United States Patent
Gill et al.

(10) Patent No.: US 11,952,352 B2
(45) Date of Patent: Apr. 9, 2024

(54) RAS INHIBITORS

(71) Applicant: Revolution Medicines, Inc., Redwood City, CA (US)

(72) Inventors: Adrian L. Gill, Atherton, CA (US); James Cregg, Belmont, CA (US); Elena S. Koltun, Foster City, CA (US); Yang Liu, Foster City, CA (US)

(73) Assignee: Revolution Medicines, Inc., Redwood City, CA (US)

( * ) Notice: Subject to any disclaimer, the term of this patent is extended or adjusted under 35 U.S.C. 154(b) by 0 days.

(21) Appl. No.: 18/161,266

(22) Filed: Jan. 30, 2023

(65) Prior Publication Data

US 2023/0234929 A1 Jul. 27, 2023

Related U.S. Application Data

(63) Continuation of application No. 17/089,035, filed on Nov. 4, 2020, now Pat. No. 11,566,007.

(60) Provisional application No. 63/043,588, filed on Jun. 24, 2020, provisional application No. 63/011,636, filed on Apr. 17, 2020, provisional application No. 63/000,357, filed on Mar. 26, 2020, provisional application No. 62/951,652, filed on Dec. 20, 2019, provisional application No. 62/930,355, filed on Nov. 4, 2019.

(51) Int. Cl.
*C07D 487/08* (2006.01)
*A61K 31/504* (2006.01)
*A61P 35/00* (2006.01)
*C07D 245/04* (2006.01)

(52) U.S. Cl.
CPC ............ *C07D 245/04* (2013.01); *A61P 35/00* (2018.01)

(58) Field of Classification Search
CPC ............................ C07D 487/08; A61K 31/504
See application file for complete search history.

(56) References Cited

U.S. PATENT DOCUMENTS

| | | |
|---|---|---|
| 6,183,965 B1 | 2/2001 | Verdine et al. |
| 6,372,712 B1 | 4/2002 | Briesewitz et al. |
| 6,686,454 B1 | 2/2004 | Yatscoff et al. |
| 6,713,607 B2 | 3/2004 | Caggiano et al. |
| 7,220,552 B1 | 5/2007 | Crabtree et al. |
| 7,396,660 B2 | 7/2008 | Huang et al. |
| 7,851,183 B2 | 12/2010 | Zotchev et al. |
| 8,664,186 B2 | 3/2014 | Aigle et al. |
| 9,119,853 B2 | 9/2015 | Moss et al. |
| 9,211,291 B2 | 12/2015 | Berkenblit et al. |
| 9,250,237 B2 | 2/2016 | Liu et al. |
| 9,260,484 B2 | 2/2016 | Briesewitz et al. |
| 9,428,845 B1 | 8/2016 | Verdine et al. |
| 9,989,535 B2 | 6/2018 | Verdine et al. |
| 10,039,839 B2 | 8/2018 | Verdine et al. |
| 10,203,323 B2 | 2/2019 | Verdine et al. |
| 10,466,249 B2 | 11/2019 | Verdine et al. |
| 10,533,016 B2 | 1/2020 | Verdine et al. |
| 10,800,787 B2 | 10/2020 | Bodhuri et al. |
| 10,948,495 B2 | 3/2021 | Verdine et al. |
| 10,989,710 B2 | 4/2021 | Verdine et al. |
| 11,059,830 B2 | 7/2021 | Verdine et al. |
| 11,608,346 B2 | 3/2023 | Koltun et al. |
| 11,644,460 B2 | 5/2023 | Verdine et al. |
| 11,690,915 B2 | 7/2023 | Aay et al. |
| 11,739,074 B2 | 8/2023 | Aggen et al. |
| 2002/0110874 A1 | 8/2002 | Khosla et al. |
| 2002/0147133 A1 | 10/2002 | Briesewitz et al. |
| 2003/0153053 A1 | 8/2003 | Reid |
| 2003/0175901 A1 | 9/2003 | Reeves et al. |
| 2004/0087496 A1 | 5/2004 | Kim et al. |
| 2004/0157768 A1 | 8/2004 | Or et al. |
| 2005/0233431 A1 | 10/2005 | Ashley et al. |
| 2007/0203168 A1 | 8/2007 | Zhao |
| 2007/0218502 A1 | 9/2007 | Hahn et al. |
| 2007/0265333 A1 | 11/2007 | Fu et al. |
| 2011/0117606 A1 | 5/2011 | Jorgensen et al. |
| 2012/0208720 A1 | 8/2012 | Kashiwagi et al. |
| 2012/0270800 A1 | 10/2012 | Verdine et al. |
| 2013/0072439 A1 | 3/2013 | Nash et al. |
| 2014/0073581 A1 | 3/2014 | Liu et al. |
| 2014/0316104 A1 | 10/2014 | Fischer et al. |
| 2015/0250896 A1 | 9/2015 | Zhao |
| 2015/0307855 A1 | 10/2015 | Yuzawa et al. |
| 2016/0083373 A1 | 3/2016 | Xu |
| 2016/0199506 A1 | 7/2016 | Verdine et al. |
| 2016/0296528 A1 | 10/2016 | Pastor Fernandez et al. |
| 2016/0341719 A1 | 11/2016 | Verdine et al. |
| 2017/0190734 A1 | 7/2017 | Aciro et al. |
| 2018/0318434 A1 | 11/2018 | Verdine et al. |
| 2020/0197391 A1 | 6/2020 | Jin et al. |
| 2020/0199102 A1 | 6/2020 | Mulvihill et al. |
| 2021/0130303 A1 | 5/2021 | Koltun et al. |

(Continued)

FOREIGN PATENT DOCUMENTS

| | | |
|---|---|---|
| EP | 0194972 A2 | 9/1986 |
| EP | 0393934 A1 | 10/1990 |

(Continued)

OTHER PUBLICATIONS

U.S. Appl. No. 61/418,038, Johns Hopkins University.

(Continued)

*Primary Examiner* — Bruck Kifle

(74) *Attorney, Agent, or Firm* — Clark & Elbing LLP

(57) ABSTRACT

The disclosure features macrocyclic compounds, and pharmaceutical compositions and protein complexes thereof, capable of inhibiting Ras proteins, and their uses in the treatment of cancers.

4 Claims, 6 Drawing Sheets

(56) References Cited

U.S. PATENT DOCUMENTS

| | | |
|---|---|---|
| 2021/0130326 A1 | 5/2021 | Aggen et al. |
| 2021/0130369 A1 | 5/2021 | Koltun et al. |
| 2021/0285955 A1 | 9/2021 | Mulvihill et al. |
| 2021/0405060 A1 | 12/2021 | Verdine et al. |
| 2022/0082556 A1 | 3/2022 | Verdine et al. |
| 2022/0105185 A1 | 4/2022 | Aay et al. |
| 2022/0143202 A1 | 5/2022 | Verdine et al. |
| 2022/0144849 A1 | 5/2022 | Verdine et al. |
| 2023/0100838 A1 | 3/2023 | Pitzen et al. |
| 2023/0106174 A1 | 4/2023 | Koltun et al. |

FOREIGN PATENT DOCUMENTS

| | | |
|---|---|---|
| EP | 0562853 A1 | 9/1993 |
| EP | 1079859 B1 | 7/2010 |
| KR | 10-2009-0041971 A | 4/2009 |
| WO | WO-86/02080 A1 | 4/1986 |
| WO | WO-95/32294 A1 | 11/1995 |
| WO | WO-96/20216 A1 | 7/1996 |
| WO | WO-98/01546 A2 | 1/1998 |
| WO | WO-98/07743 A1 | 2/1998 |
| WO | WO-98/12217 A1 | 3/1998 |
| WO | WO-99/61055 A1 | 12/1999 |
| WO | WO-00/47724 A2 | 8/2000 |
| WO | WO-01/36460 A2 | 5/2001 |
| WO | WO-01/36612 A1 | 5/2001 |
| WO | WO-01/90070 A2 | 11/2001 |
| WO | WO-03/033010 A1 | 4/2003 |
| WO | WO-2008/069824 A2 | 6/2008 |
| WO | WO-2010/031185 A1 | 3/2010 |
| WO | WO-2010/034243 A1 | 4/2010 |
| WO | WO-2010/088573 A1 | 8/2010 |
| WO | WO-2012/075048 A2 | 6/2012 |
| WO | WO-2012/078915 A1 | 6/2012 |
| WO | WO-2012/174489 A2 | 12/2012 |
| WO | WO-2013/001310 A1 | 1/2013 |
| WO | WO-2013/022818 A1 | 2/2013 |
| WO | WO-2013/185090 A1 | 12/2013 |
| WO | WO-2013/185093 A1 | 12/2013 |
| WO | WO-2013/185103 A1 | 12/2013 |
| WO | WO-2014/009774 A1 | 1/2014 |
| WO | WO-2014/187959 A2 | 11/2014 |
| WO | WO-2015/132784 A1 | 9/2015 |
| WO | WO-2016/112279 A1 | 7/2016 |
| WO | WO-2016/112295 A1 | 7/2016 |
| WO | WO-2016/160362 A1 | 10/2016 |
| WO | WO-2017/059207 A1 | 4/2017 |
| WO | WO-2018/081592 A2 | 5/2018 |
| WO | WO-2018/091634 A1 | 5/2018 |
| WO | WO-2018/187401 A1 | 10/2018 |
| WO | WO-2018/187423 A1 | 10/2018 |
| WO | WO-2018/217651 A1 | 11/2018 |
| WO | WO-2020/101736 A1 | 5/2020 |
| WO | WO-2020/132597 A1 | 6/2020 |
| WO | WO-2021/091956 A1 | 5/2021 |
| WO | WO-2021/091967 A1 | 5/2021 |
| WO | WO-2021/091982 A1 | 5/2021 |
| WO | WO-2021/108683 A1 | 6/2021 |
| WO | WO-2022/060583 A1 | 3/2022 |
| WO | WO-2022/060836 A1 | 3/2022 |

OTHER PUBLICATIONS

"Registration No. 333-235968: Amendment No. 2 to Form S-1 Registration Statement Under The Securities Act of 1933 for Revolution Medicines, Inc.," United States Securities and Exchange Commission, Washington, D.C., 20549, dated Feb. 11, 2020 (354 pages).

"SMART™ Drugs: Engineering Nature's Solution to the Undruggable Target Challenge," WarpDrive Bio, 2016, available <http://www.warpdrivebio.com/docs/Warp%20Drive%20Bio_SMART%20Drugs%20Platform_2016.pdf> (31 pages).

"Substructure Search Report on Specifically Substituted Macrocycles—Substances Only," prepared by Science IP, dated Dec. 17, 2014 (6177 pages).

"Translating Frontier Oncology Targets to Outsmart Cancer™," Corporate Overview Q3-2020, Revolution Medicines, Aug. 20, 2020 (35 pages).

Aebi et al., "Synthesis, Conformation, and Immunosuppressive Activities of Three Analogues of Cyclosporin A Modified in the 1-Position," J Med Chem. 33(3):999-1009 (1990).

Allain et al., "Cyclophilin B mediates cyclosporin A incorporation in human blood T-lymphocytes through the specific binding of complexed drug to the cell surface," Biochem J. 317 (Pt 2):565-70 (1996).

Andrei et al., "Stabilization of protein-protein interactions in drug discovery," Expert Opin Drug Discov. 12(9):925-40 (2017) (17 pages).

Antunes et al., "A mutational analysis defines Vibrio fischeri LuxR binding sites," J Bacteriol. 190(13):4392-7 (2008).

Archibald et al., "Discovery and Evaluation of Potent, Cysteine-based alpha4beta1 Integrin Antagonists," Bioorg Med Chem Lett. 10(9):993-995 (2000).

Baillie, "Targeted Covalent Inhibitors for Drug Design," Covalent Inhibitor Drug Discovery & Development Symposium PBSS, Feb. 7, Foster City, California. (2019) (16 pages).

Banaszynski et al., "Characterization of the FKBP.rapamycin.FRB ternary complex," J Am Chem Soc. 127(13):4715-21 (2005).

Baranasic et al., "Draft Genome Sequence of Streptomyces rapamycinicus Strain NRRL 5491, the Producer of the Immunosuppressant Rapamycin," Genome Announc. 1(4):e00581-13 (2013) (2 pages).

Bayle et al., "Rapamycin analogs with differential binding specificity permit orthogonal control of protein activity," Chem Biol. 13(1):99-107 (2006).

Bender et al., "Periodate Oxidation of alpha-Keto gamma-Lactams. Enol Oxidation and beta-Lactam Formation. Mechanism of Periodate Hydroxylation Reactions," J Org Chem. 43(17):3354-3362 (1978).

Benjamin et al., "Rapamycin passes the torch: a new generation of mTOR inhibitors," Nat Rev Drug Discov. 10(11):868-80 (2011).

Bhuyan et al., "Antioxidant activity of peptide-based angiotensin converting enzyme inhibitors," Org Biomol Chem. 10(11):2237-47 (2012).

Blodgett et al., "Unusual transformations in the biosynthesis of the antibiotic phosphinothricin tripeptide," Nat Chem Biol. 3(8):480-5 (2007).

Briesewitz et al., "Affinity modulation of small-molecule ligands by borrowing endogenous protein surfaces," Proc Natl Acad Sci U.S.A. 96(5):1953-8 (1999).

Bruce, "In vivo protein complex topologies: sights through a cross-linking lens," Proteomics. 12(10):1565-75 (2012).

Burgess et al., "Controlled translocation of palladium(II) within a 22 ring atom macrocyclic ligand," Dalton Trans. 43(45):17006-16 (2014) (12 pages).

Chaurasia et al., "Molecular insights into the stabilization of protein-protein interactions with small molecule: The FKBP12-rapamycin-FRB case study," Chem Phys Lett. 587:68-74 (2013).

Che et al., "Inducing protein-protein interactions with molecular glues," Bioorg Med Chem Lett. 28(15):2585-92 (2018) (18 pages).

Chevalier et al., "Straightforward synthesis of bioconjugatable azo dyes. Part 1: Black Hole Quencher-1 (BHQ-1) scaffold," Tetrahedron Lett. 55(50):6759-63 (2014).

Ding et al., "Insights into Bacterial 6-Methylsalicylic Acid Synthase and Its Engineering to Orsellinic Acid Synthase for Spirotetronate Generation," Chem Biol. 17(5):495-503 (2010).

Eberle et al., "Preparation of Functionalized Ethers of Cyclosporin A," Tetrahedron Lett. 35(35):6477-6480 (1994).

Extended European Search Report for European Application No. 16735480.2, dated Aug. 8, 2018 (9 pages).

Extended European Search Report for European Application No. 16852685.3, dated Feb. 4, 2019 (8 pages).

Extended European Search Report for European Patent Application No. 17783058.5, dated Aug. 22, 2019 (15 pages).

Findlay et al., "The structure of demethoxyrapamycin," Can J Chem. 60:2046-7 (1982).

(56) References Cited

OTHER PUBLICATIONS

Garg et al., "Elucidation of the Cryptic Epimerase Activity of Redox-Inactive Ketoreductase Domains from Modular Polyketide Synthases by Tandem Equilibrium Isotope Exchange," J Am Chem Soc. 136(29):10190-10193 (2014).

Gill et al., "Discovery of Small Molecule Inhibitors of the Oncogenic, GTP-Bound (ON) Form of $KRAS^{G12C}$ and $KRAS^{G13C}$," Revolution Medicines (Sep. 2019) (1 page).

Gill, "Discovery of Small Molecule Inhibitors of Oncogenic Mutants of RAS," Revolution Medicines, ACS, Apr. 2, Orlando (2019) (23 pages).

Gordon et al., "A SARS-CoV-2 Protein Interaction Map Reveals Targets for Drug Repurposing," Nature. 583(7816):459-68 (Apr. 2020).

Guerra et al., "LAL regulators SCO0877 and SCO7173 as pleiotropic modulators of phosphate starvation response and actinorhodin biosynthesis in Streptomyces coelicolor," PLoS One. 7(2):e31475 (2012) (11 pages).

Guo et al., "Rapamycin-inspired macrocycles with new target specificity," Nat Chem. 11(3):254-263 (Mar. 2019) (13 pages).

Hansson et al., "Bioengineering and Semisynthesis of an Optimized Cyclophilin Inhibitor for Treatment of Chronic Viral Infection," Chem Biol. 22(2):285-92 (2015) (24 pages).

He et al., "The LuxR family members GdmRI and GdmRII are positive regulators of geldanamycin biosynthesis in Streptomyces hygroscopicus 17997," Arch Microbiol. 189(5):501-10 (2008).

Hong et al., "Evidence for an iterative module in chain elongation on the azalomycin polyketide synthase," Beilstein J Org Chem. 12:2164-2172 (2016).

Horn et al., "Draft Genome Sequence of Streptomyces iranensis," Genome Announc. 2(4):e00616-14 (2014) (2 Pages).

Horton et al., "Engineering hybrid genes without the use of restriction enzymes: gene splicing by overlap extension," Gene. 77(1):61-8 (1989).

Hosted et al., "Use of rpsL for dominance selection and gene replacement in *Streptomyces roseosporus*," J Bacteriol. 179(1):180-6 (1997).

Huang et al., "Conjugation to Albumin-Binding Molecule Tags as a Strategy to Improve Both Efficacy and Pharmacokinetic Properties of the Complement Inhibitor Compstatin," ChemMedChem. 9(10):2223-6 (2014).

Huang et al., "Enhanced rapamycin production in *Streptomyces hygroscopicus* by integrative expression of aveR, a LAL family transcriptional regulator," World J Microbiol Biotechnol. 27:2103-9 (2011).

Hubler et al., "Synthetic routes to $NEtXaa^4$-cyclosporin A derivatives as potential anti-HIV I drugs," Tetrahedron Lett. 41:7193-6 (2000).

International Preliminary Report on Patentability for International Application No. PCT/US2016/012631, dated Jul. 20, 2017 (7 pages).

International Preliminary Report on Patentability for International Application No. PCT/US2017/027215, dated Oct. 25, 2018 (7 pages).

International Search Report and Written Opinion for International Application No. PCT/US17/58805, dated Aug. 27, 2018 (16 pages).

International Search Report and Written Opinion for International Application No. PCT/US2016/012631, dated Mar. 16, 2016 (13 pages).

International Search Report and Written Opinion for International Application No. PCT/US2016/012656, dated Mar. 21, 2016 (14 pages).

International Search Report and Written Opinion for International Application No. PCT/US2016/054691, dated Feb. 15, 2017 (28 pages).

International Search Report and Written Opinion for International Application No. PCT/US2017/027215, dated Jul. 10, 2017 (13 pages).

International Search Report and Written Opinion for International Application No. PCT/US2017/058800, dated Apr. 3, 2018 (21 pages).

International Search Report and Written Opinion for International Application No. PCT/US2018/025991, dated Jun. 26, 2018 (13 pages).

International Search Report and Written Opinion for International Application No. PCT/US2018/026014, dated Aug. 7, 2018 (31 pages).

International Search Report and Written Opinion for International Application No. PCT/US2019/068100, dated Feb. 24, 2020 (16 pages).

International Search Report and Written Opinion for International Application No. PCT/US2020/058841, dated Jan. 11, 2021 (15 pages).

Ishizawa et al., "TRAP display: a high-speed selection method for the generation of functional polypeptides," J Am Chem. 135(14):5433-40 (2013).

Jarvis, "Have drug hunters finally cracked KRas?—After decades of failures, researchers see promise in fresh approaches to developing drugs that block cancer's toughest target," Chemical & Engineering News. 94(23):28-33. <https://cen.acs.org/articles/94/123/drug-hunters-finally-cracked-KRas.html>, retrieved on Oct. 14, 2018 (2016) (9 pages).

Kawakami et al., "In vitro selection of multiple libraries created by genetic code reprogramming to discover macrocyclic peptides that antagonize VEGFR2 activity in living cells," ACS Chem Biol. 8(6):1205-14 (2013).

Kelsey, "Approaches to Inhibiting RAS-Driven Tumors Beyond $KRAS^{G12D}$," RAS Targeted Drug Development, Revolution Medicines, Sep. 16, 2020 (24 pages).

Kendrew et al., "Recombinant strains for the enhanced production of bioengineered rapalogs," Metab Eng. 15:167-73 (2013).

Kuhn et al., "Synthesis of Functional Ras Lipoproteins and Fluorescent Derivatives," J Am Chem Soc. 123(6):1023-35 (2001).

Kuramochi et al., "Identification of Small Molecule Binding Molecules by Affinity Purification Using a Specific Ligand Immobilized on PEGA Resin," Bioconjug Chem. 19(12):2417-26 (2008).

Laureti et al., "Identification of a bioactive 51-membered macrolide complex by activation of a silent polyketide synthase in Streptomyces ambofaciens," Proc Natl Acad Sci USA. 108(15):6258- 63 (2011).

Laureti et al., Supporting Material for "Identification of a bioactive 51-membered macrolide complex by activation of a silent polyketide synthase in Streptomyces ambofaciens," Proc Natl Acad Sci U.S.A. 108(15):6258-63 (2011), accessed via <https://www.pnas.org/content/suppl/2011/03/24/1019077108.DCSupplemental> (41 pages).

Lee et al., "Current implications of cyclophilins in human cancers," J Exp Clin Cancer Res. 29(1):97 (2010) (6 pages).

Leskiw et al., "TTA codons in some genes prevent their expression in a class of developmental, antibiotic-negative, *Streptomyces* mutants," Proc Natl Acad Sci USA. 88(6):2461-5 (1991).

Li et al., "A simple and efficient route to the FKBP-binding domain from rapamycin," available in PMC Sep. 28, 2012, published in final edited form as: Tetrahedron Lett. 52(39):5070-2 (2011) (7 pages).

Luengo et al., "Structure-activity studies of rapamycin analogs: evidence that the C-7 methoxy group is part of the effector domain and positioned at the FKBP12-FRAP interface," Chem Biol. 2(7):471-81 (1995).

Mackman et al., "Discovery of a Potent and Orally Bioavailable Cyclophilin Inhibitor Derived from the Sanglifehrin Macrocycle," J Med Chem. 61(21):9473-9499 (2018).

Majumder et al. "Interaction of aryl hydrocarbon receptor-interacting protein-like 1 with the farnesyl moiety," J Biol Chem. 288(29):21320-21328 (2013).

McGregor et al., "Expanding the Scope of Electrophiles Capable of Targeting K-Ras Oncogenes," Biochemistry. 56(25):3178-3183 (2017).

Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46):14059-67 (2012) (10 pages).

Mo et al., "Interspecies Complementation of the LuxR Family Pathway-Specific Regulator Involved in Macrolide Biosynthesis," J Microbiol Biotechnol. 26(1):66-71 (2016).

(56) References Cited

OTHER PUBLICATIONS

Moore et al., "RAS-targeted therapies: is the undruggable drugged?" available in PMC Feb. 1, 2021, published in final edited form as: Nat Rev Drug Discov. 19(8):533-52 (Aug. 2020) (43 pages).
Mullard, "Cracking KRAS," Nature Publishing Group 18(12) (Nov. 2019) (14 pages).
Murphy et al., "Isolation and characterisation of amphotericin B analogues and truncated polyketide intermediates produced by genetic engineering of *Streptomyces nodosus*," Org Biomol Chem. 8(16):3758-70 (2010).
Non-Final Office Action for U.S. Appl. No. 15/974,923, dated Apr. 15, 2019 (6 pages).
Notification of Reasons for Rejection for Japanese Application No. 2017-555427, dated Aug. 28, 2018 (12 pages).
Ochi et al., "New strategies for drug discovery: activation of silent or weakly expressed microbial gene clusters," Appl Microbiol Biotechnol. 97(1):87-98 (2013).
Ostrem et al., "Direct small-molecule inhibitors of KRAS: from structural insights to mechanism-based design," Nat Rev Drug Discov. 15(11):771-785 (2016).
Ostrem et al., "K-Ras(G12C) inhibitors allosterically control GTP affinity and effector interactions," Nature. 503(7477):548-51 (2013) (14 pages).
Papageorgiou et al., "Improved binding affinity for cyclophilin A by a cyclosporin derivative singly modified at its effector domain," J Med Chem. 37(22):3674-6 (1994).
Pfeifer et al., "Biosynthesis of complex polyketides in a metabolically engineered strain of *E. coli*," Science. 291(5509):1790-2 (2001) (4 pages).
Power et al., "Engineered Synthesis of 7-Oxo- and 15-Deoxy-15-Oxo-Amphotericins: Insights into Structure-Activity Relationships in Polyene Antibiotics," Chem Biol. 15(1):78-86 (2008).
PubChem CID 130196149, <https://pubchem.ncbi.nlm.nih.gov/compound/130196149>, retrieved on Apr. 1, 2020 (10 pages).
Quesniaux et al., "Cyclophilin binds to the region of cyclosporine involved in its immunosuppressive activity," Eur J Immunol. 17(9):1359-65 (1987).
Quesniaux et al., "Study of the conformation of cyclosporine in aqueous medium by means of monoclonal antibodies," Int J Pept Protein Res. 31(2):173-85 (1988).
Ranganathan et al., "Knowledge-based design of bimodular and trimodular polyketide synthases based on domain and module swaps: a route to simple statin analogues," Chem Biol. 6(10):731-41 (1999).
Ray et al., "New Electrophiles and Strategies for Mechanism-Based and Targeted Covalent Inhibitor Design," Biochemistry. 58: 5234-5244 (Dec. 2019).
Reid et al. "A model of structure and catalysis for ketoreductase domains in modular polyketide synthases," Biochemistry. 42(1):72-79 (2003).
Revill et al., "Genetically engineered analogs of ascomycin for nerve regeneration," J Pharmacol Exp Ther. 302(3):1278-85 (2002).
Revolution Medicines, "Translating Frontier Oncology Targets to *Outsmart Cancer*™: Corporate Overview Q4-2020," dated Nov. 12, 2020 (30 pages).
Ruan et al., "Binding of rapamycin analogs to calcium channels and FKBP52 contributes to their neuroprotective activities," Proc Natl Acad Sci U S A. 105(1):33-8 (2008).
Rudolph, "Covalent Modification In Drug Discovery—A Chemist's Perspective," Pharmaceutical & BioScience Society. Dated Feb. 7, 2019 (39 pages).
Schulze et al., "Tri-Complex Inhibitors of the Oncogenic, GTP-Bound Form of KRAS$^{G12C}$ Overcome RTK-Mediated Escape Mechanisms and Drive Tumor Regressions in Vivo," Revolution Medicines (Oct. 2019) (1 page).
Schutt, "Safety Considerations for Covalent Inhibitors," Pharmaceutical & BioScience Society. Dated Feb. 7, 2019 (36 pages).
Schwecke et al., "The biosynthetic gene cluster for the polyketide immunosuppressant rapamycin," Proc Natl Acad Sci U S A. 92(17):7839-43 (1995).
Sebastiano et al., "Impact of Dynamically Exposed Polarity on Permeability and Solubility of Chameleonic Drugs Beyond the Rule of 5," J Med Chem. 61:4189-4202 (2018).
Shigdel et al., "Genomic discovery of an evolutionarily programmed modality for small-molecule targeting of an intractable protein surface," Proc Natl Acad Sci U S A. 117(29):17195-203 (Jul. 2020).
Sieber et al., "Novel inhibitors of the calcineurin/NFATc hub—alternatives to CsA and FK506?" Cell Commun Signal. 7:25 (2009) (19 pages).
Simanshu et al., "RAS Proteins and Their Regulators in Human Disease," available in PMC Jun. 29, 2018, published in final edited form as: Cell. 170(1):17-33 (2017) (34 pages).
Smith, "Translating Frontier Oncology Targets to Outsmart Cancer," RAS-Targeted Drug Discovery Summit, Revolution Medicines, Sep. 19, 2019 (29 pages).
Smulik et al., "Synthesis of cyclosporin A-derived affinity reagents by olefin metathesis," Org Lett. 4(12):2051-4 (2002).
Steadman et al., "Discovery of Potent Cyclophilin Inhibitors Based on the Structural Simplification of Sanglifehrin A," J Med Chem. 60:1000-1017 (2017).
Stewart et al., "Development of Inhibitors of the Activated Form of KRAS$^{G12C}$," AACR Targeting RAS-Driven Cancers, Dec. 9-12, San Diego, California. Poster B37 (2018) (1 page).
Sun et al. "Design and structure-based study of new potential FKBP12 inhibitors," Biophys J. 85(5):3194-3201 (2003).
Supplementary European Search Report for European Application No. 16852685.3, dated Feb. 4, 2019 (8 pages).
Supplementary Partial European Search Report for European Application No. 17863519.9, dated Jun. 15, 2020 (16 pages).
Supplementary Partial European Search Report for European Patent Application No. 17865512.2, dated May 7, 2020 (20 pages).
Sweeney et al., "From chemical tools to clinical medicines: non-immunosuppressive cyclophilin inhibitors derived from the cyclosporin and sanglifehrin scaffolds," J Med Chem. 57(17):7145-59 (2014) (63 pages).
Sànchez-Tilló et al., "Cyclophilin A is required for M-CSF-dependent macrophage proliferation," Eur J Immunol. 36(9):2515-24 (2006).
Takakusagi et al., "Efficient one-cycle affinity selection of binding proteins or peptides specific for a small-molecule using a T7 phage display pool," Bioorg Med Chem. 16(22):9837-46 (2008).
Tanaka et al., "Clinical Acquired Resistance to KRAS$^{G12C}$ Inhibition through a Novel KRAS Switch-II Pocket Mutation and Polyclonal Alterations Converging on RAS-MAPK Reactivation," Cancer Discov. 11(8):1913-1922 (Apr. 6, 2021).
Tang et al., "Generation of New Epothilones by Genetic Engineering of a Polyketide Synthase in Myxococcus xanthus," J Antibiot (Tokyo). 58(3):178-184 (2005).
UniProtKB Accession No. A0A061A6I8, Sep. 3, 2014, available <http://www.uniprot.org/uniprot/A0A061A6I8>, (12 pages).
UniProtKB Accession No. Q54296, "Polyketide synthase," <https://www.uniprot.org/uniprot/A0A61A618.txt?version=14>, retrieved May 29, 2020 (12 pages).
UniProtKB Accession No. Q54296, Nov. 1, 1996, available <http://www.uniprot.org/uniprot/Q54296>, (12 pages).
UniProtKB Accession No. Q54297, Nov. 1, 1996, available <https://www.uniprot.org/uniprot/Q54297.txt>, (3 pages).
Upadhyaya et al., "Direct Ras Inhibitors Identified From a Structurally Rigidified Bicyclic Peptide Library," available in PMC Oct. 21, 2015, published in final edited form as: Tetrahedron. 70(42):7714-7720 (2014) (15 pages).
Vakiti et al., "Stereoselective synthesis of C17-C34 fragment of antascomicin A," Tetrahedron Lett. 55(47):6438-40 (2014).
Vignot et al., "mTOR-targeted therapy of cancer with rapamycin derivatives," Ann Oncol. 16(4):525-37 (2005).
Wagner et al., "New naturally occurring amino acids," Angew Chem Int Ed Engl. 22(11):816-28 (1983).
Wang et al., "Thermodynamic analysis of cyclosporin a binding to cyclophilin a in a lung tumor tissue lysate," Anal Chem. 76(15):4343-8 (2004).
Weissman et al., "Combinatorial biosynthesis of reduced polyketides," Nat Rev Microbiol. 3(12):925-36 (2005).

(56) References Cited

OTHER PUBLICATIONS

Weissman, "Genetic engineering of modular PKSs: from combinatorial biosynthesis to synthetic biology," Nat Prod Rep. 33(2):203-230 (2016).
Wilson et al., "Comparative X-ray structures of the major binding protein for the immunosuppressant FK506 (tacrolimus) in unliganded form and in complex with FK506 and rapamycin," Acta Cryst. D51:511-21 (1995).
Wright et al., "Multivalent binding in the design of bioactive compounds," Curr Org Chem. 5(11):1107-31 (2001).
Wu et al., "Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).
Wu et al., "Inhibition of ras-effector interactions by cyclic peptides," Med Chem Commun. 4(2):378-82 (2013).
Wu et al., "Synthesis of Ketone Analogues of Prolyl and Pipecolyl Ester FKBP12 Ligands," J Med Chem. 45(16):3558-3568 (2002).
Zhang et al., "Bifunctional Small-Molecule Ligands of K-Ras Induce Its Association with Immunophilin Proteins," Angew Chem Int Ed Engl. 131:16460-5 (Nov. 2019).
Zhou et al., "Biophysical and biochemical characterization of $KRAS^{G12C}$ inhibition through a novel modality," AACR Targeting RAS-Driven Cancers, Dec. 9-12, San Diego, California. Poster A06 (2018) (1 page).
Banteli et al., "A synthesis of the C1-N12 tripeptide fragment of sanglifehrin A," Tetrahedron Letters. 40(11):2109-2112 (Mar. 12, 1999).
Doak et al., "Cyclophilin Succumbs to a Macrocyclic Chameleon," J Med Chem. 61(21):9469-9472 (Nov. 2018).
Halford, "Covalent drugs go from fringe field to fashionable endeavor: Designing molecules that make bonds with their biological targets is in vogue," Chemical and Engineering News, 98(43) (Nov. 2020) (6 pages).
Janes et al., "Targeting KRAS Mutant Cancers with a Covalent G12C-Specific Inhibitor," Cell., 172(3):578-589.e17 (Jan. 2018) (30 pages).
Pei et al., "Targeting Ras with Macromolecules," Cold Spring Harb Perspect Med. 8(3):a031476 (Mar. 2018) (13 pages).
Pollock et al., "Development of Inhibitors of the Activated Form of $KRAS^{G12C}$," AACR Targeting RAS-Driven Cancers, Dec. 9-12, San Diego, California (Dec. 2018) (Abstract Included) (2 pages).
Wildes et al., "Inhibition of the Oncogenic, GTP-Bound Form of $KRAS^{G12C}$ by Second Generation, Tri-Complex Inhibitors Overcomes RTK-Mediated Escape Mechanisms," The FASEB Regulation and Function of Small GTPases Conference, Jun. 23-28, Olean, New York (Abstract Included) (Jun. 2019) (2 pages).

CTG H358 EC50 µM Matched Pairs

Formula AA          Formula BB

RAS INHIBITORS

CROSS-REFERENCE TO RELATED APPLICATIONS

The present application claims the benefit of priority to U.S. Application No. 62/930,355, filed on Nov. 4, 2019; U.S. Application No. 62/951,652, filed on Dec. 20, 2019; U.S. Application No. 63/000,357, filed on Mar. 26, 2020; U.S. Application No. 63/011,636, filed on Apr. 17, 2020; and U.S. Application No. 63/043,588, filed on Jun. 24, 2020, all of which are hereby incorporated by reference in their entirety.

BACKGROUND

The vast majority of small molecule drugs act by binding a functionally important pocket on a target protein, thereby modulating the activity of that protein. For example, cholesterol-lowering drugs known as statins bind the enzyme active site of HMG-CoA reductase, thus preventing the enzyme from engaging with its substrates. The fact that many such drug/target interacting pairs are known may have misled some into believing that a small molecule modulator could be discovered for most, if not all, proteins provided a reasonable amount of time, effort, and resources. This is far from the case. Current estimates are that only about 10% of all human proteins are targetable by small molecules. Bojadzic and Buchwald, Curr Top Med Chem 18: 674-699 (2019). The other 90% are currently considered refractory or intractable toward above-mentioned small molecule drug discovery. Such targets are commonly referred to as "undruggable." These undruggable targets include a vast and largely untapped reservoir of medically important human proteins. Thus, there exists a great deal of interest in discovering new molecular modalities capable of modulating the function of such undruggable targets.

It has been well established in literature that Ras proteins (K-Ras, H-Ras and N-Ras) play an essential role in various human cancers and are therefore appropriate targets for anticancer therapy. Indeed, mutations in Ras proteins account for approximately 30% of all human cancers in the United States, many of which are fatal. Dysregulation of Ras proteins by activating mutations, overexpression or upstream activation is common in human tumors, and activating mutations in Ras are frequently found in human cancer. For example, activating mutations at codon 12 in Ras proteins function by inhibiting both GTPase-activating protein (GAP)-dependent and intrinsic hydrolysis rates of GTP, significantly skewing the population of Ras mutant proteins to the "on" (GTP-bound) state (Ras(ON)), leading to oncogenic MAPK signaling. Notably, Ras exhibits a picomolar affinity for GTP, enabling Ras to be activated even in the presence of low concentrations of this nucleotide. Mutations at codons 13 (e.g., G13D) and 61 (e.g., Q61K) of Ras are also responsible for oncogenic activity in some cancers.

Despite extensive drug discovery efforts against Ras during the last several decades, a drug directly targeting Ras is still not approved. Additional efforts are needed to uncover additional medicines for cancers driven by the various Ras mutations.

SUMMARY

Provided herein are Ras inhibitors. The approach described herein entails formation of a high affinity three-component complex, or conjugate, between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex, or conjugate, between the Ras protein and the widely expressed cytosolic chaperone, cyclophilin A (CYPA). Without being bound by theory, the inventors believe that one way the inhibitory effect on Ras is effected by compounds of the invention and the complexes, or conjugates, they form is by steric occlusion of the interaction site between Ras and downstream effector molecules, such as RAF and PI3K, which are required for propagating the oncogenic signal.

As such, in some embodiments, the disclosure features a compound, or pharmaceutically acceptable salt thereof, of structural Formula I:

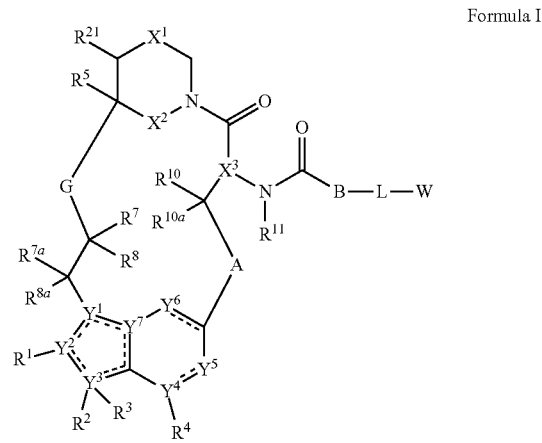

Formula I wherein the dotted lines represent zero, one, two, three, or four non-adjacent double bonds;

A is —N(H or $CH_3$)C(O)—$(CH_2)$— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is absent, —CH($R^9$)—, >C=C$R^9R^{9'}$, or >C$R^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a vinyl ketone, a vinyl sulfone, an ynone, a haloacetal, or an alkynyl sulfone;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, CH$_2$, or N;

$Y^6$ is C(O), CH, CH$_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^{9'}$ is H, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; or $R^9$ and L combine with the atoms to which they are attached to form an optionally substituted 3 to 14-membered heterocycloalkyl;

$R^{9'}$ is hydrogen or optionally substituted $C_1$-$C_6$ alkyl; or $R^9$ and $R^{9'}$, combined with the atoms to which they are attached, form a 3 to 6-membered cycloalkyl or a 3 to 6-membered heterocycloalkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl; and $R^{21}$ is hydrogen or $C_1$-$C_3$ alkyl (e.g., methyl).

Also provided are pharmaceutical compositions comprising a compound of Formula I, or a pharmaceutically acceptable salt thereof, and a pharmaceutically acceptable excipient.

Further provided is a conjugate, or salt thereof, comprising the structure of Formula IV:

M-L-P      Formula IV wherein L is a linker;

P is a monovalent organic moiety; and

M has the structure of Formula V:

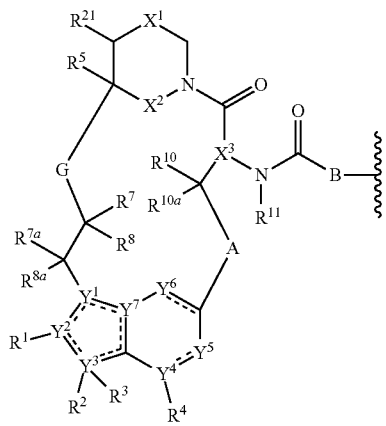

Formula V wherein the dotted lines represent zero, one, two, three, or four non-adjacent double bonds;

A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is absent, —CH(R$^9$)—, >C=CR$^9$R$^{9'}$, or >CR$^9$R$^{9'}$ where the carbon is bound to the carbonyl carbon of —N(R$^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

$X^1$ is optionally substituted $C_1$-$C_2$ alkylene, NR, O, or $S(O)_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, CH$_2$, or N;

$Y^6$ is C(O), CH, CH$_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is H, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl; or $R^9$ and $R^{9'}$, combined with the atoms to which they are attached, form a 3 to 6-membered cycloalkyl or a 3 to 6-membered heterocycloalkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl; and $R^{21}$ is H or $C_1$-$C_3$ alkyl.

Also provided is a method of treating cancer in a subject in need thereof, the method comprising administering to the subject a therapeutically effective amount of a compound of the present invention, or a pharmaceutically acceptable salt thereof.

In some embodiments, a method is provided of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

BRIEF DESCRIPTION OF THE DRAWINGS

FIG. 2A shows Compound A dosed at 100 mg/kg by daily oral gavage led to tumor regression in NCI-H358 KRASG12C xenograft model, which is a sensitive model to KRASG12C inhibition alone. The spaghetti titer plot (FIG. 2B) displaying individual tumor growth is shown next to the tumor volume plot (FIG. 2A).

FIG. 3A shows the combination of intermittent intravenous administration of Compound B at 50 mg/kg plus daily oral administration of cobimetinib at 2.5 mg/kg drove tumor regression, whereas each single agent led to tumor growth inhibition. End of study responses were shown as waterfall plots (FIG. 3B), which indicate 6 out 10 mice had tumor regression in the combination group, whereas no tumor regressions recorded in each single agent group.

In FIG. 4A, the combinatorial activity of once weekly intravenous administration of Compound C at 60 mg/kg plus daily oral administration of SHP2 inhibitor at 30 mg/kg is shown. End of study responses in individual tumors were plotted as a waterfall plot (FIG. 4B).

DEFINITIONS AND CHEMICAL TERMS

Figure 1A:
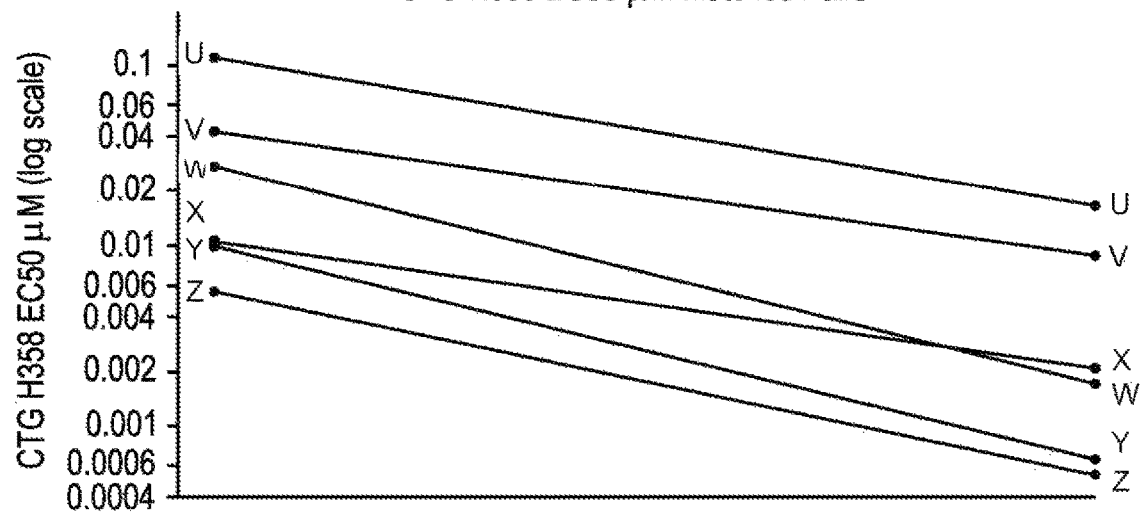
FIG. 1A and FIG. 1B: These figures illustrate a matched pair analysis of potencies of certain compounds of the present invention (Formula BB) (points on the right) and corresponding compounds of Formula AA (points on the left) wherein a H is replaced with (S)Me in the context of two different cell-based assays. The y axes represent pERK EC50 (FIG. 1A) or CTG IC50 (FIG. 1B) as measured in an H358 cell line.
Figure 1A:
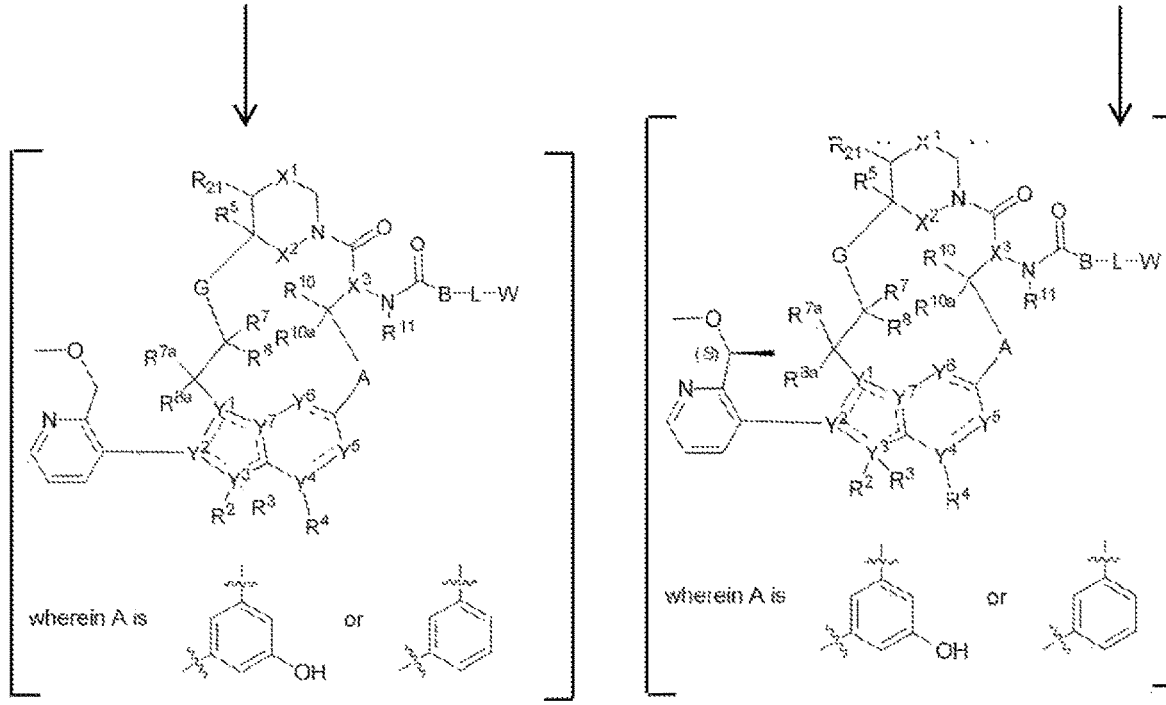

In this application, unless otherwise clear from context, (i) the term "a" means "one or more"; (ii) the term "or" is used to mean "and/or" unless explicitly indicated to refer to alternatives only or the alternative are mutually exclusive, although the disclosure supports a definition that refers to only alternatives and "and/or"; (iii) the terms "comprising" and "including" are understood to encompass itemized components or steps whether presented by themselves or together with one or more additional components or steps; and (iv) where ranges are provided, endpoints are included.

As used herein, the term "about" is used to indicate that a value includes the standard deviation of error for the device or method being employed to determine the value. In certain embodiments, the term "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

As used herein, the term "adjacent" in the context of describing adjacent atoms refers to bivalent atoms that are directly connected by a covalent bond.

A "compound of the present invention" and similar terms as used herein, whether explicitly noted or not, refers to Ras inhibitors described herein, including compounds of Formula I and subformula thereof, and compounds of Table 1 and Table 2, as well as salts (e.g., pharmaceutically acceptable salts), solvates, hydrates, stereoisomers (including atropisomers), and tautomers thereof.

The term "wild-type" refers to an entity having a structure or activity as found in nature in a "normal" (as contrasted with mutant, diseased, altered, etc) state or context. Those of ordinary skill in the art will appreciate that wild-type genes and polypeptides often exist in multiple different forms (e.g., alleles).

Those skilled in the art will appreciate that certain compounds described herein can exist in one or more different isomeric (e.g., stereoisomers, geometric isomers, atropisomers, tautomers) or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{32}$P, $^{33}$P, $^{35}$S, $^{18}$F, $^{36}$Cl, $^{123}$I and $^{125}$I. Isotopically-labeled compounds (e.g., those labeled with $^3$H and $^{14}$C) can be useful in compound or substrate tissue distribution assays. Tritiated (i.e., $^3$H) and carbon-14 (i.e., $^{14}$C) isotopes can be useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements). In some embodiments, one or more hydrogen atoms are replaced by $^2$H or $^3$H, or one or more carbon atoms are replaced by $^{13}$C- or $^{14}$C-enriched carbon. Positron emitting isotopes such as 150, $^{13}$N, $^{11}$C, and $^{18}$F are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

At various places in the present specification, substituents of compounds of the present disclosure are disclosed in groups or in ranges. It is specifically intended that the present disclosure include each and every individual sub-combination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substituents are disclosed in groups or in ranges, unless otherwise indicated, the present disclosure is intended to cover individual compounds and groups of compounds (e.g., genera and subgenera) containing each and every individual subcombination of members at each position.

The term "optionally substituted X" (e.g., "optionally substituted alkyl") is intended to be equivalent to "X, wherein X is optionally substituted" (e.g., "alkyl, wherein said alkyl is optionally substituted"). It is not intended to mean that the feature "X" (e.g., alkyl) per se is optional. As described herein, certain compounds of interest may contain one or more "optionally substituted" moieties. In general, the term "substituted", whether preceded by the term "optionally" or not, means that one or more hydrogens of the designated moiety are replaced with a suitable substituent, e.g., any of the substituents or groups described herein. Unless otherwise indicated, an "optionally substituted" group may have a suitable substituent at each substitutable position of the group, and when more than one position in any given structure may be substituted with more than one substituent selected from a specified group, the substituent may be either the same or different at every position. For example, in the term "optionally substituted $C_1$-$C_6$ alkyl-$C_2$-$C_9$ heteroaryl," the alkyl portion, the heteroaryl portion, or both, may be optionally substituted. Combinations of substituents envisioned by the present disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group may be, independently, deuterium; halogen; —(CH$_2$)$_{0-4}$R$^\circ$; —(CH$_2$)$_{0-4}$OR$^\circ$; —O(CH$_2$)$_{0-4}$R$^\circ$; —O—(CH$_2$)$_{0-4}$C(O) OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; 4-8 membered saturated or unsaturated heterocycloalkyl (e.g., pyridyl); 3-8 membered saturated or unsaturated cycloalkyl (e.g., cyclopropyl, cyclobutyl, or cyclopentyl); —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O) NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S) R$^\circ$; —(CH$_2$)$_{0-4}$C(O)OR$^\circ$; —(CH$_2$)$_{0-4}$—C(O)—N(R$^\circ$)$_2$; —(CH$_2$)$_{0-4}$—C(O)—N(R$^\circ$)—S(O)$_2$—R$^\circ$; —C(NCN) NR$^\circ$$_2$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR$^\circ$; —SC(S) SR$^\circ$; —(CH$_2$)$_{0-4}$SC(O)R$^\circ$; —(CH$_2$)$_{0-4}$C(O)NR$^\circ$$_2$; —C(S) NR$^\circ$$_2$; —C(S)SR$^\circ$; —(CH$_2$)$_{0-4}$OC(O) NR$^\circ$$_2$; —C(O)N (OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$ NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NOR$^\circ$)NR$^\circ$$_2$; —C(NH)NR$^\circ$$_2$; —P(O)$_2$R$^\circ$; —P(O)R$^\circ$$_2$; —P(O)(OR$^\circ$)$_2$; —OP(O)R$^\circ$$_2$; —OP(O)(OR$^\circ$)$_2$; —OP(O)(OR$^\circ$)R$^\circ$, —SiR$^\circ$$_3$; —(C$_{1-4}$ straight or branched alkylene)O—N (R$^\circ$)$_2$; or —(C$_{1-4}$ straight or branched alkylene)C(O)O—N (R$^\circ$)$_2$, wherein each R$^\circ$ may be substituted as defined below and is independently hydrogen, —C$_{1-6}$ aliphatic, —CH$_2$Ph, —O(CH$_2$)$_{0-1}$Ph, —CH$_2$-(5-6 membered heteroaryl ring), or a 3-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), may be, independently, halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$2, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 3-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on an aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^†$ include =O and =S.

The term "acetyl," as used herein, refers to the group —C(O)CH$_3$.

The term "alkoxy," as used herein, refers to a —O—C$_1$-C$_{20}$ alkyl group, wherein the alkoxy group is attached to the remainder of the compound through an oxygen atom.

The term "alkyl," as used herein, refers to a saturated, straight or branched monovalent hydrocarbon group containing from 1 to 20 (e.g., from 1 to 10 or from 1 to 6) carbons. In some embodiments, an alkyl group is unbranched (i.e., is linear); in some embodiments, an alkyl group is branched. Alkyl groups are exemplified by, but not limited to, methyl, ethyl, n- and iso-propyl, n-, sec-, iso- and tert-butyl, and neopentyl.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like. The term "C$_x$-C$_y$ alkylene" represents alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., C$_1$-C$_6$, C$_1$-C$_{10}$, C$_2$-C$_{20}$, C$_2$-C$_6$, C$_2$-C$_{10}$, or C$_2$-C$_{20}$ alkylene). In some embodiments, the alkylene can be further substituted with 1, 2, 3, or 4 substituent groups as defined herein.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. The term "alkenylene," as used herein, represents a divalent straight or branched chain groups of, unless otherwise specified, from 2 to 20 carbons (e.g., from 2 to 6 or from 2 to 10 carbons) containing one or more carbon-carbon double bonds.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, and 1-propynyl.

The term "alkynyl sulfone," as used herein, represents a group comprising the structure

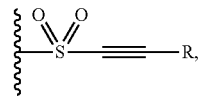

wherein R is any chemically feasible substituent described herein.

The term "amino," as used herein, represents —N(R$^†$)$_2$, e.g., —NH$_2$ and —N(CH$_3$)$_2$.

The term "aminoalkyl," as used herein, represents an alkyl moiety substituted on one or more carbon atoms with one or more amino moieties.

The term "amino acid," as described herein, refers to a molecule having a side chain, an amino group, and an acid group (e.g., —CO$_2$H or —SO$_3$H), wherein the amino acid is attached to the parent molecular group by the side chain, amino group, or acid group (e.g., the side chain). As used herein, the term "amino acid" in its broadest sense, refers to any compound or substance that can be incorporated into a polypeptide chain, e.g., through formation of one or more peptide bonds. In some embodiments, an amino acid has the general structure H$_2$N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. Exemplary amino acids include alanine, arginine, asparagine, aspartic acid, cysteine, glutamic acid, glutamine, glycine, histidine, optionally substituted hydroxylnorvaline, isoleucine, leucine, lysine, methionine, norvaline, ornithine, phenylalanine, proline, pyrrolysine, selenocysteine, serine, taurine, threonine, tryptophan, tyrosine, and valine.

The term "aryl," as used herein, represents a monovalent monocyclic, bicyclic, or multicyclic ring system formed by carbon atoms, wherein the ring attached to the pendant group is aromatic. Examples of aryl groups are phenyl, naphthyl, phenanthrenyl, and anthracenyl. An aryl ring can be attached to its pendant group at any heteroatom or carbon ring atom that results in a stable structure and any of the ring atoms can be optionally substituted unless otherwise specified.

The term "C$_0$," as used herein, represents a bond. For example, part of the term —N(C(O)—(C$_0$-C$_5$ alkylene-H)— includes —N(C(O)—(C₀ alkylene-H)—, which is also represented by —N(C(O)—H)—.

The terms "carbocyclic" and "carbocyclyl," as used herein, refer to a monovalent, optionally substituted $C_3$-$C_{12}$ monocyclic, bicyclic, or tricyclic ring structure, which may be bridged, fused or spirocyclic, in which all the rings are formed by carbon atoms and at least one ring is non-aromatic. Carbocyclic structures include cycloalkyl, cycloalkenyl, and cycloalkynyl groups. Examples of carbocyclyl groups are cyclohexyl, cyclohexenyl, cyclooctynyl, 1,2-dihydronaphthyl, 1,2,3,4-tetrahydronaphthyl, fluorenyl, indenyl, indanyl, decalinyl, and the like. A carbocyclic ring can be attached to its pendant group at any ring atom that results in a stable structure and any of the ring atoms can be optionally substituted unless otherwise specified.

The term "carbonyl," as used herein, represents a C(O) group, which can also be represented as C=O.

The term "carboxyl," as used herein, means —CO₂H, (C=O)(OH), COOH, or C(O)OH or the unprotonated counterparts.

The term "cyano," as used herein, represents a —CN group.

The term "cycloalkyl," as used herein, represents a monovalent saturated cyclic hydrocarbon group, which may be bridged, fused or spirocyclic having from three to eight ring carbons, unless otherwise specified, and is exemplified by cyclopropyl, cyclobutyl, cyclopentyl, cyclohexyl, cycloheptyl, and cycloheptyl.

The term "cycloalkenyl," as used herein, represents a monovalent, non-aromatic, saturated cyclic hydrocarbon group, which may be bridged, fused or spirocyclic having from three to eight ring carbons, unless otherwise specified, and containing one or more carbon-carbon double bonds.

The term "diastereomer," as used herein, means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "guanidinyl," refers to a group having the structure:

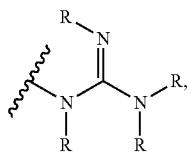

wherein each R is, independently, any chemically feasible substituent described herein.

The term "guanidinoalkyl alkyl," as used herein, represents an alkyl moiety substituted on one or more carbon atoms with one or more guanidinyl moieties.

The term "haloacetyl," as used herein, refers to an acetyl group wherein at least one of the hydrogens has been replaced by a halogen.

The term "haloalkyl," as used herein, represents an alkyl moiety substituted on one or more carbon atoms with one or more of the same of different halogen moieties.

The term "halogen," as used herein, represents a halogen selected from bromine, chlorine, iodine, or fluorine.

The term "heteroalkyl" as used herein, refers to an "alkyl" group, as defined herein, in which at least one carbon atom has been replaced with a heteroatom (e.g., an O, N, or S atom). The heteroatom may appear in the middle or at the end of the radical.

The term "heteroaryl," as used herein, represents a monovalent, monocyclic or polycyclic ring structure that contains at least one fully aromatic ring: i.e., they contain 4n+2 pi electrons within the monocyclic or polycyclic ring system and contains at least one ring heteroatom selected from N, O, or S in that aromatic ring. Exemplary unsubstituted heteroaryl groups are of 1 to 12 (e.g., 1 to 11, 1 to 10, 1 to 9, 2 to 12, 2 to 11, 2 to 10, or 2 to 9) carbons. The term "heteroaryl" includes bicyclic, tricyclic, and tetracyclic groups in which any of the above heteroaromatic rings is fused to one or more, aryl or carbocyclic rings, e.g., a phenyl ring, or a cyclohexane ring. Examples of heteroaryl groups include, but are not limited to, pyridyl, pyrazolyl, benzooxazolyl, benzoimidazolyl, benzothiazolyl, imidazolyl, thiazolyl, quinolinyl, tetrahydroquinolinyl, and 4-azaindolyl. A heteroaryl ring can be attached to its pendant group at any ring atom that results in a stable structure and any of the ring atoms can be optionally substituted unless otherwise specified. In some embodiment, the heteroaryl is substituted with 1, 2, 3, or 4 substituents groups.

The term "heterocycloalkyl," as used herein, represents a monovalent monocyclic, bicyclic or polycyclic ring system, which may be bridged, fused or spirocyclic, wherein at least one ring is non-aromatic and wherein the non-aromatic ring contains one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocycloalkyl groups are of 1 to 12 (e.g., 1 to 11, 1 to 10, 1 to 9, 2 to 12, 2 to 11, 2 to 10, or 2 to 9) carbons. The term "heterocycloalkyl" also represents a heterocyclic compound having a bridged multicyclic structure in which one or more carbons or heteroatoms bridges two non-adjacent members of a monocyclic ring, e.g., a quinuclidinyl group. The term "heterocycloalkyl" includes bicyclic, tricyclic, and tetracyclic groups in which any of the above heterocyclic rings is fused to one or more aromatic, carbocyclic, heteroaromatic, or heterocyclic rings, e.g., an aryl ring, a cyclohexane ring, a cyclohexene ring, a cyclopentane ring, a cyclopentene ring, a pyridine ring, or a pyrrolidine ring. Examples of heterocycloalkyl groups are pyrrolidinyl, piperidinyl, 1,2,3,4-tetrahydroquinolinyl, decahydroquinolinyl, dihydropyrrolopyridine, and decahydronapthyridinyl. A heterocycloalkyl ring can be attached to its pendant group at any ring atom that results in a stable structure and any of the ring atoms can be optionally substituted unless otherwise specified.

The term "hydroxy," as used herein, represents a —OH group.

The term "hydroxyalkyl," as used herein, represents an alkyl moiety substituted on one or more carbon atoms with one or more —OH moieties.

The term "isomer," as used herein, means any tautomer, stereoisomer, atropismer, enantiomer, or diastereomer of any compound of the invention. It is recognized that the compounds of the invention can have one or more chiral centers or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

As used herein, the term "linker" refers to a divalent organic moiety connecting moiety B to moiety W in a compound of Formula I, such that the resulting compound is capable of achieving an IC50 of 2 uM or less in the Ras-RAF disruption assay protocol provided in the Examples below, and provided here: The purpose of this biochemical assay is to measure the ability of test compounds to facilitate ternary complex formation between a nucleotide-loaded Ras isoform and cyclophilin A; the resulting ternary complex disrupts binding to a BRAF$^{RBD}$ construct, inhibiting Ras signaling through a RAF effector.

In assay buffer containing 25 mM HEPES pH 7.3, 0.002% Tween20, 0.1% BSA, 100 mM NaCl and 5 mM MgCl$_2$, tagless Cyclophilin A, His6-K-Ras-GMPPNP (or other Ras variant), and GST-BRAF$^{RBD}$ are combined in a 384-well assay plate at final concentrations of 25 µM, 12.5 nM and 50 nM, respectively. Compound is present in plate wells as a 10-point 3-fold dilution series starting at a final concentration of 30 µM. After incubation at 25° C. for 3 hours, a mixture of Anti-His Eu-W1024 and anti-GST allophycocyanin is then added to assay sample wells at final concentrations of 10 nM and 50 nM, respectively, and the reaction incubated for an additional 1.5 hours. TR-FRET signal is read on a microplate reader (Ex 320 nm, Em 665/615 nm). Compounds that facilitate disruption of a Ras:RAF complex are identified as those eliciting a decrease in the TR-FRET ratio relative to DMSO control wells.

In some embodiments, the linker comprises 20 or fewer linear atoms. In some embodiments, the linker comprises 15 or fewer linear atoms. In some embodiments, the linker comprises 10 or fewer linear atoms. In some embodiments, the linker has a molecular weight of under 500 g/mol. In some embodiments, the linker has a molecular weight of under 400 g/mol. In some embodiments, the linker has a molecular weight of under 300 g/mol. In some embodiments, the linker has a molecular weight of under 200 g/mol. In some embodiments, the linker has a molecular weight of under 100 g/mol. In some embodiments, the linker has a molecular weight of under 50 g/mol.

As used herein, a "monovalent organic moiety" is less than 500 kDa. In some embodiments, a "monovalent organic moiety" is less than 400 kDa. In some embodiments, a "monovalent organic moiety" is less than 300 kDa. In some embodiments, a "monovalent organic moiety" is less than 200 kDa. In some embodiments, a "monovalent organic moiety" is less than 100 kDa. In some embodiments, a "monovalent organic moiety" is less than 50 kDa. In some embodiments, a "monovalent organic moiety" is less than 25 kDa. In some embodiments, a "monovalent organic moiety" is less than 20 kDa. In some embodiments, a "monovalent organic moiety" is less than 15 kDa. In some embodiments, a "monovalent organic moiety" is less than 10 kDa. In some embodiments, a "monovalent organic moiety" is less than 1 kDa. In some embodiments, a "monovalent organic moiety" is less than 500 g/mol. In some embodiments, a "monovalent organic moiety" ranges between 500 g/mol and 500 kDa.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers or conformers of the basic molecular structure, including atropisomers. Some compounds of the present invention may exist in different tautomeric forms, all of the latter being included within the scope of the present invention.

The term "sulfonyl," as used herein, represents an —S(O)$_2$— group.

The term "thiocarbonyl," as used herein, refers to a —C(S)— group.

The term "vinyl ketone," as used herein, refers to a group comprising a carbonyl group directly connected to a carbon-carbon double bond.

The term "vinyl sulfone," as used herein, refers to a group comprising a sulfonyl group directed connected to a carbon-carbon double bond.

The term "ynone," as used herein, refers to a group comprising the structure

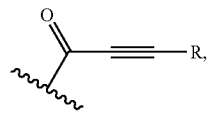

wherein R is any chemically feasible substituent described herein.

Those of ordinary skill in the art, reading the present disclosure, will appreciate that certain compounds described herein may be provided or utilized in any of a variety of forms such as, for example, salt forms, protected forms, pro-drug forms, ester forms, isomeric forms (e.g., optical or structural isomers), isotopic forms, etc. In some embodiments, reference to a particular compound may relate to a specific form of that compound. In some embodiments, reference to a particular compound may relate to that compound in any form. In some embodiments, for example, a preparation of a single stereoisomer of a compound may be considered to be a different form of the compound than a racemic mixture of the compound; a particular salt of a compound may be considered to be a different form from another salt form of the compound; a preparation containing one conformational isomer ((Z) or (E)) of a double bond may be considered to be a different form from one containing the other conformational isomer ((E) or (Z)) of the double bond; a preparation in which one or more atoms is a different isotope than is present in a reference preparation may be considered to be a different form.

DETAILED DESCRIPTION

Compounds

Provided herein are Ras inhibitors. The approach described herein entails formation of a high affinity three-component complex, or conjugate, between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex, or conjugate, between the Ras protein and the widely expressed cytosolic chaperone, cyclophilin A (CYPA). Without being bound by theory, the inventors believe that one way the inhibitory effect on Ras is effected by compounds of the invention and the complexes, or conjugates, they form is by steric occlusion of the interaction site between Ras and downstream effector molecules, such as RAF, which are required for propagating the oncogenic signal.

Without being bound by theory, the inventors postulate that both covalent and non-covalent interactions of a compound of the present invention with Ras and the chaperone protein (e.g., cyclophilin A) may contribute to the inhibition of Ras activity. In some embodiments, a compound of the present invention forms a covalent adduct with a side chain of a Ras protein (e.g., a sulfhydryl side chain of the cysteine at position 12 or 13 of a mutant Ras protein). Covalent adducts may also be formed with other side chains of Ras. In addition, or alternatively, non-covalent interactions may be at play: for example, van der Waals, hydrophobic, hydrophilic and hydrogen bond interactions, and combinations thereof, may contribute to the ability of the compounds of the present invention to form complexes and act as Ras inhibitors. Accordingly, a variety of Ras proteins may be inhibited by compounds of the present invention (e.g., K-Ras, N-Ras, H-Ras, and mutants thereof at positions 12, 13 and 61, such as G12C, G12D, G12V, G12S, G13C, G13D, and Q61L, and others described herein).

Methods of determining covalent adduct formation are known in the art. One method of determining covalent adduct formation is to perform a "cross-linking" assay, such as under these conditions (Note—the following protocol describes a procedure for monitoring cross-linking of K-Ras G12C (GMP-PNP) to a compound of the invention. This protocol may also be executed substituting other Ras proteins or nucleotides).

The purpose of this biochemical assay is to measure the ability of test compounds to covalently label nucleotide-loaded K-Ras isoforms. In assay buffer containing 12.5 mM HEPES pH 7.4, 75 mM NaCl, 1 mM MgCl$_2$, 1 mM BME, 5 μM Cyclophilin A and 2 μM test compound, a 5 μM stock of GMP-PNP-loaded K-Ras (1-169) G12C is diluted 10-fold to yield a final concentration of 0.5 μM; with final sample volume being 100 μL.

The sample is incubated at 25° C. for a time period of up to 24 hours prior to quenching by the addition of 10 μL of 5% Formic Acid. Quenched samples are centrifuged at 15000 rpm for 15 minutes in a benchtop centrifuge before injecting a 10 μL aliquot onto a reverse phase C4 column and eluting into the mass spectrometer with an increasing acetonitrile gradient in the mobile phase. Analysis of raw data may be carried out using Waters MassLynx MS software, with % bound calculated from the deconvoluted protein peaks for labeled and unlabeled K-Ras.

Accordingly, provided herein is a compound, or pharmaceutically acceptable salt thereof, having the structure of Formula I:

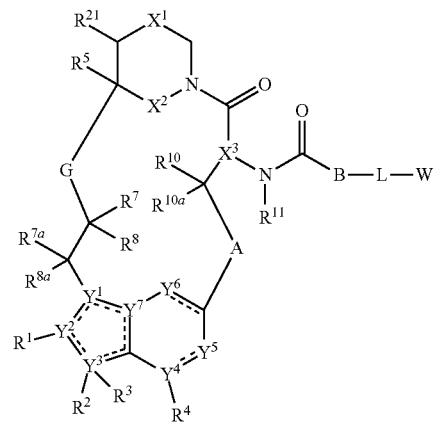

Formula I wherein the dotted lines represent zero, one, two, three, or four non-adjacent double bonds;

A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is absent, —CH(R$^9$)—, >C=CR$^9$R$^{9'}$, or >CR$^9$R$^{9'}$ where the carbon is bound to the carbonyl carbon of —N(R$^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene; G is optionally substituted C$_1$-C$_4$ alkylene, optionally substituted C$_1$-C$_4$ alkenylene, optionally substituted C$_1$-C$_4$ heteroalkylene, —C(O)O—CH(R$^6$)— where C is bound to —C(R$^7$R$^8$)—, —C(O)NH—CH(R$^6$)— where C is bound to —C(R$^7$R$^8$)—, optionally substituted C$_1$-C$_4$ heteroalkylene, or 3 to 8-membered heteroarylene;

L is absent or a linker;

W is a cross-linking group comprising a vinyl ketone, a vinyl sulfone, an ynone, a haloacetal, or an alkynyl sulfone;

X$^1$ is optionally substituted C$_1$-C$_2$ alkylene, NR, O, or S(O)$_n$;

X$^2$ is O or NH;

X$^3$ is N or CH;

n is 0, 1, or 2;

R is hydrogen, cyano, optionally substituted C$_1$-C$_4$ alkyl, optionally substituted C$_2$-C$_4$ alkenyl, optionally substituted C$_2$-C$_4$ alkynyl, C(O)R', C(O)OR', C(O)N(R')$_2$, S(O)R', S(O)$_2$R', or S(O)$_2$N(R')$_2$;

each R' is, independently, H or optionally substituted C$_1$-C$_4$ alkyl;

Y$^1$ is C, CH, or N;

Y$^2$, Y$^3$, Y$^4$, and Y$^7$ are, independently, C or N;

Y$^5$ is CH, CH$_2$, or N;

Y$^6$ is C(O), CH, CH$_2$, or N;

R$^1$ is cyano, optionally substituted C$_1$-C$_6$ alkyl, optionally substituted C$_1$-C$_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or R¹ and R² combine with the atoms to which they are attached to form an optionally substituted 3 to 14-membered heterocycloalkyl;

R² is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; R³ is absent, or R² and R³ combine with the atom to which they are attached to form an optionally substituted 3 to 8-membered cycloalkyl or optionally substituted 3 to 14-membered heterocycloalkyl;

R⁴ is absent, hydrogen, halogen, cyano, or methyl optionally substituted with 1 to 3 halogens;

R⁵ is hydrogen, $C_1$-$C_4$ alkyl optionally substituted with halogen, cyano, hydroxy, or $C_1$-$C_4$ alkoxy, cyclopropyl, or cyclobutyl;

R⁶ is hydrogen or methyl; R⁷ is hydrogen, halogen, or optionally substituted $C_1$-$C_3$ alkyl, or R⁶ and R⁷ combine with the carbon atoms to which they are attached to form an optionally substituted 3 to 6-membered cycloalkyl or optionally substituted 3 to 7-membered heterocycloalkyl;

R⁸ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R⁷ and R⁸ combine with the carbon atom to which they are attached to form C=CR⁷'R⁸'; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

R⁷ᵃ and R⁸ᵃ are, independently, hydrogen, halo, optionally substituted $C_1$-$C_3$ alkyl, or combine with the carbon to which they are attached to form a carbonyl;

R⁷' is hydrogen, halogen, or optionally substituted $C_1$-$C_3$ alkyl; R⁸' is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R⁷' and R⁸' combine with the carbon atom to which they are attached to form optionally substituted 3 to 6-membered cycloalkyl or optionally substituted 3 to 7-membered heterocycloalkyl;

R⁹ is H, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or R⁹ and L combine with the atoms to which they are attached to form an optionally substituted 3 to 14-membered heterocycloalkyl;

R⁹' is hydrogen or optionally substituted $C_1$-$C_6$ alkyl; or R⁹ and R⁹', combined with the atoms to which they are attached, form a 3 to 6-membered cycloalkyl or a 3 to 6-membered heterocycloalkyl;

R¹⁰ is hydrogen, halo, hydroxy, $C_1$-$C_3$ alkoxy, or $C_1$-$C_3$ alkyl;

R¹⁰ᵃ is hydrogen or halo;

R¹¹ is hydrogen or $C_1$-$C_3$ alkyl; and

R²¹ is hydrogen or $C_1$-$C_3$ alkyl (e.g., methyl).

In some embodiments, R⁹ is H, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

In some embodiments, R²¹ is hydrogen.

In some embodiments, provided herein is a compound, or pharmaceutically acceptable salt thereof, having the structure of Formula Ia:

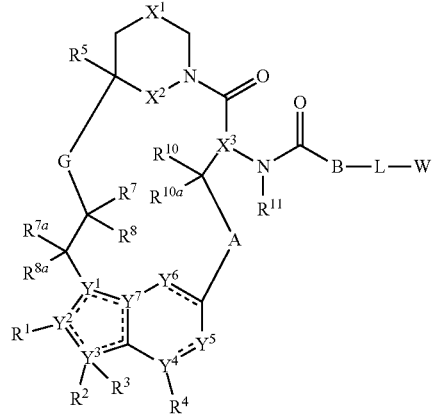

Formula Ia wherein the dotted lines represent zero, one, two, three, or four non-adjacent double bonds;

A is —N(H or CH₃)C(O)—(CH₂)— where the amino nitrogen is bound to the carbon atom of —CH(R¹⁰)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is —CH(R⁹)— or >C=CR⁹R⁹' where the carbon is bound to the carbonyl carbon of —N(R¹¹)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH(R⁶)— where C is bound to —C(R⁷R⁸)—, —C(O)NH—CH(R⁶)— where C is bound to —C(R⁷R⁸)—, optionally substituted $C_1$-$C_4$ heteroalkylene, or 3 to 8-membered heteroarylene;

L is absent or a linker;

W is a cross-linking group comprising a vinyl ketone, a vinyl sulfone, an ynone, a haloacetal, or an alkynyl sulfone;

X¹ is optionally substituted $C_1$-$C_2$ alkylene, NR, O, or S(O)ₙ;

X² is O or NH;

X³ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')₂, S(O)R', S(O)₂R', or S(O)₂N(R')₂;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo; and $R^{11}$ is hydrogen or $C_1$-$C_3$ alkyl.

In some embodiments, the disclosure features a compound, or pharmaceutically acceptable salt thereof, of structural Formula Ib:

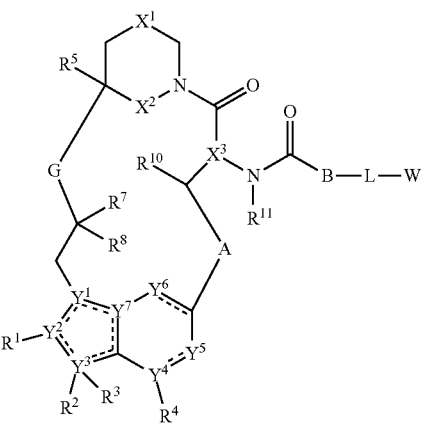

Formula Ib wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a vinyl ketone, a vinyl sulfone, an ynone, a haloacetal, or an alkynyl sulfone;

$X^1$ is optionally substituted $C_1$-$C_2$ alkylene, NR, O, or $S(O)_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', $S(O)_2R'$, or $S(O)_2N(R')_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^{10}$ is hydrogen, hydroxy, $C_1$-$C_3$ alkoxy, or $C_1$-$C_3$ alkyl; and $R^{11}$ is hydrogen or $C_1$-$C_3$ alkyl.

In some embodiments of compounds of the present invention, G is optionally substituted $C_1$-$C_4$ heteroalkylene.

In some embodiments, a compound having the structure of Formula Ic is provided, or a pharmaceutically acceptable salt thereof:

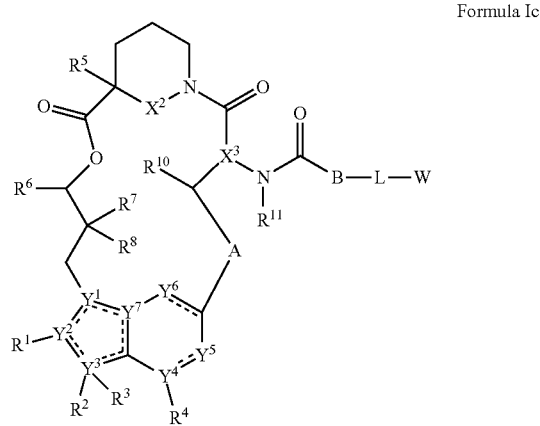

Formula Ic wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a vinyl ketone, a vinyl sulfone, an ynone, or an alkynyl sulfone;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^{10}$ is hydrogen, hydroxy, $C_1$-$C_3$ alkoxy, or $C_1$-$C_3$ alkyl; and $R^{11}$ is hydrogen or $C_1$-$C_3$ alkyl.

In some embodiments of compounds of the present invention, $X^2$ is NH. In some embodiments, $X^3$ is CH. In some embodiments, $R^{11}$ is hydrogen. In some embodiments, $R^{11}$ is $C_1$-$C_3$ alkyl. In some embodiments, $R^{11}$ is methyl.

In some embodiments, a compound of the present invention has the structure of Formula Id, or a pharmaceutically acceptable salt thereof:

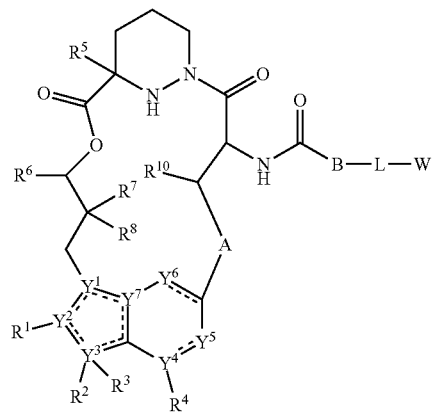

Formula Id wherein the dotted lines represent zero, one, two, three, or four non-adjacent double bonds;

A is —N(H or $CH_3$)C(O)—$(CH_2)$— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a vinyl ketone, a vinyl sulfone, an ynone, or an alkynyl sulfone;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $R^{10}$ is hydrogen, hydroxy, $C_1$-$C_3$ alkoxy, or $C_1$-$C_3$ alkyl.

In some embodiments of a compound of the present invention, $X^1$ is optionally substituted $C_1$-$C_2$ alkylene. In some embodiments, $X^1$ is methylene. In some embodiments, $X^1$ is methylene substituted with a $C_1$-$C_6$ alkyl group or a halogen. In some embodiments, $X^1$ is —CH(Br)—. In some embodiments, $X^1$ is —CH(CH$_3$)—. In some embodiments, $R^5$ is hydrogen. In some embodiments, $R^5$ is $C_1$-$C_4$ alkyl optionally substituted with halogen. In some embodiments, $R^5$ is methyl. In some embodiments, $Y^4$ is C. In some embodiments, $R^4$ is hydrogen. In some embodiments, $Y^5$ is CH.

In some embodiments, $Y^6$ is CH. In some embodiments, $Y^1$ is C. In some embodiments, $Y^2$ is C. In some embodiments, $Y^3$ is N. In some embodiments, $R^3$ is absent. In some embodiments, $Y^7$ is C.

In some embodiments, a compound of the present invention has the structure of Formula Ie, or a pharmaceutically acceptable salt thereof:

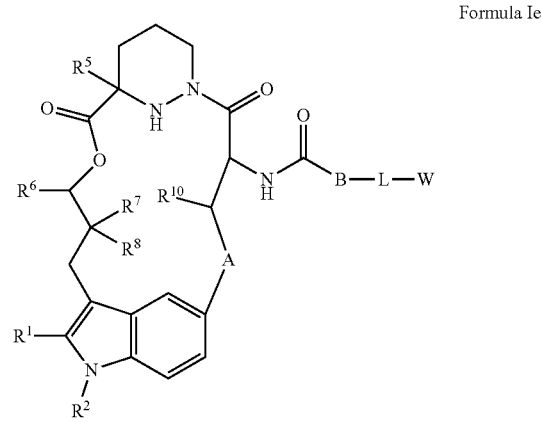

Formula Ie wherein A is —N(H or CH$_3$)C(O)—(CH$_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a vinyl ketone, a vinyl sulfone, an ynone, or an alkynyl sulfone;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $R^{10}$ is hydrogen, hydroxy, $C_1$-$C_3$ alkoxy, or $C_1$-$C_3$ alkyl.

In some embodiments of a compound of the present invention, $R^6$ is hydrogen. In some embodiments, $R^2$ is hydrogen, cyano, optionally substituted $C_1$-$C_6$ alkyl, optionally substituted 3 to 6-membered cycloalkyl, or optionally substituted 3 to 6-membered heterocycloalkyl. In some embodiments, $R^2$ is optionally substituted $C_1$-$C_6$ alkyl. In some embodiments, $R^2$ is fluoroalkyl. In some embodiments, $R^2$ is ethyl. In some embodiments, $R^2$ is —$CH_2CF_3$. In some embodiments, $R^2$ is $C_2$-$C_6$ alkynyl. In some embodiments, $R^2$ is —CHC≡CH. In some embodiments, $R^2$ is —$CH_2$C≡$CCH_3$. In some embodiments, $R^7$ is optionally substituted $C_1$-$C_3$ alkyl. In some embodiments, $R^7$ is $C_1$-$C_3$ alkyl. In some embodiments, $R^8$ is optionally substituted $C_1$-$C_3$ alkyl. In some embodiments, $R^8$ is $C_1$-$C_3$ alkyl.

In some embodiments, a compound of the present invention has the structure of Formula If, or a pharmaceutically acceptable salt thereof:

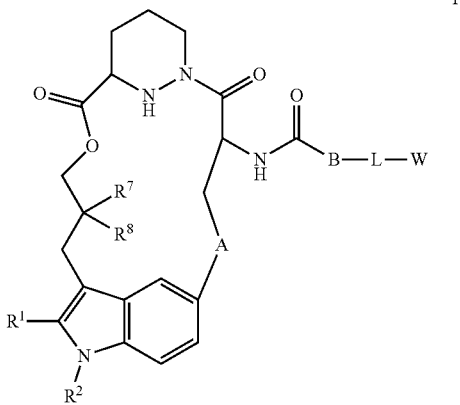

Formula If wherein A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a vinyl ketone, a vinyl sulfone, an ynone, or an alkynyl sulfone;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is $C_1$-$C_6$ alkyl or 3 to 6-membered cycloalkyl; $R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

In some embodiments of a compound of the present invention, $R^1$ is optionally substituted 6 to 10-membered aryl, optionally substituted 3 to 6-membered cycloalkenyl, or optionally substituted 5 to 10-membered heteroaryl. In some embodiments, $R^1$ is optionally substituted 6-membered aryl, optionally substituted 6-membered cycloalkenyl, or optionally substituted 6-membered heteroaryl.

In some embodiments of a compound of the present invention, $R_1$ is

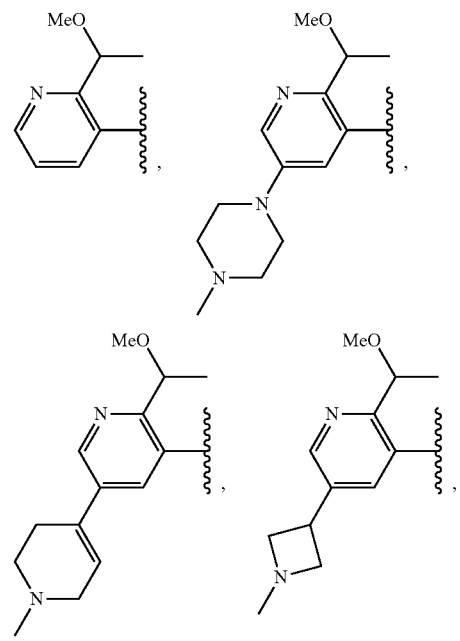

-continued

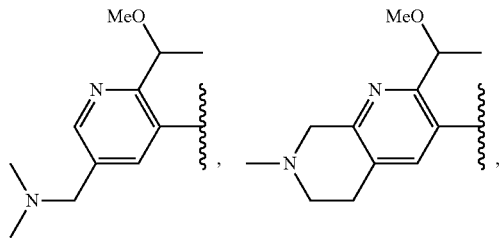

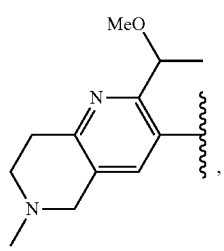

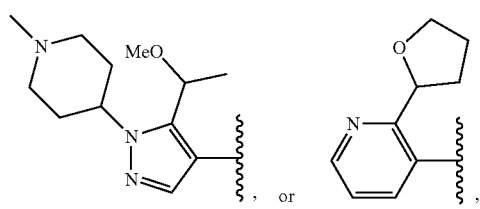

or a stereoisomer (e.g., atropisomer) thereof.

In some embodiments of a compound of the present invention, $R_1$ is

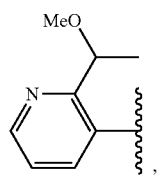 [SMILES: *c1cccnc1C(C)OC]

or a stereoisomer (e.g., atropisomer) thereof. In some embodiments of a compound of the present invention, $R_1$ is

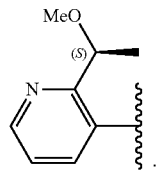

In some embodiments, a compound of the present invention has the structure of Formula Ig, or a pharmaceutically acceptable salt thereof:

Formula Ig

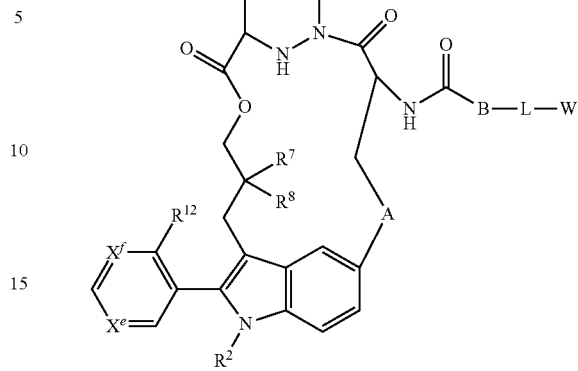

wherein A is —N(H or $CH_3$)C(O)—($CH_2$)— where the amino nitrogen is bound to the carbon atom of —CH ($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a vinyl ketone, a vinyl sulfone, an ynone, or an alkynyl sulfone;

$R^2$ is $C_1$-$C_6$ alkyl, $C_1$-$C_6$ fluoroalkyl, or 3 to 6-membered cycloalkyl; $R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl $X^e$ and $X^f$ are, independently, N or CH; and $R^{12}$ is optionally substituted $C_1$-$C_6$ alkyl, optionally substituted $C_1$-$C_6$ heteroalkyl, or optionally substituted 3 to 6-membered heterocycloalkylene.

In some embodiments of a compound of the present invention, $X^e$ is N and $X^f$ is CH. In some embodiments, $X^e$ is CH and $X^f$ is N.

In some embodiments of a compound of the present invention, $R^{12}$ is optionally substituted $C_1$-$C_6$ heteroalkyl. In some embodiments, $R^{12}$ is

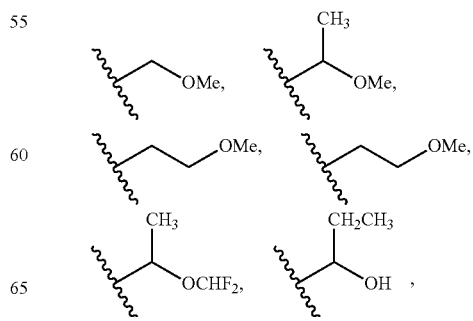

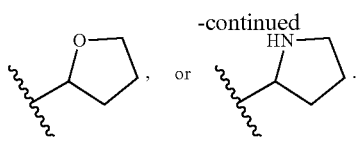, or

In some embodiments, $R^{12}$ is

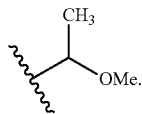

In some embodiments, a compound of the present invention has the structure of Formula VI, or a pharmaceutically acceptable salt thereof:

Formula VI

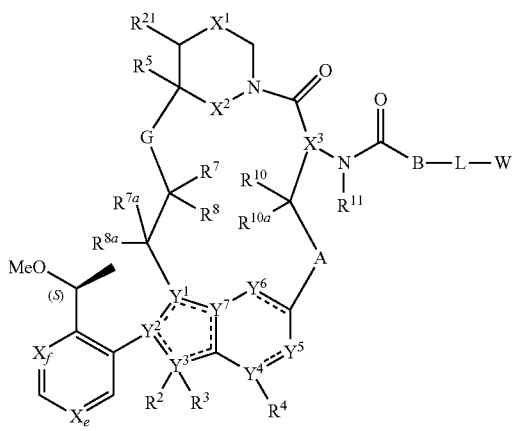

wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene (e.g., phenyl or phenol), or optionally substituted 5 to 10-membered heteroarylene;

B is absent, —CH($R^9$)—, >C=$CR^9R^{9'}$, or >$CR^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a vinyl ketone, a vinyl sulfone, an ynone, a haloacetal, or an alkynyl sulfone;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

R⁹ is H, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; or R⁹ and L combine with the atoms to which they are attached to form an optionally substituted 3 to 14-membered heterocycloalkyl;

R⁹' is hydrogen or optionally substituted $C_1$-$C_6$ alkyl; or

R⁹ and R⁹', combined with the atoms to which they are attached, form a 3 to 6-membered cycloalkyl or a 3 to 6-membered heterocycloalkyl;

R¹⁰ is hydrogen, halo, hydroxy, $C_1$-$C_3$ alkoxy, or $C_1$-$C_3$ alkyl;

R¹⁰ᵃ is hydrogen or halo;

R¹¹ is hydrogen or $C_1$-$C_3$ alkyl;

R²¹ is hydrogen or $C_1$-$C_3$ alkyl (e.g., methyl); and

Xᵉ and Xᶠ are, independently, N or CH.

In some embodiments, a compound of the present invention has the structure of Formula VIa, or a pharmaceutically acceptable salt thereof:

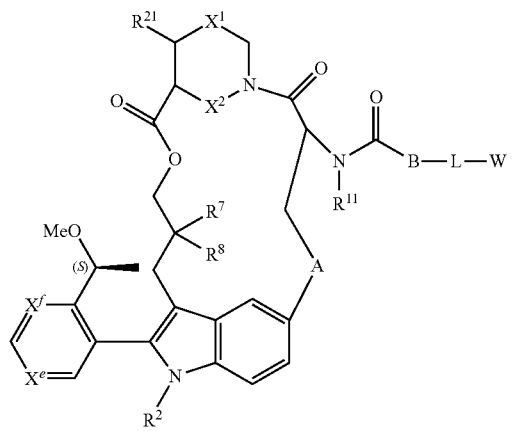

Formula VIa wherein A optionally substituted 3 to 6-membered cycloalkylene, optionally substituted 3 to 6-membered heterocycloalkylene, optionally substituted 6-membered arylene (e.g., phenyl or phenol), or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a vinyl ketone, a vinyl sulfone, an ynone, or an alkynyl sulfone;

X¹ is optionally substituted $C_1$-$C_2$ alkylene, NR, O, or $S(O)_n$;

X² is O or NH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')₂, S(O)R', S(O)₂R', or S(O)₂N(R')₂;

each R' is, independently, H or optionally substituted $C_1$-$C_4$ alkyl;

R² is $C_1$-$C_6$ alkyl, $C_1$-$C_6$ fluoroalkyl, or 3 to 6-membered cycloalkyl;

R⁷ is $C_1$-$C_3$ alkyl;

R⁸ is $C_1$-$C_3$ alkyl; and

R⁹ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

Xᵉ and Xᶠ are, independently, N or CH;

R¹¹ is hydrogen or $C_1$-$C_3$ alkyl; and

R²¹ is hydrogen or $C_1$-$C_3$ alkyl.

In some embodiments of a compound of the present invention, Xᵉ is N and Xᶠ is CH. In some embodiments, Xᵉ is CH and Xᶠ is N.

In some embodiments, a compound of the present invention has the structure of Formula VIb, or a pharmaceutically acceptable salt thereof:

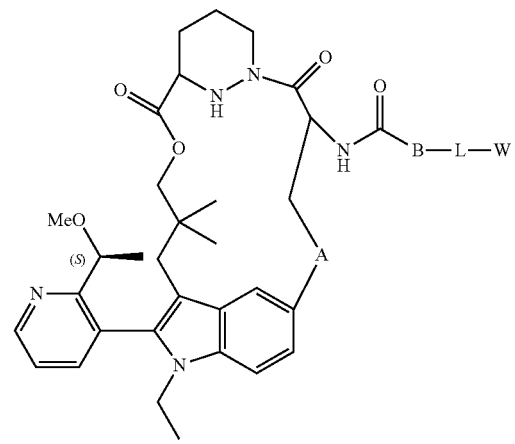

Formula VIb wherein A optionally substituted 3 to 6-membered cycloalkylene, optionally substituted 3 to 6-membered heterocycloalkylene, optionally substituted 6-membered arylene (e.g., phenyl or phenol), or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

R⁹ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

L is absent or a linker; and

W is a cross-linking group comprising a vinyl ketone, a vinyl sulfone, an ynone, or an alkynyl sulfone. In some embodiments of a compound of the present invention, A is optionally substituted 6-membered arylene.

In some embodiments, a compound of the present invention has the structure of Formula VIc (corresponding for Formula BB of FIG. 1A and FIG. 1B), or a pharmaceutically acceptable salt thereof:

Formula VIc

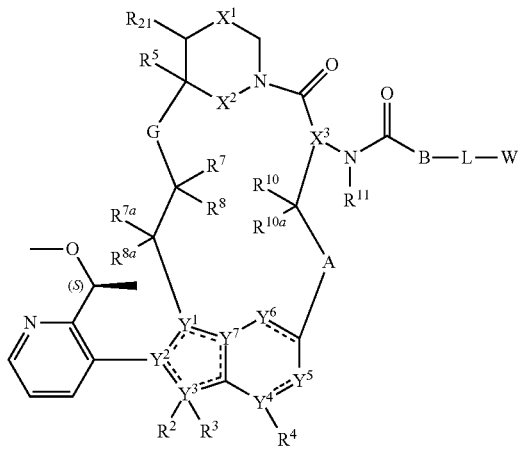

wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene (e.g., phenyl or phenol), or optionally substituted 5 to 10-membered heteroarylene;

B is absent, —CH($R^9$)—, >C=$CR^9R^{9'}$, or >$CR^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a vinyl ketone, a vinyl sulfone, an ynone, a haloacetal, or an alkynyl sulfone;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is H, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; or $R^9$ and L combine with the atoms to which they are attached to form an optionally substituted 3 to 14-membered heterocycloalkyl;

$R^{9'}$ is hydrogen or optionally substituted $C_1$-$C_6$ alkyl; or $R^9$ and $R^{9'}$, combined with the atoms to which they are attached, form a 3 to 6-membered cycloalkyl or a 3 to 6-membered heterocycloalkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl; and $R^{21}$ is hydrogen or $C_1$-$C_3$ alkyl (e.g., methyl).

In some embodiments, A has the structure:

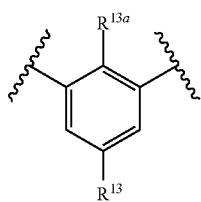

wherein R[13] is hydrogen, halo, hydroxy, amino, optionally substituted $C_1$-$C_6$ alkyl, or optionally substituted $C_1$-$C_6$ heteroalkyl; and R[13a] is hydrogen or halo. In some embodiments, R[13] is hydrogen. In some embodiments, R[13] and R[13a] are each hydrogen. In some embodiments, R[13] is hydroxy, methyl, fluoro, or difluoromethyl.

In some embodiments, A is optionally substituted 5 to 6-membered heteroarylene. In some embodiments, A is:

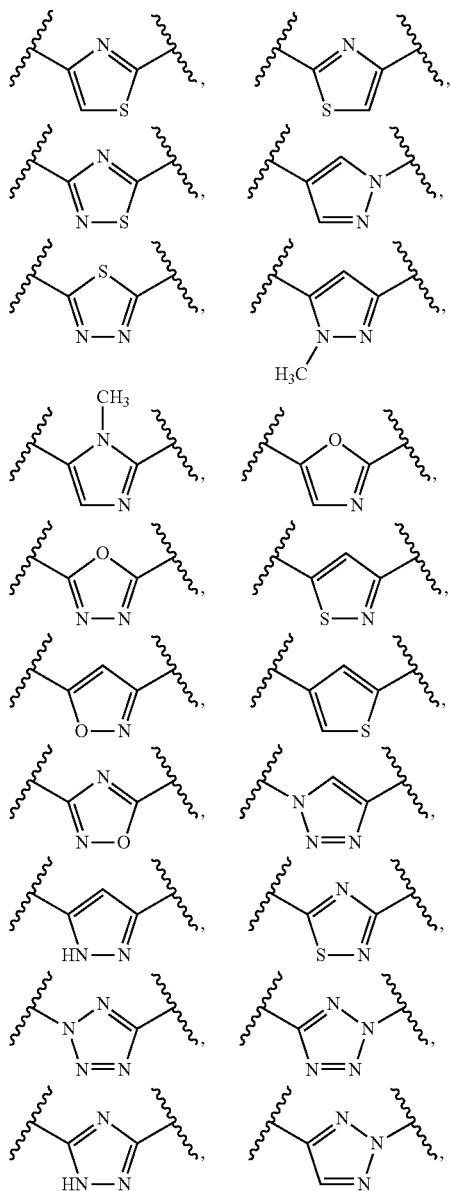

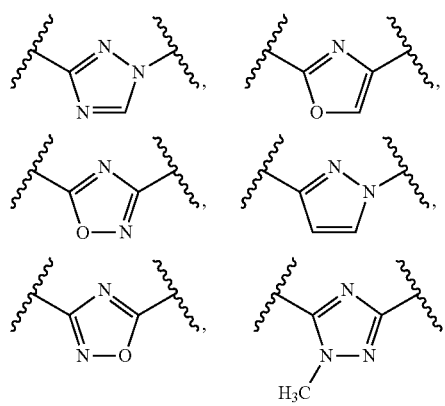

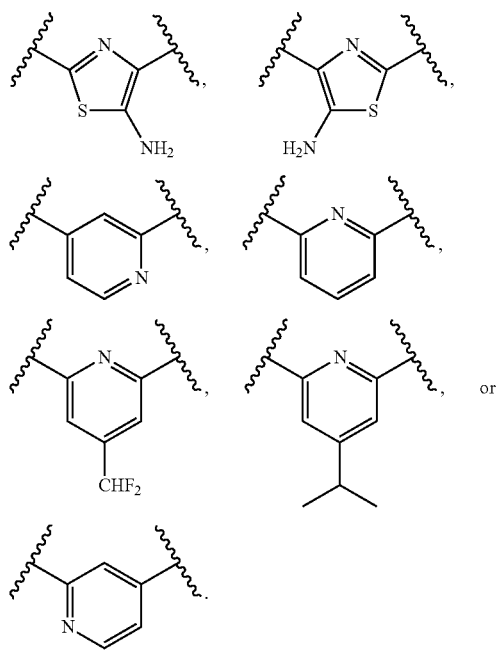

In some embodiments, A is optionally substituted $C_1$-$C_4$ heteroalkylene. In some embodiments, A is:

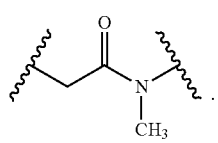

In some embodiments, A is optionally substituted 3 to 6-membered heterocycloalkylene. In some embodiments, A is:

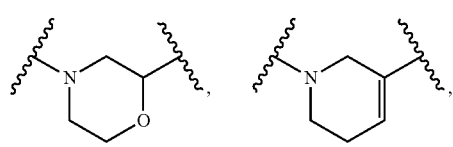

-continued

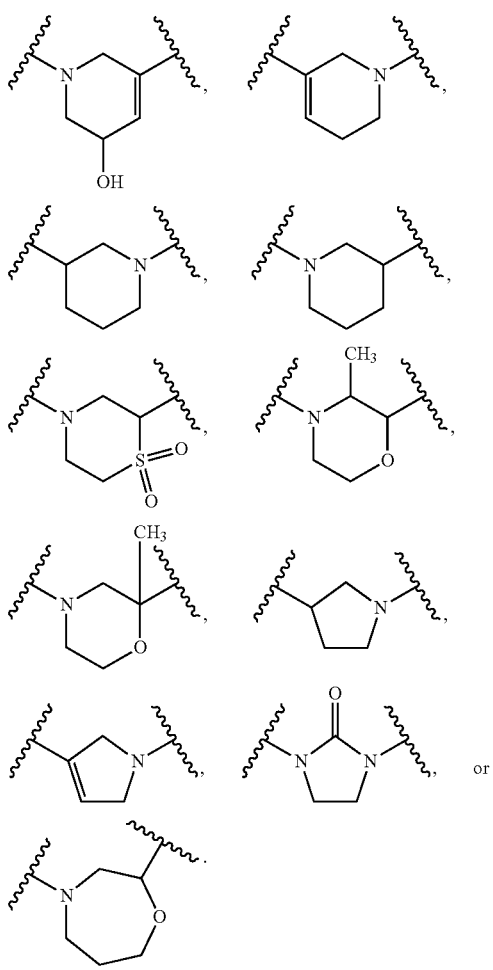

In some embodiments, A is

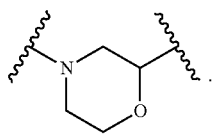 [SMILES: *C1CN(*)CCO1]

In some embodiments of a compound of the present invention, B is —CHR$^9$—. In some embodiments, R$^9$ is H, F, optionally substituted C$_1$-C$_6$ alkyl, optionally substituted C$_1$-C$_6$ heteroalkyl, optionally substituted 3 to 6-membered cycloalkyl, or optionally substituted 3 to 7-membered heterocycloalkyl. In some embodiments, R$^9$ is:

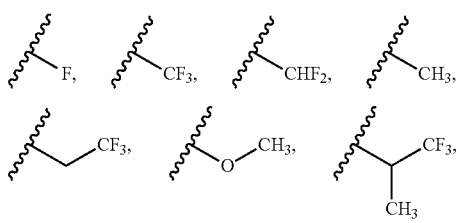

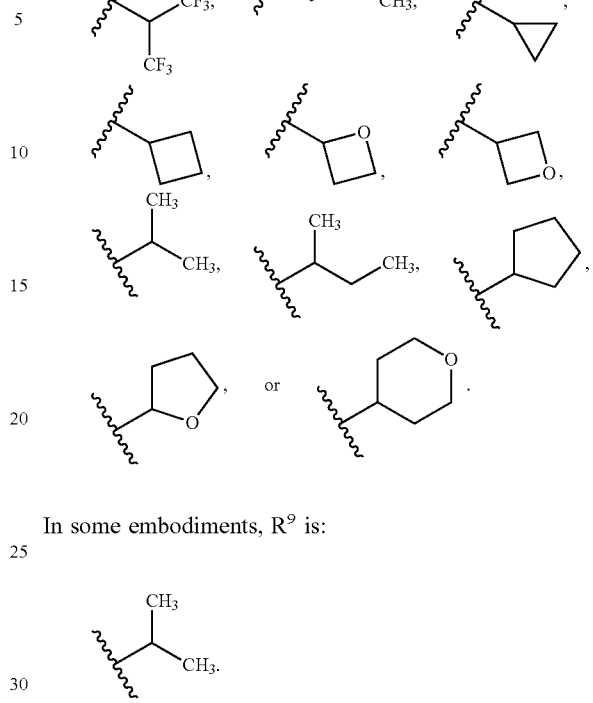

In some embodiments, R$^9$ is:

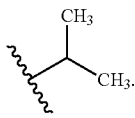

In some embodiments, R$^9$ is H, optionally substituted C$_1$-C$_6$ alkyl, optionally substituted C$_1$-C$_6$ heteroalkyl, optionally substituted 3 to 6-membered cycloalkyl, or optionally substituted 3 to 7-membered heterocycloalkyl.

In some embodiments of a compound of the present invention, B is optionally substituted 6-membered arylene. In some embodiments, B is 6-membered arylene. In some embodiments, B is:

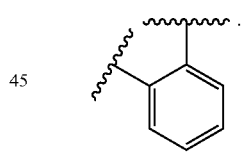

In some embodiments of a compound of the present invention, R$^7$ is methyl.

In some embodiments of a compound of the present invention, R$^8$ is methyl.

In some embodiments, R$^{21}$ is hydrogen.

In some embodiments of a compound of the present invention, the linker is the structure of Formula II:

$$A^1\text{-}(B^1)_f\text{—}(C^1)_g\text{—}(B^2)_h\text{-}(D^1)\text{-}(B^3)_i\text{—}(C^2)_j\text{—}(B^4)_k\text{-}A^2 \quad \text{Formula II}$$

where A$^1$ is a bond between the linker and B; A$^2$ is a bond between W and the linker; B$^1$, B$^2$, B$^3$, and B$^4$ each, independently, is selected from optionally substituted C$_1$-C$_2$ alkylene, optionally substituted C$_1$-C$_3$ heteroalkylene, O, S, and NR$^N$; R$^N$ is hydrogen, optionally substituted C$_{1-4}$ alkyl, optionally substituted C$_2$-C$_4$ alkenyl, optionally substituted C$_2$-C$_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$—$(C^1)_g$—$(B^2)_h$- to —$(B^3)_i$—$(C^2)_j$—$(B^4)_k$-$A^2$. In some embodiments, the linker is acyclic. In some embodiments, linker has the structure of Formula IIa:

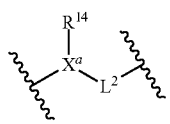

Formula IIa wherein $X^a$ is absent or N;
$R^{14}$ is absent, hydrogen or optionally substituted $C_1$-$C_6$ alkyl; and
$L^2$ is absent, —$SO_2$—, optionally substituted $C_1$-$C_4$ alkylene or optionally substituted $C_1$-$C_4$ heteroalkylene, wherein at least one of $X^a$, $R^{14}$, or $L^2$ is present. In some embodiments, the linker has the structure:

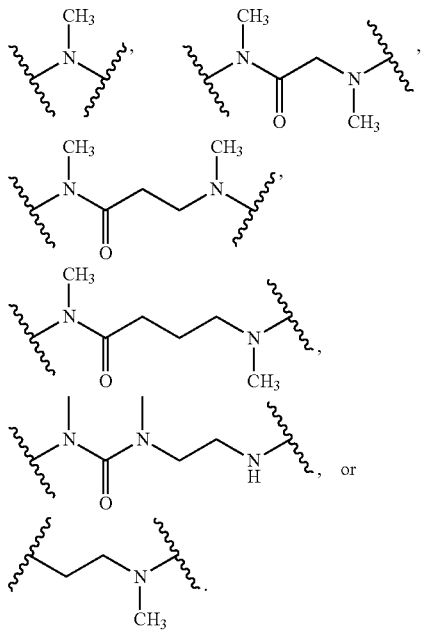

In some embodiments, the linker is or comprises a cyclic moiety. In some embodiments, the linker has the structure of Formula IIb:

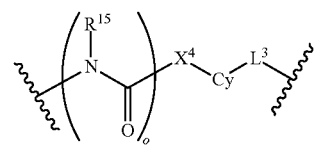

Formula IIb wherein o is 0 or 1;
$R^{15}$ is hydrogen or optionally substituted $C_1$-$C_6$ alkyl, optionally substituted 3 to 8-membered cycloalkylene, or optionally substituted 3 to 8-membered heterocycloalkylene;
$X^4$ is absent, optionally substituted $C_1$-$C_4$ alkylene, O, $NCH_3$, or optionally substituted $C_1$-$C_4$ heteroalkylene;
Cy is optionally substituted 3 to 8-membered cycloalkylene, optionally substituted 3 to 8-membered heterocycloalkylene, optionally substituted 6-10 membered arylene, or optionally substituted 5 to 10-membered heteroarylene; and
$L^3$ is absent, —$SO_2$—, optionally substituted $C_1$-$C_4$ alkylene or optionally substituted $C_1$-$C_4$ heteroalkylene.

In some embodiments, the linker has the structure of Formula IIb-1:

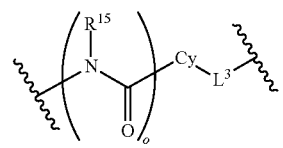

Formula IIb-1 wherein o is 0 or 1;
$R^{15}$ is hydrogen or optionally substituted $C_1$-$C_6$ alkyl, optionally substituted 3 to 8-membered cycloalkylene, or optionally substituted 3 to 8-membered heterocycloalkylene;
Cy is optionally substituted 3 to 8-membered cycloalkylene, optionally substituted 3 to 8-membered heterocycloalkylene, optionally substituted 6-10 membered arylene, or optionally substituted 5 to 10-membered heteroarylene; and
$L^3$ is absent, —$SO_2$—, optionally substituted $C_1$-$C_4$ alkylene or optionally substituted $C_1$-$C_4$ heteroalkylene.

In some embodiments, the linker has the structure of Formula IIc:

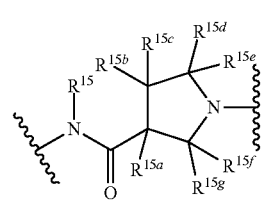

Formula IIc wherein $R^{15}$ is hydrogen, optionally substituted $C_1$-$C_6$ alkyl, optionally substituted 3 to 8-membered cycloalkylene, or optionally substituted 3 to 8-membered heterocycloalkylene; and $R^{15a}$, $R^{15b}$, $R^{15c}$, $R^{15d}$, $R^{15e}$, $R^{15f}$, and $R^{15g}$ are, independently, hydrogen, halo, hydroxy, cyano, amino, optionally substituted $C_1$-$C_6$ alkyl, optionally substituted $C_1$-$C_6$ alkoxy, or, or $R^{15b}$ and $R^{15d}$ combine with the carbons to which they are attached to form an optionally substituted 3 to 8-membered cycloalkylene, or optionally substituted 3 to 8-membered heterocycloalkylene.

In some embodiments, the linker has the structure:

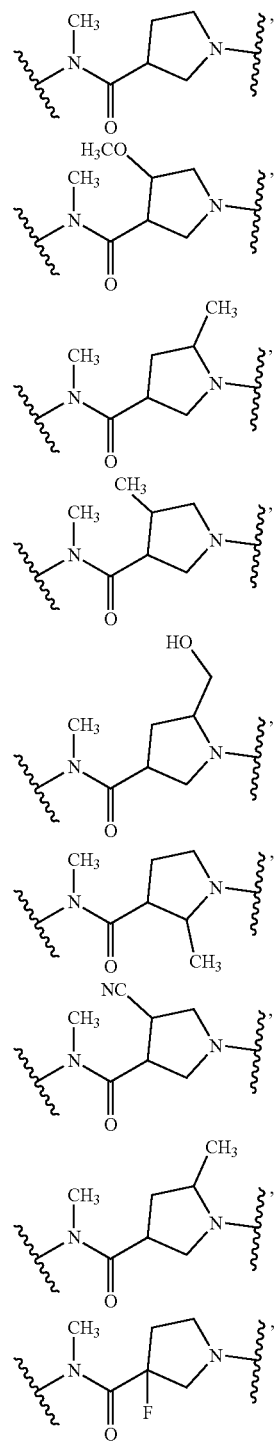

-continued

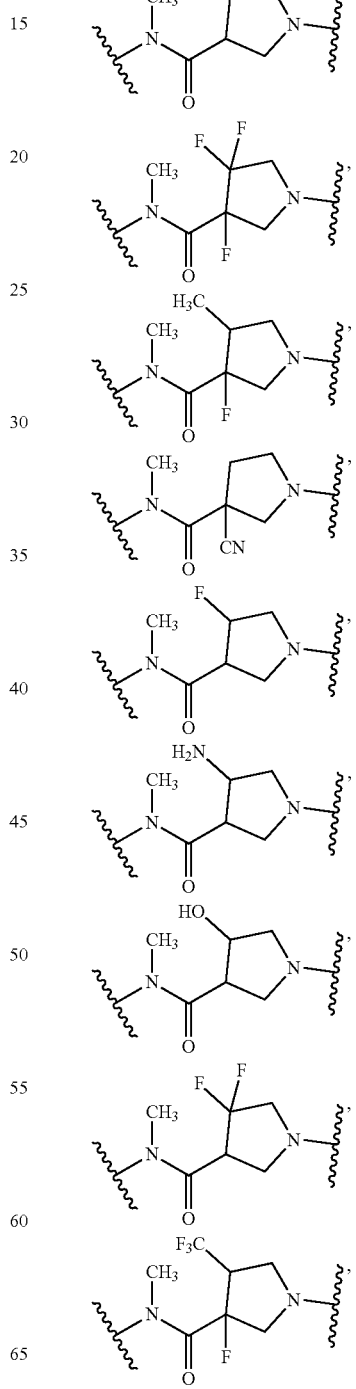

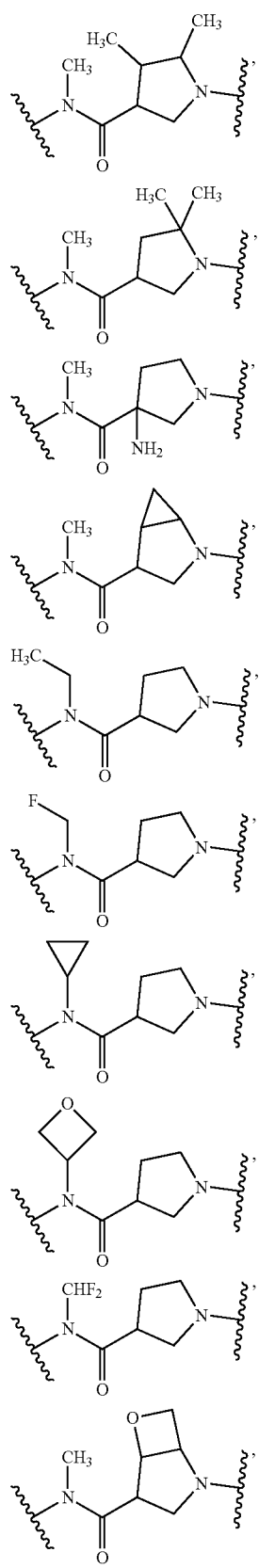
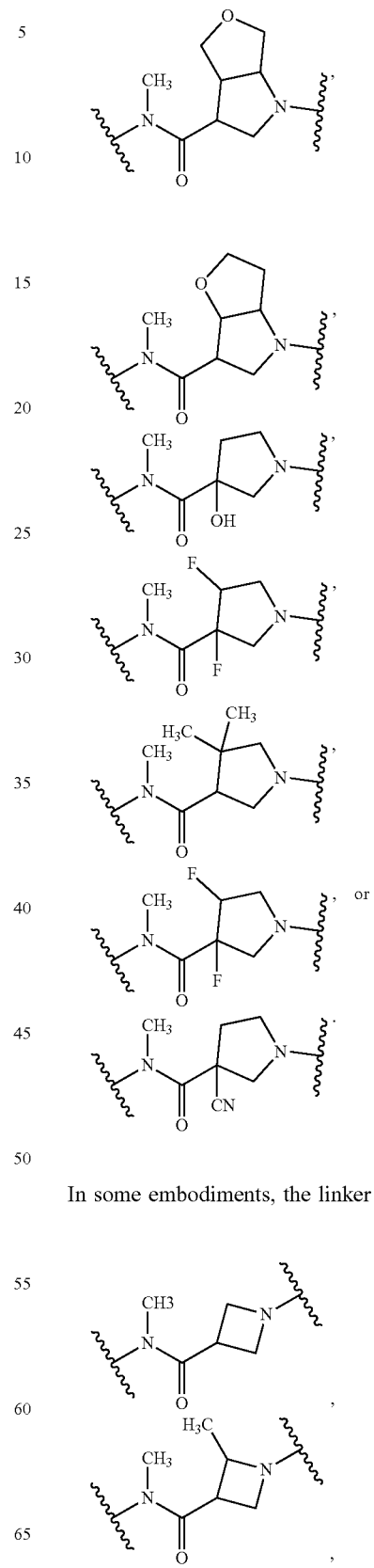
In some embodiments, the linker has the structure:

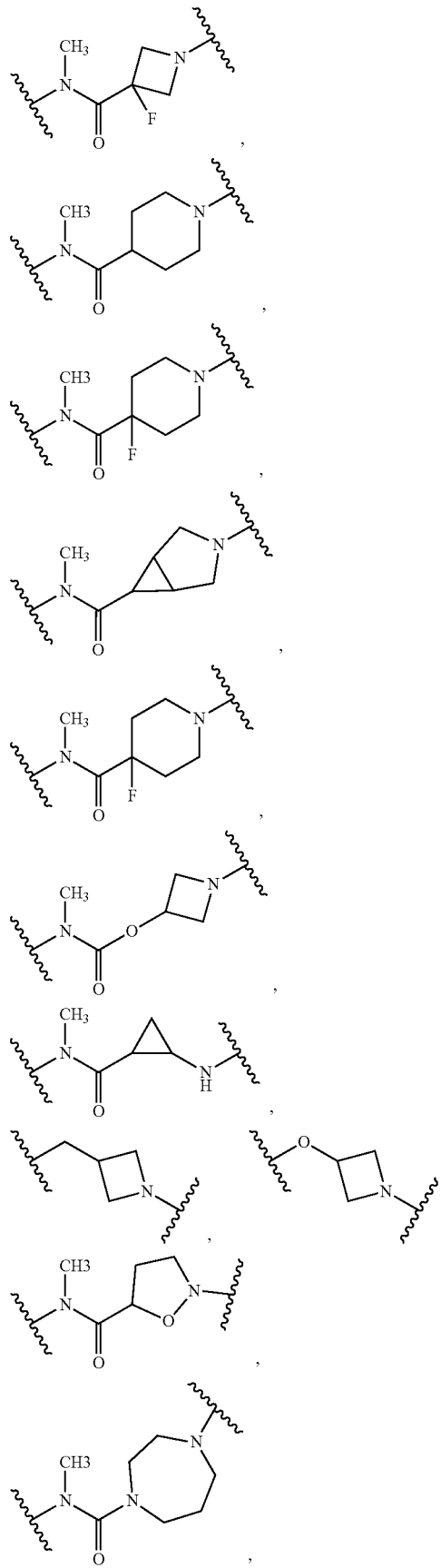
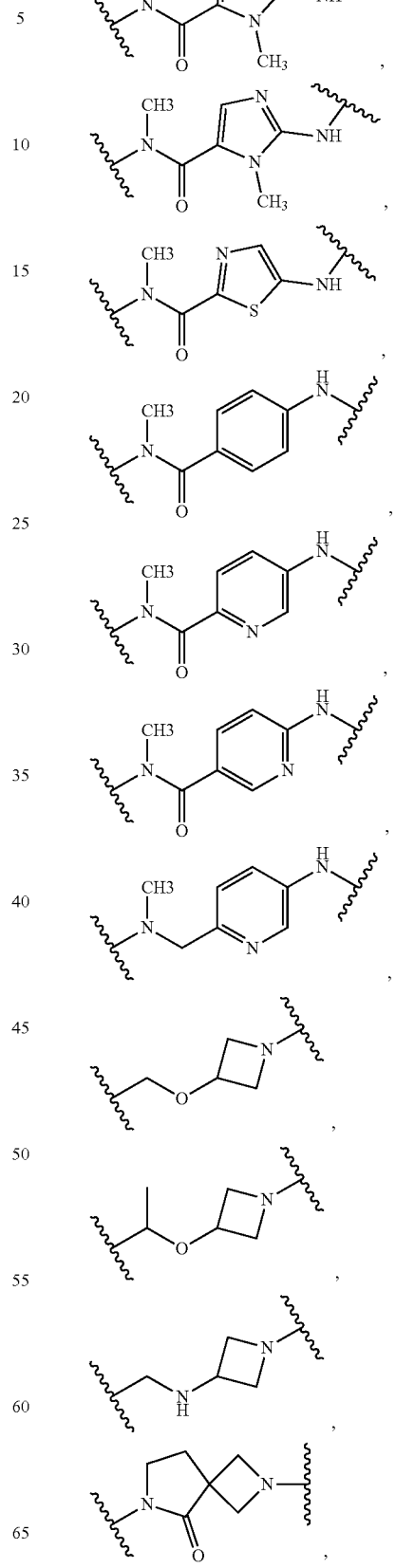

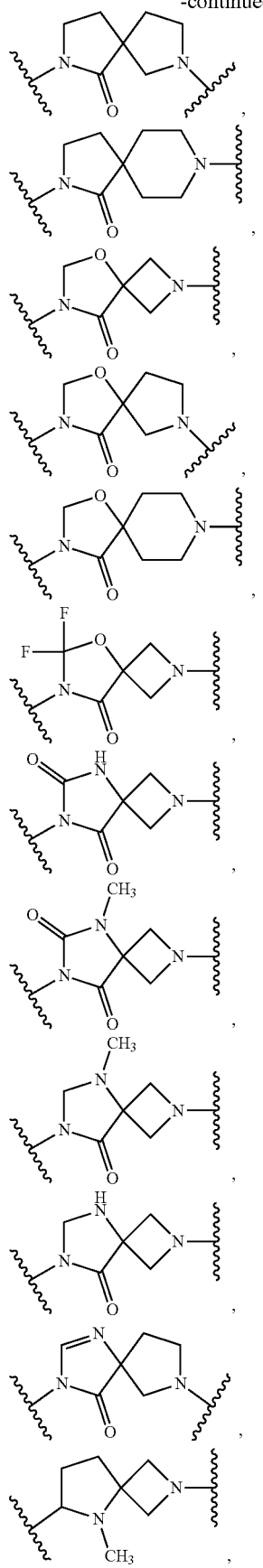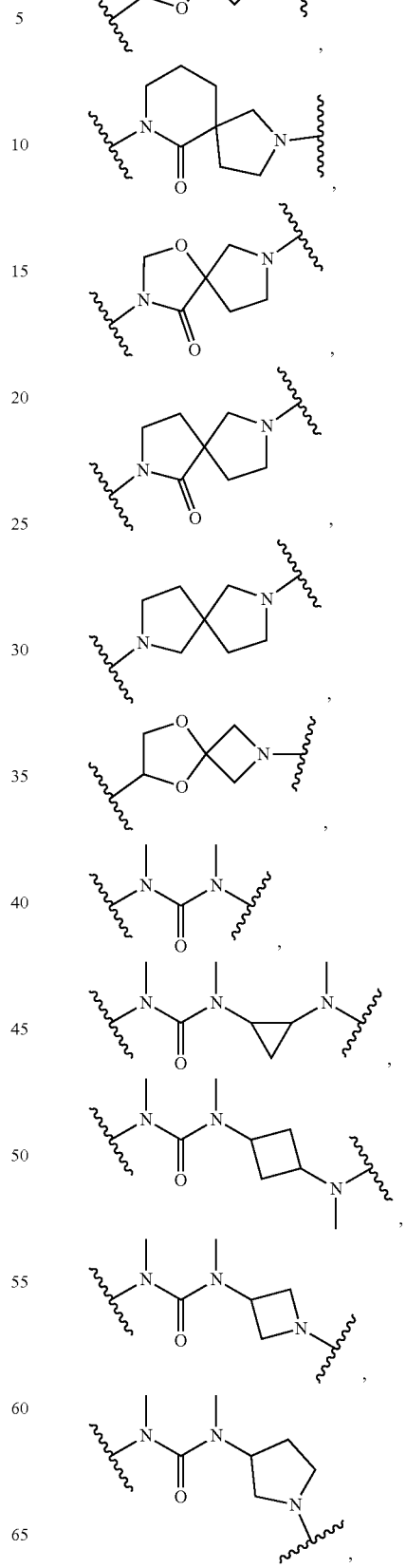

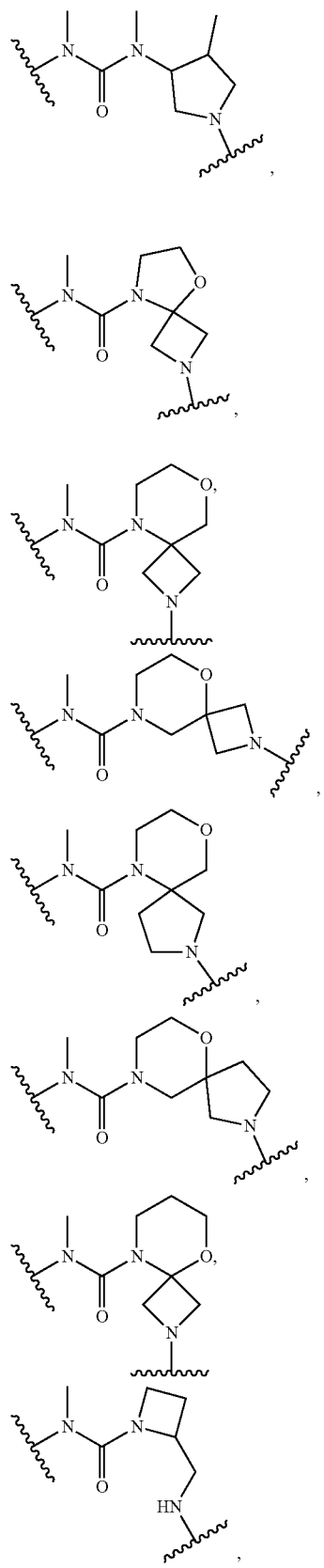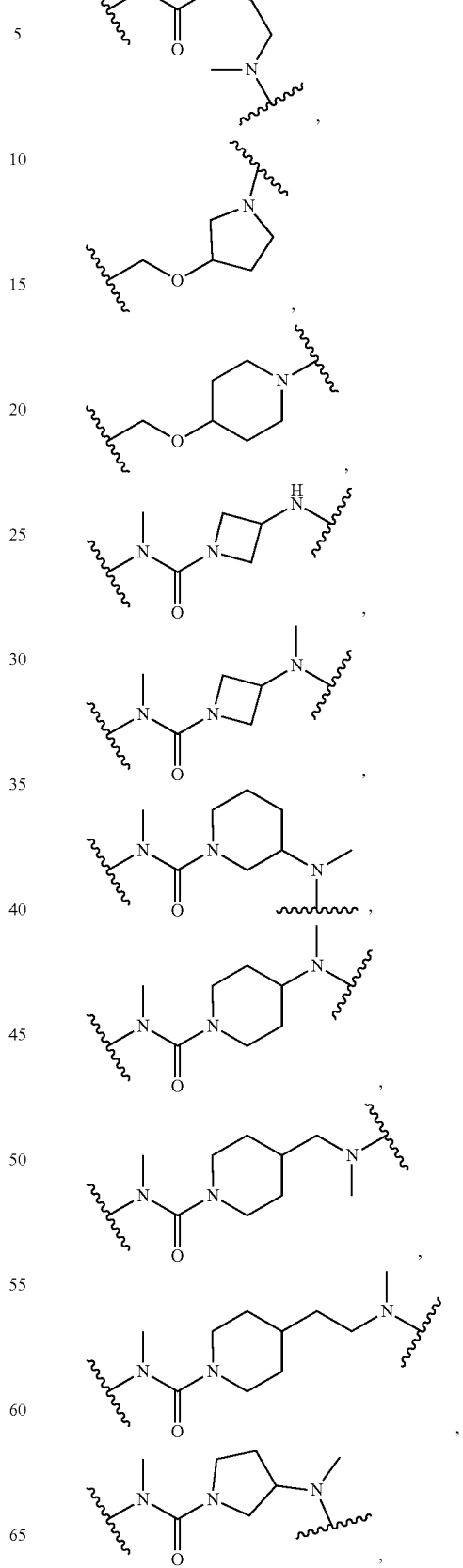

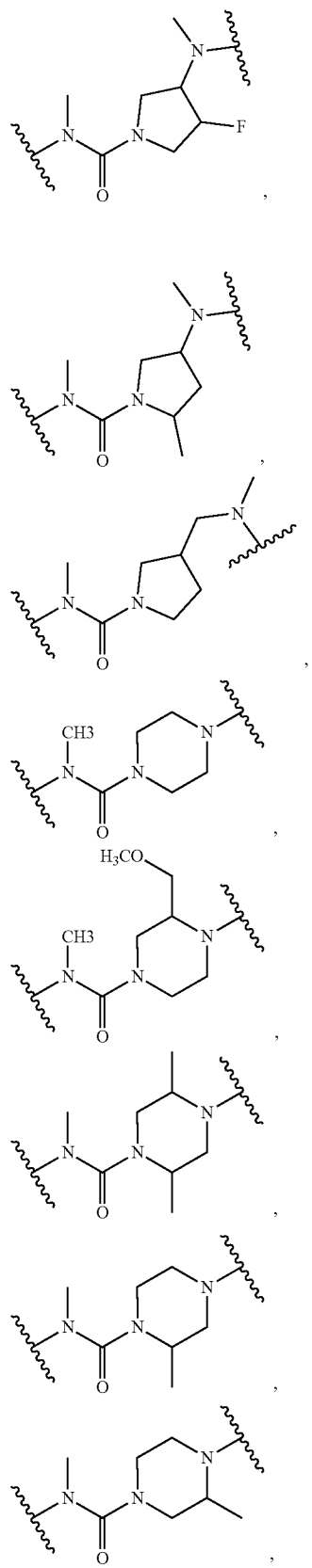
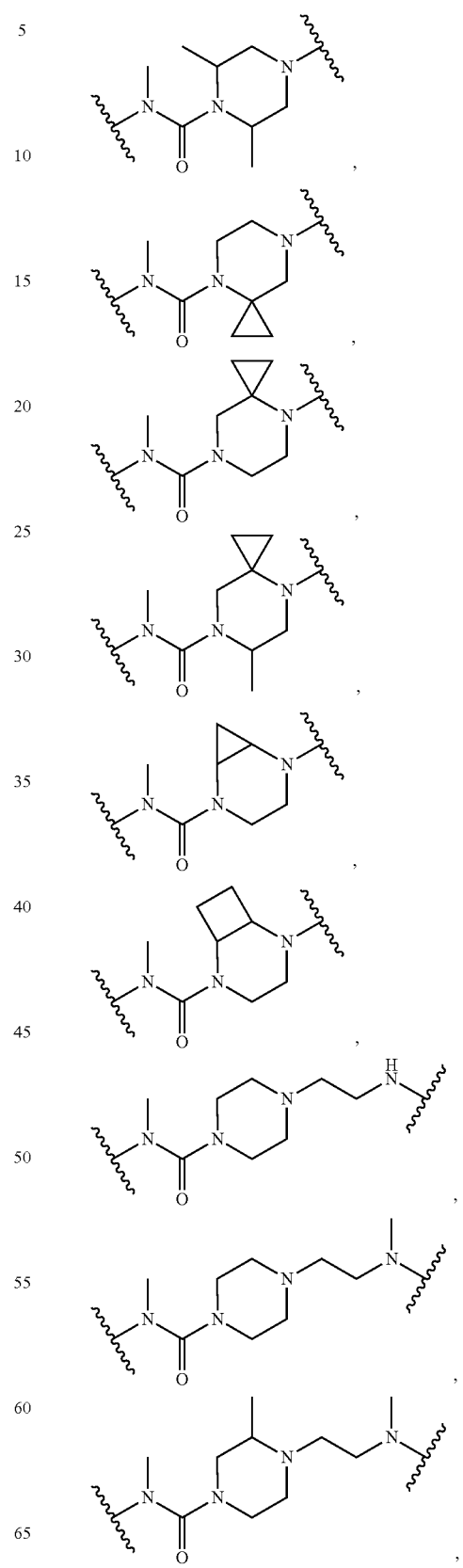

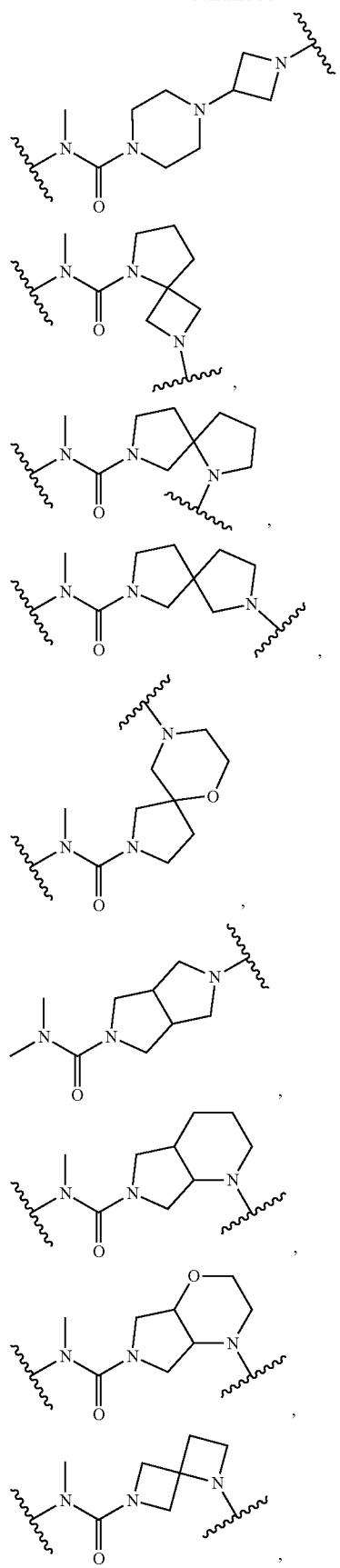
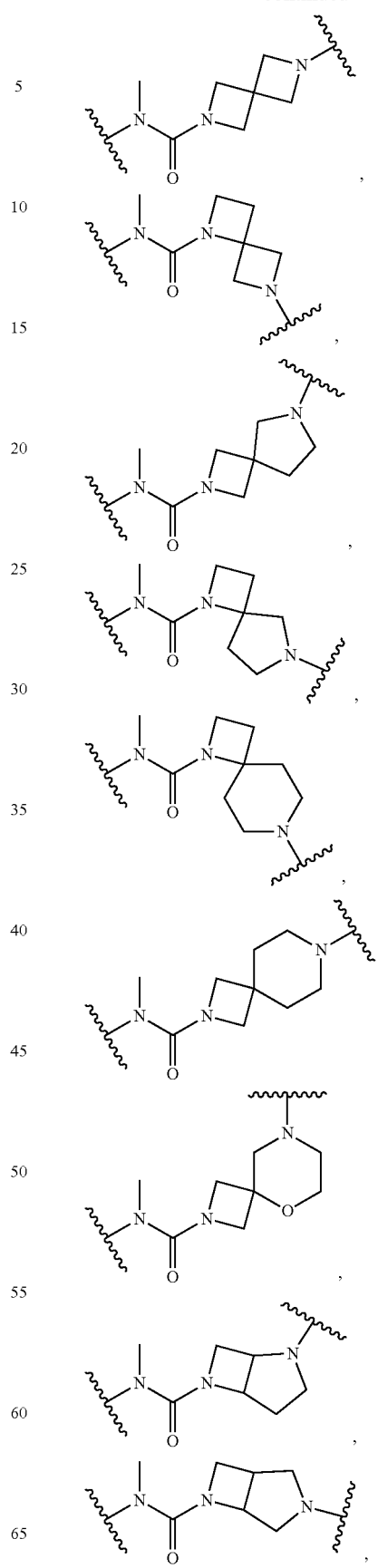

-continued
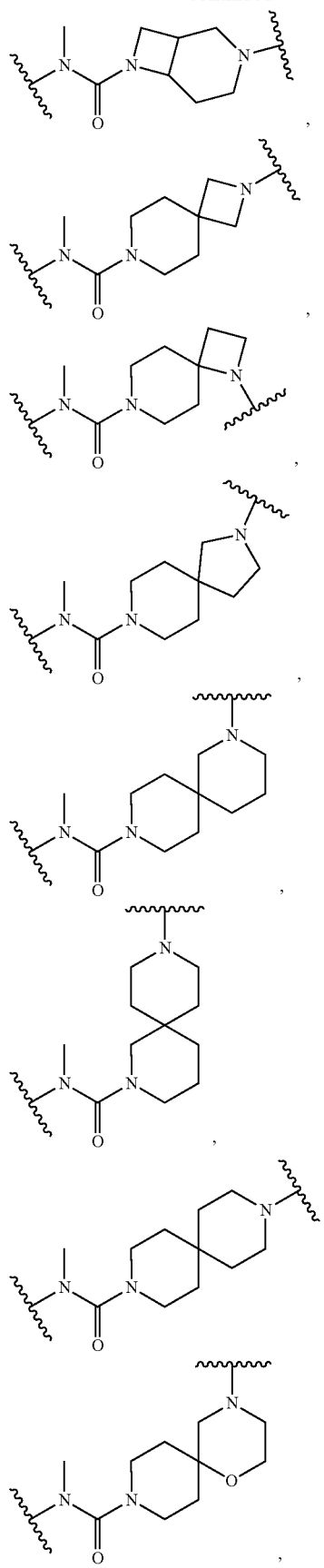
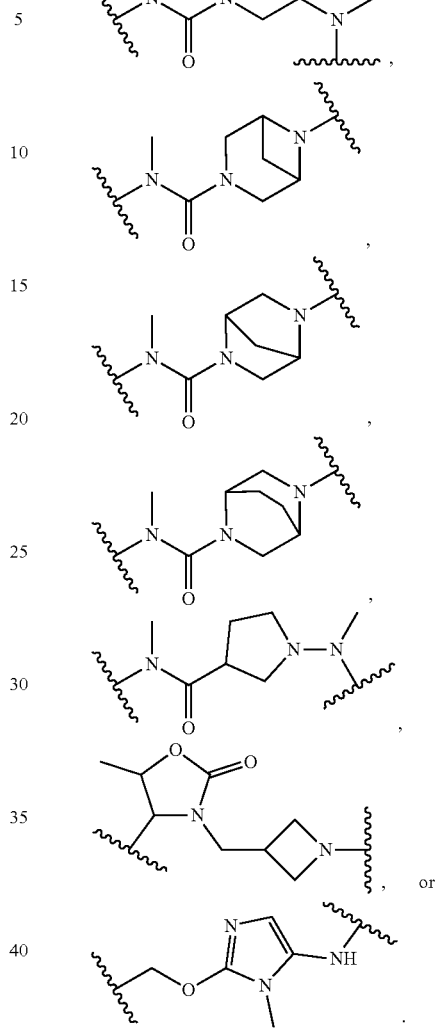
In some embodiments, the linker has the structure
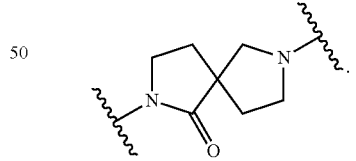
In some embodiments, the linker has the structure
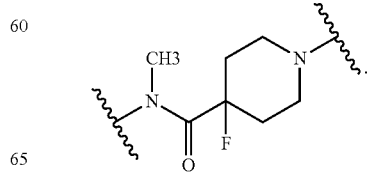

In some embodiments of a compound of the present invention, W is a cross-linking group comprising a vinyl ketone. In some embodiments, W has the structure of Formula IIIa:

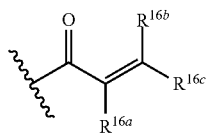

Formula IIIa wherein $R^{16a}$, $R^{16b}$, and $R^{16c}$ are, independently, hydrogen, —CN, halogen, or —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated heterocycloalkyl. In some embodiments, W is:

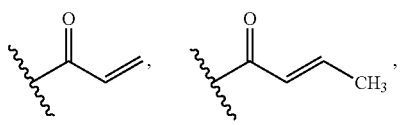

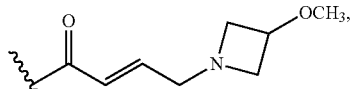

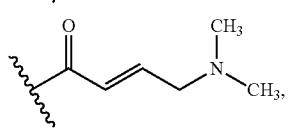

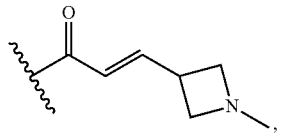

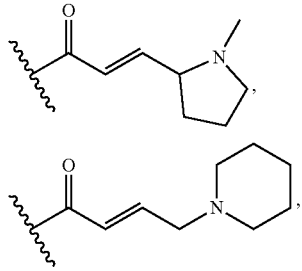

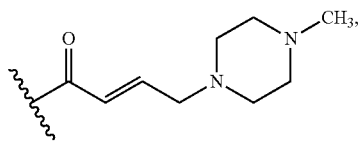

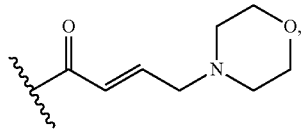

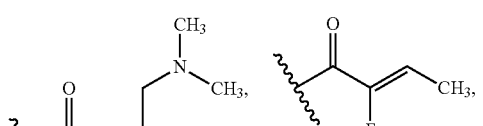

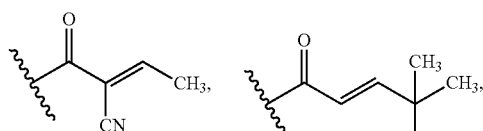

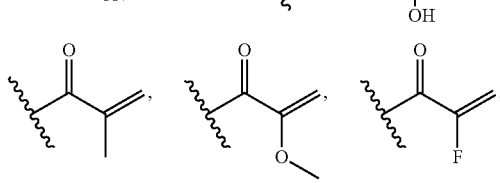

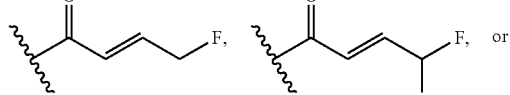

, or

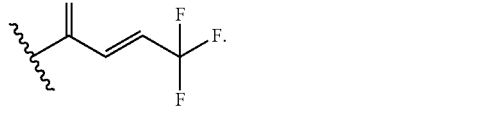

In some embodiments, W is a cross-linking group comprising an ynone. In some embodiments, W has the structure of Formula IIIb:

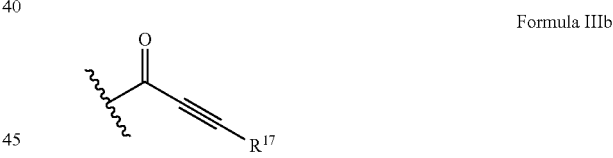

Formula IIIb wherein $R^{17}$ is hydrogen, —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated heterocycloalkyl, or a 4 to 7-membered saturated heterocycloalkyl. In some embodiments, W is:

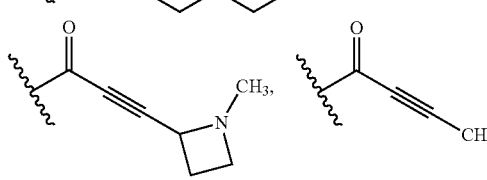

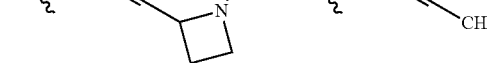

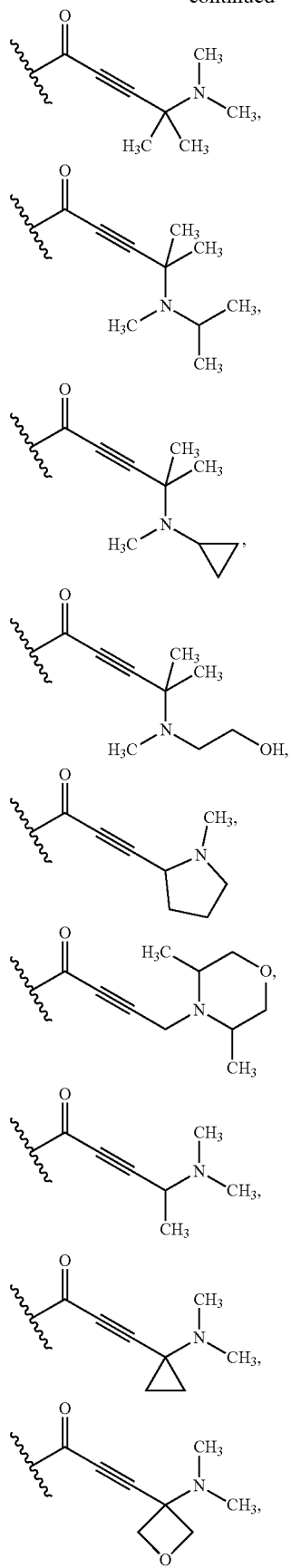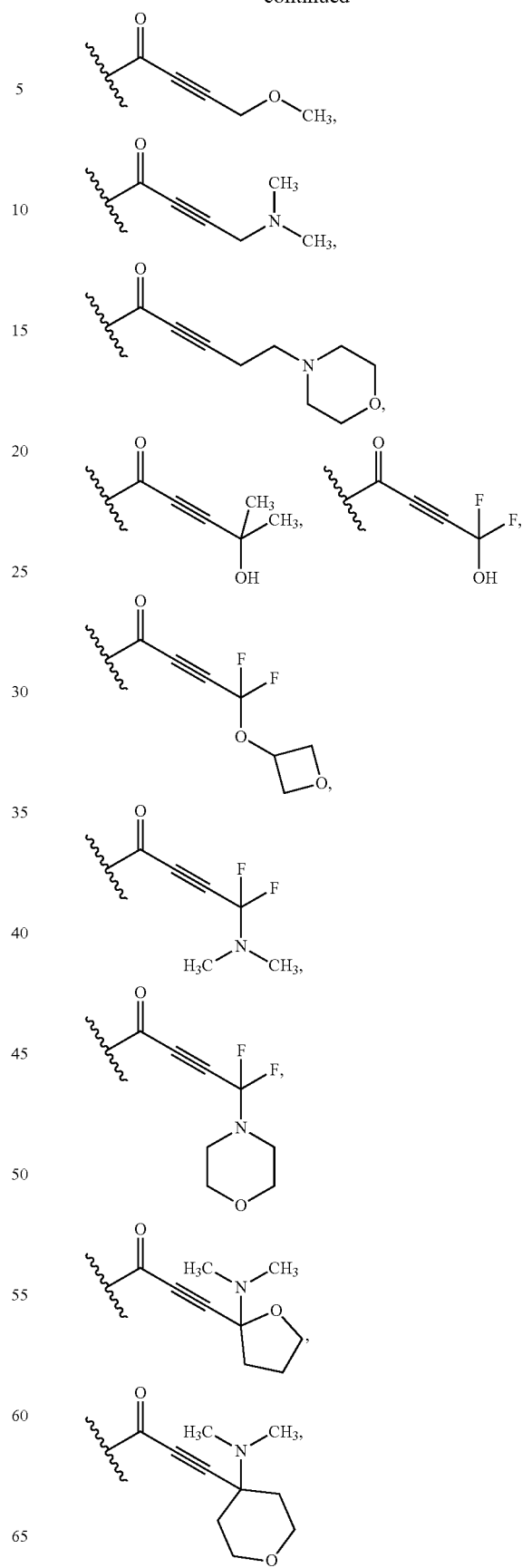

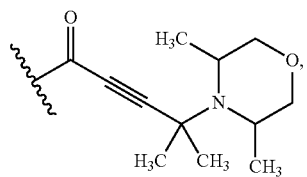
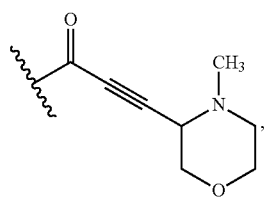
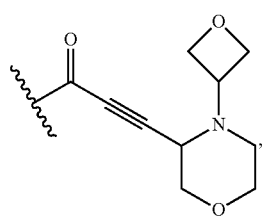
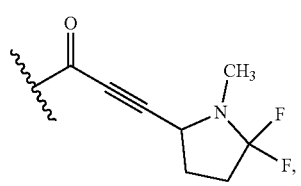
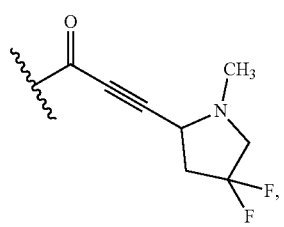
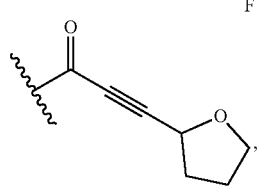
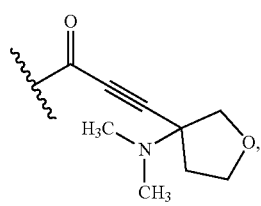
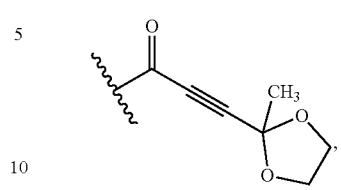
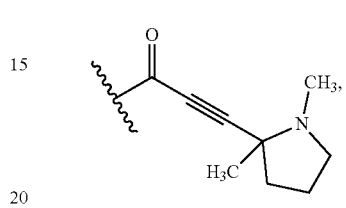
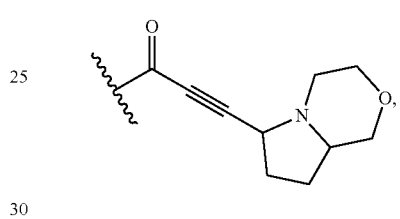
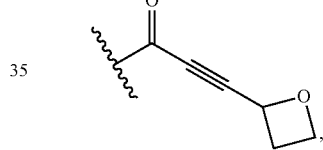
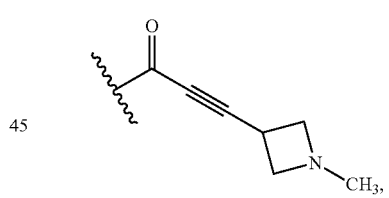
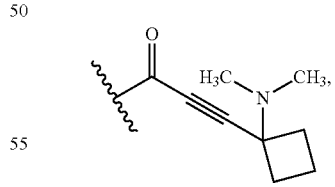
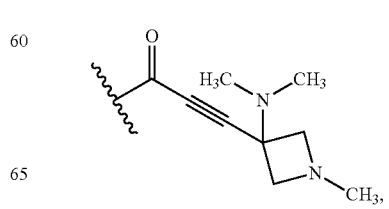

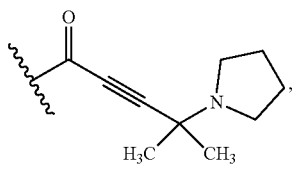

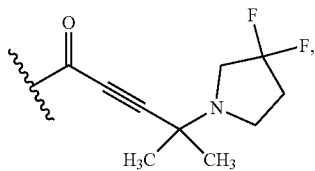

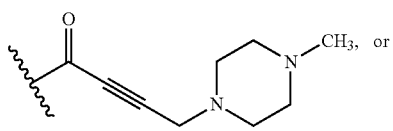

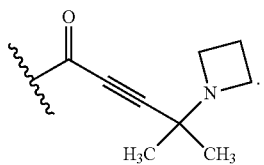

In some embodiments, W is

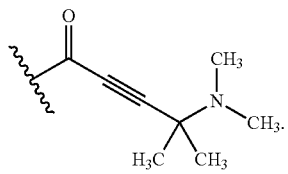 [SMILES: *C(=O)C#CC(C)(C)N(C)C]

In some embodiments, W is a cross-linking group comprising a vinyl sulfone. In some embodiments, W has the structure of Formula IIIc:

Formula IIIc

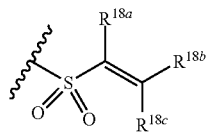

wherein $R^{18a}$, $R^{18b}$, and $R^{18c}$ are, independently, hydrogen, —CN, or —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated heterocycloalkyl. In some embodiments, W is:

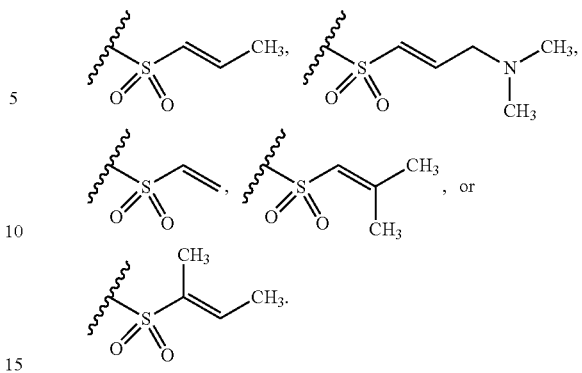

In some embodiments, W is a cross-linking group comprising an alkynyl sulfone. In some embodiments, W has the structure of Formula IIId:

Formula IIId

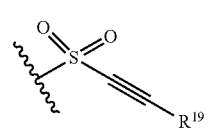

wherein $R^{19}$ is hydrogen, —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated heterocycloalkyl, or a 4 to 7-membered saturated heterocycloalkyl. In some embodiments, W is:

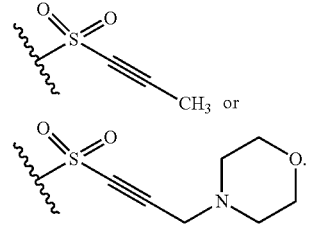

In some embodiments, W has the structure of Formula IIIe:

Formula IIIe

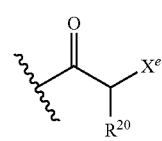

wherein $X^e$ is a halogen; and
$R^{20}$ is hydrogen, —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated heterocycloalkyl. In some embodiments, W is haloacetal. In some embodiments, W is not haloacetal.

In some embodiments, a compound of the present invention is selected from Table 1, or a pharmaceutically acceptable salt or stereoisomer thereof. In some embodiments, a compound of the present invention is selected from Table 1, or a pharmaceutically acceptable salt or atropisomer thereof.

TABLE 1
Certain Compounds of the Present Invention
| Ex# | Structure |
|---|---|
| A1 | 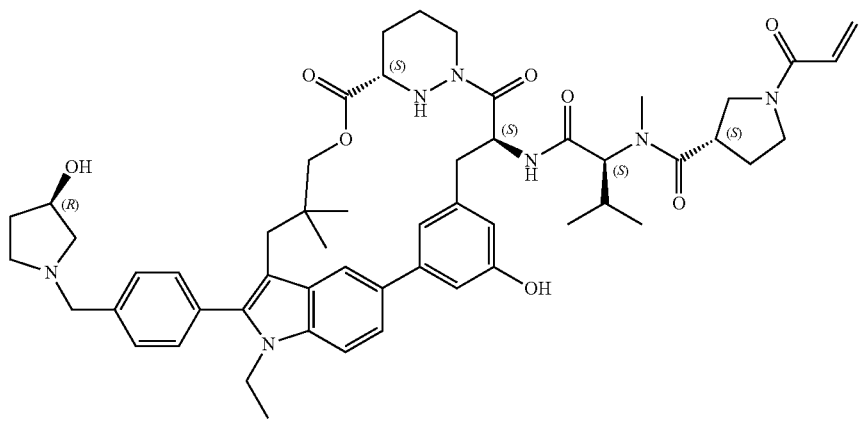 |
| A2 | 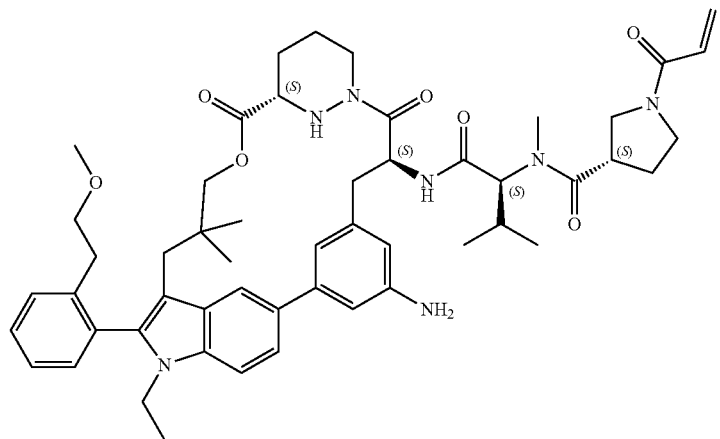 |
| A3 | 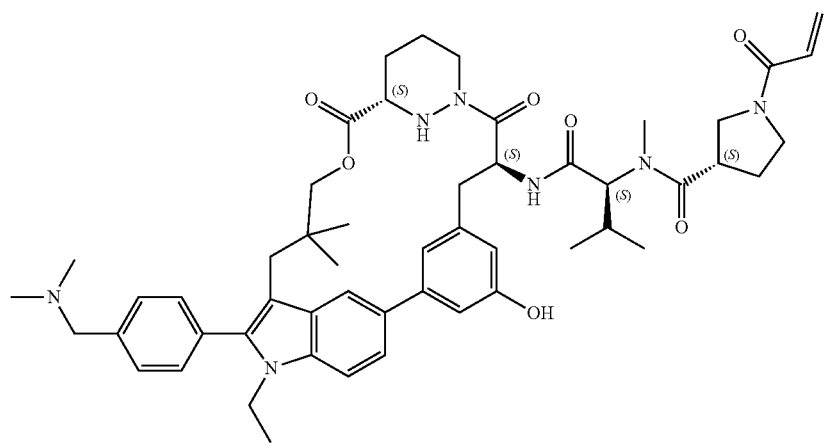 |

TABLE 1-continued
Certain Compounds of the Present Invention
| Ex# | Structure |
|---|---|
| A4 | 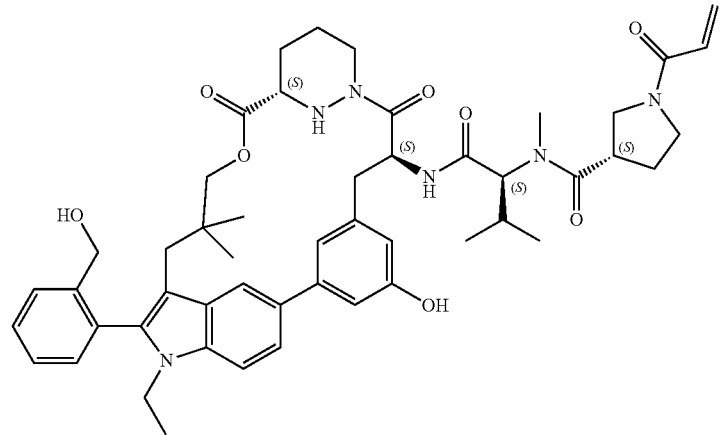 |
| A5 | 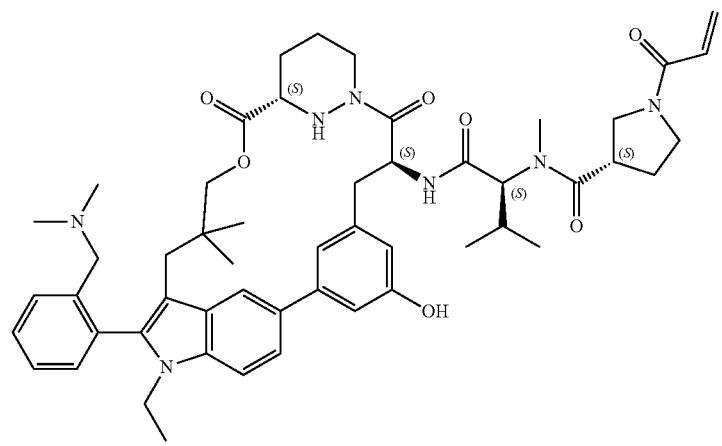 |
| A6 | 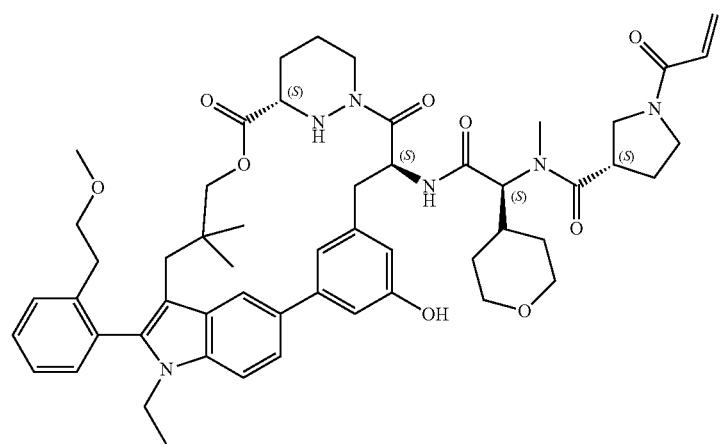 |

TABLE 1-continued
Certain Compounds of the Present Invention
| Ex# | Structure |
|---|---|
| A7 | 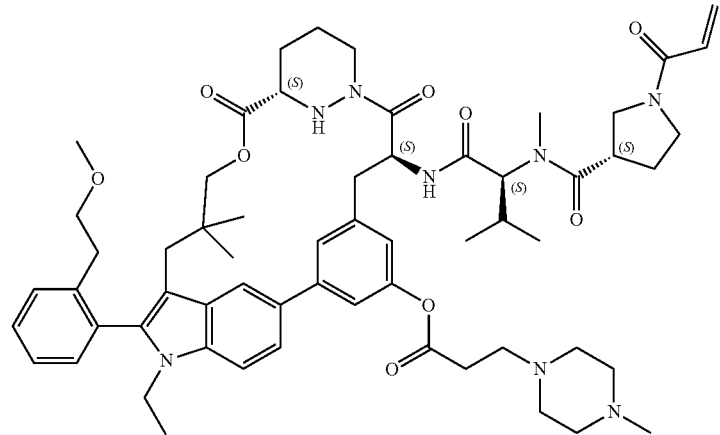 |
| A8 | 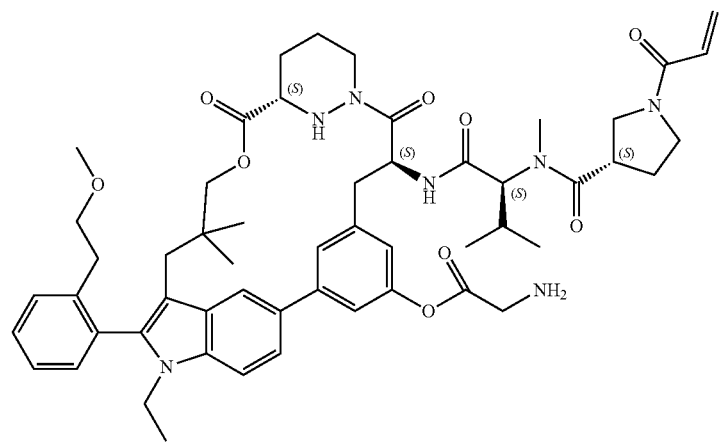 |
| A9 | 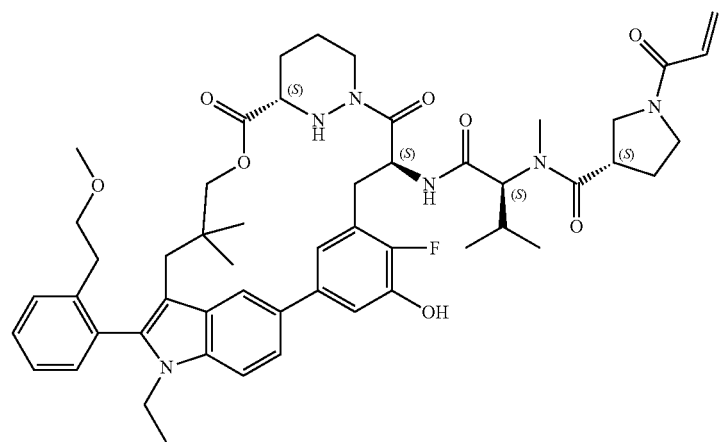 |

TABLE 1-continued
Certain Compounds of the Present Invention
| Ex# | Structure |
|---|---|
| A10 | 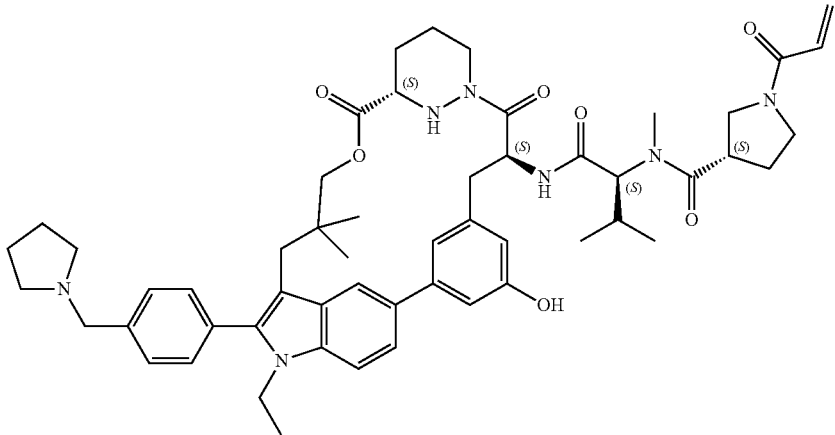 |
| A11 | 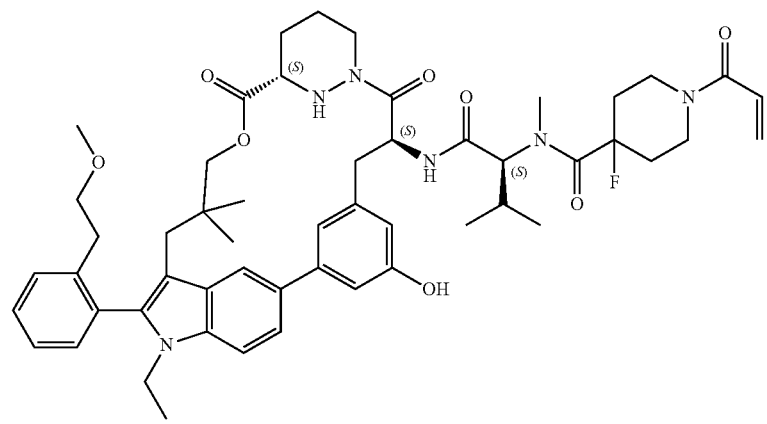 |
| A12 | 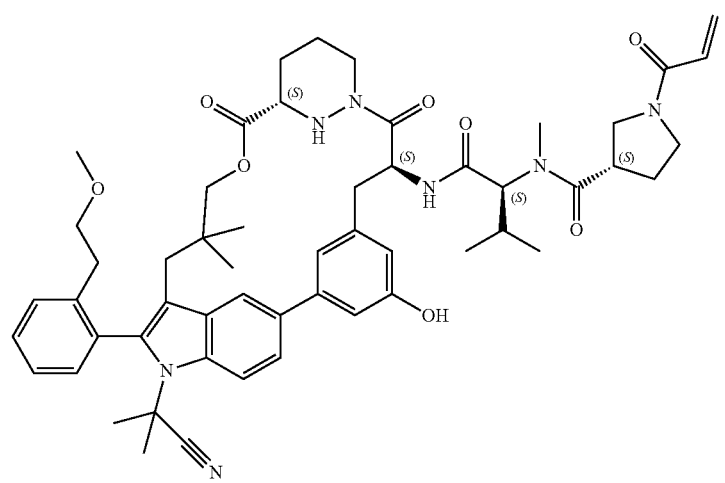 |

TABLE 1-continued
Certain Compounds of the Present Invention
| Ex# | Structure |
|---|---|
| A13 | 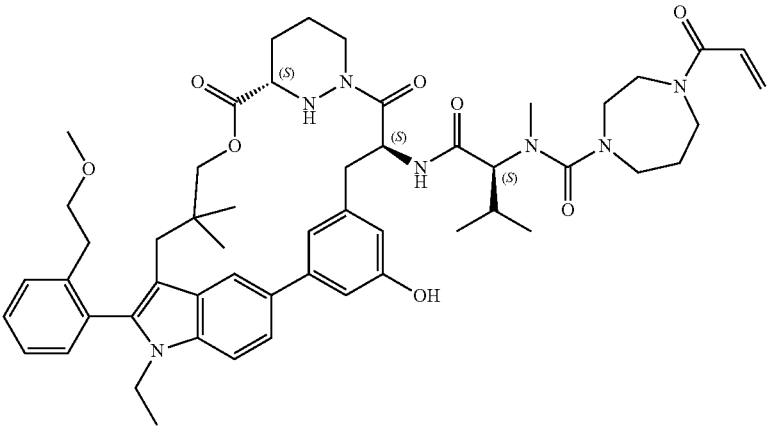 |
| A14 | 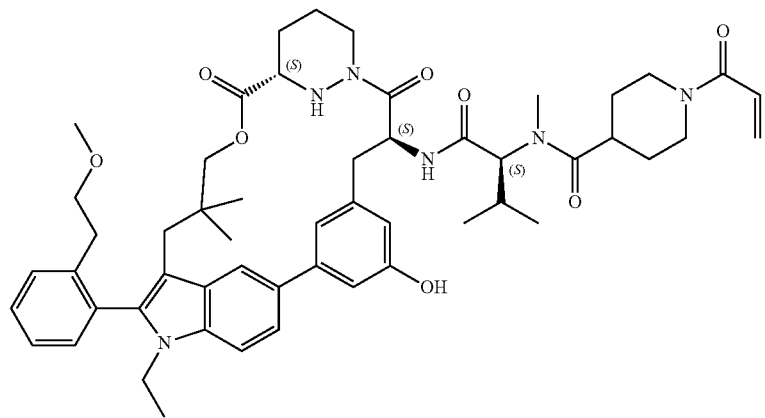 |
| A15 | 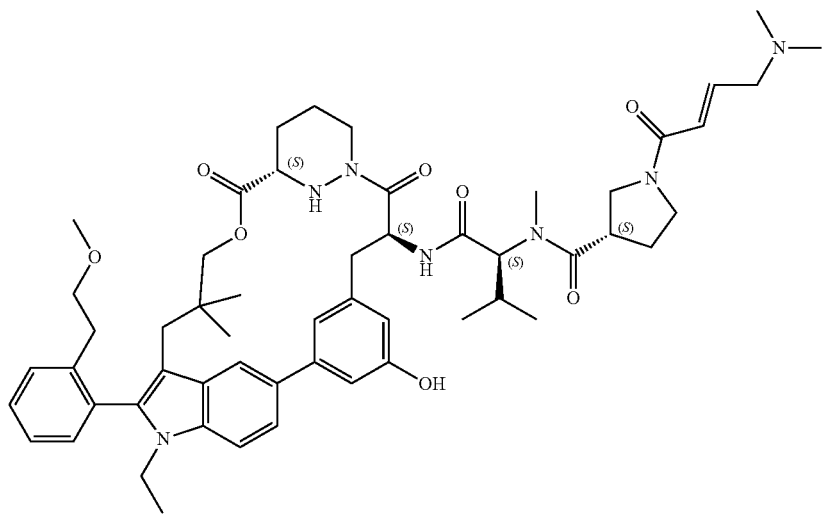 |

US 11,952,352 B2
79                                                                 80
TABLE 1-continued
Certain Compounds of the Present Invention
| Ex# | Structure |
|-----|-----------|
| A16 | 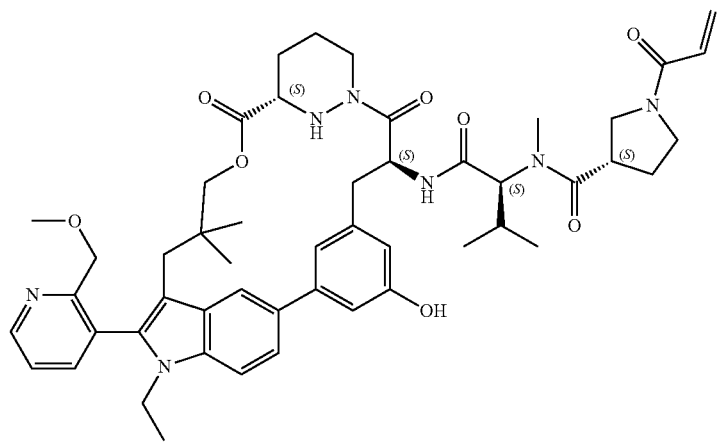 |
| A17 | 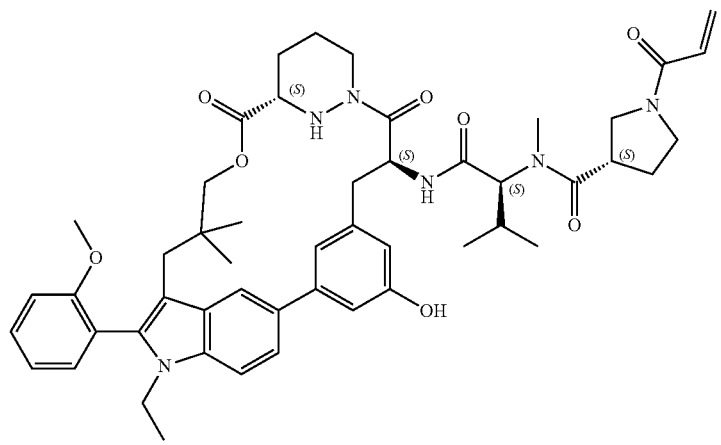 |
| A18 | 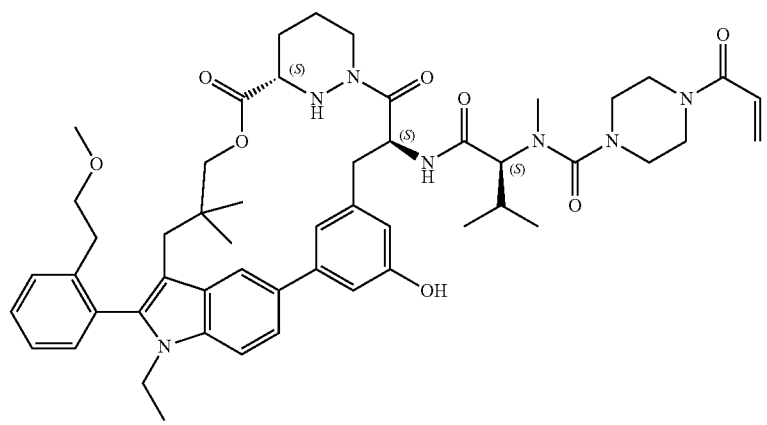 |

TABLE 1-continued
Certain Compounds of the Present Invention
| Ex# | Structure |
|---|---|
| A19 | 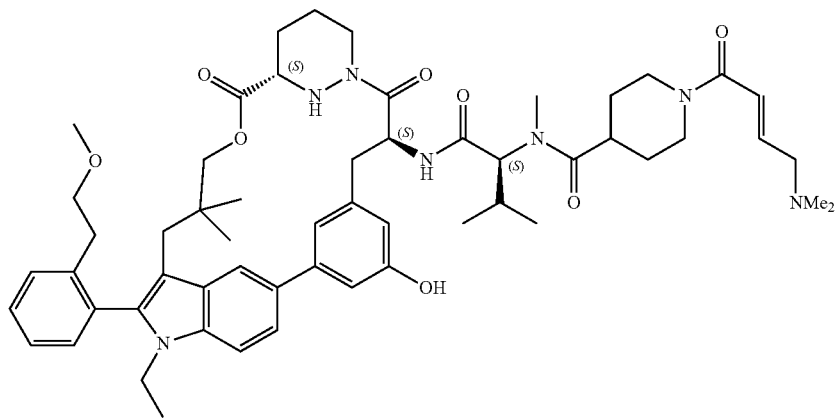 |
| A20 | 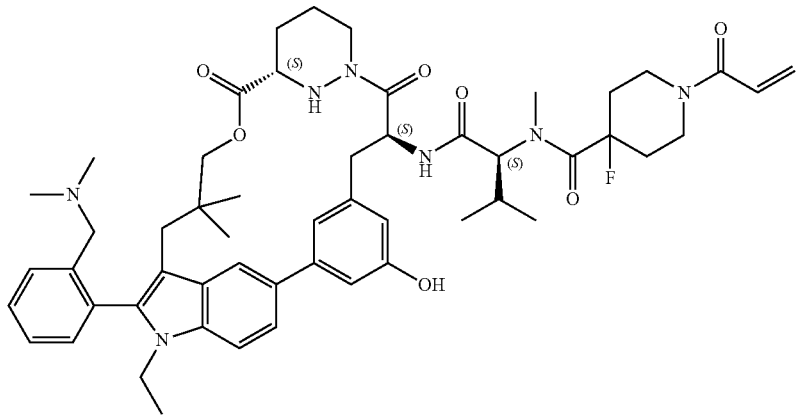 |
| A21 | 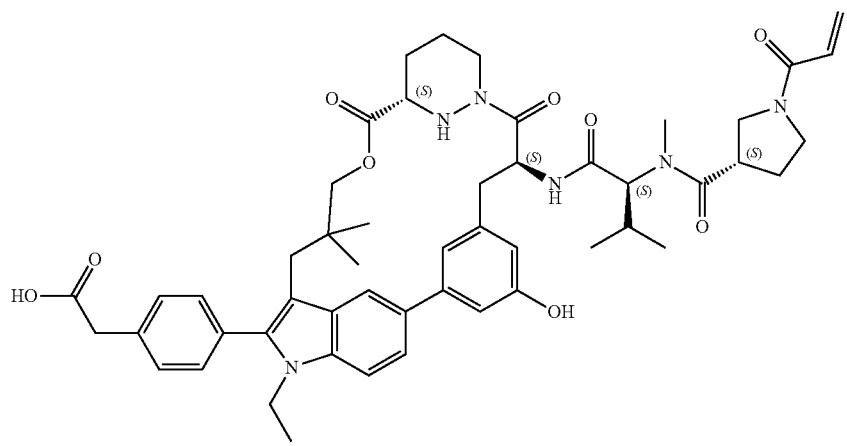 |

TABLE 1-continued

Certain Compounds of the Present Invention

| Ex# | Structure |
|---|---|
| A22 | 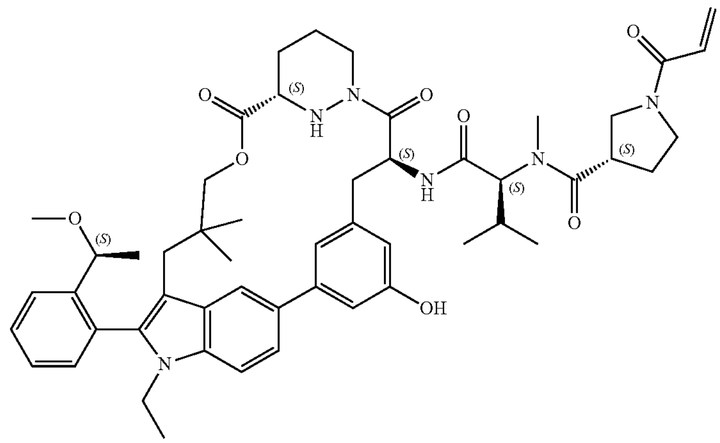 |
| A23 | 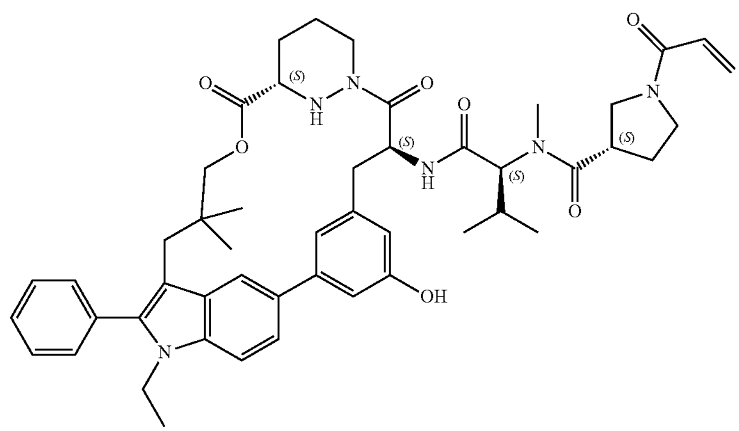 |
| A24 | 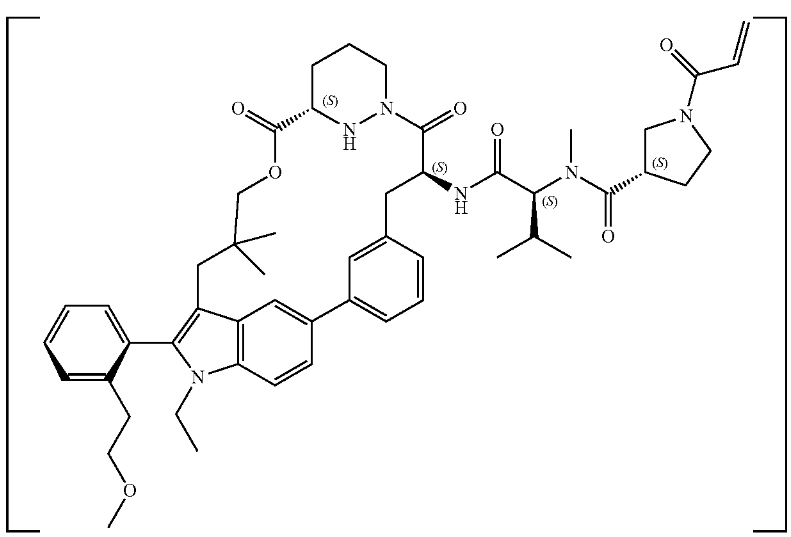 |

TABLE 1-continued
Certain Compounds of the Present Invention
| Ex# | Structure |
|---|---|
| A25 | 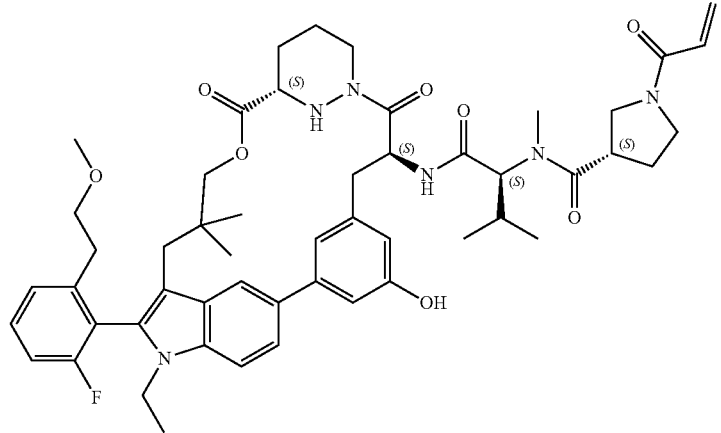 |
| A26 | 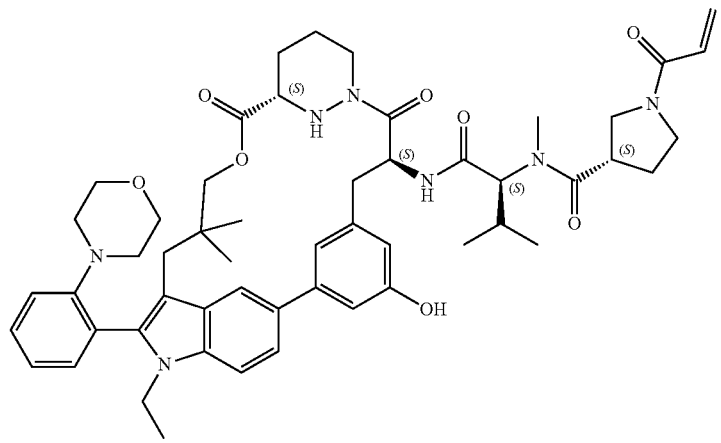 |
| A27 | 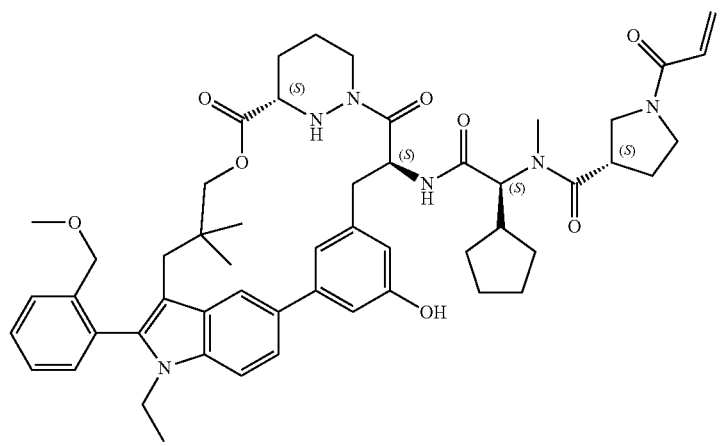 |

TABLE 1-continued
Certain Compounds of the Present Invention
| Ex# | Structure |
|---|---|
| A28 | 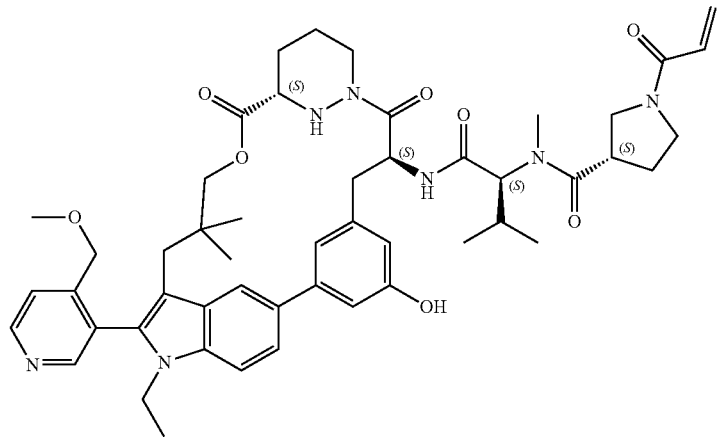 |
| A29 | 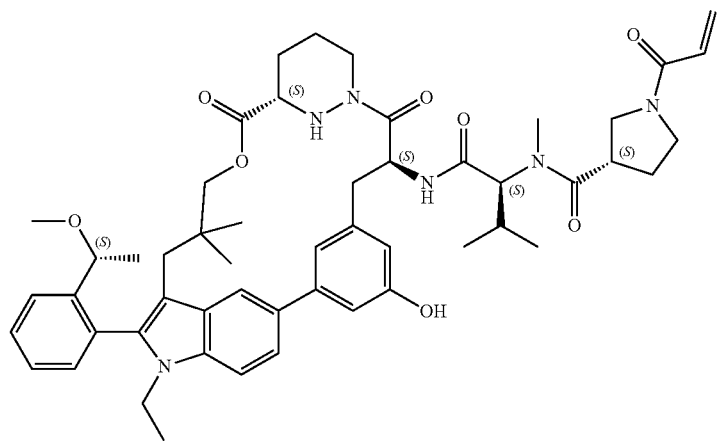 |
| A30 | 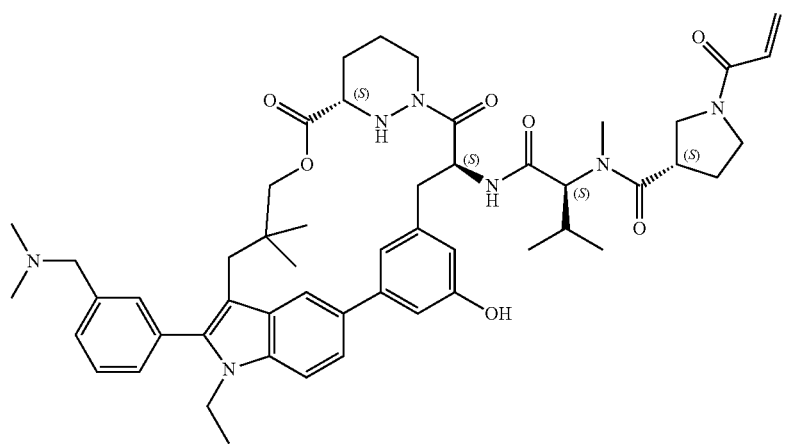 |

TABLE 1-continued
Certain Compounds of the Present Invention
| Ex# | Structure |
|---|---|
| A31 | 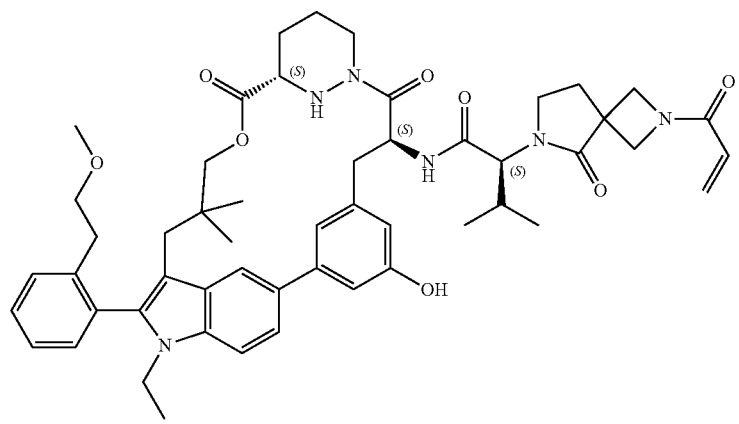 |
| A32 | 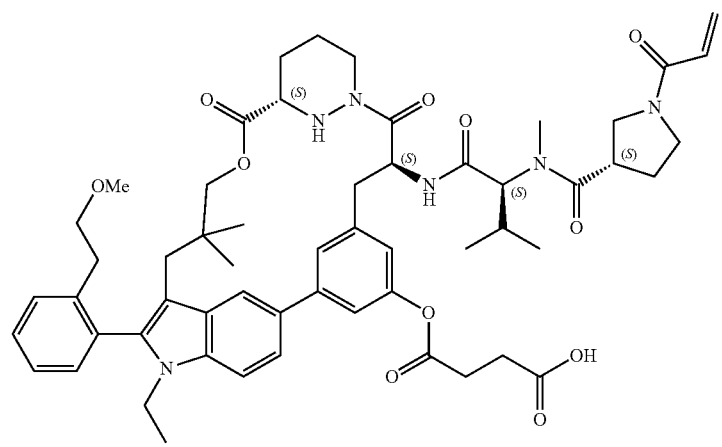 |
| A33 | 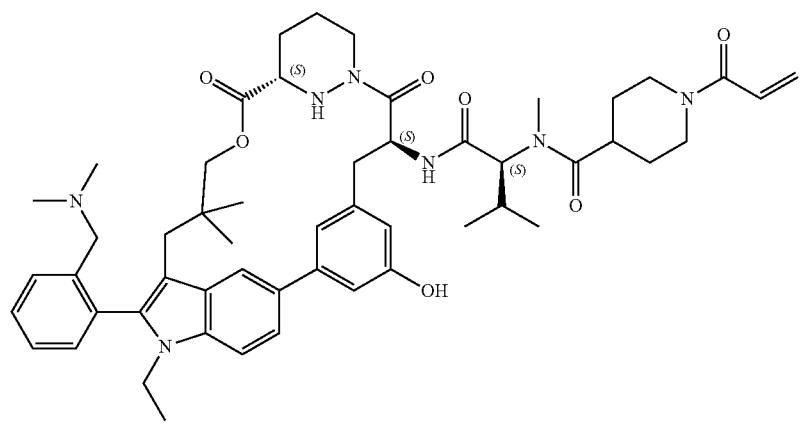 |

TABLE 1-continued
Certain Compounds of the Present Invention
| Ex# | Structure |
|---|---|
| A34 | 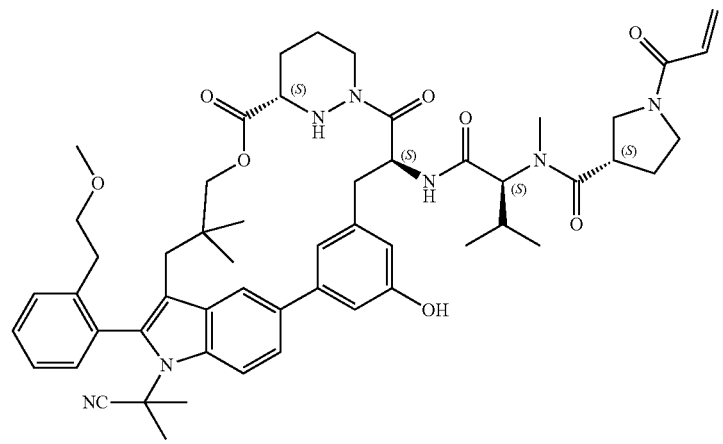 |
| A35 | 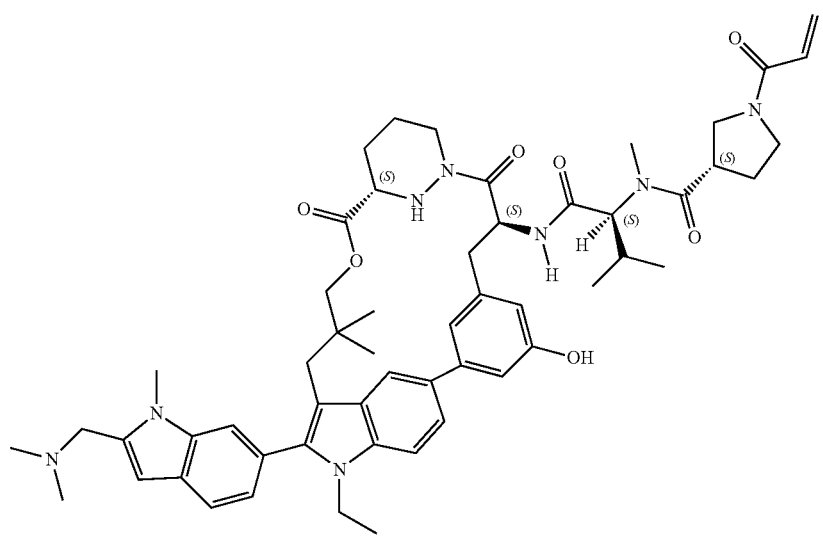 |
| A36 | 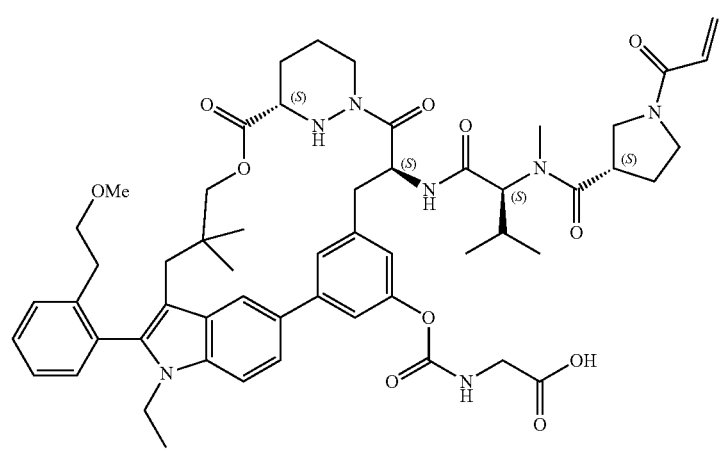 |

TABLE 1-continued
Certain Compounds of the Present Invention
| Ex# | Structure |
|---|---|
| A37 | 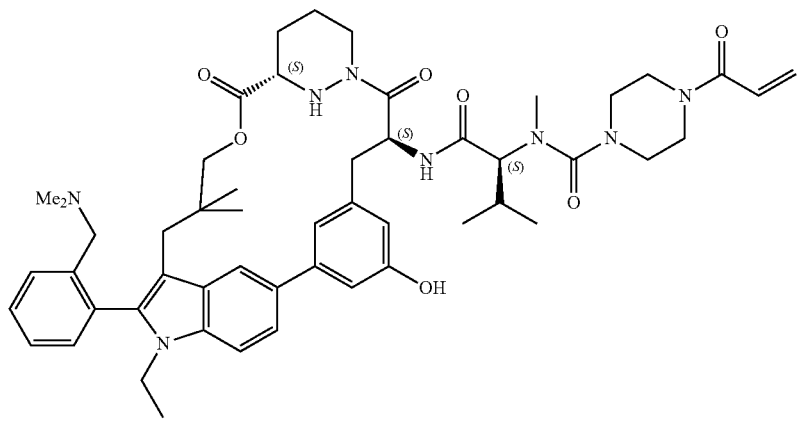 |
| A38 | 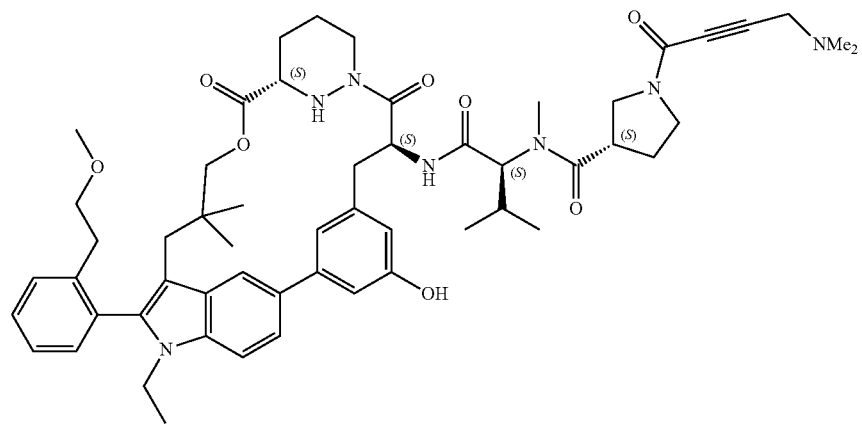 |
| A39 | 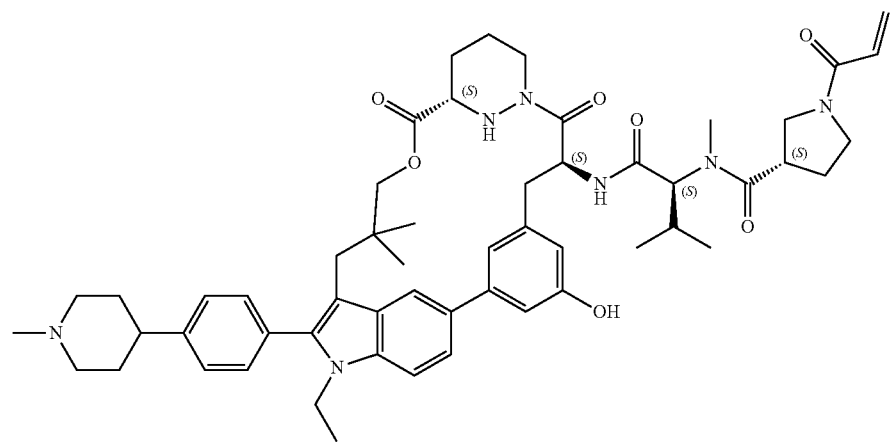 |

TABLE 1-continued
Certain Compounds of the Present Invention
| Ex# | Structure |
|---|---|
| A40 | 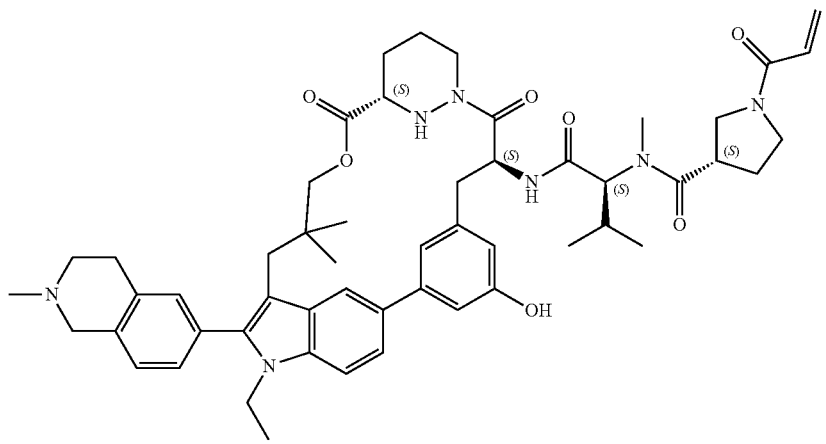 |
| A41 | 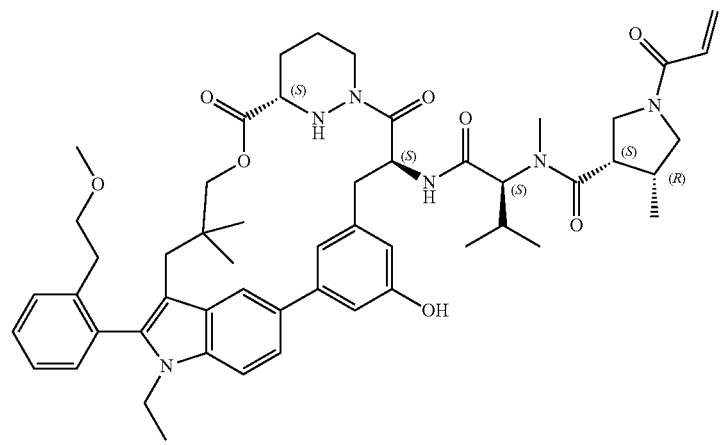 |
| A42 | 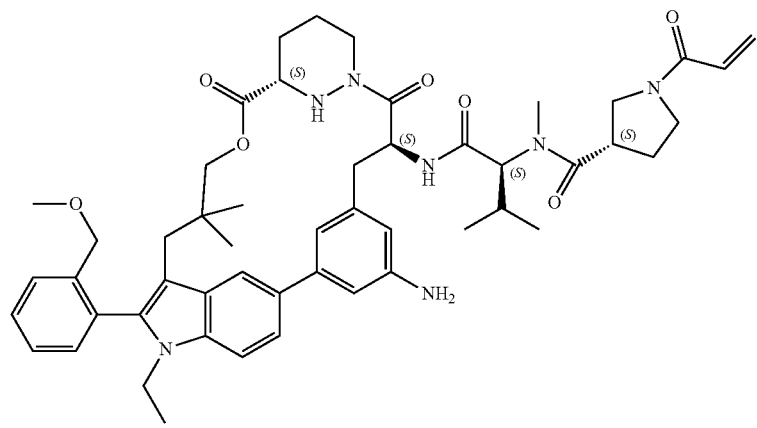 |

TABLE 1-continued
Certain Compounds of the Present Invention
| Ex# | Structure |
|---|---|
| A43 | 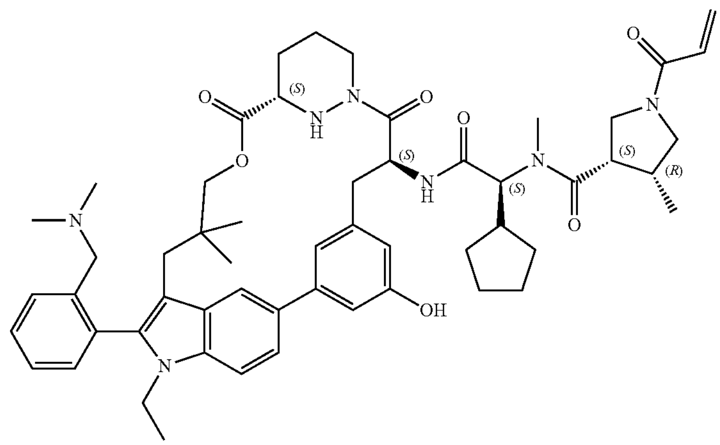 |
| A44 | 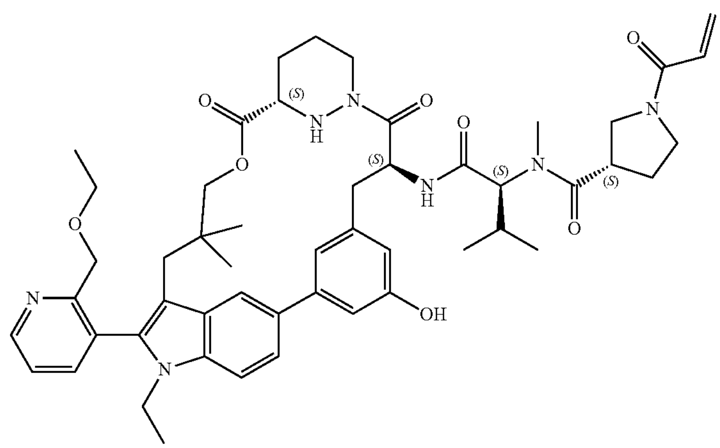 |
| A45 | 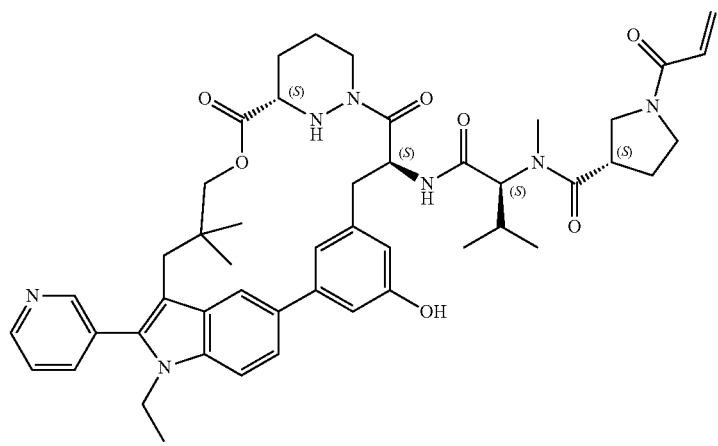 |

TABLE 1-continued
Certain Compounds of the Present Invention
| Ex# | Structure |
|---|---|
| A46 | 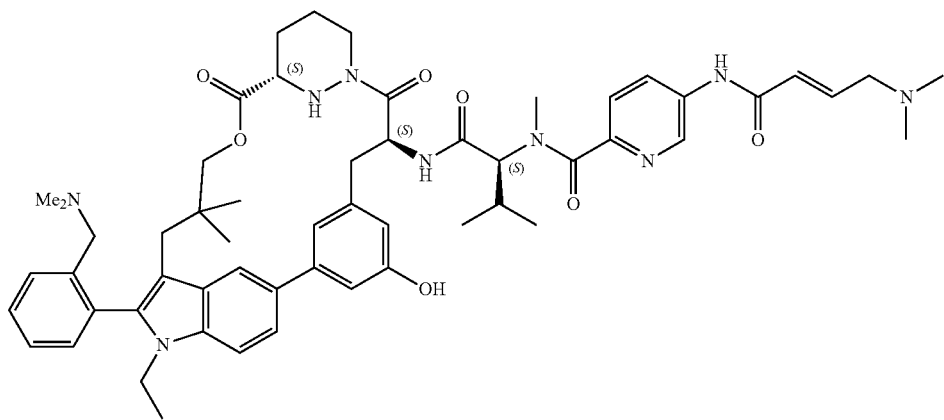 |
| A47 | 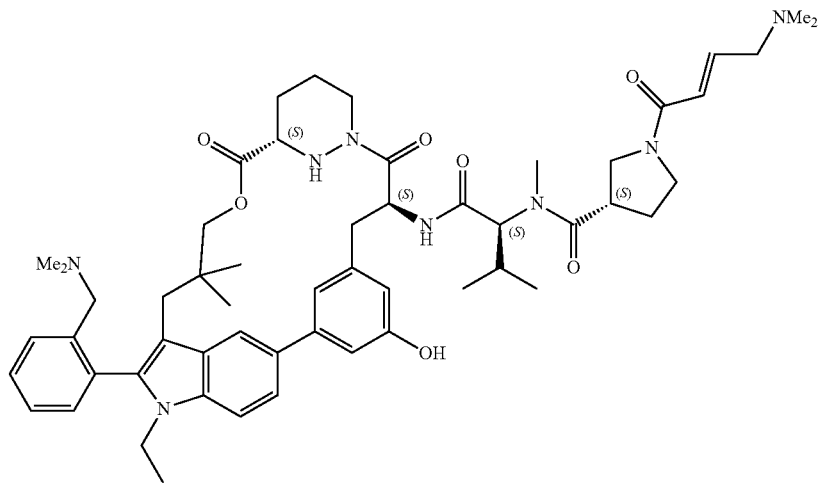 |
| A48 | 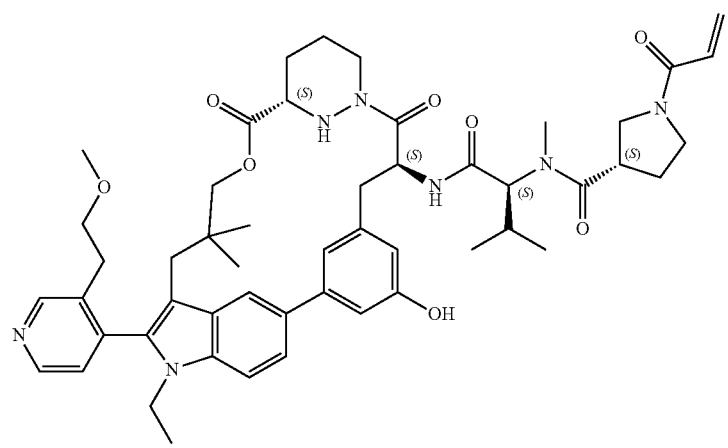 |

TABLE 1-continued
Certain Compounds of the Present Invention
| Ex# | Structure |
| --- | --- |
| A49 | 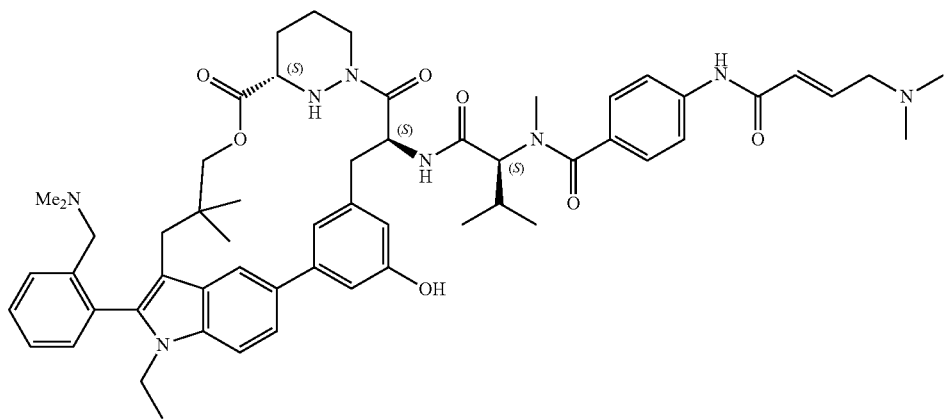 |
| A50 | 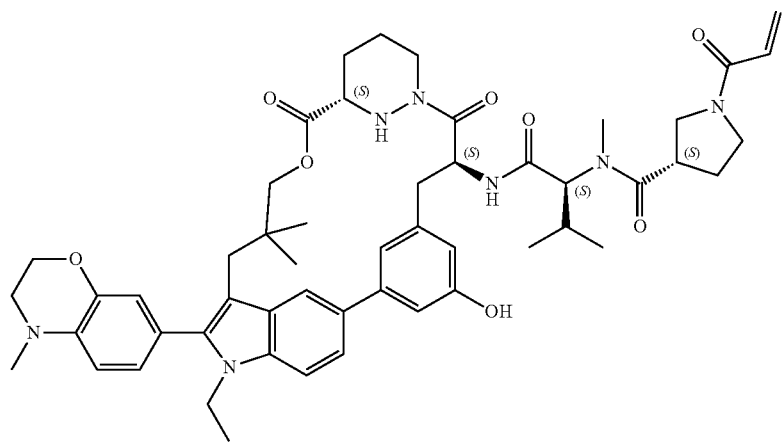 |
| A51 | 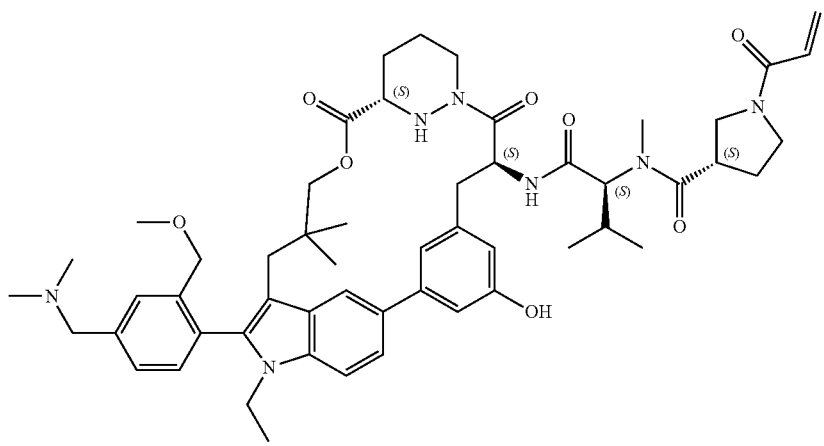 |

TABLE 1-continued
Certain Compounds of the Present Invention
| Ex# | Structure |
|---|---|
| A52 | 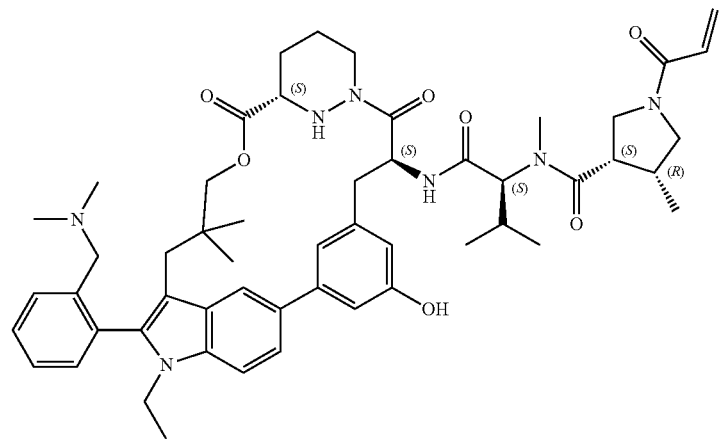 |
| A53 | 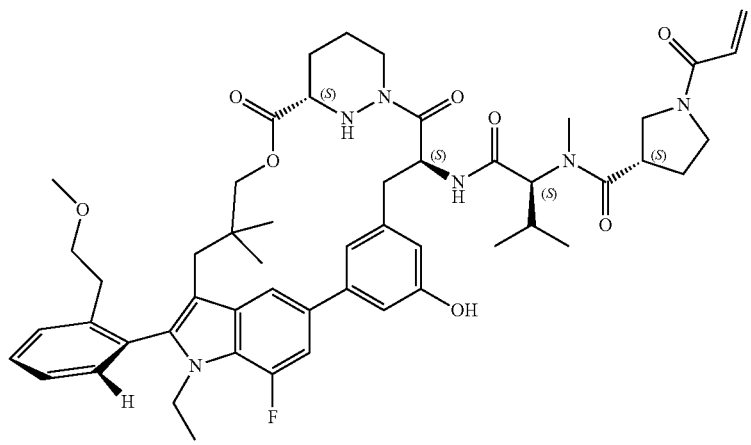 |
| A54 | 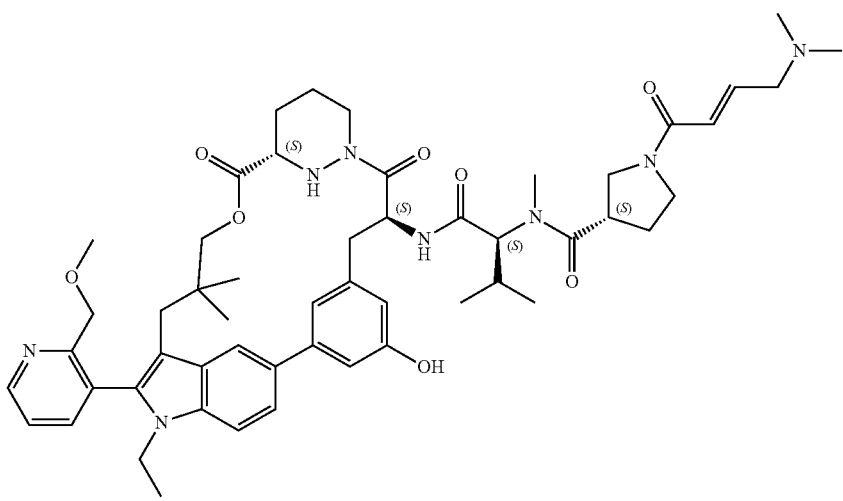 |

TABLE 1-continued
Certain Compounds of the Present Invention
| Ex# | Structure |
|---|---|
| A55 | 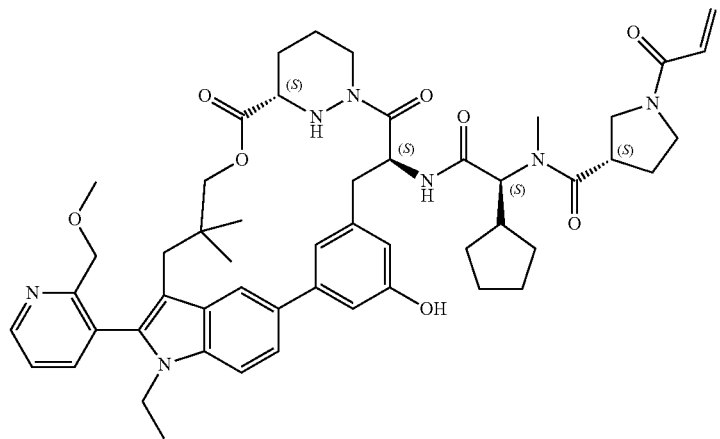 |
| A56 | 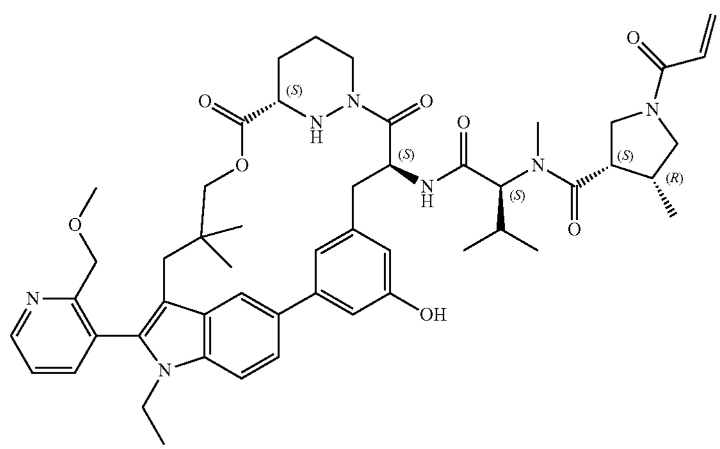 |
| A57 | 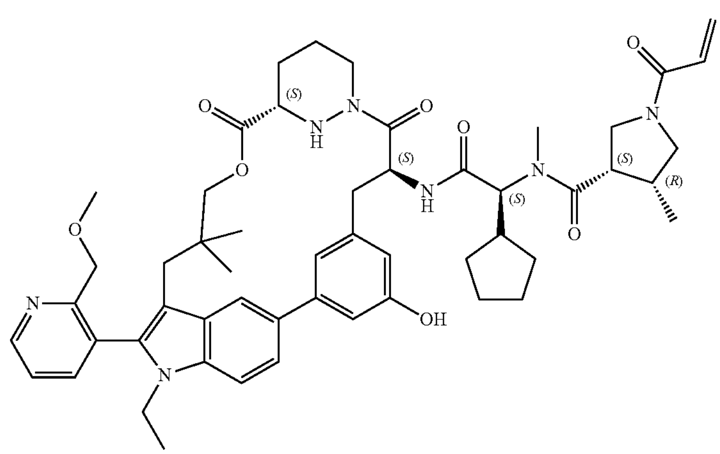 |

TABLE 1-continued
Certain Compounds of the Present Invention
| Ex# | Structure |
|---|---|
| A58 | 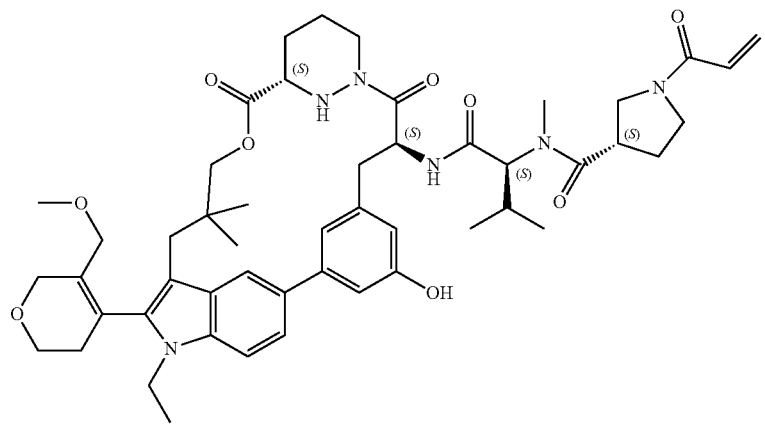 |
| A59 | 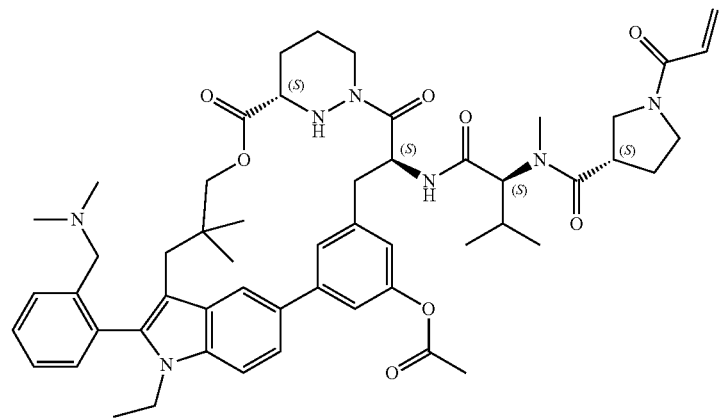 |
| A60 | 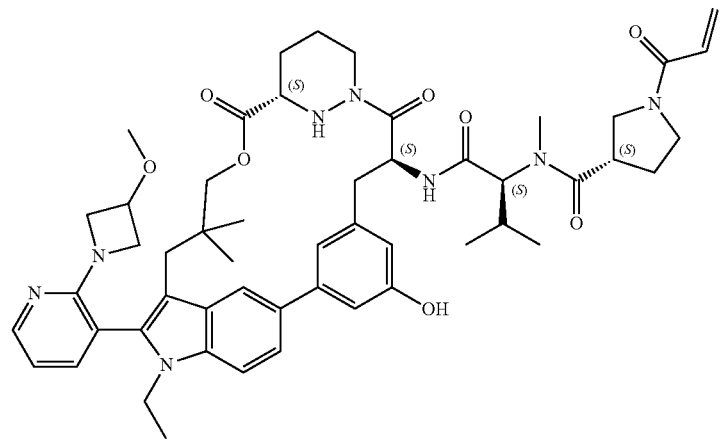 |

TABLE 1-continued
Certain Compounds of the Present Invention
| Ex# | Structure |
|---|---|
| A61 | 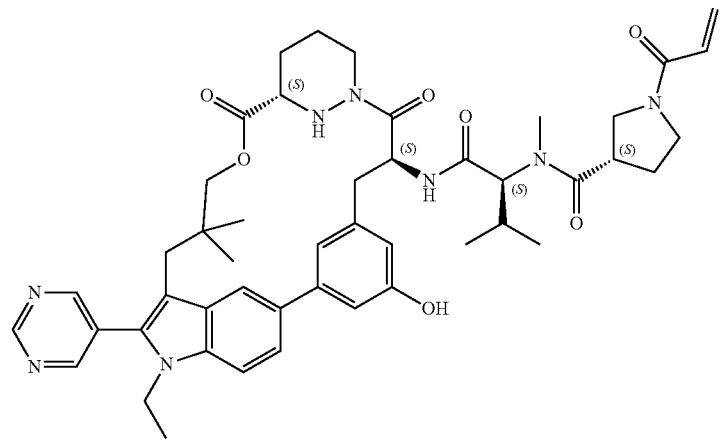 |
| A62 | 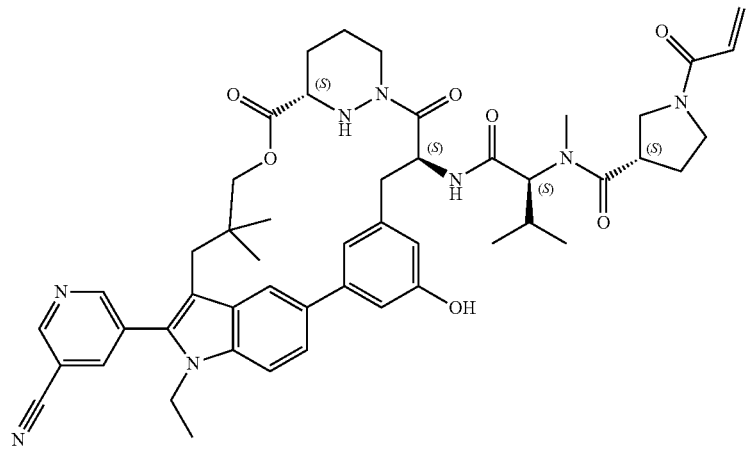 |
| A63 | 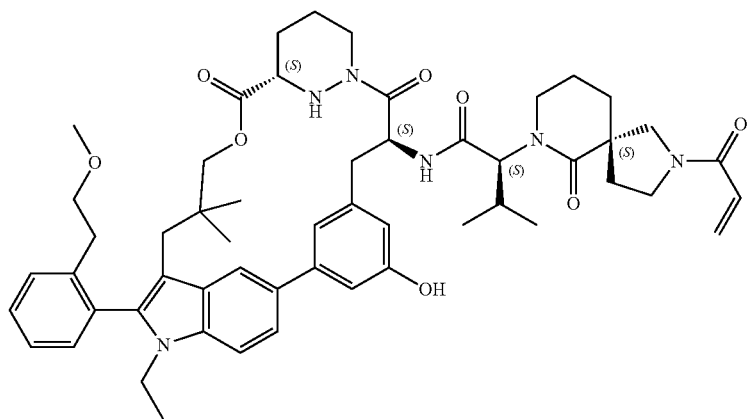 |

TABLE 1-continued
Certain Compounds of the Present Invention
| Ex# | Structure |
|---|---|
| A64 | 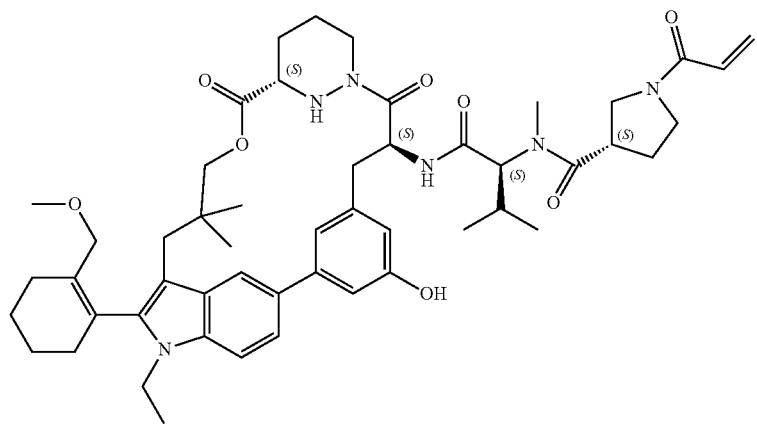 |
| A65 | 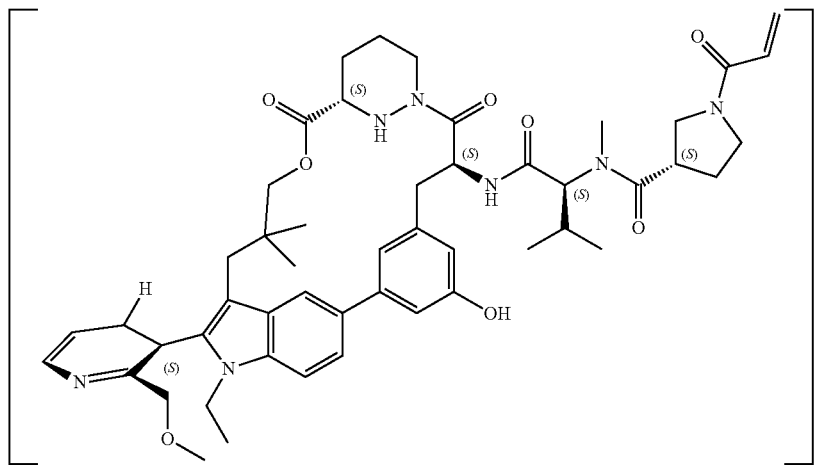 |
| A66 | 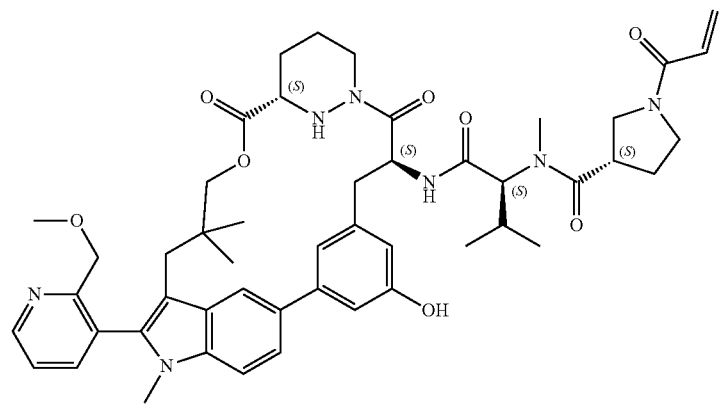 |

TABLE 1-continued
Certain Compounds of the Present Invention
| Ex# | Structure |
|---|---|
| A67 | 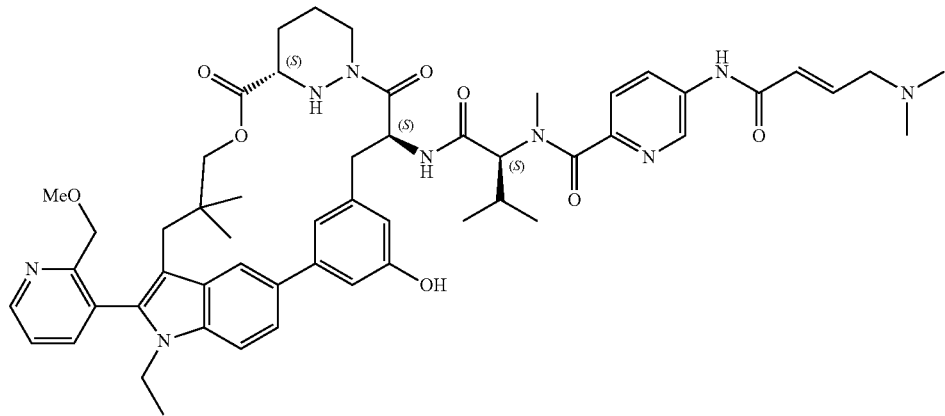 |
| A68 | 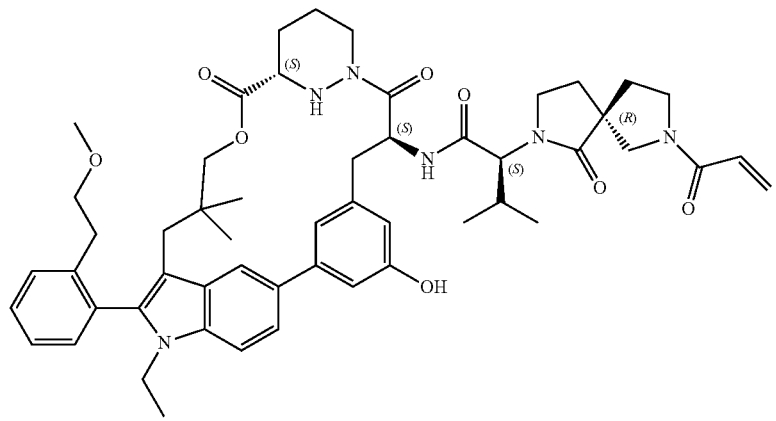 |
| A69 | 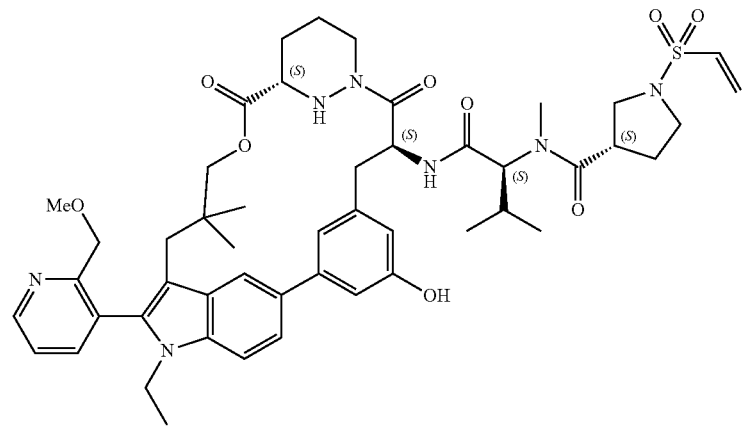 |

US 11,952,352 B2
115                                                                 116
TABLE 1-continued
Certain Compounds of the Present Invention
| Ex# | Structure |
|---|---|
A70
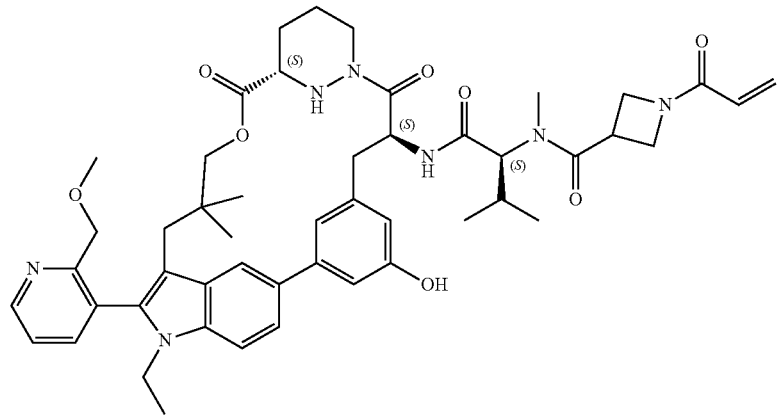
A71
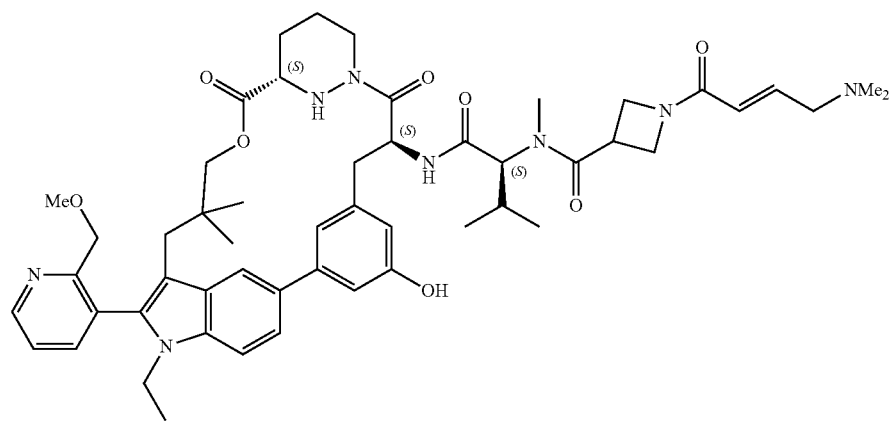
A72
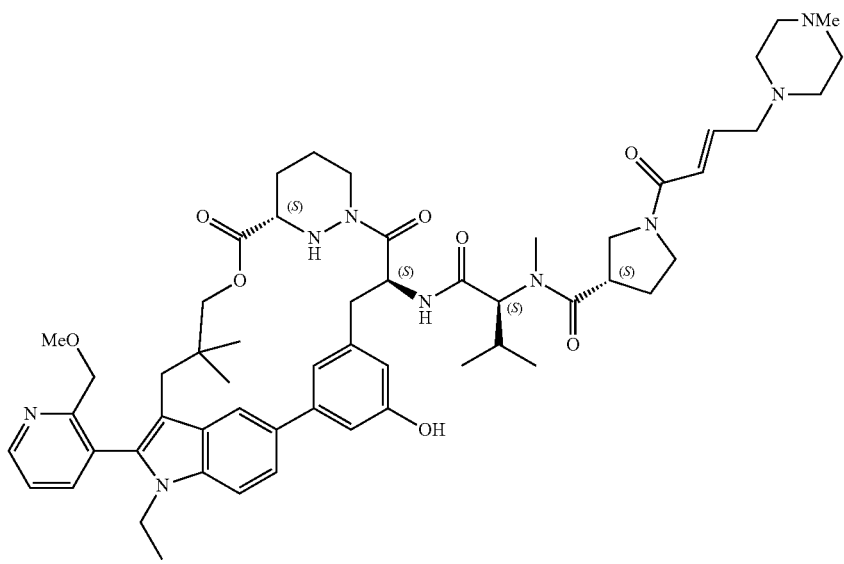

TABLE 1-continued

Certain Compounds of the Present Invention

| Ex# | Structure |
|---|---|
| A73 | 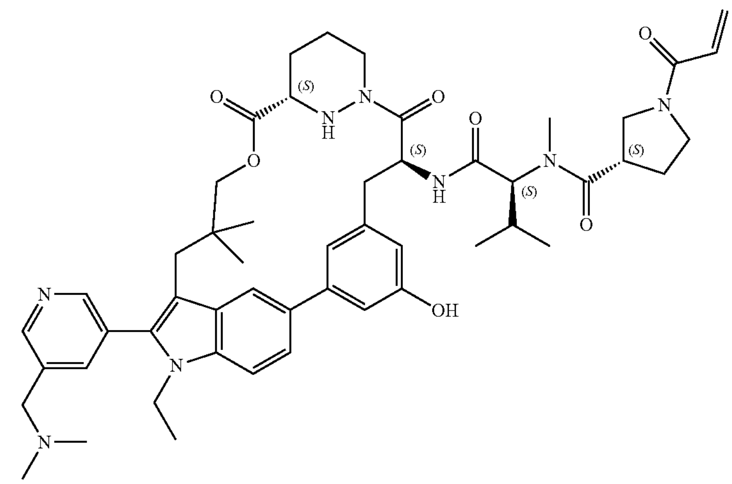 |
| A74 | 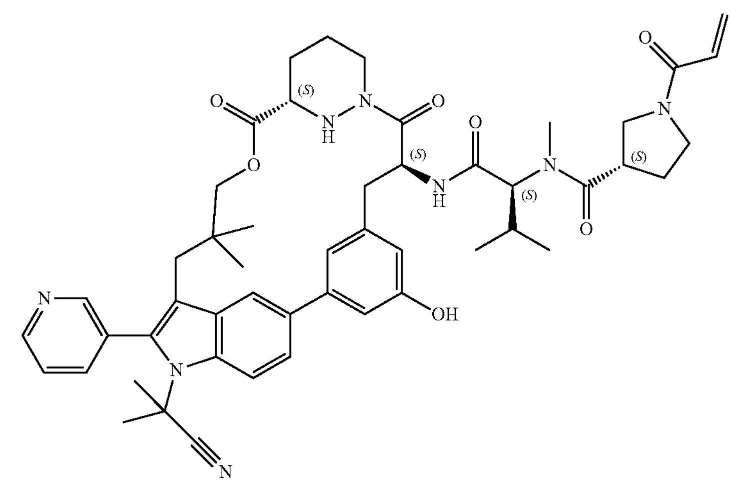 |
| A75 | 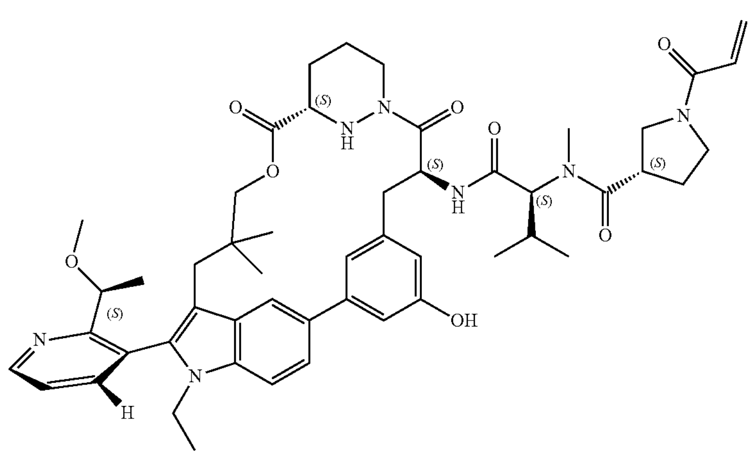 |

TABLE 1-continued

Certain Compounds of the Present Invention

| Ex# | Structure |
|---|---|
| A76 | 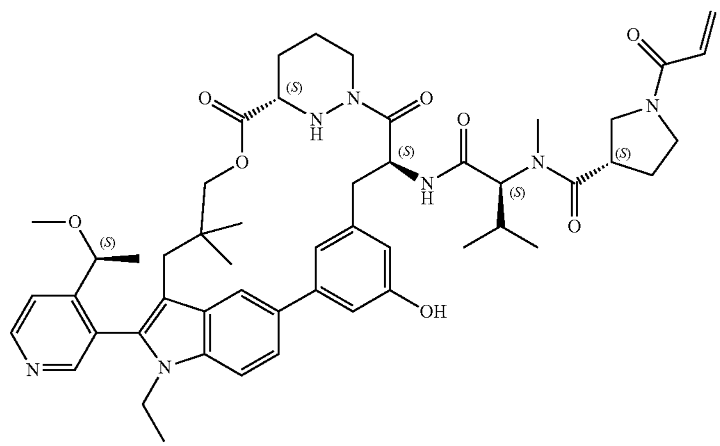 |
| A77 | 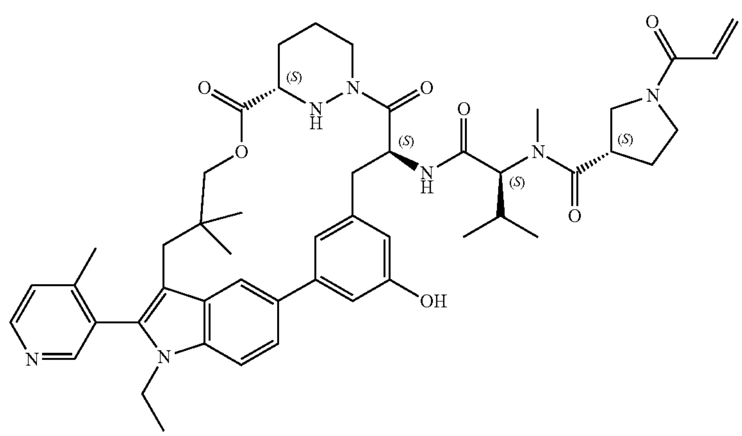 |
| A78 | 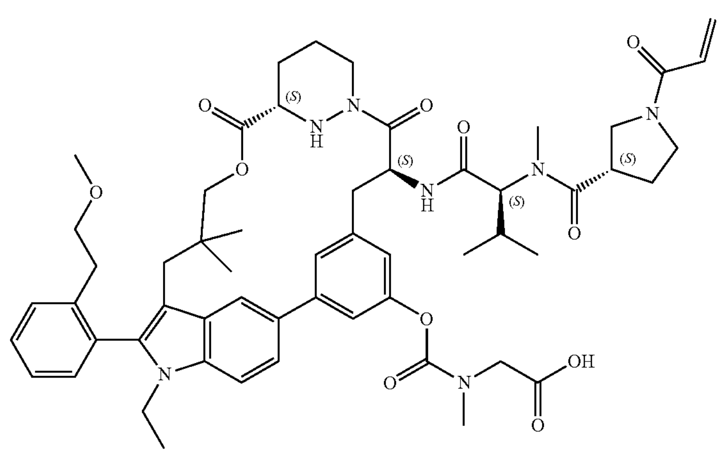 |

TABLE 1-continued

Certain Compounds of the Present Invention

| Ex# | Structure |
| --- | --- |
| A79 | 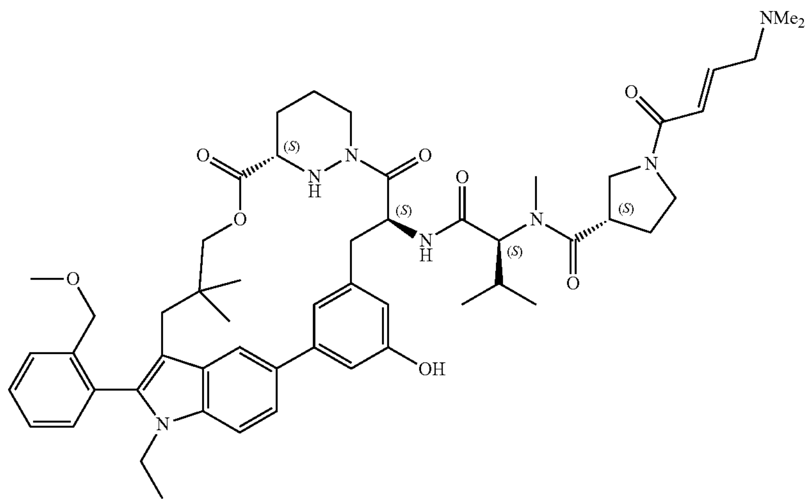 |
| A80 | 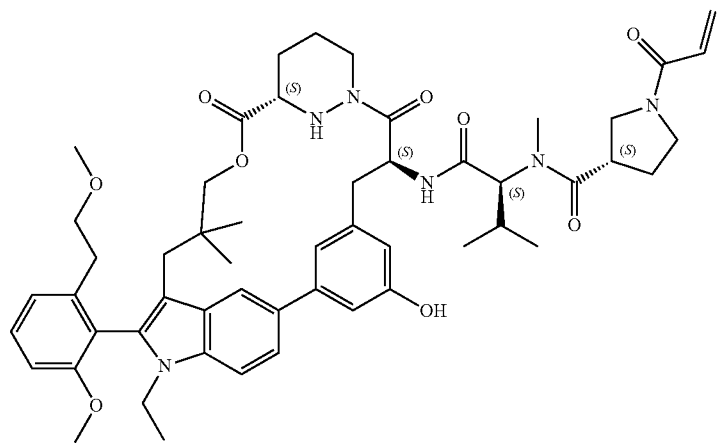 |
| A81 | 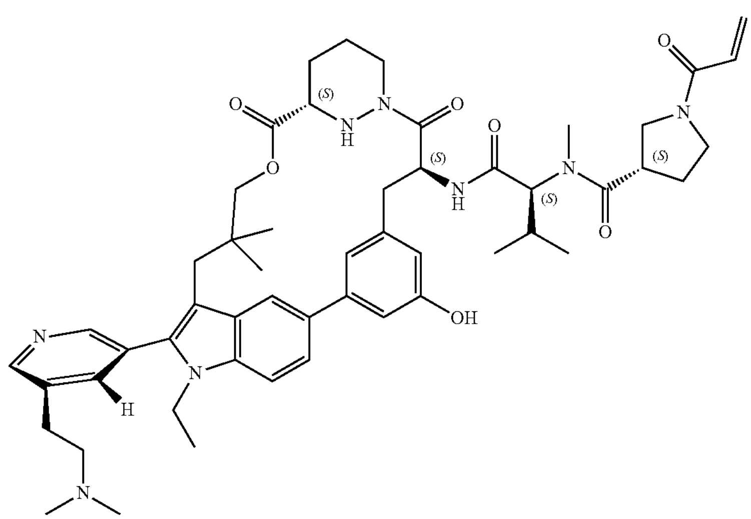 |

TABLE 1-continued
Certain Compounds of the Present Invention
| Ex# | Structure |
|---|---|
| A82 | 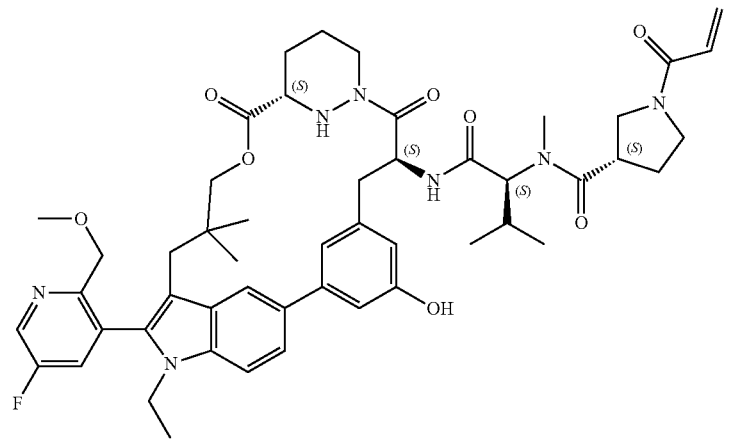 |
| A83 | 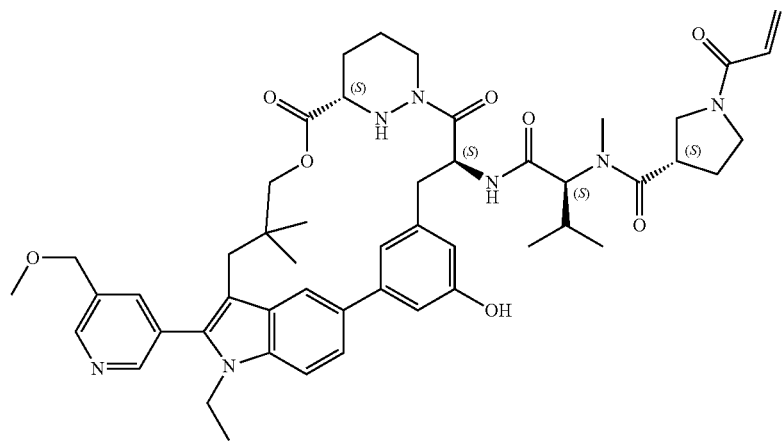 |
| A84 | 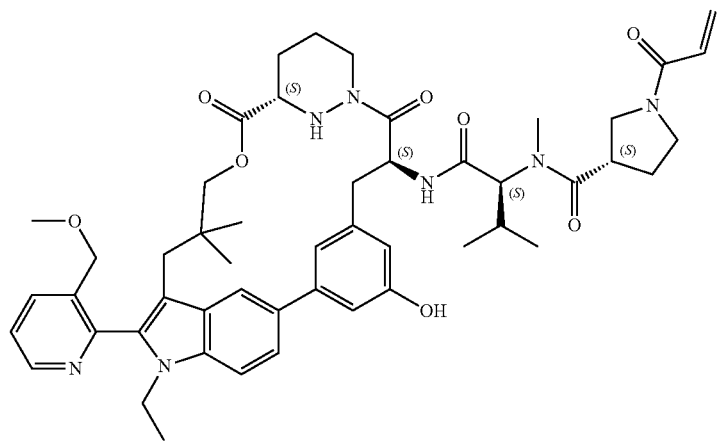 |

TABLE 1-continued
Certain Compounds of the Present Invention
| Ex# | Structure |
|---|---|
| A85 | 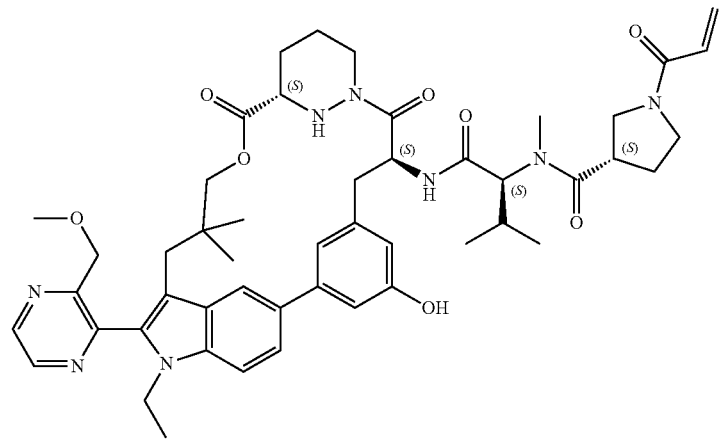 |
| A86 | 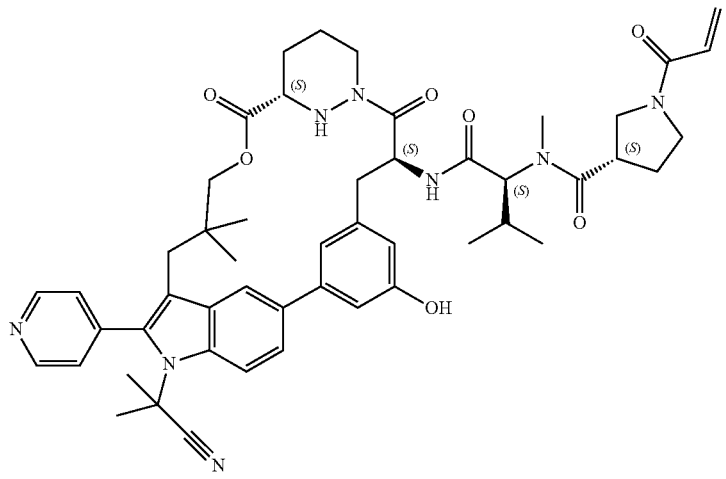 |
| A87 | 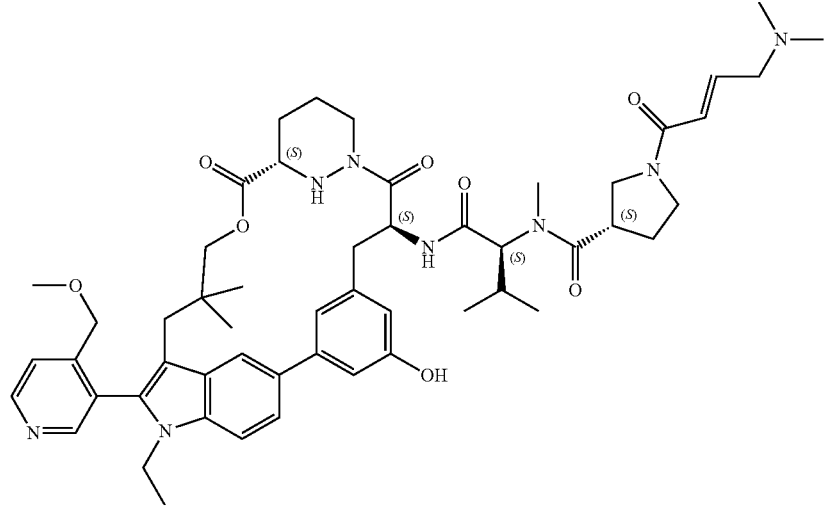 |

TABLE 1-continued
Certain Compounds of the Present Invention
| Ex# | Structure |
|---|---|
| A88 | 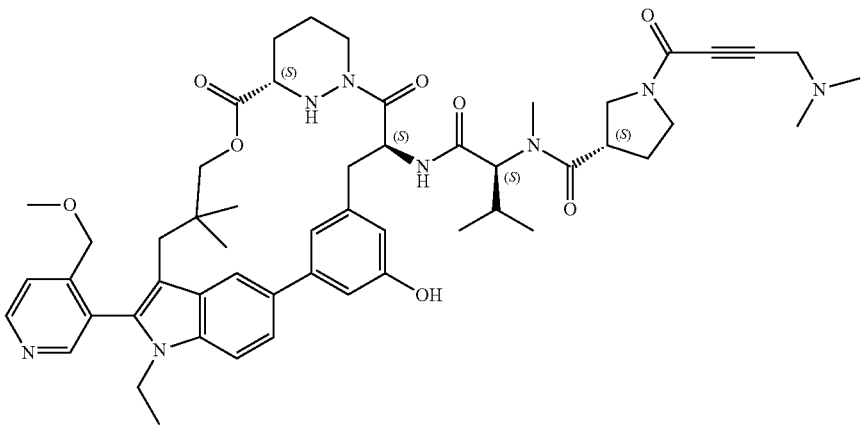 |
| A89 | 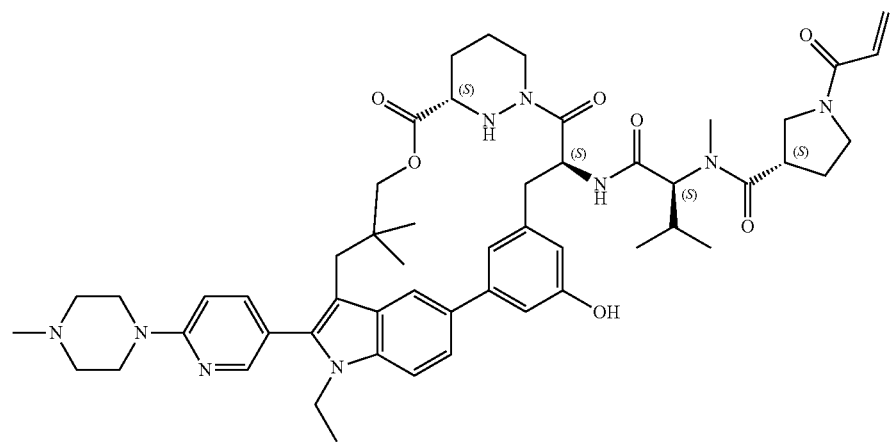 |
| A90 | 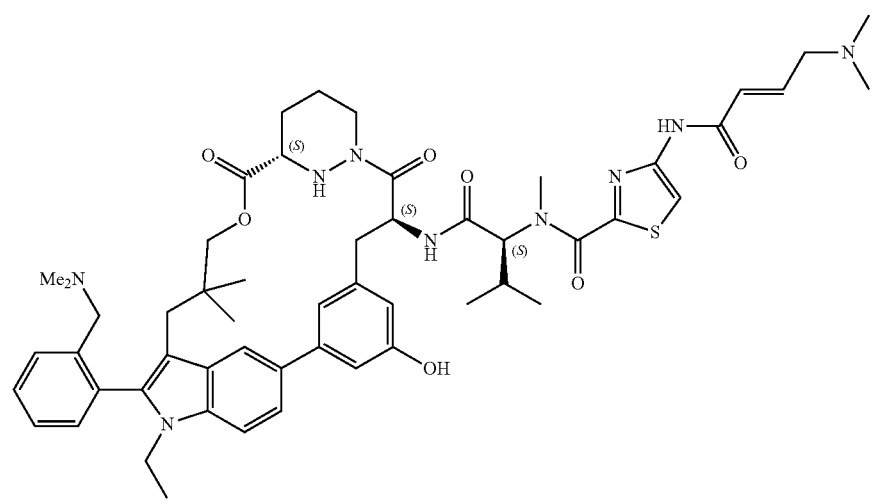 |

TABLE 1-continued
Certain Compounds of the Present Invention
| Ex# | Structure |
|---|---|
| A91 | 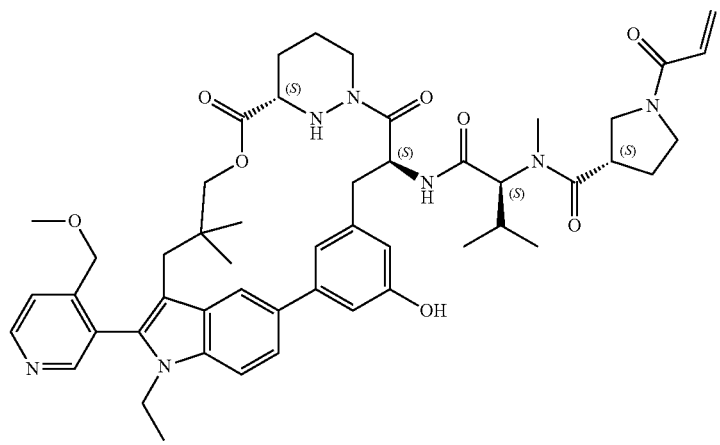 |
| A92 | 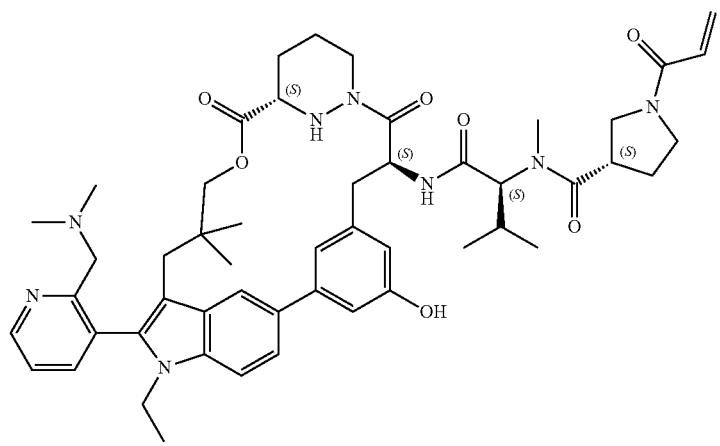 |
| A93 | 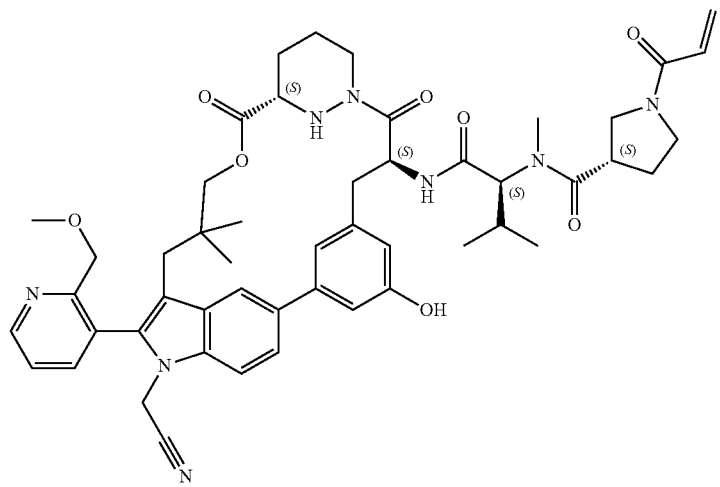 |

US 11,952,352 B2
131                                                                      132
TABLE 1-continued
Certain Compounds of the Present Invention
| Ex# | Structure |
|-----|-----------|
| A94 | 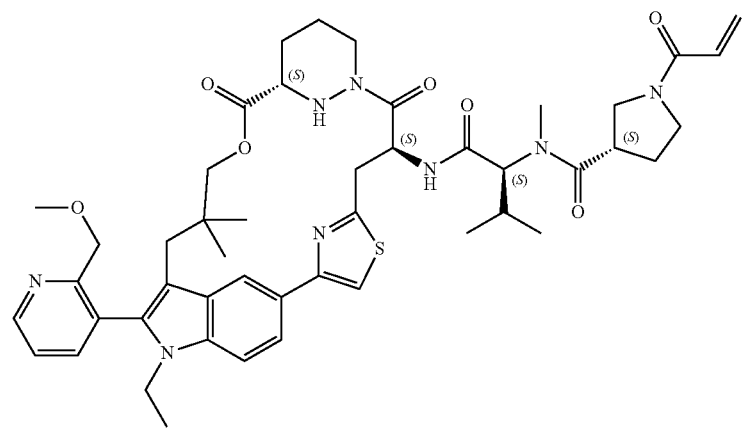 |
| A95 | 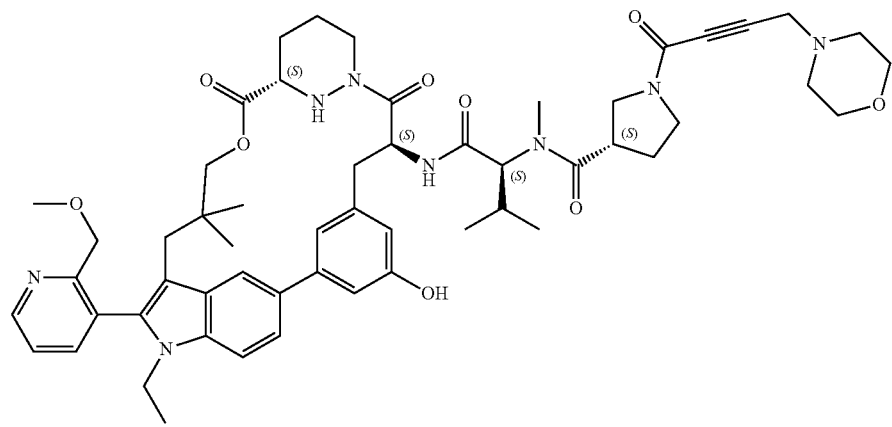 |
| A96 | 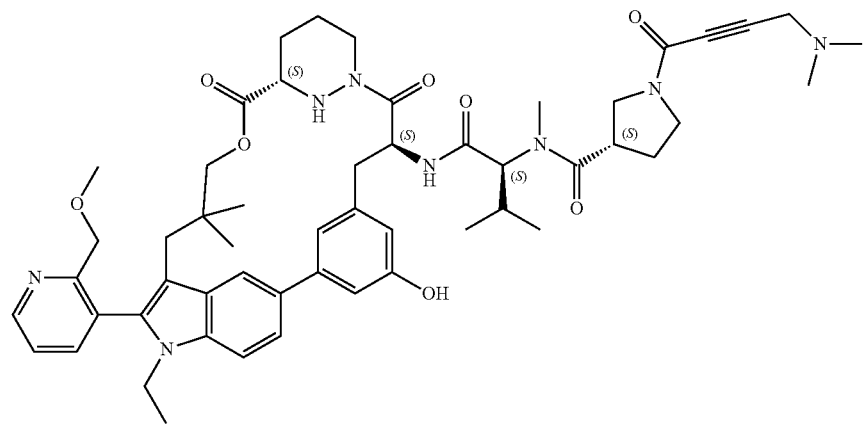 |

TABLE 1-continued
Certain Compounds of the Present Invention
| Ex# | Structure |
|---|---|
| A97 | 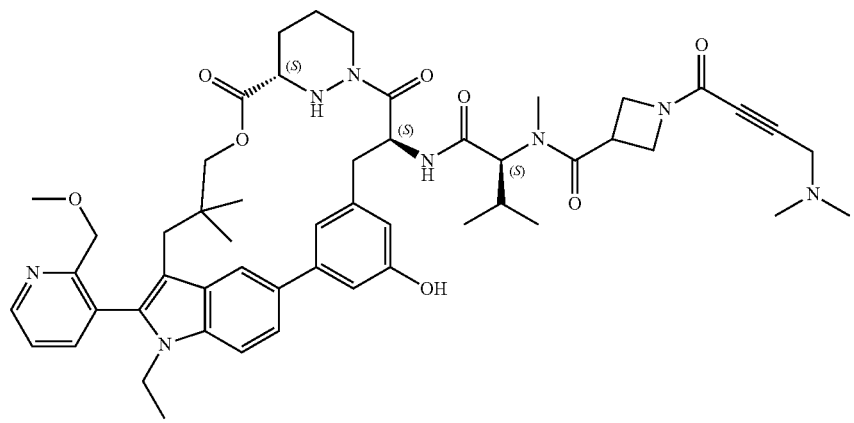 |
| A98 | 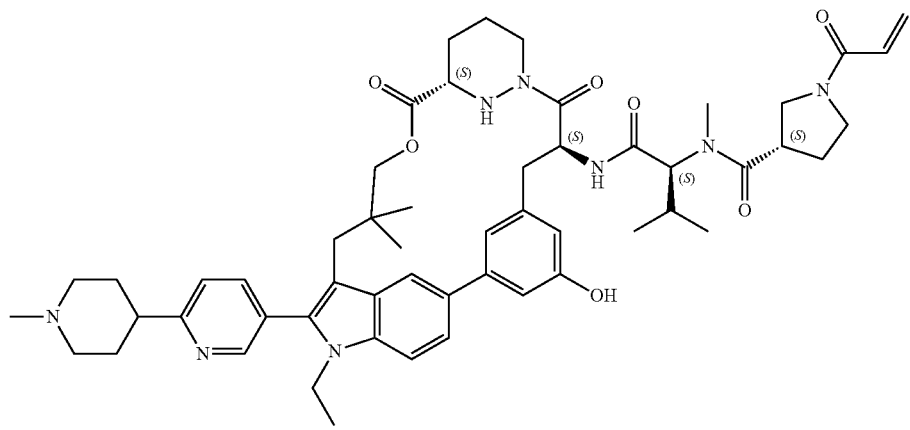 |
| A99 | 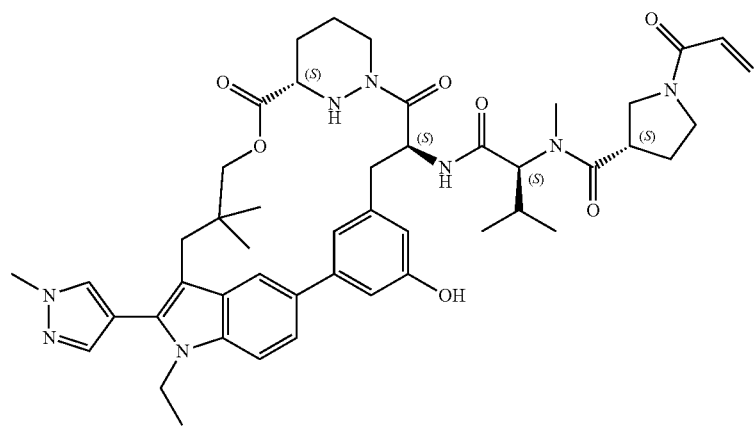 |

TABLE 1-continued
Certain Compounds of the Present Invention
| Ex# | Structure |
|---|---|
| A100 | 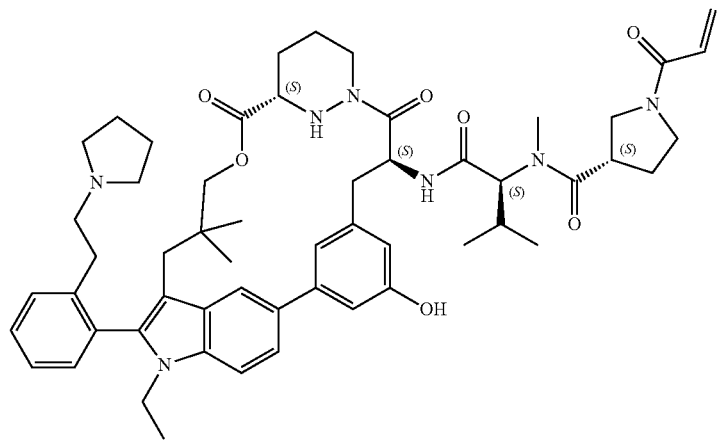 |
| A101 | 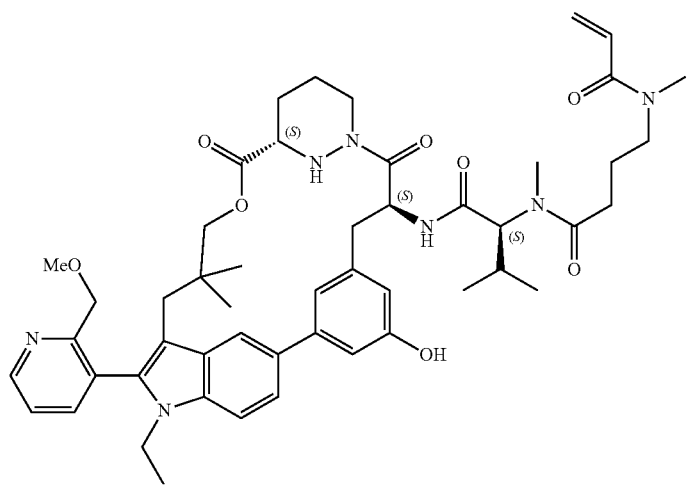 |
| A102 | 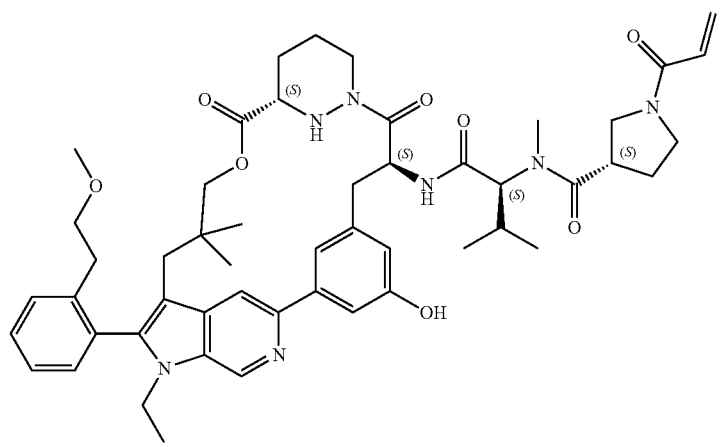 |

TABLE 1-continued
Certain Compounds of the Present Invention
| Ex# | Structure |
|---|---|
| A103 | 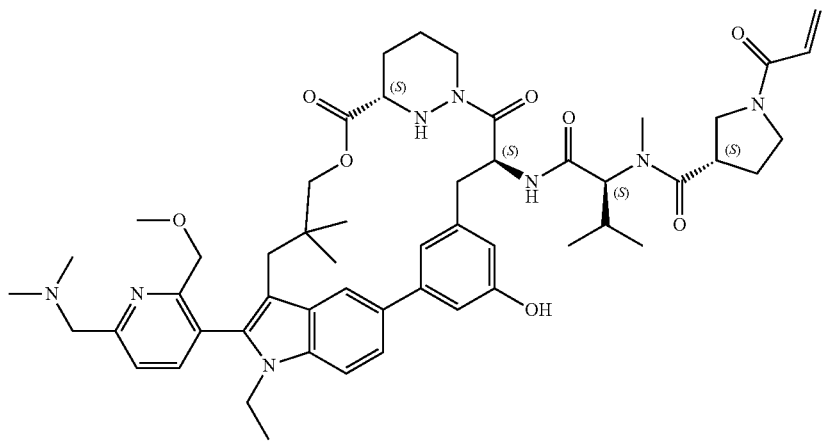 |
| A104 | 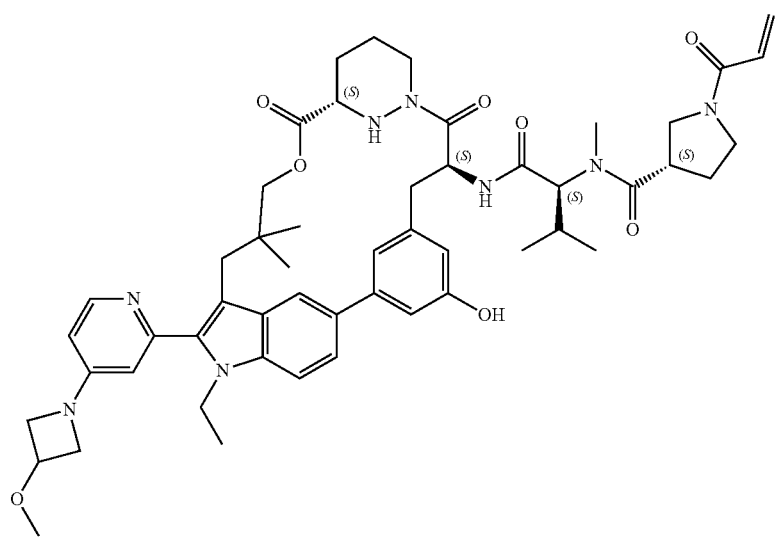 |
| A105 | 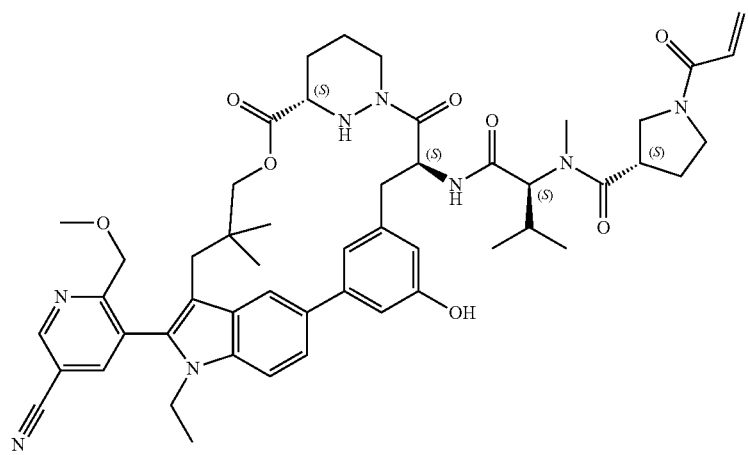 |

TABLE 1-continued
Certain Compounds of the Present Invention
| Ex# | Structure |
|---|---|
| A106 | 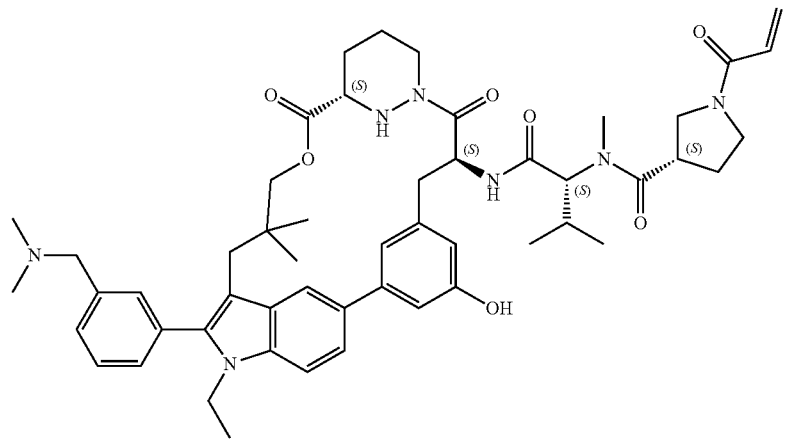 |
| A107 | 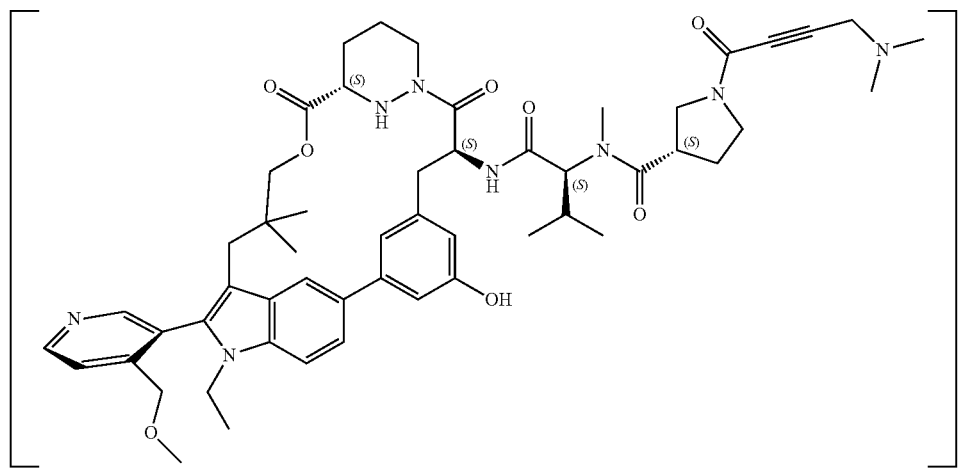 |
| A108 | 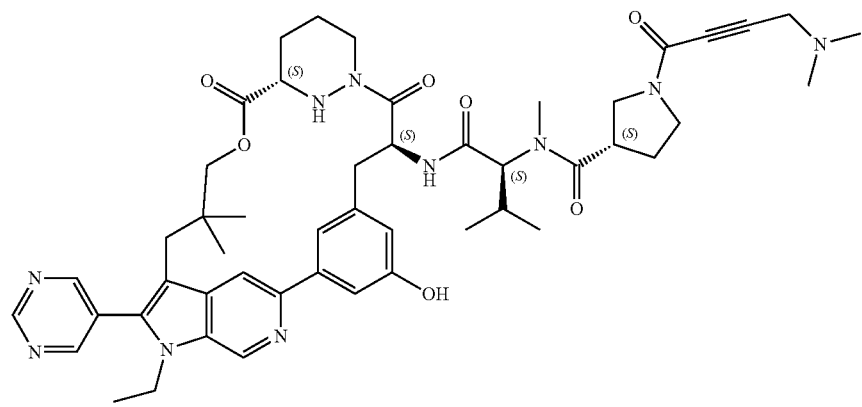 |

TABLE 1-continued
Certain Compounds of the Present Invention
| Ex# | Structure |
|---|---|
| A109 | 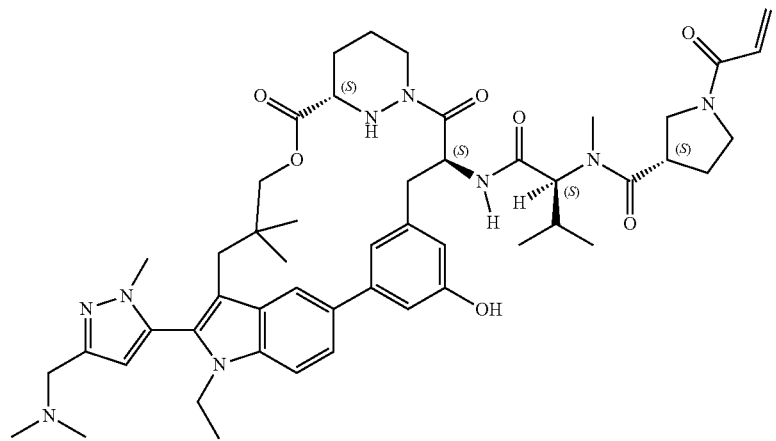 |
| A110 | 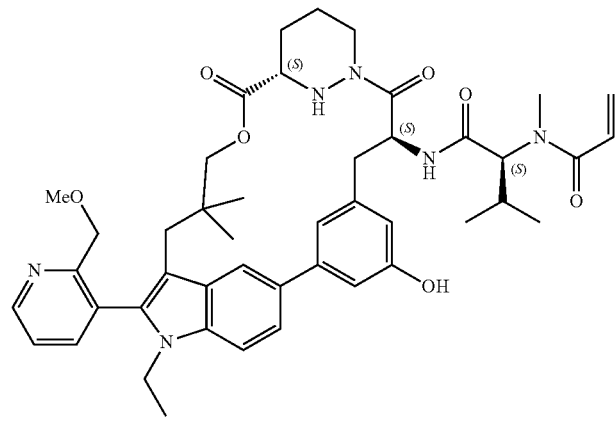 |
| A111 | 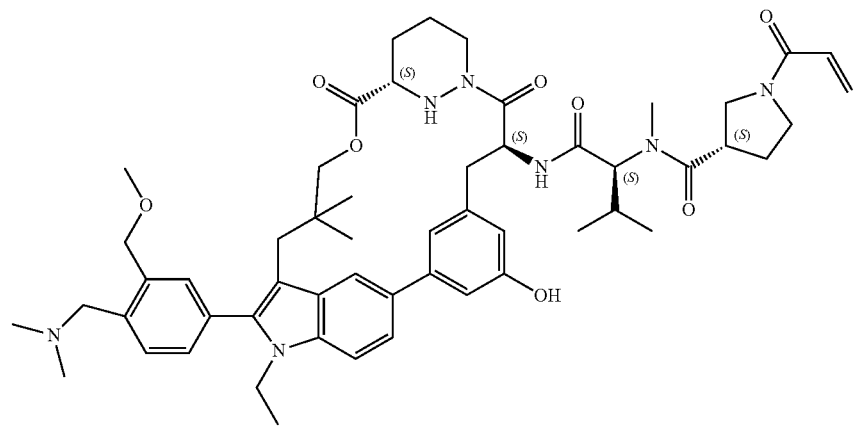 |

TABLE 1-continued
Certain Compounds of the Present Invention
| Ex# | Structure |
|---|---|
| A112 | 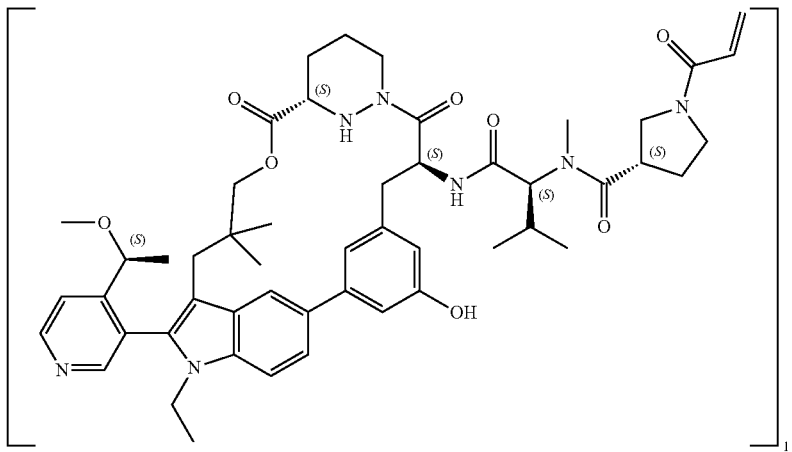 |
| A113 | 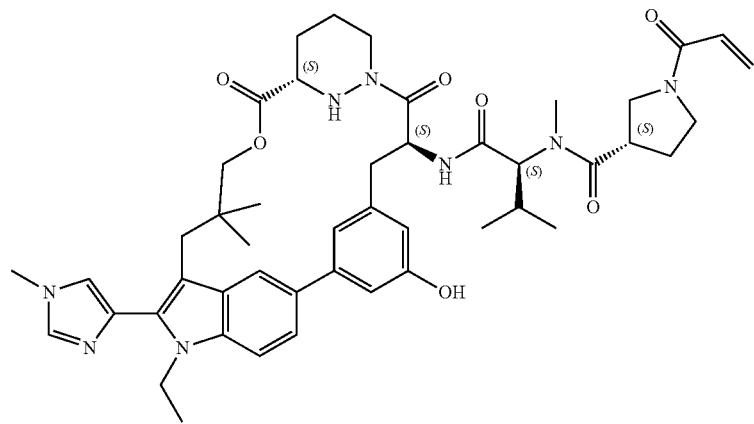 |
| A114 | 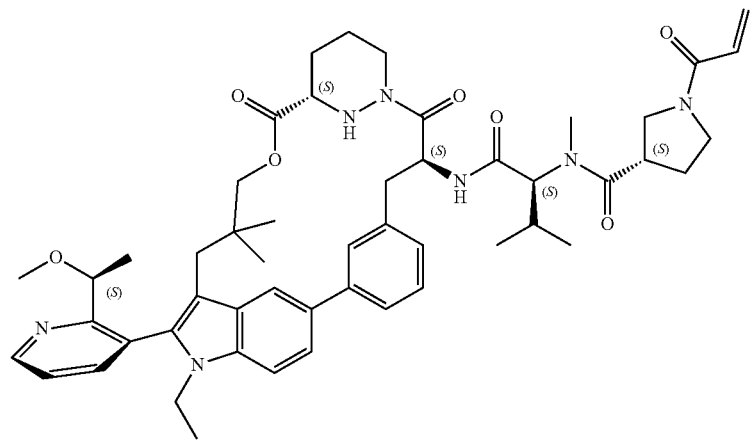 |

TABLE 1-continued
Certain Compounds of the Present Invention
| Ex# | Structure |
|---|---|
| A115 | 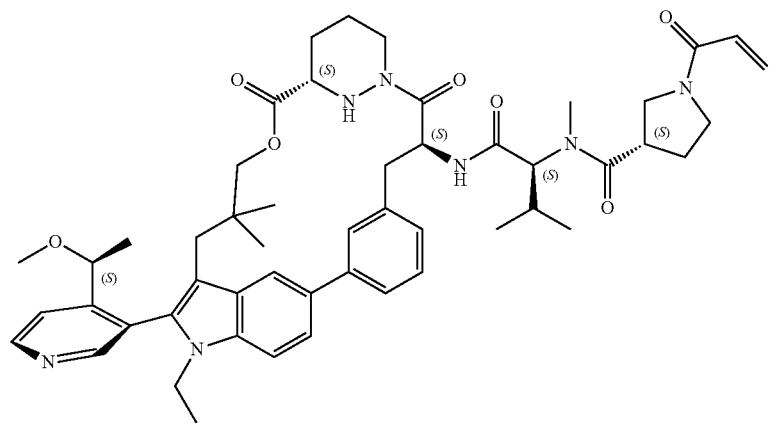 |
| A116 | 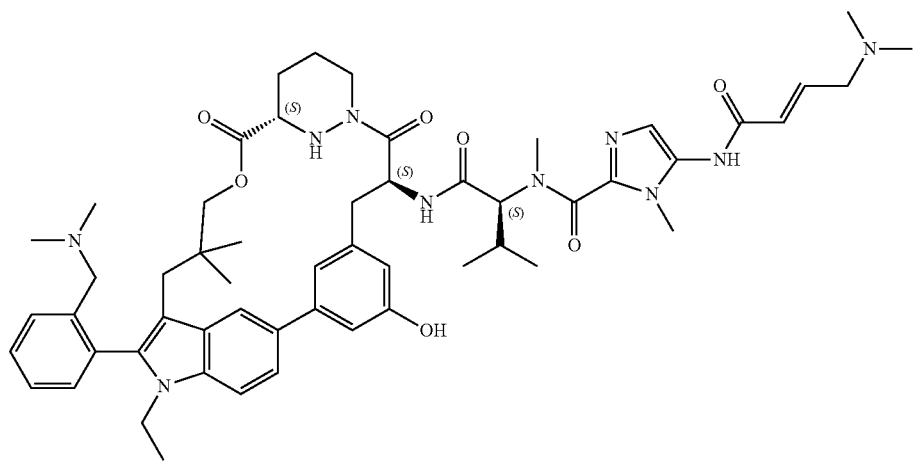 |
| A117 | 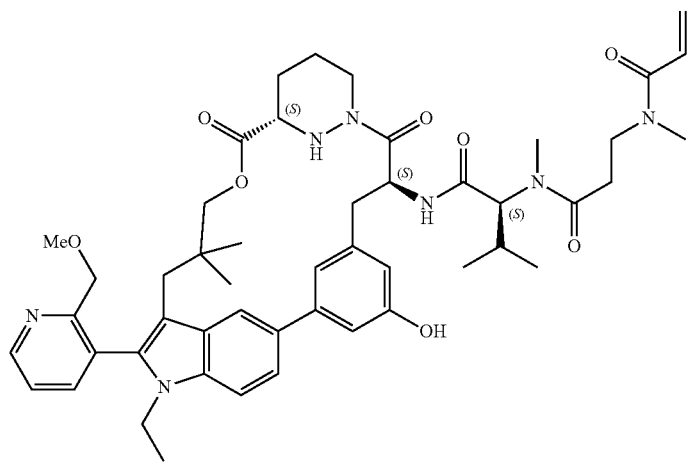 |

US 11,952,352 B2
147 148
TABLE 1-continued
Certain Compounds of the Present Invention
| Ex# | Structure |
|---|---|
| A118 | 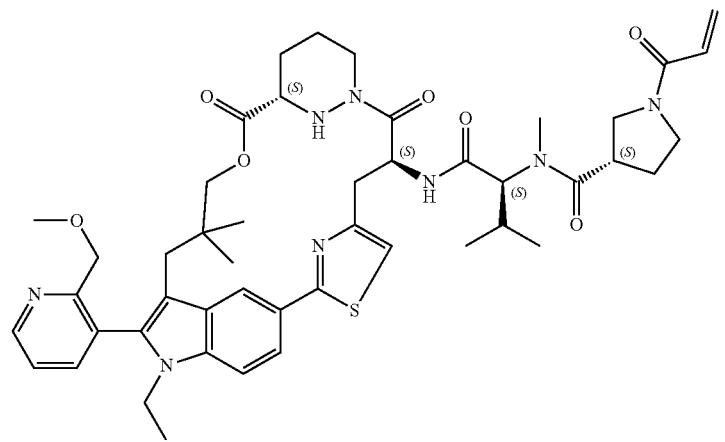 |
| A119 | 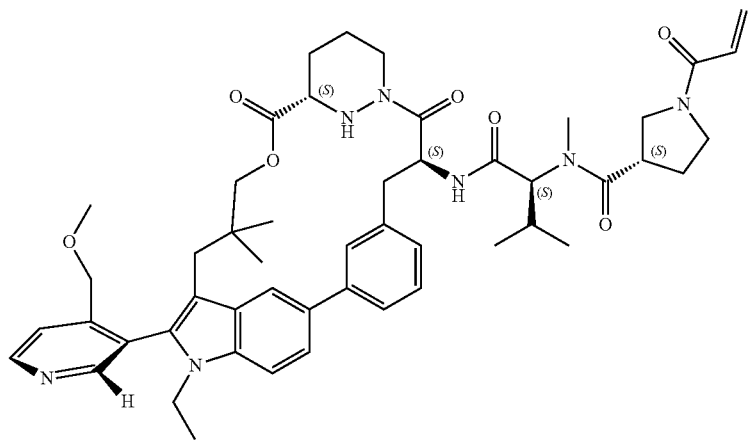 |
| A120 | 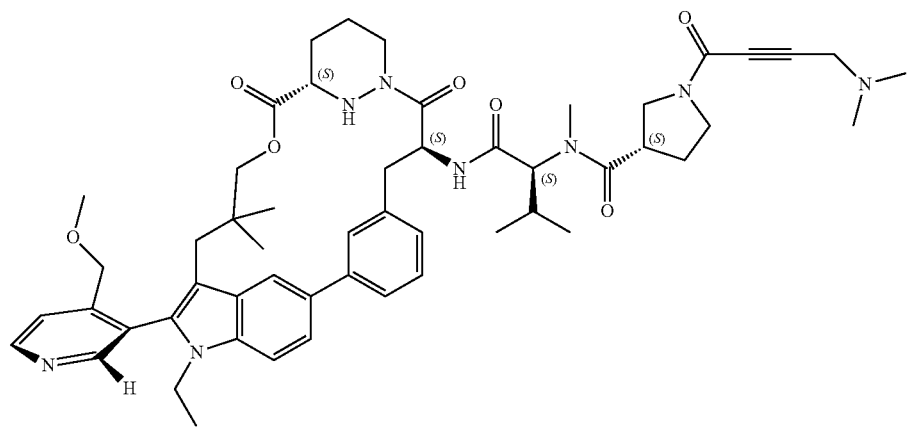 |

TABLE 1-continued
Certain Compounds of the Present Invention
| Ex# | Structure |
|---|---|
| A121 | 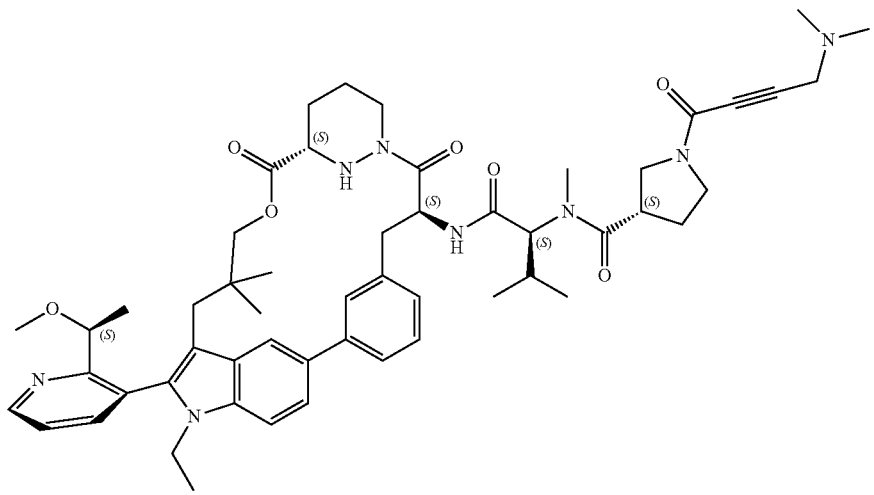 |
| A122 | 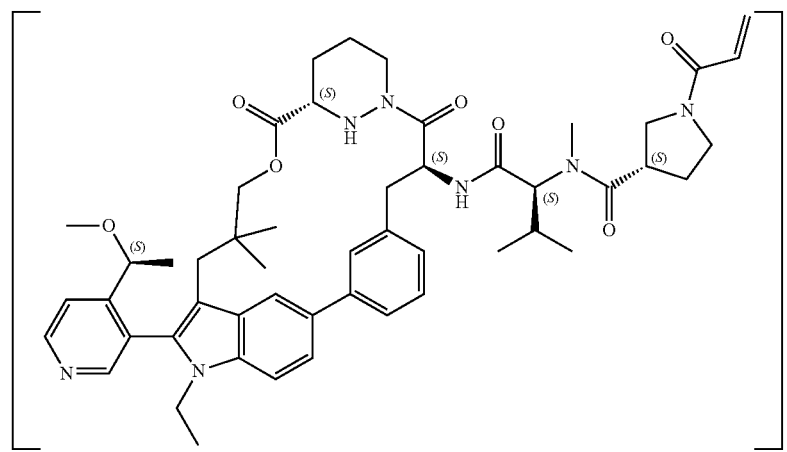 |
| A123 | 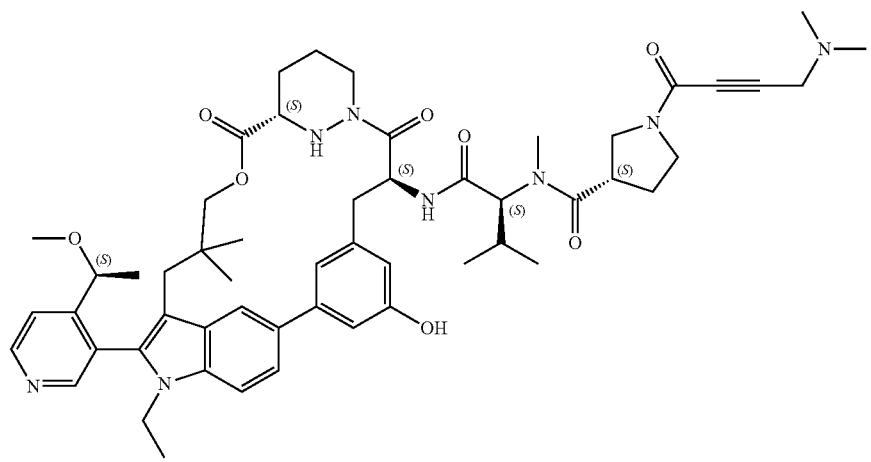 |

TABLE 1-continued
Certain Compounds of the Present Invention
| Ex# | Structure |
|---|---|
| A124 | 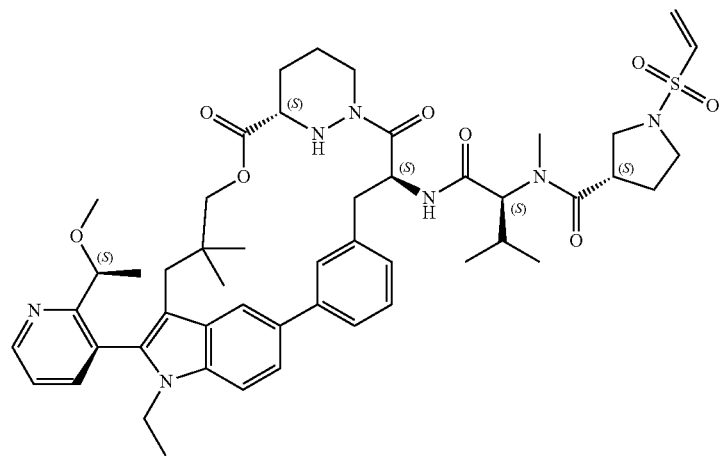 |
| A125 | 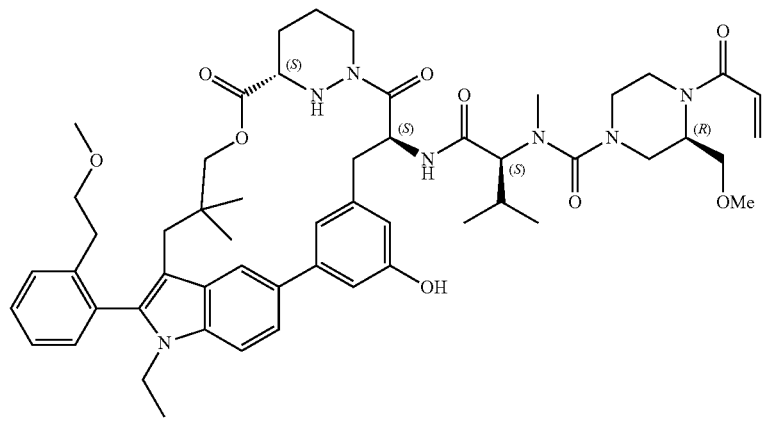 |
| A126 | 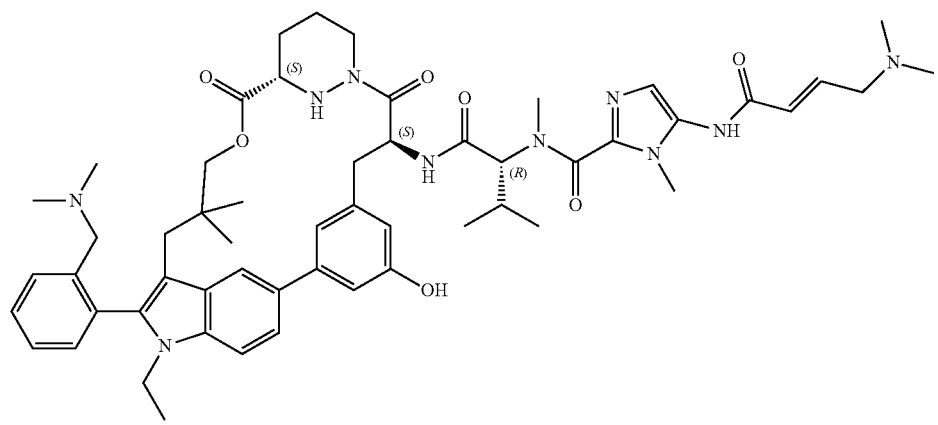 |

TABLE 1-continued
Certain Compounds of the Present Invention
| Ex# | Structure |
|---|---|
| A127 | 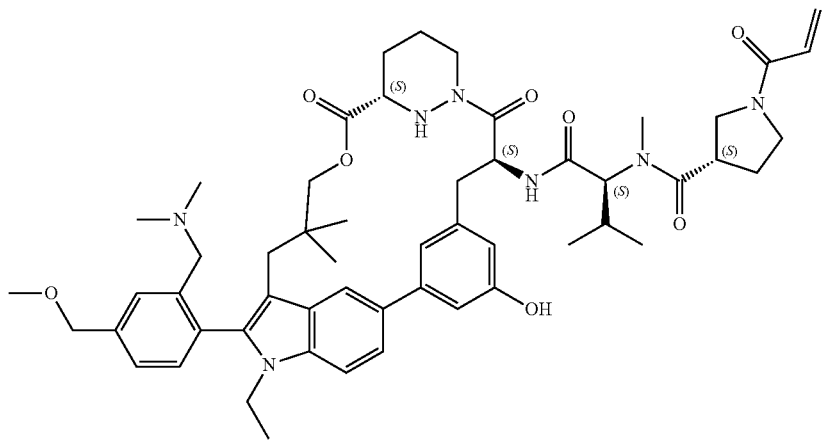 |
| A128 | 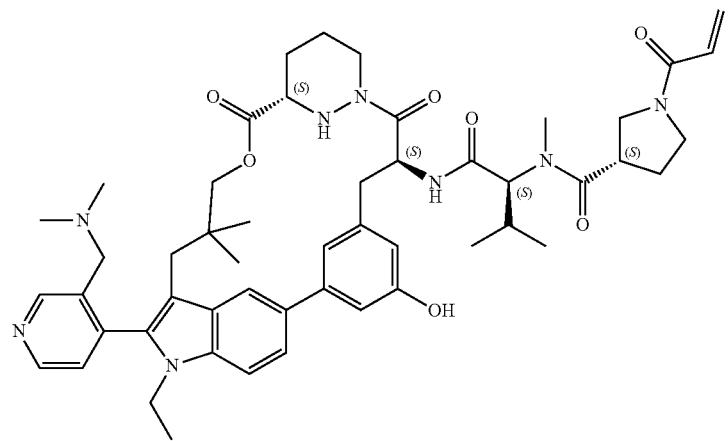 |
| A129 | 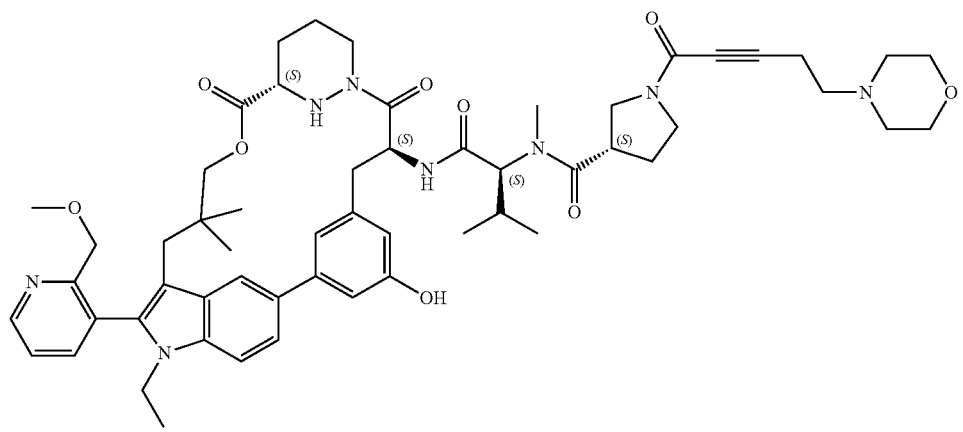 |

TABLE 1-continued

Certain Compounds of the Present Invention

| Ex# | Structure |
|---|---|
| A130 | 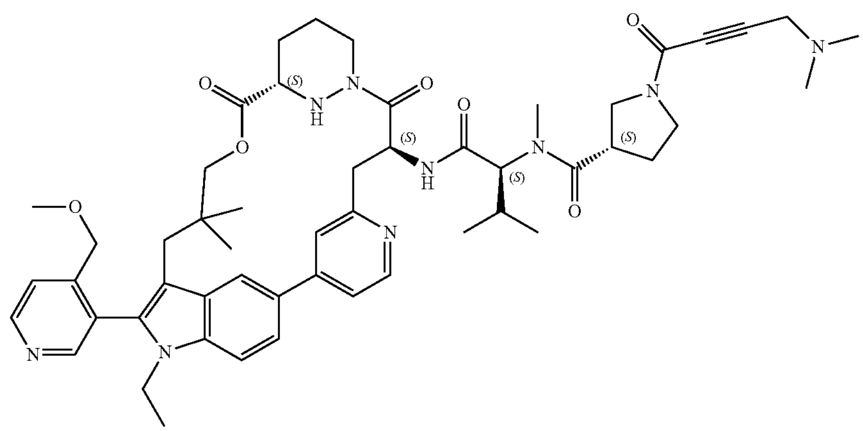 |
| A131 | 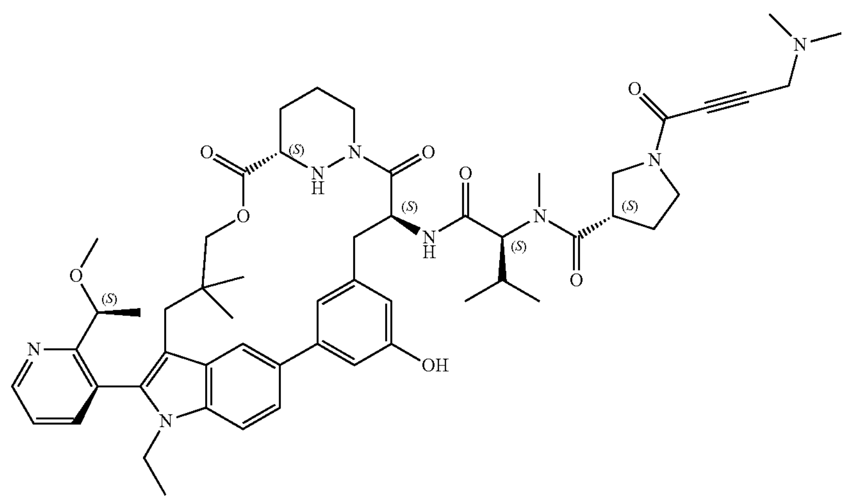 |
| A132 | 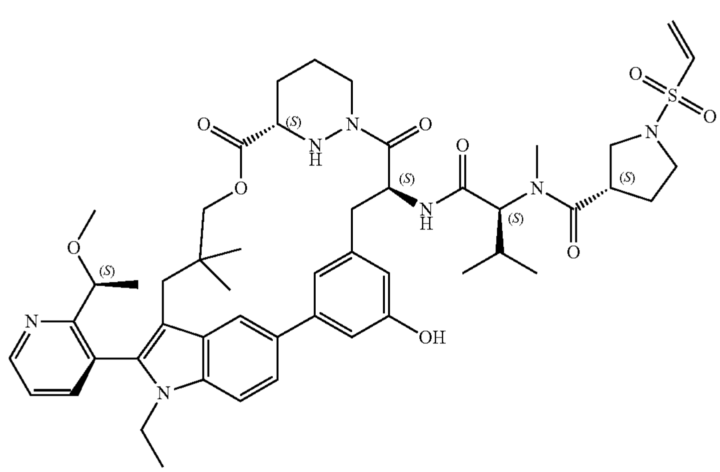 |

… TABLE 1-continued
Certain Compounds of the Present Invention
| Ex# | Structure |
|---|---|
| A133 | 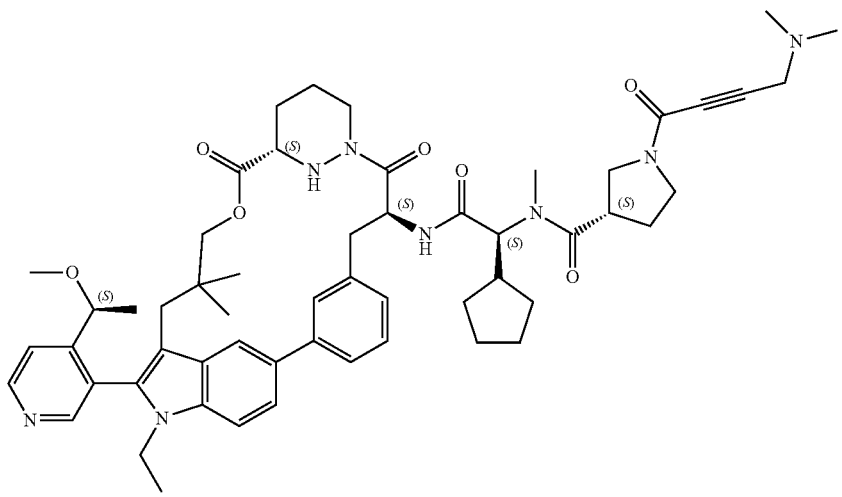 |
| A134 | 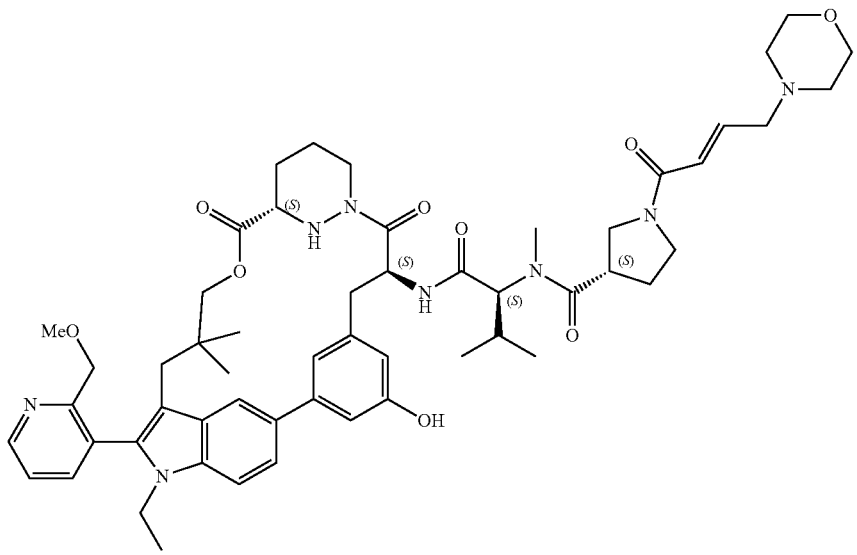 |
| A135 | 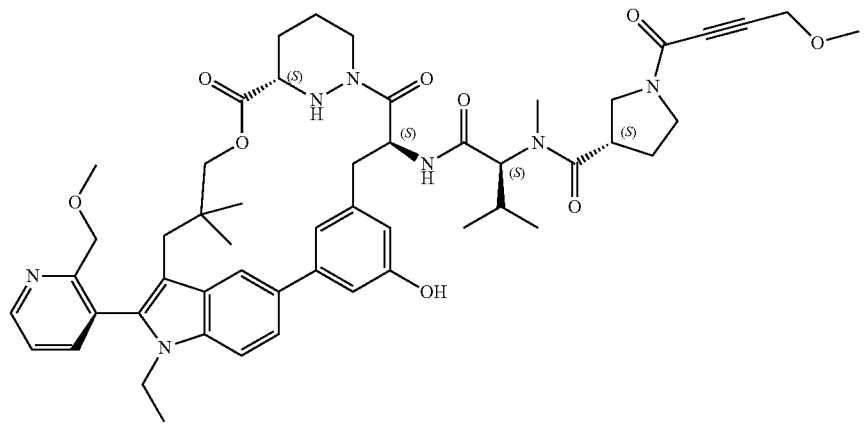 |

TABLE 1-continued
Certain Compounds of the Present Invention
| Ex# | Structure |
|---|---|
| A136 | 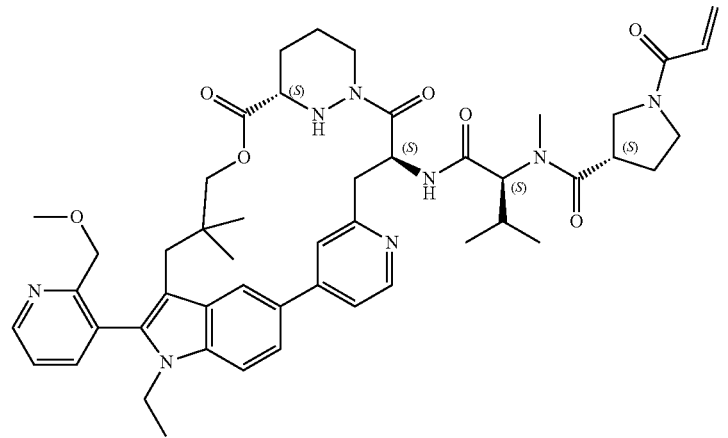 |
| A137 | 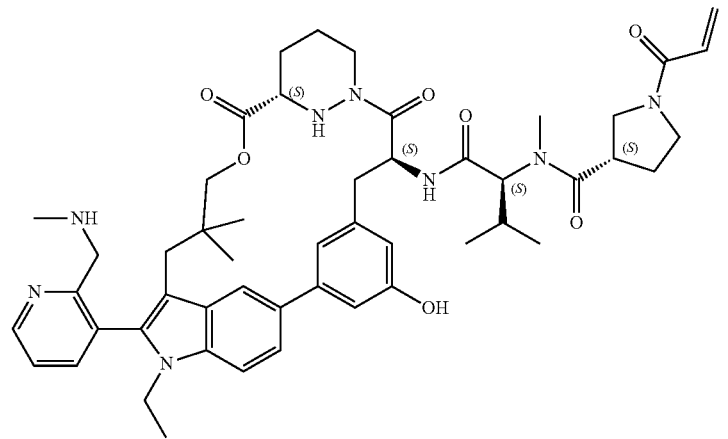 |
| A138 | 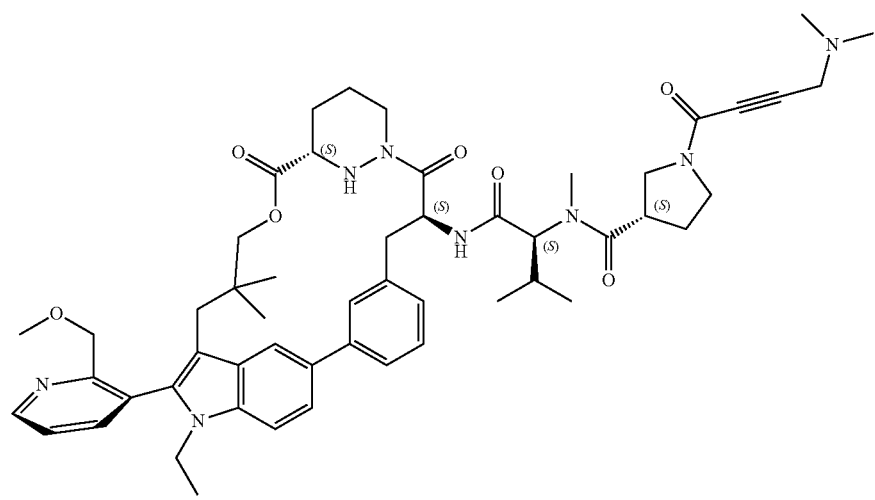 |

TABLE 1-continued
Certain Compounds of the Present Invention
| Ex# | Structure |
|---|---|
| A139 | 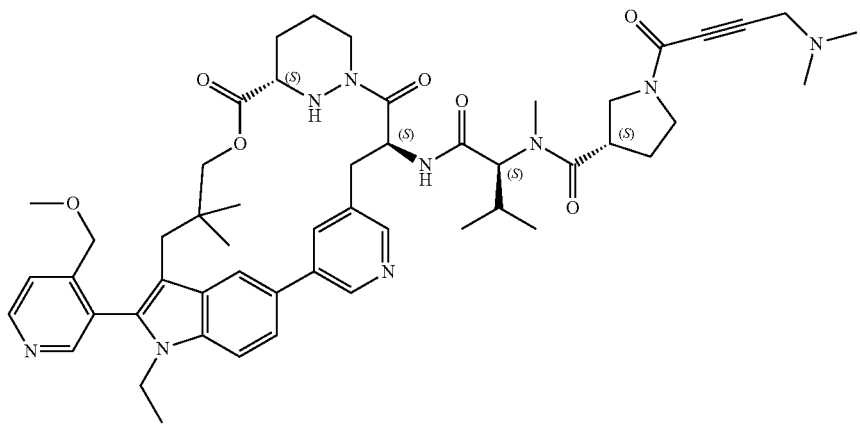 |
| A140 | 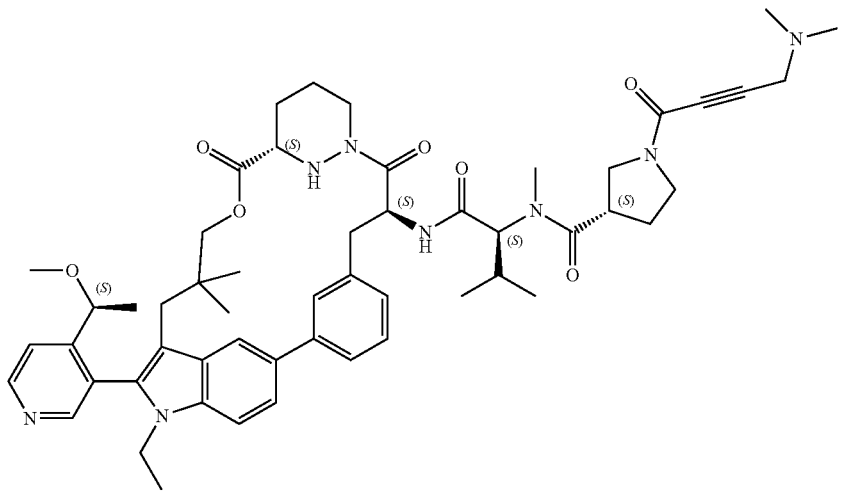 |
| A141 | 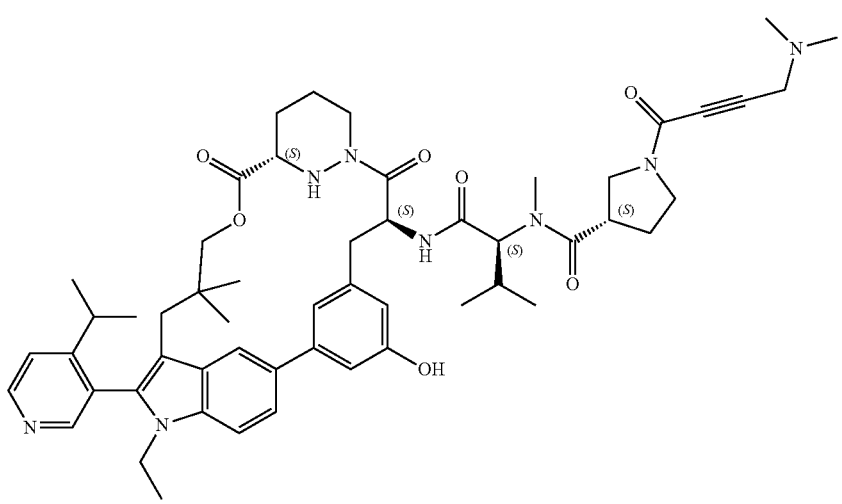 |

| Ex# | Structure |
|---|---|
| A142 | 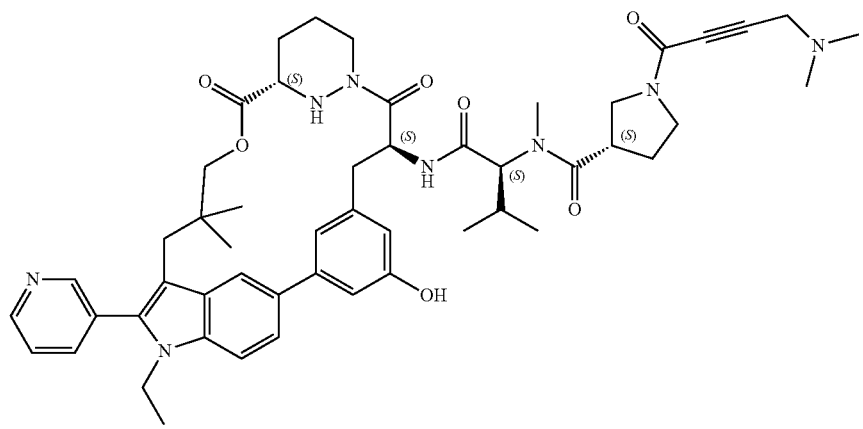 |
| A143 | 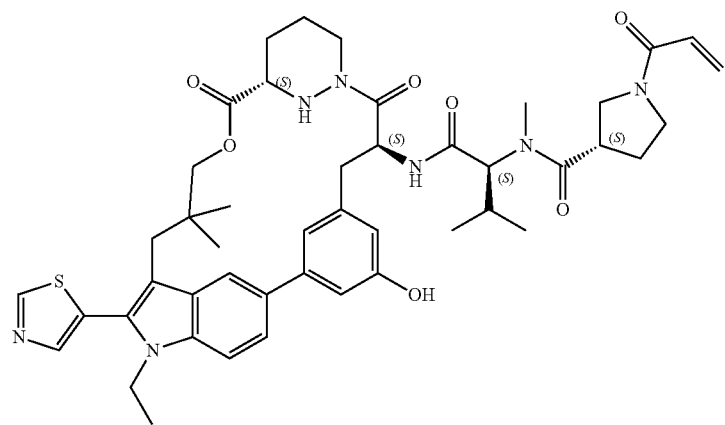 |
| A144 | 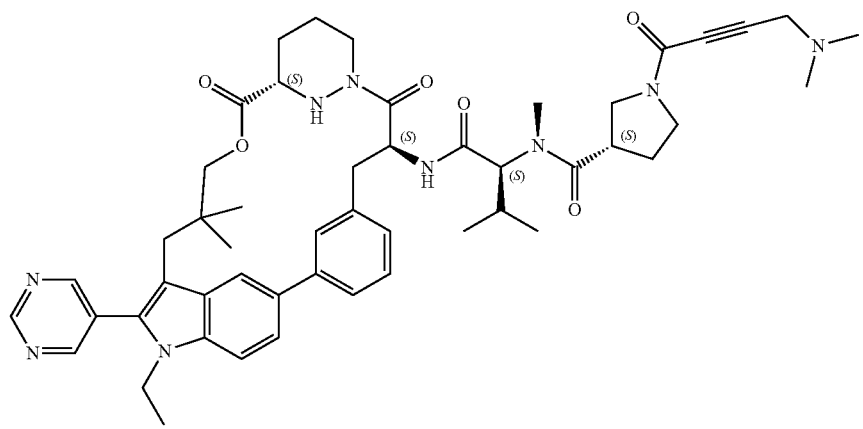 |

TABLE 1-continued

Certain Compounds of the Present Invention

| Ex# | Structure |
|---|---|
| A145 | 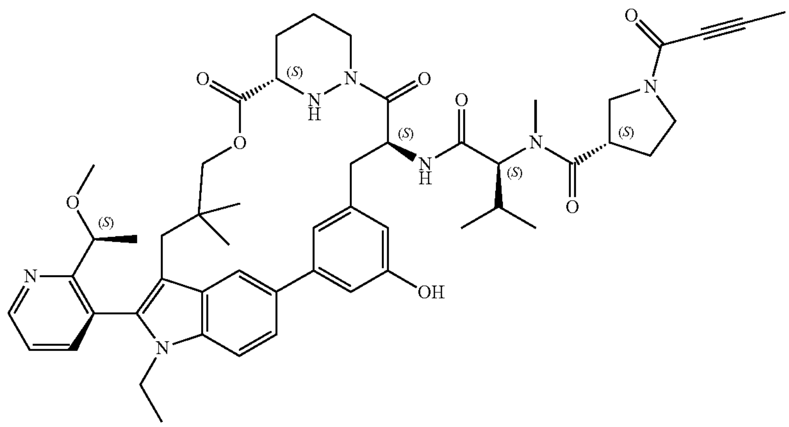 |
| A146 | 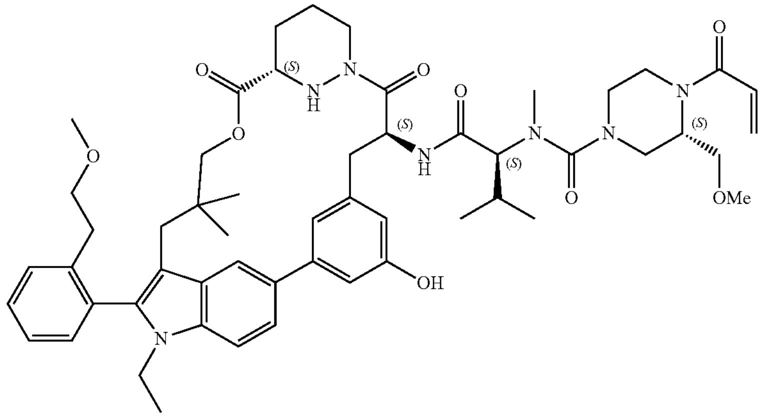 |
| A147 | 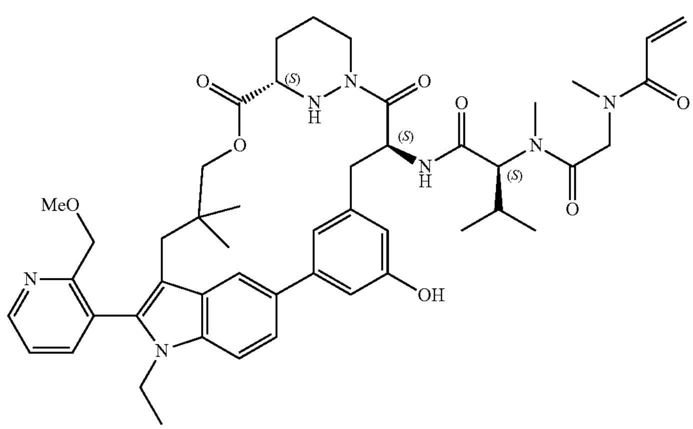 |

TABLE 1-continued

Certain Compounds of the Present Invention

| Ex# | Structure |
|---|---|
| A148 | 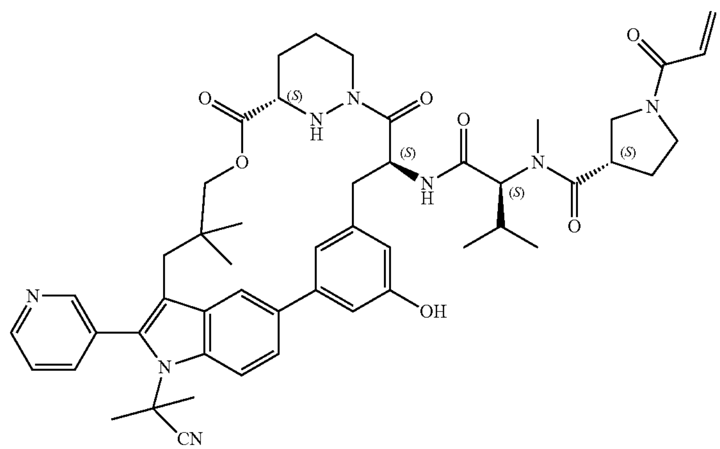 |
| A149 | 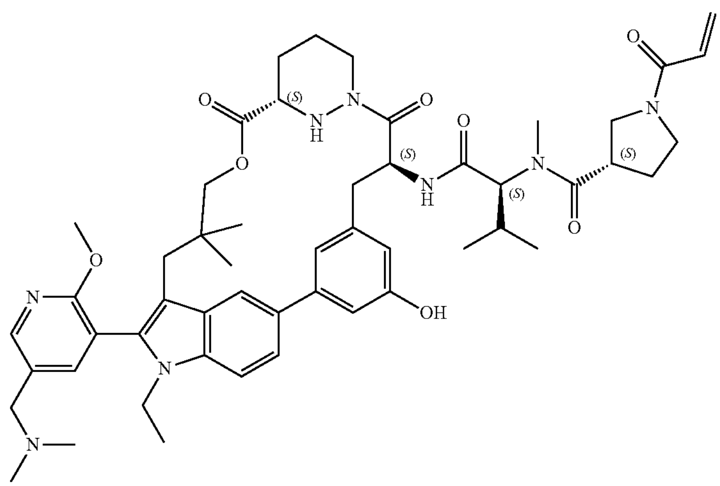 |
| A150 | 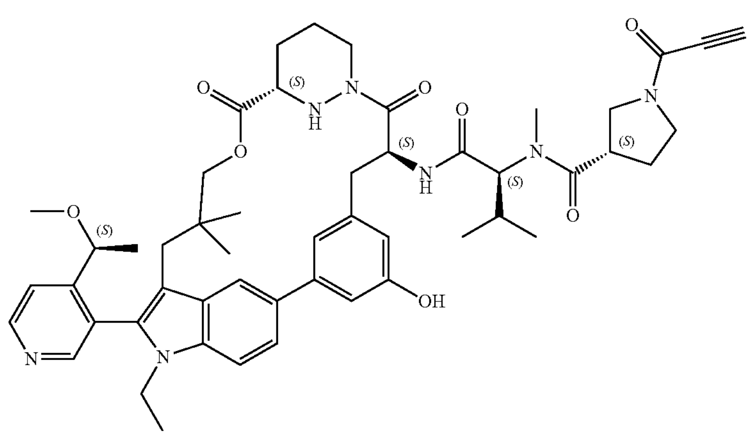 |

TABLE 1-continued

Certain Compounds of the Present Invention

| Ex# | Structure |
|---|---|
| A151 | 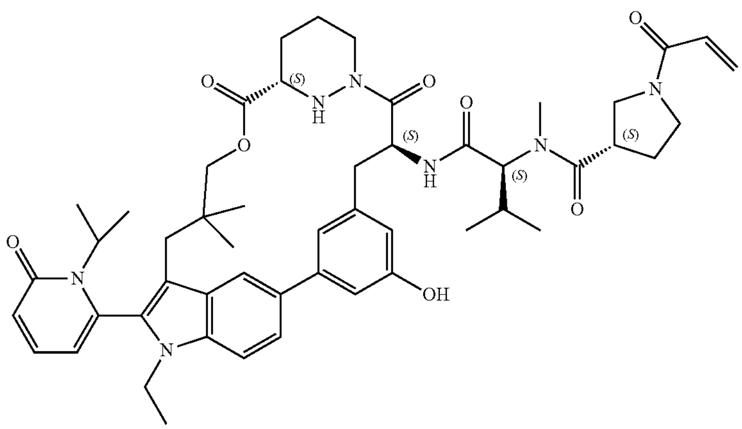 |
| A152 | 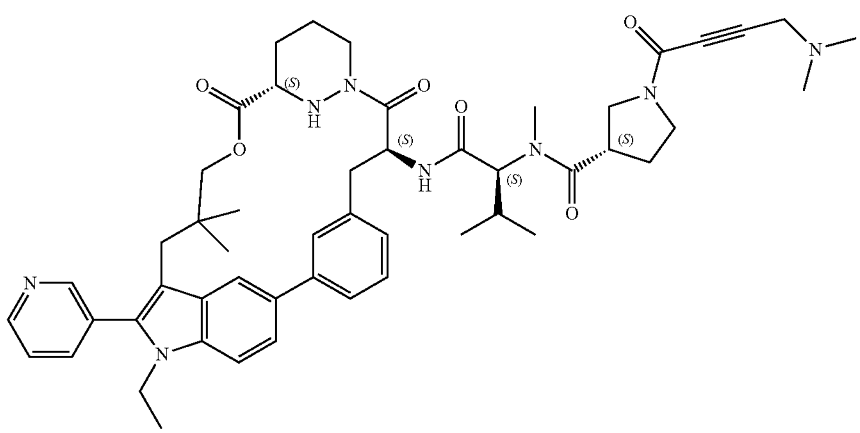 |
| A153 | 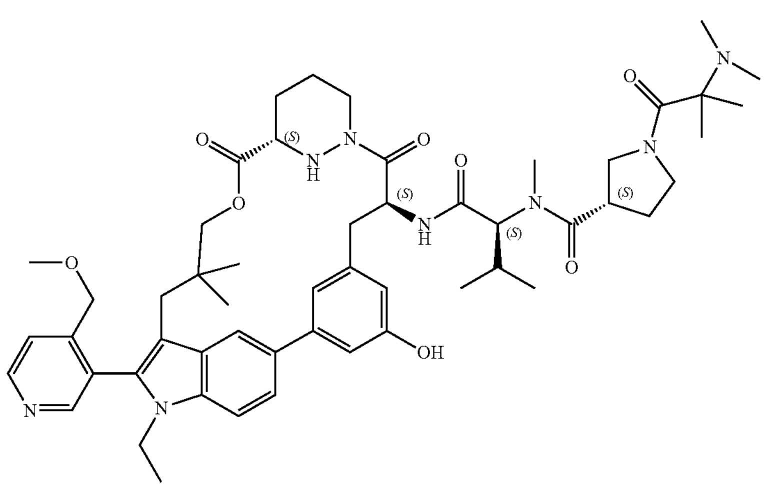 |

TABLE 1-continued
Certain Compounds of the Present Invention
| Ex# | Structure |
|---|---|
| A154 | 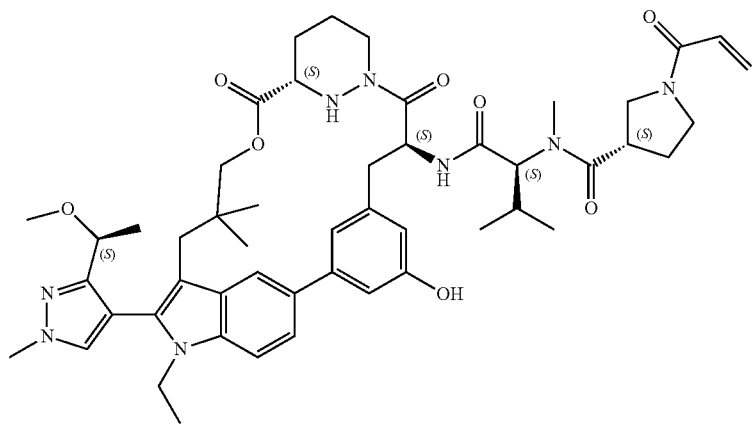 |
| A155 | 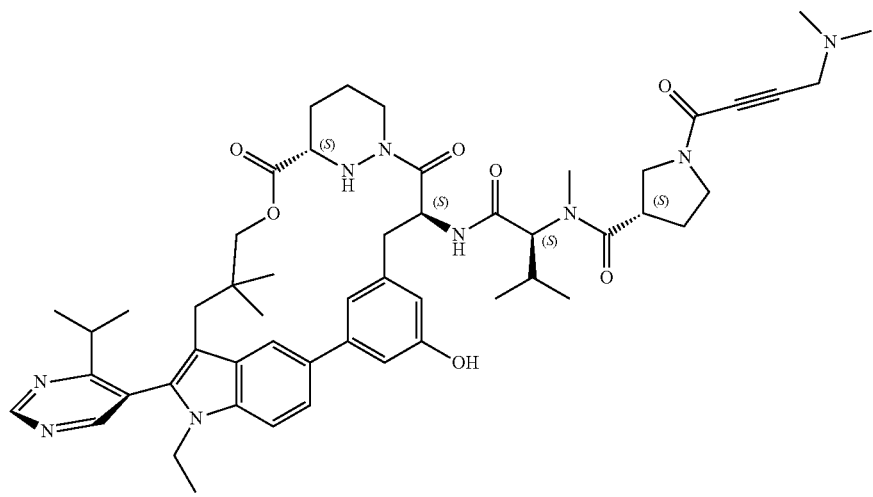 |
| A156 | 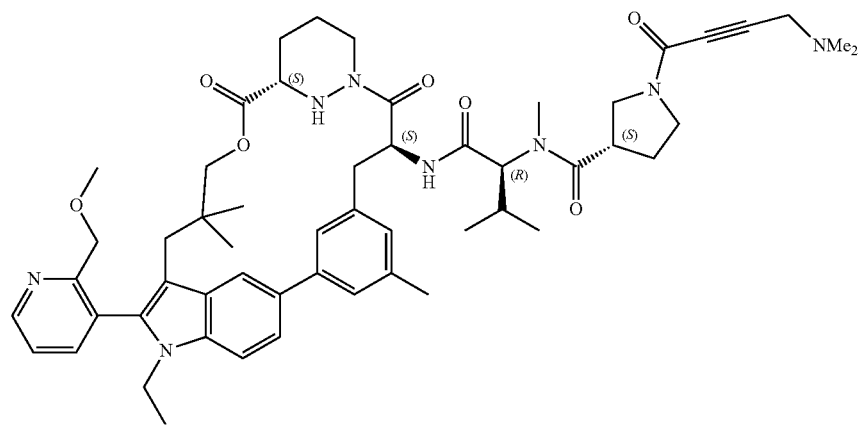 |

TABLE 1-continued
Certain Compounds of the Present Invention
| Ex# | Structure |
|---|---|
| A157 | 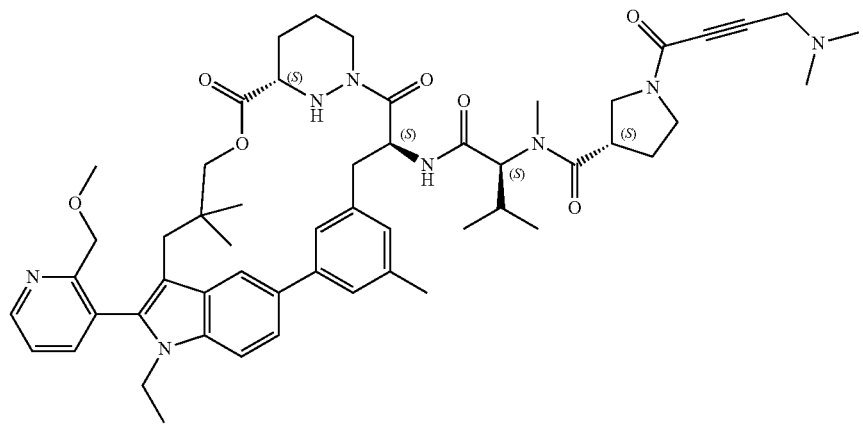 |
| A158 | 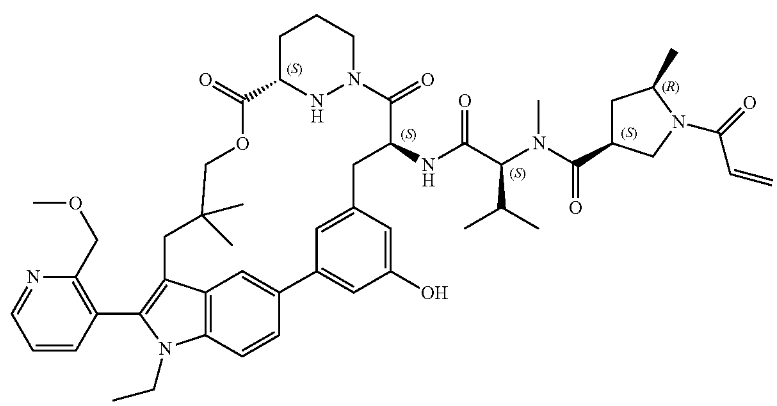 |
| A159 | 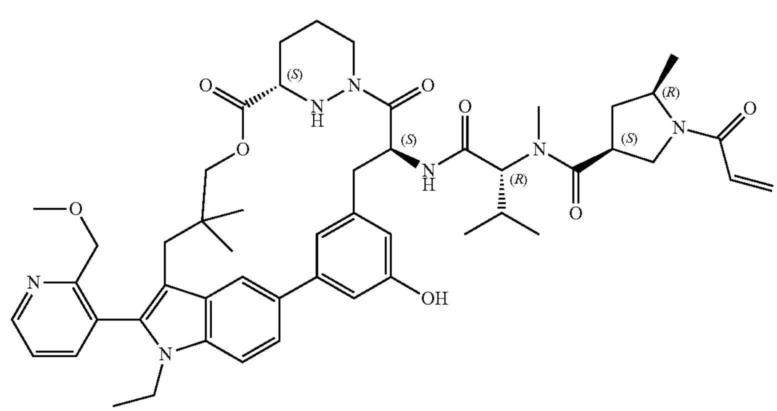 |

TABLE 1-continued
Certain Compounds of the Present Invention
| Ex# | Structure |
|---|---|
| A160 | 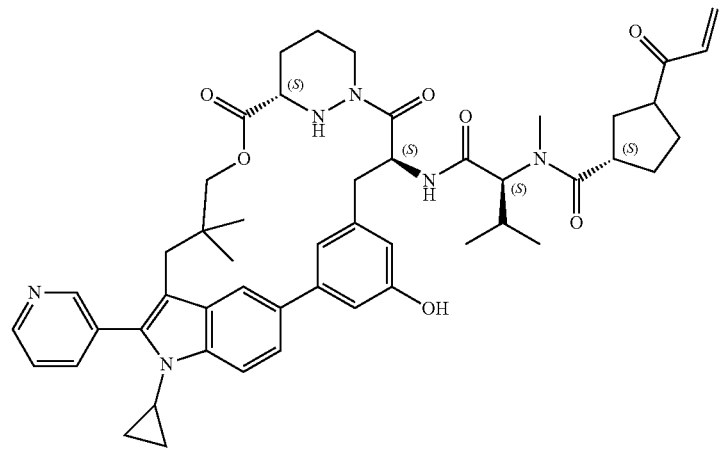 |
| A161 | 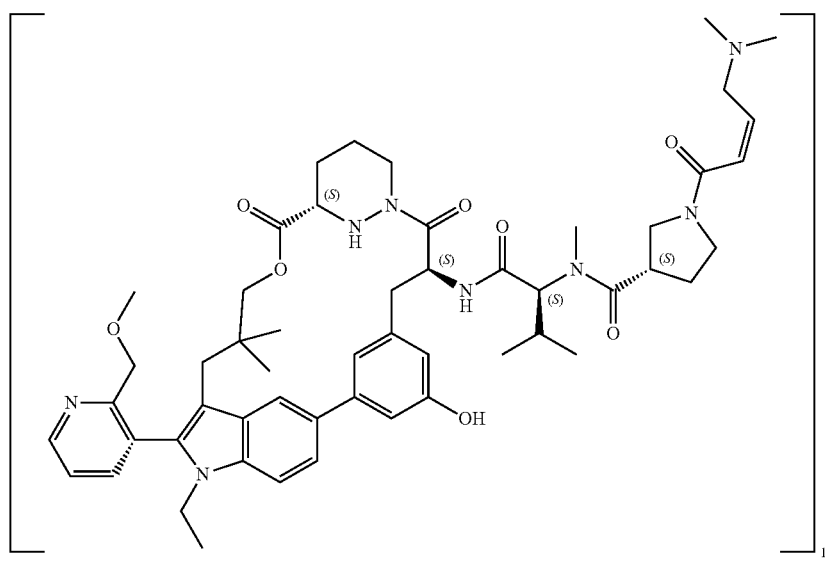 |
| A162 | 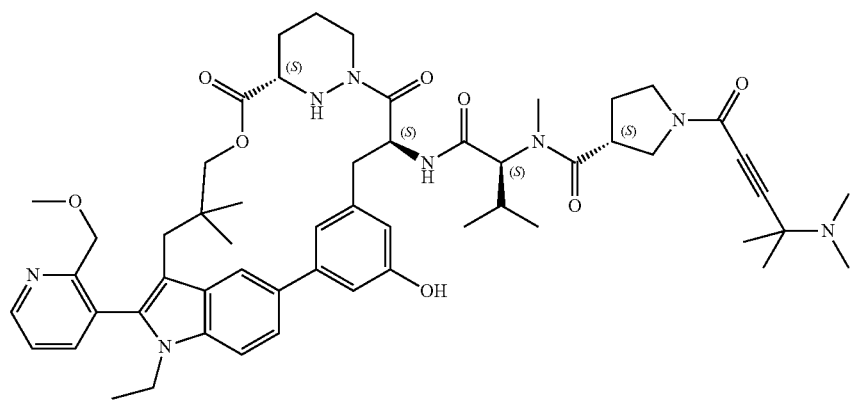 |

TABLE 1-continued
Certain Compounds of the Present Invention
| Ex# | Structure |
|---|---|
| A163 | 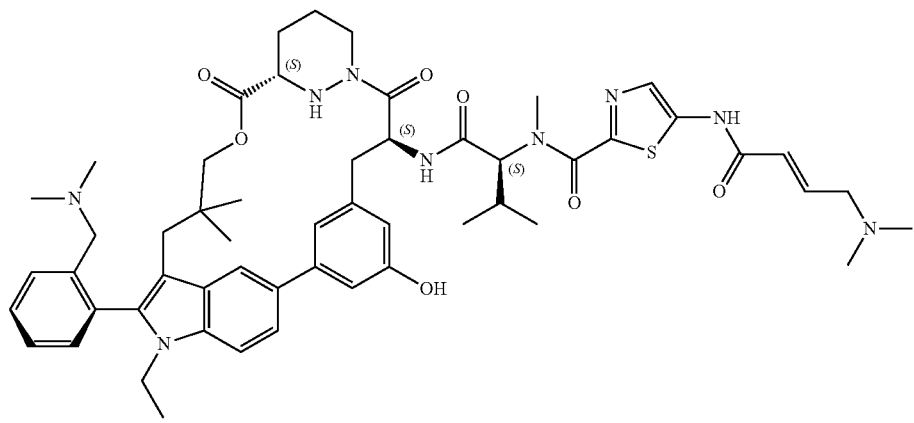 |
| A164 | 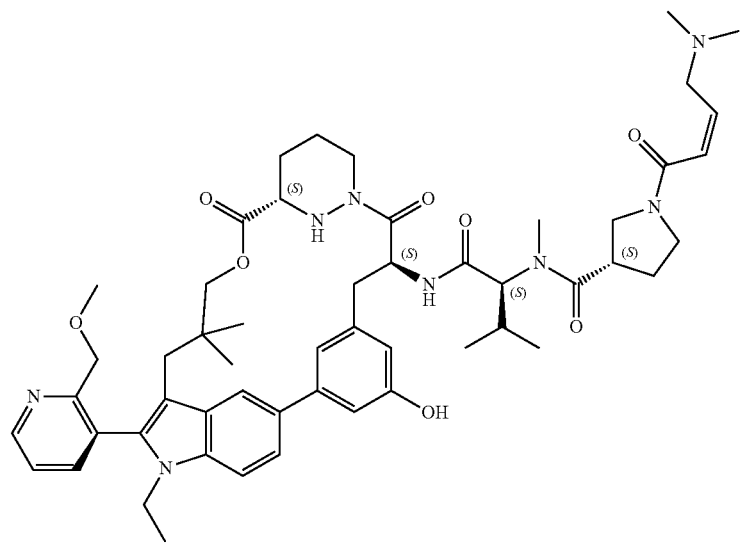 |
| A165 | 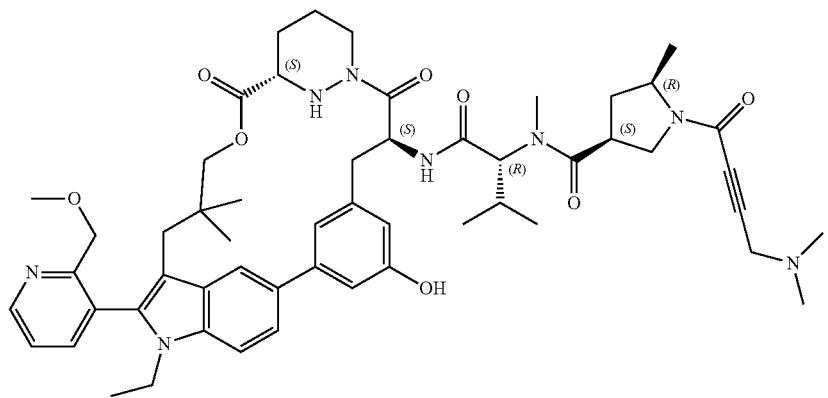 |

TABLE 1-continued
Certain Compounds of the Present Invention
| Ex# | Structure |
|---|---|
| A166 | 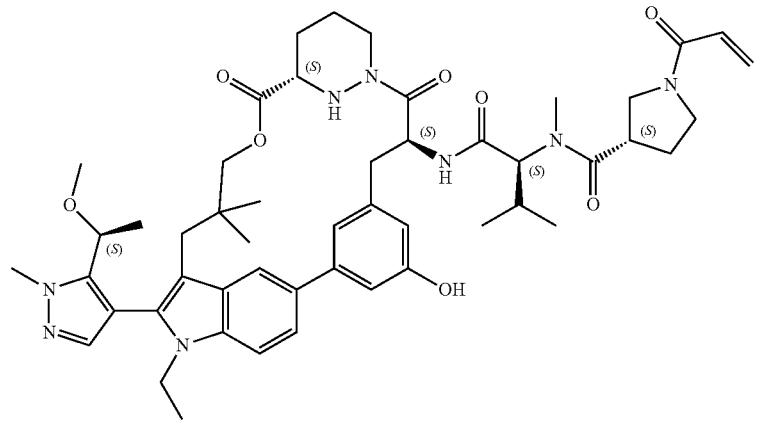 |
| A167 | 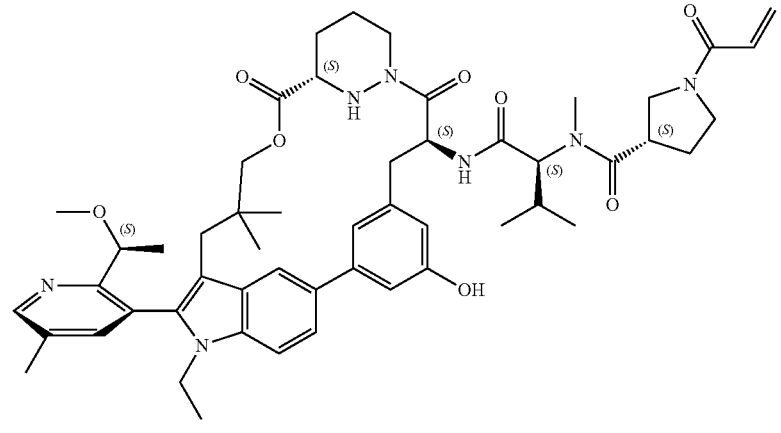 |
| A168 | 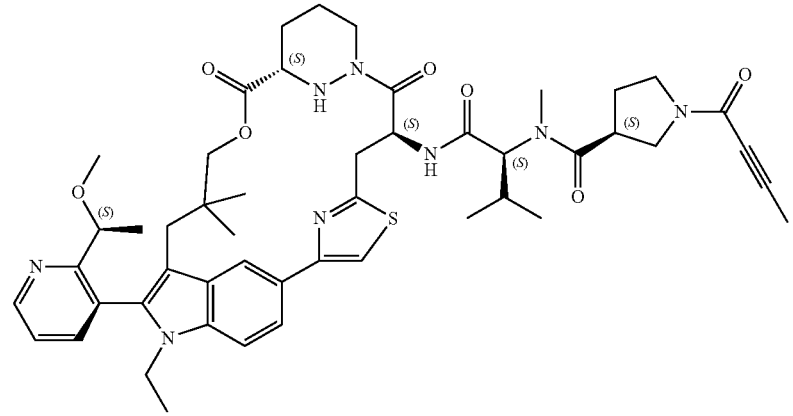 |

181 182
TABLE 1-continued
Certain Compounds of the Present Invention
| Ex# | Structure |
|---|---|
| A169 | 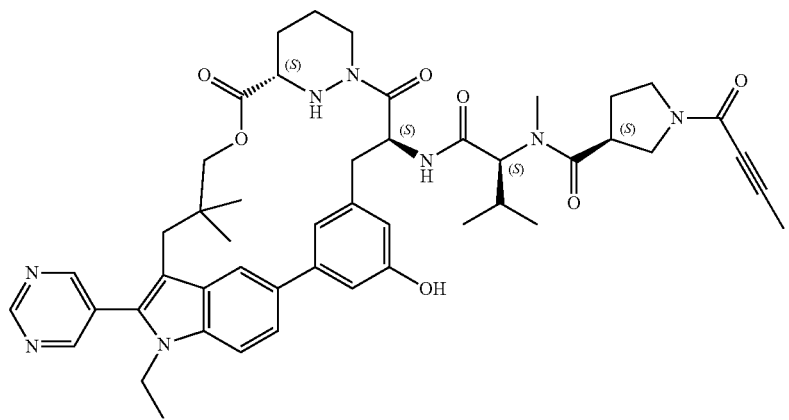 |
| A170 | 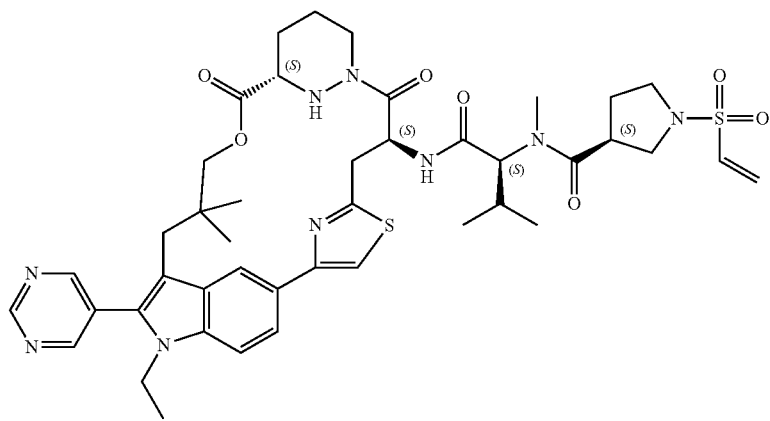 |
| A171 | 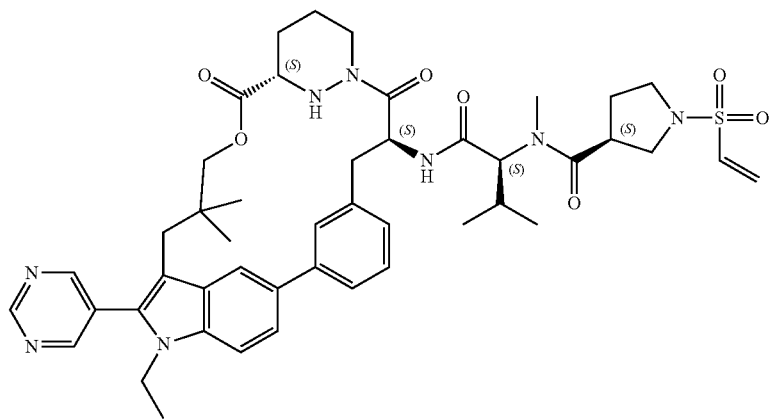 |

US 11,952,352 B2
183                                                                                              184
TABLE 1-continued
Certain Compounds of the Present Invention
| Ex# | Structure |
| --- | --- |
A172
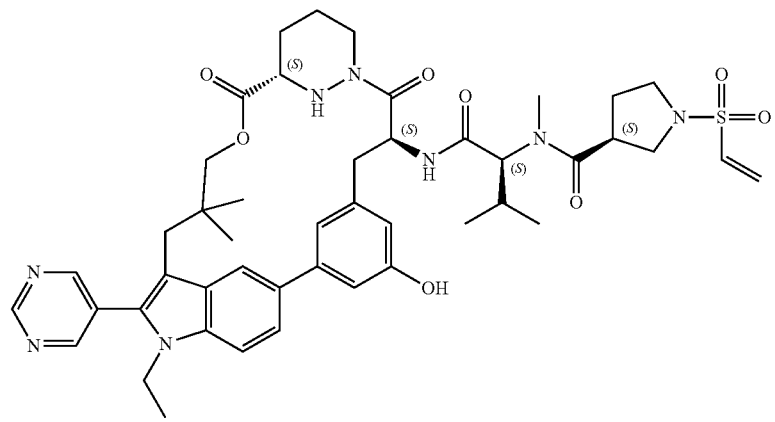
A173
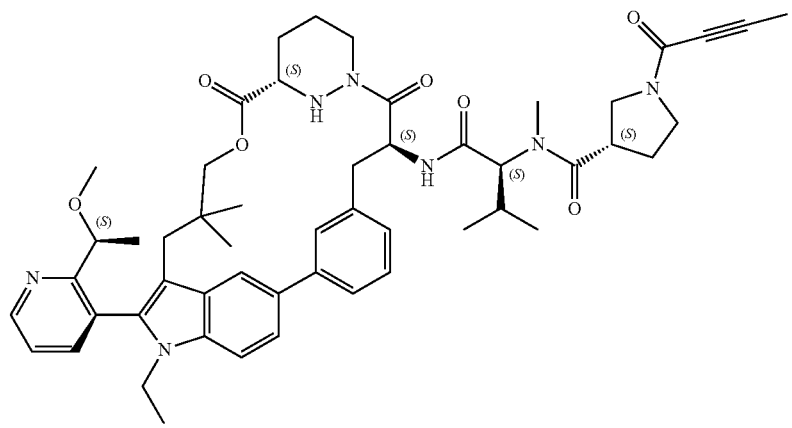
A174
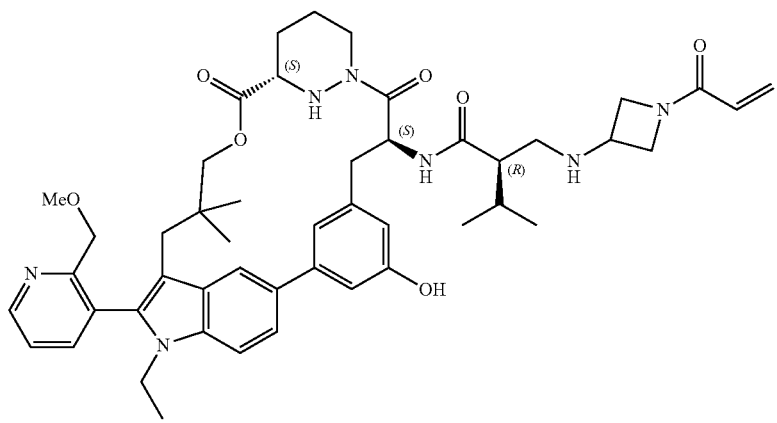

TABLE 1-continued
Certain Compounds of the Present Invention
| Ex# | Structure |
|---|---|
| A175 | 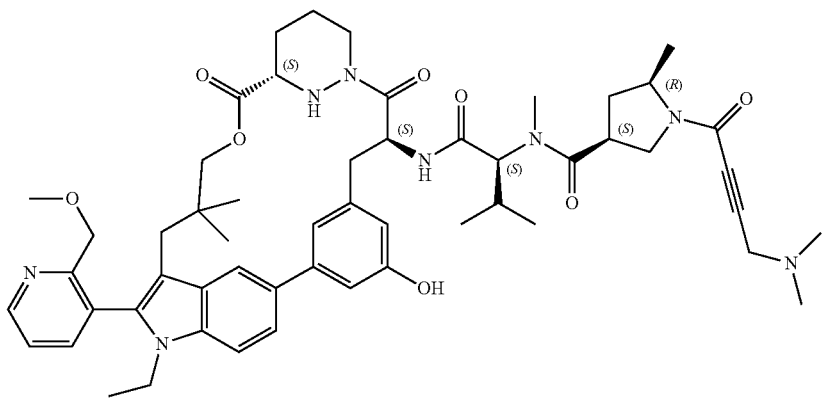 |
| A176 | 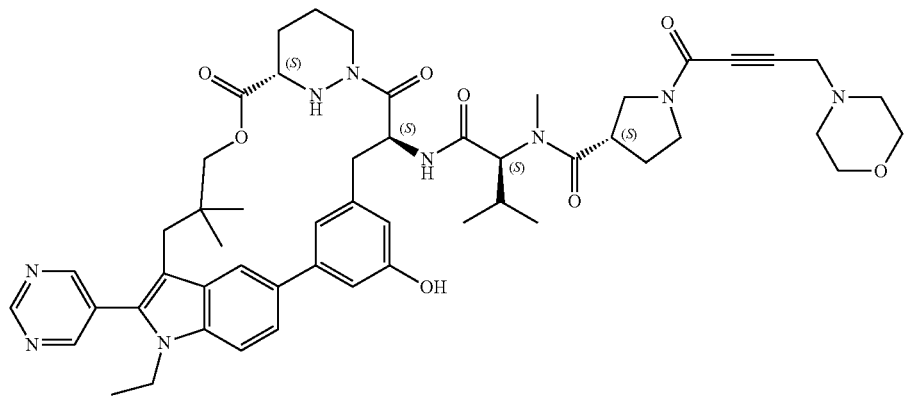 |
| A177 | 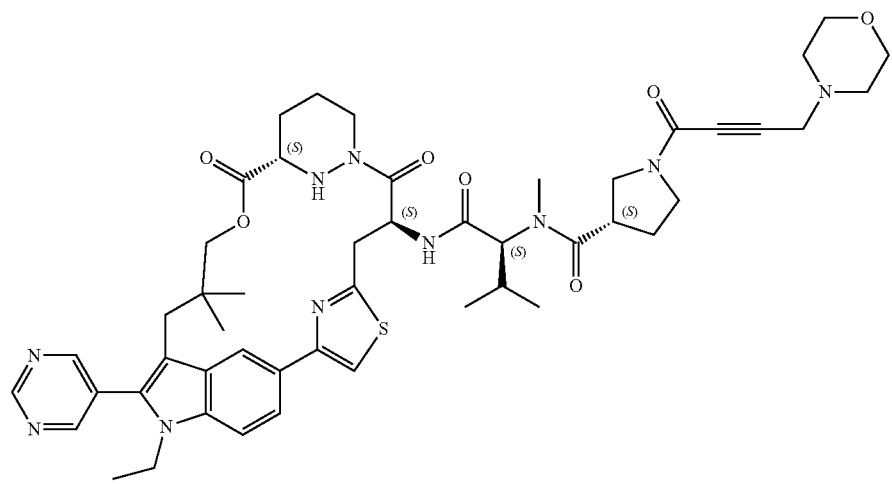 |

TABLE 1-continued
Certain Compounds of the Present Invention
| Ex# | Structure |
|---|---|
| A178 | 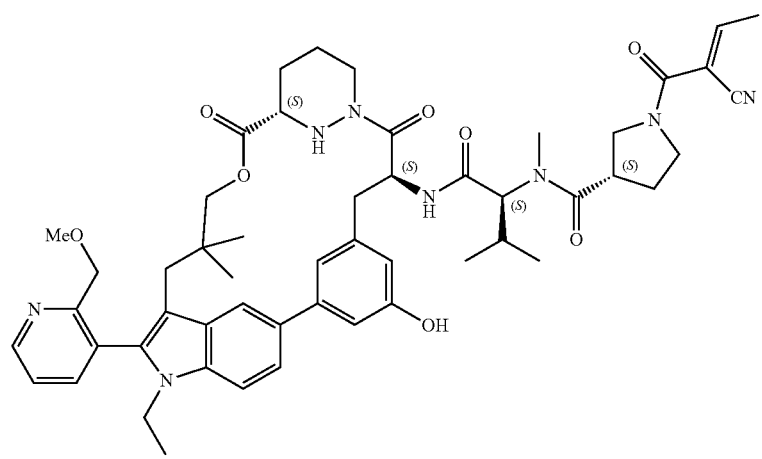 |
| A179 | 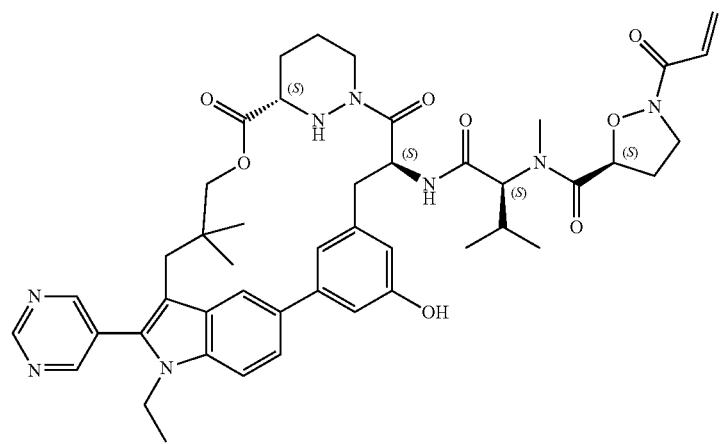 |
| A180 | 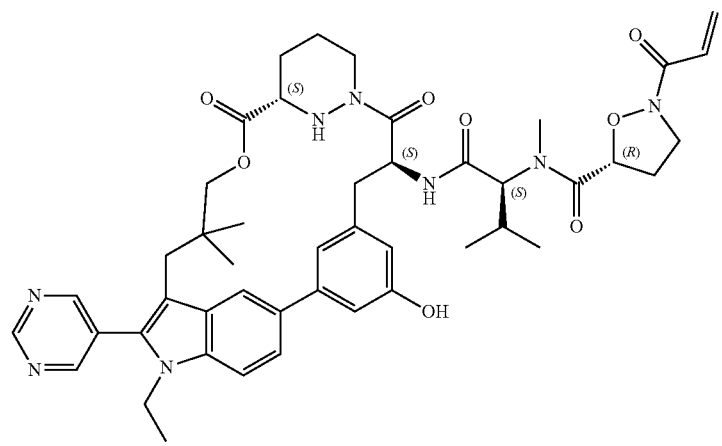 |

TABLE 1-continued
Certain Compounds of the Present Invention
| Ex# | Structure |
|---|---|
| A181 | 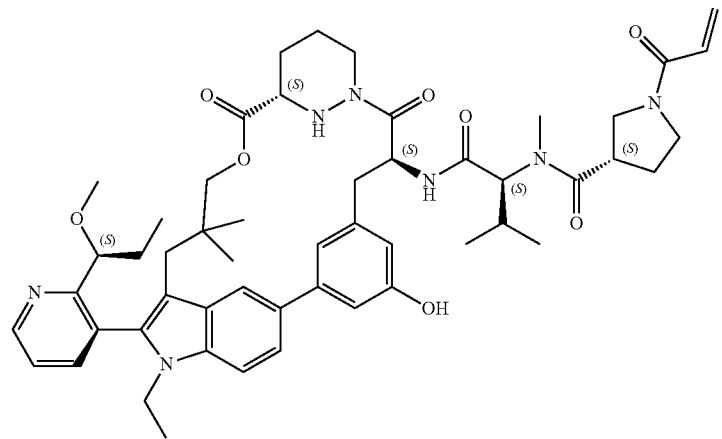 |
| A182 | 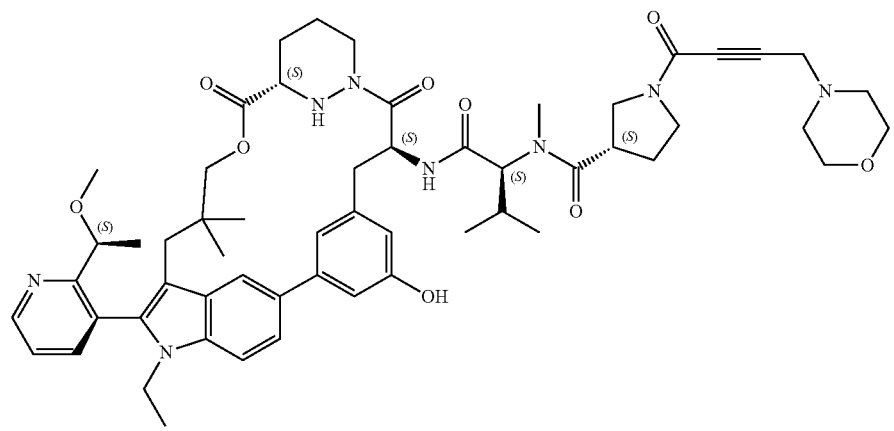 |
| A183 | 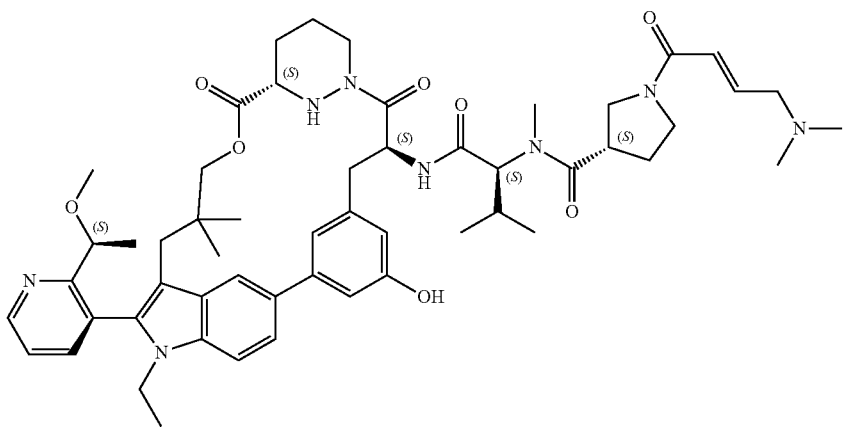 |

TABLE 1-continued
Certain Compounds of the Present Invention
| Ex# | Structure |
|---|---|
| A184 | 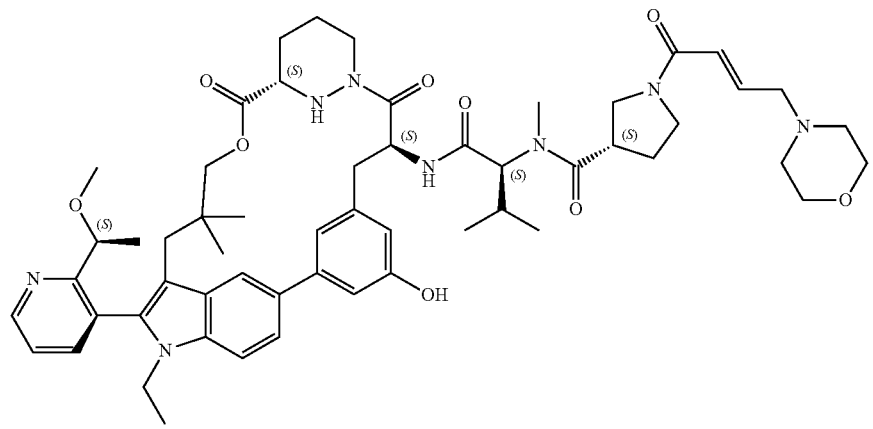 |
| A185 | 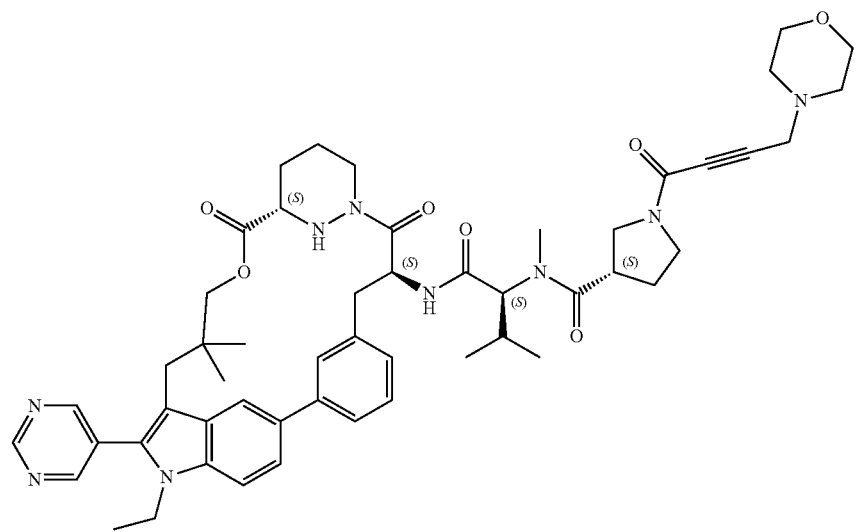 |
| A186 | 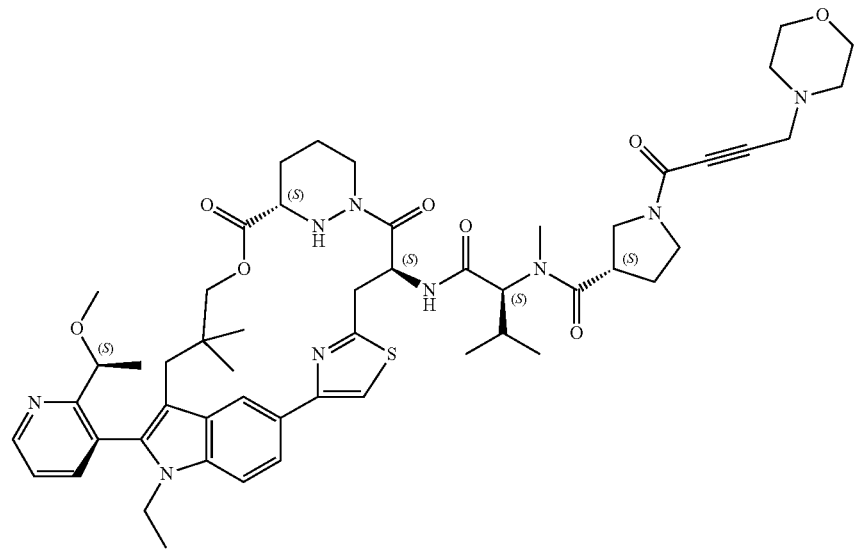 |

TABLE 1-continued
Certain Compounds of the Present Invention
| Ex# | Structure |
|---|---|
| A187 | 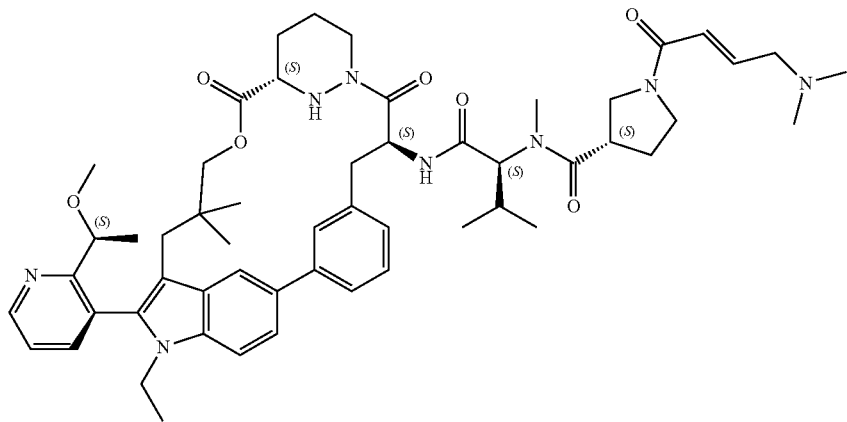 |
| A188 | 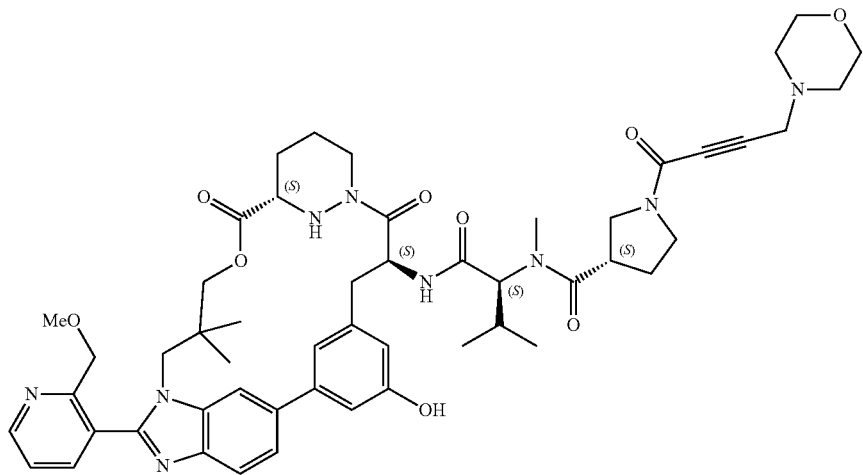 |
| A189 | 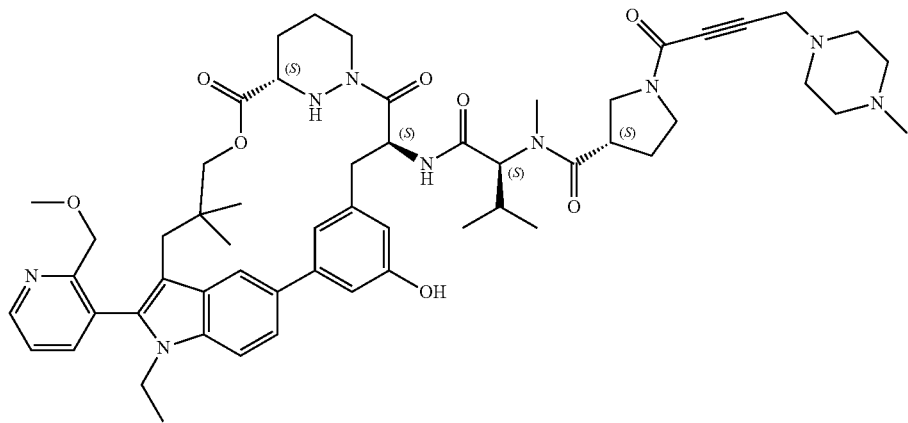 |

TABLE 1-continued
Certain Compounds of the Present Invention
| Ex# | Structure |
|---|---|
| A190 | 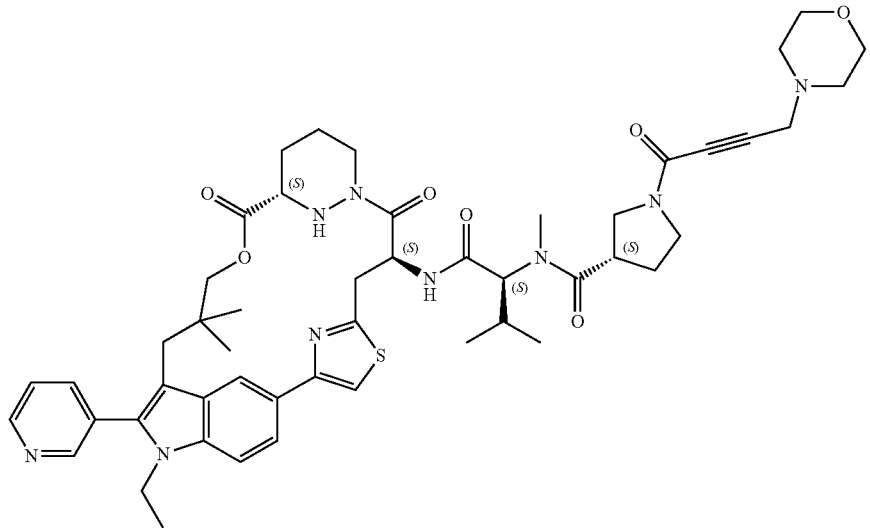 |
| A191 | 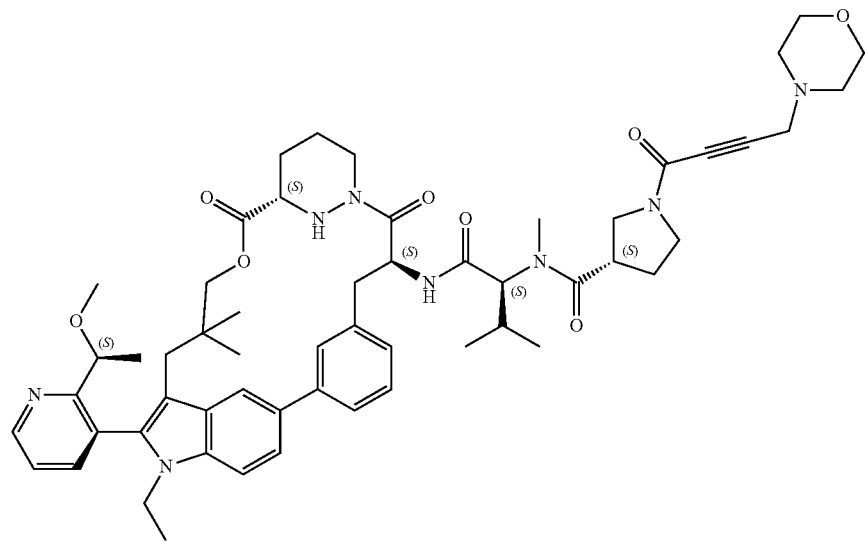 |
| A192 | 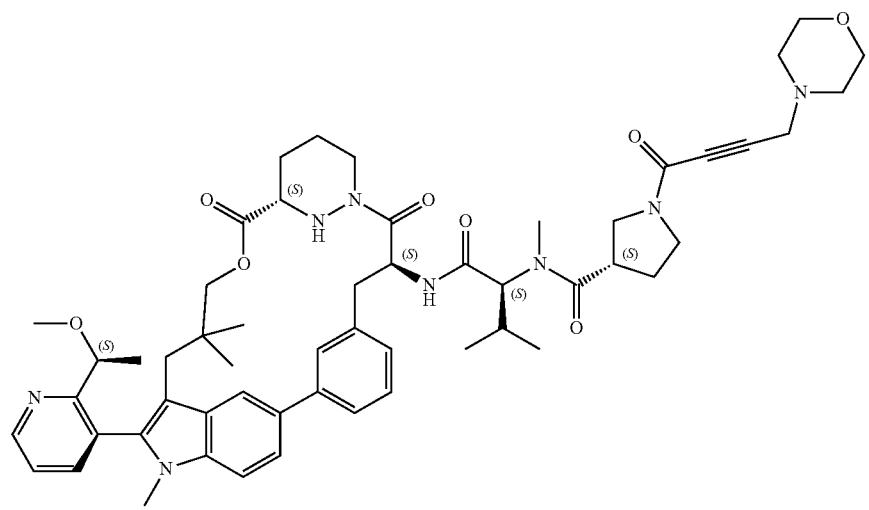 |

TABLE 1-continued
Certain Compounds of the Present Invention
| Ex# | Structure |
|---|---|
A193
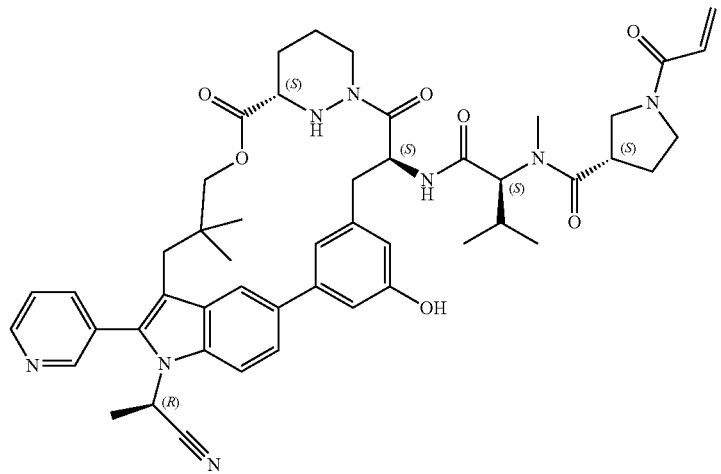
A194
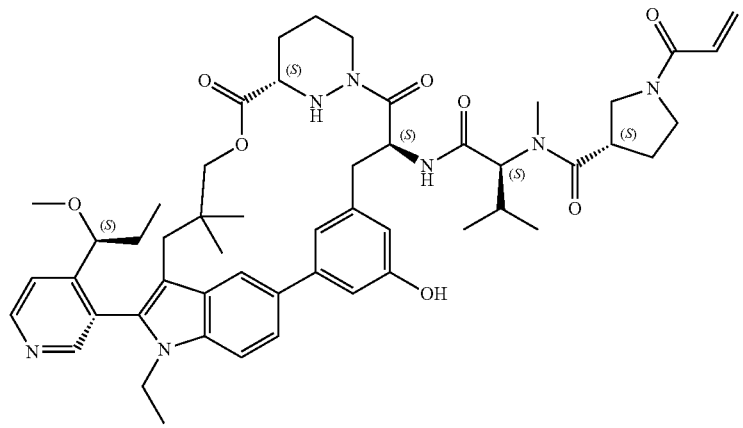
A195
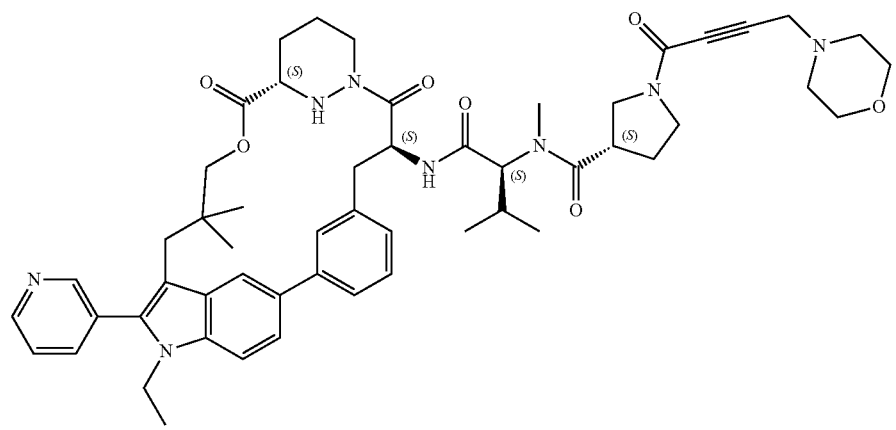

TABLE 1-continued
Certain Compounds of the Present Invention
| Ex# | Structure |
|---|---|
| A196 | 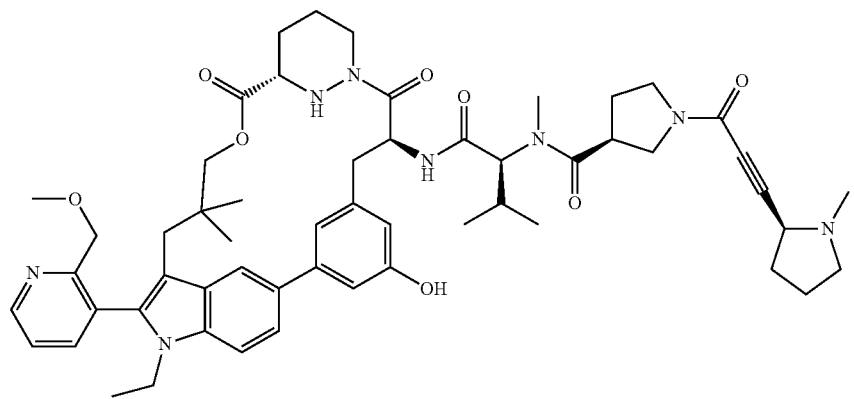 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#C[C@@H]3CCCN3C)C1)C(=O)N1CCC[C@H](N1)C(=O)OCC(C)(C)C2] |
| A197 | 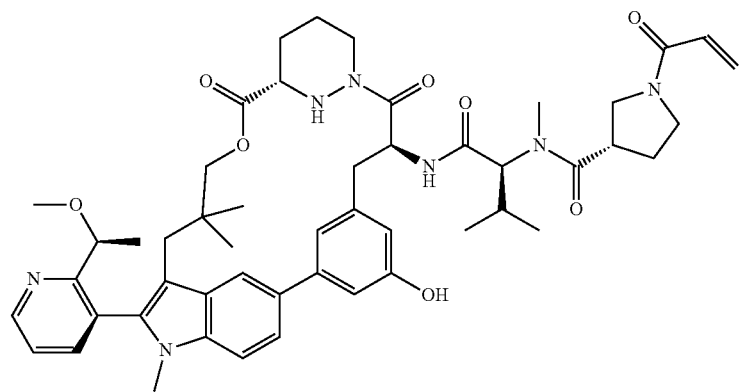 |
| A198 | 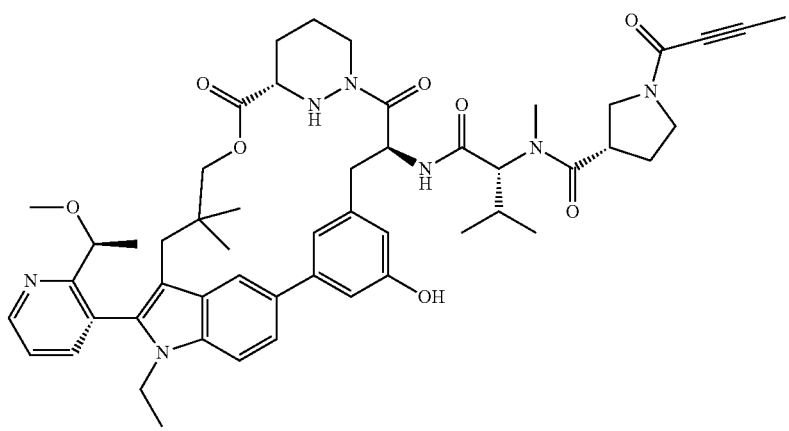 |

TABLE 1-continued
Certain Compounds of the Present Invention
| Ex# | Structure |
|---|---|
| A199 | 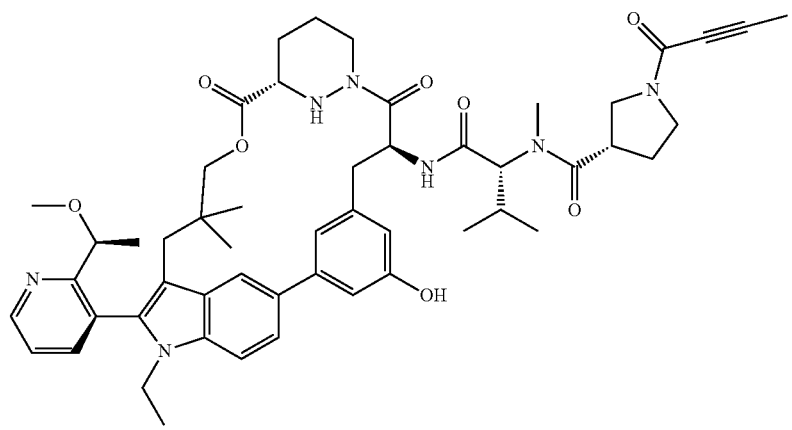 |
| A200 | 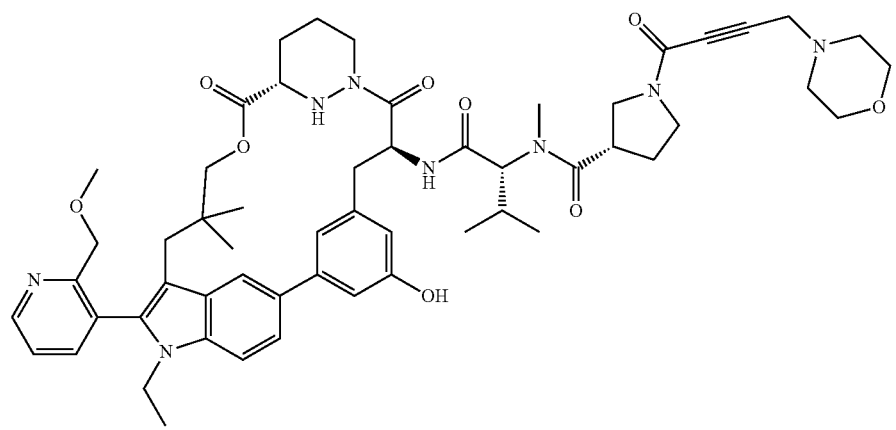 [SMILES: CCn1c(-c2cccnc2COC)c2c3cc(ccc31)-c1cc(O)cc(c1)C[C@H](NC(=O)[C@@H](C(C)C)N(C)C(=O)[C@H]1CCN(C(=O)C#CCN3CCOCC3)C1)C(=O)N1CCC[C@H](N1)C(=O)OCC(C)(C)C2] |
| A201 | 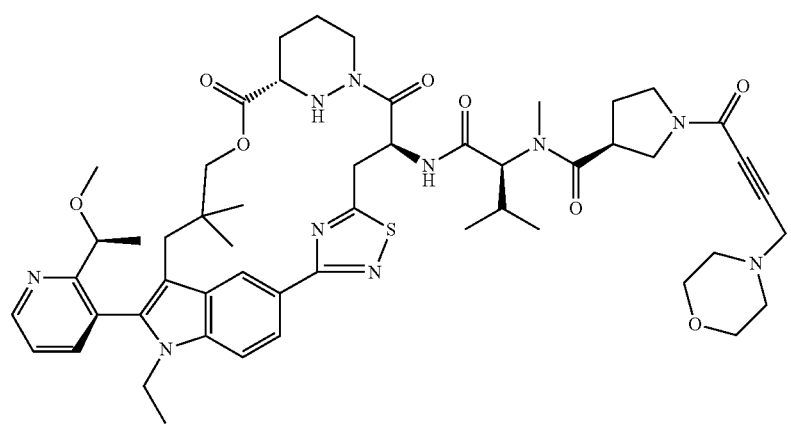 |

TABLE 1-continued
Certain Compounds of the Present Invention
| Ex# | Structure |
|---|---|
| A202 | 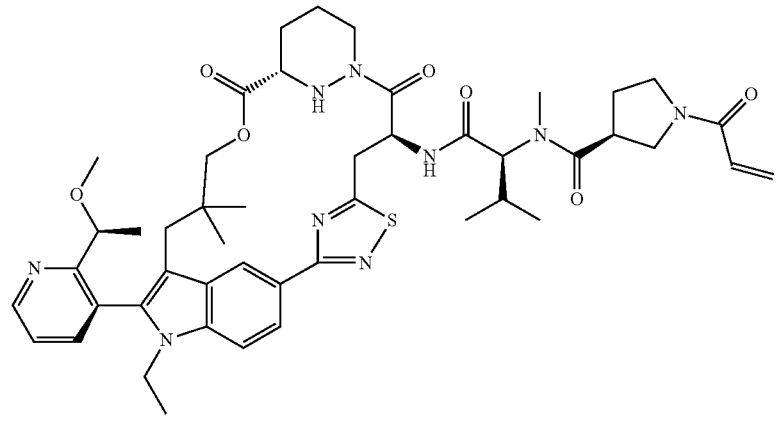 |
| A203 | 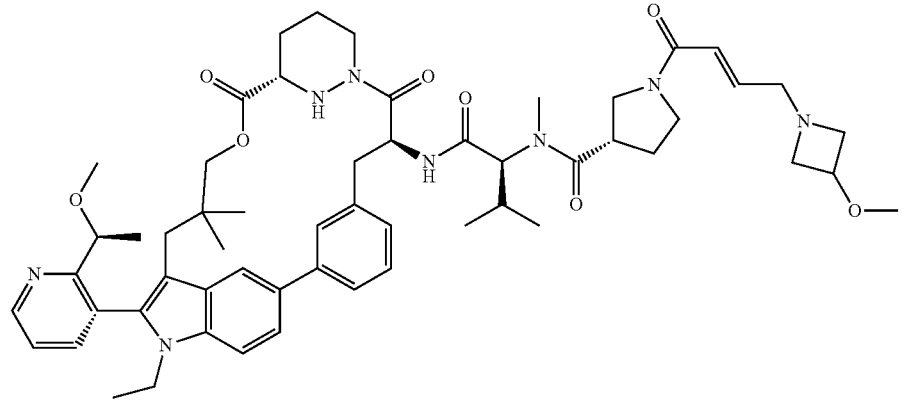 |
| A204 | 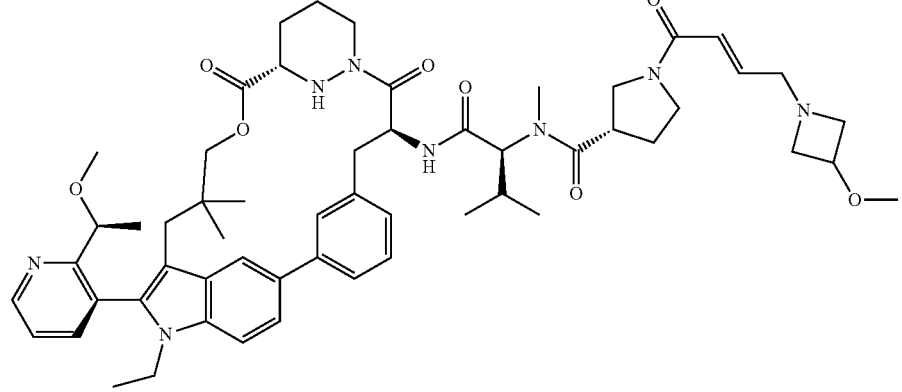 |

TABLE 1-continued
Certain Compounds of the Present Invention
| Ex# | Structure |
|---|---|
| A205 | 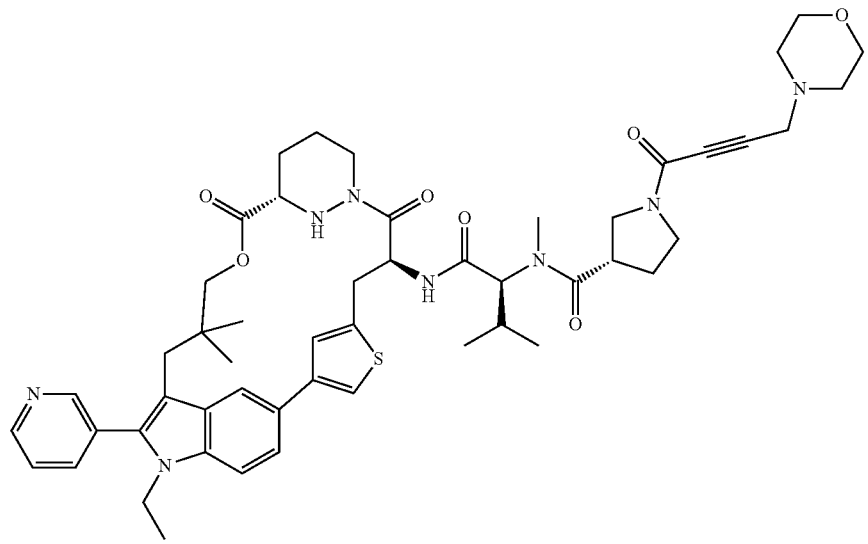 [SMILES: CCn1c(-c2cccnc2)c2c3cc(ccc31)-c1csc(c1)C[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |
| A206 | 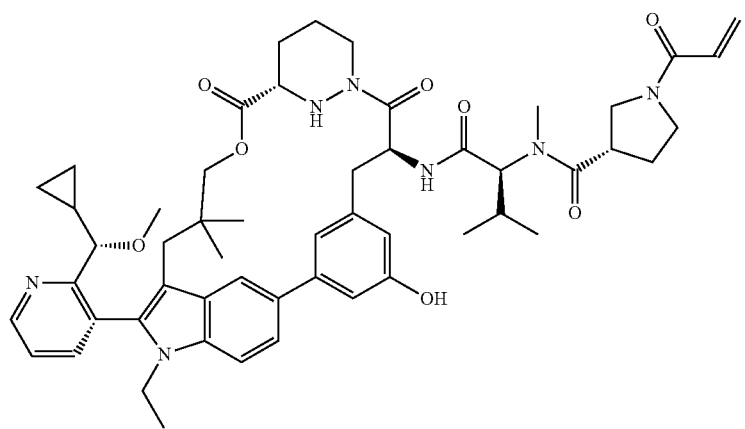 |
| A207 | 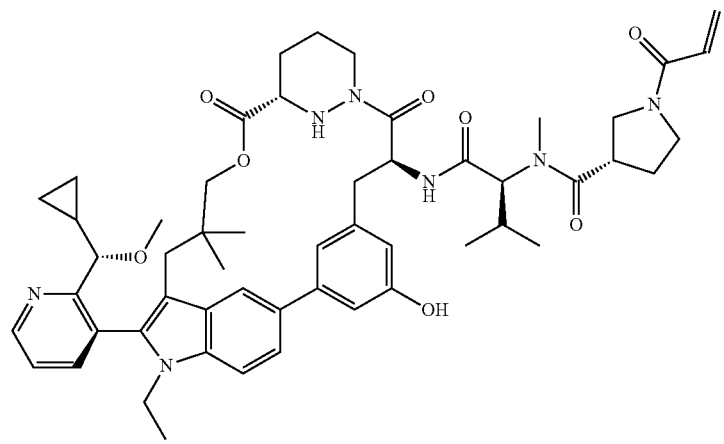 |

TABLE 1-continued
Certain Compounds of the Present Invention
| Ex# | Structure |
|---|---|
| A208 | 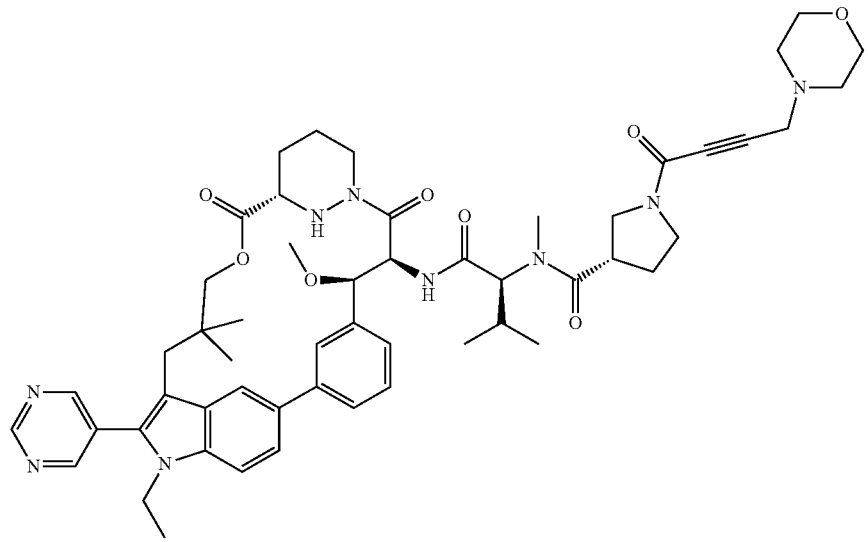 [SMILES: CCn1c(-c2cncnc2)c2c3cc(ccc31)-c1cccc(c1)[C@@H](OC)[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |
| A209 | 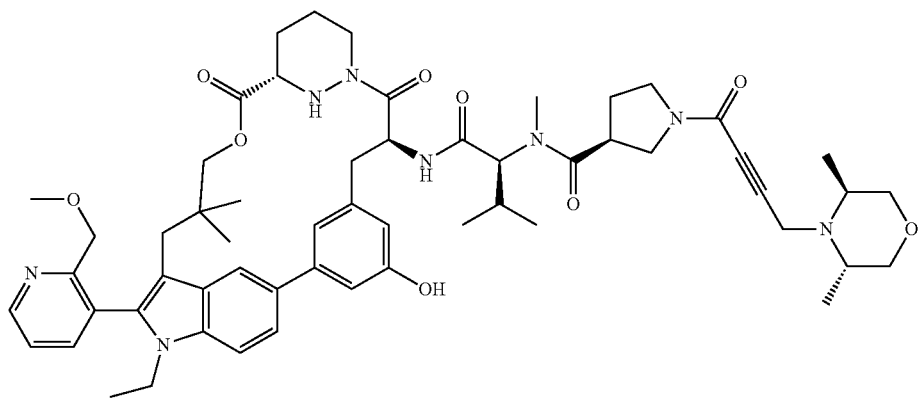 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#CCN3[C@@H](C)COC[C@@H]3C)C1)C(=O)N1CCC[C@H](N1)C(=O)OCC(C)(C)C2] |
| A210 | 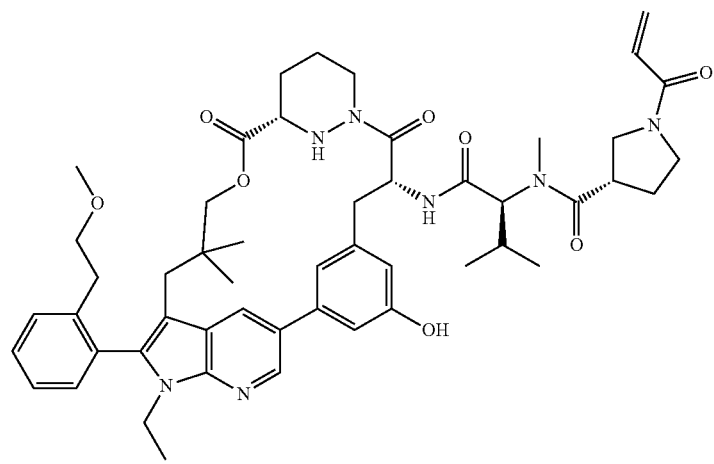 [SMILES: C=CC(=O)N1CC[C@H](C(=O)N(C)[C@H](C(=O)N[C@@H]2Cc3cc(O)cc(c3)-c3cnc4c(c3)c(c(-c3ccccc3CCOC)n4CC)CC(C)(C)COC(=O)[C@@H]3CCCN(N3)C2=O)C(C)C)C1] |

TABLE 1-continued
Certain Compounds of the Present Invention
| Ex# | Structure |
| --- | --- |
| A211 | 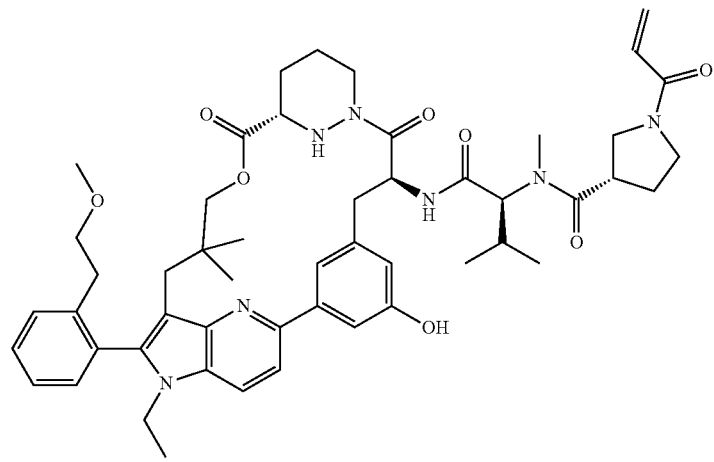 [SMILES: C=CC(=O)N1CC[C@H](C(=O)N(C)[C@H](C(=O)N[C@H]2Cc3cc(O)cc(c3)-c3ccc4c(n3)c(c(-c3ccccc3CCOC)n4CC)CC(C)(C)COC(=O)[C@@H]3CCCN(N3)C2=O)C(C)C)C1] |
| A212 | 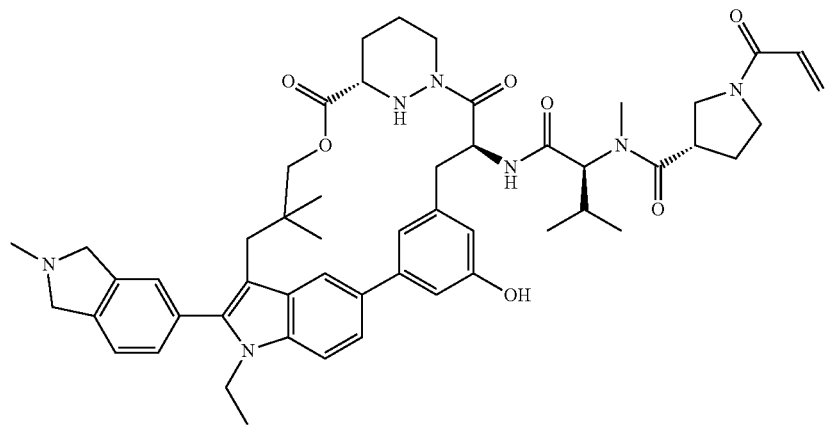 [SMILES: C=CC(=O)N1CC[C@H](C(=O)N(C)[C@H](C(=O)N[C@H]2Cc3cc(O)cc(c3)-c3ccc4c(c3)c(c(-c3ccc5c(c3)CN(C)C5)n4CC)CC(C)(C)COC(=O)[C@@H]3CCCN(N3)C2=O)C(C)C)C1] |
| A213 | 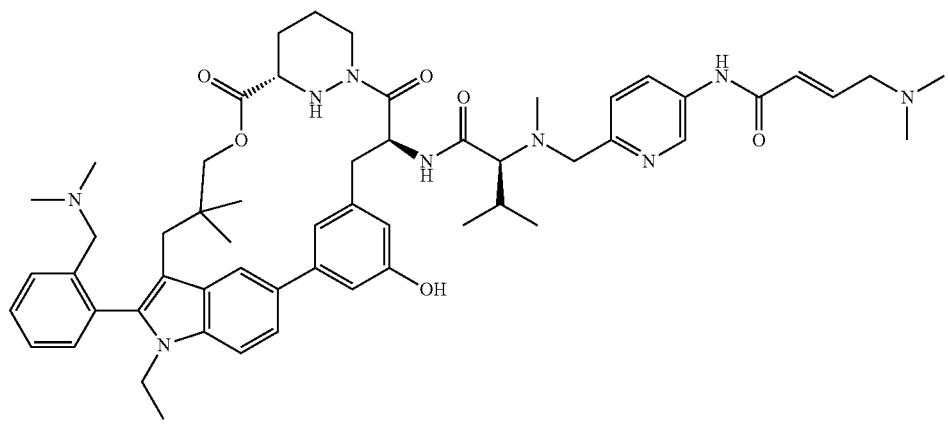 [SMILES: CCn1c(-c2ccccc2CN(C)C)c2c3cc(ccc31)-c1cc(O)cc(c1)C[C@H](NC(=O)[C@H](C(C)C)N(C)Cc1ccc(NC(=O)/C=C/CN(C)C)cn1)C(=O)N1CCC[C@H](N1)C(=O)OCC(C)(C)C2] |

TABLE 1-continued
Certain Compounds of the Present Invention
| Ex# | Structure |
|---|---|
| A214 | 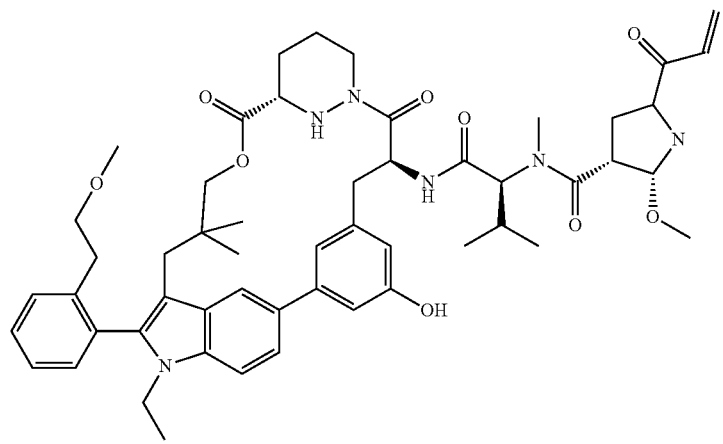 [SMILES: C=CC(=O)C1C[C@@H](C(=O)N(C)[C@H](C(=O)N[C@H]2Cc3cc(O)cc(c3)-c3ccc4c(c3)c(c(-c3ccccc3CCOC)n4CC)CC(C)(C)COC(=O)[C@@H]3CCCN(N3)C2=O)C(C)C)[C@@H](OC)N1] |
| A215 | 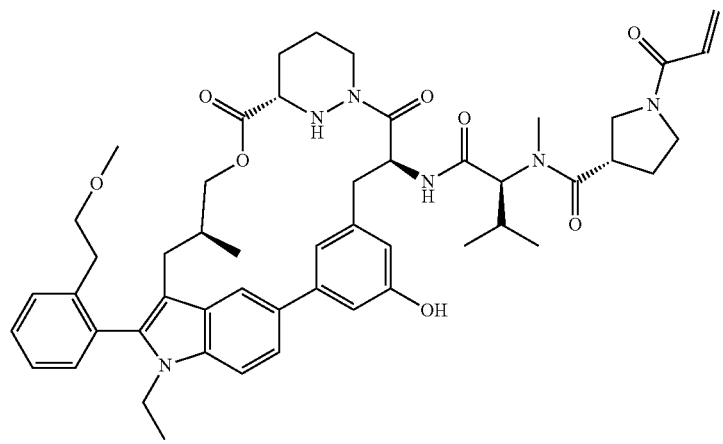 [SMILES: C=CC(=O)N1CC[C@H](C(=O)N(C)[C@H](C(=O)N[C@H]2Cc3cc(O)cc(c3)-c3ccc4c(c3)c(c(-c3ccccc3CCOC)n4CC)C[C@H](C)COC(=O)[C@@H]3CCCN(N3)C2=O)C(C)C)C1] |
| A216 | 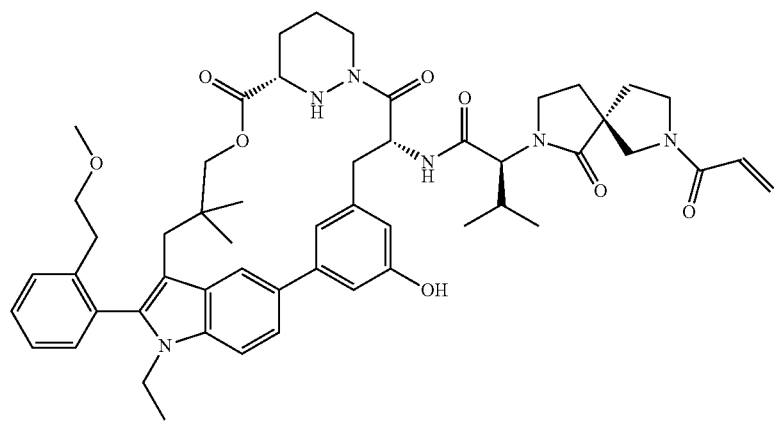 [SMILES: C=CC(=O)N1CC[C@]2(CCN([C@H](C(=O)N[C@@H]3Cc4cc(O)cc(c4)-c4ccc5c(c4)c(c(-c4ccccc4CCOC)n5CC)CC(C)(C)COC(=O)[C@@H]4CCCN(N4)C3=O)C(C)C)C2=O)C1] |

US 11,952,352 B2
213                                                                                                                                             214
TABLE 1-continued
Certain Compounds of the Present Invention
| Ex# | Structure |
| --- | --- |
A217
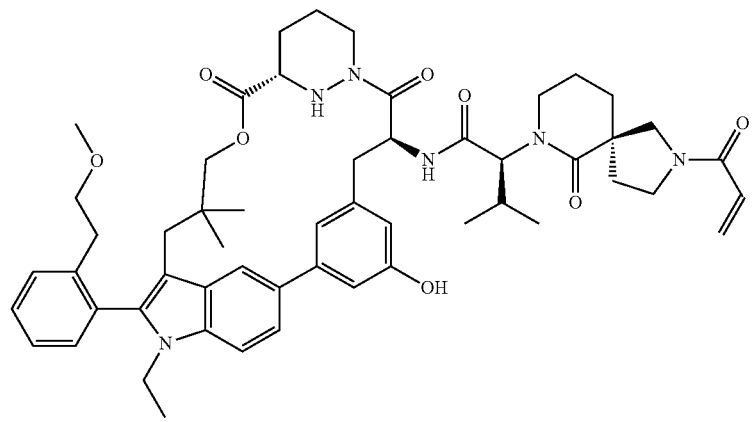 [SMILES: C=CC(=O)N1CC[C@]2(CCCN([C@H](C(=O)N[C@H]3Cc4cc(O)cc(c4)-c4ccc5c(c4)c(c(-c4ccccc4CCOC)n5CC)CC(C)(C)COC(=O)[C@@H]4CCCN(N4)C3=O)C(C)C)C2=O)C1]
A218
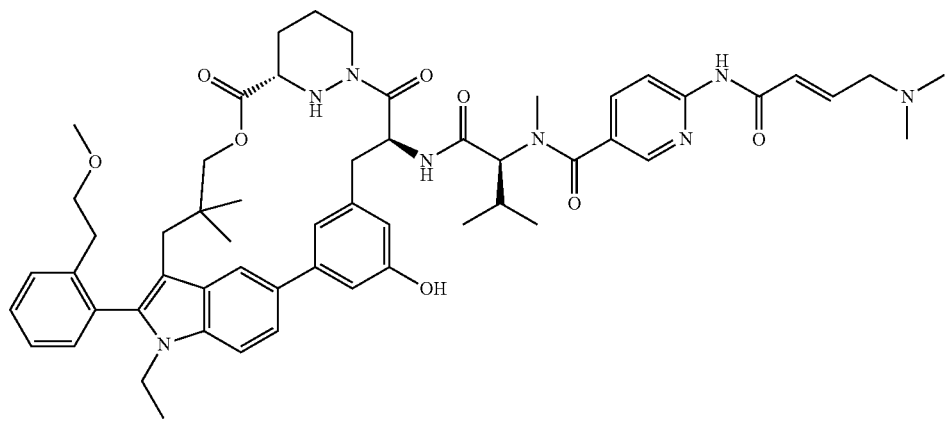 [SMILES: CCn1c(-c2ccccc2CCOC)c2c3cc(ccc31)-c1cc(O)cc(c1)C[C@H](NC(=O)[C@H](C(C)C)N(C)C(=O)c1ccc(NC(=O)/C=C/CN(C)C)nc1)C(=O)N1CCC[C@H](N1)C(=O)OCC(C)(C)C2]
A219
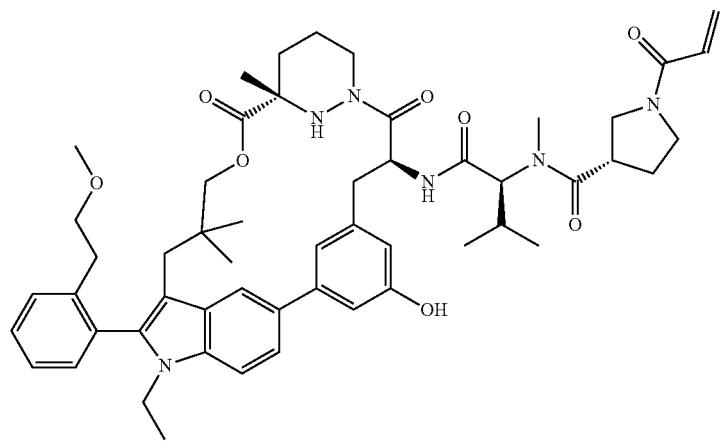 [SMILES: C=CC(=O)N1CC[C@H](C(=O)N(C)[C@H](C(=O)N[C@H]2Cc3cc(O)cc(c3)-c3ccc4c(c3)c(c(-c3ccccc3CCOC)n4CC)CC(C)(C)COC(=O)[C@]3(C)CCCN(N3)C2=O)C(C)C)C1]

TABLE 1-continued
Certain Compounds of the Present Invention
| Ex# | Structure |
|---|---|
| A220 | 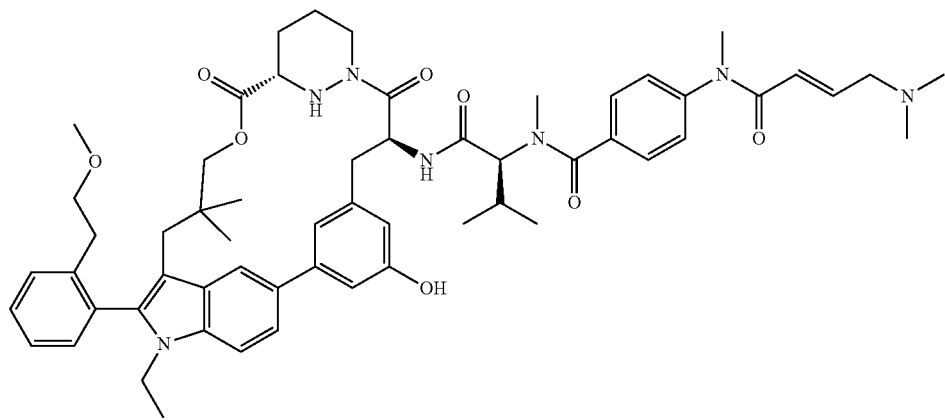 [SMILES: CCn1c(-c2ccccc2CCOC)c2c3cc(ccc31)-c1cc(O)cc(c1)C[C@H](NC(=O)[C@H](C(C)C)N(C)C(=O)c1ccc(N(C)C(=O)/C=C/CN(C)C)cc1)C(=O)N1CCC[C@H](N1)C(=O)OCC(C)(C)C2] |
| A221 | 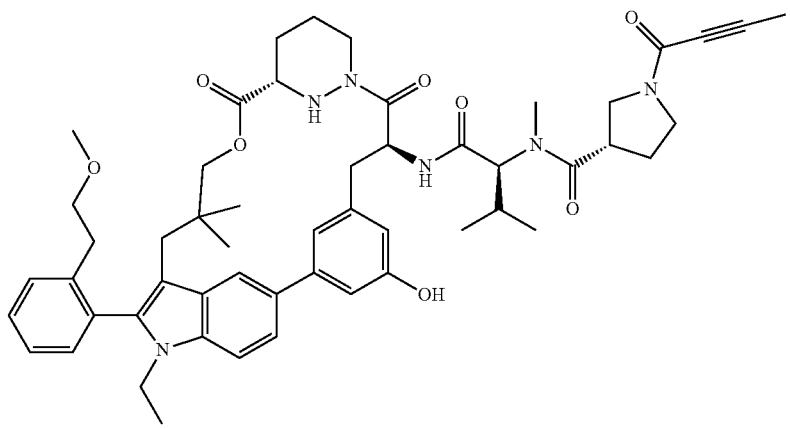 [SMILES: CC#CC(=O)N1CC[C@H](C(=O)N(C)[C@H](C(=O)N[C@H]2Cc3cc(O)cc(c3)-c3ccc4c(c3)c(c(-c3ccccc3CCOC)n4CC)CC(C)(C)COC(=O)[C@@H]3CCCN(N3)C2=O)C(C)C)C1] |
| A222 | 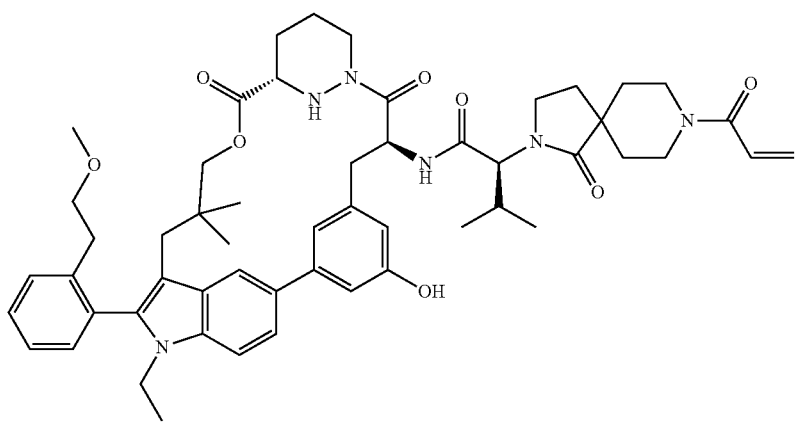 [SMILES: C=CC(=O)N1CCC2(CC1)CCN([C@H](C(=O)N[C@H]1Cc3cc(O)cc(c3)-c3ccc4c(c3)c(c(-c3ccccc3CCOC)n4CC)CC(C)(C)COC(=O)[C@@H]3CCCN(N3)C1=O)C(C)C)C2=O] |

TABLE 1-continued
Certain Compounds of the Present Invention
| Ex# | Structure |
| --- | --- |
| A223 | 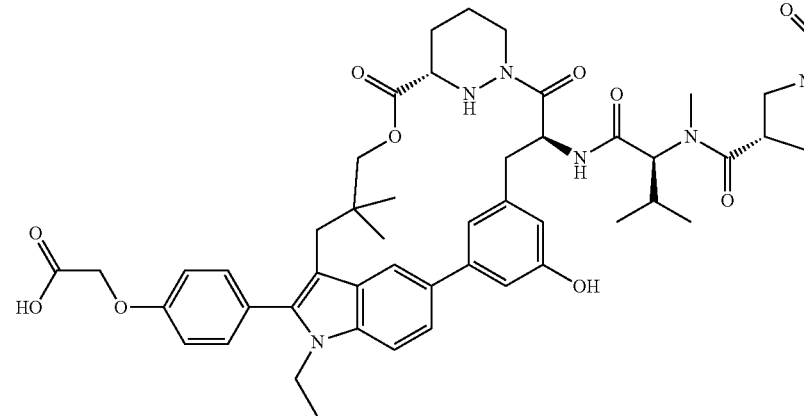 |
| A224 | 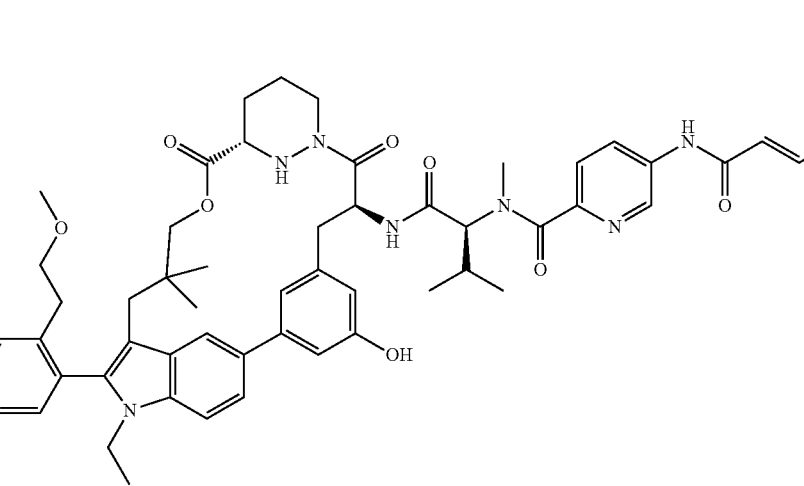 |
| A225 | 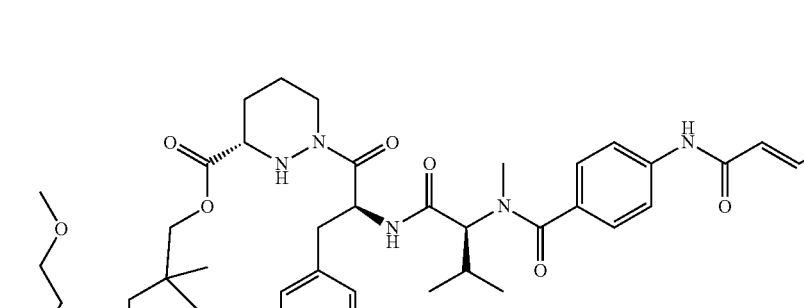 |

TABLE 1-continued
Certain Compounds of the Present Invention
| Ex# | Structure |
|---|---|
| A226 | 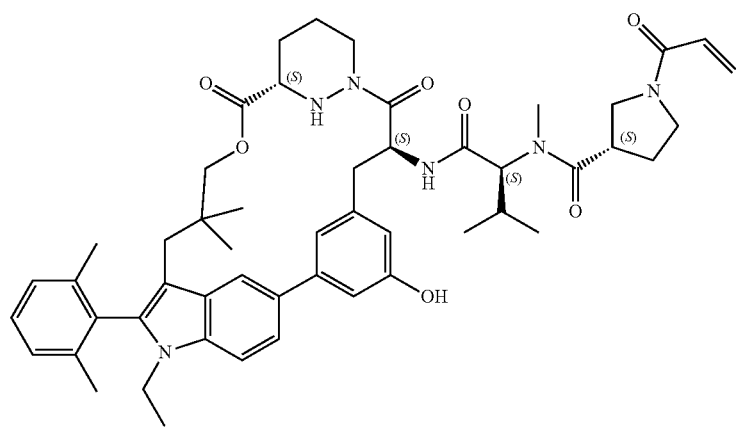 |
| A227 | 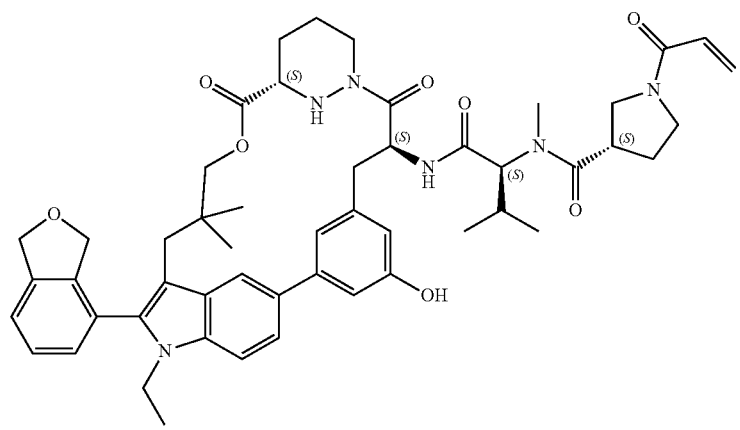 |
| A228 | 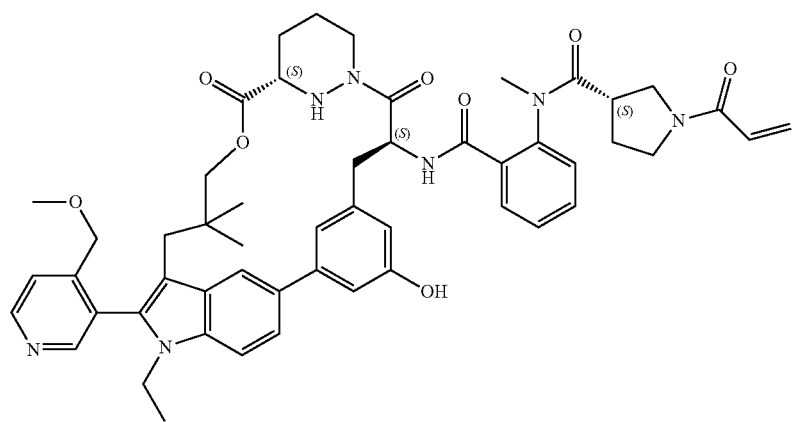 |

TABLE 1-continued
Certain Compounds of the Present Invention
| Ex# | Structure |
|---|---|
| A229 | 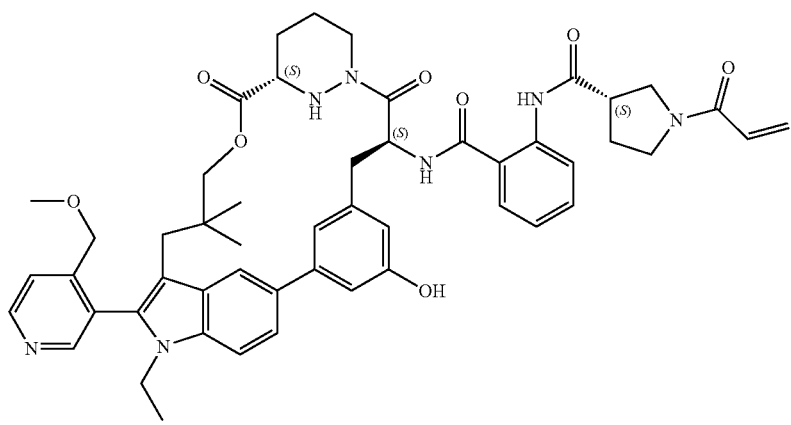 |
| A230 | 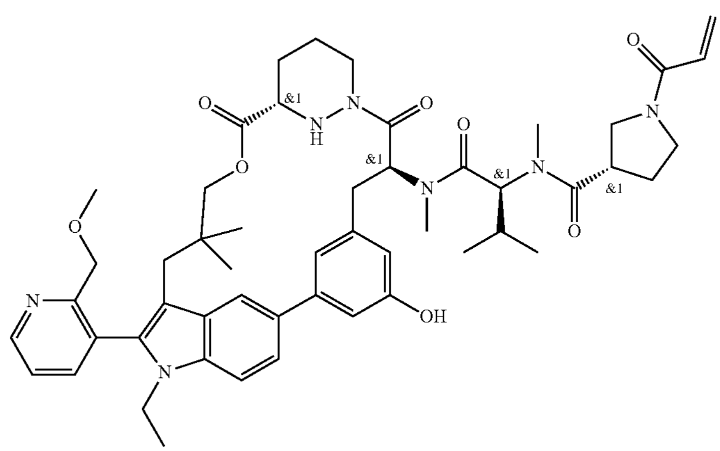 [SMILES: C=CC(=O)N1CC[C@H](C(=O)N(C)[C@H](C(=O)N(C)[C@H]2Cc3cc(O)cc(c3)-c3ccc4c(c3)c(c(-c3cccnc3COC)n4CC)CC(C)(C)COC(=O)[C@@H]3CCCN(N3)C2=O)C(C)C)C1] |
| A231 | 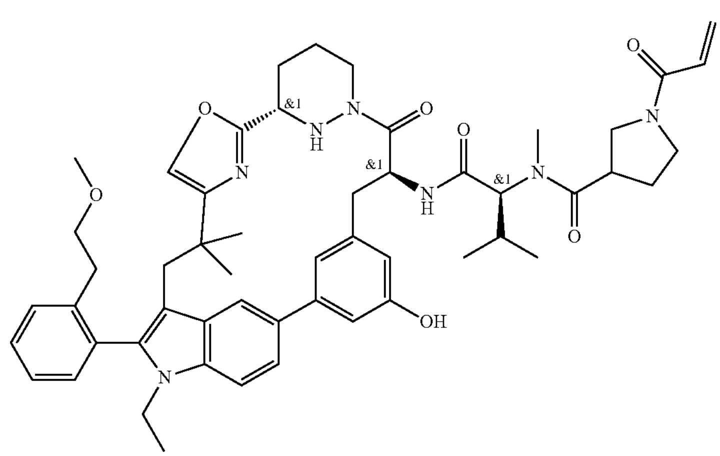 [SMILES: C=CC(=O)N1CCC(C(=O)N(C)[C@H](C(=O)N[C@H]2Cc3cc(O)cc(c3)-c3ccc4c(c3)c(c(-c3ccccc3CCOC)n4CC)CC(C)(C)c3coc(n3)[C@@H]3CCCN(N3)C2=O)C(C)C)C1] |

TABLE 1-continued
Certain Compounds of the Present Invention
| Ex# | Structure |
|---|---|
| A232 | 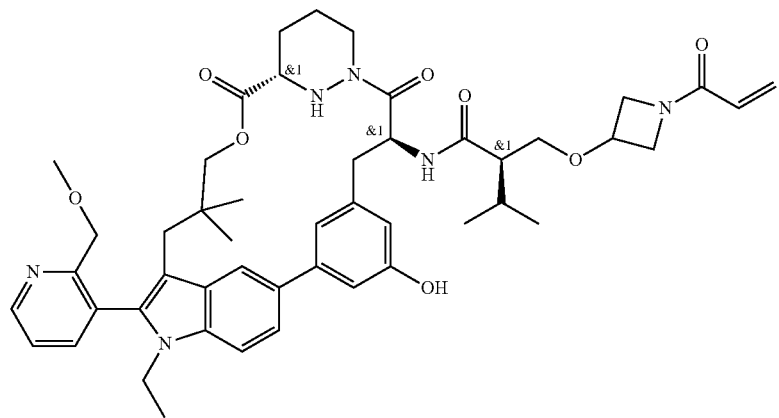 [SMILES: C=CC(=O)N1CC(OC[C@H](C(=O)N[C@H]2Cc3cc(O)cc(c3)-c3ccc4c(c3)c(c(-c3cccnc3COC)n4CC)CC(C)(C)COC(=O)[C@@H]3CCCN(N3)C2=O)C(C)C)C1] |
| A233 | 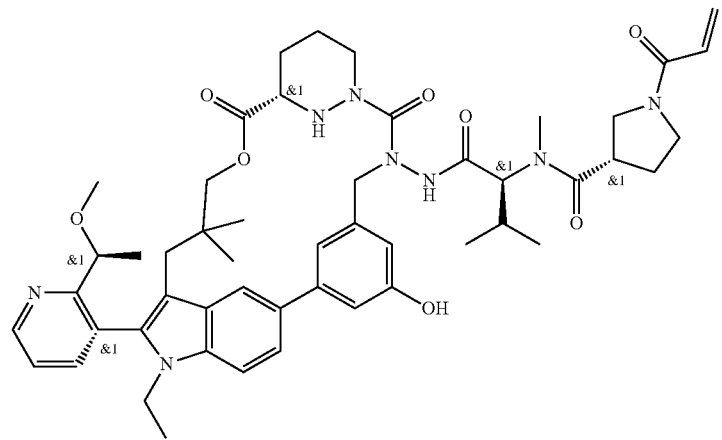 |
| A234 | 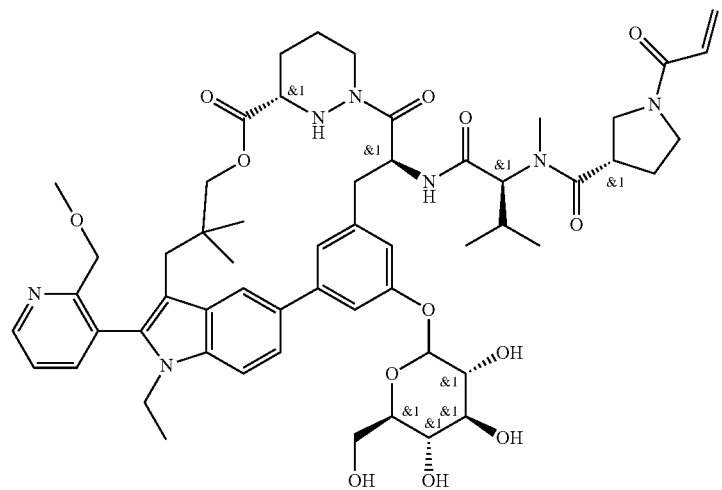 [SMILES: C=CC(=O)N1CC[C@H](C(=O)N(C)[C@H](C(=O)N[C@H]2Cc3cc(OC4O[C@H](CO)[C@@H](O)[C@H](O)[C@H]4O)cc(c3)-c3ccc4c(c3)c(c(-c3cccnc3COC)n4CC)CC(C)(C)COC(=O)[C@@H]3CCCN(N3)C2=O)C(C)C)C1] |

TABLE 1-continued

Certain Compounds of the Present Invention

| Ex# | Structure |
|---|---|
| A235 | 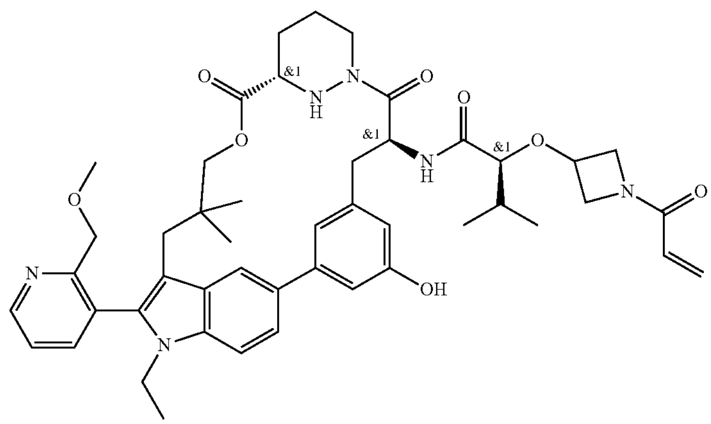 [SMILES: C=CC(=O)N1CC(O[C@H](C(=O)N[C@H]2Cc3cc(O)cc(c3)-c3ccc4c(c3)c(c(-c3cccnc3COC)n4CC)CC(C)(C)COC(=O)[C@@H]3CCCN(N3)C2=O)C(C)C)C1] |
| A236 | 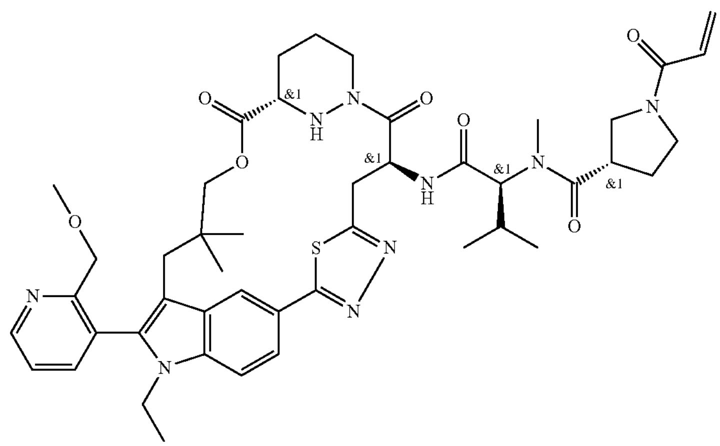 [SMILES: C=CC(=O)N1CC[C@H](C(=O)N(C)[C@H](C(=O)N[C@H]2CC3=NN=C(S3)c3ccc4c(c3)c(c(-c3cccnc3COC)n4CC)CC(C)(C)COC(=O)[C@@H]3CCCN(N3)C2=O)C(C)C)C1] |
| A237 | 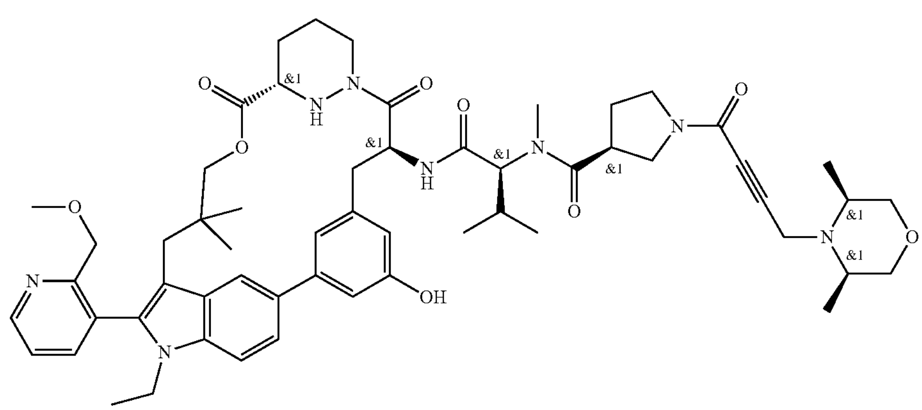 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#CCN3[C@H](C)COC[C@@H]3C)C1)C(=O)N1CCC[C@H](N1)C(=O)OCC(C)(C)C2] |

US 11,952,352 B2
TABLE 1-continued
Certain Compounds of the Present Invention
| Ex# | Structure |
|---|---|
| A238 | 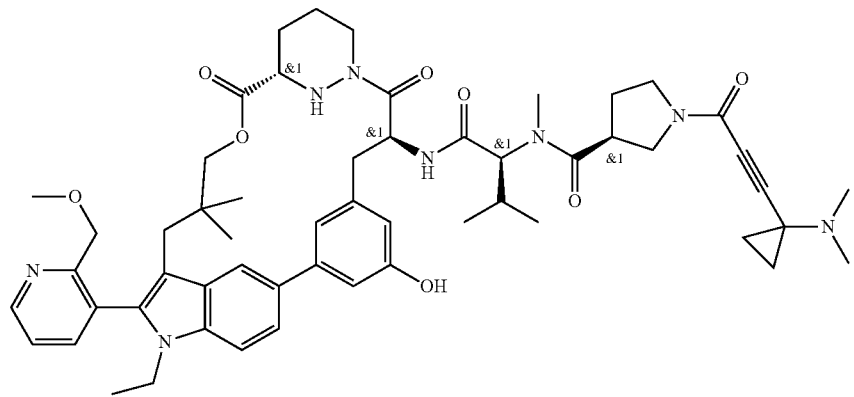 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#CC3(N(C)C)CC3)C1)C(=O)N1CCC[C@H](N1)C(=O)OCC(C)(C)C2] |
| A239 | 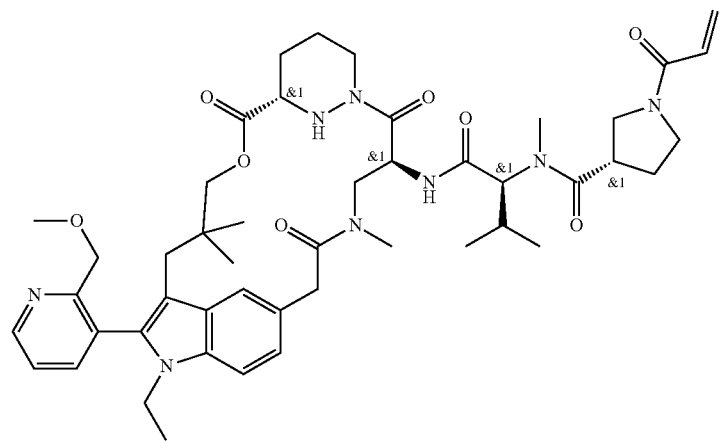 [SMILES: C=CC(=O)N1CC[C@H](C(=O)N(C)[C@H](C(=O)N[C@H]2CN(C)C(=O)Cc3ccc4c(c3)c(c(-c3cccnc3COC)n4CC)CC(C)(C)COC(=O)[C@@H]3CCCN(N3)C2=O)C(C)C)C1] |
| A240 | 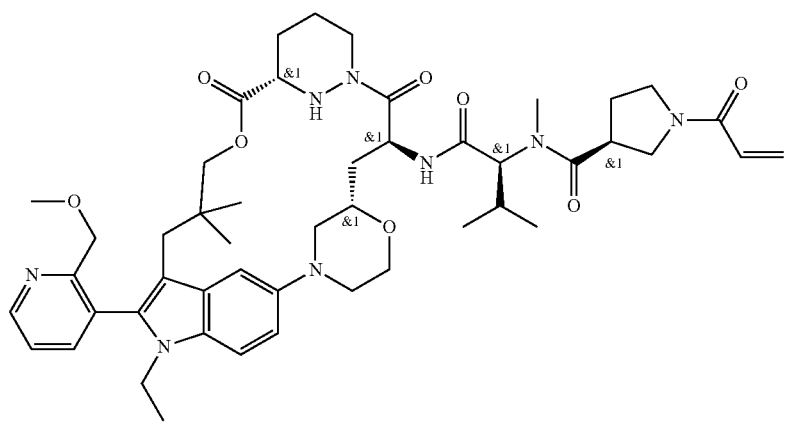 [SMILES: C=CC(=O)N1CC[C@H](C(=O)N(C)[C@H](C(=O)N[C@H]2C[C@H]3CN(CCO3)c3ccc4c(c3)c(c(-c3cccnc3COC)n4CC)CC(C)(C)COC(=O)[C@@H]3CCCN(N3)C2=O)C(C)C)C1] |

TABLE 1-continued

Certain Compounds of the Present Invention

| Ex# | Structure |
|---|---|
| A241 | 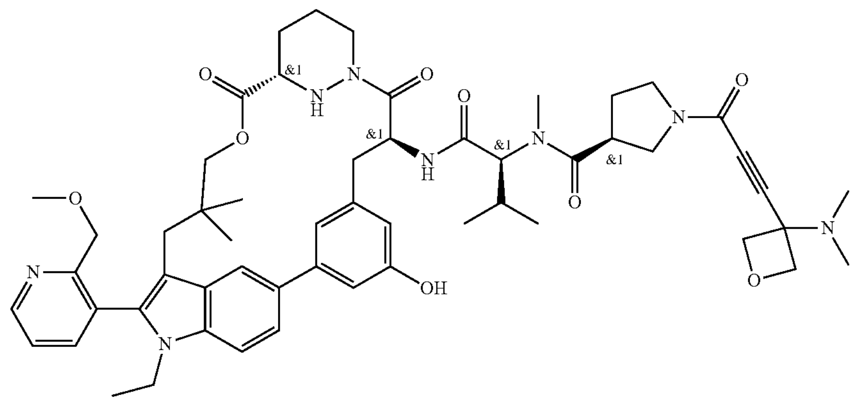 [SMILES: CCn1c(-c2cccnc2COC)c2c3cc(ccc31)-c1cc(O)cc(c1)C[C@H](NC(=O)[C@H](C(C)C)N(C)C(=O)[C@H]1CCN(C(=O)C#CC3(N(C)C)COC3)C1)C(=O)N1CCC[C@H](N1)C(=O)OCC(C)(C)C2] |
| A242 | 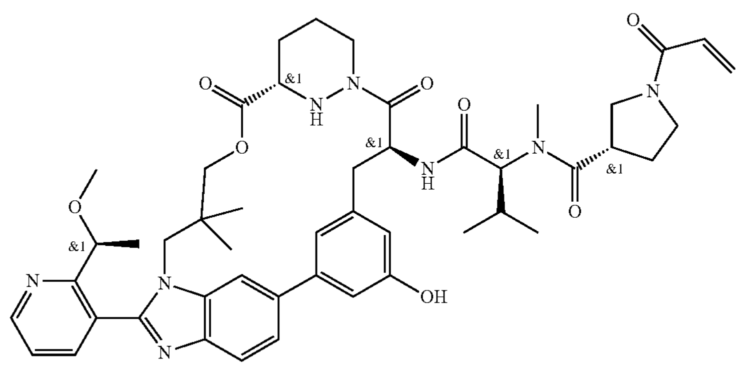 [SMILES: C=CC(=O)N1CC[C@H](C(=O)N(C)[C@H](C(=O)N[C@H]2Cc3cc(O)cc(c3)-c3ccc4nc(-c5cccnc5[C@H](C)OC)n(c4c3)CC(C)(C)COC(=O)[C@@H]3CCCN(N3)C2=O)C(C)C)C1] |
| A243 | 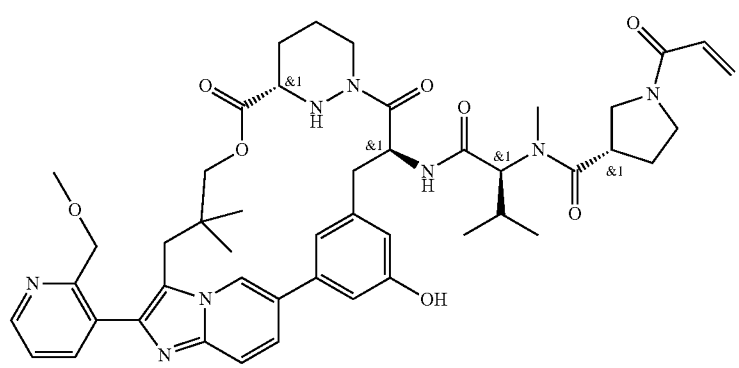 [SMILES: C=CC(=O)N1CC[C@H](C(=O)N(C)[C@H](C(=O)N[C@H]2Cc3cc(O)cc(c3)-c3ccc4nc(-c5cccnc5COC)c(n4c3)CC(C)(C)COC(=O)[C@@H]3CCCN(N3)C2=O)C(C)C)C1] |
| A244 | 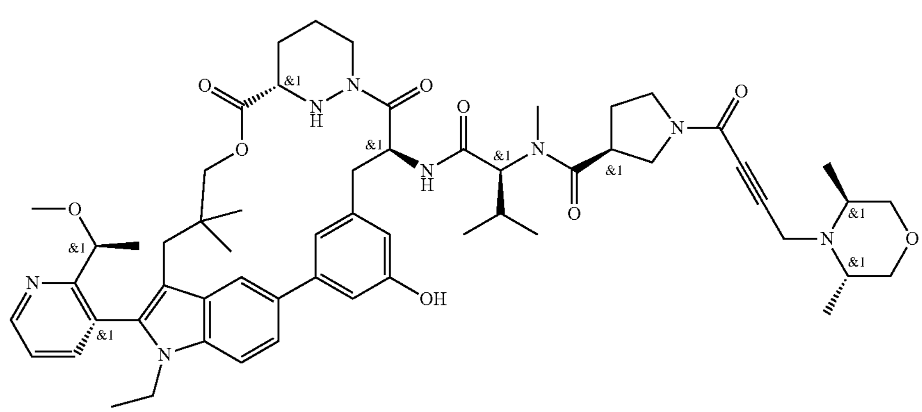 |

US 11,952,352 B2
231                                                                                         232
TABLE 1-continued
Certain Compounds of the Present Invention
| Ex# | Structure |
|---|---|
| A245 | 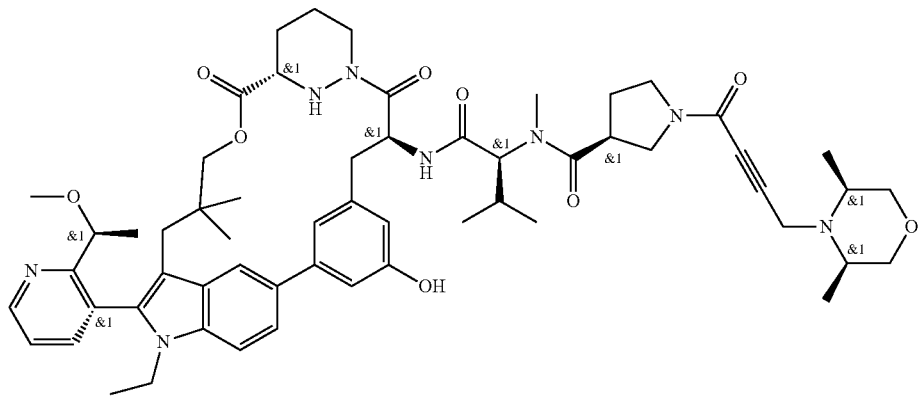 |
| A246 | 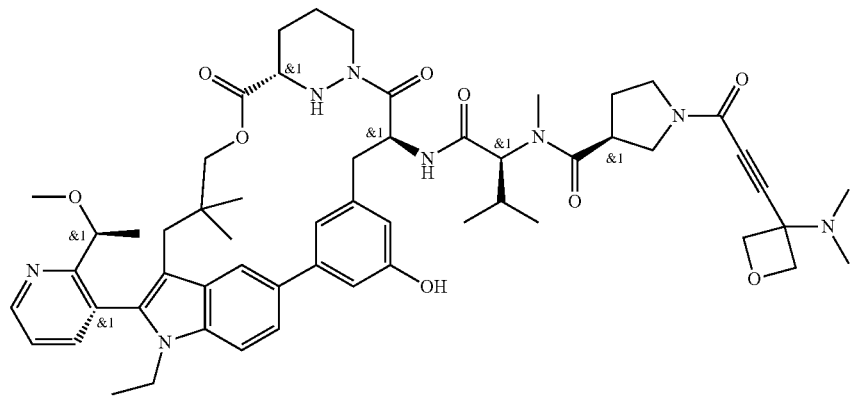 |
| A247 | 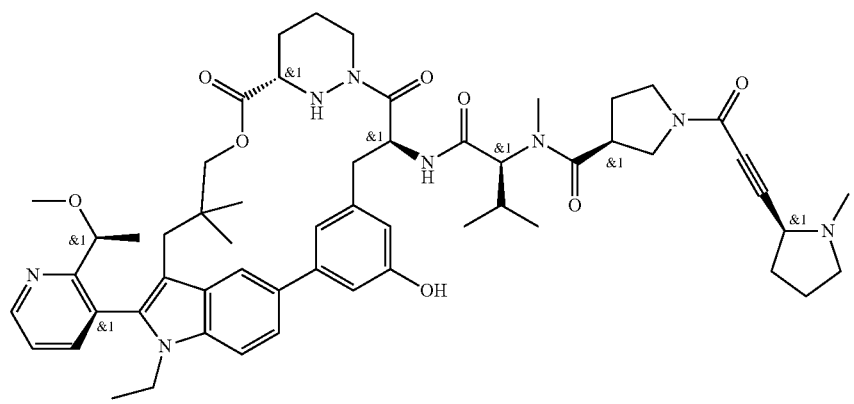 |

TABLE 1-continued

Certain Compounds of the Present Invention

| Ex# | Structure |
|---|---|
| A248 | 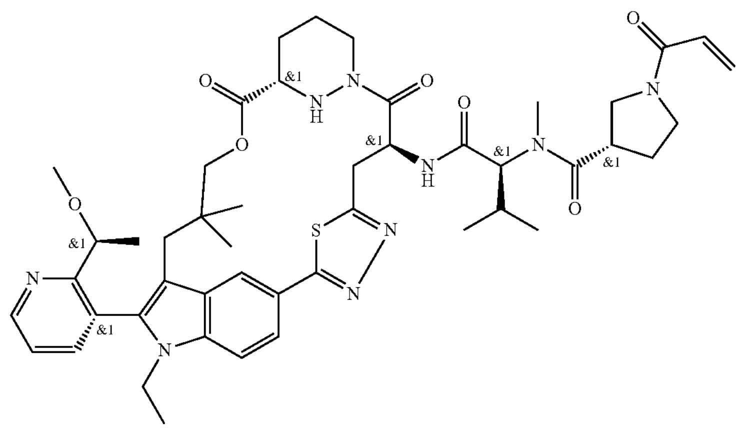 |
| A249 | 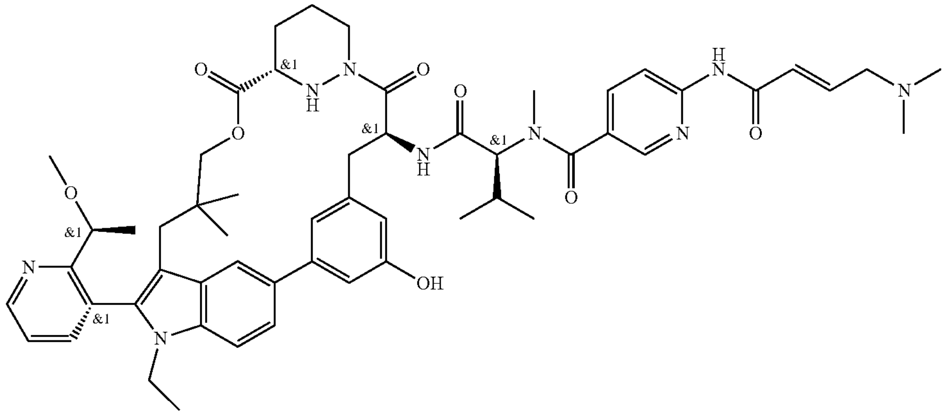 |
| A250 | 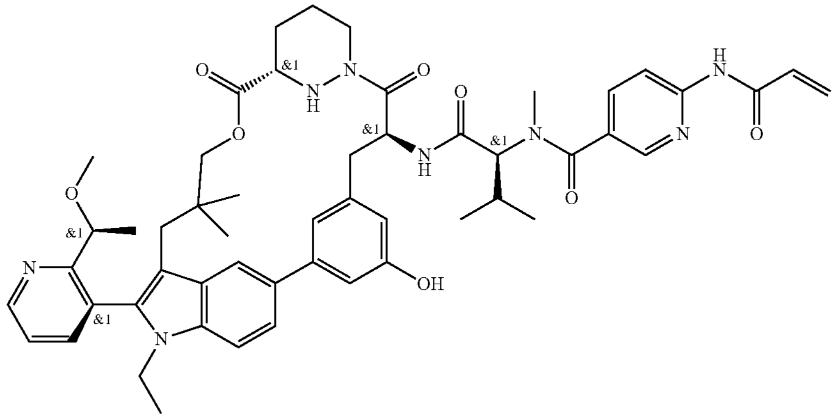 |

TABLE 1-continued
Certain Compounds of the Present Invention
| Ex# | Structure |
|---|---|
| A251 | 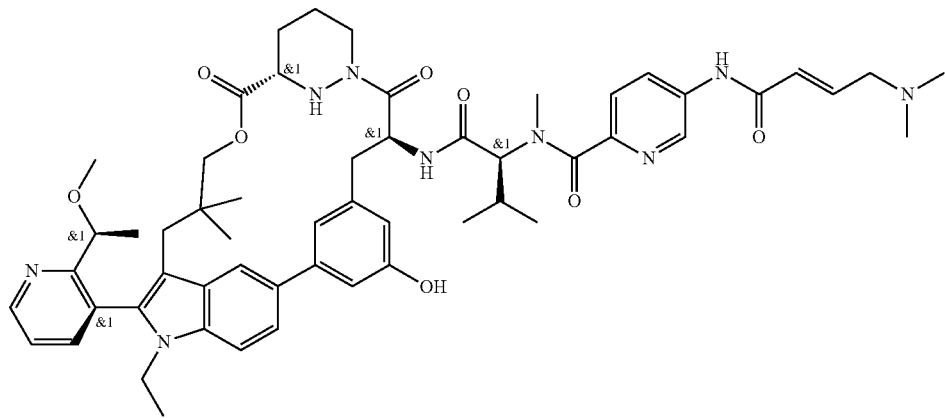 |
| A252 | 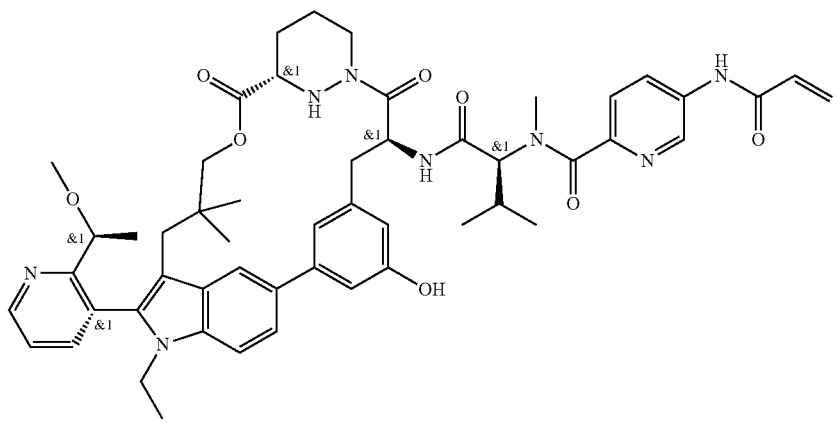 |
| A253 | 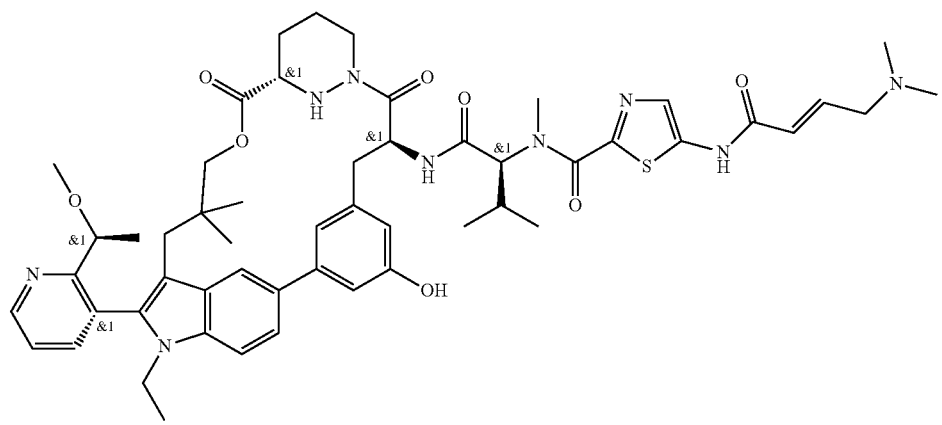 |

TABLE 1-continued
Certain Compounds of the Present Invention
| Ex# | Structure |
|---|---|
| A254 | 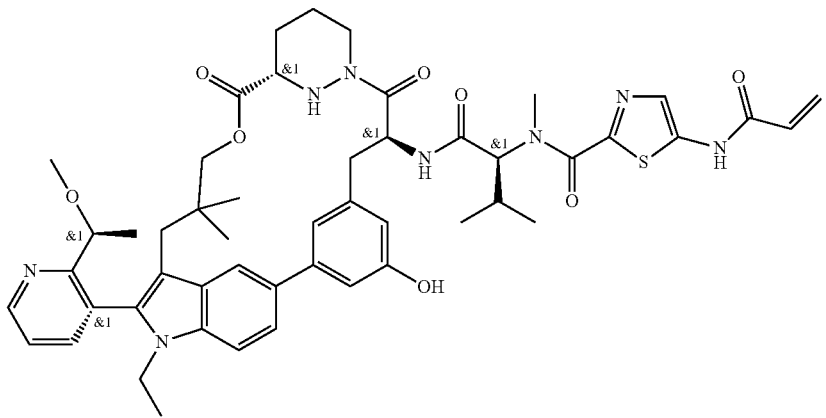 |
| A255 | 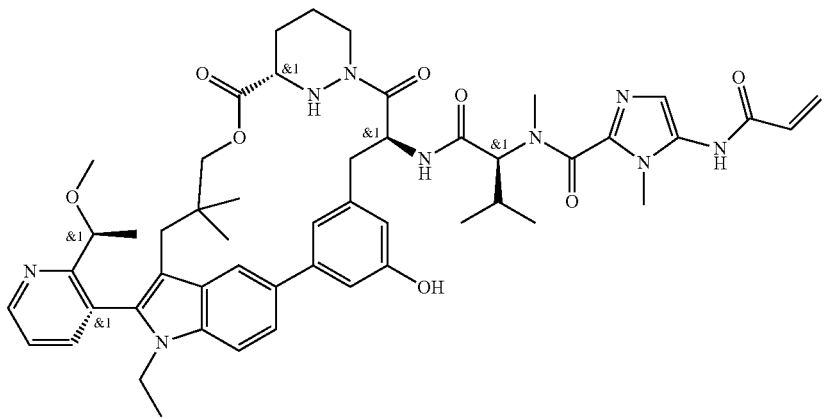 |
| A256 | 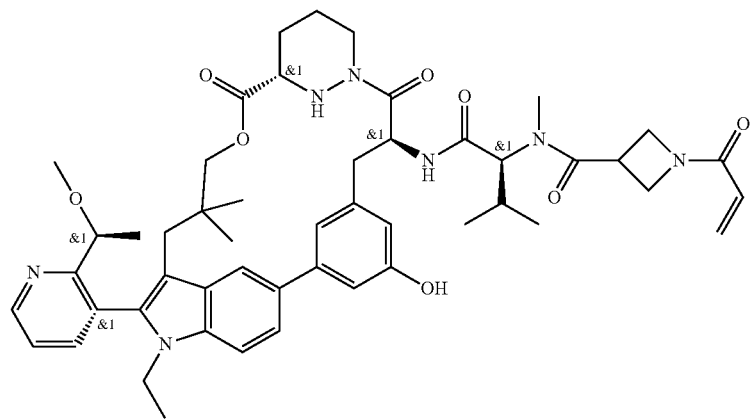 |

TABLE 1-continued
Certain Compounds of the Present Invention
| Ex# | Structure |
|---|---|
| A257 | 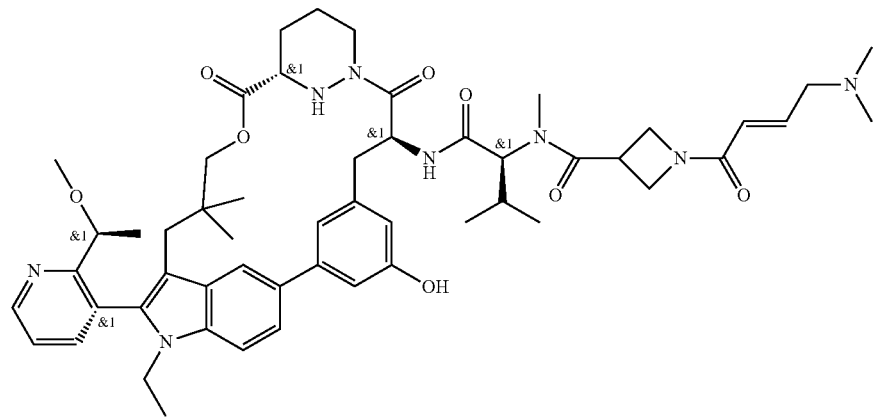 |
| A258 | 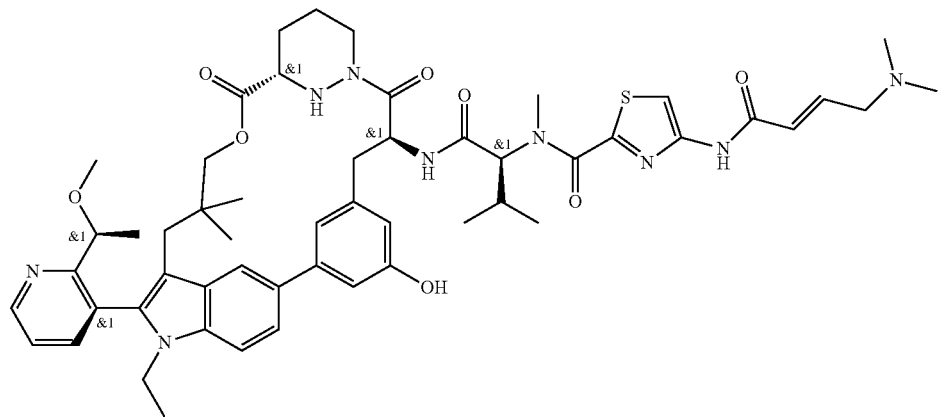 |
| A259 | 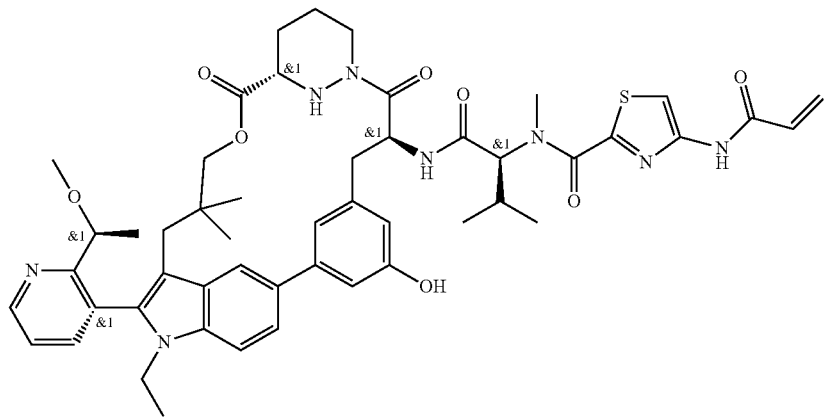 |

TABLE 1-continued
Certain Compounds of the Present Invention
| Ex# | Structure |
|---|---|
| A260 | 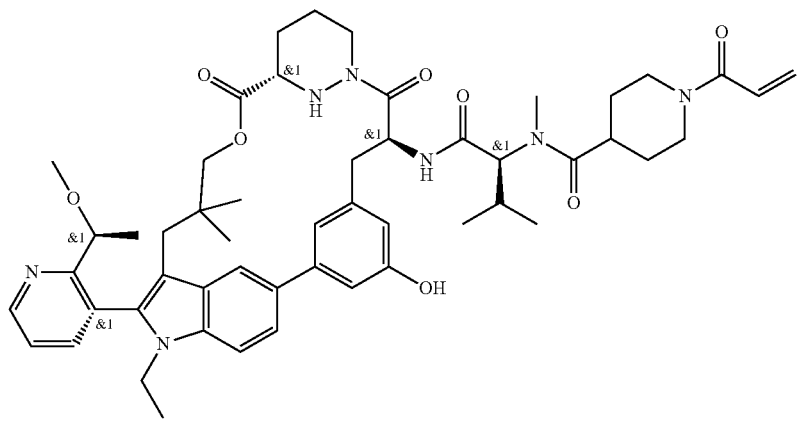 |
| A261 | 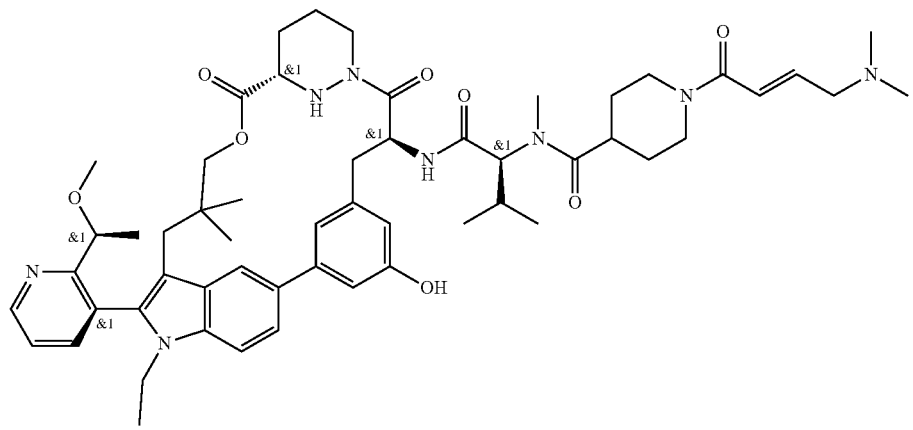 |
| A262 | 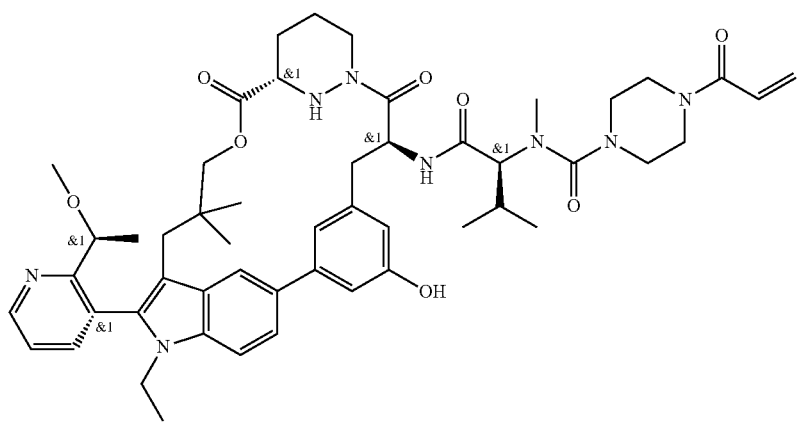 |

TABLE 1-continued
Certain Compounds of the Present Invention
| Ex# | Structure |
|---|---|
| A263 | 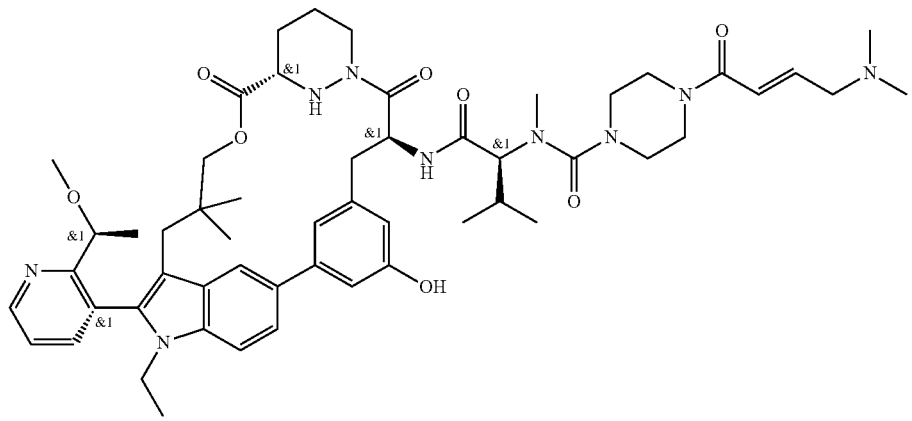 |
| A264 | 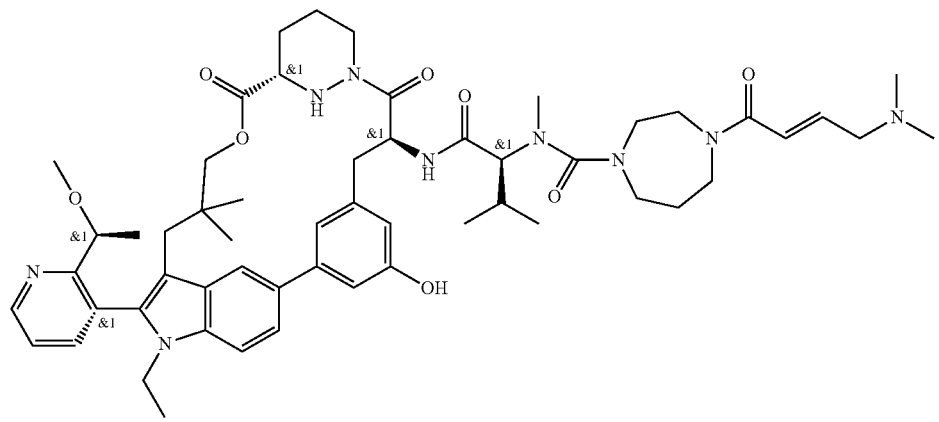 |
| A265 | 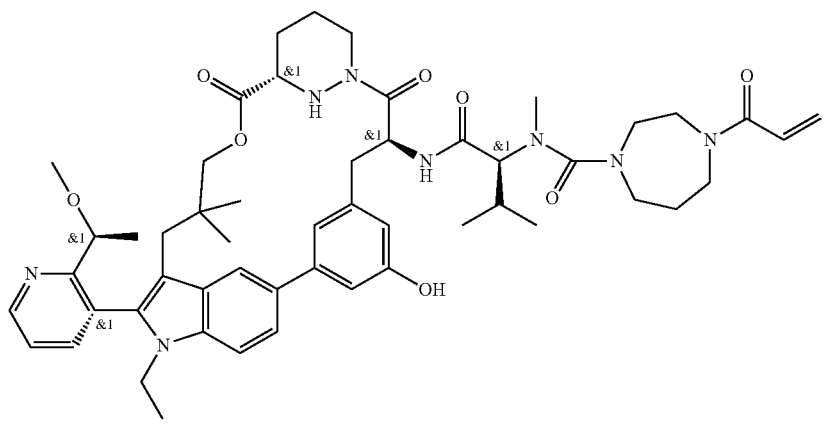 |

US 11,952,352 B2
245                                                                                               246
TABLE 1-continued
Certain Compounds of the Present Invention
| Ex# | Structure |
|---|---|
A266
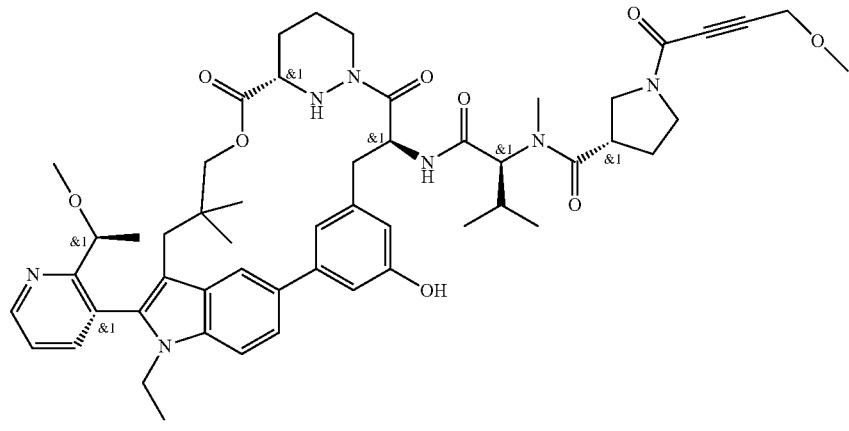
A267
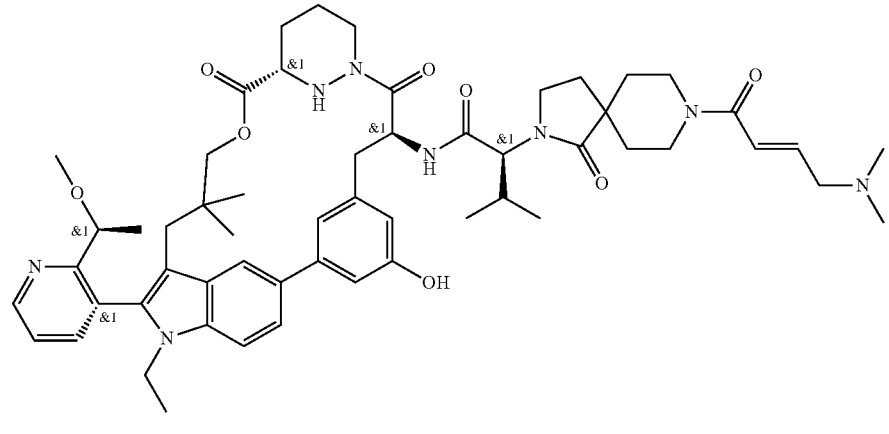
A268
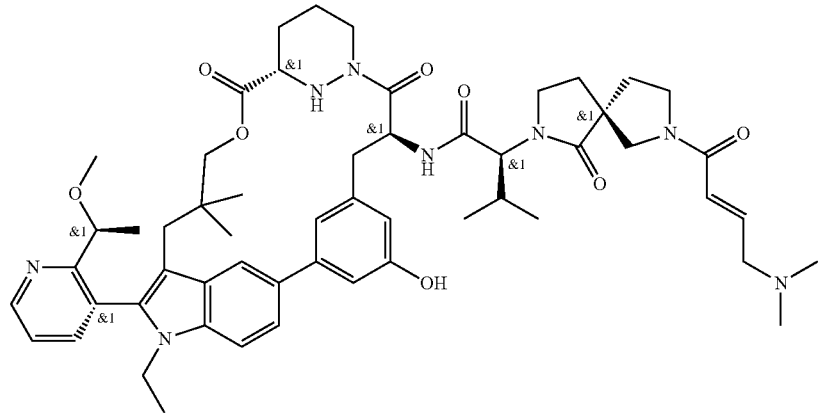

TABLE 1-continued
Certain Compounds of the Present Invention
| Ex# | Structure |
| --- | --- |
| A269 | 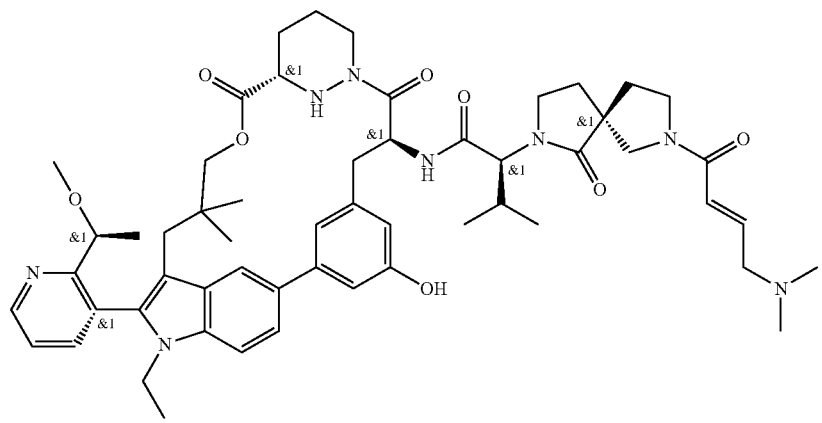 |
| A270 | 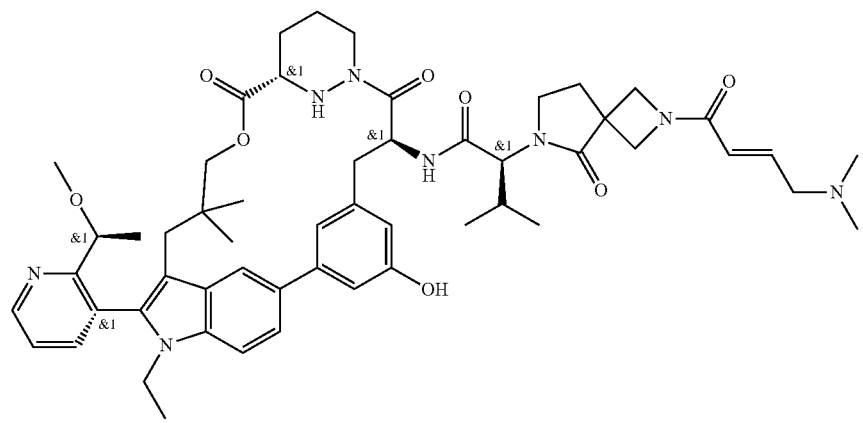 |
| A271 | 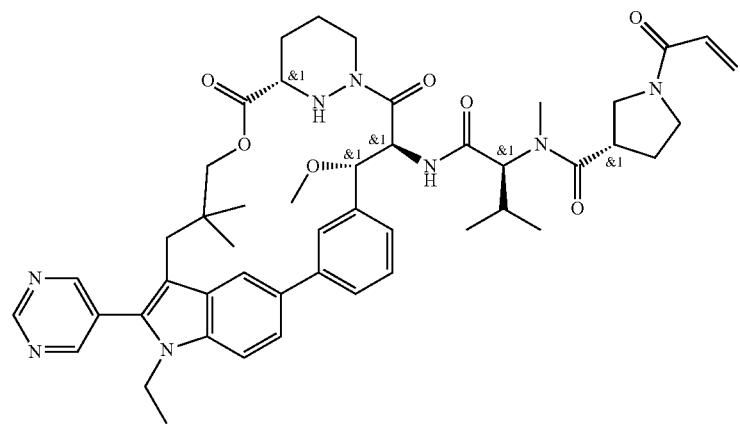 [SMILES: C=CC(=O)N1CC[C@H](C(=O)N(C)[C@H](C(=O)N[C@@H]2C(=O)N3CCC[C@H](N3)C(=O)OCC(C)(C)Cc3c(-c4cncnc4)n(CC)c4ccc(cc34)-c3cccc(c3)[C@@H]2OC)C(C)C)C1] |

US 11,952,352 B2
TABLE 1-continued
Certain Compounds of the Present Invention
| Ex# | Structure |
|---|---|
| A272 | 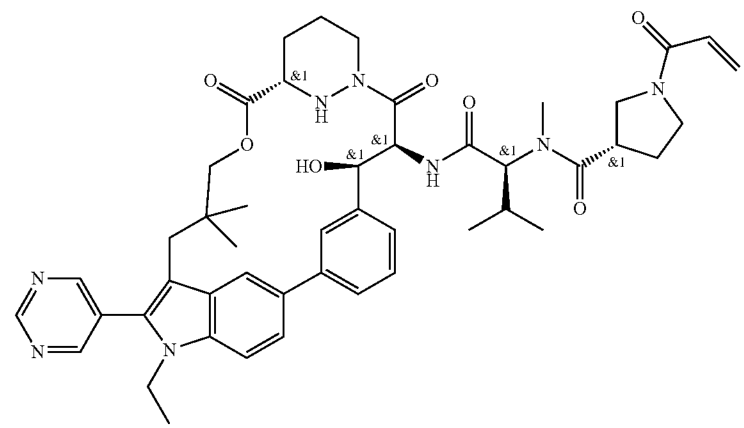 [SMILES: C=CC(=O)N1CC[C@H](C(=O)N(C)[C@H](C(=O)N[C@@H]2C(=O)N3CCC[C@H](N3)C(=O)OCC(C)(C)Cc3c(-c4cncnc4)n(CC)c4ccc(cc34)-c3cccc(c3)[C@H]2O)C(C)C)C1] |
| A273 | 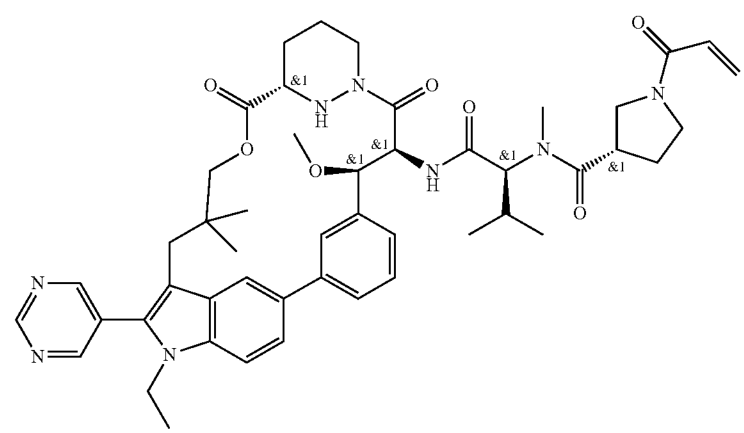 [SMILES: C=CC(=O)N1CC[C@H](C(=O)N(C)[C@H](C(=O)N[C@@H]2C(=O)N3CCC[C@H](N3)C(=O)OCC(C)(C)Cc3c(-c4cncnc4)n(CC)c4ccc(cc34)-c3cccc(c3)[C@H]2OC)C(C)C)C1] |
| A274 | 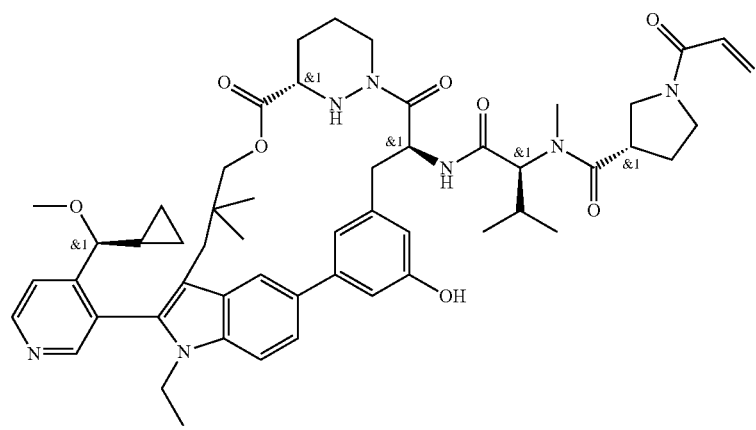 [SMILES: C=CC(=O)N1CC[C@H](C(=O)N(C)[C@H](C(=O)N[C@H]2Cc3cc(O)cc(c3)-c3ccc4c(c3)c(c(-c3cnccc3[C@@H](OC)C3CC3)n4CC)CC(C)(C)COC(=O)[C@@H]3CCCN(N3)C2=O)C(C)C)C1] |

TABLE 1-continued
Certain Compounds of the Present Invention
| Ex# | Structure |
|---|---|
| A275 | 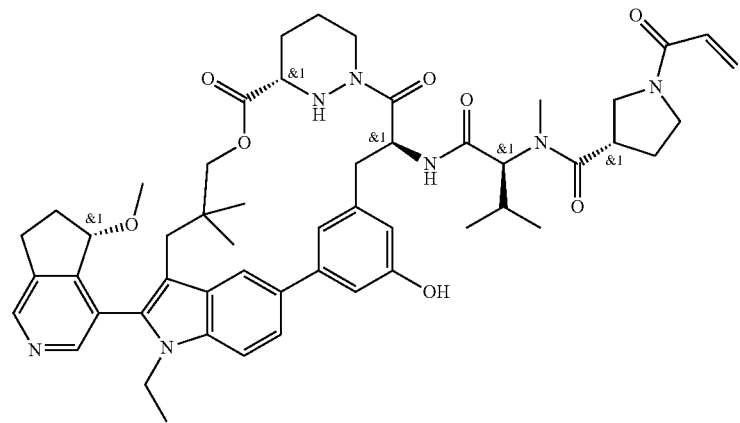 [SMILES: C=CC(=O)N1CC[C@H](C(=O)N(C)[C@H](C(=O)N[C@H]2Cc3cc(O)cc(c3)-c3ccc4c(c3)c(c(-c3cncc5c3[C@@H](OC)CC5)n4CC)CC(C)(C)COC(=O)[C@@H]3CCCN(N3)C2=O)C(C)C)C1] |
| A276 | 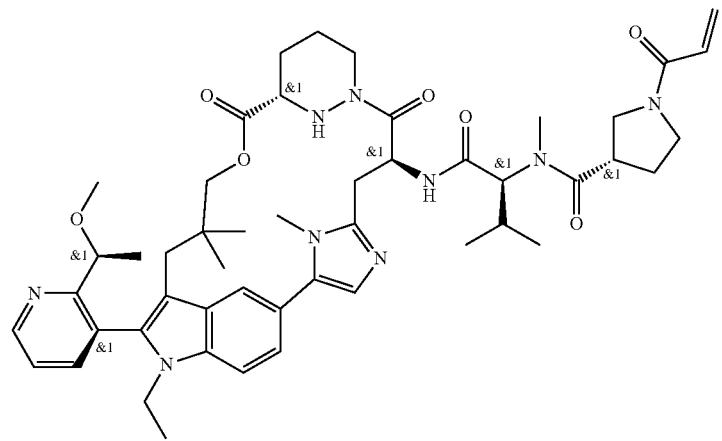 |
| A277 | 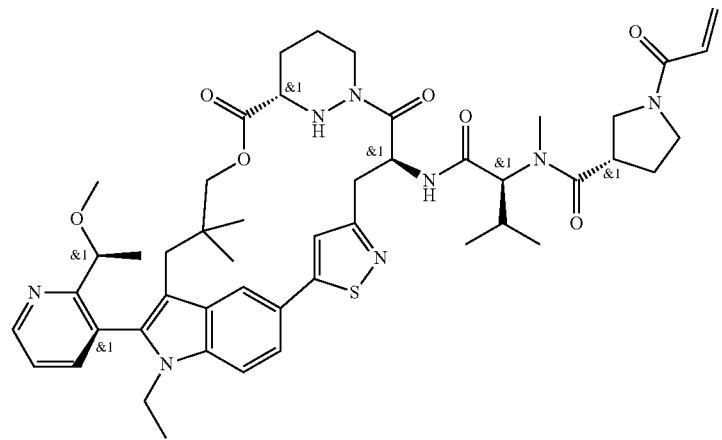 |

TABLE 1-continued
Certain Compounds of the Present Invention
| Ex# | Structure |
|---|---|
| A278 | 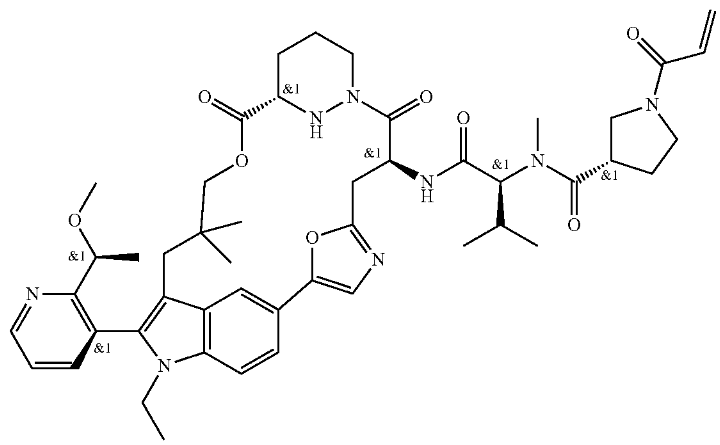 |
| A279 | 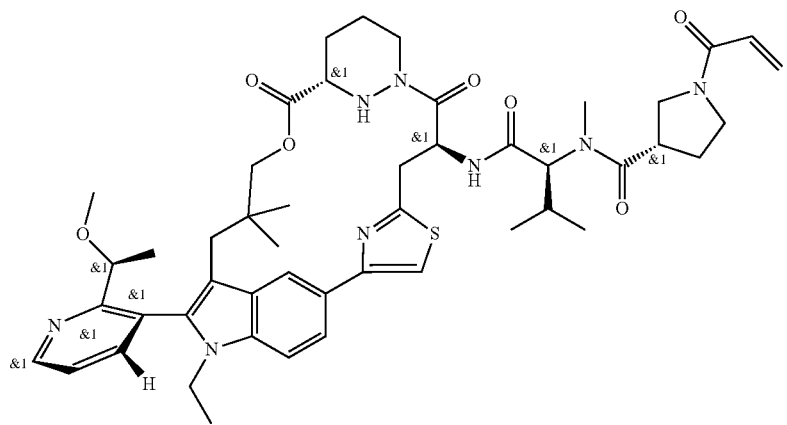 |
| A280 | 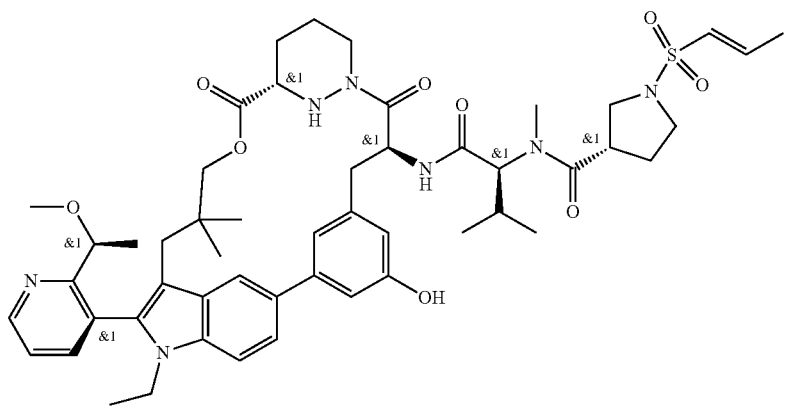 |

TABLE 1-continued
Certain Compounds of the Present Invention
| Ex# | Structure |
|---|---|
| A281 | 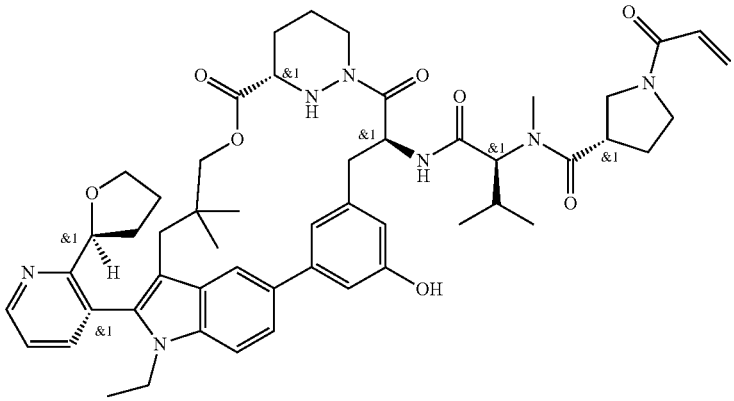 |
| A282 | 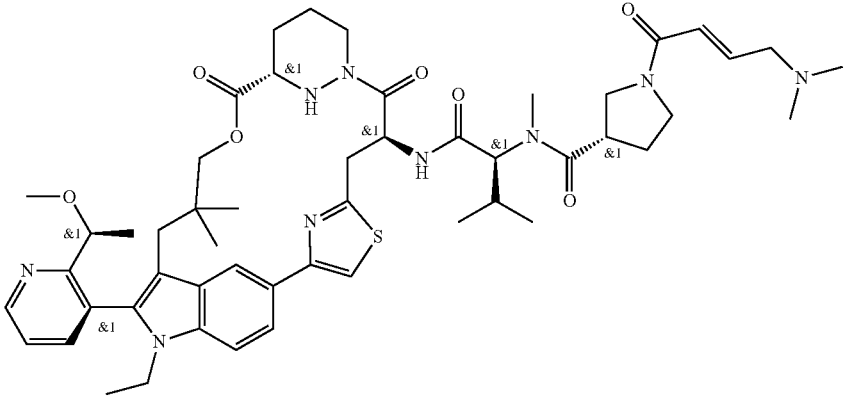 |
| A283 | 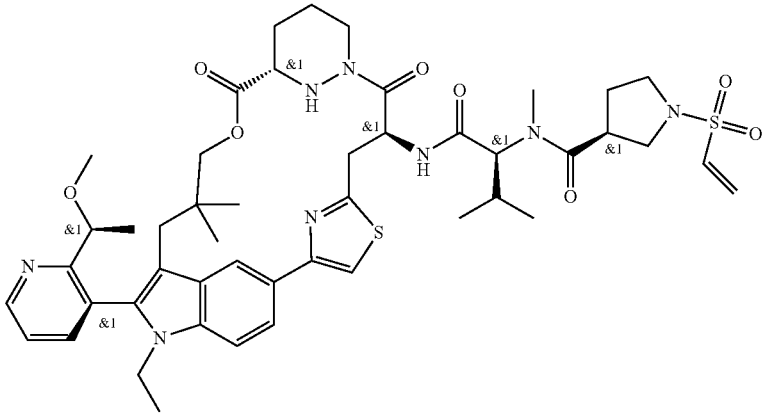 |

US 11,952,352 B2
TABLE 1-continued
Certain Compounds of the Present Invention
| Ex# | Structure |
|---|---|
| A284 | 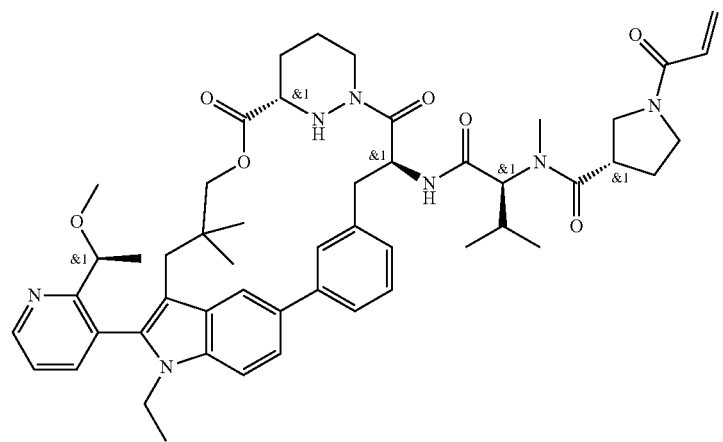 [SMILES: C=CC(=O)N1CC[C@H](C(=O)N(C)[C@H](C(=O)N[C@H]2Cc3cccc(c3)-c3ccc4c(c3)c(c(-c3cccnc3[C@H](C)OC)n4CC)CC(C)(C)COC(=O)[C@@H]3CCCN(N3)C2=O)C(C)C)C1] |
| A285 | 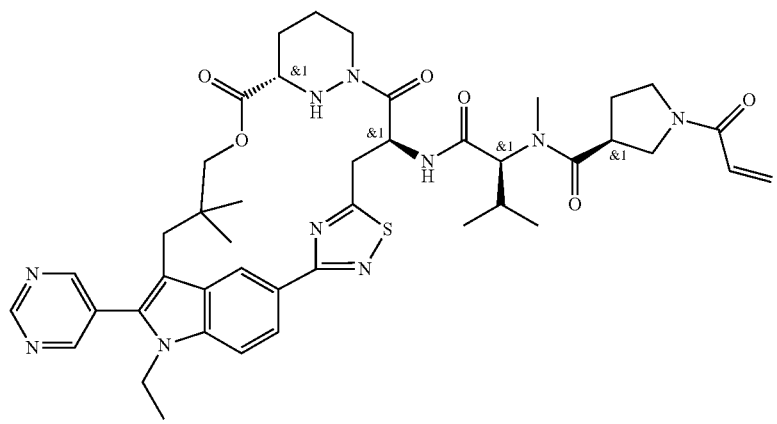 [SMILES: C=CC(=O)N1CC[C@H](C(=O)N(C)[C@H](C(=O)N[C@H]2Cc3nc(ns3)-c3ccc4c(c3)c(c(-c3cncnc3)n4CC)CC(C)(C)COC(=O)[C@@H]3CCCN(N3)C2=O)C(C)C)C1] |
| A286 | 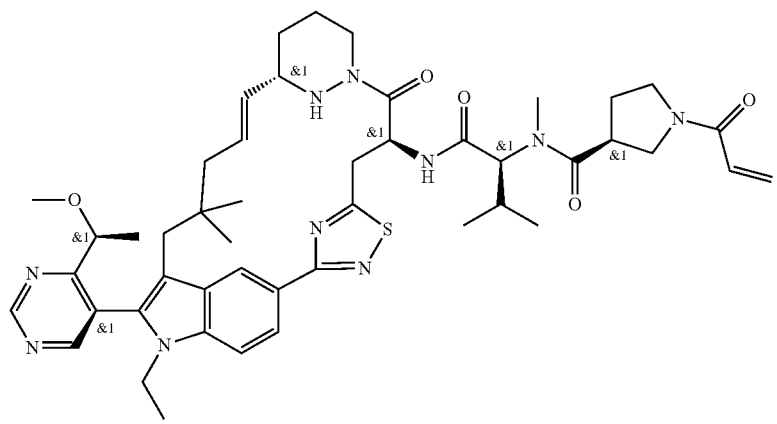 |

TABLE 1-continued
Certain Compounds of the Present Invention
| Ex# | Structure |
|---|---|
| A287 | 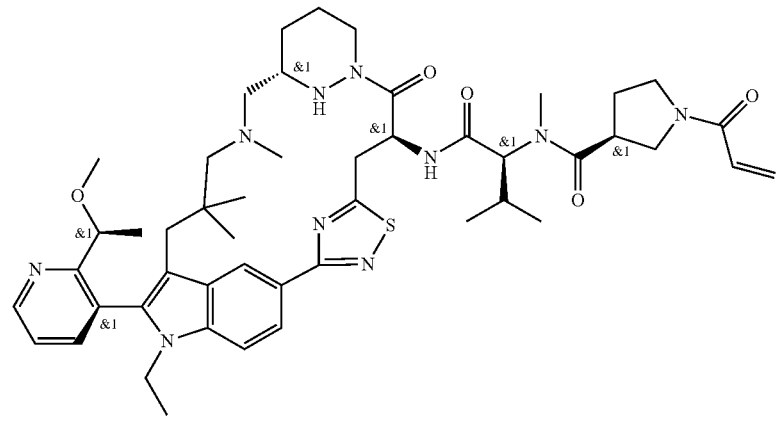 |
| A288 | 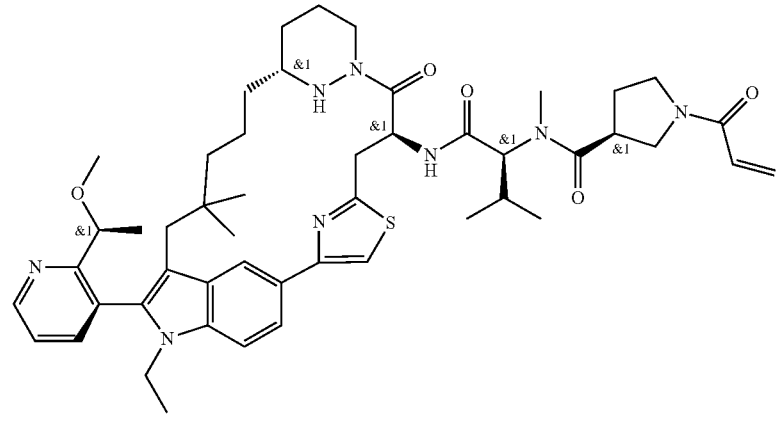 |
| A289 | 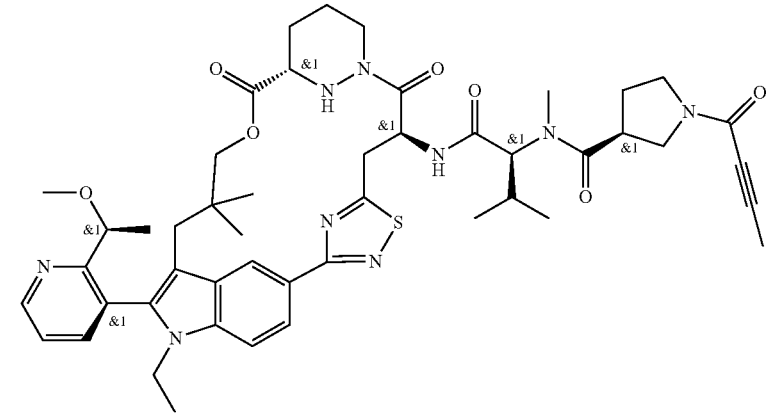 |

TABLE 1-continued
Certain Compounds of the Present Invention
| Ex# | Structure |
|---|---|
| A290 | 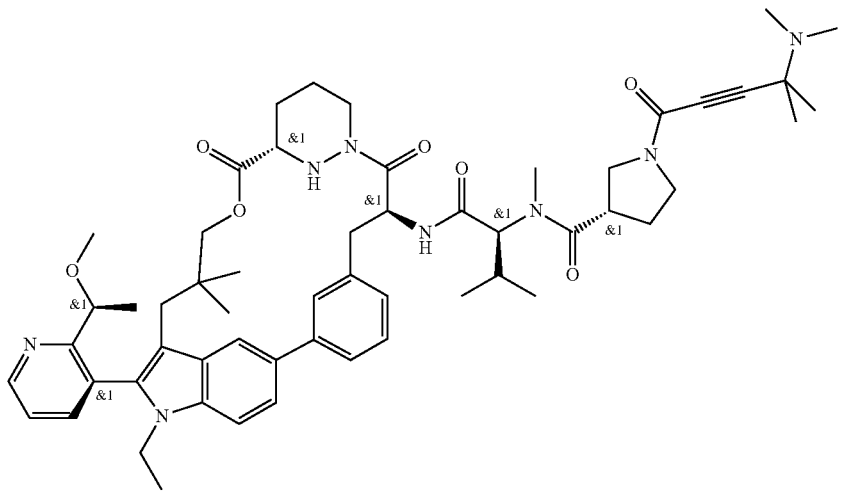 |
| A291 | 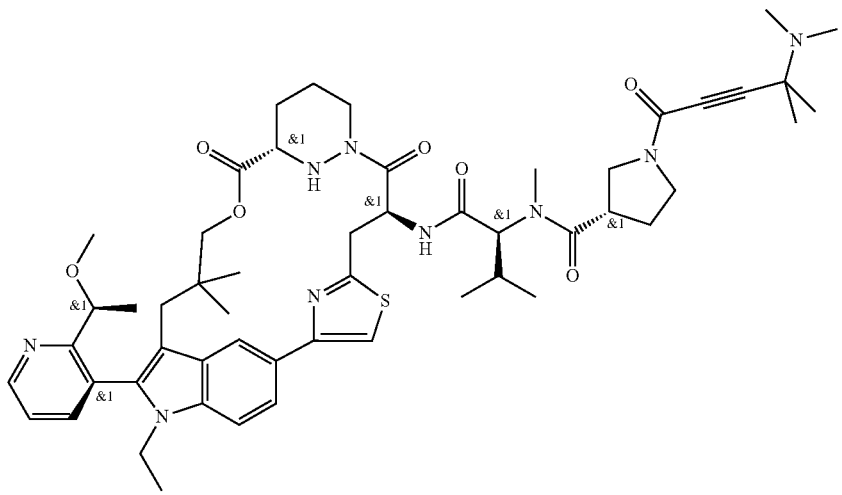 |
| A292 | 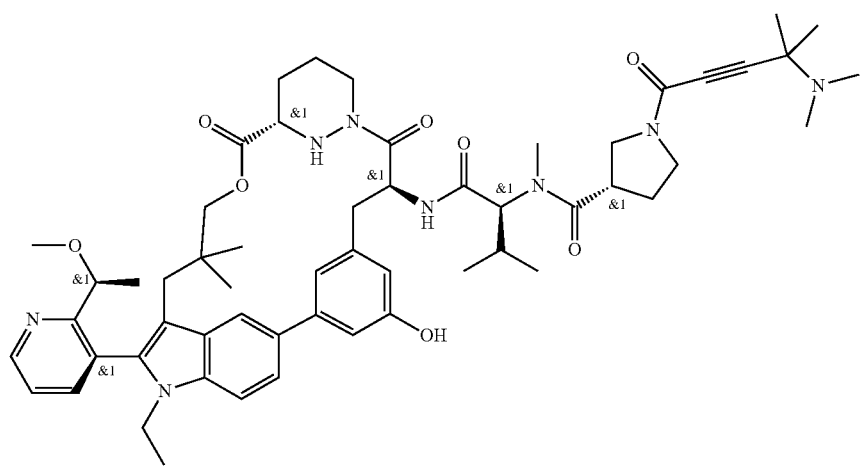 |

TABLE 1-continued
Certain Compounds of the Present Invention
| Ex# | Structure |
|---|---|
| A293 | 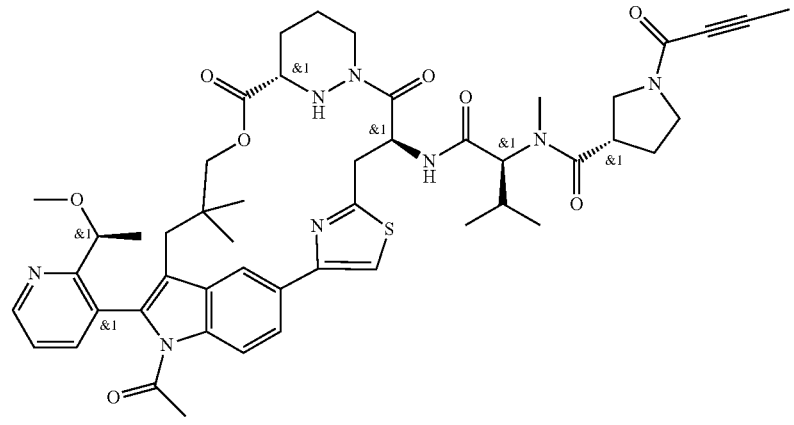 [SMILES: CC#CC(=O)N1CC[C@H](C(=O)N(C)[C@H](C(=O)N[C@H]2Cc3nc(cs3)-c3ccc4c(c3)c(c(-c3cccnc3[C@H](C)OC)n4C(C)=O)CC(C)(C)COC(=O)[C@@H]3CCCN(N3)C2=O)C(C)C)C1] |
| A294 | 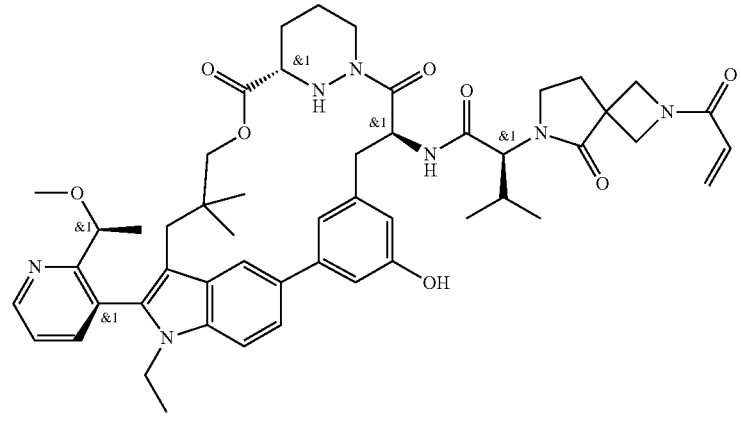 |
| A295 | 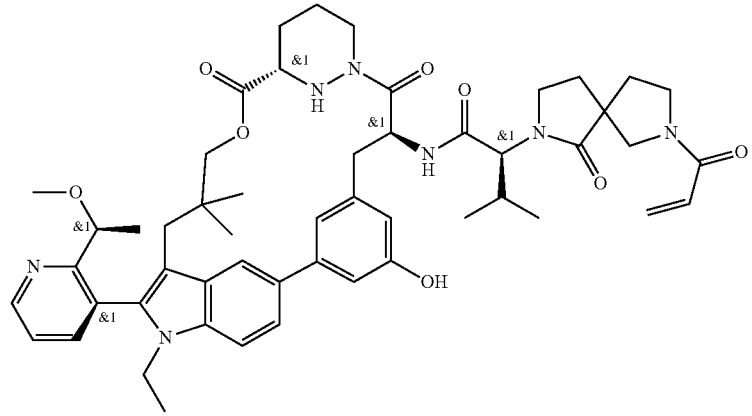 |

TABLE 1-continued
Certain Compounds of the Present Invention
| Ex# | Structure |
|---|---|
| A296 | 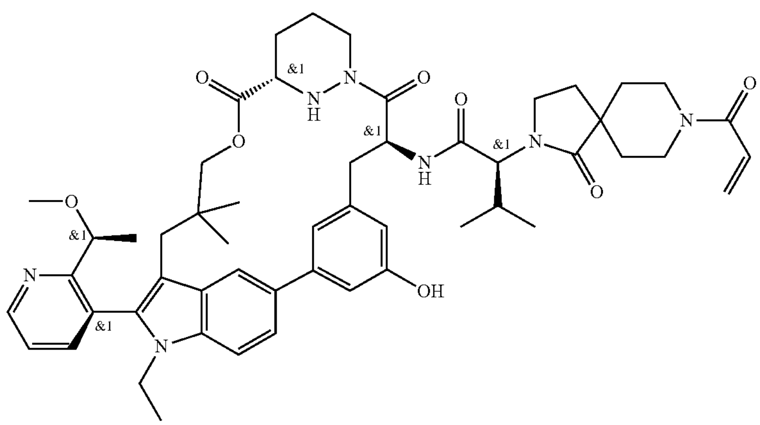 |
| A297 | 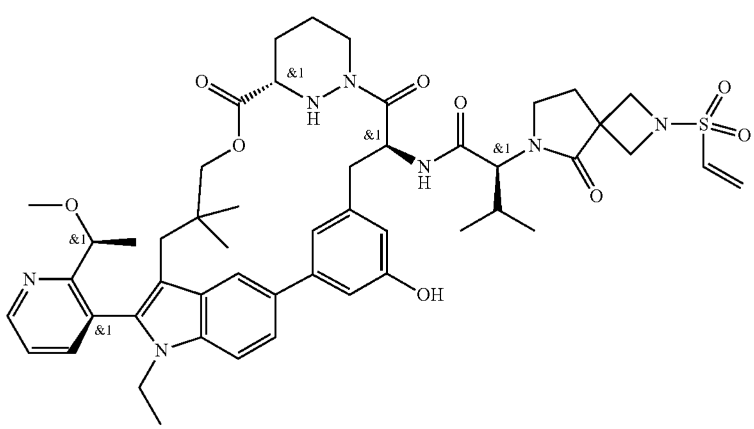 |
| A298 | 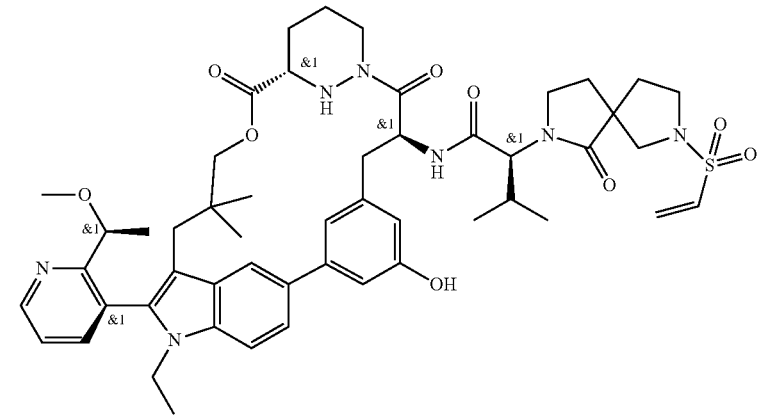 |

TABLE 1-continued
Certain Compounds of the Present Invention
| Ex# | Structure |
|---|---|
| A299 | 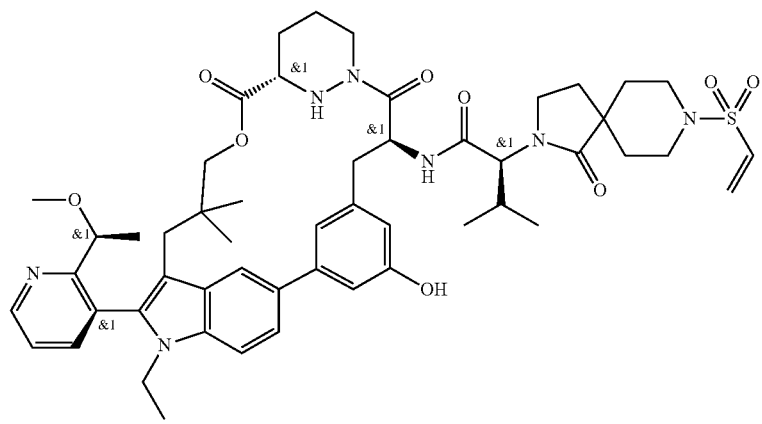 |
| A300 | 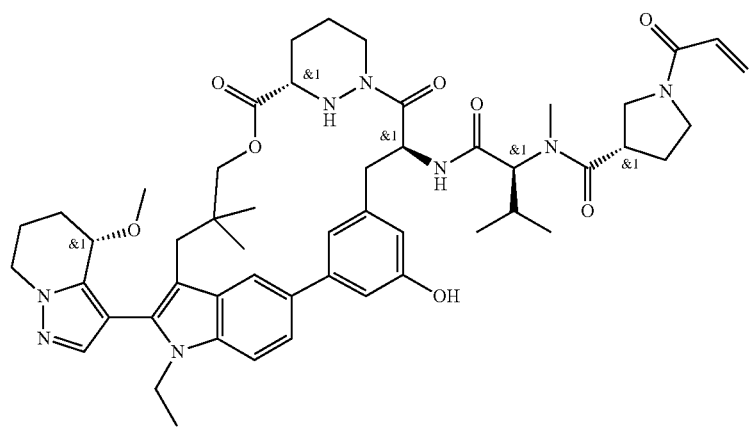 [SMILES: C=CC(=O)N1CC[C@H](C(=O)N(C)[C@H](C(=O)N[C@H]2Cc3cc(O)cc(c3)-c3ccc4c(c3)c(c(-c3cnn5c3[C@@H](OC)CCC5)n4CC)CC(C)(C)COC(=O)[C@@H]3CCCN(N3)C2=O)C(C)C)C1] |
| A301 | 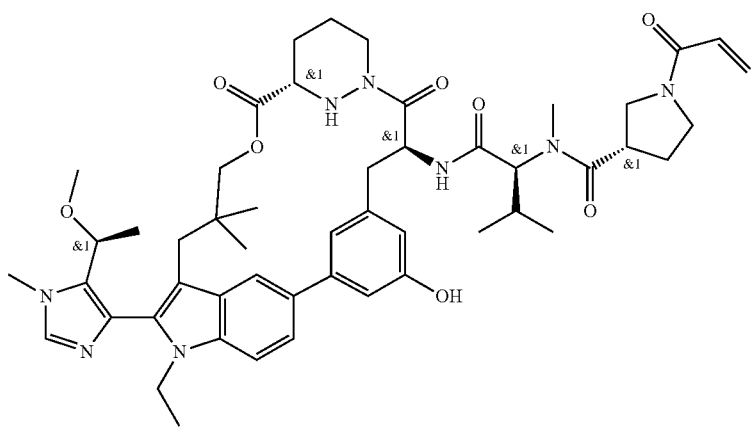 [SMILES: C=CC(=O)N1CC[C@H](C(=O)N(C)[C@H](C(=O)N[C@H]2Cc3cc(O)cc(c3)-c3ccc4c(c3)c(c(-c3ncn(C)c3[C@H](C)OC)n4CC)CC(C)(C)COC(=O)[C@@H]3CCCN(N3)C2=O)C(C)C)C1] |

TABLE 1-continued
Certain Compounds of the Present Invention
| Ex# | Structure |
|---|---|
| A302 | 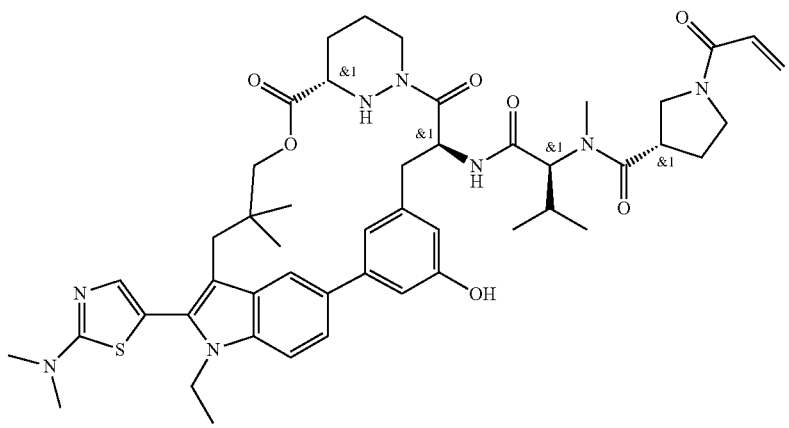 [SMILES: C=CC(=O)N1CC[C@H](C(=O)N(C)[C@H](C(=O)N[C@H]2Cc3cc(O)cc(c3)-c3ccc4c(c3)c(c(-c3cnc(N(C)C)s3)n4CC)CC(C)(C)COC(=O)[C@@H]3CCCN(N3)C2=O)C(C)C)C1] |
| A303 | 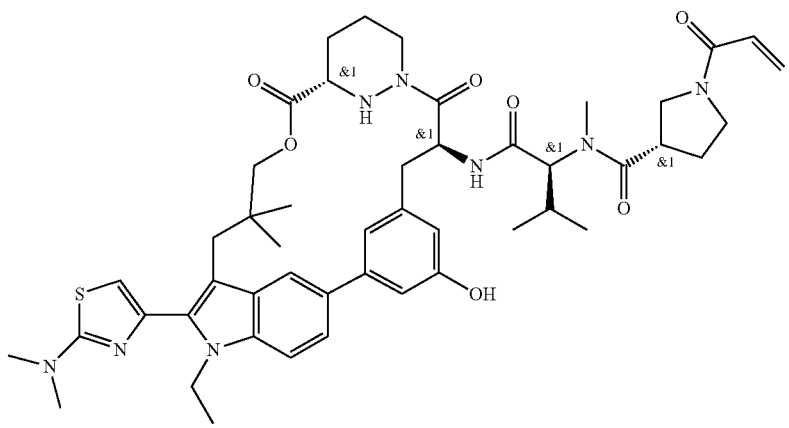 [SMILES: C=CC(=O)N1CC[C@H](C(=O)N(C)[C@H](C(=O)N[C@H]2Cc3cc(O)cc(c3)-c3ccc4c(c3)c(c(-c3csc(N(C)C)n3)n4CC)CC(C)(C)COC(=O)[C@@H]3CCCN(N3)C2=O)C(C)C)C1] |
| A304 | 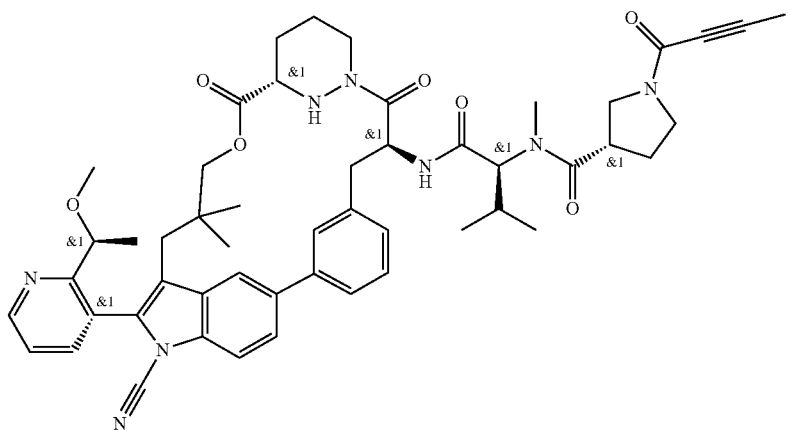 |

TABLE 1-continued
Certain Compounds of the Present Invention
| Ex# | Structure |
|---|---|
| A305 | 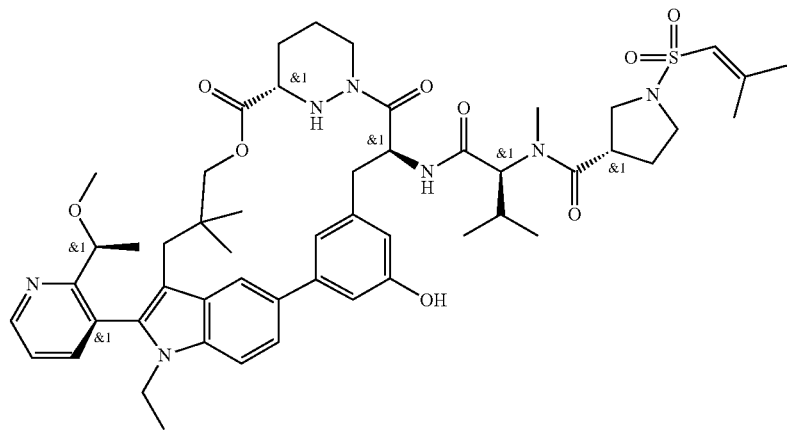 |
| A306 | 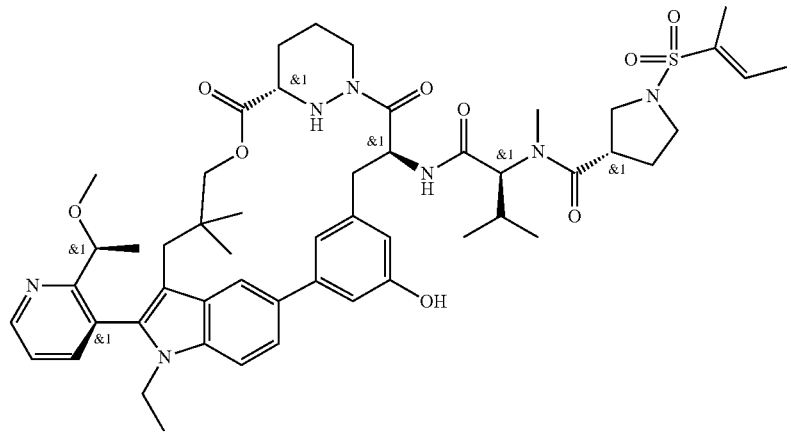 |
| A307 | 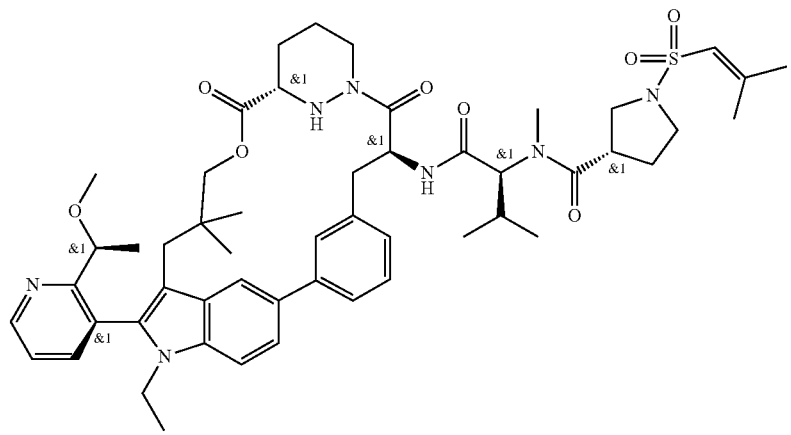 |

TABLE 1-continued
Certain Compounds of the Present Invention
| Ex# | Structure |
|---|---|
| A308 | 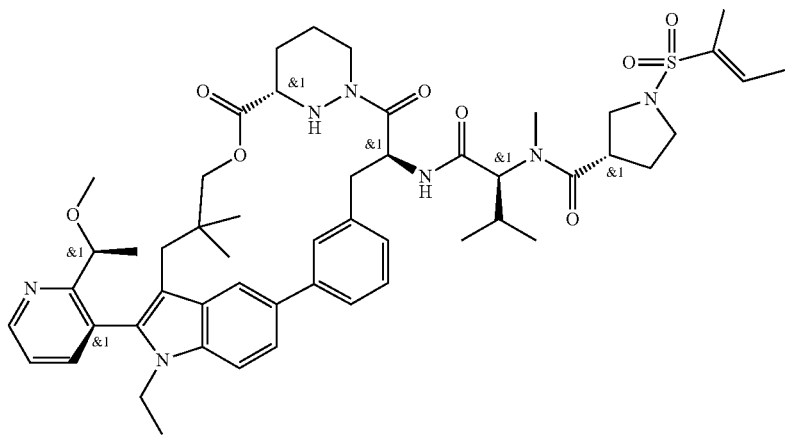 |
| A309 | 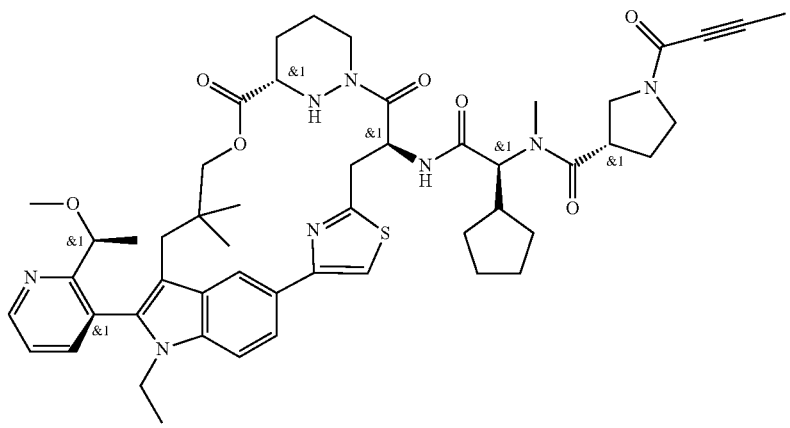 |
| A310 | 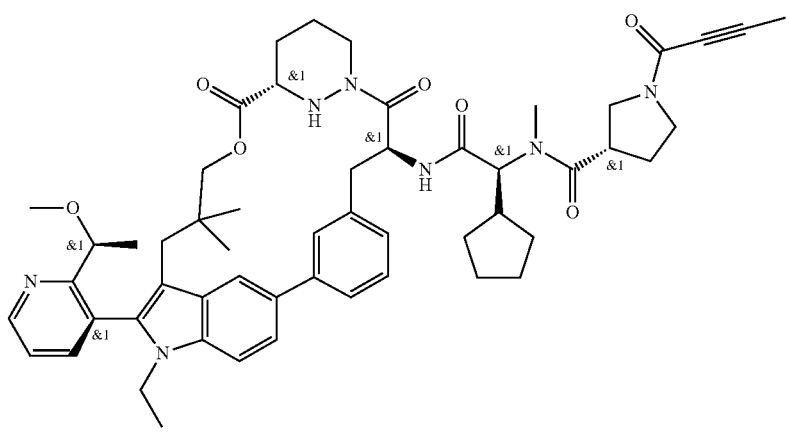 |

TABLE 1-continued
Certain Compounds of the Present Invention
| Ex# | Structure |
|---|---|
| A311 | 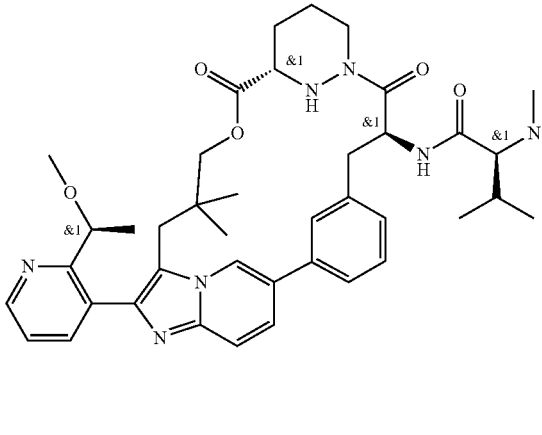 |
| A312 | 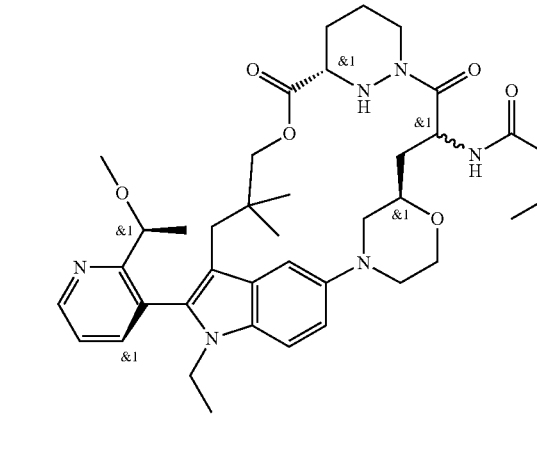 |
| A313 | 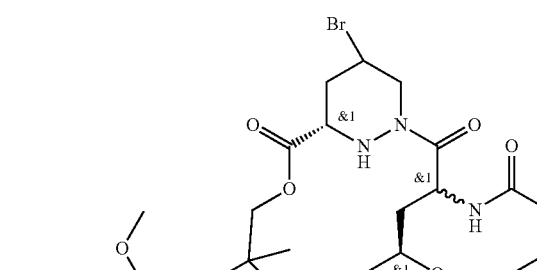 |

TABLE 1-continued
Certain Compounds of the Present Invention
| Ex# | Structure |
|---|---|
| A314 | 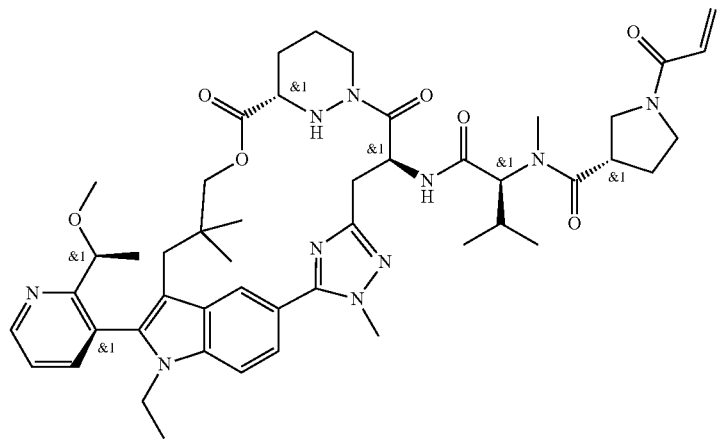 |
| A316 | 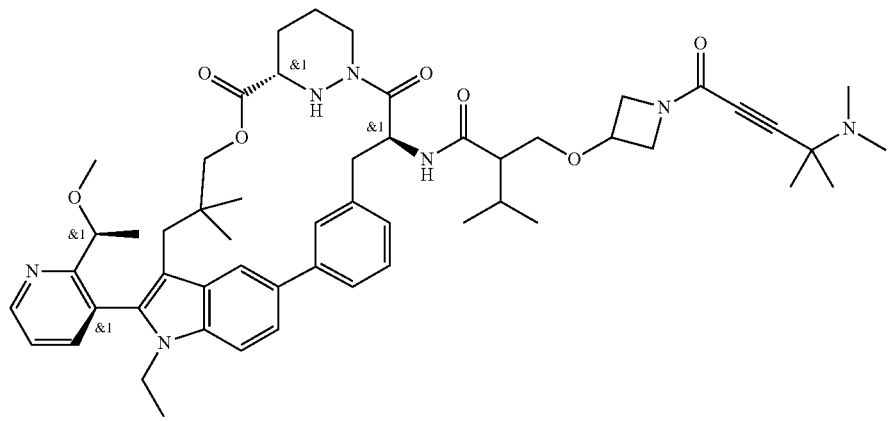 |
| A317 | 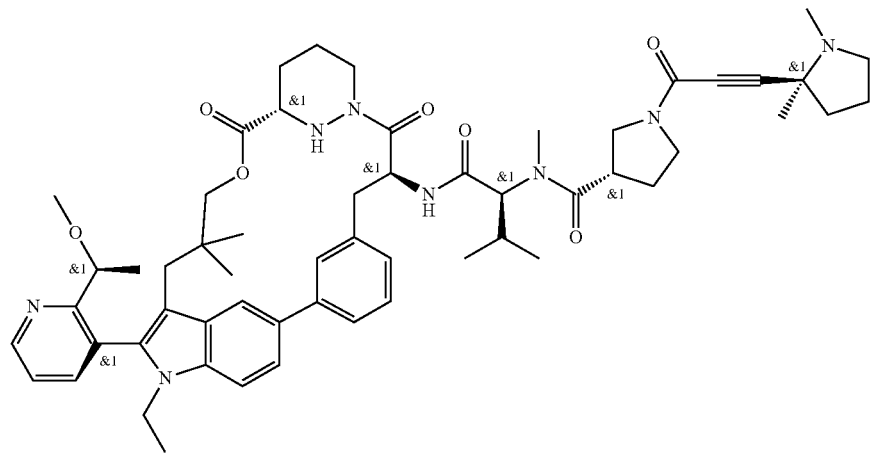 |

TABLE 1-continued
Certain Compounds of the Present Invention
| Ex# | Structure |
|---|---|
| A318 | 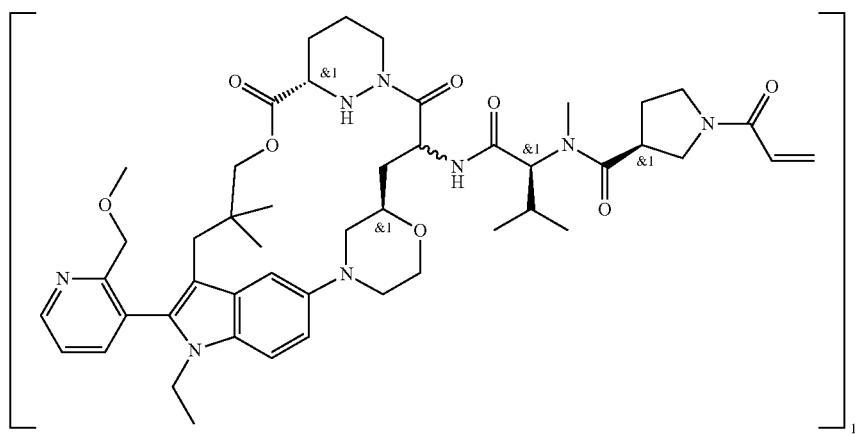 |
| A319 | 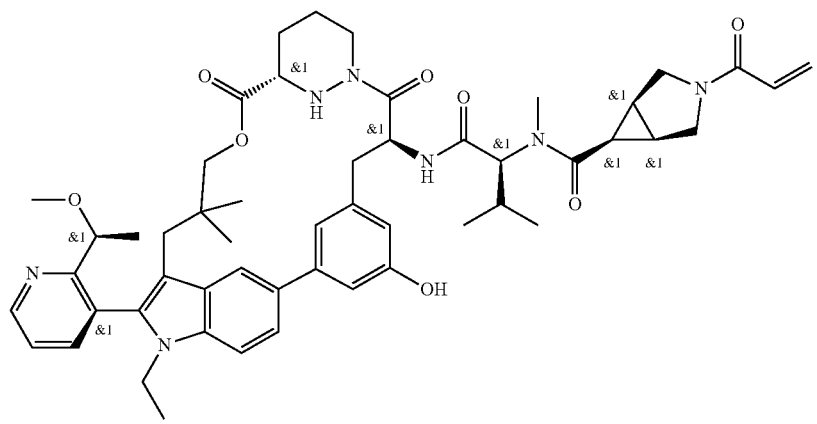 |
| A320 | 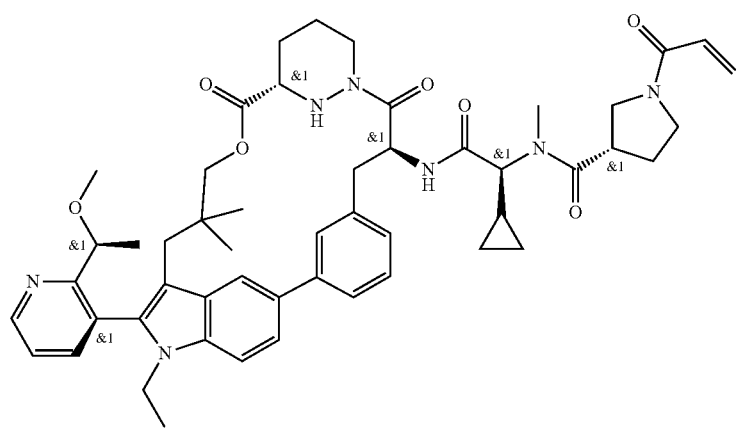 |

| Ex# | Structure |
|---|---|
| A321 | 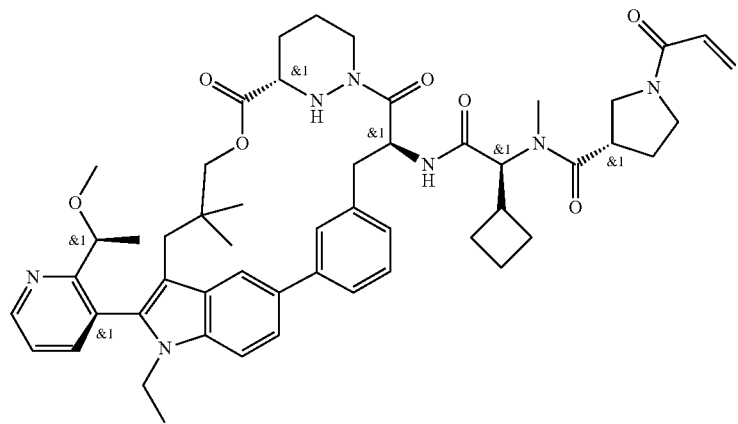 |
| A322 | 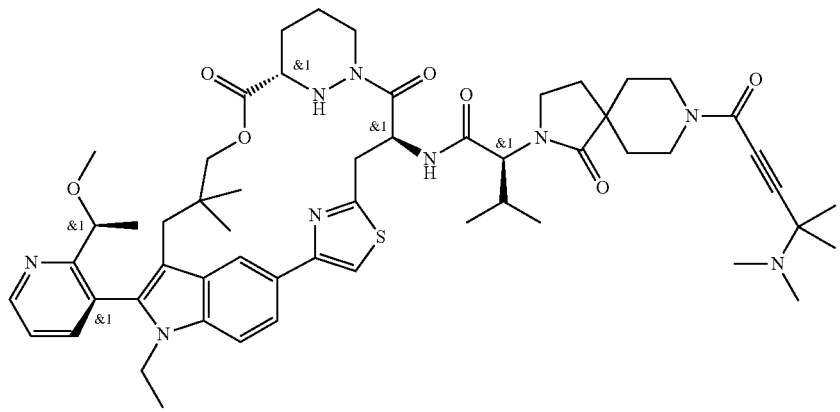 |
| A323 | 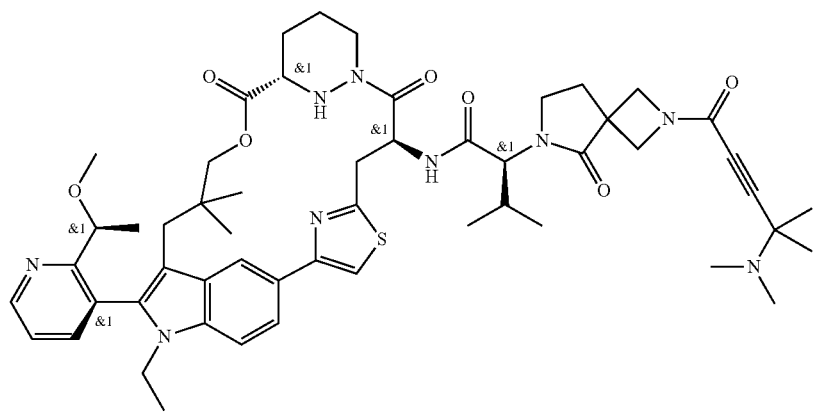 |

US 11,952,352 B2
283 284
TABLE 1-continued
Certain Compounds of the Present Invention
| Ex# | Structure |
|---|---|
| A324 | 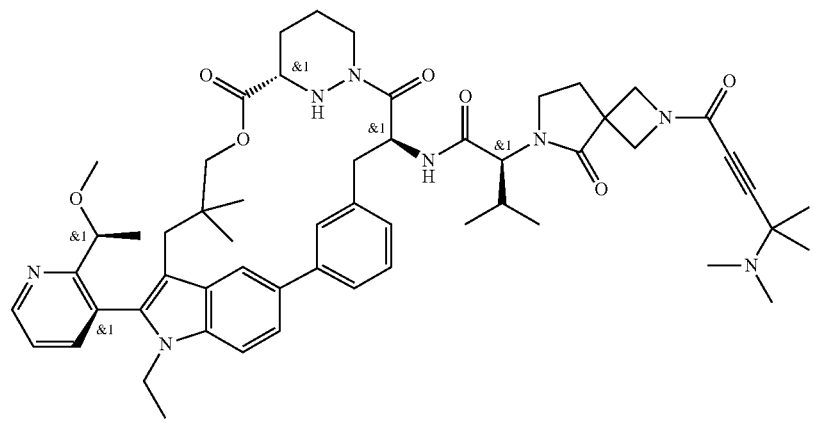 |
| A325 | 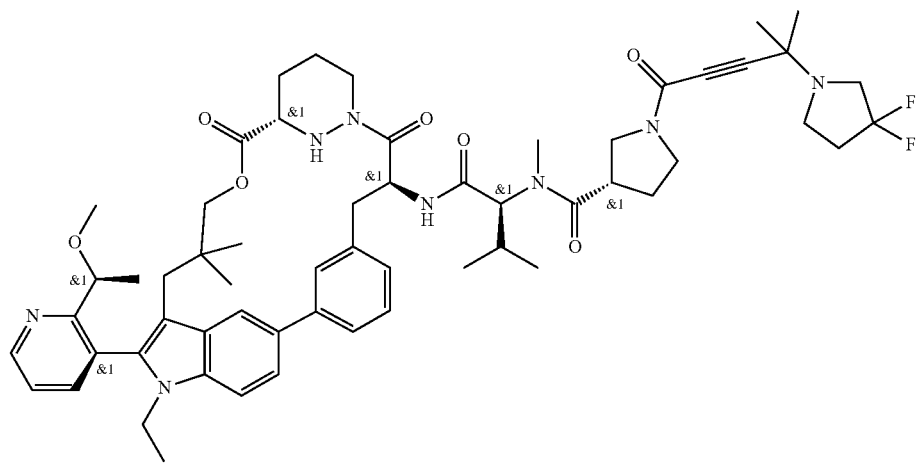 |
| A326 | 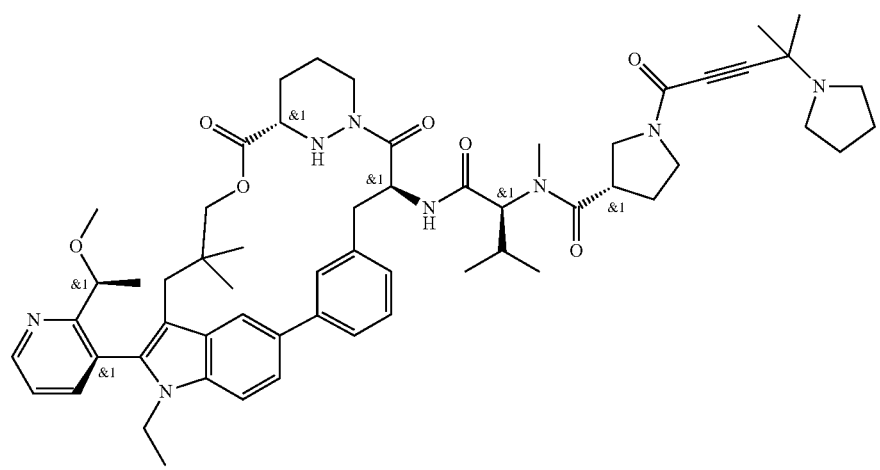 |

TABLE 1-continued
Certain Compounds of the Present Invention
| Ex# | Structure |
|---|---|
| A327 | 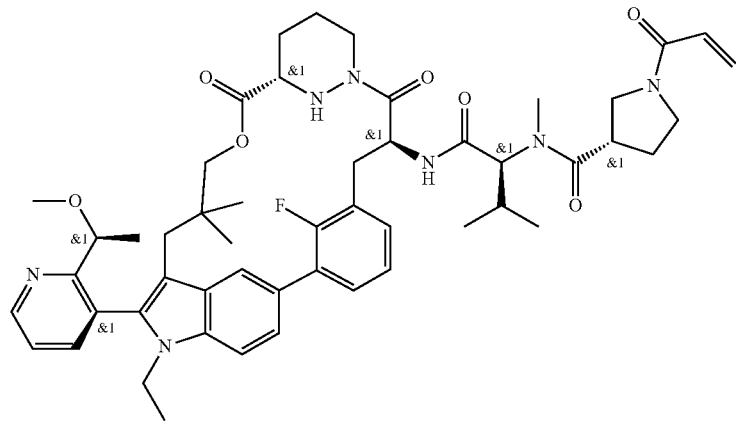 |
| A328 | 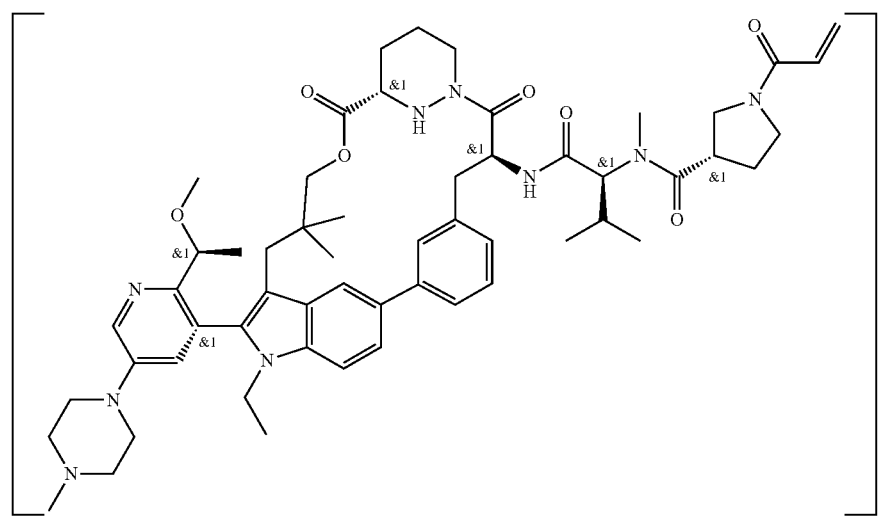 |
| A329 | 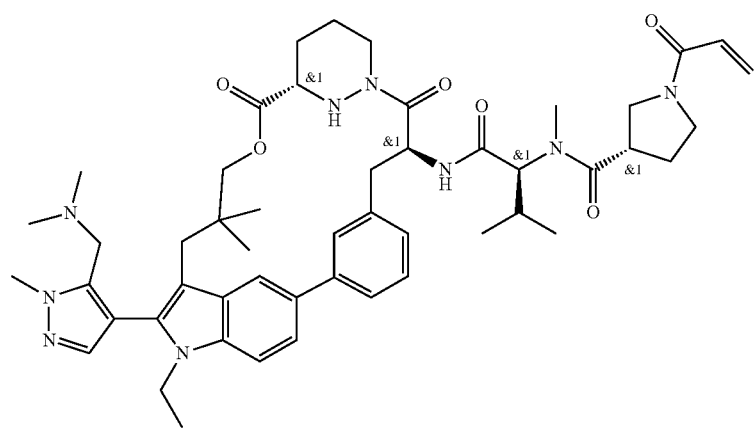 [SMILES: C=CC(=O)N1CC[C@H](C(=O)N(C)[C@H](C(=O)N[C@H]2Cc3cccc(c3)-c3ccc4c(c3)c(c(-c3cnn(C)c3CN(C)C)n4CC)CC(C)(C)COC(=O)[C@@H]3CCCN(N3)C2=O)C(C)C)C1] |

TABLE 1-continued
Certain Compounds of the Present Invention
| Ex# | Structure |
|---|---|
| A330 | 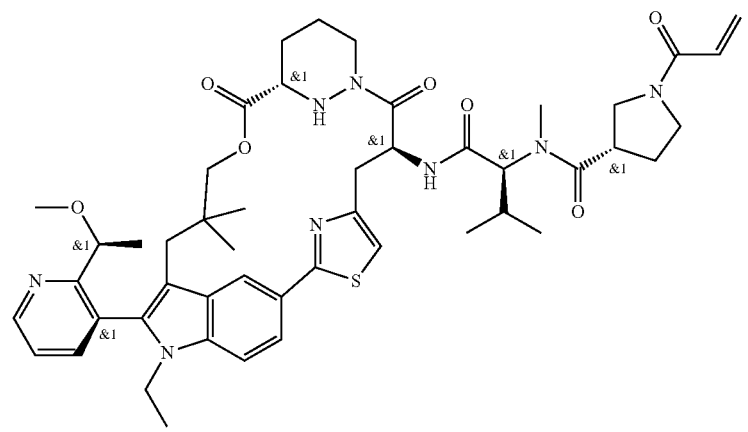 |
| A331 | 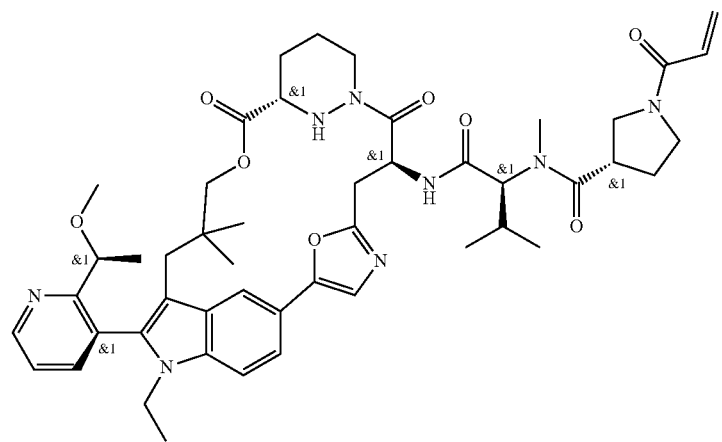 |
| A332 | 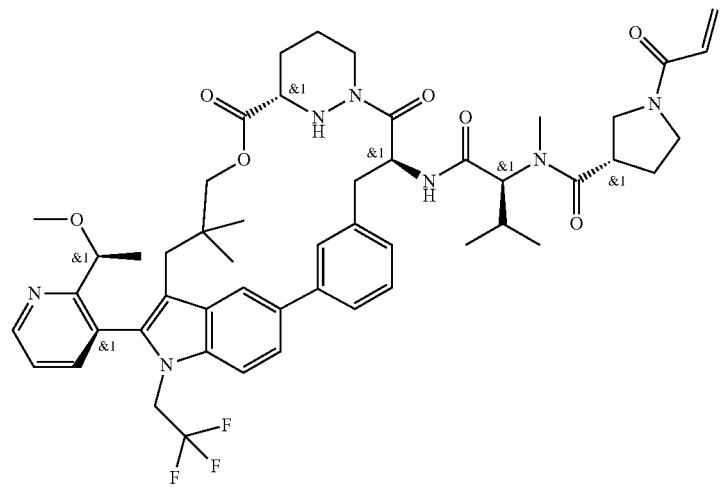 |

TABLE 1-continued
Certain Compounds of the Present Invention
| Ex# | Structure |
|---|---|
| A333 | 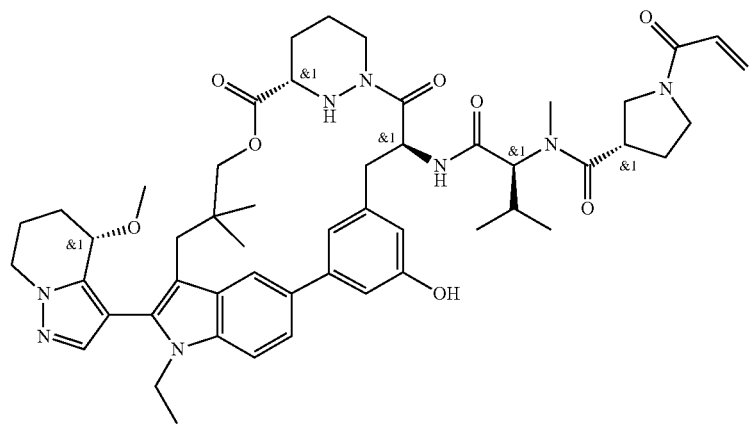 [SMILES: C=CC(=O)N1CC[C@H](C(=O)N(C)[C@H](C(=O)N[C@H]2Cc3cc(O)cc(c3)-c3ccc4c(c3)c(c(-c3cnn5c3[C@@H](OC)CCC5)n4CC)CC(C)(C)COC(=O)[C@@H]3CCCN(N3)C2=O)C(C)C)C1] |
| A334 | 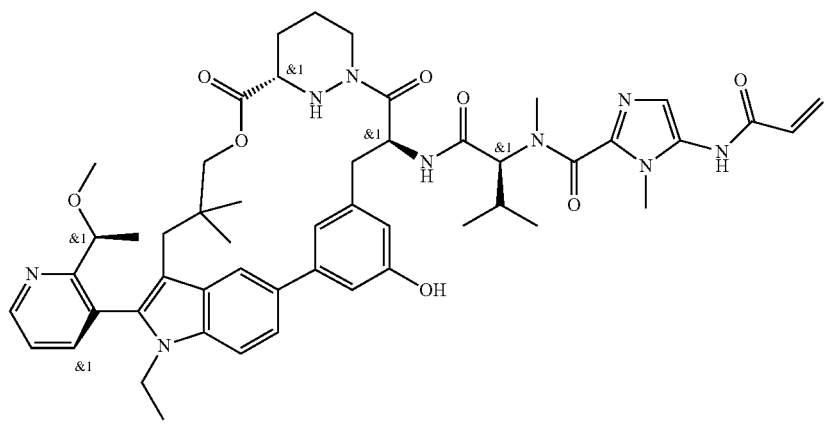 |
| A335 | 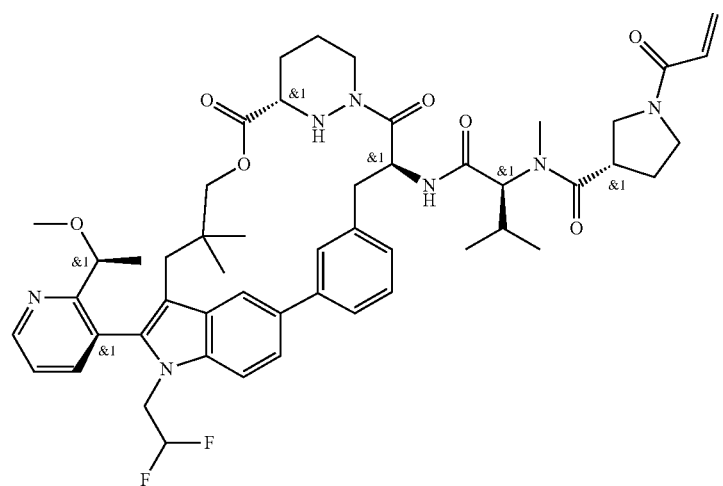 |

TABLE 1-continued
Certain Compounds of the Present Invention
| Ex# | Structure |
|---|---|
| A336 | 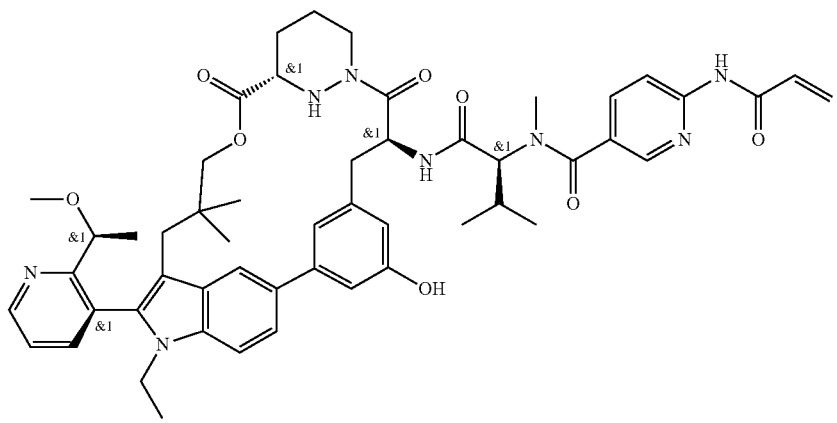 |
| A337 | 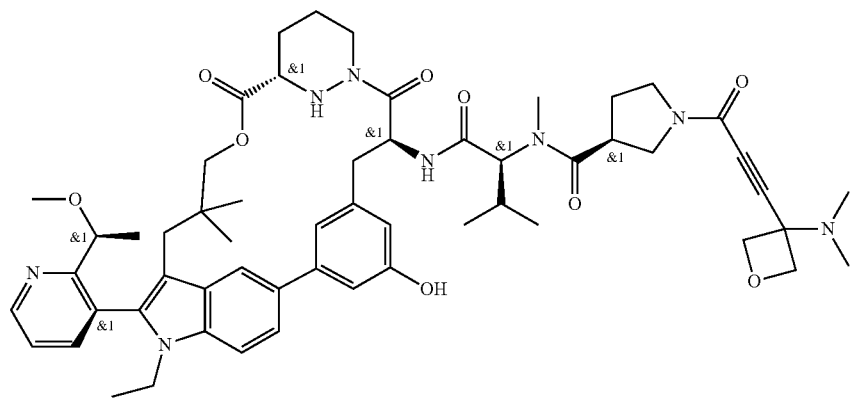 |
| A338 | 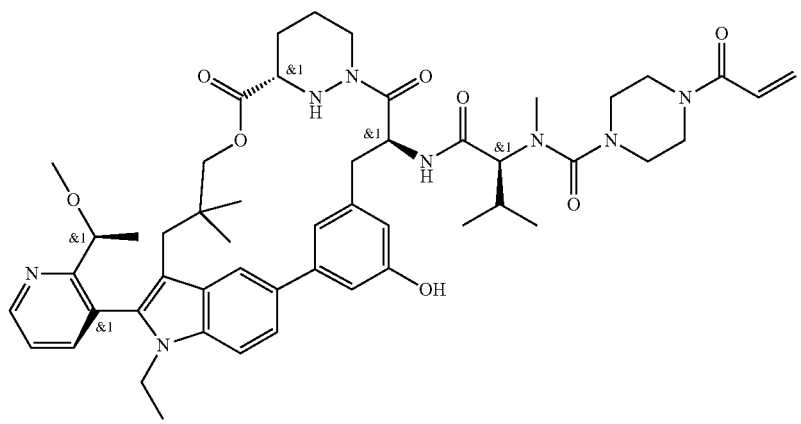 |

TABLE 1-continued
Certain Compounds of the Present Invention
| Ex# | Structure |
|---|---|
| A339 | 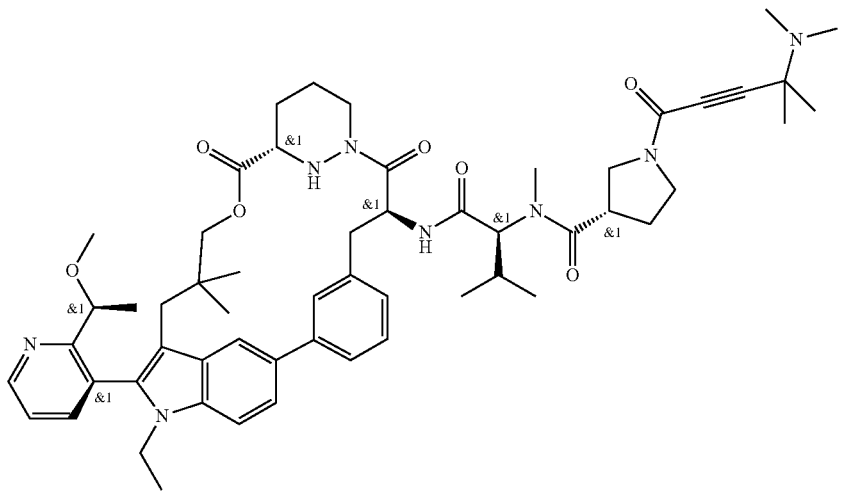 |
| A340 | 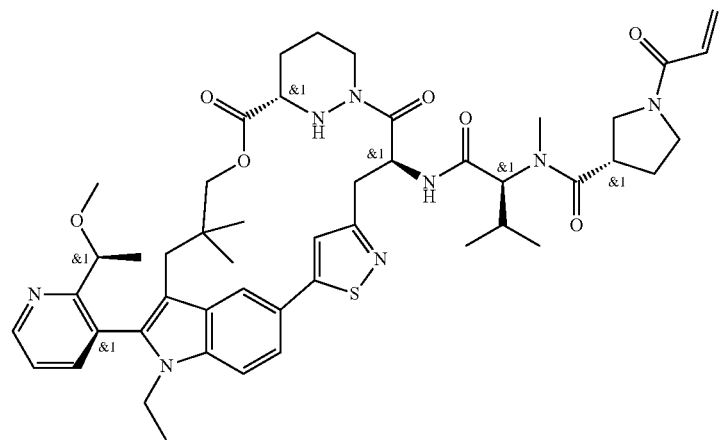 |
| A341 | 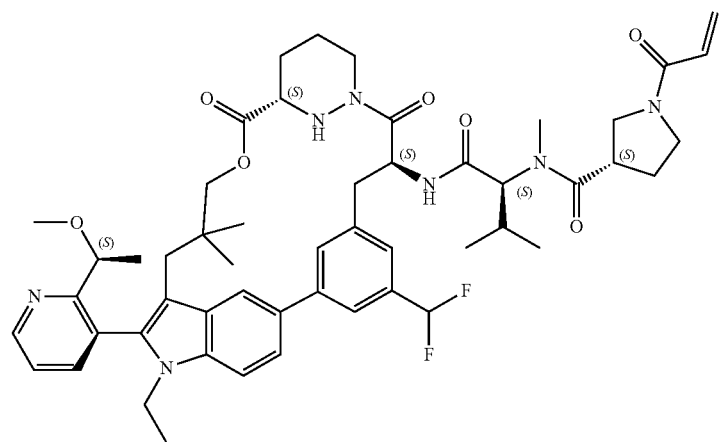 |

TABLE 1-continued
Certain Compounds of the Present Invention
| Ex# | Structure |
|---|---|
| A342 | 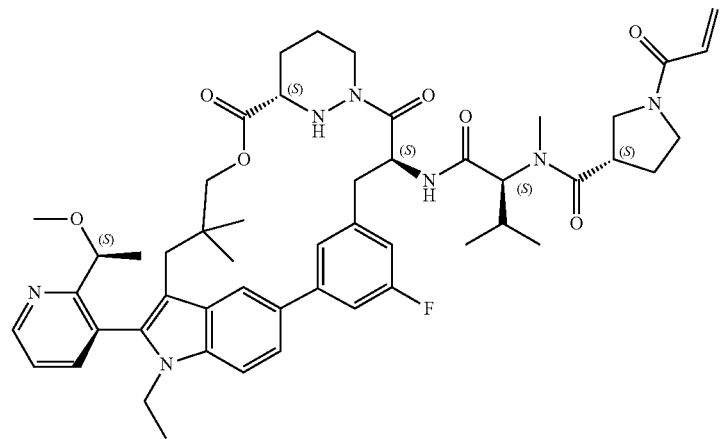 |
| A343 | 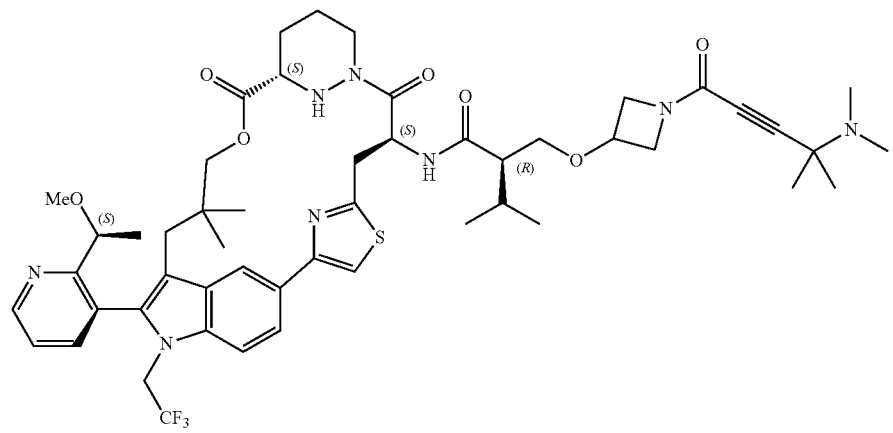 |
| A344 | 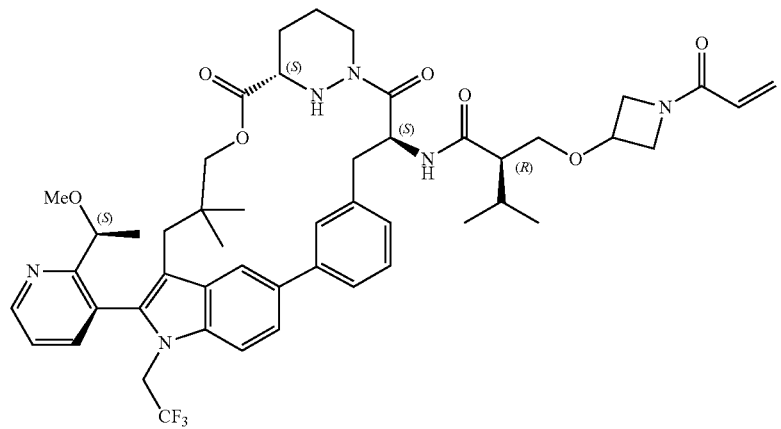 |

TABLE 1-continued

Certain Compounds of the Present Invention

| Ex# | Structure |
|---|---|
| A345 | 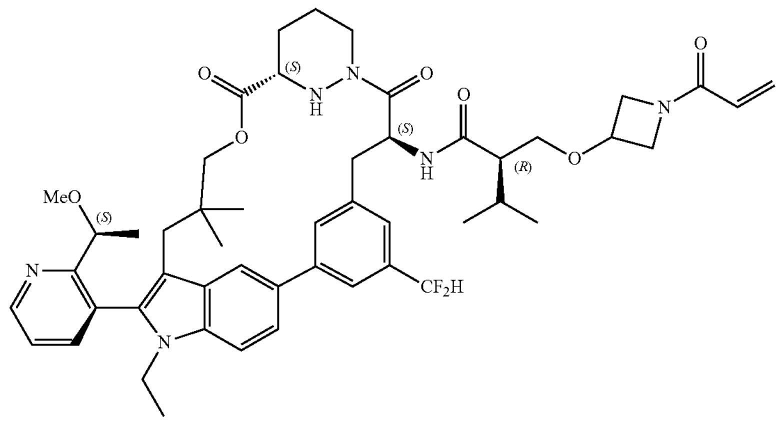 |
| A346 | 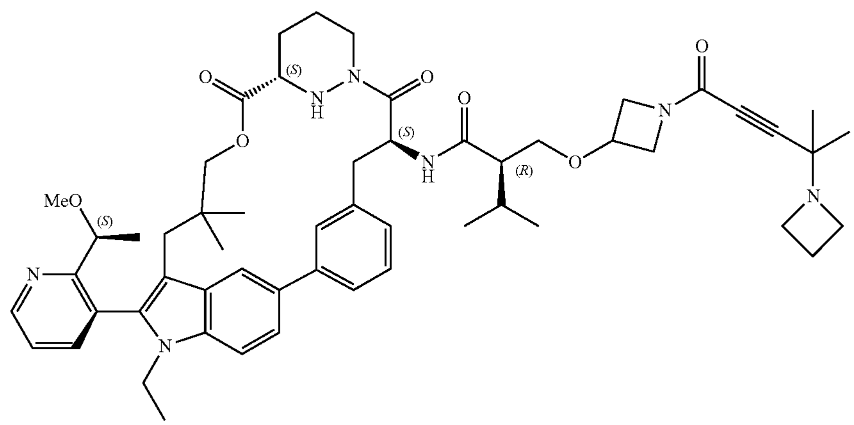 |
| A347 | 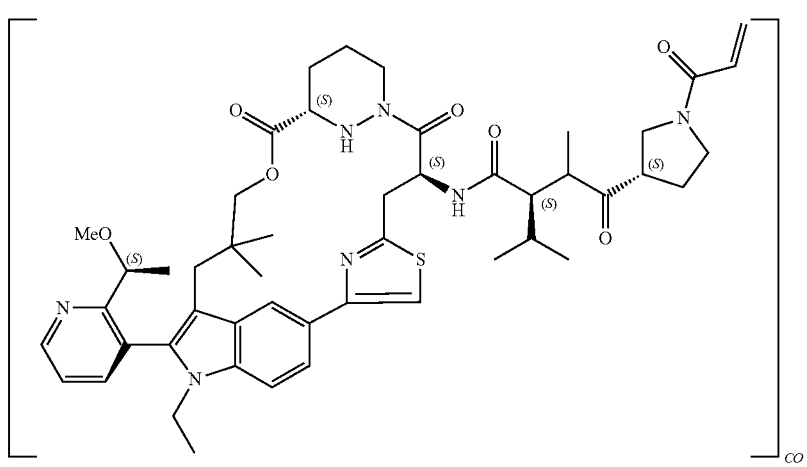 |

TABLE 1-continued
Certain Compounds of the Present Invention
| Ex# | Structure |
|---|---|
| A348 | 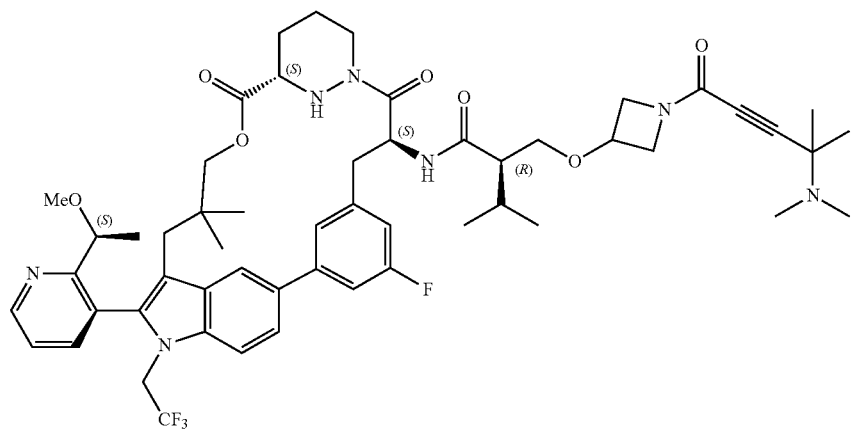 |
| A349 | 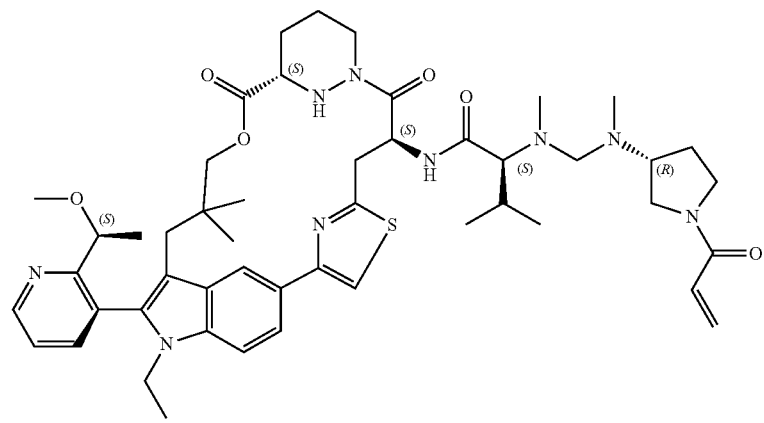 |
| A350 | 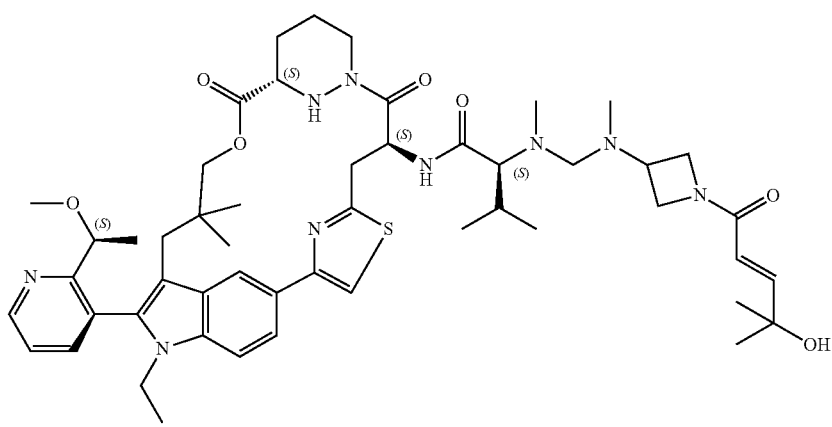 |

TABLE 1-continued
Certain Compounds of the Present Invention
| Ex# | Structure |
|---|---|
| A351 | 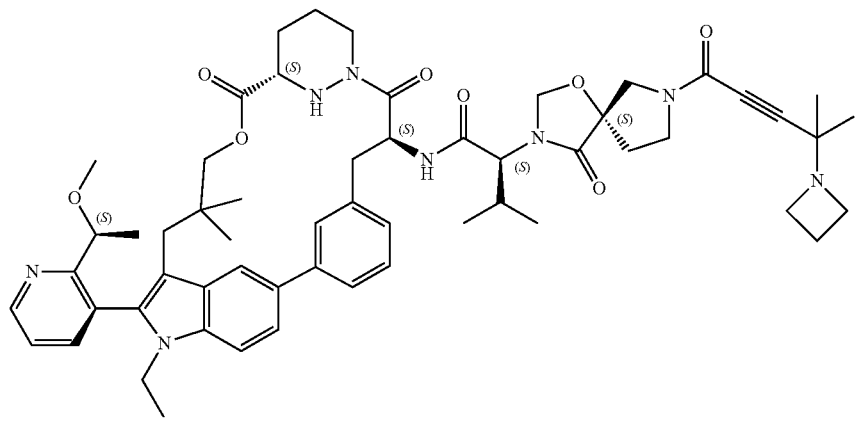 |
| A352 | 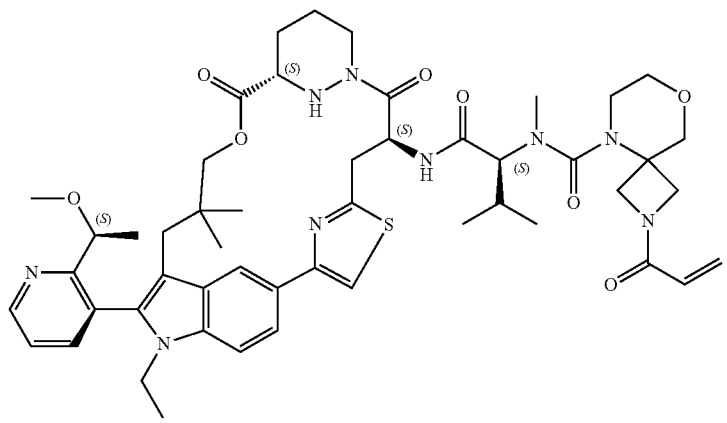 |
| A353 | 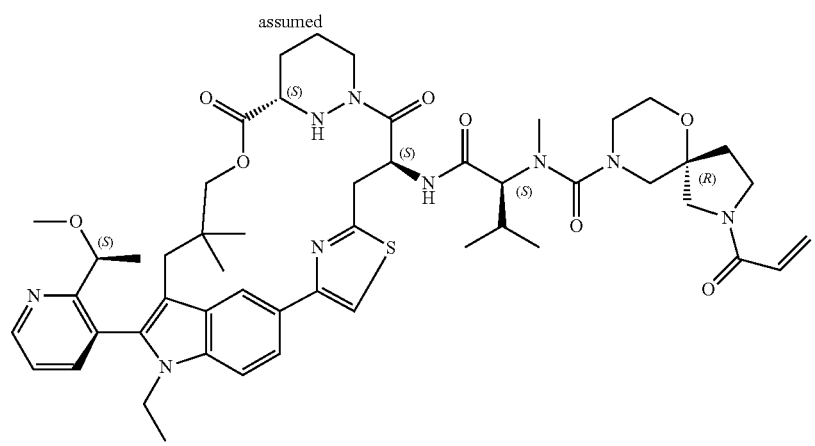 |

TABLE 1-continued
Certain Compounds of the Present Invention
| Ex# | Structure |
|---|---|
| A354 | 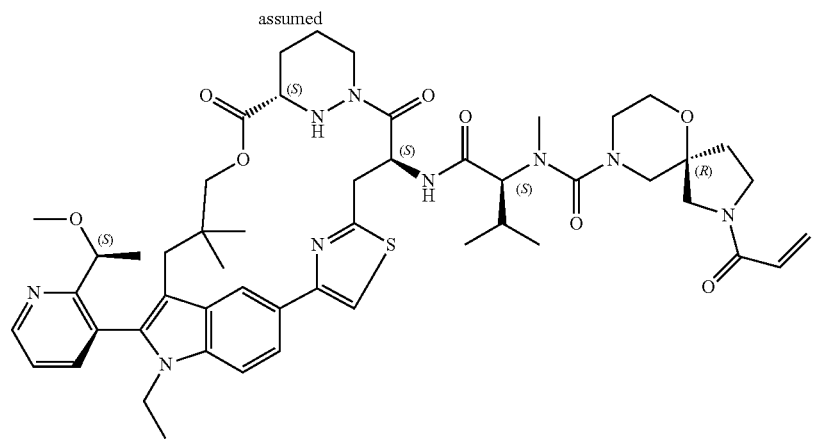 |
| A355 | 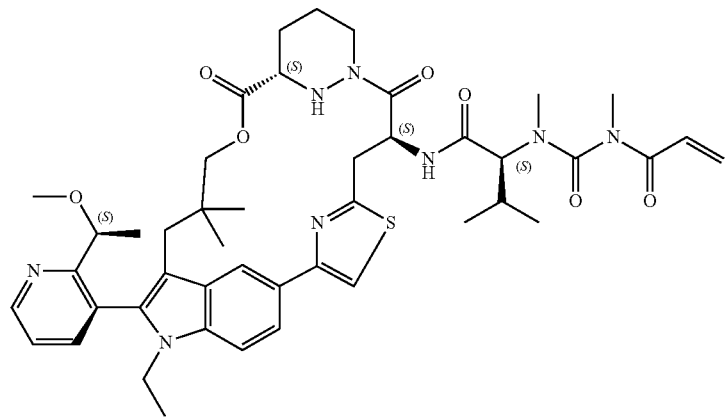 |
| A356 | 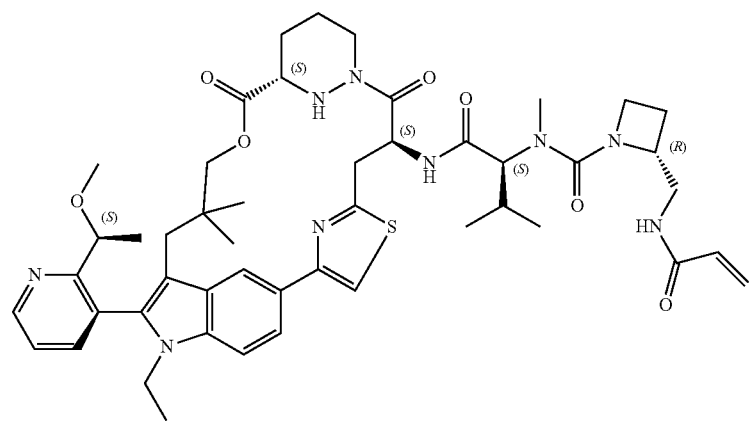 |

TABLE 1-continued
Certain Compounds of the Present Invention
| Ex# | Structure |
|---|---|
| A357 | 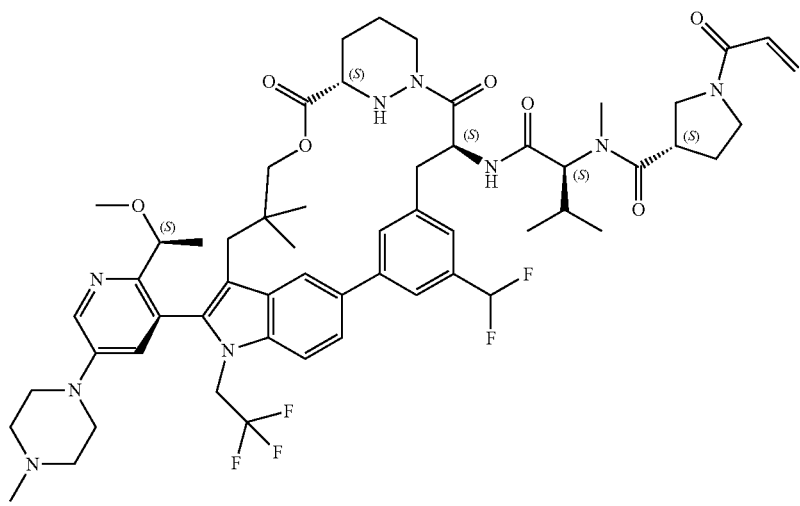 |
| A358 | 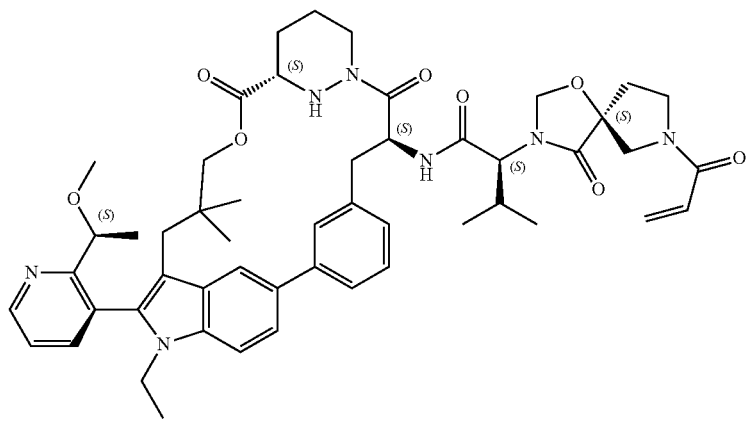 |
| A359 | 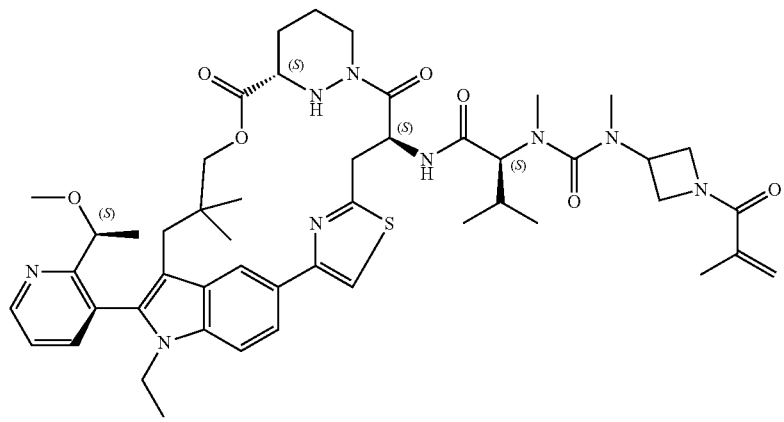 |

TABLE 1-continued
Certain Compounds of the Present Invention
| Ex# | Structure |
|---|---|
| A360 | 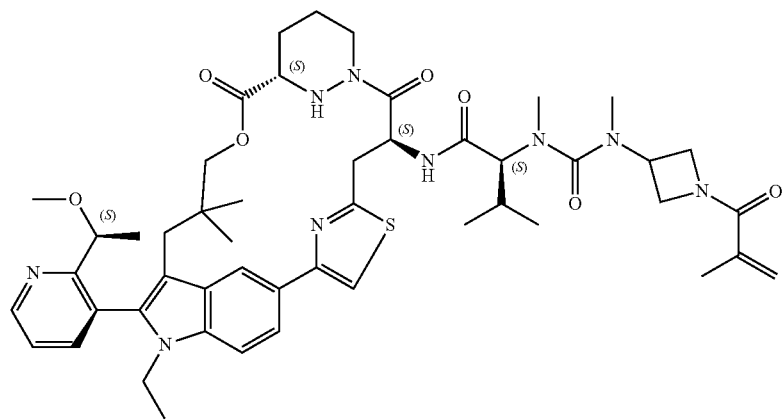 |
| A361 | 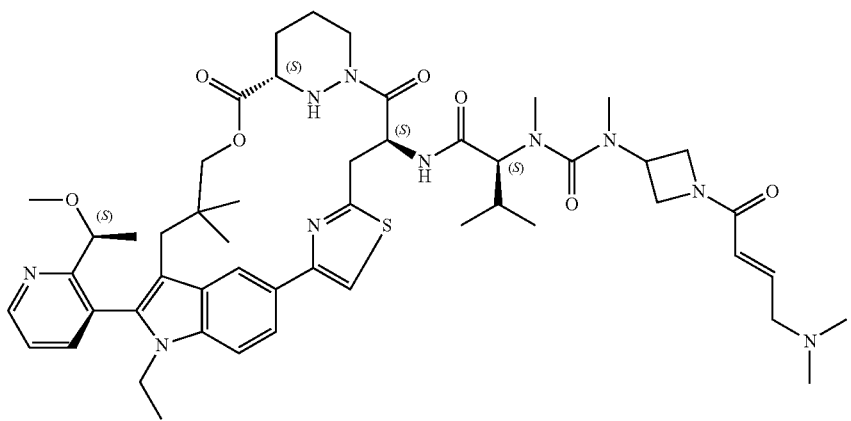 |
| A362 | 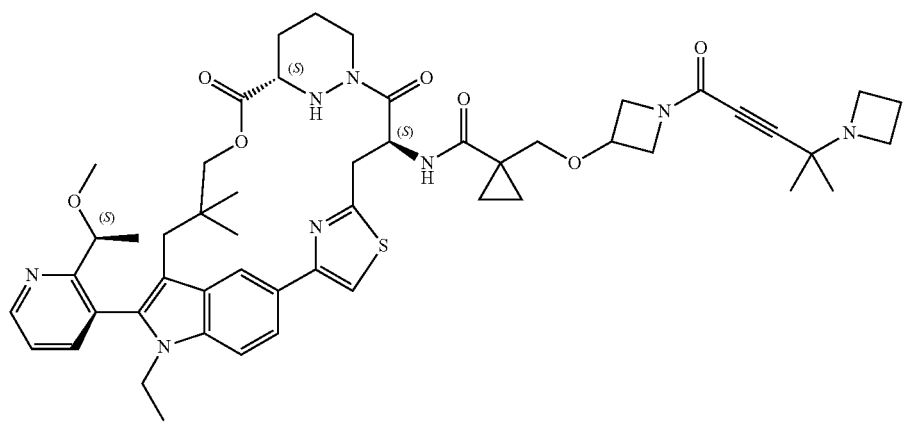 |

TABLE 1-continued
Certain Compounds of the Present Invention
| Ex# | Structure |
|---|---|
| A363 | 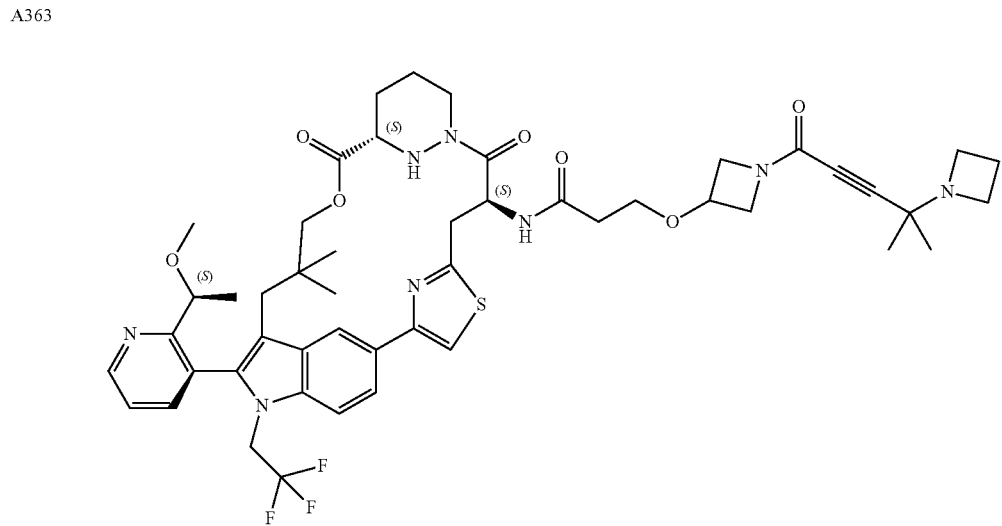 |
| A364 | 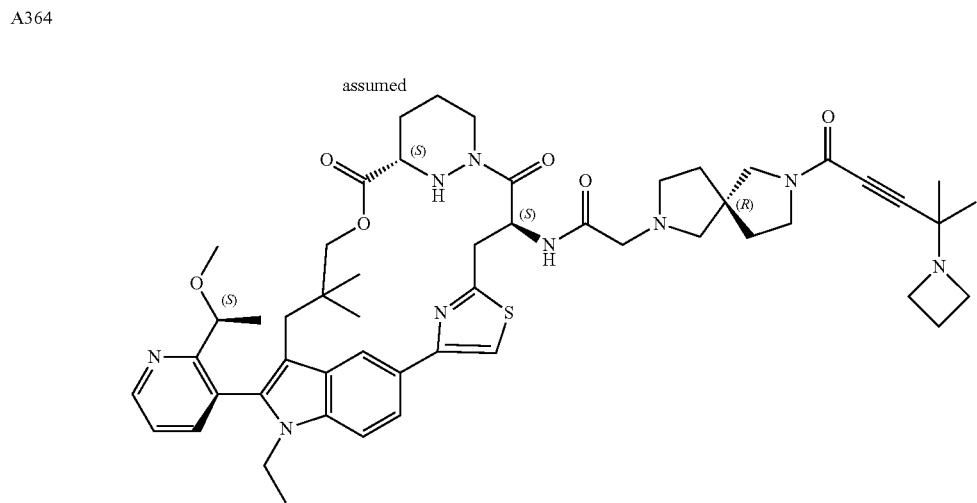 |
| A365 | 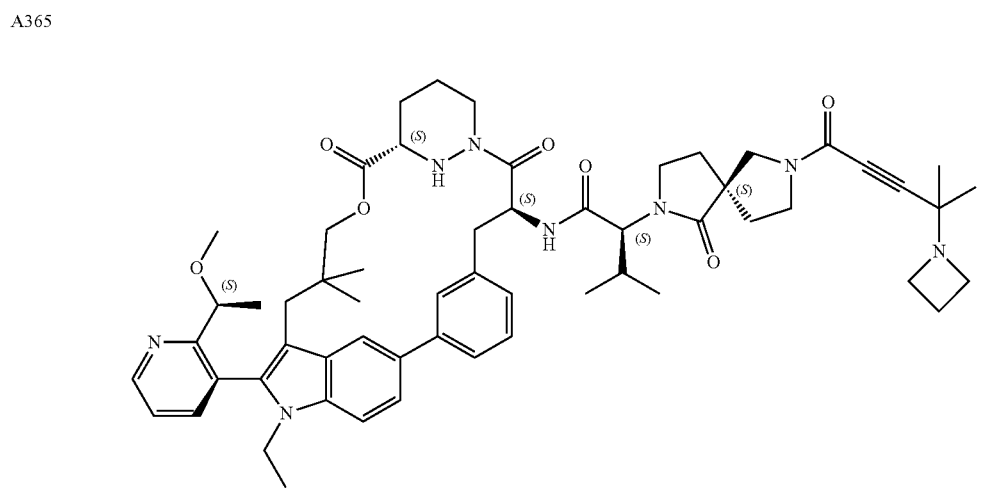 |

TABLE 1-continued
Certain Compounds of the Present Invention
| Ex# | Structure |
|---|---|
| A366 | 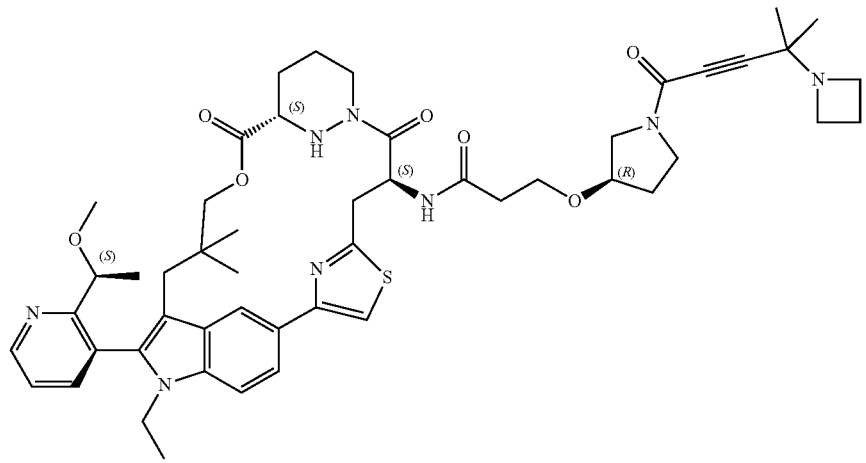 |
| A367 | 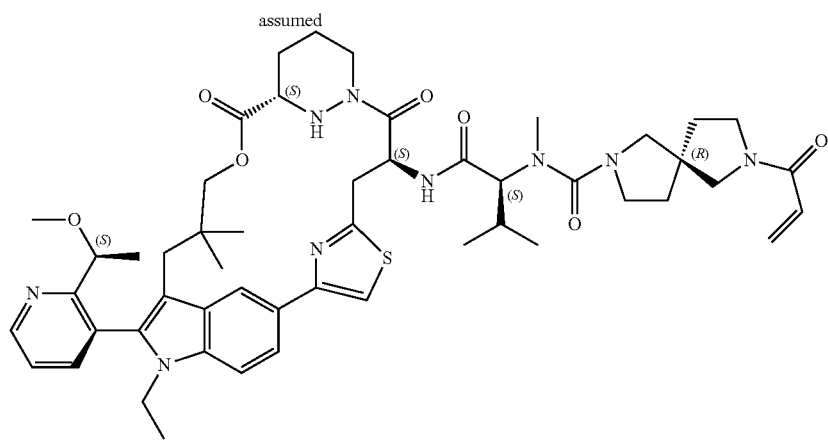 |
| A368 | 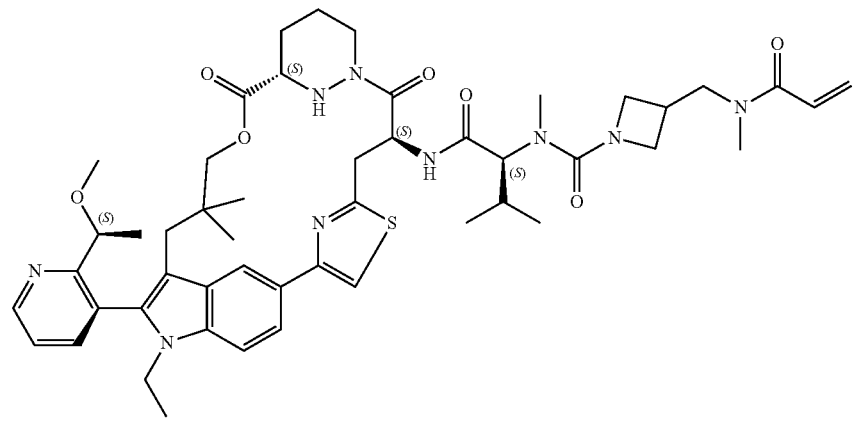 |

TABLE 1-continued
Certain Compounds of the Present Invention
| Ex# | Structure |
|---|---|
| A369 | 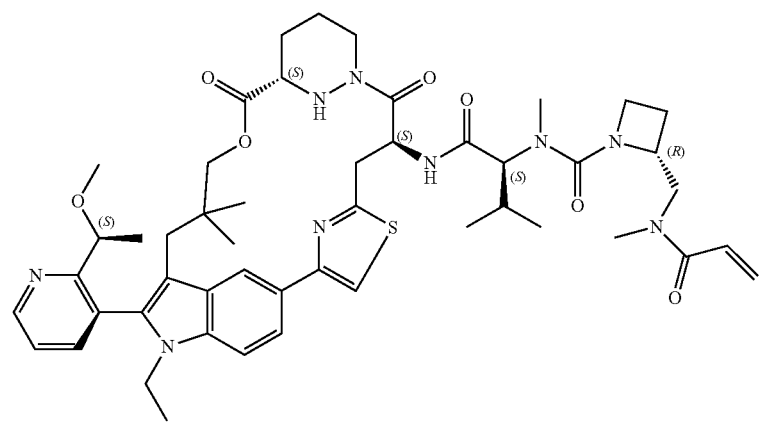 |
| A370 | 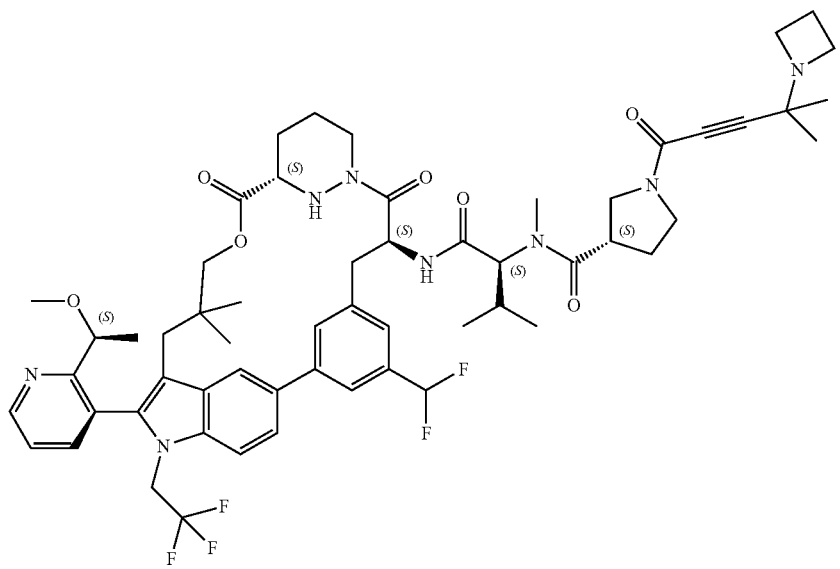 |
| A371 | 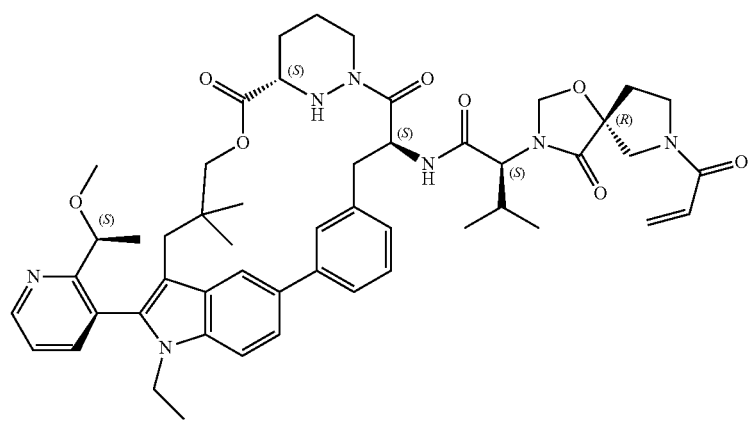 |

TABLE 1-continued
Certain Compounds of the Present Invention
| Ex# | Structure |
|---|---|
| A372 | 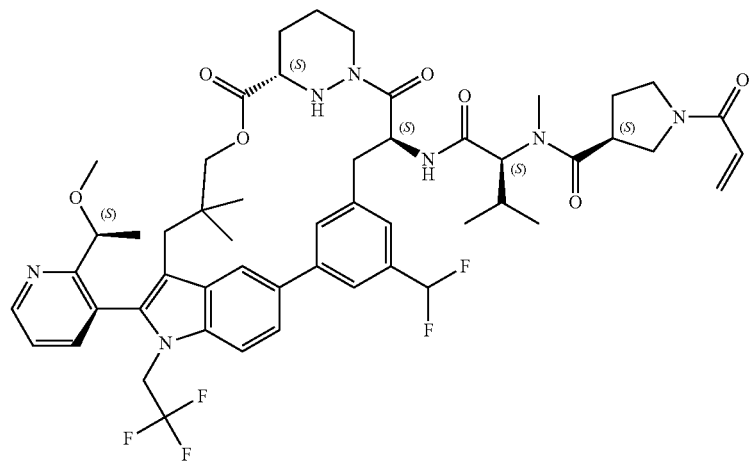 |
| A373 | 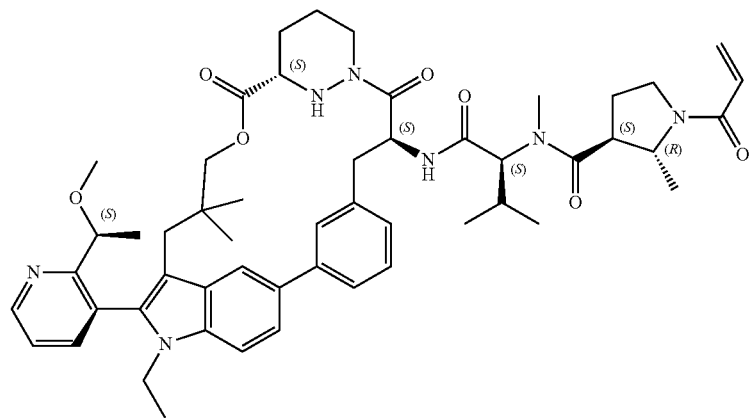 |
| A374 | 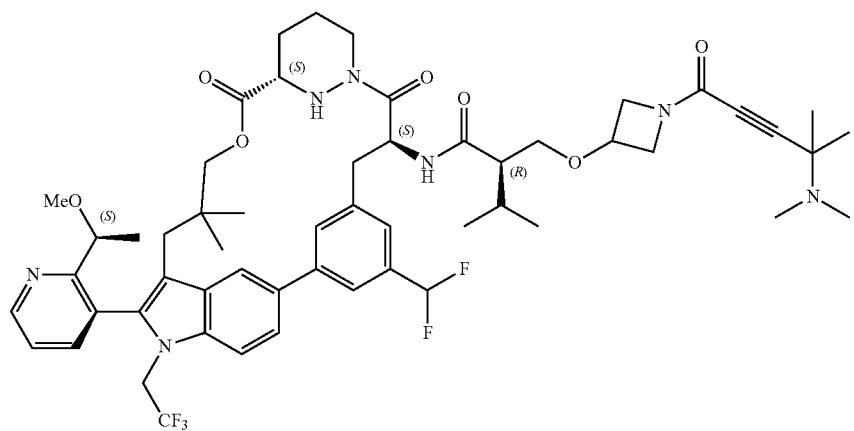 |

TABLE 1-continued
Certain Compounds of the Present Invention
| Ex# | Structure |
|---|---|
| A375 | 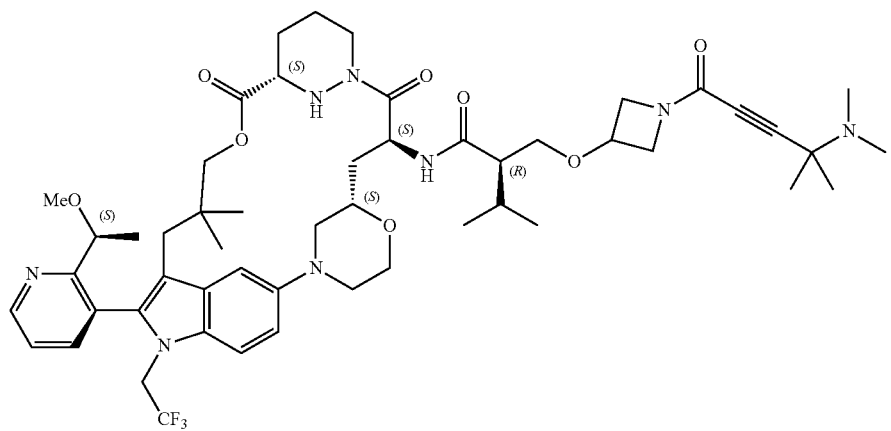 |
| A376 | 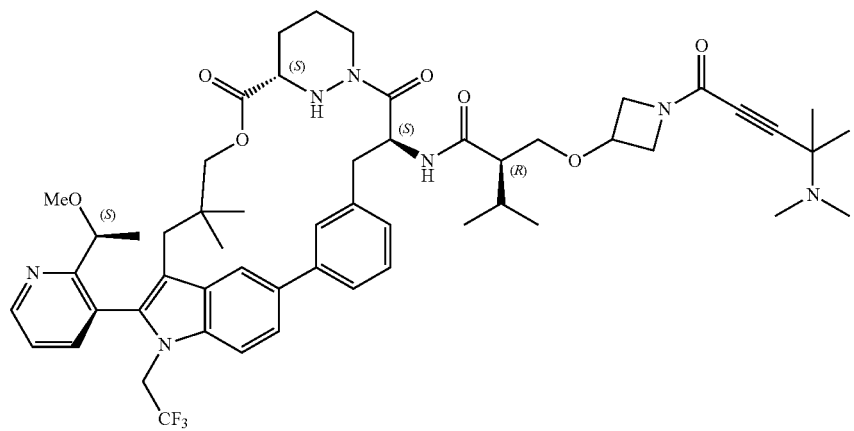 |
| A377 | 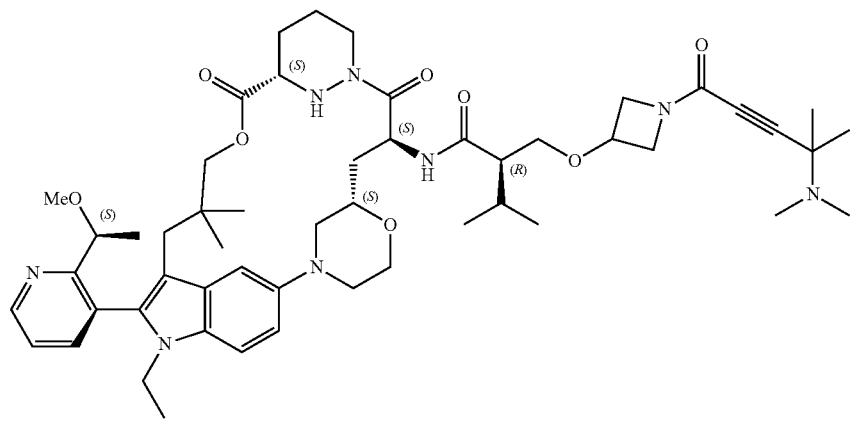 |

TABLE 1-continued
Certain Compounds of the Present Invention
| Ex# | Structure |
|---|---|
| A378 | 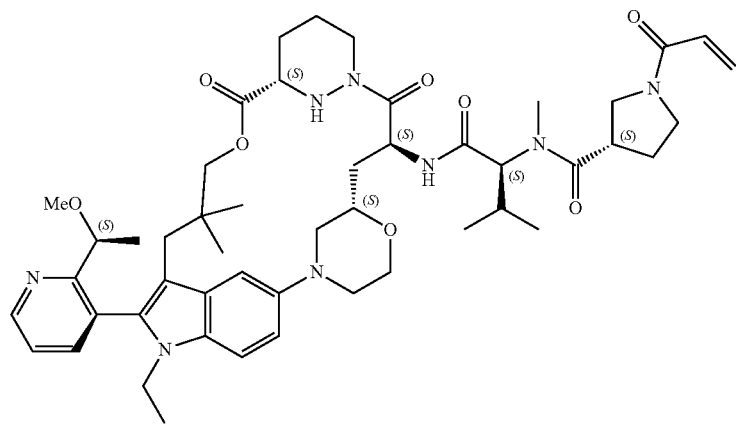 |
| A379 | 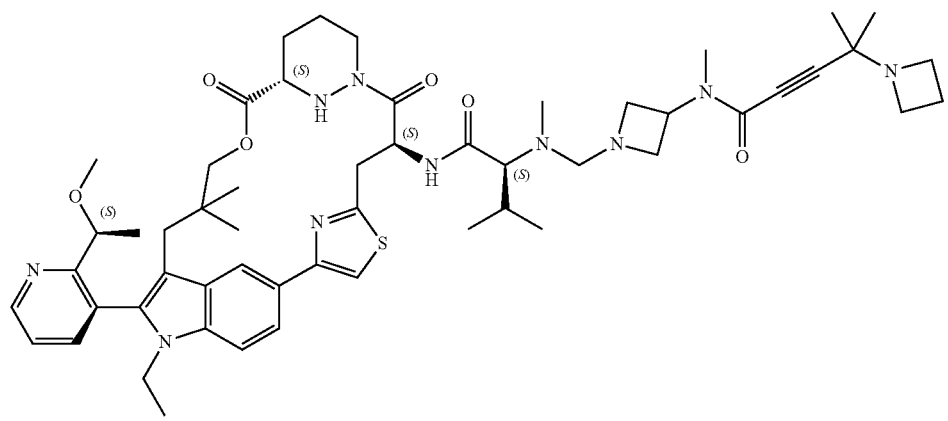 |
| A380 | 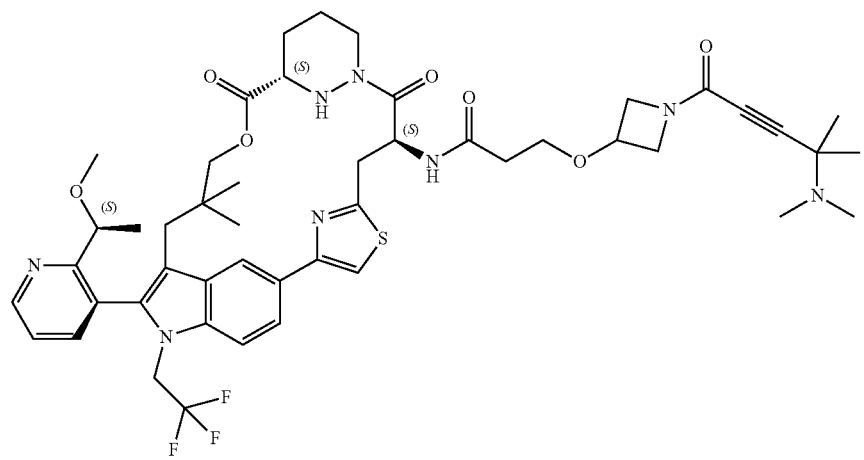 |

TABLE 1-continued
Certain Compounds of the Present Invention
| Ex# | Structure |
|---|---|
| A381 | 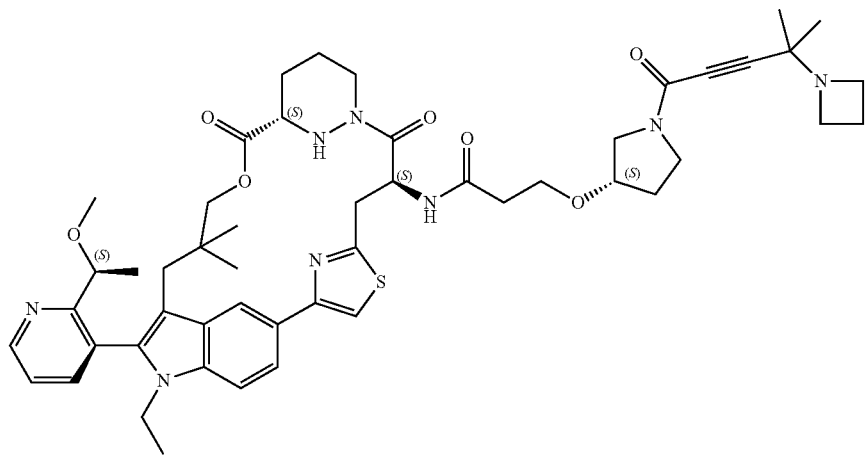 |
| A382 | 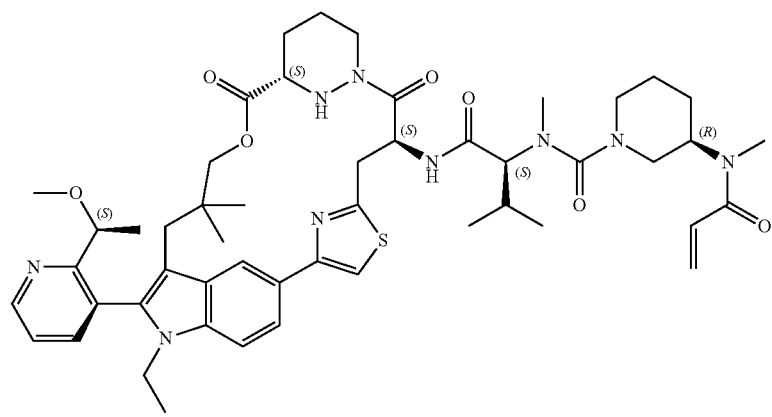 |
| A383 | 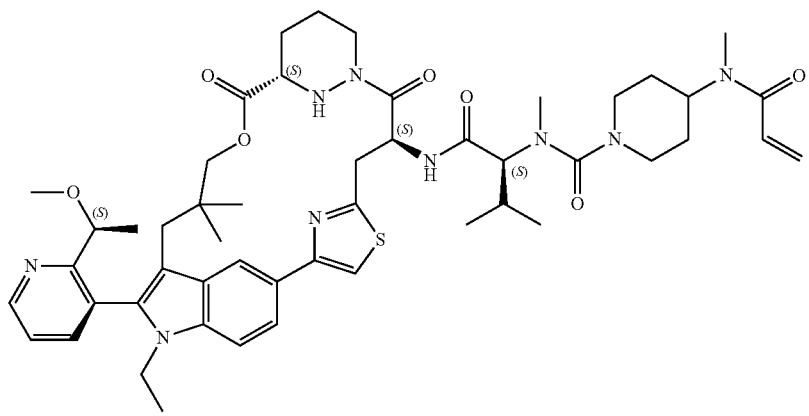 |

TABLE 1-continued
Certain Compounds of the Present Invention
| Ex# | Structure |
|---|---|
| A384 | 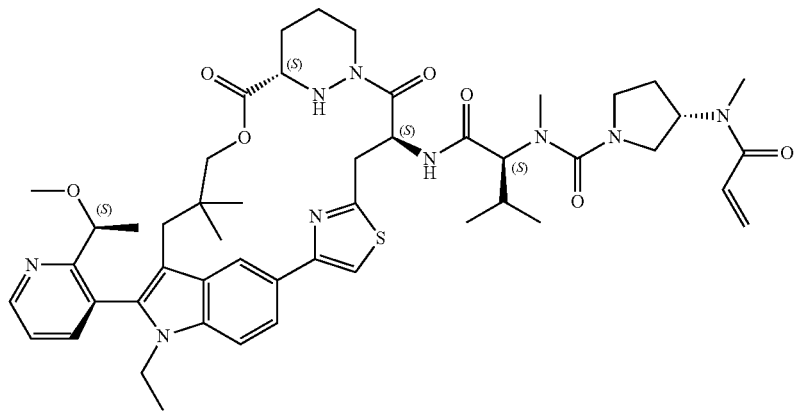 |
| A385 | 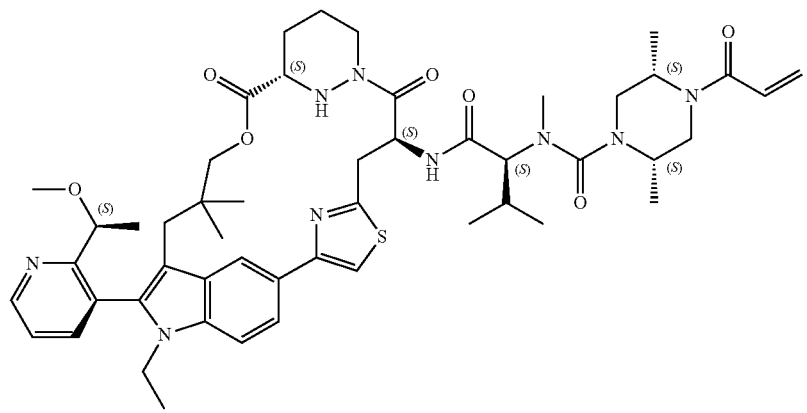 |
| A386 | 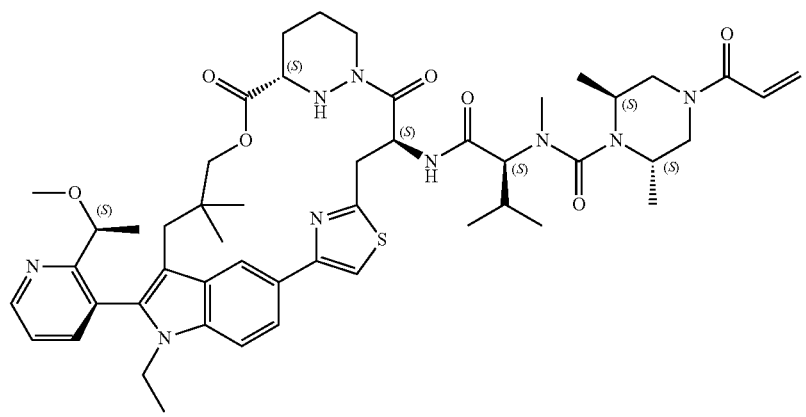 |

TABLE 1-continued

Certain Compounds of the Present Invention

| Ex# | Structure |
|---|---|
| A387 | 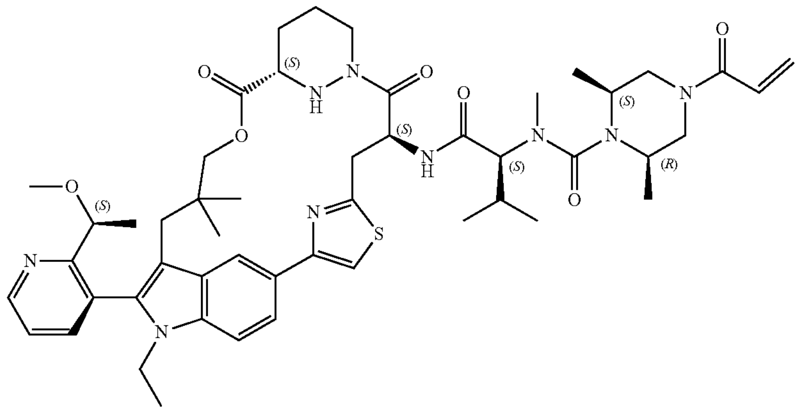 |
| A388 | 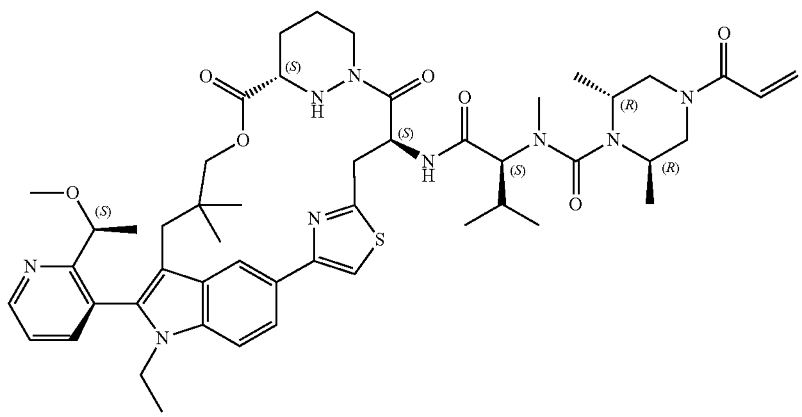 |
| A389 | 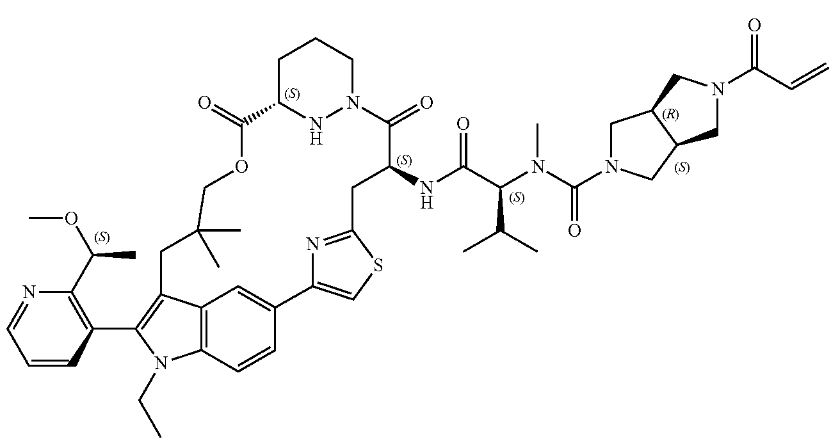 |

TABLE 1-continued
Certain Compounds of the Present Invention
| Ex# | Structure |
|---|---|
| A390 | 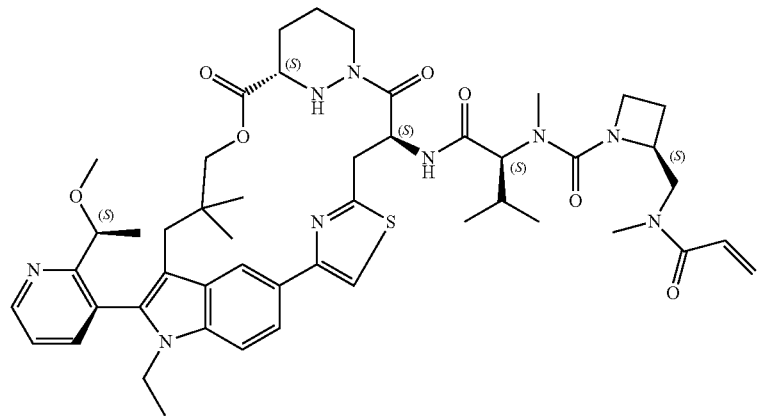 |
| A391 | 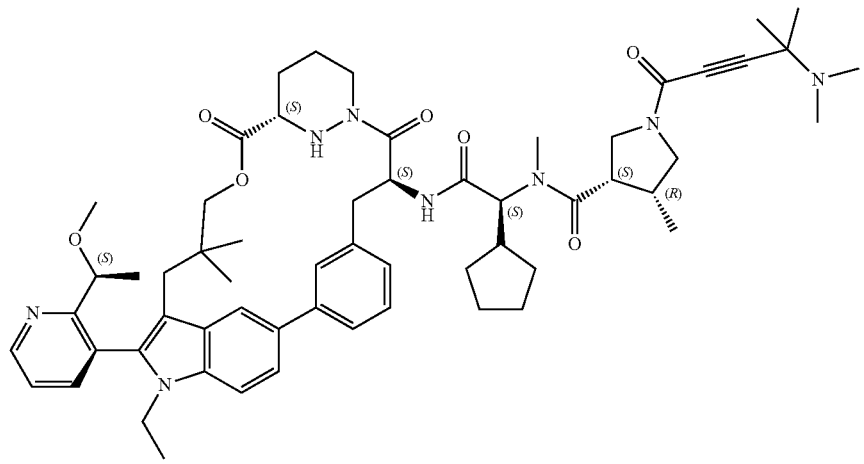 |
| A392 | 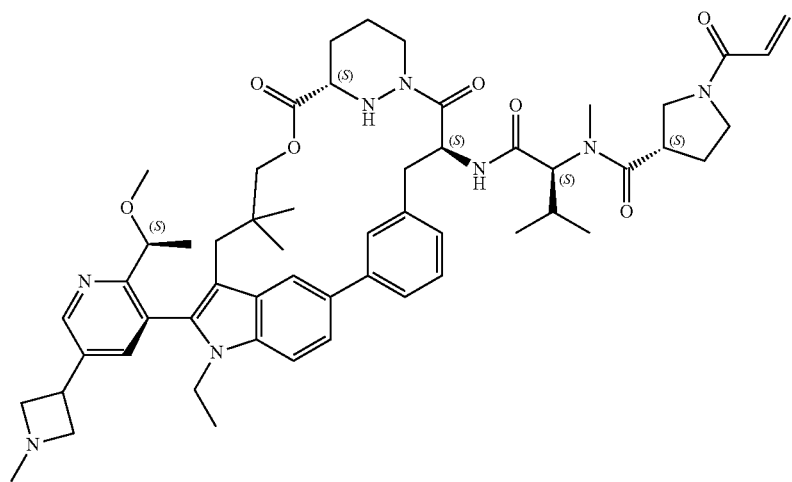 |

TABLE 1-continued
Certain Compounds of the Present Invention
| Ex# | Structure |
|---|---|
| A393 | 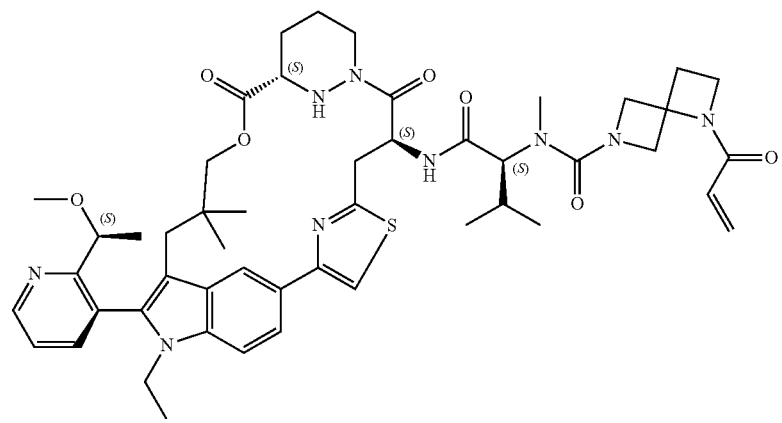 |
| A394 | 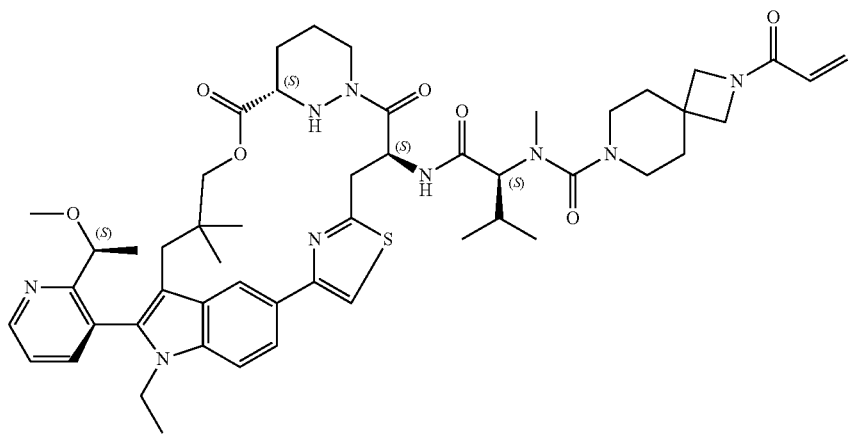 |
| A395 | 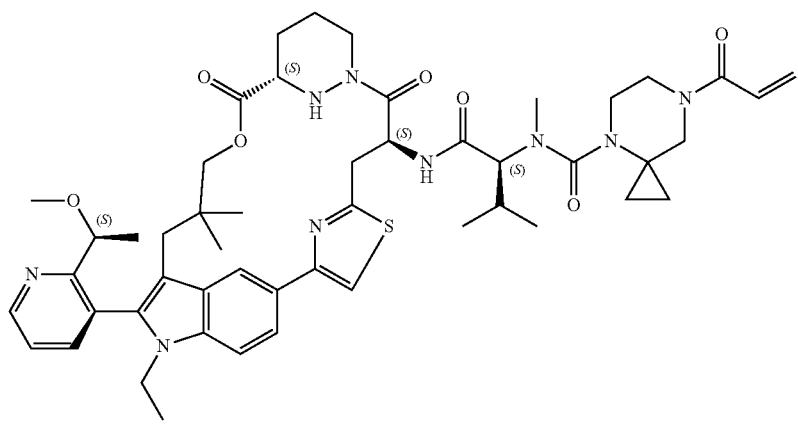 |

TABLE 1-continued
Certain Compounds of the Present Invention
| Ex# | Structure |
|---|---|
| A396 | 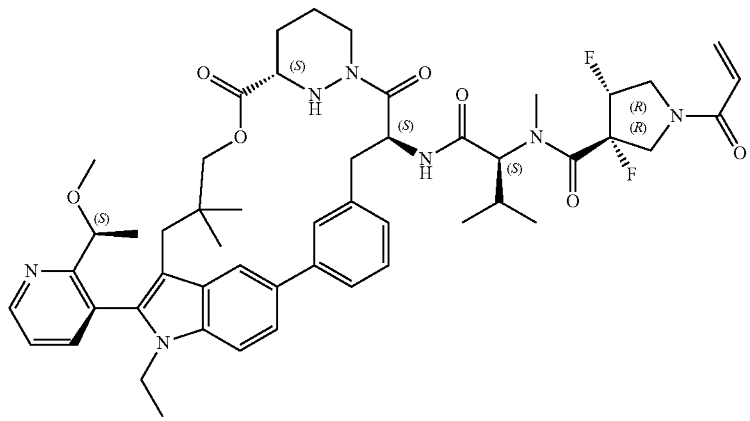 |
| A397 | 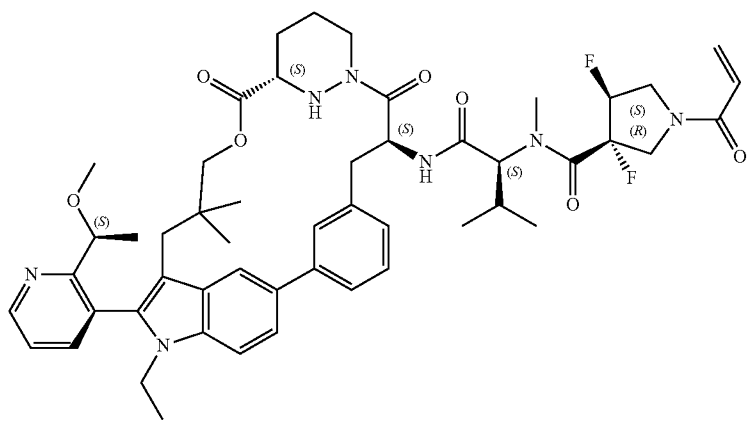 |
| A398 | 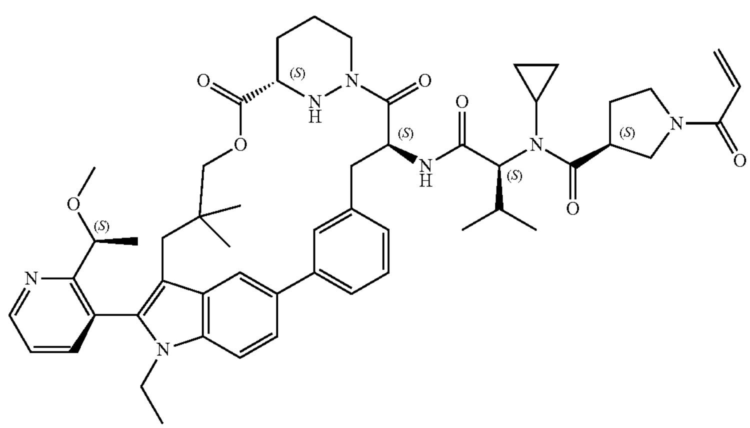 |

333
TABLE 1-continued
Certain Compounds of the Present Invention
| Ex# | Structure |
|---|---|
| A399 | 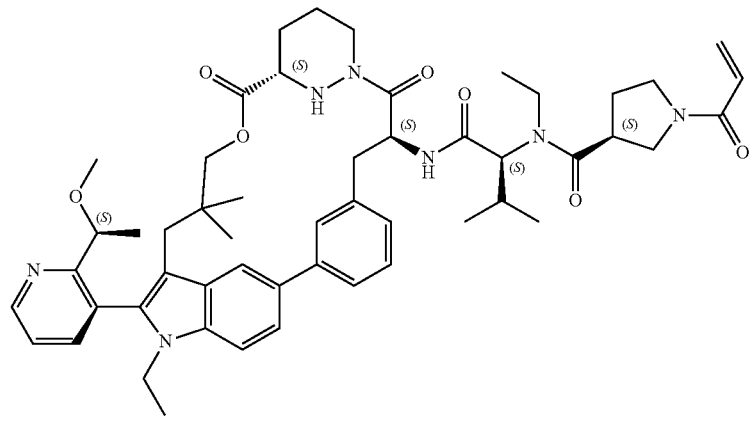 |
| A400 | 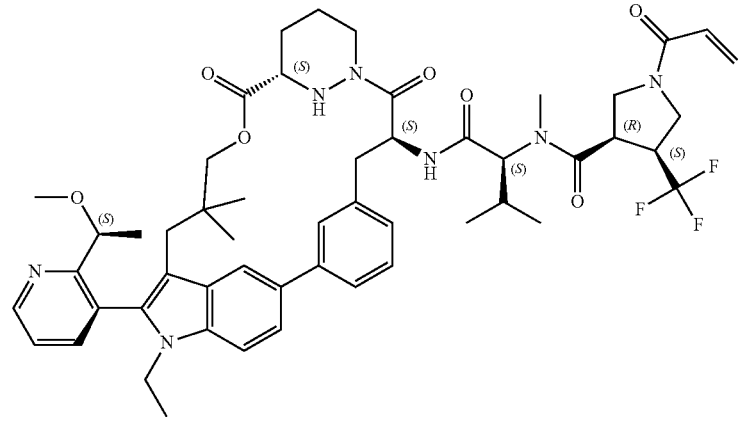 |
| A401 | 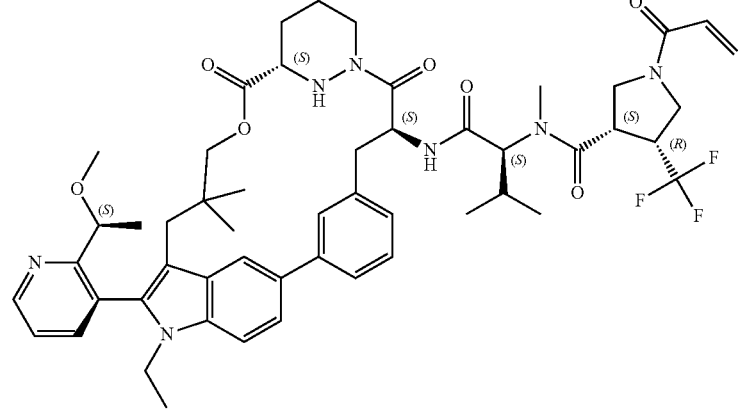 |

TABLE 1-continued
Certain Compounds of the Present Invention
| Ex# | Structure |
|---|---|
| A402 | 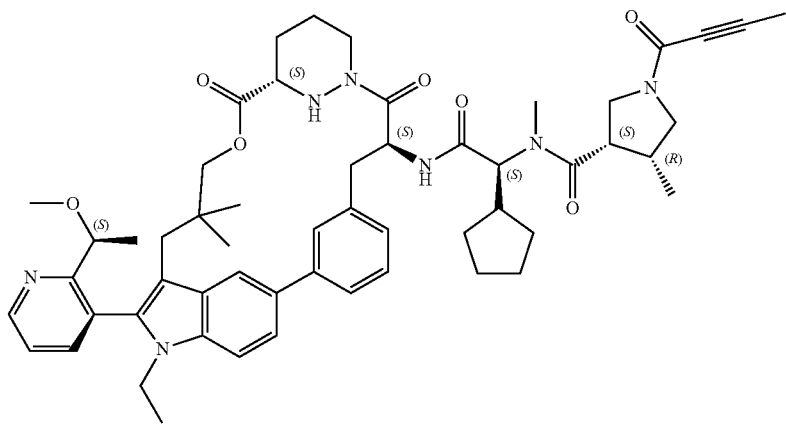 |
| A403 | 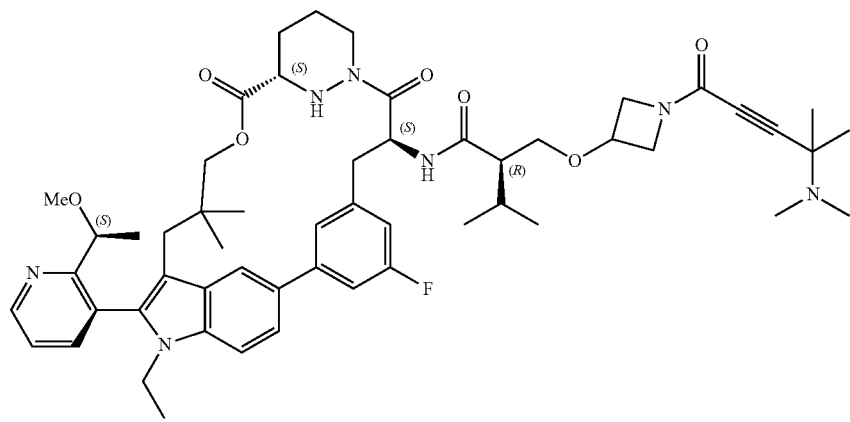 |
| A404 | 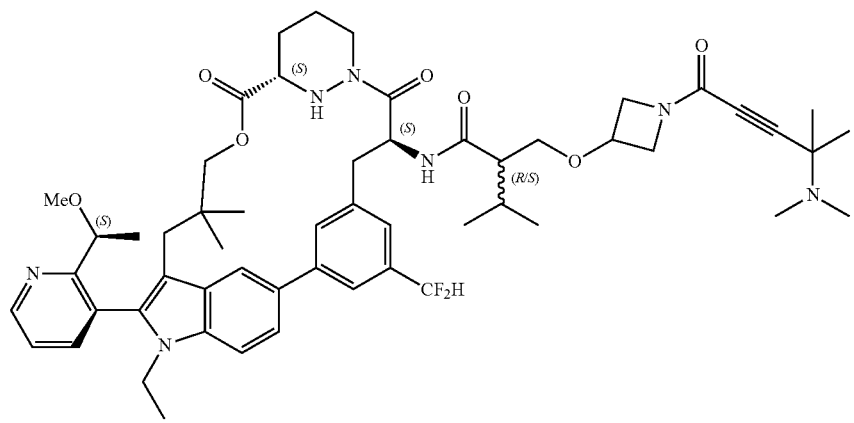 |

TABLE 1-continued
Certain Compounds of the Present Invention
| Ex# | Structure |
|---|---|
| A405 | 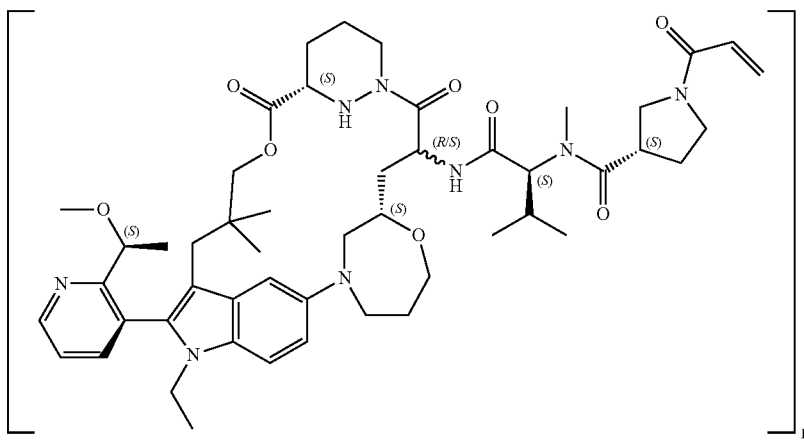 |
| A406 | 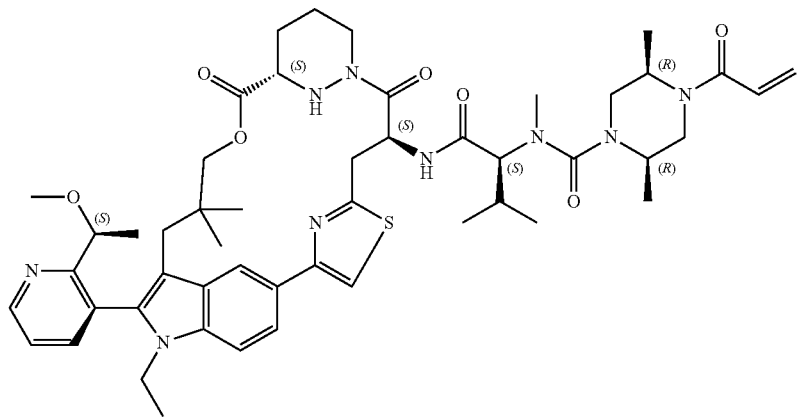 |
| A407 | 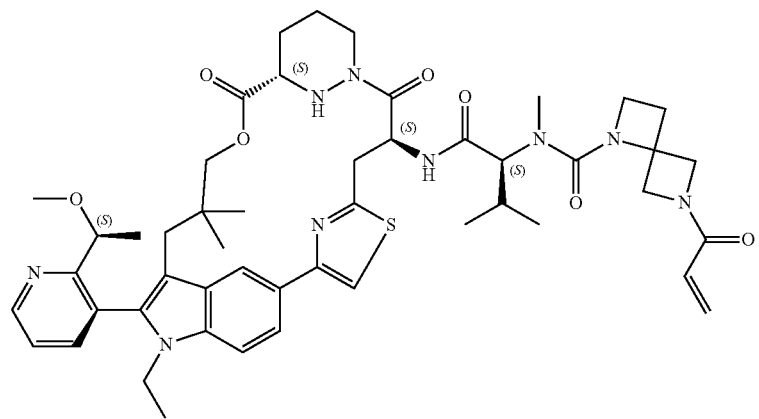 |

TABLE 1-continued
Certain Compounds of the Present Invention
| Ex# | Structure |
|---|---|
| A408 | 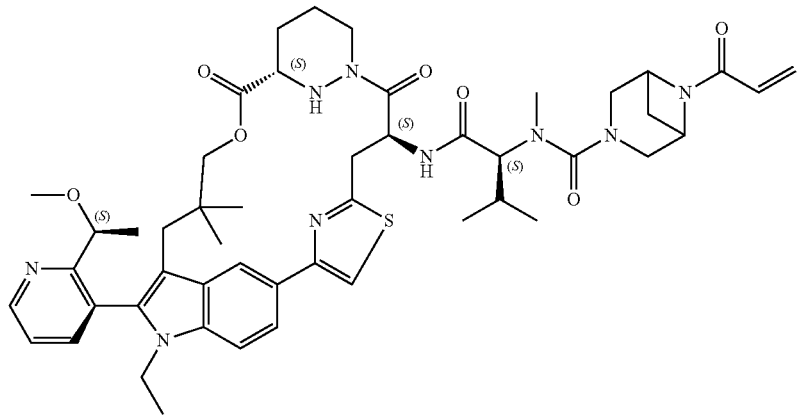 |
| A409 | 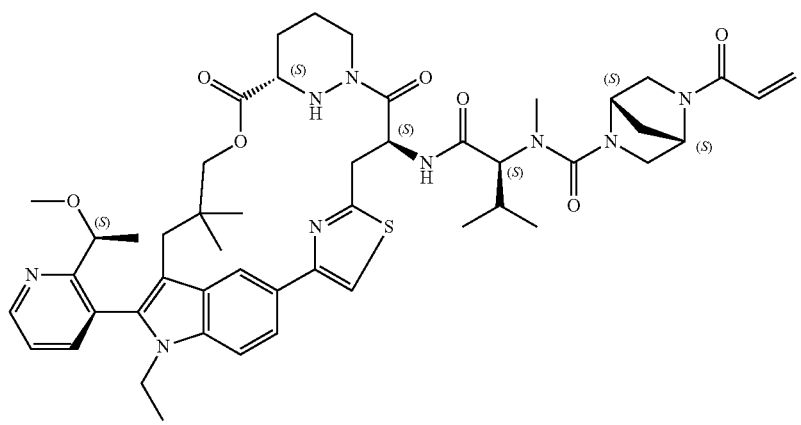 |
| A410 | 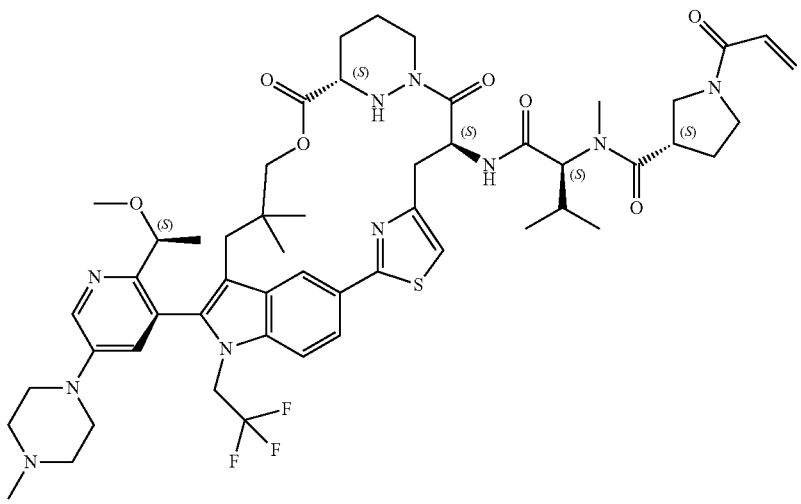 |

341 342
TABLE 1-continued
Certain Compounds of the Present Invention
| Ex# | Structure |
|---|---|
| A411 | 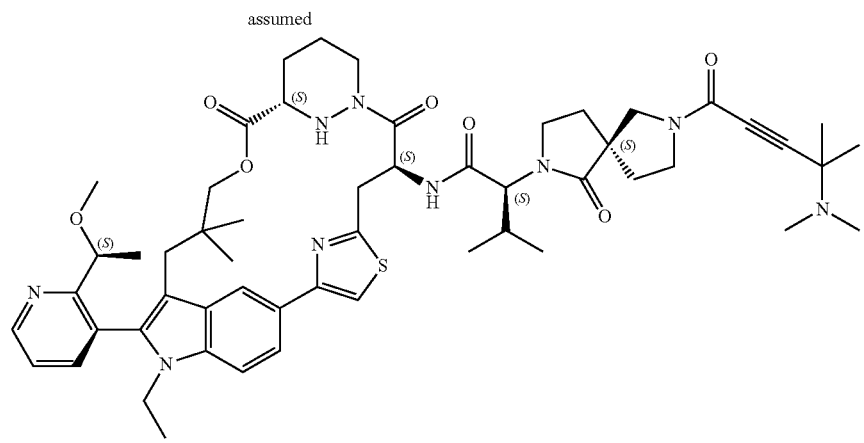 |
| A412 | 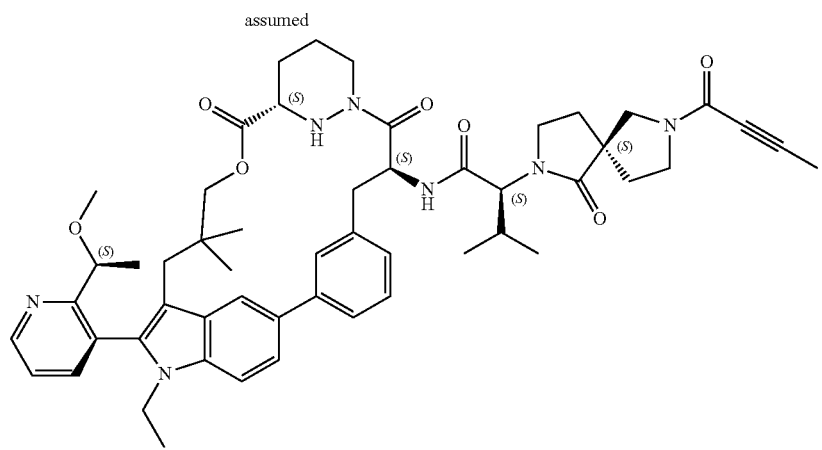 |
| A413 | 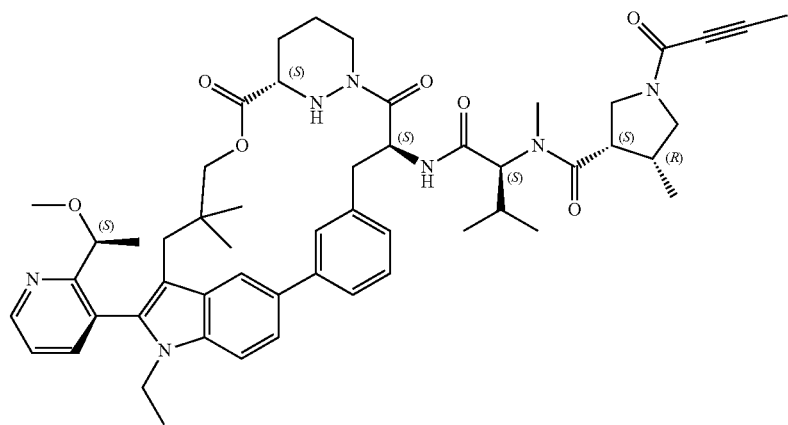 |

TABLE 1-continued

Certain Compounds of the Present Invention

| Ex# | Structure |
| --- | --- |
| A414 | 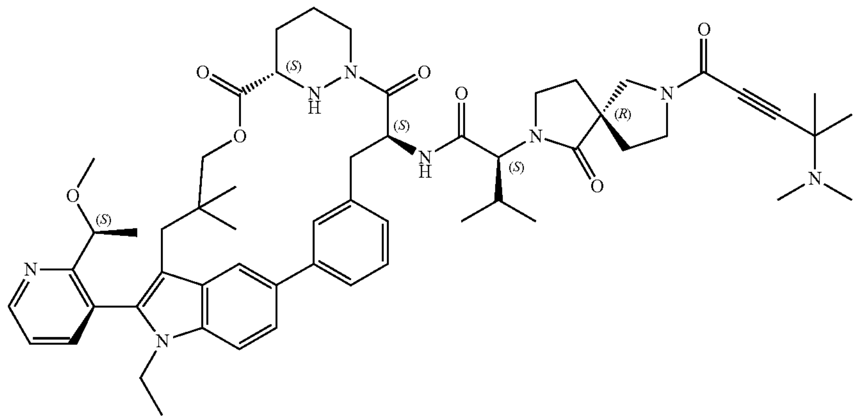 |
| A415 | 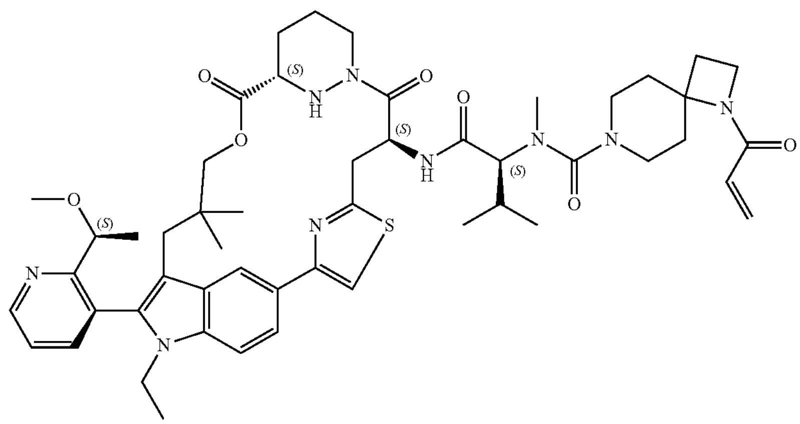 |
| A416 | 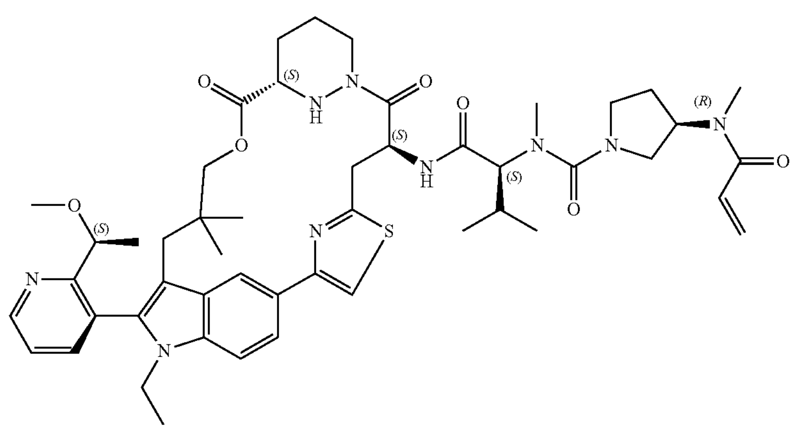 |

TABLE 1-continued
Certain Compounds of the Present Invention
| Ex# | Structure |
|---|---|
| A417 | 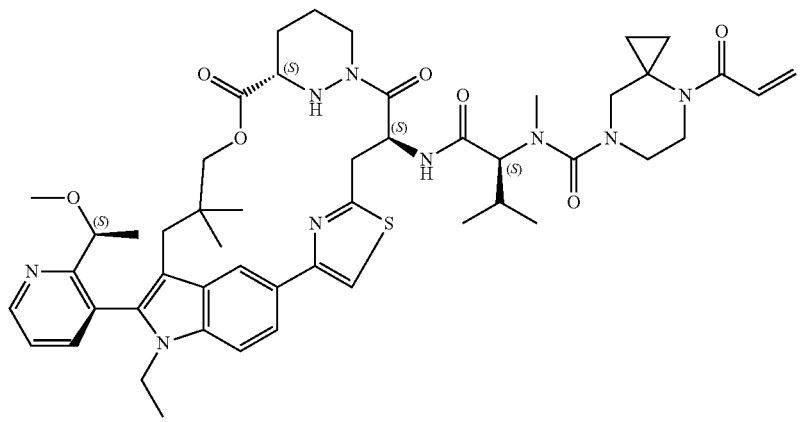 |
| A418 | 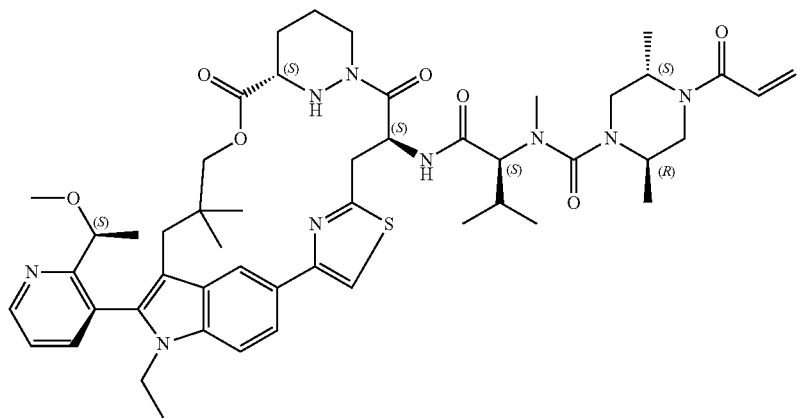 |
| A419 | 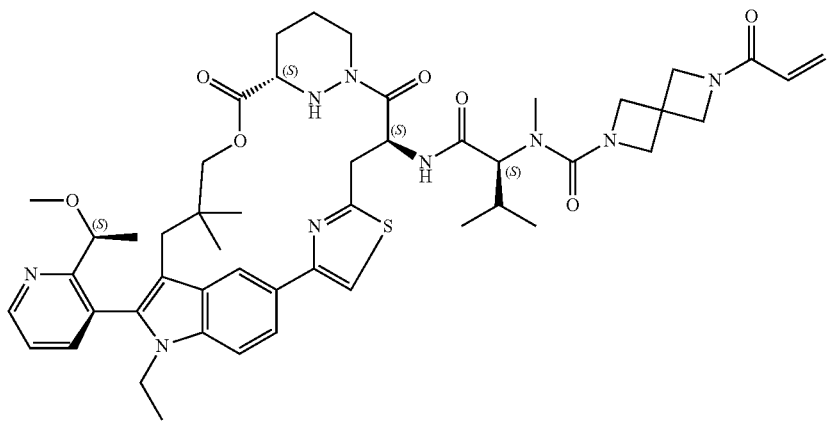 |

TABLE 1-continued
Certain Compounds of the Present Invention
| Ex# | Structure |
|---|---|
| A420 | 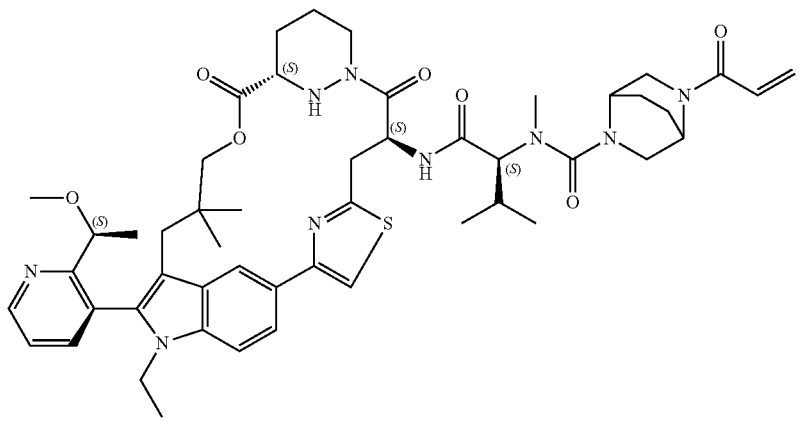 |
| A421 | 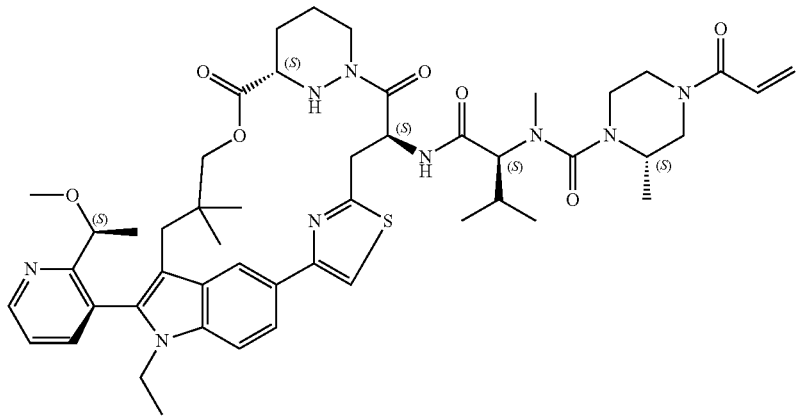 |
| A422 | 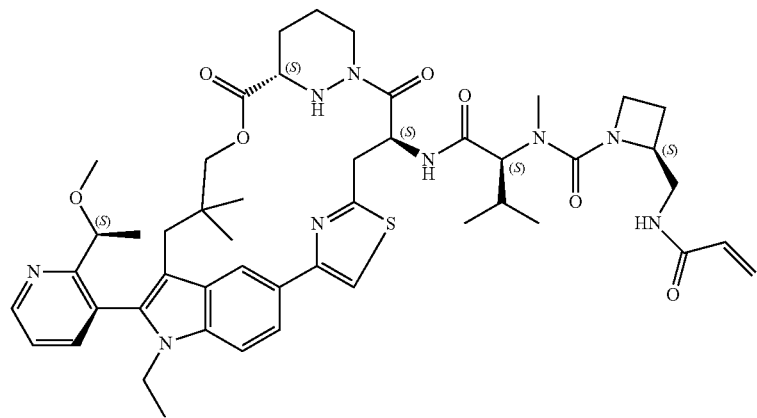 |

TABLE 1-continued
Certain Compounds of the Present Invention
| Ex# | Structure |
|---|---|
| A423 | 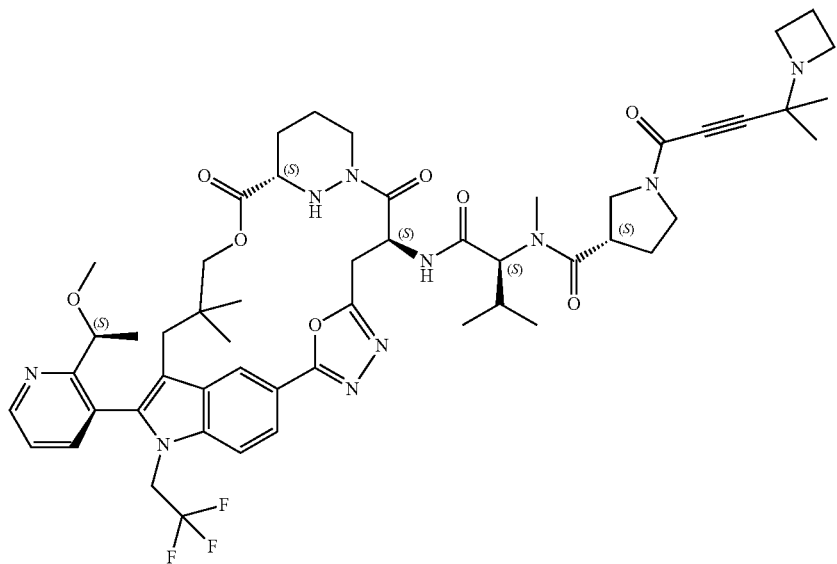 |
| A424 | 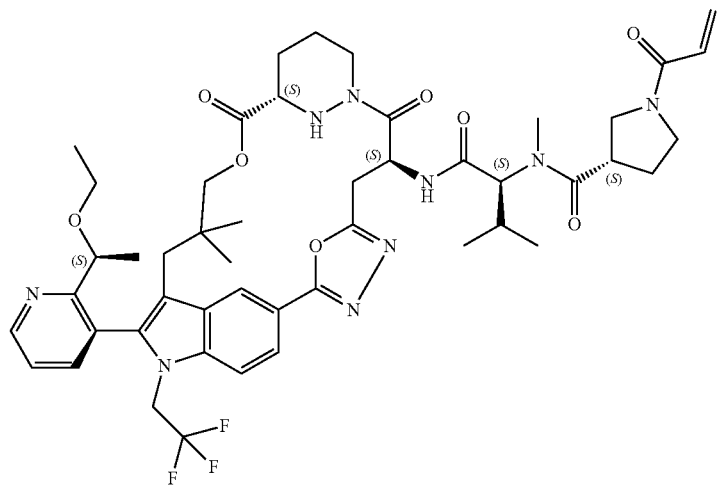 |
| A425 | 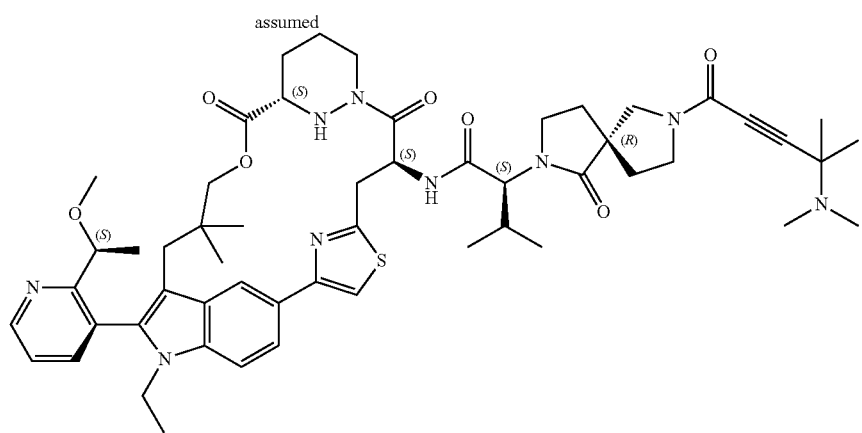 |

TABLE 1-continued
Certain Compounds of the Present Invention
| Ex# | Structure |
|---|---|
| A426 | 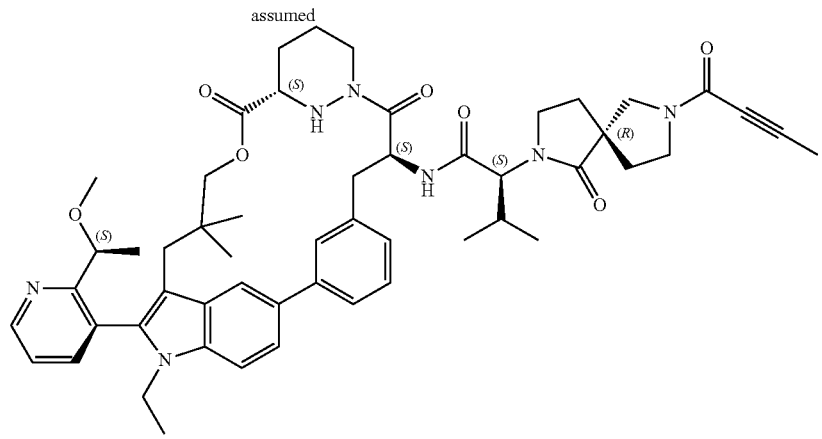 |
| A427 | 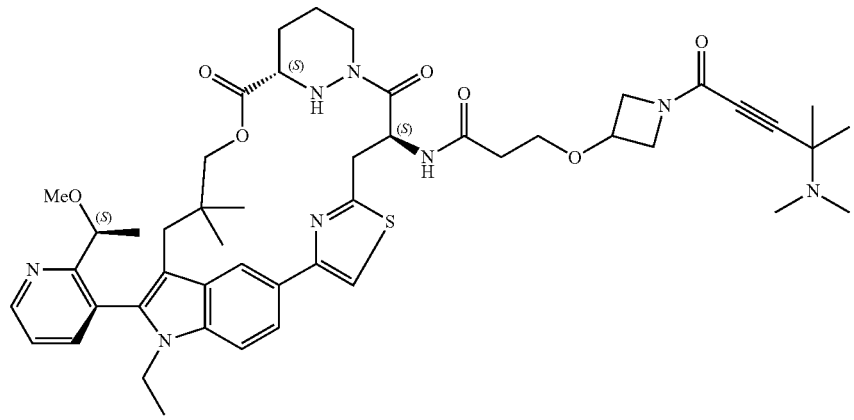 |
| A428 | 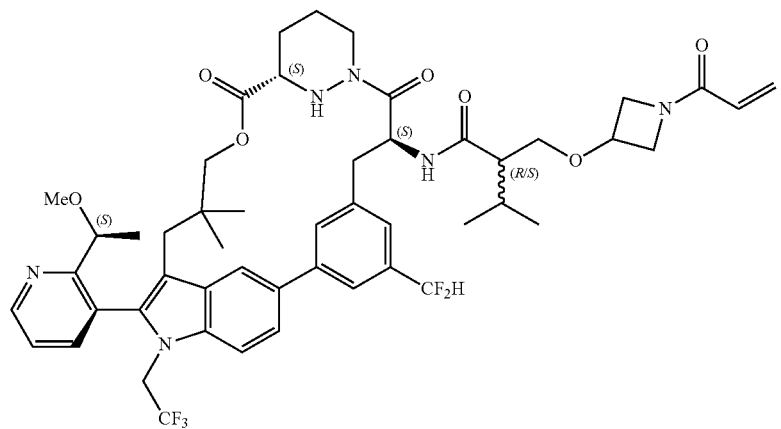 |

TABLE 1-continued
Certain Compounds of the Present Invention
| Ex# | Structure |
|---|---|
| A429 | 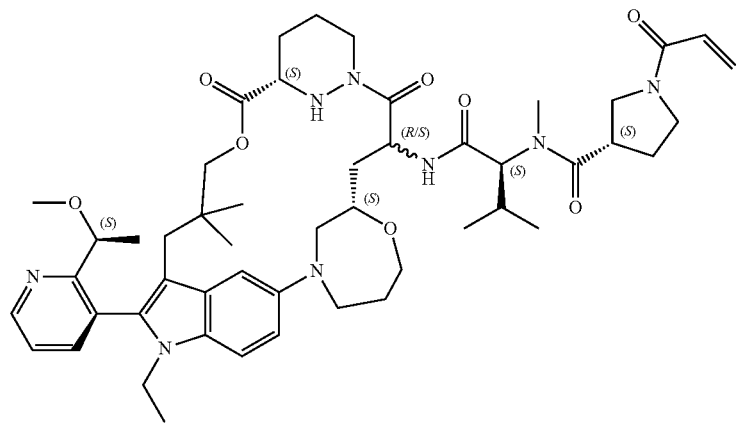 |
| A430 | 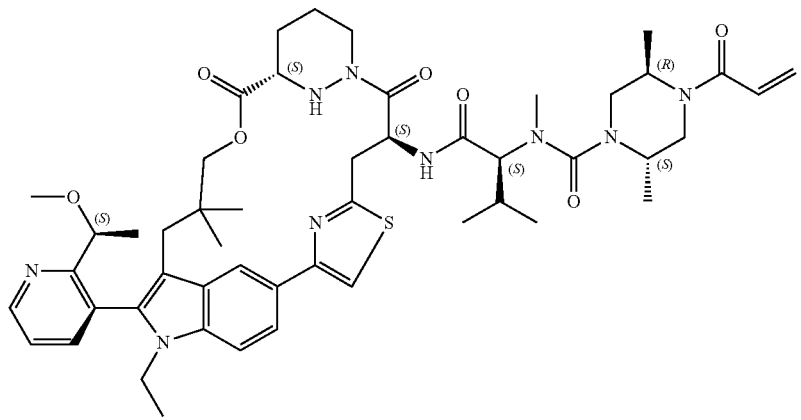 |
| A431 | 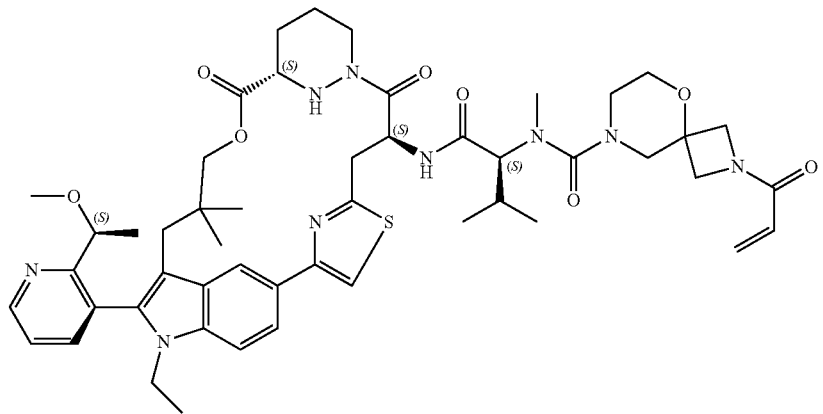 |

TABLE 1-continued

Certain Compounds of the Present Invention

| Ex# | Structure |
|---|---|
| A432 | 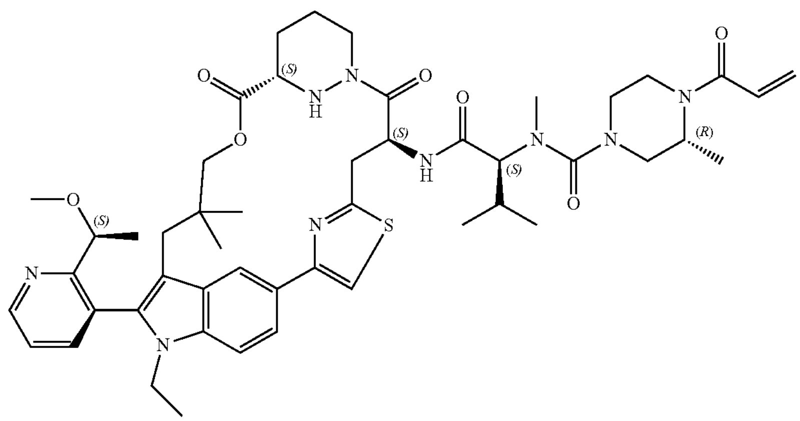 |
| A433 | 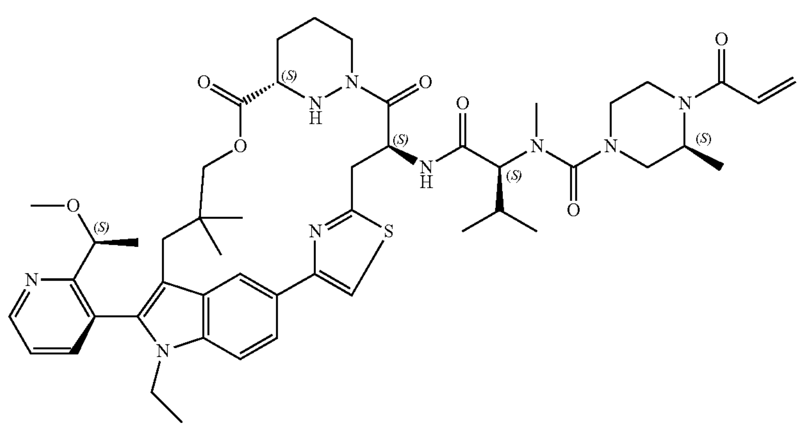 |
| A334 | 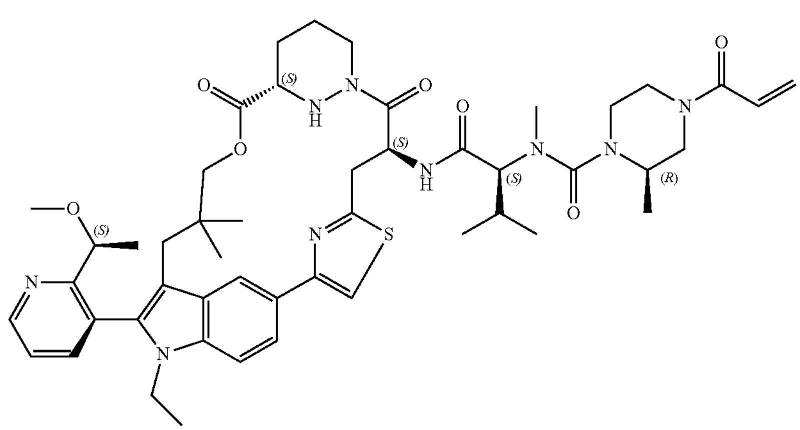 |

TABLE 1-continued
Certain Compounds of the Present Invention
| Ex# | Structure |
|---|---|
| A435 | 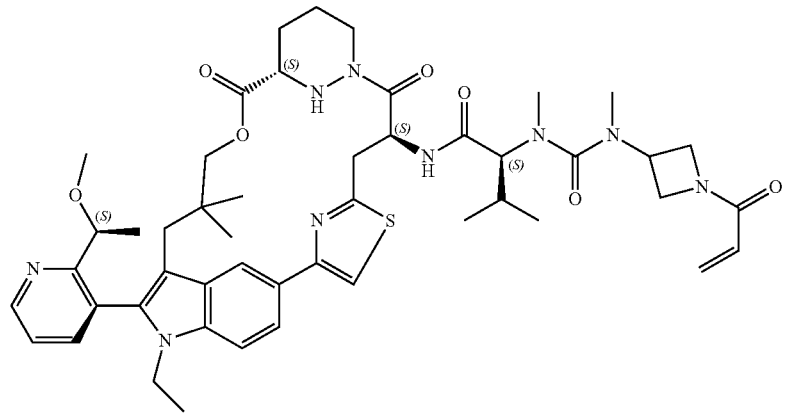 |
| A436 | 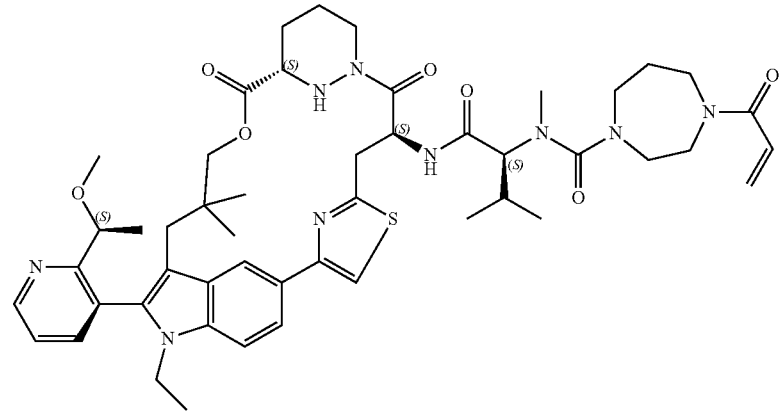 |
| A437 | 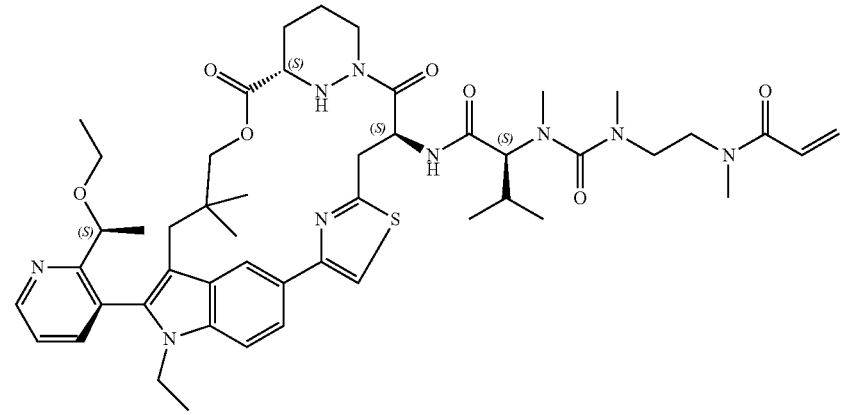 |

TABLE 1-continued

Certain Compounds of the Present Invention

| Ex# | Structure |
|---|---|
| A438 | 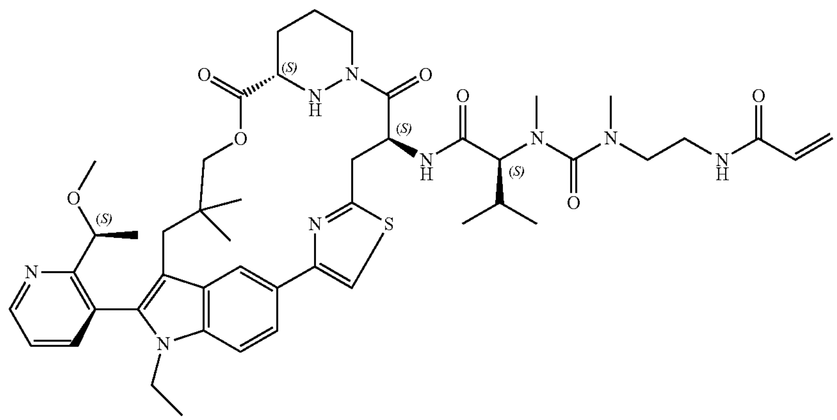 |
| A439 | 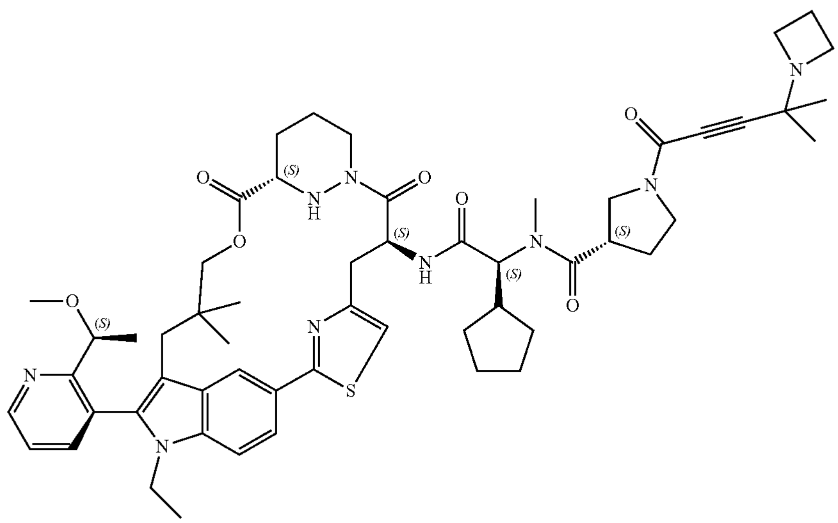 |
| A440 | 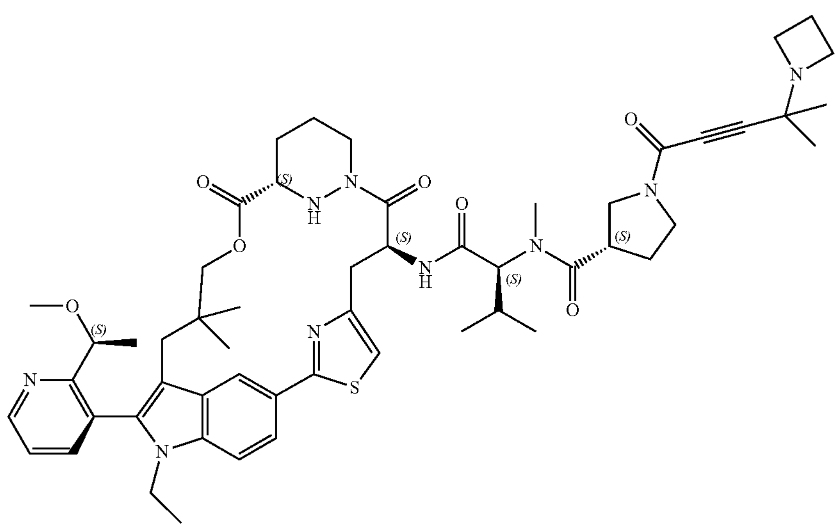 |

TABLE 1-continued

Certain Compounds of the Present Invention

| Ex# | Structure |
|---|---|
| A441 | 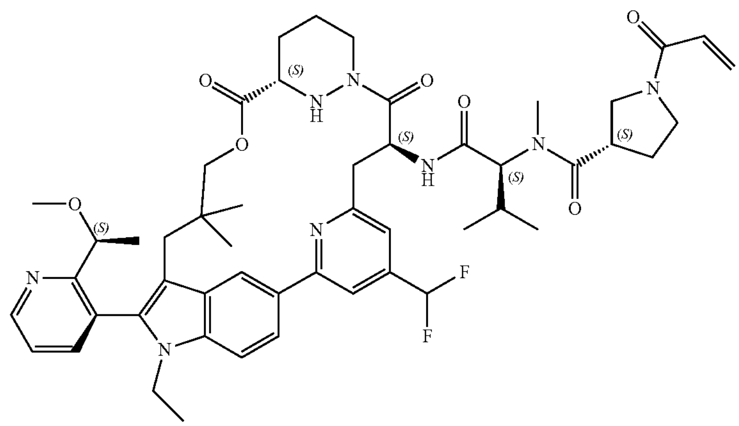 |
| A442 | 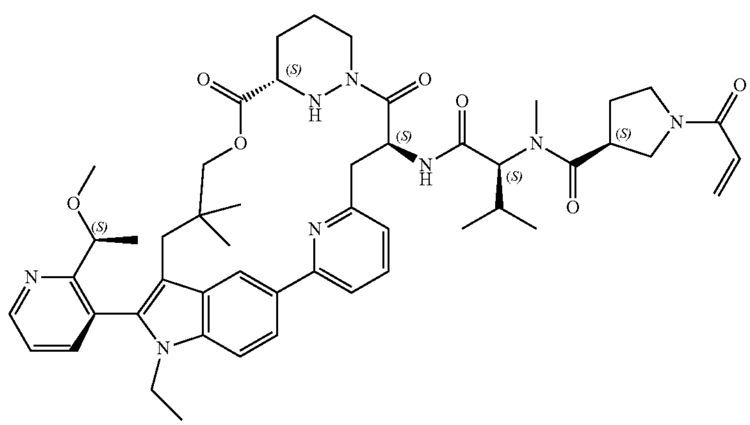 |
| A443 | 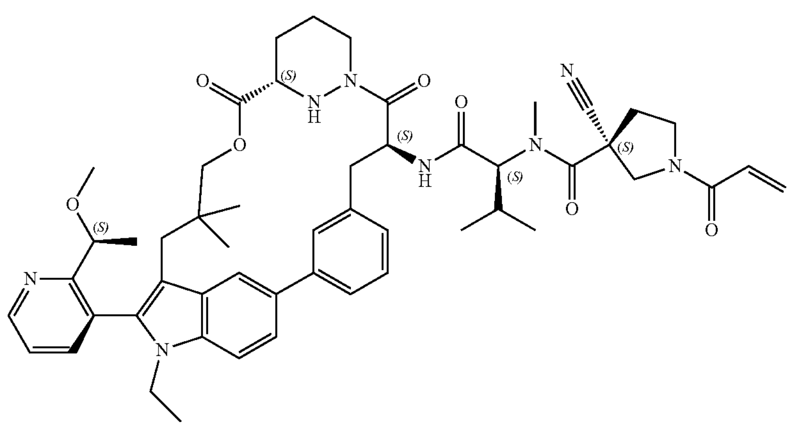 |

US 11,952,352 B2
363                                                                  364
TABLE 1-continued
Certain Compounds of the Present Invention
| Ex# | Structure |
|---|---|
| A444 | 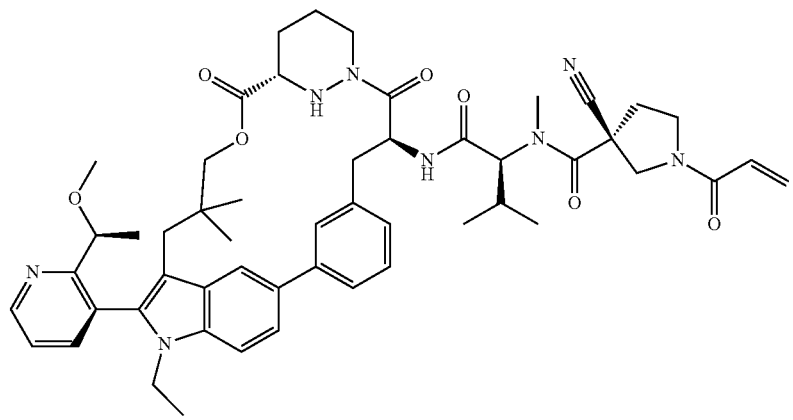 |
| A445 | 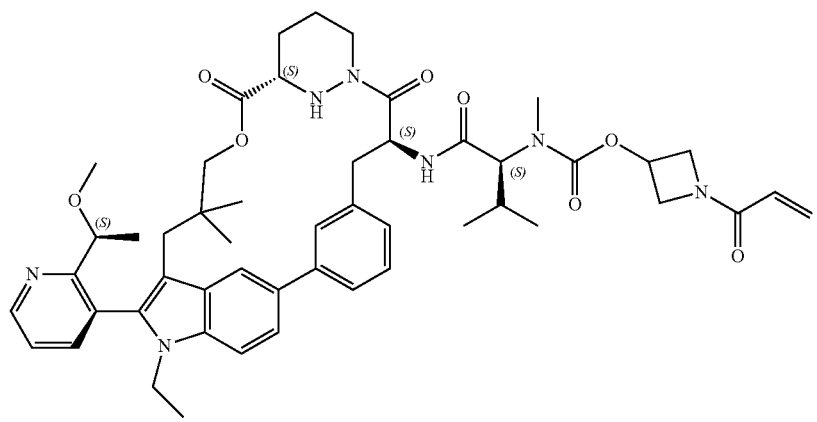 |
| A446 | 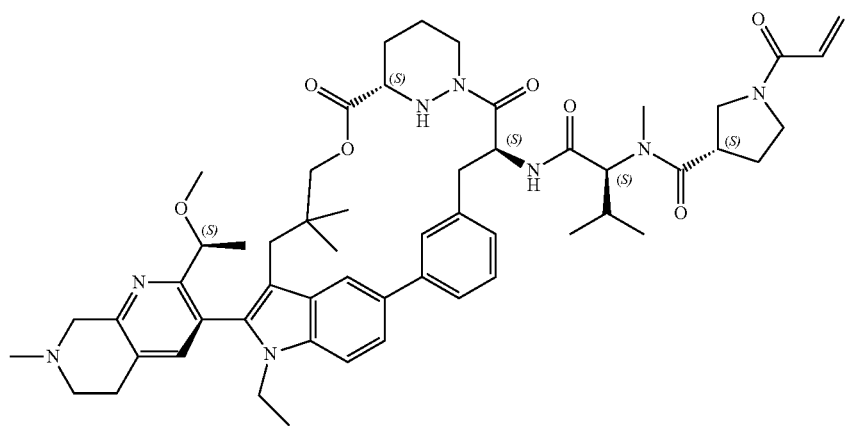 |

TABLE 1-continued
Certain Compounds of the Present Invention
| Ex# | Structure |
|---|---|
| A447 | 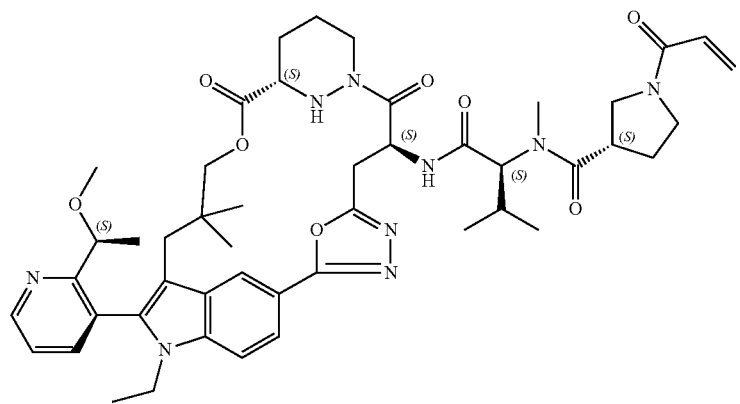 |
| A448 | 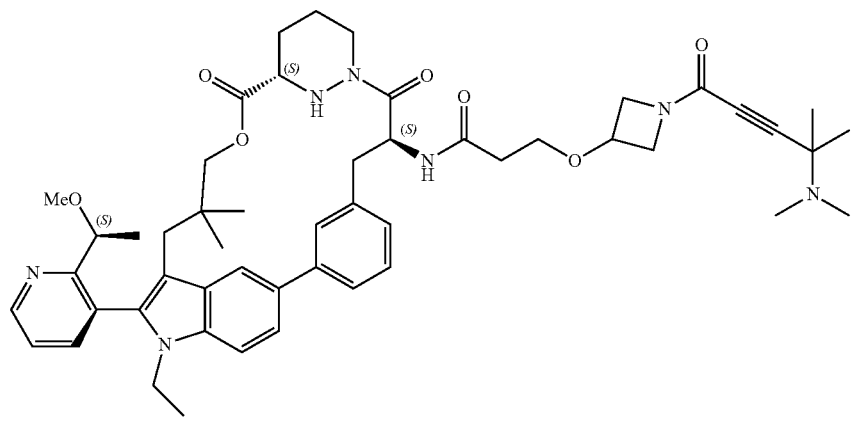 |
| A449 | 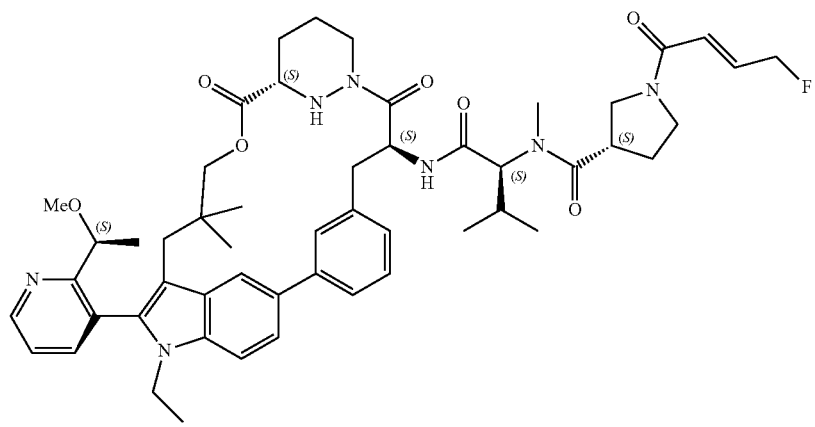 |

TABLE 1-continued

Certain Compounds of the Present Invention

| Ex# | Structure |
|---|---|
| A450 | 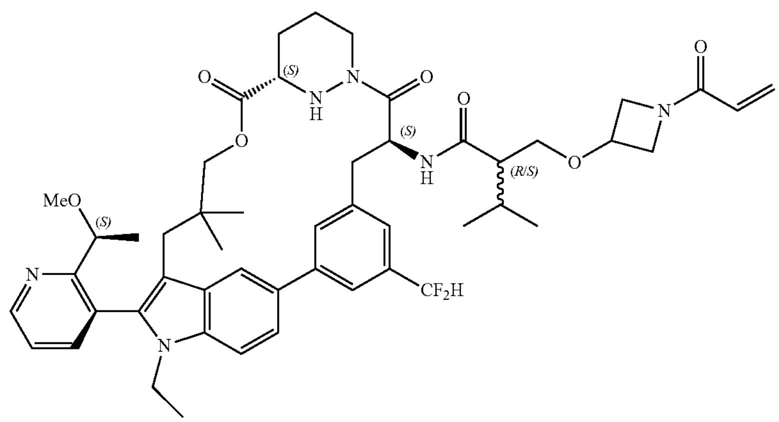 |
| A451 | 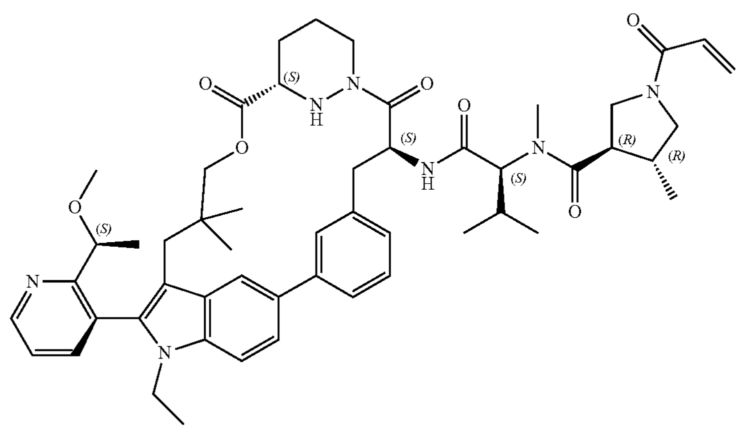 |
| A452 | 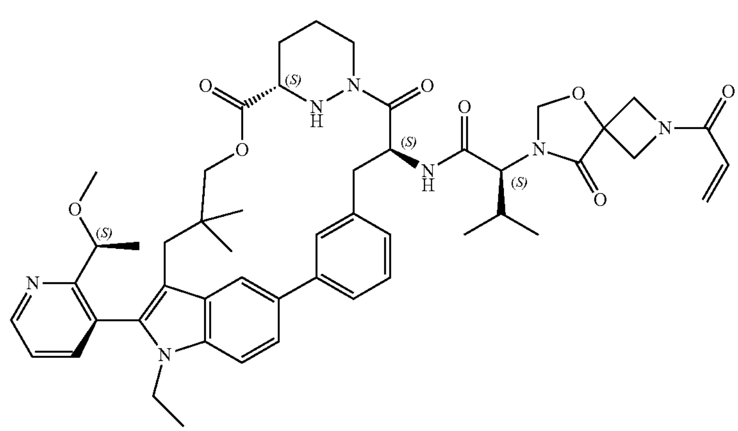 |

TABLE 1-continued
Certain Compounds of the Present Invention
| Ex# | Structure |
|---|---|
| A453 | 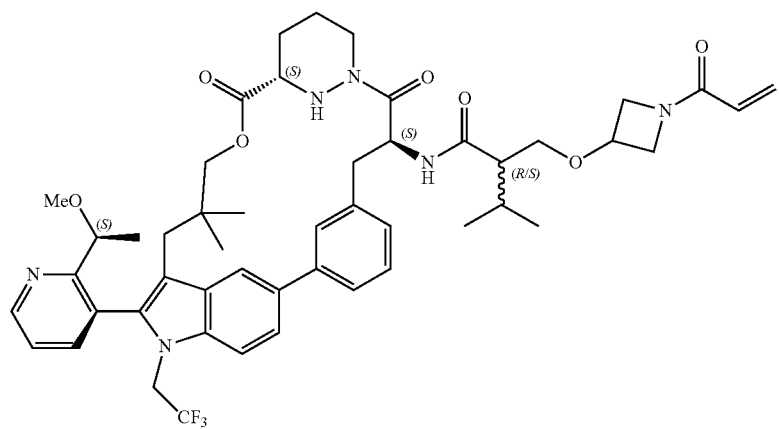 |
| A454 | 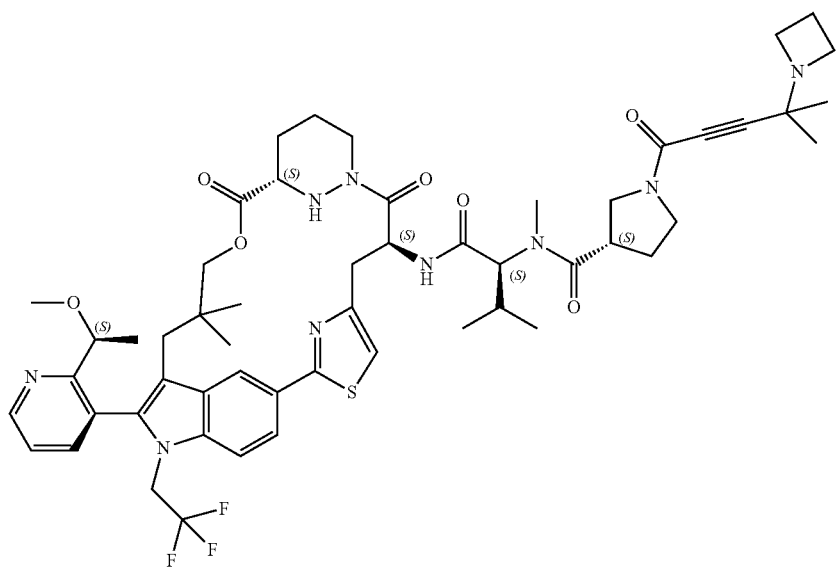 |
| A455 | 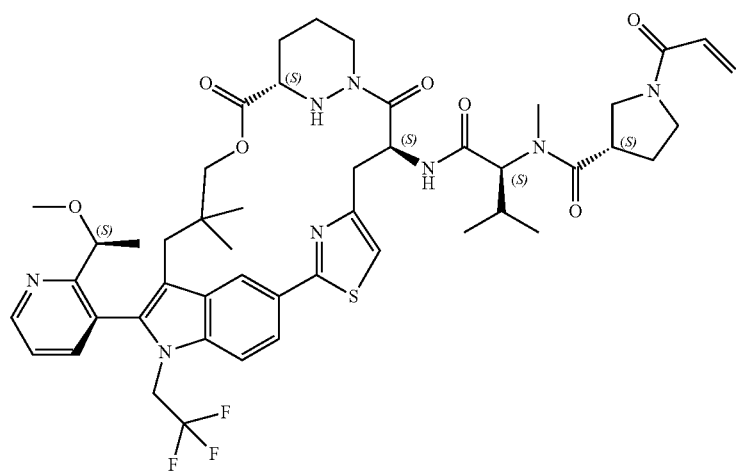 |

TABLE 1-continued
Certain Compounds of the Present Invention
| Ex# | Structure |
|---|---|
| A456 | 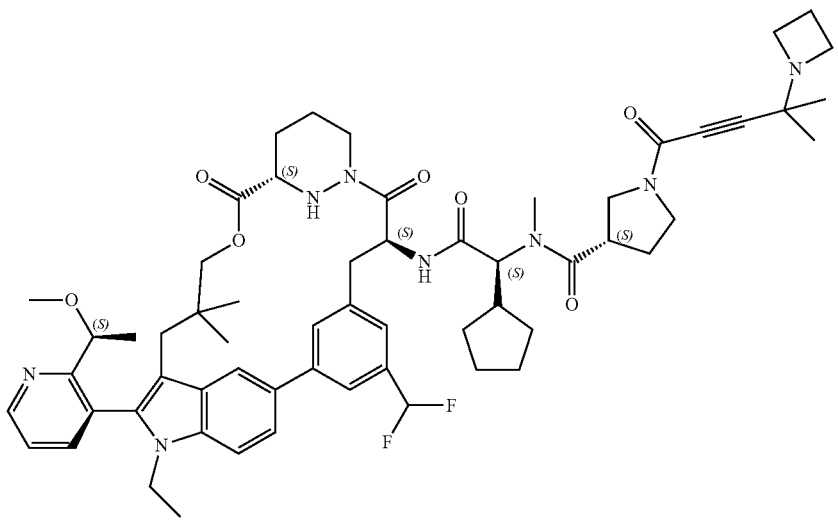 |
| A457 | 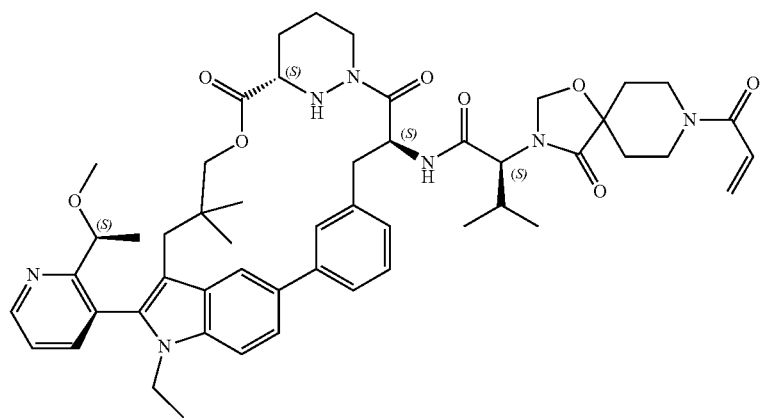 |
| A458 | 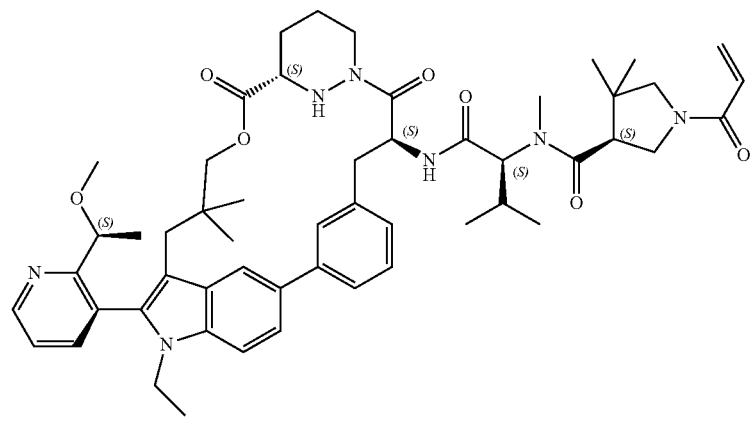 |

TABLE 1-continued
Certain Compounds of the Present Invention
| Ex# | Structure |
|---|---|
| A459 | 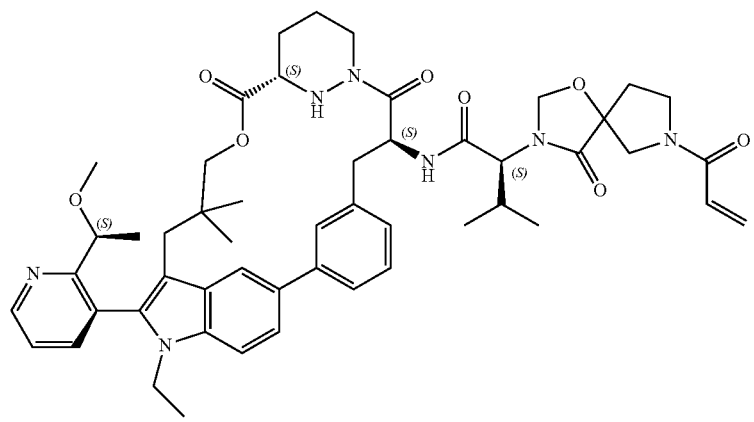 |
| A460 | 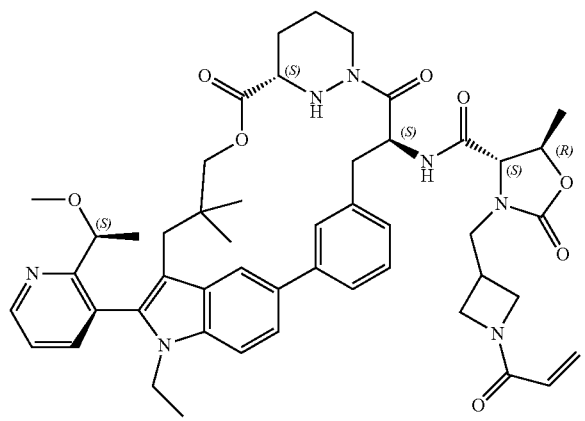 |
| A461 | 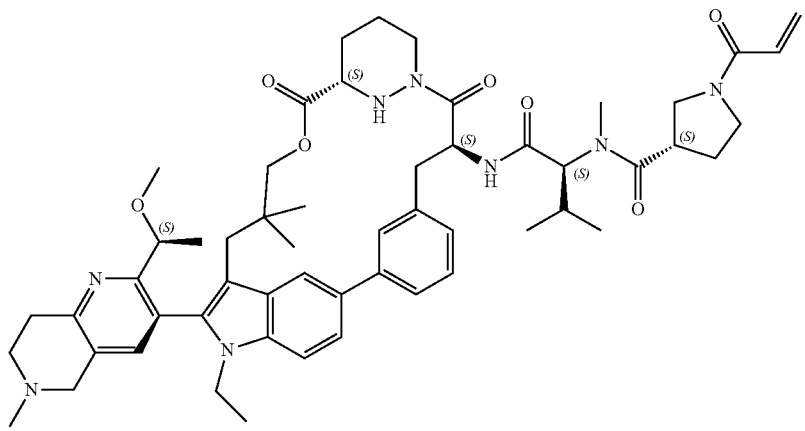 |

TABLE 1-continued
Certain Compounds of the Present Invention
| Ex# | Structure |
|---|---|
| A462 | 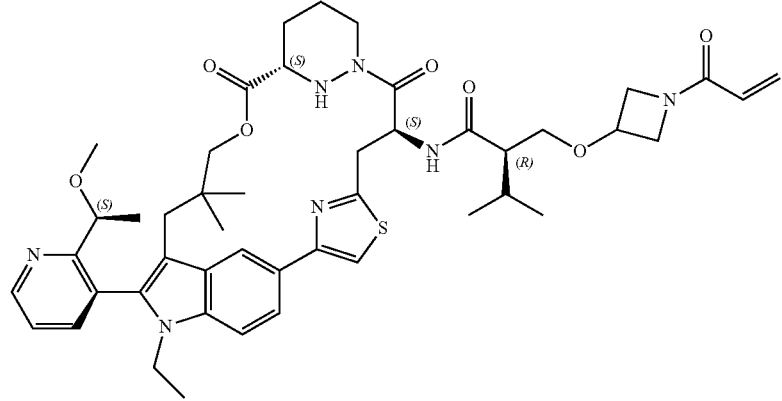 |
| A463 | 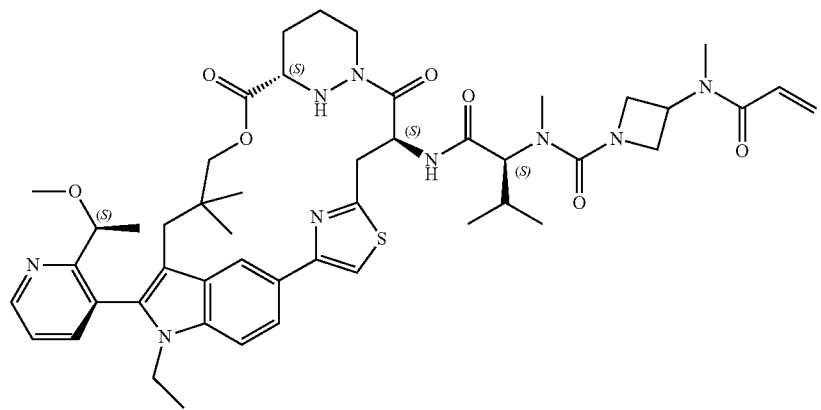 |
| A464 | 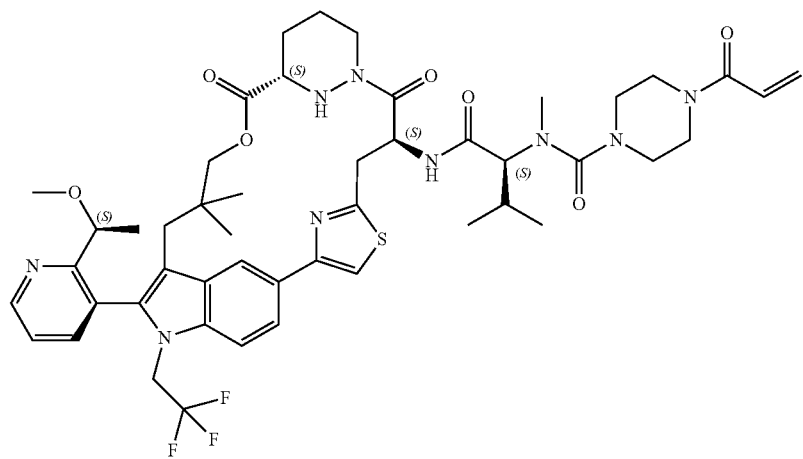 |

TABLE 1-continued
Certain Compounds of the Present Invention
| Ex# | Structure |
|---|---|
| A465 | 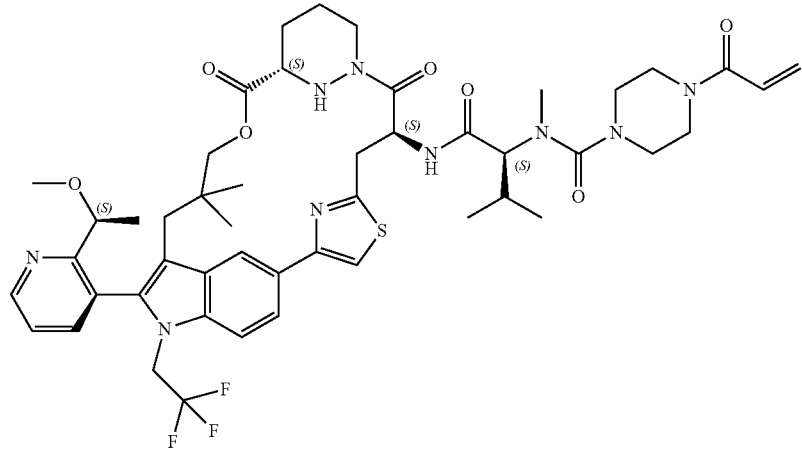 |
| A466 | 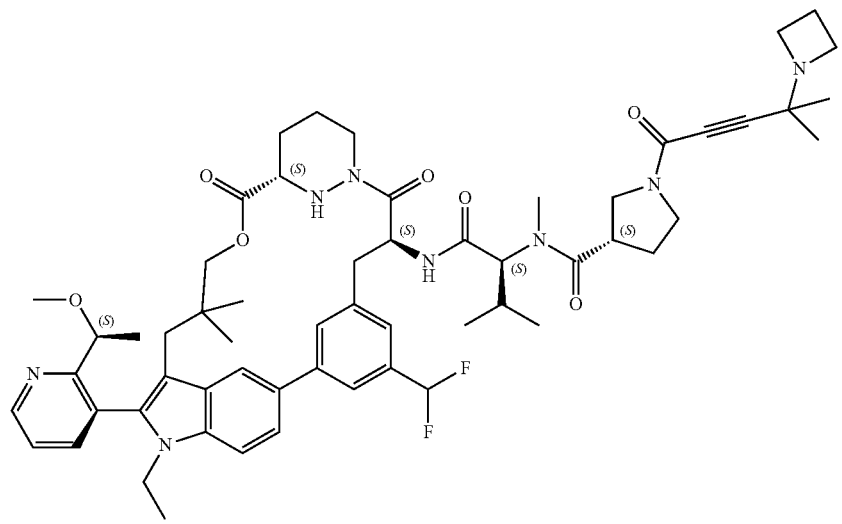 |
| A467 | 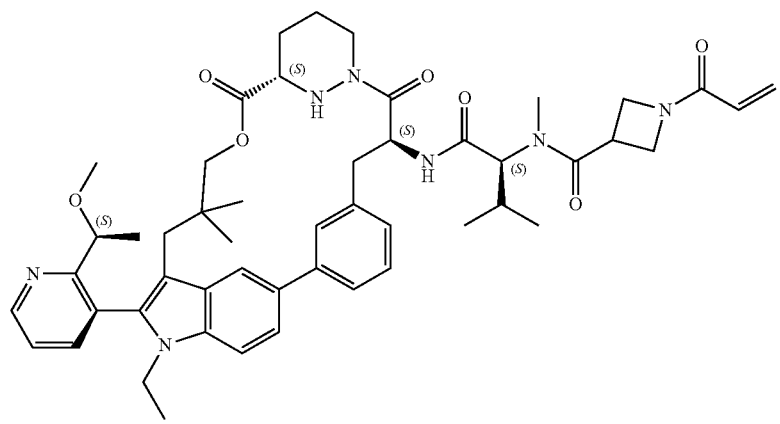 |

TABLE 1-continued
Certain Compounds of the Present Invention
| Ex# | Structure |
|---|---|
| A468 | 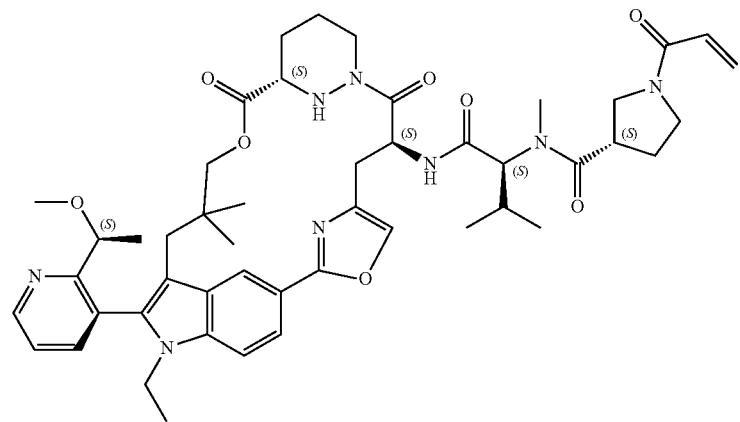 |
| A469 | 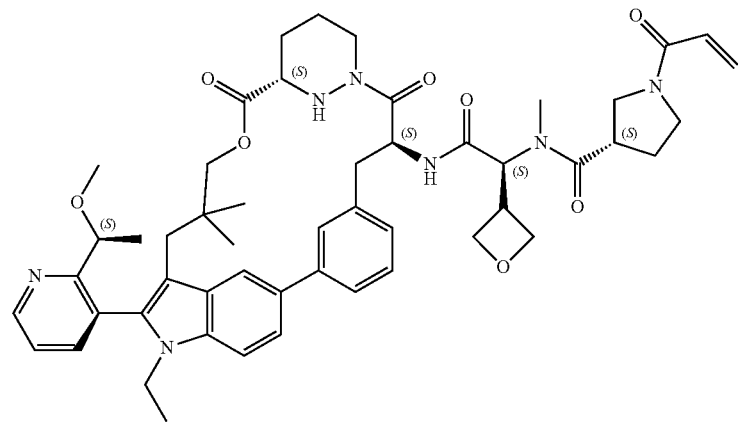 |
| A470 | 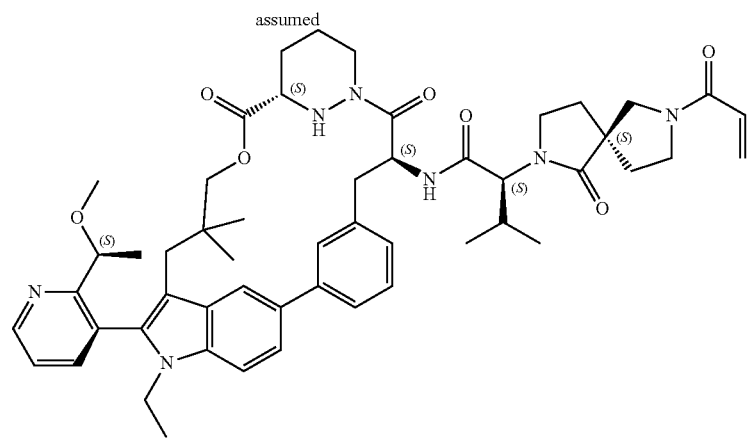 |

TABLE 1-continued
Certain Compounds of the Present Invention
| Ex# | Structure |
|---|---|
| A471 | 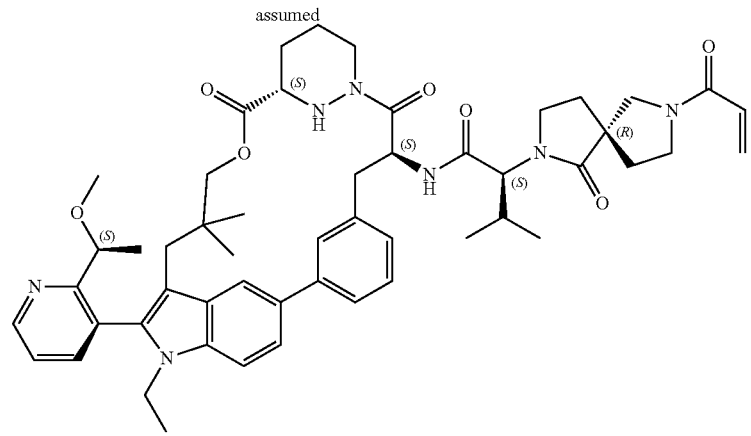 |
| A472 | 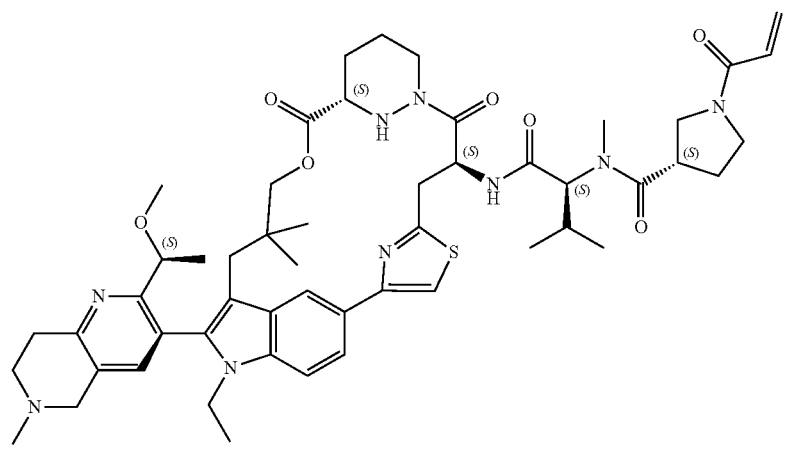 |
| A473 | 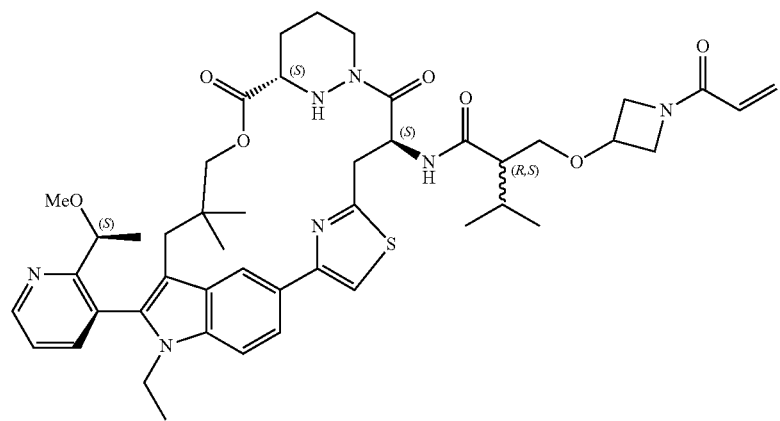 |

TABLE 1-continued
Certain Compounds of the Present Invention
| Ex# | Structure |
|---|---|
| A474 | 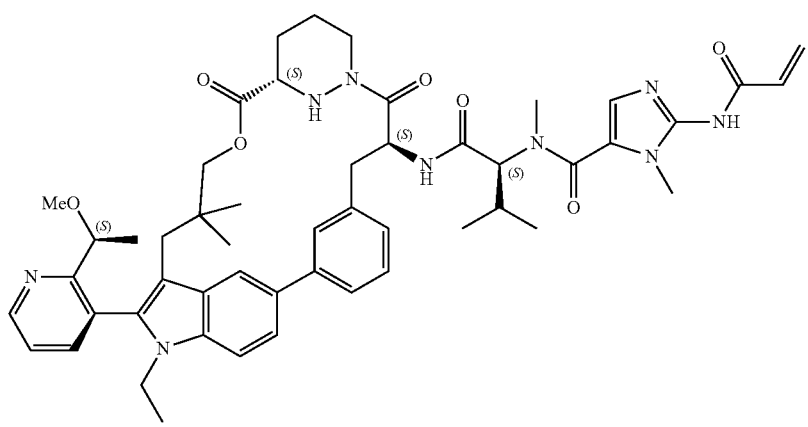 |
| A475 | 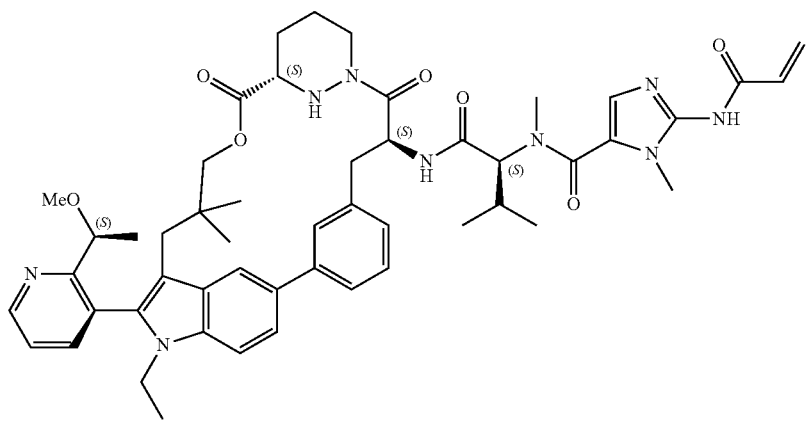 |
| A476 | 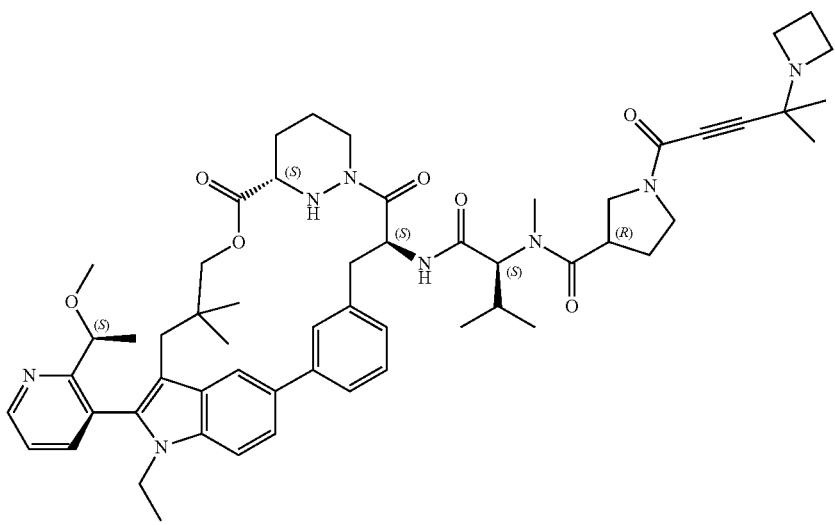 |

TABLE 1-continued

Certain Compounds of the Present Invention

| Ex# | Structure |
|---|---|
| A477 | 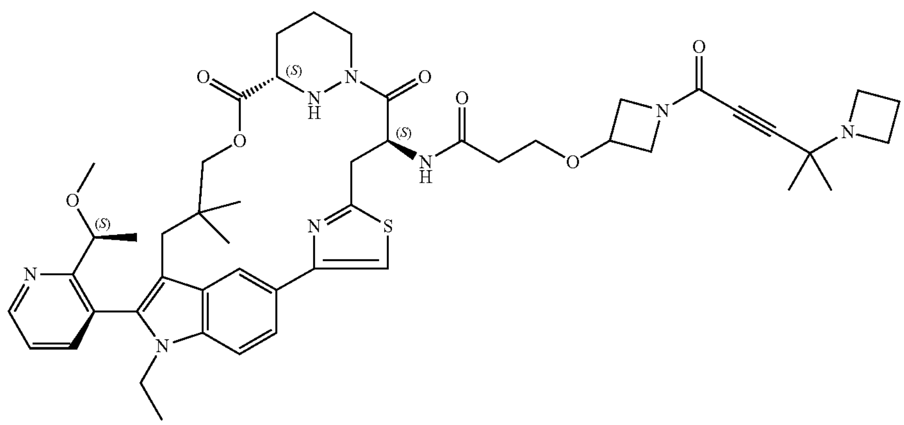 |
| A478 | 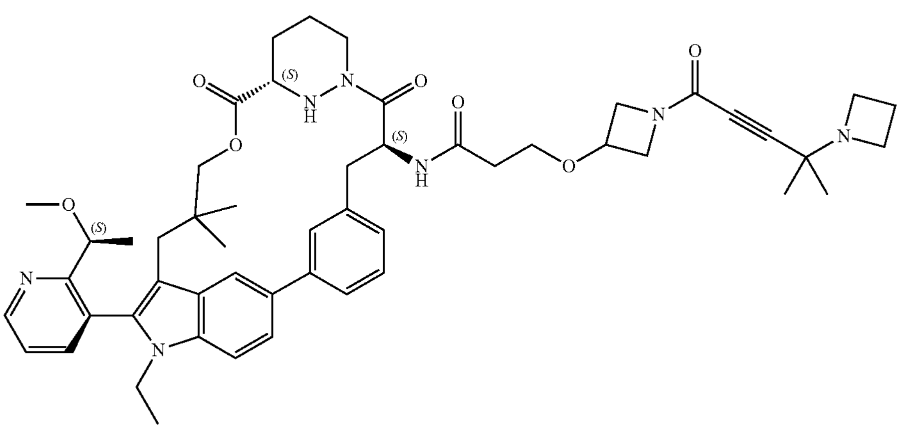 |
| A479 | 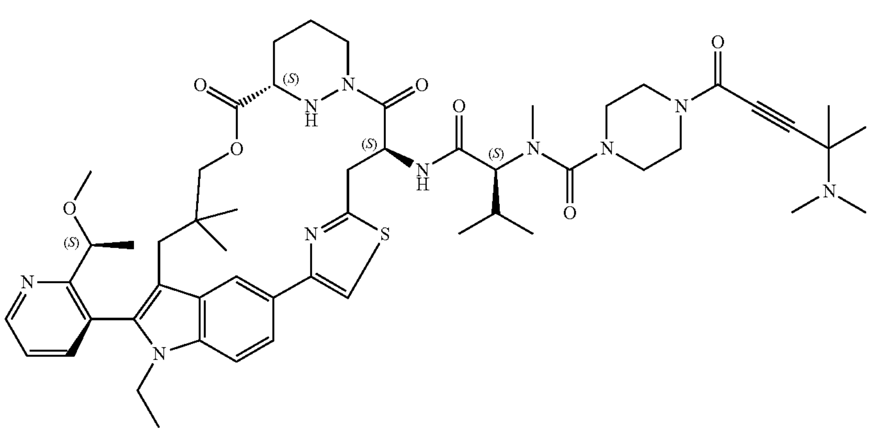 |

TABLE 1-continued
Certain Compounds of the Present Invention
| Ex# | Structure |
|---|---|
| A480 | 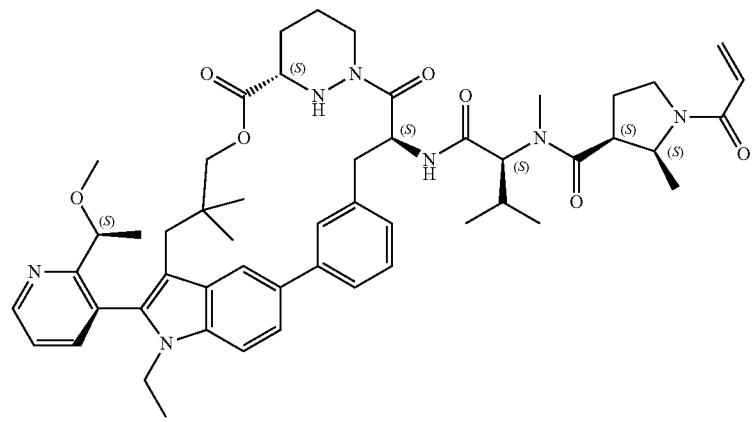 |
| A481 | 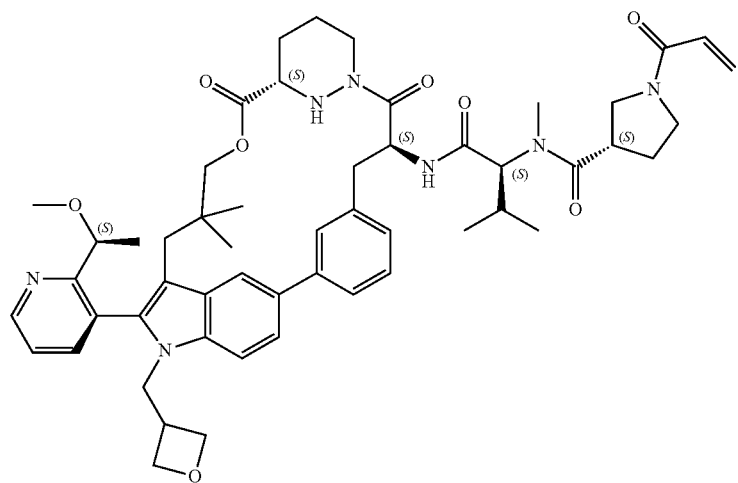 |
| A482 | 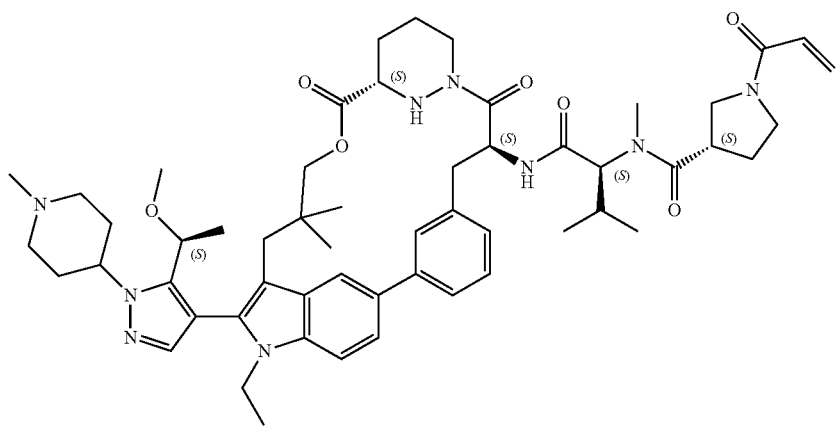 |

TABLE 1-continued
Certain Compounds of the Present Invention
| Ex# | Structure |
|---|---|
| A483 | 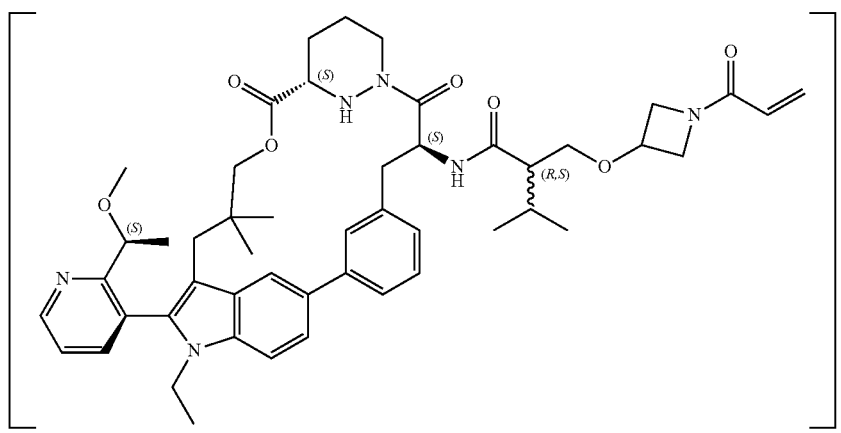 |
| A484 | 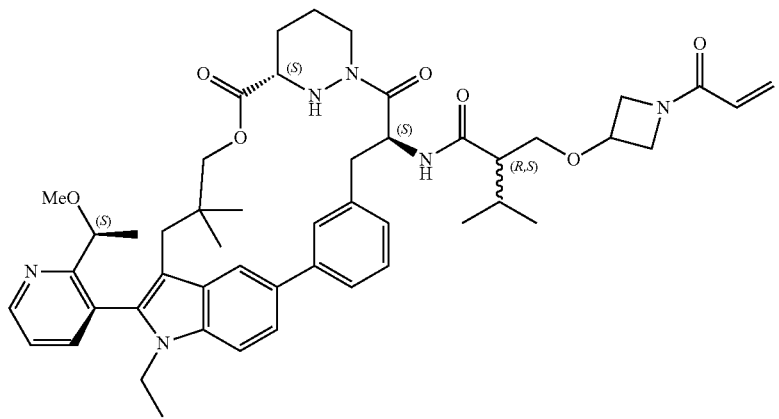 |
| A485 | 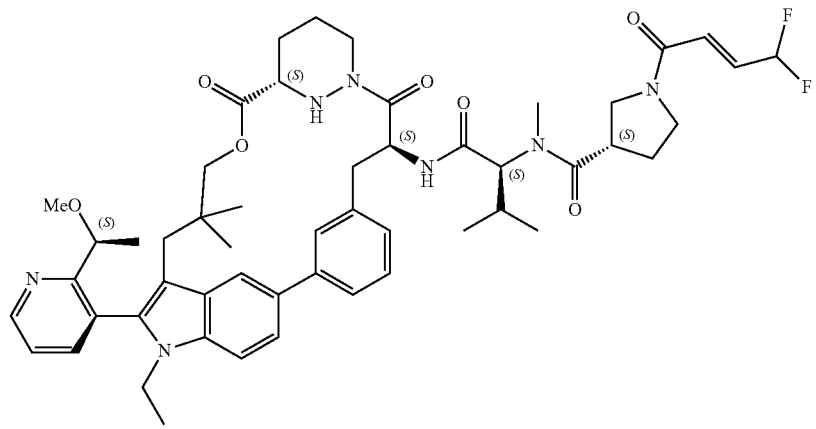 |

TABLE 1-continued
Certain Compounds of the Present Invention
| Ex# | Structure |
|---|---|
| A486 | 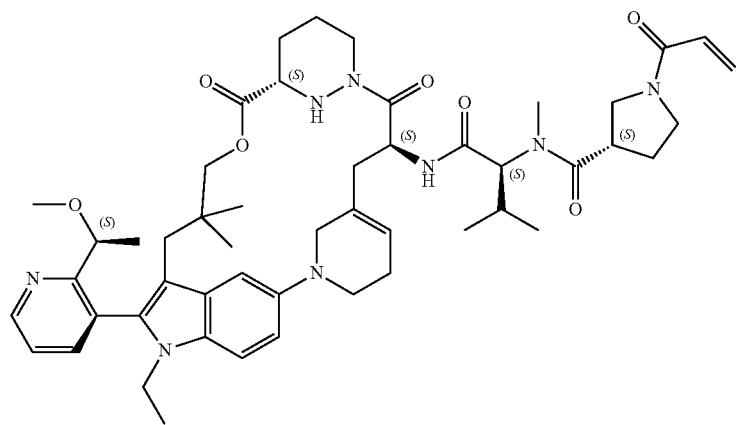 |
| A487 | 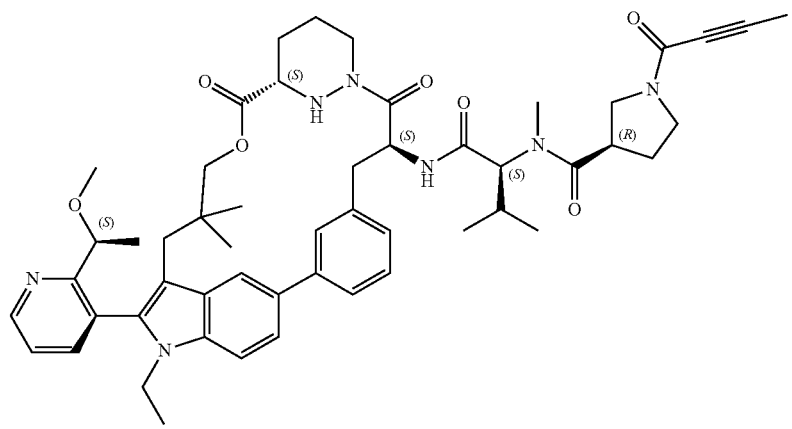 |
| A488 | 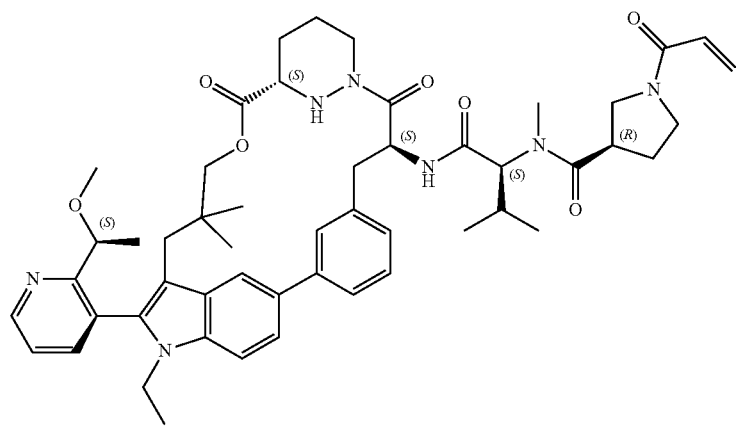 |

TABLE 1-continued
Certain Compounds of the Present Invention
| Ex# | Structure |
|---|---|
| A489 | 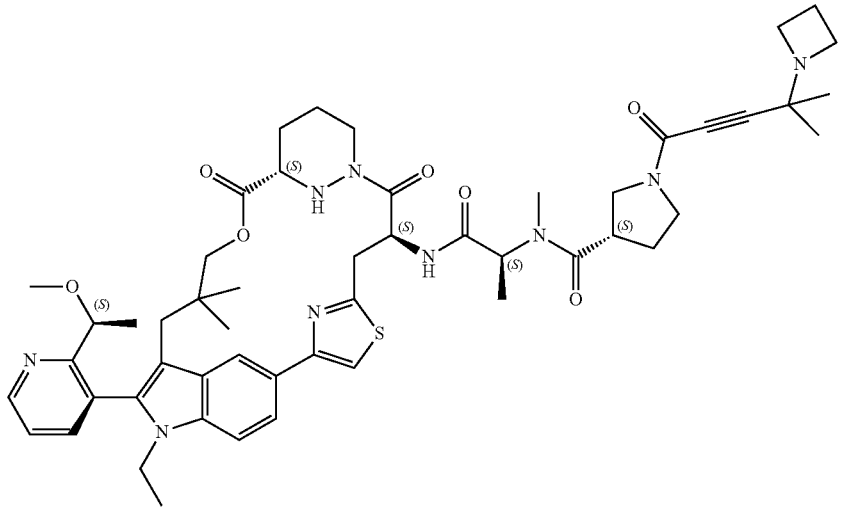 |
| A490 | 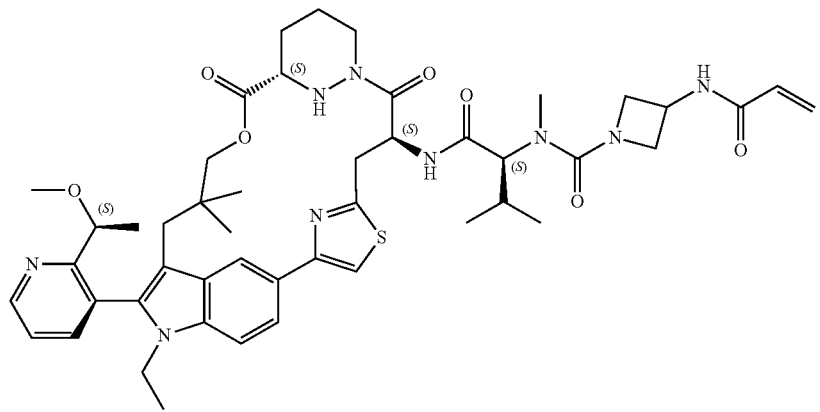 |
| A491 | 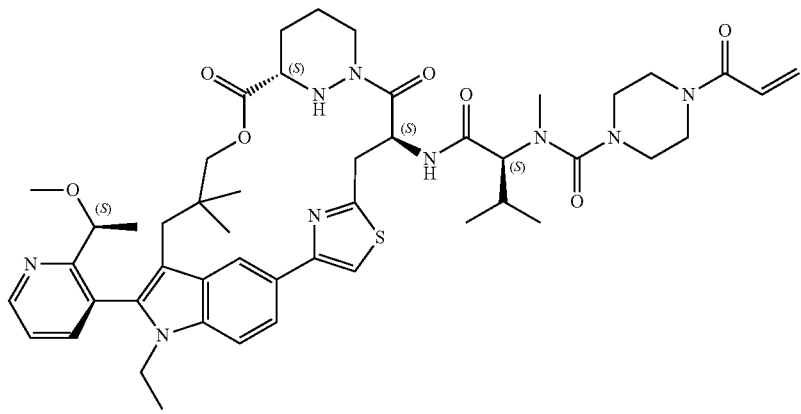 |

TABLE 1-continued
Certain Compounds of the Present Invention
| Ex# | Structure |
|---|---|
| A492 | 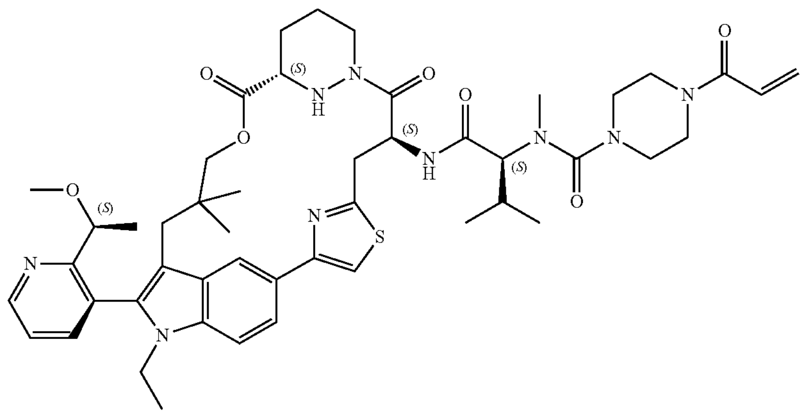 |
| A493 | 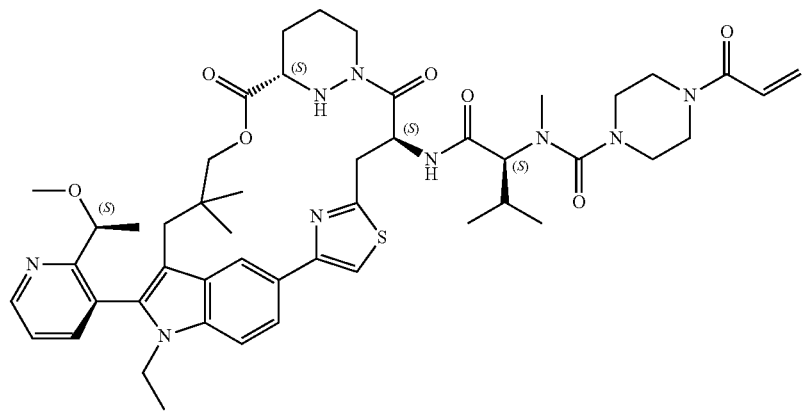 |
| A494 | 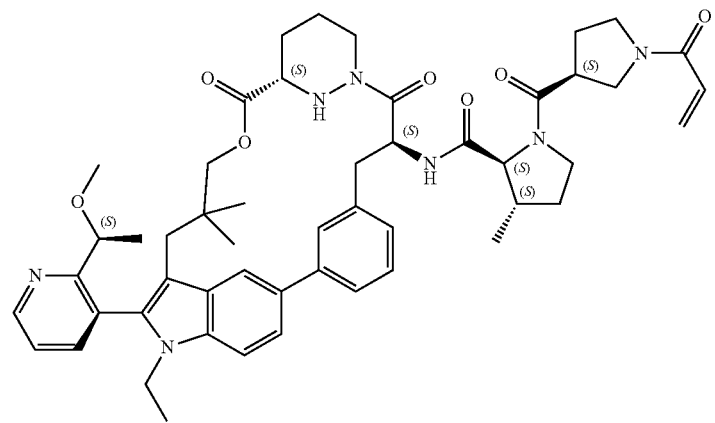 |

TABLE 1-continued

Certain Compounds of the Present Invention

| Ex# | Structure |
|---|---|
| A495 | 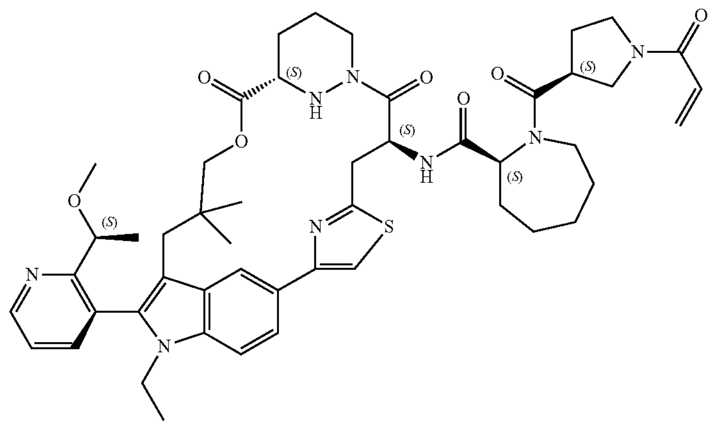 |
| A496 | 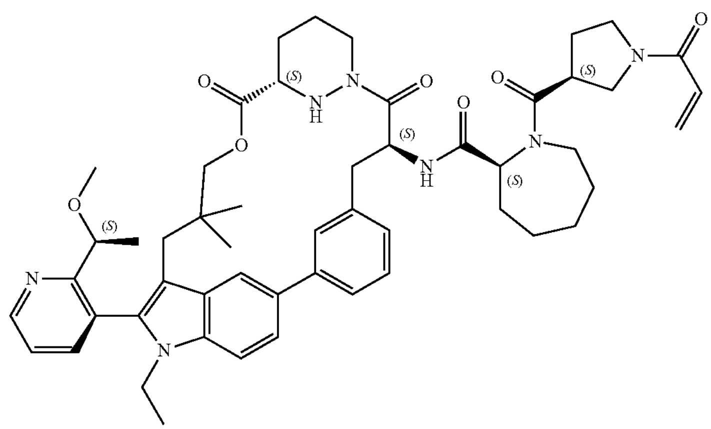 |
| A497 | 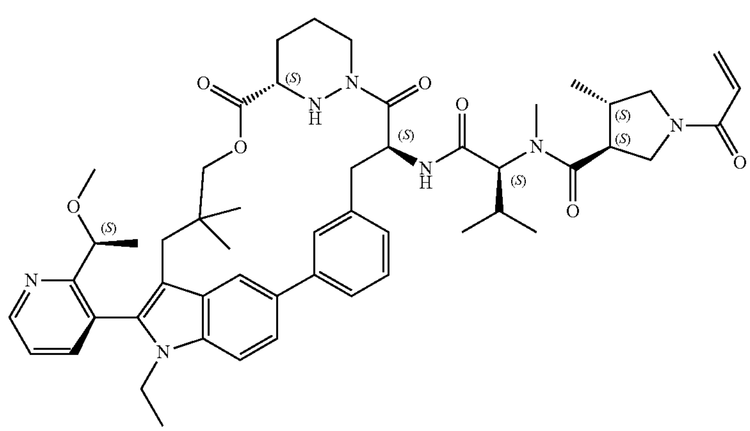 |

TABLE 1-continued
Certain Compounds of the Present Invention
| Ex# | Structure |
|---|---|
| A498 | 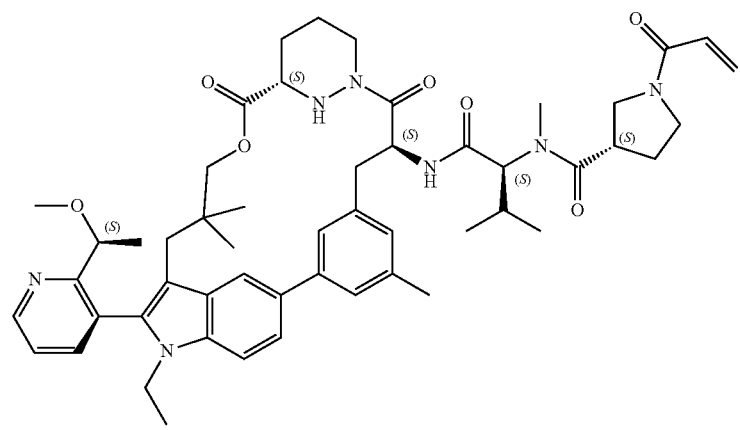 |
| A499 | 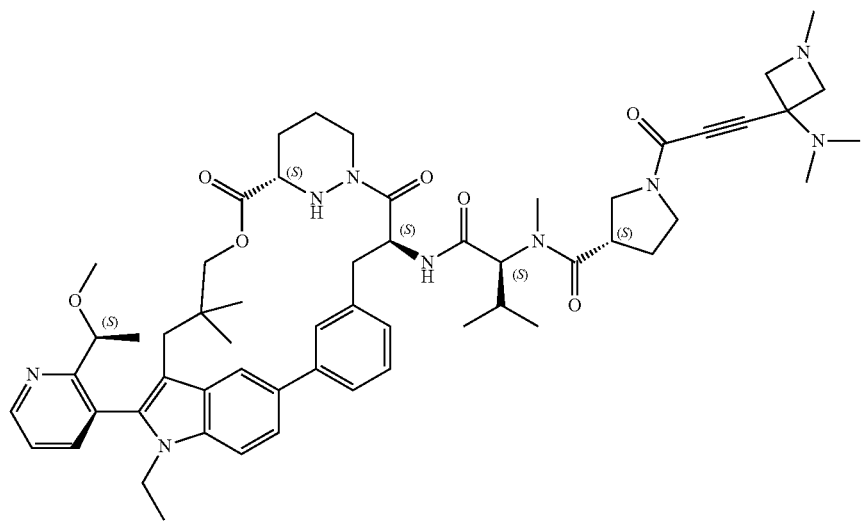 |
| A500 | 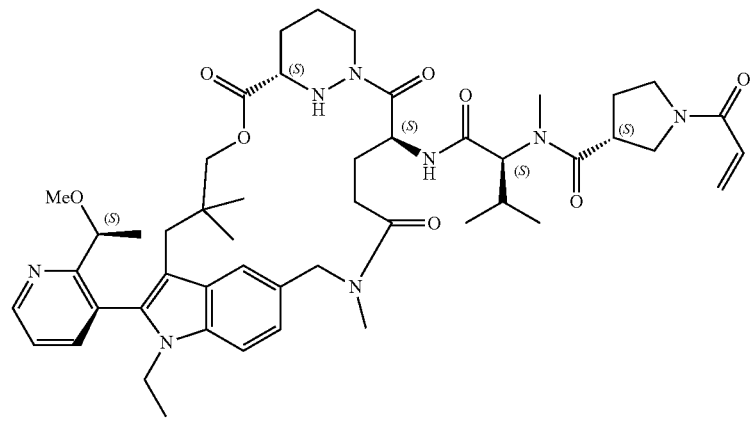 |

TABLE 1-continued
Certain Compounds of the Present Invention
| Ex# | Structure |
|---|---|
| A501 | 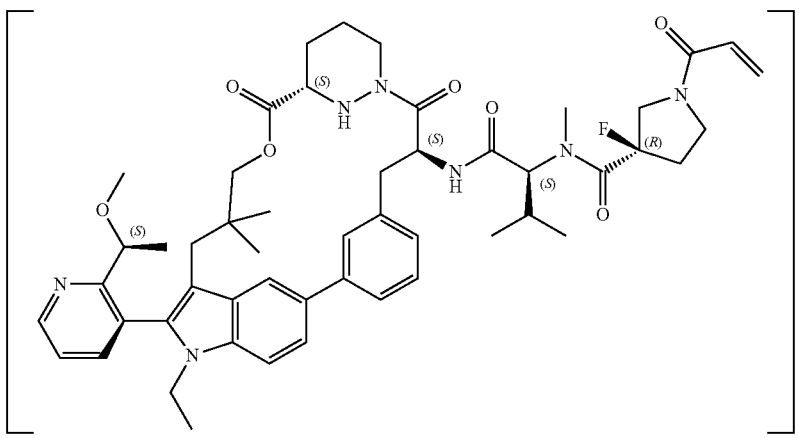 |
| A502 | 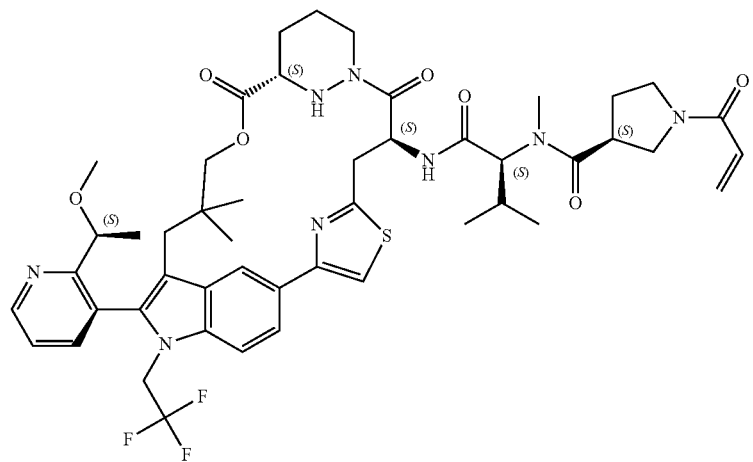 |
| A503 | 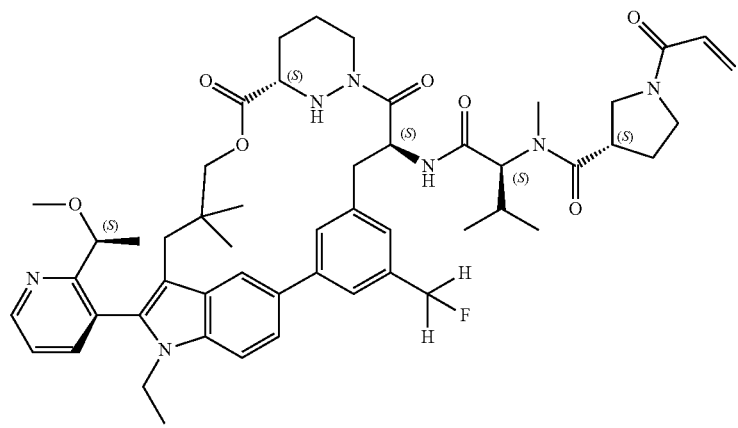 |

TABLE 1-continued
Certain Compounds of the Present Invention
| Ex# | Structure |
|---|---|
| A504 | 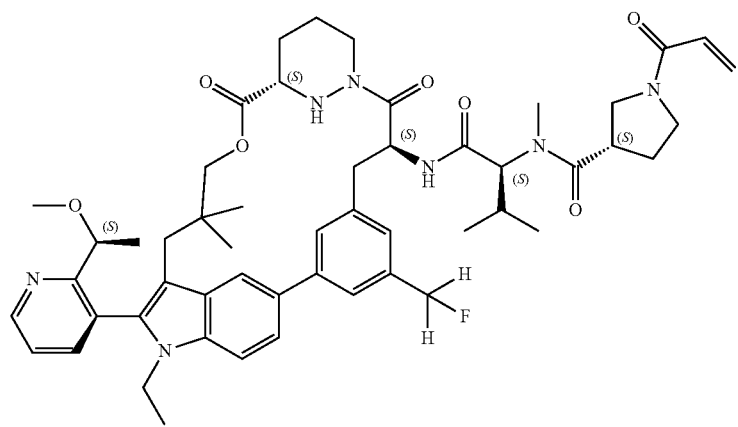 |
| A505 | 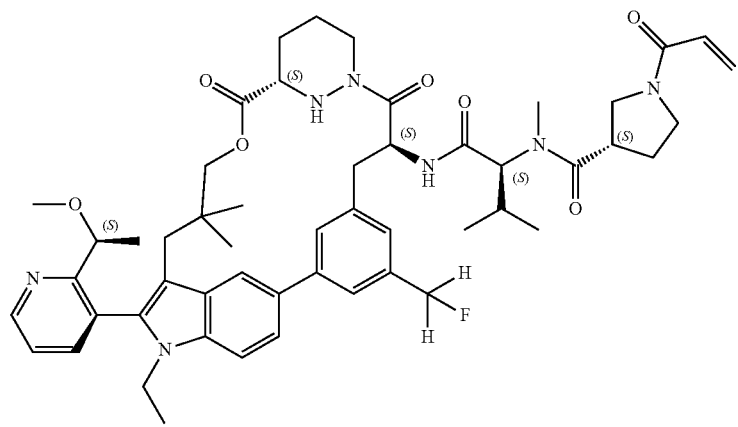 |
| A506 | 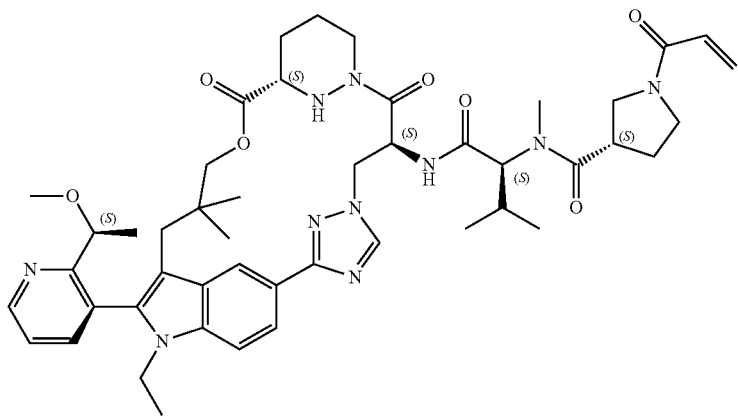 |

TABLE 1-continued
Certain Compounds of the Present Invention
| Ex# | Structure |
|---|---|
| A507 | 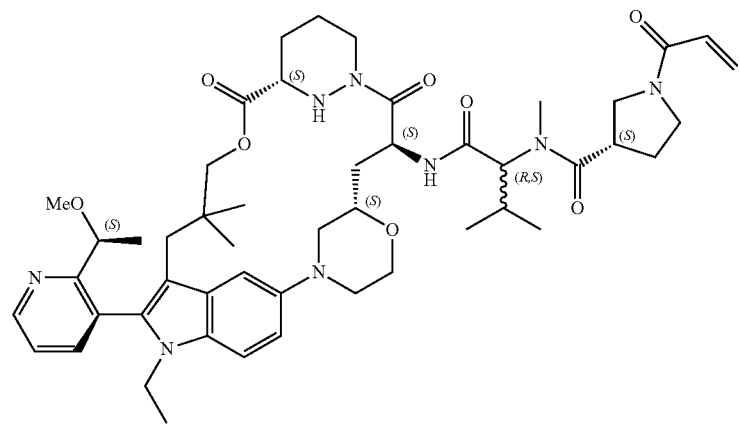 |
| A508 | 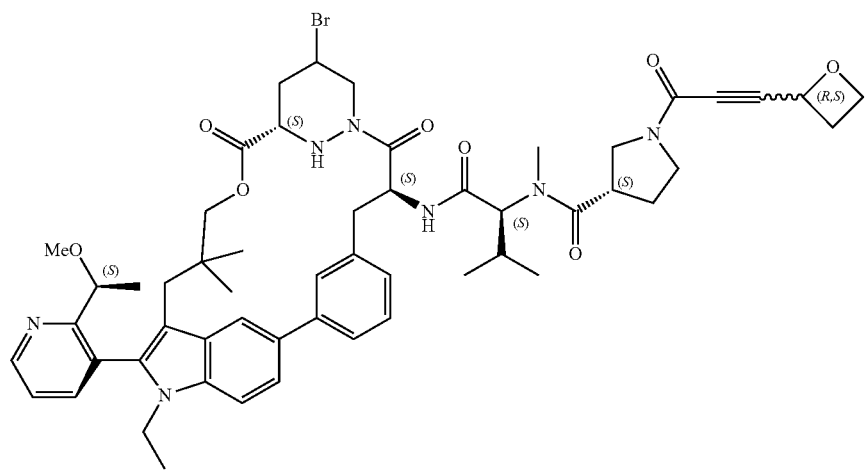 |
| A509 | 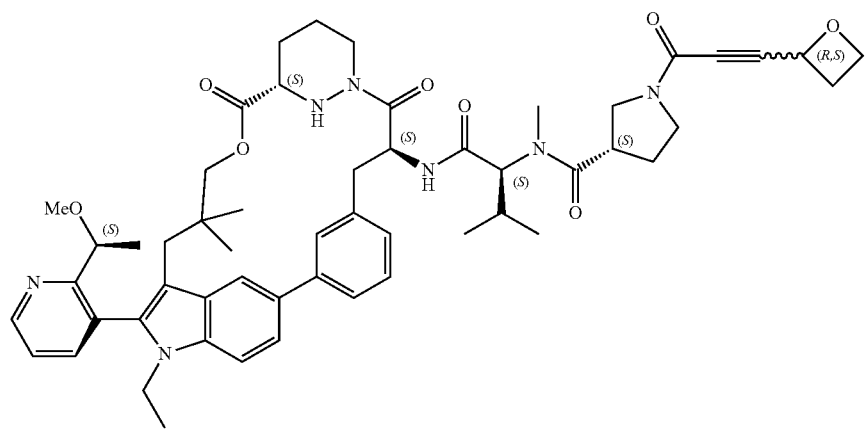 |

TABLE 1-continued
Certain Compounds of the Present Invention
| Ex# | Structure |
|---|---|
| A510 | 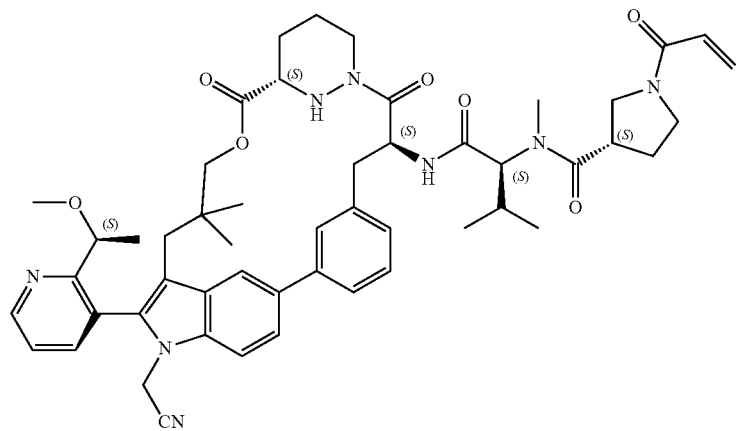 |
| A511 | 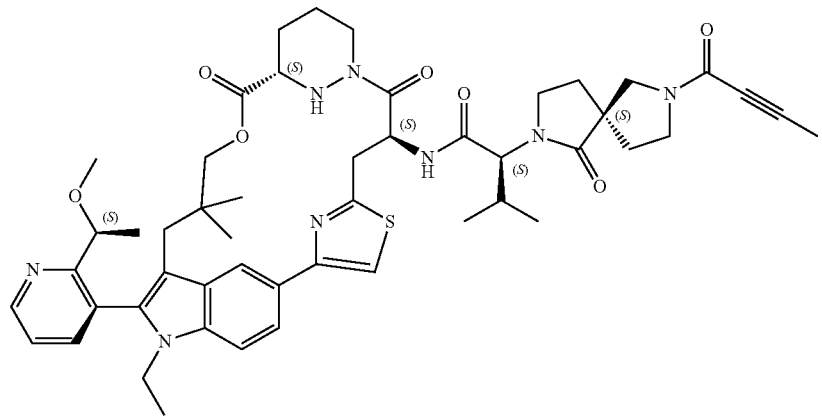 |
| A512 | 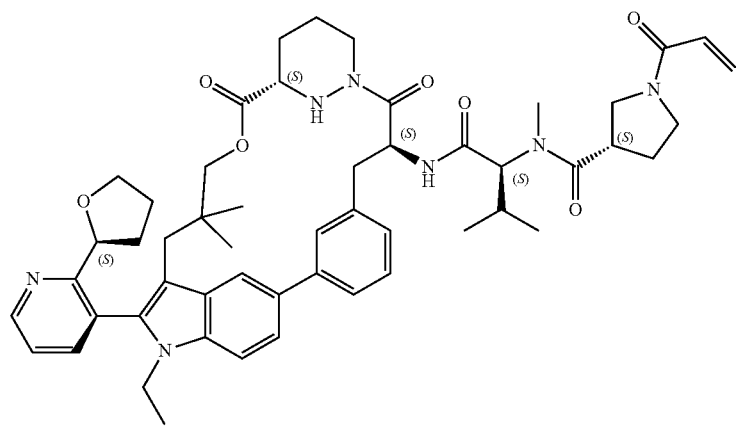 |

TABLE 1-continued

Certain Compounds of the Present Invention

| Ex# | Structure |
|---|---|
| A513 | 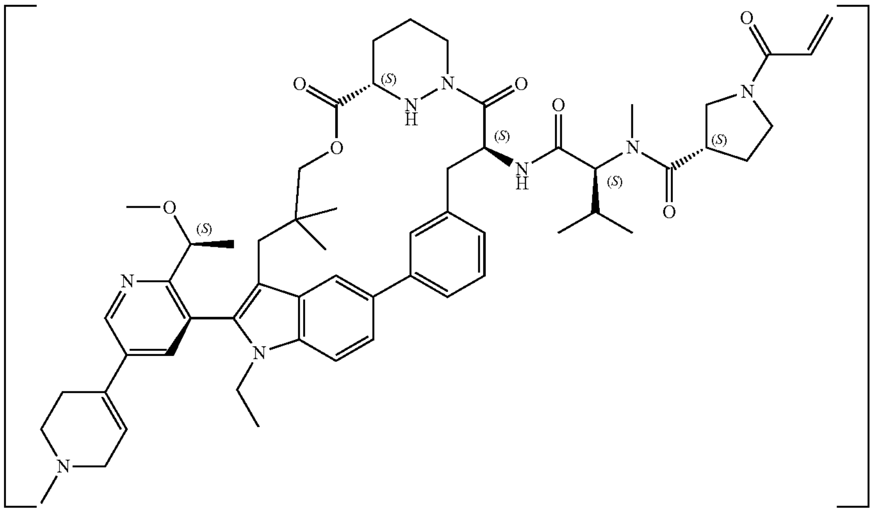 |
| A514 | 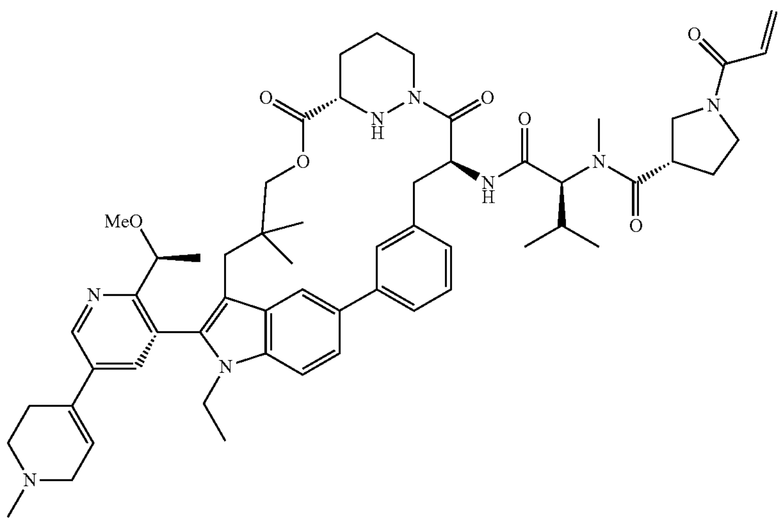 |
| A515 | 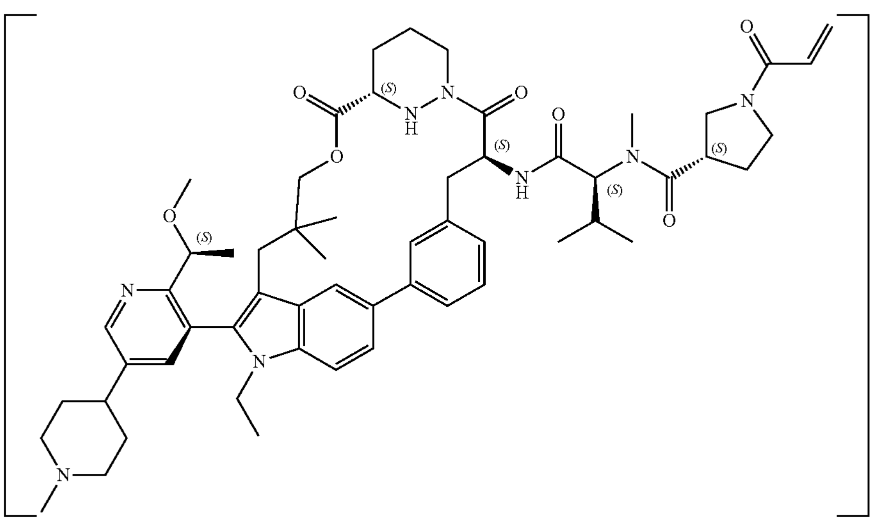 |

TABLE 1-continued
Certain Compounds of the Present Invention
| Ex# | Structure |
|---|---|
| A516 | 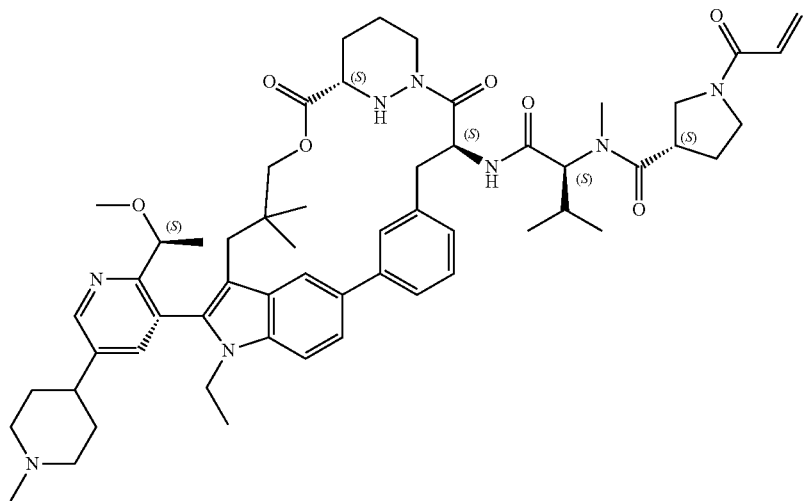 |
| A517 | 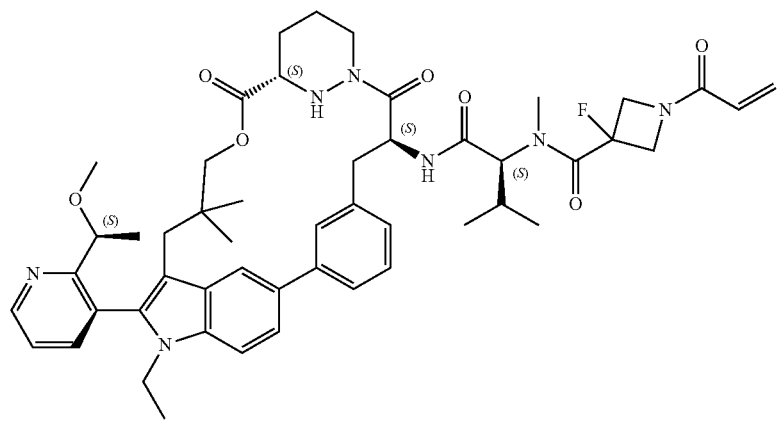 |
| A518 | 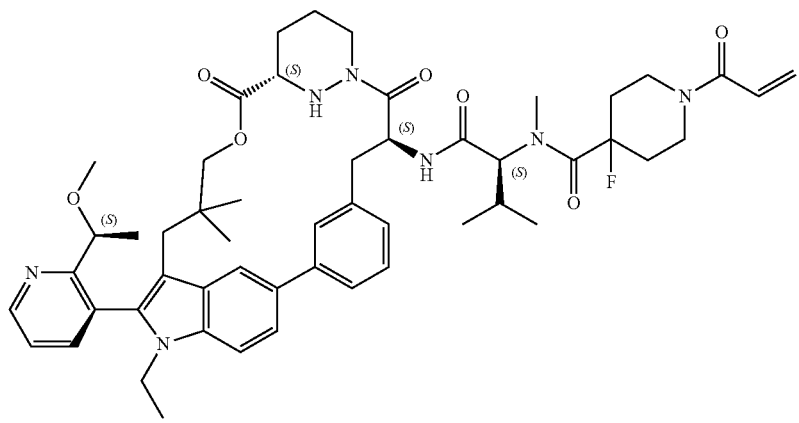 |

TABLE 1-continued

Certain Compounds of the Present Invention

| Ex# | Structure |
|---|---|
| A519 | 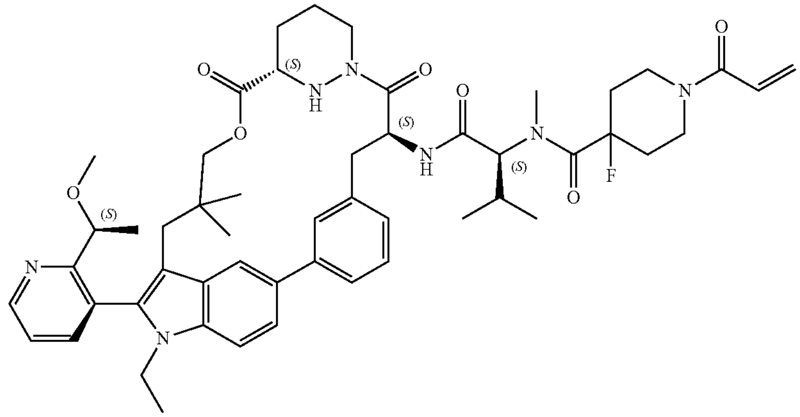 |
| A520 | 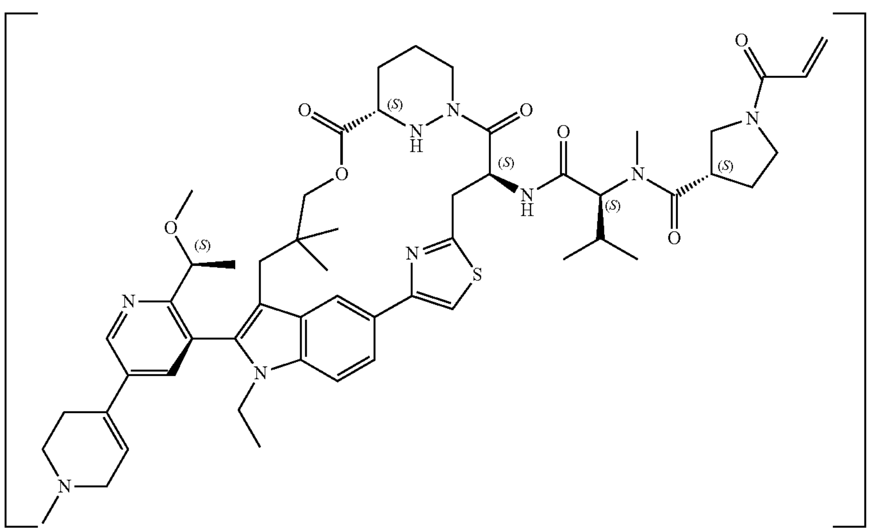 |
| A521 | 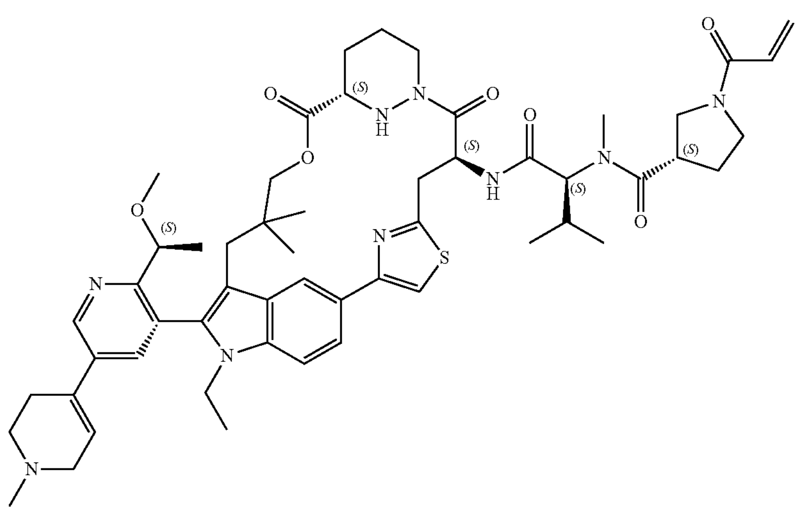 |

TABLE 1-continued
Certain Compounds of the Present Invention
| Ex# | Structure |
|---|---|
| A522 | 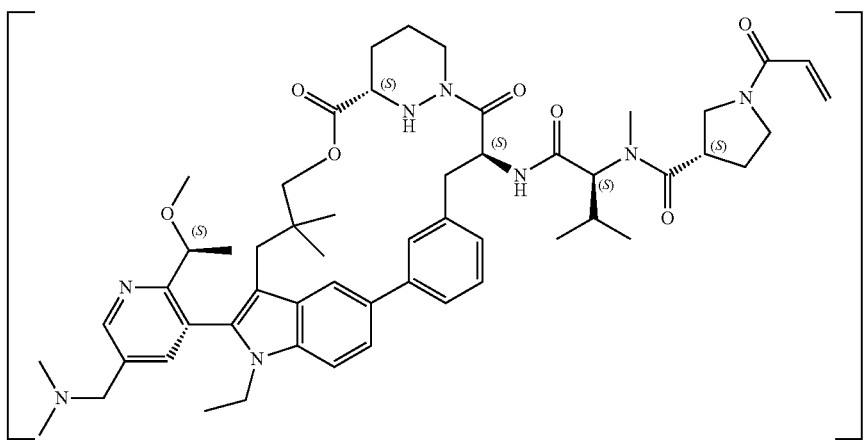 |
| A523 | 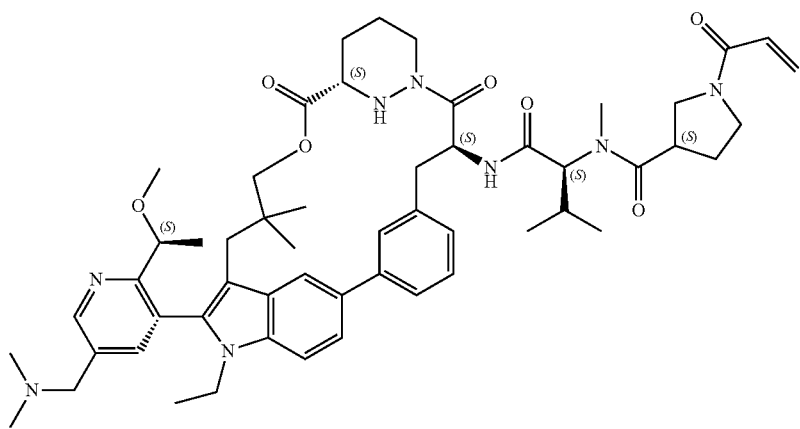 |
| A524 | 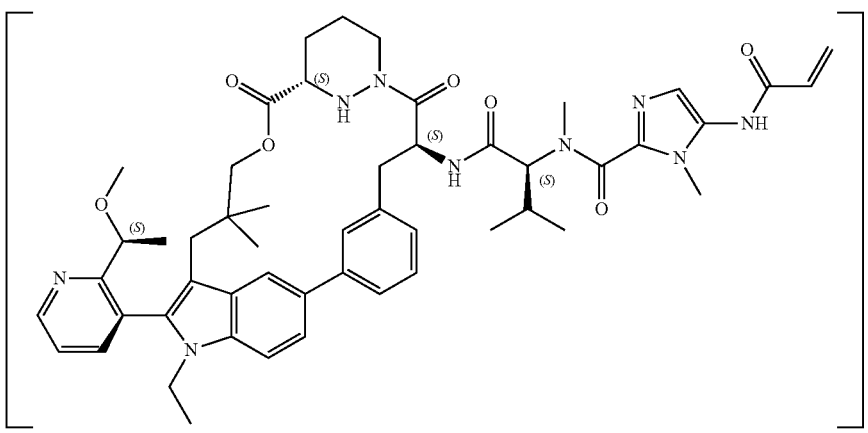 |

TABLE 1-continued
Certain Compounds of the Present Invention
| Ex# | Structure |
|---|---|
| A525 | 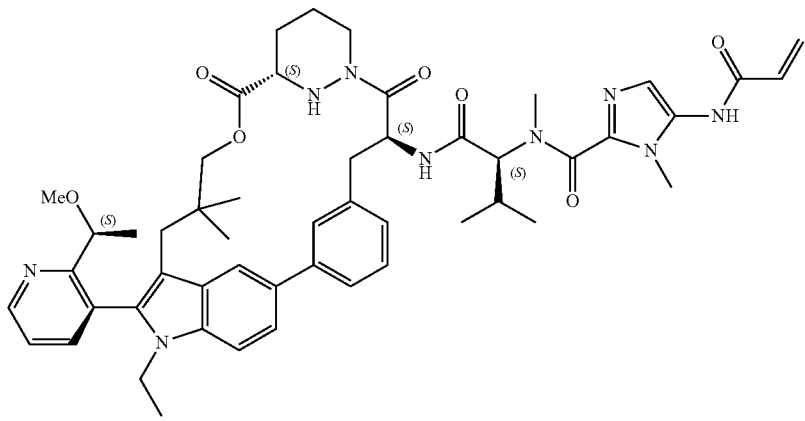 |
| A526 | 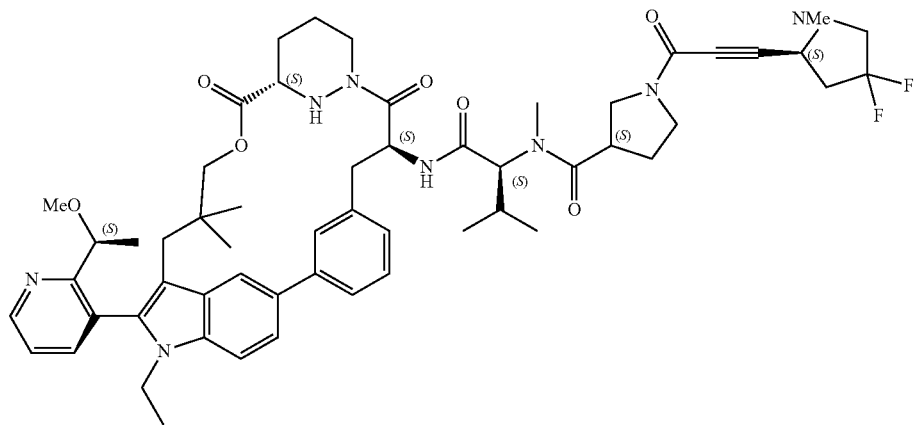 |
| A527 | 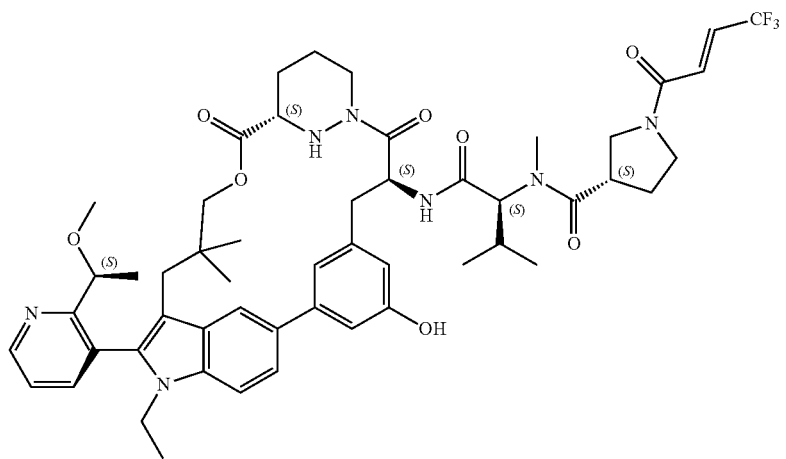 |

TABLE 1-continued

Certain Compounds of the Present Invention

| Ex# | Structure |
|---|---|
| A528 | 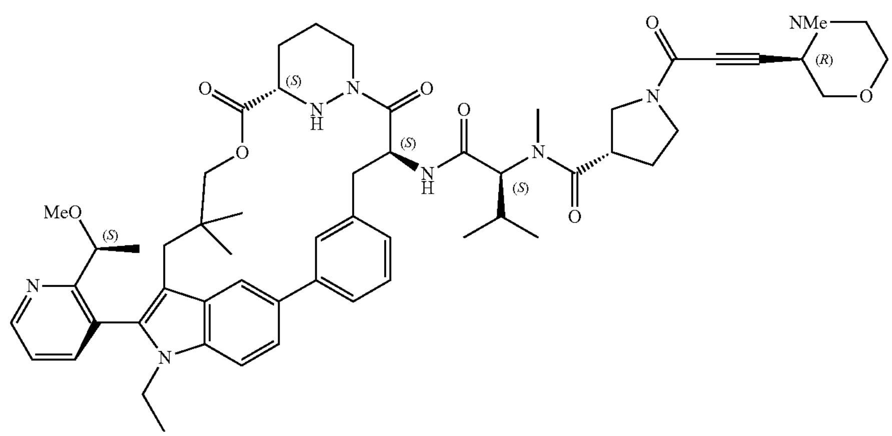 |
| A529 | 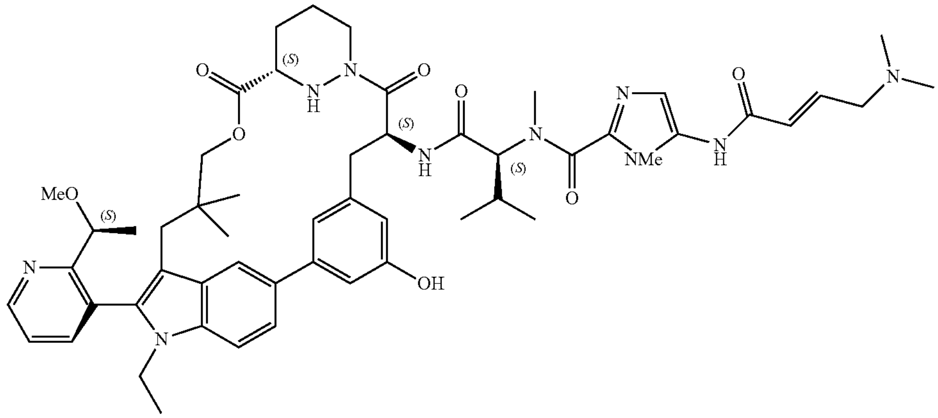 |
| A530 | 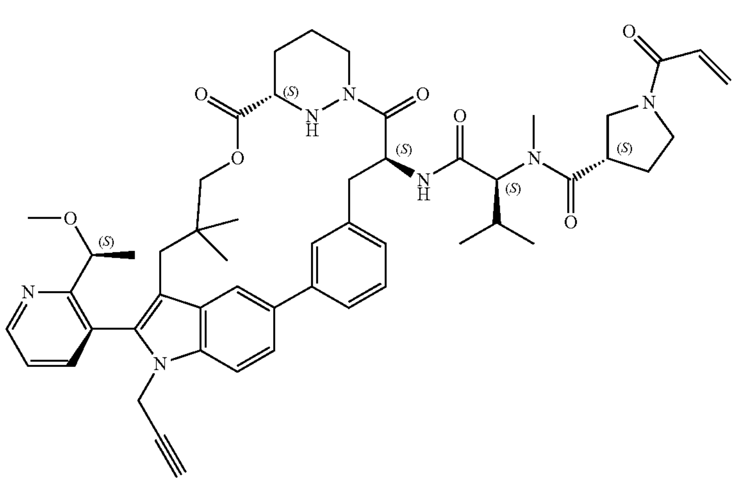 |

TABLE 1-continued
Certain Compounds of the Present Invention
| Ex# | Structure |
|---|---|
| A531 | 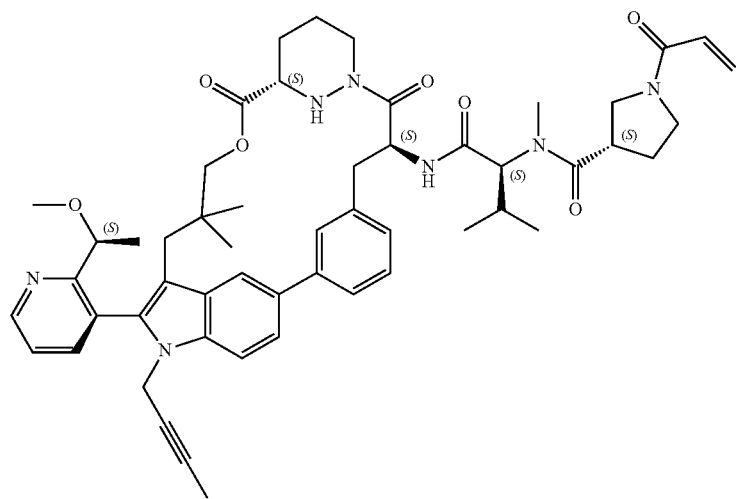 |
| A532 | 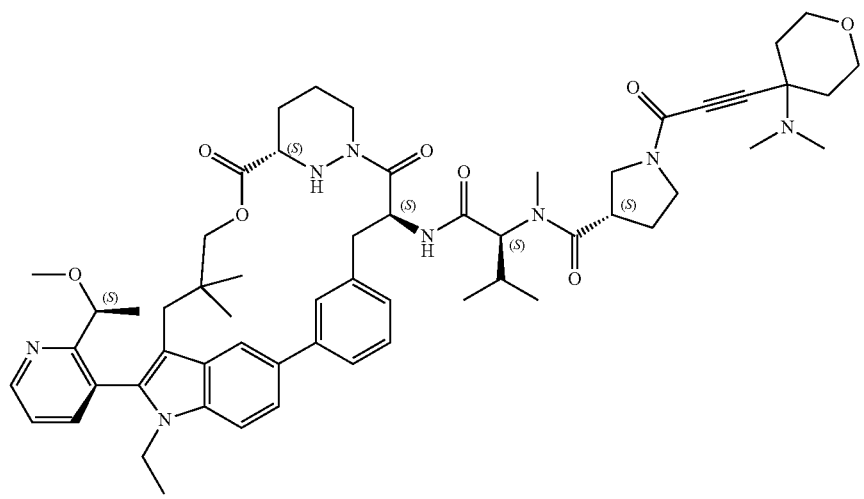 |
| A533 | 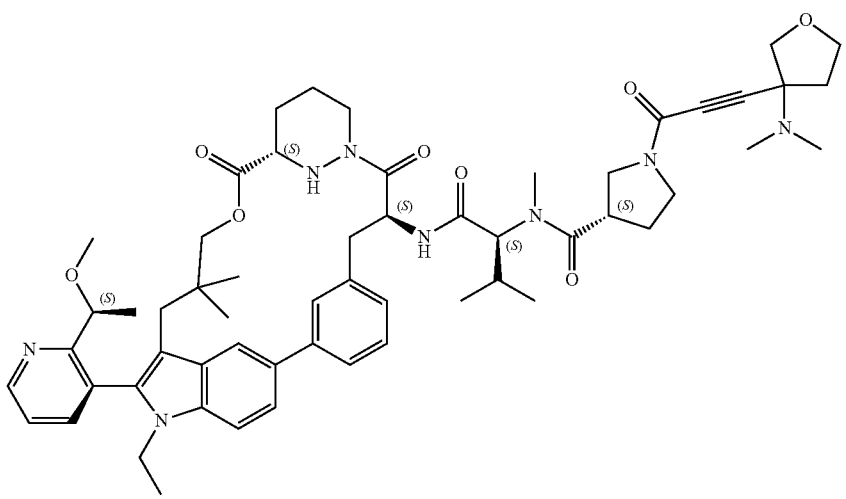 |

TABLE 1-continued
Certain Compounds of the Present Invention
| Ex# | Structure |
|---|---|
| A534 | 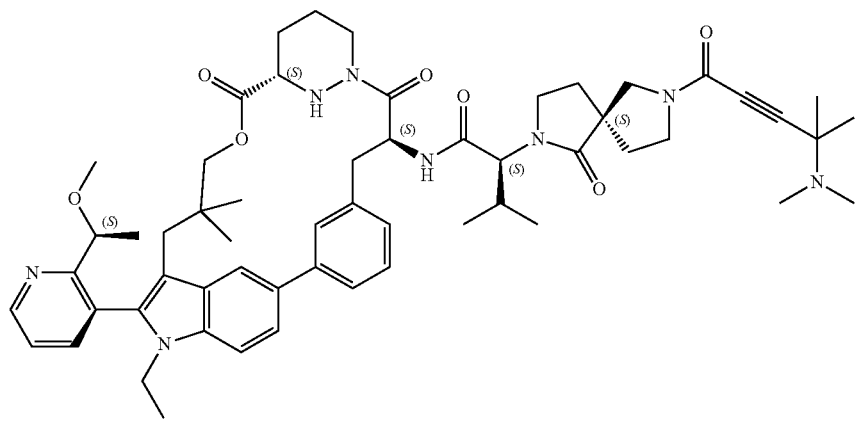 |
| A535 | 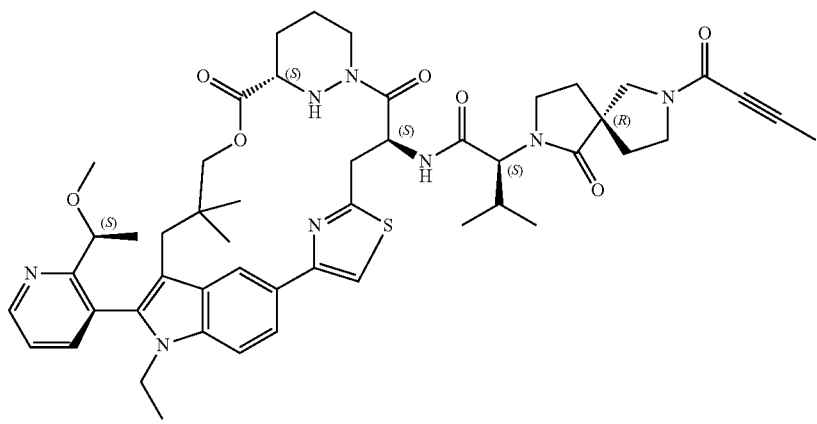 |
| A536 | 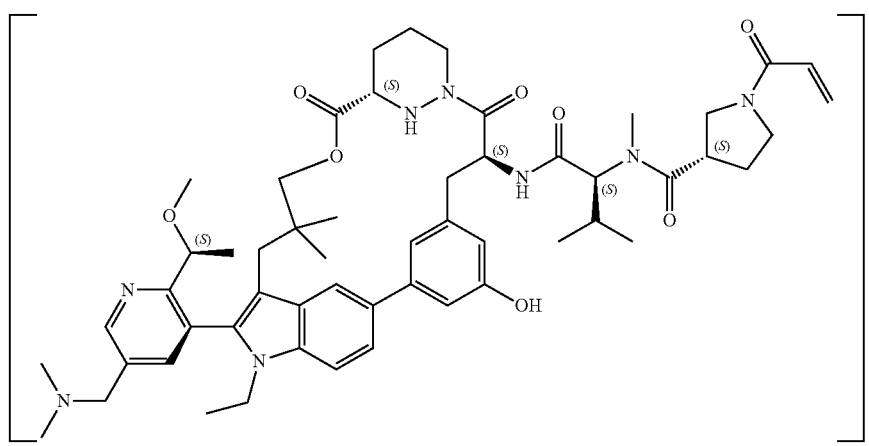 |

TABLE 1-continued
Certain Compounds of the Present Invention
| Ex# | Structure |
|---|---|
| A537 | 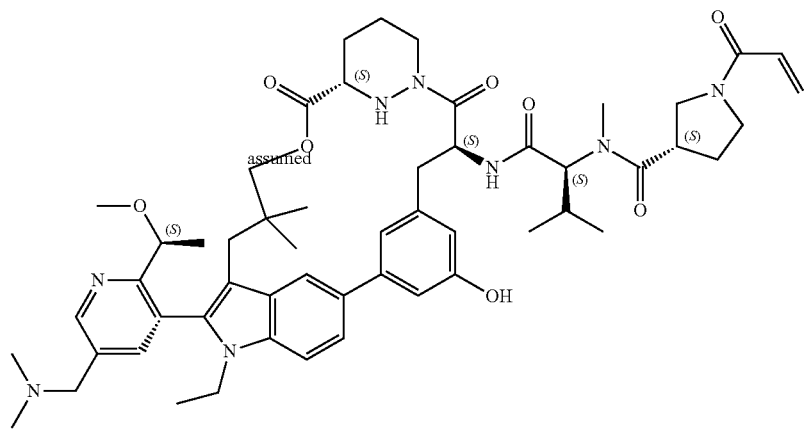 |
| A538 | 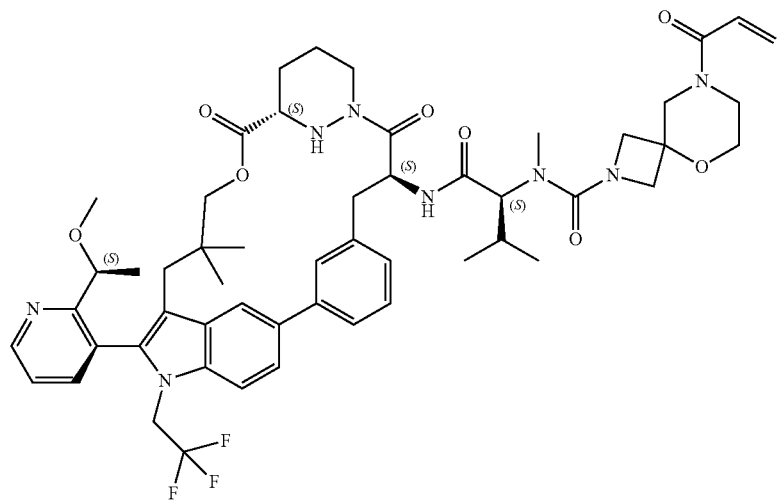 |
| A539 | 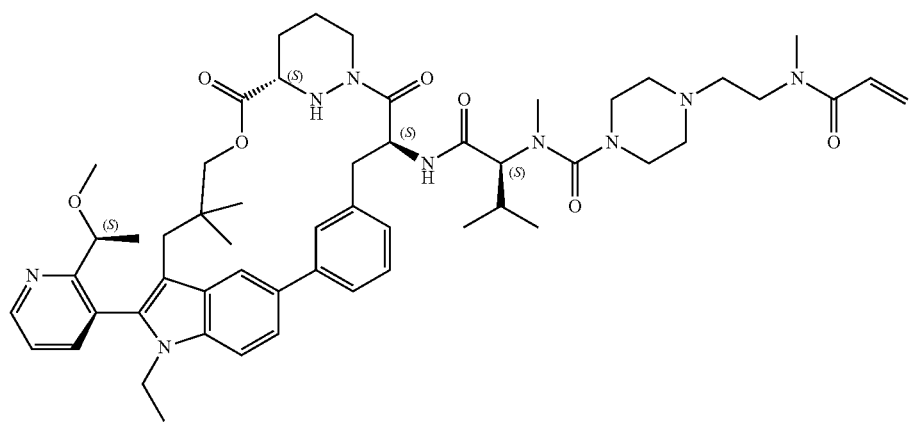 |

TABLE 1-continued
Certain Compounds of the Present Invention
| Ex# | Structure |
| --- | --- |
| A540 | 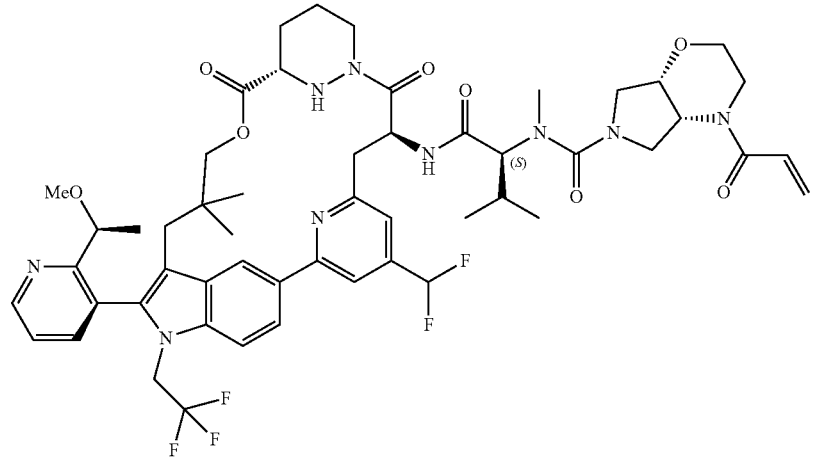 |
| A541 | 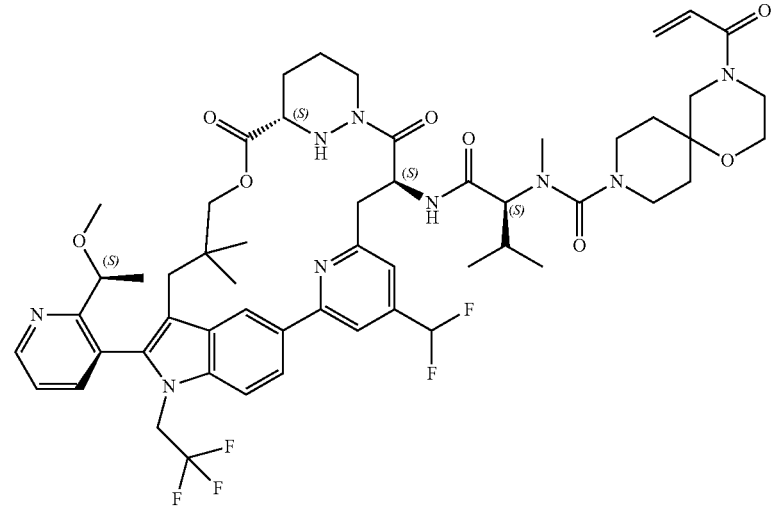 |
| A542 | 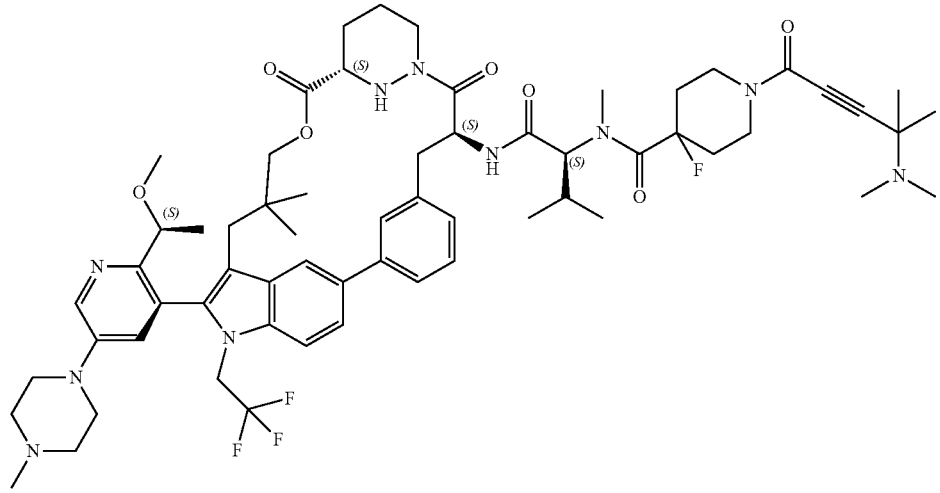 |

| Ex# | Structure |
|---|---|
| A543 | 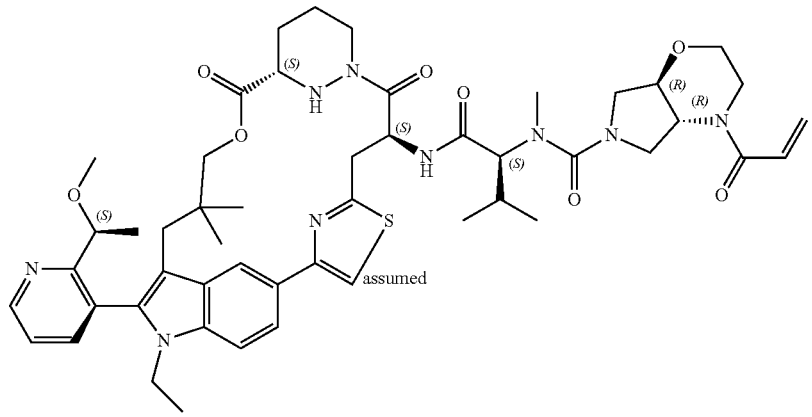 |
| A544 | 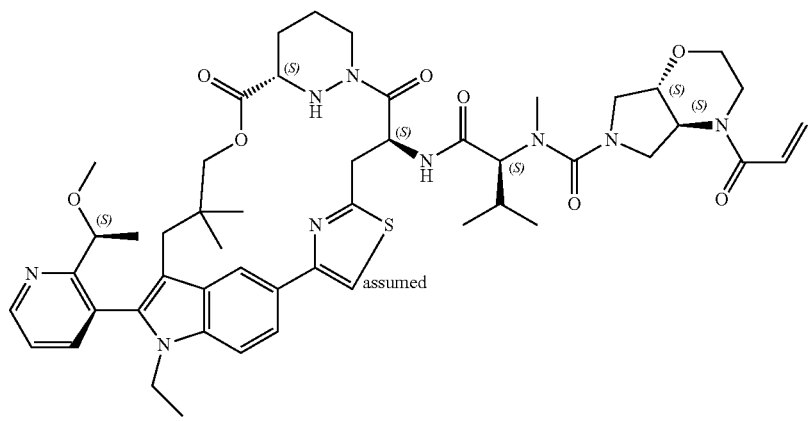 |
| A545 | 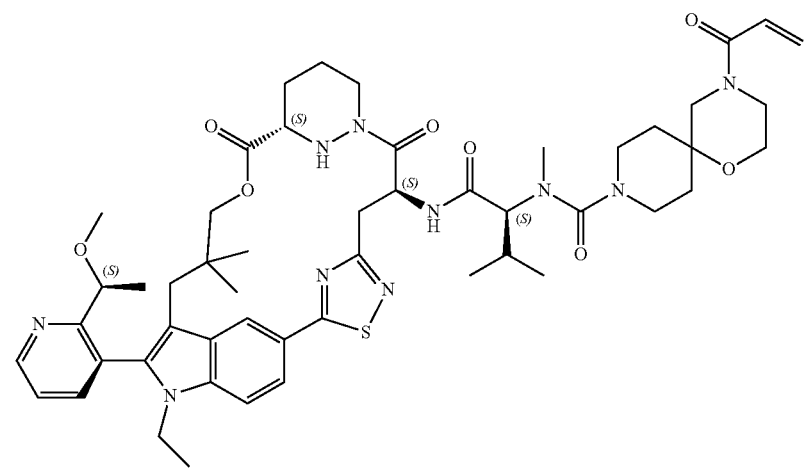 |

TABLE 1-continued

Certain Compounds of the Present Invention

| Ex# | Structure |
|---|---|
| A546 | 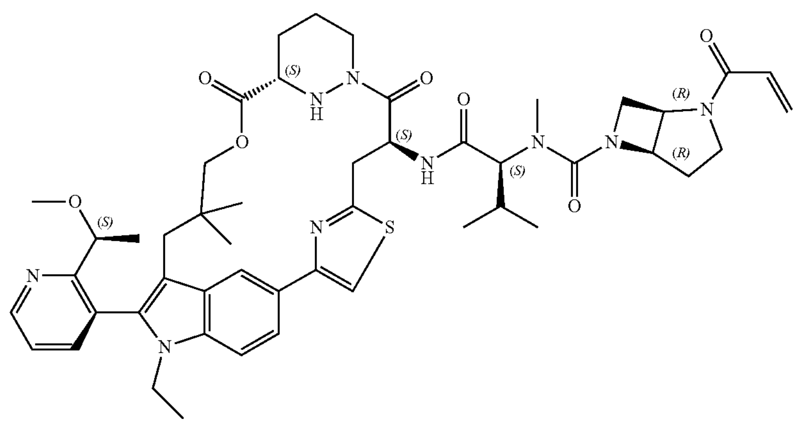 |
| A547 | 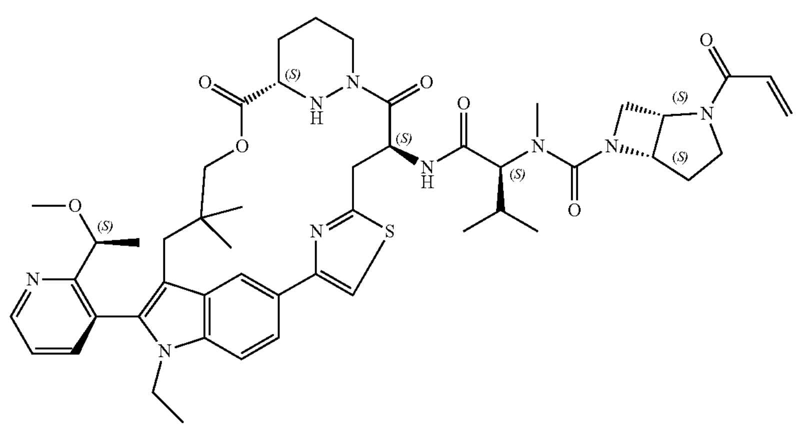 |
| A548 | 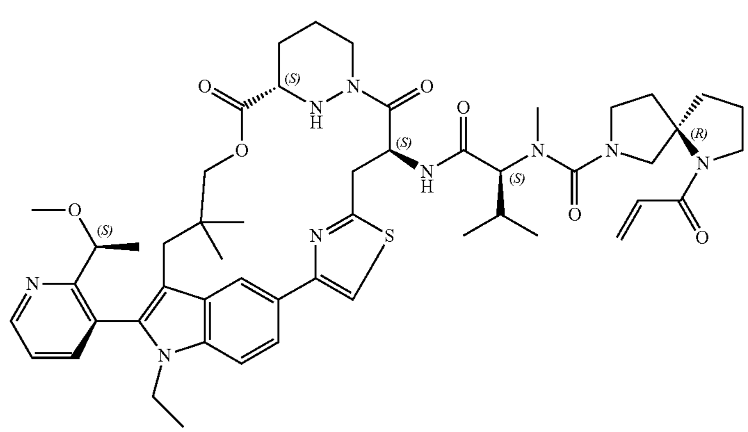 |

TABLE 1-continued

Certain Compounds of the Present Invention

| Ex# | Structure |
|---|---|
| A549 | 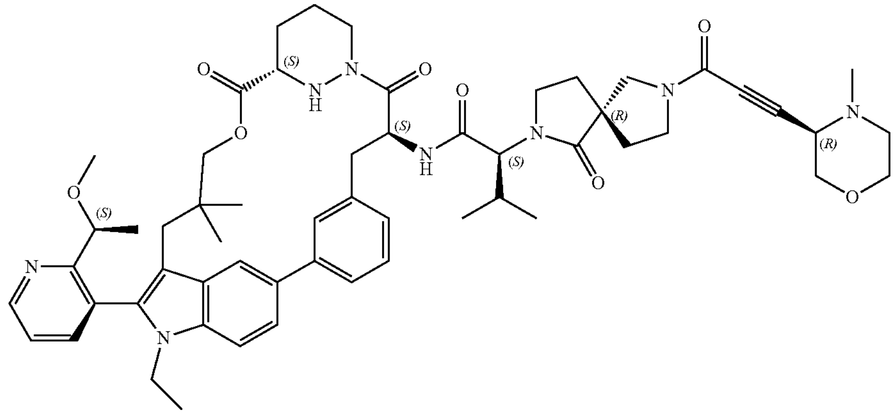 |
| A550 | 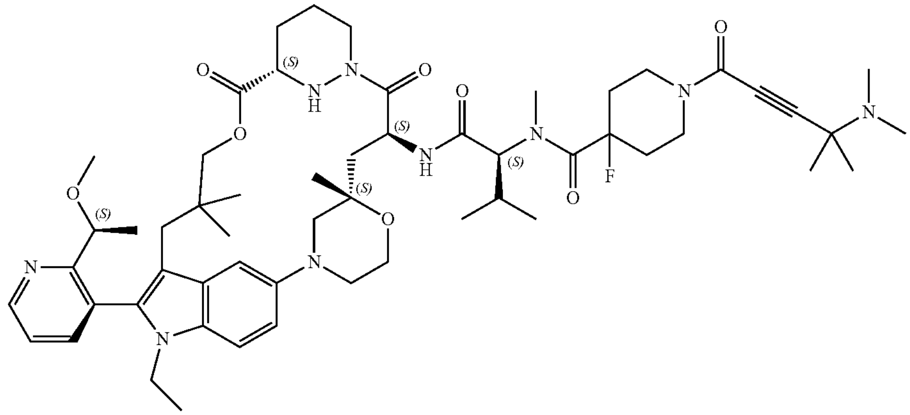 |
| A551 | 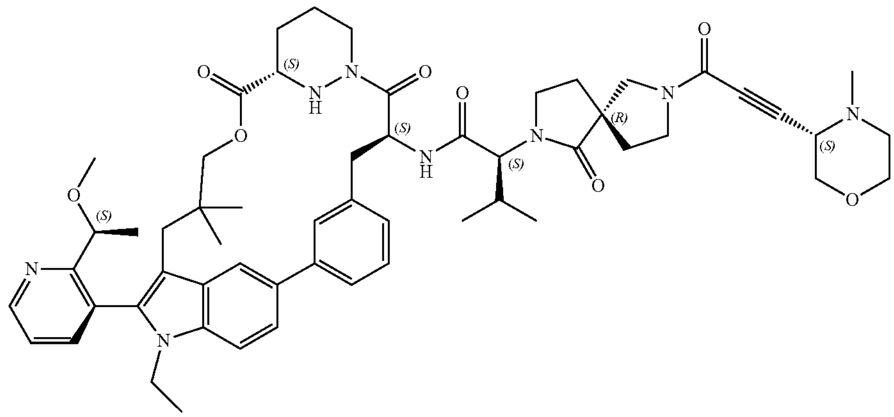 |

TABLE 1-continued
Certain Compounds of the Present Invention
| Ex# | Structure |
|---|---|
| A552 | 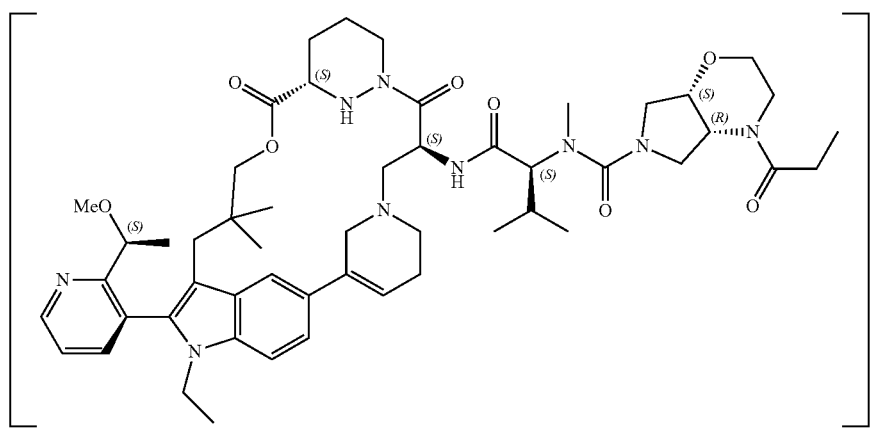 |
| A553 | 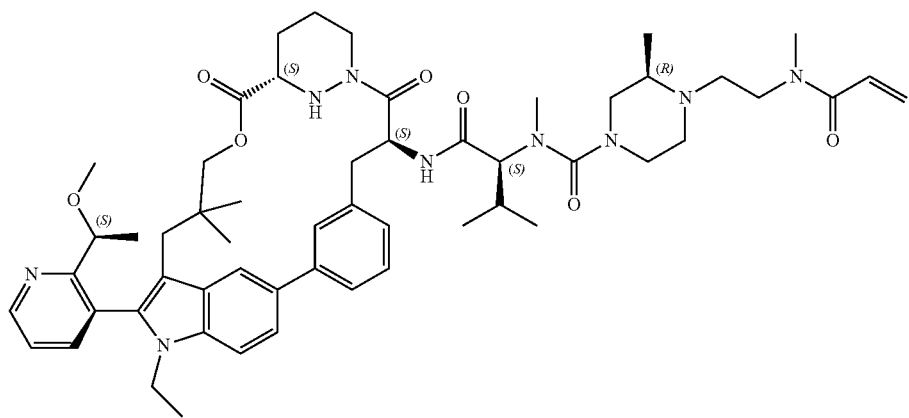 |
| A554 | 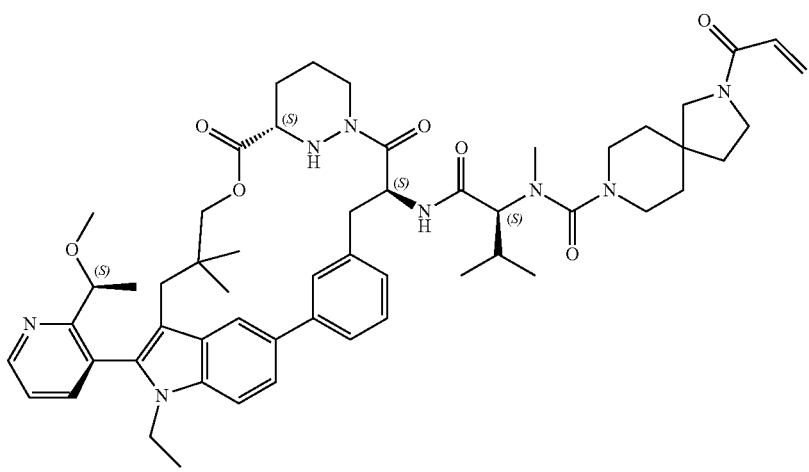 |

TABLE 1-continued
Certain Compounds of the Present Invention
| Ex# | Structure |
|---|---|
| A555 | 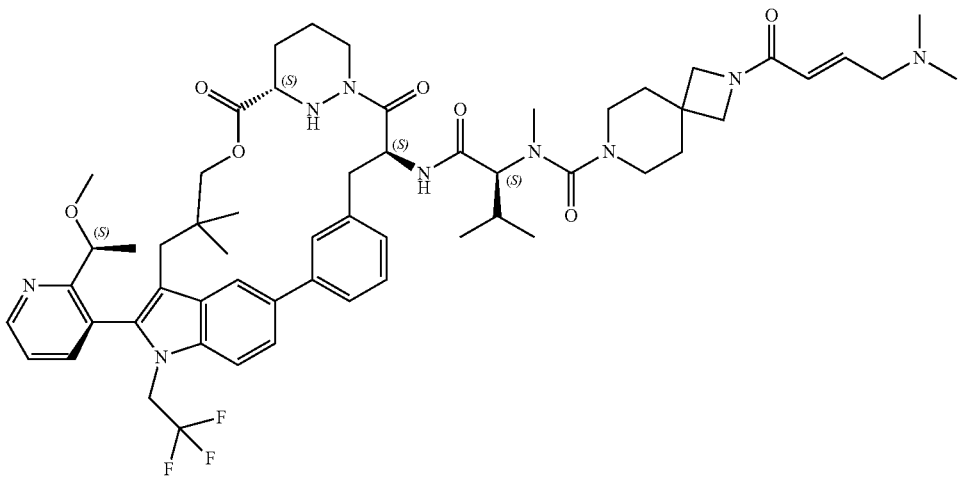 |
| A556 | 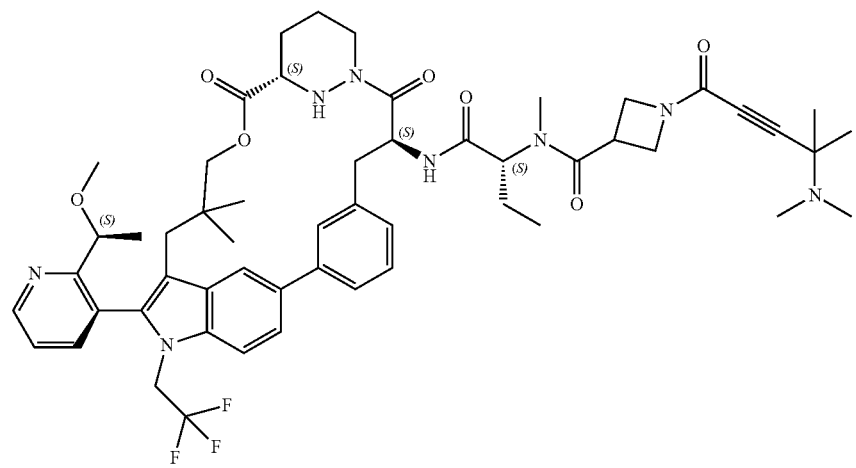 |
| A557 | 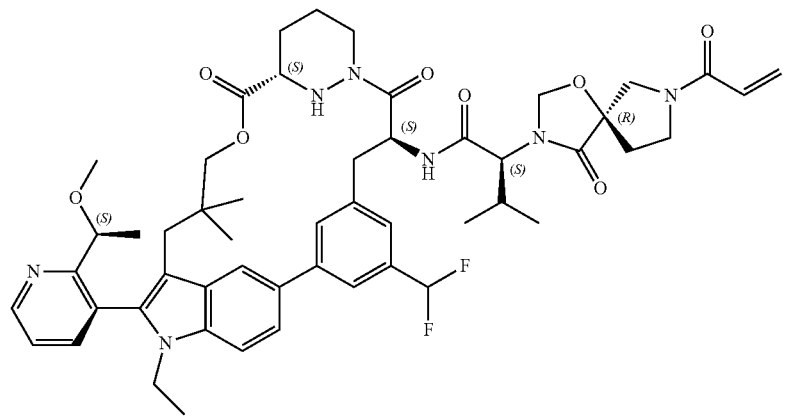 |

TABLE 1-continued

Certain Compounds of the Present Invention

| Ex# | Structure |
|---|---|
| A558 | 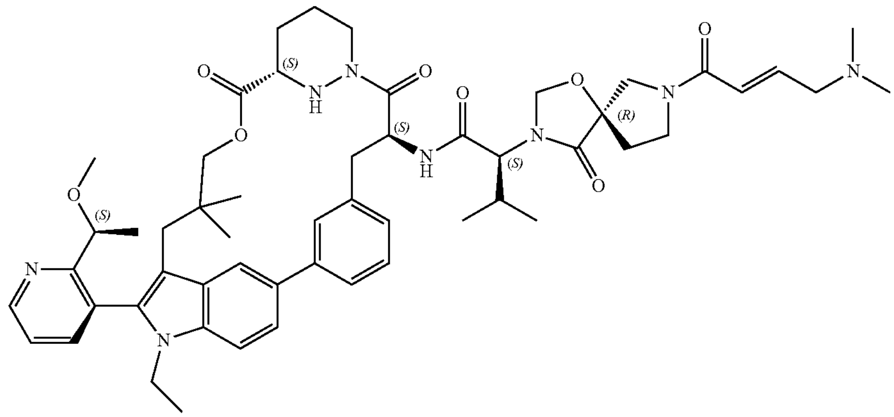 |
| A559 | 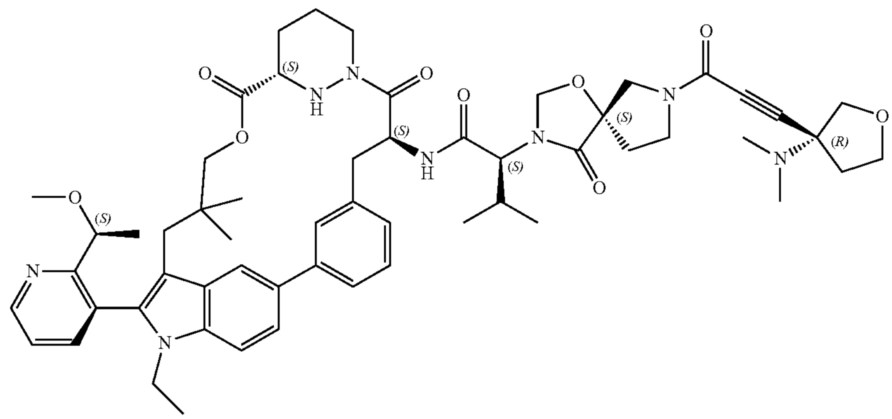 |
| A560 | 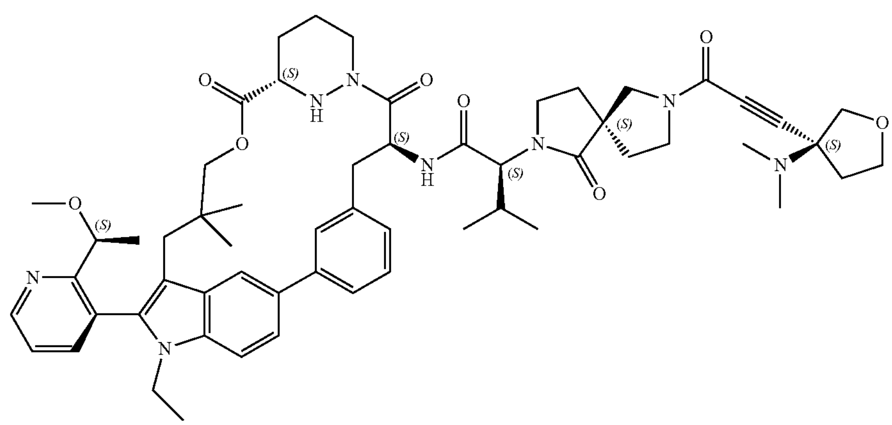 |

441 442
TABLE 1-continued
Certain Compounds of the Present Invention
| Ex# | Structure |
|---|---|
| A561 | 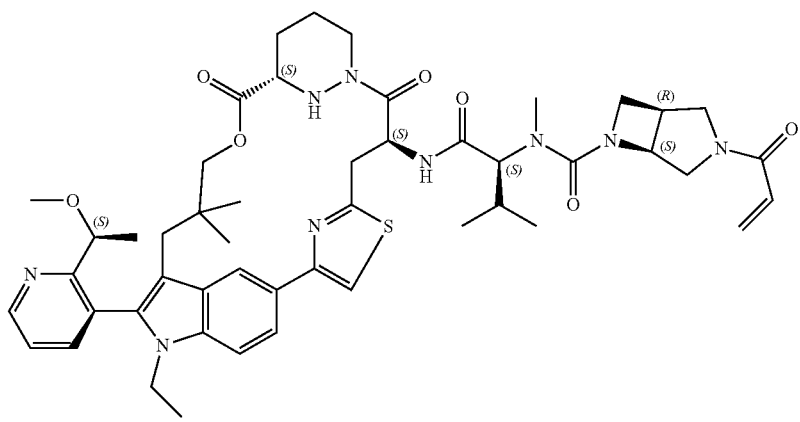 |
| A562 | 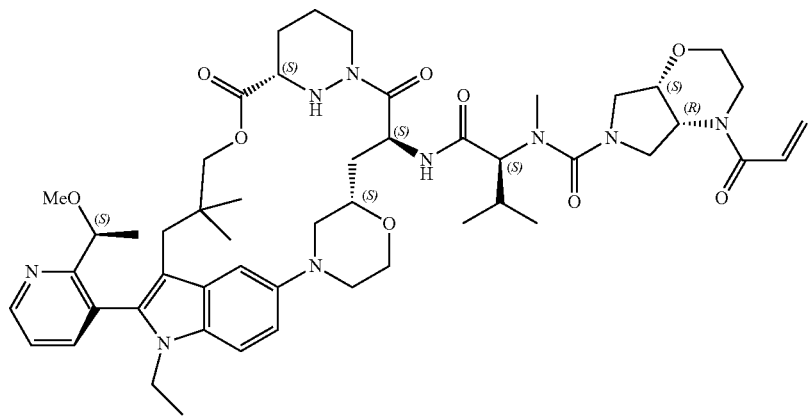 |
| A563 | 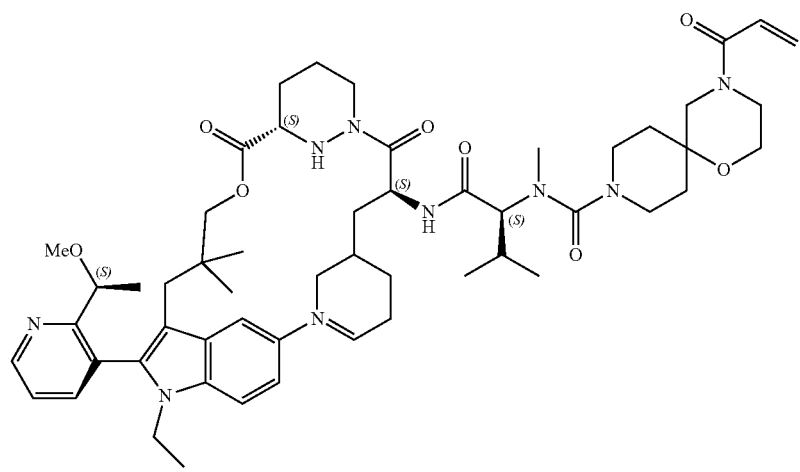 |

TABLE 1-continued
Certain Compounds of the Present Invention
| Ex# | Structure |
|---|---|
| A564 | 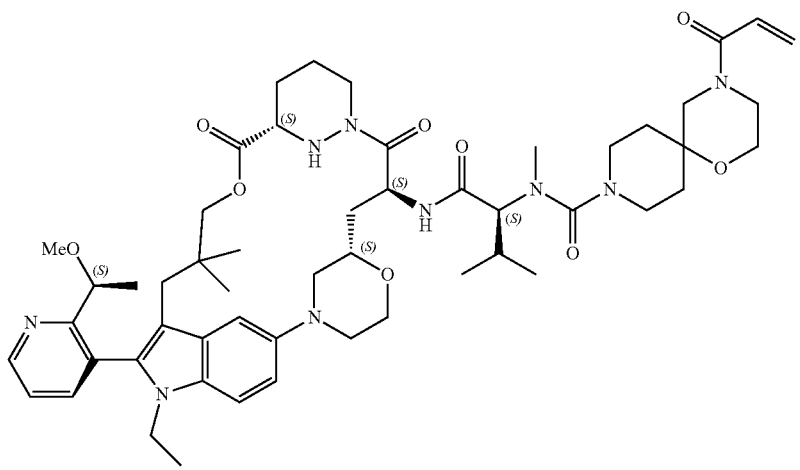 |
| A565 | 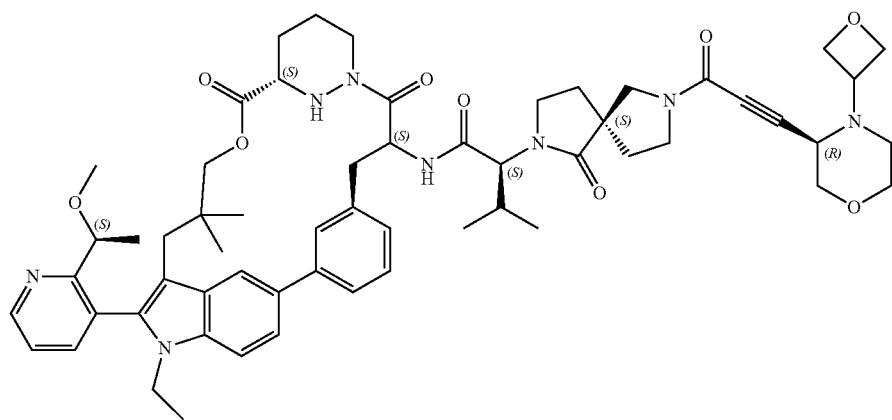 |
| A566 | 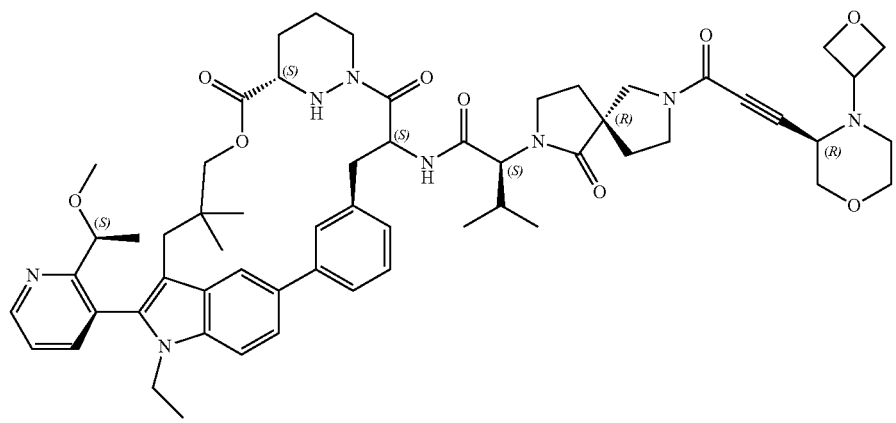 |

TABLE 1-continued

Certain Compounds of the Present Invention

| Ex# | Structure |
|---|---|
| A567 | 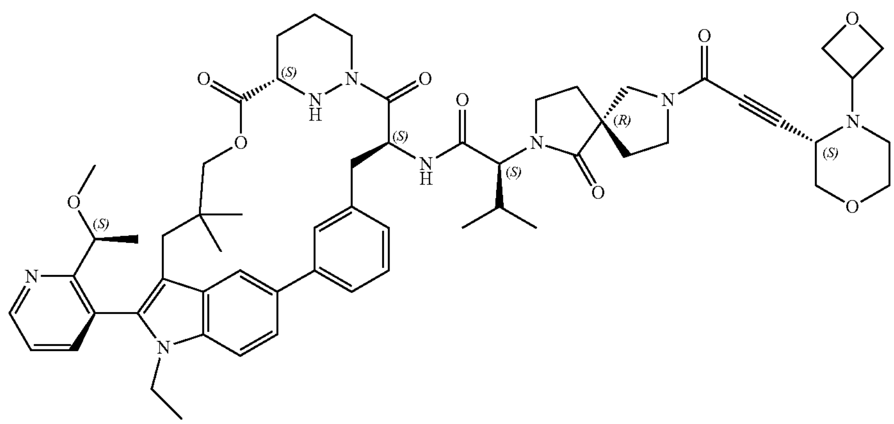 |
| A568 | 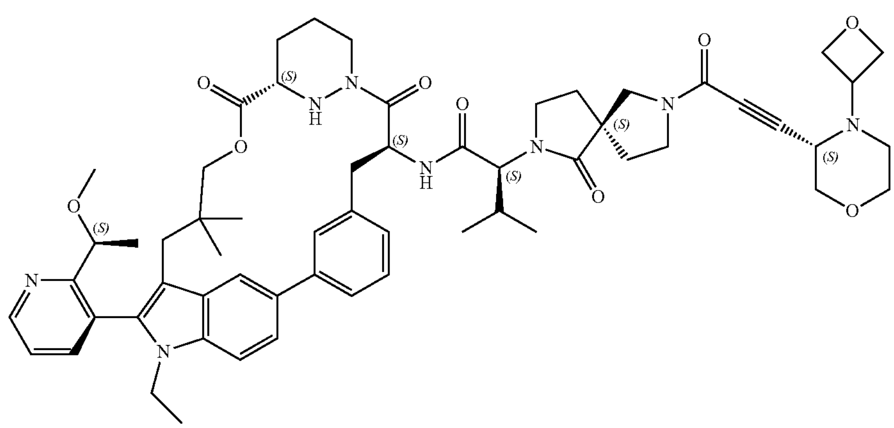 |
| A569 | 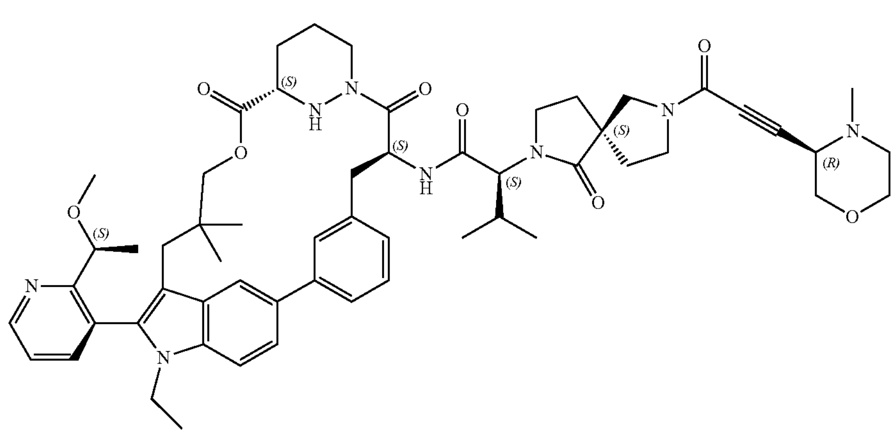 |

TABLE 1-continued
Certain Compounds of the Present Invention
| Ex# | Structure |
|---|---|
| A570 | 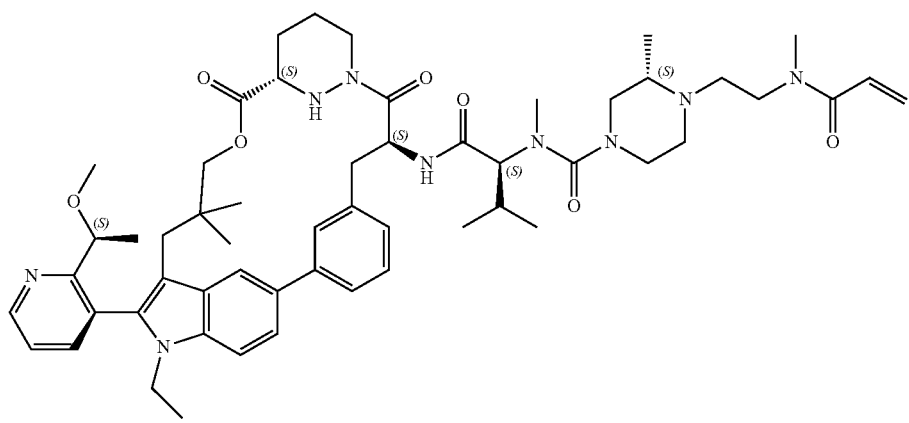 |
| A571 | 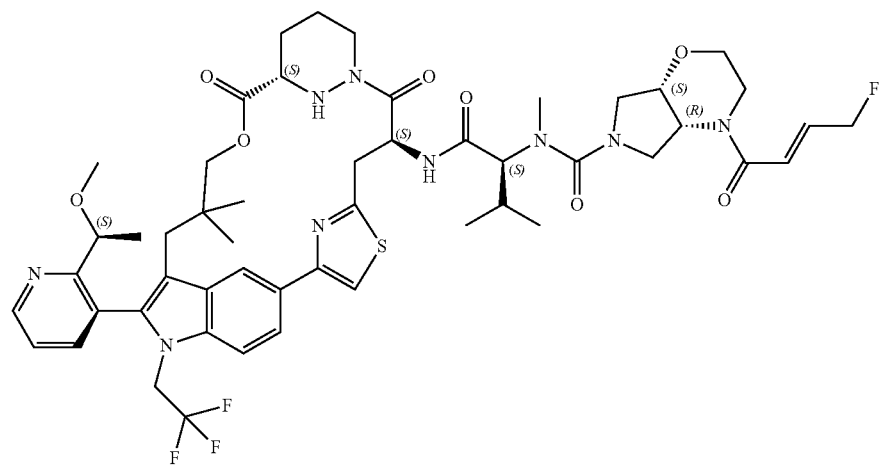 |
| A572 | 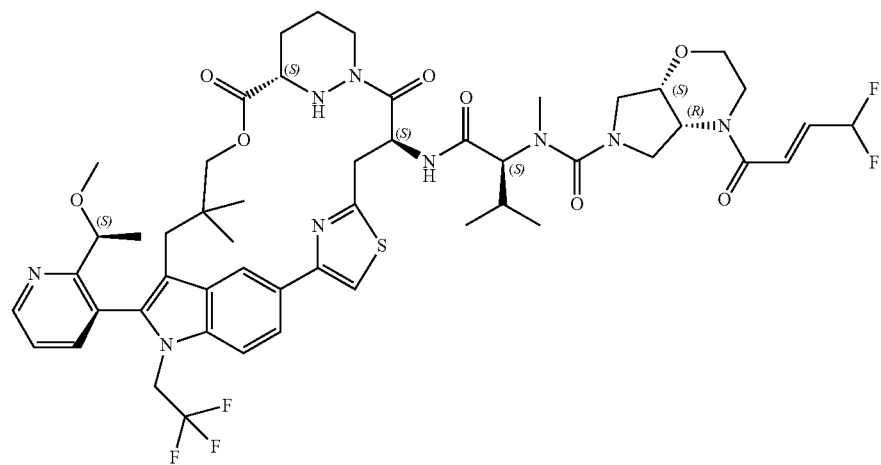 |

/ TABLE 1-continued
Certain Compounds of the Present Invention
| Ex# | Structure |
| --- | --- |
| A573 | 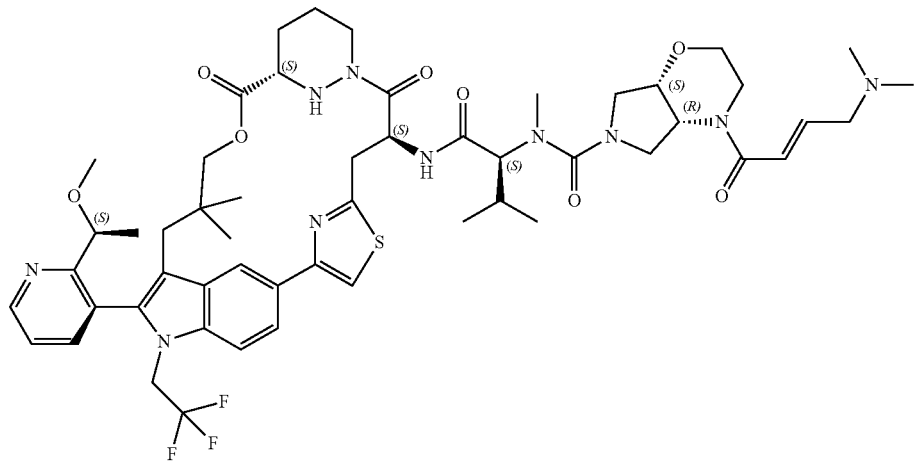 |
| A574 | 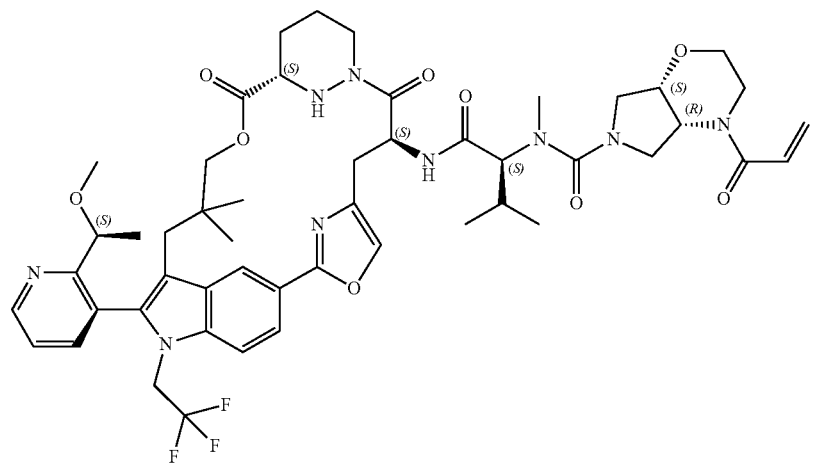 |
| A575 | 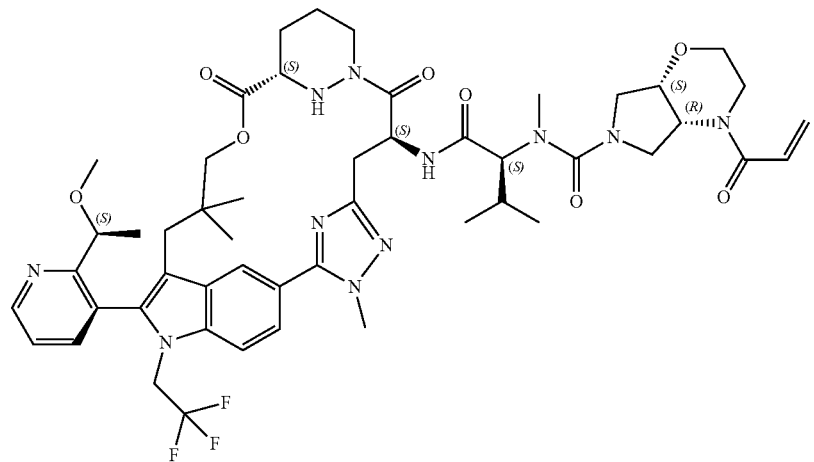 |

TABLE 1-continued
Certain Compounds of the Present Invention
| Ex# | Structure |
|---|---|
| A576 | 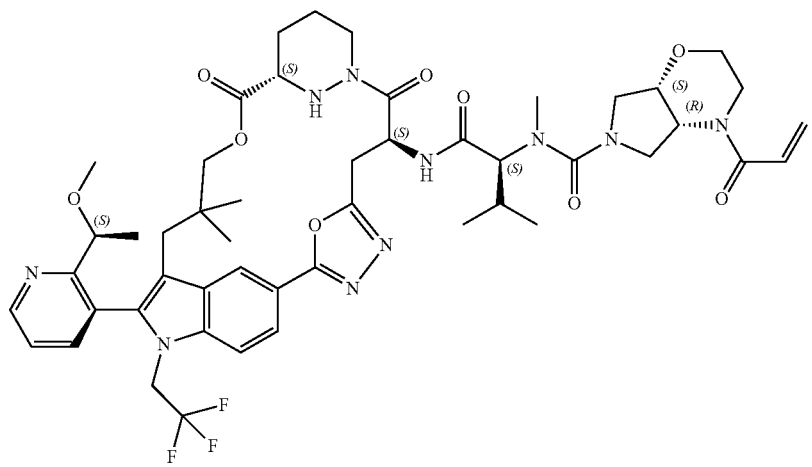 |
| A577 | 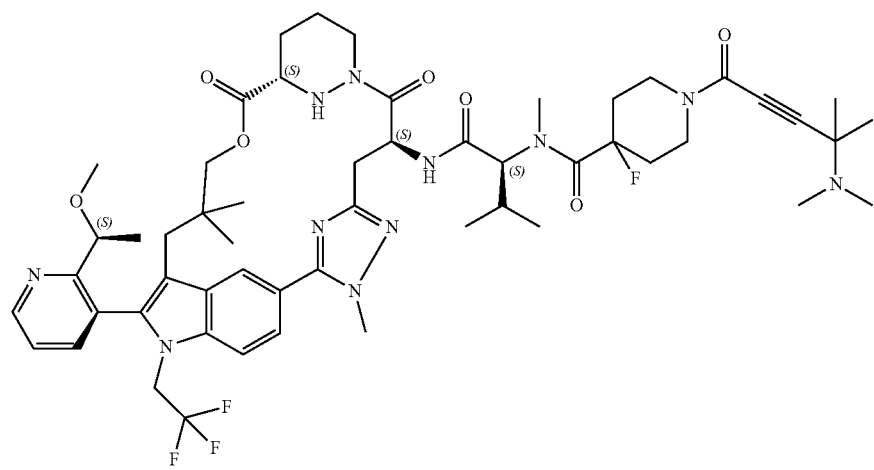 |
| A578 | 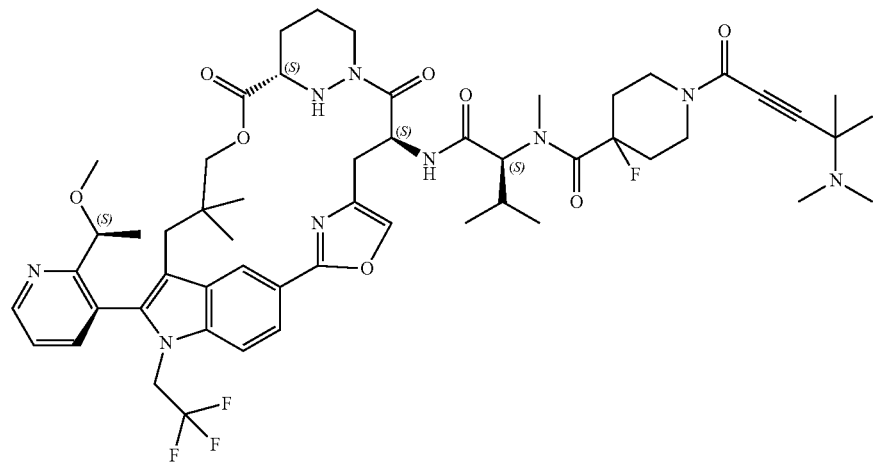 |

454
TABLE 1-continued
Certain Compounds of the Present Invention
| Ex# | Structure |
|---|---|
| A579 | 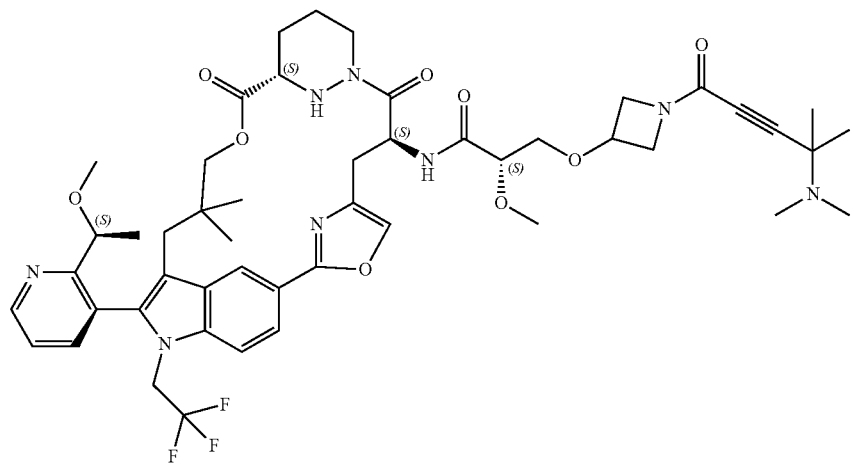 |
| A580 | 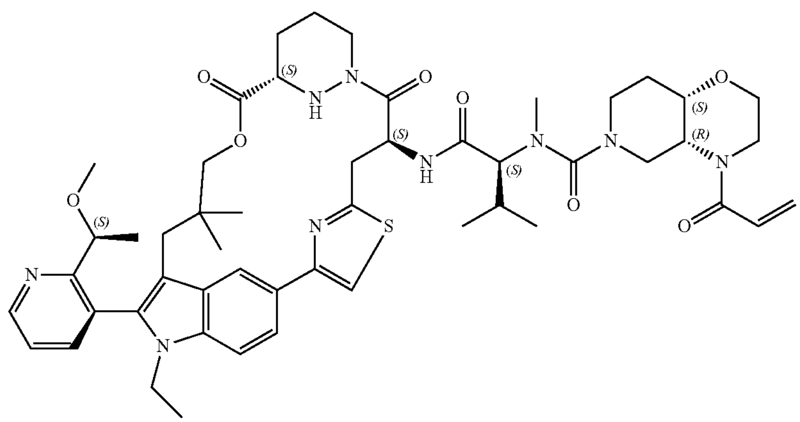 |
| A581 | 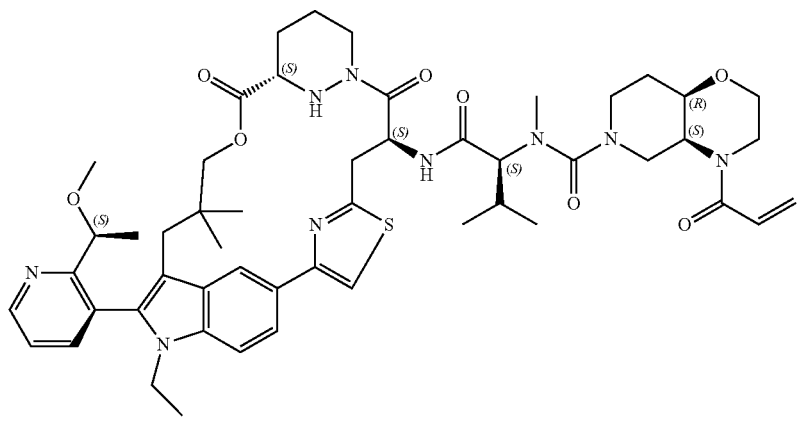 |

TABLE 1-continued
Certain Compounds of the Present Invention
| Ex# | Structure |
|---|---|
| A582 | 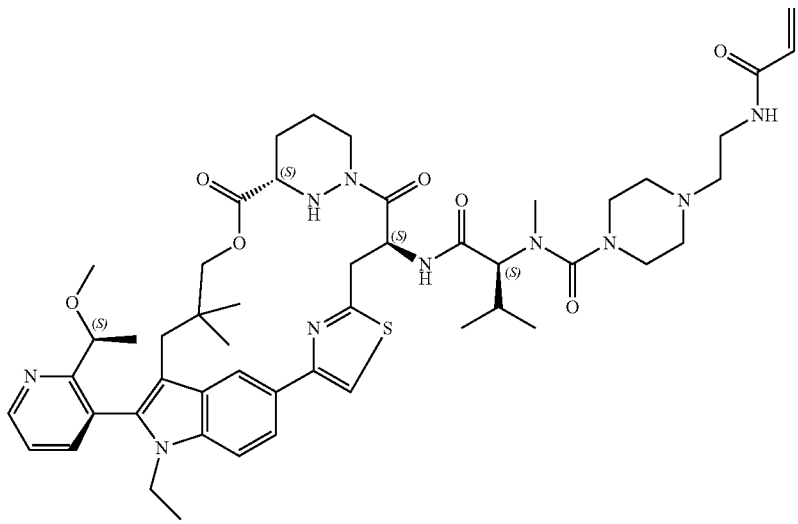 |
| A583 | 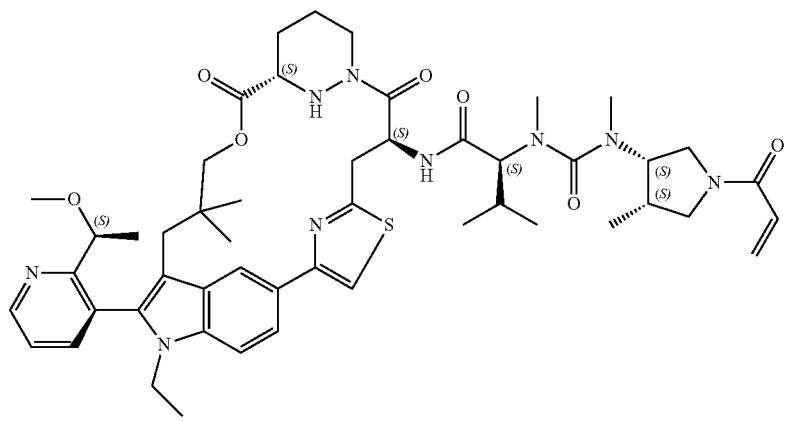 |
| A584 | 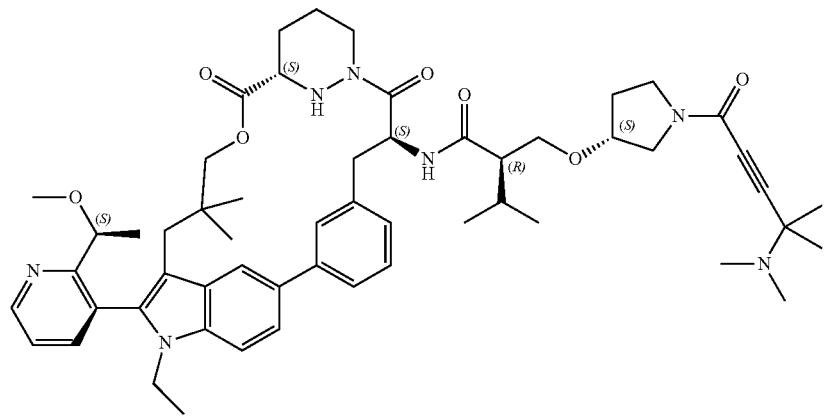 |

US 11,952,352 B2
457 458
TABLE 1-continued
Certain Compounds of the Present Invention
| Ex# | Structure |
|---|---|
| A585 | 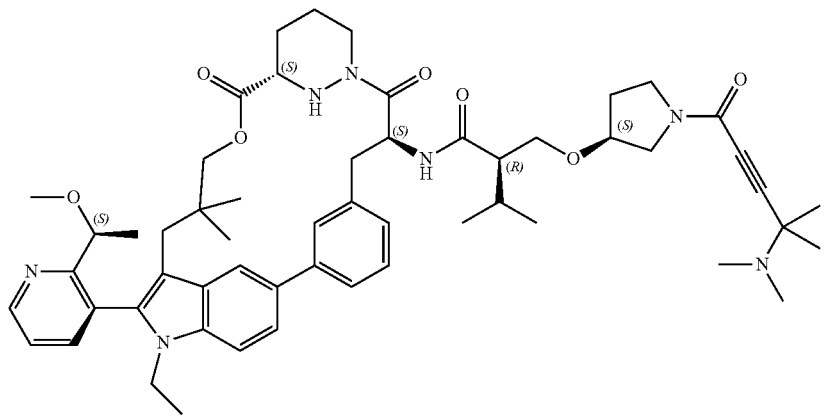 |
| A586 | 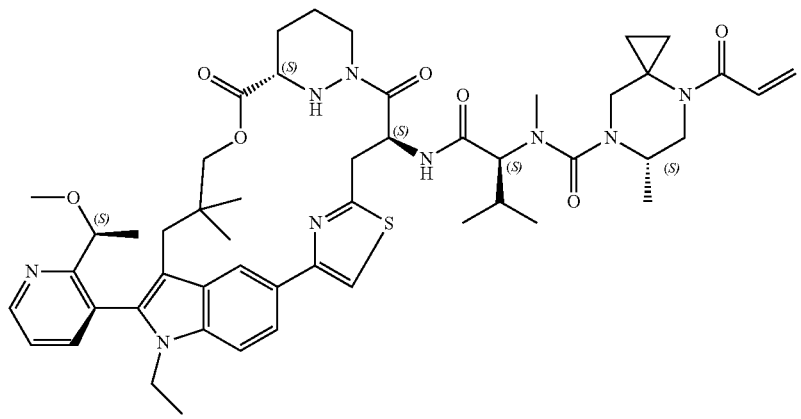 |
| A587 | 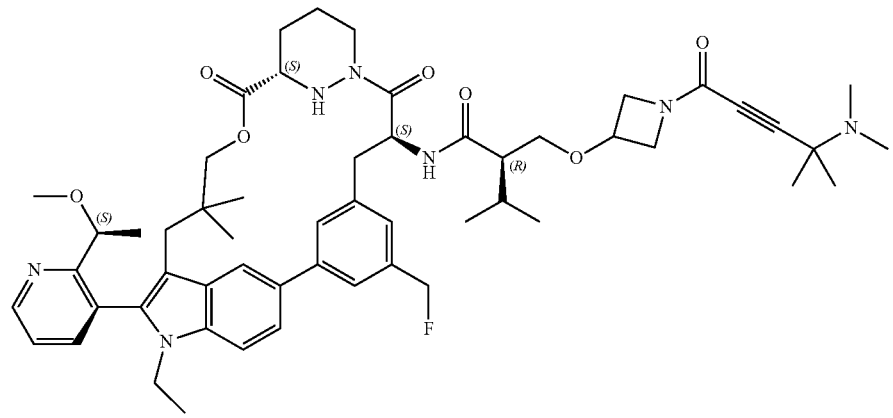 |

TABLE 1-continued
Certain Compounds of the Present Invention
| Ex# | Structure |
|---|---|
| A588 | 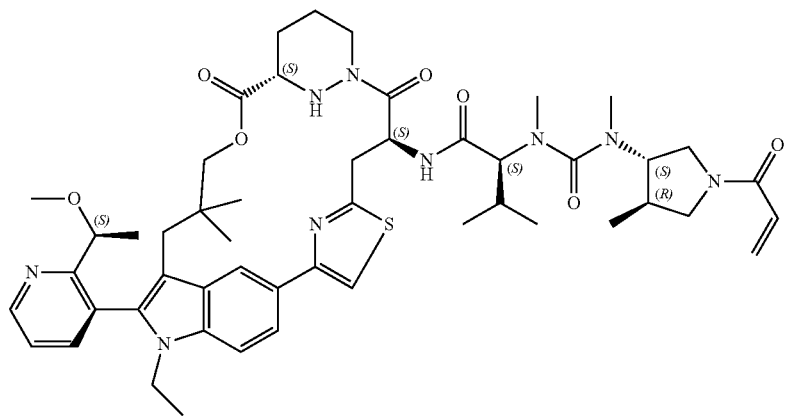 |
| A589 | 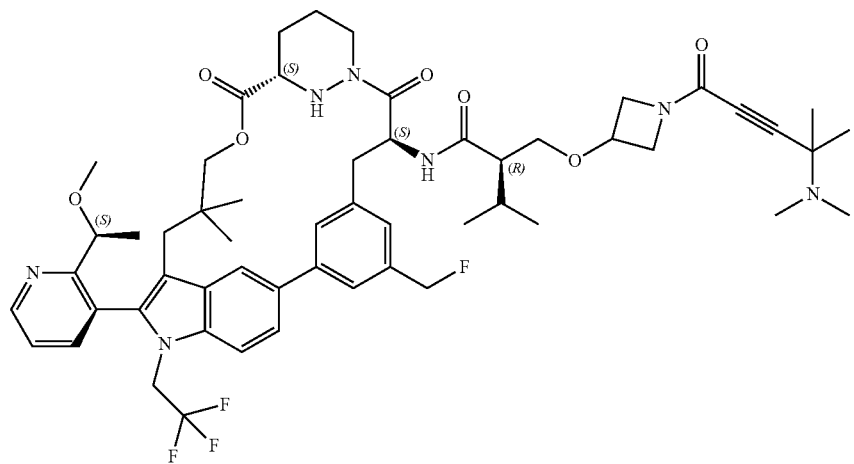 |
| A590 | 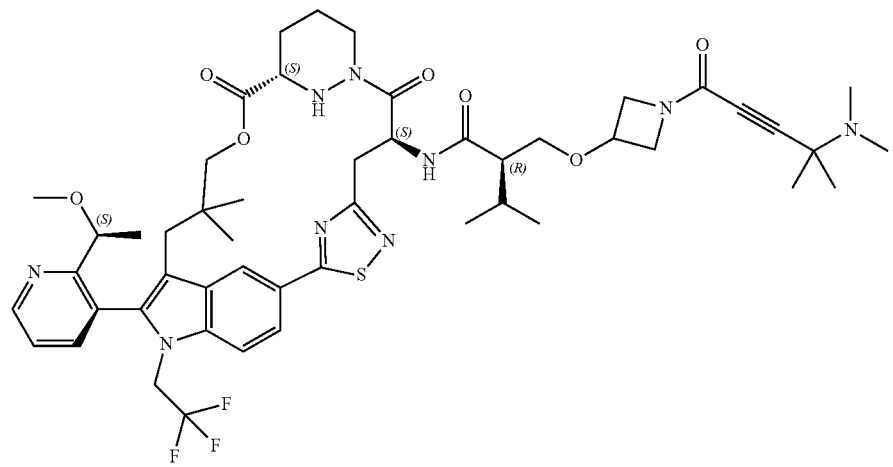 |

TABLE 1-continued
Certain Compounds of the Present Invention
| Ex# | Structure |
|---|---|
| A591 | 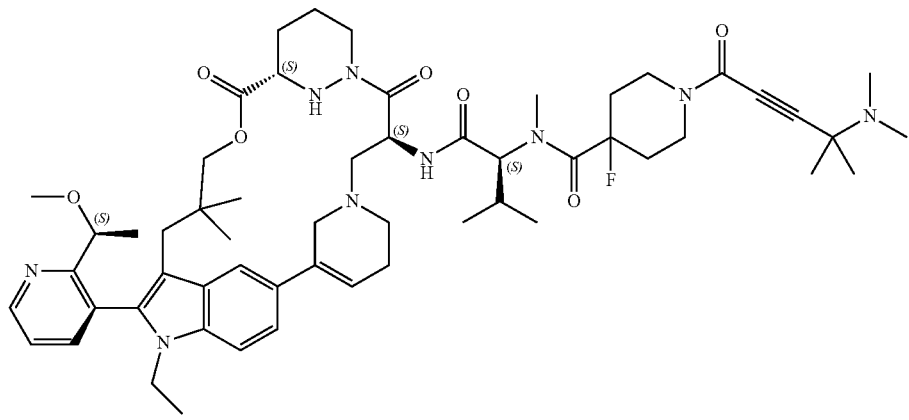 |
| A592 | 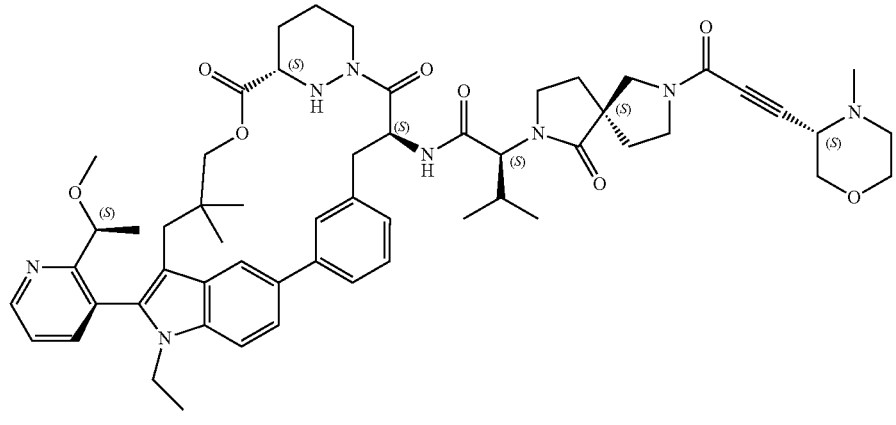 |
| A593 | 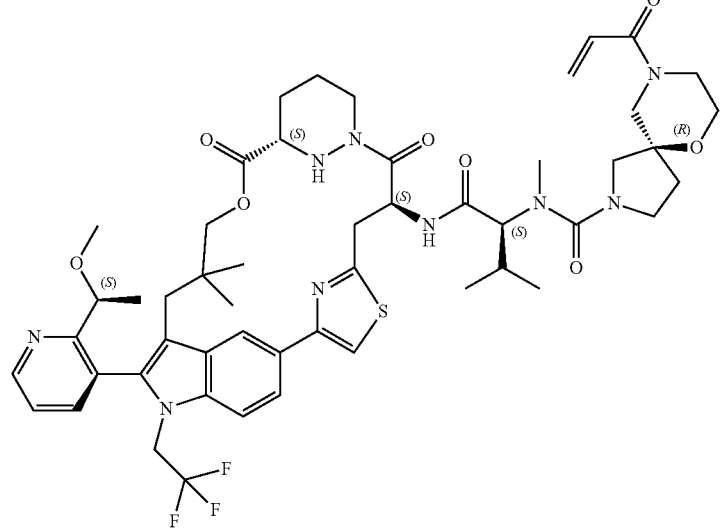 |

TABLE 1-continued
Certain Compounds of the Present Invention
| Ex# | Structure |
|---|---|
| A594 | 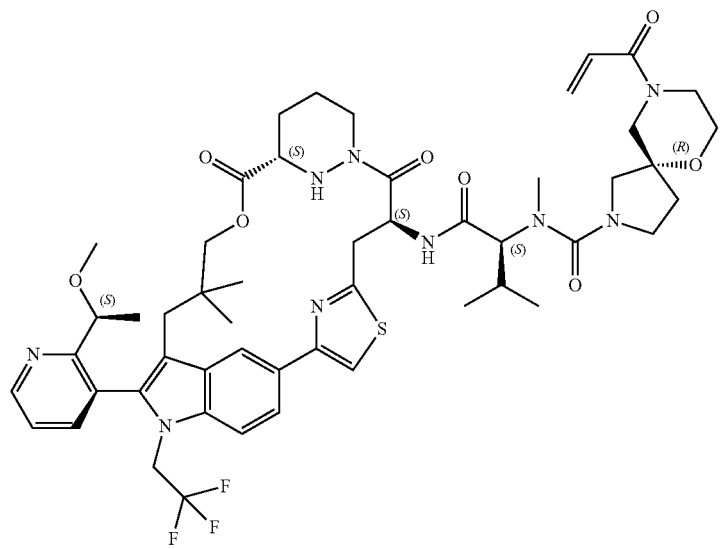 |
| A595 | 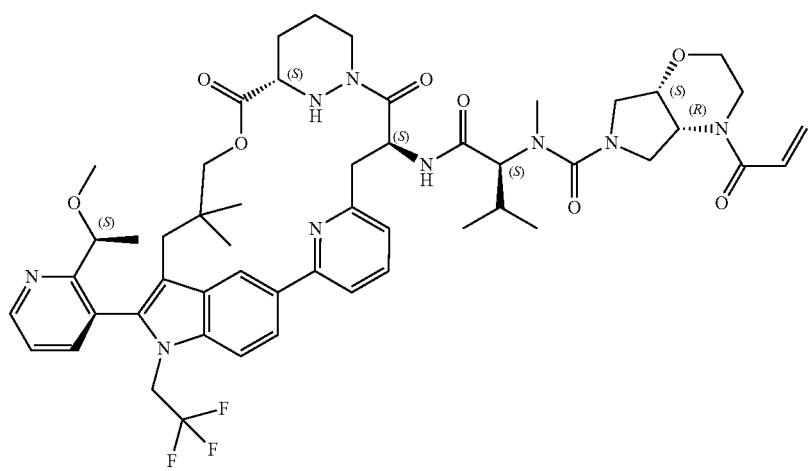 |
| A596 | 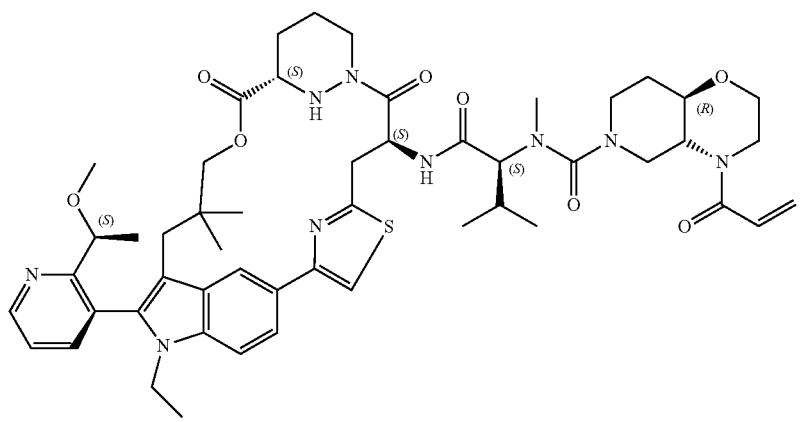 |

TABLE 1-continued
Certain Compounds of the Present Invention
| Ex# | Structure |
|---|---|
| A597 | 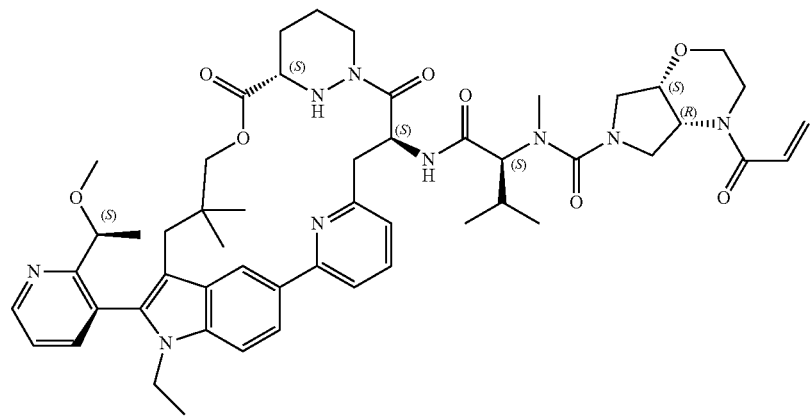 |
| A598 | 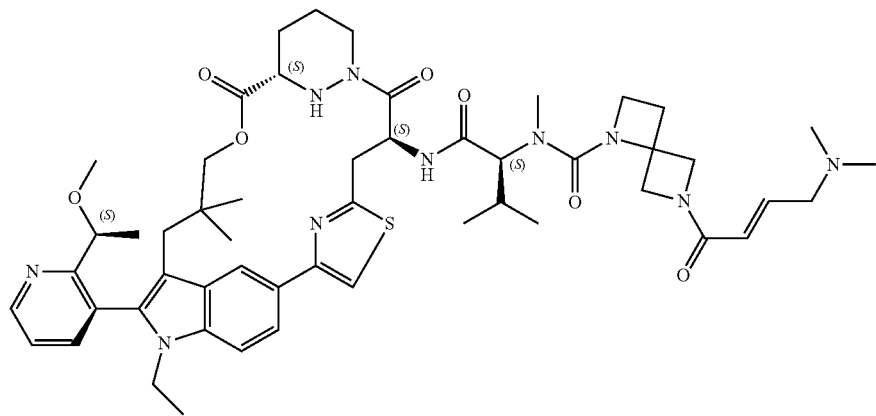 |
| A599 | 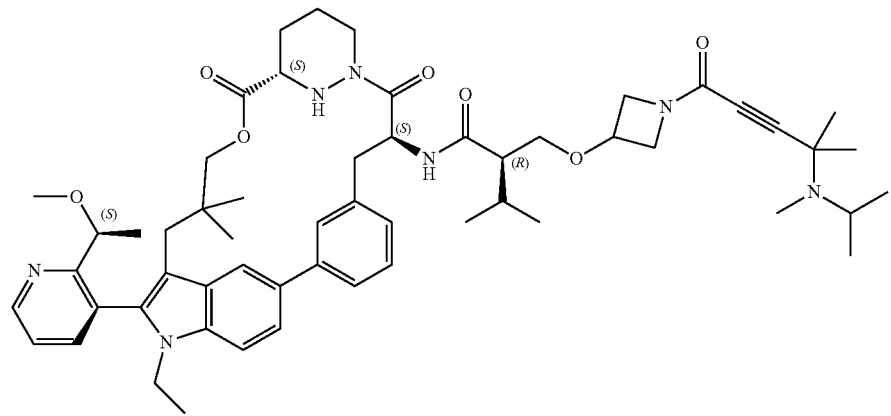 |

TABLE 1-continued

Certain Compounds of the Present Invention

| Ex# | Structure |
|---|---|
| A600 | 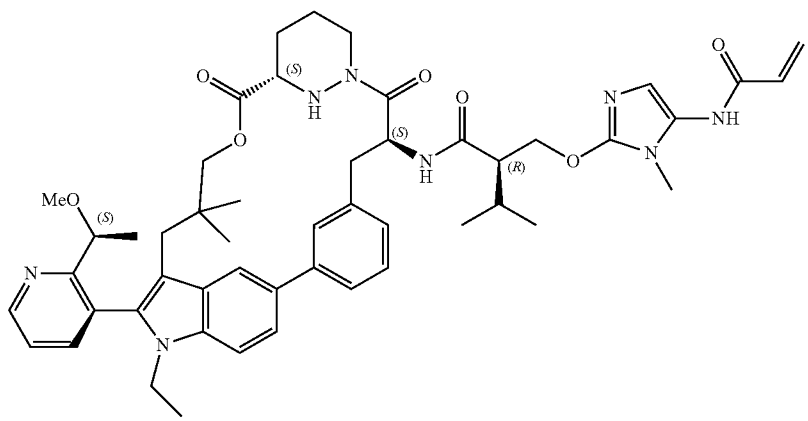 |
| A601 | 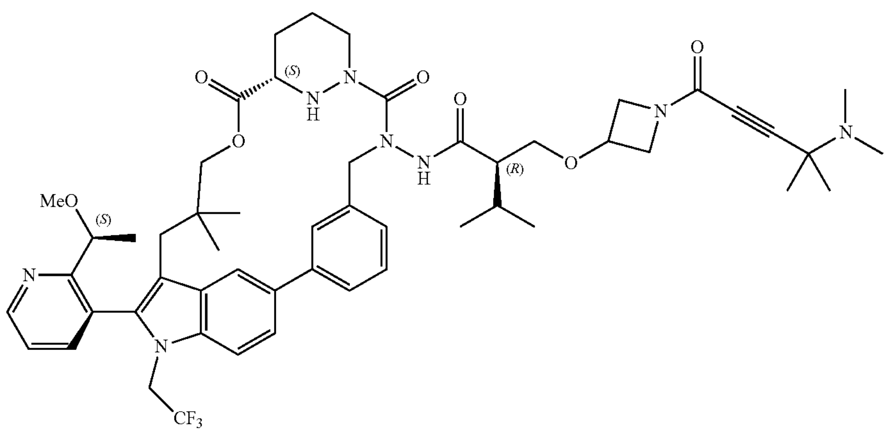 |
| A602 | 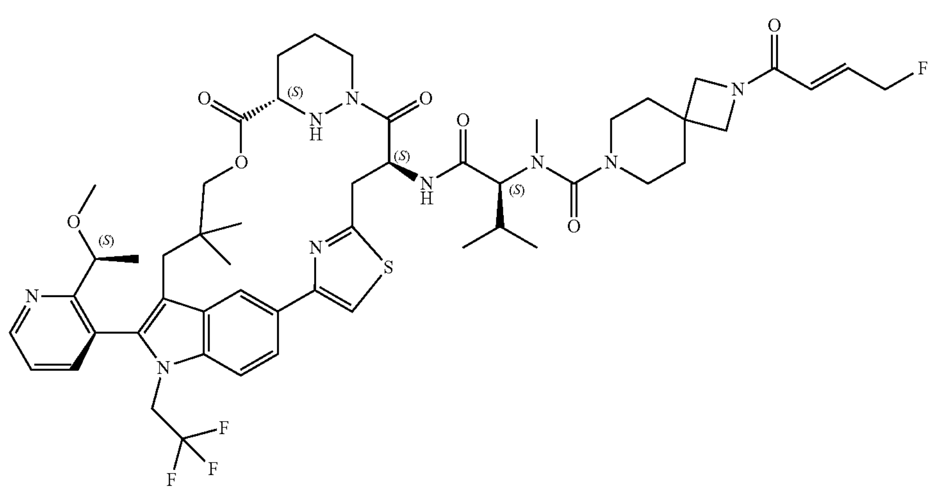 |

TABLE 1-continued
Certain Compounds of the Present Invention
| Ex# | Structure |
|---|---|
| A603 | 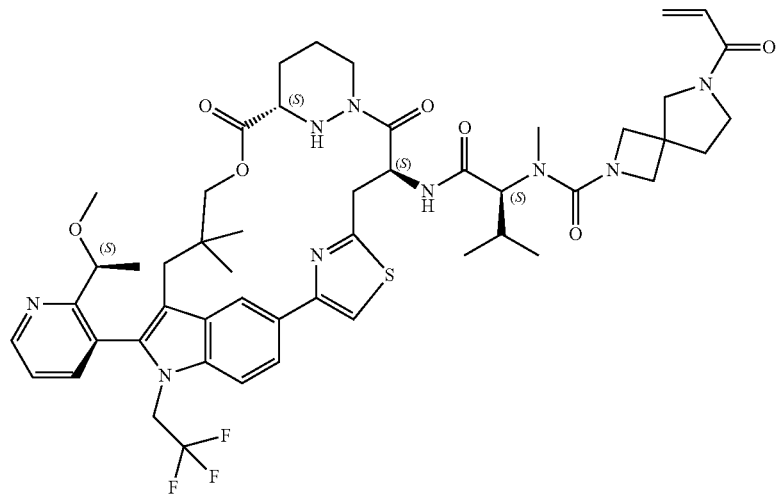 |
| A604 | 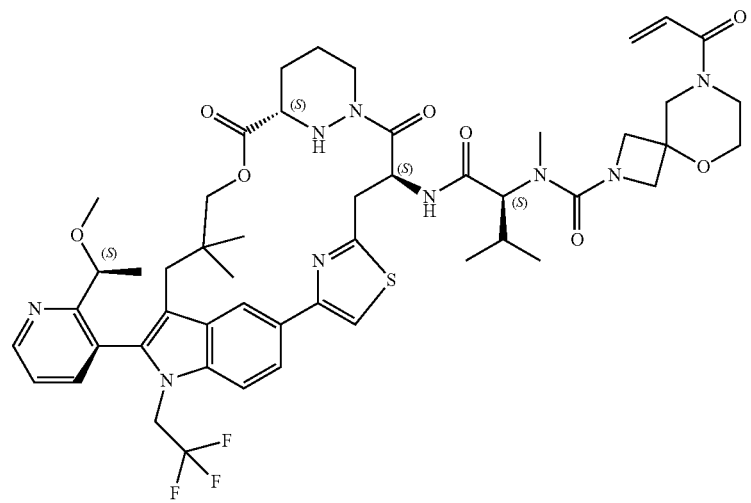 |
| A605 | 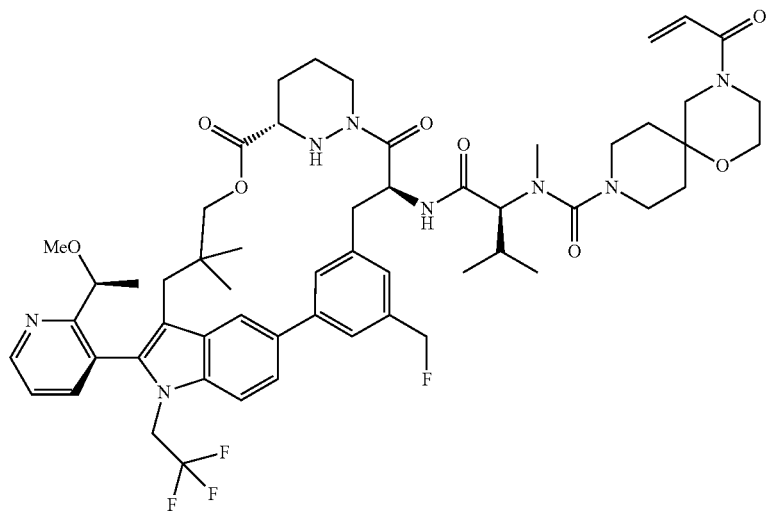 |

TABLE 1-continued

Certain Compounds of the Present Invention

| Ex# | Structure |
| --- | --- |
| A606 | 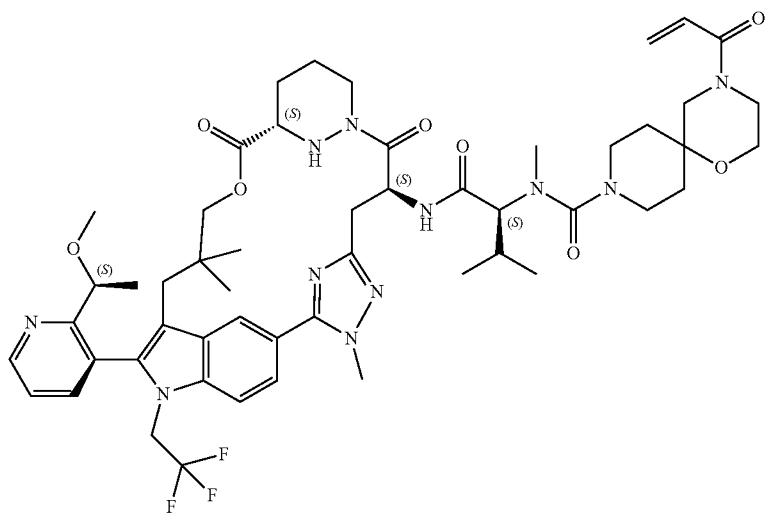 |
| A607 | 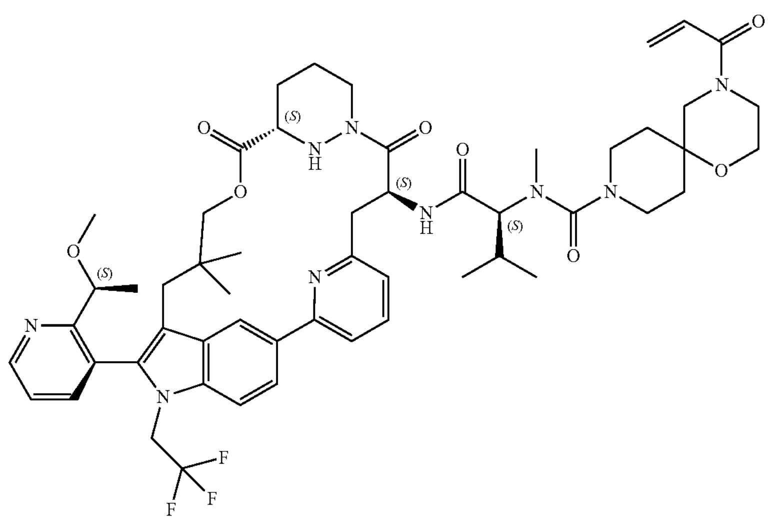 |
| A608 | 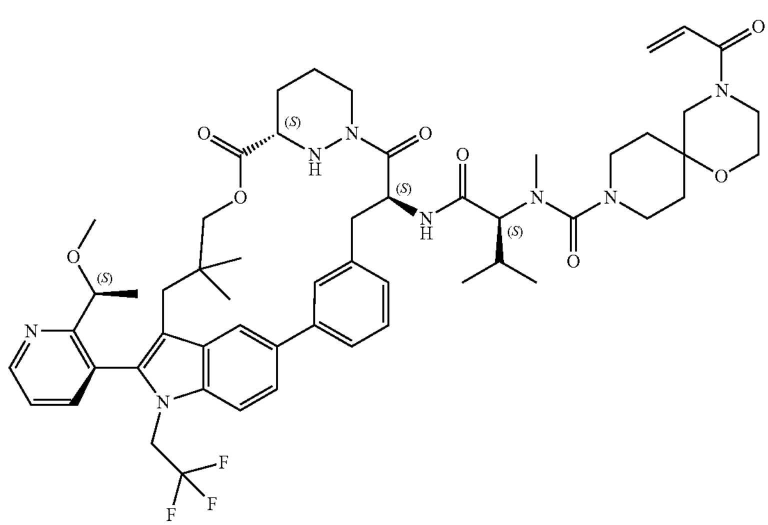 |

TABLE 1-continued

Certain Compounds of the Present Invention

| Ex# | Structure |
|---|---|
| A609 | 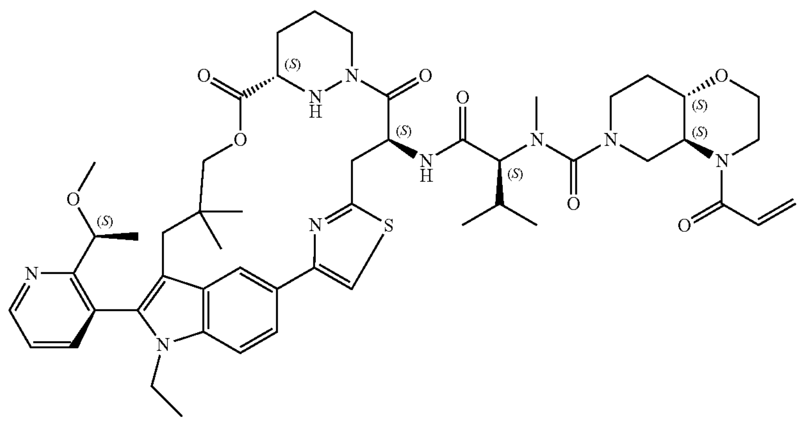 |
| A610 | 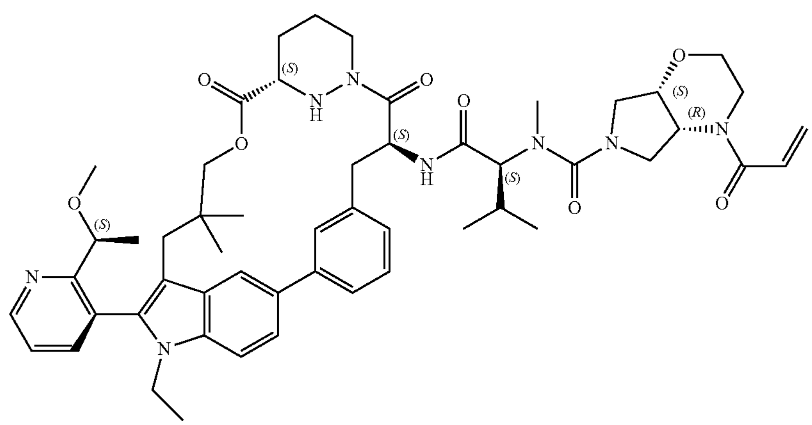 |
| A611 | 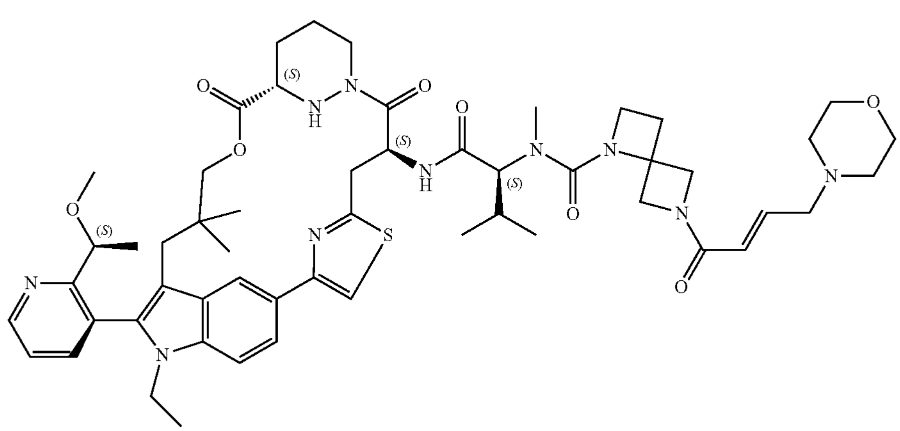 |

TABLE 1-continued

Certain Compounds of the Present Invention

| Ex# | Structure |
|---|---|
| A612 | 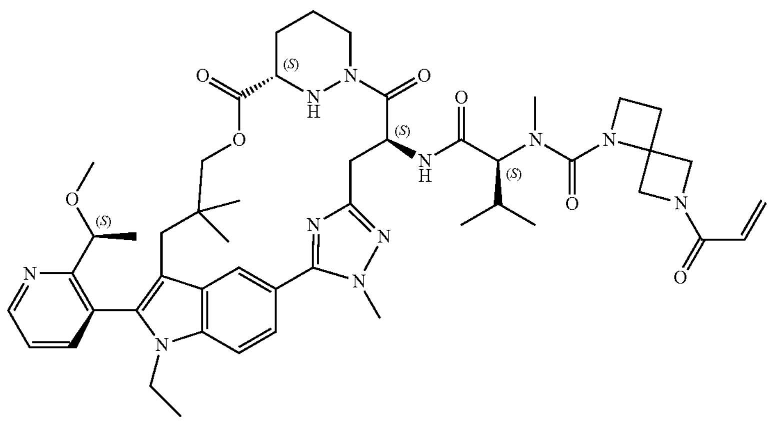 |
| A613 | 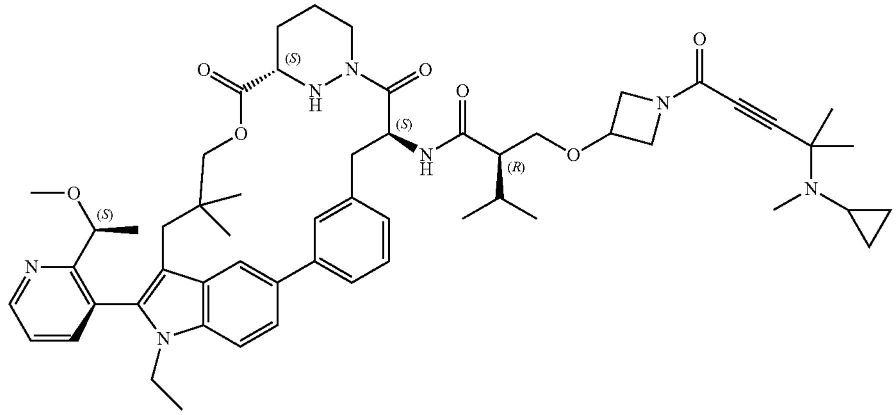 |
| A614 | 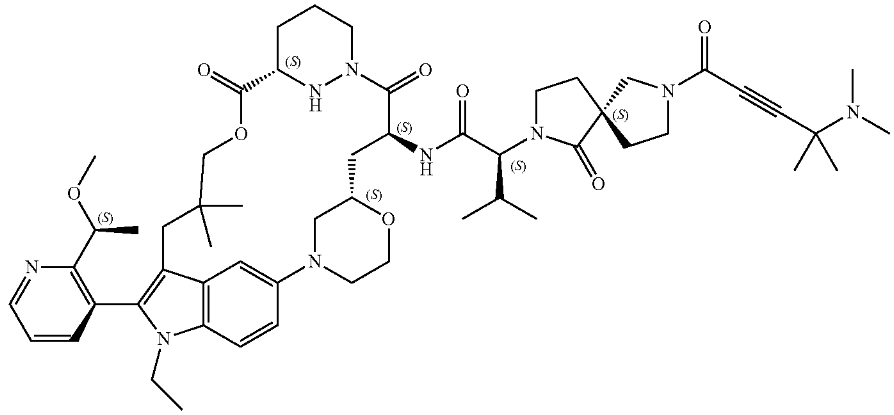 |

TABLE 1-continued
Certain Compounds of the Present Invention
| Ex# | Structure |
| --- | --- |
| A615 | 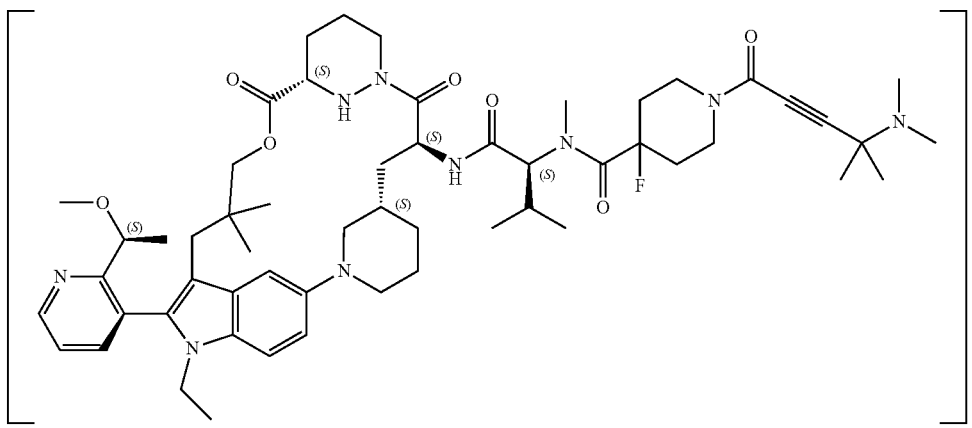 |
| A616 | 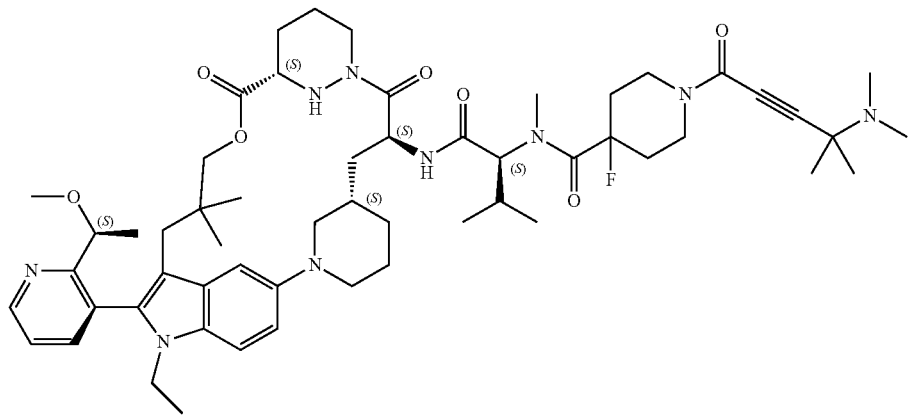 |
| A617 | 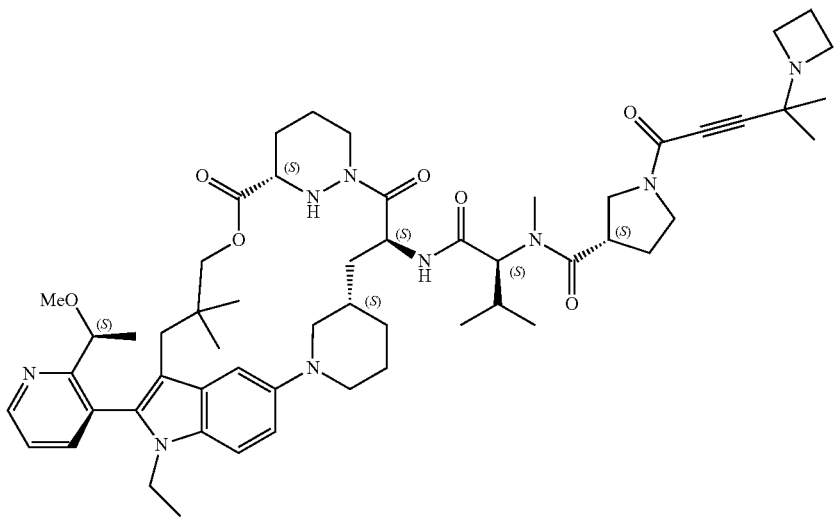 |

TABLE 1-continued

Certain Compounds of the Present Invention

| Ex# | Structure |
|---|---|
| A618 | 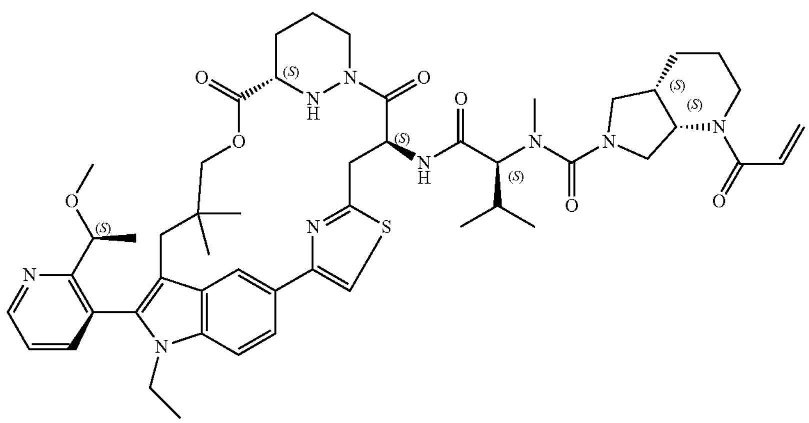 |
| A619 | 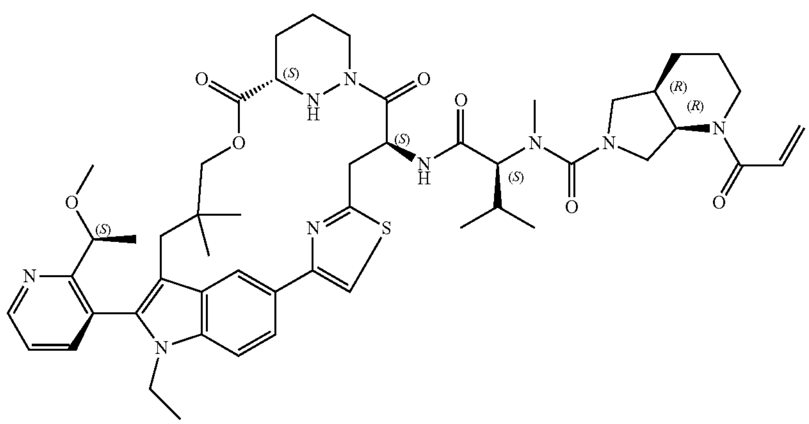 |
| A620 | 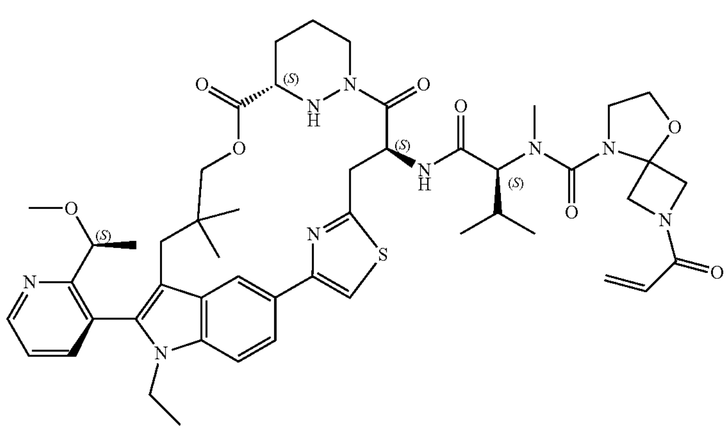 |

TABLE 1-continued
Certain Compounds of the Present Invention
| Ex# | Structure |
|---|---|
| A621 | 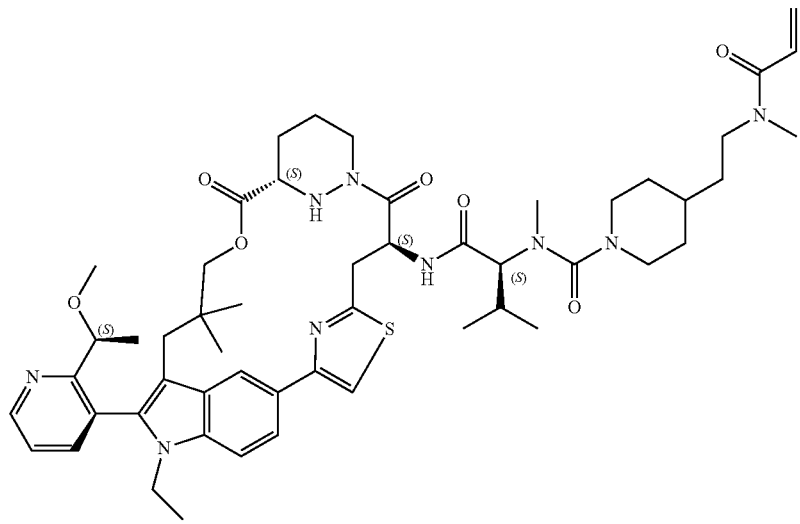 |
| A622 | 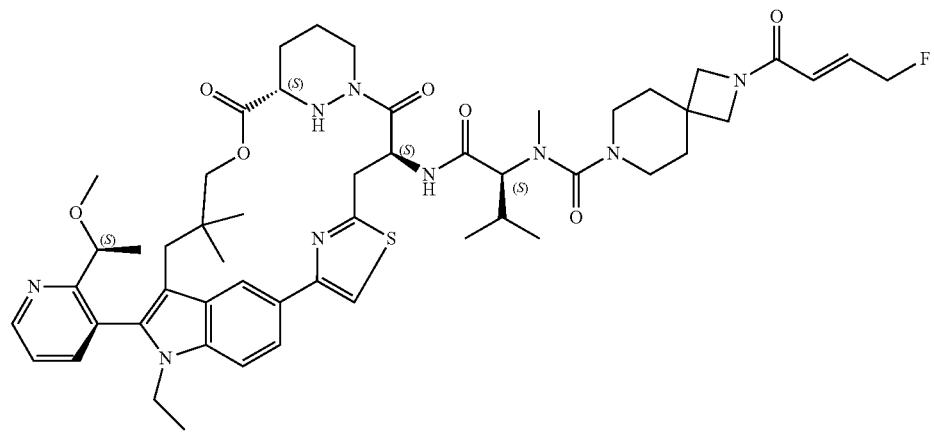 |
| A623 | 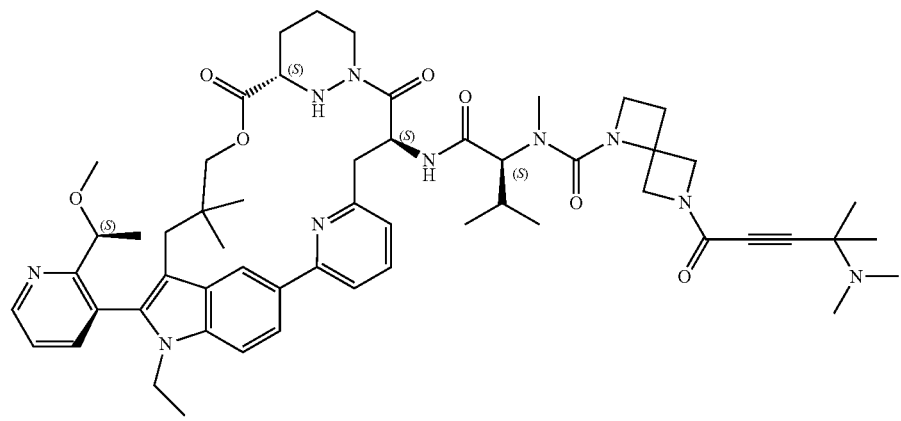 |

TABLE 1-continued
Certain Compounds of the Present Invention
| Ex# | Structure |
|---|---|
| A624 | 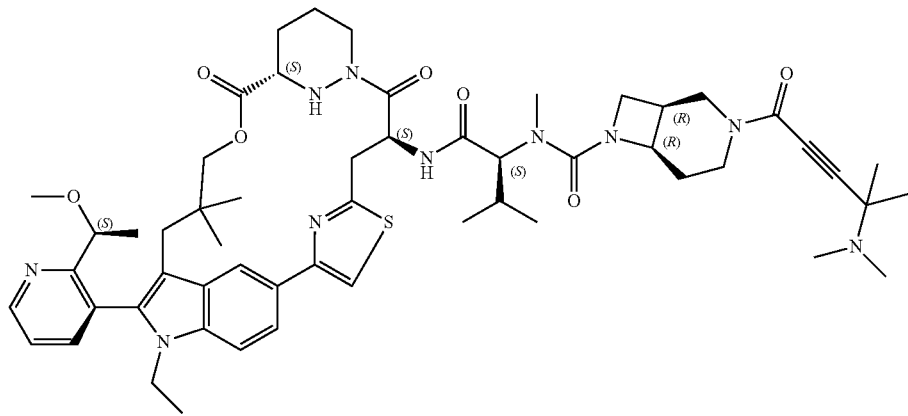 |
| A625 | 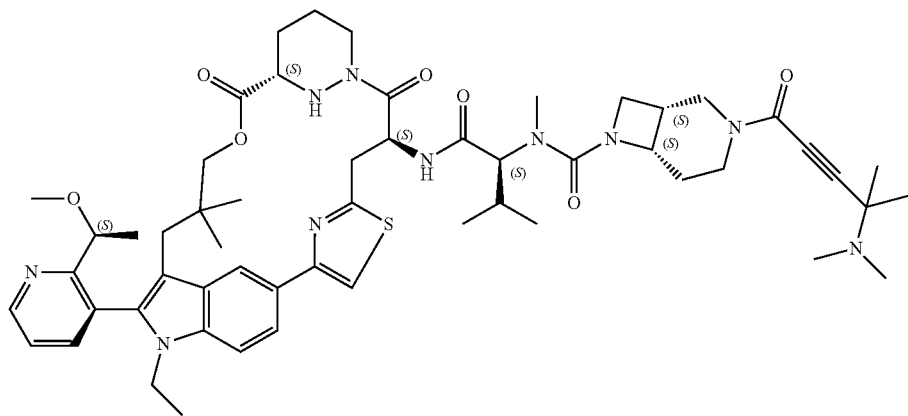 |
| A626 | 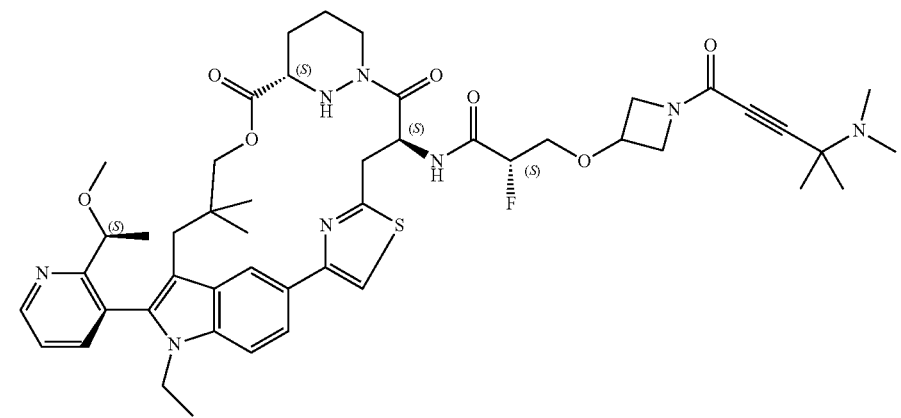 |

TABLE 1-continued

Certain Compounds of the Present Invention

| Ex# | Structure |
|---|---|
| A627 | 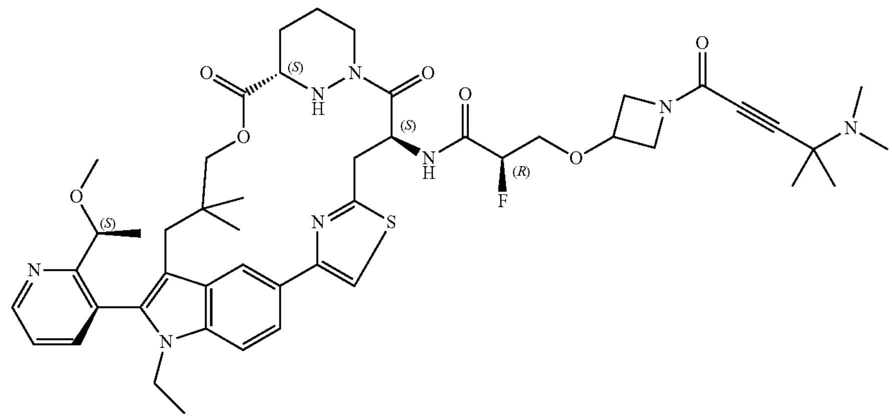 |
| A628 | 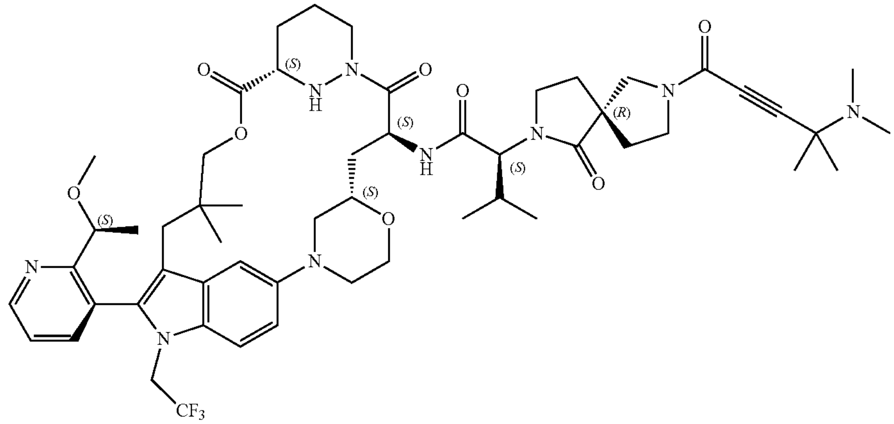 |
| A629 | 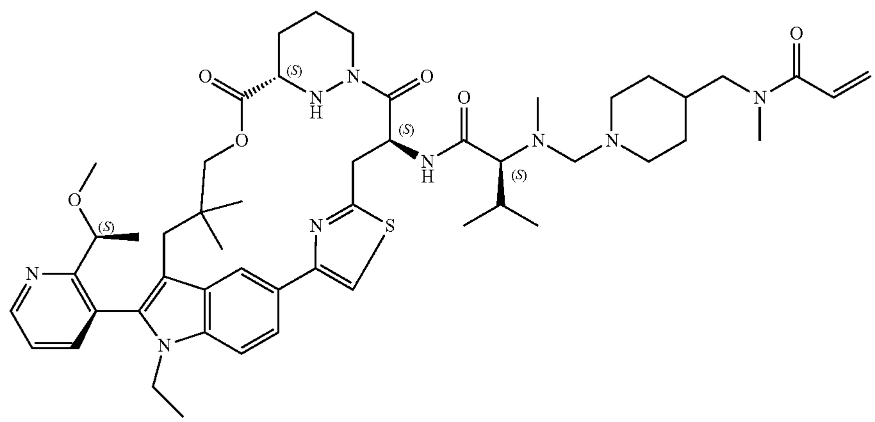 |

TABLE 1-continued
Certain Compounds of the Present Invention
| Ex# | Structure |
|---|---|
| A630 | 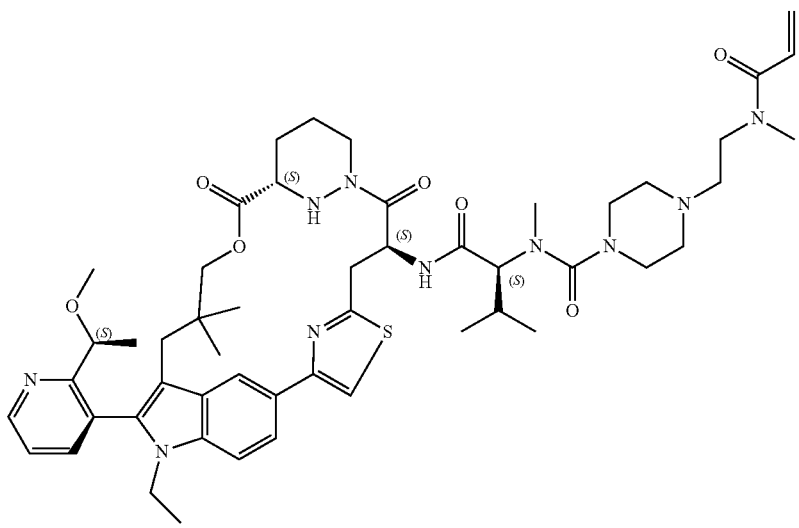 |
| A631 | 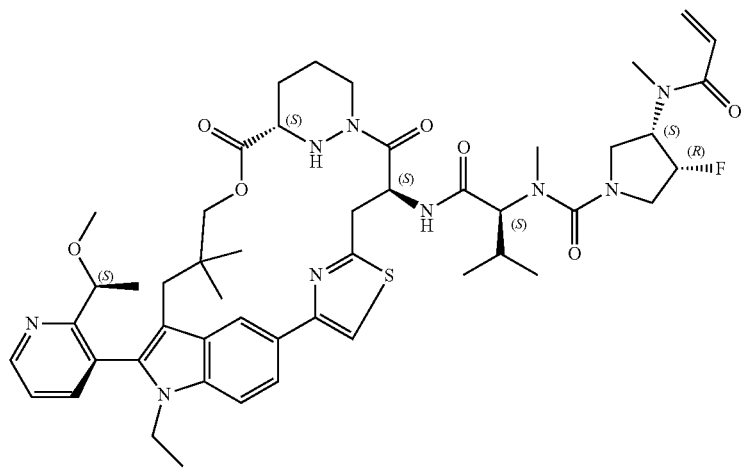 |
| A632 | 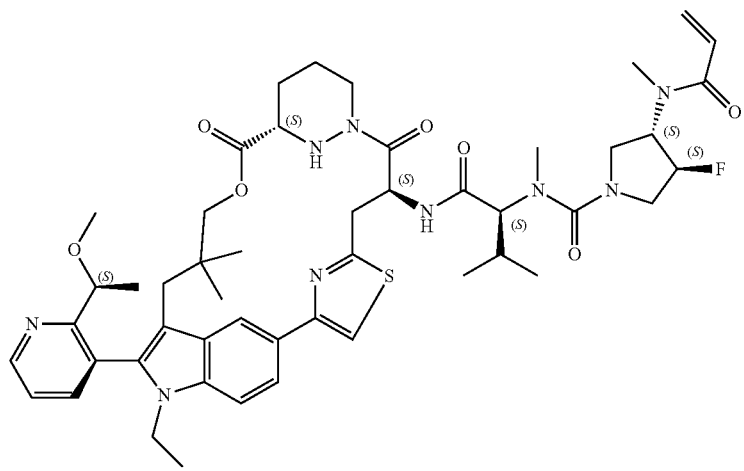 |

TABLE 1-continued

Certain Compounds of the Present Invention

| Ex# | Structure |
|---|---|
| A633 | 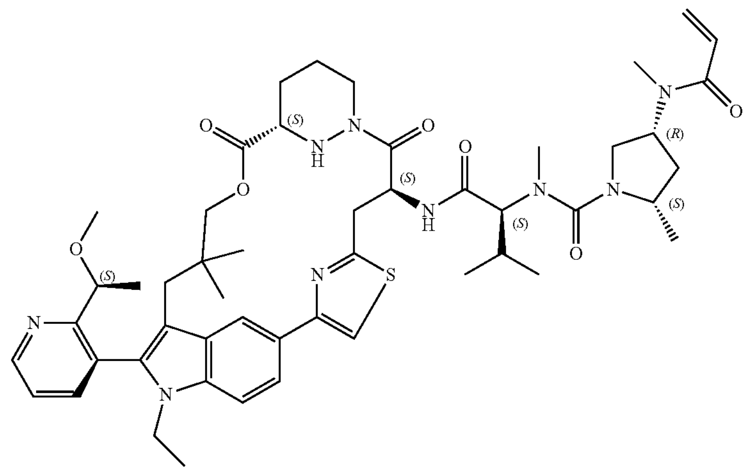 |
| A634 | 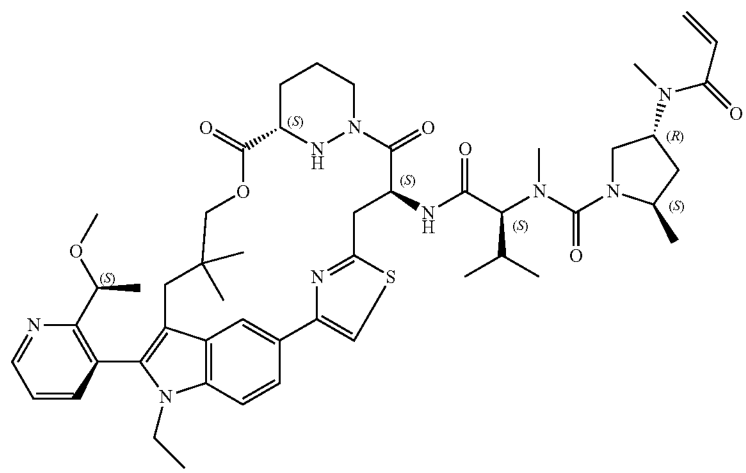 |
| A635 | 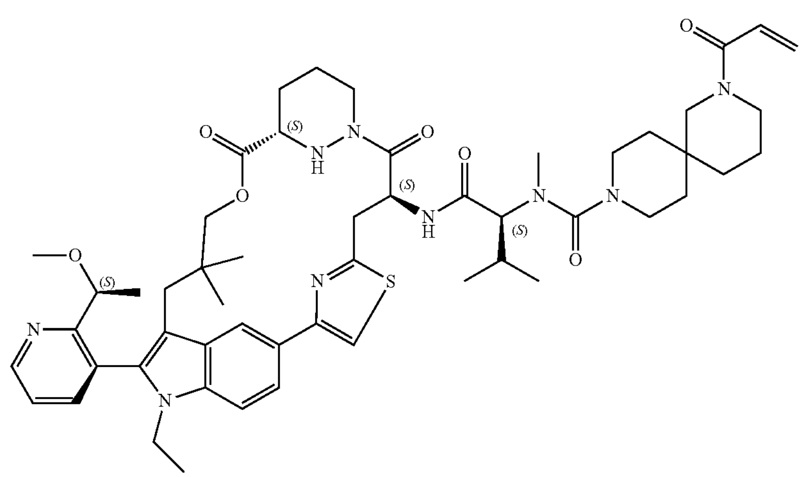 |

TABLE 1-continued

Certain Compounds of the Present Invention

| Ex# | Structure |
|---|---|
| A636 | 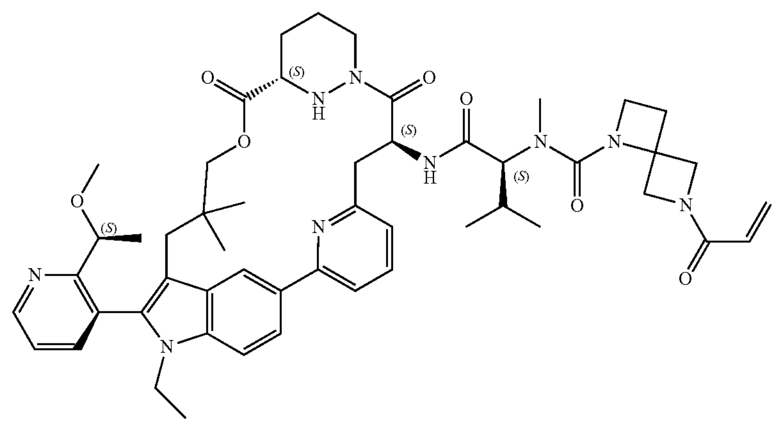 |
| A637 | 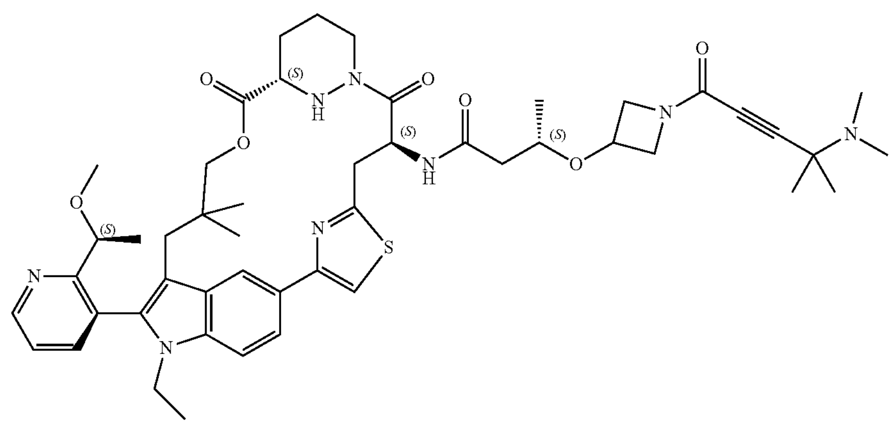 |
| A638 | 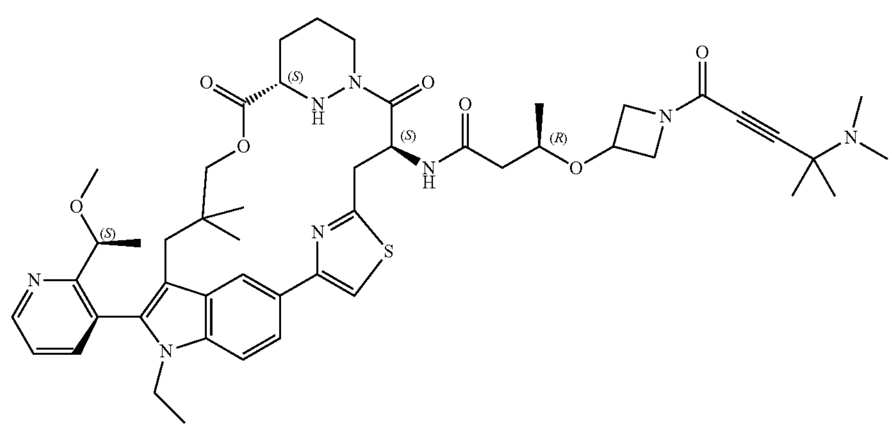 |

TABLE 1-continued

Certain Compounds of the Present Invention

| Ex# | Structure |
|---|---|
| A639 | 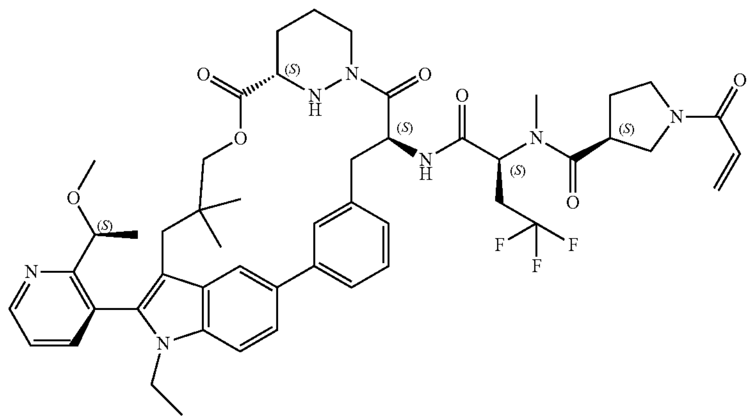 |
| A640 | 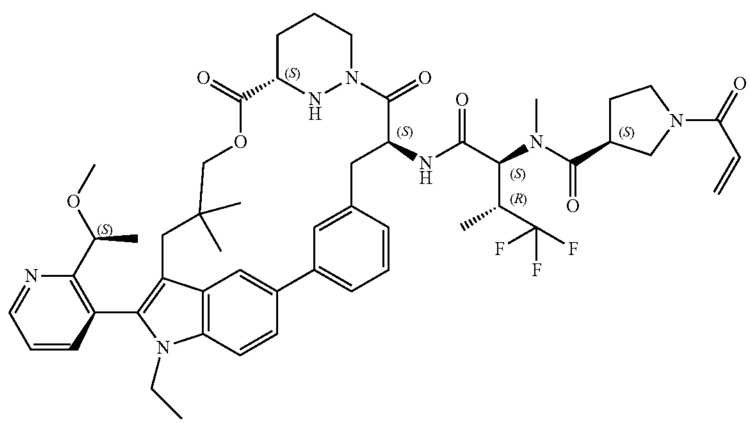 |
| A641 | 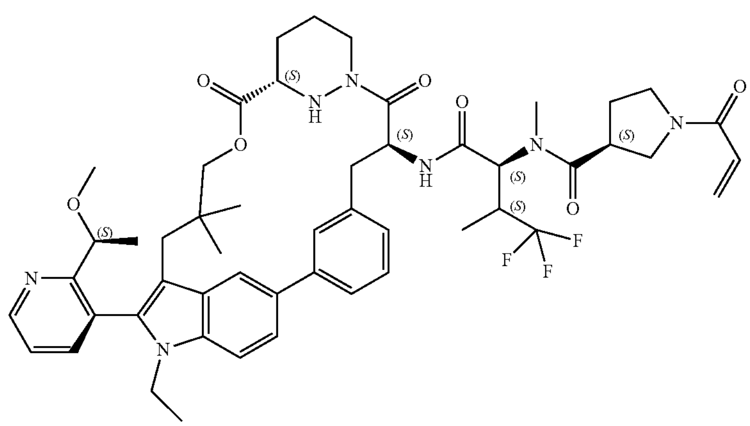 |

TABLE 1-continued

Certain Compounds of the Present Invention

| Ex# | Structure |
|---|---|
| A642 | 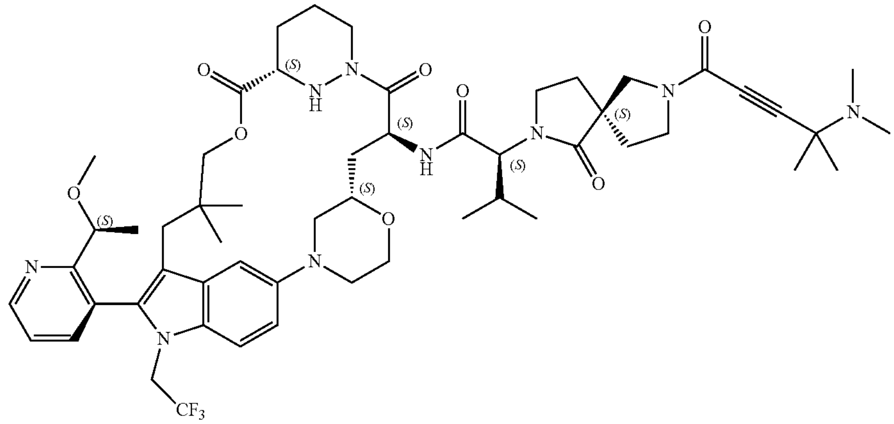 |
| A643 | 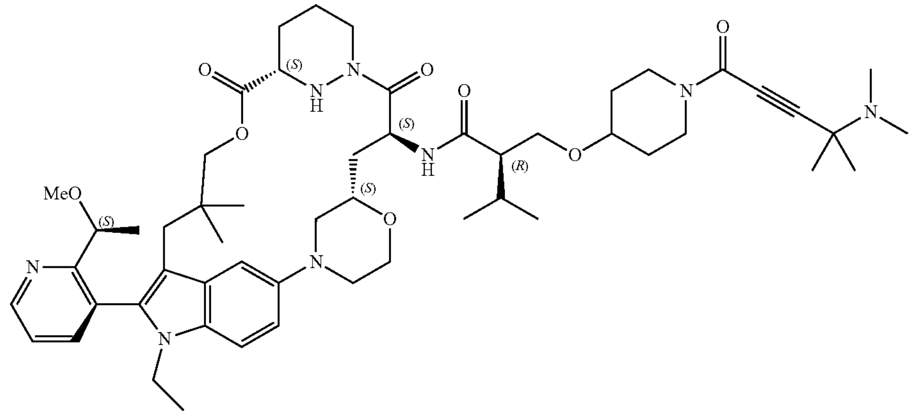 |
| A644 | 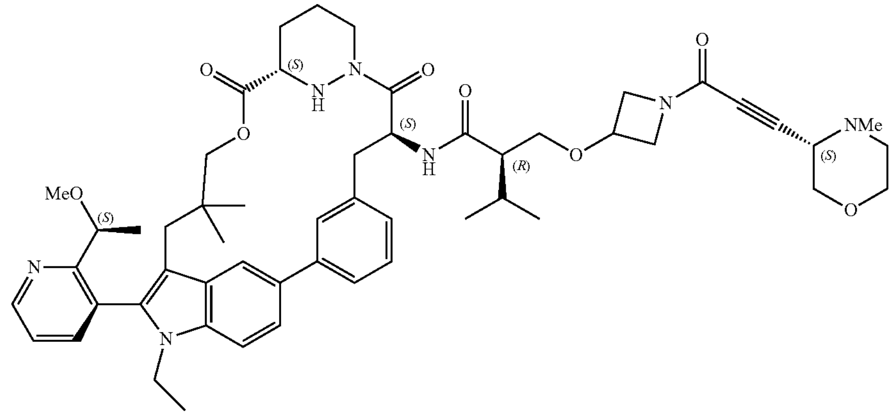 |

TABLE 1-continued

Certain Compounds of the Present Invention

| Ex# | Structure |
| --- | --- |
| A645 | 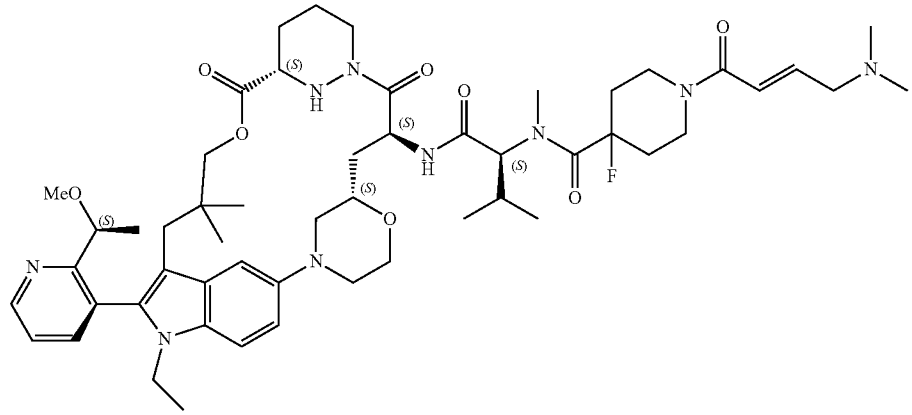 |
| A646 | 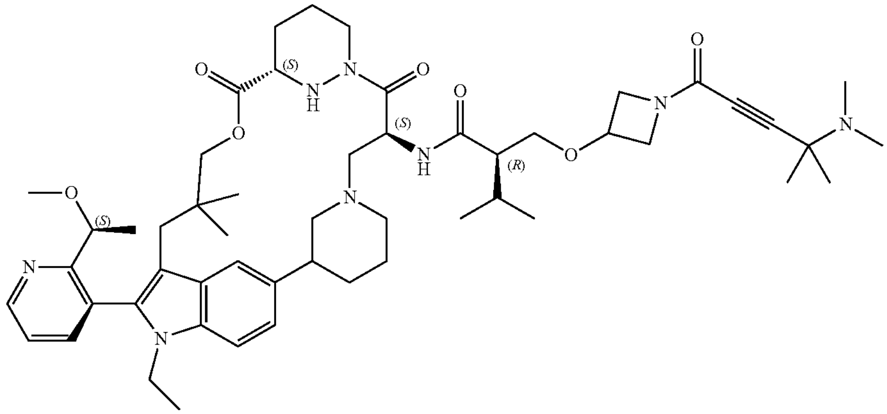 |
| A647 | 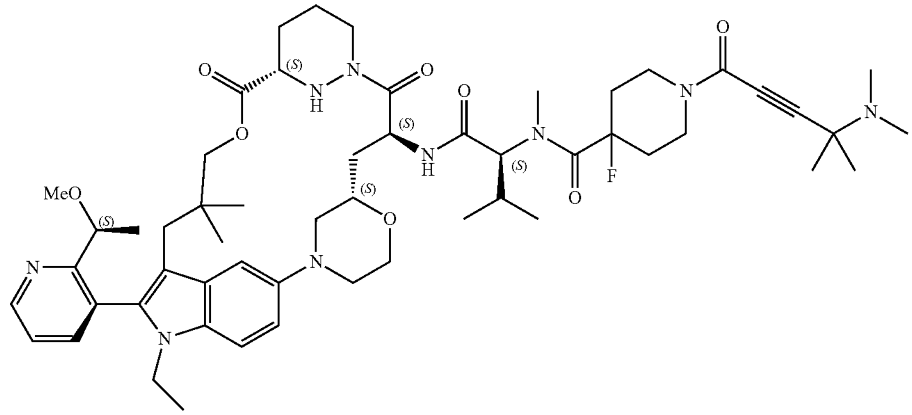 |

TABLE 1-continued
Certain Compounds of the Present Invention
| Ex# | Structure |
|---|---|
| A648 | 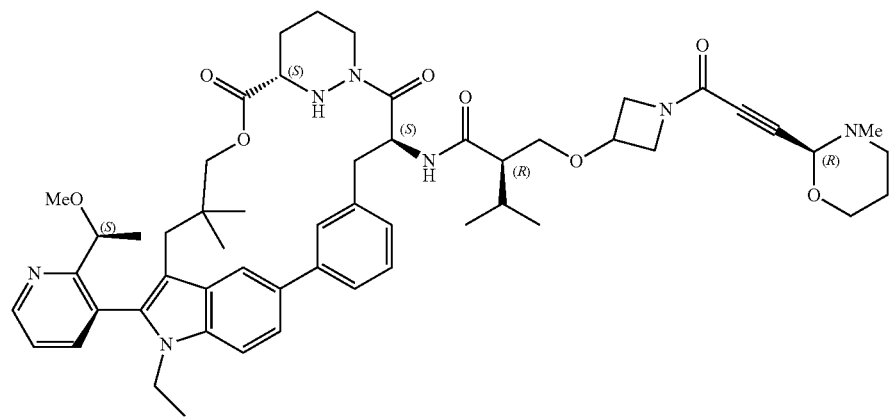 |
| A649 | 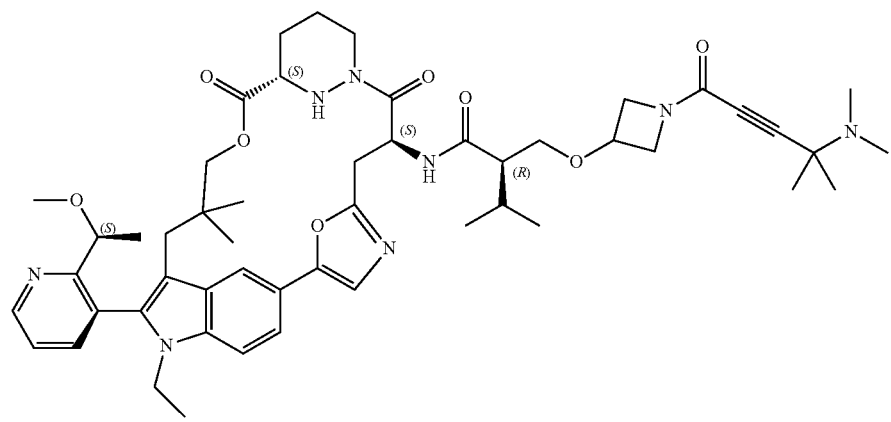 |
| A650 | 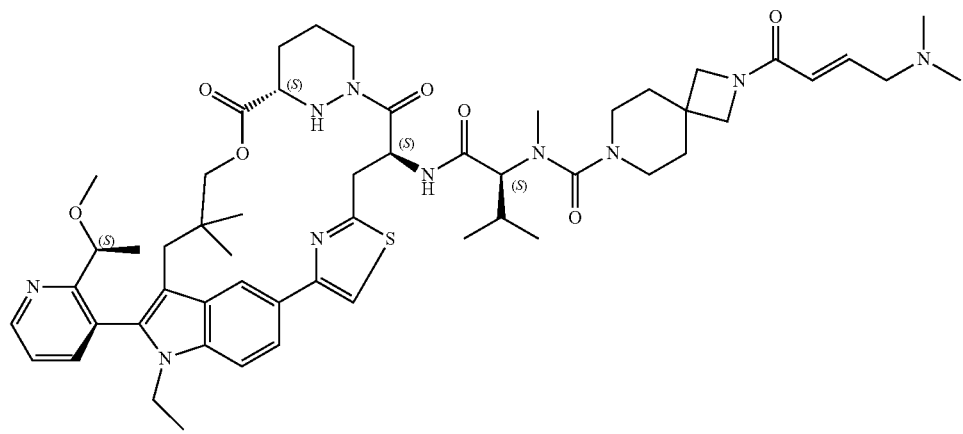 |

TABLE 1-continued
Certain Compounds of the Present Invention
| Ex# | Structure |
|---|---|
| A651 | 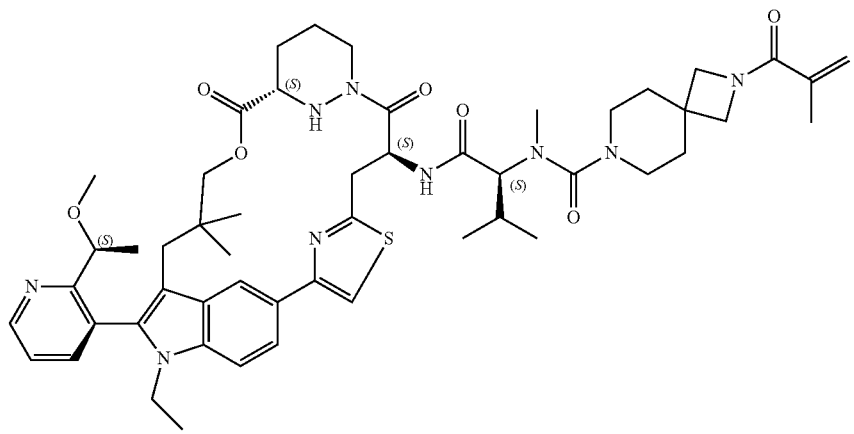 |
| A652 | 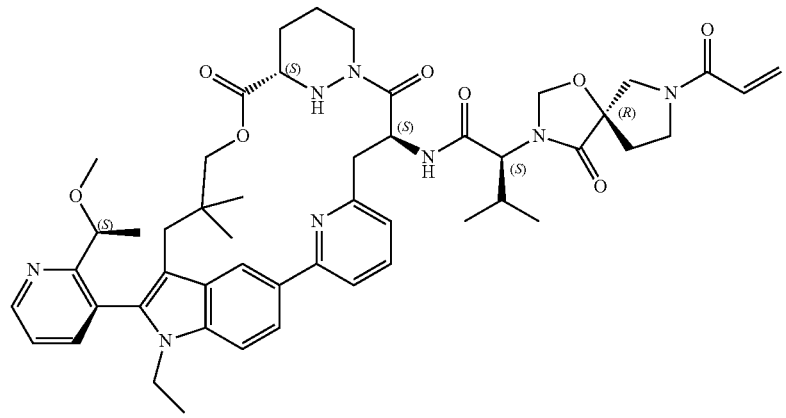 |
| A653 | 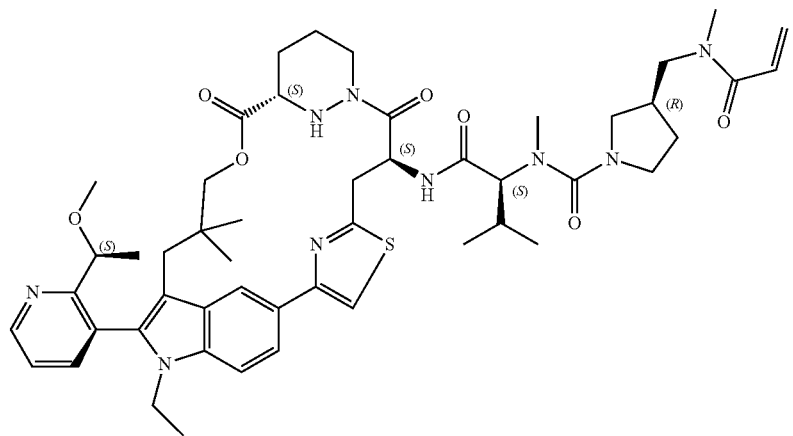 |

TABLE 1-continued
Certain Compounds of the Present Invention
| Ex# | Structure |
|---|---|
| A654 | 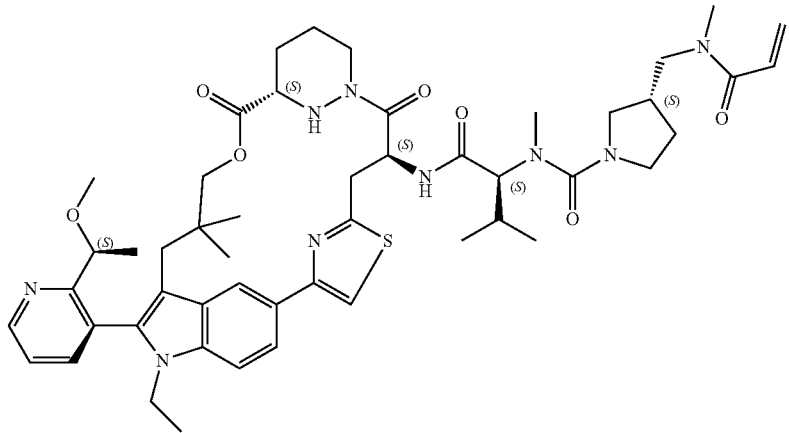 |
| A655 | 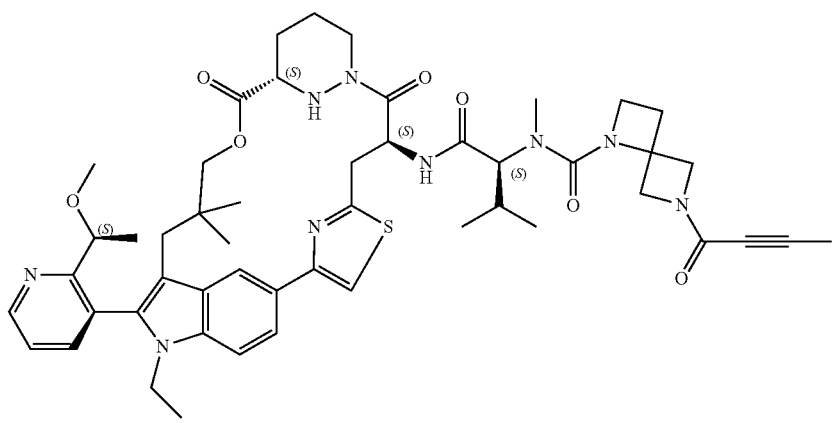 |
| A656 | 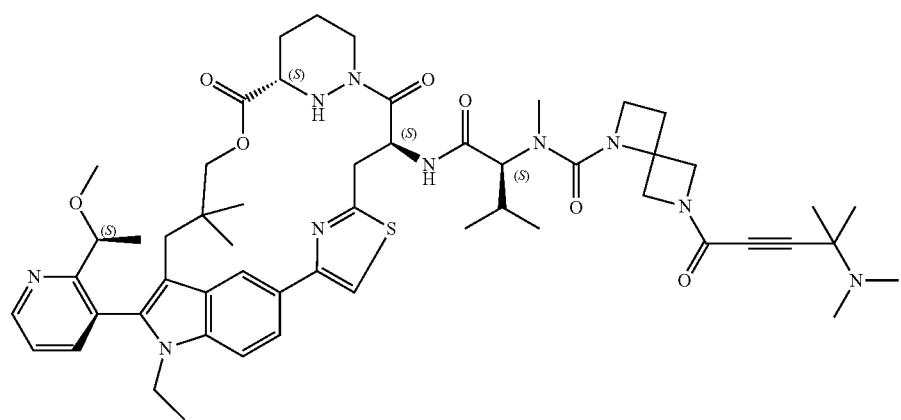 |

TABLE 1-continued
Certain Compounds of the Present Invention
| Ex# | Structure |
|---|---|
| A657 | 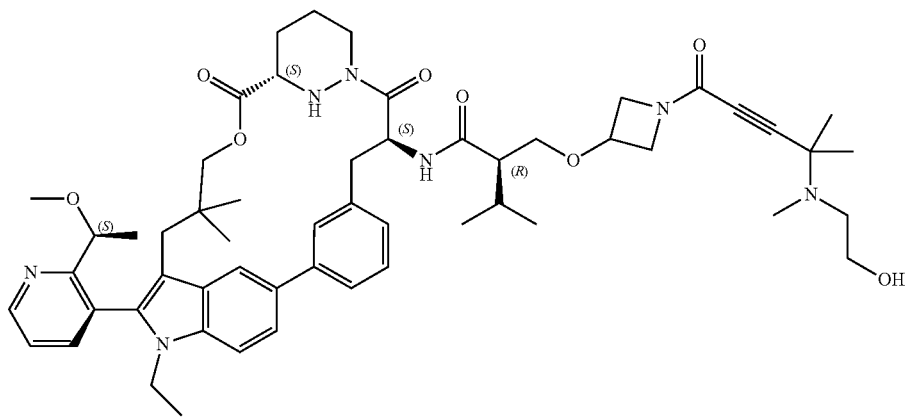 |
| A658 | 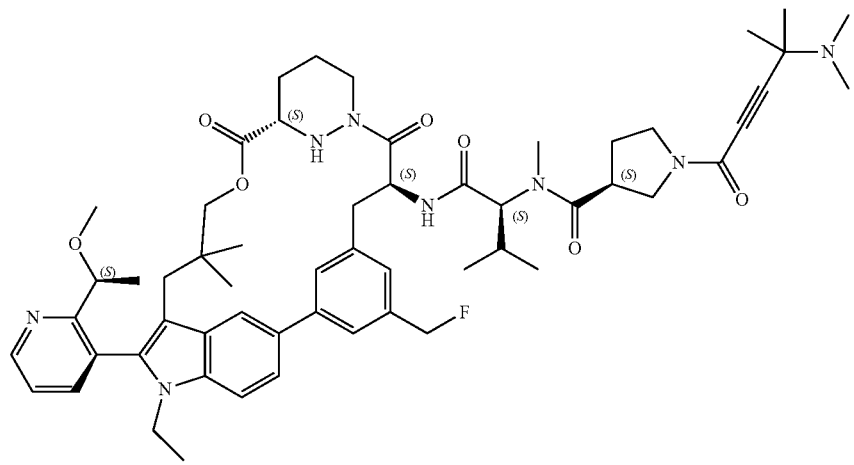 |
| A659 | 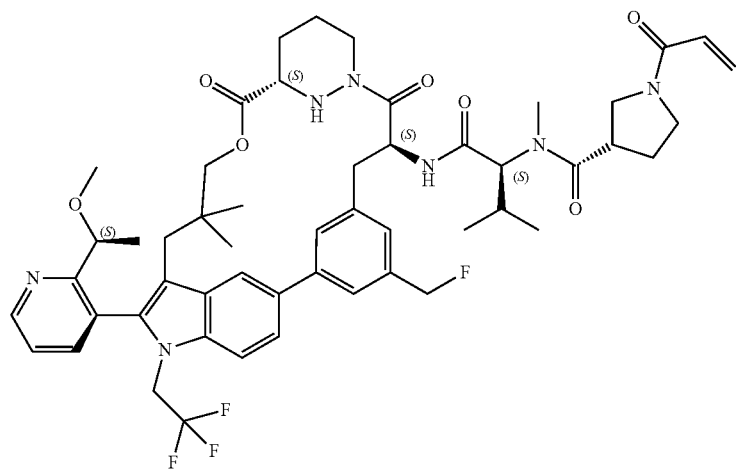 |

TABLE 1-continued
Certain Compounds of the Present Invention
| Ex# | Structure |
|---|---|
| A660 | 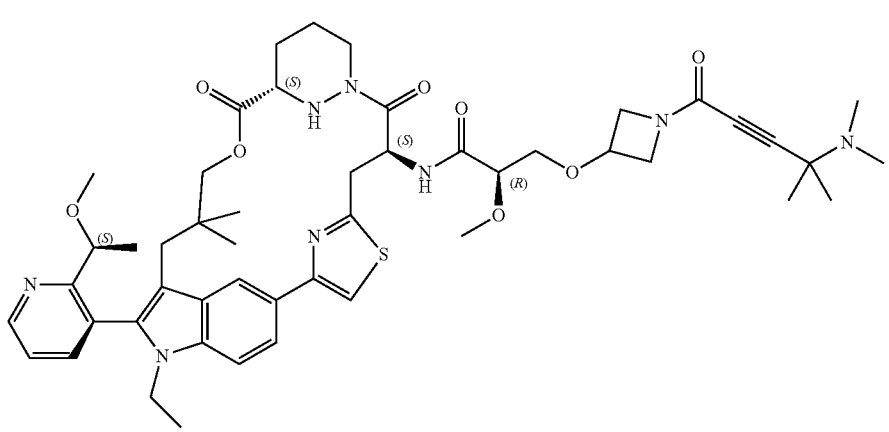 |
| A661 | 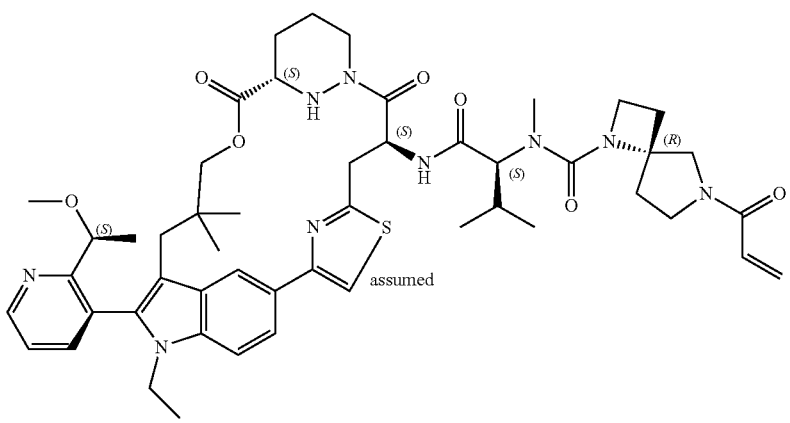 |
| A662 | 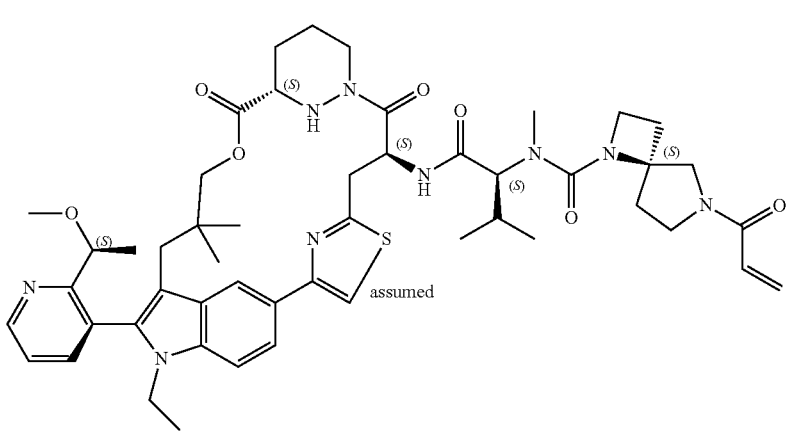 |

TABLE 1-continued
Certain Compounds of the Present Invention
| Ex# | Structure |
|---|---|
| A663 | 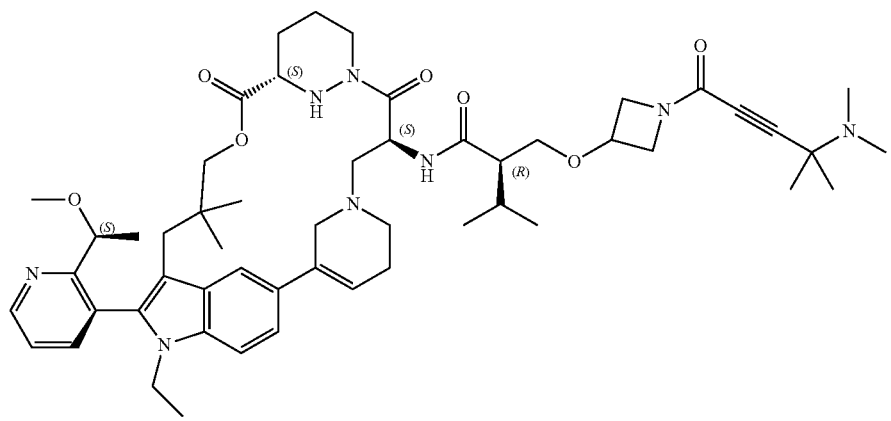 |
| A664 | 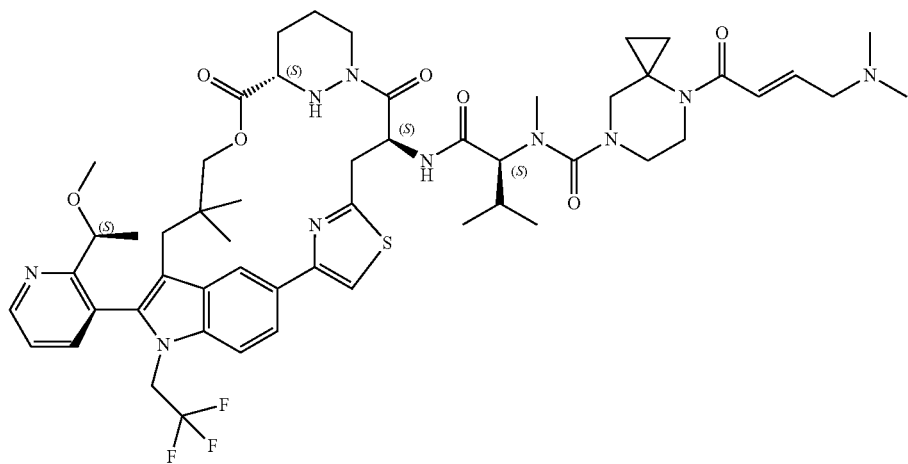 |
| A665 | 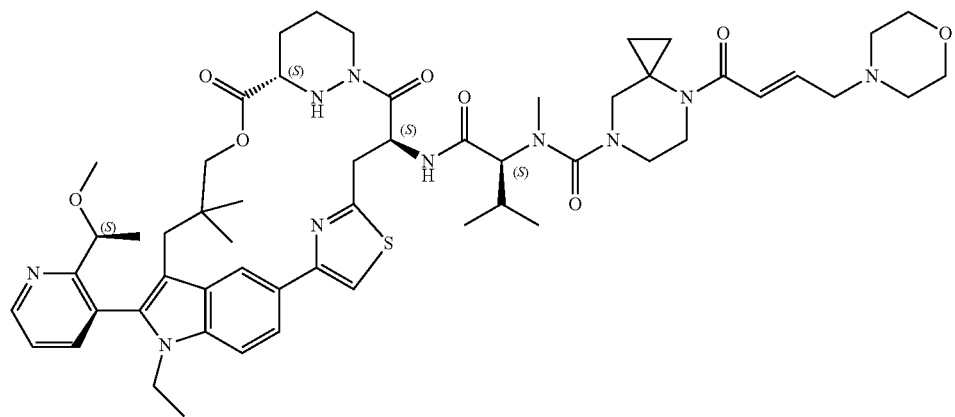 |

TABLE 1-continued
Certain Compounds of the Present Invention
| Ex# | Structure |
|---|---|
| A666 | 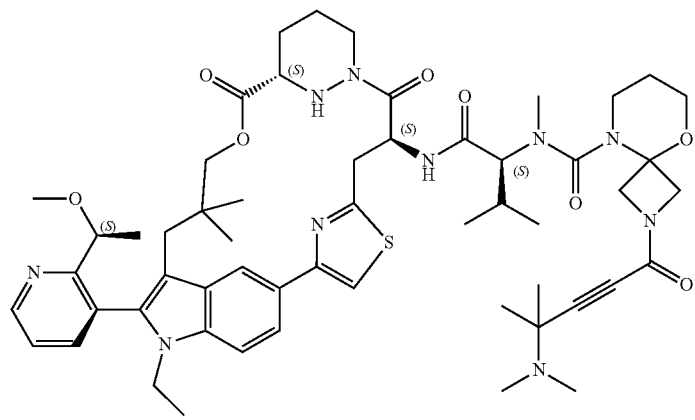 |
| A667 | 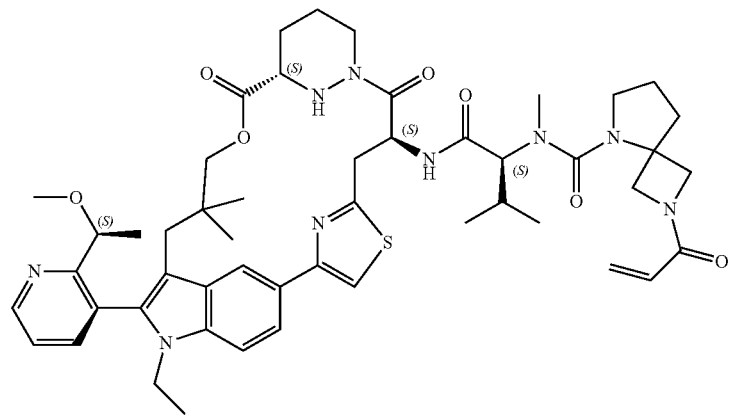 |
| A668 | 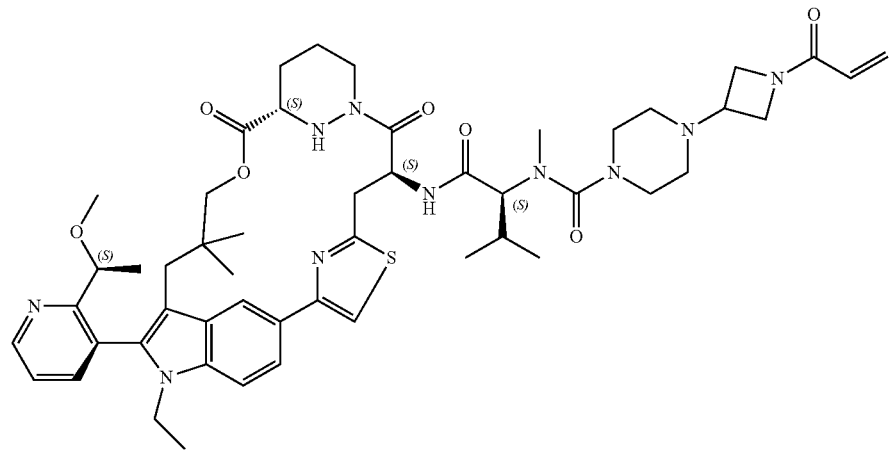 |

TABLE 1-continued
Certain Compounds of the Present Invention
| Ex# | Structure |
|---|---|
| A669 | 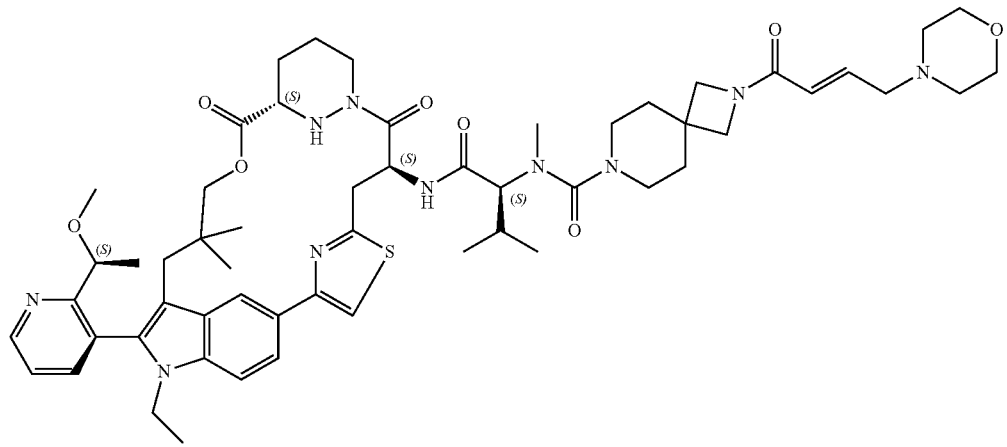 |
| A670 | 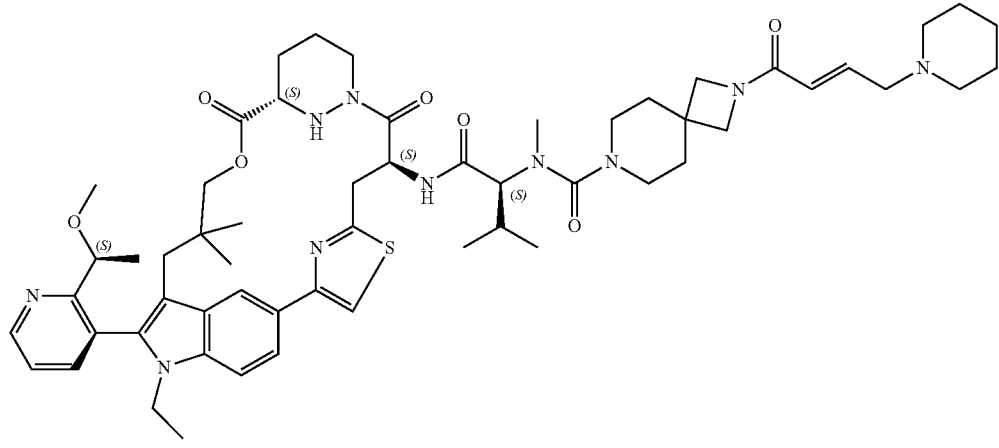 |
| A671 | 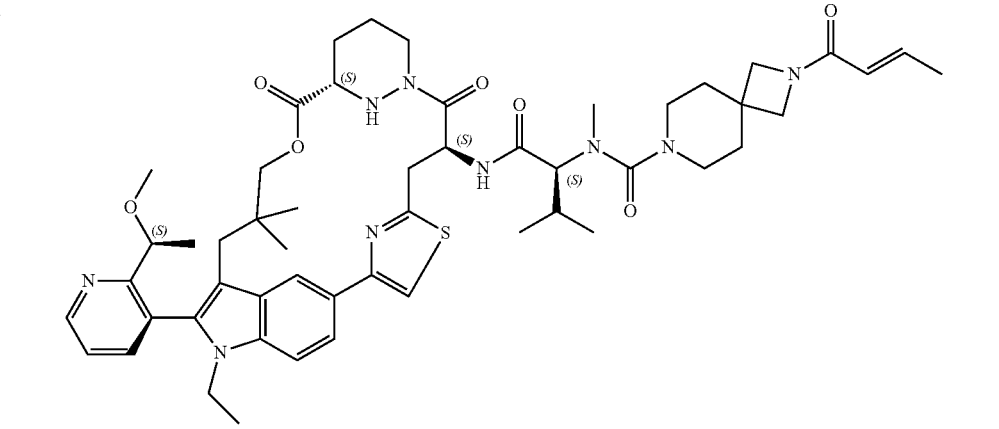 |

TABLE 1-continued
Certain Compounds of the Present Invention
| Ex# | Structure |
|---|---|
| A672 | 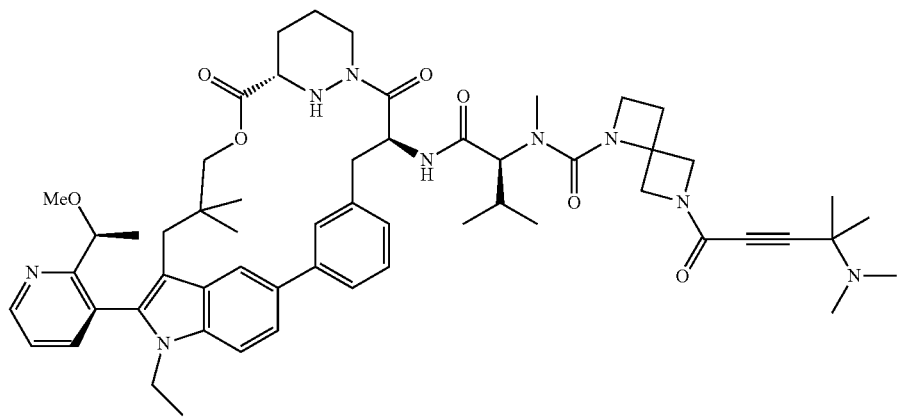 |
| A673 | 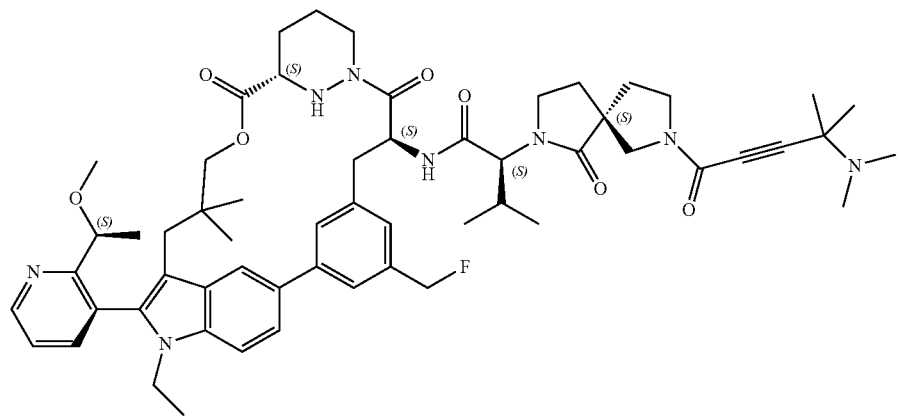 |
| A674 | 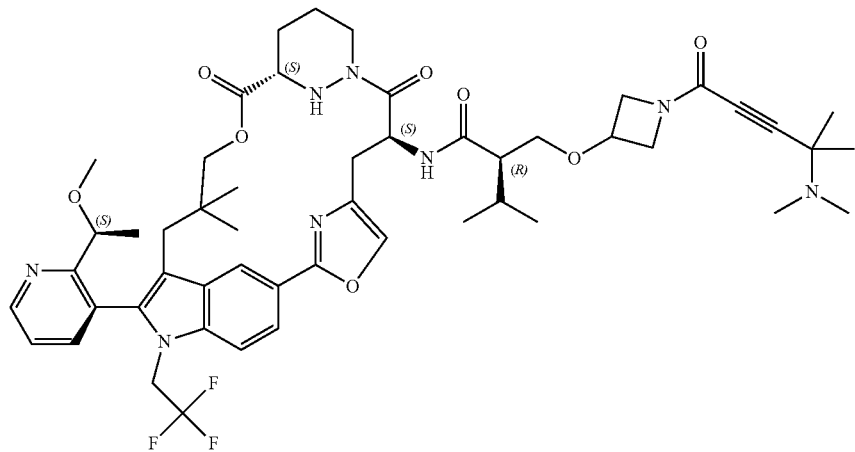 |

TABLE 1-continued

Certain Compounds of the Present Invention

| Ex# | Structure |
|---|---|
| A675 | 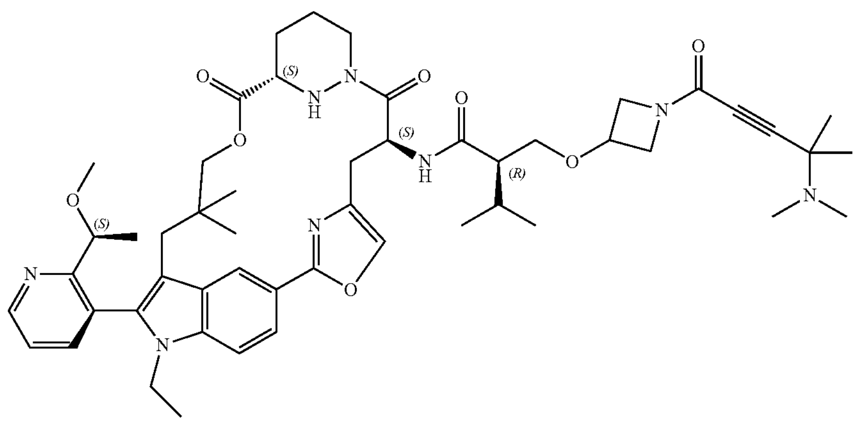 |
| A676 | 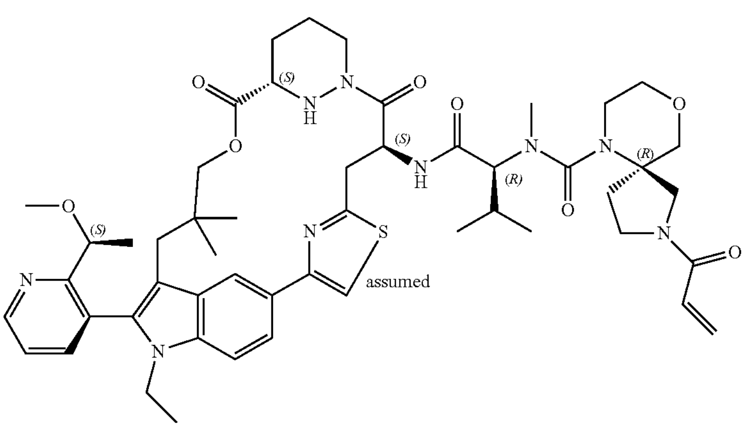 |
| A677 | 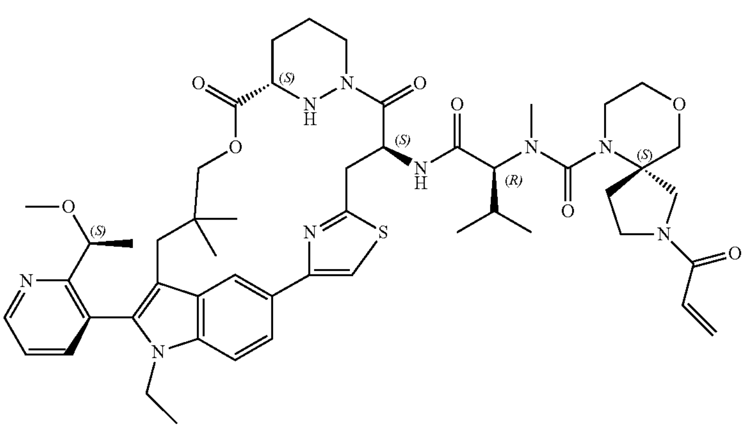 |

TABLE 1-continued
Certain Compounds of the Present Invention
| Ex# | Structure |
| --- | --- |
| A678 | 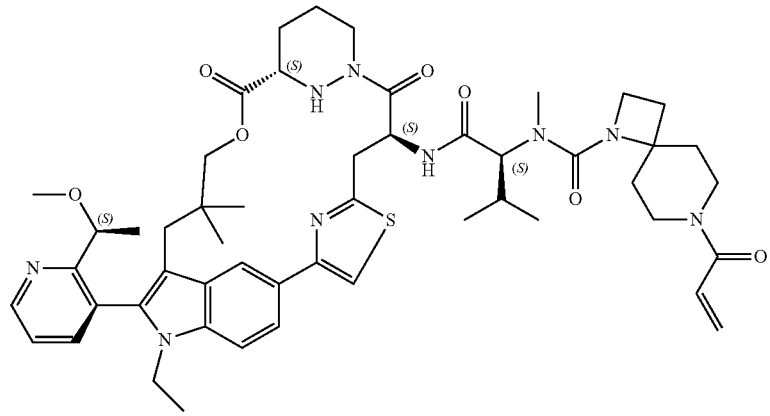 |
| A679 | 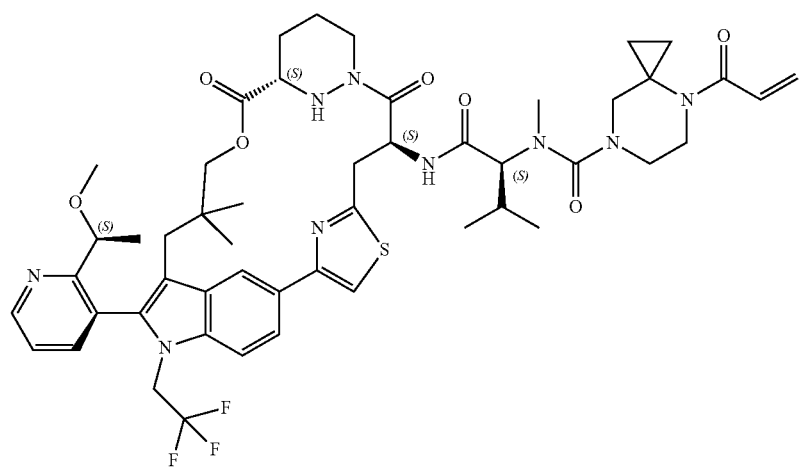 |
| A680 | 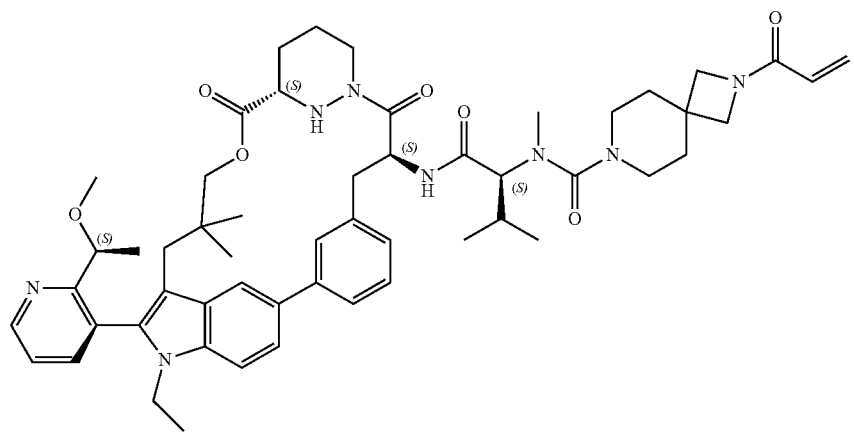 |

TABLE 1-continued
Certain Compounds of the Present Invention
| Ex# | Structure |
| --- | --- |
| A681 | 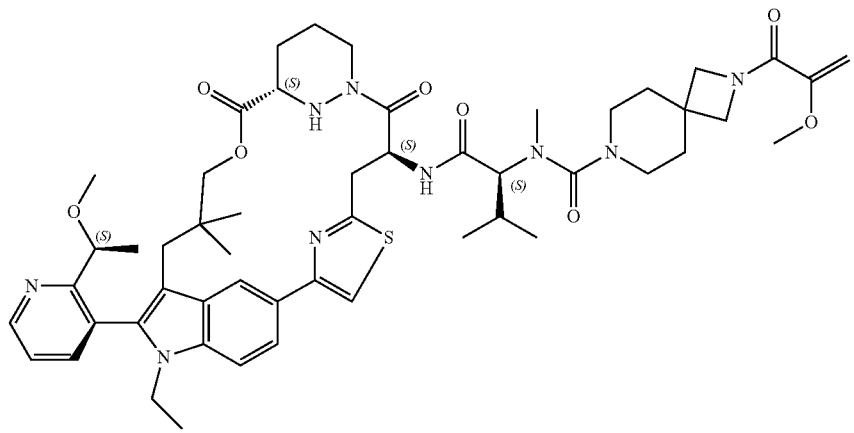 |
| A682 | 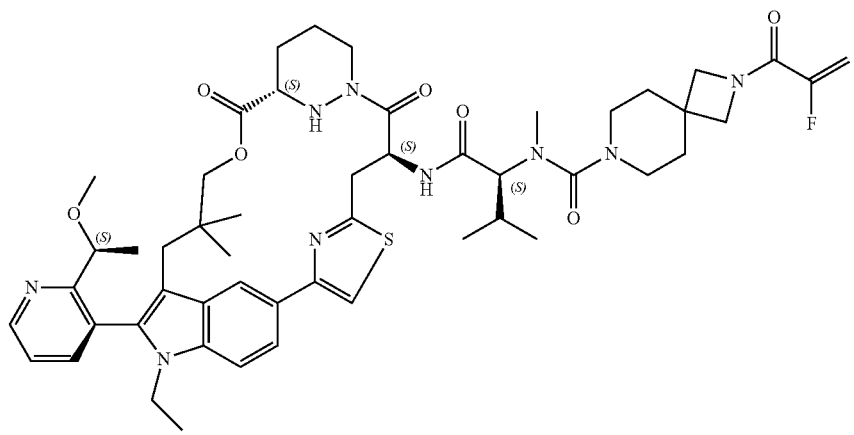 |
| A683 | 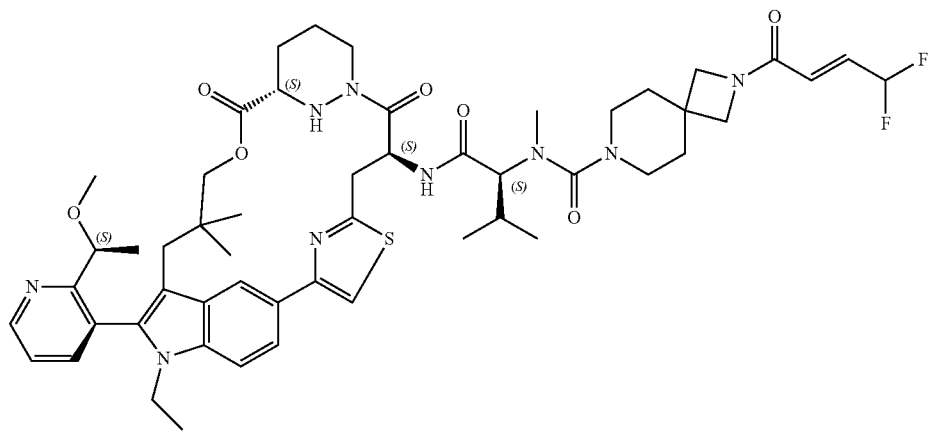 |

TABLE 1-continued
Certain Compounds of the Present Invention
| Ex# | Structure |
|---|---|
| A684 | 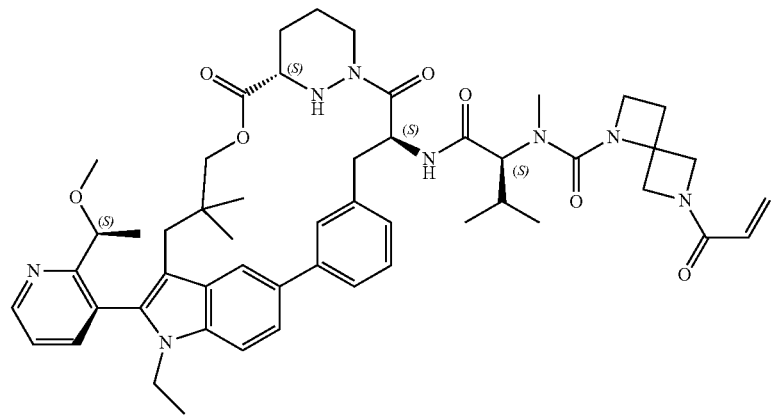 |
| A685 | 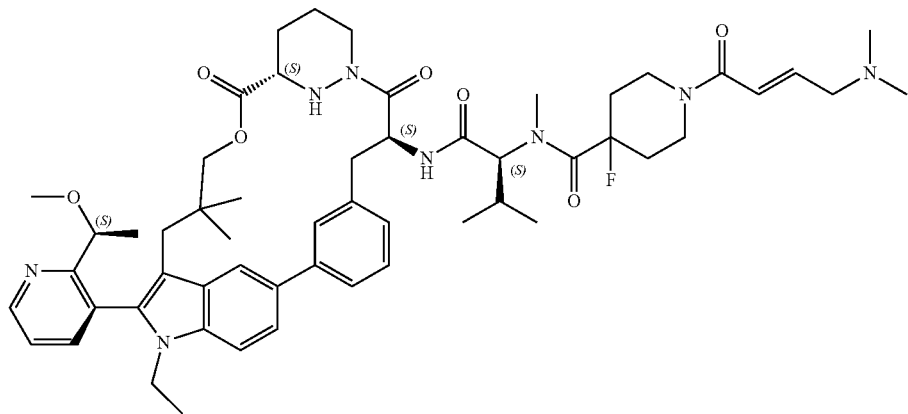 |
| A686 | 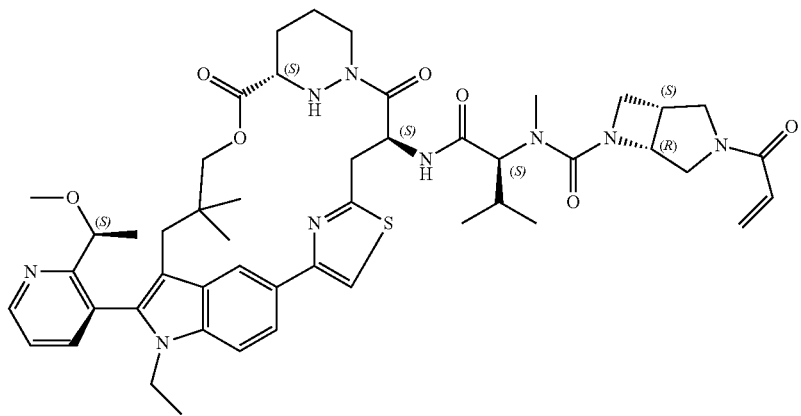 |

TABLE 1-continued
Certain Compounds of the Present Invention
| Ex# | Structure |
|---|---|
| A687 | 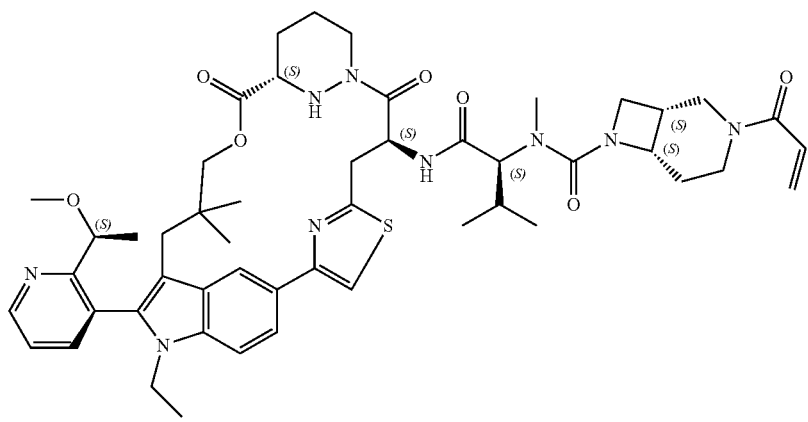 |
| A688 | 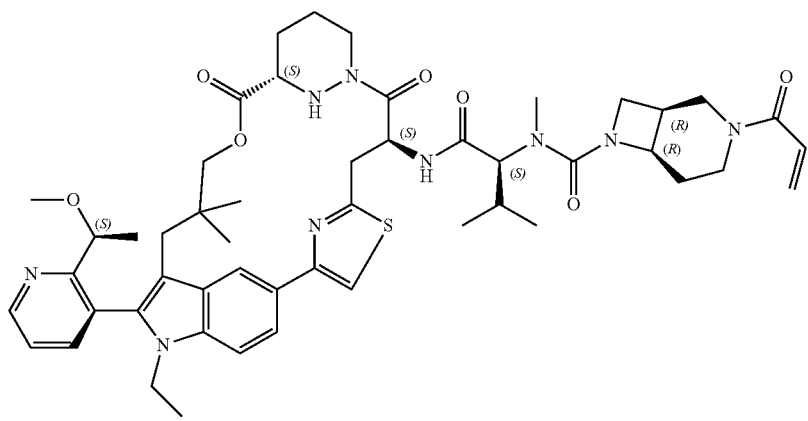 |
| A689 | 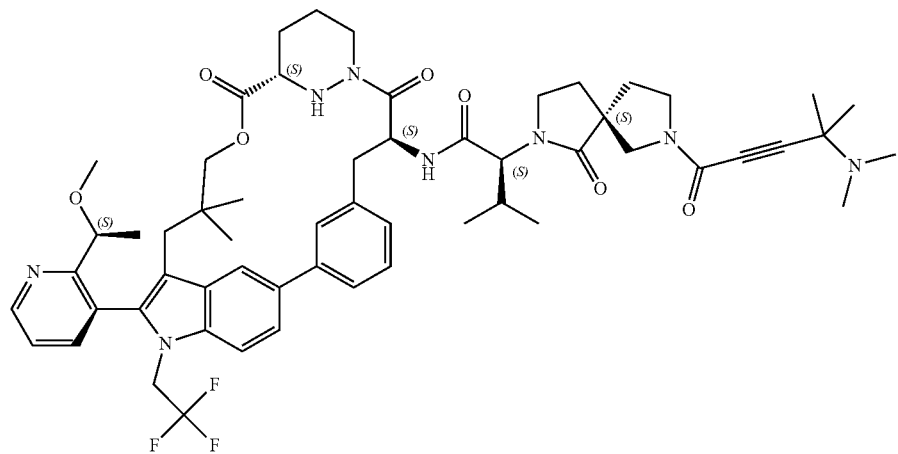 |

TABLE 1-continued
Certain Compounds of the Present Invention
| Ex# | Structure |
|---|---|
| A690 | 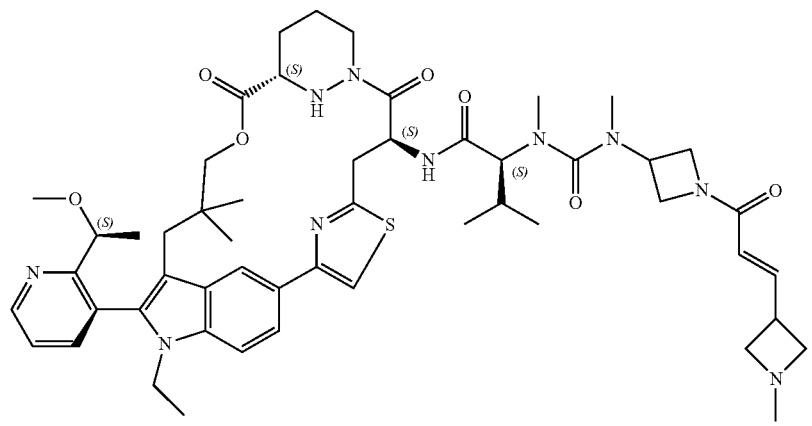 |
| A691 | 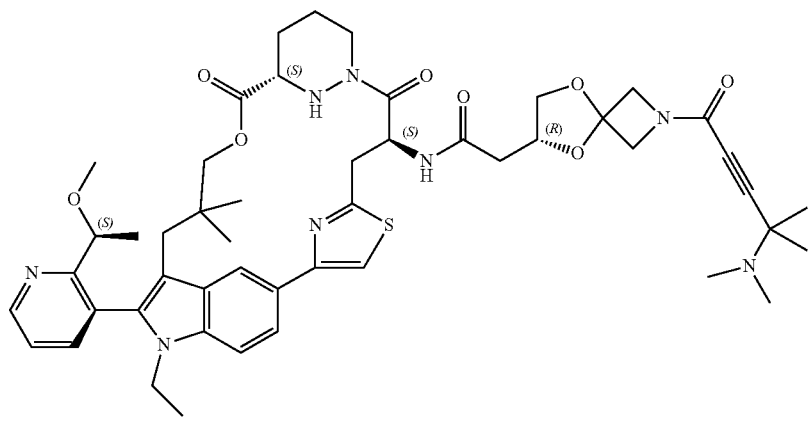 |
| A692 | 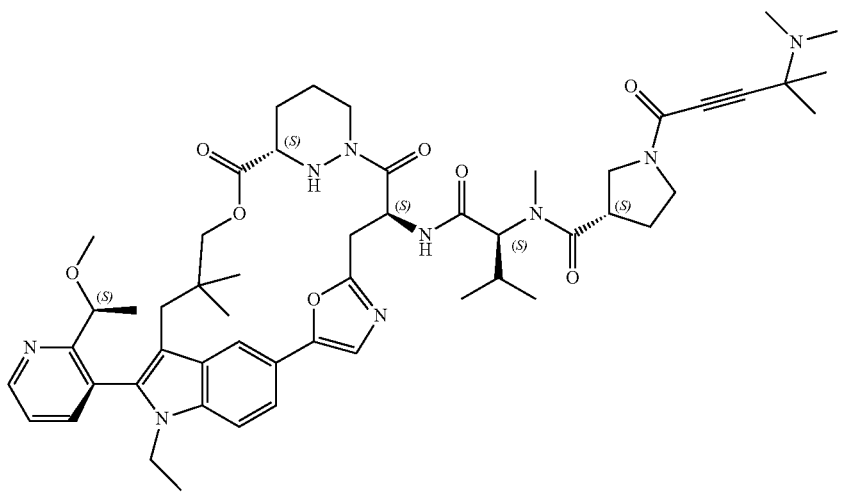 |

TABLE 1-continued
Certain Compounds of the Present Invention
| Ex# | Structure |
|---|---|
| A693 | 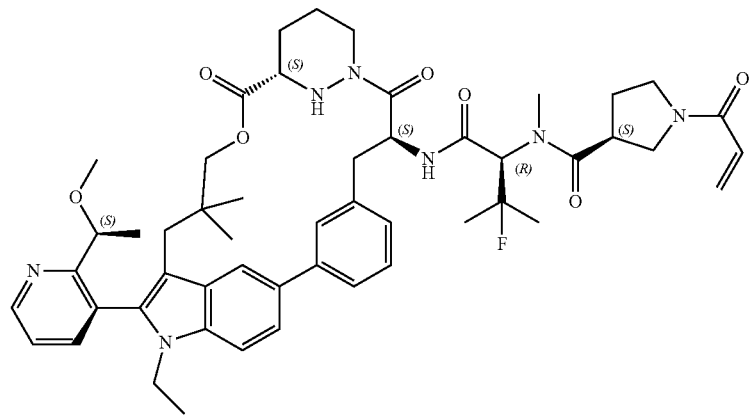 |
| A694 | 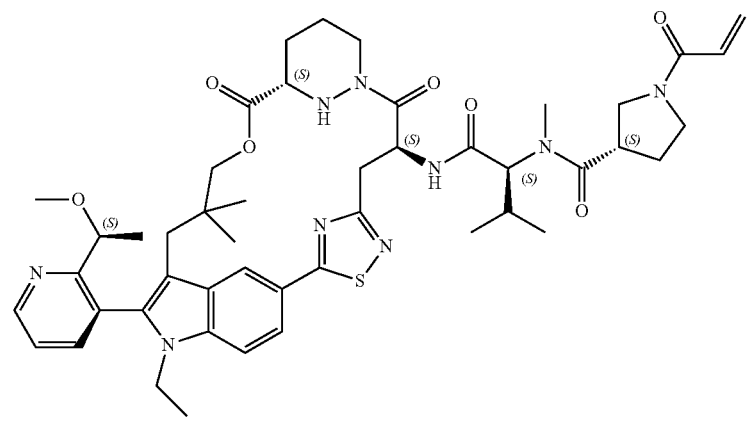 |
| A695 | 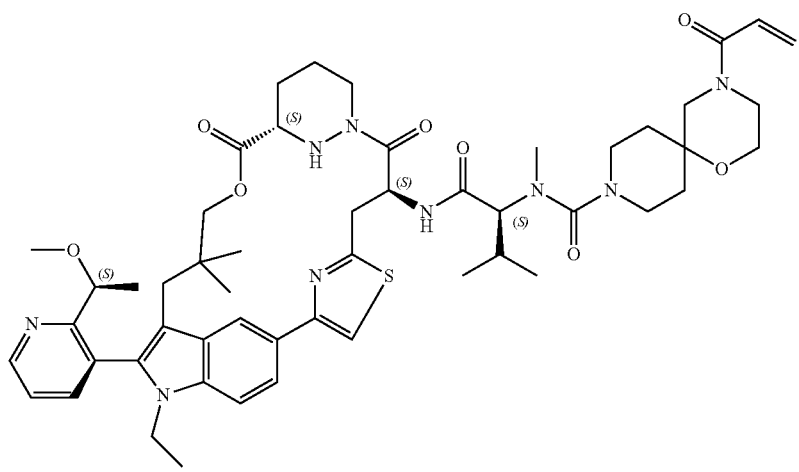 |

TABLE 1-continued
Certain Compounds of the Present Invention
| Ex# | Structure |
|---|---|
| A696 | 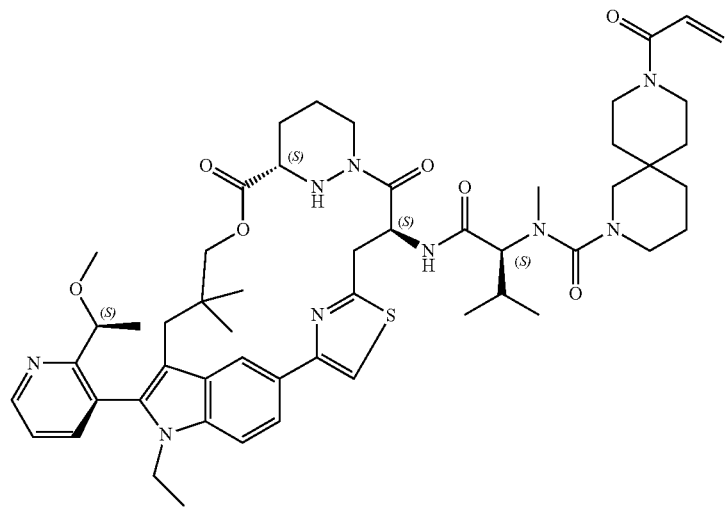 |
| A697 | 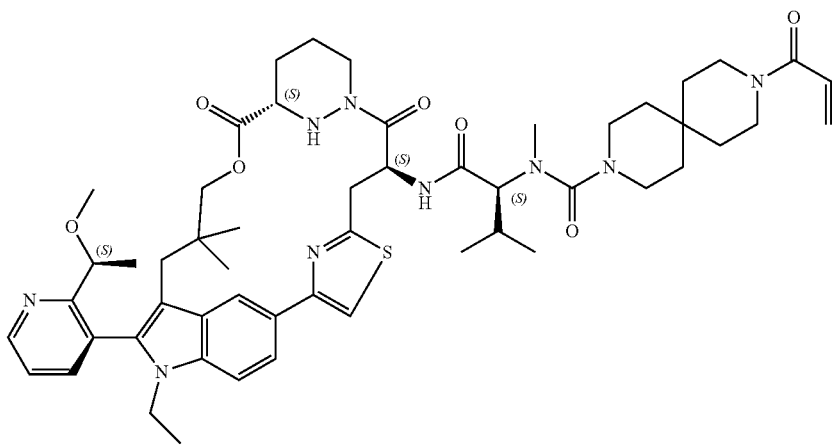 |
| A698 | 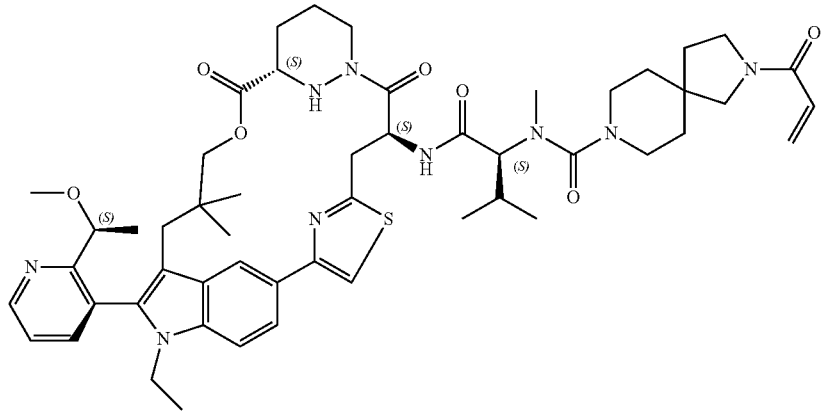 |

TABLE 1-continued
Certain Compounds of the Present Invention
| Ex# | Structure |
|---|---|
| A699 | 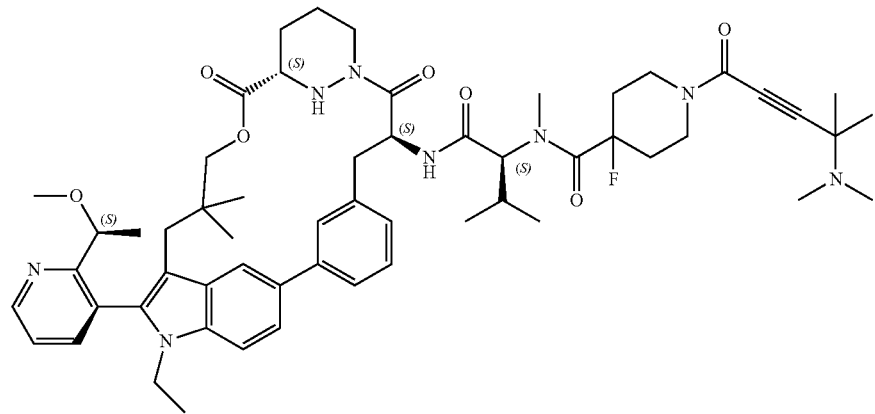 |
| A700 | 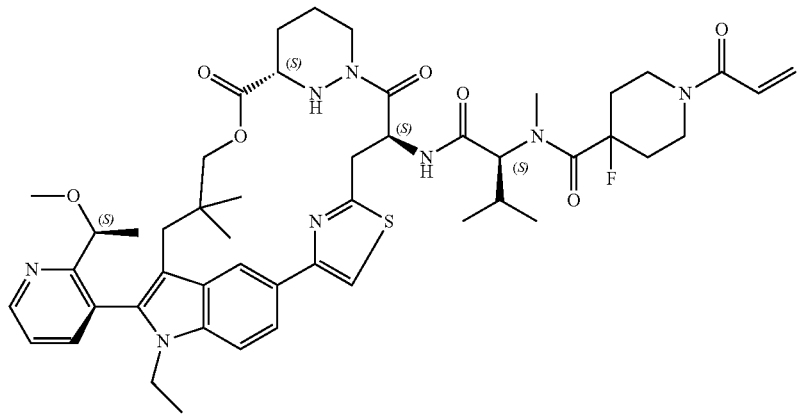 |
| A701 | 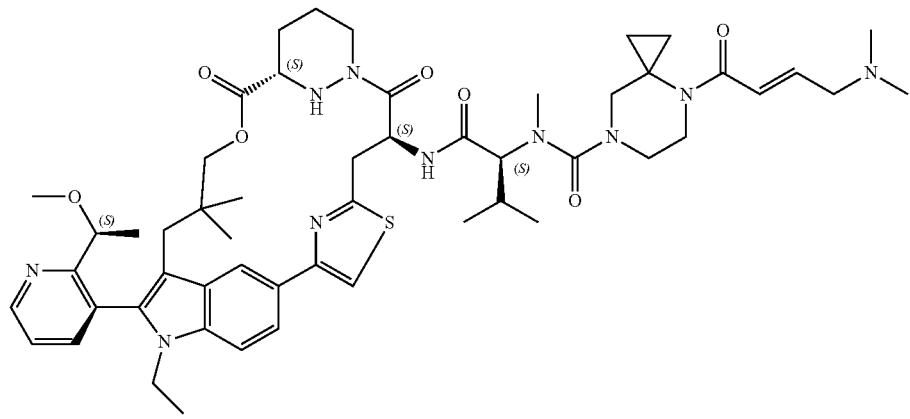 |

TABLE 1-continued
Certain Compounds of the Present Invention
| Ex# | Structure |
|---|---|
| A702 | 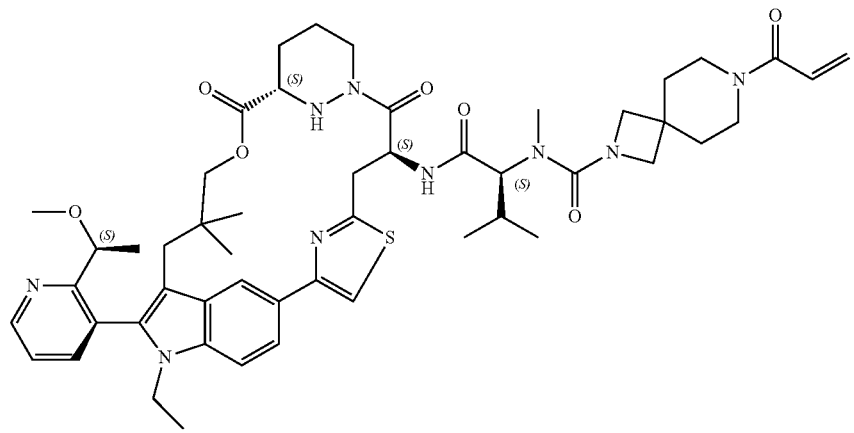 |
| A703 | 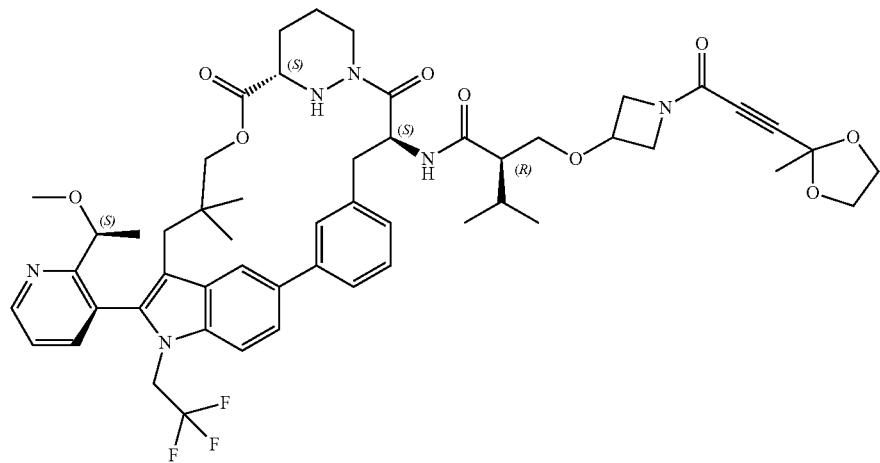 |
| A704 | 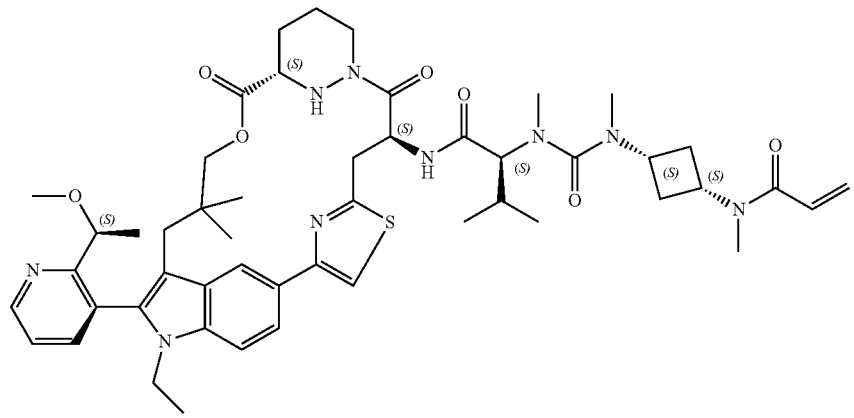 |

TABLE 1-continued
Certain Compounds of the Present Invention
| Ex# | Structure |
|---|---|
| A705 | 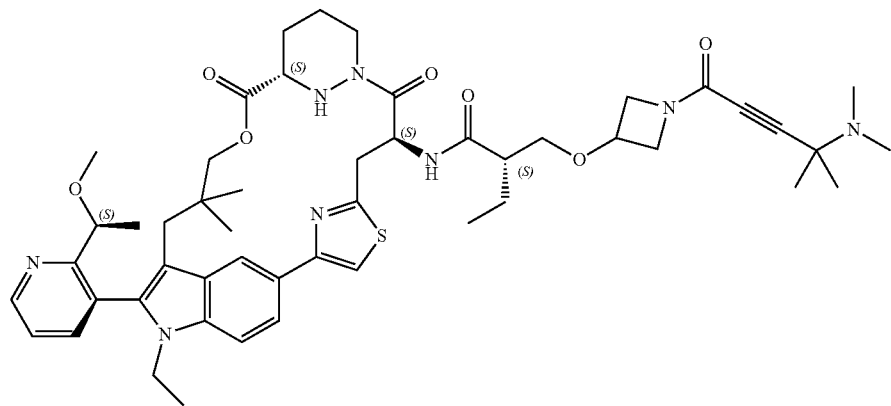 |
| A706 | 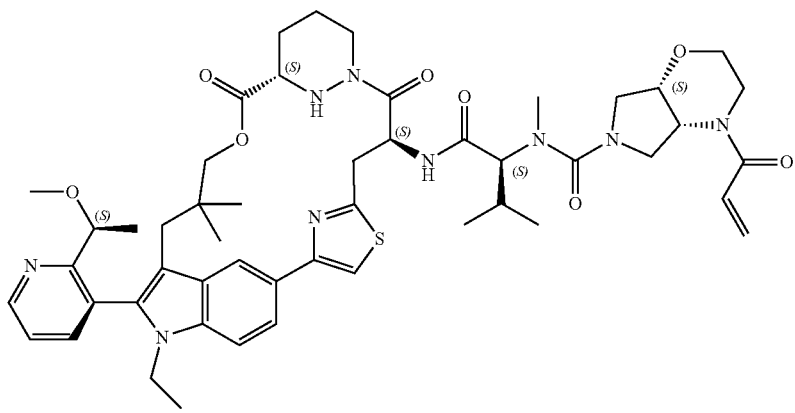 |
| A707 | 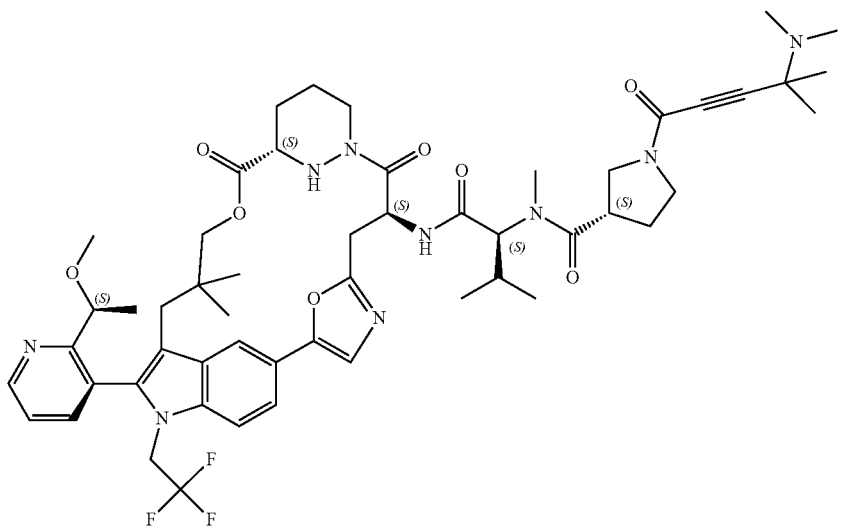 |

TABLE 1-continued
Certain Compounds of the Present Invention
| Ex# | Structure |
|---|---|
| A708 | 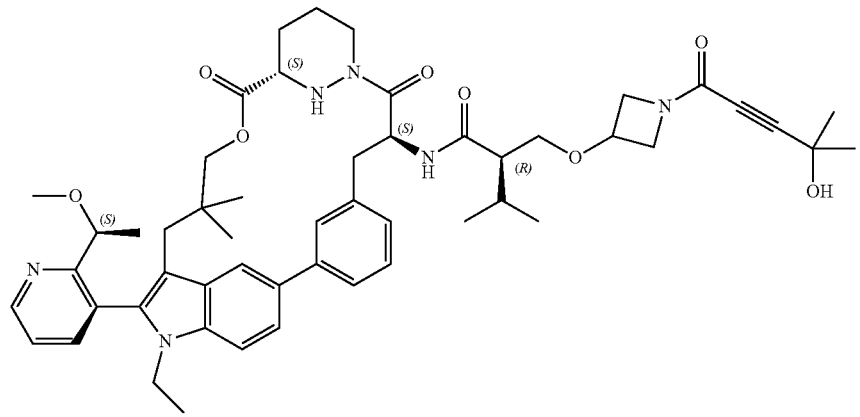 |
| A709 | 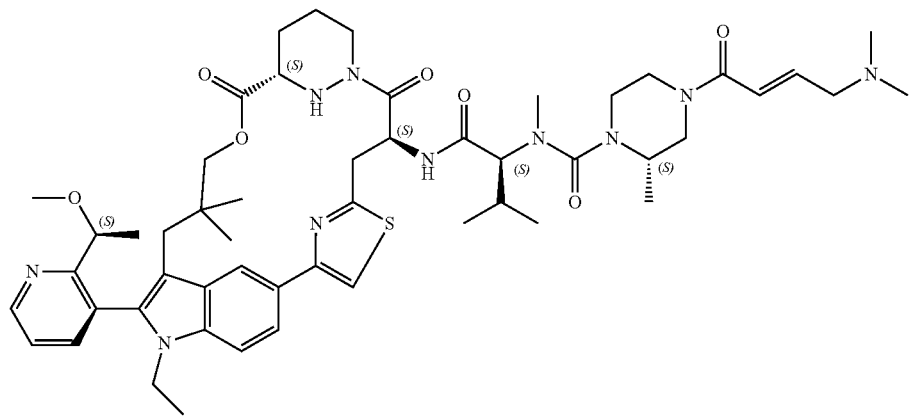 |
| A710 | 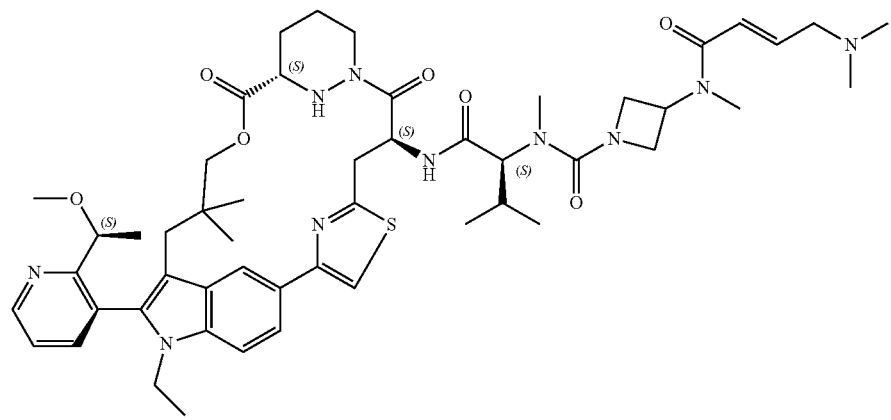 |

TABLE 1-continued
Certain Compounds of the Present Invention
| Ex# | Structure |
|---|---|
| A711 | 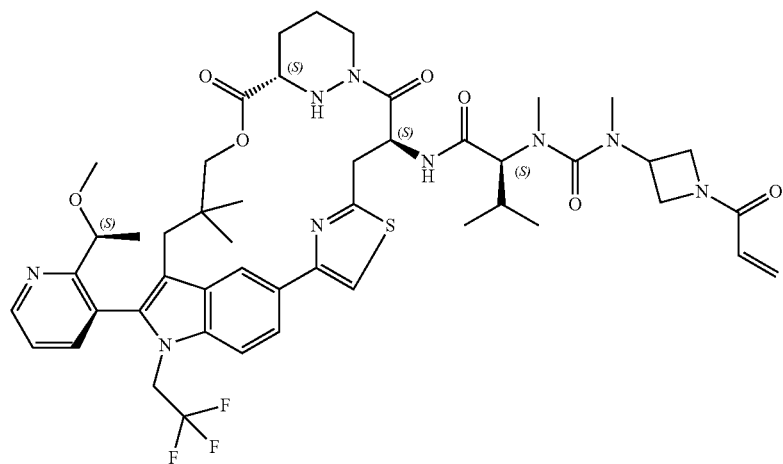 |
| A712 | 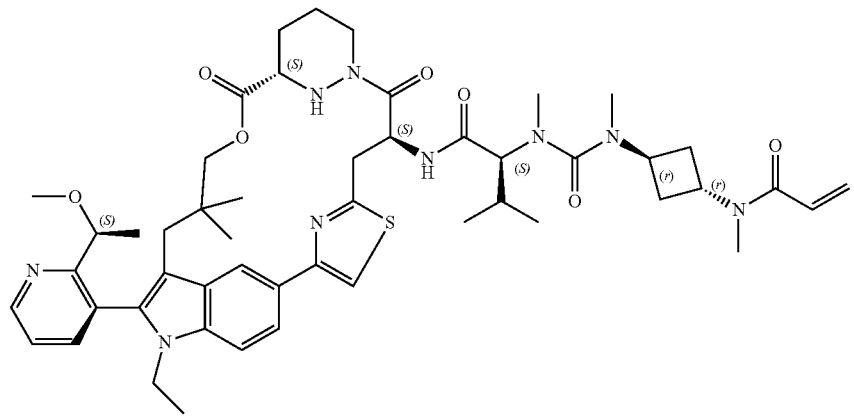 |
| A713 | 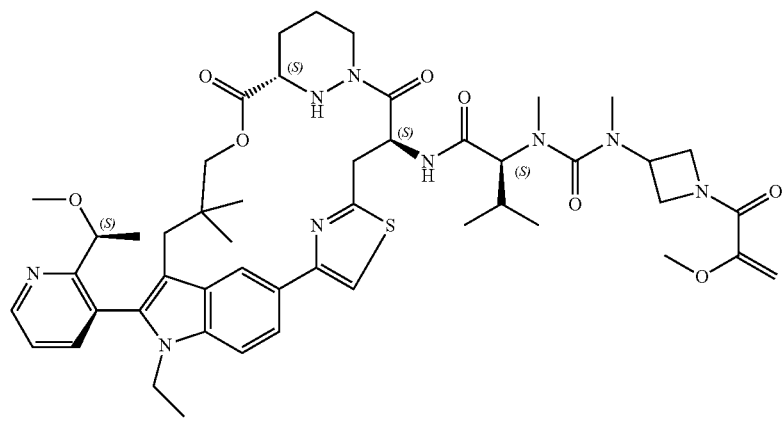 |

TABLE 1-continued

Certain Compounds of the Present Invention

| Ex# | Structure |
|---|---|
| A714 | 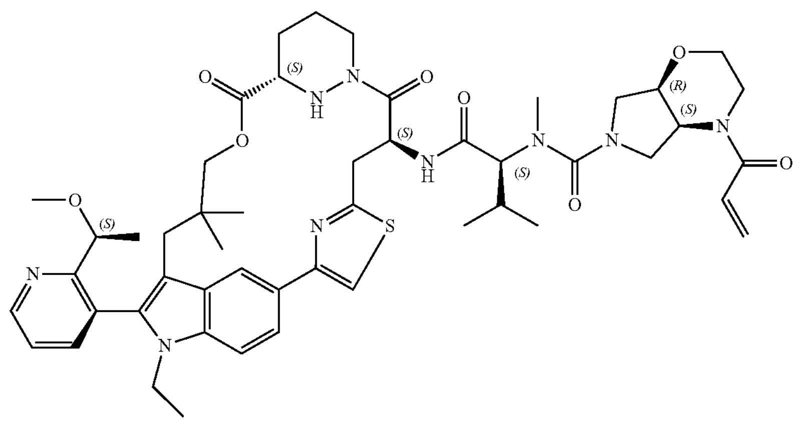 |
| A715 | 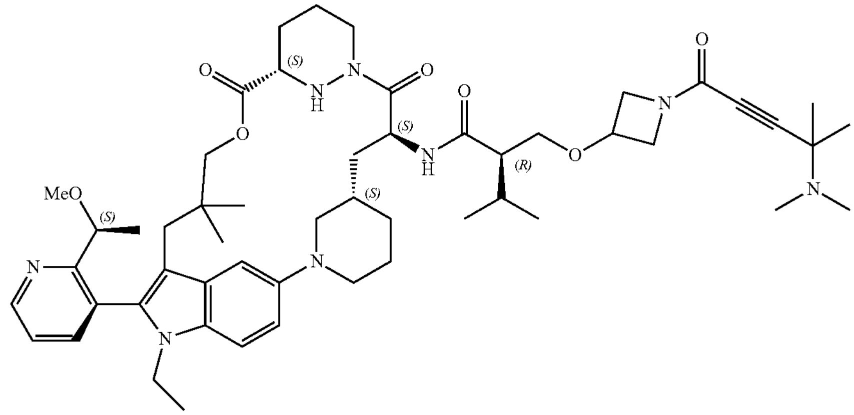 |
| A716 | 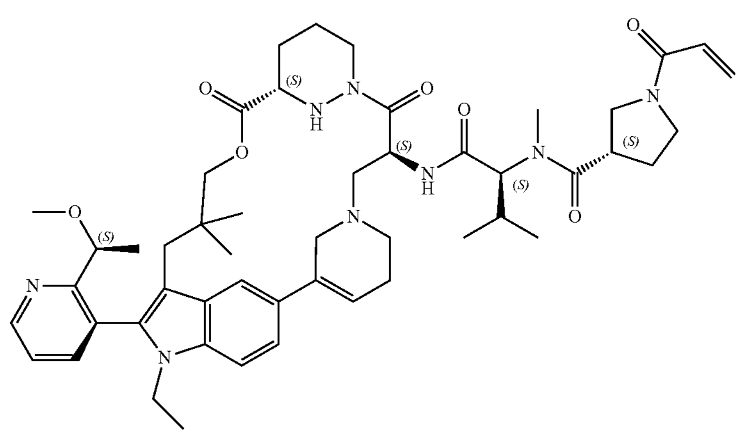 |

TABLE 1-continued

Certain Compounds of the Present Invention

| Ex# | Structure |
|---|---|
| A717 | 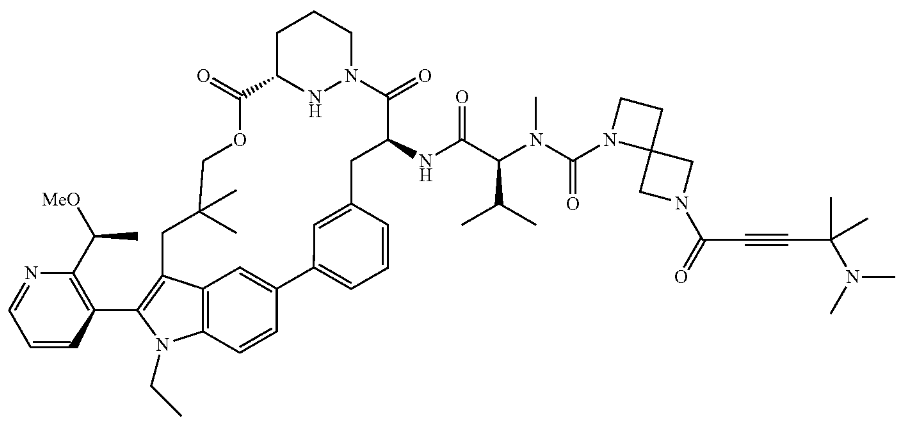 |
| A718 | 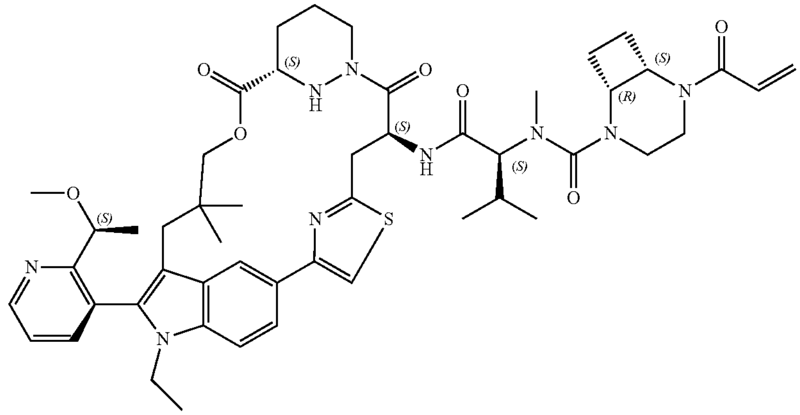 |
| A719 | 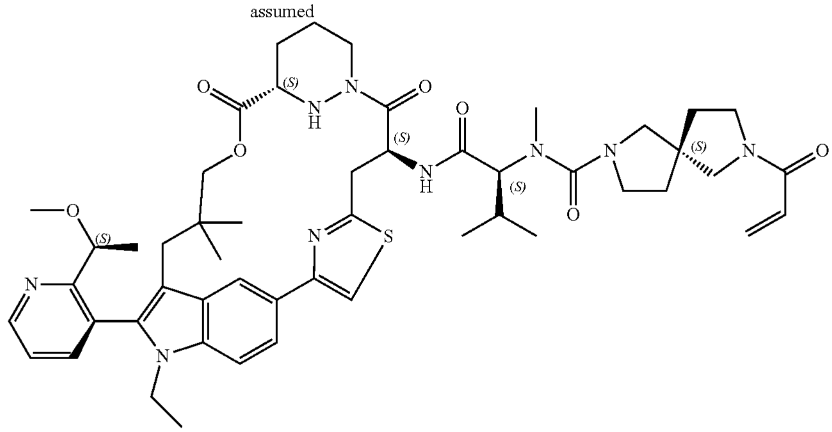 |

TABLE 1-continued

Certain Compounds of the Present Invention

| Ex# | Structure |
|---|---|
| A720 | 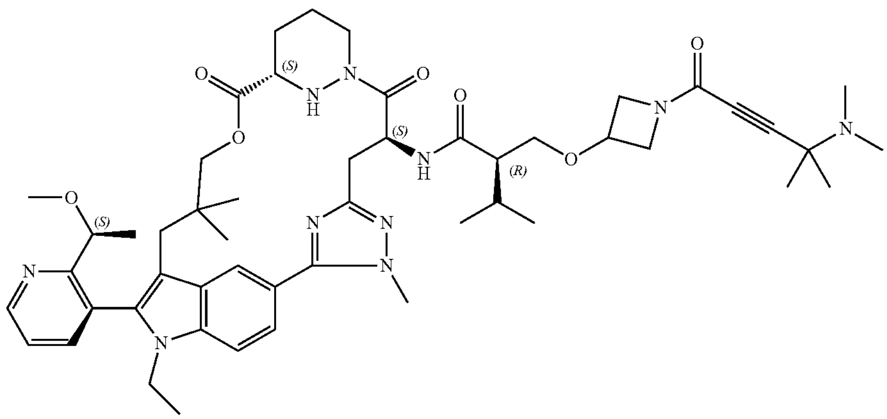 |
| A721 | 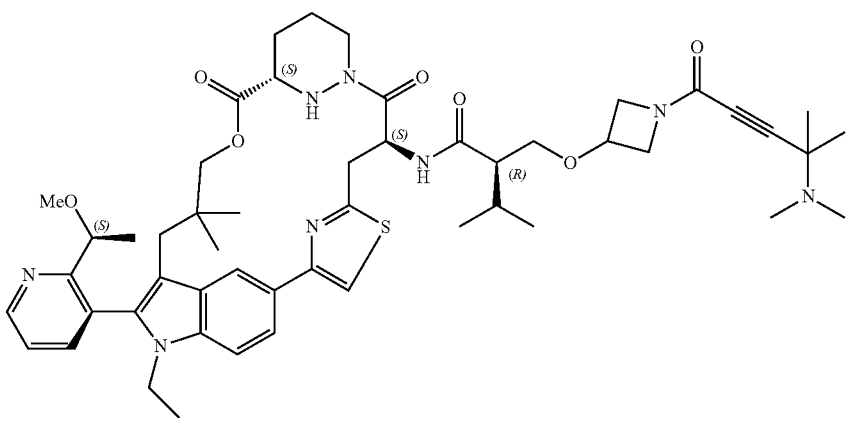 |
| A722 | 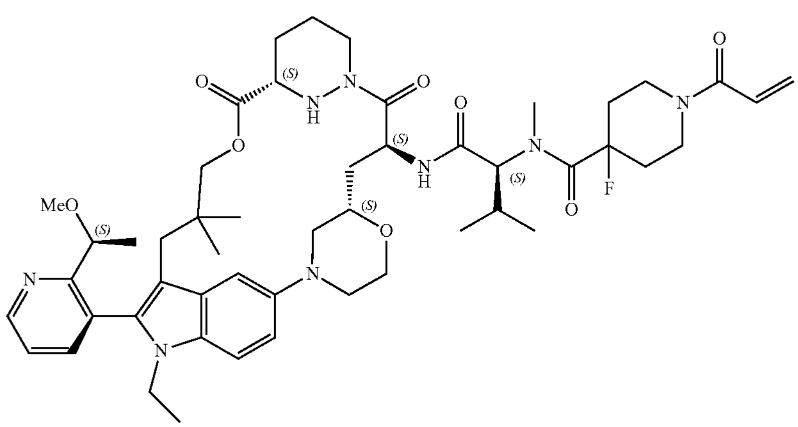 |

TABLE 1-continued
Certain Compounds of the Present Invention
| Ex# | Structure |
|---|---|
| A723 | 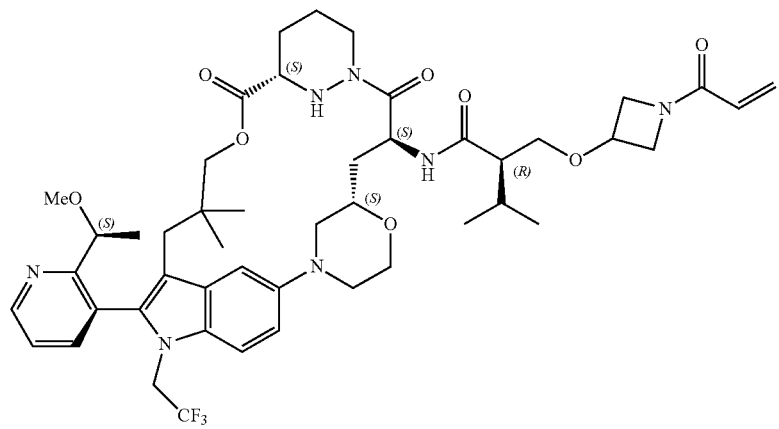 |
| A724 | 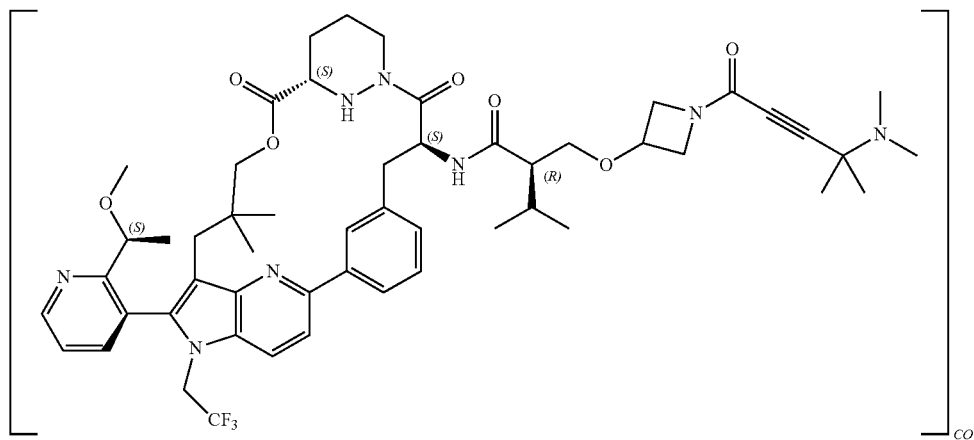 |
| A725 | 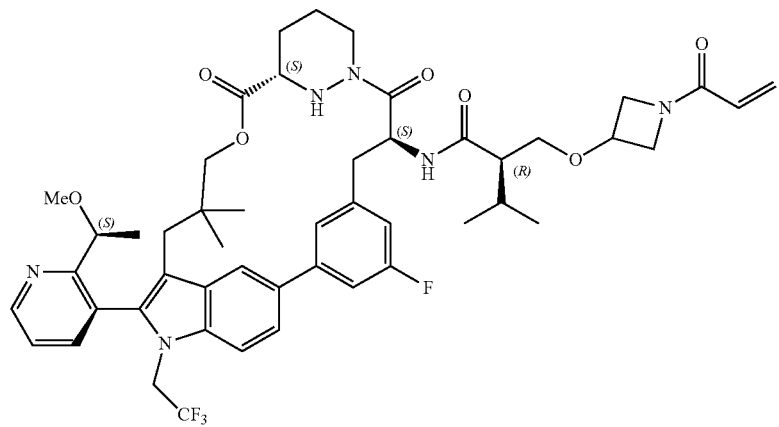 |

TABLE 1-continued
Certain Compounds of the Present Invention
| Ex# | Structure |
|---|---|
| A726 | 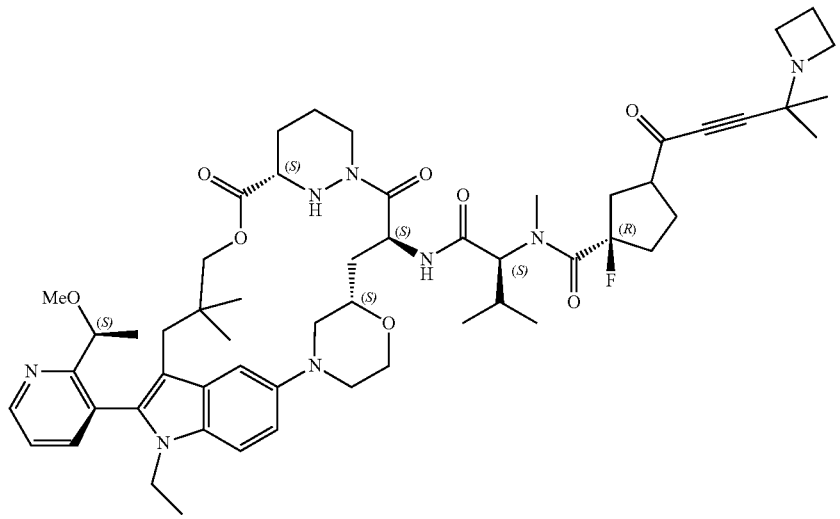 |
| A727 | 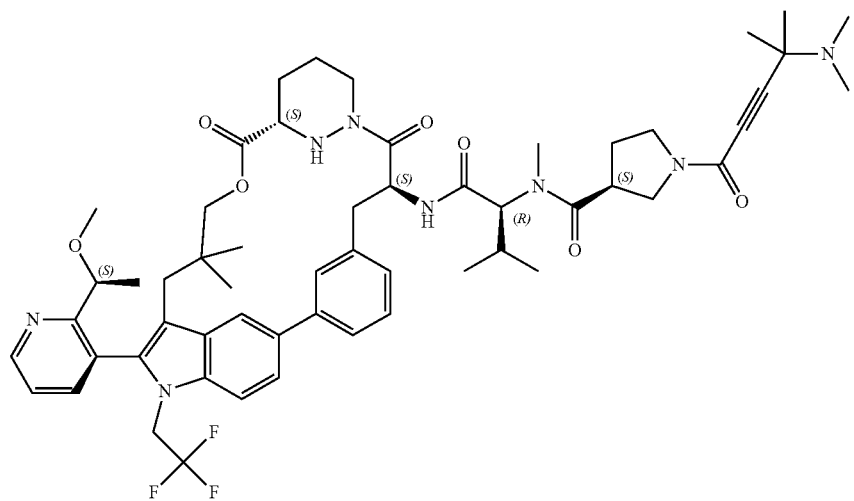 |
| A728 | 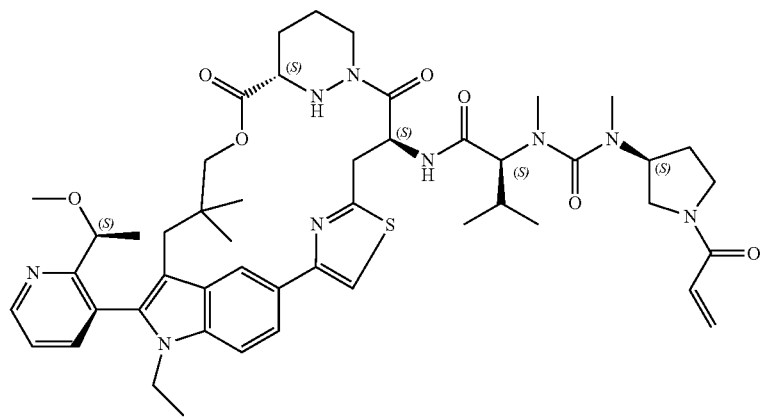 |

US 11,952,352 B2
553                                                                                                       554
TABLE 1-continued
Certain Compounds of the Present Invention
| Ex# | Structure |
|---|---|
| A729 | 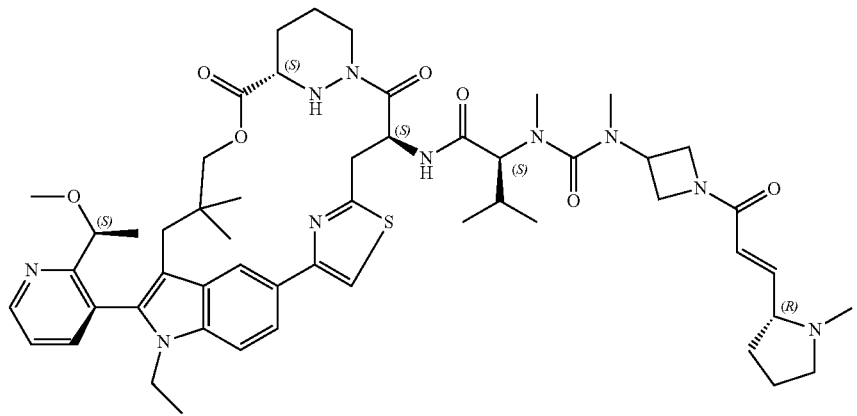 |
| A730 | 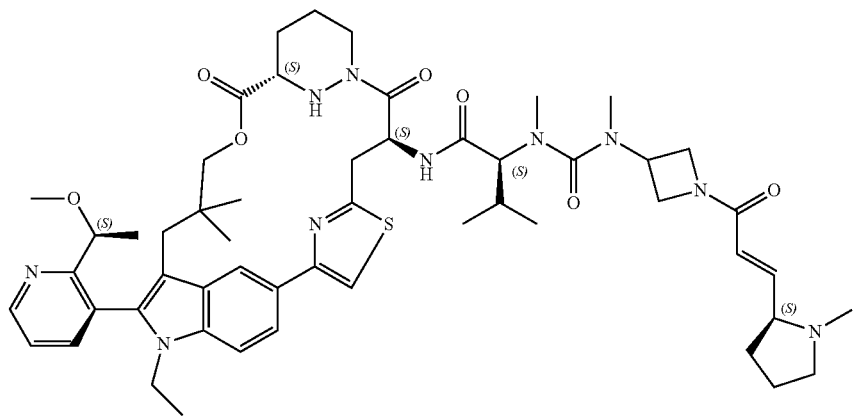 |
| A731 | 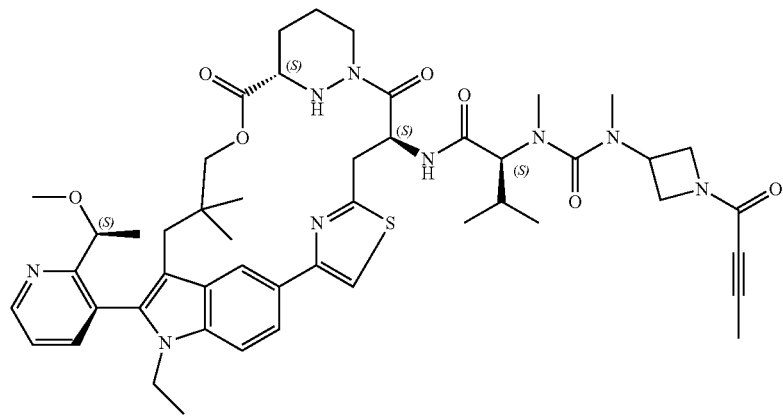 |

TABLE 1-continued

Certain Compounds of the Present Invention

| Ex# | Structure |
|---|---|
| A732 | 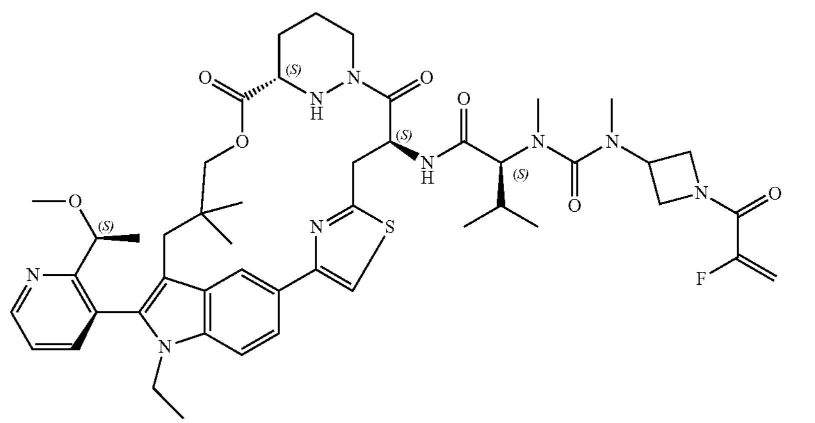 |
| A733 | 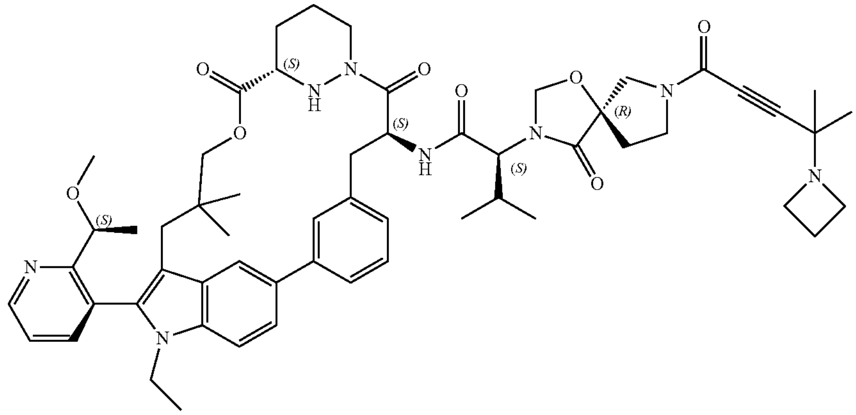 |
| A734 | 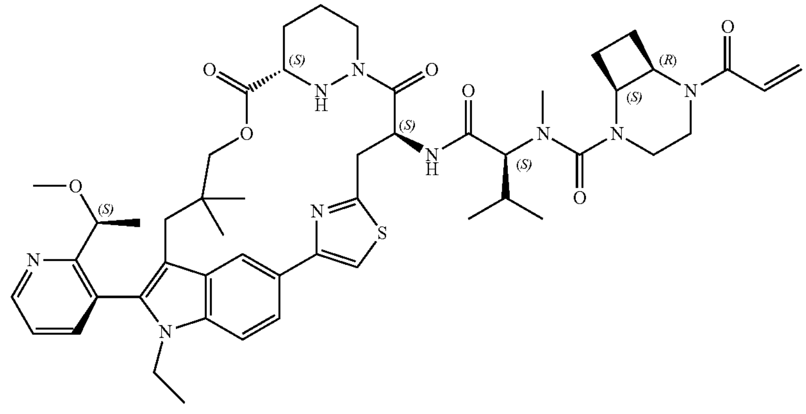 |

TABLE 1-continued
Certain Compounds of the Present Invention
| Ex# | Structure |
|---|---|
| A735 | 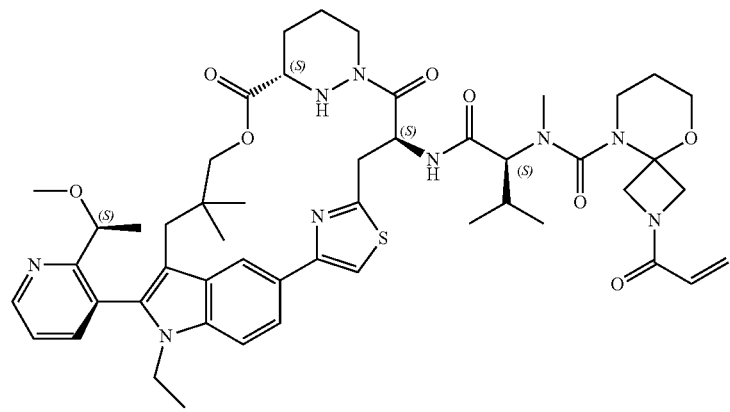 |
| A736 | 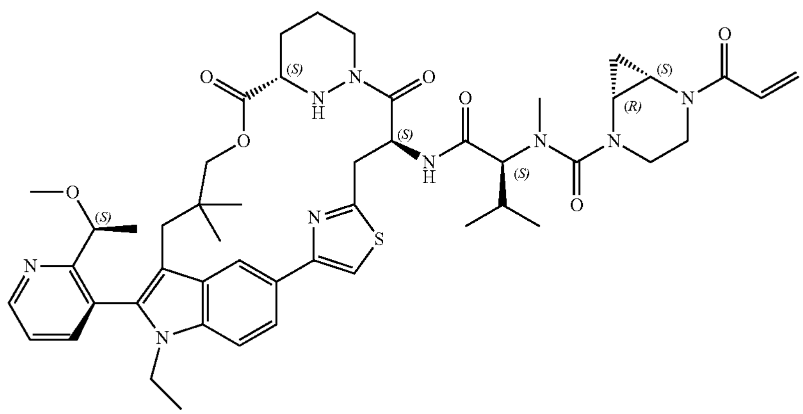 |
| A737 | 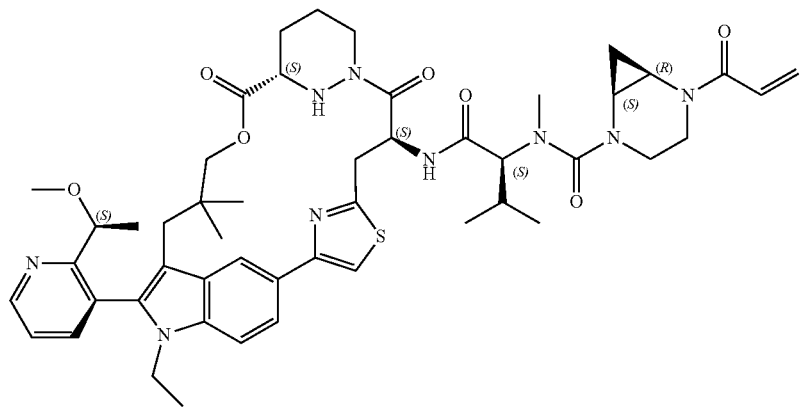 |

TABLE 1-continued
Certain Compounds of the Present Invention
| Ex# | Structure |
|---|---|
| A738 | 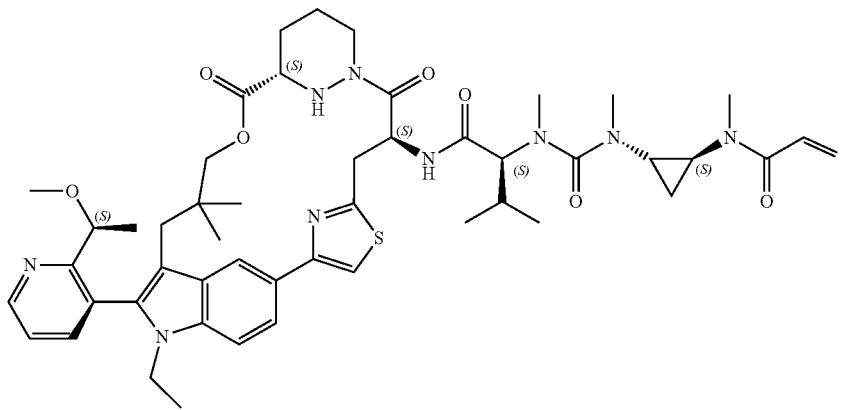 |
| A739 | 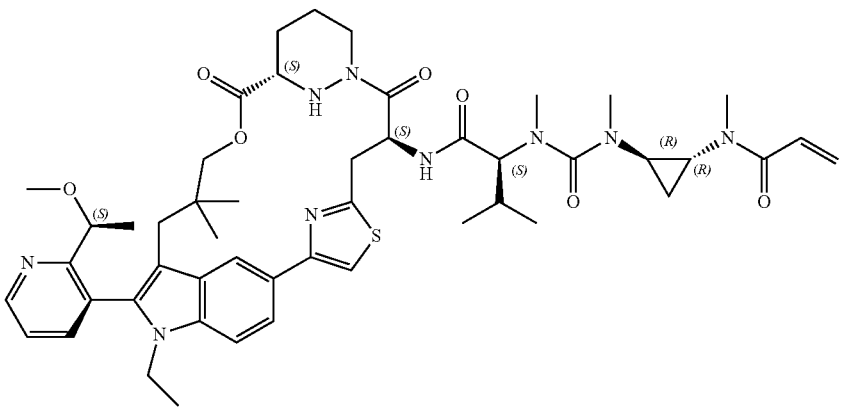 |
| A740 | 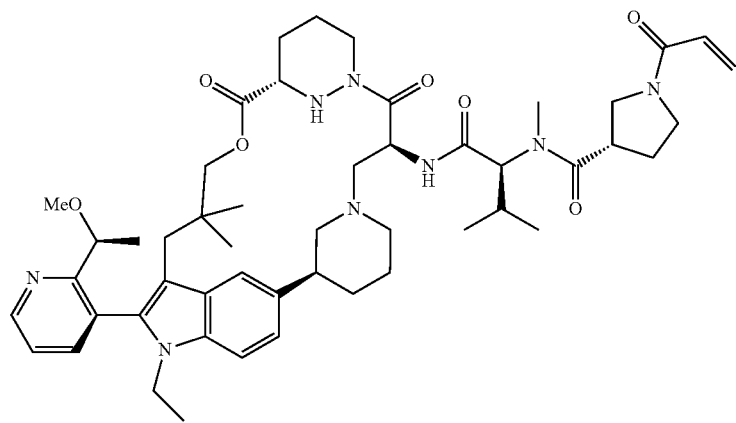 |

TABLE 1-continued

Certain Compounds of the Present Invention

| Ex# | Structure |
|---|---|
| A741 | 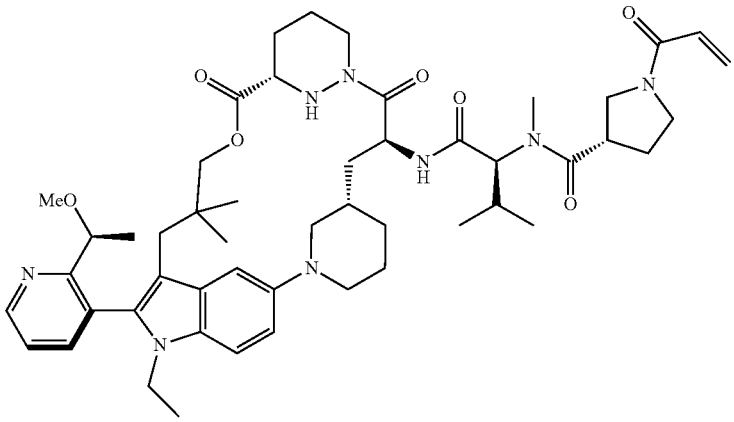 |

Note
that some compounds are shown with bonds as flat or wedged. In some instances, the relative stereochemistry of stereoisomers has been determined; in some instances, the absolute stereochemistry has been determined. In some instances, a single Example number corresponds to a mixture of stereoisomers. All stereoisomers of the compounds of the foregoing table are contemplated by the present invention. In particular embodiments, an atropisomer of a compound of the foregoing table is contemplated.
Brackets are to be ignored.
*The activity of this stereoisomer may, in fact, be attributable to the presence of a small amount of the stereoisomer with the (S) configuration at the —NC(O)—C̲H(CH$_3$)$_2$—N(CH$_3$)— position.

In some embodiments, a compound of Table 2 is provided, or a pharmaceutically acceptable salt thereof. In some embodiments, a compound of the present invention is selected from Table 2, or a pharmaceutically acceptable salt or atropisomer thereof.

TABLE 2

Certain Compounds of the Present Invention

| Ex # | Structure |
|---|---|
| B1 | 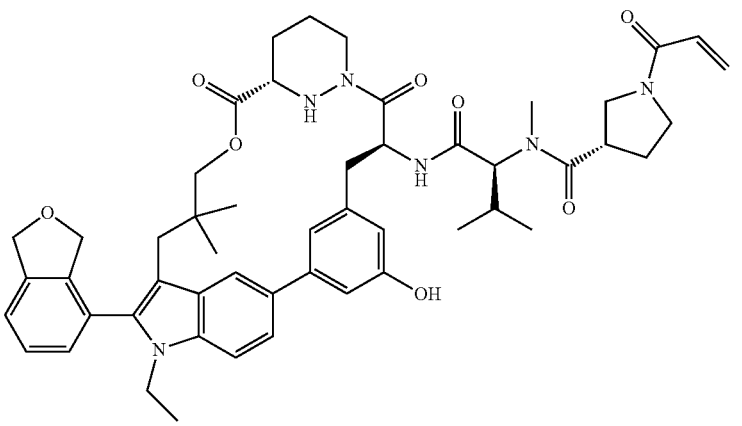 [SMILES: C=CC(=O)N1CC[C@H](C(=O)N(C)[C@H](C(=O)N[C@H]2Cc3cc(O)cc(c3)-c3ccc4c(c3)c(c(-c3cccc5c3COC5)n4CC)CC(C)(C)COC(=O)[C@@H]3CCCN(N3)C2=O)C(C)C)C1] |

TABLE 2-continued
Certain Compounds of the Present Invention
| Ex # | Structure |
|---|---|
| B2 | 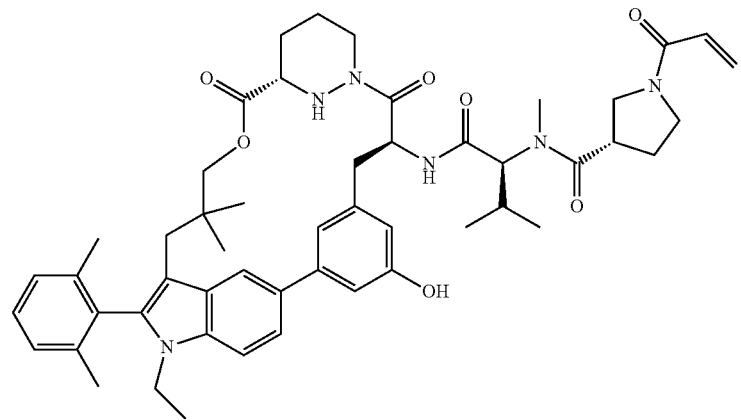 [SMILES: C=CC(=O)N1CC[C@H](C(=O)N(C)[C@H](C(=O)N[C@H]2Cc3cc(O)cc(c3)-c3ccc4c(c3)c(c(-c3c(C)cccc3C)n4CC)CC(C)(C)COC(=O)[C@@H]3CCCN(N3)C2=O)C(C)C)C1] |
| B3 | 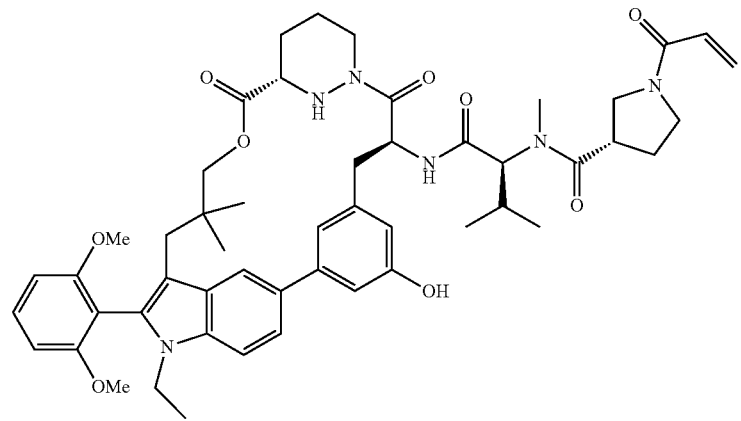 [SMILES: C=CC(=O)N1CC[C@H](C(=O)N(C)[C@H](C(=O)N[C@H]2Cc3cc(O)cc(c3)-c3ccc4c(c3)c(c(-c3c(OC)cccc3OC)n4CC)CC(C)(C)COC(=O)[C@@H]3CCCN(N3)C2=O)C(C)C)C1] |
| B4 | 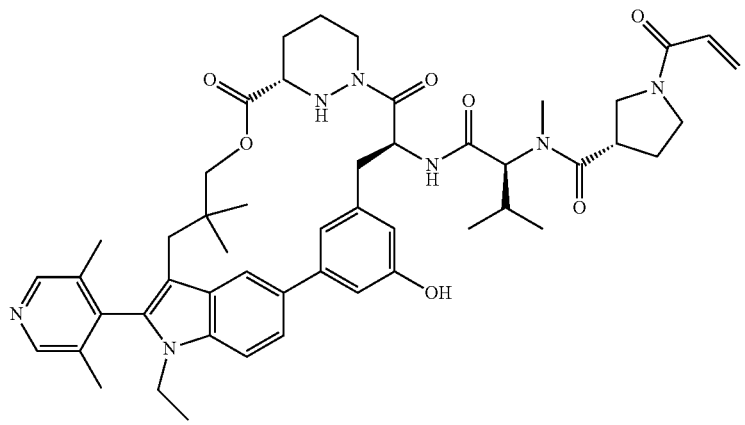 [SMILES: C=CC(=O)N1CC[C@H](C(=O)N(C)[C@H](C(=O)N[C@H]2Cc3cc(O)cc(c3)-c3ccc4c(c3)c(c(-c3c(C)cncc3C)n4CC)CC(C)(C)COC(=O)[C@@H]3CCCN(N3)C2=O)C(C)C)C1] |

TABLE 2-continued

Certain Compounds of the Present Invention

| Ex # | Structure |
|---|---|
| B5 | 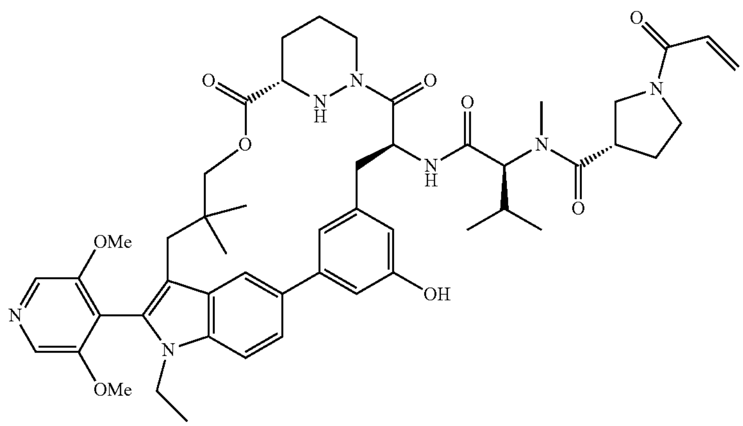 [SMILES: C=CC(=O)N1CC[C@H](C(=O)N(C)[C@H](C(=O)N[C@H]2Cc3cc(O)cc(c3)-c3ccc4c(c3)c(c(-c3c(OC)cncc3OC)n4CC)CC(C)(C)COC(=O)[C@@H]3CCCN(N3)C2=O)C(C)C)C1] |
| B6 | 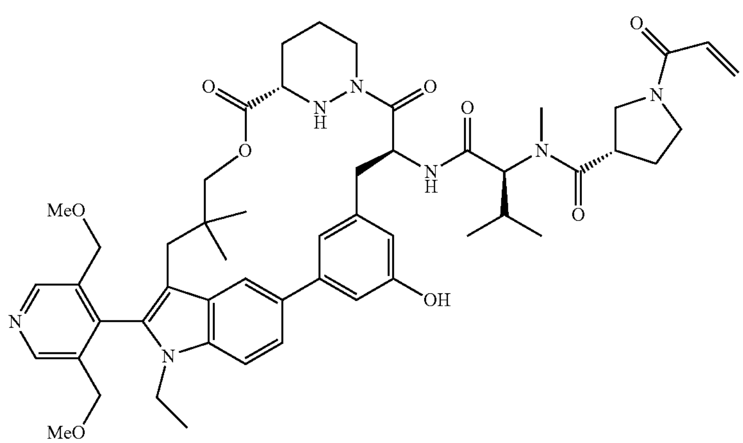 [SMILES: C=CC(=O)N1CC[C@H](C(=O)N(C)[C@H](C(=O)N[C@H]2Cc3cc(O)cc(c3)-c3ccc4c(c3)c(c(-c3c(COC)cncc3COC)n4CC)CC(C)(C)COC(=O)[C@@H]3CCCN(N3)C2=O)C(C)C)C1] |
| B7 | 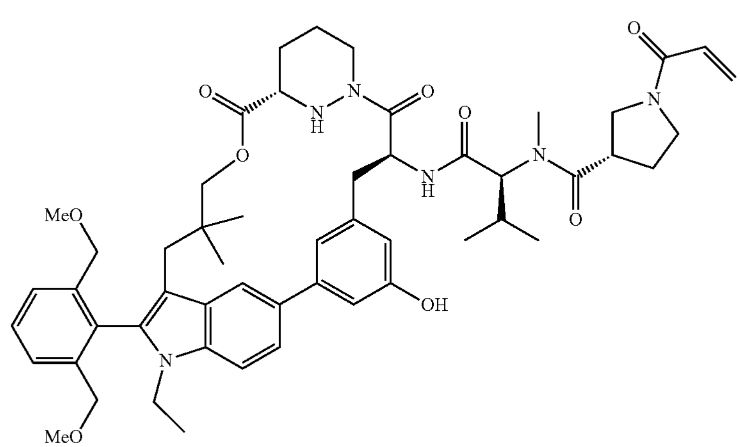 [SMILES: C=CC(=O)N1CC[C@H](C(=O)N(C)[C@H](C(=O)N[C@H]2Cc3cc(O)cc(c3)-c3ccc4c(c3)c(c(-c3c(COC)cccc3COC)n4CC)CC(C)(C)COC(=O)[C@@H]3CCCN(N3)C2=O)C(C)C)C1] |

TABLE 2-continued

Certain Compounds of the Present Invention

| Ex # | Structure |
|---|---|
| B11 | 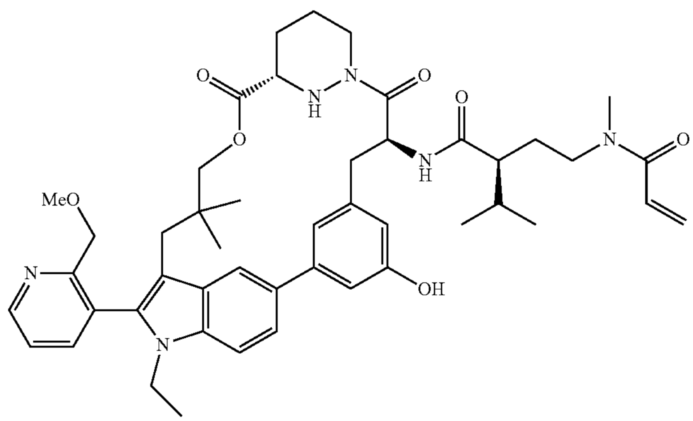 [SMILES: C=CC(=O)N(C)CC[C@H](C(=O)N[C@H]1Cc2cc(O)cc(c2)-c2ccc3c(c2)c(c(-c2cccnc2COC)n3CC)CC(C)(C)COC(=O)[C@@H]2CCCN(N2)C1=O)C(C)C] |
| B12 | 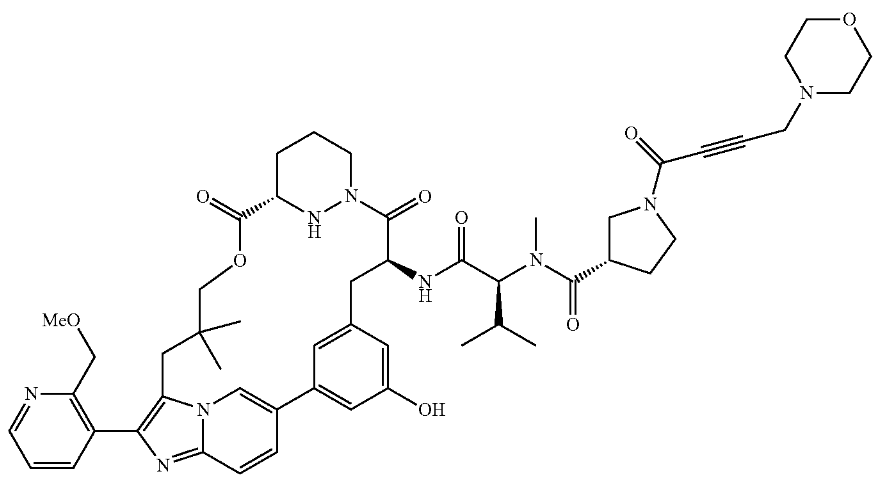 [SMILES: COCc1ncccc1-c1nc2ccc3cn2c1CC(C)(C)COC(=O)[C@@H]1CCCN(N1)C(=O)[C@@H](NC(=O)[C@H](C(C)C)N(C)C(=O)[C@H]1CCN(C(=O)C#CCN2CCOCC2)C1)Cc1cc(O)cc-3c1] |
| B13 | 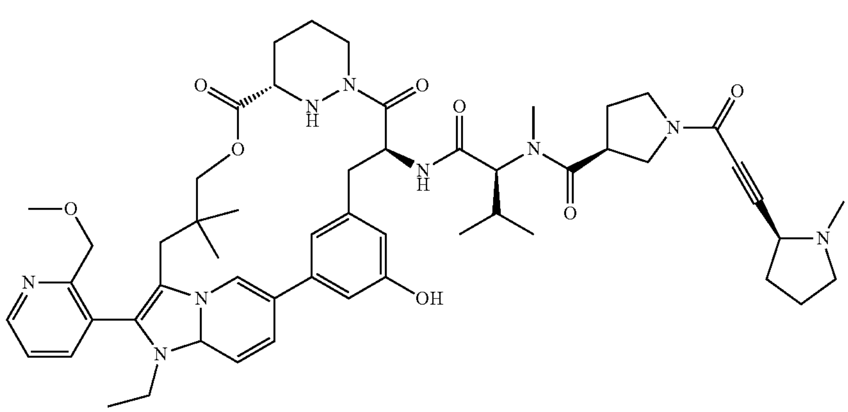 [SMILES: CCN1C(c2cccnc2COC)=C2CC(C)(C)COC(=O)[C@@H]3CCCN(N3)C(=O)[C@@H](NC(=O)[C@H](C(C)C)N(C)C(=O)[C@H]3CCN(C(=O)C#C[C@@H]4CCCN4C)C3)Cc3cc(O)cc(c3)C3=CN2C1C=C3] |

TABLE 2-continued

Certain Compounds of the Present Invention

| Ex # | Structure |
|---|---|
| B18 | 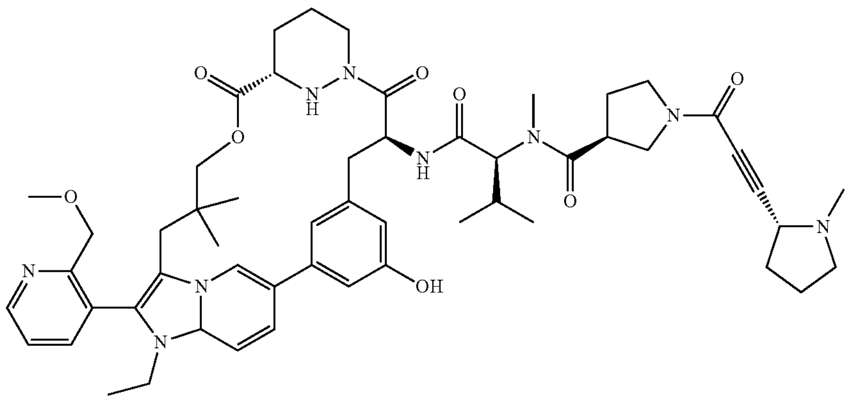 [SMILES: CCN1C(c2cccnc2COC)=C2CC(C)(C)COC(=O)[C@@H]3CCCN(N3)C(=O)[C@@H](NC(=O)[C@H](C(C)C)N(C)C(=O)[C@H]3CCN(C(=O)C#C[C@H]4CCCN4C)C3)Cc3cc(O)cc(c3)C3=CN2C1C=C3] |
| B21 | 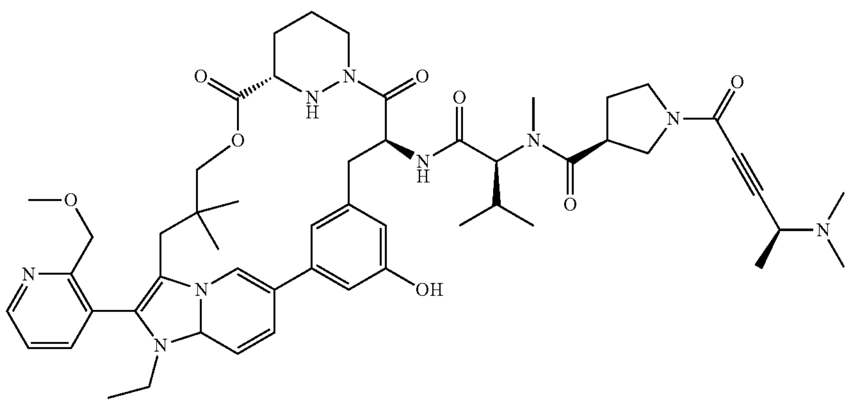 [SMILES: CCN1C(c2cccnc2COC)=C2CC(C)(C)COC(=O)[C@@H]3CCCN(N3)C(=O)[C@@H](NC(=O)[C@H](C(C)C)N(C)C(=O)[C@H]3CCN(C(=O)C#C[C@H](C)N(C)C)C3)Cc3cc(O)cc(c3)C3=CN2C1C=C3] |
| B22 | 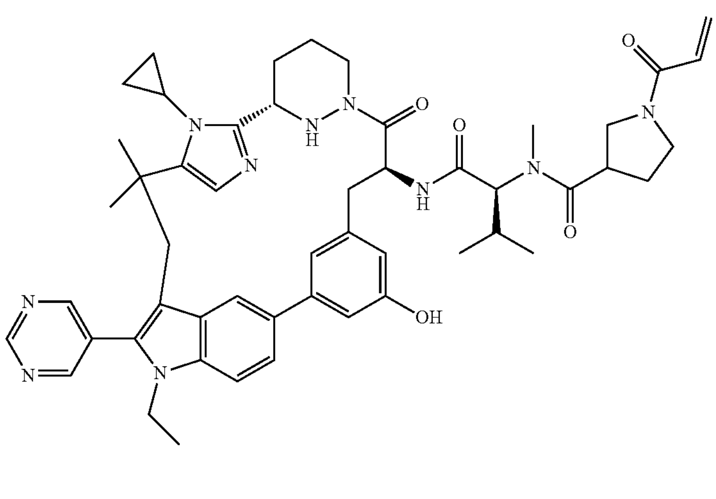 [SMILES: C=CC(=O)N1CCC(C(=O)N(C)[C@H](C(=O)N[C@H]2Cc3cc(O)cc(c3)-c3ccc4c(c3)c(c(-c3cncnc3)n4CC)CC(C)(C)c3cnc(n3C3CC3)[C@@H]3CCCN(N3)C2=O)C(C)C)C1] |

TABLE 2-continued
Certain Compounds of the Present Invention
| Ex # | Structure |
|---|---|
| B25 | 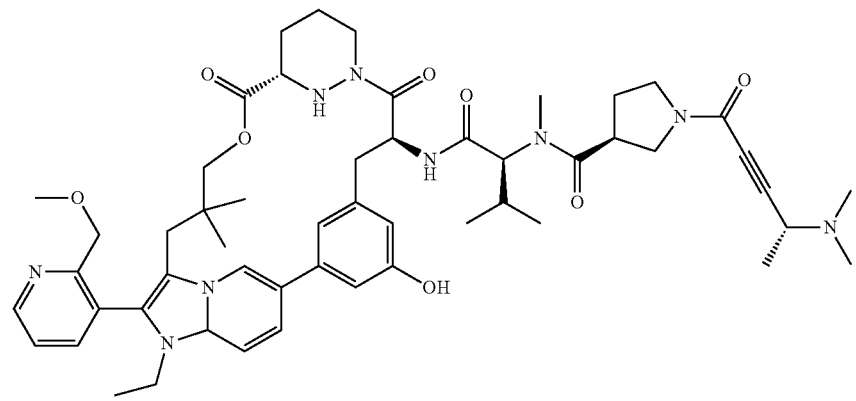 [SMILES: CCN1C(c2cccnc2COC)=C2CC(C)(C)COC(=O)[C@@H]3CCCN(N3)C(=O)[C@@H](NC(=O)[C@H](C(C)C)N(C)C(=O)[C@H]3CCN(C(=O)C#C[C@@H](C)N(C)C)C3)Cc3cc(O)cc(c3)C3=CN2C1C=C3] |
| B27 | 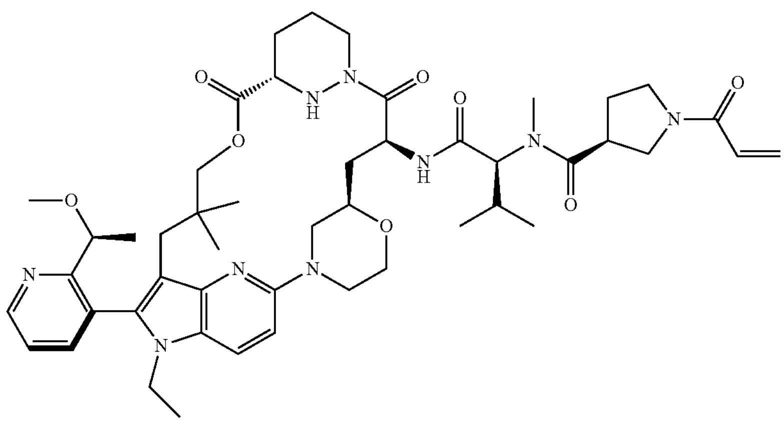 |
| B28 | 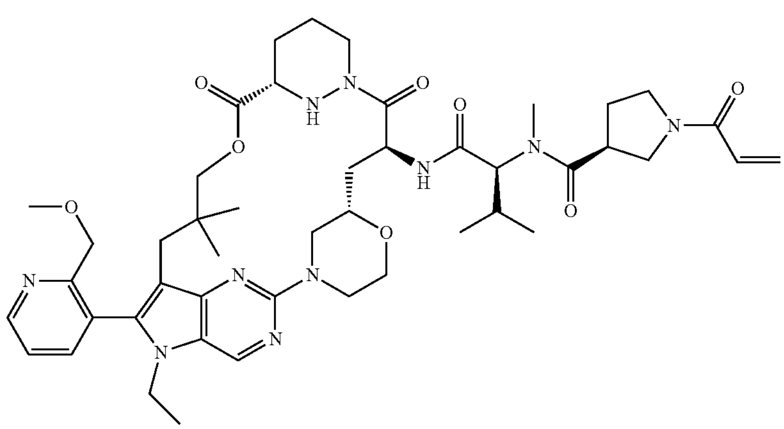 [SMILES: C=CC(=O)N1CC[C@H](C(=O)N(C)[C@H](C(=O)N[C@H]2C[C@H]3CN(CCO3)c3ncc4c(n3)c(c(-c3cccnc3COC)n4CC)CC(C)(C)COC(=O)[C@@H]3CCCN(N3)C2=O)C(C)C)C1] |

TABLE 2-continued

Certain Compounds of the Present Invention

| Ex # | Structure |
|---|---|
| B29 | 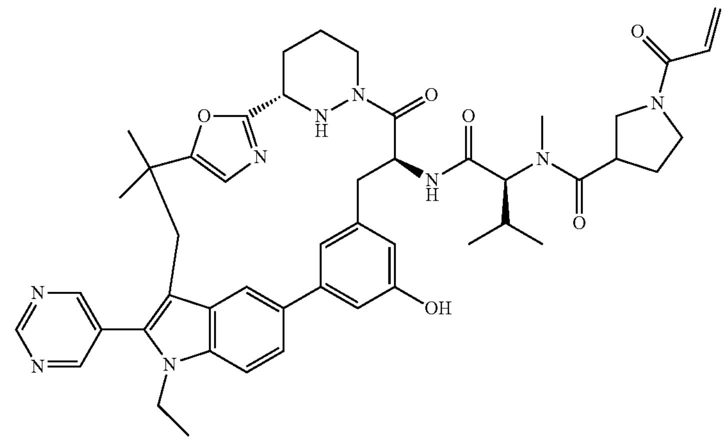 [SMILES: C=CC(=O)N1CCC(C(=O)N(C)[C@H](C(=O)N[C@H]2Cc3cc(O)cc(c3)-c3ccc4c(c3)c(c(-c3cncnc3)n4CC)CC(C)(C)C3=CN=C(O3)[C@@H]3CCCN(N3)C2=O)C(C)C)C1] |
| B30 | 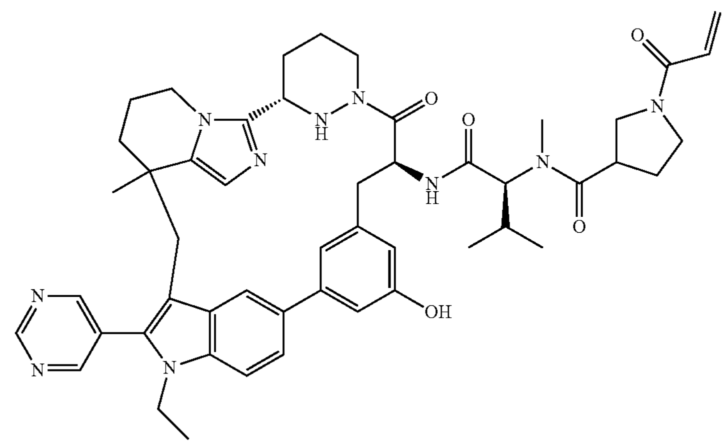 [SMILES: C=CC(=O)N1CCC(C(=O)N(C)[C@H](C(=O)N[C@H]2Cc3cc(O)cc(c3)-c3ccc4c(c3)c(c(-c3cncnc3)n4CC)CC3(C)CCCn4c3cnc4[C@@H]3CCCN(N3)C2=O)C(C)C)C1] |
| B32 | 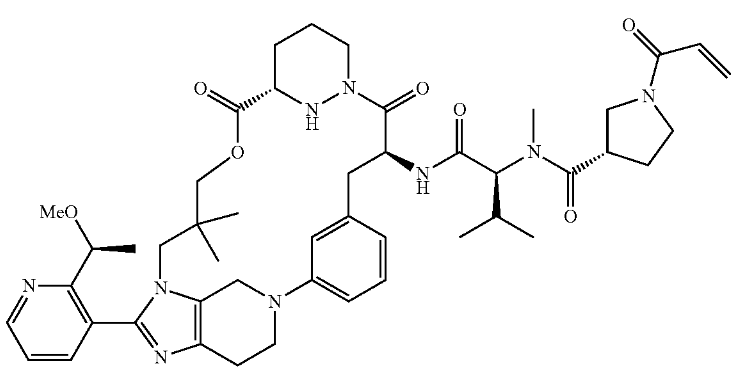 [SMILES: C=CC(=O)N1CC[C@H](C(=O)N(C)[C@H](C(=O)N[C@H]2Cc3cccc(c3)N3CCc4nc(-c5cccnc5[C@H](C)OC)n(c4C3)CC(C)(C)COC(=O)[C@@H]3CCCN(N3)C2=O)C(C)C)C1] |

TABLE 2-continued
Certain Compounds of the Present Invention
| Ex # | Structure |
|---|---|
| B34 | 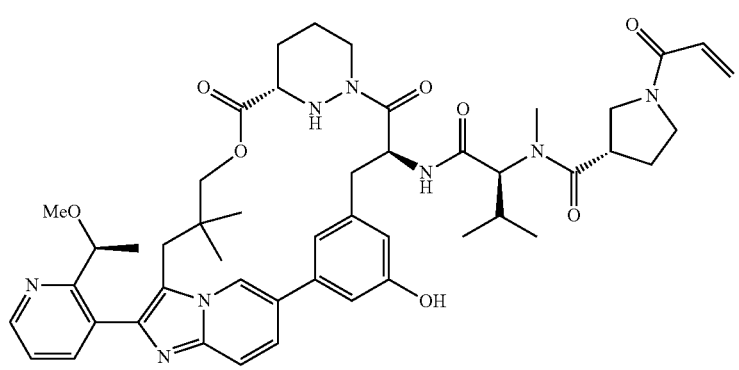 [SMILES: C=CC(=O)N1CC[C@H](C(=O)N(C)[C@H](C(=O)N[C@H]2Cc3cc(O)cc(c3)-c3ccc4nc(-c5cccnc5[C@H](C)OC)c(n4c3)CC(C)(C)COC(=O)[C@@H]3CCCN(N3)C2=O)C(C)C)C1] |
| B38 | 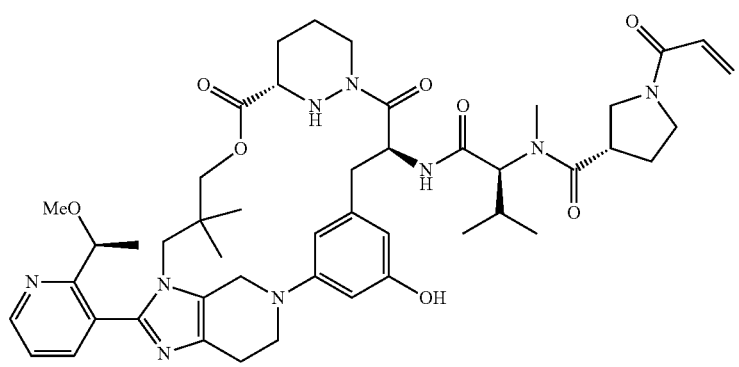 [SMILES: C=CC(=O)N1CC[C@H](C(=O)N(C)[C@H](C(=O)N[C@H]2Cc3cc(O)cc(c3)N3CCc4nc(-c5cccnc5[C@H](C)OC)n(c4C3)CC(C)(C)COC(=O)[C@@H]3CCCN(N3)C2=O)C(C)C)C1] |
| B47 | 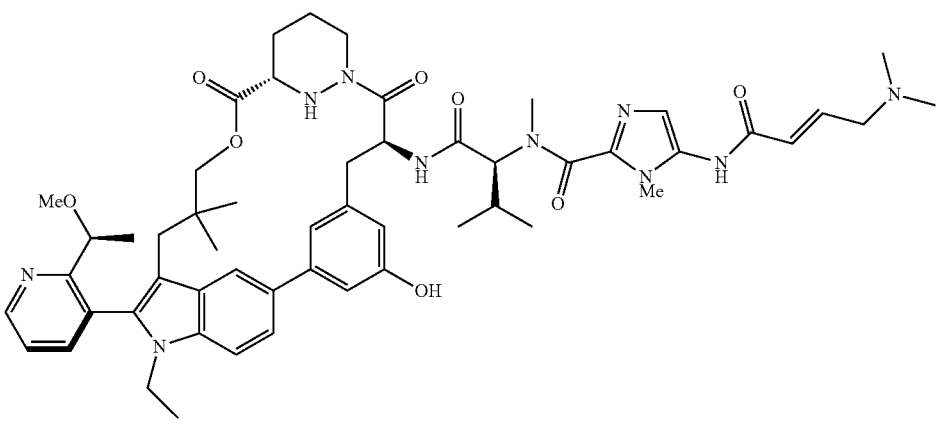 |

TABLE 2-continued

Certain Compounds of the Present Invention

| Ex # | Structure |
|------|-----------|
| B64 | 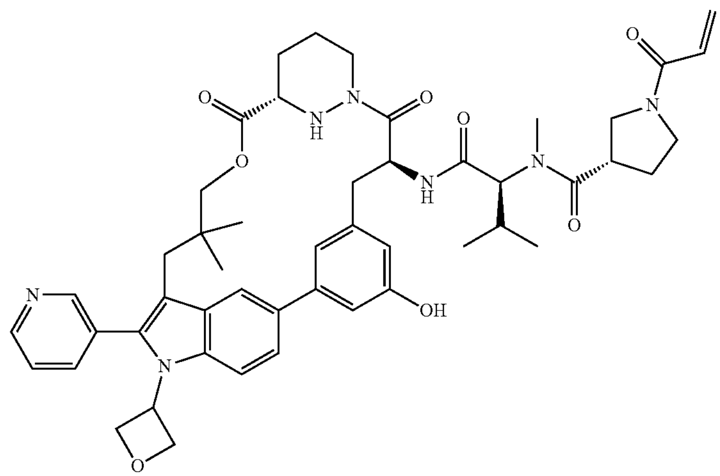 [SMILES: C=CC(=O)N1CC[C@H](C(=O)N(C)[C@H](C(=O)N[C@H]2Cc3cc(O)cc(c3)-c3ccc4c(c3)c(c(-c3cccnc3)n4C3COC3)CC(C)(C)COC(=O)[C@@H]3CCCN(N3)C2=O)C(C)C)C1] |
| B65 | 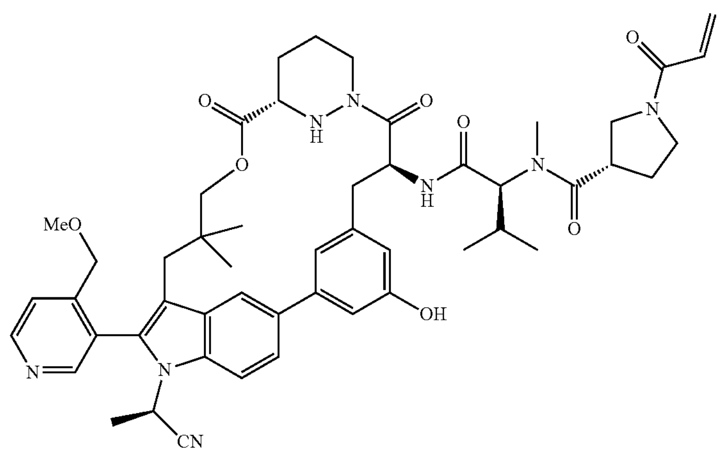 [SMILES: C=CC(=O)N1CC[C@H](C(=O)N(C)[C@H](C(=O)N[C@H]2Cc3cc(O)cc(c3)-c3ccc4c(c3)c(c(-c3cnccc3COC)n4[C@H](C)C#N)CC(C)(C)COC(=O)[C@@H]3CCCN(N3)C2=O)C(C)C)C1] |
| B66 | 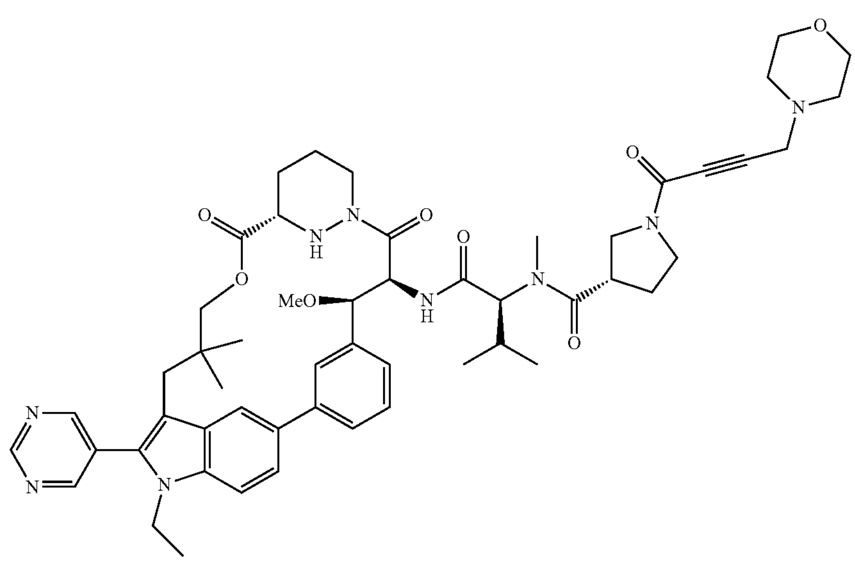 [SMILES: CCn1c(-c2cncnc2)c2c3cc(ccc31)-c1cccc(c1)[C@@H](OC)[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |

TABLE 2-continued

Certain Compounds of the Present Invention

| Ex # | Structure |
|---|---|
| B70 | 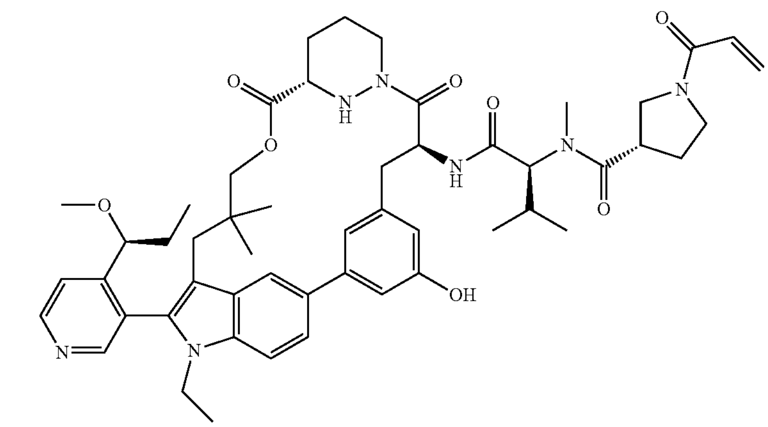 [SMILES: C=CC(=O)N1CC[C@H](C(=O)N(C)[C@H](C(=O)N[C@H]2Cc3cc(O)cc(c3)-c3ccc4c(c3)c(c(-c3cnccc3[C@H](CC)OC)n4CC)CC(C)(C)COC(=O)[C@@H]3CCCN(N3)C2=O)C(C)C)C1] |
| B73 | 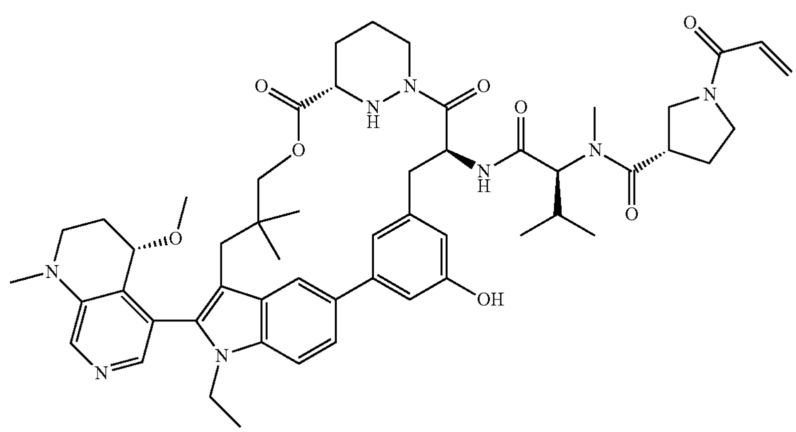 [SMILES: C=CC(=O)N1CC[C@H](C(=O)N(C)[C@H](C(=O)N[C@H]2Cc3cc(O)cc(c3)-c3ccc4c(c3)c(c(-c3cncc5c3[C@@H](OC)CCN5C)n4CC)CC(C)(C)COC(=O)[C@@H]3CCCN(N3)C2=O)C(C)C)C1] |
| B74 | 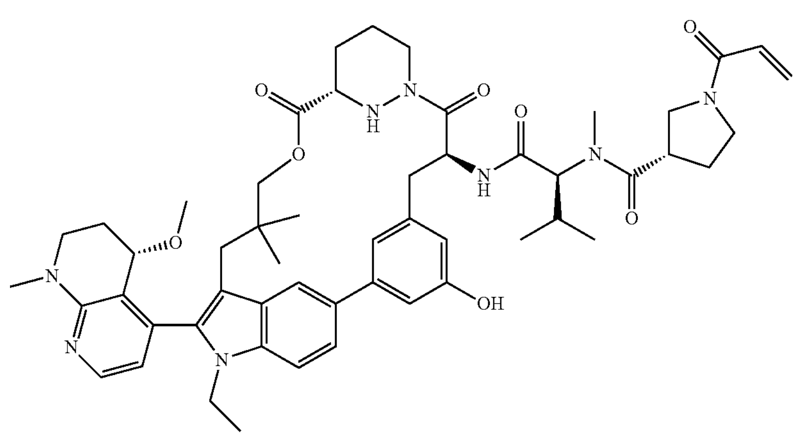 [SMILES: C=CC(=O)N1CC[C@H](C(=O)N(C)[C@H](C(=O)N[C@H]2Cc3cc(O)cc(c3)-c3ccc4c(c3)c(c(-c3ccnc5c3[C@@H](OC)CCN5C)n4CC)CC(C)(C)COC(=O)[C@@H]3CCCN(N3)C2=O)C(C)C)C1] |

TABLE 2-continued

Certain Compounds of the Present Invention

| Ex # | Structure |
|---|---|
| B75 | 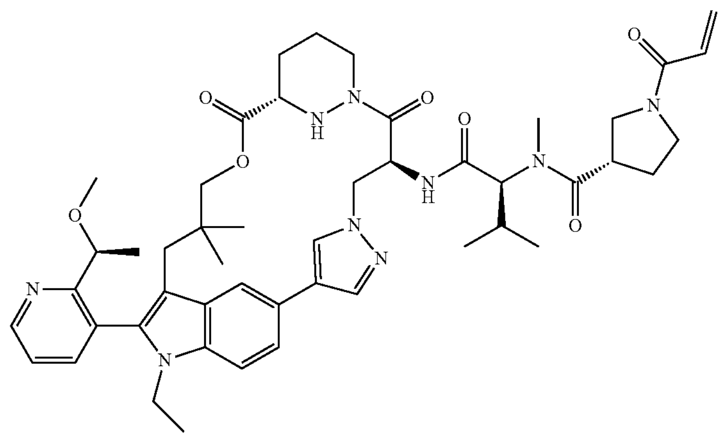 [SMILES: C=CC(=O)N1CC[C@H](C(=O)N(C)[C@H](C(=O)N[C@H]2Cn3cc(cn3)-c3ccc4c(c3)c(c(-c3cccnc3[C@H](C)OC)n4CC)CC(C)(C)COC(=O)[C@@H]3CCCN(N3)C2=O)C(C)C)C1] |
| B76 | 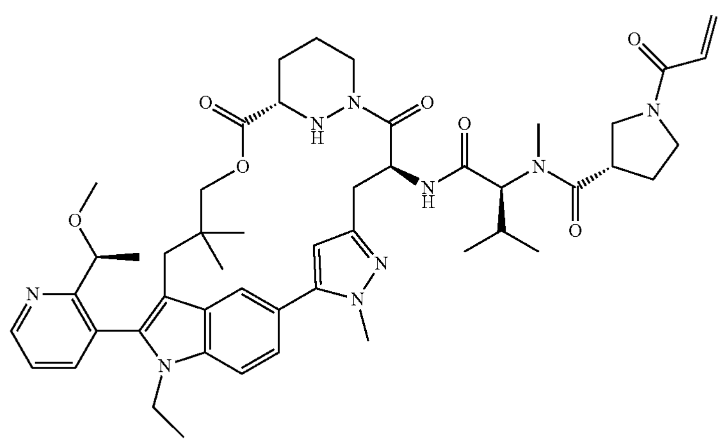 [SMILES: C=CC(=O)N1CC[C@H](C(=O)N(C)[C@H](C(=O)N[C@H]2Cc3cc(n(C)n3)-c3ccc4c(c3)c(c(-c3cccnc3[C@H](C)OC)n4CC)CC(C)(C)COC(=O)[C@@H]3CCCN(N3)C2=O)C(C)C)C1] |
| B77 | 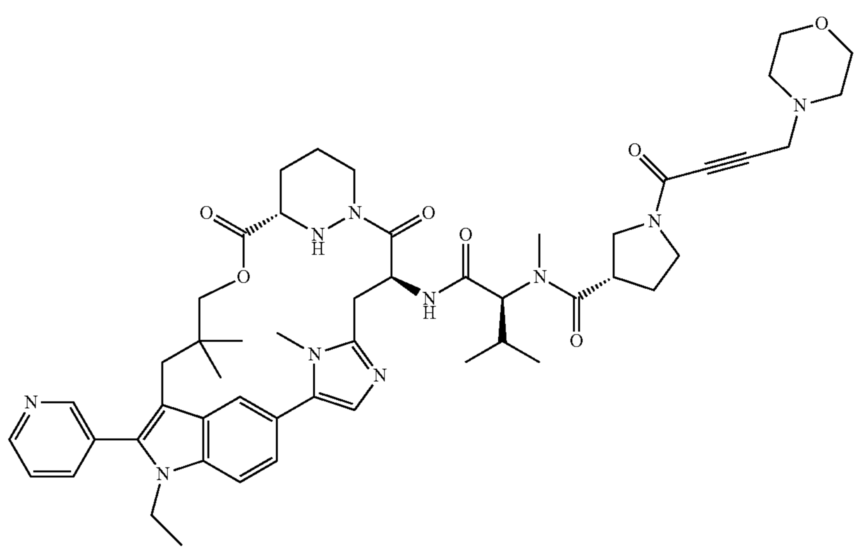 [SMILES: CCn1c(-c2cccnc2)c2c3cc(ccc31)-c1cnc(n1C)C[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |

TABLE 2-continued
Certain Compounds of the Present Invention
| Ex # | Structure |
|---|---|
| B81 | 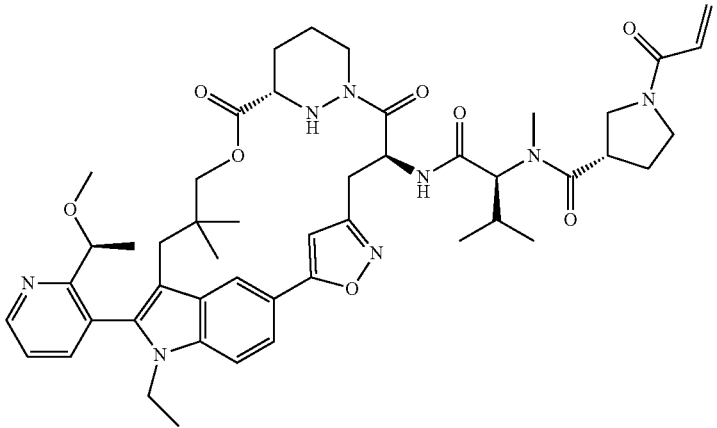 [SMILES: C=CC(=O)N1CC[C@H](C(=O)N(C)[C@H](C(=O)N[C@H]2Cc3cc(on3)-c3ccc4c(c3)c(c(-c3cccnc3[C@H](C)OC)n4CC)CC(C)(C)COC(=O)[C@@H]3CCCN(N3)C2=O)C(C)C)C1] |
| B83 | 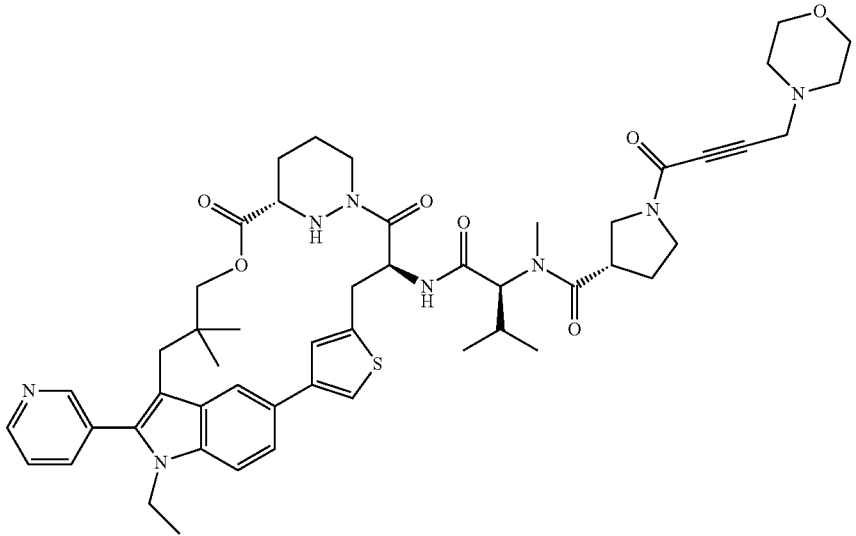 [SMILES: CCn1c(-c2cccnc2)c2c3cc(ccc31)-c1csc(c1)C[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |
| B85 | 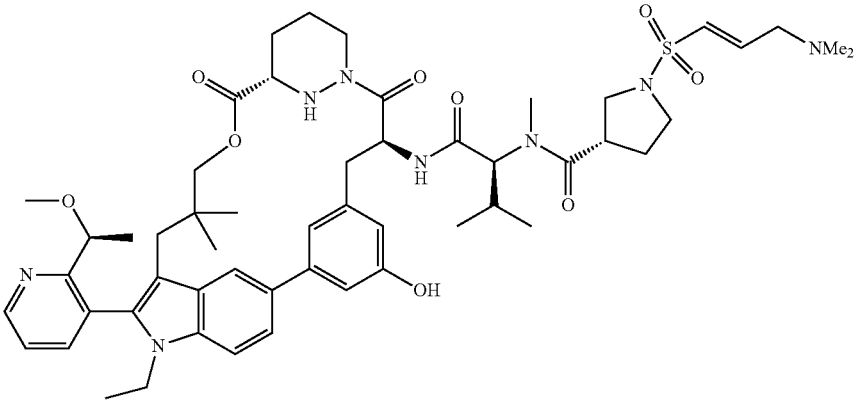 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(S(=O)(=O)/C=C/CN(C)C)C1)C(=O)N1CCC[C@H](N1)C(=O)OCC(C)(C)C2] |

TABLE 2-continued
Certain Compounds of the Present Invention
| Ex # | Structure |
|---|---|
| B86 | 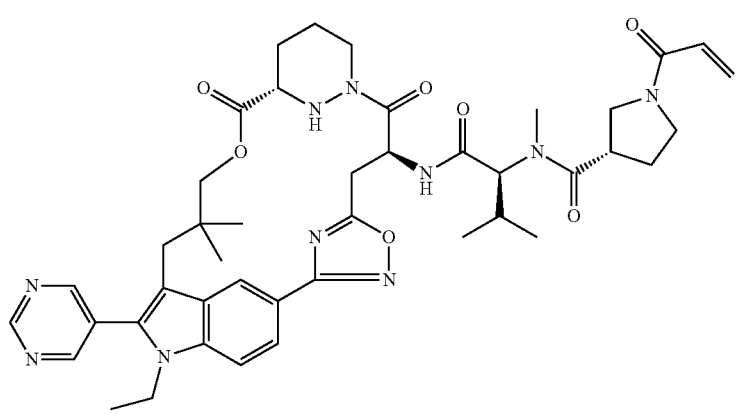 [SMILES: C=CC(=O)N1CC[C@H](C(=O)N(C)[C@H](C(=O)N[C@H]2Cc3nc(no3)-c3ccc4c(c3)c(c(-c3cncnc3)n4CC)CC(C)(C)COC(=O)[C@@H]3CCCN(N3)C2=O)C(C)C)C1] |
| B87 | 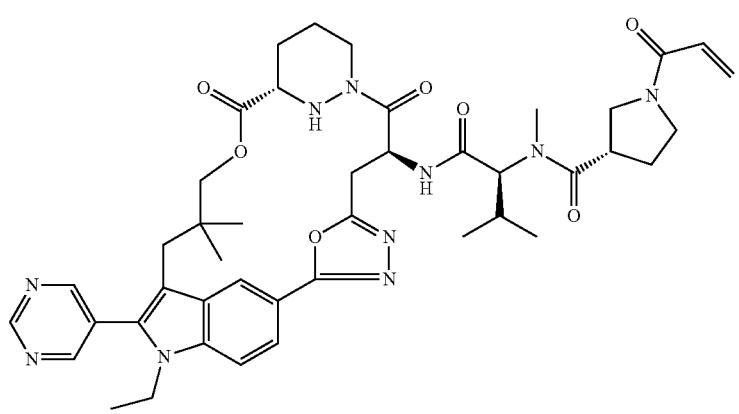 [SMILES: C=CC(=O)N1CC[C@H](C(=O)N(C)[C@H](C(=O)N[C@H]2CC3=NN=C(O3)c3ccc4c(c3)c(c(-c3cncnc3)n4CC)CC(C)(C)COC(=O)[C@@H]3CCCN(N3)C2=O)C(C)C)C1] |
| B88 | 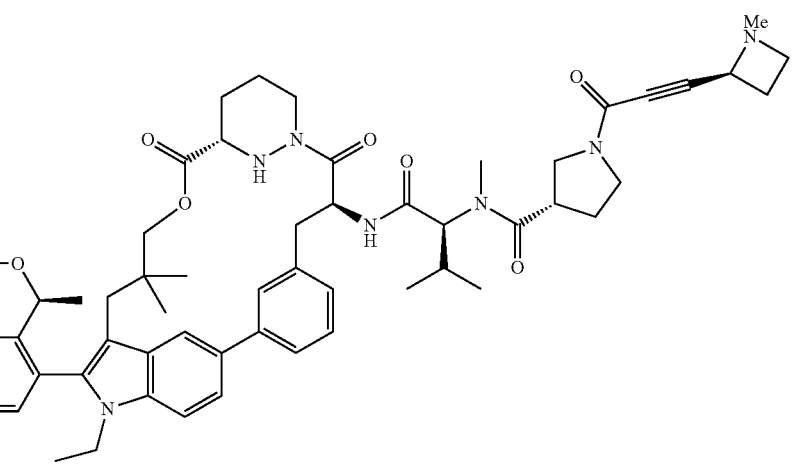 |

TABLE 2-continued
Certain Compounds of the Present Invention
| Ex # | Structure |
|---|---|
| B89 | 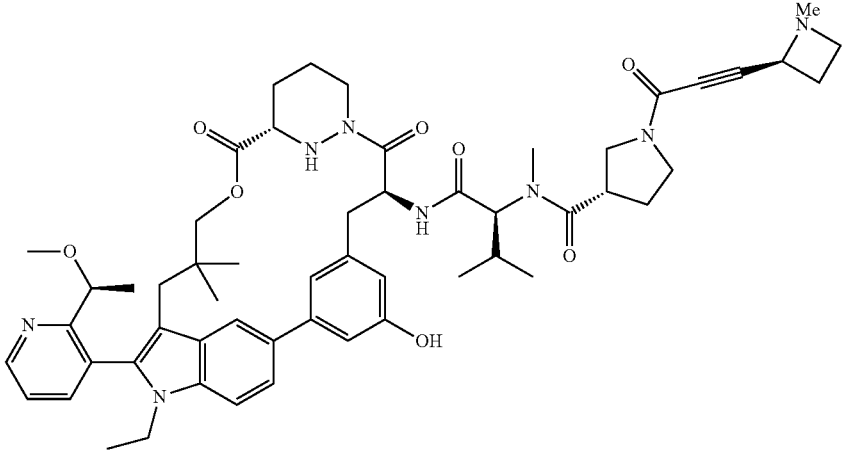 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(C(=O)C#C[C@@H]3CCN3C)C1)C(=O)N1CCC[C@H](N1)C(=O)OCC(C)(C)C2] |
| B90 | 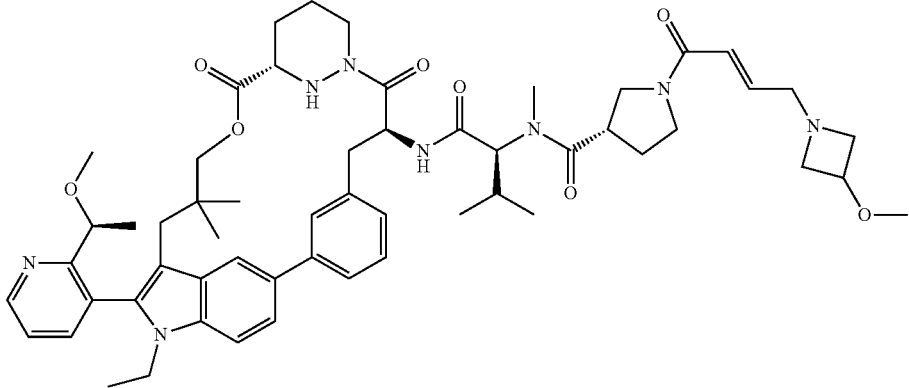 [SMILES: CCn1c(-c2cccnc2[C@H](C)OC)c2c3cc(ccc31)-c1cccc(c1)C[C@H](NC(=O)[C@H](C(C)C)N(C)C(=O)[C@H]1CCN(C(=O)/C=C/CN3CC(OC)C3)C1)C(=O)N1CCC[C@H](N1)C(=O)OCC(C)(C)C2] |
| B91 | 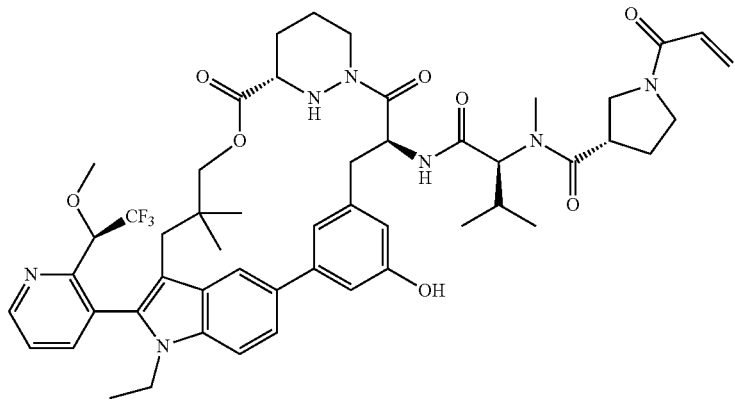 [SMILES: C=CC(=O)N1CC[C@H](C(=O)N(C)[C@H](C(=O)N[C@H]2Cc3cc(O)cc(c3)-c3ccc4c(c3)c(c(-c3cccnc3[C@@H](OC)C(F)(F)F)n4CC)CC(C)(C)COC(=O)[C@@H]3CCCN(N3)C2=O)C(C)C)C1] |

TABLE 2-continued

Certain Compounds of the Present Invention

| Ex # | Structure |
|---|---|
| B96 | 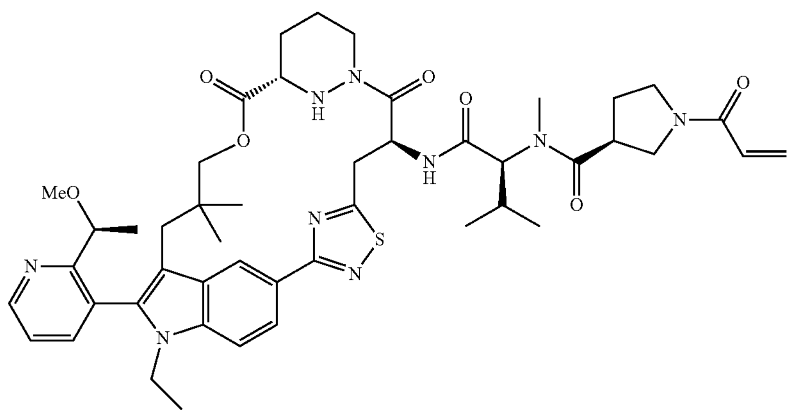 [SMILES: C=CC(=O)N1CC[C@H](C(=O)N(C)[C@H](C(=O)N[C@H]2Cc3nc(ns3)-c3ccc4c(c3)c(c(-c3cccnc3[C@H](C)OC)n4CC)CC(C)(C)COC(=O)[C@@H]3CCCN(N3)C2=O)C(C)C)C1] |
| B97 | 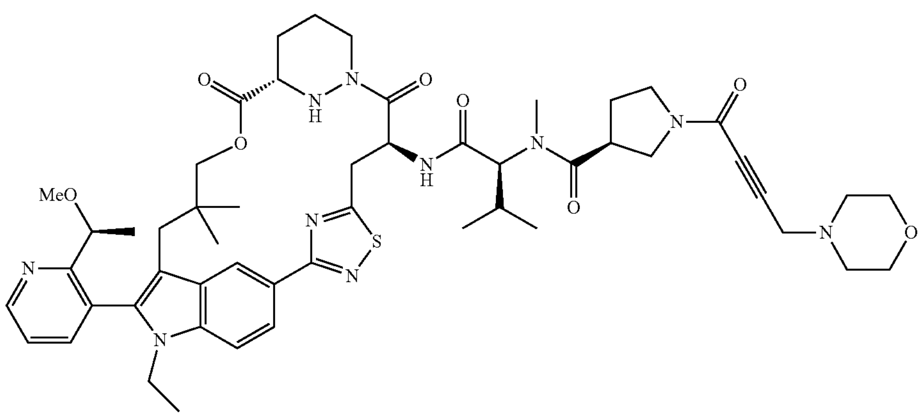 [SMILES: CCn1c(-c2cccnc2[C@H](C)OC)c2c3cc(ccc31)-c1nsc(n1)C[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |
| B102 | 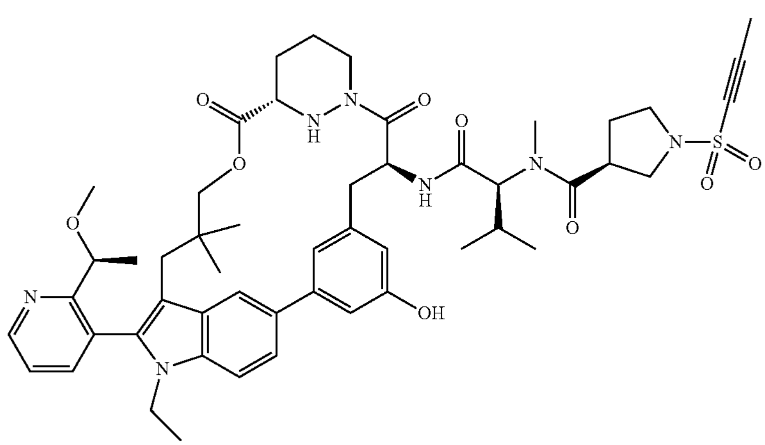 [SMILES: CC#CS(=O)(=O)N1CC[C@H](C(=O)N(C)[C@H](C(=O)N[C@H]2Cc3cc(O)cc(c3)-c3ccc4c(c3)c(c(-c3cccnc3[C@H](C)OC)n4CC)CC(C)(C)COC(=O)[C@@H]3CCCN(N3)C2=O)C(C)C)C1] |

TABLE 2-continued
Certain Compounds of the Present Invention
| Ex # | Structure |
|---|---|
| B103 | 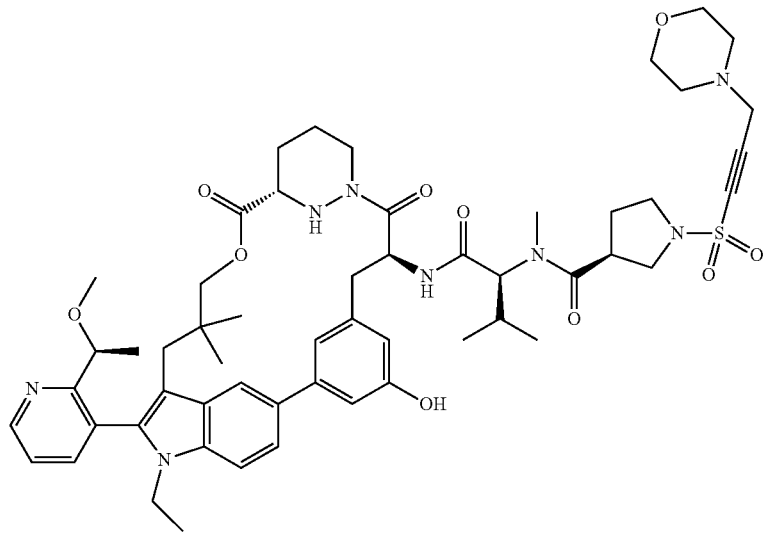 [SMILES: CCn1c(-c2cccnc2[C@H](C)OC)c2c3cc(ccc31)-c1cc(O)cc(c1)C[C@H](NC(=O)[C@H](C(C)C)N(C)C(=O)[C@H]1CCN(S(=O)(=O)C#CCN3CCOCC3)C1)C(=O)N1CCC[C@H](N1)C(=O)OCC(C)(C)C2] |
| B104 | 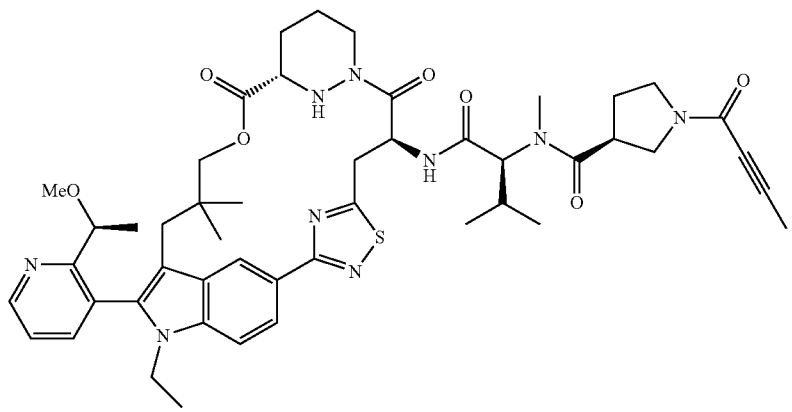 [SMILES: CC#CC(=O)N1CC[C@H](C(=O)N(C)[C@H](C(=O)N[C@H]2Cc3nc(ns3)-c3ccc4c(c3)c(c(-c3cccnc3[C@H](C)OC)n4CC)CC(C)(C)COC(=O)[C@@H]3CCCN(N3)C2=O)C(C)C)C1] |
| B106 | 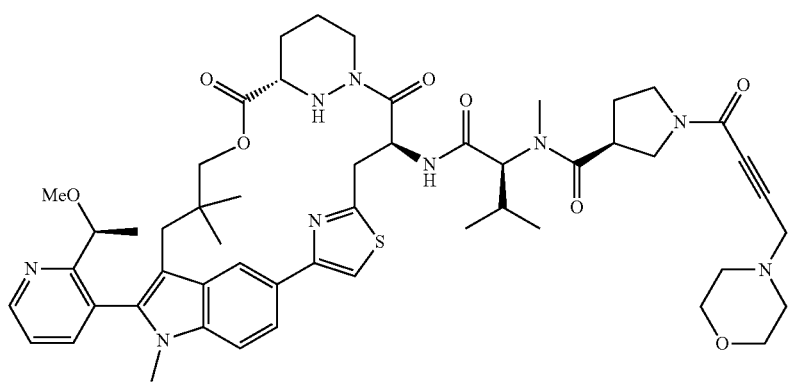 [SMILES: CO[C@@H](C)c1ncccc1-c1c2c3cc(ccc3n1C)-c1csc(n1)C[C@H](NC(=O)[C@H](C(C)C)N(C)C(=O)[C@H]1CCN(C(=O)C#CCN3CCOCC3)C1)C(=O)N1CCC[C@H](N1)C(=O)OCC(C)(C)C2] |

TABLE 2-continued
Certain Compounds of the Present Invention
| Ex # | Structure |
|---|---|
| B107 | 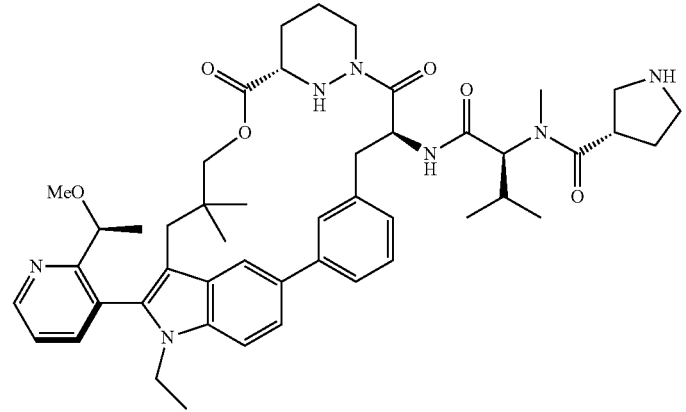 |
| B109 | 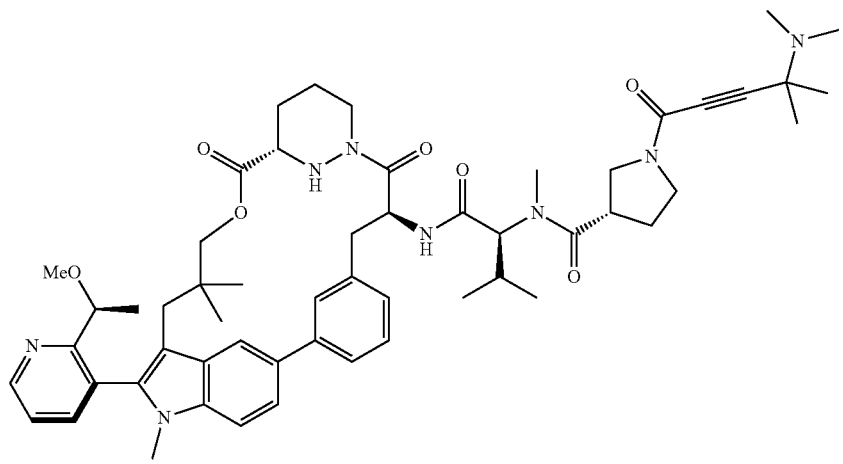 |
| B111 | 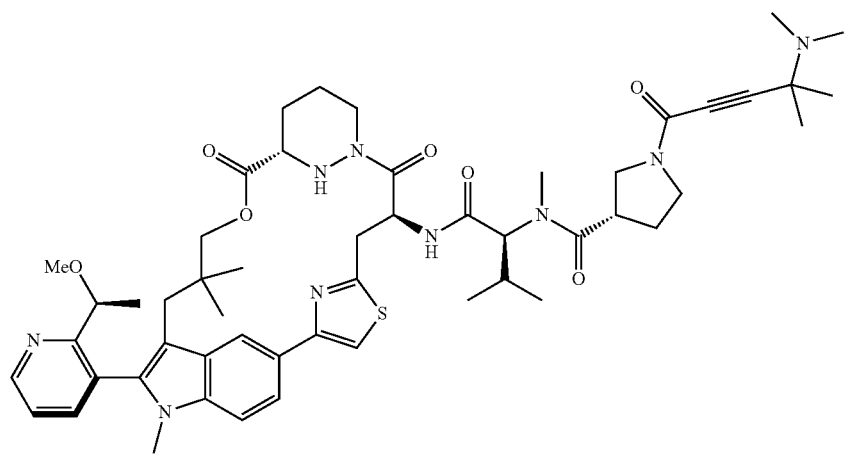 |

TABLE 2-continued
Certain Compounds of the Present Invention
| Ex # | Structure |
|---|---|
| B112 | 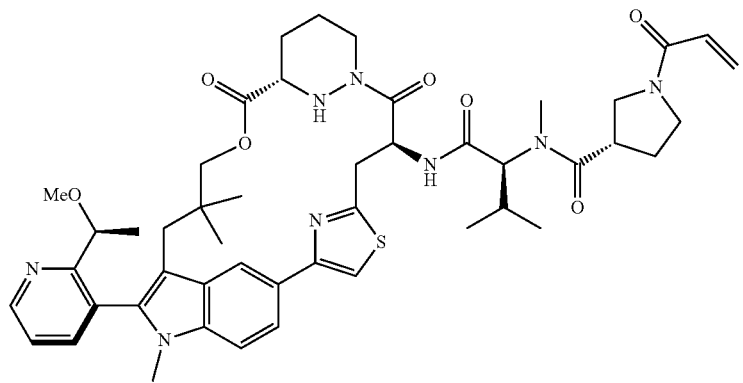 |
| B113 | 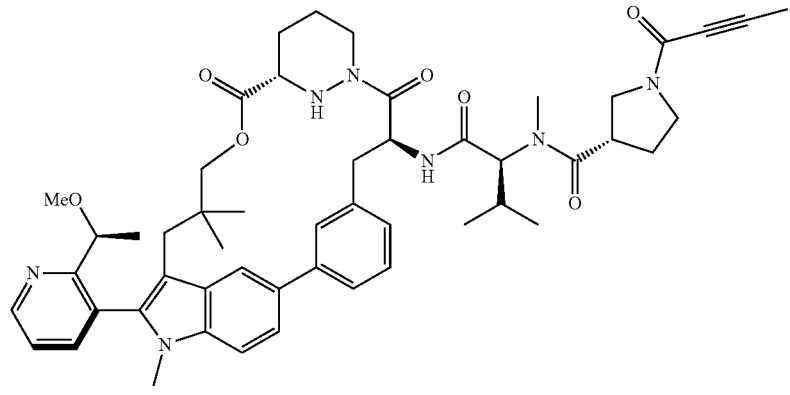 |
| B115 | 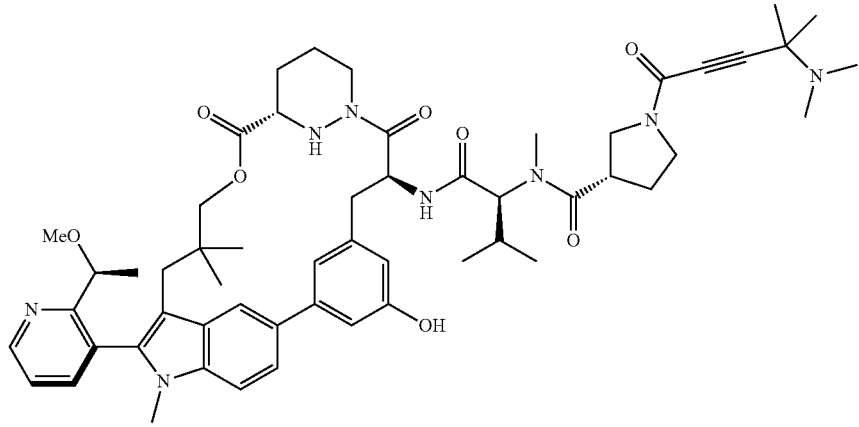 |

TABLE 2-continued

Certain Compounds of the Present Invention

| Ex # | Structure |
|---|---|
| B116 | 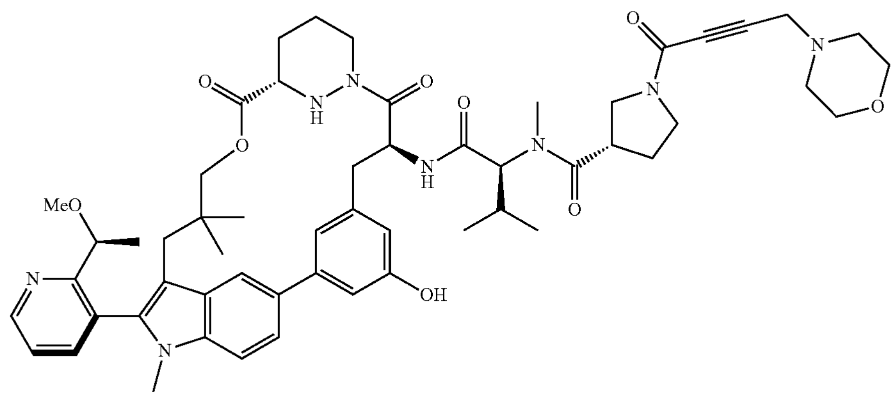 |
| B117 | 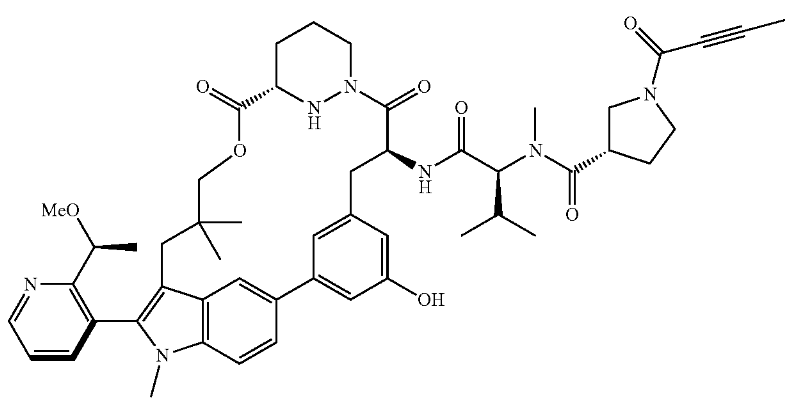 |
| B118 | 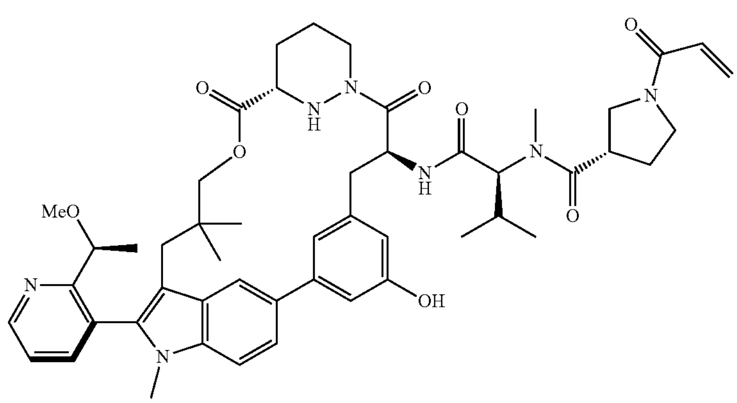 |

TABLE 2-continued
Certain Compounds of the Present Invention
| Ex # | Structure |
|---|---|
| B119 | 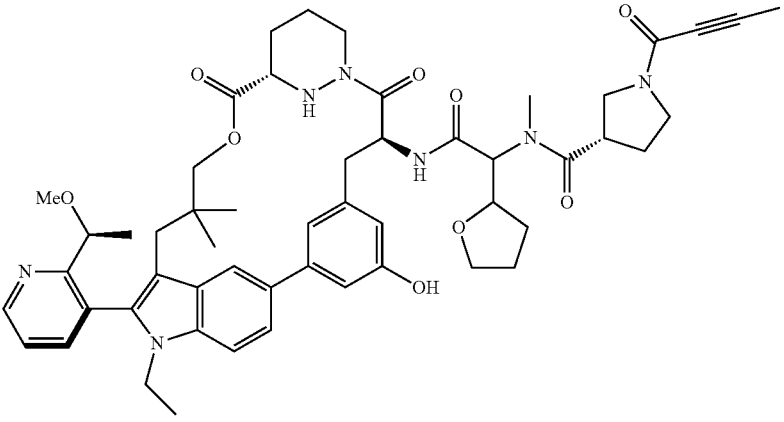 |
| B120 | 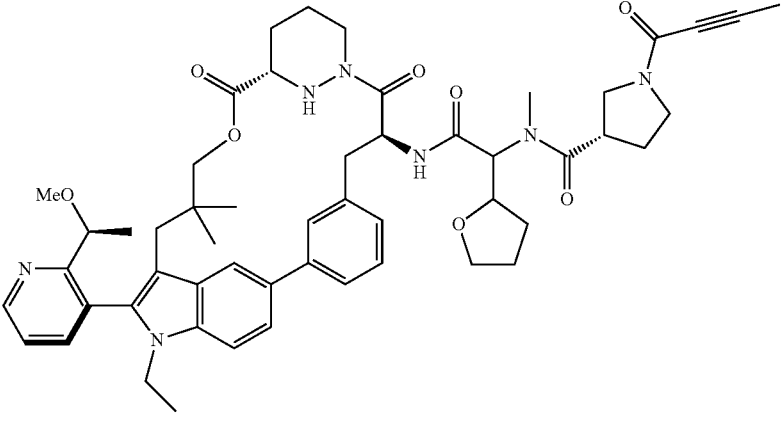 |
| B121 | 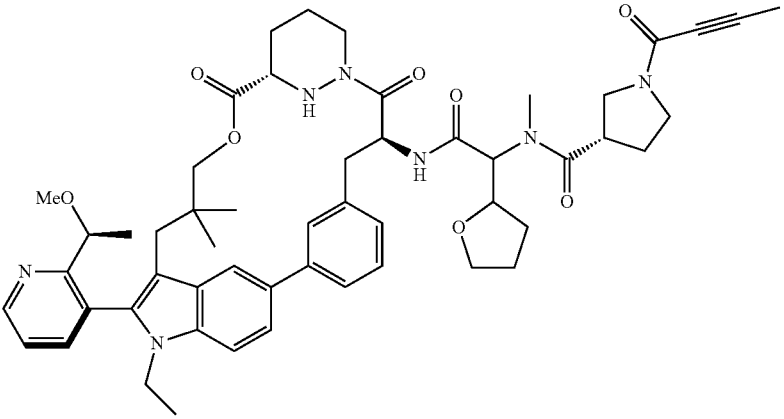 |

TABLE 2-continued

Certain Compounds of the Present Invention

| Ex # | Structure |
|---|---|
| B122 | 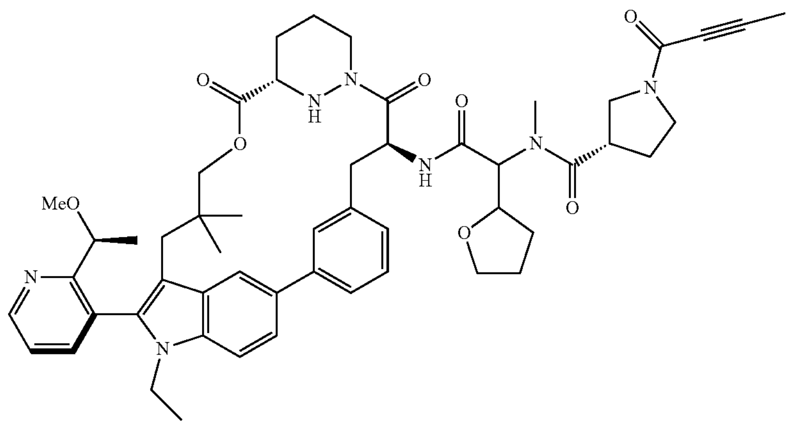 |
| B123 | 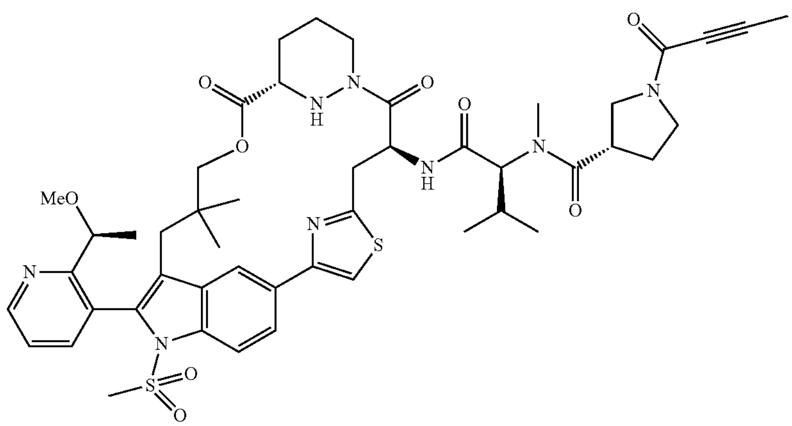 [SMILES: CC#CC(=O)N1CC[C@H](C(=O)N(C)[C@H](C(=O)N[C@H]2Cc3nc(cs3)-c3ccc4c(c3)c(c(-c3cccnc3[C@H](C)OC)n4S(C)(=O)=O)CC(C)(C)COC(=O)[C@@H]3CCCN(N3)C2=O)C(C)C)C1] |
| B124 | 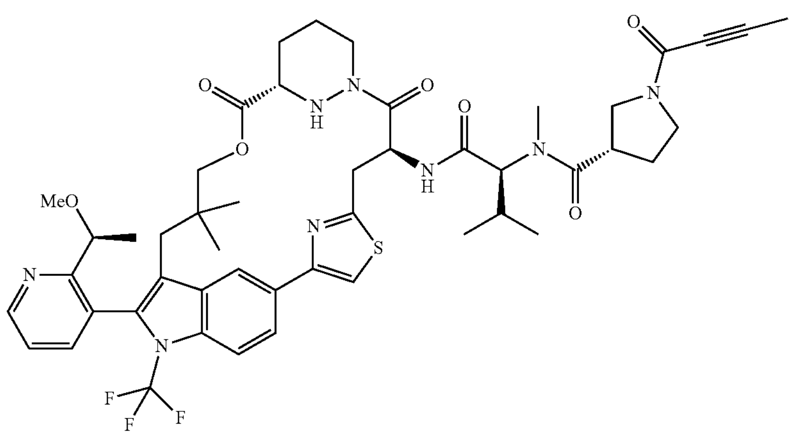 [SMILES: CC#CC(=O)N1CC[C@H](C(=O)N(C)[C@H](C(=O)N[C@H]2Cc3nc(cs3)-c3ccc4c(c3)c(c(-c3cccnc3[C@H](C)OC)n4C(F)(F)F)CC(C)(C)COC(=O)[C@@H]3CCCN(N3)C2=O)C(C)C)C1] |

TABLE 2-continued

Certain Compounds of the Present Invention

| Ex # | Structure |
|---|---|
| B126 | 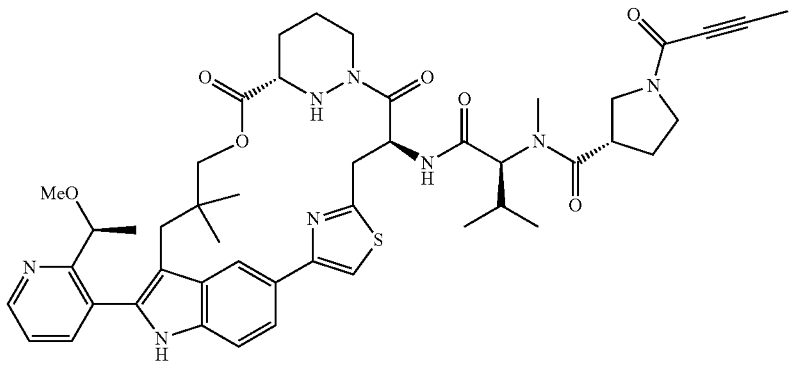 [SMILES: CC#CC(=O)N1CC[C@H](C(=O)N(C)[C@H](C(=O)N[C@H]2Cc3nc(cs3)-c3ccc4[nH]c(-c5cccnc5[C@H](C)OC)c(c4c3)CC(C)(C)COC(=O)[C@@H]3CCCN(N3)C2=O)C(C)C)C1] |
| B127 | 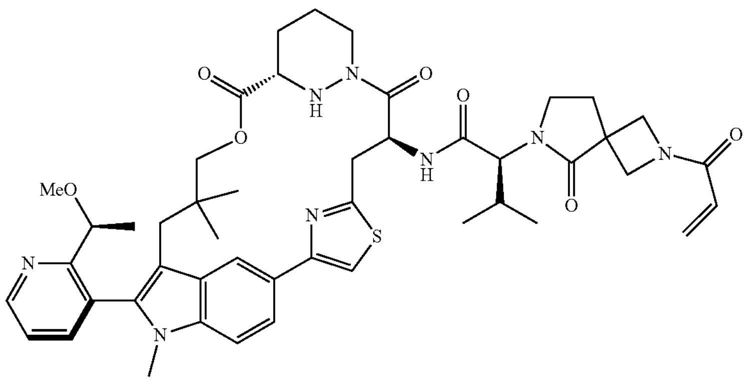 |
| B128 | 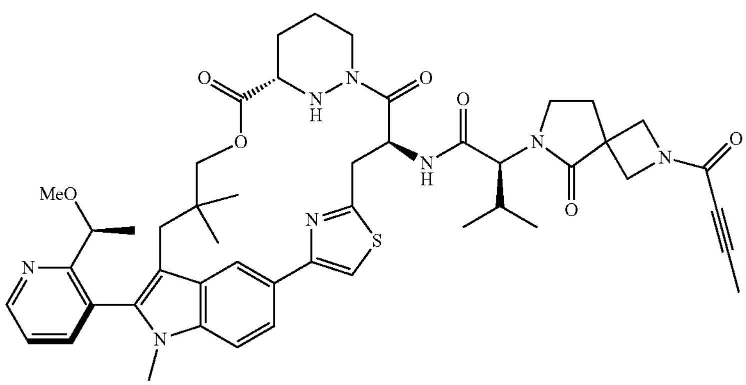 |
| B129 | 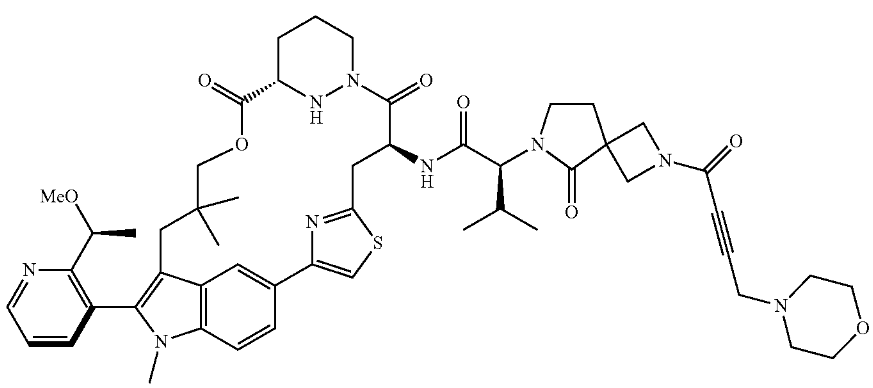 |

TABLE 2-continued
Certain Compounds of the Present Invention
| Ex # | Structure |
|---|---|
| B130 | 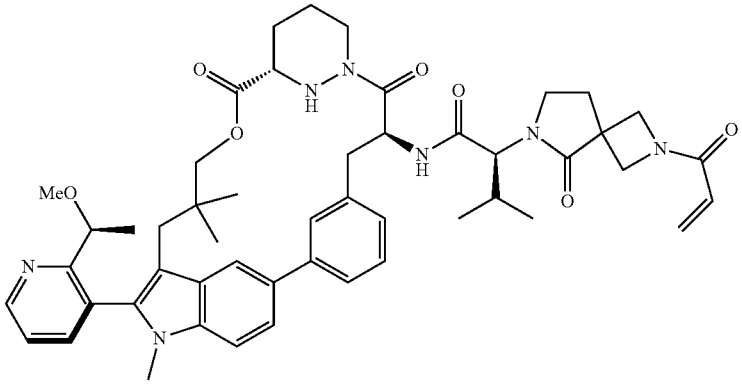 |
| B131 | 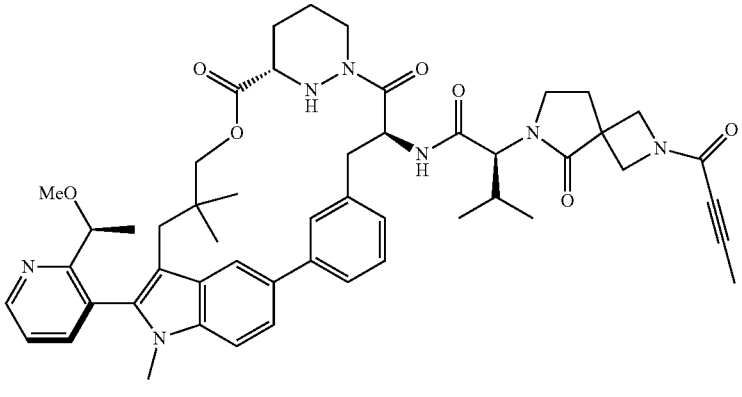 |
| B132 | 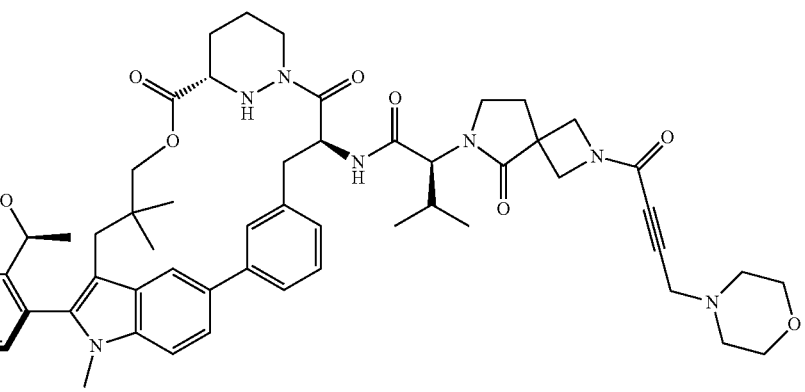 |
| B139 | 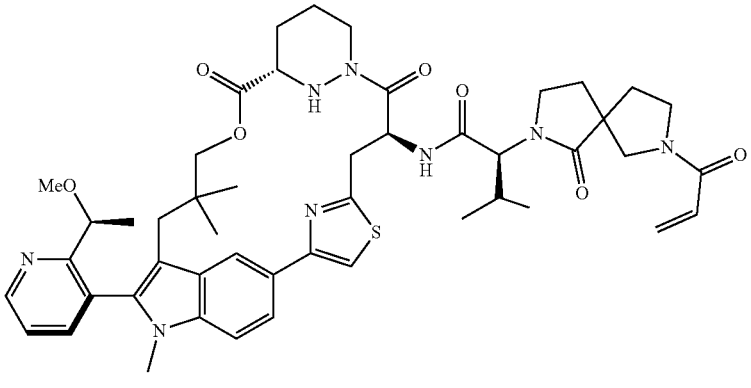 |

TABLE 2-continued
Certain Compounds of the Present Invention
| Ex # | Structure |
|------|-----------|
| B140 | 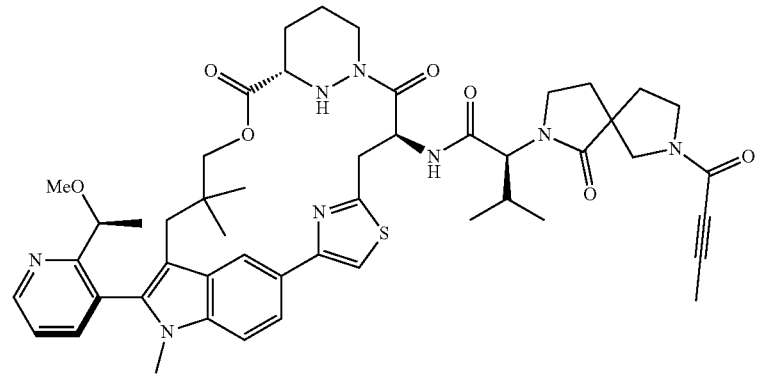 |
| B141 | 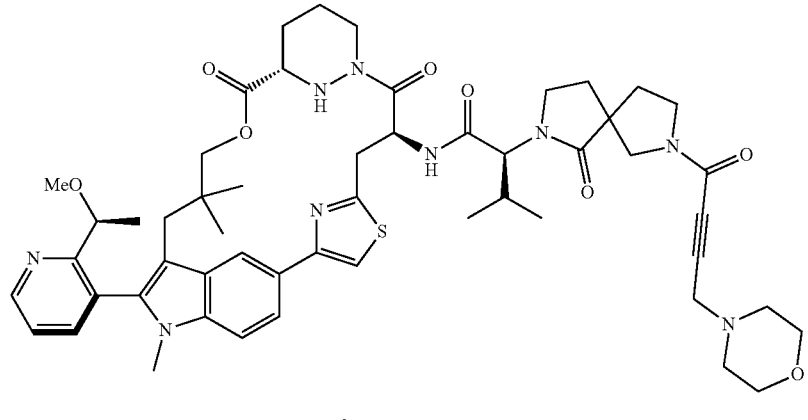 |
| B142 | 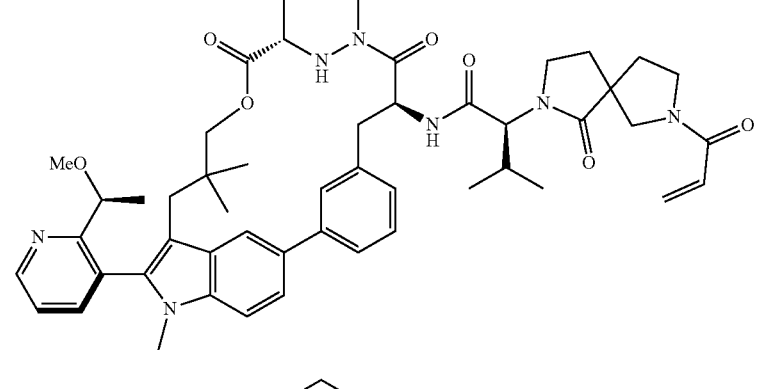 |
| B143 | 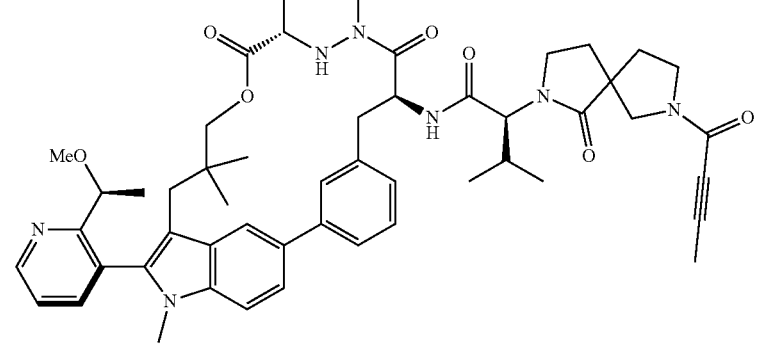 |

TABLE 2-continued
Certain Compounds of the Present Invention
| Ex # | Structure |
|---|---|
| B144 | 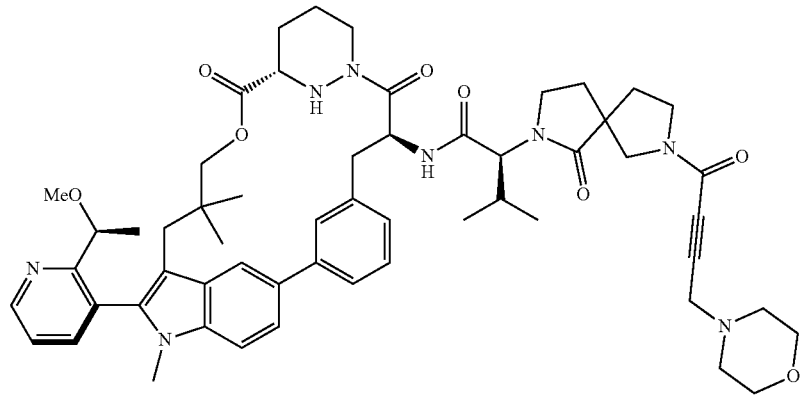 |
| B145 | 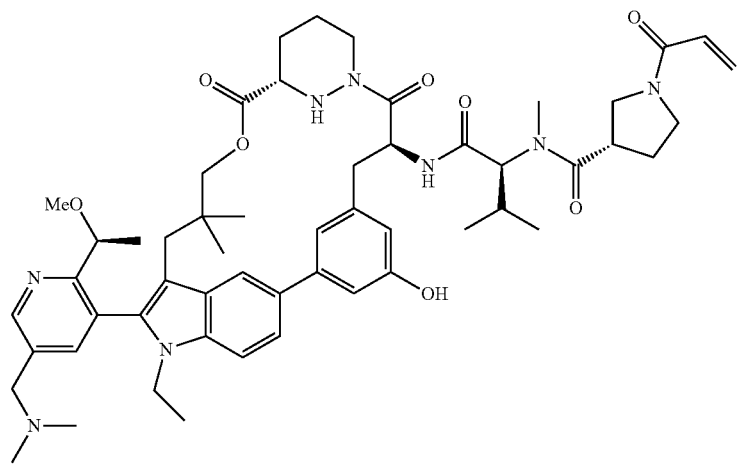 [SMILES: C=CC(=O)N1CC[C@H](C(=O)N(C)[C@H](C(=O)N[C@H]2Cc3cc(O)cc(c3)-c3ccc4c(c3)c(c(-c3cc(CN(C)C)cnc3[C@H](C)OC)n4CC)CC(C)(C)COC(=O)[C@@H]3CCCN(N3)C2=O)C(C)C)C1] |
| B146 | 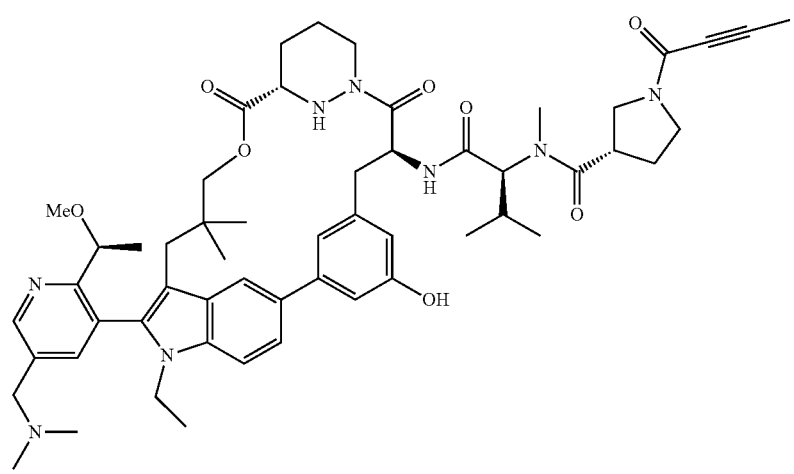 [SMILES: CC#CC(=O)N1CC[C@H](C(=O)N(C)[C@H](C(=O)N[C@H]2Cc3cc(O)cc(c3)-c3ccc4c(c3)c(c(-c3cc(CN(C)C)cnc3[C@H](C)OC)n4CC)CC(C)(C)COC(=O)[C@@H]3CCCN(N3)C2=O)C(C)C)C1] |

TABLE 2-continued
Certain Compounds of the Present Invention
| Ex # | Structure |
|---|---|
| B147 | 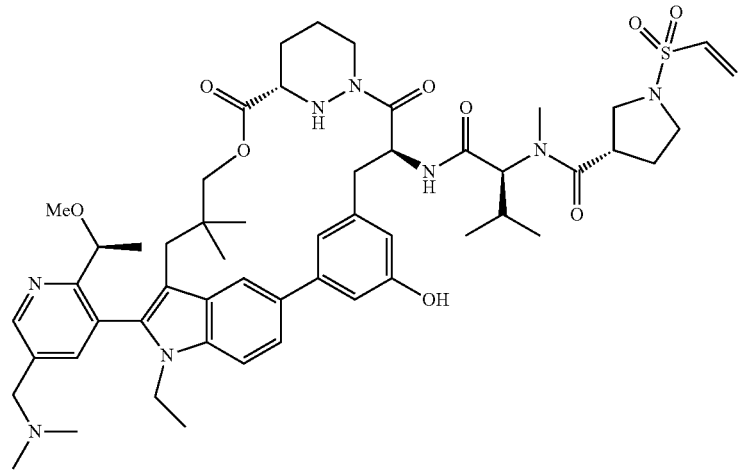 [SMILES: C=CS(=O)(=O)N1CC[C@H](C(=O)N(C)[C@H](C(=O)N[C@H]2Cc3cc(O)cc(c3)-c3ccc4c(c3)c(c(-c3cc(CN(C)C)cnc3[C@H](C)OC)n4CC)CC(C)(C)COC(=O)[C@@H]3CCCN(N3)C2=O)C(C)C)C1] |
| B148 | 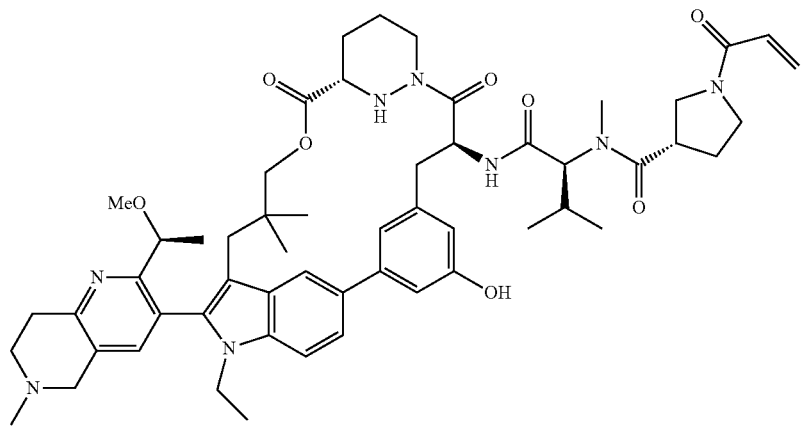 [SMILES: C=CC(=O)N1CC[C@H](C(=O)N(C)[C@H](C(=O)N[C@H]2Cc3cc(O)cc(c3)-c3ccc4c(c3)c(c(-c3cc5c(nc3[C@H](C)OC)CCN(C)C5)n4CC)CC(C)(C)COC(=O)[C@@H]3CCCN(N3)C2=O)C(C)C)C1] |
| B149 | 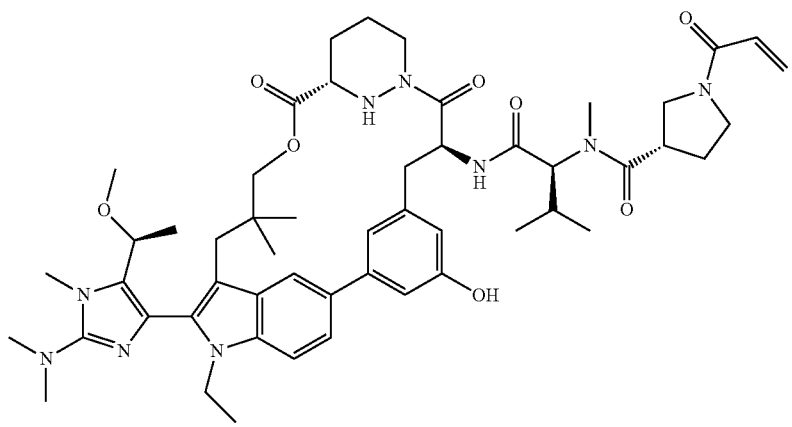 [SMILES: C=CC(=O)N1CC[C@H](C(=O)N(C)[C@H](C(=O)N[C@H]2Cc3cc(O)cc(c3)-c3ccc4c(c3)c(c(-c3nc(N(C)C)n(C)c3[C@H](C)OC)n4CC)CC(C)(C)COC(=O)[C@@H]3CCCN(N3)C2=O)C(C)C)C1] |

TABLE 2-continued

Certain Compounds of the Present Invention

| Ex # | Structure |
|---|---|
| B150 | 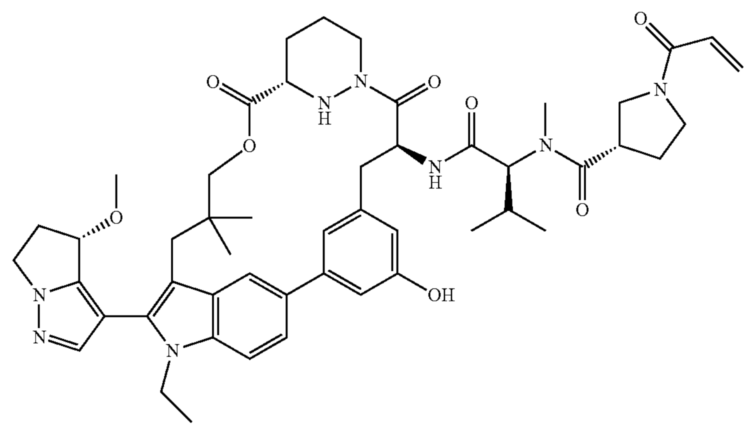 [SMILES: C=CC(=O)N1CC[C@H](C(=O)N(C)[C@H](C(=O)N[C@H]2Cc3cc(O)cc(c3)-c3ccc4c(c3)c(c(-c3cnn5c3[C@@H](OC)CC5)n4CC)CC(C)(C)COC(=O)[C@@H]3CCCN(N3)C2=O)C(C)C)C1] |
| B161 | 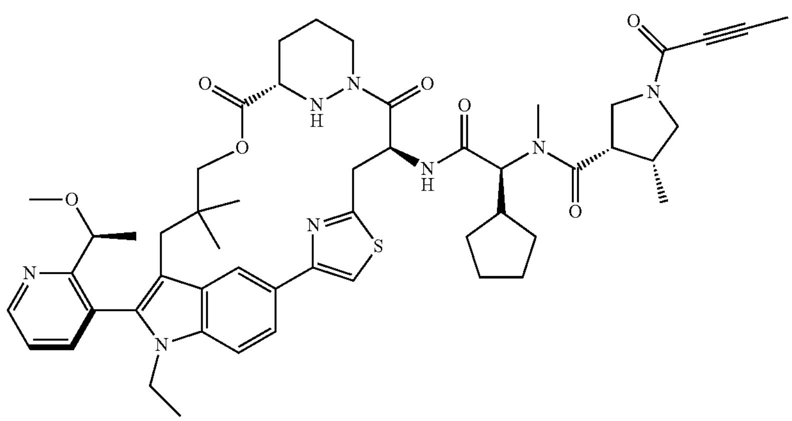 |
| B162 | 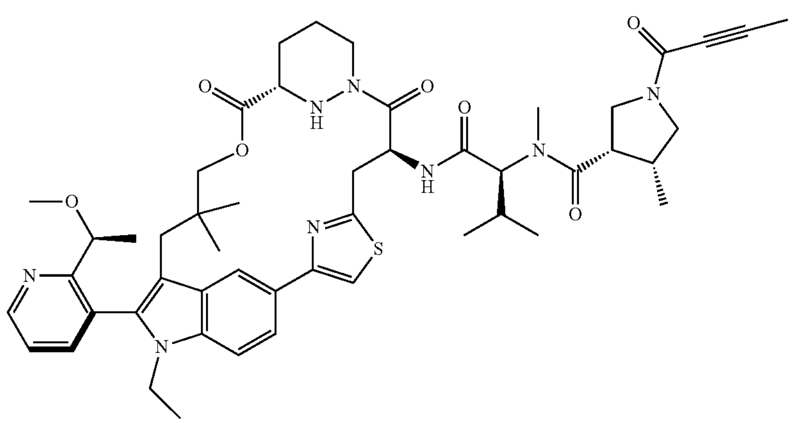 |

TABLE 2-continued
Certain Compounds of the Present Invention
| Ex # | Structure |
|---|---|
| B163 | 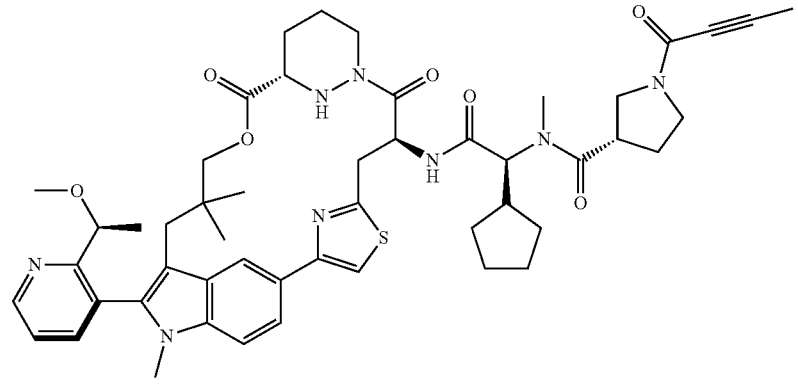 |
| B164 | 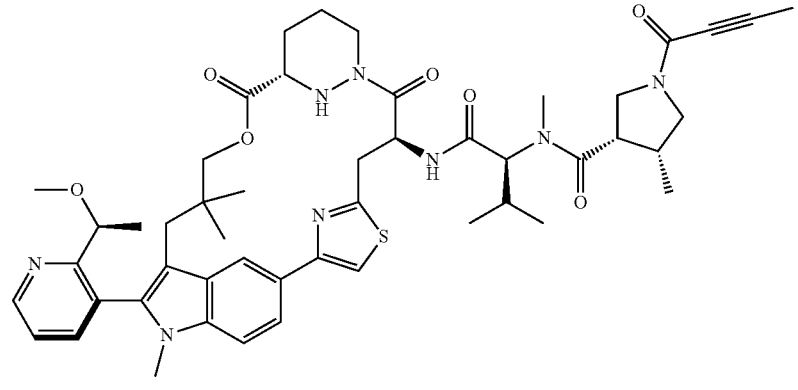 |
| B165 | 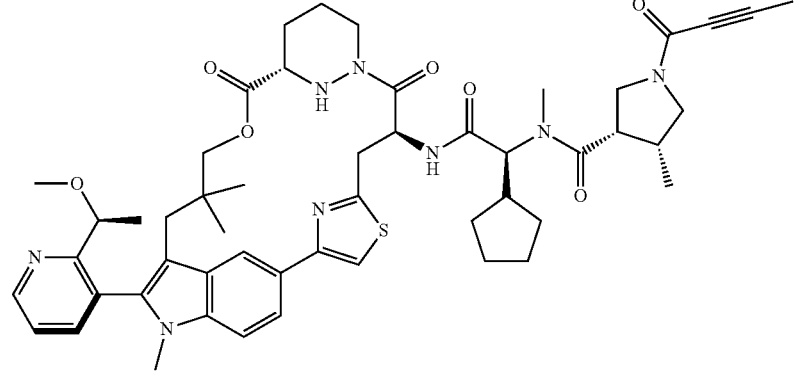 |
| B167 | 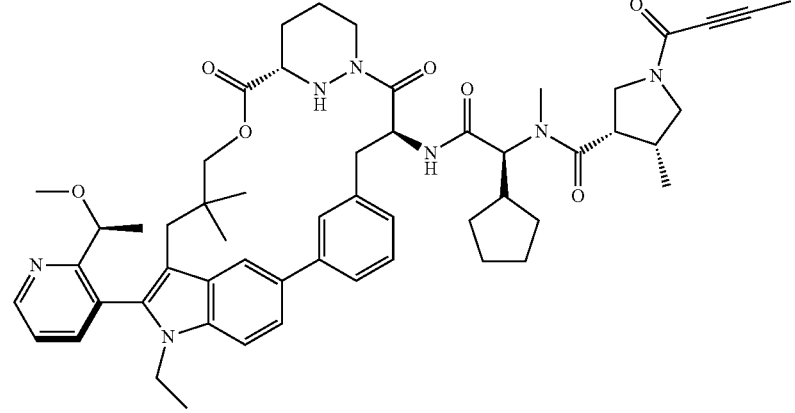 |

US 11,952,352 B2
TABLE 2-continued
Certain Compounds of the Present Invention
| Ex # | Structure |
|---|---|
B168
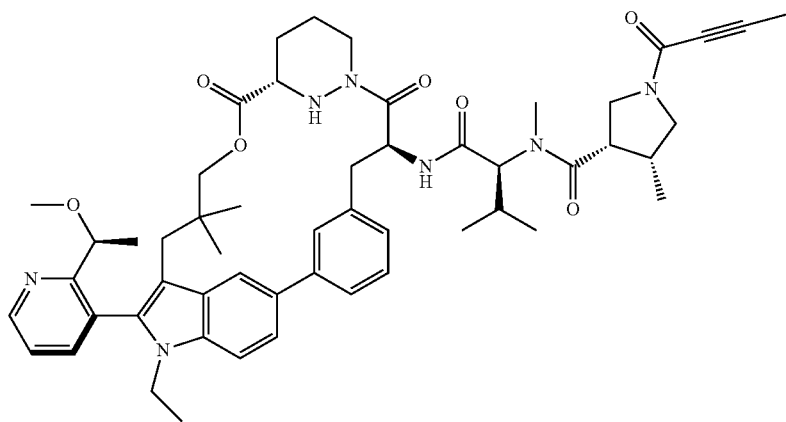
B169
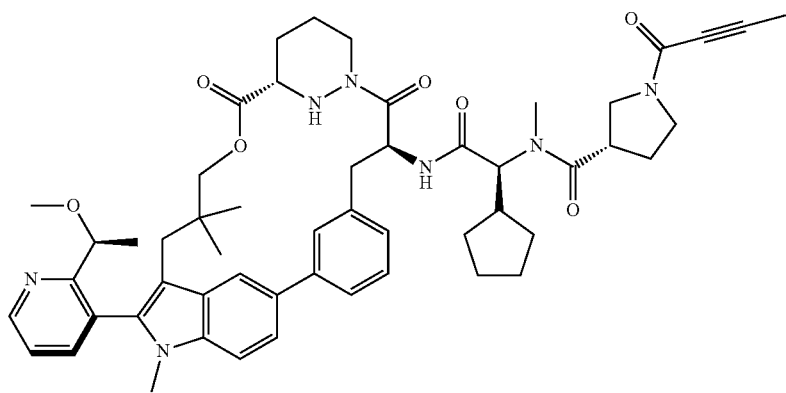
B170
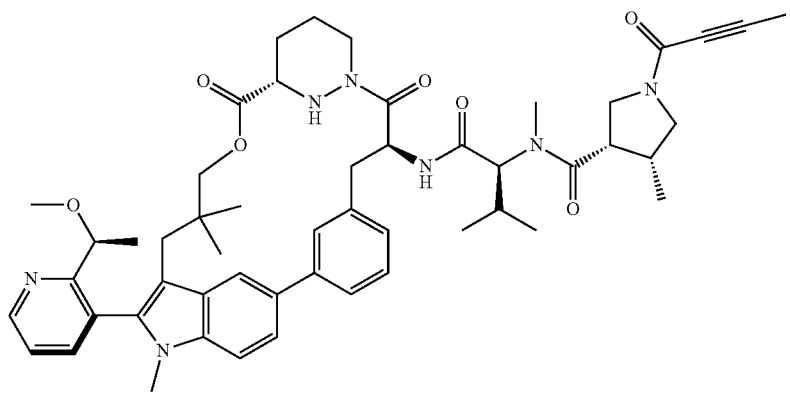

TABLE 2-continued

Certain Compounds of the Present Invention

| Ex # | Structure |
|---|---|
| B171 | 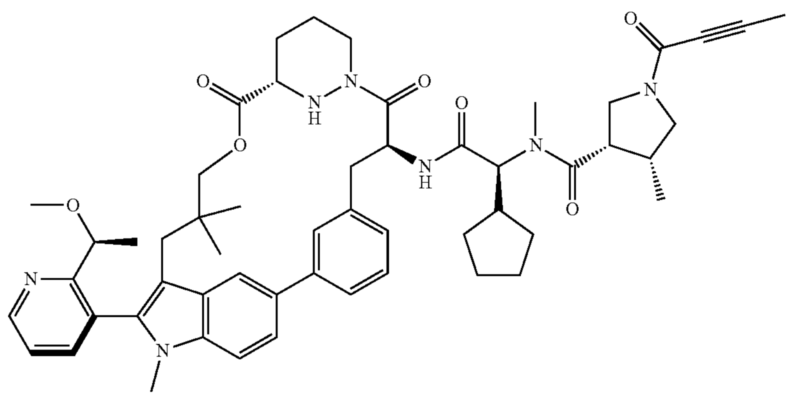 |
| B172 | 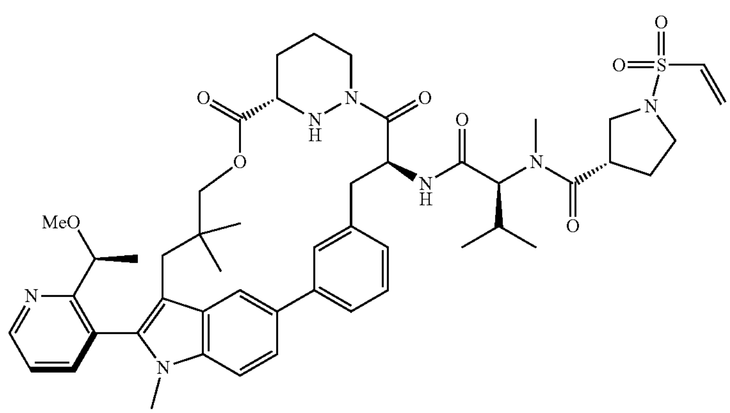 |
| B173 | 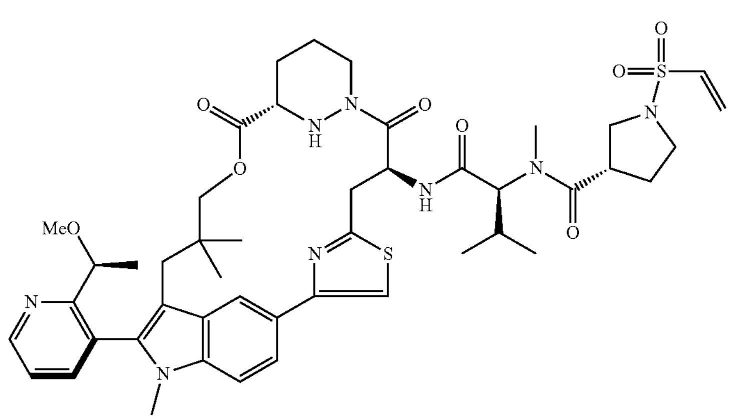 |

TABLE 2-continued

Certain Compounds of the Present Invention

| Ex # | Structure |
|---|---|
| B174 | 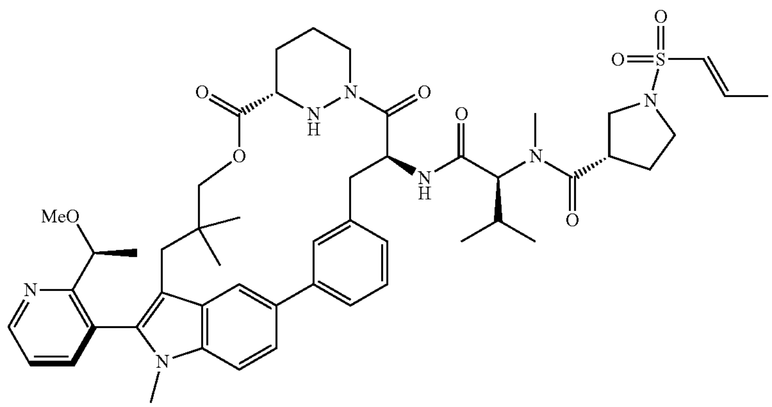 |
| B175 | 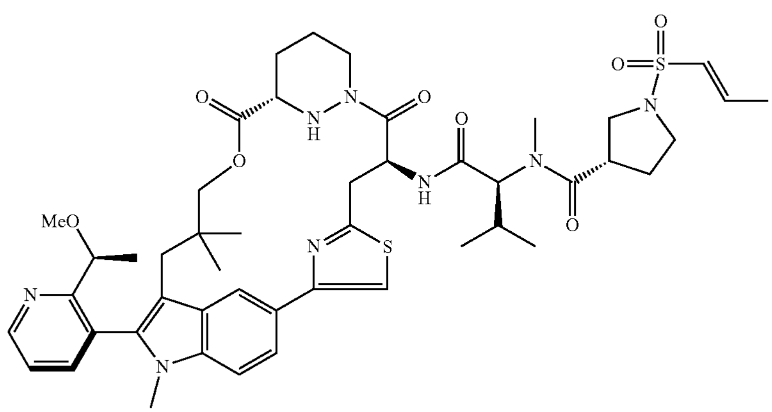 |
| B176 | 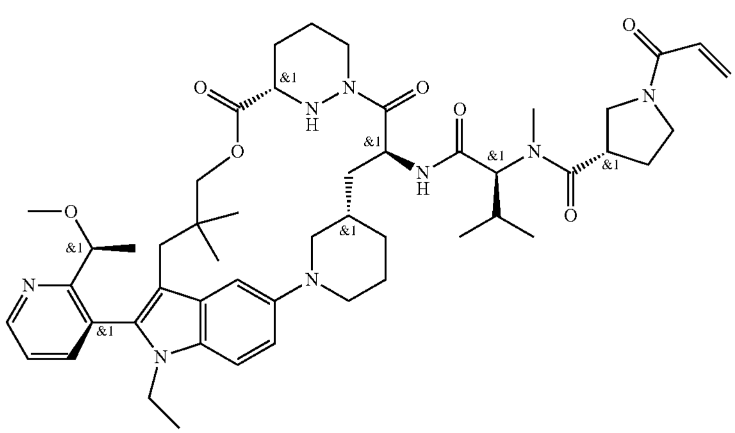 |

TABLE 2-continued

Certain Compounds of the Present Invention

| Ex # | Structure |
|---|---|
| B177 | 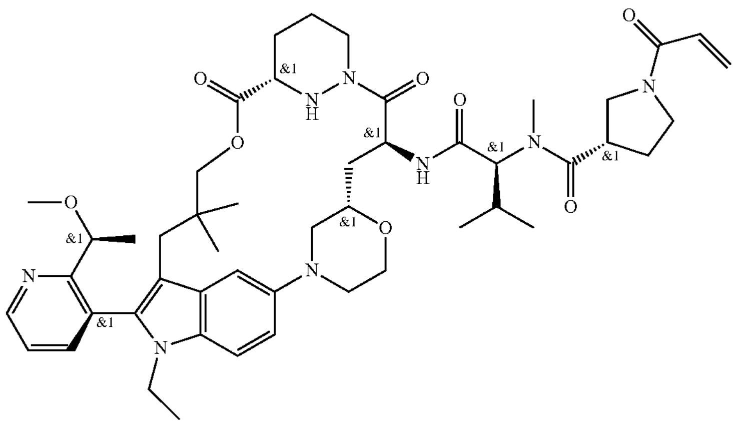 |
| B178 | 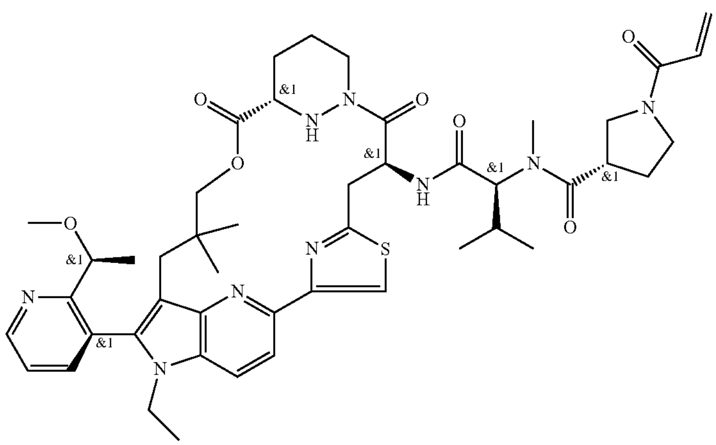 |
| B179 | 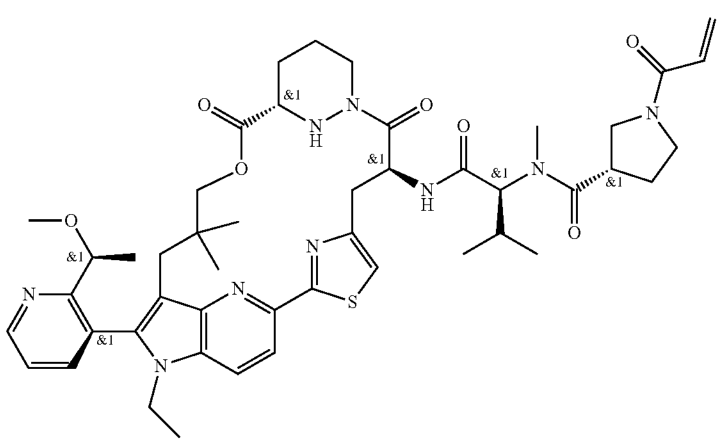 |

TABLE 2-continued

Certain Compounds of the Present Invention

| Ex # | Structure |
|---|---|
| B180 | 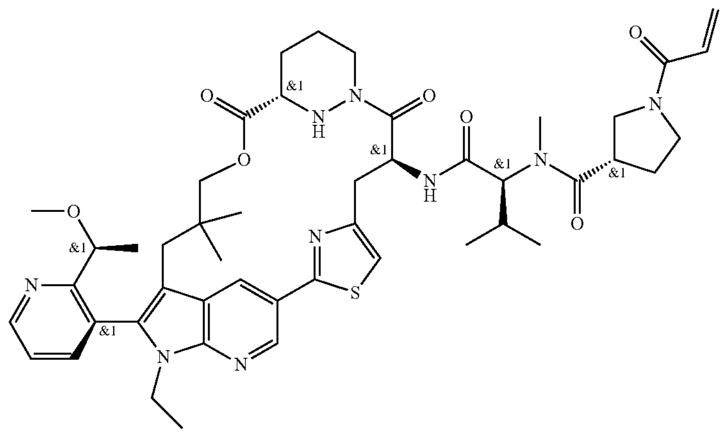 |
| B181 | 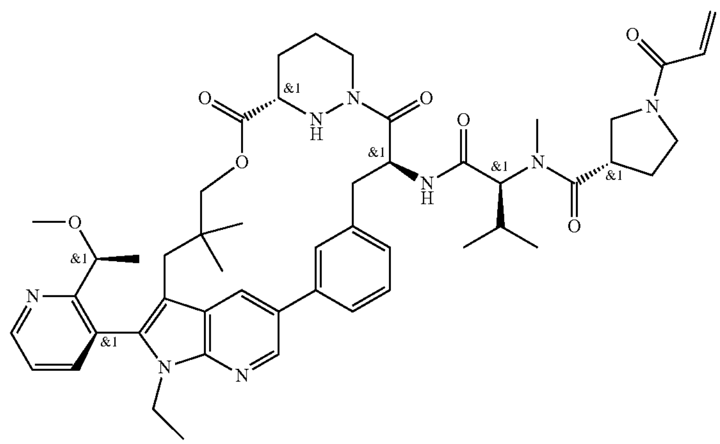 |
| B182 | 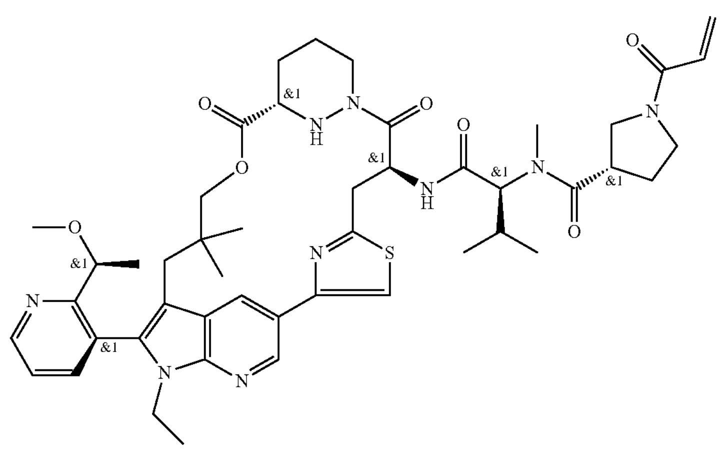 |

TABLE 2-continued

Certain Compounds of the Present Invention

| Ex # | Structure |
|---|---|
| B183 | 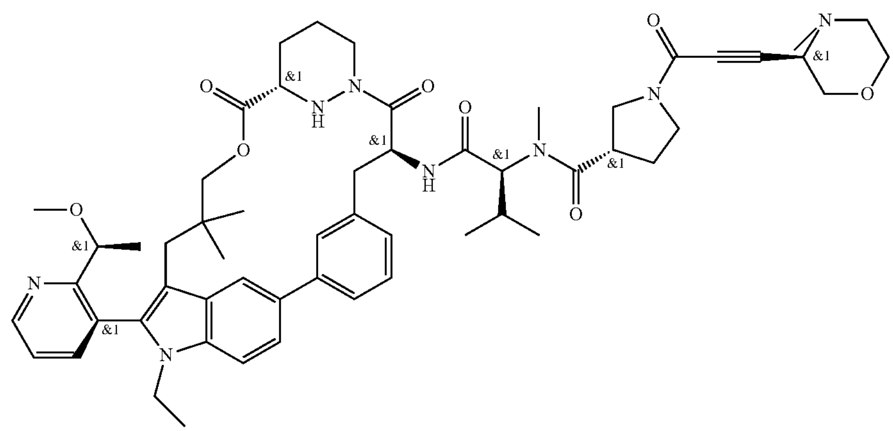 |
| B184 | 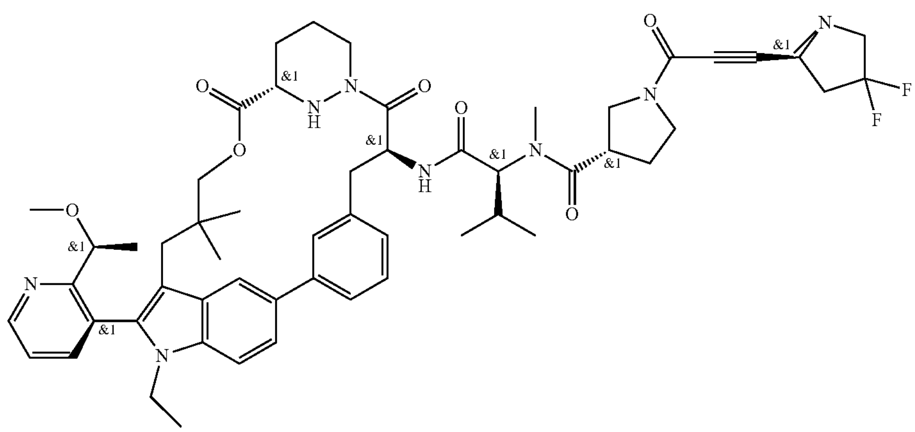 |
| B185 | 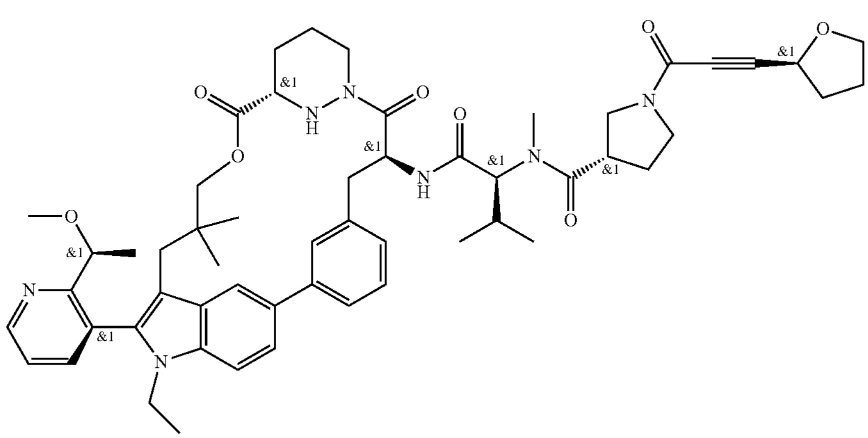 |

TABLE 2-continued
Certain Compounds of the Present Invention
| Ex # | Structure |
|---|---|
| B186 | 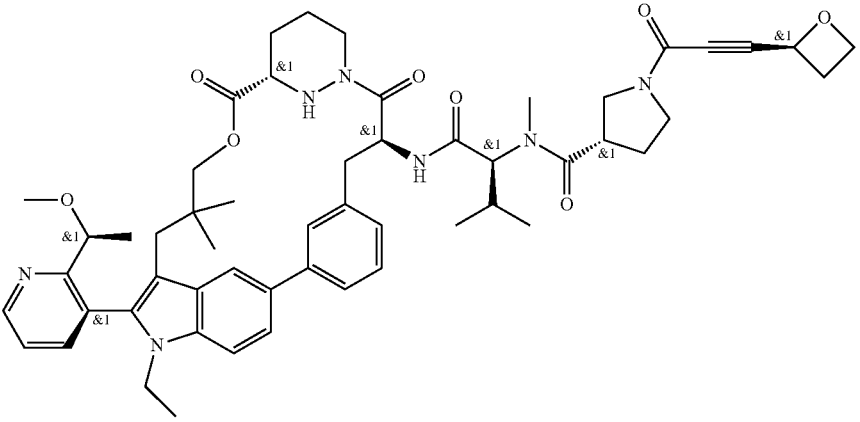 |
| B187 | 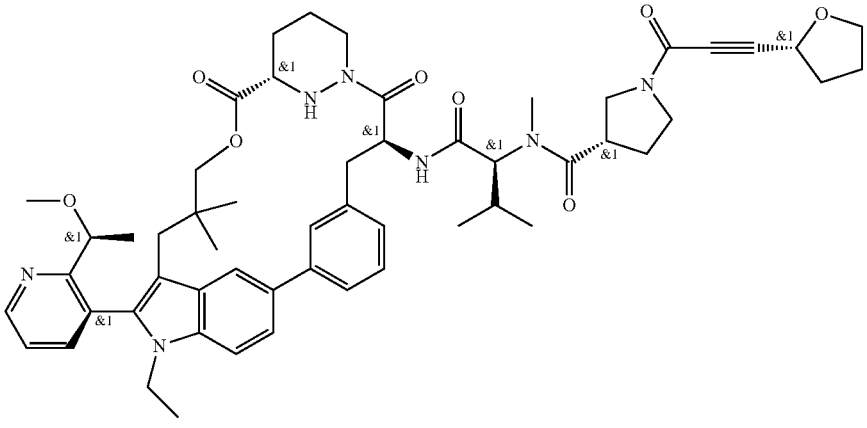 |
| B188 | 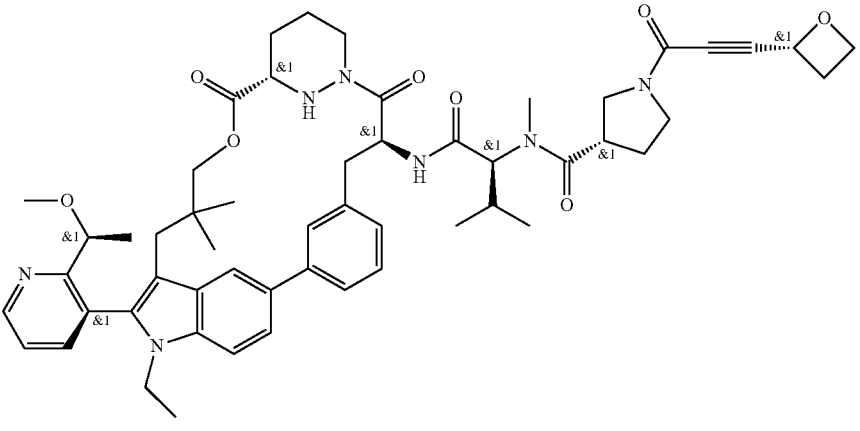 |

TABLE 2-continued

Certain Compounds of the Present Invention

| Ex # | Structure |
|---|---|
| B189 | 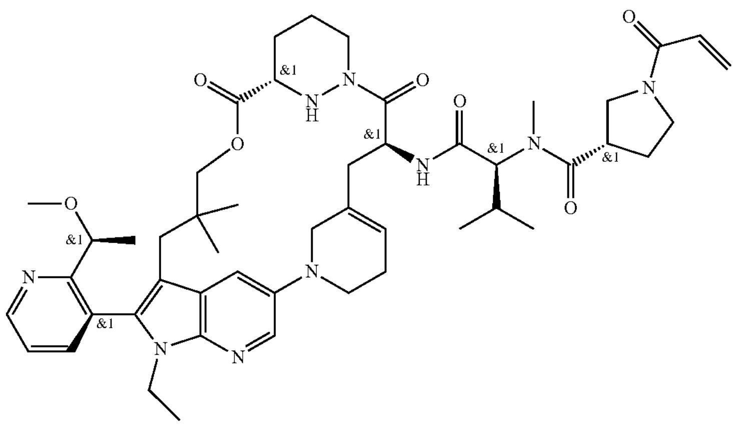 |
| B190 | 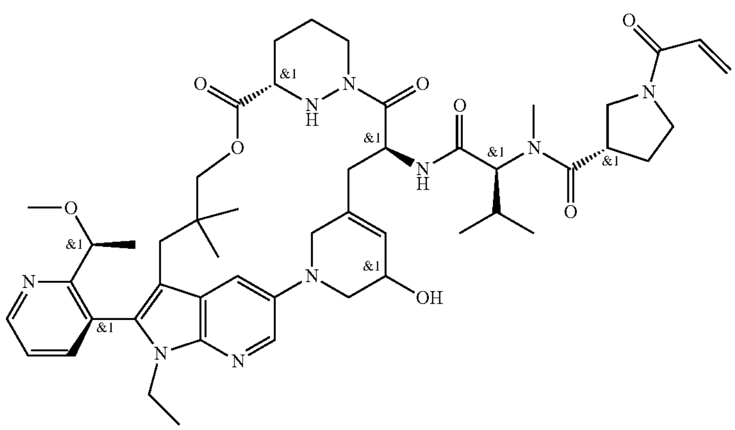 |
| B191 | 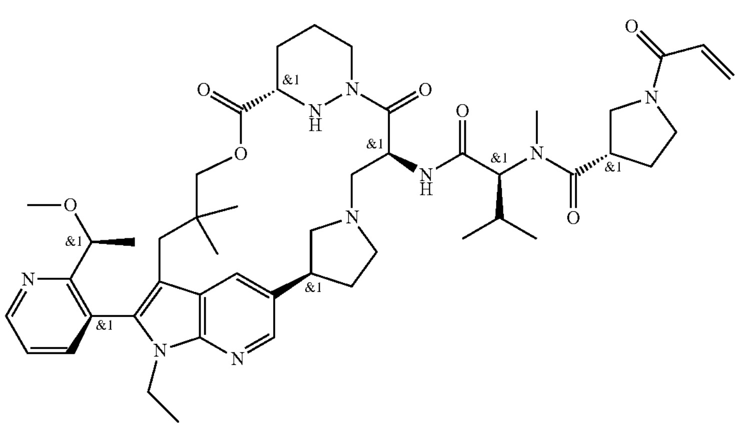 |

TABLE 2-continued

Certain Compounds of the Present Invention

| Ex # | Structure |
|---|---|
| B192 | 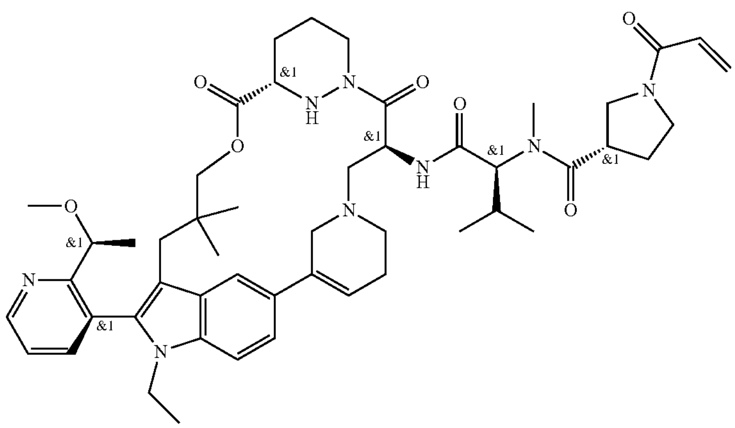 |
| B194 | 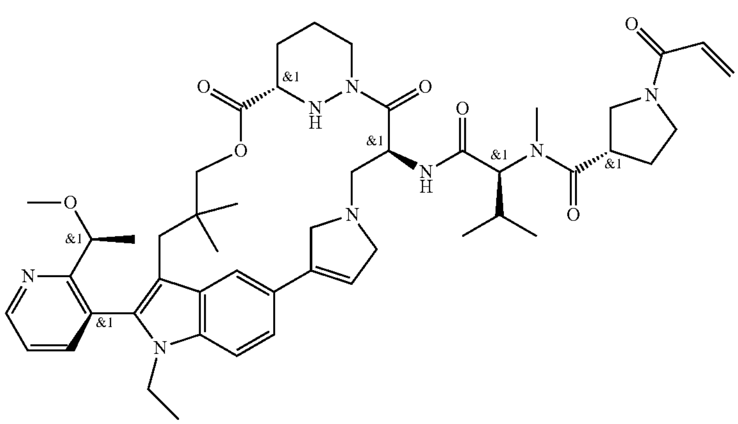 |
| B195 | 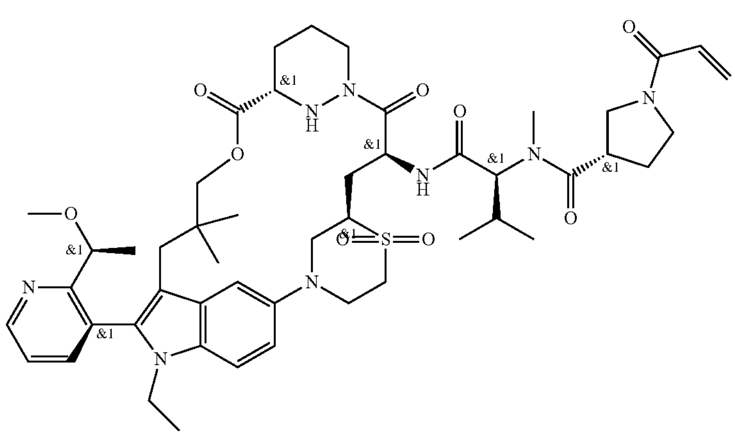 |

TABLE 2-continued

Certain Compounds of the Present Invention

| Ex # | Structure |
|---|---|
| B196 | 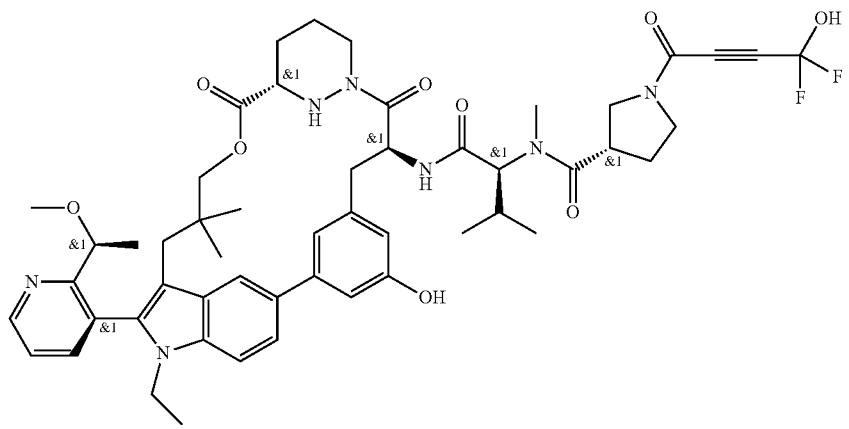 |
| B197 | 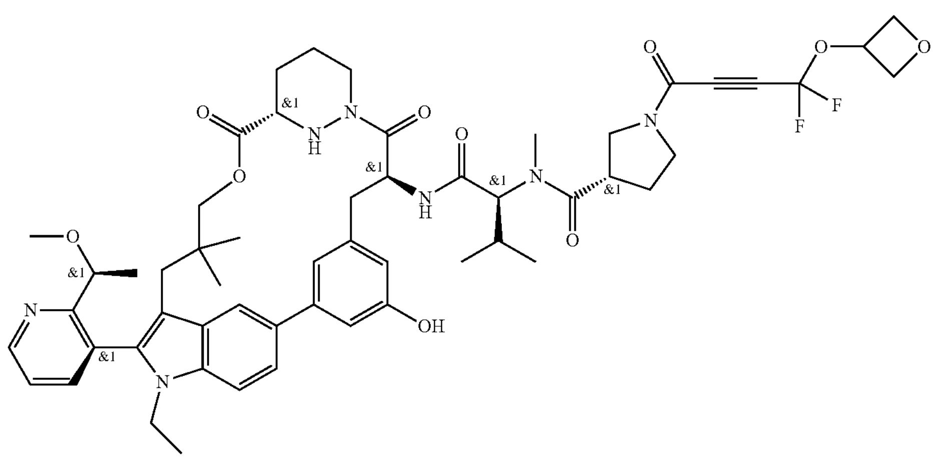 |
| B198 | 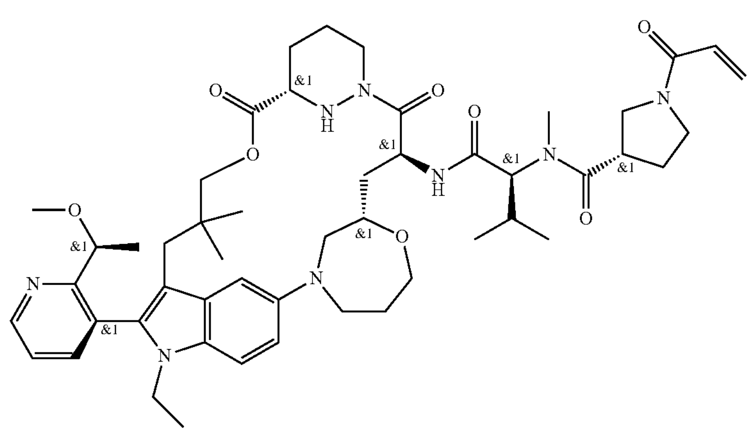 |

TABLE 2-continued

Certain Compounds of the Present Invention

| Ex # | Structure |
|------|-----------|
| B199 | 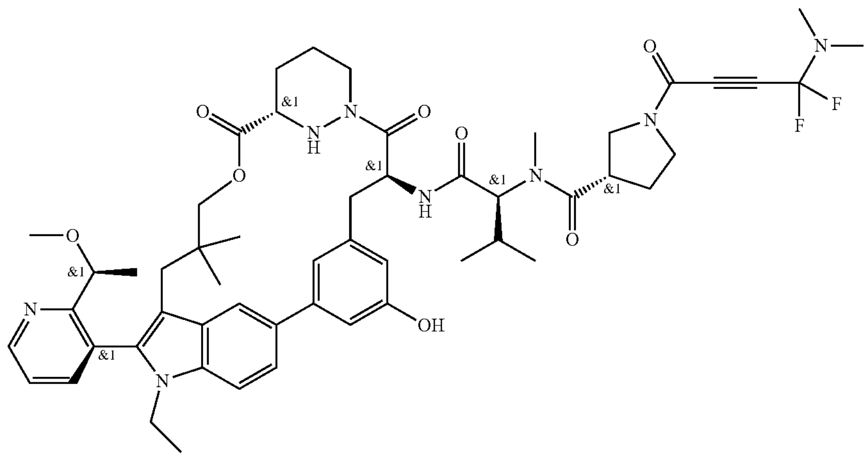 |
| B200 | 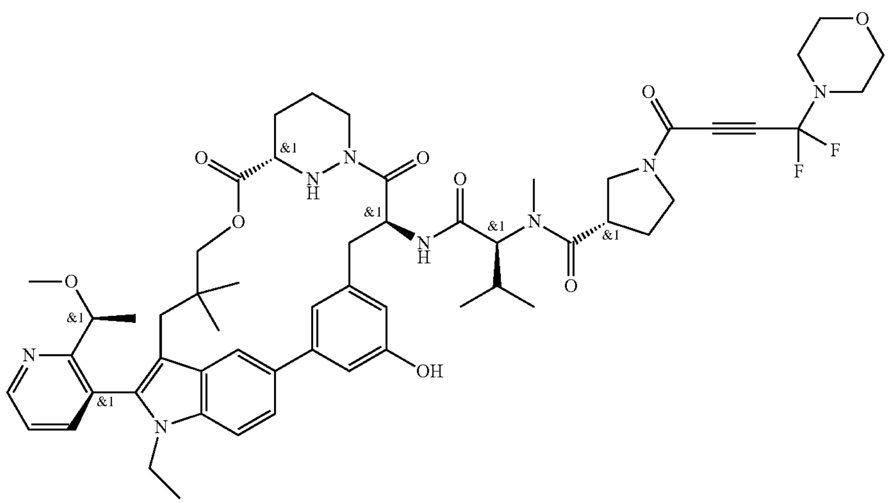 |
| B201 | 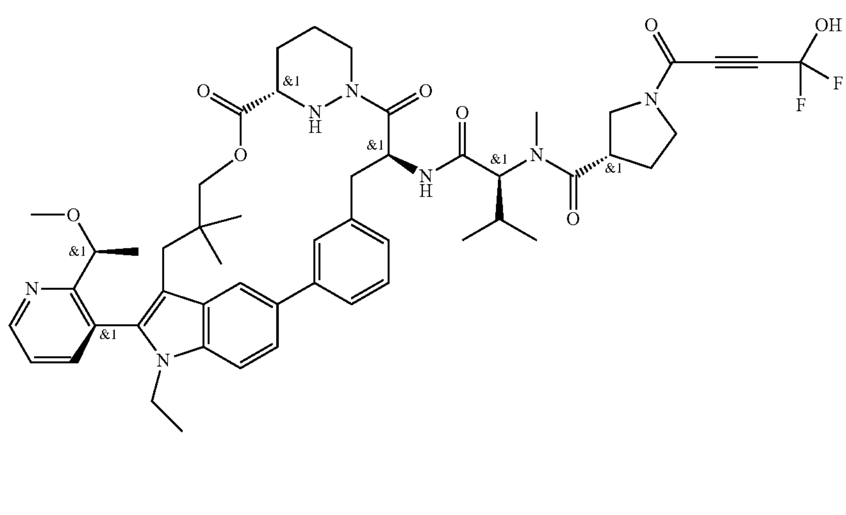 |

TABLE 2-continued
Certain Compounds of the Present Invention
| Ex # | Structure |
|---|---|
| B202 | 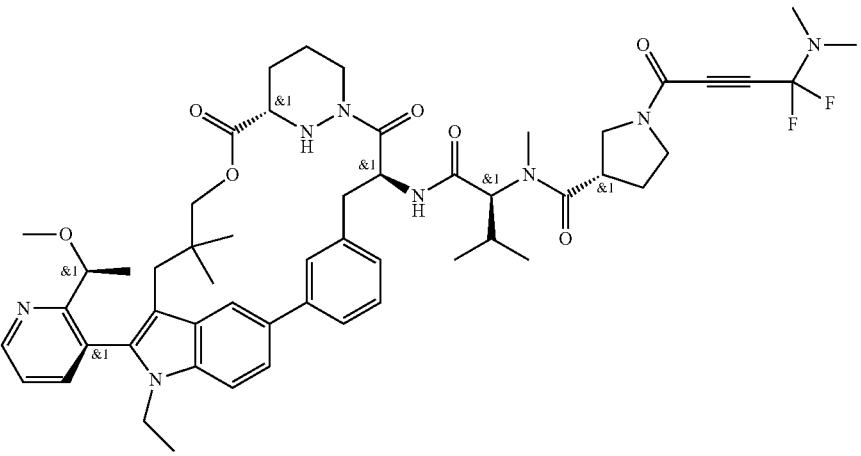 |
| B203 | 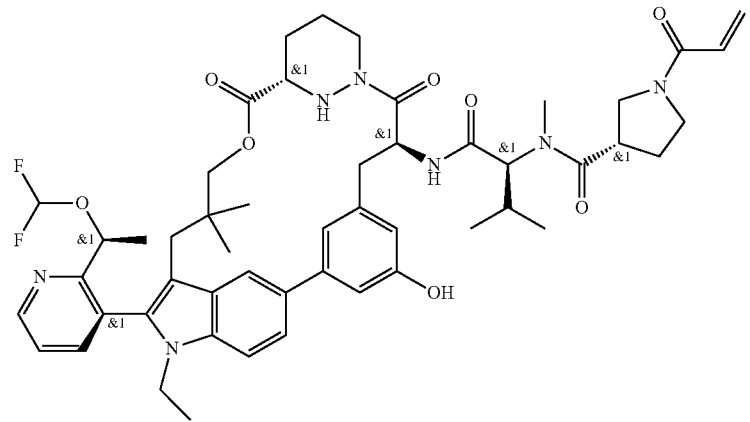 |
| B204 | 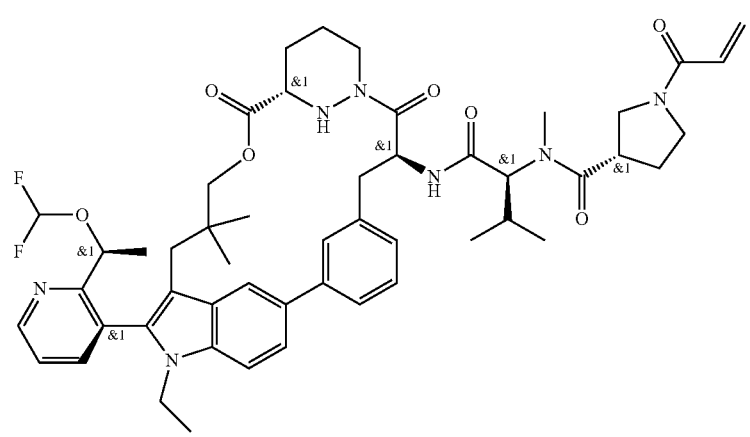 |

TABLE 2-continued

Certain Compounds of the Present Invention

| Ex # | Structure |
|---|---|
| B205 | 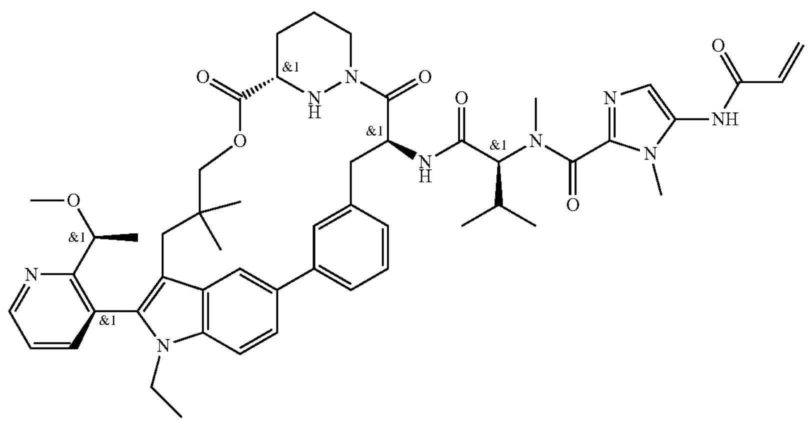 |
| B206 | 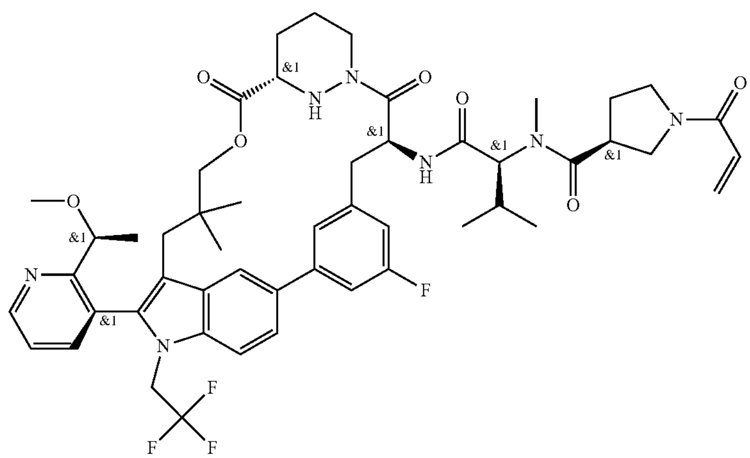 |
| B207 | 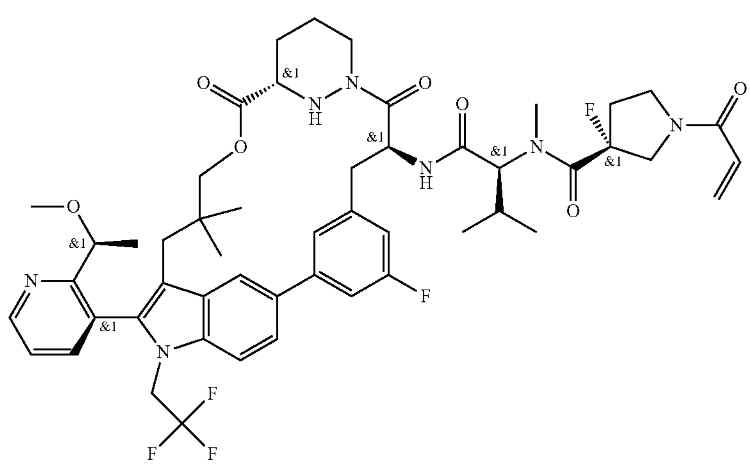 |

TABLE 2-continued

Certain Compounds of the Present Invention

| Ex # | Structure |
|------|-----------|
| B208 | 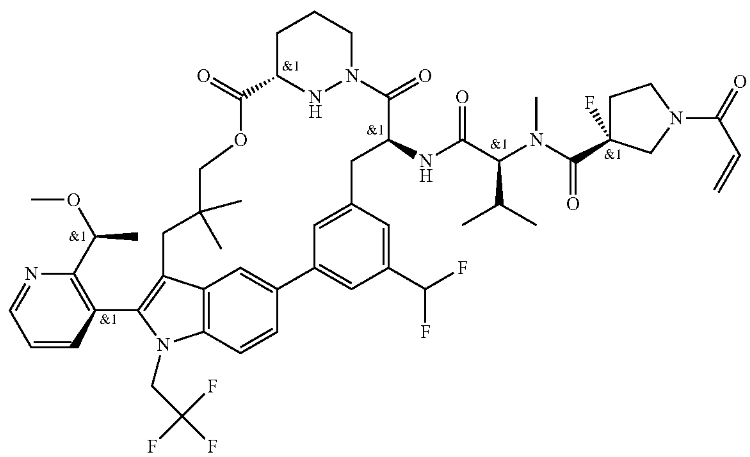 |
| B209 | 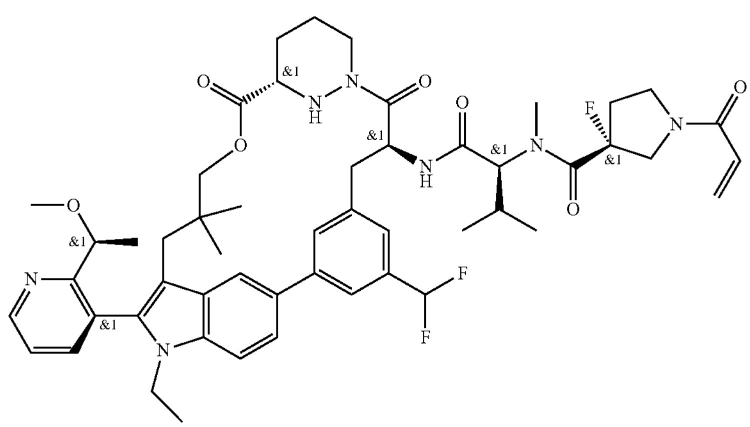 |
| B210 | 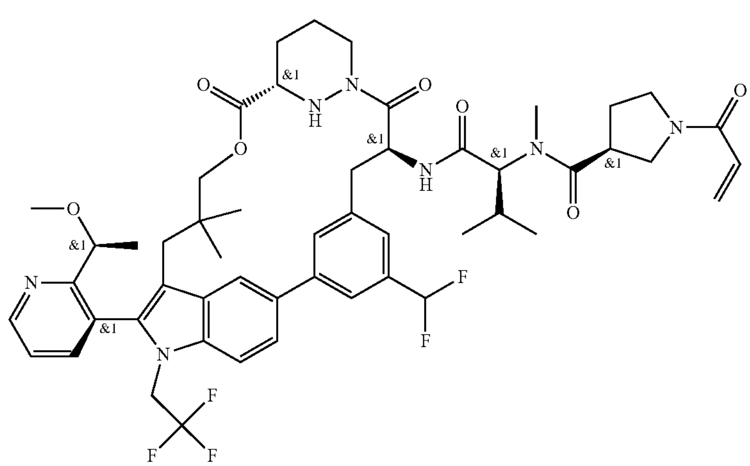 |

TABLE 2-continued

Certain Compounds of the Present Invention

| Ex # | Structure |
|------|-----------|
| B211 | 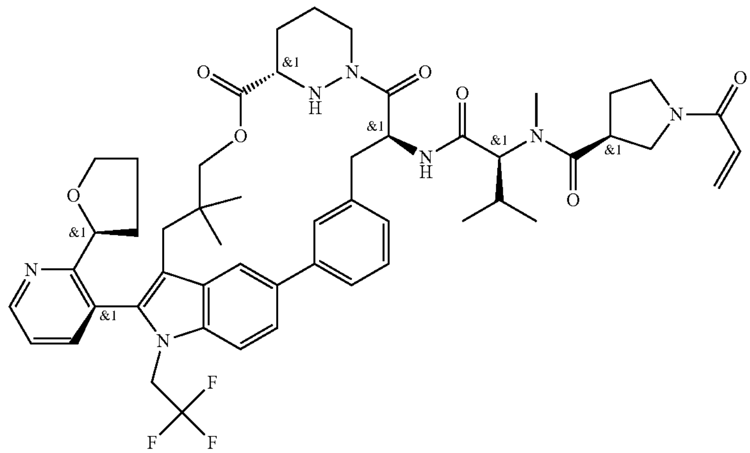 |
| B212 | 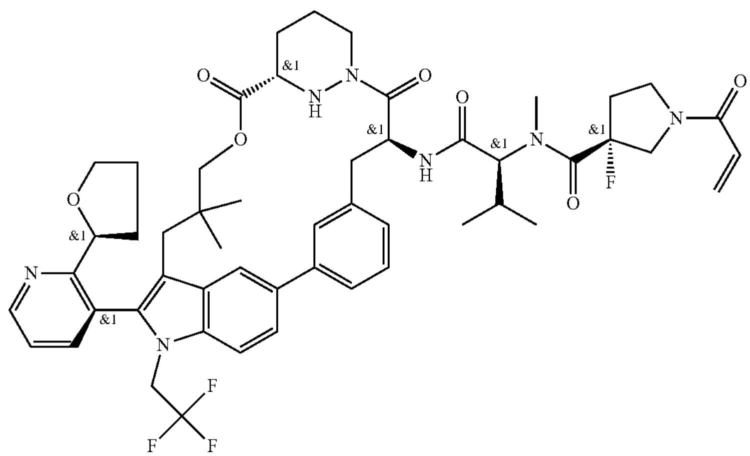 |
| B213 | 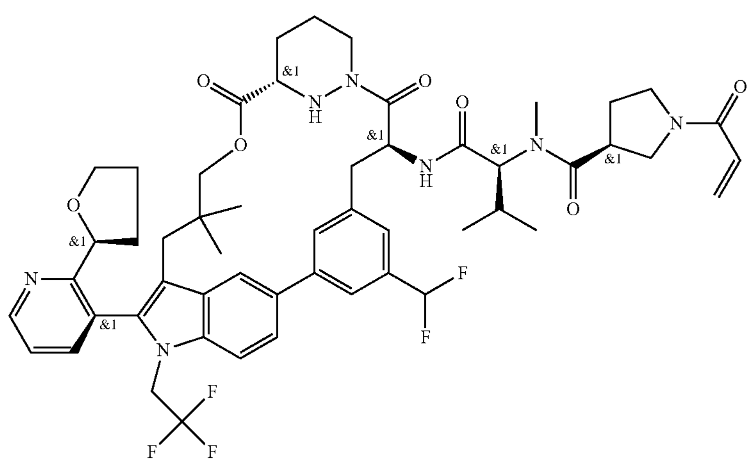 |

TABLE 2-continued
Certain Compounds of the Present Invention
| Ex # | Structure |
|---|---|
| B214 | 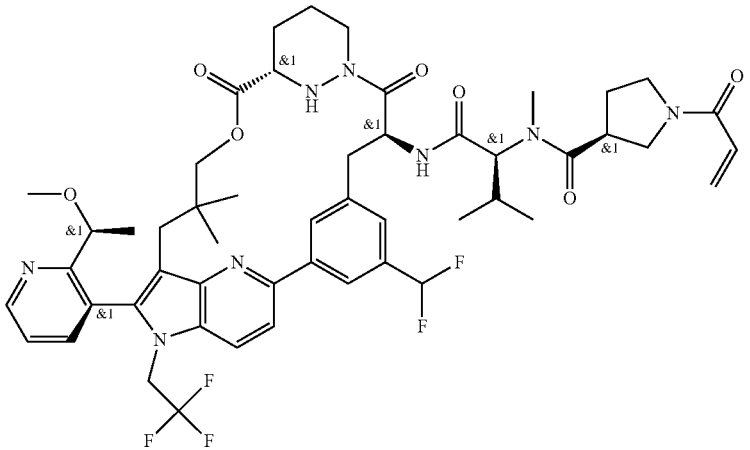 |
| B215 | 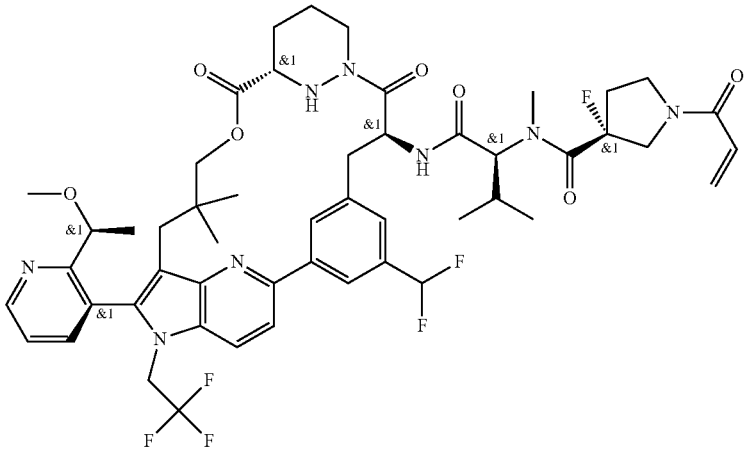 |
| B216 | 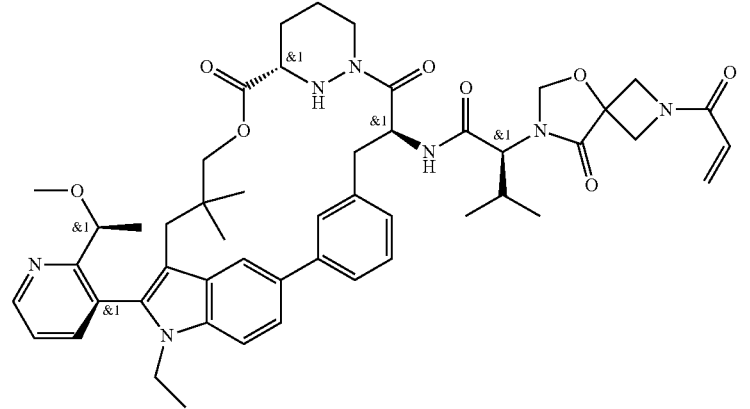 |

TABLE 2-continued
Certain Compounds of the Present Invention
| Ex # | Structure |
|---|---|
| B217 | 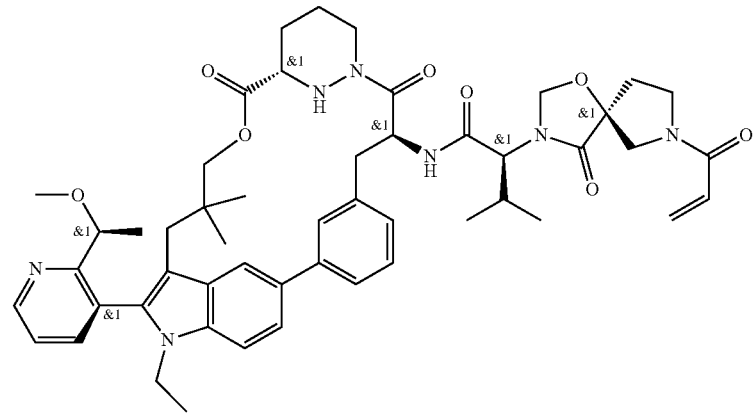 |
| B218 | 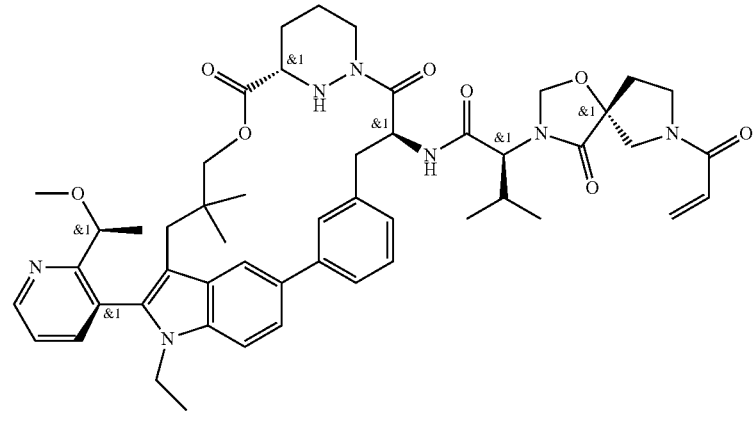 |
| B219 | 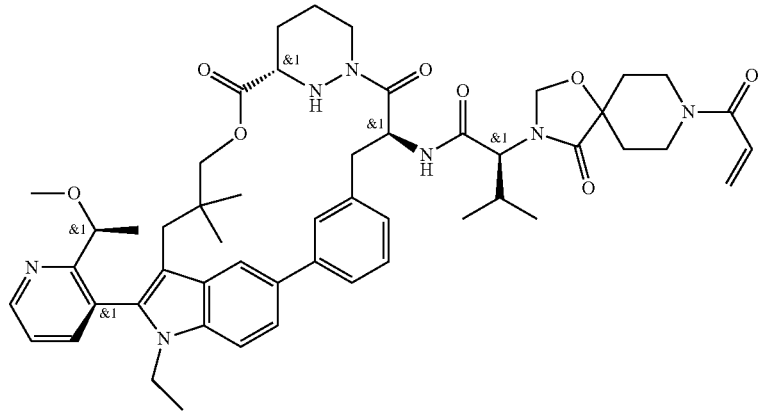 |

TABLE 2-continued

Certain Compounds of the Present Invention

| Ex # | Structure |
|---|---|
| B220 | 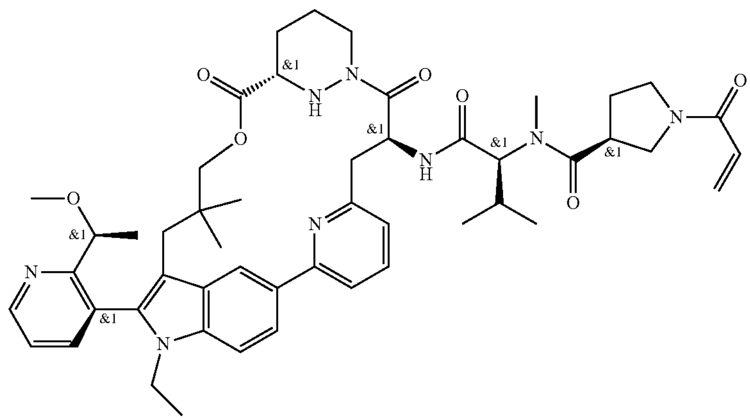 |
| B221 | 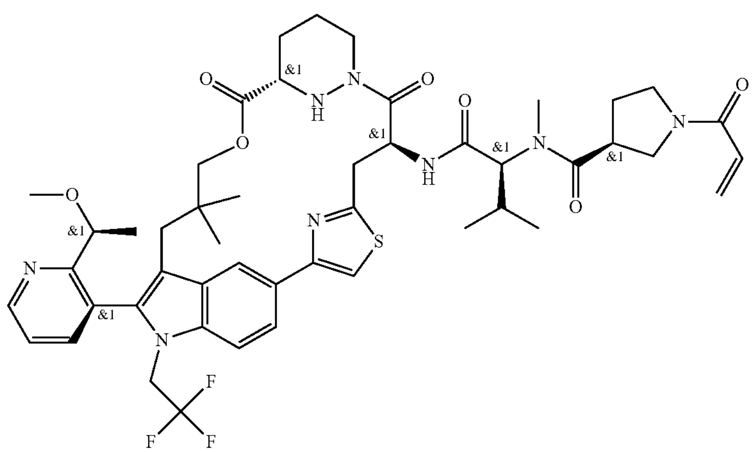 |
| B222 | 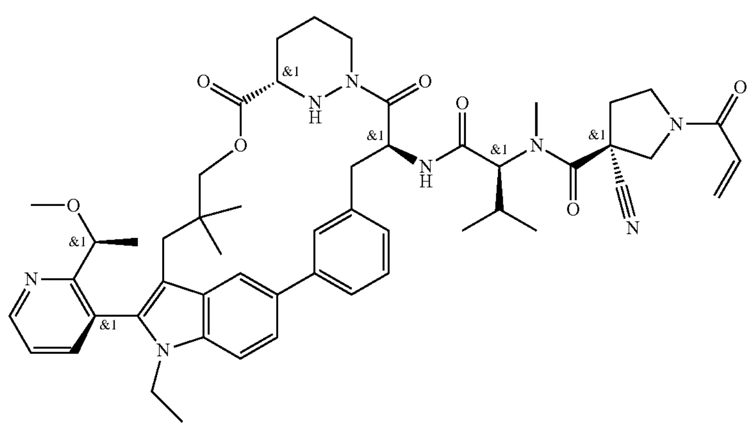 |

TABLE 2-continued

Certain Compounds of the Present Invention

| Ex # | Structure |
| --- | --- |
| B223 | 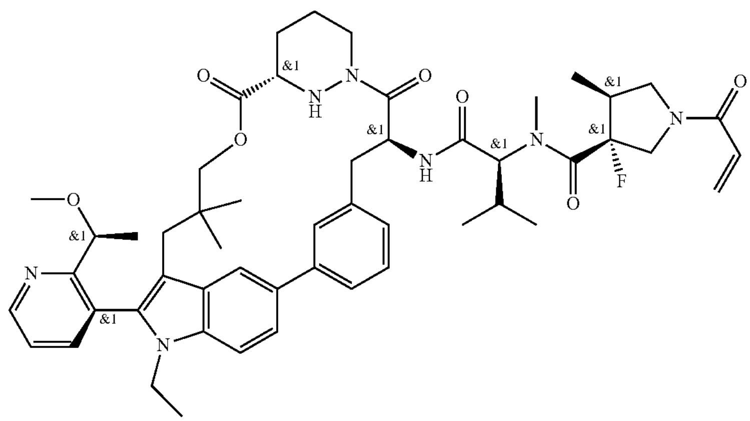 |
| B224 | 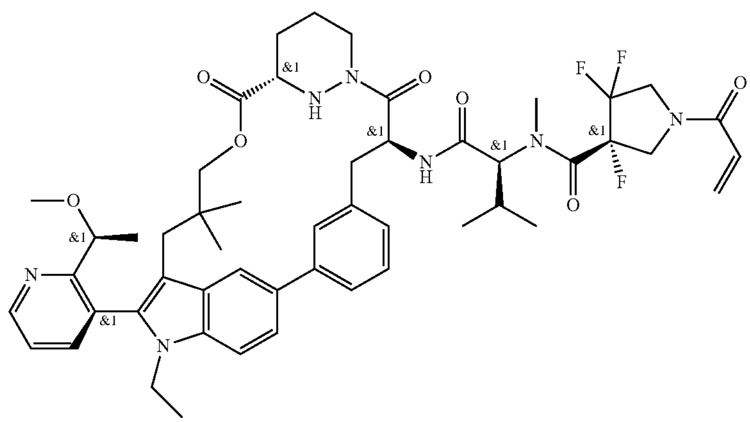 |
| B225 | 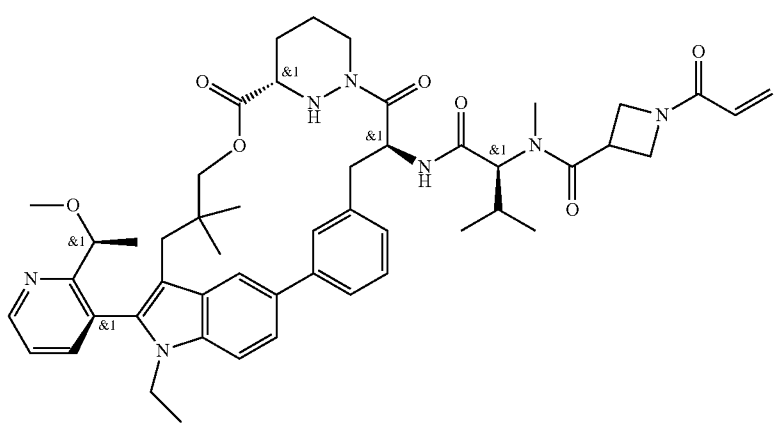 |

TABLE 2-continued
Certain Compounds of the Present Invention
| Ex # | Structure |
|---|---|
| B226 | 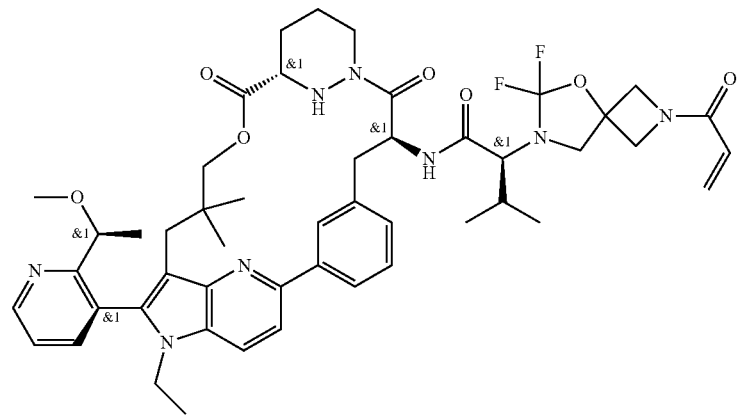 |
| B227 | 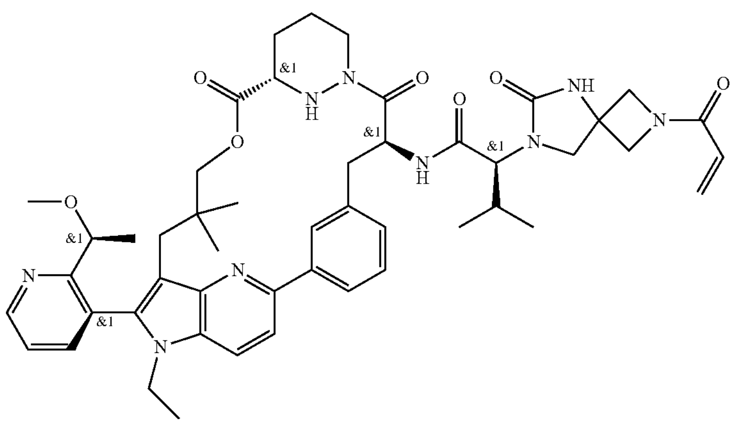 |
| B228 | 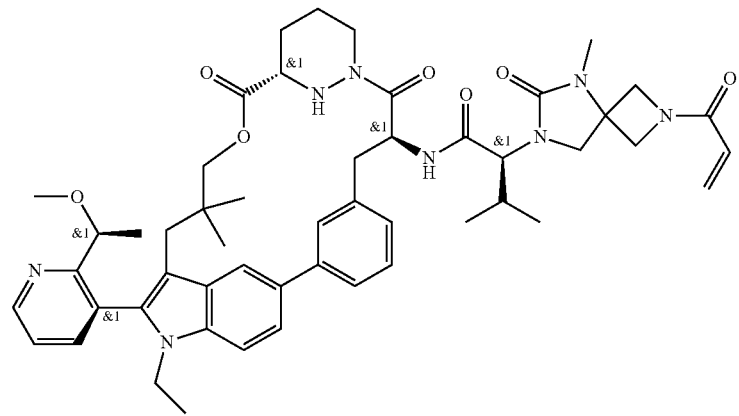 |

TABLE 2-continued

Certain Compounds of the Present Invention

| Ex # | Structure |
|------|-----------|
| B229 | 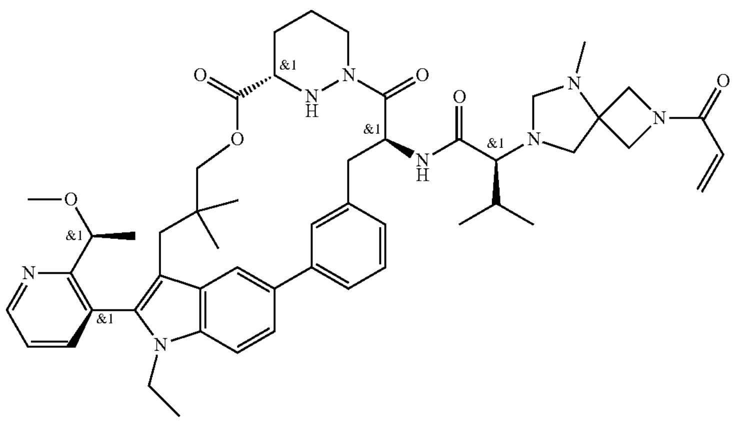 |
| B230 | 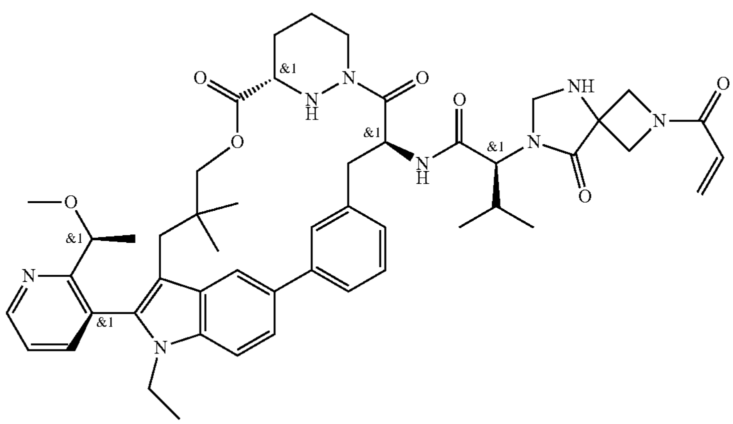 |
| B231 | 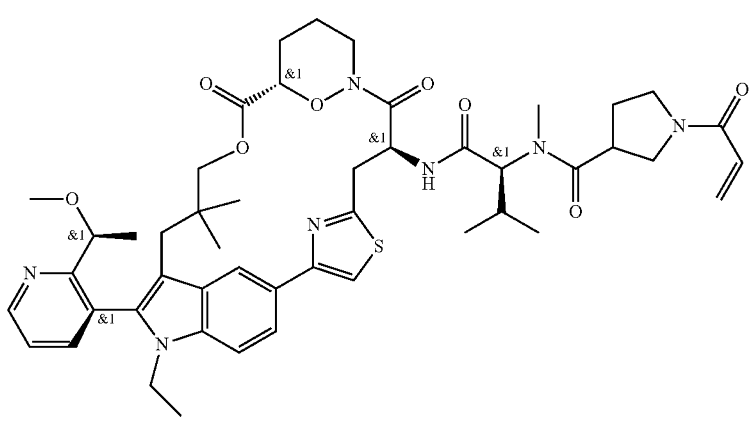 |

TABLE 2-continued
Certain Compounds of the Present Invention
| Ex # | Structure |
|---|---|
| B232 | 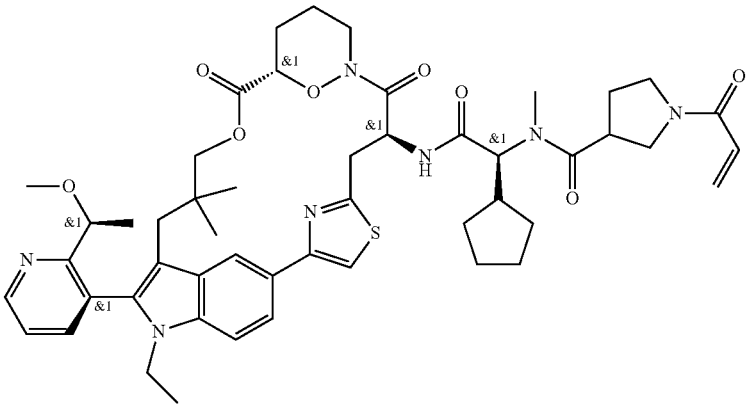 |
| B233 | 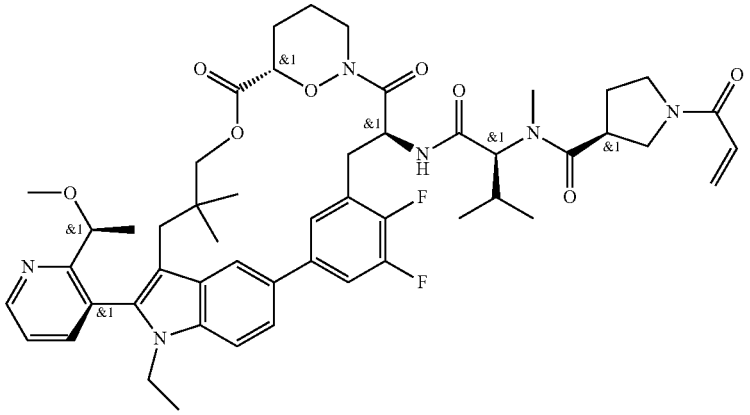 |
| B234 | 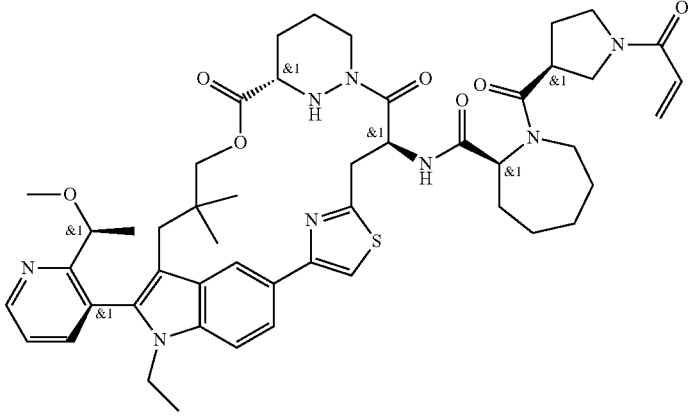 |

TABLE 2-continued
Certain Compounds of the Present Invention
| Ex # | Structure |
|---|---|
| B235 | 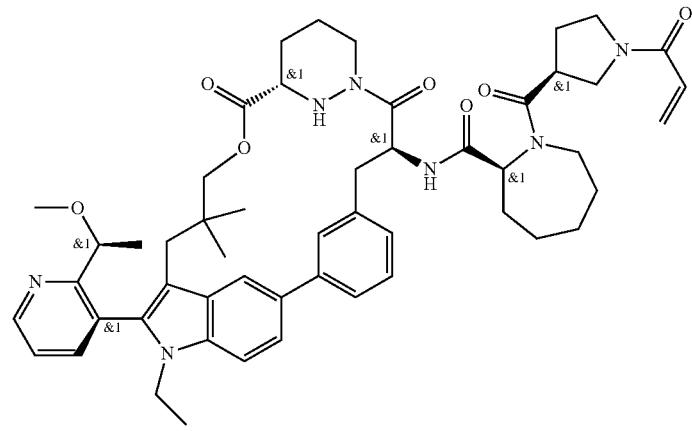 |
| B236 | 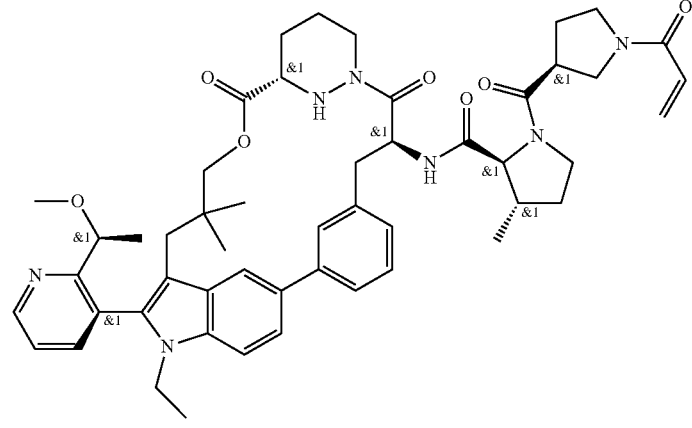 |
| B237 | 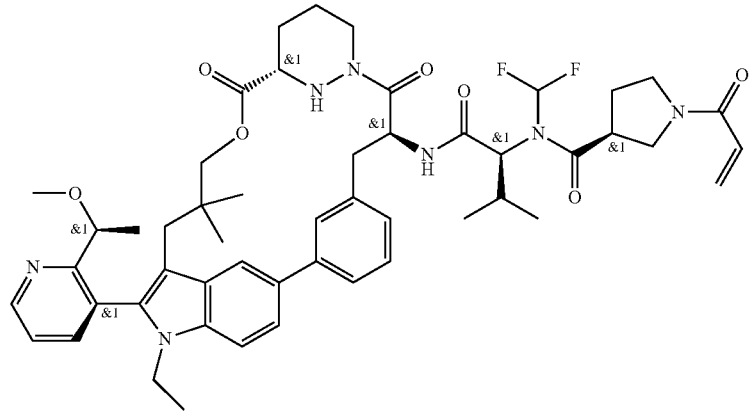 |

TABLE 2-continued

Certain Compounds of the Present Invention

| Ex # | Structure |
|------|-----------|
| B238 | 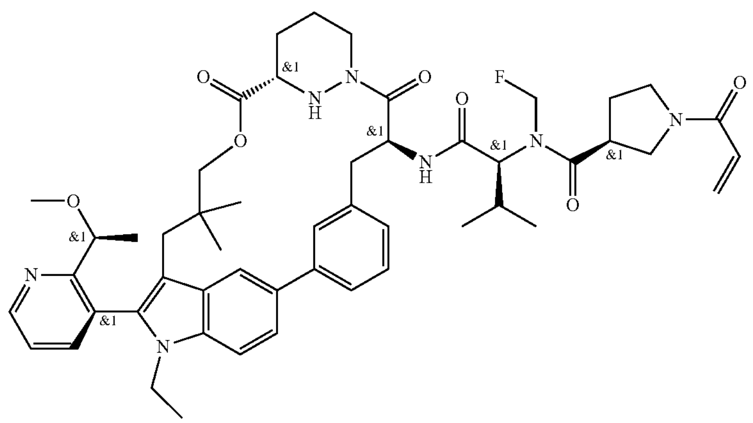 |
| B239 | 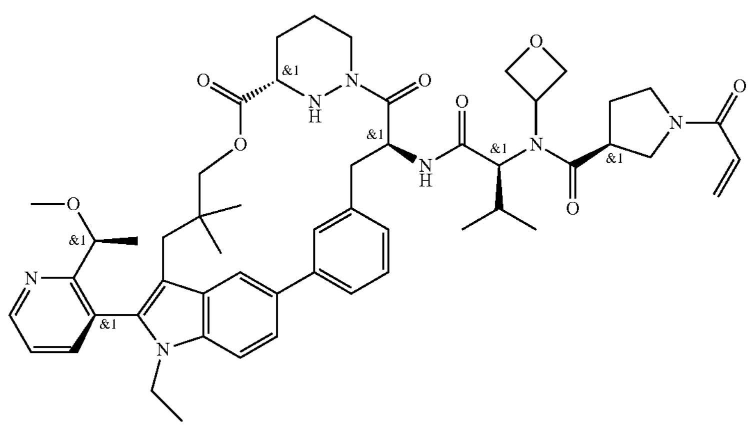 |
| B240 | 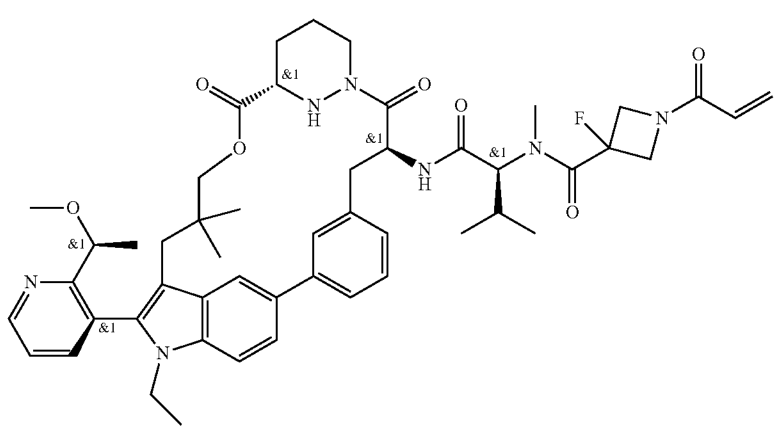 |

TABLE 2-continued
Certain Compounds of the Present Invention
| Ex # | Structure |
|---|---|
| B241 | 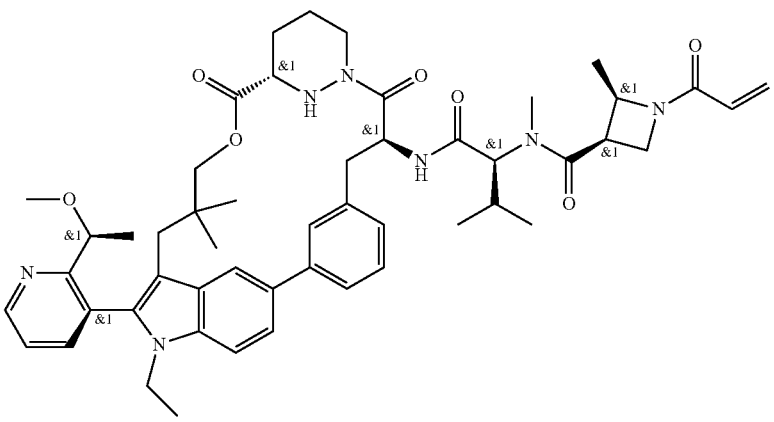 |
| B242 | 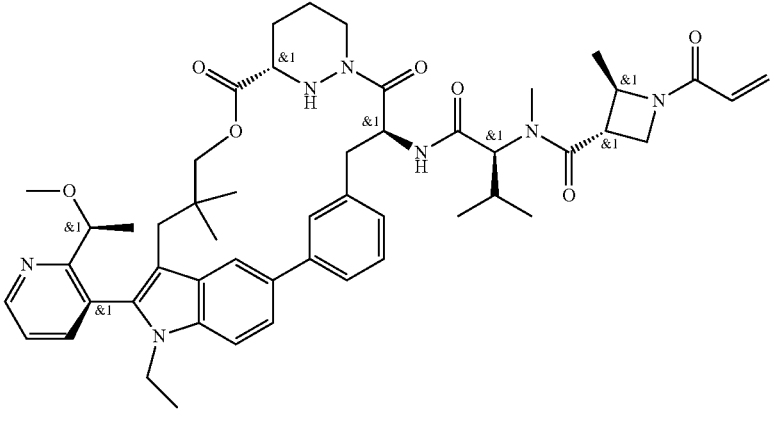 |
| B243 | 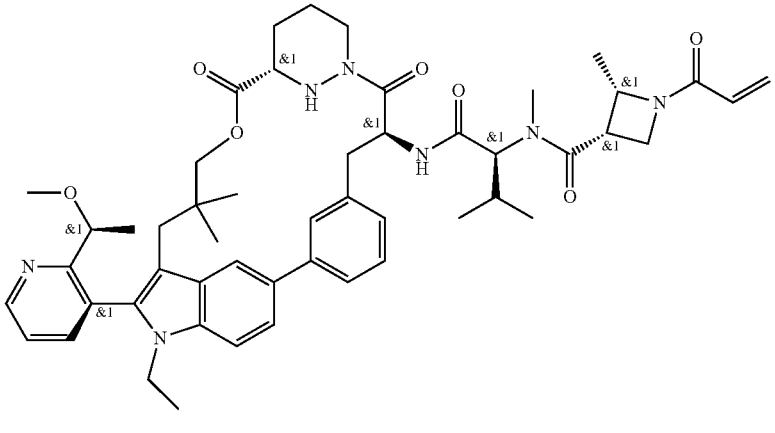 |

TABLE 2-continued
Certain Compounds of the Present Invention
| Ex # | Structure |
|---|---|
| B244 | 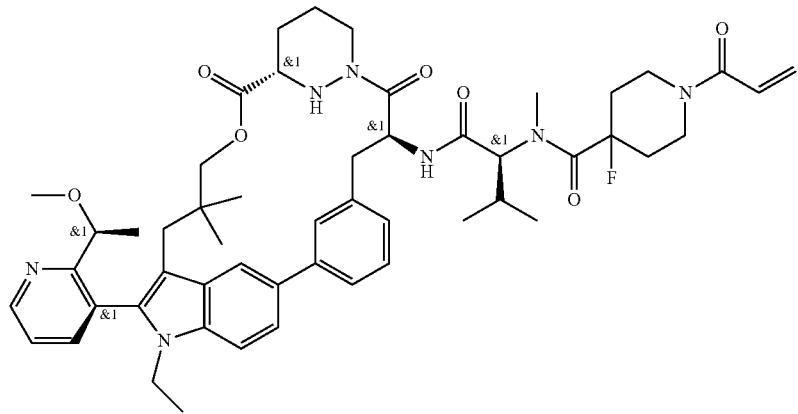 |
| B245 | 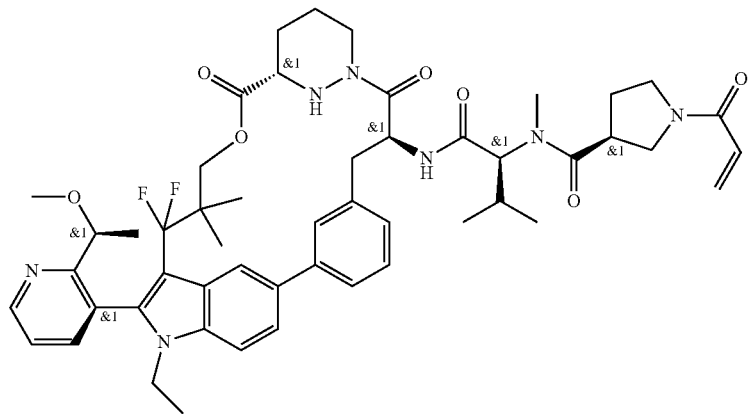 |
| B246 | 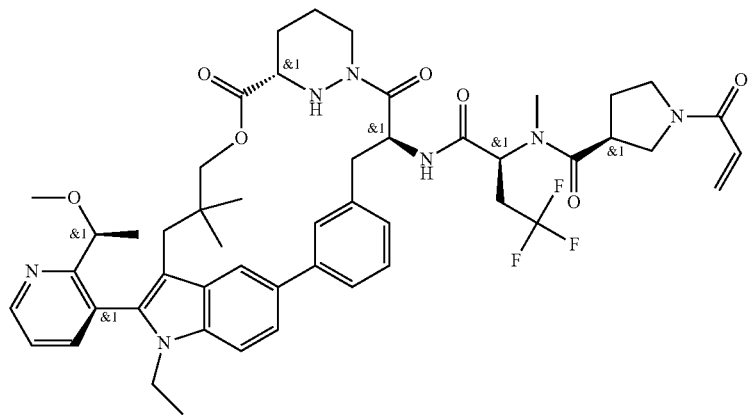 |

TABLE 2-continued
Certain Compounds of the Present Invention
| Ex # | Structure |
|---|---|
| B247 | 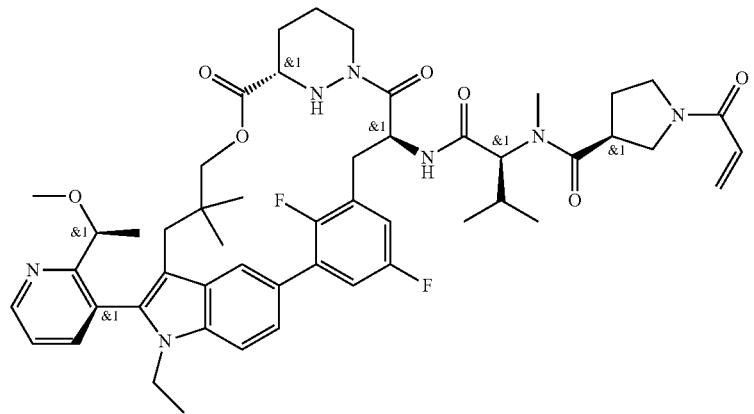 |
| B248 | 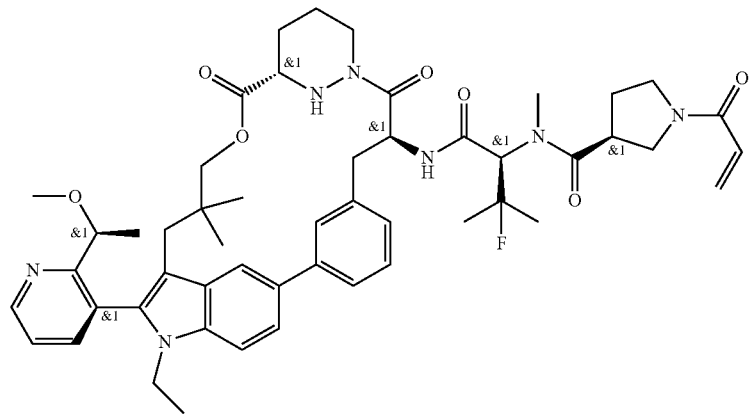 |
| B249 | 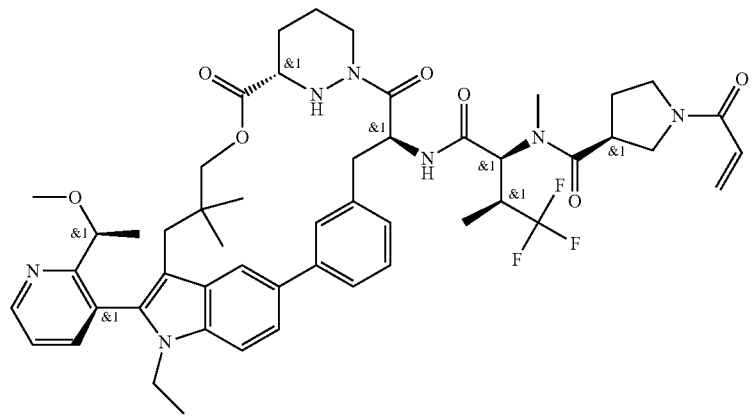 |

TABLE 2-continued
Certain Compounds of the Present Invention
| Ex # | Structure |
|---|---|
| B250 | 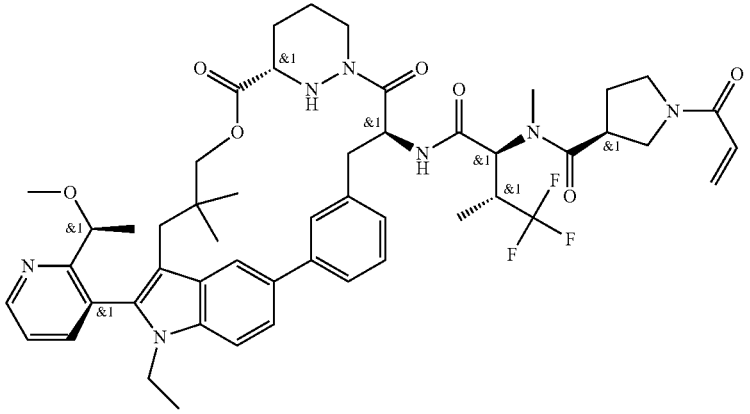 |
| B251 | 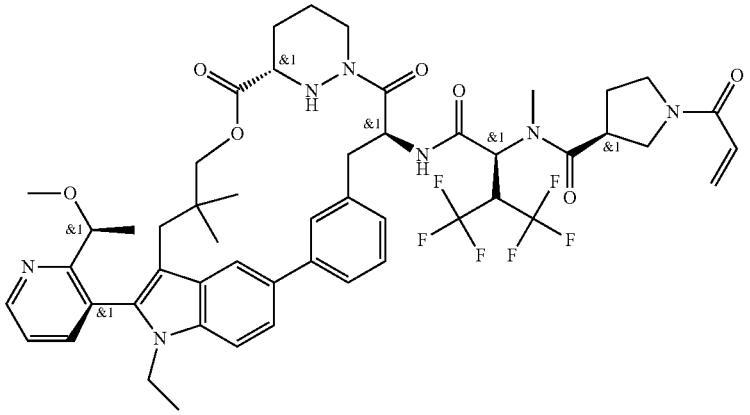 |
| B252 | 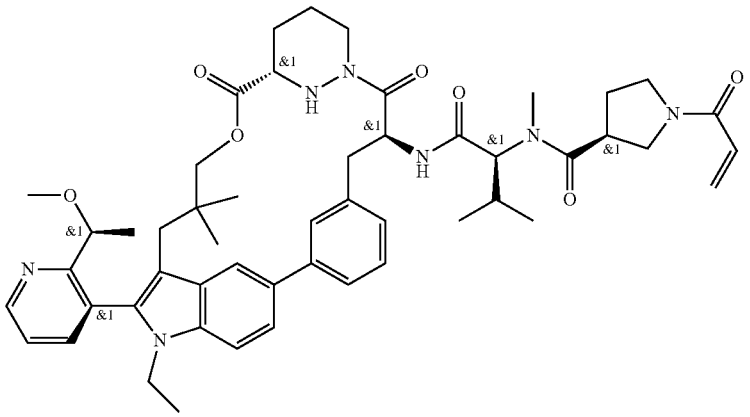 |

TABLE 2-continued
Certain Compounds of the Present Invention
| Ex # | Structure |
|---|---|
| B253 | 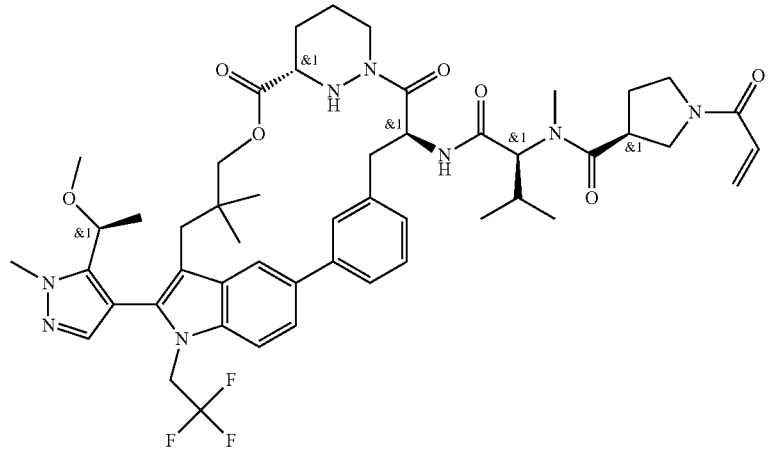 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)OC)n4CC(F)(F)F)CC(C)(C)COC(=O)[C@@H]3CCCN(N3)C2=O)C(C)C)C1] |
| B254 | 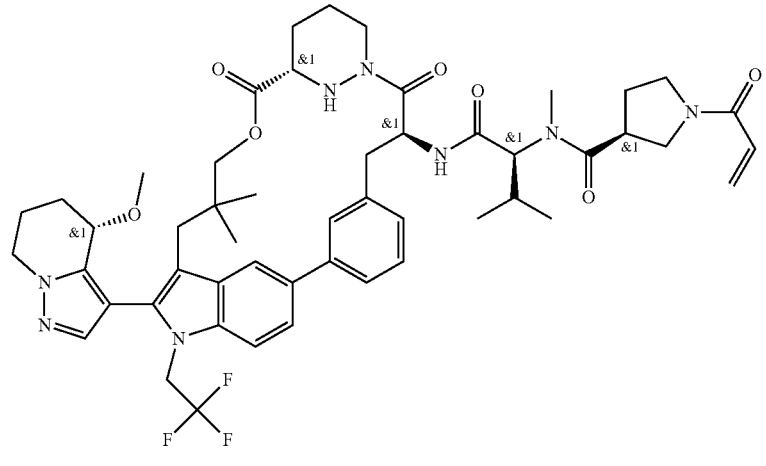 [SMILES: C=CC(=O)N1CC[C@H](C(=O)N(C)[C@H](C(=O)N[C@H]2Cc3cccc(c3)-c3ccc4c(c3)c(c(-c3cnn5c3[C@@H](OC)CCC5)n4CC(F)(F)F)CC(C)(C)COC(=O)[C@@H]3CCCN(N3)C2=O)C(C)C)C1] |
| B255 | 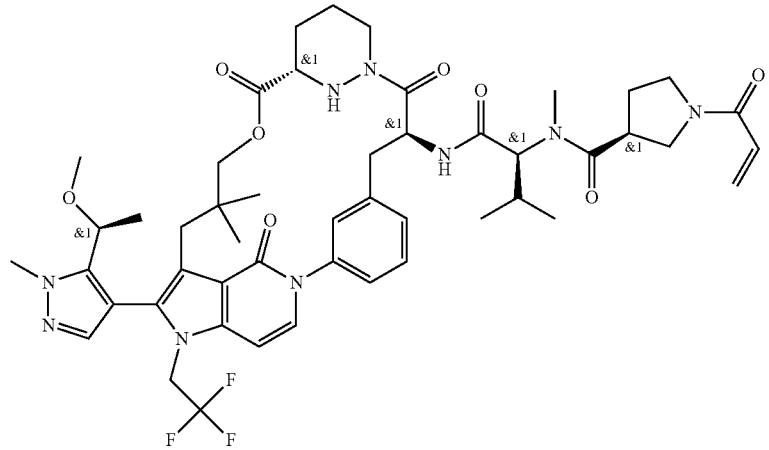 [SMILES: C=CC(=O)N1CC[C@H](C(=O)N(C)[C@H](C(=O)N[C@H]2Cc3cccc(c3)-n3ccc4c(c(c(-c5cnn(C)c5[C@H](C)OC)n4CC(F)(F)F)CC(C)(C)COC(=O)[C@@H]4CCCN(N4)C2=O)c3=O)C(C)C)C1] |

TABLE 2-continued

Certain Compounds of the Present Invention

| Ex # | Structure |
| --- | --- |
| B256 | 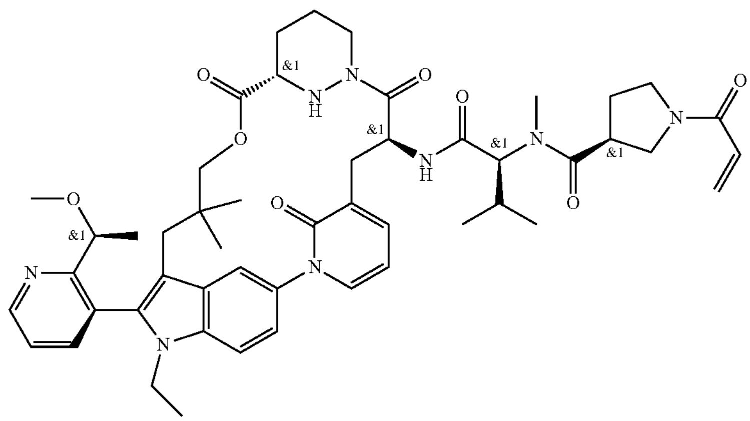 |
| B257 | 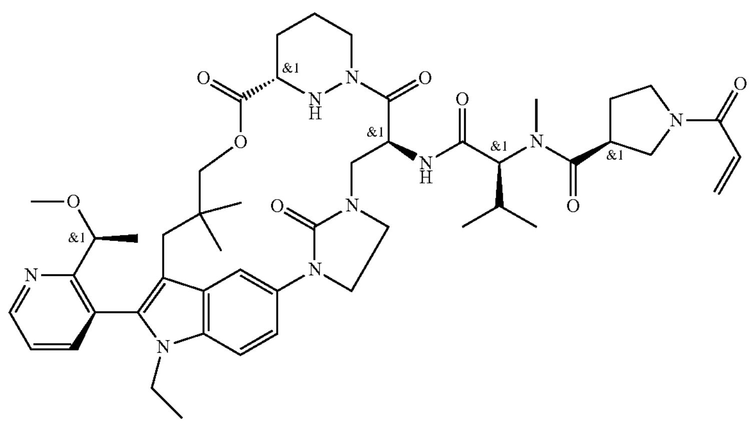 |
| B258 | 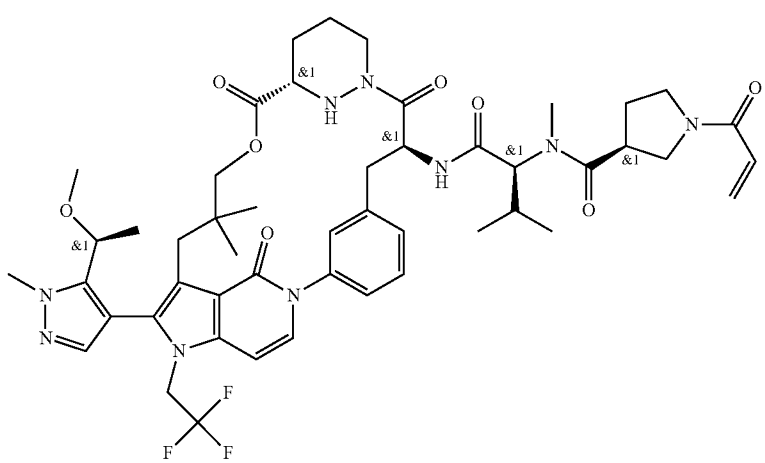 [SMILES: C=CC(=O)N1CC[C@H](C(=O)N(C)[C@H](C(=O)N[C@H]2Cc3cccc(c3)-n3ccc4c(c(c(-c5cnn(C)c5[C@H](C)OC)n4CC(F)(F)F)CC(C)(C)COC(=O)[C@@H]4CCCN(N4)C2=O)c3=O)C(C)C)C1] |

TABLE 2-continued
Certain Compounds of the Present Invention
| Ex # | Structure |
|---|---|
| B259 | 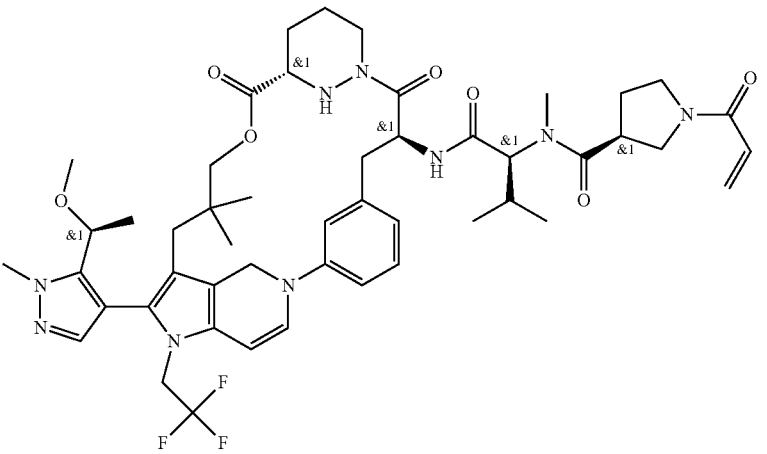 [SMILES: C=CC(=O)N1CC[C@H](C(=O)N(C)[C@H](C(=O)N[C@H]2Cc3cccc(c3)N3C=Cc4c(c(c(-c5cnn(C)c5[C@H](C)OC)n4CC(F)(F)F)CC(C)(C)COC(=O)[C@@H]4CCCN(N4)C2=O)C3)C(C)C)C1] |
| B260 | 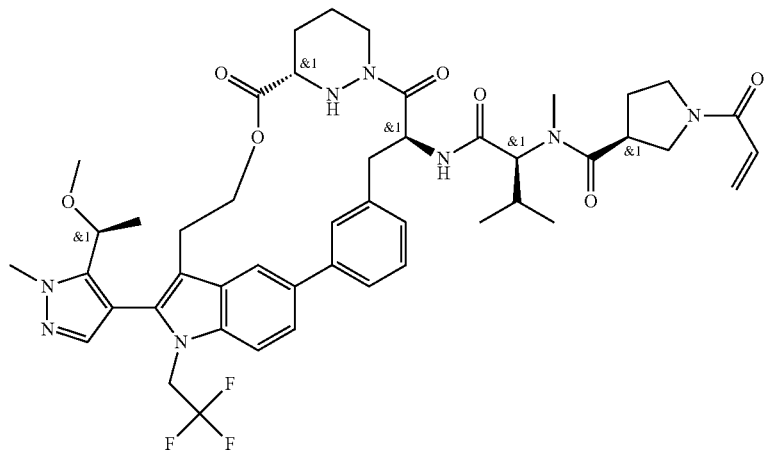 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)OC)n4CC(F)(F)F)CCOC(=O)[C@@H]3CCCN(N3)C2=O)C(C)C)C1] |
| B261 | 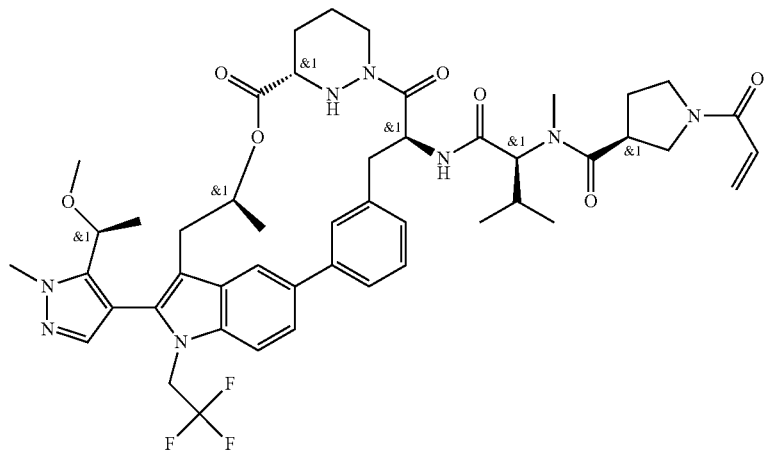 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)OC)n4CC(F)(F)F)C[C@H](C)OC(=O)[C@@H]3CCCN(N3)C2=O)C(C)C)C1] |

TABLE 2-continued

Certain Compounds of the Present Invention

| Ex # | Structure |
|---|---|
| B262 | 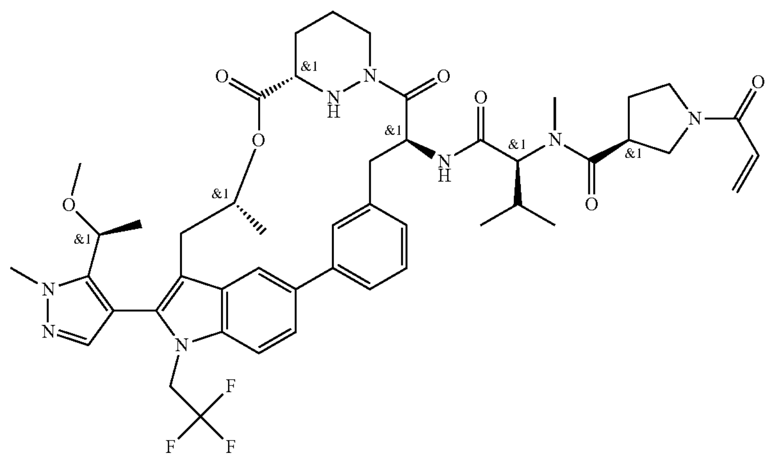 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)OC)n4CC(F)(F)F)C[C@@H](C)OC(=O)[C@@H]3CCCN(N3)C2=O)C(C)C)C1] |
| B263 | 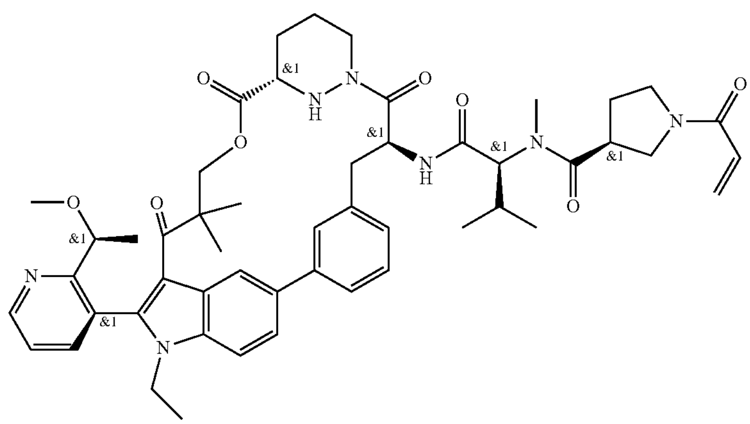 |
| B264 | 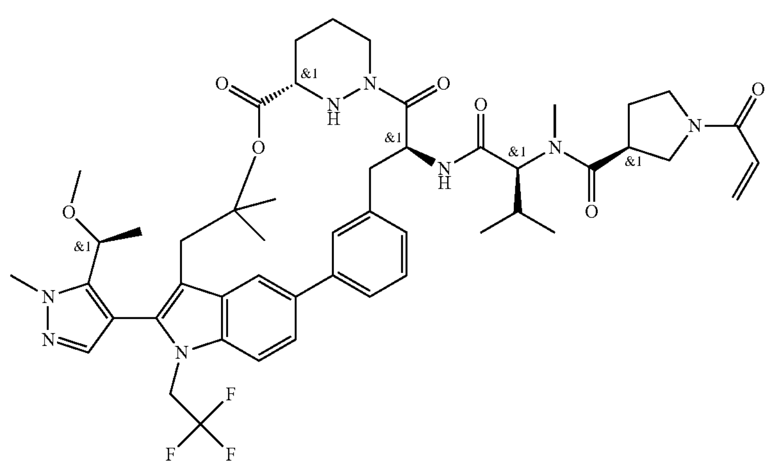 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)OC)n4CC(F)(F)F)CC(C)(C)OC(=O)[C@@H]3CCCN(N3)C2=O)C(C)C)C1] |

TABLE 2-continued
Certain Compounds of the Present Invention
| Ex # | Structure |
|---|---|
| B265 | 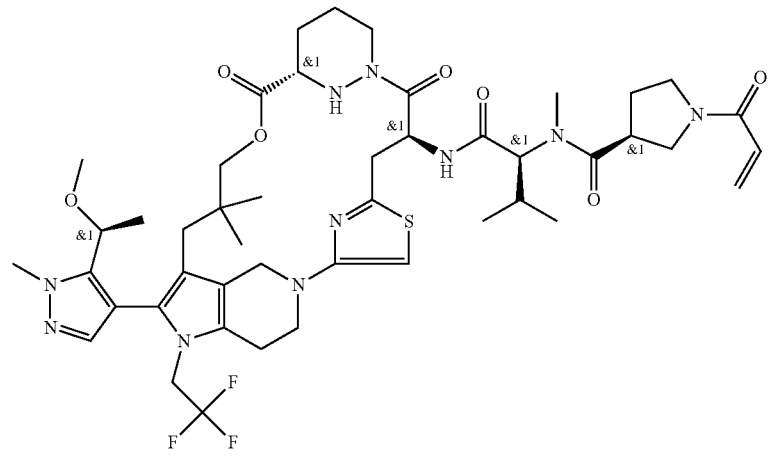 [SMILES: C=CC(=O)N1CC[C@H](C(=O)N(C)[C@H](C(=O)N[C@H]2Cc3nc(cs3)N3CCc4c(c(c(-c5cnn(C)c5[C@H](C)OC)n4CC(F)(F)F)CC(C)(C)COC(=O)[C@@H]4CCCN(N4)C2=O)C3)C(C)C)C1] |
| B266 | 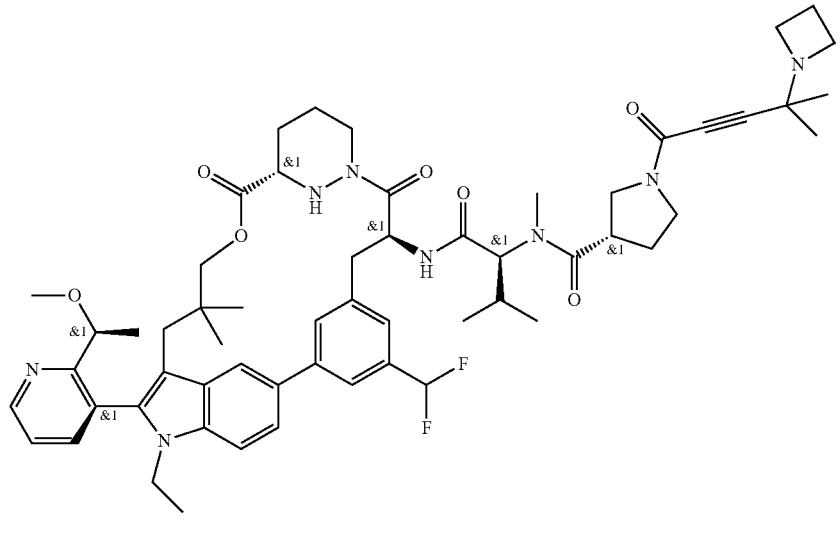 |
| B267 | 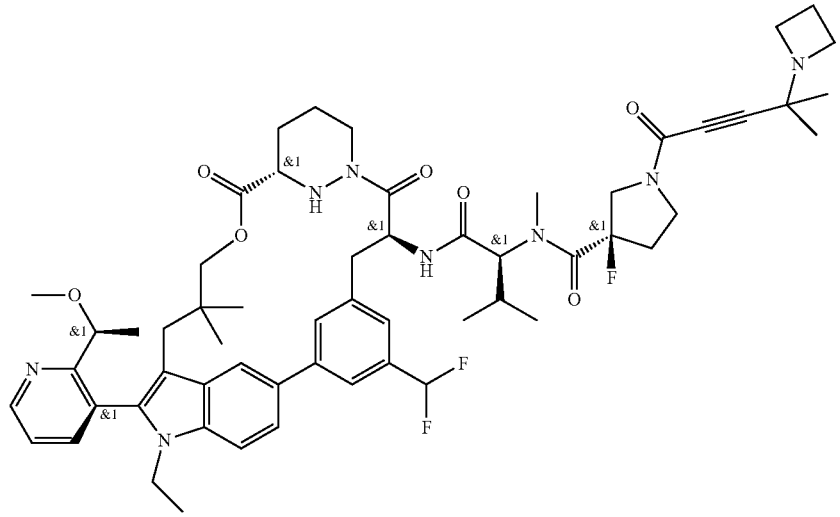 |

TABLE 2-continued

Certain Compounds of the Present Invention

| Ex # | Structure |
|------|-----------|
| B268 | 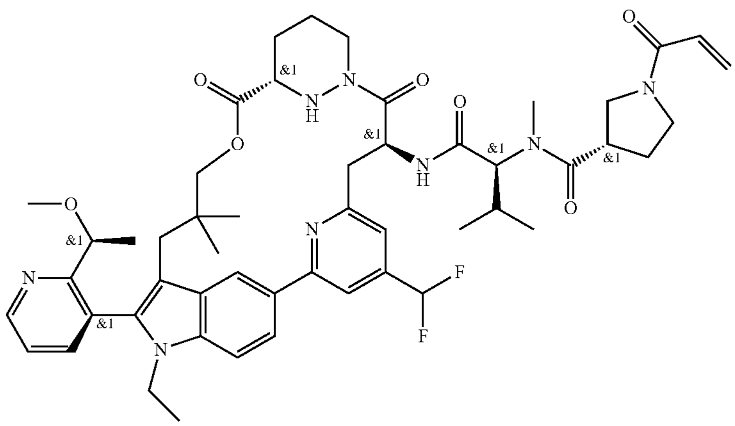 |
| B269 | 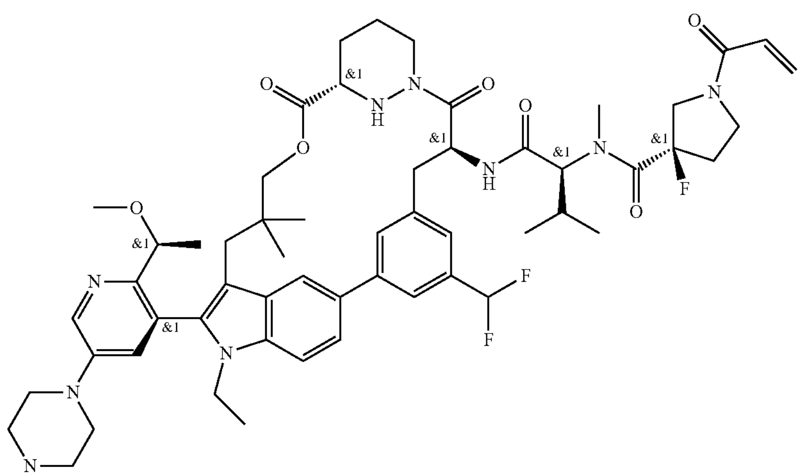 |
| B270 | 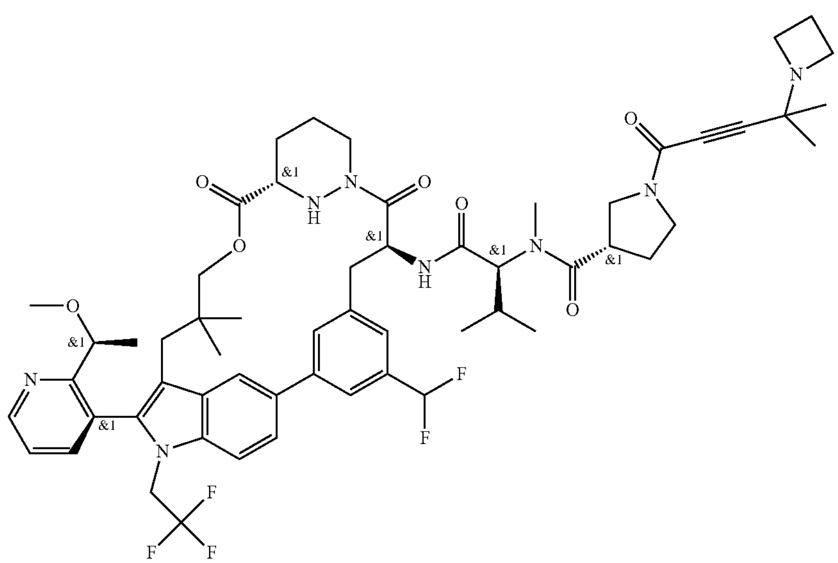 |

TABLE 2-continued

Certain Compounds of the Present Invention

| Ex # | Structure |
|---|---|
| B271 | 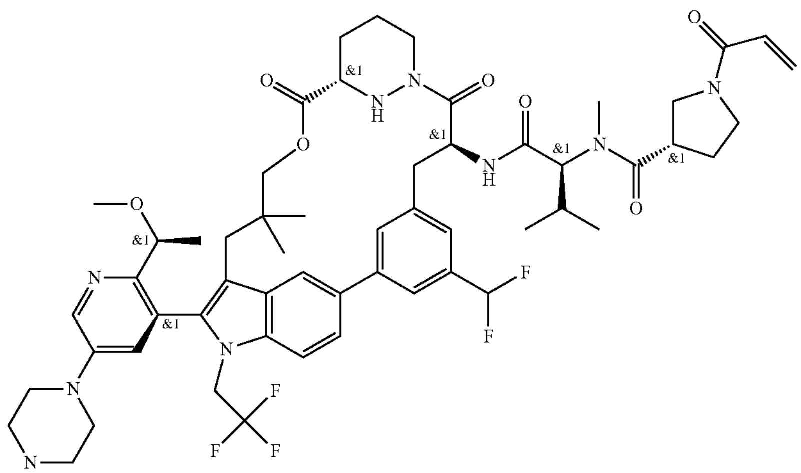 |
| B272 | 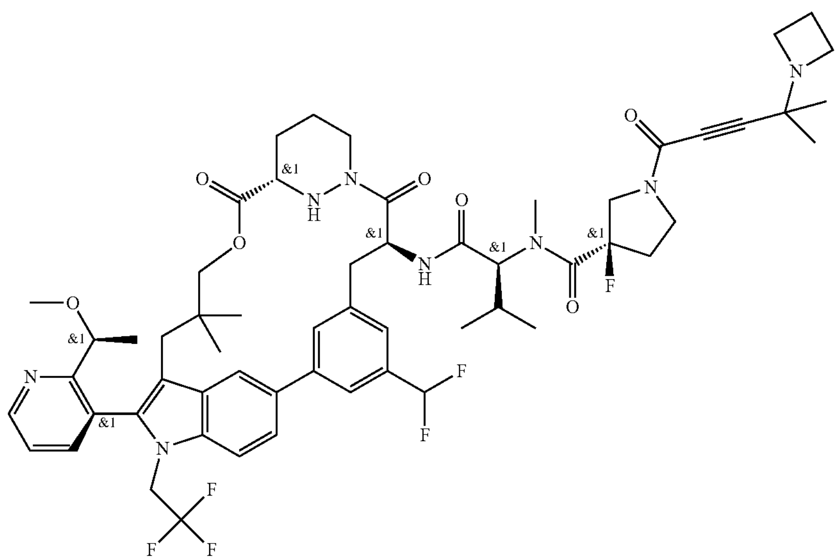 |
| B273 | 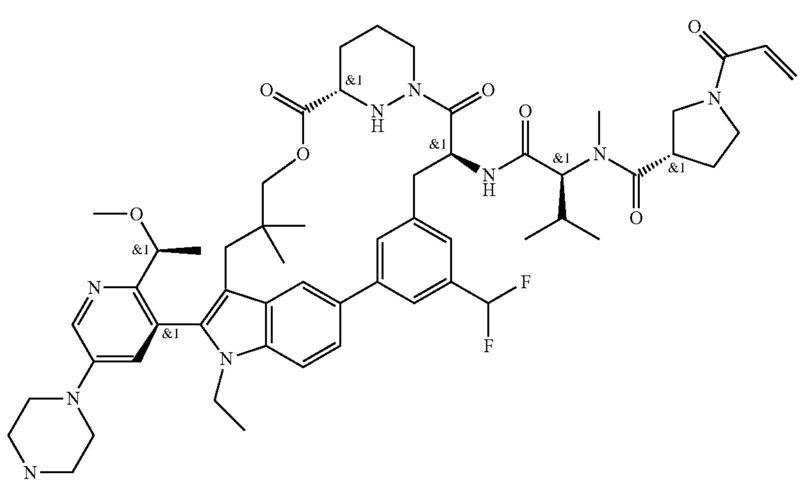 |

TABLE 2-continued

Certain Compounds of the Present Invention

| Ex # | Structure |
|---|---|
| B274 | 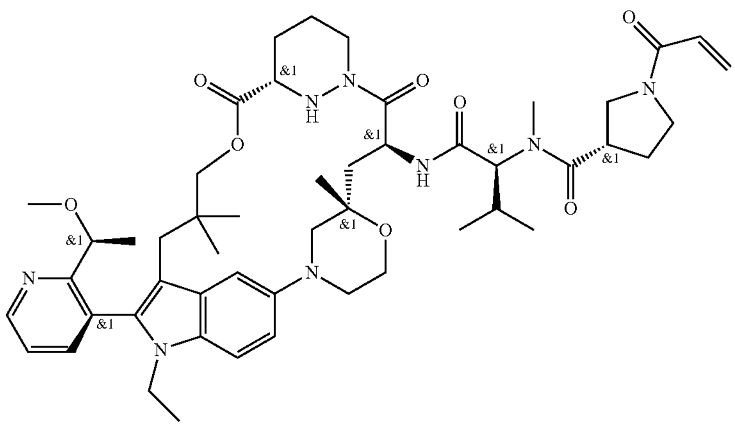 |
| B275 | 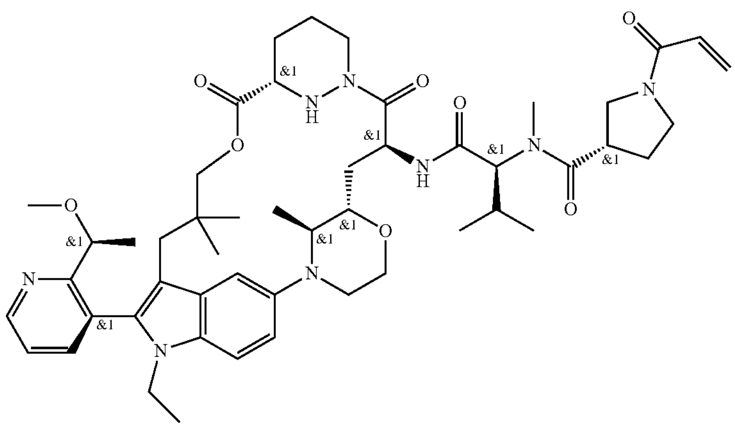 |
| B276 | 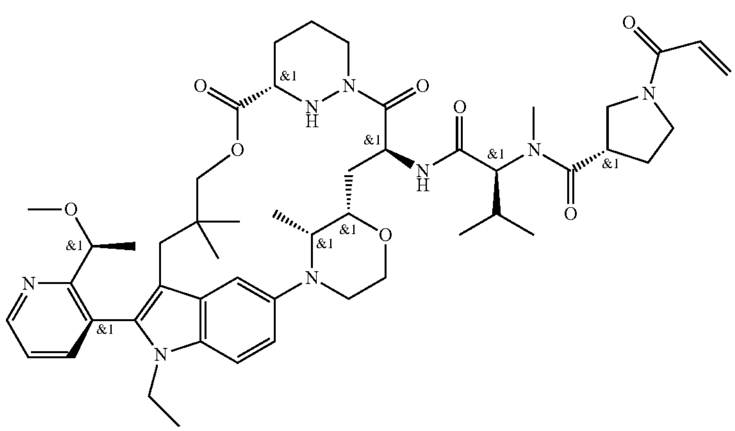 |

TABLE 2-continued
Certain Compounds of the Present Invention
| Ex # | Structure |
|---|---|
| B277 | 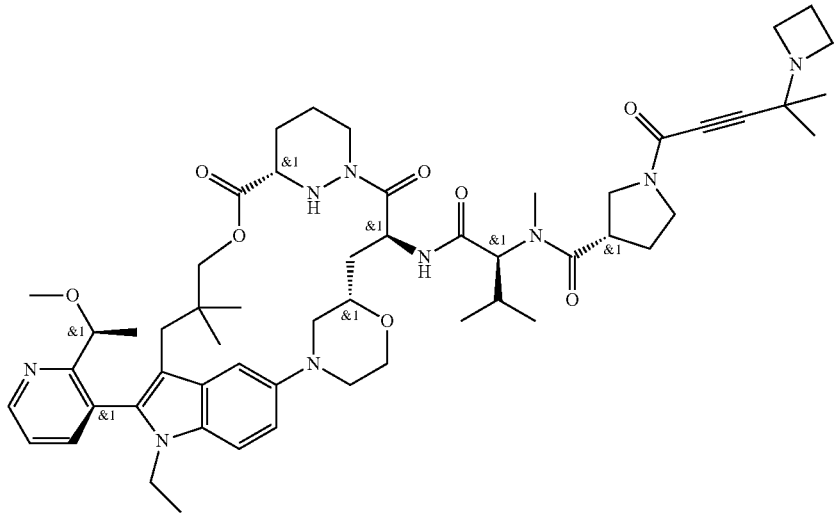 |
| B278 | 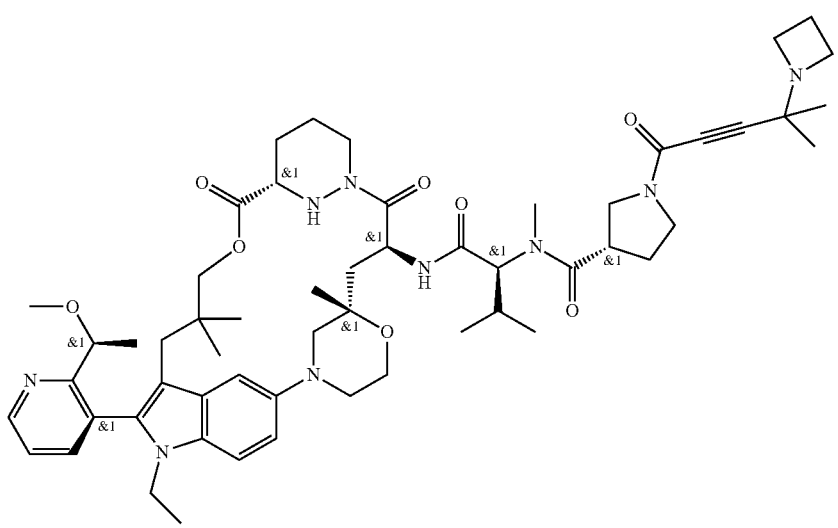 |
| B279 | 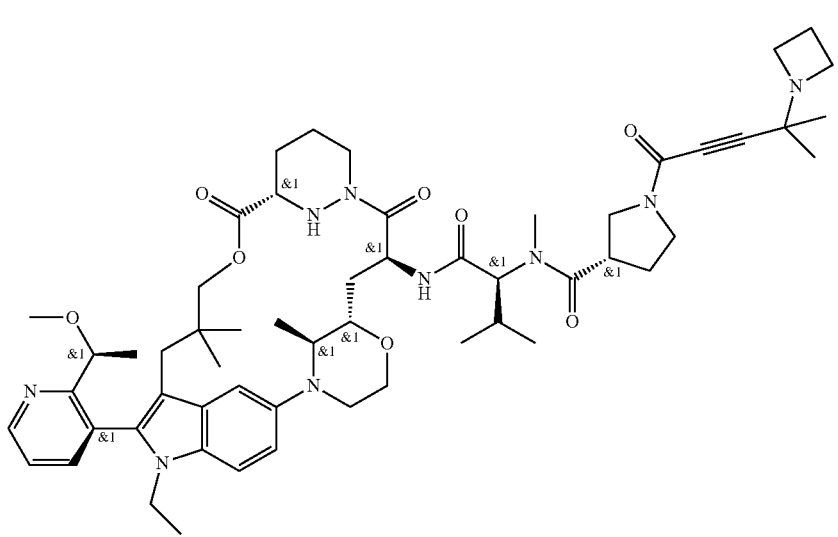 |

TABLE 2-continued
Certain Compounds of the Present Invention
| Ex # | Structure |
|---|---|
| B280 | 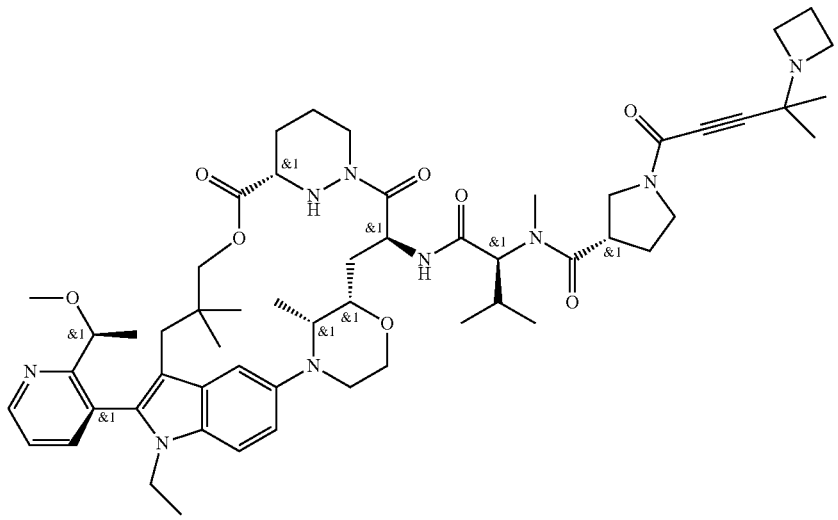 |
| B282 | 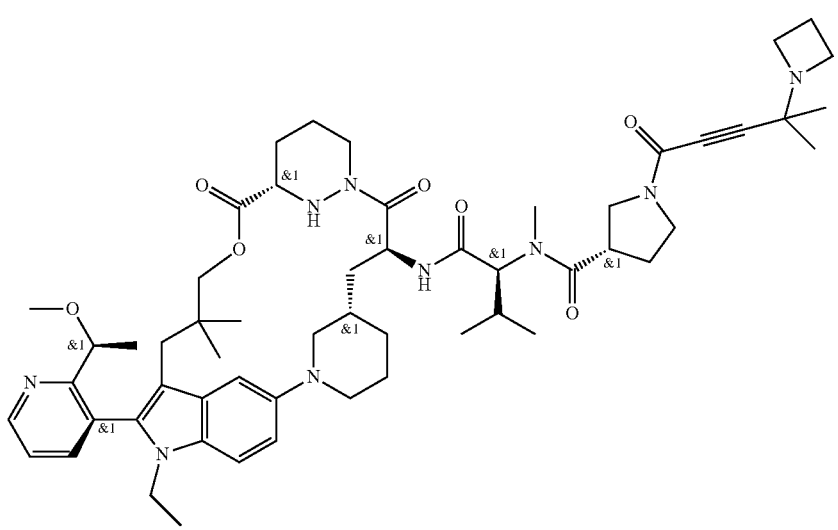 |
| B283 | 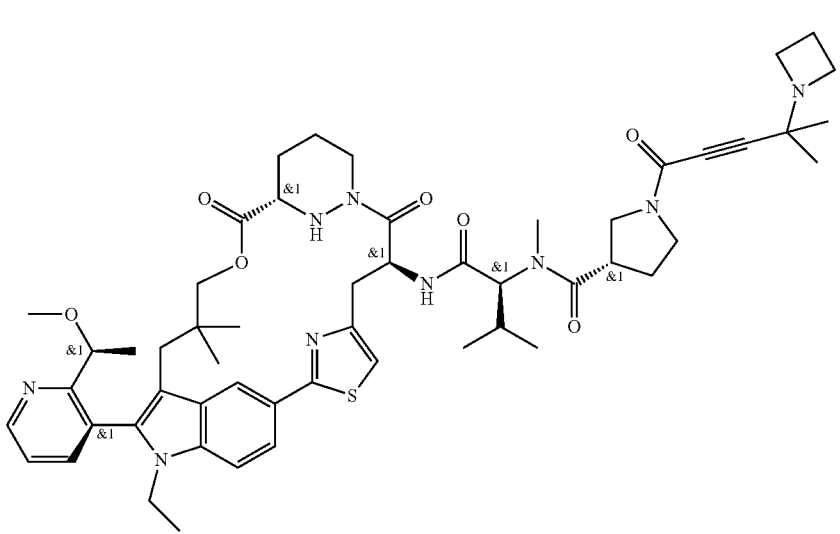 |

TABLE 2-continued

Certain Compounds of the Present Invention

| Ex # | Structure |
|------|-----------|
| B284 | 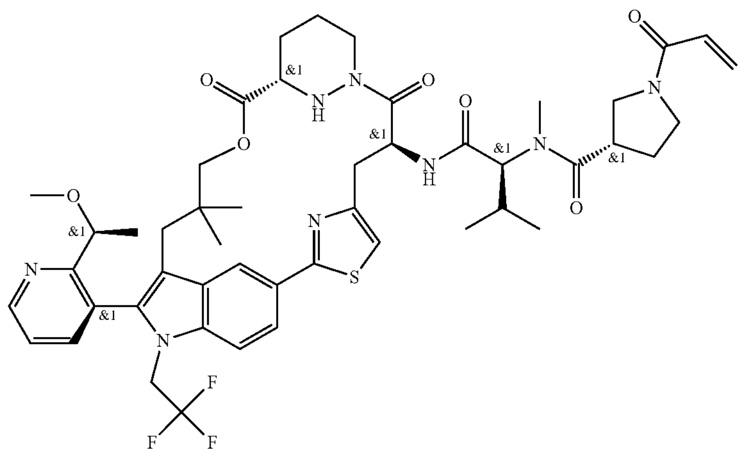 |
| B285 | 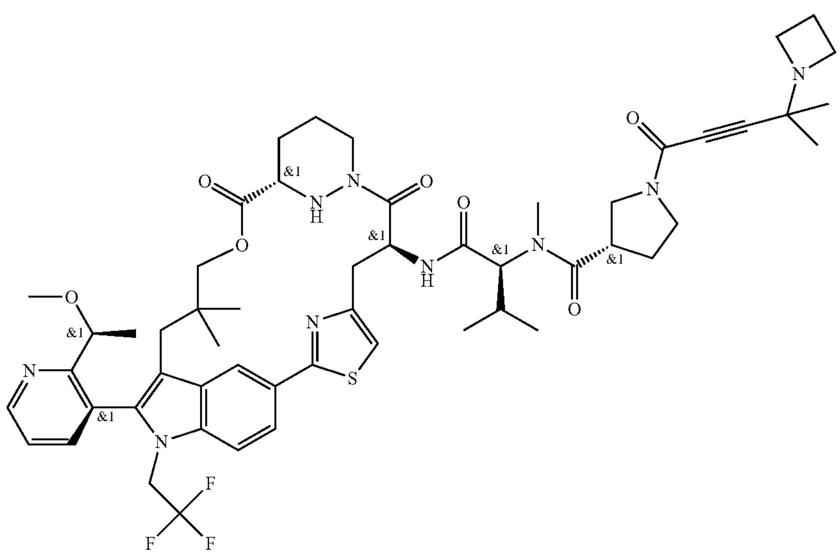 |
| B286 | 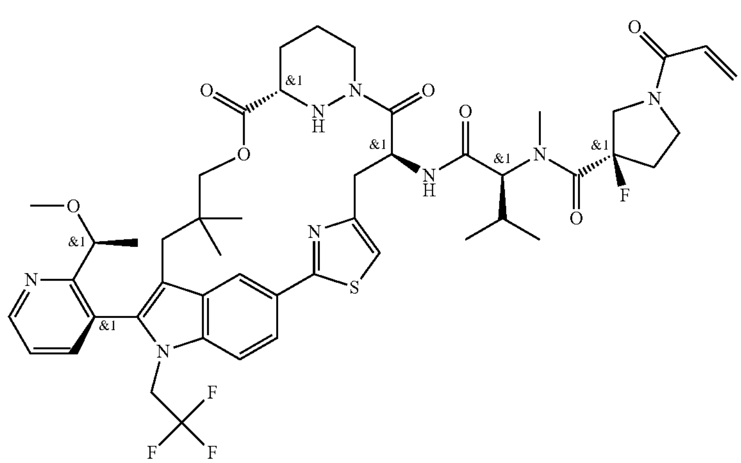 |

TABLE 2-continued

Certain Compounds of the Present Invention

| Ex # | Structure |
|------|-----------|
| B287 | 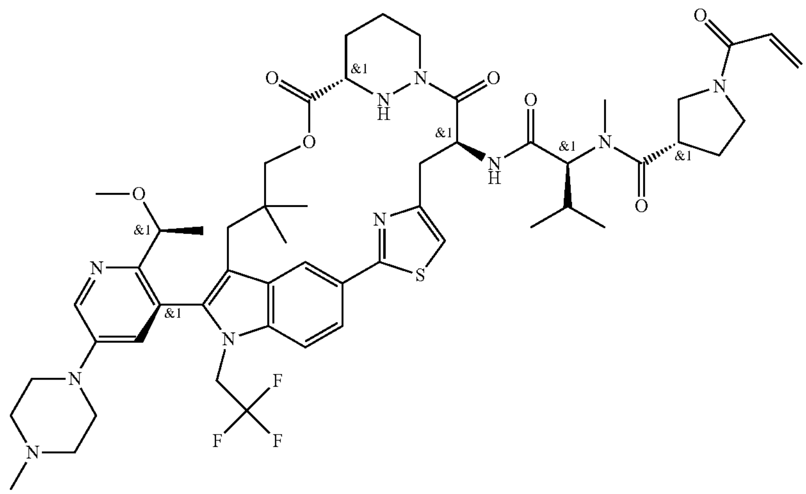 |
| B288 | 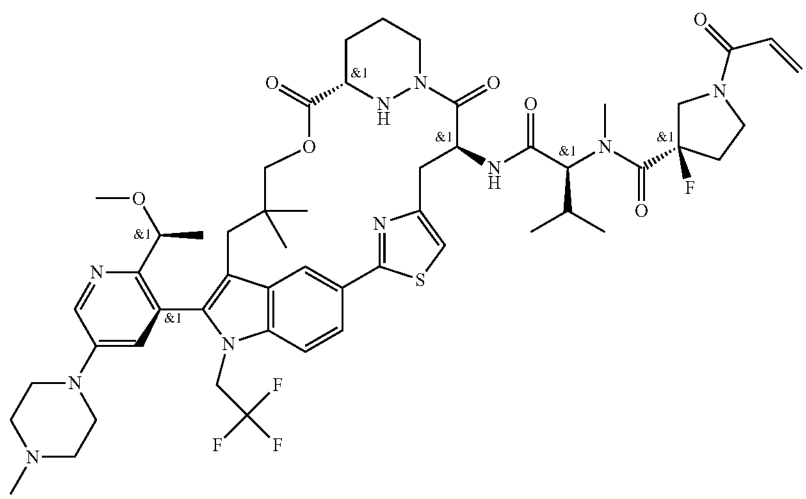 |
| B289 | 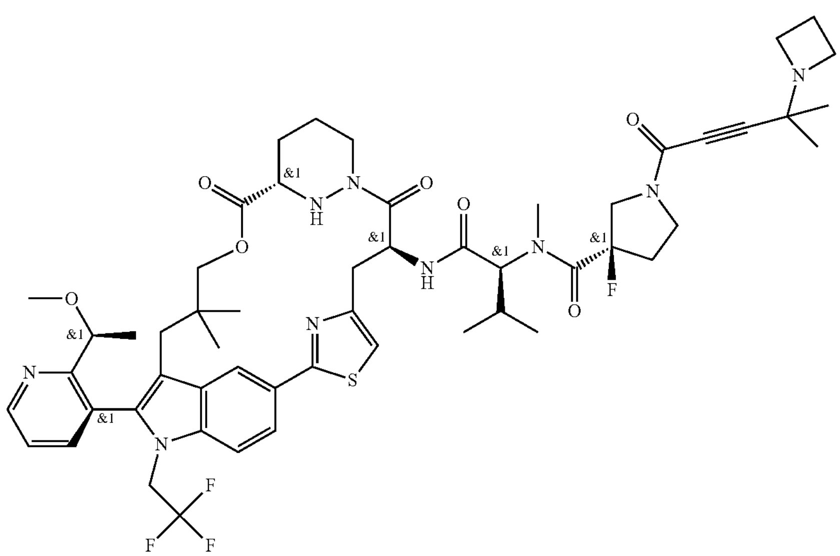 |

TABLE 2-continued
Certain Compounds of the Present Invention
| Ex # | Structure |
|------|-----------|
| B290 | 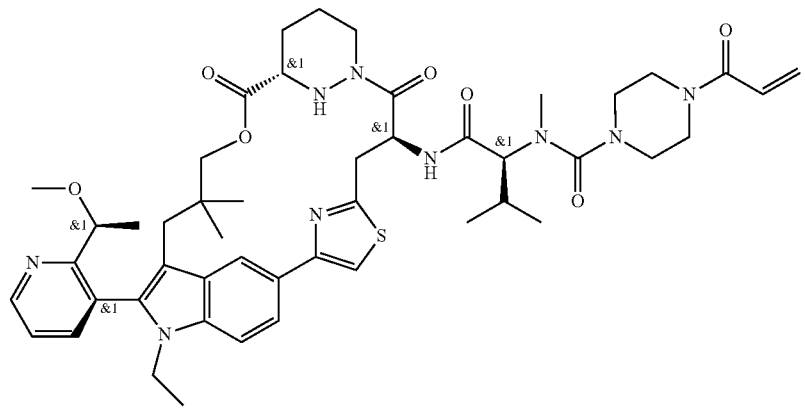 |
| B291 | 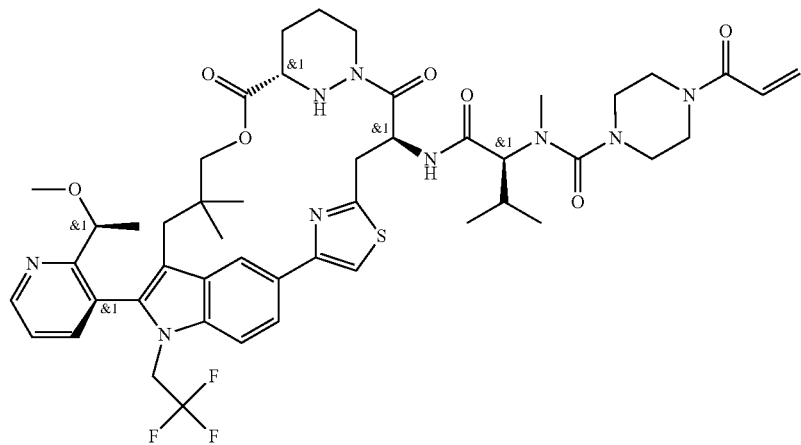 |
| B292 | 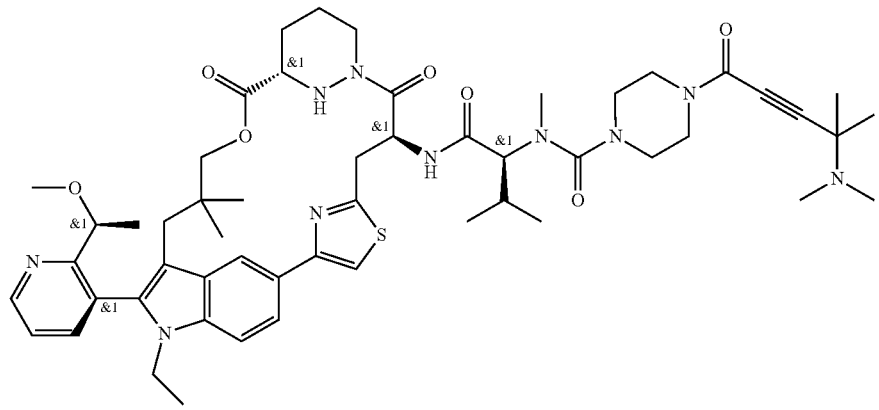 |

| Ex # | Structure |
|---|---|
| B293 | 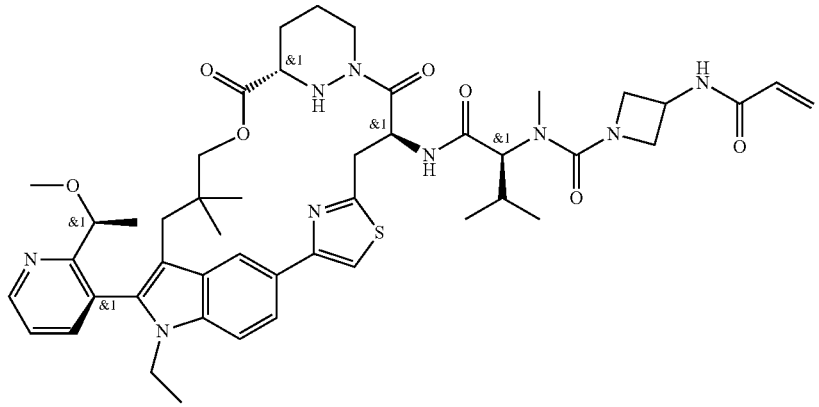 |
| B294 | 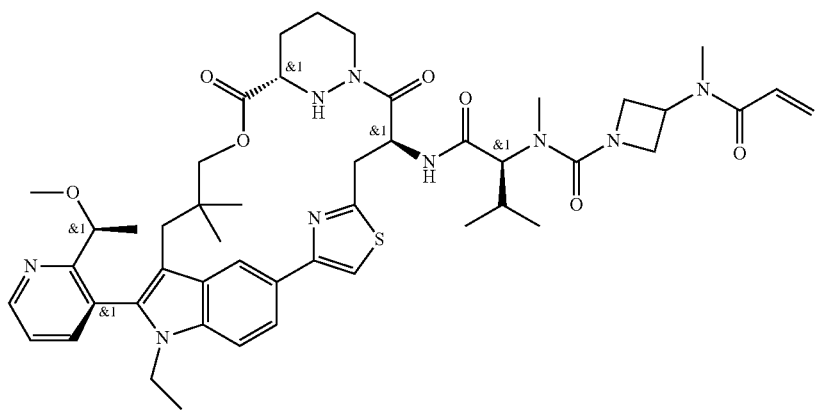 |
| B295 | 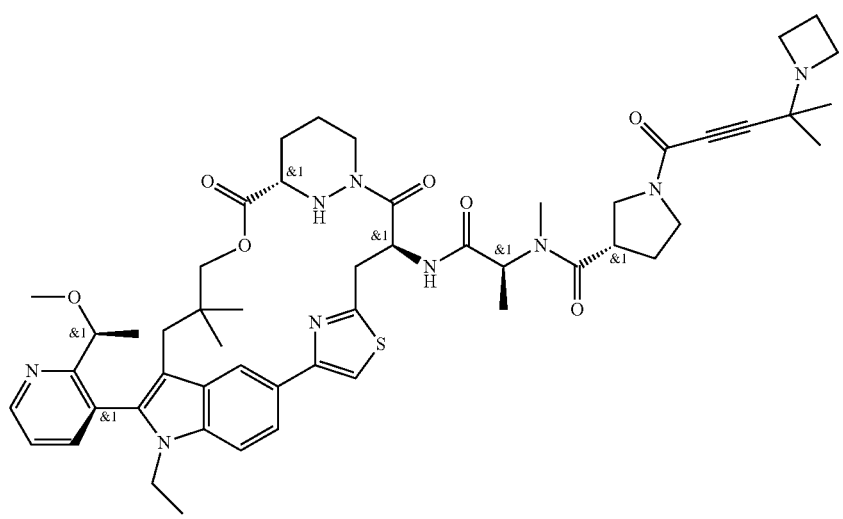 |

TABLE 2-continued
Certain Compounds of the Present Invention
| Ex # | Structure |
|---|---|
| B296 | 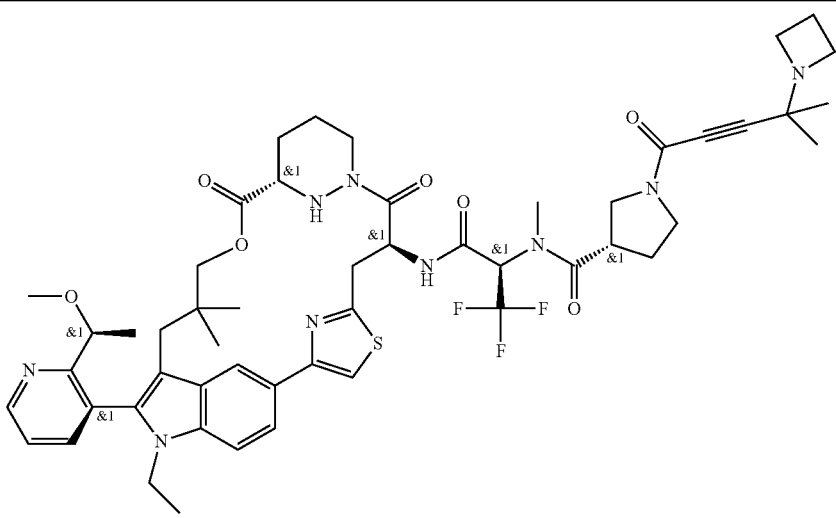 |
| B297 | 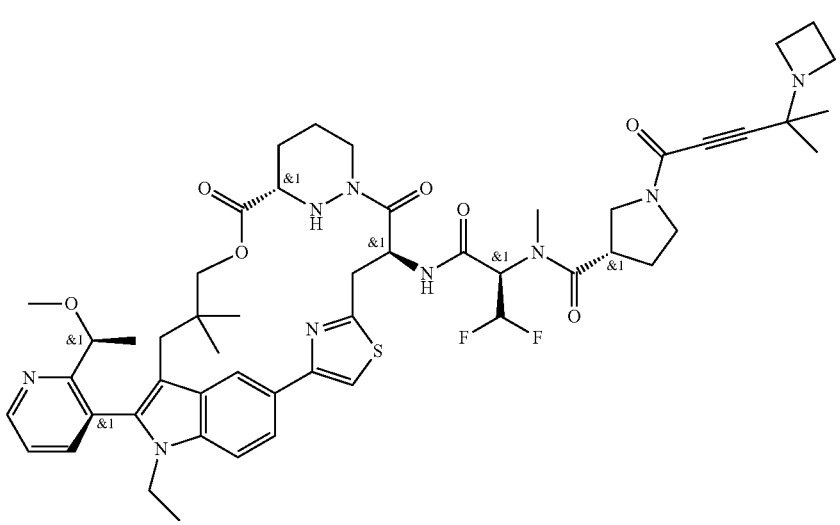 |
| B298 | 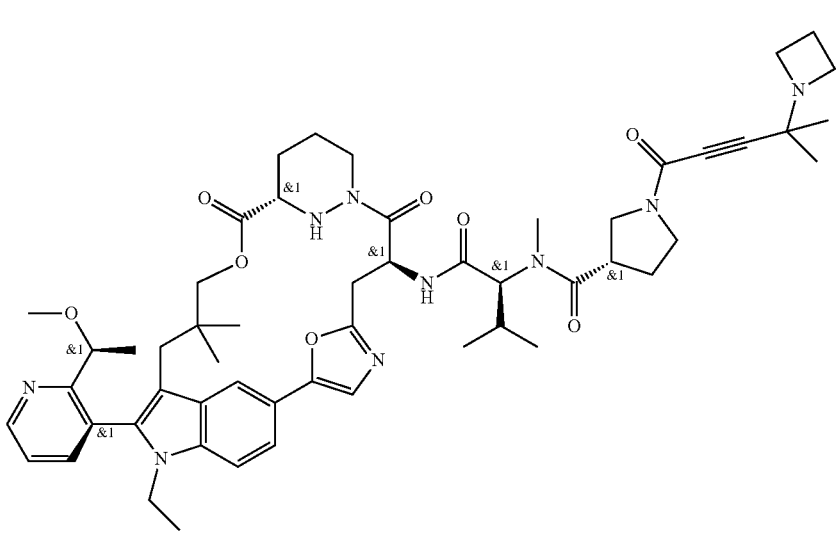 |

TABLE 2-continued

Certain Compounds of the Present Invention

| Ex # | Structure |
|---|---|
| B299 | 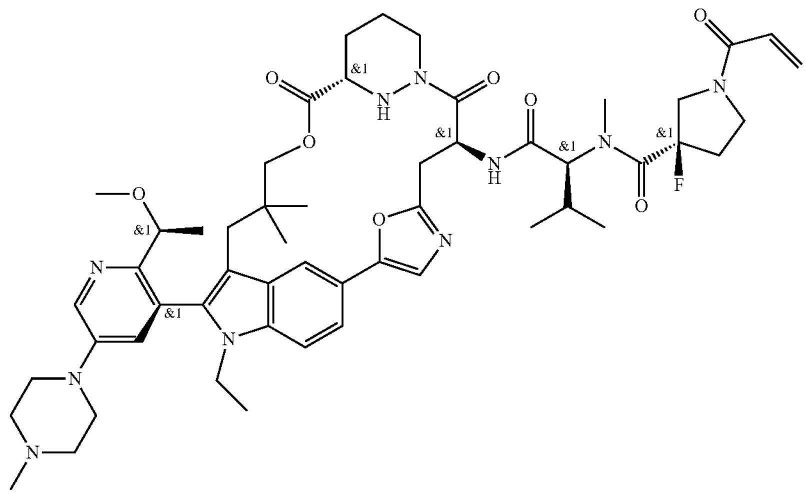 |
| B300 | 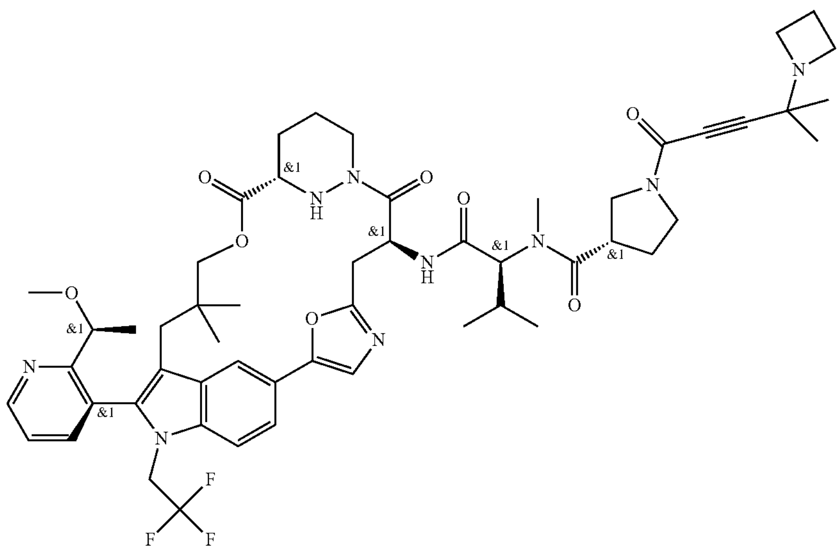 |
| B301 | 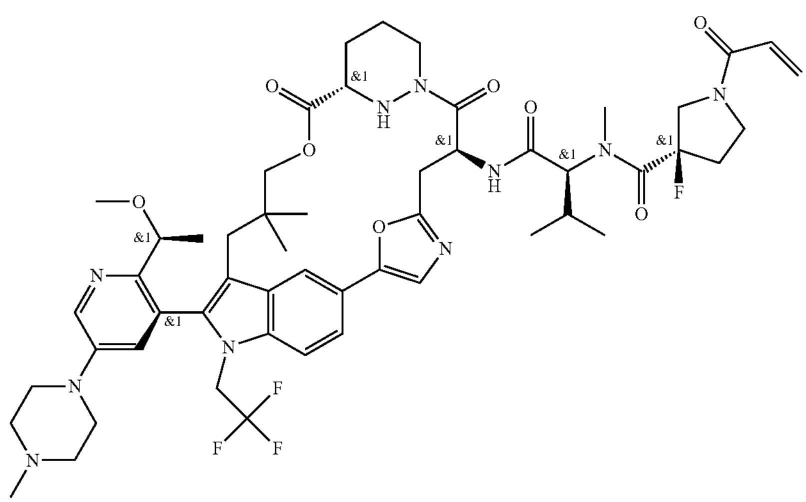 |

TABLE 2-continued
Certain Compounds of the Present Invention
| Ex # | Structure |
|---|---|
| B302 | 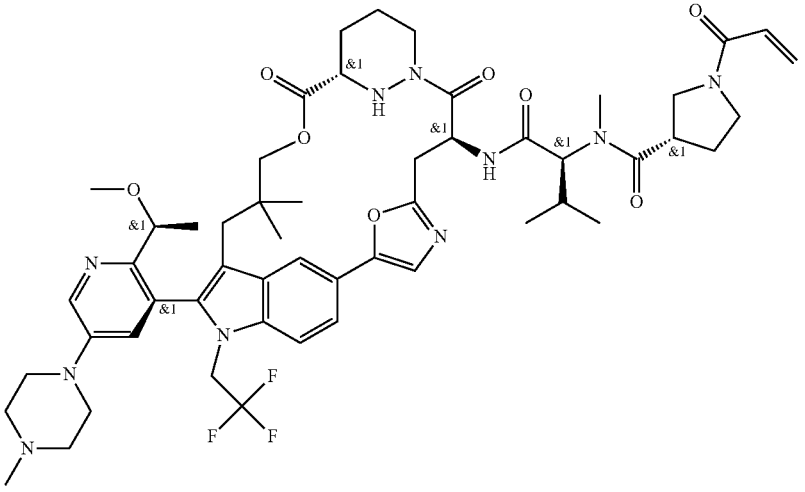 |
| B303 | 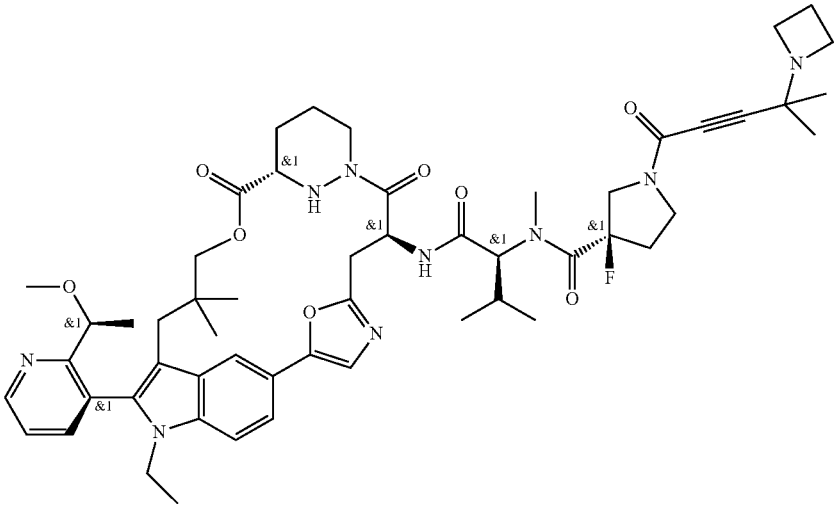 |
| B304 | 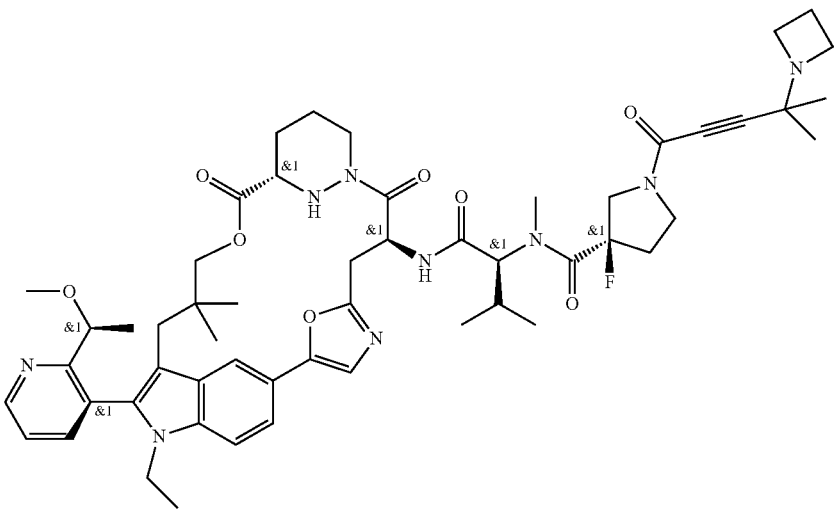 |

TABLE 2-continued

Certain Compounds of the Present Invention

| Ex # | Structure |
|---|---|
| B305 | 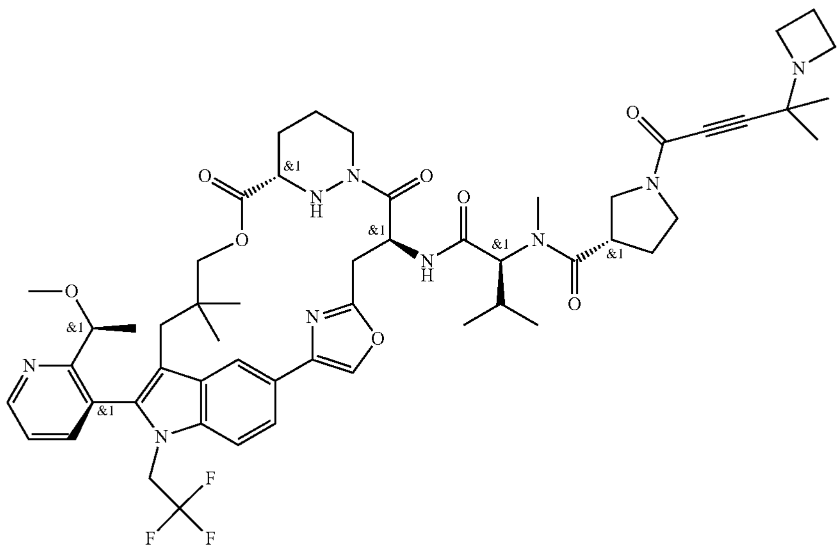 |
| B306 | 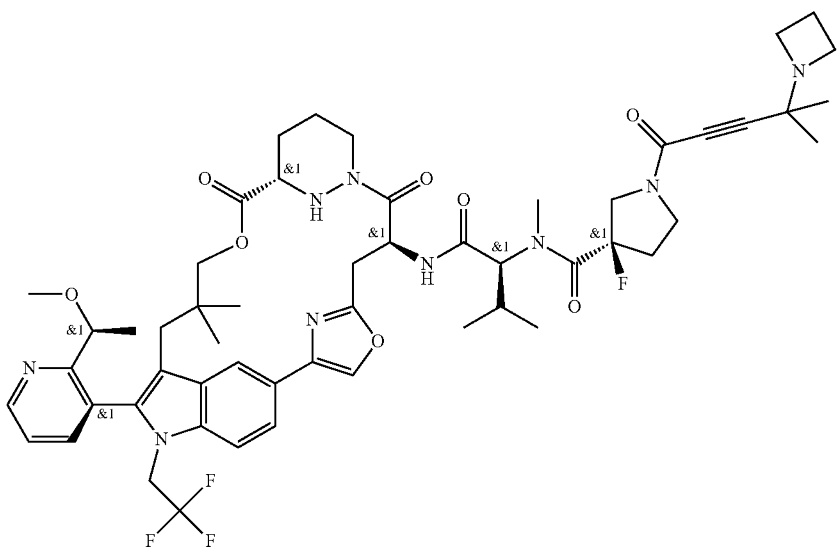 |
| B307 | 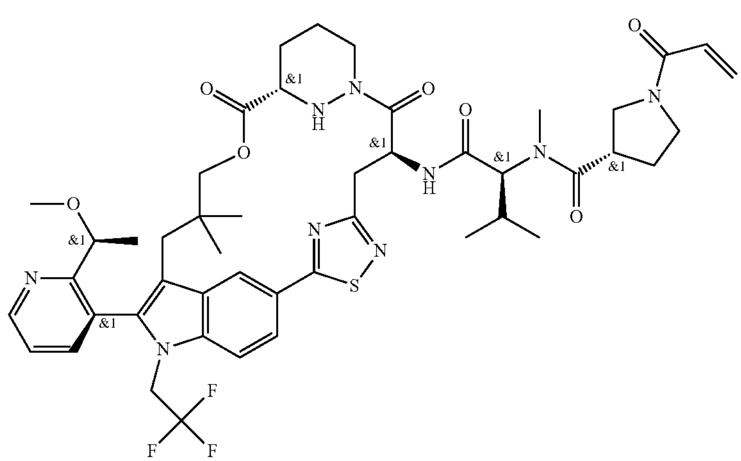 |

TABLE 2-continued
Certain Compounds of the Present Invention
| Ex # | Structure |
| --- | --- |
| B308 | 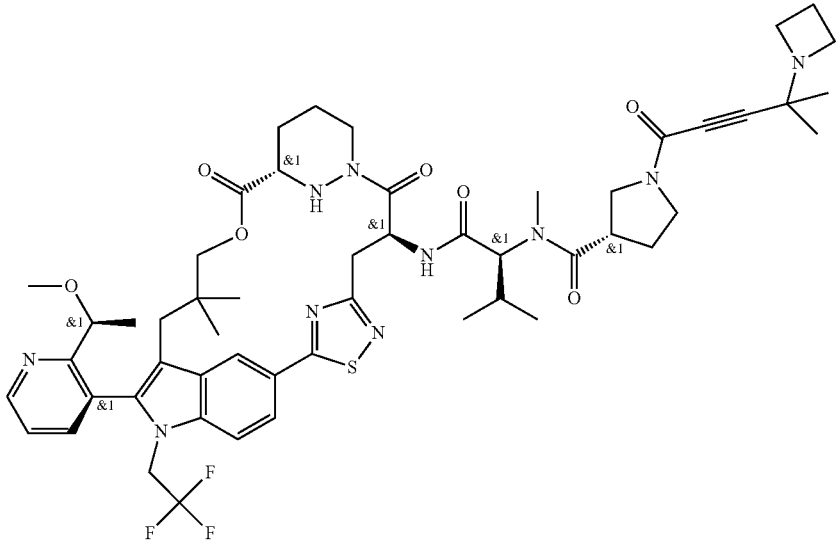 |
| B309 | 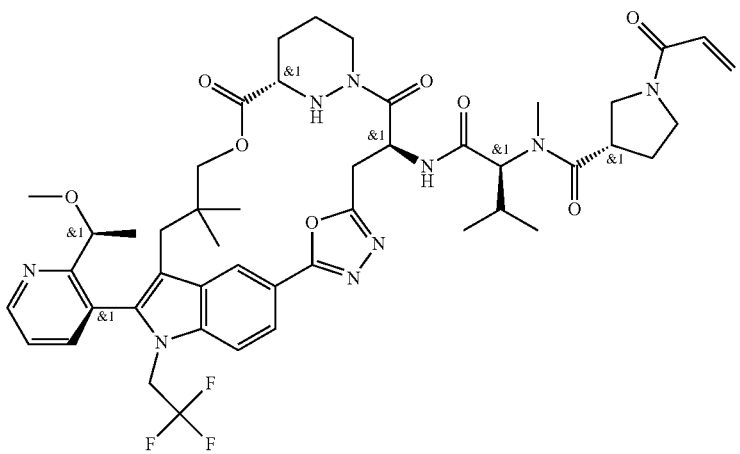 |
| B310 | 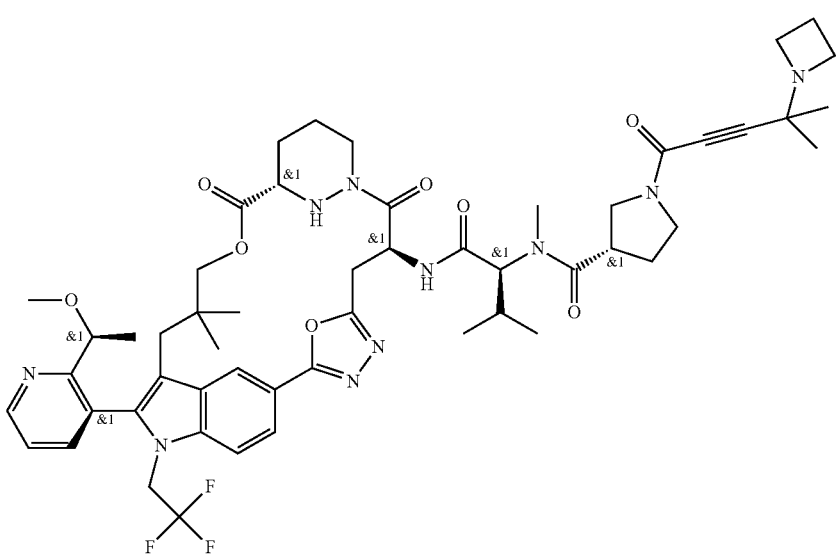 |

TABLE 2-continued
Certain Compounds of the Present Invention
| Ex # | Structure |
|---|---|
| B311 | 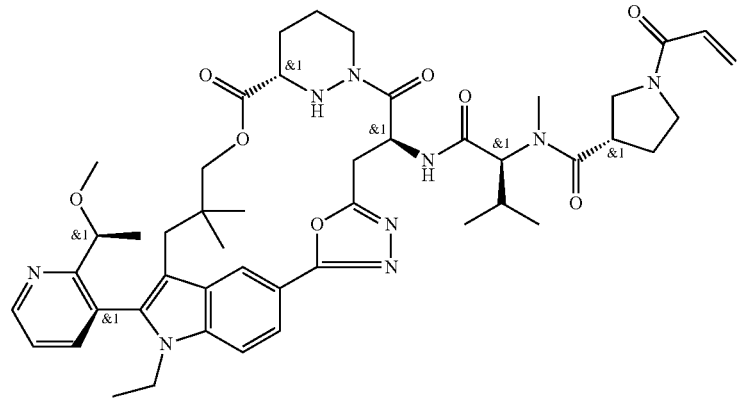 |
| B312 | 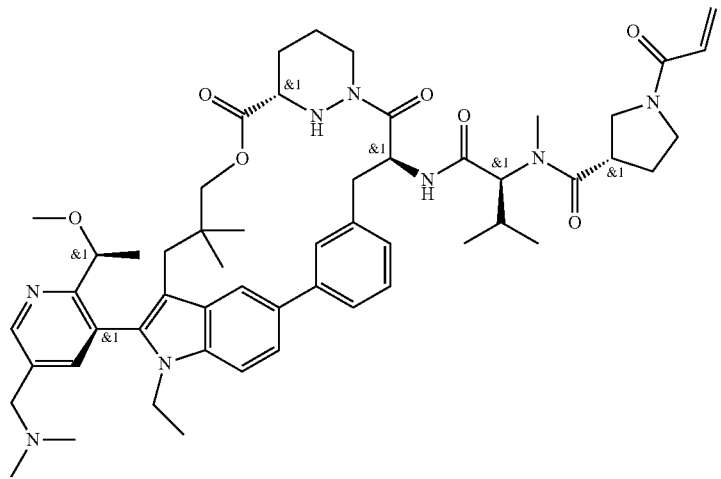 |
| B313 | 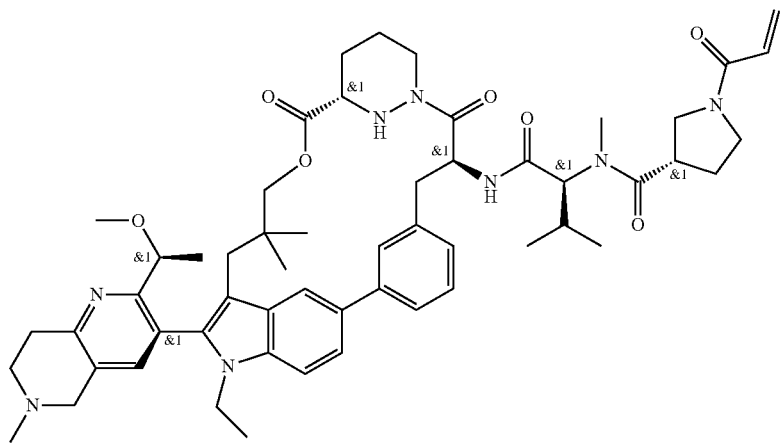 |

TABLE 2-continued

Certain Compounds of the Present Invention

| Ex # | Structure |
|---|---|
| B314 | 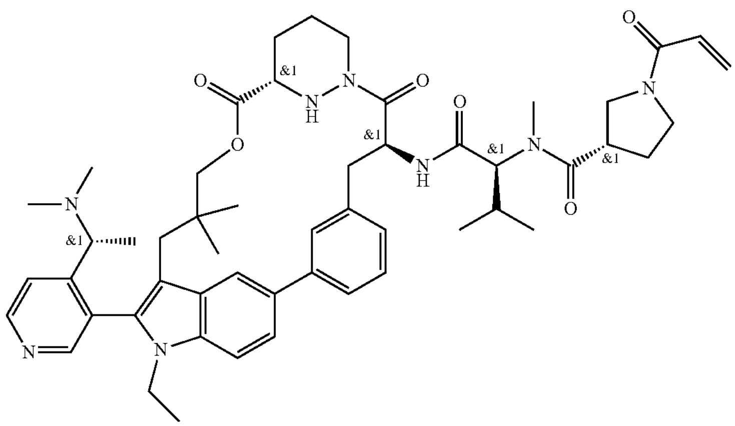 [SMILES: C=CC(=O)N1CC[C@H](C(=O)N(C)[C@H](C(=O)N[C@H]2Cc3cccc(c3)-c3ccc4c(c3)c(c(-c3cnccc3[C@@H](C)N(C)C)n4CC)CC(C)(C)COC(=O)[C@@H]3CCCN(N3)C2=O)C(C)C)C1] |
| B315 | 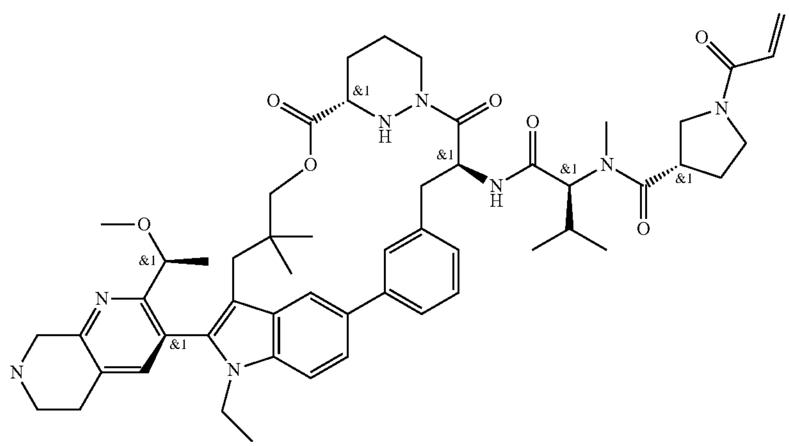 |
| B316 | 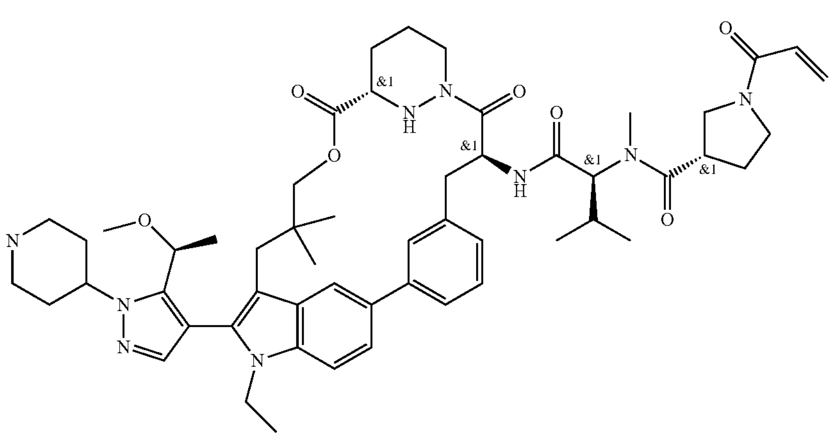 [SMILES: C=CC(=O)N1CC[C@H](C(=O)N(C)[C@H](C(=O)N[C@H]2Cc3cccc(c3)-c3ccc4c(c3)c(c(-c3cnn(C5CCNCC5)c3[C@H](C)OC)n4CC)CC(C)(C)COC(=O)[C@@H]3CCCN(N3)C2=O)C(C)C)C1] |

TABLE 2-continued
Certain Compounds of the Present Invention
| Ex # | Structure |
|---|---|
| B317 | 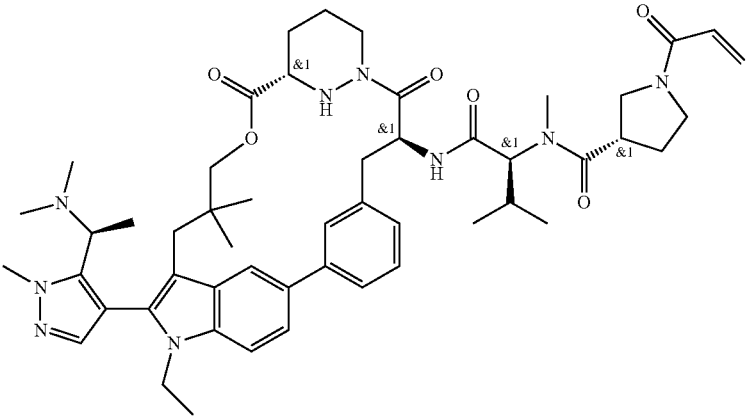 [SMILES: C=CC(=O)N1CC[C@H](C(=O)N(C)[C@H](C(=O)N[C@H]2Cc3cccc(c3)-c3ccc4c(c3)c(c(-c3cnn(C)c3[C@H](C)N(C)C)n4CC)CC(C)(C)COC(=O)[C@@H]3CCCN(N3)C2=O)C(C)C)C1] |
| B318 | 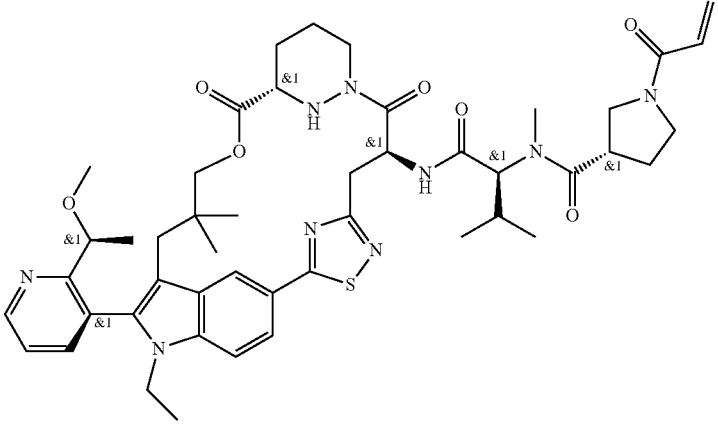 |
| B319 | 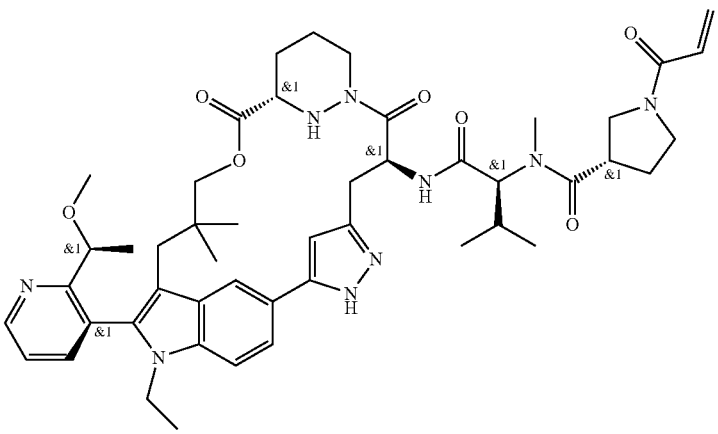 |

TABLE 2-continued
Certain Compounds of the Present Invention
| Ex # | Structure |
|---|---|
| B320 | 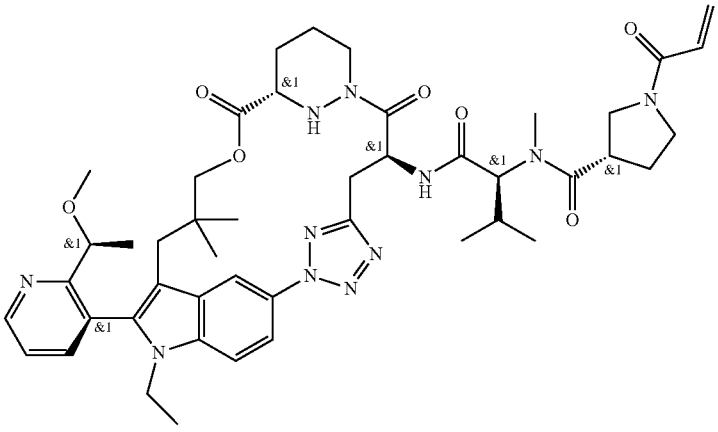 |
| B321 | 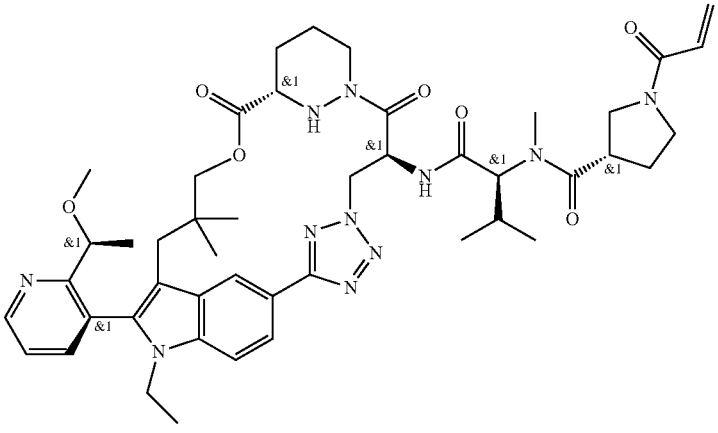 |
| B322 | 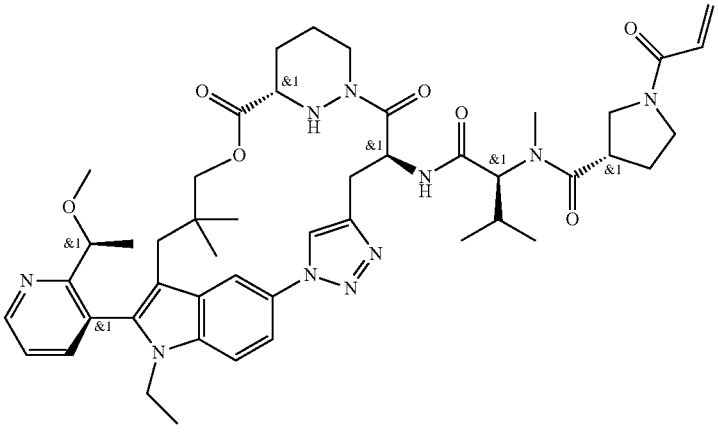 |

TABLE 2-continued
Certain Compounds of the Present Invention
| Ex # | Structure |
|---|---|
| B323 | 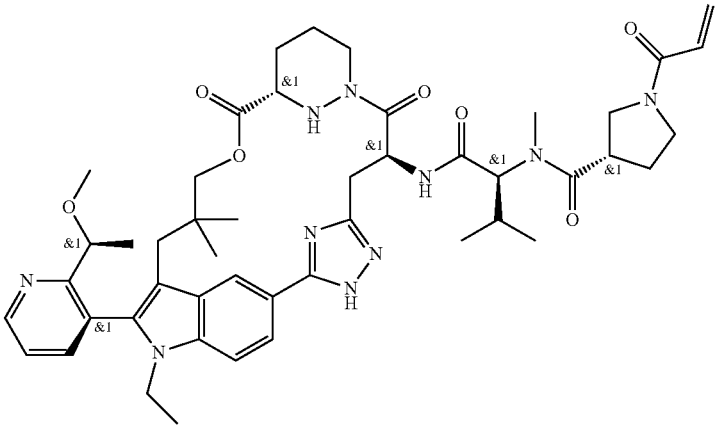 |
| B324 | 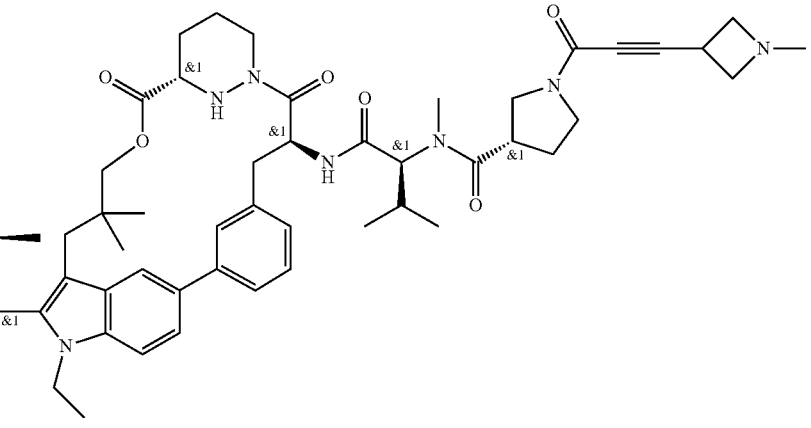 |
| B325 | 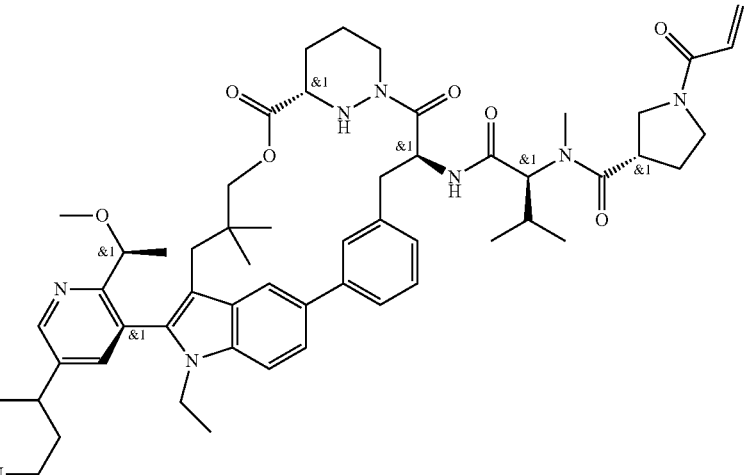 |

TABLE 2-continued

Certain Compounds of the Present Invention

| Ex # | Structure |
|------|-----------|
| B326 | 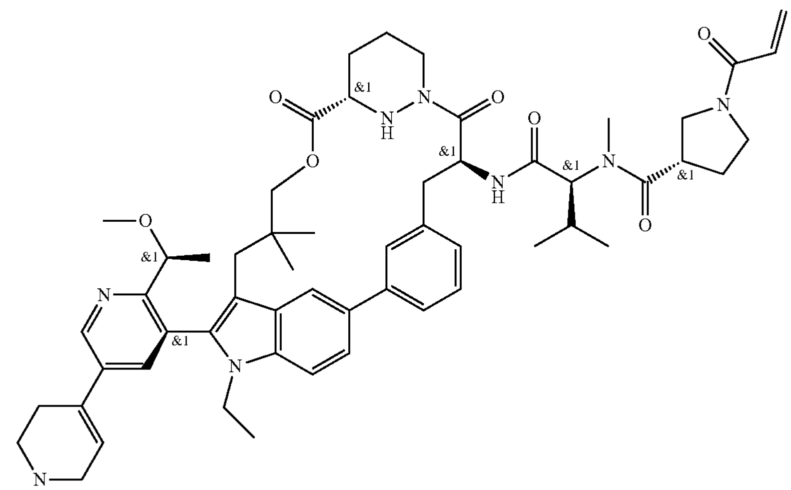 |
| B327 | 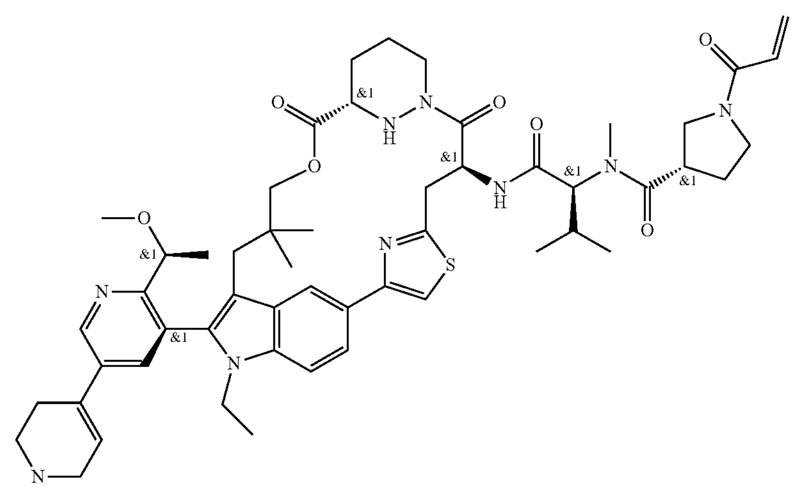 |
| B328 | 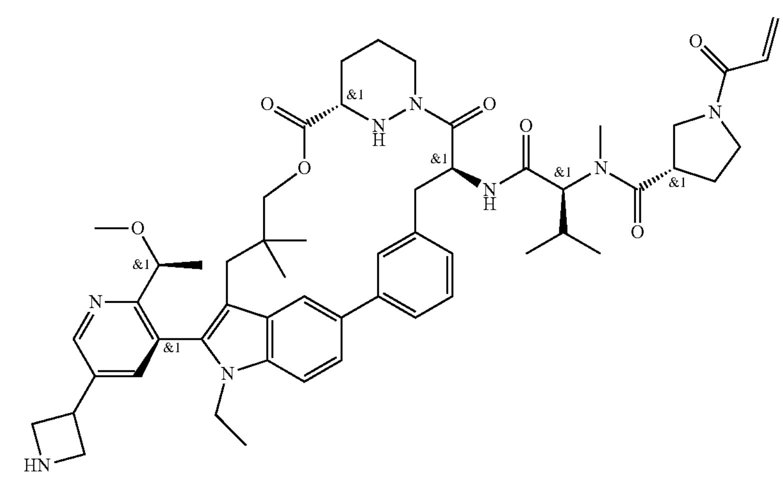 |

US 11,952,352 B2
TABLE 2-continued
Certain Compounds of the Present Invention
| Ex # | Structure |
|---|---|
| B329 | 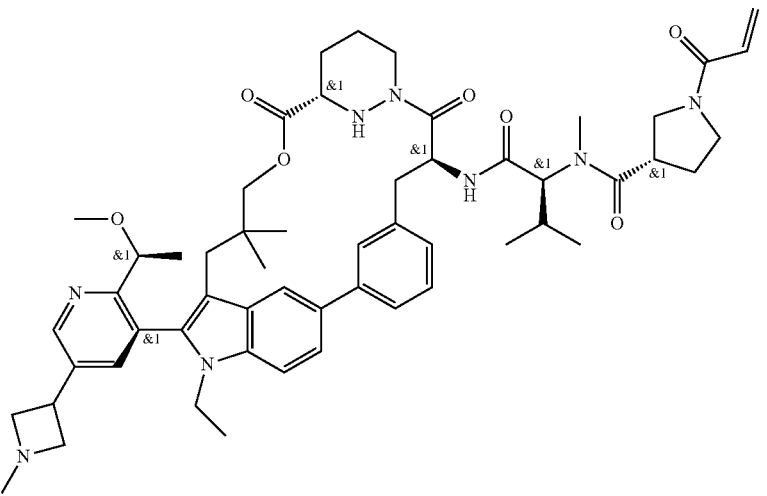 |
| B330 | 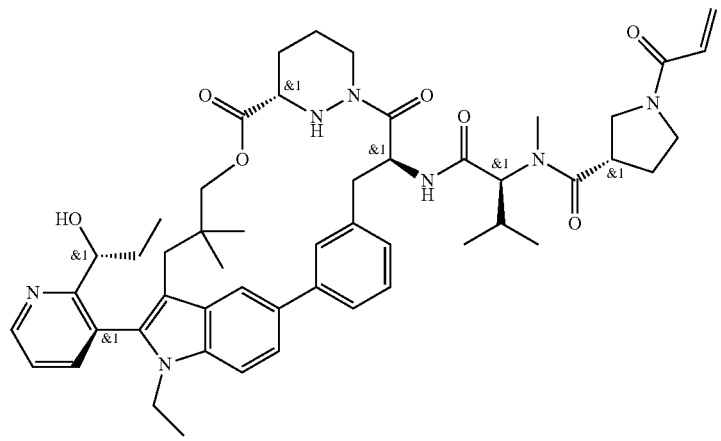 |
| B331 | 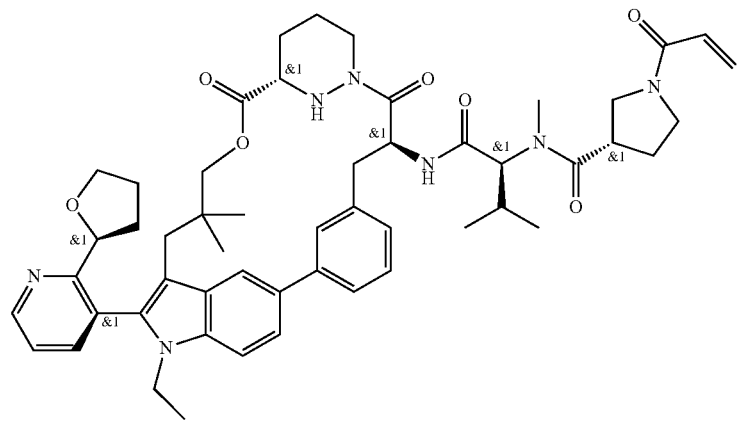 |

TABLE 2-continued

Certain Compounds of the Present Invention

| Ex # | Structure |
|------|-----------|
| B332 | 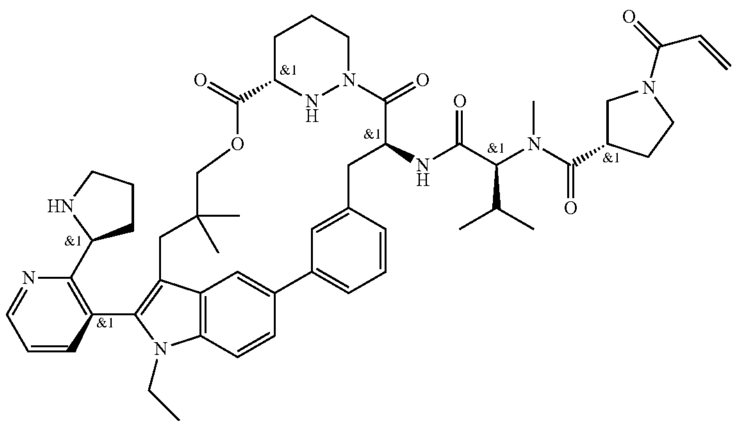 |
| B333 | 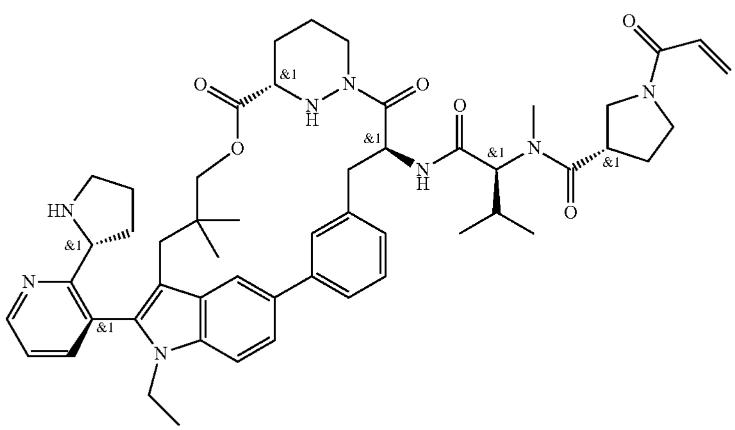 |
| B334 | 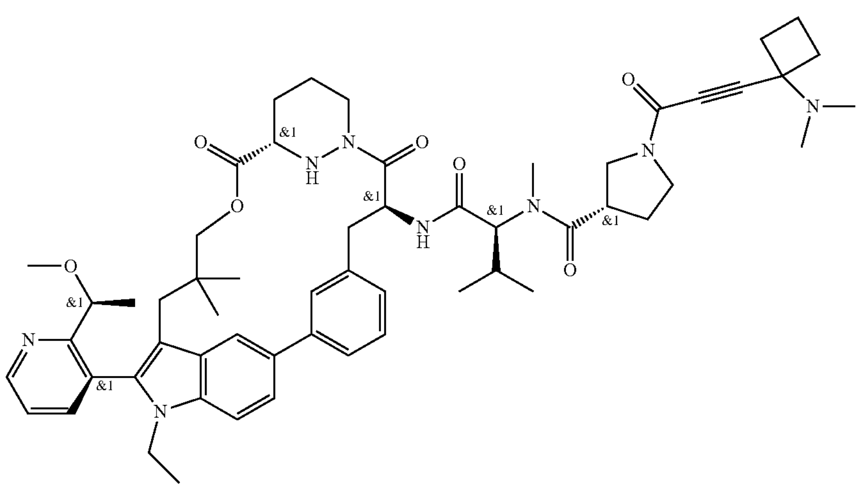 |

TABLE 2-continued

Certain Compounds of the Present Invention

| Ex # | Structure |
|------|-----------|
| B335 | 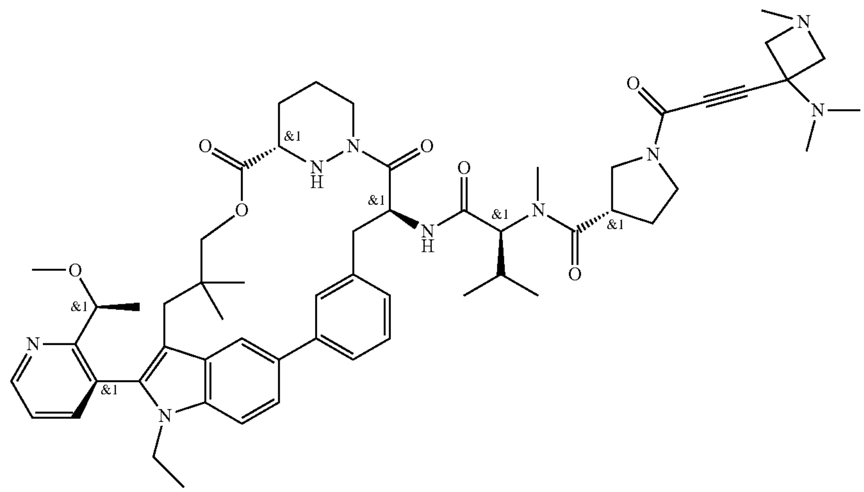 |
| B336 | 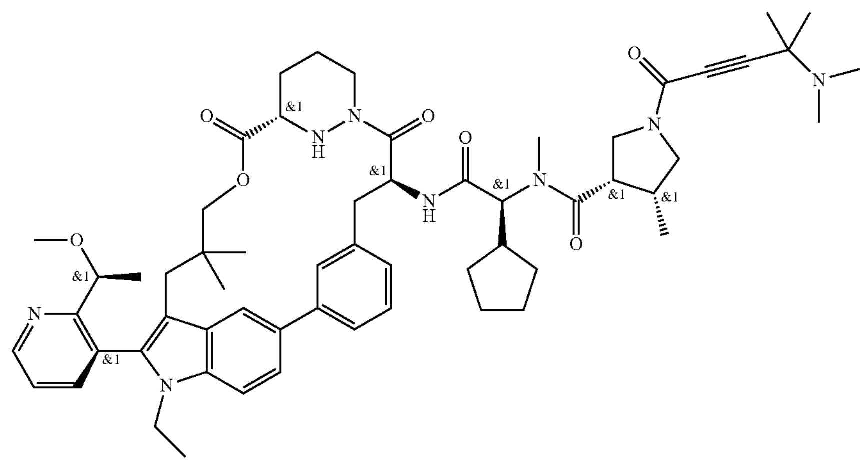 |
| B337 | 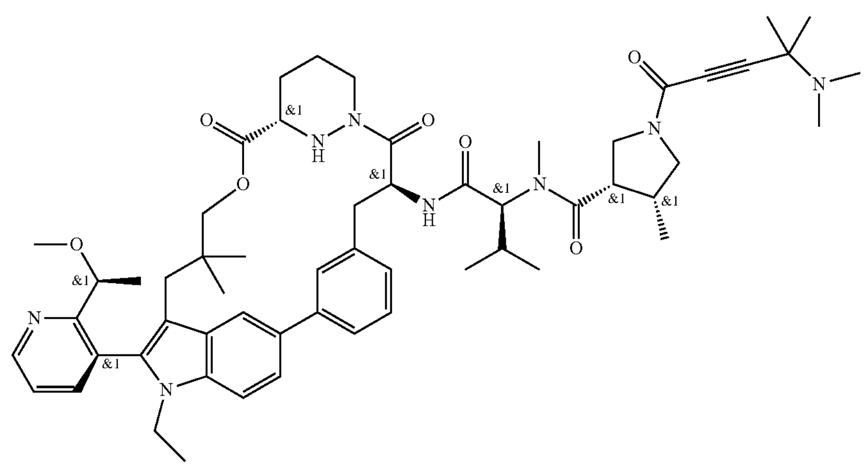 |

TABLE 2-continued
Certain Compounds of the Present Invention
| Ex # | Structure |
|---|---|
| B338 | 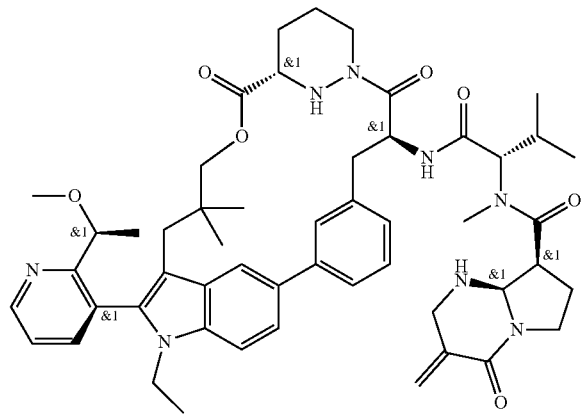 |
| B339 | 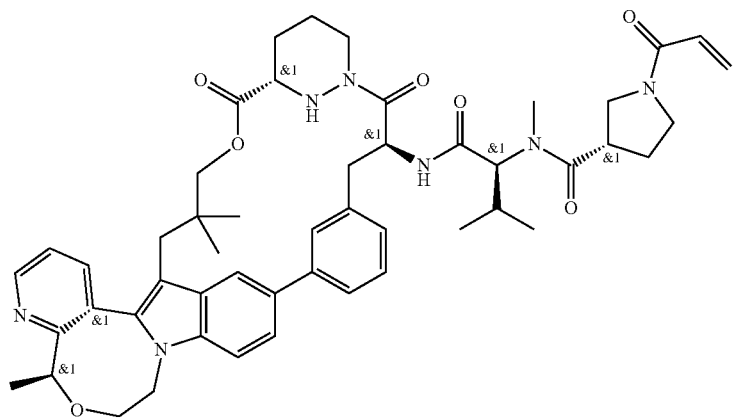 |
| B340 | 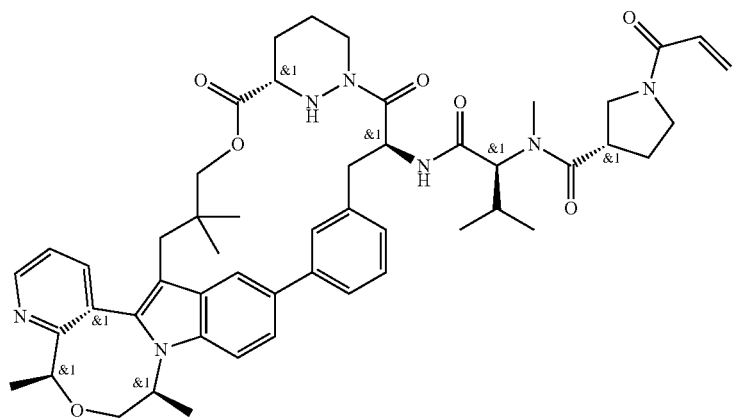 |

US 11,952,352 B2
731                                                                                                                          732
TABLE 2-continued
Certain Compounds of the Present Invention
| Ex # | Structure |
|------|-----------|
| B341 | 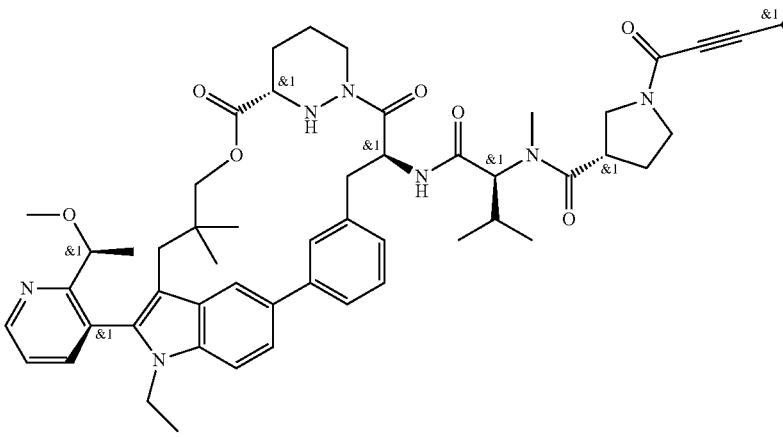 |
| B342 | 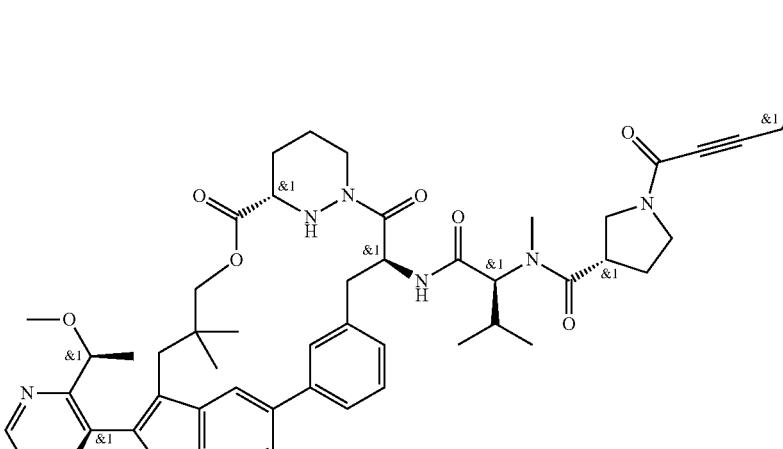 |
| B343 | 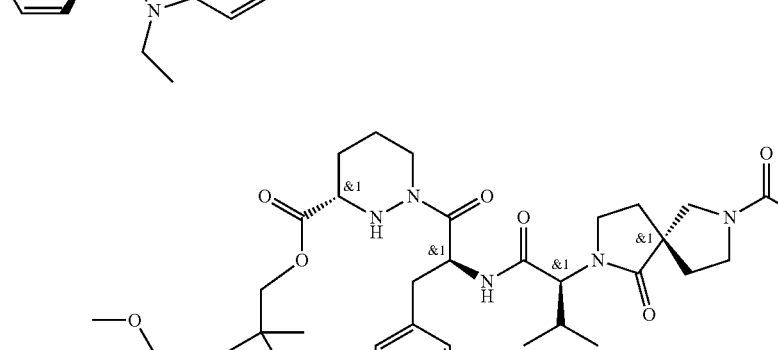 |

TABLE 2-continued
Certain Compounds of the Present Invention
| Ex # | Structure |
|---|---|
| B344 | 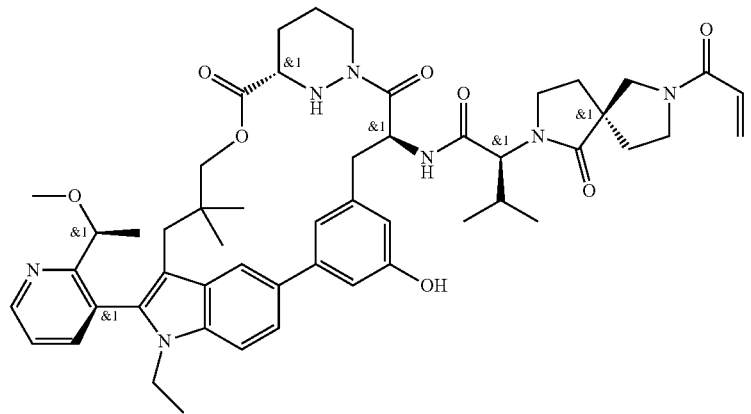 |
| B345 | 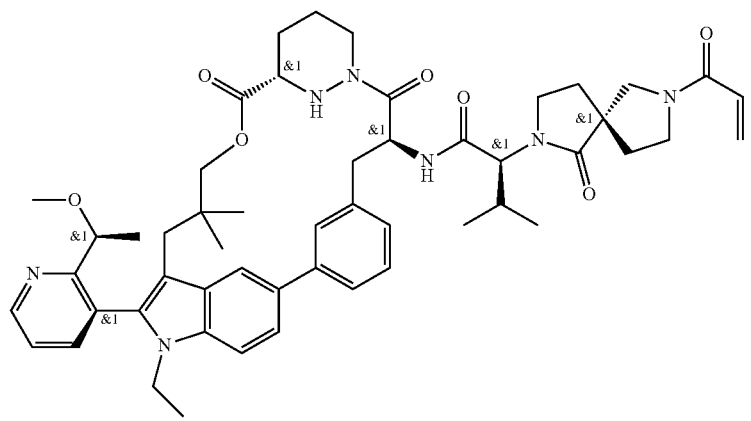 |
| B346 | 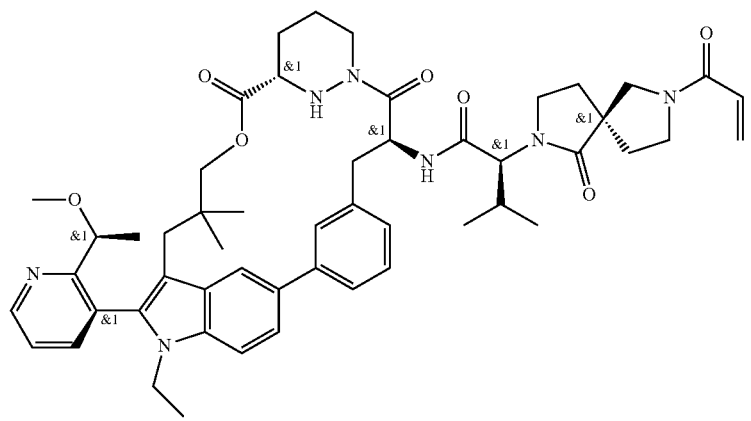 |

TABLE 2-continued
Certain Compounds of the Present Invention
| Ex # | Structure |
|---|---|
| B347 | 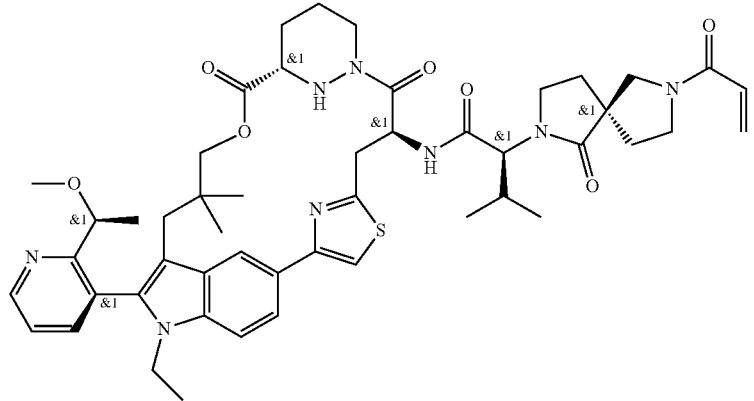 |
| B348 | 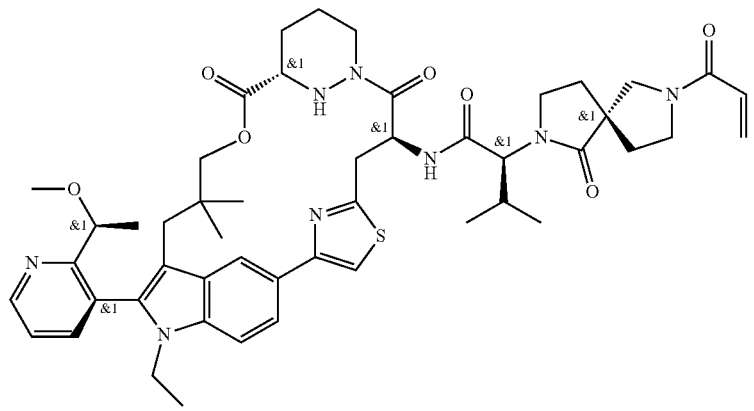 |
| B349 | 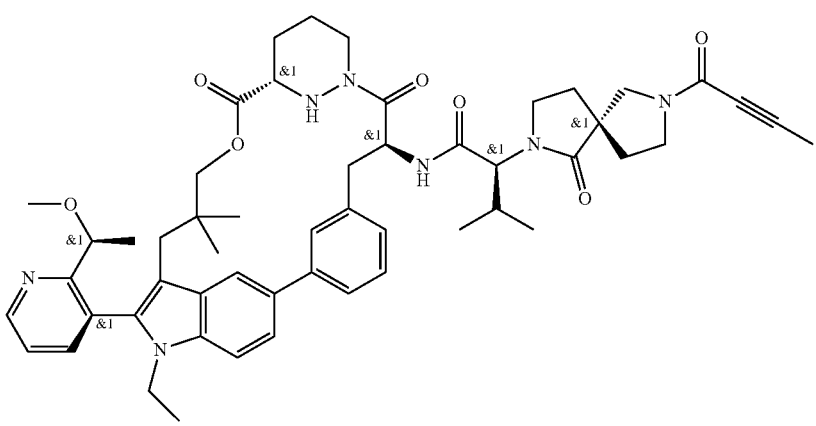 |

TABLE 2-continued

Certain Compounds of the Present Invention

| Ex # | Structure |
|------|-----------|
| B350 | 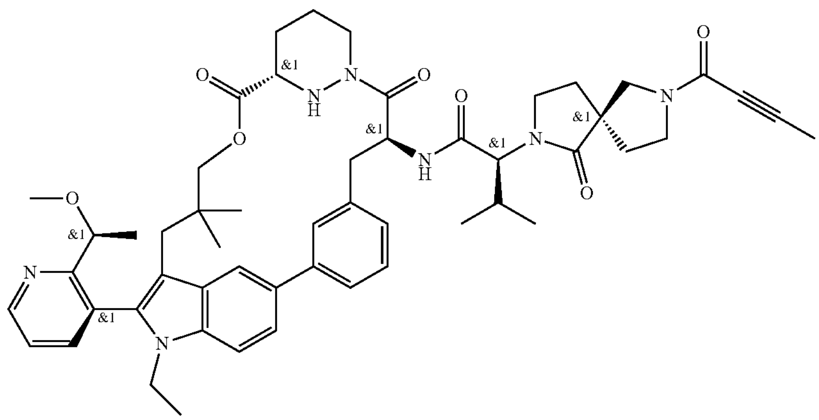 |
| B351 | 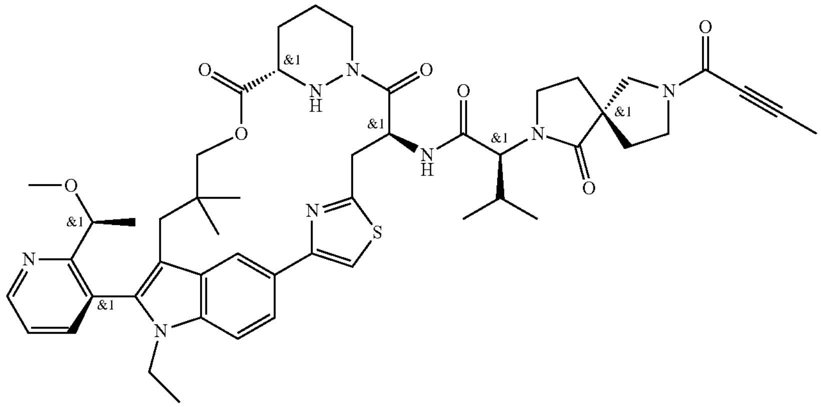 |
| B352 | 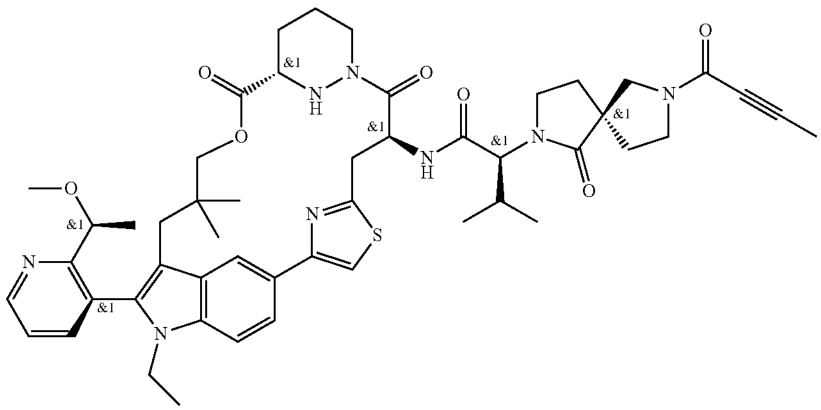 |

TABLE 2-continued

Certain Compounds of the Present Invention

| Ex # | Structure |
|---|---|
| B353 | 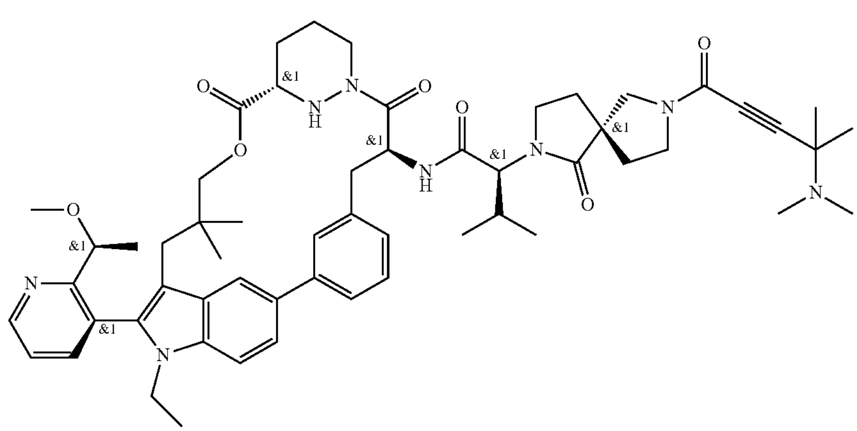 |
| B354 | 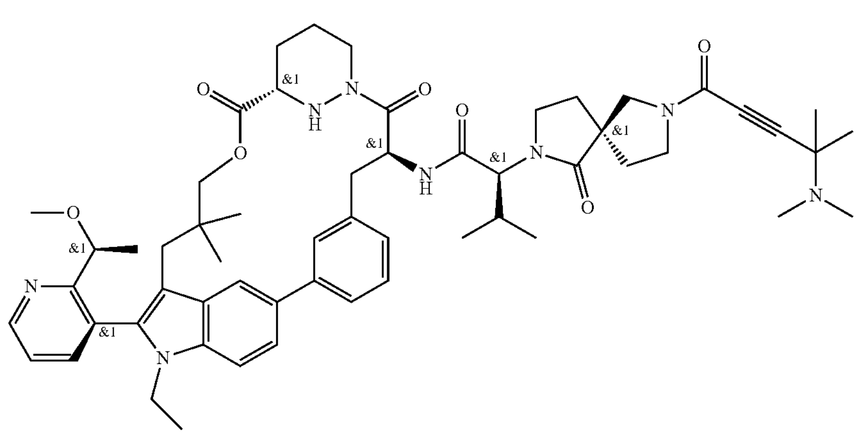 |
| B355 | 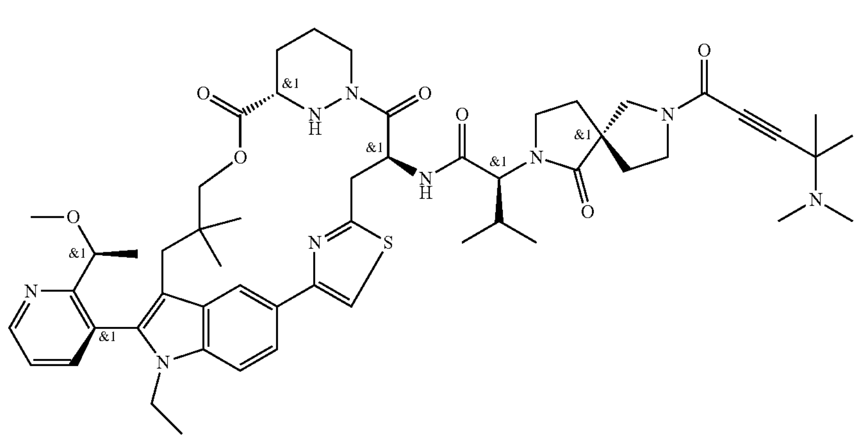 |

TABLE 2-continued

Certain Compounds of the Present Invention

| Ex # | Structure |
|---|---|
| B356 | 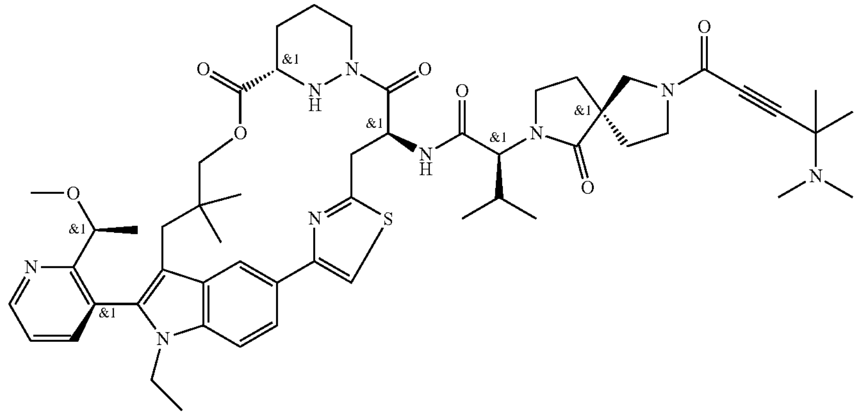 |
| B357 | 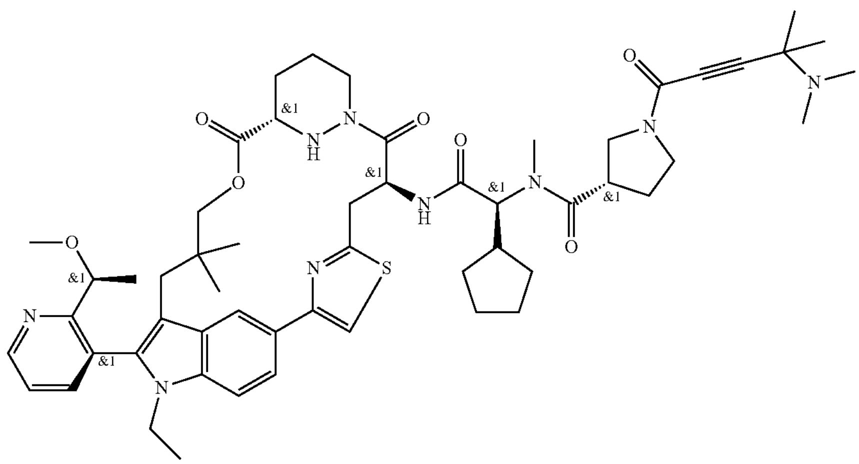 |
| B358 | 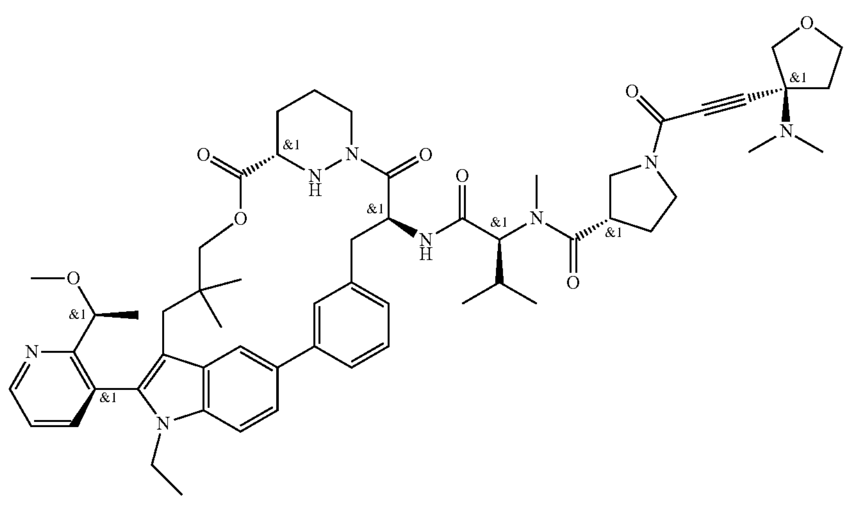 |

TABLE 2-continued

Certain Compounds of the Present Invention

| Ex # | Structure |
|---|---|
| B359 | 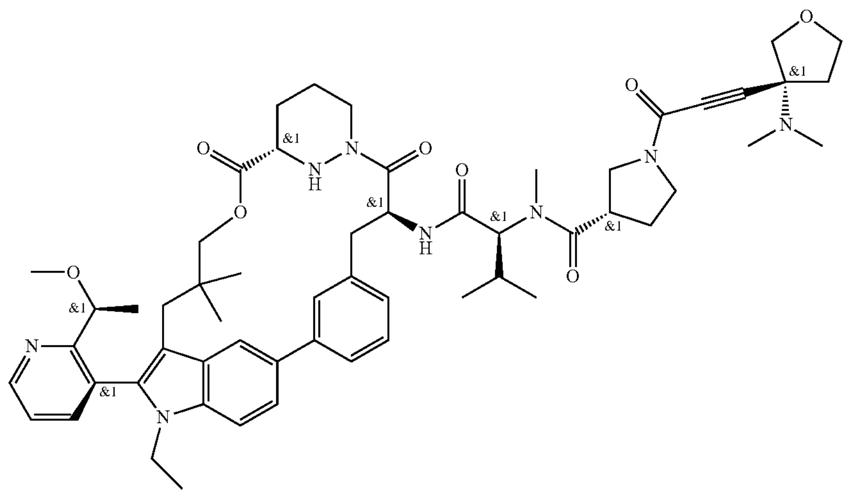 |
| B360 | 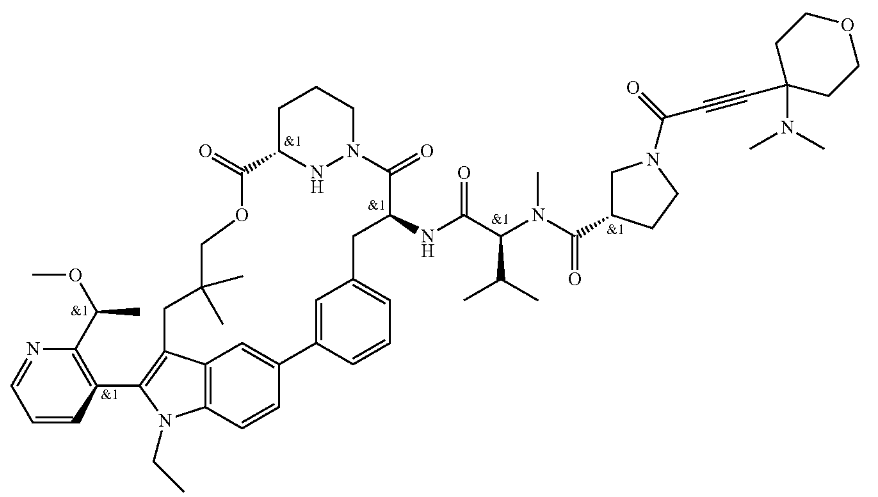 |
| B361 | 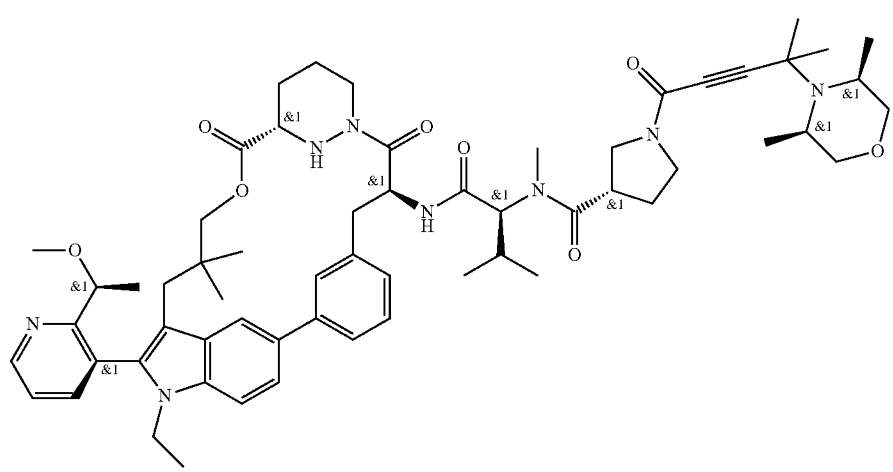 |

TABLE 2-continued
Certain Compounds of the Present Invention
| Ex # | Structure |
|---|---|
| B362 | 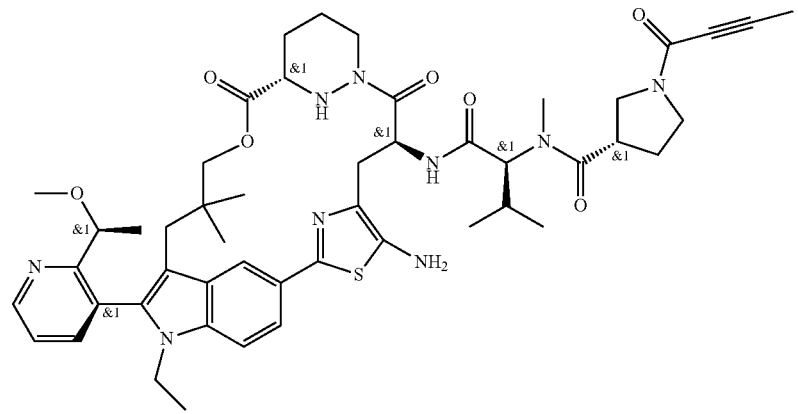 |
| B363 | 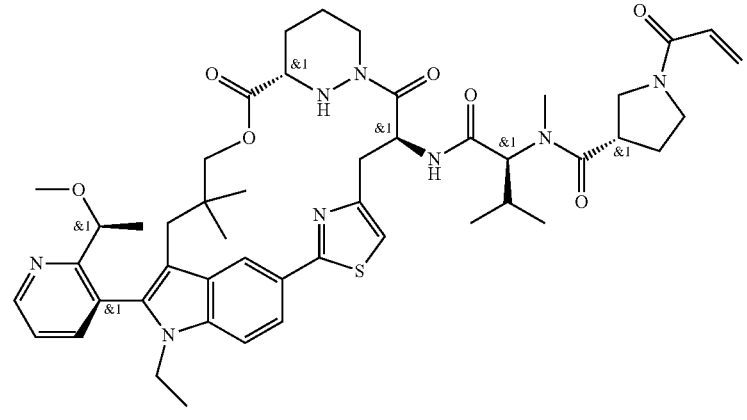 |
| B364 | 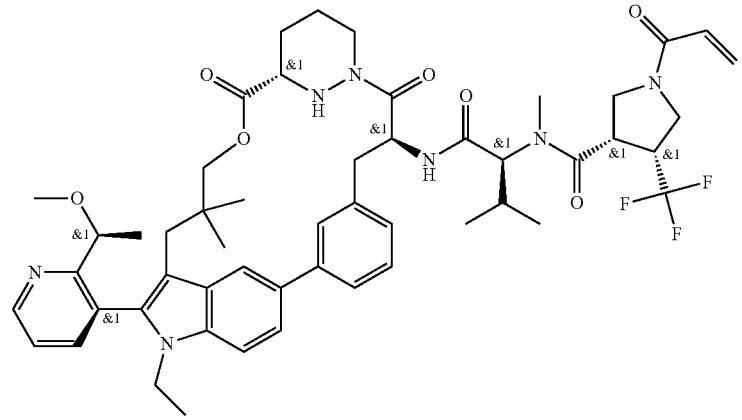 |

TABLE 2-continued

Certain Compounds of the Present Invention

| Ex # | Structure |
|---|---|
| B365 | 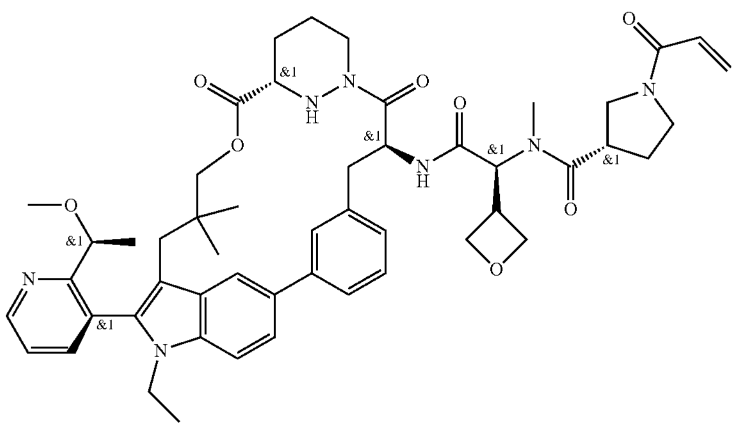 |
| B366 | 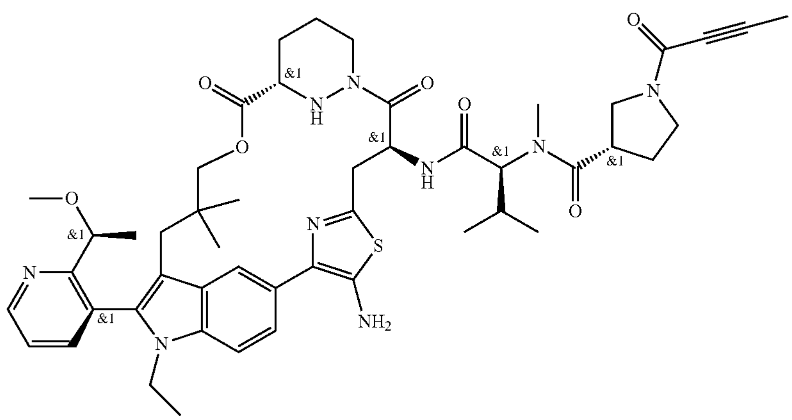 |
| B367 | 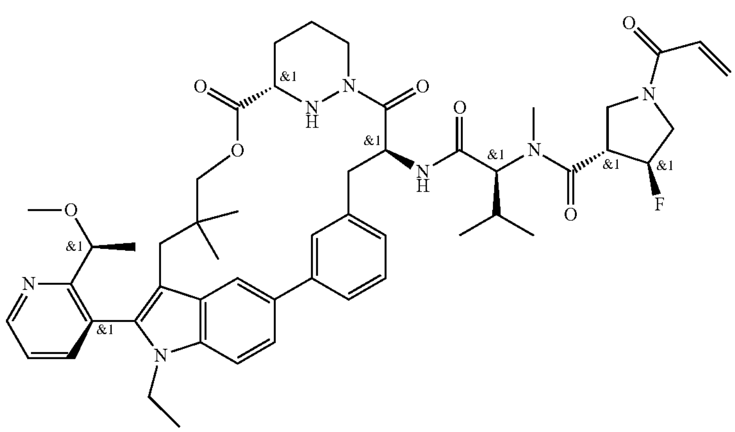 |

TABLE 2-continued

Certain Compounds of the Present Invention

| Ex # | Structure |
|---|---|
| B368 | 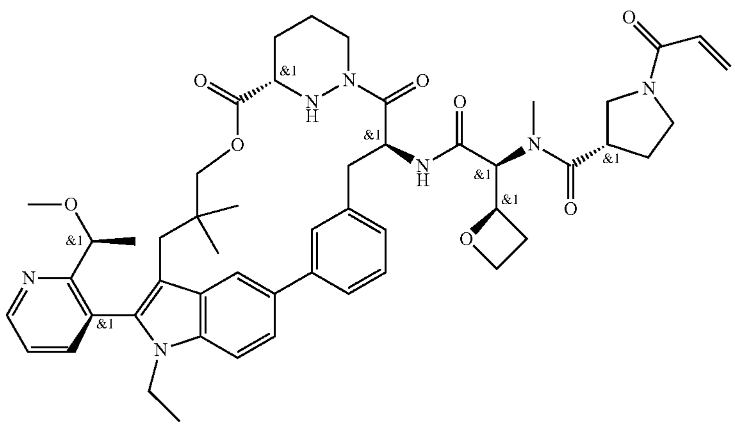 |
| B369 | 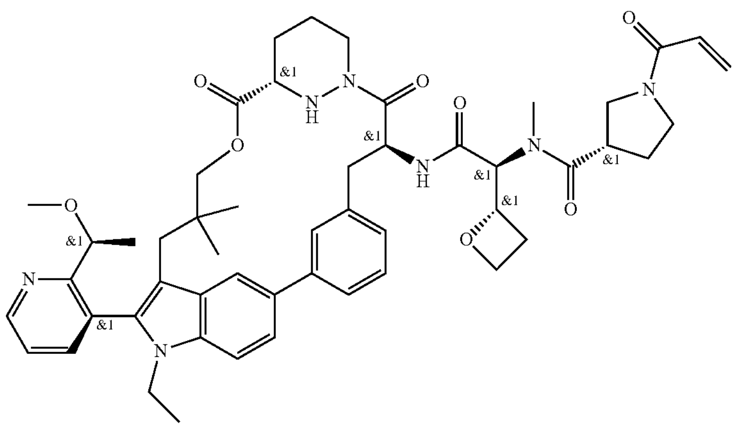 |
| B370 | 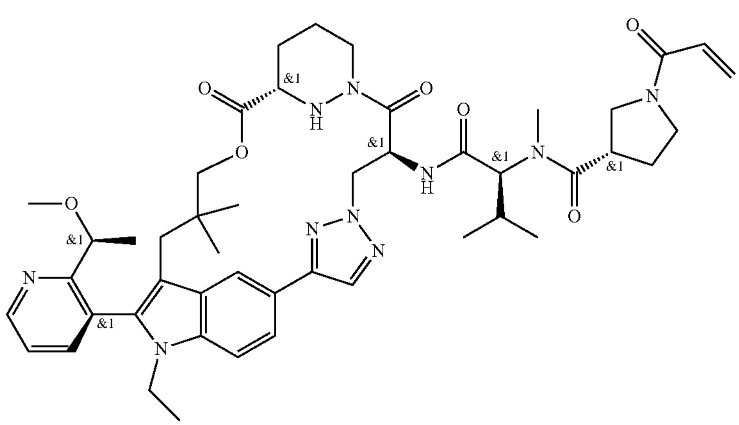 |

TABLE 2-continued

Certain Compounds of the Present Invention

| Ex # | Structure |
|---|---|
| B371 | 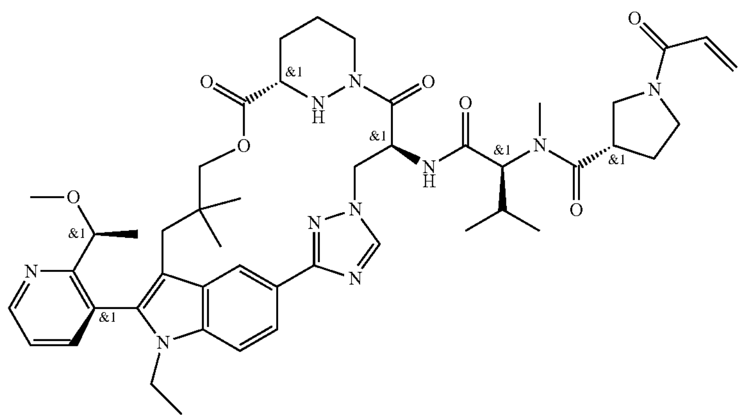 |
| B372 | 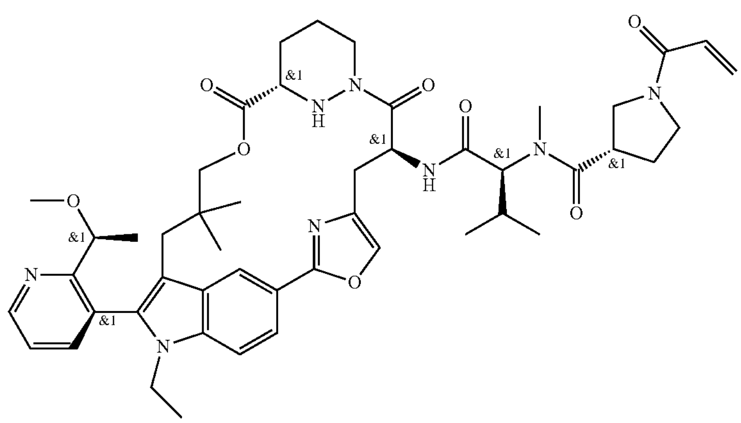 |
| B373 | 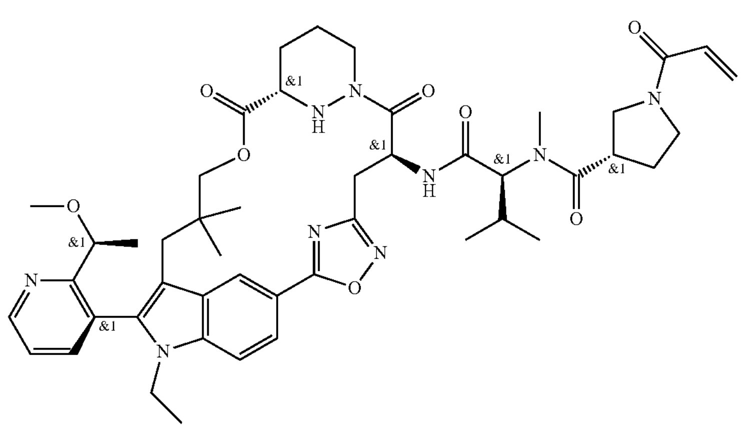 |

TABLE 2-continued
Certain Compounds of the Present Invention
| Ex # | Structure |
|---|---|
| B374 | 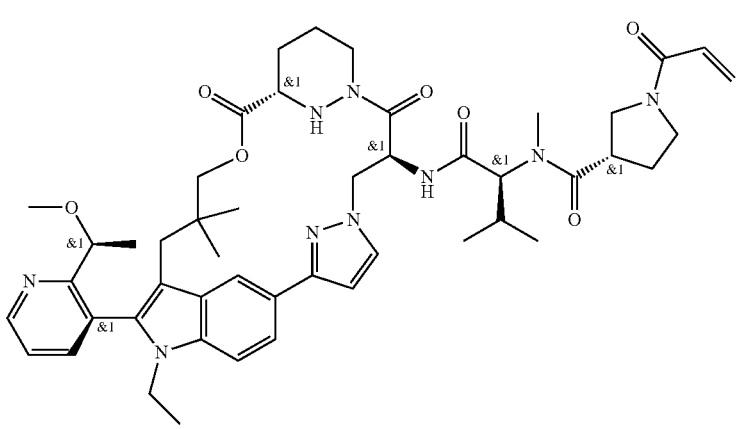 |
| B375 | 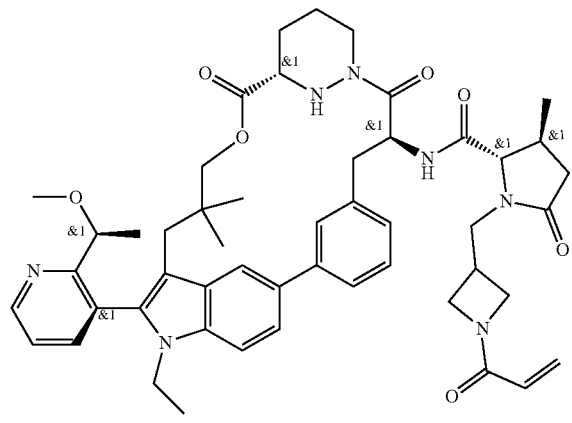 |
| B376 | 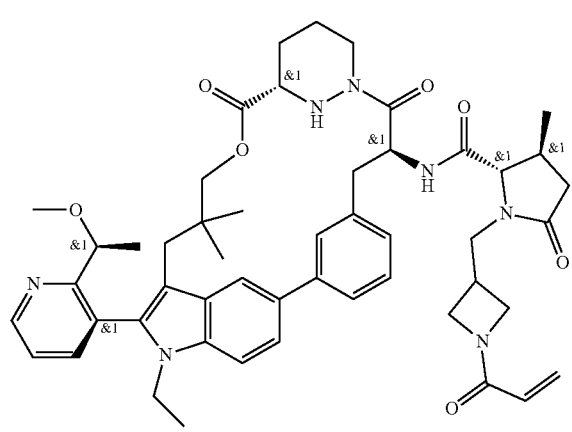 |

TABLE 2-continued
Certain Compounds of the Present Invention
| Ex # | Structure |
|---|---|
| B377 | 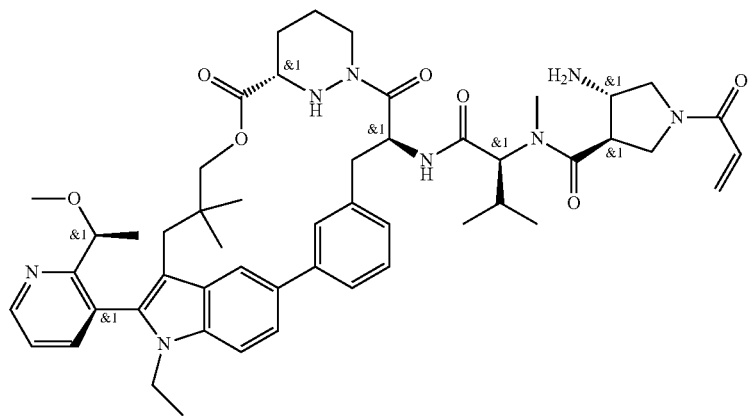 |
| B378 | 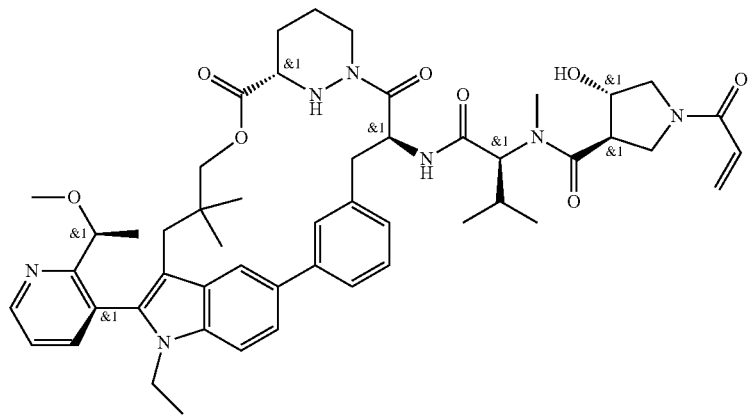 |
| B379 | 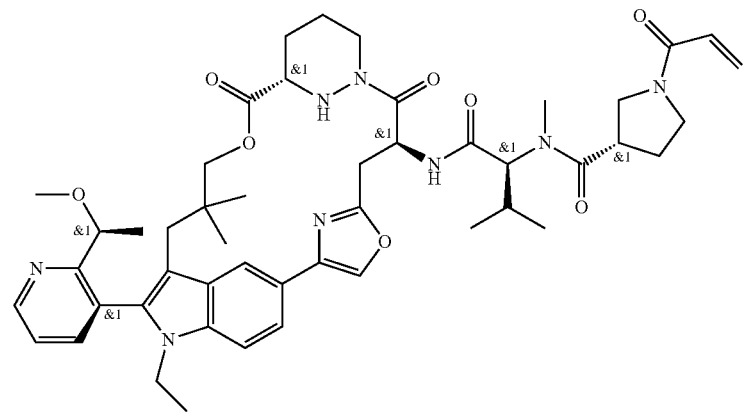 |

TABLE 2-continued

Certain Compounds of the Present Invention

| Ex # | Structure |
|---|---|
| B380 | 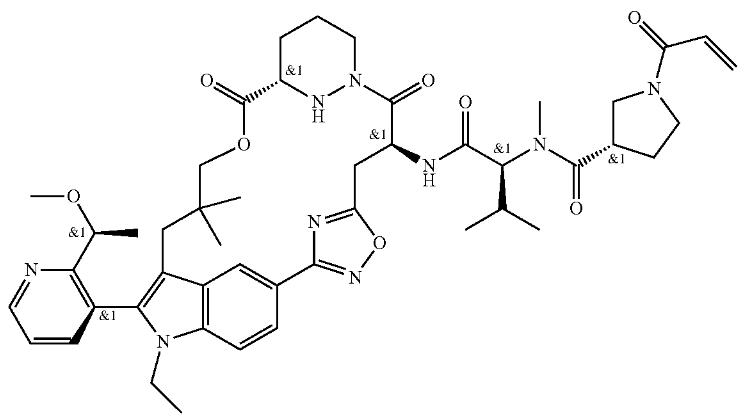 |
| B381 | 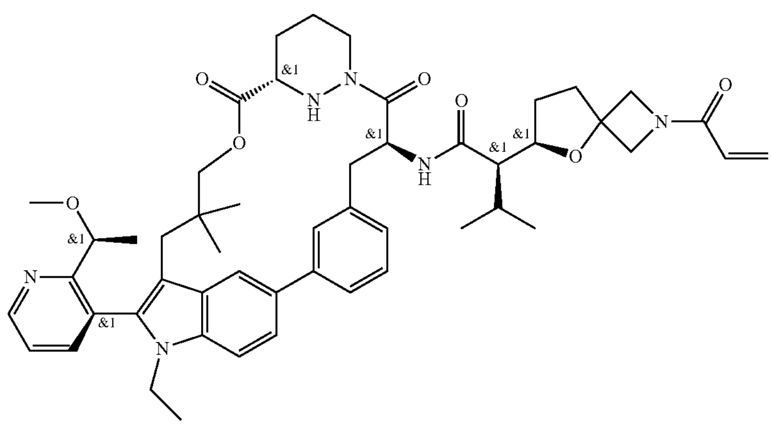 |
| B382 | 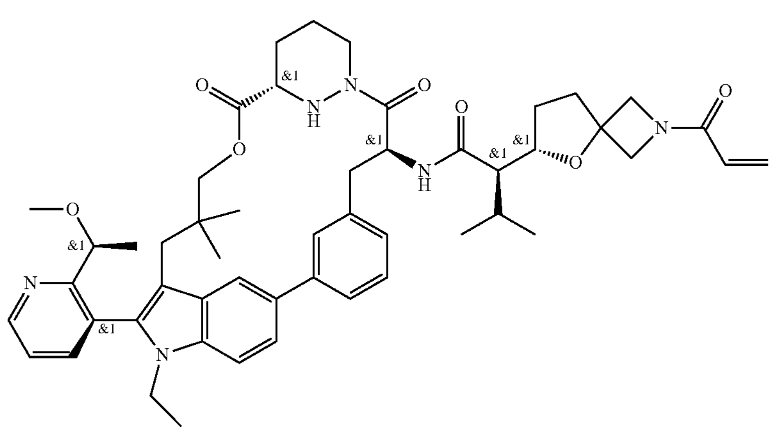 |

TABLE 2-continued

Certain Compounds of the Present Invention

| Ex # | Structure |
|---|---|
| B383 | 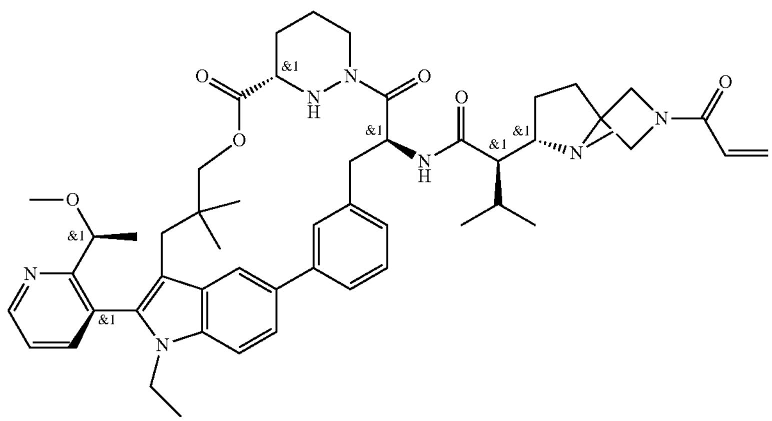 |
| B384 | 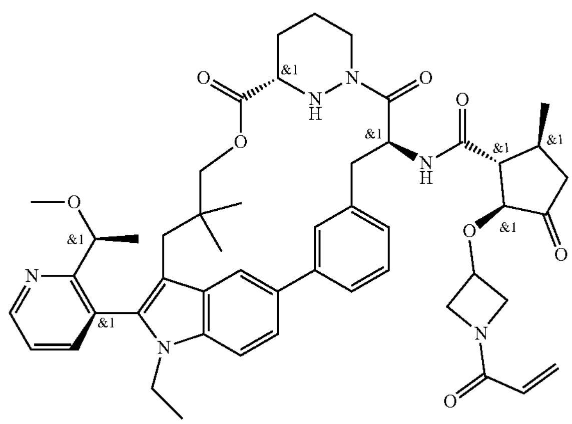 |
| B385 | 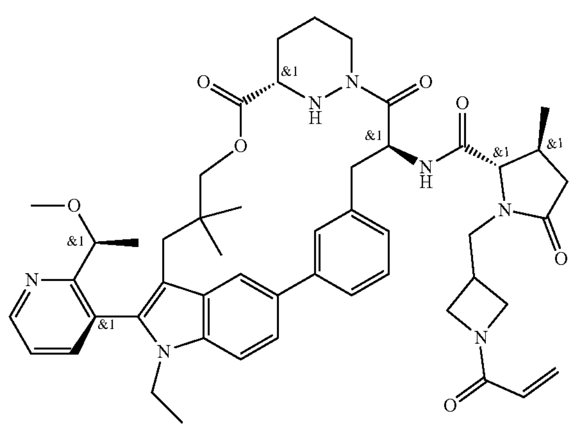 |

TABLE 2-continued
Certain Compounds of the Present Invention
| Ex # | Structure |
| --- | --- |
| B386 | 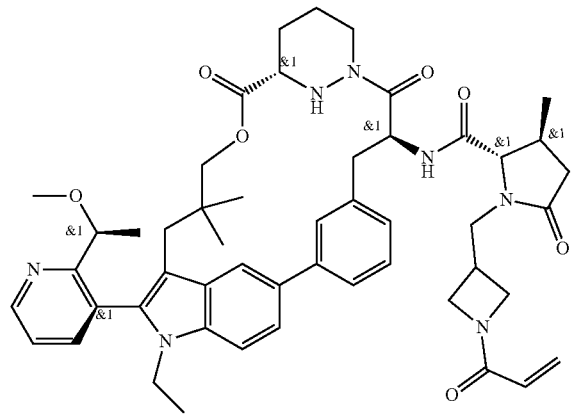 |
| B387 | 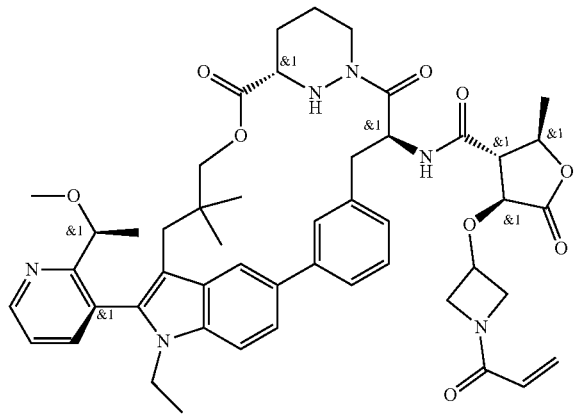 |
| B388 | 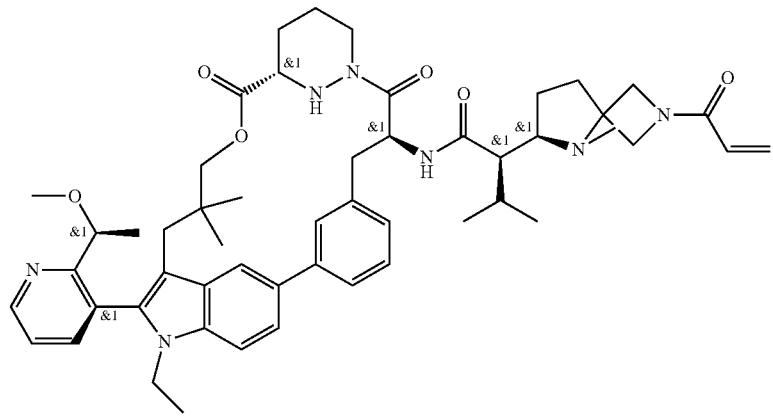 |

TABLE 2-continued
Certain Compounds of the Present Invention
| Ex # | Structure |
|---|---|
| B389 | 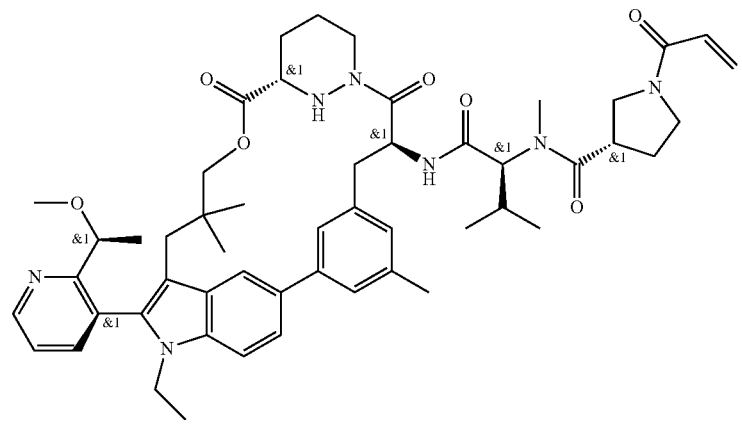 |
| B390 | 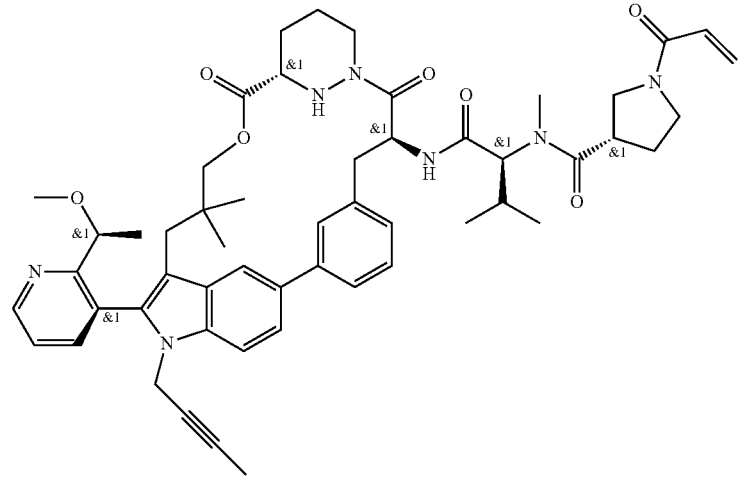 |
| B391 | 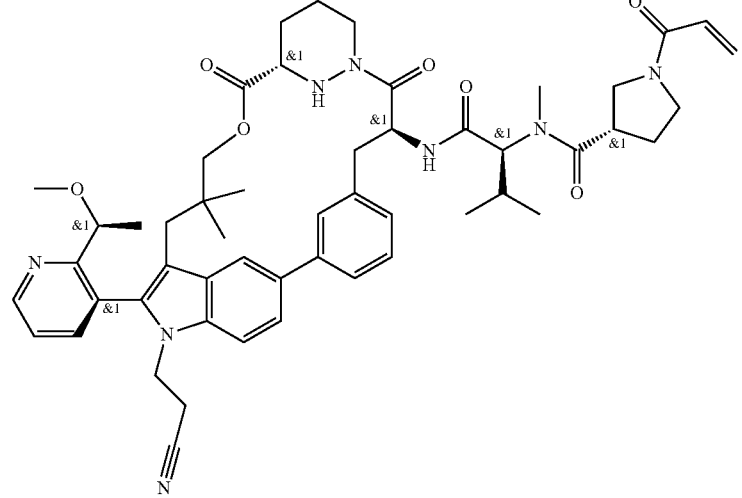 |

TABLE 2-continued

Certain Compounds of the Present Invention

| Ex # | Structure |
|------|-----------|
| B392 | 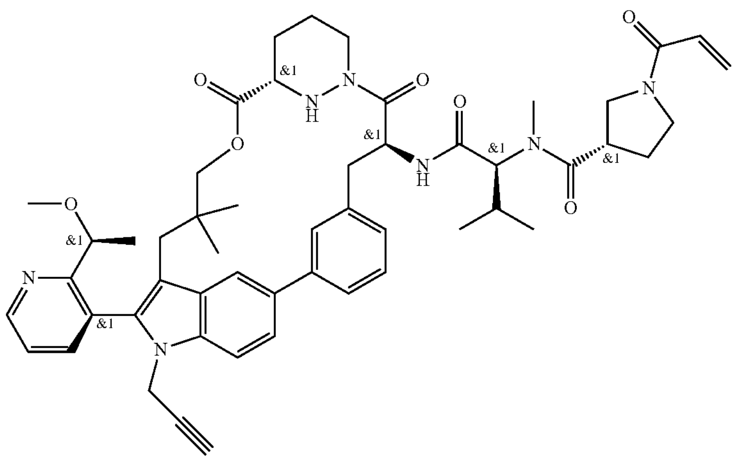 |
| B393 | 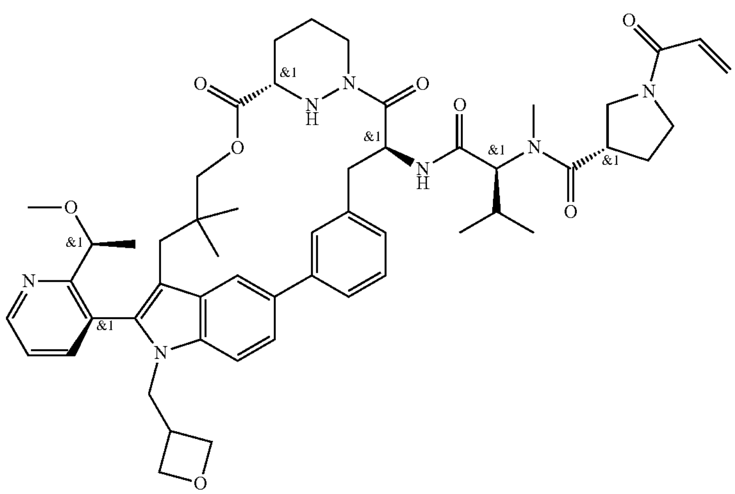 |
| B394 | 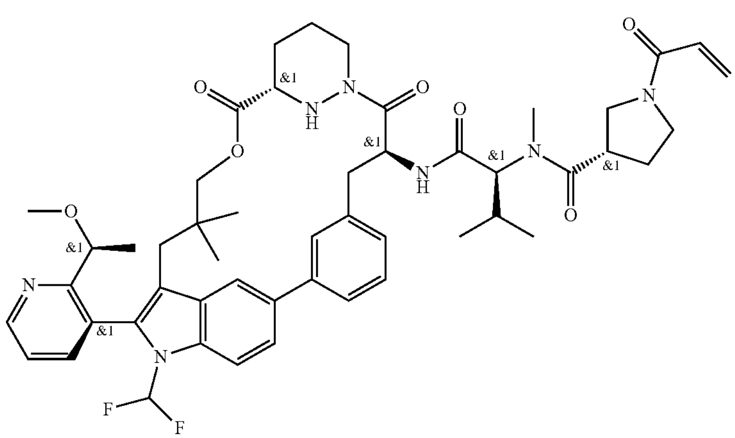 |

TABLE 2-continued

Certain Compounds of the Present Invention

| Ex # | Structure |
|---|---|
| B395 | 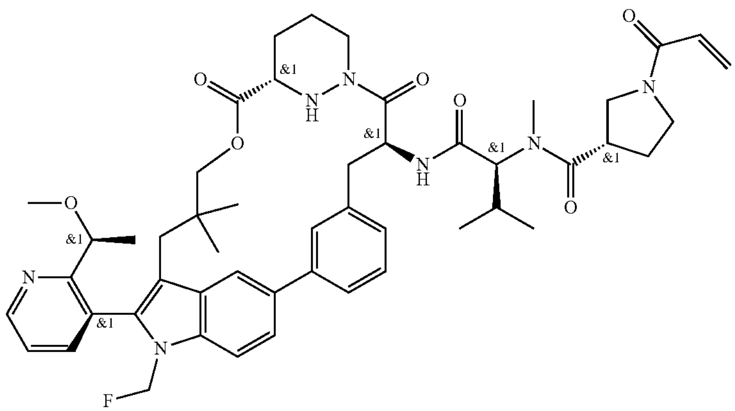 |
| B396 | 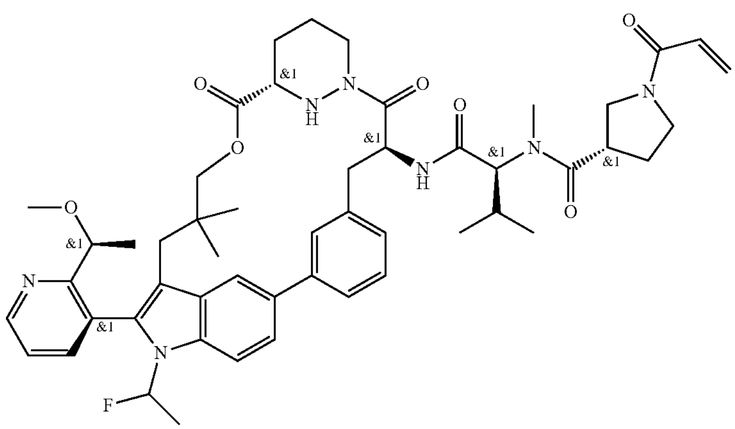 |
| B397 | 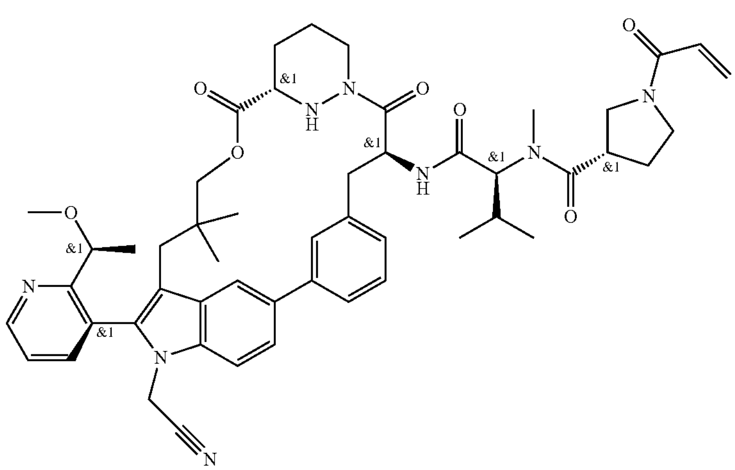 |

TABLE 2-continued

Certain Compounds of the Present Invention

| Ex # | Structure |
|---|---|
| B398 | 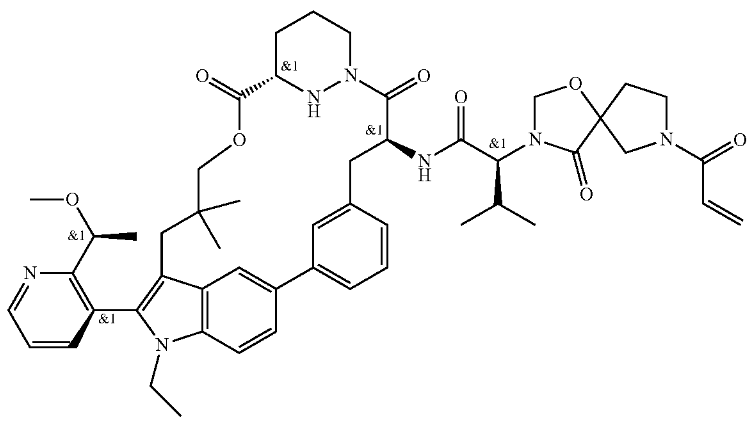 |
| B399 | 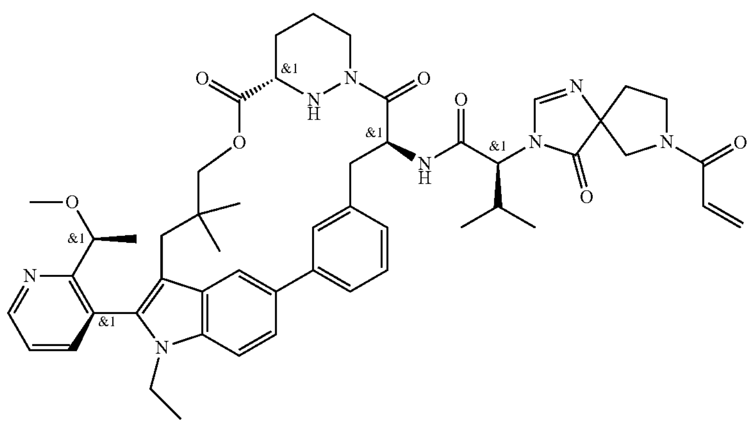 |
| B400 | 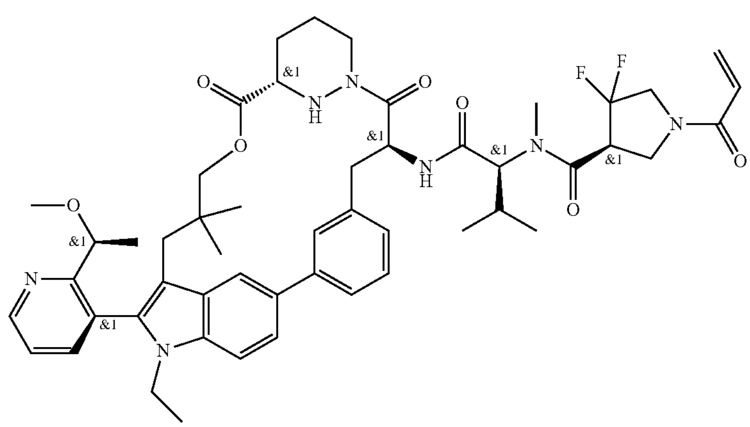 |

US 11,952,352 B2
TABLE 2-continued
Certain Compounds of the Present Invention
| Ex # | Structure |
|---|---|
| B401 | 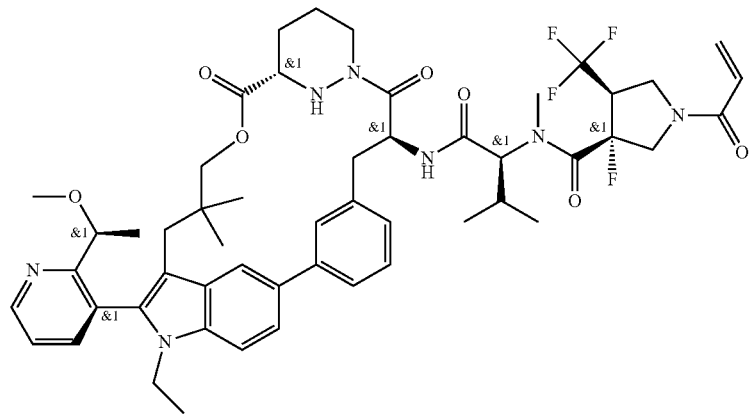 |
| B402 | 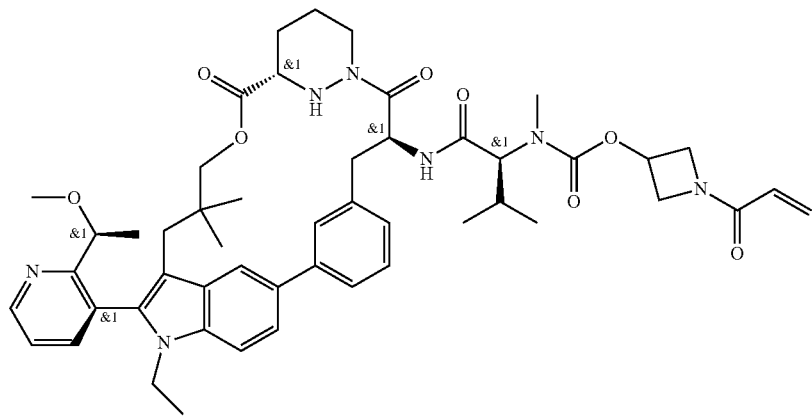 |
| B403 | 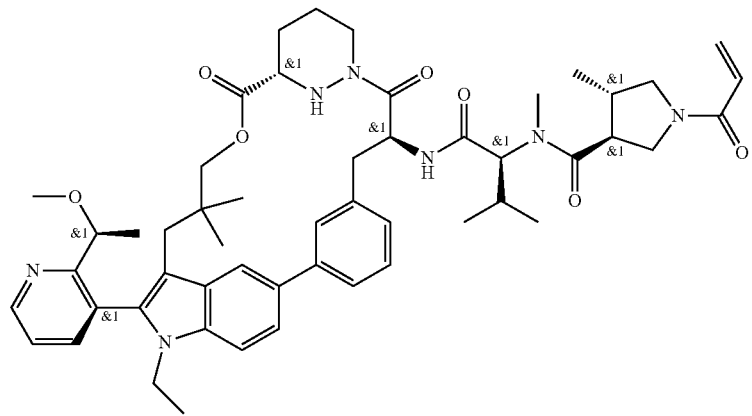 |

TABLE 2-continued
Certain Compounds of the Present Invention
| Ex # | Structure |
|---|---|
| B404 | 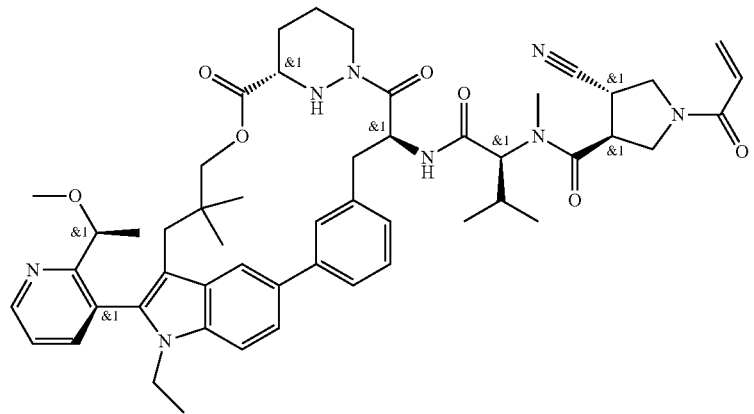 |
| B405 | 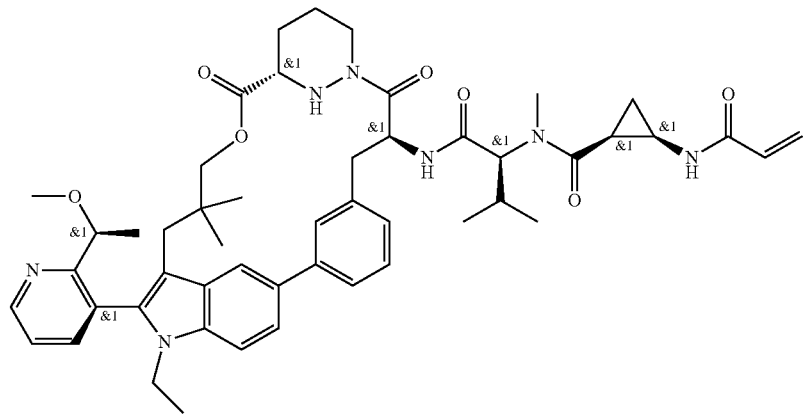 |
| B406 | 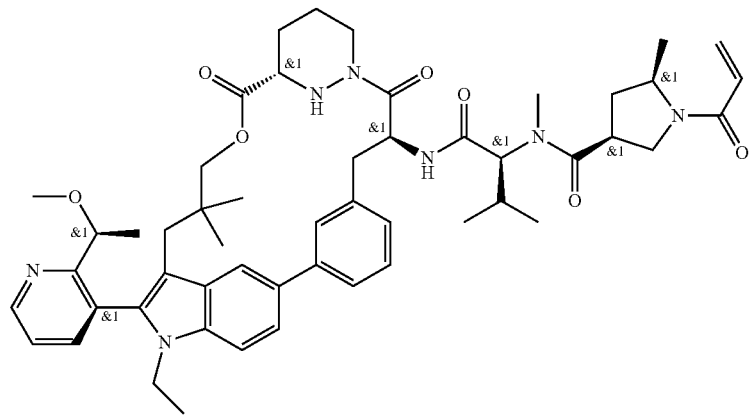 |

TABLE 2-continued

Certain Compounds of the Present Invention

| Ex # | Structure |
|---|---|
| B407 | 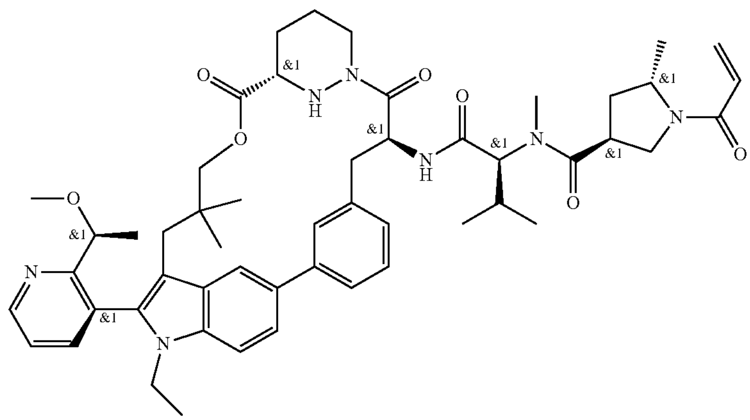 |
| B408 | 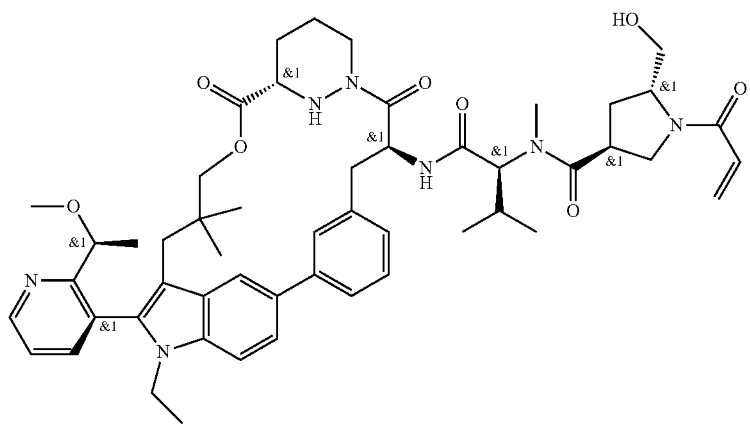 |
| B409 | 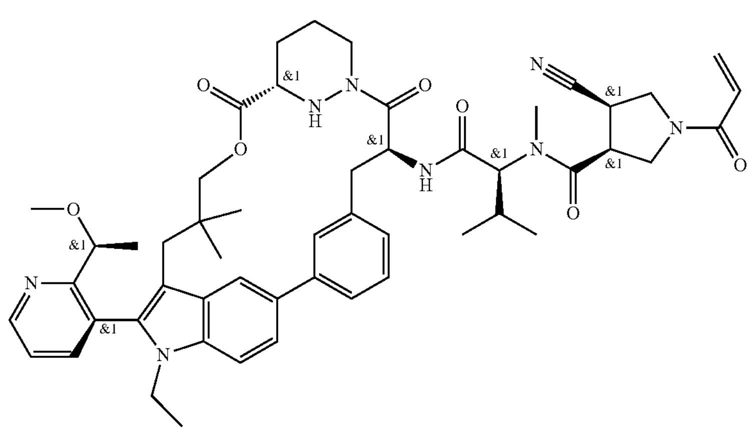 |

TABLE 2-continued

Certain Compounds of the Present Invention

| Ex # | Structure |
|------|-----------|

B410

B411

B412

TABLE 2-continued

Certain Compounds of the Present Invention

| Ex # | Structure |
|------|-----------|
| B413 | 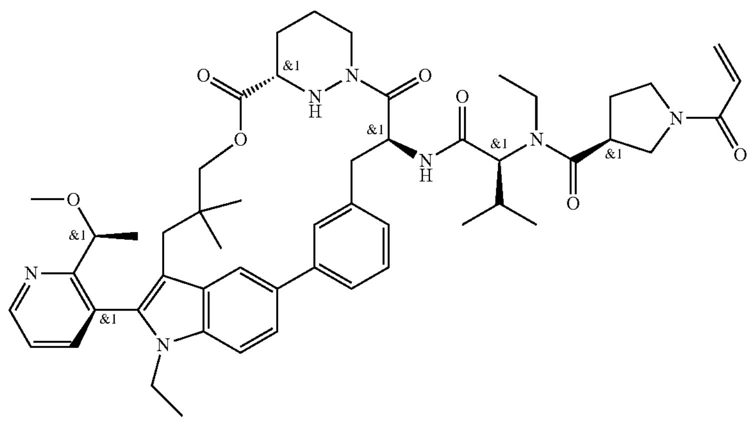 |
| B414 | 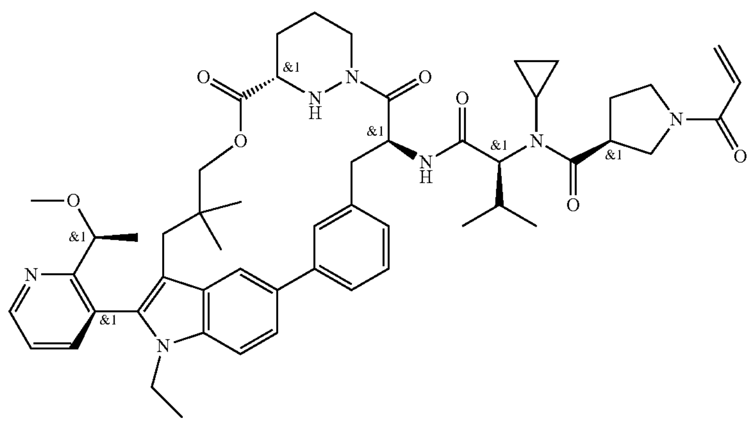 |
| B415 | 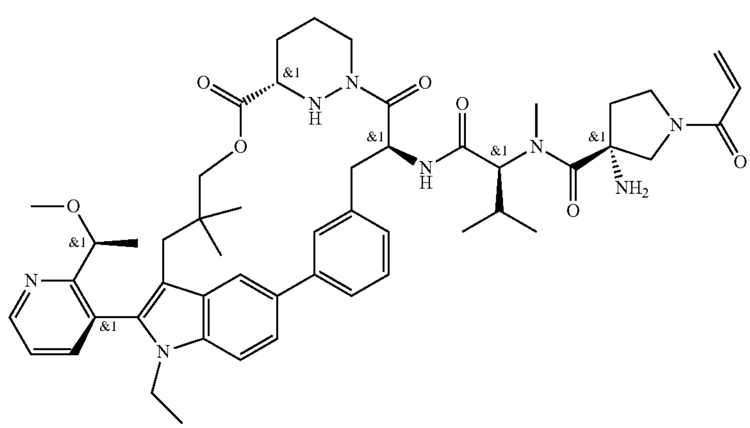 |

TABLE 2-continued

Certain Compounds of the Present Invention

| Ex # | Structure |
|------|-----------|

B416

B417

B418

TABLE 2-continued
Certain Compounds of the Present Invention
| Ex # | Structure |
|---|---|
| B419 | 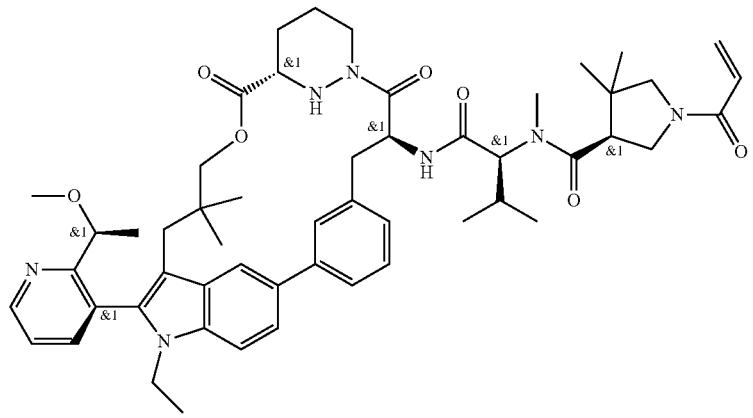 |
| B420 | 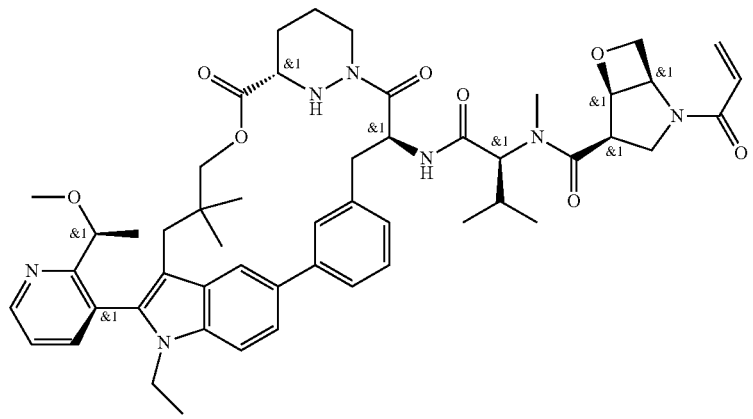 |
| B421 | 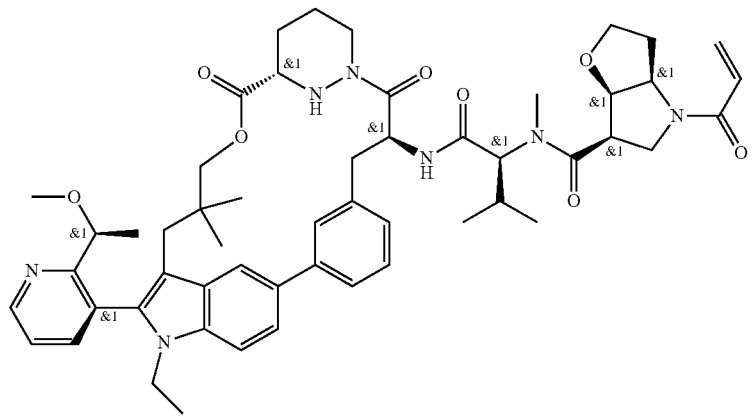 |

TABLE 2-continued

Certain Compounds of the Present Invention

| Ex # | Structure |
|---|---|
| B422 | 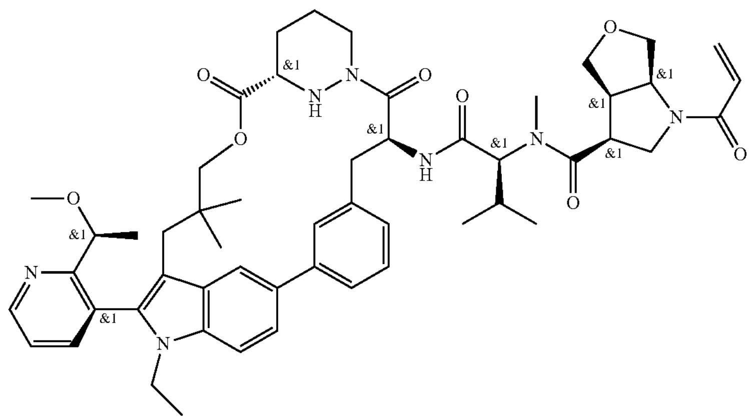 |
| B423 | 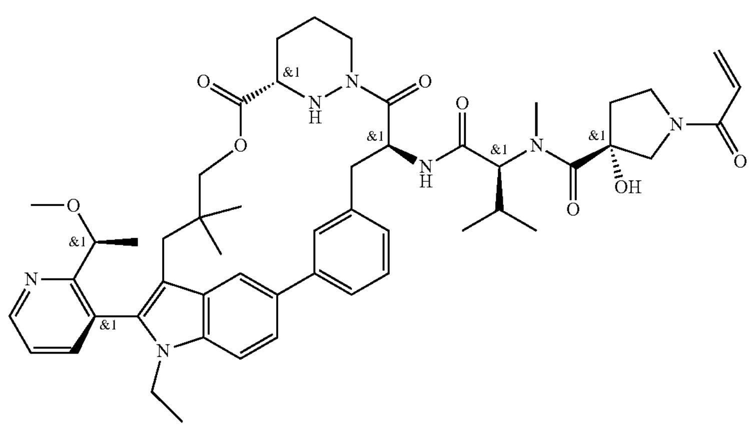 |
| B424 | 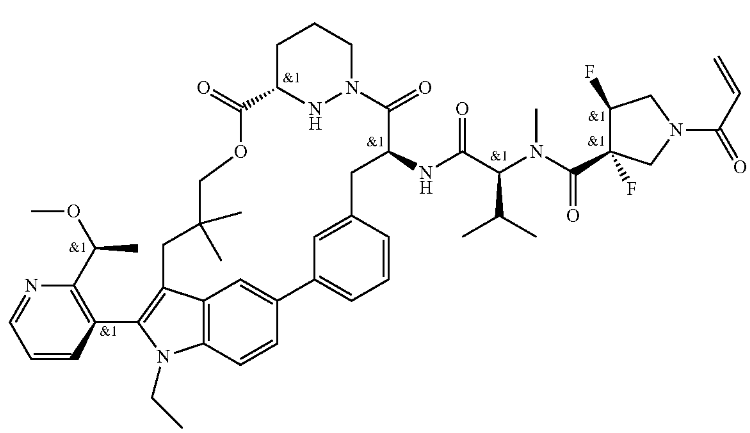 |

TABLE 2-continued

Certain Compounds of the Present Invention

| Ex # | Structure |
|---|---|
| B425 | 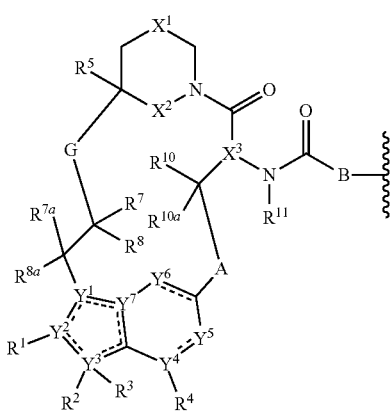 |

Note
that some compounds are shown with bonds as flat or wedged. In some instances, the relative stereochemistry of stereoisomers has been determined; in some instances, the absolute stereochemistry has been determined. All stereoisomers of the compounds of the foregoing table are contemplated by the present invention. In particular embodiments, an atropisomer of a compound of the foregoing table is contemplated.

In some embodiments, a compound of the present invention is or acts as a prodrug, such as with respect to administration to a cell or to a subject in need thereof.

Also provided are pharmaceutical compositions comprising a compound of the present invention, or a pharmaceutically acceptable salt thereof, and a pharmaceutically acceptable excipient.

Further provided is a conjugate, or salt thereof, comprising the structure of Formula IV:

M-L-P      Formula IV wherein L is a linker;
P is a monovalent organic moiety; and
M has the structure of Formula Va:

Formula Va wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is absent, —CH($R^9$)—, >C=$CR^9R^{9'}$, or >$CR^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

$X^1$ is optionally substituted $C_1$-$C_2$ alkylene, NR, O, or $S(O)_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted C$_2$-C$_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; R$^3$ is absent, or R$^2$ and R$^3$ combine with the atom to which they are attached to form an optionally substituted 3 to 8-membered cycloalkyl or optionally substituted 3 to 14-membered heterocycloalkyl;

R$^4$ is absent, hydrogen, halogen, cyano, or methyl optionally substituted with 1 to 3 halogens;

R$^5$ is hydrogen, C$_1$-C$_4$ alkyl optionally substituted with halogen, cyano, hydroxy, or C$_1$-C$_4$ alkoxy, cyclopropyl, or cyclobutyl;

R$^6$ is hydrogen or methyl; R$^7$ is hydrogen, halogen, or optionally substituted C$_1$-C$_3$ alkyl, or R$^6$ and R$^7$ combine with the carbon atoms to which they are attached to form an optionally substituted 3 to 6-membered cycloalkyl or optionally substituted 3 to 7-membered heterocycloalkyl;

R$^8$ is hydrogen, halogen, hydroxy, cyano, optionally substituted C$_1$-C$_3$ alkoxy, optionally substituted C$_1$-C$_3$ alkyl, optionally substituted C$_2$-C$_6$ alkenyl, optionally substituted C$_2$-C$_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R$^7$ and R$^8$ combine with the carbon atom to which they are attached to form C=CR$^{7'}$R$^{8'}$; C=N(OH), C=N(O—C$_1$-C$_3$ alkyl), C=O, C=S, C=NH, optionally substituted 3 to 6-membered cycloalkyl, or optionally substituted 3 to 7-membered heterocycloalkyl;

R$^{7a}$ and R$^{8a}$ are, independently, hydrogen, halo, optionally substituted C$_1$-C$_3$ alkyl, or combine with the carbon to which they are attached to form a carbonyl;

R$^{7'}$ is hydrogen, halogen, or optionally substituted C$_1$-C$_3$ alkyl; R$^{8'}$ is hydrogen, halogen, hydroxy, cyano, optionally substituted C$_1$-C$_3$ alkoxy, optionally substituted C$_1$-C$_3$ alkyl, optionally substituted C$_2$-C$_6$ alkenyl, optionally substituted C$_2$-C$_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R$^{7'}$ and R$^{8'}$ combine with the carbon atom to which they are attached to form optionally substituted 3 to 6-membered cycloalkyl or optionally substituted 3 to 7-membered heterocycloalkyl;

R$^9$ is H, optionally substituted C$_1$-C$_6$ alkyl, optionally substituted C$_1$-C$_6$ heteroalkyl, optionally substituted 3 to 6-membered cycloalkyl, or optionally substituted 3 to 7-membered heterocycloalkyl, or R$^9$ and L combine with the atoms to which they are attached to form an optionally substituted 3 to 14-membered heterocycloalkyl;

R$^{9'}$ is hydrogen or optionally substituted C$_1$-C$_6$ alkyl; or

R$^9$ and R$^{9'}$, combined with the atoms to which they are attached, form a 3 to 6-membered cycloalkyl or a 3 to 6-membered heterocycloalkyl;

R$^{10}$ is hydrogen, halo, hydroxy, C$_1$-C$_3$ alkoxy, or C$_1$-C$_3$ alkyl;

R$^{10a}$ is hydrogen or halo; and

R$^{11}$ is hydrogen or C$_1$-C$_3$ alkyl.

In some embodiments the conjugate, or salt thereof, comprises the structure of Formula IV:

M-L-P      Formula IV wherein L is a linker;
P is a monovalent organic moiety; and
M has the structure of Formula Vb:

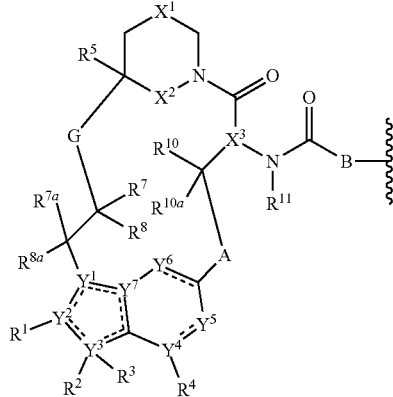

Formula Vb wherein the dotted lines represent zero, one, two, three, or four non-adjacent double bonds;

A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R$^9$)— or >C=CR$^9$R$^{9'}$ where the carbon is bound to the carbonyl carbon of —N(R$^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted C$_1$-C$_4$ alkylene, optionally substituted C$_1$-C$_4$ alkenylene, optionally substituted C$_1$-C$_4$ heteroalkylene, —C(O)O—CH(R$^6$)— where C is bound to —C(R$^7$R$^8$)—, —C(O)NH—CH(R$^6$)— where C is bound to —C(R$^7$R$^8$)—, optionally substituted C$_1$-C$_4$ heteroalkylene, or 3 to 8-membered heteroarylene;

X$^1$ is optionally substituted C$_1$-C$_2$ alkylene, NR, O, or S(O)$_n$;

X$^2$ is O or NH;

X$^3$ is N or CH;

n is 0, 1, or 2;

R is hydrogen, cyano, optionally substituted C$_1$-C$_4$ alkyl, optionally substituted C$_2$-C$_4$ alkenyl, optionally substituted C$_2$-C$_4$ alkynyl, C(O)R', C(O)OR', C(O)N(R')$_2$, S(O)R', S(O)$_2$R', or S(O)$_2$N(R')$_2$;

each R' is, independently, H or optionally substituted C$_1$-C$_4$ alkyl;

Y$^1$ is C, CH, or N;

Y$^2$, Y$^3$, Y$^4$, and Y$^7$ are, independently, C or N;

Y$^5$ is CH, CH$_2$, or N;

Y$^6$ is C(O), CH, CH$_2$, or N;

R$^1$ is cyano, optionally substituted C$_1$-C$_6$ alkyl, optionally substituted C$_1$-C$_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo; and $R^{11}$ is hydrogen or $C_1$-$C_3$ alkyl.

In some embodiments, the conjugate has the structure of Formula IV:

M-L-P  Formula IV wherein L is a linker;
P is a monovalent organic moiety; and
M has the structure of Formula Vc:

Formula Vc wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

R² is hydrogen, optionally substituted C₁-C₆ alkyl, optionally substituted C₂-C₆ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; R³ is absent, or R² and R³ combine with the atom to which they are attached to form an optionally substituted 3 to 8-membered cycloalkyl or optionally substituted 3 to 14-membered heterocycloalkyl;

R⁴ is absent, hydrogen, halogen, cyano, or methyl optionally substituted with 1 to 3 halogens;

R⁵ is hydrogen, C₁-C₄ alkyl optionally substituted with halogen, cyano, hydroxy, or C₁-C₄ alkoxy, cyclopropyl, or cyclobutyl;

R⁶ is hydrogen or methyl; R⁷ is hydrogen, halogen, or optionally substituted C₁-C₃ alkyl, or R⁶ and R⁷ combine with the carbon atoms to which they are attached to form an optionally substituted 3 to 6-membered cycloalkyl or optionally substituted 3 to 7-membered heterocycloalkyl;

R⁸ is hydrogen, halogen, hydroxy, cyano, optionally substituted C₁-C₃ alkoxy, optionally substituted C₁-C₃ alkyl, optionally substituted C₂-C₆ alkenyl, optionally substituted C₂-C₆ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R⁷ and R⁸ combine with the carbon atom to which they are attached to form C=CR⁷'R⁸'; C=N(OH), C=N(O—C₁-C₃ alkyl), C=O, C=S, C=NH, optionally substituted 3 to 6-membered cycloalkyl, or optionally substituted 3 to 7-membered heterocycloalkyl;

R⁷' is hydrogen, halogen, or optionally substituted C₁-C₃ alkyl; R⁸' is hydrogen, halogen, hydroxy, cyano, optionally substituted C₁-C₃ alkoxy, optionally substituted C₁-C₃ alkyl, optionally substituted C₂-C₆ alkenyl, optionally substituted C₂-C₆ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R⁷' and R⁸' combine with the carbon atom to which they are attached to form optionally substituted 3 to 6-membered cycloalkyl or optionally substituted 3 to 7-membered heterocycloalkyl;

R⁹ is optionally substituted C₁-C₆ alkyl, optionally substituted C₁-C₆ heteroalkyl, optionally substituted 3 to 6-membered cycloalkyl, or optionally substituted 3 to 7-membered heterocycloalkyl;

R¹⁰ is hydrogen, hydroxy, C₁-C₃ alkoxy, or C₁-C₃ alkyl; and

R¹¹ is hydrogen or C₁-C₃ alkyl.

In some embodiments, a compound of the present invention has the structure of of Formula IV:

M-L-P          Formula IV wherein L is a linker;

P is a monovalent organic moiety; and

M has the structure of Formula Vd:

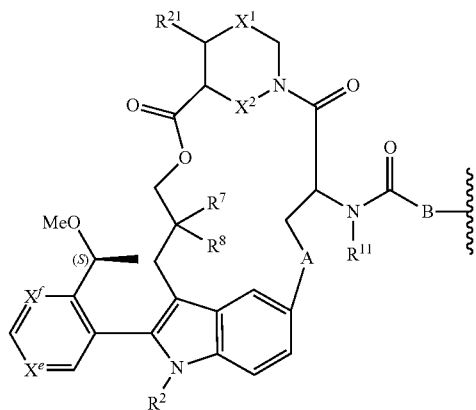

Formula Vd wherein A optionally substituted 3 to 6-membered cycloalkylene, optionally substituted 3 to 6-membered heterocycloalkylene, optionally substituted 6-membered arylene (e.g., phenyl or phenol), or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

X¹ is optionally substituted C₁-C₂ alkylene, NR, O, or S(O)ₙ;

X² is O or NH;

n is 0, 1, or 2;

R is hydrogen, cyano, optionally substituted C₁-C₄ alkyl, optionally substituted C₂-C₄ alkenyl, optionally substituted C₂-C₄ alkynyl, C(O)R', C(O)OR', C(O)N(R')₂, S(O)R', S(O)₂R', or S(O)₂N(R')₂;

each R' is, independently, H or optionally substituted C₁-C₄ alkyl;

R² is C₁-C₆ alkyl, C₁-C₆ fluoroalkyl, or 3 to 6-membered cycloalkyl; R⁷ is C₁-C₃ alkyl;

R⁸ is C₁-C₃ alkyl; and

R⁹ is optionally substituted C₁-C₆ alkyl, optionally substituted C₁-C₆ heteroalkyl, optionally substituted 3 to 6-membered cycloalkyl, or optionally substituted 3 to 7-membered heterocycloalkyl;

Xᵉ and Xᶠ are, independently, N or CH;

R¹¹ is hydrogen or C₁-C₃ alkyl; and

R²¹ is hydrogen or C₁-C₃ alkyl.

In some embodiments of a compound of the present invention, Xᵉ is N and Xᶠ is CH. In some embodiments, Xᵉ is CH and Xᶠ is N.

In some embodiments, a compound of the present invention has the structure of Formula IV:

M-L-P          Formula IV wherein L is a linker;
P is a monovalent organic moiety; and
M has the structure of Formula Ve:

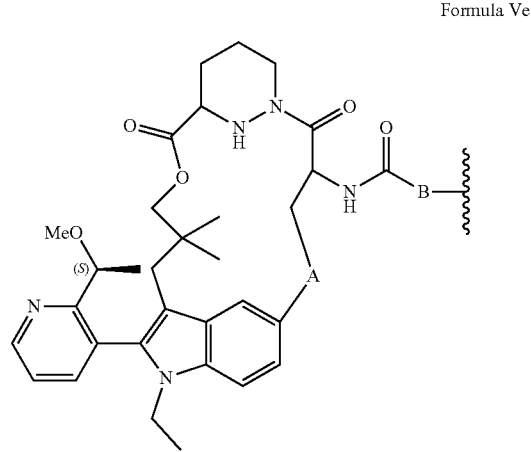

Formula Ve wherein A is optionally substituted 3 to 6-membered cycloalkylene, optionally substituted 3 to 6-membered heterocycloalkylene, optionally substituted 6-membered arylene (e.g., phenyl or phenol), or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

In some embodiments of a conjugate of the present invention, the linker has the structure of Formula II:

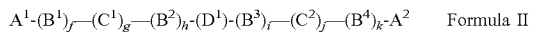

Formula II where $A^1$ is a bond between the linker and B; $A^2$ is a bond between P and the linker; $B^1$, $B^2$, $B^3$, and $B^4$ each, independently, is selected from optionally substituted $C_1$-$C_2$ alkylene, optionally substituted $C_1$-$C_3$ heteroalkylene, O, S, and $NR^N$; $R^N$ is hydrogen, optionally substituted $C_1$-$C_4$ alkyl, optionally substituted $C_2$-$C_4$ alkenyl, optionally substituted $C_2$-$C_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$-$(C^1)_g$—$(B^2)_h$- to -$(B^3)_i$—$(C^2)_j$—$(B^4)_k$-$A^2$.

In some embodiments of a conjugate of the present invention, the monovalent organic moiety is a protein, such as a Ras protein. In some embodiments, the Ras protein is K-Ras G12C, K-Ras G13C, H-Ras G12C, H-Ras G13C, N-Ras G12C, or N-Ras G13C. Other Ras proteins are described herein. In some embodiments, the linker is bound to the monovalent organic moiety through a bond to a sulfhydryl group of an amino acid residue of the monovalent organic moiety. In some embodiments, the linker is bound to the monovalent organic moiety through a bond to a carboxyl group of an amino acid residue of the monovalent organic moiety.

Further provided is a method of treating cancer in a subject in need thereof, the method comprising administering to the subject a therapeutically effective amount of a compound of the present invention, or a pharmaceutically acceptable salt thereof. The cancer may, for example, be pancreatic cancer, colorectal cancer, non-small cell lung cancer, acute myeloid leukemia, multiple myeloma, thyroid gland adenocarcinoma, a myelodysplastic syndrome, or squamous cell lung carcinoma. In some embodiments, the cancer comprises a Ras mutation, such as K-Ras G12C, K-Ras G13C, H-Ras G12C, H-Ras G13C, N-Ras G12C, or N-Ras G13C. Other Ras mutations are described herein.

Further provided is a method of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof. For example, the Ras protein is K-Ras G12C, K-Ras G13C, H-Ras G12C, H-Ras G13C, N-Ras G12C, or N-Ras G13C. Other Ras proteins are described herein. The cell may be a cancer cell, such as a pancreatic cancer cell, a colorectal cancer cell, a non-small cell lung cancer cell, an acute myeloid leukemia cell, a multiple myeloma cell, a thyroid gland adenocarcinoma cell, a myelodysplastic syndrome cell, or a squamous cell lung carcinoma cell. Other cancer types are described herein. The cell may be in vivo or in vitro.

With respect to compounds of the present invention, one stereoisomer may exhibit better inhibition than another stereoisomer. For example, one atropisomer may exhibit inhibition, whereas the other atropisomer may exhibit little or no inhibition.

In some embodiments, a method or use described herein further comprises administering an additional anti-cancer therapy. In some embodiments, the additional anti-cancer therapy is a HER2 inhibitor, an EGFR inhibitor, a second Ras inhibitor, a SHP2 inhibitor, an SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, or a combination thereof. In some embodiments, the additional anticancer therapy is a SHP2 inhibitor. Other additional anti-cancer therapies are described herein.

Methods of Synthesis

The compounds described herein may be made from commercially available starting materials or synthesized using known organic, inorganic, or enzymatic processes.

The compounds of the present invention can be prepared in a number of ways well known to those skilled in the art of organic synthesis. By way of example, compounds of the present invention can be synthesized using the methods described in the Schemes below, together with synthetic methods known in the art of synthetic organic chemistry, or variations thereon as appreciated by those skilled in the art.

These methods include but are not limited to those methods described in the Schemes below.
Scheme 1. General synthesis of macrocyclic esters
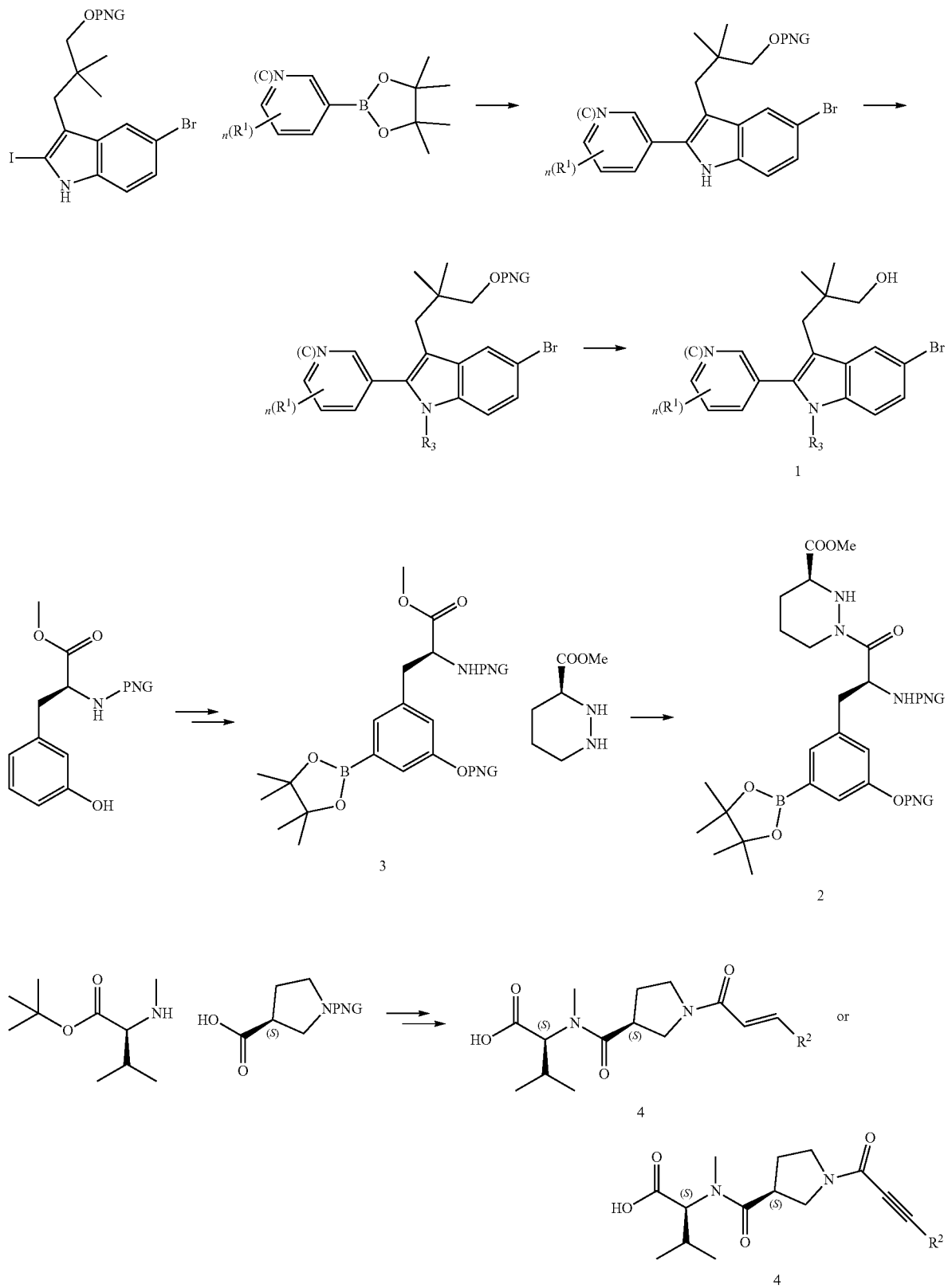

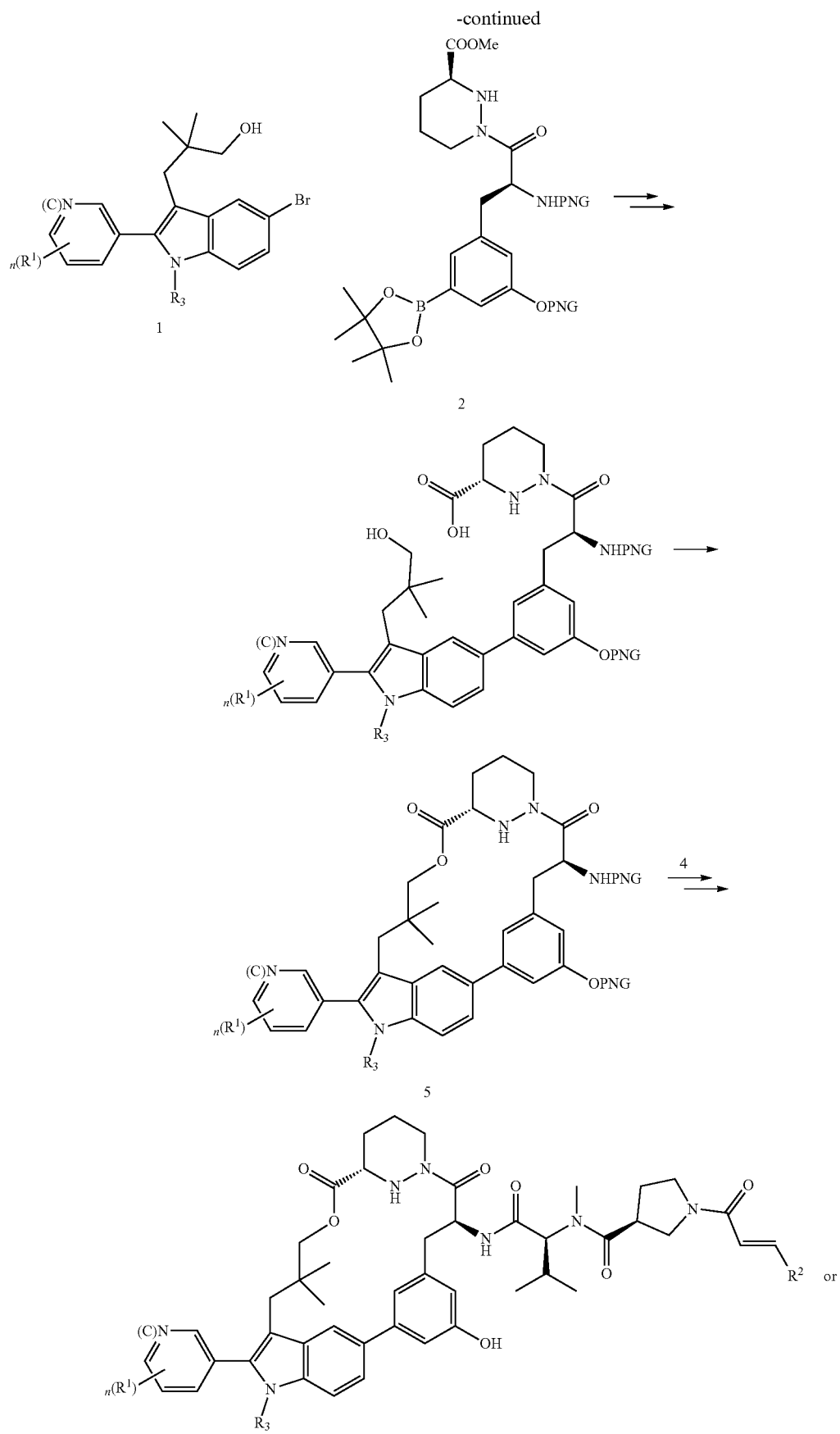

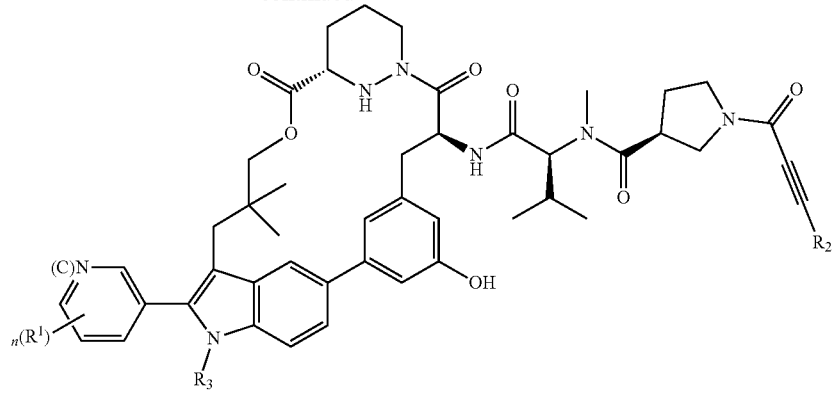

A general synthesis of macrocyclic esters is outlined in Scheme 1. An appropriately substituted aryl-3-(5-bromo-1-ethyl-1H-indol-3-yl)-2,2-dimethylpropan-1-ol (1) can be prepared in three steps starting from protected 3-(5-bromo-2-iodo-1H-indol-3-yl)-2,2-dimethylpropan-1-ol and appropriately substituted boronic acid, including palladium mediated coupling, alkylation, and de-protection reactions. Methyl-amino-hexahydropyridazine-3-carboxylate-boronic ester (2) can be prepared in three steps, including protection, iridium catalyst mediated borylation, and coupling with methyl methyl (S)-hexahydropyridazine-3-carboxylate.

An appropriately substituted acetylpyrrolidine-3-carbonyl-N-methyl-L-valine (or an alternative amino acid derivative (4) can be made by coupling of methyl-L-valinate and protected (S)-pyrrolidine-3-carboxylic acid, followed by deprotection, coupling with a carboxylic acid containing an appropriately substituted Michael acceptor, and a hydrolysis step.

The final macrocyclic esters can be made by coupling of methyl-amino-hexahydropyridazine-3-carboxylate-boronic ester (2) and aryl-3-(5-bromo-1-ethyl-1H-indol-3-yl)-2,2-dimethylpropan-1-ol (1) in the presence of a Pd catalyst followed by hydrolysis and macrolactonization steps to result in an appropriately protected macrocyclic intermediate (5). Deprotection and coupling with an appropriately substituted intermediate 4 results in a macrocyclic product. Additional deprotection and/or functionalization steps can be required to produce the final compound.

Scheme 2. Alternative general synthesis of macrocyclic esters

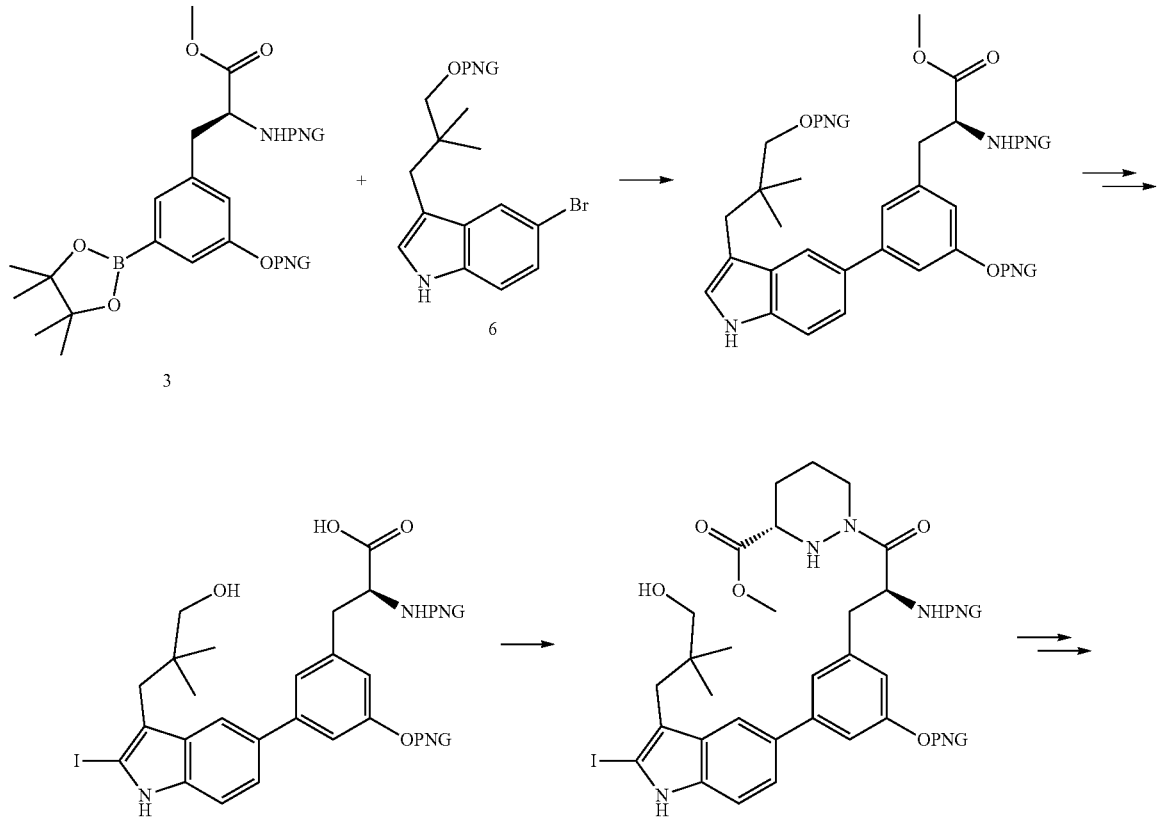

-continued

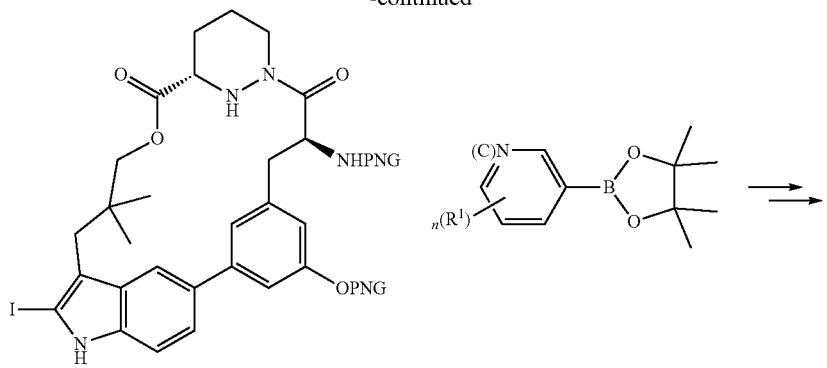

7

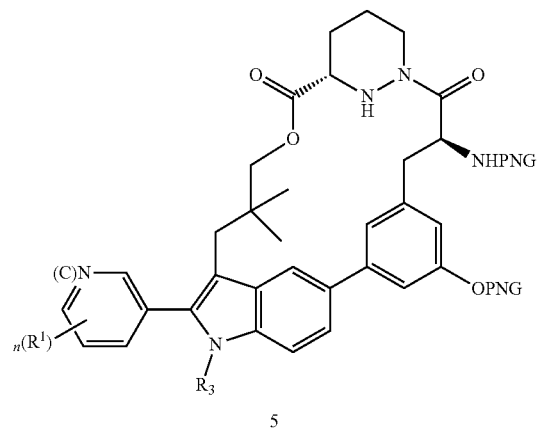

5

Alternatively, macrocyclic ester can be prepared as described in Scheme 2. An appropriately protected bromoindolyl (6) coupled in the presence of a Pd catalyst with boronic ester (3), followed by iodination, deprotection, and ester hydrolysis. Subsequent coupling with methyl (S)-hexahydropyridazine-3-carboxylate, followed by hydrolysis and macrolactonization can result in iodo intermediate (7). Coupling in the presence of a Pd catalyst with an appropriately substituted boronic ester and alkylation can yield fully protected macrocycle (5). Additional deprotection or functionalization steps are required to produce the final compound.

In addition, compounds of the disclosure can be synthesized using the methods described in the Examples below, together with synthetic methods known in the art of synthetic organic chemistry, or variations thereon as appreciated by those skilled in the art. These methods include but are not limited to those methods described in the Examples below. For example, a person of skill in the art would be able to install into a macrocyclic ester a desired -B-L-W group of a compound of Formula (I), where B, L and W are defined herein, including by using methods exemplified in the Example section herein.

Compounds of Table 1 herein were prepared using methods disclosed herein or were prepared using methods disclosed herein combined with the knowledge of one of skill in the art. Compounds of Table 2 may be prepared using methods disclosed herein or may be prepared using methods disclosed herein combined with the knowledge of one of skill in the art.

Scheme 3. General synthesis of macrocyclic esters

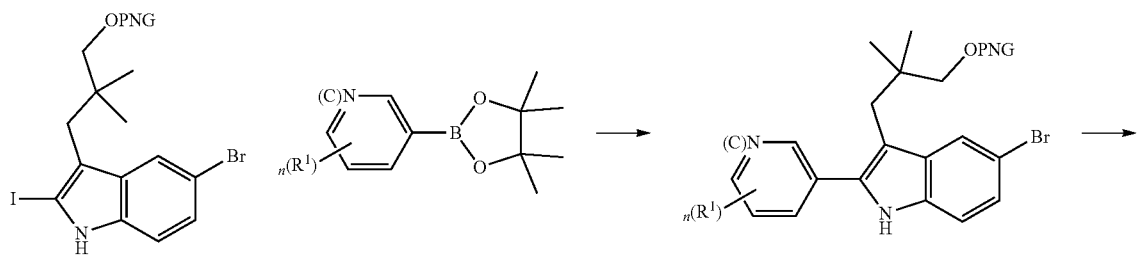

-continued
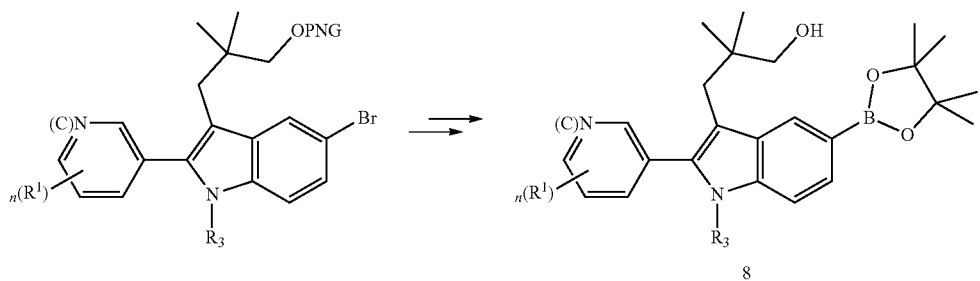
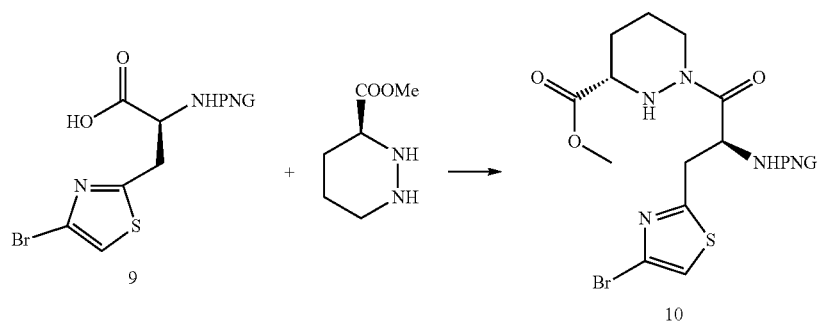
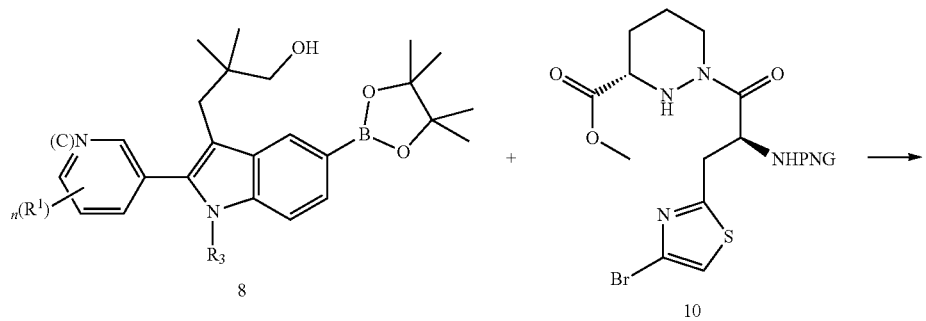
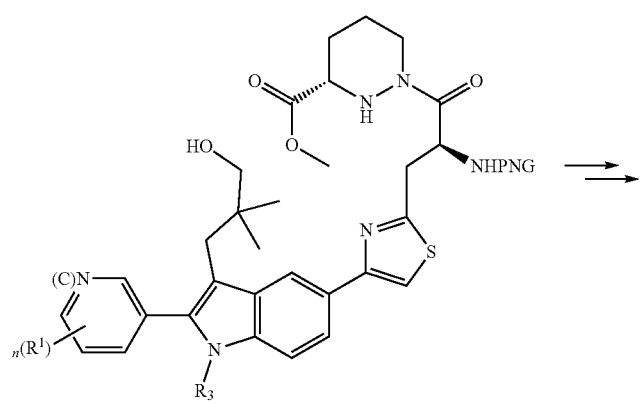

-continued

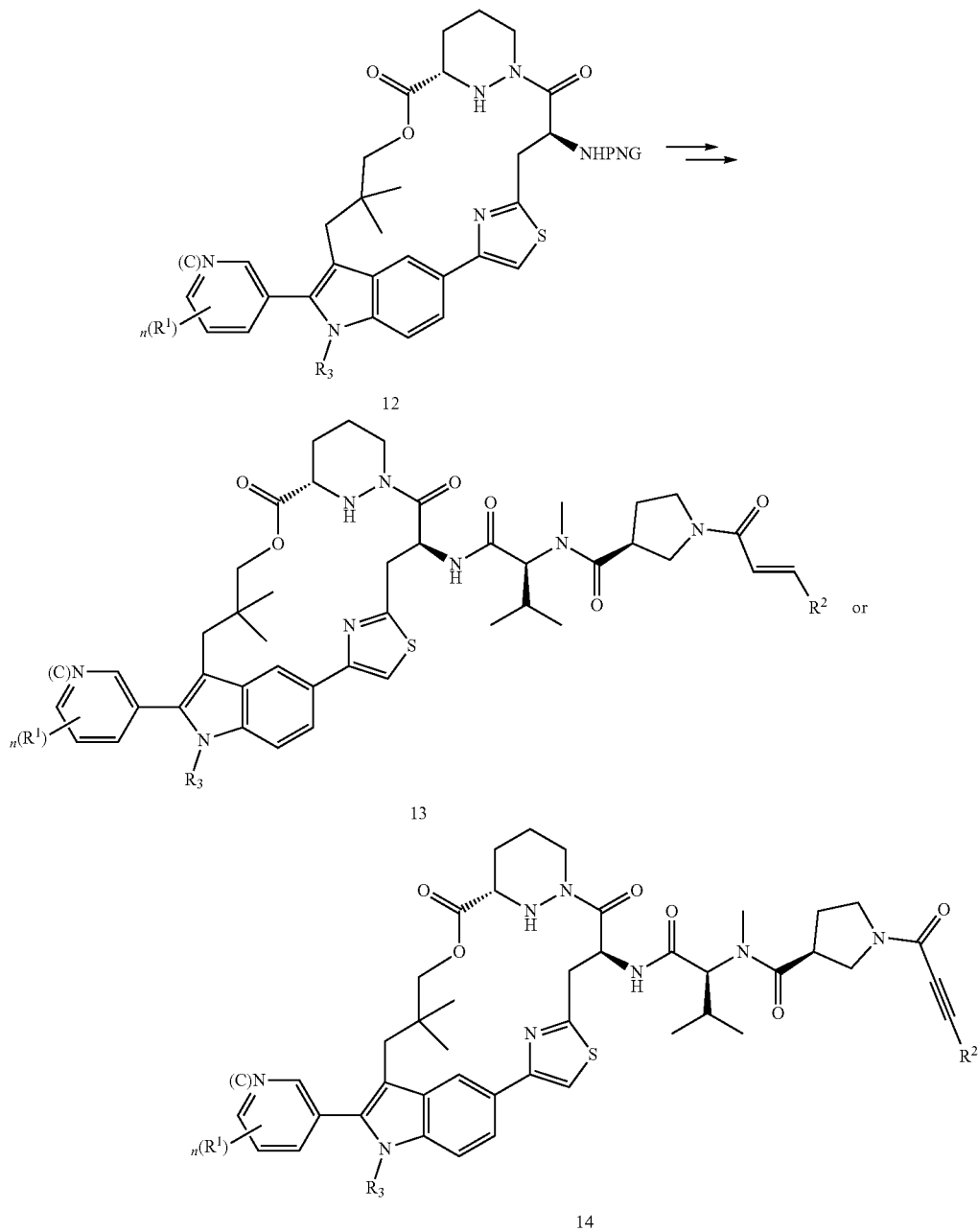

An alternative general synthesis of macrocyclic esters is outlined in Scheme 3. An appropriately substituted indolyl boronic ester (8) can be prepared in four steps starting from protected 3-(5-bromo-2-iodo-1H-indol-3-yl)-2,2-dimethyl-propan-1-ol and appropriately substituted boronic acid, including Palladium mediated coupling, alkylation, de-protection, and Palladium mediated borylation reactions.

Methyl-amino-3-(4-bromothiazol-2-yl)propanoyl)hexahydropyridazine-3-carboxylate (10) can be prepared via coupling of (S)-2-amino-3-(4-bromothiazol-2-yl)propanoic acid (9) with methyl (S)-hexahydropyridazine-3-carboxylate.

The final macrocyclic esters can be made by coupling of Methyl-amino-3-(4-bromothiazol-2-yl)propanoyl)hexahydropyridazine-3-carboxylate (10) and an appropriately substituted indolyl boronic ester (8) in the presence of Pd catalyst followed by hydrolysis and macrolactonization steps to result in an appropriately protected macrocyclic intermediate (11). Deprotection and coupling with an appropriately substituted intermediate 4 can result in a macrocyclic product. Additional deprotection or functionalization steps could be required to produce a final compound 13 or 14.

Scheme 4. General synthesis of macrocyclic esters
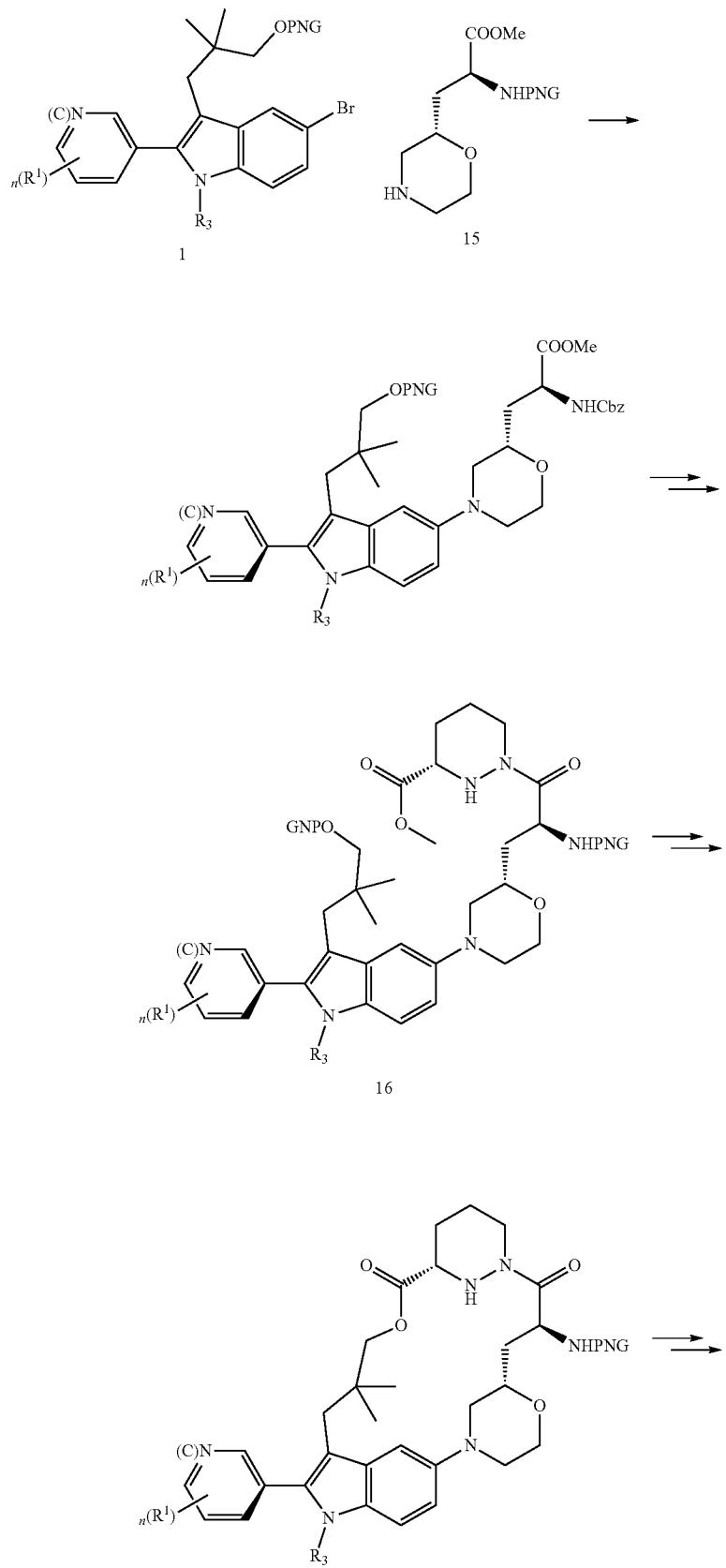

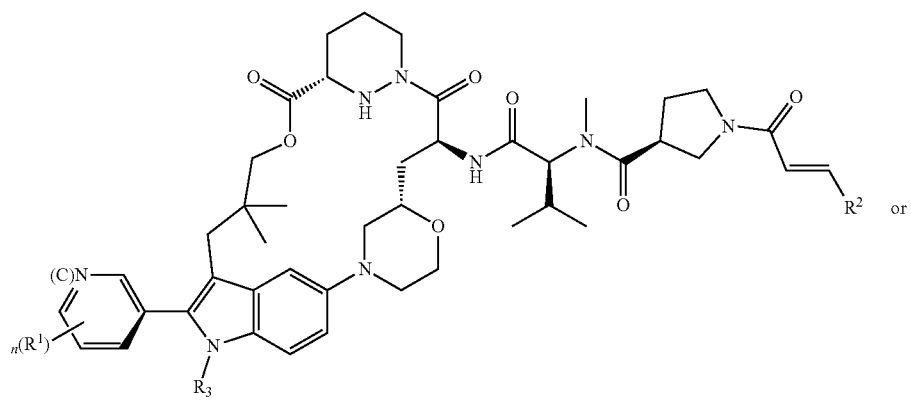

17

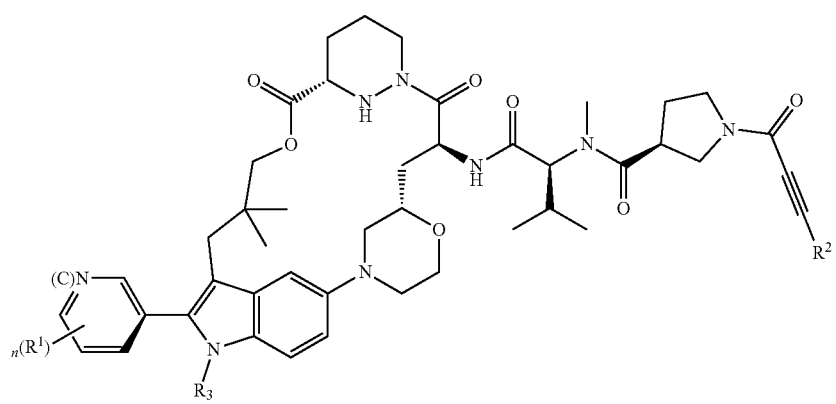

17

40

An alternative general synthesis of macrocyclic esters is outlined in Scheme 4. An appropriately substituted morpholine or an alternative herecyclic intermediate (15) can be coupled with appropriately protected Intermediate 1 via Palladium mediated coupling. Subsequent ester hydrolysis, and coupling with piperazoic ester results in intermediate 16.

The macrocyclic esters can be made by hydrolysis, deprotection and macrocyclization sequence. Subsequent deprotection and coupling with Intermediate 4 (or analogs) result in an appropriately substituted final macrocyclic products. Additional deprotection or functionalization steps could be required to produce a final compound 17.

Scheme 5. General synthesis of macrocyclic esters

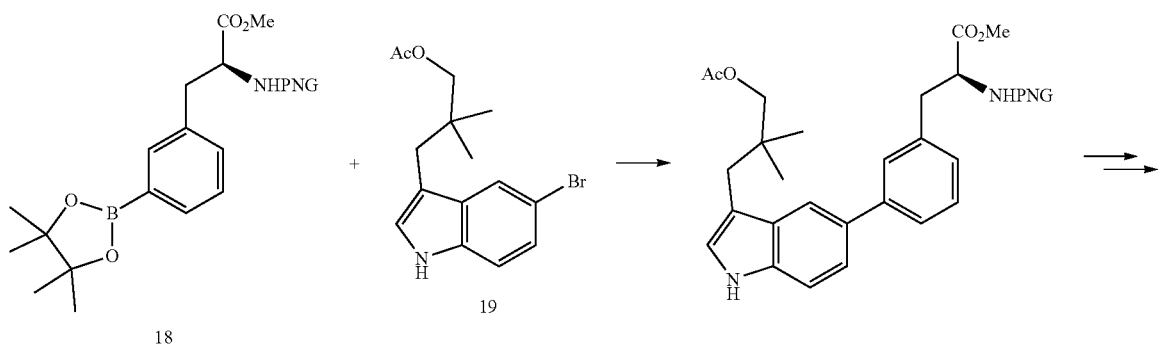

-continued
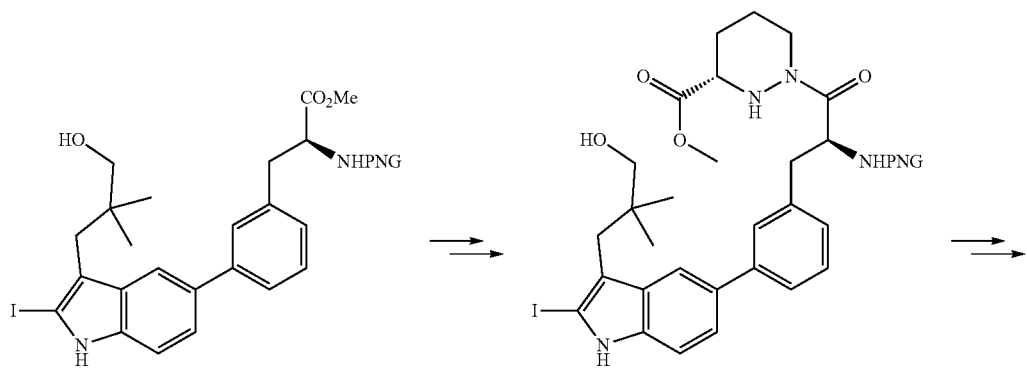
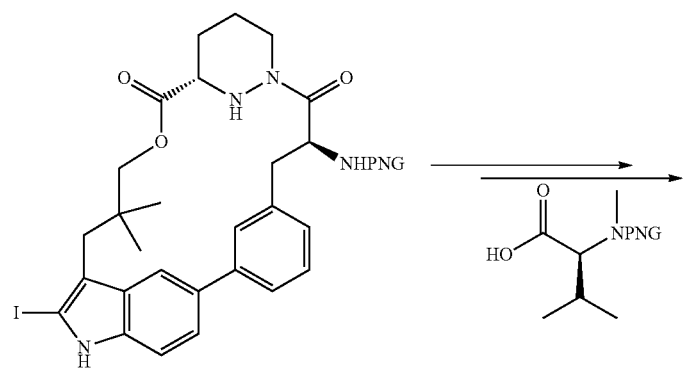
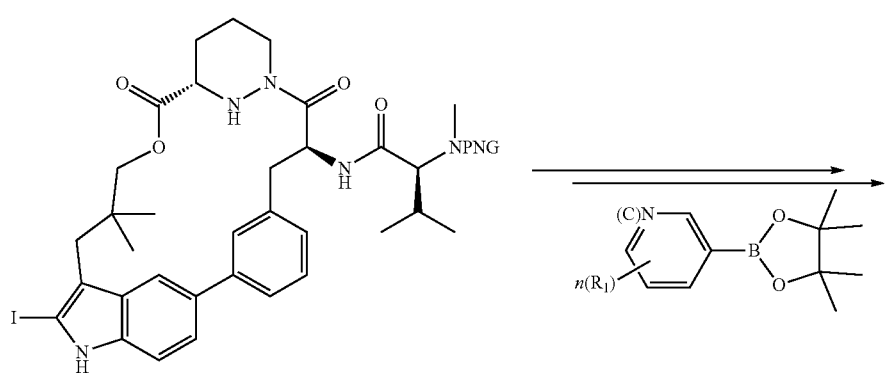
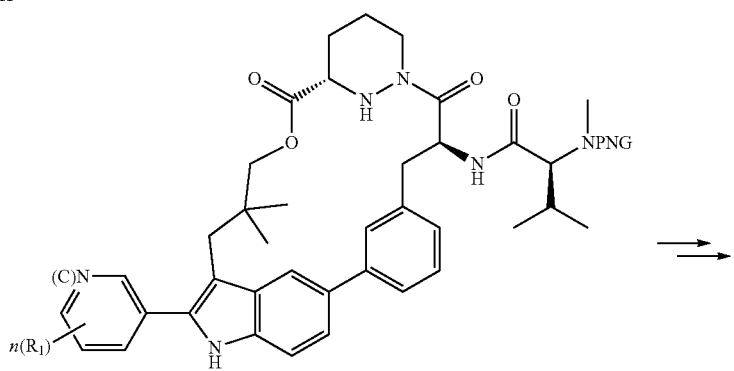

-continued

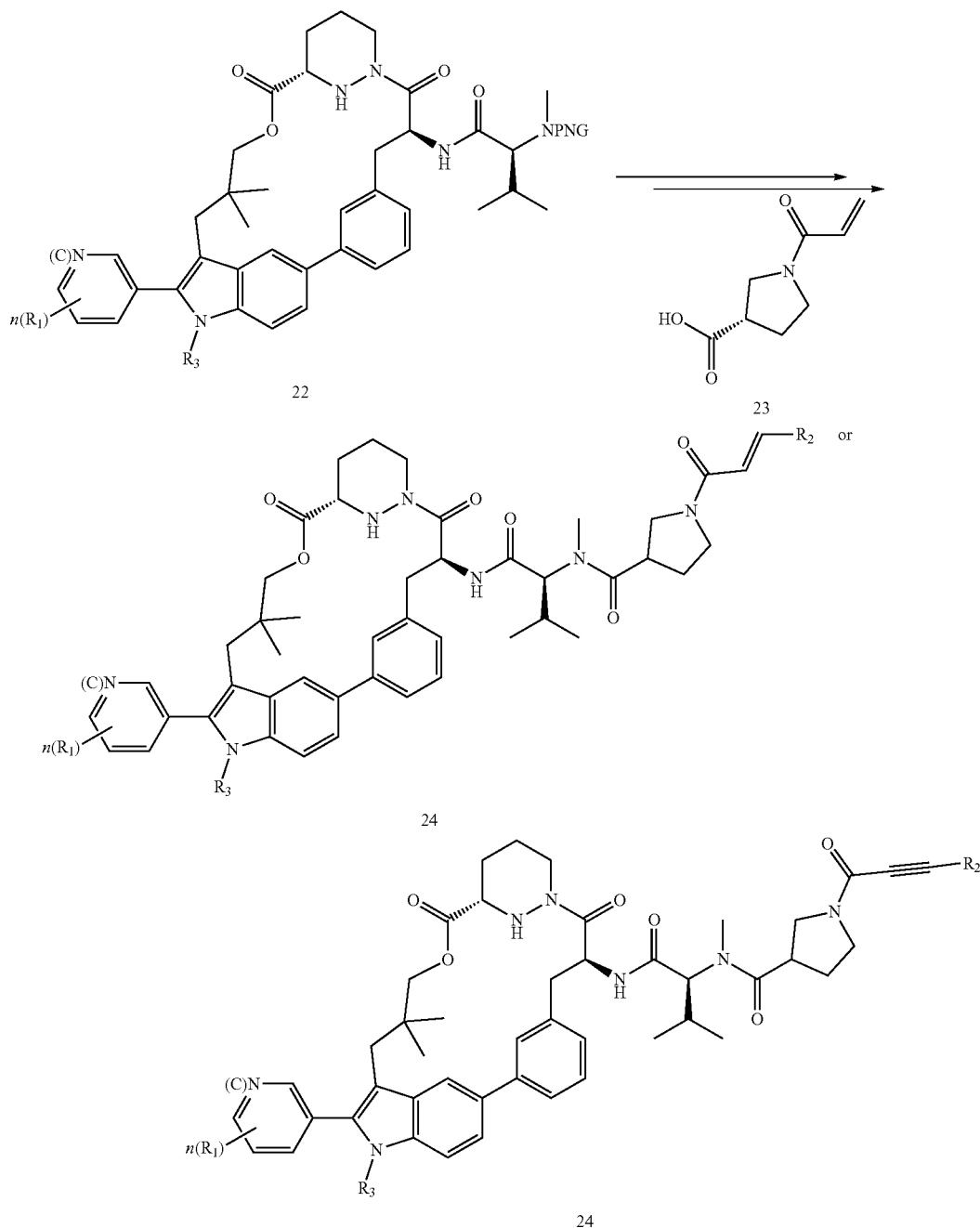

An alternative general synthesis of macrocyclic esters is outlined in Scheme 5. An appropriately substituted macrocycle (20) can be prepared starting from an appropriately protected boronic ester 18 and bromo indolyl intermediate (19), including Palladium mediated coupling, hydrolysis, coupling with piperazoic ester, hydrolysis, de-protection, and macrocyclizarion steps. Subsequent coupling with an appropriately substituted protected amino acid followed by palladium mediated coupling yields intermediate 21. Additional deprotection and derivatization steps, including alkylation may be required at this point.

The final macrocyclic esters can be made by coupling of intermediate (22) and an appropriately substituted carboxylic acid intermediate (23). Additional deprotection or functionalization steps could be required to produce a final compound (24).

In addition, compounds of the disclosure can be synthesized using the methods described in the Examples below, together with synthetic methods known in the art of synthetic organic chemistry, or variations thereon as appreciated by those skilled in the art. These methods include but are not limited to those methods described in the Examples below.

For example, a person of skill in the art would be able to install into a macrocyclic ester a desired -B-L-W group of a compound of Formula (I), where B, L and W are defined herein, including by using methods exemplified in the Example section herein.

Pharmaceutical Compositions and Methods of Use

Pharmaceutical Compositions and Methods of Administration

The compounds with which the invention is concerned are Ras inhibitors, and are useful in the treatment of cancer. Accordingly, one embodiment of the present invention provides pharmaceutical compositions containing a compound of the invention or a pharmaceutically acceptable salt thereof, and a pharmaceutically acceptable excipient, as well as methods of using the compounds of the invention to prepare such compositions.

As used herein, the term "pharmaceutical composition" refers to a compound, such as a compound of the present invention, or a pharmaceutically acceptable salt thereof, formulated together with a pharmaceutically acceptable excipient.

In some embodiments, a compound is present in a pharmaceutical composition in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Excipients include, but are not limited to: butylated optionally substituted hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, optionally substituted hydroxylpropyl cellulose, optionally substituted hydroxylpropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Those of ordinary skill in the art are familiar with a variety of agents and materials useful as excipients. See, e.g., e.g., Ansel, et al., Ansel's Pharmaceutical Dosage Forms and Drug Delivery Systems. Philadelphia: Lippincott, Williams & Wilkins, 2004; Gennaro, et al., Remington: The Science and Practice of Pharmacy. Philadelphia: Lippincott, Williams & Wilkins, 2000; and Rowe, Handbook of Pharmaceutical Excipients. Chicago, Pharmaceutical Press, 2005. In some embodiments, a composition includes at least two different pharmaceutically acceptable excipients.

Compounds described herein, whether expressly stated or not, may be provided or utilized in salt form, e.g., a pharmaceutically acceptable salt form, unless expressly stated to the contrary. The term "pharmaceutically acceptable salt," as use herein, refers to those salts of the compounds described herein that are, within the scope of sound medical judgment, suitable for use in contact with the tissues of humans and other animals without undue toxicity, irritation, allergic response and the like, and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention, be prepared from inorganic or organic bases. In some embodiments, the compounds are prepared or used as pharmaceutically acceptable salts prepared as addition products of pharmaceutically acceptable acids or bases. Suitable pharmaceutically acceptable acids and bases are well-known in the art, such as hydrochloric, sulfuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used herein, the term "subject" refers to any member of the animal kingdom. In some embodiments, "subject" refers to humans, at any stage of development. In some embodiments, "subject" refers to a human patient. In some embodiments, "subject" refers to non-human animals. In some embodiments, the non-human animal is a mammal (e.g., a rodent, a mouse, a rat, a rabbit, a monkey, a dog, a cat, a sheep, cattle, a primate, or a pig). In some embodiments, subjects include, but are not limited to, mammals, birds, reptiles, amphibians, fish, or worms. In some embodiments, a subject may be a transgenic animal, genetically-engineered animal, or a clone.

As used herein, the term "dosage form" refers to a physically discrete unit of a compound (e.g., a compound of the present invention) for administration to a subject. Each unit contains a predetermined quantity of compound. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or compound administered to a particular subject is determined by one or more attending physicians and may involve administration of multiple dosage forms.

As used herein, the term "dosing regimen" refers to a set of unit doses (typically more than one) that are administered individually to a subject, typically separated by periods of time. In some embodiments, a given therapeutic compound (e.g., a compound of the present invention) has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., a compound of the present invention) that partially or completely alleviates, ameliorates, relieves, inhibits, delays onset of, reduces severity of, or reduces incidence of one or more symptoms, features, or causes of a particular disease, disorder, or condition. In some embodiments, such treatment may be administered to a subject who does not exhibit signs of the relevant disease, disorder or condition or of a subject who exhibits only early signs of the disease, disorder, or condition. Alternatively, or additionally, in some embodiments, treatment may be administered to a subject who exhibits one or more established signs of the relevant disease, disorder, or condition. In some embodiments, treatment may be of a subject who has been diagnosed as suffering from the relevant disease, disorder, or condition. In some embodiments, treatment may be of a subject known to have one or more susceptibility factors that are statistically correlated with increased risk of development of the relevant disease, disorder, or condition.

The term "therapeutically effective amount" means an amount that is sufficient, when administered to a population suffering from or susceptible to a disease, disorder, or condition in accordance with a therapeutic dosing regimen, to treat the disease, disorder, or condition. In some embodiments, a therapeutically effective amount is one that reduces the incidence or severity of, or delays onset of, one or more symptoms of the disease, disorder, or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, a therapeutically effective amount may be formulated or administered in a single dose. In some embodiments, a therapeutically effective amount may be formulated or administered in a plurality of doses, for example, as part of a dosing regimen.

For use as treatment of subjects, the compounds of the invention, or a pharmaceutically acceptable salt thereof, can be formulated as pharmaceutical or veterinary compositions. Depending on the subject to be treated, the mode of administration, and the type of treatment desired, e.g., prevention, prophylaxis, or therapy, the compounds, or a pharmaceutically acceptable salt thereof, are formulated in ways consonant with these parameters. A summary of such techniques may be found in *Remington: The Science and Practice of Pharmacy*, 21$^{st}$ *Edition*, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

Compositions can be prepared according to conventional mixing, granulating or coating methods, respectively, and the present pharmaceutical compositions can contain from about 0.1% to about 99%, from about 5% to about 90%, or from about 1% to about 20% of a compound of the present invention, or pharmaceutically acceptable salt thereof, by weight or volume. In some embodiments, compounds, or a pharmaceutically acceptable salt thereof, described herein may be present in amounts totaling 1-95% by weight of the total weight of a composition, such as a pharmaceutical composition.

The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

As used herein, the term "administration" refers to the administration of a composition (e.g., a compound, or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, or vitreal.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. A formulation will generally include a diluent as well as, in some cases, adjuvants, buffers, preservatives and the like. Compounds, or a pharmaceutically acceptable salt thereof, can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention, or a pharmaceutically acceptable salt thereof. Suitable forms include syrups, capsules, and tablets, as is understood in the art.

Each compound, or a pharmaceutically acceptable salt thereof, as described herein, may be formulated in a variety of ways that are known in the art. For example, the first and second agents of the combination therapy may be formulated together or separately. Other modalities of combination therapy are described herein.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dose or in which the individual compounds, or a pharmaceutically acceptable salt thereof, may vary in potency as therapy progresses); or the kit may contain multiple doses suitable for administration to multiple subjects ("bulk packaging"). The kit components may be assembled in cartons, blister packs, bottles, tubes, and the like.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, optionally substituted hydroxylpropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion-controlled release can be achieved by appropriate coating of a tablet, capsule, pellet, or granulate formulation of compounds, or by incorporating the compound, or a pharmaceutically acceptable salt thereof, into an appropriate matrix. A controlled release coating may include one or more of the coating substances mentioned above or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-optionally substituted hydroxylmethacrylate, methacrylate hydrogels, 1,3 butylene glycol, ethylene glycol methacrylate, or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, or halogenated fluorocarbon.

The liquid forms in which the compounds, or a pharmaceutically acceptable salt thereof, and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the invention, or a pharmaceutically acceptable salt thereof, will depend on the nature of the compound, and can readily be determined by one skilled in the art. A dosage may be, for example, about 0.001 mg to about 2000 mg per day, about 1 mg to about 1000 mg per day, about 5 mg to about 500 mg per day, about 100 mg to about 1500 mg per day, about 500 mg to about 1500 mg per day, about 500 mg to about 2000 mg per day, or any range derivable therein.

In some embodiments, the pharmaceutical composition may further comprise an additional compound having anti-proliferative activity. Depending on the mode of administration, compounds, or a pharmaceutically acceptable salt thereof, will be formulated into suitable compositions to permit facile delivery. Each compound, or a pharmaceutically acceptable salt thereof, of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

It will be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics or procedures and the desired therapeutic effect to be achieved. It will also be appreciated that the therapies employed may achieve a desired effect for the same disorder, or they may achieve different effects (e.g., control of any adverse effects).

Administration of each drug in a combination therapy, as described herein, can, independently, be one to four times daily for one day to one year, and may even be for the life of the subject. Chronic, long-term administration may be indicated.

Methods of Use

In some embodiments, the invention discloses a method of treating a disease or disorder that is characterized by aberrant Ras activity due to a Ras mutant. In some embodiments, the disease or disorder is a cancer.

Accordingly, also provided is a method of treating cancer in a subject in need thereof, the method comprising administering to the subject a therapeutically effective amount of a compound of the present invention, or a pharmaceutically acceptable salt thereof, or a pharmaceutical composition comprising such a compound or salt. In some embodiments, the cancer is colorectal cancer, non-small cell lung cancer, small-cell lung cancer, pancreatic cancer, appendiceal cancer, melanoma, acute myeloid leukemia, small bowel cancer, ampullary cancer, germ cell cancer, cervical cancer, cancer of unknown primary origin, endometrial cancer, esophagogastric cancer, GI neuroendocrine cancer, ovarian cancer, sex cord stromal tumor cancer, hepatobiliary cancer, or bladder cancer. In some embodiments, the cancer is appendiceal, endometrial or melanoma. Also provided is a method of treating a Ras protein-related disorder in a subject in need thereof, the method comprising administering to the subject a therapeutically effective amount of a compound of the present invention, or a pharmaceutically acceptable salt thereof, or a pharmaceutical composition comprising such a compound or salt.

In some embodiments, the compounds of the present invention or pharmaceutically acceptable salts thereof, pharmaceutical compositions comprising such compounds or salts, and methods provided herein may be used for the treatment of a wide variety of cancers including tumors such as lung, prostate, breast, brain, skin, cervical carcinomas, testicular carcinomas, etc. More particularly, cancers that may be treated by the compounds or salts thereof, pharmaceutical compositions comprising such compounds or salts, and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. Other cancers include, for example:

Cardiac, for example: sarcoma (angiosarcoma, fibrosarcoma, rhabdomyosarcoma, liposarcoma), myxoma, rhabdomyoma, fibroma, lipoma, and teratoma;

Lung, for example: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal, for example: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract, for example: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver, for example: hepatoma (hepatocellular carcinoma), cholangiocarcinoma, hepatoblastoma, angiosarcoma, hepatocellular adenoma, hemangioma;

Biliary tract, for example: gall bladder carcinoma, ampullary carcinoma, cholangiocarcinoma;

Bone, for example: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors;

Nervous system, for example: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, neurofibromatosis type 1, meningioma, glioma, sarcoma);

Gynecological, for example: uterus (endometrial carcinoma, uterine carcinoma, uterine corpus endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic, for example: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma);

Skin, for example: malignant melanoma, basal cell carcinoma, squamous cell carcinoma, Kaposi's sarcoma, moles dysplastic nevi, lipoma, angioma, dermatofibroma, keloids, psoriasis; and Adrenal glands, for example: neuroblastoma.

In some embodiments, the Ras protein is wild-type ($Ras^{WT}$). Accordingly, in some embodiments, a compound of the present invention is employed in a method of treating a patient having a cancer comprising a $Ras^{WT}$ (e.g., K-$Ras^{WT}$, H-$Ras^{WT}$ or N-$Ras^{WT}$). In some embodiments, the Ras protein is Ras amplification (e.g., K-$Ras^{amp}$). Accordingly, in some embodiments, a compound of the present invention is employed in a method of treating a patient having a cancer comprising a $Ras^{amp}$ (K-$Ras^{amp}$, H-$Ras^{amp}$ or N-$Ras^{amp}$). In some embodiments, the cancer comprises a Ras mutation, such as a Ras mutation described herein. In some embodiments, a mutation is selected from:

(a) the following K-Ras mutants: G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V, and combinations thereof;

(b) the following H-Ras mutants: Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R, and combinations thereof; and (c) the following N-Ras mutants: Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T, and combinations thereof;

or a combination of any of the foregoing. In some embodiments, the cancer comprises a K-Ras mutation selected from the group consisting of G12C, G12D, G13C, G12V, G13D, G12R, G12S, Q61H, Q61K and Q61 L. In some embodiments, the cancer comprises an N-Ras mutation selected from the group consisting of G12C, Q61H, Q61K, Q61L, Q61P and Q61R. In some embodiments, the cancer comprises an H-Ras mutation selected from the group consisting of Q61H and Q61 L. In some embodiments, the cancer comprises a Ras mutation selected from the group consisting of G12C, G13C, G12A, G12D, G13D, G12S, G13S, G12V and G13V. In some embodiments, the cancer comprises at least two Ras mutations selected from the group consisting of G12C, G13C, G12A, G12D, G13D, G12S, G13S, G12V and G13V. In some embodiments, a compound of the present invention inhibits more than one Ras mutant. For example, a compound may inhibit both K-Ras G12C and K-Ras G13C. A compound may inhibit both N-Ras G12C and K-Ras G12C. In some embodiments, a compound may inhibit both K-Ras G12C and K-Ras G12D. In some embodiments, a compound may inhibit both K-Ras G12V and K-Ras G12C. In some embodiments, a compound may inhibit both K-Ras G12V and K-Ras G12S. In some embodiments, a compound of the present invention inhibits $Ras^{WT}$ in addition to one or more additional Ras mutations (e.g., K-, H- or N-$Ras^{WT}$ and K-Ras G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V; K, H or N-$Ras^{WT}$ and H-Ras Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R; or K, H or N-$Ras^{WT}$ and N-Ras Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T). In some embodiments, a compound of the present invention inhibits $Ras^{amp}$ in addition to one or more additional Ras mutations (e.g., K-, H- or N-$Ras^{amp}$ and K-Ras G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V; K, H or N-$Ras^{amp}$ and H-Ras Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R; or K, H or N-$Ras^{amp}$ and N-Ras Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T).

Methods of detecting Ras mutations are known in the art. Such means include, but are not limited to direct sequencing, and utilization of a high-sensitivity diagnostic assay (with CE-IVD mark), e.g., as described in Domagala, et al., Pol J Pathol 3: 145-164 (2012), incorporated herein by reference in its entirety, including TheraScreen PCR; AmoyDx; PNA-Clamp; RealQuality; EntroGen; LightMix; StripAssay; Hybcell plexA; Devyser; Surveyor; Cobas; and TheraScreen Pyro. See, also, e.g., WO 2020/106640.

In some embodiments, the cancer is non-small cell lung cancer and the Ras mutation comprises a K-Ras mutation, such as K-Ras G12C, K-Ras G12V or K-Ras G12D. In some embodiments, the cancer is colorectal cancer and the Ras mutation comprises a K-Ras mutation, such as K-Ras G12C, K-Ras G12V or K-Ras G12D. In some embodiments, the cancer is pancreatic cancer and the Ras mutation comprises an K-Ras mutation, such as K-Ras G12D or K-Ras G12V. In some embodiments, the cancer is pancreatic cancer and the Ras mutation comprises an N-Ras mutation, such as N-Ras G12D. In some embodiments, the cancer is melanoma and the Ras mutation comprises an N-Ras mutation, such as N-Ras Q61R or N-Ras Q61K. In some embodiments, the cancer is non-small cell lung cancer and the Ras protein is K-$Ras^{amp}$. In any of the foregoing if not already specified, a compound may inhibit $Ras^{WT}$ (e.g., K-, H- or N-$Ras^{WT}$) or $Ras^{amp}$ (e.g., K-, H- or N-$Ras^{amp}$) as well.

In some embodiments, a cancer comprises a Ras mutation and an $STK11^{LOF}$, a KEAP1, an EPHA5 or an NF1 mutation. In some embodiments, the cancer is non-small cell lung cancer and comprises a K-Ras G12C mutation. In some embodiments, the cancer is non-small cell lung cancer and comprises a K-Ras G12C mutation and an $STK11^{LOF}$ mutation. In some embodiments, the cancer is non-small cell lung cancer and comprises a K-Ras G12C mutation and an STK11$^{LOF}$ mutation. In some embodiments, a cancer comprises a K-Ras G13C Ras mutation and an STK11$^{LOF}$, a KEAP1, an EPHA5 or an NF1 mutation. In some embodiments, the cancer is non-small cell lung cancer and comprises a K-Ras G12D mutation. In some embodiments, the cancer is non-small cell lung cancer and comprises a K-Ras G12V mutation. In some embodiments, the cancer is colorectal cancer and comprises a K-Ras G12C mutation. In some embodiments, the cancer is pancreatic cancer and comprises a K-Ras G12C or K-Ras G12D mutation. In some embodiments, the cancer is pancreatic cancer and comprises a a K-Ras G12V mutation. In some embodiments, the cancer is endometrial cancer, ovarian cancer, cholangiocarcinoma, or mucinous appendiceal cancer and comprises a K-Ras G12C mutation. In some embodiments, the cancer is gastric cancer and comprises a K-Ras G12C mutation. In any of the foregoing, a compound may inhibit Ras$^{WT}$ (e.g., K-, H- or N-Ras$^{WT}$) or Ras$^{amp}$ (e.g., K-, H- or N-Ras$^{amp}$) as well.

Also provided is a method of inhibiting a Ras protein in a cell, the method comprising contacting the cell with an effective amount of a compound of the present invention, or a pharmaceutically acceptable salt thereof. A method of inhibiting RAF-Ras binding, the method comprising contacting the cell with an effective amount of a compound of the present invention, or a pharmaceutically acceptable salt thereof, is also provided. The cell may be a cancer cell. The cancer cell may be of any type of cancer described herein. The cell may be in vivo or in vitro.

Combination Therapy

The methods of the invention may include a compound of the invention used alone or in combination with one or more additional therapies (e.g., non-drug treatments or therapeutic agents). The dosages of one or more of the additional therapies (e.g., non-drug treatments or therapeutic agents) may be reduced from standard dosages when administered alone. For example, doses may be determined empirically from drug combinations and permutations or may be deduced by isobolographic analysis (e.g., Black et al., *Neurology* 65:S3-S6 (2005)).

A compound of the present invention may be administered before, after, or concurrently with one or more of such additional therapies. When combined, dosages of a compound of the invention and dosages of the one or more additional therapies (e.g., non-drug treatment or therapeutic agent) provide a therapeutic effect (e.g., synergistic or additive therapeutic effect). A compound of the present invention and an additional therapy, such as an anti-cancer agent, may be administered together, such as in a unitary pharmaceutical composition, or separately and, when administered separately, this may occur simultaneously or sequentially. Such sequential administration may be close or remote in time.

In some embodiments, the additional therapy is the administration of side-effect limiting agents (e.g., agents intended to lessen the occurrence or severity of side effects of treatment. For example, in some embodiments, the compounds of the present invention can also be used in combination with a therapeutic agent that treats nausea. Examples of agents that can be used to treat nausea include: dronabinol, granisetron, metoclopramide, ondansetron, and prochlorperazine, or pharmaceutically acceptable salts thereof.

In some embodiments, the one or more additional therapies includes a non-drug treatment (e.g., surgery or radiation therapy). In some embodiments, the one or more additional therapies includes a therapeutic agent (e.g., a compound or biologic that is an anti-angiogenic agent, signal transduction inhibitor, antiproliferative agent, glycolysis inhibitor, or autophagy inhibitor). In some embodiments, the one or more additional therapies includes a non-drug treatment (e.g., surgery or radiation therapy) and a therapeutic agent (e.g., a compound or biologic that is an anti-angiogenic agent, signal transduction inhibitor, antiproliferative agent, glycolysis inhibitor, or autophagy inhibitor). In other embodiments, the one or more additional therapies includes two therapeutic agents. In still other embodiments, the one or more additional therapies includes three therapeutic agents. In some embodiments, the one or more additional therapies includes four or more therapeutic agents.

In this Combination Therapy section, all references are incorporated by reference for the agents described, whether explicitly stated as such or not.

Non-Drug Therapies

Examples of non-drug treatments include, but are not limited to, radiation therapy, cryotherapy, hyperthermia, surgery (e.g., surgical excision of tumor tissue), and T cell adoptive transfer (ACT) therapy.

In some embodiments, the compounds of the invention may be used as an adjuvant therapy after surgery. In some embodiments, the compounds of the invention may be used as a neo-adjuvant therapy prior to surgery.

Radiation therapy may be used for inhibiting abnormal cell growth or treating a hyperproliferative disorder, such as cancer, in a subject (e.g., mammal (e.g., human)). Techniques for administering radiation therapy are known in the art Radiation therapy can be administered through one of several methods, or a combination of methods, including, without limitation, external-beam therapy, internal radiation therapy, implant radiation, stereotactic radiosurgery, systemic radiation therapy, radiotherapy, and permanent or temporary interstitial brachy therapy. The term "brachy therapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as 1-125, 1-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, or Y-90. Moreover, the radionuclide(s) can be embodied in a gel or radioactive micro spheres.

In some embodiments, the compounds of the present invention can render abnormal cells more sensitive to treatment with radiation for purposes of killing or inhibiting the growth of such cells.

Accordingly, this invention further relates to a method for sensitizing abnormal cells in a mammal to treatment with radiation which comprises administering to the mammal an amount of a compound of the present invention, which amount is effective to sensitize abnormal cells to treatment with radiation. The amount of the compound in this method can be determined according to the means for ascertaining effective amounts of such compounds described herein. In some embodiments, the compounds of the present invention may be used as an adjuvant therapy after radiation therapy or as a neo-adjuvant therapy prior to radiation therapy.

In some embodiments, the non-drug treatment is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 7,572,631; 5,883,223; 6,905,874; 6,797,514; and 6,867,041.

Therapeutic Agents

A therapeutic agent may be a compound used in the treatment of cancer or symptoms associated therewith.

For example, a therapeutic agent may be a steroid. Accordingly, in some embodiments, the one or more additional therapies includes a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, fiucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts or derivatives thereof.

Further examples of therapeutic agents that may be used in combination therapy with a compound of the present invention include compounds described in the following patents: U.S. Pat. Nos. 6,258,812, 6,630,500, 6,515,004, 6,713,485, 5,521,184, 5,770,599, 5,747,498, 5,990,141, 6,235,764, and 8,623,885, and International Patent Applications WO01/37820, WO01/32651, WO02/68406, WO02/66470, WO02/55501, WO04/05279, WO04/07481, WO04/07458, WO04/09784, WO02/59110, WO99/45009, WO00/59509, WO99/61422, WO00/12089, and WO00/02871.

A therapeutic agent may be a biologic (e.g., cytokine (e.g., interferon or an interleukin such as IL-2)) used in treatment of cancer or symptoms associated therewith. In some embodiments, the biologic is an immunoglobulin-based biologic, e.g., a monoclonal antibody (e.g., a humanized antibody, a fully human antibody, an Fc fusion protein, or a functional fragment thereof) that agonizes a target to stimulate an anti-cancer response or antagonizes an antigen important for cancer. Also included are antibody-drug conjugates.

A therapeutic agent may be a T-cell checkpoint inhibitor. In one embodiment, the checkpoint inhibitor is an inhibitory antibody (e.g., a monospecific antibody such as a monoclonal antibody). The antibody may be, e.g., humanized or fully human. In some embodiments, the checkpoint inhibitor is a fusion protein, e.g., an Fc-receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein. In some embodiments, the checkpoint inhibitor is an inhibitor (e.g., an inhibitory antibody or small molecule inhibitor) of CTLA-4 (e.g., an anti-CTLA-4 antibody or fusion a protein). In some embodiments, the checkpoint inhibitor is an inhibitor or antagonist (e.g., an inhibitory antibody or small molecule inhibitor) of PD-1. In some embodiments, the checkpoint inhibitor is an inhibitor or antagonist (e.g., an inhibitory antibody or small molecule inhibitor) of PDL-1. In some embodiments, the checkpoint inhibitor is an inhibitor or antagonist (e.g., an inhibitory antibody or Fc fusion or small molecule inhibitor) of PDL-2 (e.g., a PDL-2/Ig fusion protein). In some embodiments, the checkpoint inhibitor is an inhibitor or antagonist (e.g., an inhibitory antibody or small molecule inhibitor) of B7-H3, B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the checkpoint inhibitor is pembrolizumab, nivolumab, PDR001 (NVS), REGN2810 (Sanofi/Regeneron), a PD-L1 antibody such as, e.g., avelumab, durvalumab, atezolizumab, pidilizumab, JNJ-63723283 (JNJ), BGB-A317 (BeiGene & Celgene) or a checkpoint inhibitor disclosed in Preusser, M. et al. (2015) Nat. Rev. Neurol., including, without limitation, ipilimumab, tremelimumab, nivolumab, pembrolizumab, AMP224, AMP514/MEDI0680, BMS936559, MEDI4736, MPDL3280A, MSB0010718C, BMS986016, IMP321, lirilumab, IPH2101, 1-7F9, and KW-6002.

A therapeutic agent may be an anti-TIGIT antibody, such as MBSA43, BMS-986207, MK-7684, COM902, AB154, MTIG7192A or OMP-313M32 (etigilimab).

A therapeutic agent may be an agent that treats cancer or symptoms associated therewith (e.g., a cytotoxic agent, non-peptide small molecules, or other compound useful in the treatment of cancer or symptoms associated therewith, collectively, an "anti-cancer agent"). Anti-cancer agents can be, e.g., chemotherapeutics or targeted therapy agents.

Anti-cancer agents include mitotic inhibitors, intercalating antibiotics, growth factor inhibitors, cell cycle inhibitors, enzymes, topoisomerase inhibitors, biological response modifiers, alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Further anti-cancer agents include leucovorin (LV), irenotecan, oxaliplatin, capecitabine, paclitaxel, and doxetaxel. In some embodiments, the one or more additional therapies includes two or more anti-cancer agents. The two or more anti-cancer agents can be used in a cocktail to be administered in combination or administered separately. Suitable dosing regimens of combination anti-cancer agents are known in the art and described in, for example, Saltz et al., *Proc. Am. Soc. Clin. Oncol.* 18:233a (1999), and Douillard et al., *Lancet* 355(9209):1041-1047 (2000).

Other non-limiting examples of anti-cancer agents include Gleevec® (Imatinib Mesylate); Kyprolis® (carfilzomib); Velcade® (bortezomib); Casodex (bicalutamide); Iressa® (gefitinib); alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; sarcodictyin A; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gammall and calicheamicin omegall (see, e.g., *Agnew, Chem. Intl. Ed Engl.* 33:183-186 (1994)); dynemicin such as dynemicin A; bisphosphonates such as clodronate; an esperamicin; neocarzinostatin chromophore and related chromoprotein enediyne antibiotic chromophores, aclacinomysins, actinomycin, authramycin, azaserine, bleomycins, cactinomycin, calicheamicin, carabicin, caminomycin, carminomycin, carzinophilin, chromomycins, dactinomycin, daunorubicin, detorubicin, 6-diazo-5-oxo-L-norleucine, adriamycin (doxorubicin), morpholino-doxorubicin, cyanomorpholino-doxorubicin, 2-pyrrolino-doxorubicin, deoxydoxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone such as epothilone B; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes such as T-2 toxin, verracurin A, roridin A and anguidine; urethane; vindesine; dacarbazine; mannomustine; mitobronitol; mitolactol; pipobroman; gacytosine; arabinoside ("Ara-C"); cyclophosphamide; thiotepa; taxoids, e.g., Taxol® (paclitaxel), Abraxane® (cremophor-free, albumin-engineered nanoparticle formulation of paclitaxel), and Taxotere® (doxetaxel); chloranbucil; tamoxifen (Nolvadex™); raloxifene; aromatase inhibiting 4(5)-imidazoles; 4-hydroxytamoxifen; trioxifene; keoxifene; LY 117018; onapristone; toremifene (Fareston®); flutamide, nilutamide, bicalutamide, leuprolide, goserelin; chlorambucil; Gemzar® gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; Navelbine® (vinorelbine); novantrone; teniposide; edatrexate; daunomycin; aminopterin; ibandronate; irinotecan (e.g., CPT-11); topoisomerase inhibitor RFS 2000; difluoromethylornithine (DMFO); retinoids such as retinoic acid; esperamicins; capecitabine (e.g., Xeloda®); and pharmaceutically acceptable salts of any of the above.

Additional non-limiting examples of anti-cancer agents include trastuzumab (Herceptin®), bevacizumab (Avastin®), cetuximab (Erbitux®), rituximab (Rituxan®), Taxol®, Arimidex®, ABVD, avicine, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastics (e.g., cell-cycle nonspecific antineoplastic agents, and other antineoplastics described herein), antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, dichloroacetic acid, discodermolide, elsamitrucin, enocitabine, eribulin, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitors, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

Further non-limiting examples of anti-cancer agents include natural products such as vinca alkaloids (e.g., vinblastine, vincristine, and vinorelbine), epidipodophyllotoxins (e.g., etoposide and teniposide), antibiotics (e.g., dactinomycin (actinomycin D), daunorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., a CDK4/6 inhibitor such as abemaciclib, ribociclib, palbociclib; seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs, pyrimidine analogs (e.g., fluorouracil, floxuridine, and cytarabine), purine analogs and related inhibitors (e.g., mercaptopurine, thioguanine, pentostatin, and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTOR inhibitors (e.g., vistusertib, temsirolimus, everolimus, ridaforolimus, and sirolimus), KSP(Eg5) inhibitors (e.g., Array 520), DNA binding agents (e.g., Zalypsis®), PI3K inhibitors such as PI3K delta inhibitor (e.g., GS-1101 and TGR-1202), PI3K delta and gamma inhibitor (e.g., CAL-130), copanlisib, alpelisib and idelalisib; multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CSI (e.g., elotuzumab), HSP90 inhibitors (e.g., 17 AAG and KOS 953), PI3K/Akt inhibitors (e.g., perifosine), Akt inhibitors (e.g., GSK-2141795), PKC inhibitors (e.g., enzastaurin), FTIs (e.g., Zamestra™), anti-CD138 (e.g., BT062), Torcl/2 specific kinase inhibitors (e.g., INK128), ER/UPR targeting agents (e.g., MKC-3946), cFMS inhibitors (e.g., ARRY-382), JAK1/2 inhibitors (e.g., CYT387), PARP inhibitors (e.g., olaparib and veliparib (ABT-888)), and BCL-2 antagonists.

In some embodiments, an anti-cancer agent is selected from mechlorethamine, camptothecin, ifosfamide, tamoxifen, raloxifene, gemcitabine, Navelbine®, sorafenib, or any analog or derivative variant of the foregoing.

In some embodiments, the anti-cancer agent is a HER2 inhibitor. Non-limiting examples of HER2 inhibitors include monoclonal antibodies such as trastuzumab (Herceptin®) and pertuzumab (Perjeta®); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, and JNJ-26483327.

In some embodiments, an anti-cancer agent is an ALK inhibitor. Non-limiting examples of ALK inhibitors include ceritinib, TAE-684 (NVP-TAE694), PF02341066 (crizotinib or 1066), alectinib; brigatinib; entrectinib; ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in examples 3-39 of WO05016894.

In some embodiments, an anti-cancer agent is an inhibitor of a member downstream of a Receptor Tyrosine Kinase (RTK)/Growth Factor Receptor (e.g., a SHP2 inhibitor (e.g., SHP099, TNO155, RMC-4550, RMC-4630, JAB-3068, RLY-1971), a SOS1 inhibitor (e.g., BI-1701963, BI-3406), a Raf inhibitor, a MEK inhibitor, an ERK inhibitor, a PI3K inhibitor, a PTEN inhibitor, an AKT inhibitor, or an mTOR inhibitor (e.g., mTORC1 inhibitor or mTORC2 inhibitor). In some embodiments, the anti-cancer agent is JAB-3312. In some embodiments, an anti-cancer agent is an additional Ras inhibitor (e.g., AMG 510, MRTX1257, MRTX849, JNJ-74699157 (ARS-3248), LY3499446, ARS-853, or ARS-1620), or a Ras vaccine, or another therapeutic modality designed to directly or indirectly decrease the oncogenic activity of Ras. Other examples of Ras inhibitors that may be combined with a Ras inhibitor of the present invention are provided in the following, incorporated herein by reference in their entireties: WO 2020050890, WO 2020047192, WO 2020035031, WO 2020028706, WO 2019241157, WO 2019232419, WO 2019217691, WO 2019217307, WO 2019215203, WO 2019213526, WO 2019213516, WO 2019155399, WO 2019150305, WO 2019110751, WO 2019099524, WO 2019051291, WO 2018218070, WO 2018217651, WO 2018218071, WO 2018218069, WO 2018206539, WO 2018143315, WO 2018140600, WO 2018140599, WO 2018140598, WO 2018140514, WO 2018140513, WO 2018140512, WO 2018119183, WO 2018112420, WO 2018068017, WO 2018064510, WO 2017201161, WO 2017172979, WO 2017100546, WO 2017087528, WO 2017058807, WO 2017058805, WO 2017058728, WO 2017058902, WO 2017058792, WO 2017058768, WO 2017058915, WO 2017015562, WO 2016168540, WO 2016164675, WO 2016049568, WO 2016049524, WO 2015054572, WO 2014152588, WO 2014143659 and WO 2013155223.

In some embodiments, a therapeutic agent that may be combined with a compound of the present invention is an inhibitor of the MAP kinase (MAPK) pathway (or "MAPK inhibitor"). MAPK inhibitors include, but are not limited to, one or more MAPK inhibitor described in Cancers (Basel) 2015 September; 7(3): 1758-1784. For example, the MAPK inhibitor may be selected from one or more of trametinib, binimetinib, selumetinib, cobimetinib, LErafAON (NeoPharm), ISIS 5132; vemurafenib, pimasertib, TAK733, RO4987655 (CH4987655); CI-1040; PD-0325901; CH5126766; MAP855; AZD6244; refametinib (RDEA 119/ BAY 86-9766); GDC-0973/XL581; AZD8330 (ARRY-424704/ARRY-704); RO5126766 (Roche, described in PLoS One. 2014 Nov. 25; 9(11)); and GSK1120212 (or JTP-74057, described in Clin Cancer Res. 2011 Mar. 1; 17(5):989-1000). The MAPK inhibitor may be PLX8394, LXH254, GDC-5573, or LY3009120.

In some embodiments, an anti-cancer agent is a disrupter or inhibitor of the RAS-RAF-ERK or PI3K-AKT-TOR or PI3K-AKT signaling pathways. The PI3K/AKT inhibitor may include, but is not limited to, one or more PI3K/AKT inhibitor described in Cancers (Basel) 2015 September; 7(3): 1758-1784. For example, the PI3K/AKT inhibitor may be selected from one or more of NVP-BEZ235; BGT226; XL765/SAR245409; SF1126; GDC-0980; PI-103; PF-04691502; PKI-587; GSK2126458.

In some embodiments, an anti-cancer agent is a PD-1 or PD-L1 antagonist.

In some embodiments, additional therapeutic agents include ALK inhibitors, HER2 inhibitors, EGFR inhibitors, IGF-1R inhibitors, MEK inhibitors, PI3K inhibitors, AKT inhibitors, TOR inhibitors, MCL-1 inhibitors, BCL-2 inhibitors, SHP2 inhibitors, proteasome inhibitors, and immune therapies. In some embodiments, a therapeutic agent may be a pan-RTK inhibitor, such as afatinib.

IGF-1R inhibitors include linsitinib, or a pharmaceutically acceptable salt thereof.

EGFR inhibitors include, but are not limited to, small molecule antagonists, antibody inhibitors, or specific antisense nucleotide or siRNA. Useful antibody inhibitors of EGFR include cetuximab (Erbitux®), panitumumab (Vectibix®), zalutumumab, nimotuzumab, and matuzumab. Further antibody-based EGFR inhibitors include any anti-EGFR antibody or antibody fragment that can partially or completely block EGFR activation by its natural ligand. Non-limiting examples of antibody-based EGFR inhibitors include those described in Modjtahedi et al., Br. J. Cancer 1993, 67:247-253; Teramoto et al., Cancer 1996, 77:639-645; Goldstein et al., Clin. Cancer Res. 1995, 1:1311-1318; Huang et al., 1999, Cancer Res. 15:59(8):1935-40; and Yang et al., Cancer Res. 1999, 59:1236-1243. The EGFR inhibitor can be monoclonal antibody Mab E7.6.3 (Yang, 1999 supra), or Mab C225 (ATCC Accession No. HB-8508), or an antibody or antibody fragment having the binding specificity thereof.

Small molecule antagonists of EGFR include gefitinib (Iressa®), erlotinib (Tarceva®), and lapatinib (TykerB®). See, e.g., Yan et al., Pharmacogenetics and Pharmacogenomics In Oncology Therapeutic Antibody Development, BioTechniques 2005, 39(4):565-8; and Paez et al., EGFR Mutations In Lung Cancer Correlation With Clinical Response To Gefitinib Therapy, Science 2004, 304(5676): 1497-500. In some embodiments, the EGFR inhibitor is osimertinib (Tagrisso®). Further non-limiting examples of small molecule EGFR inhibitors include any of the EGFR inhibitors described in the following patent publications, and all pharmaceutically acceptable salts of such EGFR inhibitors: EP 0520722; EP 0566226; WO96/33980; U.S. Pat. No. 5,747,498; WO96/30347; EP 0787772; WO97/30034; WO97/30044; WO97/38994; WO97/49688; EP 837063; WO98/02434; WO97/38983; WO95/19774; WO95/19970; WO97/13771; WO98/02437; WO98/02438; WO97/32881; DE 19629652; WO98/33798; WO97/32880; WO97/32880; EP 682027; WO97/02266; WO97/27199; WO98/07726; WO97/34895; WO96/31510; WO98/14449; WO98/14450; WO98/14451; WO95/09847; WO97/19065; WO98/17662; U.S. Pat. Nos. 5,789,427; 5,650,415; 5,656,643; WO99/35146; WO99/35132; WO99/07701; and WO92/20642. Additional non-limiting examples of small molecule EGFR inhibitors include any of the EGFR inhibitors described in Traxler et al., Exp. Opin. Ther. Patents 1998, 8(12):1599-1625. In some embodiments, an EGFR inhibitor is an ERBB inhibitor. In humans, the ERBB family contains HER1 (EGFR, ERBB1), HER2 (NEU, ERBB2), HER3 (ERBB3), and HER (ERBB4).

MEK inhibitors include, but are not limited to, pimasertib, selumetinib, cobimetinib (Cotellic®), trametinib (Mekinist®), and binimetinib (Mektovi®). In some embodiments, a MEK inhibitor targets a MEK mutation that is a Class I MEK1 mutation selected from D67N; P124L; P124S; and L177V. In some embodiments, the MEK mutation is a Class II MEK1 mutation selected from ΔE51-Q58; ΔF53-Q58; E203K; L177M; C121S; F53L; K57E; Q56P; and K57N.

PI3K inhibitors include, but are not limited to, wortmannin; 17-hydroxywortmannin analogs described in WO06/044453; 4-[2-(1H-Indazol-4-yl)-6-[[4-(methylsulfonyl)piperazin-1-yl]methyl]thieno[3,2-d]pyrimidin-4-yl]morpholine (also known as pictilisib or GDC-0941 and described in WO09/036082 and WO09/055730); 2-methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in WO06/122806); (S)—I-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in WO08/070740); LY294002 (2-(4-morpholinyl)-8-phenyl-4H-1-benzopyran-4-one (available from Axon Medchem); PI 103 hydrochloride (3-[4-(4-morpholinylpyrido-[3',2':4,5]furo[3,2-d]pyrimidin-2-yl] phenol hydrochloride (available from Axon Medchem); PIK 75 (2-methyl-5-nitro-2-[(6-bromoimidazo[1,2-a]pyridin-3-yl)methylene]-1-methylhydrazide-benzenesulfonic acid, monohydrochloride) (available from Axon Medchem); PIK 90 (N-(7,8-dimethoxy-2,3-dihydro-imidazo[1,2-c]quinazolin-5-yl)-nicotinamide (available from Axon Medchem); AS-252424 (5-[1-[5-(4-fluoro-2-hydroxy-phenyl)-furan-2-yl]-meth-(Z)-ylidene]-thiazolidine-2,4-dione (available from Axon Medchem); TGX-221 (7-methyl-2-(4-morpholinyl)-9-[1-(phenylamino)ethyl]-4H-pyrido-[1,2-a] pyrimidin-4-one (available from Axon Medchem); XL-765; and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors include, but are not limited to, Akt-1-1 (inhibits Akt1) (Barnett et al., Biochem. J. 2005, 385(Pt. 2): 399-408); Akt-1-1,2 (inhibits Ak1 and 2) (Barnett et al., Biochem. J. 2005, 385(Pt. 2): 399-408); API-59CJ-Ome (e.g., Jin et al., Br. J. Cancer 2004, 91:1808-12); 1-H-imidazo[4,5-c]pyridinyl compounds (e.g., WO 05/011700); indole-3-carbinol and derivatives thereof (e.g., U.S. Pat. No. 6,656,963; Sarkar and Li J Nutr. 2004, 134(12 Suppl): 3493S-3498S); perifosine (e.g., interferes with Akt membrane localization; Dasmahapatra et al. Clin. Cancer Res. 2004, 10(15):5242-52); phosphatidylinositol ether lipid analogues (e.g., Gills and Dennis Expert. Opin. Investig. Drugs 2004, 13:787-97); and triciribine (TCN or API-2 or NCI identifier: NSC 154020; Yang et al., Cancer Res. 2004, 64:4394-9).

mTOR inhibitors include, but are not limited to, ATP-competitive mTORC1/mTORC2 inhibitors, e.g., PI-103, PP242, PP30; Torin 1; FKBP12 enhancers; 4H-1-benzopyran-4-one derivatives; and rapamycin (also known as sirolimus) and derivatives thereof, including: temsirolimus (Torisel®); everolimus (Afinitor®; WO94/09010); ridaforolimus (also known as deforolimus or AP23573); rapalogs, e.g., as disclosed in WO98/02441 and WO01/14387, e.g. AP23464 and AP23841; 40-(2-hydroxyethyl)rapamycin; 40-[3-hydroxy(hydroxymethyl)methylpropanoate]-rapamycin (also known as CC1779); 40-epi-(tetrazolyt)-rapamycin (also called ABT578); 32-deoxorapamycin; 16-pentynyloxy-32(S)-dihydrorapanycin; derivatives disclosed in WO05/005434; derivatives disclosed in U.S. Pat. Nos. 5,258,389, 5,118,677, 5,118,678, 5,100,883, 5,151,413, 5,120,842, and 5,256,790, and in WO94/090101, WO92/05179, WO93/111130, WO94/02136, WO94/02485, WO95/14023, WO94/02136, WO95/16691, WO96/41807, WO96/41807, and WO2018204416; and phosphorus-containing rapamycin derivatives (e.g., WO05/016252). In some embodiments, the mTOR inhibitor is a bisteric inhibitor (see, e.g., WO2018204416, WO2019212990 and WO2019212991), such as RMC-5552.

BRAF inhibitors that may be used in combination with compounds of the invention include, for example, vemurafenib, dabrafenib, and encorafenib. A BRAF may comprise a Class 3 BRAF mutation. In some embodiments, the Class 3 BRAF mutation is selected from one or more of the following amino acid substitutions in human BRAF: D287H; P367R; V459L; G466V; G466E; G466A; S467L; G469E; N581 S; N581 I; D594N; D594G; D594A; D594H; F595L; G596D; G596R and A762E.

MCL-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

In some embodiments, the additional therapeutic agent is a SHP2 inhibitor. SHP2 is a non-receptor protein tyrosine phosphatase encoded by the PTPN11 gene that contributes to multiple cellular functions including proliferation, differentiation, cell cycle maintenance and migration. SHP2 has two N-terminal Src homology 2 domains (N—SH2 and C—SH2), a catalytic domain (PTP), and a C-terminal tail.

The two SH2 domains control the subcellular localization and functional regulation of SHP2. The molecule exists in an inactive, self-inhibited conformation stabilized by a binding network involving residues from both the N—SH2 and PTP domains. Stimulation by, for example, cytokines or growth factors acting through receptor tyrosine kinases (RTKs) leads to exposure of the catalytic site resulting in enzymatic activation of SHP2.

SHP2 is involved in signaling through the RAS-mitogen-activated protein kinase (MAPK), the JAK-STAT or the phosphoinositol 3-kinase-AKT pathways. Mutations in the PTPN11 gene and subsequently in SHP2 have been identified in several human developmental diseases, such as Noonan Syndrome and Leopard Syndrome, as well as human cancers, such as juvenile myelomonocytic leukemia, neuroblastoma, melanoma, acute myeloid leukemia and cancers of the breast, lung and colon.

Some of these mutations destabilize the auto-inhibited conformation of SHP2 and promote autoactivation or enhanced growth factor driven activation of SHP2. SHP2, therefore, represents a highly attractive target for the development of novel therapies for the treatment of various diseases including cancer. A SHP2 inhibitor (e.g., RMC-4550 or SHP099) in combination with a RAS pathway inhibitor (e.g., a MEK inhibitor) have been shown to inhibit the proliferation of multiple cancer cell lines in vitro (e.g., pancreas, lung, ovarian and breast cancer). Thus, combination therapy involving a SHP2 inhibitor with a RAS pathway inhibitor could be a general strategy for preventing tumor resistance in a wide range of malignancies.

Non-limiting examples of such SHP2 inhibitors that are known in the art, include: Chen et al. *Mol Pharmacol.* 2006, 70, 562; Sarver et al., *J. Med. Chem.* 2017, 62, 1793; Xie et al., *J. Med. Chem.* 2017, 60, 113734; and Igbe et al., *Oncotarget,* 2017, 8, 113734; and PCT applications: WO2015107493; WO2015107494; WO2015107495; WO2016203404; WO2016203405; WO2016203406; WO2011022440; WO2017156397; WO2017079723; WO2017211303; WO2012041524; WO2017211303; WO2019051084; WO2017211303; US20160030594; US20110281942; WO2010011666; WO2014113584; WO2014176488; WO2017100279; WO2019051469; U.S. Pat. No. 8,637,684; WO2007117699; WO2015003094; WO2005094314; WO2008124815; WO2009049098; WO2009135000; WO2016191328; WO2016196591; WO2017078499; WO2017210134; WO2018013597; WO2018129402; WO2018130928; WO20181309928; WO2018136264; WO2018136265; WO2018160731; WO2018172984; and WO2010121212, each of which is incorporated herein by reference.

In some embodiments, a SHP2 inhibitor binds in the active site. In some embodiments, a SHP2 inhibitor is a mixed-type irreversible inhibitor. In some embodiments, a SHP2 inhibitor binds an allosteric site e.g., a non-covalent allosteric inhibitor. In some embodiments, a SHP2 inhibitor is a covalent SHP2 inhibitor, such as an inhibitor that targets the cysteine residue (C333) that lies outside the phosphatase's active site. In some embodiments a SHP2 inhibitor is a reversible inhibitor. In some embodiments, a SHP2 inhibitor is an irreversible inhibitor. In some embodiments, the SHP2 inhibitor is SHP099. In some embodiments, the SHP2 inhibitor is TNO155. In some embodiments, the SHP2 inhibitor is RMC-4550. In some embodiments, the SHP2 inhibitor is RMC-4630. In some embodiments, the SHP2 inhibitor is JAB-3068. In some embodiments, the SHP2 inhibitor is RLY-1971.

In some embodiments, the additional therapeutic agent is selected from the group consisting of a MEK inhibitor, a HER2 inhibitor, a SHP2 inhibitor, a CDK4/6 inhibitor, an mTOR inhibitor, a SOS1 inhibitor, and a PD-L1 inhibitor. In some embodiments, the additional therapeutic agent is selected from the group consisting of a MEK inhibitor, a SHP2 inhibitor, and a PD-L1 inhibitor. See, e.g., Hallin et al., Cancer Discovery, DOI: 10.1158/2159-8290 (Oct. 28, 2019) and Canon et al., Nature, 575:217 (2019). In some embodiments, a Ras inhibitor of the present invention is used in combination with a MEK inhibitor and a SOS1 inhibitor. In some embodiments, a Ras inhibitor of the present invention is used in combination with a PDL-1 inhibitor and a SOS1 inhibitor. In some embodiments, a Ras inhibitor of the present invention is used in combination with a PDL-1 inhibitor and a SHP2 inhibitor. In some embodiments, a Ras inhibitor of the present invention is used in combination with a MEK inhibitor and a SHP2 inhibitor. In some embodiments, the cancer is colorectal cancer and the treatment comprises administration of a Ras inhibitor of the present invention in combination with a second or third therapeutic agent.

Proteasome inhibitors include, but are not limited to, carfilzomib (Kyprolis®), bortezomib (Velcade®), and oprozomib.

Immune therapies include, but are not limited to, monoclonal antibodies, immunomodulatory imides (IMiDs), GITR agonists, genetically engineered T-cells (e.g., CAR-T cells), bispecific antibodies (e.g., BiTEs), and anti-PD-1, anti-PDL-1, anti-CTLA4, anti-LAGI, and anti-OX40 agents).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., Blood 2007, 110(1):186-192; Thompson et al., Clin. Cancer Res. 2007, 13(6):1757-1761; and WO06/121168 A1), as well as described elsewhere herein.

GITR agonists include, but are not limited to, GITR fusion proteins and anti-GITR antibodies (e.g., bivalent anti-GITR antibodies), such as, a GITR fusion protein described in U.S. Pat. Nos. 6,111,090, 8,586,023, WO2010/003118 and WO2011/090754; or an anti-GITR antibody described, e.g., in U.S. Pat. No. 7,025,962, EP 1947183, U.S. Pat. Nos. 7,812,135, 8,388,967, 8,591,886, 7,618,632, EP 1866339, and WO2011/028683, WO2013/039954, WO05/007190, WO07/133822, WO05/055808, WO99/40196, WO01/03720, WO99/20758, WO06/083289, WO05/115451, and WO2011/051726.

Another example of a therapeutic agent that may be used in combination with the compounds of the invention is an anti-angiogenic agent. Anti-angiogenic agents are inclusive of, but not limited to, in vitro synthetically prepared chemical compositions, antibodies, antigen binding regions, radionuclides, and combinations and conjugates thereof. An anti-angiogenic agent can be an agonist, antagonist, allosteric modulator, toxin or, more generally, may act to inhibit or stimulate its target (e.g., receptor or enzyme activation or inhibition), and thereby promote cell death or arrest cell growth. In some embodiments, the one or more additional therapies include an anti-angiogenic agent.

Anti-angiogenic agents can be MMP-2 (matrix-metalloproteinase 2) inhibitors, MMP-9 (matrix-metalloprotienase 9) inhibitors, and COX-II (cyclooxygenase 11) inhibitors. Non-limiting examples of anti-angiogenic agents include rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO96/33172, WO96/27583, WO98/07697, WO98/03516, WO98/34918, WO98/34915, WO98/33768, WO98/30566, WO90/05719, WO99/52910, WO99/52889, WO99/29667, WO99007675, EP0606046, EP0780386, EP1786785, EP1181017, EP0818442, EP1004578, and US20090012085, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors are AG-3340, RO 32-3555, and RS 13-0830.

Further exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF (e.g., bevacizumab), or soluble VEGF receptors or a ligand binding region thereof) such as VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix® (panitumumab), erlotinib (Tarceva®), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). Other anti-angiogenic agents include Campath, IL-8, B-FGF, Tek antagonists (US2003/0162712; U.S. Pat. No. 6,413,932), anti-TWEAK agents (e.g., specifically binding antibodies or antigen binding regions, or soluble TWEAK receptor antagonists; see U.S. Pat. No. 6,727,225), ADAM distintegrin domain to antagonize the binding of integrin to its ligands (US 2002/0042368), specifically binding anti-eph receptor or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Additional anti-angiogenic agents include: SD-7784 (Pfizer, USA); cilengitide (Merck KGaA, Germany, EPO 0770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands), DACantiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 0970070); ARGENT technology (Ariad, USA); YIGSR-Stealth (Johnson & Johnson, USA); fibrinogen-E fragment (BioActa, UK); angiogenic inhibitor (Trigen, UK); TBC-1635 (Encysive Pharmaceuticals, USA); SC-236 (Pfizer, USA); ABT-567 (Abbott, USA); Metastatin (EntreMed, USA); maspin (Sosei, Japan); 2-methoxyestradiol (Oncology Sciences Corporation, USA); ER-68203-00 (IV AX, USA); BeneFin (Lane Labs, USA); Tz-93 (Tsumura, Japan); TAN-1120 (Takeda, Japan); FR-111142 (Fujisawa, Japan, JP 02233610); platelet factor 4 (RepliGen, USA, EP 407122); vascular endothelial growth factor antagonist (Borean, Denmark); bevacizumab (pINN) (Genentech, USA); angiogenic inhibitors (SUGEN, USA); XL 784 (Exelixis, USA); XL 647 (Exelixis, USA); MAb, alpha5beta3 integrin, second generation (Applied Molecular Evolution, USA and MedImmune, USA); enzastaurin hydrochloride (Lilly, USA); CEP 7055 (Cephalon, USA and Sanofi-Synthelabo, France); BC 1 (Genoa Institute of Cancer Research, Italy); rBPI 21 and BPI-derived antiangiogenic (XOMA, USA); PI 88 (Progen, Australia); cilengitide (Merck KGaA, German; Munich Technical University, Germany, Scripps Clinic and Research Foundation, USA); AVE 8062 (Ajinomoto, Japan); AS 1404 (Cancer Research Laboratory, New Zealand); SG 292, (Telios, USA); Endostatin (Boston Childrens Hospital, USA); ATN 161 (Attenuon, USA); 2-methoxyestradiol (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenic, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol; anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors; SU 11248 (Pfizer, USA and SUGEN USA); ABT 518, (Abbott, USA); YH16 (Yantai Rongchang, China); S-3APG (Boston Childrens Hospital, USA and EntreMed, USA); MAb, KDR (ImClone Systems, USA); MAb, alpha5 beta (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA) CV 247 (Ivy Medical, UK); CKD 732 (Chong Kun Dang, South Korea); irsogladine, (Nippon Shinyaku, Japan); RG 13577 (Aventis, France); WX 360 (Wilex, Germany); squalamine, (Genaera, USA); RPI 4610 (Sirna, USA); heparanase inhibitors (InSight, Israel); KL 3106 (Kolon, South Korea); Honokiol (Emory University, USA); ZK CDK (Schering AG, Germany); ZK Angio (Schering AG, Germany); ZK 229561 (Novartis, Switzerland, and Schering AG, Germany); XMP 300 (XOMA, USA); VGA 1102 (Taisho, Japan); VE-cadherin-2 antagonists(ImClone Systems, USA); Vasostatin (National Institutes of Health, USA); Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Further examples of therapeutic agents that may be used in combination with compounds of the invention include agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor, c-Met.

Another example of a therapeutic agent that may be used in combination with compounds of the invention is an autophagy inhibitor. Autophagy inhibitors include, but are not limited to chloroquine, 3-methyladenine, hydroxychloroquine (Plaquenil™), bafilomycin A1, 5-amino-4-imidazole carboxamide riboside (AlCAR), okadaic acid, autophagy-suppressive algal toxins which inhibit protein phosphatases of type 2A or type 1, analogues of cAMP, and drugs which elevate cAMP levels such as adenosine, LY204002, $N_6$-mercaptopurine riboside, and vinblastine. In addition, antisense or siRNA that inhibits expression of proteins including but not limited to ATG5 (which are implicated in autophagy), may also be used. In some embodiments, the one or more additional therapies include an autophagy inhibitor.

Another example of a therapeutic agent that may be used in combination with compounds of the invention is an anti-neoplastic agent. In some embodiments, the one or more additional therapies include an anti-neoplastic agent. Non-limiting examples of anti-neoplastic agents include acemannan, aclarubicin, aldesleukin, alemtuzumab, alitretinoin, altretamine, amifostine, aminolevulinic acid, amrubicin, amsacrine, anagrelide, anastrozole, ancer, ancestim, arglabin, arsenic trioxide, BAM-002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glyco-pine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon-1, interferon alpha, natural, interferon beta, interferon beta-la, interferon beta-Ib, interferon gamma, natural interferon gamma-Ia, interferon gamma-Ib, interleukin-1 beta, iobenguane, irinotecan, irsogladine, Ianreotide, LC 9018 (Yakult), leflunomide, lenograstim, lentinan sulfate, letrozole, leukocyte alpha interferon, leuprorelin, levamisole+fluorouracil, liarozole, lobaplatin, Ionidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, virulizin, zinostatin stimalamer, or zoledronic acid; abarelix; AE 941 (Aeterna), ambamustine, antisense oligonucleotide, bcl-2 (Genta), APC 8015 (Dendreon), decitabine, dexaminoglutethimide, diaziquone, EL 532 (Elan), EM 800 (Endorecherche), eniluracil, etanidazole, fenretinide, filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Additional examples of therapeutic agents that may be used in combination with compounds of the invention include ipilimumab (Yervoy®); tremelimumab; galiximab; nivolumab, also known as BMS-936558 (Opdivo®); pembrolizumab (Keytruda®); avelumab (Bavencio®); AMP224; BMS-936559; MPDL3280A, also known as RG7446; MEDI-570; AMG557; MGA271; IMP321; BMS- 663513; PF-05082566; CDX-1127; anti-OX40 (Providence Health Services); huMAbOX40L; atacicept; CP-870893; lucatumumab; dacetuzumab; muromonab-CD3; ipilumumab; MEDI4736 (Imfinzi®); MSB0010718C; AMP 224; adalimumab (Humira®); ado-trastuzumab emtansine (Kadcyla®); aflibercept (Eylea®); alemtuzumab (Campath®); basiliximab (Simulect®); belimumab (Benlysta®); basiliximab (Simulect®); belimumab (Benlysta®); brentuximab vedotin (Adcetris®); canakinumab (Ilaris®); certolizumab pegol (Cimzia®); daclizumab (Zenapax®); daratumumab (Darzalex®); denosumab (Prolia®); eculizumab (Soliris®); efalizumab (Raptiva®); gemtuzumab ozogamicin (Mylotarg®); golimumab (Simponi®); ibritumomab tiuxetan (Zevalin®); infliximab (Remicade®); motavizumab (Numax®); natalizumab (Tysabri®); obinutuzumab (Gazyva®); ofatumumab (Arzerra®); omalizumab (Xolair®); palivizumab (Synagis®); pertuzumab (Perjeta®); pertuzumab (Perjeta®); ranibizumab (Lucentis®); raxibacumab (Abthrax®); tocilizumab (Actemra®); tositumomab; tositumomab-i-131; tositumomab and tositumomab-i-131 (Bexxar®); ustekinumab (Stelara®); AMG 102; AMG 386; AMG 479; AMG 655; AMG 706; AMG 745; and AMG 951.

The compounds described herein can be used in combination with the agents disclosed herein or other suitable agents, depending on the condition being treated. Hence, in some embodiments the one or more compounds of the disclosure will be co-administered with other therapies as described herein. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described herein can be formulated together in the same dosage form and administered simultaneously. Alternatively, a compound of the invention and any of the therapies described herein can be simultaneously administered, wherein both the agents are present in separate formulations. In another alternative, a compound of the present disclosure can be administered and followed by any of the therapies described herein, or vice versa. In some embodiments of the separate administration protocol, a compound of the invention and any of the therapies described herein are administered a few minutes apart, or a few hours apart, or a few days apart.

In some embodiments of any of the methods described herein, the first therapy (e.g., a compound of the invention) and one or more additional therapies are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours, up to 24 hours, or up to 1-7, 1-14, 1-21 or 1-30 days before or after the one or more additional therapies.

The invention also features kits including (a) a pharmaceutical composition including an agent (e.g., a compound of the invention) described herein, and (b) a package insert with instructions to perform any of the methods described herein. In some embodiments, the kit includes (a) a pharmaceutical composition including an agent (e.g., a compound of the invention) described herein, (b) one or more additional therapies (e.g., non-drug treatment or therapeutic agent), and (c) a package insert with instructions to perform any of the methods described herein.

As one aspect of the present invention contemplates the treatment of the disease or symptoms associated therewith with a combination of pharmaceutically active compounds that may be administered separately, the invention further relates to combining separate pharmaceutical compositions in kit form. The kit may comprise two separate pharmaceutical compositions: a compound of the present invention, and one or more additional therapies. The kit may comprise a container for containing the separate compositions such as a divided bottle or a divided foil packet. Additional examples of containers include syringes, boxes, and bags. In some embodiments, the kit may comprise directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

Numbered Embodiments

[1] A compound, or pharmaceutically acceptable salt thereof, having the structure of Formula I:

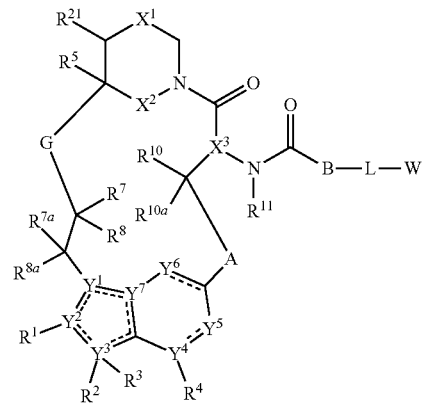

Formula I wherein the dotted lines represent zero, one, two, three, or four non-adjacent double bonds;

A is —N(H or $CH_3$)C(O)—$(CH_2)$— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is absent, —CH($R^9$)—, >C=$CR^9R^{9'}$, or >$CR^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a vinyl ketone, a vinyl sulfone, an ynone, or an alkynyl sulfone;

$X^1$ is optionally substituted $C_1$-$C_2$ alkylene, NR, O, or $S(O)_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^7R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is H, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl; or $R^9$ and $R^{9'}$, combined with the atoms to which they are attached, form a 3 to 6-membered cycloalkyl or a 3 to 6-membered heterocycloalkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl; and $R^{21}$ is H or $C_1$-$C_3$ alkyl.

[2] The compound, or pharmaceutically acceptable salt thereof, of paragraph [1], wherein G is optionally substituted $C_1$-$C_4$ heteroalkylene.

[3] The compound, or pharmaceutically acceptable salt thereof, of paragraph [1] or [2], wherein the compound has the structure of Formula Ic:

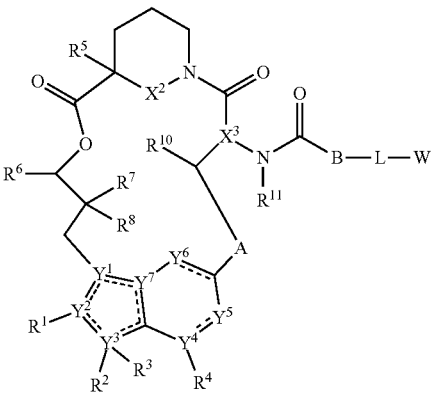

Formula Ic wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;
L is absent or a linker;
W is a cross-linking group comprising a vinyl ketone, a vinyl sulfone, an ynone, or an alkynyl sulfone;
$X^2$ is O or NH;
$X^3$ is N or CH;
n is 0, 1, or 2;
R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;
each R' is, independently, H or optionally substituted $C_1$-$C_4$ alkyl;
$Y^1$ is C, CH, or N;
$Y^2$, $Y^3$, $Y^4$, and $Y^7$ are, independently, C or N; $Y^5$ and $Y^6$ are, independently, CH or N;
$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;
$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or
$R^2$ and $R^3$ combine with the atom to which they are attached to form an optionally substituted 3 to 8-membered cycloalkyl or optionally substituted 3 to 14-membered heterocycloalkyl;
$R^4$ is absent, hydrogen, halogen, cyano, or methyl optionally substituted with 1 to 3 halogens;
$R^5$ is hydrogen, $C_1$-$C_4$ alkyl optionally substituted with halogen, cyano, hydroxy, or $C_1$-$C_4$ alkoxy, cyclopropyl, or cyclobutyl;
$R^6$ is hydrogen or methyl; $R^7$ is hydrogen, halogen, or optionally substituted $C_1$-$C_3$ alkyl, or
$R^6$ and $R^7$ combine with the carbon atoms to which they are attached to form an optionally substituted 3 to 6-membered cycloalkyl or optionally substituted 3 to 7-membered heterocycloalkyl;
$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or
$R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;
$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;
$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;
$R^{10}$ is hydrogen, hydroxy, $C_1$-$C_3$ alkoxy, or $C_1$-$C_3$ alkyl; and
$R^{11}$ is hydrogen or $C_1$-$C_3$ alkyl.

[4] The compound, or pharmaceutically acceptable salt thereof, of any one of paragraphs [1] to [3], wherein $X^2$ is NH.

[5] The compound, or pharmaceutically acceptable salt thereof, of any one of paragraphs [1] to [4], wherein $X^3$ is CH.

[6] The compound, or pharmaceutically acceptable salt thereof, of any one of paragraphs [1] to [5], wherein $R^{11}$ is hydrogen.

[7] The compound, or pharmaceutically acceptable salt thereof, of any one of paragraphs [1] to [5], wherein $R^{11}$ is $C_1$-$C_3$ alkyl.

[8] The compound, or pharmaceutically acceptable salt thereof, of paragraph [7], wherein $R^{11}$ is methyl.

[9] The compound, or pharmaceutically acceptable salt thereof, of any one of paragraphs [1] to [6], wherein the compound has the structure of Formula Id:

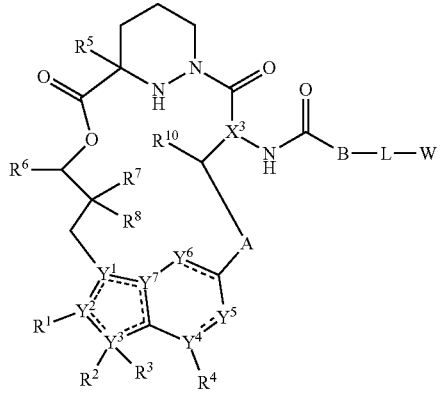

Formula Id wherein the dotted lines represent zero, one, two, three, or four non-adjacent double bonds;
A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;
B is —CH(R$^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;
L is absent or a linker;
W is a cross-linking group comprising a vinyl ketone, a vinyl sulfone, an ynone, or an alkynyl sulfone;
n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N; $Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl; $R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $R^{10}$ is hydrogen, hydroxy, $C_1$-$C_3$ alkoxy, or $C_1$-$C_3$ alkyl.

[10] The compound, or pharmaceutically acceptable salt thereof, of any one of paragraphs [1] to [9] wherein $X^1$ is optionally substituted $C_1$-$C_2$ alkylene.

[11] The compound, or pharmaceutically acceptable salt thereof, of paragraph [10], wherein $X^1$ is methylene.

[12] The compound, or pharmaceutically acceptable salt thereof, of any one of paragraphs [1] to 35 [11], wherein $R^5$ is hydrogen.

[13] The compound, or pharmaceutically acceptable salt thereof, of any one of paragraphs [1] to [11], wherein $R^5$ is $C_1$-$C_4$ alkyl optionally substituted with halogen.

[14] The compound, or pharmaceutically acceptable salt thereof, of paragraph [13], wherein $R^5$ is methyl.

[15] The compound, or pharmaceutically acceptable salt thereof, of any one of paragraphs [1] to [14], wherein $Y^4$ is C.

[16] The compound, or pharmaceutically acceptable salt thereof, of any one of paragraphs [1] to [15], wherein $R^4$ is hydrogen.

[17] The compound, or pharmaceutically acceptable salt thereof, of any one of paragraphs [1] to [16], wherein $Y^5$ is CH.

[18] The compound, or pharmaceutically acceptable salt thereof, of any one of paragraphs [1] to [17], wherein $Y^6$ is CH.

[19] The compound, or pharmaceutically acceptable salt thereof, of any one of paragraphs [1] to [18], wherein $Y^1$ is C.

[20] The compound, or pharmaceutically acceptable salt thereof, of any one of paragraphs [1] to [19] wherein $Y^2$ is C.

[21] The compound, or pharmaceutically acceptable salt thereof, of any one of paragraphs [1] to [20] wherein $Y^3$ is N.

[22] The compound, or pharmaceutically acceptable salt thereof, of any one of paragraphs [1] to [21], wherein $R^3$ is absent.

[23] The compound, or pharmaceutically acceptable salt thereof, of any one of paragraphs [1] to [22], wherein $Y^7$ is C.

[24] The compound, or pharmaceutically acceptable salt thereof, of any one of paragraphs [1] to [6] or [9] to [23], wherein the compound has the structure of Formula Ie:

Formula Ie wherein A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a vinyl ketone, a vinyl sulfone, an ynone, or an alkynyl sulfone;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $R^{10}$ is hydrogen, hydroxy, $C_1$-$C_3$ alkoxy, or $C_1$-$C_3$ alkyl.

[25] The compound, or pharmaceutically acceptable salt thereof, of any one of paragraphs [3] to [24], wherein $R^6$ is hydrogen.

[26] The compound, or pharmaceutically acceptable salt thereof, of any one of paragraphs [1] to [25], wherein $R^2$ is hydrogen, cyano, optionally substituted $C_1$-$C_6$ alkyl, optionally substituted 3 to 6-membered cycloalkyl, or optionally substituted 3 to 6-membered heterocycloalkyl.

[27] The compound, or pharmaceutically acceptable salt thereof, of paragraph [26], wherein $R^2$ is optionally substituted $C_1$-$C_6$ alkyl.

[28] The compound, or pharmaceutically acceptable salt thereof, of paragraph [27], wherein $R^2$ is ethyl.

[29] The compound, or pharmaceutically acceptable salt thereof, of any one of paragraphs [1] to [28], wherein $R^7$ is optionally substituted $C_1$-$C_3$ alkyl.

[30] The compound, or pharmaceutically acceptable salt thereof, of paragraph 29, wherein $R^7$ is $C_1$-$C_3$ alkyl.

[31] The compound, or pharmaceutically acceptable salt thereof, of any one of paragraphs [1] to 30, wherein $R^8$ is optionally substituted $C_1$-$C_3$ alkyl.

[32] The compound, or pharmaceutically acceptable salt thereof, of paragraph [31], wherein $R^8$ is $C_1$-$C_3$ alkyl.

[33] The compound, or pharmaceutically acceptable salt thereof, of any one of paragraphs [1] to [32], wherein the compound has the structure of Formula If:

Formula If wherein A is —N(H or CH$_3$)C(O)—(CH$_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a vinyl ketone, a vinyl sulfone, an ynone, or an alkynyl sulfone;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is $C_1$-$C_6$ alkyl or 3 to 6-membered cycloalkyl;

$R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

[34] The compound, or pharmaceutically acceptable salt thereof, of any one of paragraphs [1] to [33], wherein $R^1$ is optionally substituted 6 to 10-membered aryl, optionally substituted 3 to 6-membered cycloalkenyl, or optionally substituted 5 to 10-membered heteroaryl.

[35] The compound, or pharmaceutically acceptable salt thereof, of paragraph [34], wherein $R^1$ is optionally substituted 6-membered aryl, optionally substituted 6-membered cycloalkenyl, or optionally substituted 6-membered heteroaryl.

[36] The compound, or pharmaceutically acceptable salt thereof, of paragraph [35], wherein $R^1$ is

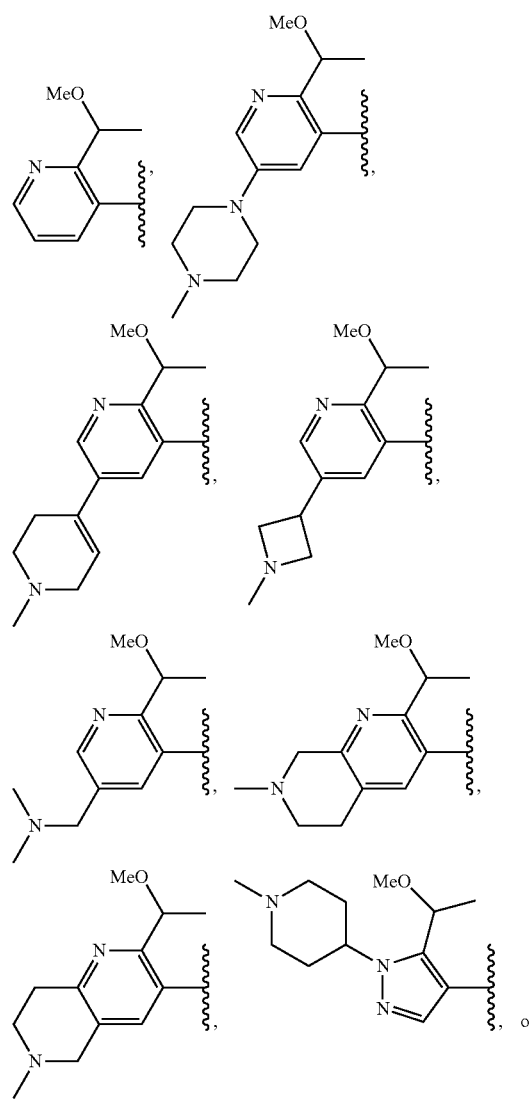

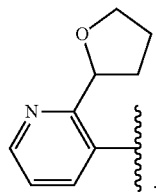

[37] The compound, or pharmaceutically acceptable salt thereof, of paragraph [36], wherein $R^1$ is

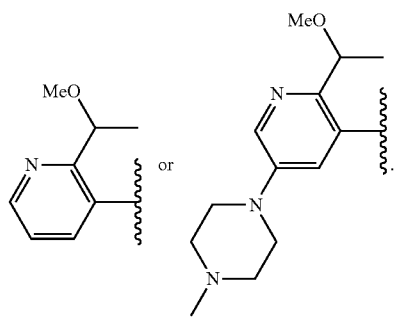 [SMILES: *c1cccnc1C(C)OC ; *c1cc(N2CCN(C)CC2)cnc1C(C)OC]

[38] The compound, or pharmaceutically acceptable salt thereof, of any one of paragraphs [1] to [37], wherein the compound has the structure of Formula II:

Formula Ig

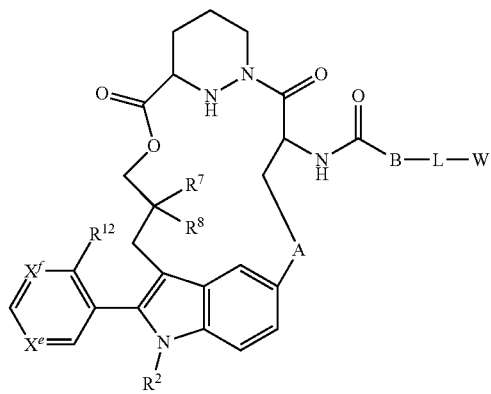

wherein A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a vinyl ketone, a vinyl sulfone, an ynone, or an alkynyl sulfone;

$R^2$ is $C_1$-$C_6$ alkyl, $C_1$-$C_6$ fluoroalkyl, or 3 to 6-membered cycloalkyl;

R⁷ is $C_1$-$C_3$ alkyl;
R⁸ is $C_1$-$C_3$ alkyl; and
R⁹ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl
$X^e$ and $X^f$ are, independently, N or CH; and
$R^{12}$ is optionally substituted $C_1$-$C_6$ alkyl, optionally substituted $C_1$-$C_6$ heteroalkyl, or optionally substituted 3 to 7-membered heterocycloalkyl.

[39] The compound, or pharmaceutically acceptable salt thereof, of paragraph [38], wherein $X^e$ is N and $X^f$ is CH.

[40] The compound, or pharmaceutically acceptable salt thereof, of paragraph [38], wherein $X^e$ is CH and $X^f$ is N.

[41] The compound, or pharmaceutically acceptable salt thereof, of any one of paragraphs [38] to [40], wherein $R^{12}$ is optionally substituted $C_1$-$C_6$ heteroalkyl.

[42] The compound, or pharmaceutically acceptable salt thereof, of any one of paragraphs [38] to [41], wherein $R^{12}$ is

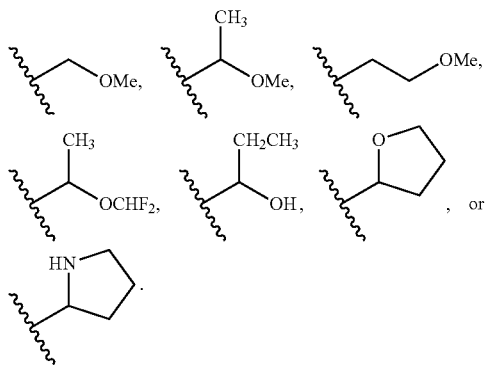

[43] The compound, or pharmaceutically acceptable salt thereof, of paragraph [1] or [2], wherein the compound has the structure of Formula VI:

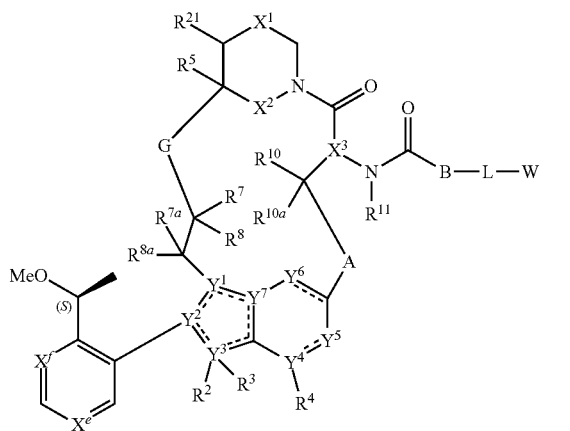

Formula VI wherein the dotted lines represent zero, one, two, three, or four non-adjacent double bonds;
A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;
B is absent, —CH($R^9$)—, >C=C$R^9R^{9'}$, or >C$R^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;
G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;
L is absent or a linker;
W is a cross-linking group comprising a vinyl ketone, a vinyl sulfone, an ynone, a haloacetal, or an alkynyl sulfone;
$X^1$ is optionally substituted $C_1$-$C_2$ alkylene, NR, O, or S(O)$_n$;
$X^2$ is O or NH;
$X^3$ is N or CH;
n is 0, 1, or 2;
R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;
each R' is, independently, H or optionally substituted $C_1$-$C_4$ alkyl;
$Y^1$ is C, CH, or N;
$Y^2$, $Y^3$, $Y^4$, and $Y^7$ are, independently, C or N;
$Y^5$ is CH, $CH_2$, or N;
$Y^6$ is C(O), CH, $CH_2$, or N;
$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or
$R^2$ and $R^3$ combine with the atom to which they are attached to form an optionally substituted 3 to 8-membered cycloalkyl or optionally substituted 3 to 14-membered heterocycloalkyl;
$R^4$ is absent, hydrogen, halogen, cyano, or methyl optionally substituted with 1 to 3 halogens;
$R^5$ is hydrogen, $C_1$-$C_4$ alkyl optionally substituted with halogen, cyano, hydroxy, or $C_1$-$C_4$ alkoxy, cyclopropyl, or cyclobutyl;
$R^6$ is hydrogen or methyl; $R^7$ is hydrogen, halogen, or optionally substituted $C_1$-$C_3$ alkyl, or
$R^6$ and $R^7$ combine with the carbon atoms to which they are attached to form an optionally substituted 3 to 6-membered cycloalkyl or optionally substituted 3 to 7-membered heterocycloalkyl;
$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or
$R^7$ and $R^8$ combine with the carbon atom to which they are attached to form C=C$R^7R^{8'}$; C=N(OH), C=N(O—

C₁-C₃ alkyl), C=O, C=S, C=NH, optionally substituted 3 to 6-membered cycloalkyl, or optionally substituted 3 to 7-membered heterocycloalkyl;

R$^{7a}$ and R$^{8a}$ are, independently, hydrogen, halo, optionally substituted C₁-C₃ alkyl, or combine with the carbon to which they are attached to form a carbonyl;

R$^{7'}$ is hydrogen, halogen, or optionally substituted C₁-C₃ alkyl; R$^{8'}$ is hydrogen, halogen, hydroxy, cyano, optionally substituted C₁-C₃ alkoxy, optionally substituted C₁-C₃ alkyl, optionally substituted C₂-C₆ alkenyl, optionally substituted C₂-C₆ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or R$^{7'}$ and R$^{8'}$ combine with the carbon atom to which they are attached to form optionally substituted 3 to 6-membered cycloalkyl or optionally substituted 3 to 7-membered heterocycloalkyl;

R⁹ is H, F, optionally substituted C₁-C₆ alkyl, optionally substituted C₁-C₆ heteroalkyl, optionally substituted 3 to 6-membered cycloalkyl, or optionally substituted 3 to 7-membered heterocycloalkyl; or R⁹ and L combine with the atoms to which they are attached to form an optionally substituted 3 to 14-membered heterocycloalkyl;

R$^{9'}$ is hydrogen or optionally substituted C₁-C₆ alkyl; or R⁹ and R$^{9'}$, combined with the atoms to which they are attached, form a 3 to 6-membered cycloalkyl or a 3 to 6-membered heterocycloalkyl;

R¹⁰ is hydrogen, halo, hydroxy, C₁-C₃ alkoxy, or C₁-C₃ alkyl;

R$^{10a}$ is hydrogen or halo;

R¹¹ is hydrogen or C₁-C₃ alkyl;

R²¹ is hydrogen or C₁-C₃ alkyl (e.g., methyl); and

X$^e$ and X$^f$ are, independently, N or CH.

[44] The compound, or pharmaceutically acceptable salt thereof, of paragraph [43], wherein the compound has the structure of Formula VIa:

Formula VIa

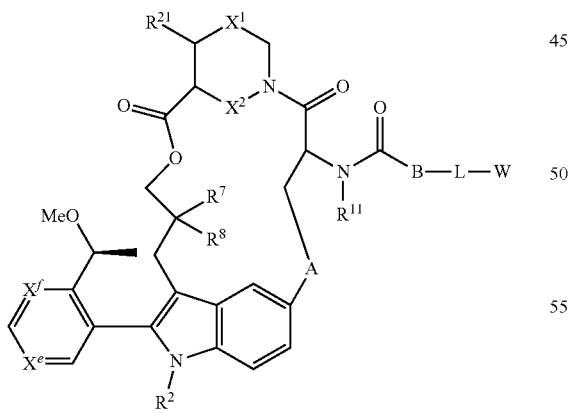

wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a vinyl ketone, a vinyl sulfone, an ynone, or an alkynyl sulfone;

X¹ is optionally substituted C₁-C₂ alkylene, NR, O, or S(O)$_n$;

X² is O or NH;

n is 0, 1, or 2;

R is hydrogen, cyano, optionally substituted C₁-C₄ alkyl, optionally substituted C₂-C₄ alkenyl, optionally substituted C₂-C₄ alkynyl, C(O)R', C(O)OR', C(O)N(R')₂, S(O)R', S(O)₂R', or S(O)₂N(R')₂;

each R' is, independently, H or optionally substituted C₁-C₄ alkyl;

R² is C₁-C₆ alkyl, C₁-C₆ fluoroalkyl, or 3 to 6-membered cycloalkyl;

R⁷ is C₁-C₃ alkyl;

R⁸ is C₁-C₃ alkyl; and

R⁹ is optionally substituted C₁-C₆ alkyl, optionally substituted C₁-C₆ heteroalkyl, optionally substituted 3 to 6-membered cycloalkyl, or optionally substituted 3 to 7-membered heterocycloalkyl;

X$^e$ and X$^f$ are, independently, N or CH;

R¹¹ is hydrogen or C₁-C₃ alkyl; and

R²¹ is hydrogen or C₁-C₃ alkyl.

[45] The compound, or pharmaceutically acceptable salt thereof, of paragraph [43] or [44], wherein the compound has the structure of Formula VIb:

Formula VIb wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

R⁹ is optionally substituted C₁-C₆ alkyl, optionally substituted C₁-C₆ heteroalkyl, optionally substituted 3 to 6-membered cycloalkyl, or optionally substituted 3 to 7-membered heterocycloalkyl;

L is absent or a linker; and

W is a cross-linking group comprising a vinyl ketone, a vinyl sulfone, an ynone, or an alkynyl sulfone.

[46] The compound, or pharmaceutically acceptable salt thereof, of any one of paragraphs [1] to [45], wherein A is optionally substituted 6-membered arylene.

[47] The compound, or pharmaceutically acceptable salt thereof, of paragraph [46], wherein A has the structure:

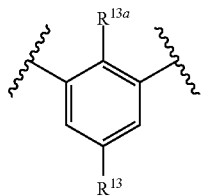

wherein $R^{13}$ is hydrogen, halo, hydroxy, amino, optionally substituted $C_1$-$C_6$ alkyl, or optionally substituted $C_1$-$C_6$ heteroalkyl; and $R^{13a}$ is hydrogen or halo.

[48] The compound, or pharmaceutically acceptable salt thereof, of paragraph [47], wherein $R^{13}$ and $R^{13a}$ are each hydrogen.

[49] The compound, or pharmaceutically acceptable salt thereof, of paragraph [47], wherein $R^{13}$ is hydroxy, methyl, fluoro, or difluoromethyl.

[50] The compound, or pharmaceutically acceptable salt thereof, of any one of paragraphs [1] to [45], wherein A is optionally substituted 5 to 6-membered heteroarylene.

[51] The compound, or pharmaceutically acceptable salt thereof, of paragraph [50], wherein A is:

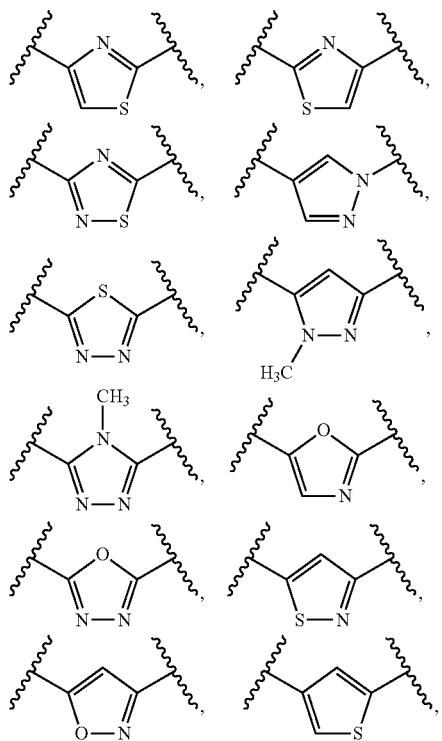

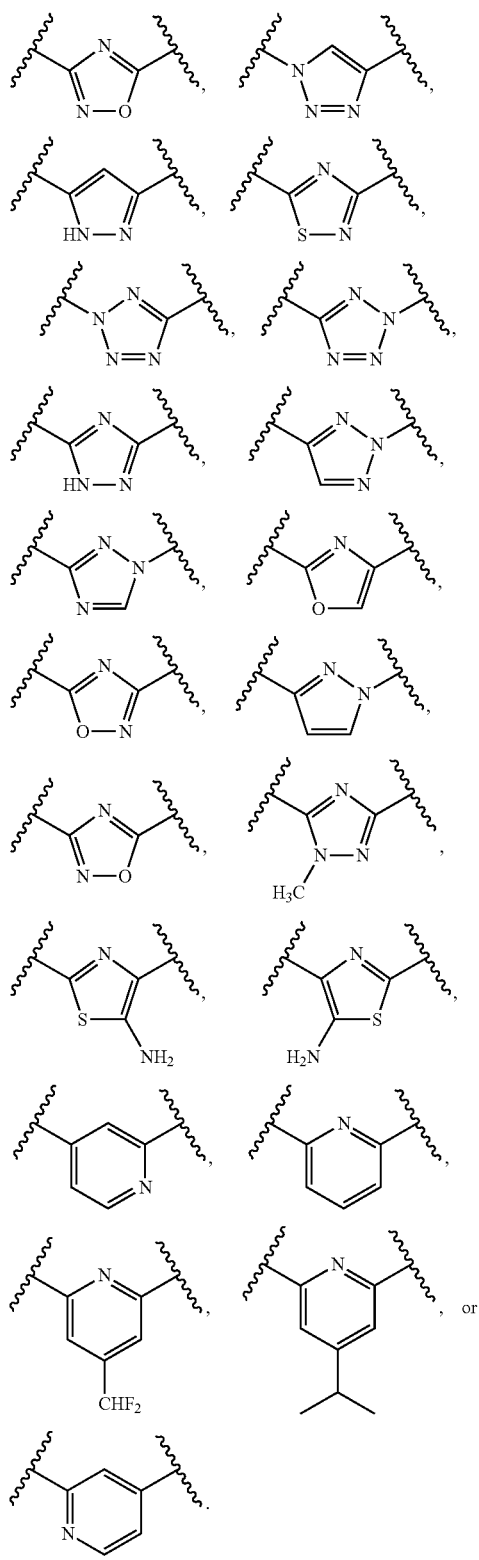

[52] The compound, or pharmaceutically acceptable salt thereof, of any one of paragraphs [1] to [45], wherein A is optionally substituted $C_1$-$C_4$ heteroalkylene.

[53] The compound, or pharmaceutically acceptable salt thereof, of paragraph [52], wherein A is:

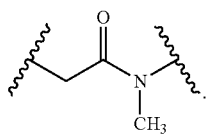 [SMILES: *CC(=O)N(*)C]

[54] The compound, or pharmaceutically acceptable salt thereof, of any one of paragraphs [1] to [45], wherein A is optionally substituted 3 to 6-membered heterocycloalkylene.

[55] The compound, or pharmaceutically acceptable salt thereof, of paragraph [54], wherein A is:

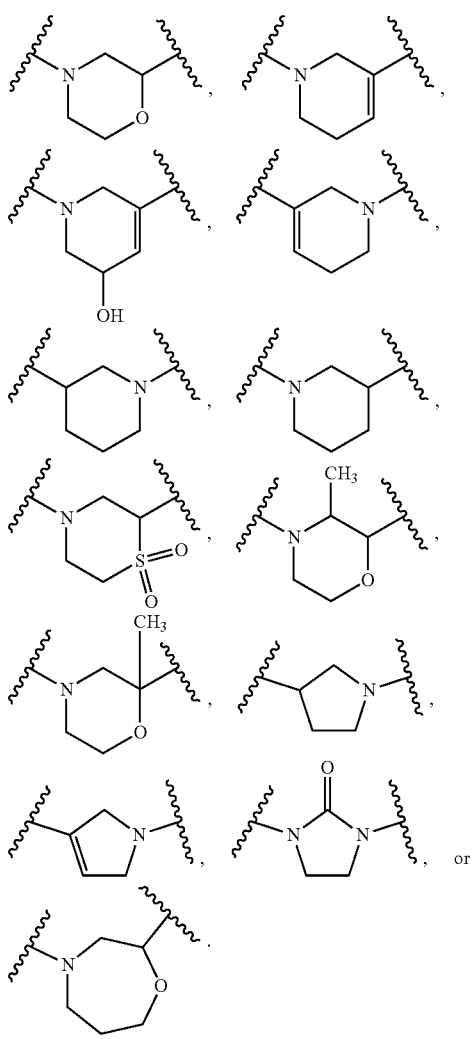

[56] The compound, or pharmaceutically acceptable salt thereof, of paragraph [55], wherein A is

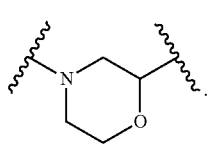 [SMILES: *C1CN(*)CCO1]

[57] The compound, or pharmaceutically acceptable salt thereof, of any one of paragraphs [1] to [56], wherein B is —CHR$^9$—.

[58] The compound, or pharmaceutically acceptable salt thereof, of paragraph [57], wherein R$^9$ is F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

[59] The compound, or pharmaceutically acceptable salt thereof, of paragraph [58], wherein R$^9$ is:

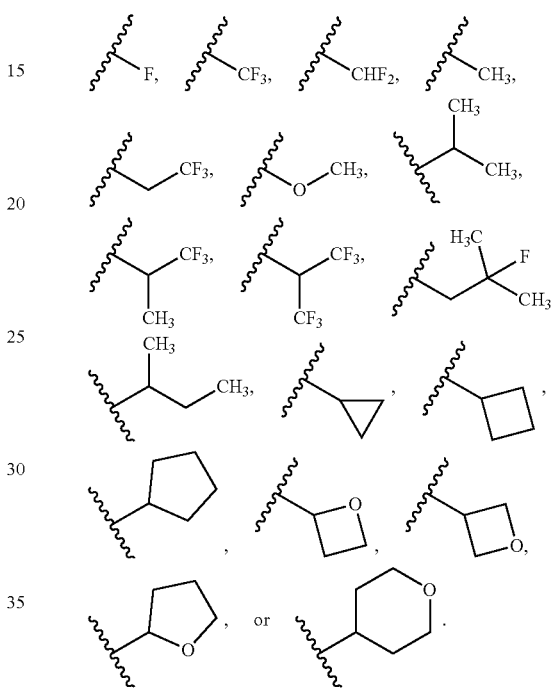

[60] The compound, or pharmaceutically acceptable salt thereof, of paragraph [59], wherein R$^9$ is:

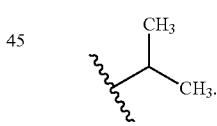

[61] The compound, or pharmaceutically acceptable salt thereof, of any one of paragraphs [1] to [56], wherein B is optionally substituted 6-membered arylene.

[62] The compound, or pharmaceutically acceptable salt thereof, of paragraph [61], wherein B is 6-membered arylene.

[63] The compound, or pharmaceutically acceptable salt thereof, of paragraph [61], wherein B is:

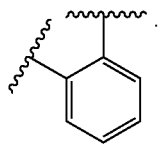

[64] The compound, or pharmaceutically acceptable salt thereof, of any one of paragraphs [1] to [63], wherein $R^7$ is methyl.

[65] The compound, or pharmaceutically acceptable salt thereof, of any one of paragraphs [1] to [64], wherein $R^8$ is methyl.

[66] The compound, or pharmaceutically acceptable salt thereof, of any one of paragraphs [1] to [65], wherein the linker is the structure of Formula II:

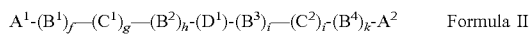

Formula II where $A^1$ is a bond between the linker and B; $A^2$ is a bond between W and the linker; $B^1$, $B^2$, $B^3$, and $B^4$ each, independently, is selected from optionally substituted $C_1$-$C_2$ alkylene, optionally substituted $C_1$-$C_3$ heteroalkylene, O, S, and $NR^N$; $R^N$ is hydrogen, optionally substituted $C_1$-$C_4$ alkyl, optionally substituted $C_2$-$C_4$ alkenyl, optionally substituted $C_2$-$C_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$—$(C^1)_g$—$(B^2)_h$- to —$(B^3)_i$—$(C^2)_j$—$(B^4)_k$-$A^2$.

[67] The compound, or a pharmaceutically acceptable salt thereof, of any one of paragraphs [1] to [66], wherein the linker is acyclic.

[68] The compound, or a pharmaceutically acceptable salt thereof, of paragraph [67], wherein the linker has the structure of Formula IIa:

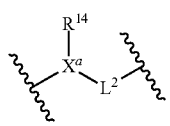

Formula IIa wherein $X^a$ is absent or N;
$R^{14}$ is absent, hydrogen or optionally substituted $C_1$-$C_6$ alkyl; and
$L^2$ is absent, —$SO_2$—, optionally substituted $C_1$-$C_4$ alkylene or optionally substituted $C_1$-$C_4$ heteroalkylene, wherein at least one of $X^a$, $R^{14}$, or $L^2$ is present.

[69] The compound, or a pharmaceutically acceptable salt thereof, of paragraph [68], wherein the linker has the structure:

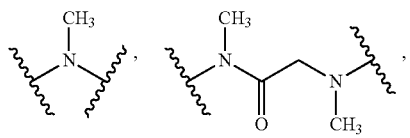

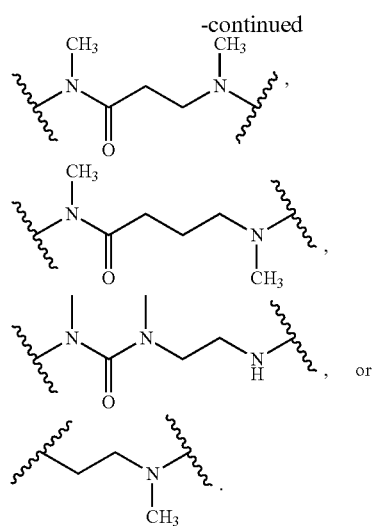

[70] The compound, or a pharmaceutically acceptable salt thereof, of any one of paragraphs [1] to [66], wherein the linker is or comprises a cyclic moiety.

[71] The compound, or a pharmaceutically acceptable salt thereof, of paragraph [70], wherein the linker has the structure of Formula IIb:

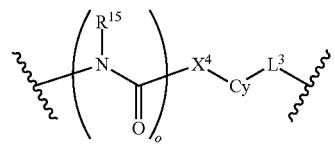

Formula IIb wherein o is 0 or 1;
$R^{15}$ is hydrogen, optionally substituted $C_1$-$C_6$ alkyl, optionally substituted 3 to 8-membered cycloalkylene, or optionally substituted 3 to 8-membered heterocycloalkylene;
$X^4$ is absent, optionally substituted $C_1$-$C_4$ alkylene, O, $NCH_3$, or optionally substituted $C_1$-$C_4$ heteroalkylene;
Cy is optionally substituted 3 to 8-membered cycloalkylene, optionally substituted 3 to 8-membered heterocycloalkylene, optionally substituted 6-10 membered arylene, or optionally substituted 5 to 10-membered heteroarylene; and
$L^3$ is absent, —$SO_2$—, optionally substituted $C_1$-$C_4$ alkylene or optionally substituted $C_1$-$C_4$ heteroalkylene.

[72] The compound, or a pharmaceutically acceptable salt thereof, of paragraph [71], wherein the linker has the structure:

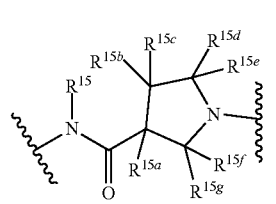

Formula IIc wherein $R^{15}$ is hydrogen, optionally substituted $C_1$-$C_6$ alkyl, optionally substituted 3 to 8-membered cycloalkylene, or optionally substituted 3 to 8-membered heterocycloalkylene; and $R^{15a}$, $R^{15b}$, $R^{15c}$, $R^{15d}$, $R^{15e}$, $R^{15f}$, and $R^{15g}$ are, independently, hydrogen, halo, hydroxy, cyano, amino, optionally substituted $C_1$-$C_6$ alkyl, optionally substituted $C_1$-$C_6$ alkoxy, or, or $R^{15b}$ and $R^{15d}$ combine with the carbons to which they are attached to form an optionally substituted 3 to 8-membered cycloalkylene, or optionally substituted 3 to 8-membered heterocycloalkylene.

[73] The compound, or a pharmaceutically acceptable salt thereof, of paragraph [72], wherein the linker has the structure:

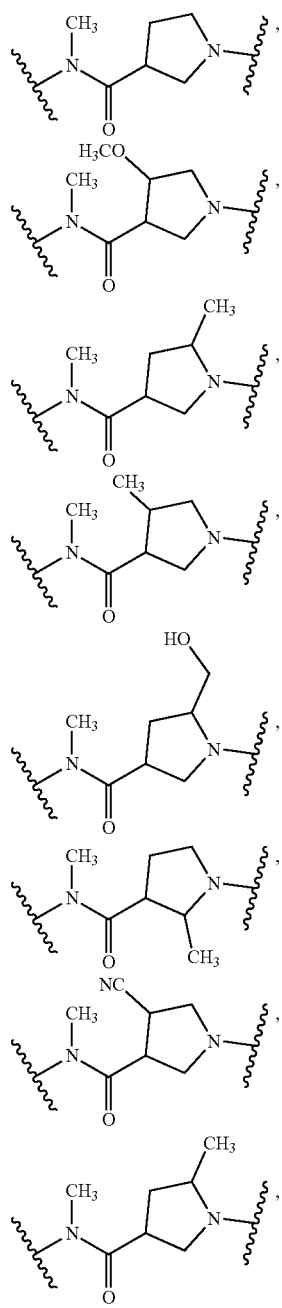

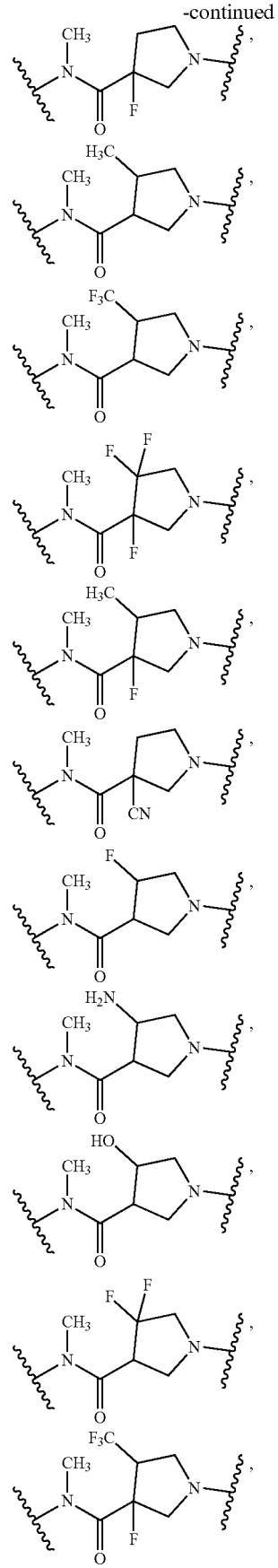

867
-continued
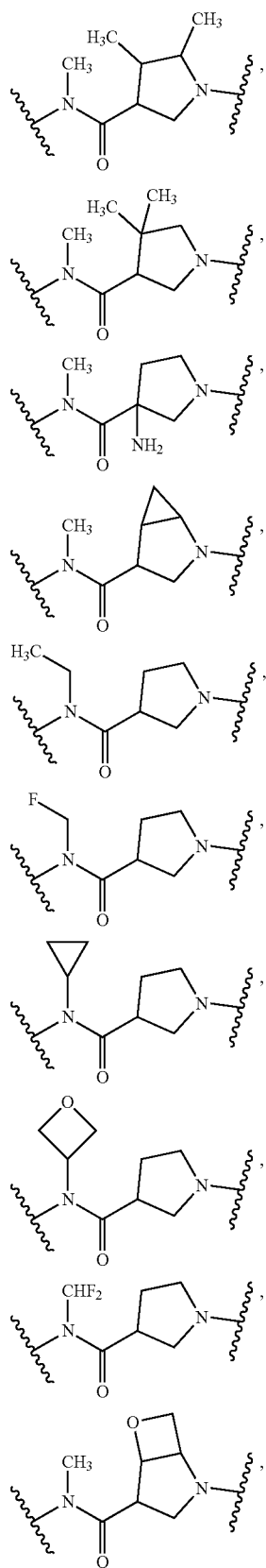
868
-continued
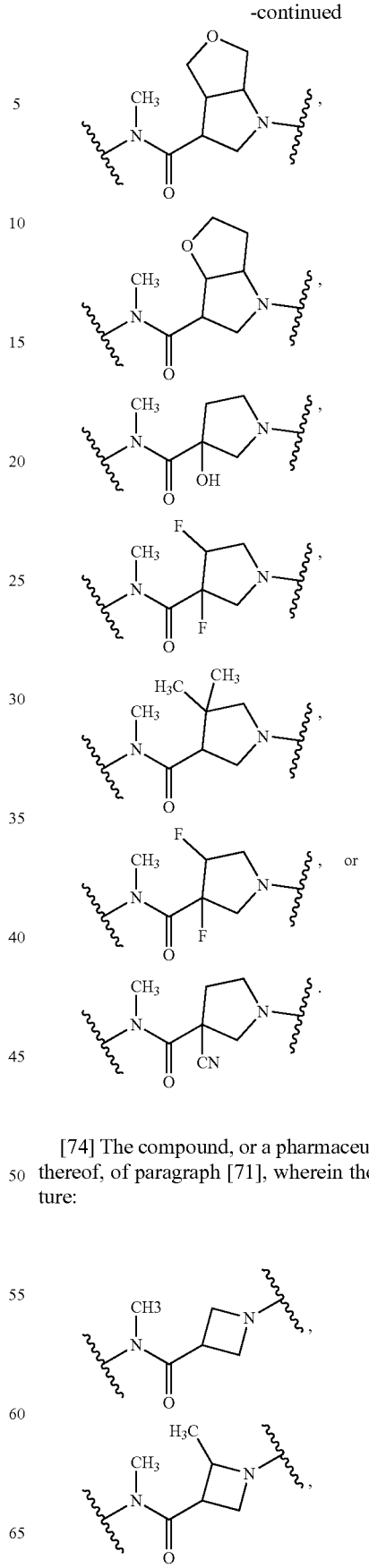
[74] The compound, or a pharmaceutically acceptable salt thereof, of paragraph [71], wherein the linker has the structure:
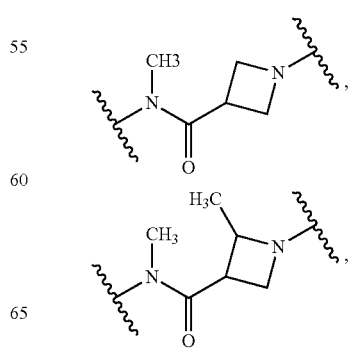

869
-continued
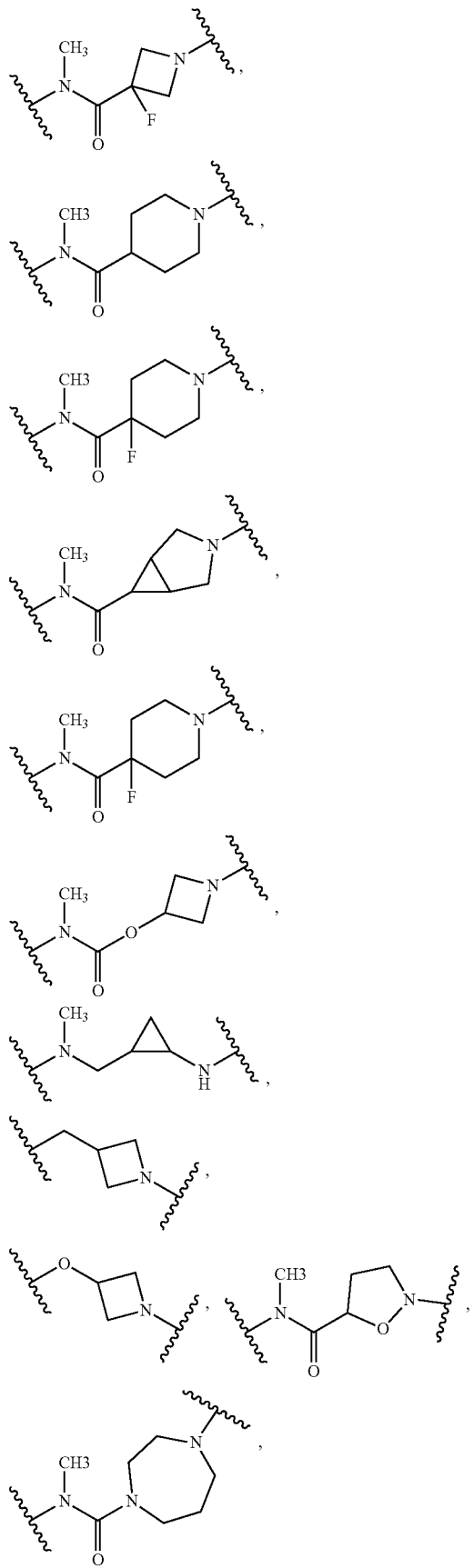
870
-continued
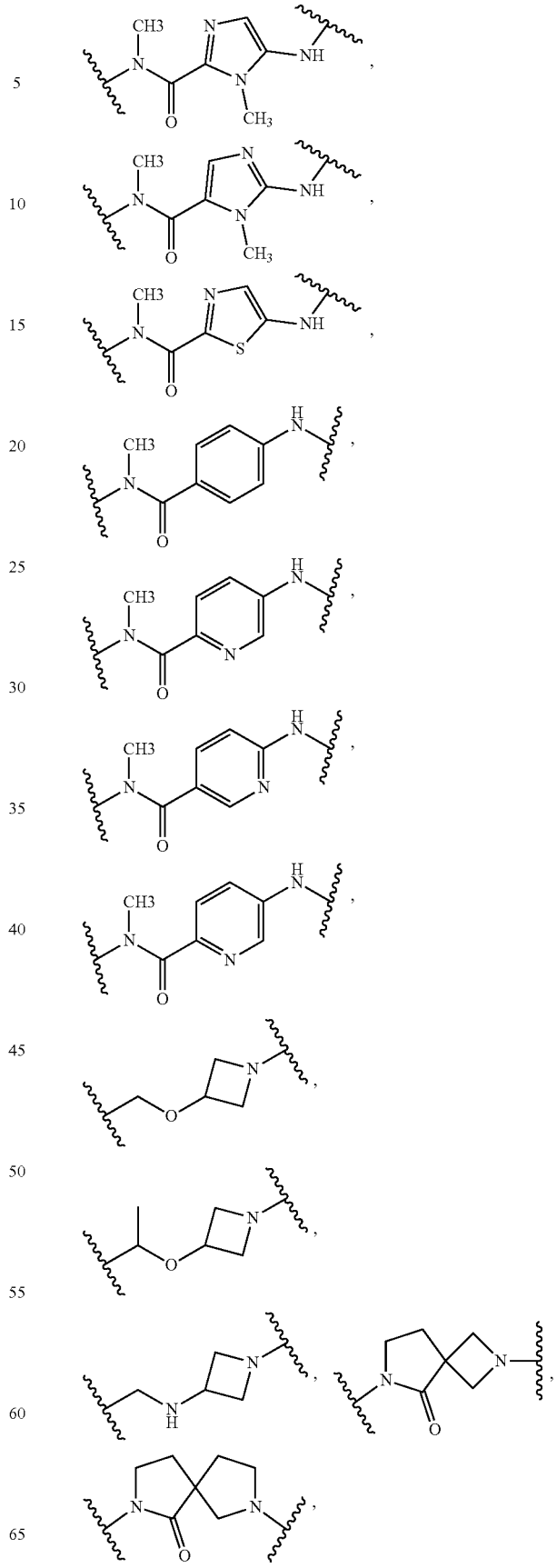

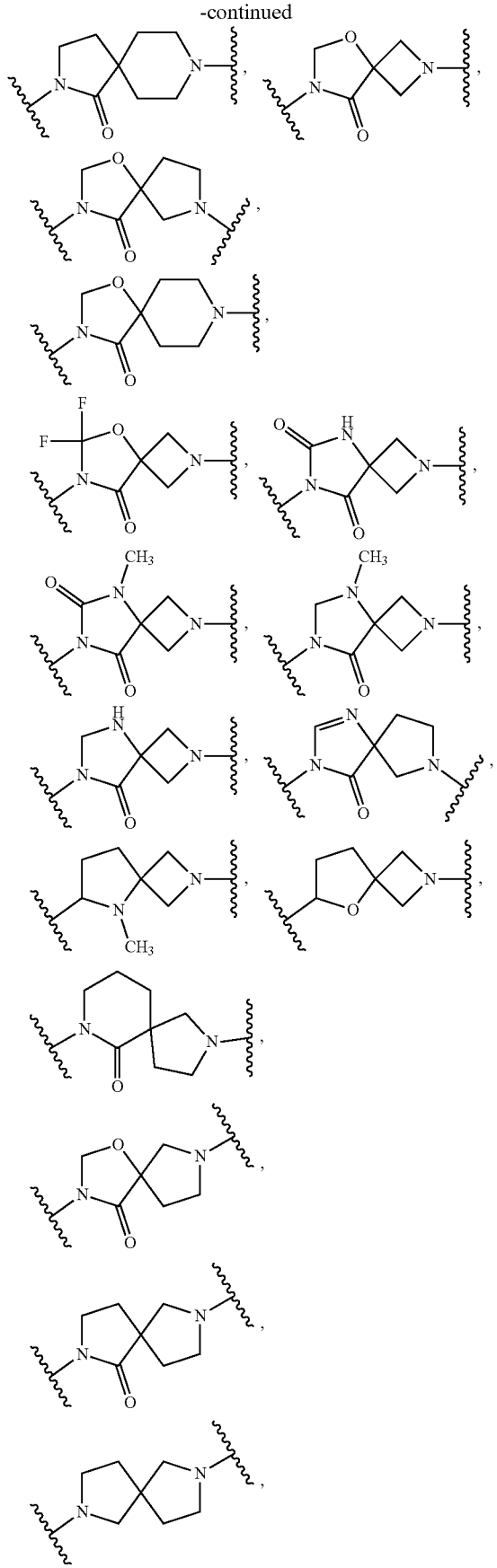
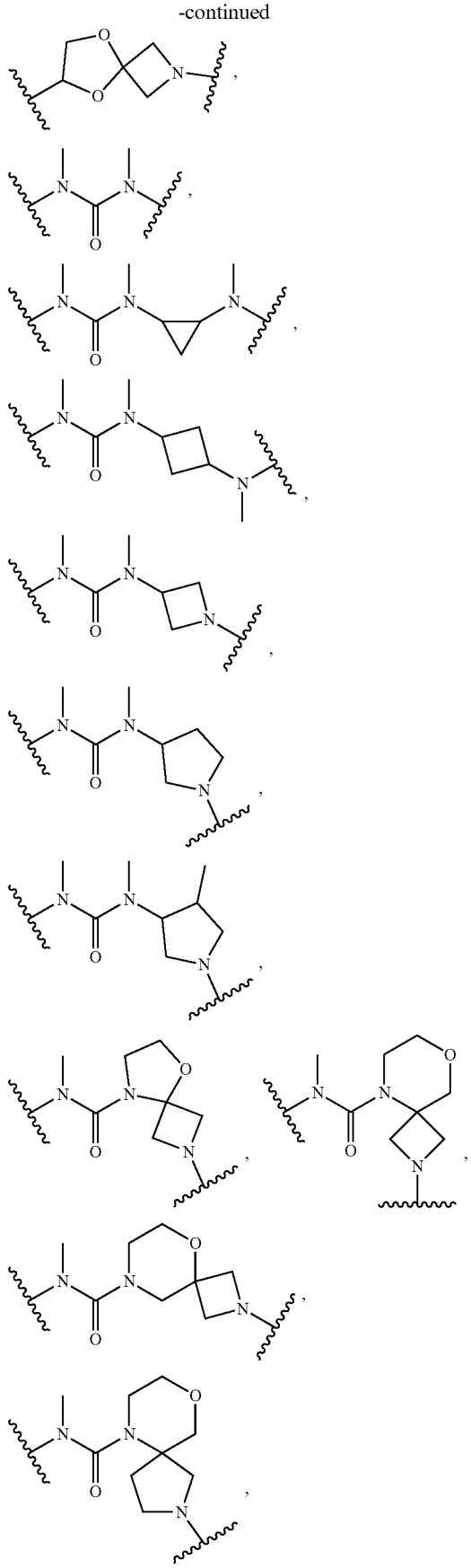

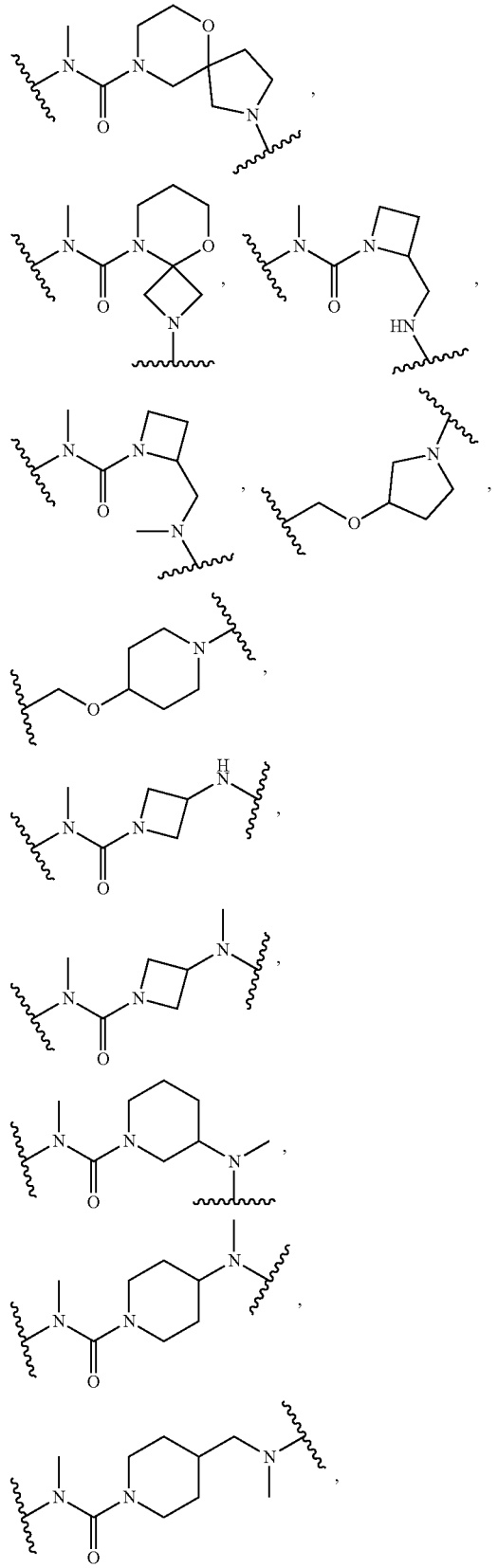
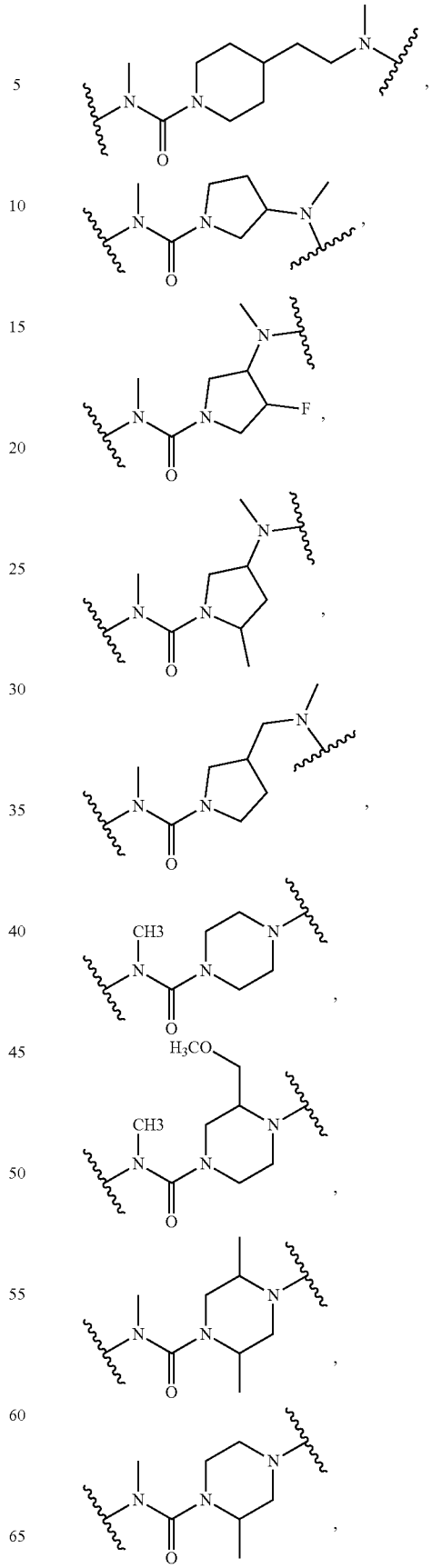

875
-continued
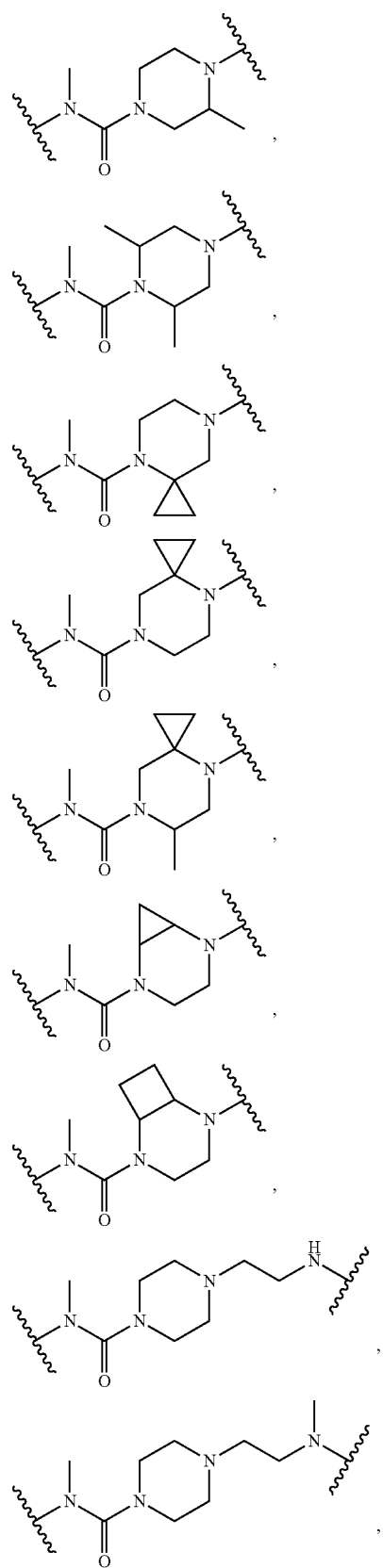
876
-continued
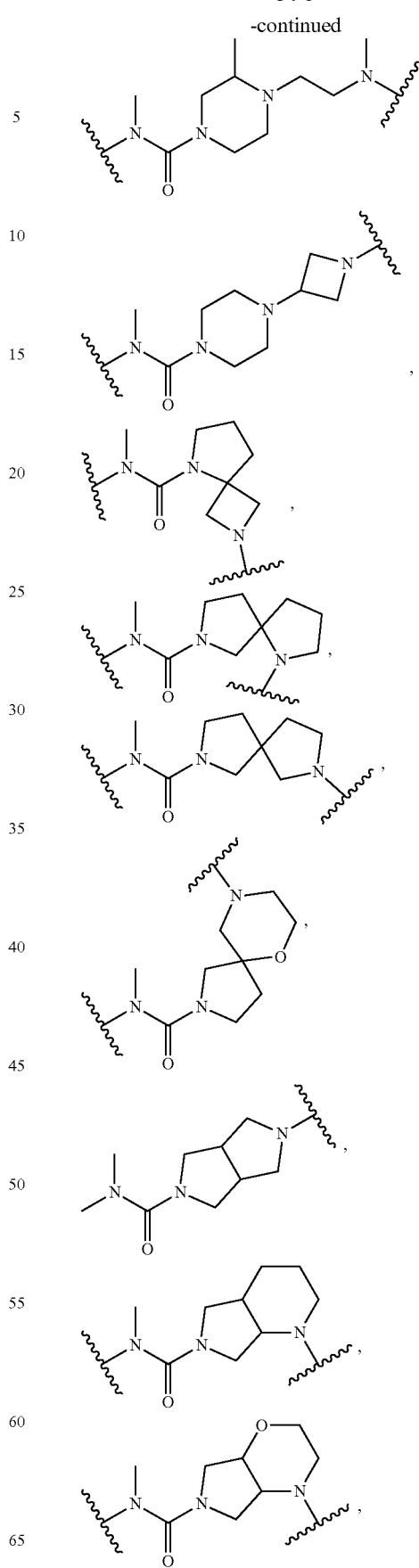

877
-continued
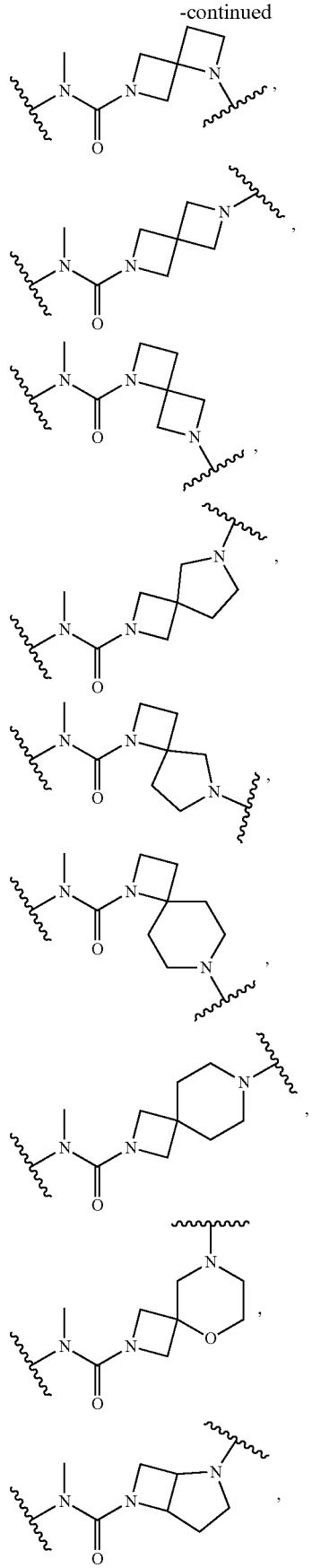
878
-continued
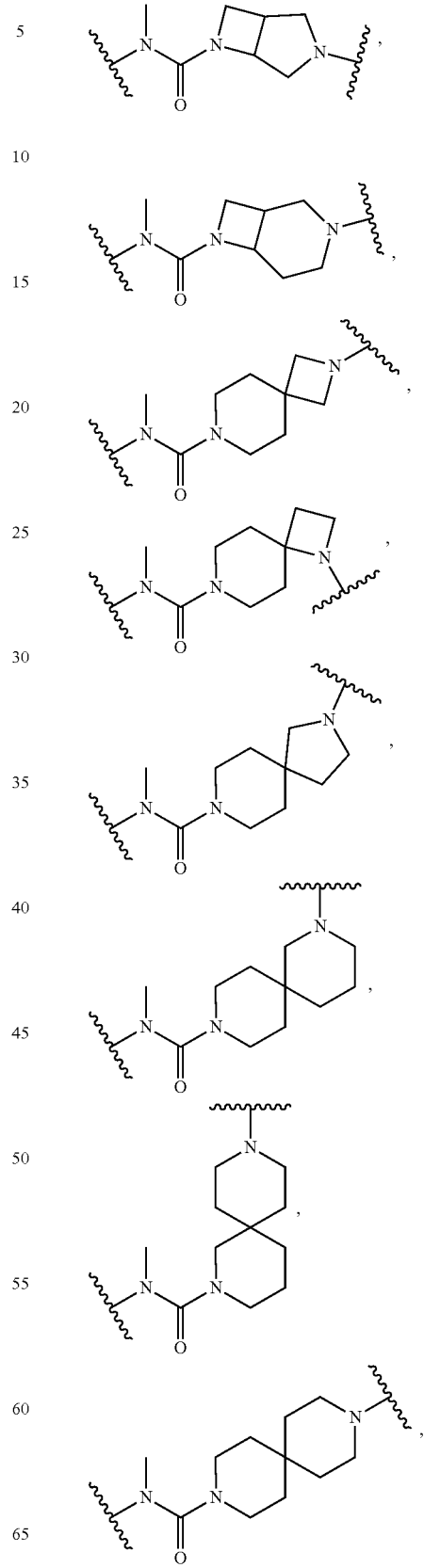

-continued

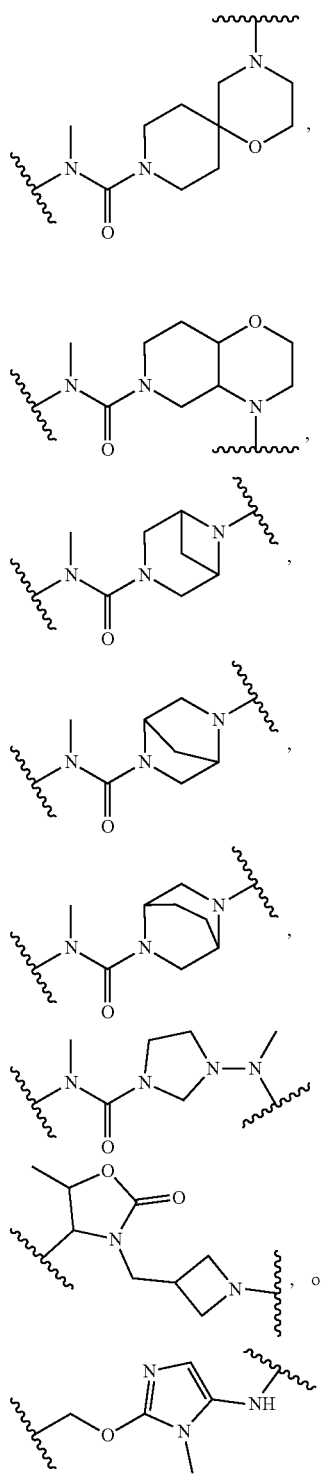

[75] The compound, or a pharmaceutically acceptable salt thereof, of any one of paragraphs [1] to [74], wherein W is a cross-linking group comprising a vinyl ketone.

[76]. The compound, or a pharmaceutically acceptable salt thereof, of paragraph [75], wherein W has the structure of Formula IIIa:

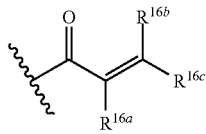

Formula IIIa wherein $R^{16a}$, $R^{16b}$, and $R^{16c}$ are, independently, hydrogen, —CN, halogen, or —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated heterocycloalkyl.

[77] The compound, or a pharmaceutically acceptable salt thereof, of paragraph [76], wherein W is:

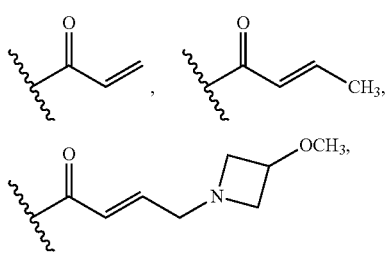

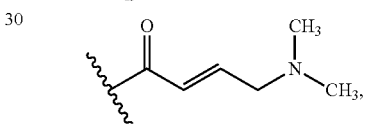

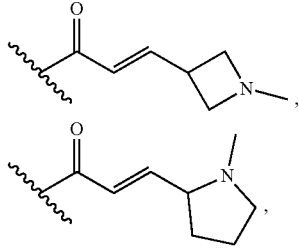

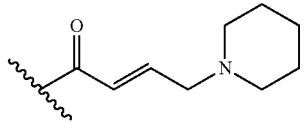

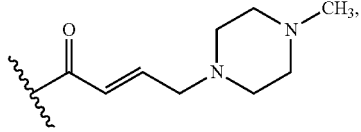

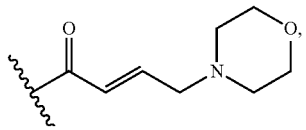

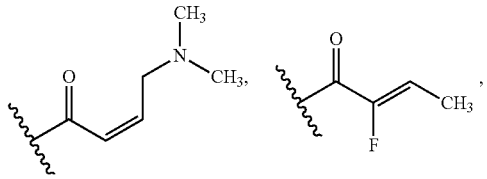

881
-continued

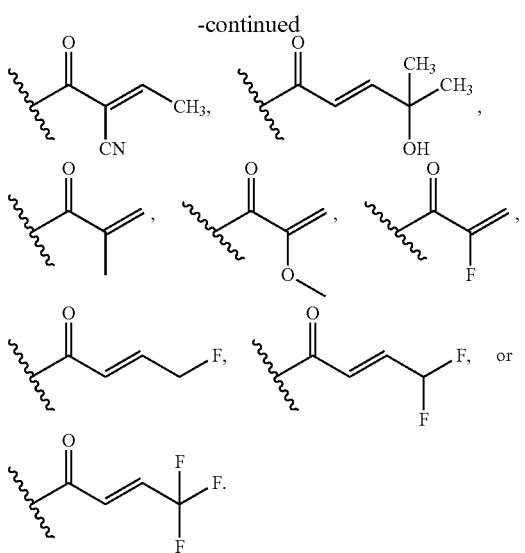

[78] The compound, or a pharmaceutically acceptable salt thereof, of any one of paragraphs [1] to [74], wherein W is a cross-linking group comprising an ynone.

[79] The compound, or a pharmaceutically acceptable salt thereof, of paragraph [78], wherein W has the structure of Formula IIIb:

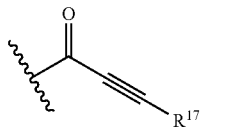

Formula IIIb wherein $R^{17}$ is hydrogen, —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated cycloalkyl, or a 4 to 7-membered saturated heterocycloalkyl.

[80] The compound, or a pharmaceutically acceptable salt thereof, of paragraph [79], wherein W is:

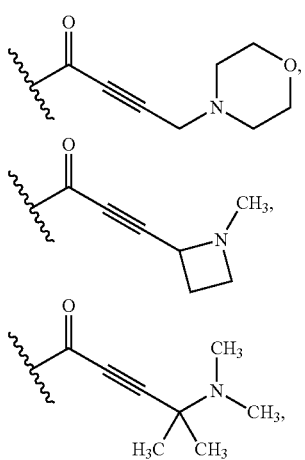

882
-continued

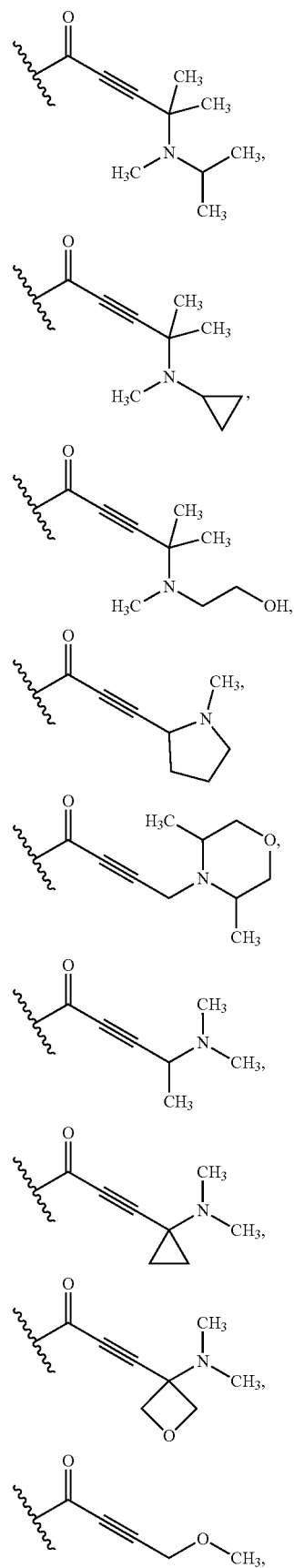

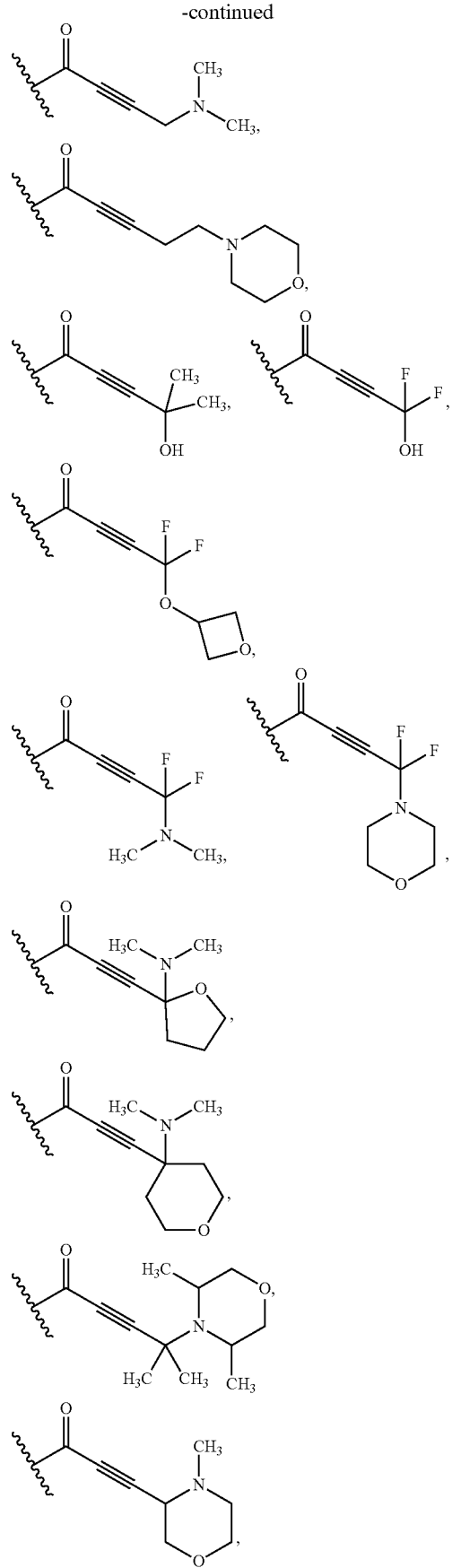
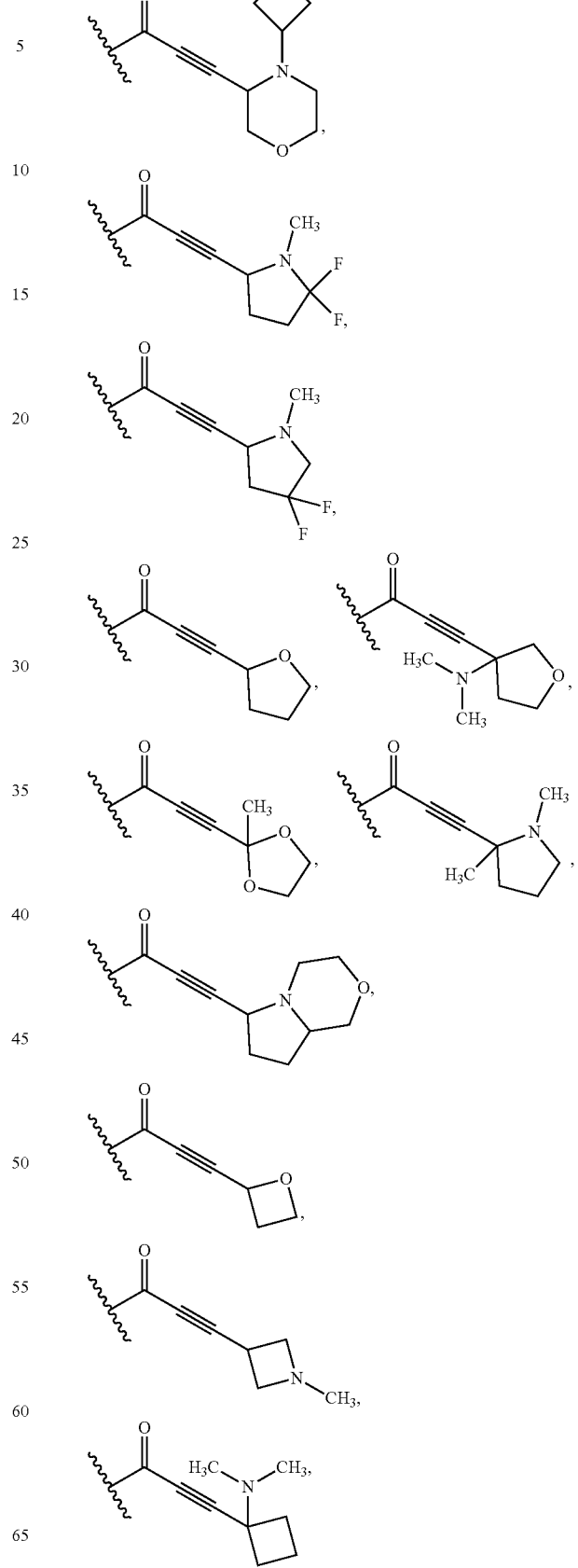

-continued

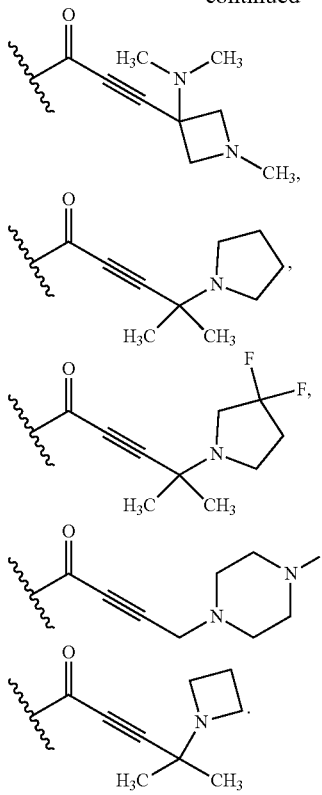

[81] The compound, or a pharmaceutically acceptable salt thereof, of any one of paragraphs [1] to [74], wherein W is a cross-linking group comprising a vinyl sulfone.

[82] The compound, or a pharmaceutically acceptable salt thereof, of paragraph [81], wherein W has the structure of Formula IIIc:

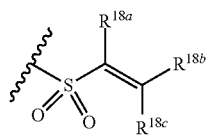

Formula IIIc wherein $R^{18a}$, $R^{18b}$, and $R^{18c}$ are, independently, hydrogen, —CN, or —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated heterocycloalkyl.

[83] The compound, or a pharmaceutically acceptable salt thereof, of paragraph [82], wherein W is:

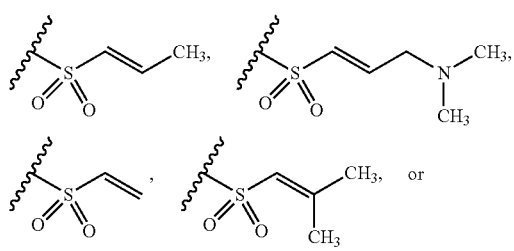

-continued

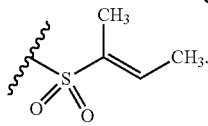

[84] The compound, or a pharmaceutically acceptable salt thereof, of any one of paragraphs [1] to [74], wherein W is a cross-linking group comprising an alkynyl sulfone.

[85] The compound, or a pharmaceutically acceptable salt thereof, of paragraph [84], wherein W has the structure of Formula IIId:

Formula IIId

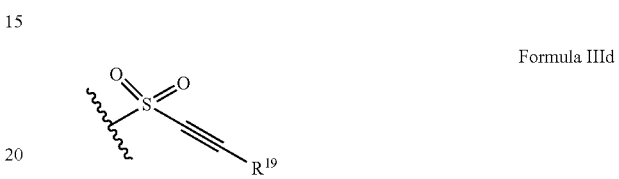

wherein $R^{19}$ is hydrogen, —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated heterocycloalkyl, or a 4 to 7-membered saturated heterocycloalkyl.

[86] The compound, or a pharmaceutically acceptable salt thereof, of paragraph [85], wherein W is:

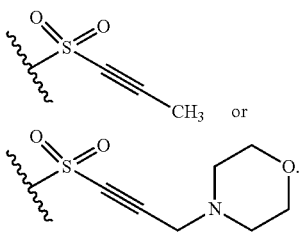

[87] The compound, or a pharmaceutically acceptable salt thereof, of any one of paragraphs [1] to [74], wherein W has the structure of Formula IIIe:

Formula IIIe

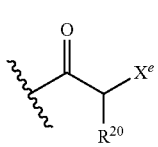

wherein $X^e$ is a halogen; and
$R^{20}$ is hydrogen, —$C_1$-$C_3$ alkyl optionally substituted with one or more substituents independently selected from —OH, —O—$C_1$-$C_3$ alkyl, —$NH_2$, —NH($C_1$-$C_3$ alkyl), —N($C_1$-$C_3$ alkyl)$_2$, or a 4 to 7-membered saturated heterocycloalkyl.

[88] A compound, or a pharmaceutically acceptable salt thereof, selected from Table 1 or Table 2.

[89] A pharmaceutical composition comprising a compound, or a pharmaceutically acceptable salt thereof, of any one of paragraphs [1] to [88], and a pharmaceutically acceptable excipient.

[90] A conjugate, or salt thereof, comprising the structure of Formula IV:

M-L-P  Formula IV wherein L is a linker;
P is a monovalent organic moiety; and
M has the structure of Formula V:

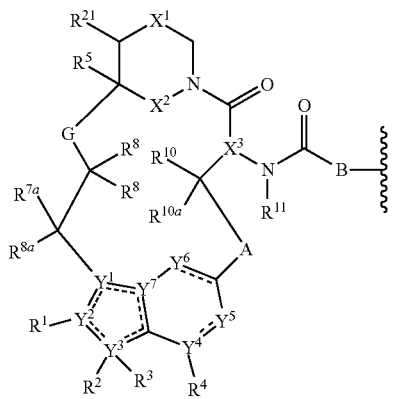

Formula V wherein the dotted lines represent zero, one, two, three, or four non-adjacent double bonds;
A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;
B is absent, —CH($R^9$)—, >C=$CR^9R^{9'}$, or >$CR^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;
G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;
$X^1$ is optionally substituted $C_1$-$C_2$ alkylene, NR, O, or S(O)$_n$;
$X^2$ is O or NH;
$X^3$ is N or CH;
n is 0, 1, or 2;
R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;
each R' is, independently, H or optionally substituted $C_1$-$C_4$ alkyl;
$Y^1$ is C, CH, or N;
$Y^2$, $Y^3$, $Y^4$, and $Y^7$ are, independently, C or N;
$Y^5$ is CH, $CH_2$, or N;
$Y^6$ is C(O), CH, $CH_2$, or N;
$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or
$R^1$ and $R^2$ combine with the atoms to which they are attached to form an optionally substituted 3 to 14-membered heterocycloalkyl;
$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or
$R^2$ and $R^3$ combine with the atom to which they are attached to form an optionally substituted 3 to 8-membered cycloalkyl or optionally substituted 3 to 14-membered heterocycloalkyl;
$R^4$ is absent, hydrogen, halogen, cyano, or methyl optionally substituted with 1 to 3 halogens;
$R^5$ is hydrogen, $C_1$-$C_4$ alkyl optionally substituted with halogen, cyano, hydroxy, or $C_1$-$C_4$ alkoxy, cyclopropyl, or cyclobutyl;
$R^6$ is hydrogen or methyl; $R^7$ is hydrogen, halogen, or optionally substituted $C_1$-$C_3$ alkyl, or
$R^6$ and $R^7$ combine with the carbon atoms to which they are attached to form an optionally substituted 3 to 6-membered cycloalkyl or optionally substituted 3 to 7-membered heterocycloalkyl;
$R^8$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or
$R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;
$R^{7a}$ and $R^{8a}$ are, independently, hydrogen, halo, optionally substituted $C_1$-$C_3$ alkyl, or combine with the carbon to which they are attached to form a carbonyl;
$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxy, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or
$R^{7'}$ and $R^{8'}$ combine with the carbon atom to which they are attached to form optionally substituted 3 to 6-membered cycloalkyl or optionally substituted 3 to 7-membered heterocycloalkyl;
$R^9$ is H, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or
$R^9$ and L combine with the atoms to which they are attached to form an optionally substituted 3 to 14-membered heterocycloalkyl;
$R^{9'}$ is hydrogen or optionally substituted $C_1$-$C_6$ alkyl; or $R^9$ and $R^{9'}$, combined with the atoms to which they are attached, form a 3 to 6-membered cycloalkyl or a 3 to 6-membered heterocycloalkyl;

$R^{10}$ is hydrogen, halo, hydroxy, $C_1$-$C_3$ alkoxy, or $C_1$-$C_3$ alkyl; $R^{10a}$ is hydrogen or halo;

$R^{11}$ is hydrogen or $C_1$-$C_3$ alkyl; and $R^{21}$ is H or $C_1$-$C_3$ alkyl.

[91] The conjugate of paragraph [90], or salt thereof, wherein M has the structure of Formula Vd:

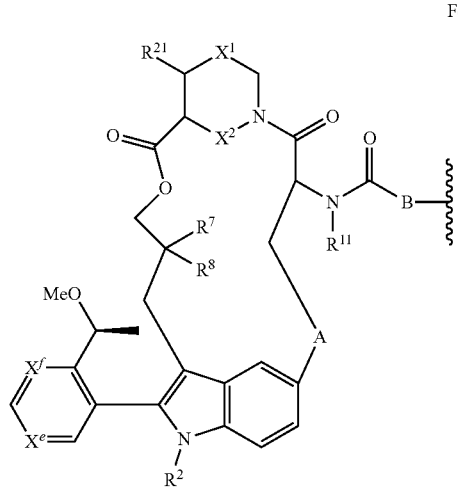

Formula Vd wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene; $X^1$ is optionally substituted $C_1$-$C_2$ alkylene, NR, O, or S(O)$_n$;

$X^2$ is O or NH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$R^2$ is $C_1$-$C_6$ alkyl, $C_1$-$C_6$ fluoroalkyl, or 3 to 6-membered cycloalkyl;

$R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$X^e$ and $X^f$ are, independently, N or CH;

$R^{11}$ is hydrogen or $C_1$-$C_3$ alkyl; and $R^{21}$ is hydrogen or $C_1$-$C_3$ alkyl.

[92] The conjugate of paragraph [91], or salt thereof, wherein M has the structure of Formula Ve:

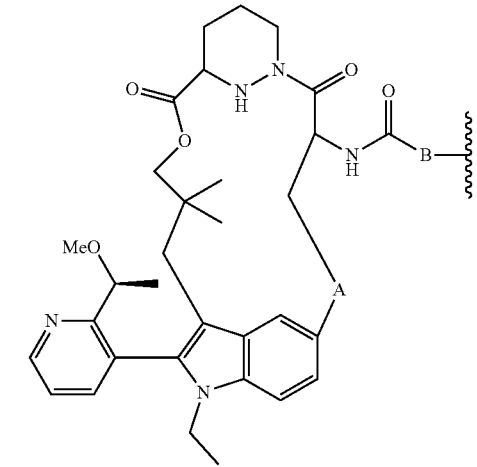

Formula Ve wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

[93] The conjugate, or salt thereof, of any one of paragraphs [90] to [92], wherein the linker has the structure of Formula II:

$$A^1\text{-}(B^1)_f\text{—}(C^1)_g\text{—}(B^2)_h\text{-}(D^1)\text{-}(B^3)_i\text{—}(C^2)_j\text{—}(B^4)_k\text{-}A^2 \quad \text{Formula II}$$

where $A^1$ is a bond between the linker and B; $A^2$ is a bond between W and the linker; $B^1$, $B^2$, $B^3$, and $B^4$ each, independently, is selected from optionally substituted $C_1$-$C_2$ alkylene, optionally substituted $C_1$-$C_3$ heteroalkylene, O, S, and NR$^N$; R$^N$ is hydrogen, optionally substituted $C_1$-$C_4$ alkyl, optionally substituted $C_2$-$C_4$ alkenyl, optionally substituted $C_2$-$C_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$—$(C^1)_g$—$(B^2)_h$- to —$(B^3)_i$—$(C^2)_j$—$(B^4)_k$-$A^2$.

[94] The conjugate, or salt thereof, of any one of paragraphs [90] to [93], wherein the monovalent organic moiety is a protein.

[95] The conjugate, or salt thereof, of paragraph [94], wherein the protein is a Ras protein.

[96] The conjugate, or salt thereof, of paragraph [95], wherein the Ras protein is K-Ras G12C, K-Ras G13C, H-Ras G12C, H-Ras G13C, N-Ras G12C, or N-Ras G13C.

[97] The conjugate, or salt thereof, of any one of paragraphs [93] to [96], wherein the linker is bound to the monovalent organic moiety through a bond to a sulfhydryl group of an amino acid residue of the monovalent organic moiety.

[98] A method of treating cancer in a subject in need thereof, the method comprising administering to the subject a therapeutically effective amount of a compound, or a pharmaceutically acceptable salt thereof, of any one of paragraphs [1] to [88] or a pharmaceutical composition of paragraph [89].

[99] The method of paragraph [98], wherein the cancer is pancreatic cancer, colorectal cancer, non-small cell lung cancer, or endometrial cancer.

[100] The method of paragraph [98] or [99], wherein the cancer comprises a Ras mutation.

[101] The method of paragraph [100], wherein the Ras mutation is K-Ras G12C, K-Ras G13C, H-Ras G12C, H-Ras G13C, N-Ras G12C, or N-Ras G13C.

[102] A method of treating a Ras protein-related disorder in a subject in need thereof, the method comprising administering to the subject a therapeutically effective amount of a compound, or a pharmaceutically acceptable salt thereof, of any one of paragraphs [1] to [88] or a pharmaceutical composition of paragraph [89].

[103] A method of inhibiting a Ras protein in a cell, the method comprising contacting the cell with an effective amount of a compound, or a pharmaceutically acceptable salt thereof, of any one of paragraphs [1] to [88] or a pharmaceutical composition of paragraph [89].

[104] The method of paragraph [102] or [103], wherein the Ras protein is K-Ras G12C, K-Ras G13C, H-Ras G12C, H-Ras G13C, N-Ras G12C, or N-Ras G13C.

[105] The method of paragraph [103] or [104], wherein the cell is a cancer cell.

[106] The method of paragraph [105], wherein the cancer cell is a pancreatic cancer cell, a colorectal cancer cell, a non-small cell lung cancer cell, or an endometrial cancer cell.

[107] The method or use of any one of paragraphs [98] to [106], wherein the method or use further comprises administering an additional anti-cancer therapy.

[108] The method of paragraph [107], wherein the additional anti-cancer therapy is an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, a HER2 inhibitor, or a combination thereof.

[109] The method of paragraph [107] or [108], wherein the additional anti-cancer therapy is a SHP2 inhibitor.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure or scope of the appended claims.

Chemical Syntheses

Definitions used in the following examples and elsewhere herein are:

| | |
|---|---|
| $CH_2Cl_2$, DCM | Methylene chloride, Dichloromethane |
| $CH_3CN$, MeCN | Acetonitrile |
| CuI | Copper (I) iodide |
| DIPEA | Diisopropylethyl amine |
| DMF | N,N-Dimethylformamide |
| EtOAc | Ethyl acetate |
| h | hour |
| $H_2O$ | Water |
| HCl | Hydrochloric acid |
| $K_3PO_4$ | Potassium phosphate (tribasic) |
| MeOH | Methanol |
| $Na_2SO_4$ | Sodium sulfate |
| NMP | N-methyl pyrrolidone |
| $Pd(dppf)Cl_2$ | [1,1'-Bis(diphenylphosphino)ferrocene]dichloropalladium(II) |

Instrumentation

Mass spectrometry data collection took place with a Shimadzu LCMS-2020, an Agilent 1260LC-6120/6125MSD, a Shimadzu LCMS-2010EV, or a Waters Acquity UPLC, with either a QDa detector or SQ Detector 2. Samples were injected in their liquid phase onto a C-18 reverse phase. The compounds were eluted from the column using an acetonitrile gradient and fed into the mass analyzer. Initial data analysis took place with either Agilent ChemStation, Shimadzu LabSolutions, or Waters MassLynx. NMR data was collected with either a Bruker AVANCE III HD 400 MHz, a Bruker Ascend 500 MHz instrument, or a Varian 400 MHz, and the raw data was analyzed with either TopSpin or Mestrelab Mnova.

Synthesis of Intermediates

Intermediate 1. Synthesis of 3-(5-bromo-1-ethyl-2-[2-[(1S)-1-methoxyethyl]pyridin-3-yl]indol-3-yl)-2,2-dimethylpropan-1-ol

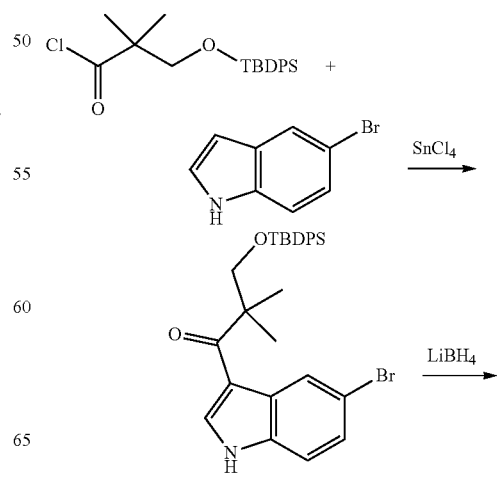

893
-continued

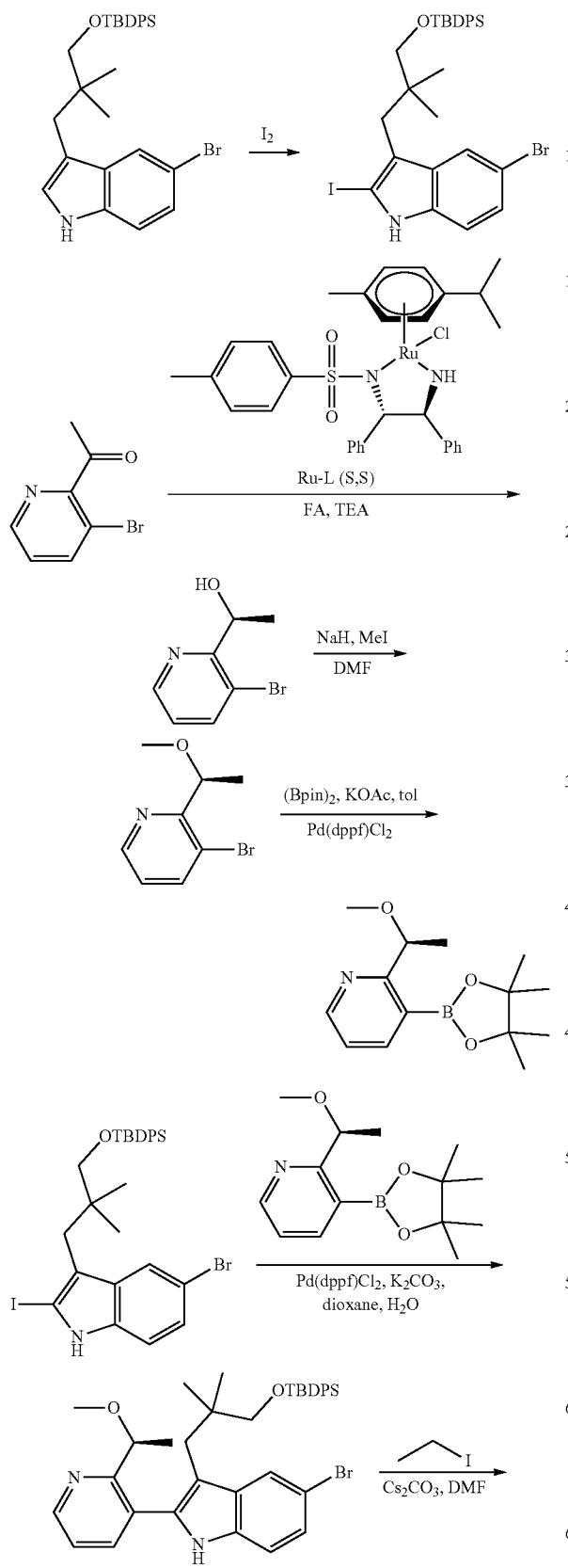

894
-continued

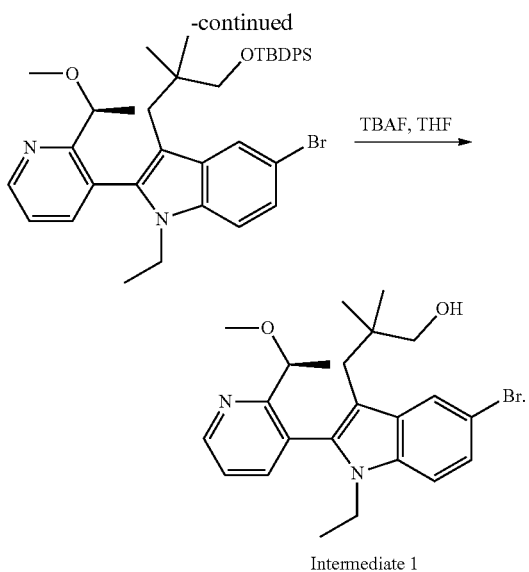

Step 1. To a mixture of 3-((tert-butyldiphenylsilyl)oxy)-2,2-dimethylpropanoyl chloride (65 g, 137 mmol, crude) in DCM (120 mL) at 0° C. under an atmosphere of N₂ was added 1M SnCl₄ in DCM (137 mL, 137 mmol) slowly. The mixture was stirred at 0° C. for 30 min, then a solution of 5-bromo-1H-indole (26.8 g, 137 mmol) in DCM (40 mL) was added dropwise. The mixture was stirred at 0° C. for 45 min, then diluted with EtOAc (300 mL), washed with brine (100 mL×4), dried over Na₂SO₄, and filtered. The filtrate was concentrated under reduced pressure and the residue was purified by silica gel column chromatography to give 1-(5-bromo-1H-indol-3-yl)-3-((tert-butyldiphenylsilyl)oxy)-2,2-dimethylpropan-1-one (55 g, 75% yield). LCMS (ESI): m/z [M+Na] calc'd for $C_{29}H_{32}BrNO_2SiNa$ 556.1; found 556.3.

Step 2. To a mixture of 1-(5-bromo-1H-indol-3-yl)-3-((tert-butyldiphenylsilyl)oxy)-2,2-dimethylpropan-1-one (50 g, 93.6 mmol) in THF (100 mL) at 0° C. under an atmosphere of N₂ was added LiBH₄ (6.1 g, 281 mmol). The mixture was heated to 60° C. and stirred for 20 h, then MeOH (10 mL) and EtOAc (100 mL) were added and the mixture washed with brine (50 mL), dried over Na₂SO₄, filtered, and the filtrate concentrated under reduced pressure. The residue was diluted with DCM (50 mL), cooled to 10° C. and diludine (9.5 g, 37.4 mmol) and TsOH·H₂O (890 mg, 4.7 mmol) added. The mixture was stirred at 10° C. for 2 h, filtered, the filtrate concentrated under reduced pressure and the residue was purified by silica gel column chromatography to give 1-(5-bromo-1H-indol-3-yl)-3-((tert-butyldiphenylsilyl)oxy)-2,2-dimethylpropan-1-one (41 g, 84% yield). LCMS (ESI): m/z [M+H] calc'd for $C_{29}H_{34}BrNOSi$ 519.2; found 520.1; ¹H NMR (400 MHz, CDCl₃) δ 7.96 (s, 1H), 7.75-7.68 (m, 5H), 7.46-7.35 (m, 6H), 7.23-7.19 (m, 2H), 6.87 (d, J=2.1 Hz, 1H), 3.40 (s, 2H), 2.72 (s, 2H), 1.14 (s, 9H), 0.89 (s, 6H).

Step 3. To a mixture of 1-(5-bromo-1H-indol-3-yl)-3-((tert-butyldiphenylsilyl)oxy)-2,2-dimethylpropan-1-one (1.5 g, 2.9 mmol) and I₂ (731 mg, 2.9 mmol) in THF (15 mL) at rt was added AgOTf (888 mg, 3.5 mmol). The mixture was stirred at rt for 2 h, then diluted with EtOAc (200 mL) and washed with saturated Na₂S₂O₃ (100 mL), dried over anhydrous Na₂SO₄, and filtered. The filtrate was concentrated under reduced pressure and the residue was purified by silica gel column chromatography to give 5-bromo-3-(3-((tert-butyldiphenylsilyl)oxy)-2,2-dimethylpropyl)-2-iodo-1H-indole (900 mg, 72% yield) as a solid. $^1$H NMR (400 MHz, DMSO-d$_6$) δ 11.70 (s, 1H), 7.68 (d, J=1.3 Hz, 1H), 7.64-7.62 (m, 4H), 7.46-7.43 (m, 6H), 7.24-7.22 (d, 1H), 7.14-7.12 (dd, J=8.6, 1.6 Hz, 1H), 3.48 (s, 2H), 2.63 (s, 2H), 1.08 (s, 9H), 0.88 (s, 6H).

Step 4. To a stirred mixture of HCOOH (66.3 g, 1.44 mol) in TEA (728 g, 7.2 mol) at 0° C. under an atmosphere of Ar was added (4S,5S)-2-chloro-2-methyl-1-(4-methylbenzenesulfonyl)-4,5-diphenyl-1,3-diaza-2-ruthenacyclopentane cymene (3.9 g, 6.0 mmol) portion-wise. The mixture was heated to 40° C. and stirred for 15 min, then cooled to rt and 1-(3-bromopyridin-2-yl)ethanone (120 g, 600 mmol) added in portions. The mixture was heated to 40° C. and stirred for an additional 2 h, then the solvent was concentrated under reduced pressure. Brine (2 L) was added to the residue, the mixture was extracted with EtOAc (4×700 mL), dried over anhydrous Na$_2$SO$_4$, and filtered. The filtrate was concentrated under reduced pressure and the residue was purified by silica gel column chromatography to give (1 S)-1-(3-bromopyridin-2-yl)ethanol (100 g, 74% yield) a an oil. LCMS (ESI): m/z [M+H] calc'd for C$_7$H$_8$BrNO 201.1; found 201.9.

Step 5. To a stirred mixture of (1 S)-1-(3-bromopyridin-2-yl)ethanol (100 g, 495 mmol) in DMF (1 L) at 0° C. was added NaH, 60% dispersion in oil (14.25 g, 594 mmol) in portions. The mixture was stirred at 0° C. for 1 h. MeI (140.5 g, 990 mmol) was added dropwise at 0° C. and the mixture was allowed to warm to rt and stirred for 2 h. The mixture was cooled to 0° C. and saturated NH$_4$Cl (5 L) was added. The mixture was extracted with EtOAc (3×1.5 L), dried over anhydrous Na$_2$SO$_4$ and filtered. The filtrate was concentrated under reduced pressure and the residue was purified by silica gel column chromatography to give 3-bromo-2-[(1S)-1-methoxyethyl]pyridine (90 g, 75% yield) as an oil. LCMS (ESI): m/z [M+H] calc'd for CH$_{10}$BrNO 215.0; found 215.9.

Step 6. To a stirred mixture of 3-bromo-2-[(1S)-1-methoxyethyl]pyridine (90 g, 417 mmol) and Pd(dppf)Cl$_2$ (30.5 g, 41.7 mmol) in toluene (900 mL) at rt under an atmosphere of Ar was added bis(pinacolato)diboron (127 g, 500 mmol) and KOAc (81.8 g, 833 mmol) in portions. The mixture was heated to 100° C. and stirred for 3 h. The filtrate was concentrated under reduced pressure and the residue was purified by Al$_2$O$_3$ column chromatography to give 2-[(1 S)-1-methoxyethyl]-3-(4,4,5,5-tetramethyl-1,3,2-dioxaborolan-2-yl)pyridine (100 g, 63% yield) as a semi-solid. LCMS (ESI): m/z [M+H] calc'd for C$_{14}$H$_{22}$BNO$_3$ 263.2; found 264.1.

Step 7. To a stirred mixture of 5-bromo-3-[3-[(tert-butyldiphenylsilyl)oxy]-2,2-dimethylpropyl]-2-iodo-1H-indole (140 g, 217 mmol) and 2-[(1 S)-1-methoxyethyl]-3-(4,4,5-5-tetramethyl-1,3,2-dioxaborolan-2-yl)pyridine (100 g, 380 mmol) in 1,4-dioxane (1.4 L) at rt under an atmosphere of Ar was added K$_2$CO$_3$ (74.8 g, 541 mmol), Pd(dppf)Cl$_2$ (15.9 g, 21.7 mmol), and H$_2$O (280 mL) in portions. The mixture was heated to 85° C. and stirred for 4 h, then cooled, H$_2$O (5 L) added, and the mixture extracted with EtOAc (3×2 L). The combined organic layers were washed with brine (2×1 L), dried over anhydrous Na$_2$SO$_4$, and filtered. The filtrate was concentrated under reduced pressure and the residue was purified by silica gel column chromatography to give 5-bromo-3-[3-[(tert-butyldiphenylsilyl)oxy]-2,2-dimethylpropyl]-2-[2-[(1 S)-1-methoxyethyl]pyridin-3-yl]-1H-indole (71 g, 45% yield) as a solid. LCMS (ESI): m/z [M+H] calc'd for C$_{37}$H$_{43}$BrN$_2$O$_2$Si 654.2; found 655.1.

Step 8. To a stirred mixture of 5-bromo-3-[3-[(tert-butyldiphenylsilyl)oxy]-2,2-dimethylpropyl]-2-[2-[(1S)-1-methoxyethyl]pyridin-3-yl]-1H-indole (71 g, 108 mmol) in DMF (0.8 L) at 0° C. under an atmosphere of N$_2$ was added Cs$_2$CO$_3$ (70.6 g, 217 mmol) and EtI (33.8 g, 217 mmol) in portions. The mixture was warmed to rt and stirred for 16 h then H$_2$O (4 L) added and the mixture extracted with EtOAc (3×1.5 L). The combined organic layers were washed with brine (2×1 L), dried over anhydrous Na$_2$SO$_4$, and filtered. The filtrate was concentrated under reduced pressure and the residue was purified by silica gel column chromatography to give 5-bromo-3-[3-[(tert-butyldiphenylsilyl)oxy]-2,2-dimethylpropyl]-1-ethyl-2-[2-[(1S)-1-methoxyethyl]pyridin-3-yl]indole (66 g, 80% yield) as an oil. LCMS (ESI): m/z [M+H] calc'd for C$_{39}$H$_{47}$BrN$_2$O$_2$Si 682.3; found 683.3.

Step 9. To a stirred mixture of TBAF (172.6 g, 660 mmol) in THF (660 mL) at rt under an atmosphere of N$_2$ was added 5-bromo-3-[3-[(tert-butyldiphenylsilyl)oxy]-2,2-dimethylpropyl]-1-ethyl-2-[2-[(1 S)-1-methoxyethyl]pyridin-3-yl]indole (66 g, 97 mmol) in portions. The mixture was heated to 50° C. for 16 h, cooled, diluted with H$_2$O (5 L), and extracted with EtOAc (3×1.5 L). The combined organic layers were washed with brine (2×1 L), dried over anhydrous Na$_2$SO$_4$, and filtered. After filtration, the filtrate was concentrated under reduced pressure. The filtrate was concentrated under reduced pressure and the residue was purified by silica gel column chromatography to give 3-(5-bromo-1-ethyl-2-[2-[(1     S)-1-methoxyethyl]pyridin-3-yl]indol-3-yl)-2,2-dimethylpropan-1-ol (30 g, 62% yield) as a solid. LCMS (ESI): m/z [M+H] calc'd for C$_{23}$H$_{29}$BrN$_2$O$_2$ 444.1; found 445.1.

Intermediate 1. Alternative Synthesis Through Fisher Indole Route

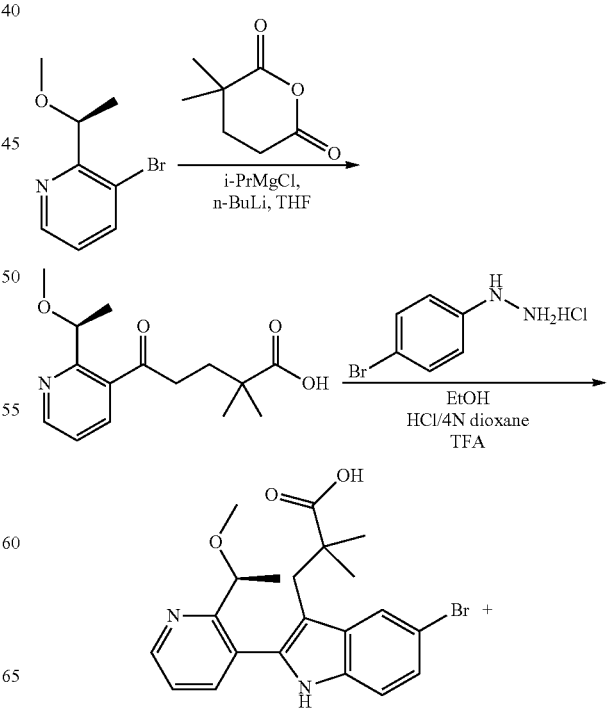

-continued

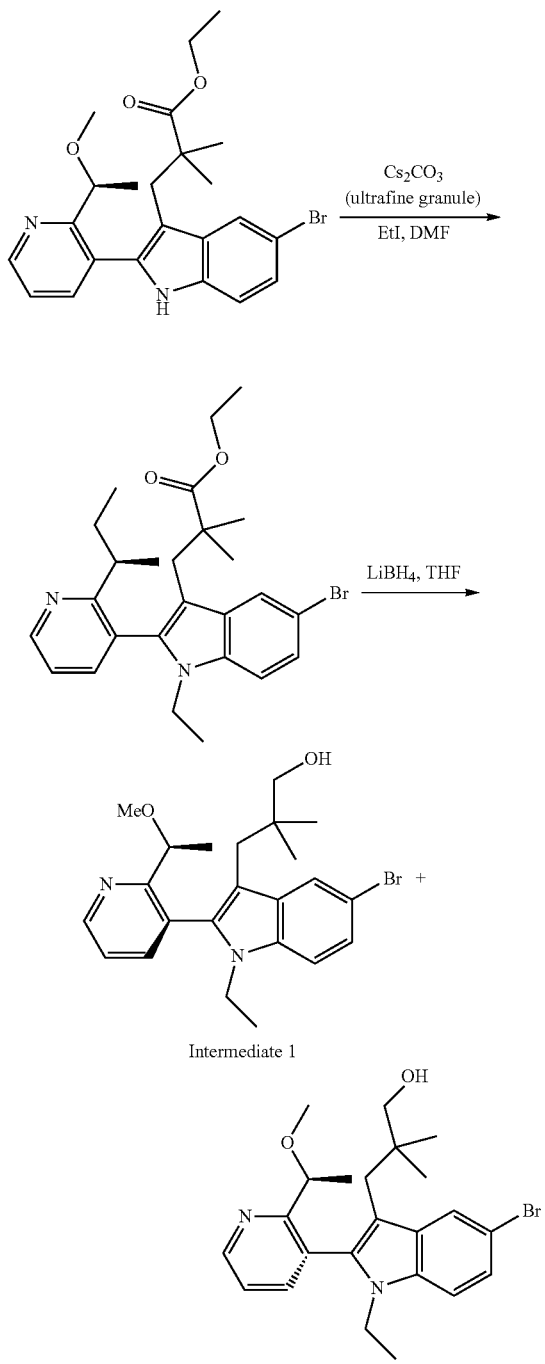

Intermediate 1

Step 1. To a mixture of i-PrMgCl (2M in in THF, 0.5 L) at −10° C. under an atmosphere of N₂ was added n-BuLi, 2.5 M in hexane (333 mL, 833 mmol) dropwise over 15 min. The mixture was stirred for 30 min at −10° C. then 3-bromo-2-[(1S)-1-methoxyethyl]pyridine (180 g, 833 mmol) in THF (0.5 L) added dropwise over 30 min at −10° C. The resulting mixture was warmed to −5° C. and stirred for 1 h, then 3,3-dimethyloxane-2,6-dione (118 g, 833 mmol) in THF (1.2 L) was added dropwise over 30 min at −5° C. The mixture was warmed to 0° C. and stirred for 1.5 h, then quenched with the addition of pre-cooled 4M HCl in 1,4-dioxane (0.6 L) at 0° C. to adjust pH ∼5. The mixture was diluted with ice-water (3 L) and extracted with EtOAc (3×2.5 L). The combined organic layers were dried over anhydrous Na₂SO₄, filtered, the filtrate was concentrated under reduced pressure, and the residue was purified by silica gel column chromatography to give 5-[2-[(1 S)-1-methoxyethyl]pyridin-3-yl]-2,2-dimethyl-5-oxopentanoic acid (87 g, 34% yield) as a solid. LCMS (ESI): m/z [M+H] calc'd for $C_{15}H_{21}NO_4$ 279.2; found 280.1.

Step 2. To a mixture of 5-[2-[(1 S)-1-methoxyethyl]pyridin-3-yl]-2,2-dimethyl-5-oxopentanoic acid (78 g, 279 mmol) in EtOH (0.78 L) at rt under an atmosphere of N₂ was added (4-bromophenyl)hydrazine HCl salt (68.7 g, 307 mmol) in portions. The mixture was heated to 85° C. and stirred for 2 h, cooled to rt, then 4M HCl in 1,4-dioxane (69.8 mL, 279 mmol) added dropwise. The mixture was heated to 85° C. and stirred for an additional 3 h, then concentrated under reduced pressure, and the residue was dissolved in TFA (0.78 L). The mixture was heated to 60° C. and stirred for 1.5 h, concentrated under reduced pressure, and the residue adjusted to pH ∼5 with saturated NaHCO₃, then extracted with EtOAc (3×1.5 L). The combined organic layers were dried over anhydrous Na₂SO₄, filtered, the filtrate concentrated under reduced pressure, and the residue was purified by silica gel column chromatography to give 3-(5-bromo-2-[2-[(1 S)-1-methoxyethyl]pyridin-3-yl]-1H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (78 g, crude). LCMS (ESI): m/z [M+H] calc'd for $C_{21}H_{23}BrN_2O_3$ 430.1 and $C_{23}H_{27}BrN_2O_3$ 458.1; found 431.1 and 459.1.

Step 3. To a mixture of 3-(5-bromo-2-[2-[(1 S)-1-methoxyethyl]pyridin-3-yl]-1H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (198 g, 459 mmol) in DMF (1.8 L) at 0° C. under an atmosphere of N₂ was added Cs₂CO₃ (449 g, 1.38 mol) in portions. EtI (215 g, 1.38 mmol) in DMF (200 mL) was then added dropwise at 0° C. The mixture was warmed to rt and stirred for 4 h then diluted with brine (5 L) and extracted with EtOAc (3×2.5 L). The combined organic layers were washed with brine (2×1.5 L), dried over anhydrous Na₂SO₄, and filtered. The filtrate was concentrated under reduced pressure and the residue was purified by silica gel column chromatography to give ethyl 3-(5-bromo-1-ethyl-2-[2-[(1 S)-1-methoxyethyl]pyridin-3-yl]indol-3-yl)-2,2-dimethylpropanoate (160 g, 57% yield) as a solid. LCMS (ESI): m/z [M+H] calc'd for $C_{25}H_{31}BrN_2O_3$ 486.2; found 487.2.

Step 4. To a mixture of ethyl 3-(5-bromo-1-ethyl-2-[2-[(1 S)-1-methoxyethyl]pyridin-3-yl]indol-3-yl)-2,2-dimethylpropanoate (160 g, 328 mmol) in THF (1.6 L) at 0° C. under an atmosphere of N₂ was added LiBH₄ (28.6 g, 1.3 mol). The mixture was heated to 60° C. for 16 h, cooled, and quenched with pre-cooled (0° C.) aqueous NH₄Cl (5 L). The mixture was extracted with EtOAc (3×2 L) and the combined organic layers were washed with brine (2×1 L), dried over anhydrous Na₂SO₄, and filtered. The filtrate was concentrated under reduced pressure and the residue was purified by silica gel column chromatography to give to two atropisomers (as single atropisomers) of 3-(5-bromo-1-ethyl-2-(2-((S)-1-methoxyethyl)pyridin-3-yl)-1H-indol-3-yl)-2,2-dimethyl-propan-1-ol (60 g, 38% yield) and (40 g, 26% yield) both as solids. LCMS (ESI): m/z [M+H] calc'd for $C_{23}H_{29}BrN_2O_2$ 444.1; found 445.2.

Intermediate 2 and Intermediate 4. Synthesis of (S)-1-((S)-2-((tert-butoxycarbonyl)amino)-3-(3-(4,4,5,5-tetramethyl-1,3,2-dioxaborolan-2-yl)-5-((triisopropylsilyl)oxy)phenyl)propanoyl)hexahydropyridazine-3-carboxylate

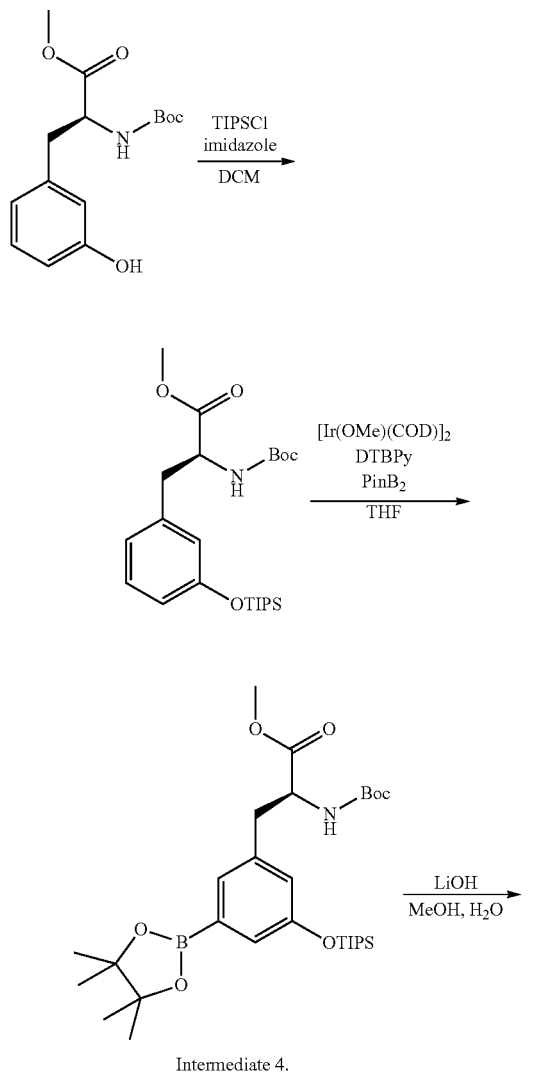

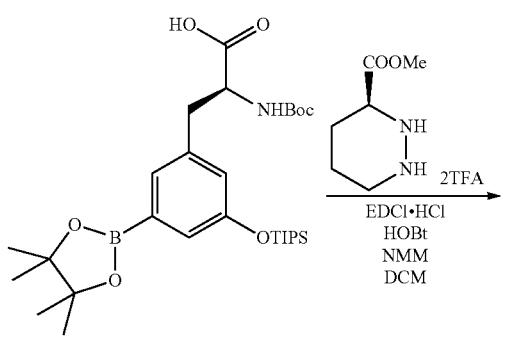

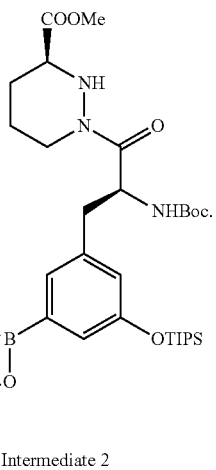

Intermediate 2

Step 1. To a mixture of (S)-methyl 2-(tert-butoxycarbonylamino)-3-(3-hydroxyphenyl)propanoate (10.0 g, 33.9 mmol) in DCM (100 mL) was added imidazole (4.6 g, 67.8 mmol) and TIPSCl (7.8 g, 40.7 mmol). The mixture was stirred at rt overnight then diluted with DCM (200 mL) and washed with $H_2O$ (150 mL×3). The organic layer was dried over anhydrous $Na_2SO_4$, filtered, concentrated under reduced pressure, and the residue was purified by silica gel column chromatography to give (S)-methyl 2-(tert-butoxycarbonylamino)-3-(3-(triisopropylsilyloxy)phenyl)-propanoate (15 g, 98% yield) as an oil. LCMS (ESI): m/z [M+Na] calc'd for $C_{24}H_{41}NO_5SiNa$ 474.3; found 474.2.

Step 2. A mixture of (S)-methyl 2-(tert-butoxycarbonylamino)-3-(3-(triisopropylsilyloxy)phenyl)-propanoate (7.5 g, 16.6 mmol), $PinB_2$ (6.3 g, 24.9 mmol), [Ir(OMe)(COD)]2 (1.1 g, 1.7 mmol), and 4-tert-butyl-2-(4-tert-butyl-2-pyridyl)pyridine (1.3 g, 5.0 mmol) was purged with Ar (×3), then THF (75 mL) was added and the mixture placed under an atmosphere of Ar and sealed. The mixture was heated to 80° C. and stirred for 16 h, concentrated under reduced pressure, and the residue was purified by silica gel column chromatography to give (S)-methyl 2-(tert-butoxycarbonylamino)-3-(3-(4,4,5,5-tetramethyl-1,3,2-dioxaborolan-2-yl)-5-(triisopropylsilyloxy)phenyl)-propanoate (7.5 g, 78% yield) as a solid. LCMS (ESI): m/z [M+Na] calc'd for $C_{30}H_{52}BNO_7SiNa$ 600.4; found 600.4; $^1H$ NMR (300 MHz, $CD_3OD$) δ 7.18 (s, 1H), 7.11 (s, 1H), 6.85 (s, 1H), 4.34 (m, 1H), 3.68 (s, 3H), 3.08 (m, 1H), 2.86 (m, 1H), 1.41-1.20 (m, 26H), 1.20-1.01 (m, 22H), 0.98-0.79 (m, 4H).

Step 3. To a mixture of triisopropylsilyl (S)-2-((tert-butoxycarbonyl)amino)-3-(3-(4,4,5,5-tetramethyl-1,3,2-dioxaborolan-2-yl)-5-((triisopropylsilyl)oxy)phenyl)propanoate (4.95 g, 6.9 mmol) in MeOH (53 mL) at 0° C. was added LiOH (840 mg, 34.4 mmol) in $H_2O$ (35 mL). The mixture was stirred at 0° C. for 2 h, then acidified to pH ~5 with 1M HCl and extracted with EtOAc (250 mL×2). The combined organic layers were washed with brine (100 mL×3), dried over anhydrous $Na_2SO_4$, filtered, and the filtrate concentrated under reduced pressure to give (S)-2-((tert-butoxycarbonyl)amino)-3-(3-(4,4,5,5-tetramethyl-1,3,2-dioxaborolan-2-yl)-5-((triisopropylsilyl)oxy)phenyl)propanoic acid (3.7 g, 95% yield), which was used directly in the next step without further purification. LCMS (ESI): m/z [M+$NH_4$] calc'd for $C_{29}H_{50}BNO_7SiNH_4$ 581.4; found 581.4.

Step 4. To a mixture of methyl (S)-hexahydropyridazine-3-carboxylate (6.48 g, 45.0 mmol) in DCM (200 mL) at 0° C. was added NMM (41.0 g, 405 mmol), (S)-2-((tert-butoxycarbonyl)amino)-3-(3-(4,4,5,5-tetramethyl-1,3,2-dioxaborolan-2-yl)-5-((triisopropylsilyl)oxy)phenyl)propanoic acid (24 g, 42.6 mmol) in DCM (50 mL) then HOBt (1.21 g, 9.0 mmol) and EDCl HCl salt (12.9 g, 67.6 mmol). The mixture was warmed to rt and stirred for 16 h, then diluted with DCM (200 mL) and washed with $H_2O$ (3×150 mL). The organic layer was dried over anhydrous $Na_2SO$, filtered, the filtrate concentrated under reduced pressure, and the residue was purified by silica gel column chromatography to give methyl (S)-1-((S)-2-((tert-butoxycarbonyl)amino)-3-(3-(4,4,5,5-tetramethyl-1,3,2-dioxaborolan-2-yl)-5-((triisopropylsilyl)oxy)phenyl)propanoyl)hexahydropyridazine-3-carboxylate (22 g, 71% yield) as an oil. LCMS (ESI): m/z [M+H] calc'd for $C_{35}H_{60}BN_3O_8Si$ 689.4; found 690.5.

Intermediate 3. Synthesis of N—((S)-1-acryloylpyrrolidine-3-carbonyl)-N-methyl-L-valine

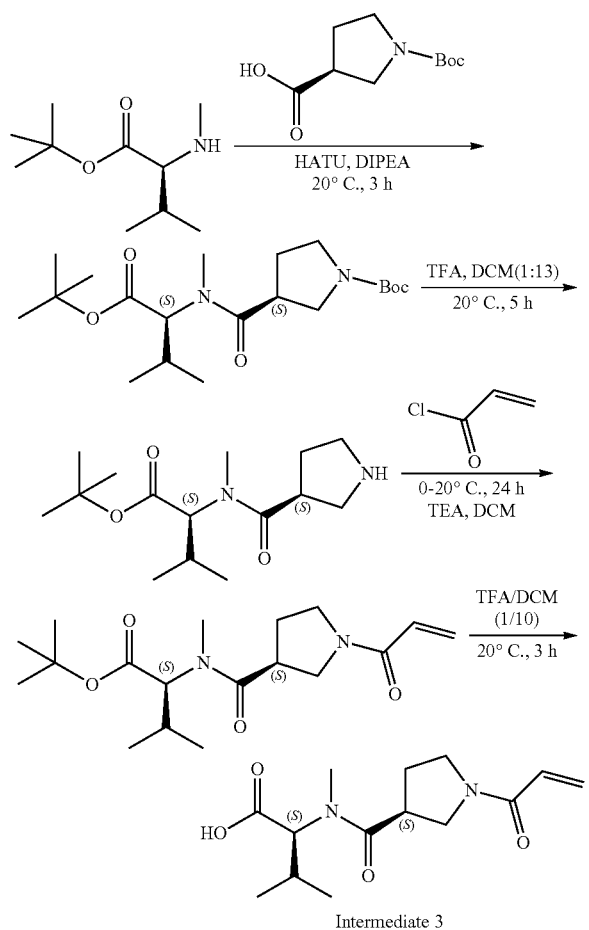

Intermediate 3

Step 1. To a mixture of (S)-1-(tert-butoxycarbonyl)pyrrolidine-3-carboxylic acid (2.2 g, 10.2 mmol) in DMF (10 mL) at rt was added HATU (7.8 g, 20.4 mmol) and DIPEA (5 mL). After stirring at rt for 10 min, tert-butyl methyl-L-valinate (3.8 g, 20.4 mmol) in DMF (10 mL) was added. The mixture was stirred at rt for 3 h, then diluted with DCM (40 mL) and $H_2O$ (30 mL). The aqueous and organic layers were separated and the organic layer was washed with $H_2O$ (3×30 mL), brine (30 mL), dried over anhydrous $Na_2SO_4$, and filtered. The filtrate was concentrated under reduced pressure and the residue was purified by silica gel column chromatography to give (S)-tert-butyl 3-(((S)-1-(tert-butoxy)-3-methyl-1-oxobutan-2-yl)(methyl)carbamoyl)pyrrolidine-1-carboxylate (3.2 g, 82% yield) as an oil. LCMS (ESI): m/z [M+Na] calc'd for $C_{20}H_{36}N_2O_5Na$ 407.3; found 407.2.

Step 2. A mixture of (S)-tert-butyl 3-(((S)-1-(tert-butoxy)-3-methyl-1-oxobutan-2-yl)(methyl)carbamoyl)pyrrolidine-1-carboxylate (3.2 g, 8.4 mmol) in DCM (13 mL) and TFA (1.05 g, 9.2 mmol) was stirred at rt for 5 h. The mixture was concentrated under reduced pressure to give (S)-tert-butyl 3-methyl-2-((S)—N-methylpyrrolidine-3-carboxamido)butanoate (2.0 g, 84% yield) as an oil. LCMS (ESI): m/z [M+H] calc'd for $C_{15}H_{28}N_2O_3$ 284.2; found 285.2.

Step 3. To a mixture of (S)-tert-butyl 3-methyl-2-((S)—N-methylpyrrolidine-3-carboxamido)butanoate (600 mg, 2.1 mmol) in DCM (6 mL) at 0° C. was added TEA (342 mg, 3.36 mmol). After stirring at 0° C. for 10 mins, acryloyl chloride (284 mg, 3.2 mmol) in DCM (10 mL) was added. The mixture was warmed to rt and stirred for 24 h, then diluted with DCM (30 mL) and $H_2O$ (30 mL). The aqueous and organic layers were separated and the organic layer was washed with $H_2O$ (3×30 mL), brine (30 mL), dried over anhydrous $Na_2SO_4$, and filtered. The filtrate was concentrated under reduced pressure and the residue was purified by silica gel column chromatography to give tert-butyl N—((S)-1-acryloylpyrrolidine-3-carbonyl)-N-methyl-L-valinate (500 mg, 70% yield) as an oil.

Step 4. To a mixture of tert-butyl N—((S)-1-acryloylpyrrolidine-3-carbonyl)-N-methyl-L-valinate (100 mg, 0.29 mmol) in DCM (3.0 mL) at 15° C. was added TFA (0.3 mL). The mixture was warmed to rt and stirred for 5 h, then the mixture was concentrated under reduced pressure to give N—((S)-1-acryloylpyrrolidine-3-carbonyl)-N-methyl-L-valine (150 mg) as a solid. The crude product was used directly in the next step without further purification. LCMS (ESI): m/z [M+H] calc'd for $C_{14}H_{22}N_2O_4$ 282.2; found 283.2.

Intermediate 5. Synthesis of tert-butyl ((63S,4S)-11-ethyl-12-(2-((S)-1-methoxyethyl)pyridin-3-yl)-10,10-dimethyl-5,7-dioxo-25-((triisopropylsilyl)oxy)-61,62,63,64,65,66-hexahydro-11H-8-oxa-1(5,3)-indola-6(1,3)-pyridazina-2(1,3)-benzenacycloundecaphane-4-yl)carbamate

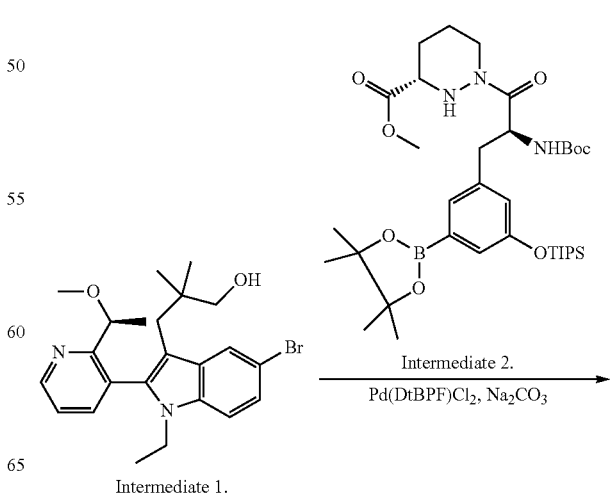

Intermediate 1.

Intermediate 2.

Pd(DtBPF)Cl$_2$, Na$_2$CO$_3$

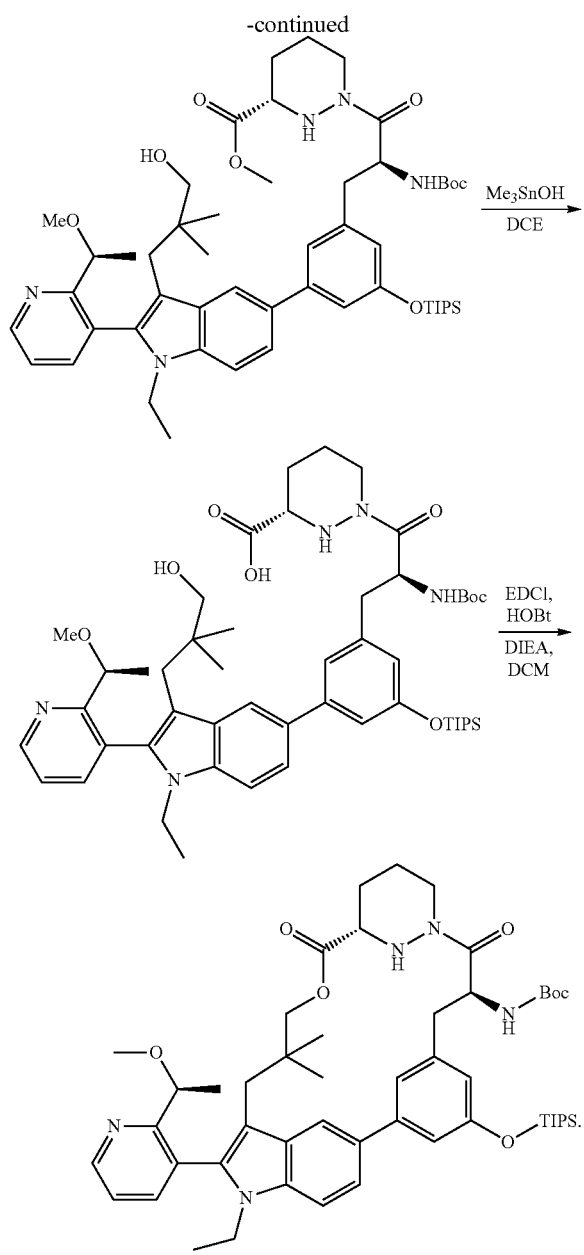

Intermediate 5

Step 1. To a stirred mixture of 3-(5-bromo-1-ethyl-2-[2-[(1 S)-1-methoxyethyl]pyridin-3-yl]indol-3-yl)-2,2-dimethylpropan-1-ol (30 g, 67 mmol) and methyl (3S)-1-[(2S)-2-[(tert-butoxycarbonyl)amino]-3-[3-(4,4,5,5-tetramethyl-1,3,2-dioxaborolan-2-yl)-5-[(triisopropylsilyl)oxy]phenyl]propanoyl]-1,2-diazinane-3-carboxylate (55.8 g, 80.8 mmol) in 1,4-dioxane (750 mL) at rt under an atmosphere of Ar was added Na$_2$CO$_3$ (17.9 g, 168.4 mmol), Pd(DtBPF)Cl$_2$ (4.39 g, 6.7 mmol), and H$_2$O (150.00 mL) in portions. The mixture was heated to 85° C. and stirred for 3 h, cooled, diluted with H$_2$O (2 L), and extracted with EtOAc (3×1 L). The combined organic layers were washed with brine (2×500 mL), dried over anhydrous Na$_2$SO$_4$, and filtered. The filtrate was concentrated under reduced pressure and the residue was purified by silica gel column chromatography to give methyl (3S)-1-[(2S)-2-[(tert-butoxycarbonyl)amino]-3-[3-[1-ethyl-3-(3-hydroxy-2,2-dimethylpropyl)-2-[2-[(1 S)-1-methoxyethyl]pyridin-3-yl]indol-5-yl]-5-[(triisopropylsilyl)oxy]phenyl]propanoyl]-1,2-diazinane-3-carboxylate (50 g, 72% yield) as a solid. LCMS (ESI): m/z [M+H] calc'd for C$_{52}$H$_{77}$N$_5$O$_8$Si 927.6; found 928.8.

Step 2. To a stirred mixture of methyl (3S)-1-[(2S)-2-[(tert-butoxycarbonyl)amino]-3-[3-[1-ethyl-3-(3-hydroxy-2,2-dimethylpropyl)-2-[2-[(1 S)-1-methoxyethyl]pyridin-3-yl]indol-5-yl]-5-[(triisopropylsilyl)oxy]phenyl]propanoyl]-1,2-diazinane-3-carboxylate (50 g, 54 mmol) in DCE (500 mL) at rt was added trimethyltin hydroxide (48.7 g, 269 mmol) in portion. The mixture was heated to 65° C. and stirred for 16 h, then filtered and the filter cake washed with DCM (3×150 mL). The filtrate was concentrated under reduced pressure to give (3S)-1-[(2S)-2-[(tert-butoxycarbonyl)amino]-3-[3-[1-ethyl-3-(3-hydroxy-2,2-dimethylpropyl)-2-[2-[(1 S)-1-methoxyethyl]pyridin-3-yl]indol-5-yl]-5-[(triisopropylsilyl)oxy]phenyl]propanoyl]-1,2-diazinane-3-carboxylic acid (70 g, crude), which was used directly in the next step without further purification. LCMS (ESI): m/z [M+H] calc'd for C$_{51}$H$_{75}$N$_5$O$_8$Si 913.5; found 914.6.

Step 3. To a stirred mixture of (3S)-1-[(2S)-2-[(tert-butoxycarbonyl)amino]-3-[3-[1-ethyl-3-(3-hydroxy-2,2-dimethylpropyl)-2-[2-[(1 S)-1-methoxyethyl]pyridin-3-yl]indol-5-yl]-5-[(triisopropylsilyl)oxy]phenyl]propanoyl]-1,2-diazinane-3-carboxylic acid (70 g) in DCM (5 L) at 0° C. under an atmosphere of N$_2$ was added DIPEA (297 g, 2.3 mol), HOBT (51.7 g, 383 mmol) and EDCl (411 g, 2.1 mol) in portions. The mixture was warmed to rt and stirred for 16 h, then diluted with DCM (1 L), washed with brine (3×1 L), dried over anhydrous Na$_2$SO$_4$, and filtered. The filtrate was concentrated under reduced pressure and the residue was purified by silica gel column chromatography to give tert-butyl ((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate (36 g, 42% yield) as a solid. LCMS (ESI): m/z [M+H] calc'd for C$_{51}$H$_{73}$N$_5$O$_7$Si 895.5; found 896.5.

Intermediate 6. Synthesis of tert-butyl N-[(8S,14S)-21-iodo-18,18-dimethyl-9,15-dioxo-4-[(triisopropylsilyl)oxy]-16-oxa-10,22,28-triazapentacyclo [18.5.2.1^[2,6]0.1^[10,14]0.0^[23,27]]nonacosa-1(26),2,4,6(29),20,23(27),24-heptaen-8-yl]carbamate

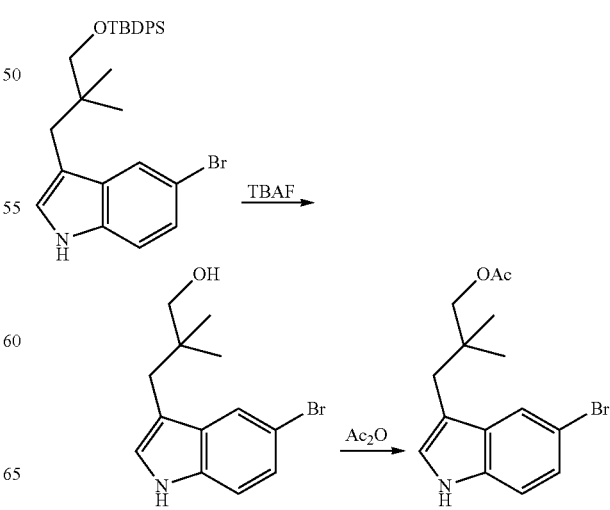

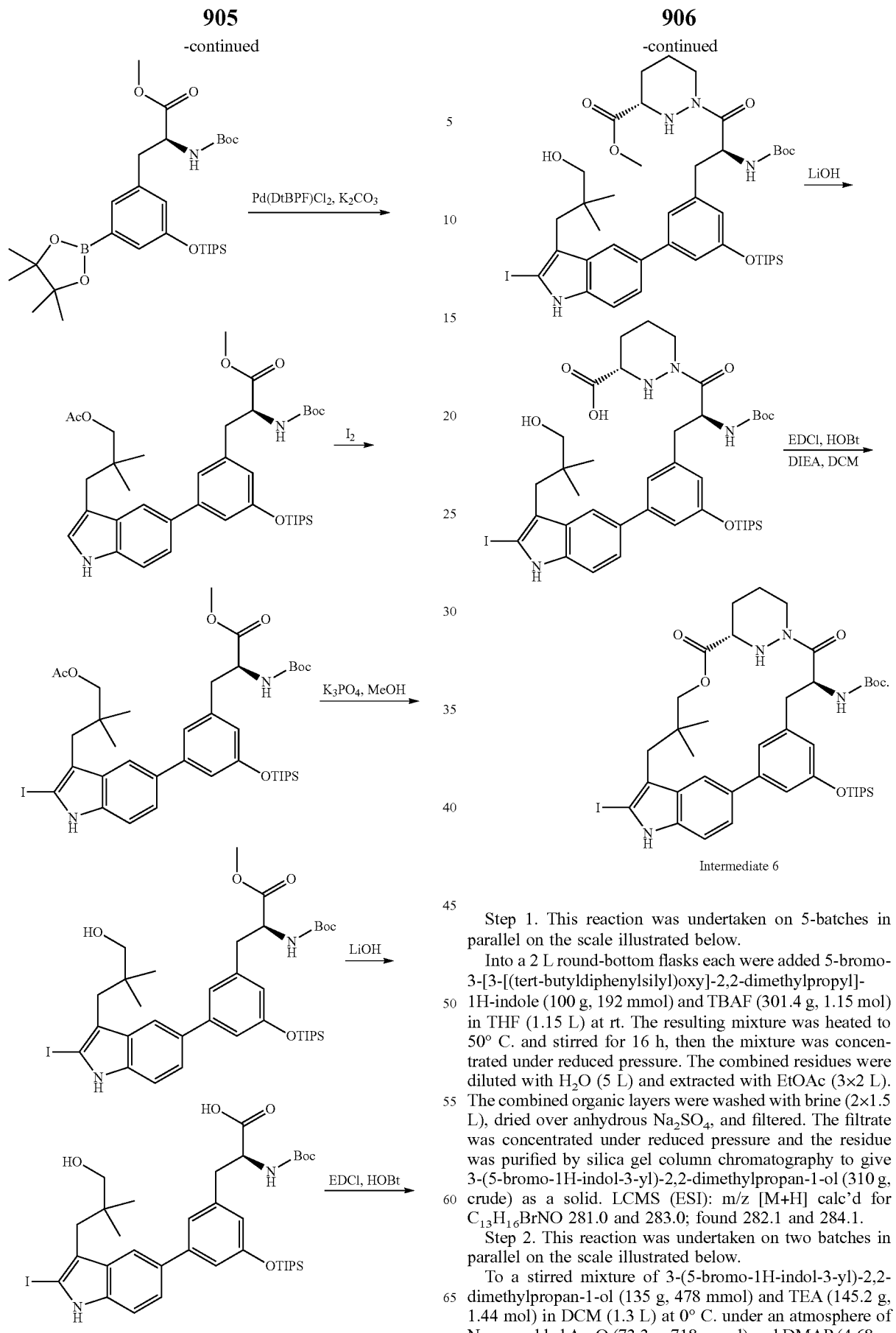

Intermediate 6

Step 1. This reaction was undertaken on 5-batches in parallel on the scale illustrated below.

Into a 2 L round-bottom flasks each were added 5-bromo-3-[3-[(tert-butyldiphenylsilyl)oxy]-2,2-dimethylpropyl]-1H-indole (100 g, 192 mmol) and TBAF (301.4 g, 1.15 mol) in THF (1.15 L) at rt. The resulting mixture was heated to 50° C. and stirred for 16 h, then the mixture was concentrated under reduced pressure. The combined residues were diluted with $H_2O$ (5 L) and extracted with EtOAc (3×2 L). The combined organic layers were washed with brine (2×1.5 L), dried over anhydrous $Na_2SO_4$, and filtered. The filtrate was concentrated under reduced pressure and the residue was purified by silica gel column chromatography to give 3-(5-bromo-1H-indol-3-yl)-2,2-dimethylpropan-1-ol (310 g, crude) as a solid. LCMS (ESI): m/z [M+H] calc'd for $C_{13}H_{16}BrNO$ 281.0 and 283.0; found 282.1 and 284.1.

Step 2. This reaction was undertaken on two batches in parallel on the scale illustrated below.

To a stirred mixture of 3-(5-bromo-1H-indol-3-yl)-2,2-dimethylpropan-1-ol (135 g, 478 mmol) and TEA (145.2 g, 1.44 mol) in DCM (1.3 L) at 0° C. under an atmosphere of $N_2$ was added $Ac_2O$ (73.3 g, 718 mmol) and DMAP (4.68 g, 38.3 mmol) in portions. The resulting mixture was stirred for 10 min at 0° C., then washed with H$_2$O (3×2 L). The organic layers from each experiment were combined and washed with brine (2×1 L), dried over anhydrous Na$_2$SO$_4$, and filtered. The filtrate was concentrated under reduced pressure and the residue was purified by column chromatography to give 3-(5-bromo-1H-indol-3-yl)-2,2-dimethylpropyl acetate (304 g, 88% yield) as a solid. $^1$H NMR (400 MHz, DMSO-d$_6$) δ 11.16-11.11 (m, 1H), 7.69 (d, J=2.0 Hz, 1H), 7.32 (d, J=8.6 Hz, 1H), 7.19-7.12 (m, 2H), 3.69 (s, 2H), 2.64 (s, 2H), 2.09 (s, 3H), 0.90 (s, 6H).

Step 3. This reaction was undertaken on four batches in parallel on the scale illustrated below.

Into a 2 L round-bottom flasks were added methyl (2S)-2-[(tert-butoxycarbonyl)amino]-3-[3-(4,4,5,5-tetramethyl-1,3,2-dioxaborolan-2-yl)-5-[(triisopropylsilyl)oxy]phenyl]propanoate (125 g, 216 mmol), 1,4-dioxane (1 L), H$_2$O (200 mL), 3-(5-bromo-1H-indol-3-yl)-2,2-dimethylpropyl acetate (73.7 g, 227 mmol), K$_2$CO$_3$ (59.8 g, 433 mmol), and Pd(DtBPF)Cl$_2$ (7.05 g, 10.8 mmol) at rt under an atmosphere of Ar. The resulting mixture was heated to 65° C. and stirred for 2 h, then diluted with H$_2$O (10 L) and extracted with EtOAc (3×3 L). The combined organic layers were washed with brine (2×2 L), dried over anhydrous Na$_2$SO$_4$, and filtered. The filtrate was concentrated under reduced pressure and the residue was purified by column chromatography to give methyl (2S)-3-(3-[3-[3-(acetyloxy)-2,2-dimethylpropyl]-1H-indol-5-yl]-5-[(triisopropylsilyl)oxy]phenyl)-2-[(tert-butoxycarbonyl)amino]propanoate (500 g, 74% yield) as an oil. LCMS (ESI): m/z [M+Na] calc'd for C$_{39}$H$_{58}$N$_2$O$_7$SiNa 717.4; found 717.3.

Step 4. This reaction was undertaken on three batches in parallel on the scale illustrated below.

To a stirred mixture of methyl (2S)-3-(3-[3-[3-(acetyloxy)-2,2-dimethylpropyl]-1H-indol-5-yl]-5-[(triisopropylsilyl)oxy]phenyl)-2-[(tert-butoxycarbonyl)amino]propanoate (150 g, 216 mmol) and NaHCO$_3$ (21.76 g, 259 mmol) in THF (1.5 L) was added AgOTf (66.5 g, 259 mmol) in THF dropwise at 0° C. under an atmosphere of nitrogen. I2 (49.3 g, 194 mmol) in THF was added dropwise over 1 h at 0° C. and the resulting mixture was stirred for an additional 10 min at 0° C. The combined experiments were diluted with aqueous Na$_2$S$_2$O$_3$ (5 L) and extracted with EtOAc (3×3 L). The combined organic layers were washed with brine (2×1.5 L), dried over anhydrous Na$_2$SO$_4$, and filtered. The filtrate was concentrated under reduced pressure and the residue was purified by column chromatography to give methyl (2S)-3-(3-[3-[3-(acetyloxy)-2,2-dimethylpropyl]-2-iodo-1H-indol-5-yl]-5-[(triisopropylsilyl)oxy]phenyl)-2-[(tert-butoxycarbonyl)amino]propanoate (420 g, 71% yield) as an oil. LCMS (ESI): m/z [M+Na] calc'd for C$_{39}$H$_{57}$IN$_2$O$_7$SiNa, 843.3; found 842.9.

Step 5. This reaction was undertaken on three batches in parallel on the scale illustrated below.

To a 2 L round-bottom flask were added methyl (2S)-3-(3-[3-[3-(acetyloxy)-2,2-dimethylpropyl]-2-iodo-1H-indol-5-yl]-5-[(triisopropylsilyl)oxy]phenyl)-2-[(tert-butoxycarbonyl)amino]propanoate (140 g, 171 mmol), MeOH (1.4 L) and K$_3$PO$_4$ (108.6 g, 512 mmol) at 0° C. The mixture was warmed to rt and stirred for 1 h, then the combined experiments were diluted with H$_2$O (9 L) and extracted with EtOAc (3×3 L).

The combined organic layers were washed with brine (2×2 L), dried over anhydrous Na$_2$SO$_4$, filtered, and the filtrate was concentrated under reduced pressure to give methyl (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoate (438 g, crude) as a solid. LCMS (ESI): m/z [M+Na] calc'd for C$_{37}$H$_{55}$IN$_2$O$_6$SiNa 801.3; found 801.6.

Step 6. This reaction was undertaken on three batches in parallel on the scale illustrated below.

To a stirred mixture of methyl (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoate (146 g, 188 mmol) in THF (1.46 L) was added LiOH (22.45 g, 937 mmol) in H$_2$O (937 mL) dropwise at 0° C. The resulting mixture was warmed to rt and stirred for 1.5 h [note: LCMS showed 15% de-TIPS product]. The mixture was acidified to pH 5 with 1M HCl (1M) and the combined experiments were extracted with EtOAc (3×3 L). The combined organic layers were washed with brine (2×2 L), dried over anhydrous Na$_2$SO$_4$, filtered, and the filtrate was concentrated under reduced pressure to give (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoic acid (402 g, crude) as a solid. LCMS (ESI): m/z [M+Na] calc'd for C$_{36}$H$_{53}$IN$_2$O$_6$SiNa 787.3; found 787.6.

Step 7. To a stirred mixture of (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoic acid (340 g, 445 mmol) and methyl (3S)-1,2-diazinane-3-carboxylate (96.1 g, 667 mmol) in DCM (3.5 L) was added NMM (225 g, 2.2 mol), EDCl (170 g, 889 mmol), and HOBT (12.0 g, 88.9 mmol) portionwise at 0° C. The mixture was warmed to rt and stirred for 16 h, then washed with H$_2$O (3×2.5 L), brine (2×1 L), dried over anhydrous Na$_2$SO$_4$ and filtered. The filtrate was concentrated under reduced pressure and the residue was purified by column chromatography to give methyl (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylate (310 g, 62% yield) as an oil. LCMS (ESI): m/z [M+H] calc'd for C$_{42}$H$_{63}$IN$_4$O$_7$Si 890.4; found 890.8.

Step 8. This reaction was undertaken on three batches in parallel on the scale illustrated below.

To a stirred mixture of methyl (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylate (85.0 g, 95.4 mmol) in THF (850 mL) each added LiOH (6.85 g, 286 mmol) in H$_2$O (410 mL) dropwise at 0° C. under an atmosphere of N$_2$. The mixture was stirred at 0° C. for 1.5 h [note: LCMS showed 15% de-TIPS product], then acidified to pH 5 with 1M HCl and the combined experiments extracted with EtOAc (3×2 L). The combined organic layers were washed with brine (2×1.5 L), dried over anhydrous Na$_2$SO$_4$, filtered, and the filtrate was concentrated under reduced pressure to give (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylic acid (240 g, crude) as a solid. LCMS (ESI): m/z [M+H] calc'd for C$_{41}$H$_{61}$IN$_4$O$_7$Si 876.3; found 877.6.

Step 9.

This reaction was undertaken on two batches in parallel on the scale illustrated below.

To a stirred mixture of (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylic acid (120 g, 137 mmol) in DCM (6 L) was added DIPEA (265 g, 2.05 mol), EDCl (394 g, 2.05 mol), and HOBT (37 g, 274 mmol) in portions at 0° C. under an atmosphere of $N_2$. The mixture was warmed to rt and stirred overnight, then the combined experiments were washed with $H_2O$ (3×6 L), brine (2×6 L), dried over anhydrous $Na_2SO_4$, and filtered. After filtration, the filtrate was concentrated under reduced pressure. The filtrate was concentrated under reduced pressure and the residue was purified by column chromatography to give tert-butyl N-[(8S,14S)-21-iodo-18,18-dimethyl-9,15-dioxo-4-[(triisopropylsilyl)oxy]-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]carbamate (140 g, 50% yield) as a solid. LCMS (ESI): m/z [M+H] calc'd for $C_{41}H_{59}IN_4O_8Si$ 858.9; found 858.3.

Intermediate 7. Synthesis of (S)-methyl 2-((tert-butoxycarbonyl)amino)-3-(4-(4,4,5,5-tetramethyl-1,3,2-dioxaborolan-2-yl)pyridin-2-yl)propanoate

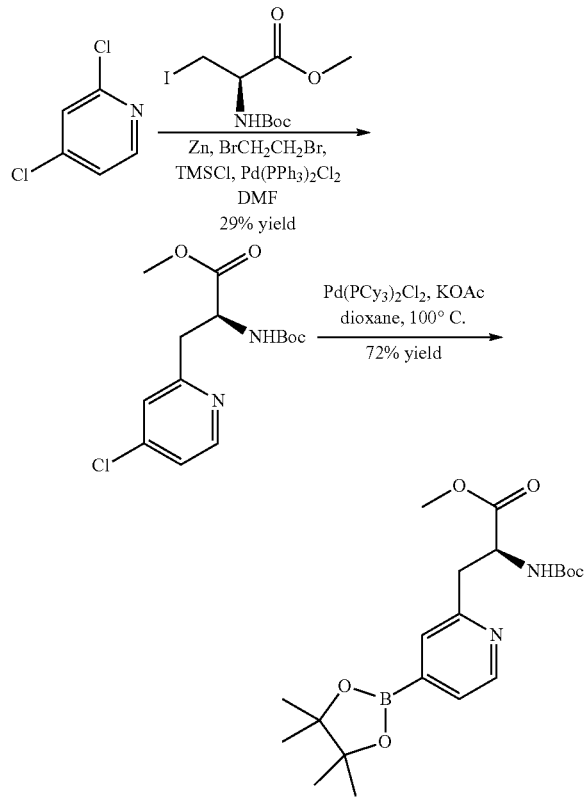

Step 1. Zn dust (28 g, 428 mmol) was added to a 1L, three necked, round bottomed flask, purged with $N_2$, and heated with a heat gun for 10 min under vacuum. The mixture was cooled to rt, and a solution of 1,2-dibromoethane (1.85 mL, 21.5 mmol) in DMF (90 mL) was added dropwise over 10 min. The mixture was heated at 90° C. for 30 min and re-cooled to rt. TMSCl (0.55 mL, 4.3 mmol) was added, and the mixture was stirred for 30 min at rt, then a mixture of (R)-methyl 2-((tert-butoxycarbonyl)amino)-3-iodopropanoate (22.5 g, 71.4 mmol) in DMF (200 mL) was added dropwise over a period of 10 min. The mixture was heated at 35° C. and stirred for 2 h, then cooled to rt, and 2,4-dichloropyridine (16 g, 109 mmol) and $Pd(PPh_3)_2Cl_2$ (4 g, 5.7 mmol) added. The mixture was heated at 45° C. and stirred for 2 h, cooled, and filtered, then $H_2O$ (1 L) and EtOAc (0.5 L) were added to the filtrate. The organic and aqueous layers were separated, and the aqueous layer was extracted with EtOAc (2×500 mL). The organic layers were dried over anhydrous $Na_2SO_4$, filtered, and concentrated under reduced pressure. The crude residue was purified by silica gel column chromatography to give (S)-methyl 2-((tert-butoxycarbonyl)amino)-3-(4-chloropyridin-2-yl)propanoate (6.5 g, 29% yield) as a solid. LCMS (ESI): m/z [M+H] calc'd for $C_{14}H_{19}ClN_2O_4$ 314.1; found 315.1.

Step 2. To a mixture of (S)-methyl 2-((tert-butoxycarbonyl)amino)-3-(4-chloropyridin-2-yl)propanoate (6.5 g, 20.6 mmol) in 1,4-dioxane (80 mL) at rt under an atmosphere of $N_2$ was added bis(pinacolato)diboron (6.3 g, 24.7 mmol), KOAc (8.1 g, 82.4 mmol), and $Pd(PCy3)_2Cl_2$ (1.9 g, 2.5 mmol). The mixture was heated to 100° C. and stirred for 3 h, then $H_2O$ (100 mL) added and the mixture extracted with EtOAc (3×200 mL). The organic layers were combined, washed with brine (2×100 mL), dried over anhydrous $Na_2SO_4$, and filtered. The filtrate was concentrated under reduced pressure and the residue was purified by silica gel column chromatography to give (S)-methyl 2-((tert-butoxycarbonyl)amino)-3-(4-(4,4,5,5-tetramethyl-1,3,2-dioxaborolan-2-yl)pyridin-2-yl)propanoate (6 g, 72% yield) as a solid. LCMS (ESI): m/z [M+H] calc'd for $C_{20}H_{31}BN_2O_6$ 406.2; found 407.3.

Synthesis of Intermediate 8

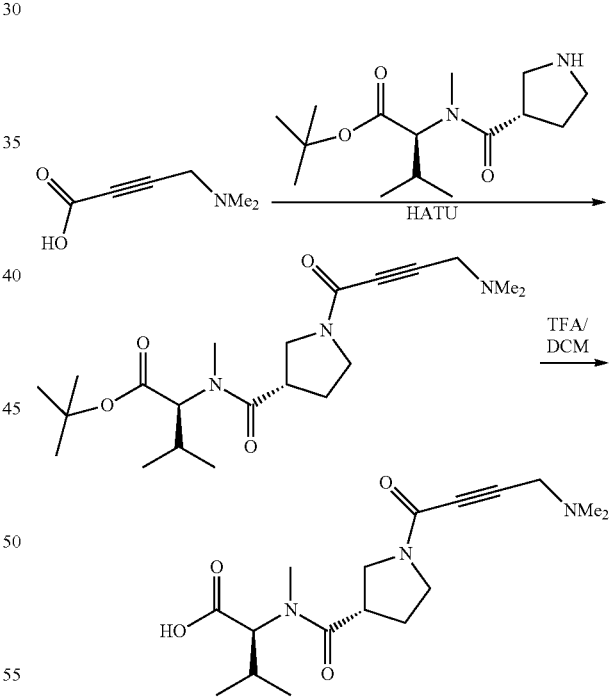

Step 1. To a mixture of 4-(dimethylamino)but-2-ynoic acid (900 mg, 7.0 mmol) in DMF (20 mL) −5° C. was added tert-butyl N-methyl-N—((S)-pyrrolidine-3-carbonyl)-L-valinate (1.0 g, 3.5 mmol), DIPEA (2.2 g, 17.6 mmol) and HATU (2.7 g, 7.0 mmol) in portions. The mixture was stirred between −5 to 5° C. for 1 h, then diluted with EtOAc (100 mL) and ice-$H_2O$ (100 mL). The aqueous and organic layers were separated and the organic layer was washed with $H_2O$ (3×100 mL), brine (100 mL), dried over anhydrous $Na_2SO_4$, and filtered. The filtrate was concentrated under reduced pressure and the residue was purified by silica gel column chromatography to give tert-butyl N—((S)-1-(4-(dimethylamino)but-2-ynoyl)pyrrolidine-3-carbonyl)-N-methyl-L-valinate (900 mg, 55% yield) as an oil. LCMS (ESI): m/z [M+H] calc'd for $C_{21}H_{35}N_3O_4$ 393.5; found 394.3.

Step 2. To a mixture of tert-butyl N—((S)-1-(4-(dimethylamino)but-2-ynoyl)pyrrolidine-3-carbonyl)-N-methyl-L-valinate (260 mg, 0.66 mmol) in DCM (6 mL) was added TFA (3 mL) at rt. The mixture was stirred at rt for 2 h, then the solvent was concentrated under reduced pressure to give (2S)-2-{1-[(3S)-1-[4-(dimethylamino)but-2-ynoyl]pyrrolidin-3-yl]-N-methylformamido}-3-methylbutanoic acid (280 mg) as an impure oil. The crude product was used directly in the next step without further purification. LCMS (ESI): m/z [M+H] calc'd for $C_{17}H_{27}N_3O_4$ 337.2; found 338.3.

Synthesis of Intermediate 9

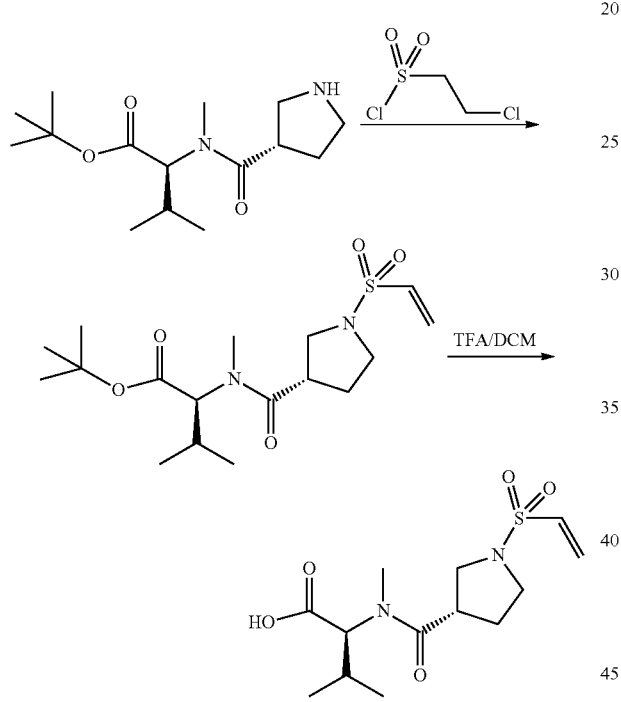

Step 1. To a mixture of tert-butyl N-methyl-N—((S)-pyrrolidine-3-carbonyl)-L-valinate (500 mg, 1.8 mmol) in DCM (8 mL) at 5° C. was added TEA (533 mg, 5.3 mmol) followed by dropwise addition of 2-chloroethane-1-sulfonyl chloride (574 mg, 3.5 mmol) in DCM (2 mL) The mixture was stirred at 5° C. for 1 h, then diluted with $H_2O$ (20 mL) and extracted with EtOAC (3×10 mL). The combined organic layers were washed with brine (10 mL), dried over anhydrous $Na_2SO_4$, and filtered. The filtrate was concentrated under reduced pressure and the residue was purified by silica gel column chromatography to give tert-butyl N-methyl-N—((S)-1-(vinylsulfonyl)pyrrolidine-3-carbonyl)-L-valinate (300 mg, 45% yield) as an oil. LCMS (ESI): m/z [M+H] calc'd for $C_{17}H_{30}N_2O_5S$ 374.2; found 375.2.

Step 2. To a mixture of tert-butyl N-methyl-N—((S)-1-(vinylsulfonyl)pyrrolidine-3-carbonyl)-L-valinate (123 mg, 0.33 mmol) in DCM (3 mL) at rt was added TFA (1 mL). The mixture was stirred at rt for 1 h, then concentrated under reduced pressure to give N-methyl-N—((S)-1-(vinylsulfonyl)pyrrolidine-3-carbonyl)-L-valine (130 mg, crude) as a solid, which was used directly in the next step without further purification. LCMS (ESI): m/z [M+H] calc'd for $C_{13}H_{22}N_2O_5S$ 318.1; found 319.1.

Synthesis of Intermediate 10

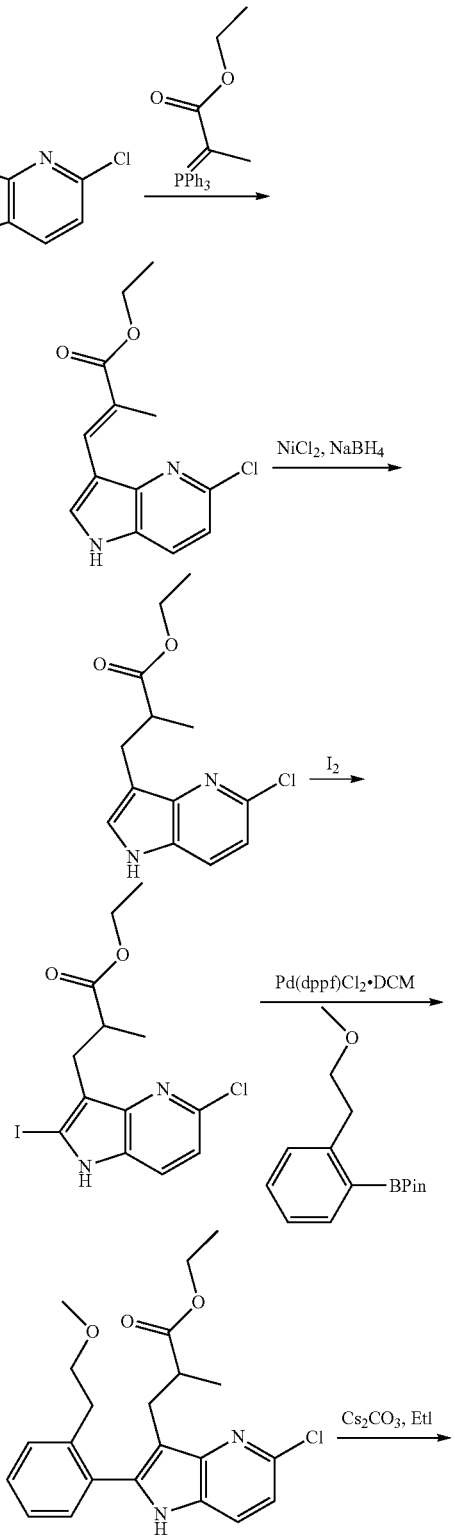

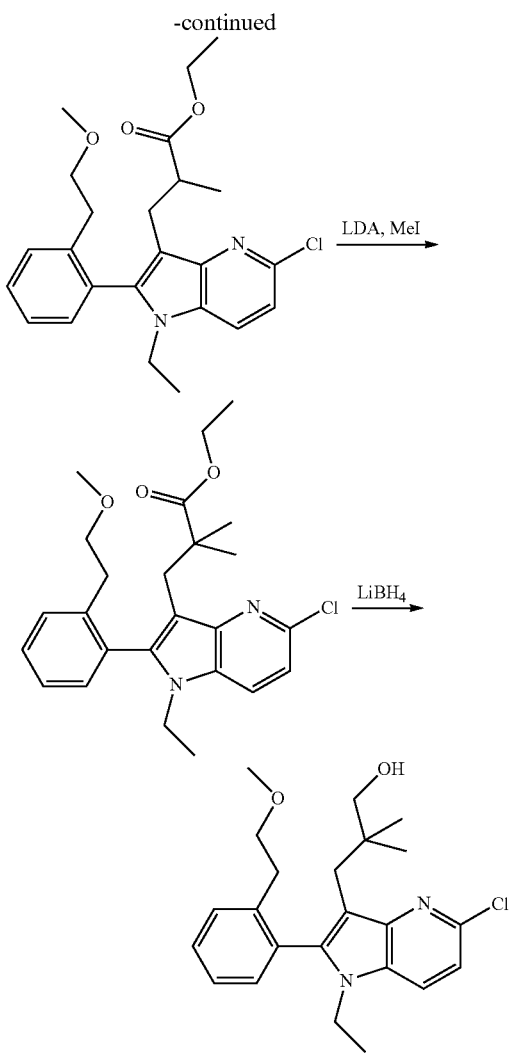

Step 1. A mixture of 5-chloro-1H-pyrrolo[3,2-b]pyridine-3-carbaldehyde (8.5 g, 47.1 mmol) and ethyl 2-(triphenylphosphoranylidene)propionate (2.56 g, 70.7 mmol) in 1,4-dioxane (120 mL) was stirred at reflux for 4 h, then concentrated under reduced pressure. EtOAc (200 mL) was added and the mixture was washed with brine, dried over $Na_2SO_4$, and filtered. The filtrate was concentrated under reduced pressure and the residue was purified by silica gel column chromatography to give ethyl (E)-3-(5-chloro-1H-pyrrolo[3,2-b]pyridin-3-yl)-2-methylacrylate (7.5 g, 60% yield) as a solid. LCMS (ESI): m/z [M+H] calc'd for $C_{13}H_{13}ClN_2O_2$ 264.1; found 265.1.

Step 2. To a mixture of ethyl (E)-3-(5-chloro-1H-pyrrolo[3,2-b]pyridin-3-yl)-2-methylacrylate (7.5 g, 28.3 mmol) and $NiCl_2$ (4.8 g, 28.3 mmol) in 1:1 THF/MeOH (300 mL) was added $NaBH_4$ (21.5 g, 566 mmol) in 20 portions every 25 minutes. After complete addition, the mixture was stirred at rt for 30 min, then diluted with EtOAc (500 mL) and washed with brine, dried over $Na_2SO_4$, and filtered. The filtrate was concentrated under reduced pressure and the residue was purified by silica gel column chromatography to give ethyl 3-(5-chloro-1H-pyrrolo[3,2-b]pyridin-3-yl)-2-methylpropanoate (3.4 g, 45% yield) as a solid. LCMS (ESI): m/z [M+H] calc'd for $C_{13}H_{15}ClN_2O_2$ 266.1; found 267.1.

Step 3. To a mixture of ethyl 3-(5-chloro-1H-pyrrolo[3,2-b]pyridin-3-yl)-2-methylpropanoate (7.0 g, 26.2 mmol) and AgOTf (6.7 g, 26.2 mmol) in THF (50 mL) at 0° C. was added 12 (6.65 g, 26.2 mol). The mixture was stirred at 0° C. for 30 min then diluted with EtOAc (100 mL), washed with $Na_2SO_3$ (50 mL), brine (50 mL), dried over $Na_2SO_4$, and filtered. The filtrate was concentrated under reduced pressure and the residue was purified by silica gel column chromatography to give ethyl 3-(5-chloro-2-iodo-1H-pyrrolo[3,2-b]pyridin-3-yl)-2-methylpropanoate (6 g, 58% yield) as white solid. LCMS (ESI): m/z [M+H] calc'd for $C_{13}H_{14}ClIN_2O_2$ 392.0; found 393.0.

Step 4. To a mixture of ethyl 3-(5-chloro-2-iodo-1H-pyrrolo[3,2-b]pyridin-3-yl)-2-methylpropanoate (6.0 g, 15.3 mmol) and 2-(2-(2-methoxyethyl)phenyl)-4,4,5,5-tetramethyl-1,3,2-dioxaborolane (5.6 g, 21.4 mmol) and $K_2CO_3$ (6.3 g, 45.9 mmol) in 1,4-dioxane (150 mL) and $H_2O$ (30 mL) under an atmosphere of $N_2$ was added Pd(dppf)$Cl_2$·DCM (1.3 g, 3.1 mmol). The mixture was heated to 80° C. and stirred for 4 h, then diluted with EtOAc (500 mL), washed with brine, dried over $Na_2SO_4$, and filtered. The filtrate was concentrated under reduced pressure and the residue was purified by silica gel column chromatography to give 3-(5-chloro-2-(2-(2-methoxyethyl)phenyl)-1H-pyrrolo[3,2-b]pyridin-3-yl)-2-methylpropanoate (5.5 g, 50% yield) as a viscous oil. LCMS (ESI): m/z [M+H] calc'd for $C_{22}H_{25}ClN_2O_3$ 400.2; found 401.2.

Step 5. A mixture of ethyl 3-(5-chloro-2-(2-(2-methoxyethyl)phenyl)-1H-pyrrolo[3,2-b]pyridin-3-yl)-2-methylpropanoate (5.5 g, 13.8 mmol), $Cs_2CO_3$ (8.9 g, 27.5 mmol), and EtI (3.5 g, 27.5 mmol) in DMF (30 mL) at rt was stirred for 10 h. The mixture was diluted with EtOAc (100 mL), washed with brine (20 mL×4), dried over $Na_2SO_4$, filtered, and concentrated in vacuo. The filtrate was concentrated under reduced pressure and the residue was purified by silica gel column chromatography to give ethyl 3-(5-chloro-1-ethyl-2-(2-(2-methoxyethyl)phenyl)-1H-pyrrolo[3,2-b]pyridin-3-yl)-2-methylpropanoate (5.6 g, 95% yield) as a viscous oil. LCMS (ESI): m/z [M+H] calc'd for $C_{25}H_{31}ClN_2O_3$ 428.2; found 429.2.

Step 6. To a mixture of ethyl 3-(5-chloro-1-ethyl-2-(2-(2-methoxyethyl)phenyl)-1H-pyrrolo[3,2-b]pyridin-3-yl)-2-methylpropanoate (5.4 g, 12.6 mmol) in THF (50 mL) at −65° C. was added 2M LDA (25 mL, 50 mmol) and stirred at −65° C. for 1 h. MeI (3.6 g, 25 mmol) was added and the mixture was stirred at −65° C. for 2.5 h, then aqueous $NH_4Cl$ and EtOAc (50 mL) were added. The aqueous and organic layers were separated and the organic layer was washed with brine (30 mL), dried over $Na_2SO_4$, and filtered. The filtrate was concentrated under reduced pressure and the residue was purified by silica gel column chromatography to give ethyl 3-(5-chloro-1-ethyl-2-(2-(2-methoxyethyl)phenyl)-1H-pyrrolo[3,2-b]pyridin-3-yl)-2,2-dimethylpropanoate (3.2 g, 57% yield) as a viscous oil. LCMS (ESI): m/z [M+H] calc'd for $C_{25}H_{31}ClN_2O_3$ 442.2; found 443.2.

Step 7. To a mixture of ethyl 3-(5-chloro-1-ethyl-2-(2-(2-methoxyethyl)phenyl)-1H-pyrrolo[3,2-b]pyridin-3-yl)-2,2-dimethylpropanoate (1.0 g, 2.3 mmol) in THF (10 mL) at 5° C. was added $LiBH_4$ (196 mg, 9.0 mmol). The mixture was heated to 65° C. and stirred for 2 h then aqueous $NH_4Cl$ and EtOAc (50 mL) added. The aqueous and organic layers were separated and the organic layer was washed with brine (30 mL), dried over $Na_2SO_4$, and filtered. The filtrate was concentrated under reduced pressure and the residue was purified by silica gel column chromatography to give 3-(5-chloro-1-ethyl-2-(2-(2-methoxyethyl)phenyl)-1H-pyrrolo[3,2-b]pyridin-3-yl)-2,2-dimethylpropan-1-ol (0.75 g, 82% yield) as a solid. LCMS (ESI): m/z [M+H] calc'd for $C_{23}H_{29}ClN_2O_2$ 400.2; found 401.2.

Intermediate 11: Methyl (3S)-1-{(2S)-2-(tert-butoxycarbonyl)amino-3-[3-fluoro-5-(4,4,5,5-tetramethyl-1,3,2-dioxaborolan-2-yl)phenyl]propanoyl}-1,2-diazinane-3-carboxylate

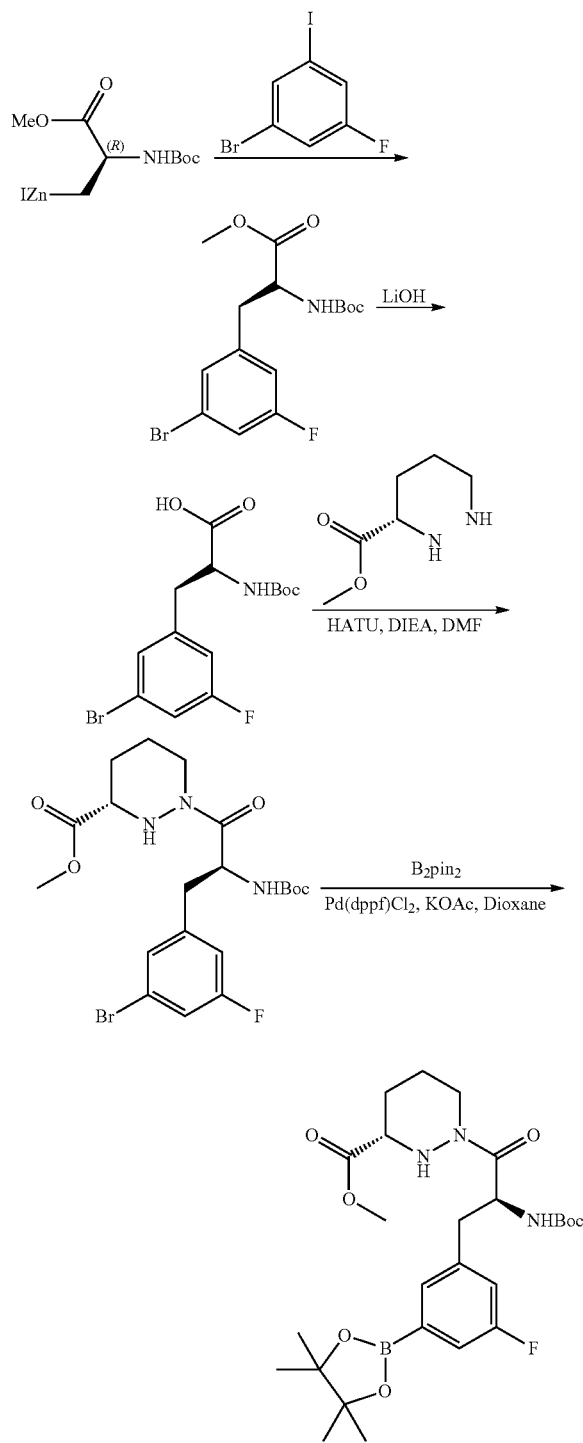

Step 1. To a stirred solution of methyl (2R)-2-{[(tert-butoxy)carbonyl]amino}-3-(iodozincio)propanoate (12 g, 30 mmol, 1.2 eq) in DMF (100 mL) was added 1-bromo-3-fluoro-5-iodobenzene (7.5 g, 25 mmol, 1 eq) and Pd(PPh$_3$)$_2$Cl$_2$ (1.7 g, 2.5 mmol, 0.1 equiv) at 20° C. under N$_2$ atmosphere. The resulting mixture was stirred for 2 hrs at 65° C. under N$_2$ atmosphere. The reaction mixture was quenched with water and extracted with EA (200 mL×2). The organic phase was washed with water (200 mL×1) and brine (100 mL×1) and concentrated to dryness to give a residue. The residue was purified by prep-TLC (PE/EA=10/1) to afford methyl 3-(3-bromo-5-fluorophenyl)-2-{[(tert-butoxy)carbonyl]amino}propanoate (6 g, 58% yield) as a colorless oil. LCMS (ESI) m/z=398.1 [M+Na]$^+$, calculated for $C_{15}H_{19}BrFNO_4$: 375.0

Step 2. To a solution of methyl 3-(3-bromo-5-fluorophenyl)-2-{[(tert-butoxy)carbonyl]amino}propanoate (3.2 g, 8.5 mmol, 1 eq) in THF (50 mL) was added Lithium hydroxide (610.7 mg, 25.5 mmol, 3 eq) in H$_2$O (10 mL). Then the reaction mixture was stirred at 20° C. for 1 h. The mixture was adjusted to pH=5.0 with 1M HCl aqueous solution. The mixture was quenched with H$_2$O (150 mL) and extracted with EA (200 mL×3). The combined organic layers was washed bine (50 mL), dried over Na$_2$SO$_4$ and concentrated to afford 3-(3-bromo-5-fluorophenyl)-2-{[(tert-butoxy)carbonyl]amino}propanoic acid (2.65 g, 68% yield) as a white solid. LCMS (ESI) m/z=384.1 [M+Na]$^+$, calculated for $C_{14}H_{15}BrFNO_4$ MW: 361.0

Step 3. To a mixture of 3-(3-bromo-5-fluorophenyl)-2-{[(tert-butoxy)carbonyl]amino}propanoic acid (2.3 g, 6.4 mmol, 1 eq) and methyl (3S)-1,2-diazinane-3-carboxylate (1.66 g, 11.5 mmol, 1.8 eq) in DMF (150 mL) was added HATU (4.9 g, 12.8 mmol, 2 eq) and DIEA (16.5 g, 128 mmol, 20 eq) in DMF (50 mL) at 0° C. Then the reaction mixture was stirred at 0° C. for 1 h. The mixture was quenched with H$_2$O (100 mL) and extracted with EA (300 mL×3). The combined organic layers was washed bine (50 mL), dried over Na$_2$SO$_4$ and concentrated to give the residue, which was purified by Pre-HPLC eluting with acetonitrile in water (0.1% FA) from 60% to 70% in 10 minutes to give methyl (3S)-1-[(2S)-3-(3-bromo-5-fluorophenyl)-2-{[(tert-butoxy)carbonyl]amino}propanoyl]-1,2-diazinane-3-carboxylate (2.7 g, 78% yield) as a pale yellow solid. LCMS (ESI) m/z=510.1 [M+Na]$^+$, calculated for $C_{20}H_{27}BrFNO_5$: 487.1.

Step 4. A mixture of methyl (S)-1-((S)-3-(3-bromo-5-fluorophenyl)-2-((tert-butoxycarbonyl)amino)propanoyl)hexahydropyridazine-3-carboxylate (3 g, 6.16 mmol, 1 eq), 4,4,5,5-tetramethyl-2-(4,4,5,5-tetramethyl-1,3,2-dioxaborolan-2-yl)-1,3,2-dioxaborolane (1.9 g, 7.4 mmol, 1.2 eq), KOAc (900 mg, 9.24 mmol, 1.5 eq) and Pd(dppf)Cl$_2$DCM (0.3 g, 0.37 mmol, 0.05 eq) in dioxane (50 mL) was heated at 100° C. for 17 h under N$_2$ atmosphere. The mixture was concentrated and purified by column chromatography (DCM/MeOH=100/1 to 40/1) to give methyl (3S)-1-(2S)-2-{(tert-butoxycarbonyl)amino-3-[3-fluoro-5-(4,4,5,5-tetramethyl-1,3,2-dioxaborolan-2-yl)phenyl]propanoyl}-1,2-diazinane-3-carboxylate (2.6 g, 79% yield) as a yellow oil. LCMS (ESI) m/z=536.2 [M+H]$^+$, calculated for $C_{26}H_{39}BFNO_7$: 535.3.

Compounds A341 and A342 may be prepared using methods disclosed herein via Intermediate 11.

Example A75. Synthesis of two atropisomers of (2S)—N-[(8S,14S,20M)-22-ethyl-4-hydroxy-21-{2-[(1S)-1-methoxyethyl]pyridin-3-yl}-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]-3-methyl-2-{N-methyl-1-[(3S)-1-(prop-2-enoyl)pyrrolidin-3-yl]formamido}butanamide
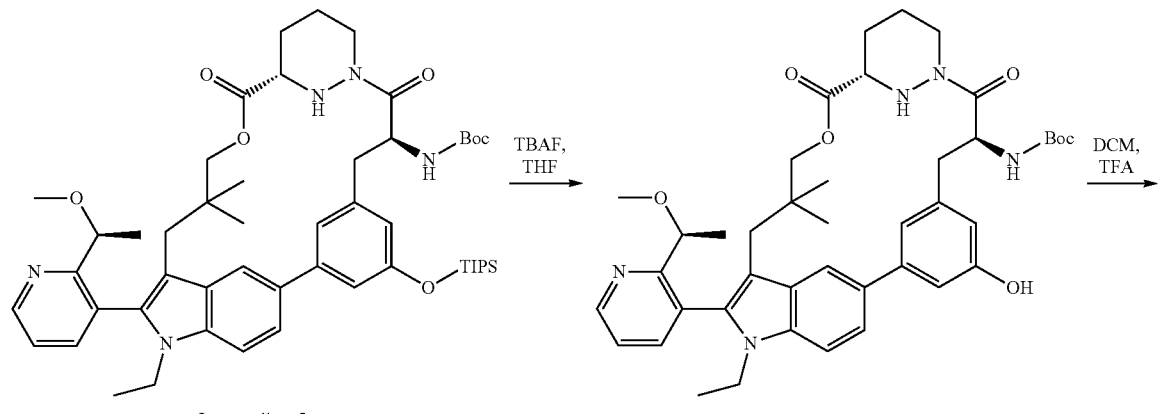
Intermediate 5.
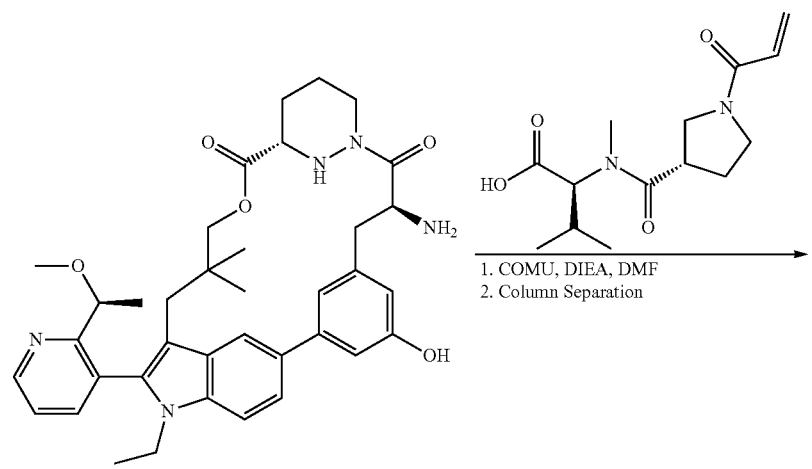
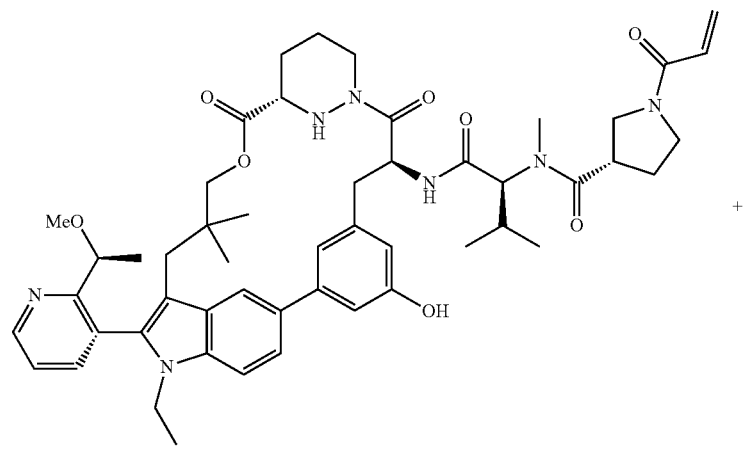
+

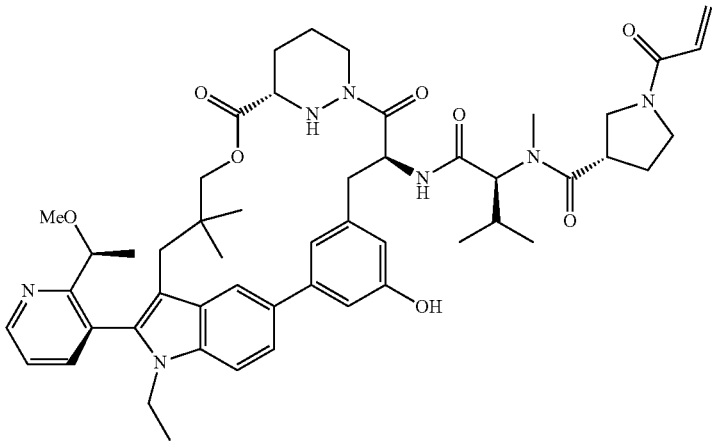

Step 1. To a stirred mixture of tert-butyl ((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (18.0 g, 20.1 mmol) in THF (180 mL) at 0° C. was added a 1M solution of TBAF in THF (24.1 mL, 24.1 mmol). The mixture was stirred at 0° C. for 1 h, then diluted with brine (1.5 L) and extracted with EtOAc (3×1 L). The combined organic layers were washed with brine (2×500 mL), dried over anhydrous Na$_2$SO$_4$, and filtered. The filtrate was concentrated under reduced pressure and the residue was purified by silica gel column chromatography to give tert-butyl ((6³S,4S)-1¹-ethyl-2⁵-hydroxy-1²-(2-((S)-1-methoxyethyl) pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1, 3)-benzenacycloundecaphane-4-yl)carbamate (11.5 g, 69% yield) as a solid. LCMS (ESI): m/z [M+H] calc'd for C$_{42}$H$_{53}$N$_5$O$_7$ 739.4; found 740.4.

Step 2. To a stirred mixture of tert-butyl ((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (11.5 g, 15.5 mmol) in DCM (120 mL) at 0° C. was added TFA (60 mL, 808 mmol). The mixture was stirred at 0° C. for 1 h, then concentrated under reduced pressure and the residue again concentrated under reduced pressure with toluene (20 mL; repeated ×3) to give (6³S,4S)-4-amino-1¹-ethyl-2⁵-hydroxy-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (12 g, crude), which was used directly in the next step without further purification. LCMS (ESI): m/z [M+H] calc'd for C$_{37}$H$_{45}$N$_5$O$_5$ 639.3; found 640.6.

Step 3. To a stirred mixture of (6³S,4S)-4-amino-1¹-ethyl-2⁵-hydroxy-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (11.9 g, 18.6 mmol) in DMF (240 mL) at 0° C. under an atmosphere of N$_2$ was added DIPEA (48.1 g, 372 mmol), (2S)-3-methyl-2-[N-methyl-1-[(3S)-1-(prop-2-enoyl)pyrrolidin-3-yl]formamido]butanoic acid (9.45 g, 33.5 mmol) and COMU (11.95 g, 27.9 mmol) in portions. The mixture was stirred ay 0° C. for 90 min, then diluted with brine (1.5 L) and extracted with EtOAc (3×1 L). The combined organic layers were washed with brine (2×500 mL), dried over anhydrous Na$_2$SO$_4$, and filtered. After filtration, the filtrate was concentrated under reduced pressure. The filtrate was concentrated under reduced pressure and the residue was purified by silica gel column chromatography (×2) to give two atropisomers of (2S)—N-[(8S,14S,20M)-22-ethyl-4-hydroxy-21-{2-[(1 S)-1-methoxyethyl]pyridin-3-yl}-18,18-dimethyl-9,15-dioxo-16-oxa-10,22,28-triazapentacyclo [18.5.2.1²,⁶0.1¹⁰,¹⁴0.0²³,²⁷]nonacosa-1(26),2,4,6(29),20,23 (27),24-heptaen-8-yl]-3-methyl-2-{N-methyl-1-[(3S)-1-(prop-2-enoyl)pyrrolidin-3-yl]formamido}butanamide (2.7 g, 15.5%, yield) and (4.2 g, 24.7% yield) both as solids. LCMS (ESI): m/z [M+H] calc'd for C$_{51}$H$_{65}$N$_7$O$_8$ 903.5; found 904.7; ¹H NMR (400 MHz, DMSO-d$_6$) δ 9.35-9.27 (m, 1H), 8.77 (dd, J=4.7, 1.7 Hz, 1H), 7.95 (dq, J=6.2, 2.0 Hz, 2H), 7.55 (ddd, J=28.0, 8.2, 4.3 Hz, 3H), 7.08 (dd, J=37.9, 6.2 Hz, 2H), 6.69-6.48 (m, 2H), 6.17 (ddt, J=16.7, 7.2, 2.3 Hz, 1H), 5.74-5.62 (m, 1H), 5.43-5.34 (m, 1H), 5.12-5.00 (m, 1H), 4.25 (d, J=12.3 Hz, 1H), 4.17-3.99 (m, 3H), 3.89-3.65 (m, 4H), 3.66-3.45 (m, 3H), 3.12 (s, 4H), 2.95-2.70 (m, 6H), 2.41-2.06 (m, 5H), 1.99-1.88 (m, 1H), 1.82 (d, J=12.1 Hz, 2H), 1.54 (t, J=12.0 Hz, 1H), 1.21 (dd, J=6.3, 2.5 Hz, 3H), 1.11 (t, J=7.1 Hz, 3H), 0.99-0.88 (m, 6H), 0.79 (ddd, J=27.8, 6.7, 2.1 Hz, 3H), 0.48 (d, J=3.7 Hz, 3H) and LCMS (ESI): m/z [M+H] calc'd for C$_{51}$H$_{65}$N$_7$O$_8$ 903.5; found 904.7; ¹H NMR (400 MHz, DMSO-d$_6$) δ 9.34-9.27 (m, 1H), 8.77 (dd, J=4.7, 1.7 Hz, 1H), 8.17-7.77 (m, 3H), 7.64-7.43 (m, 3H), 7.33 (d, J=13.7 Hz, 1H), 7.05-6.94 (m, 1H), 6.69-6.41 (m, 2H), 6.26-5.94 (m, 1H), 5.73-5.63 (m, 1H), 5.50-5.20 (m, 2H), 4.40-4.15 (m, 3H), 4.00-3.40 (m, 9H), 3.11 (d, J=4.4 Hz, 3H), 2.93-2.60 (m, 8H), 2.29-2.01 (m, 3H), 1.99 (s, 1H), 1.87-1.75 (m, 2H), 1.73-1.47 (m, 2H), 1.40 (d, J=6.0 Hz, 3H), 1.01-0.88 (m, 6H), 0.85-0.65 (m, 7H), 0.56 (s, 3H).

Example A89. Synthesis of (2S)—N-[(8S,14S)-22-ethyl-4-hydroxy-18,18-dimethyl-21-[6-(4-methylpiperazin-1-yl)pyridin-3-yl]-9,15-dioxo-16-oxa-10,22,28-triazapentacyclo[18.5.2.1²,⁶0.1¹⁰,¹⁴0.0²³,²⁷]nonacosa-1(26),2,4,6(29),20,23(27),24-heptaen-8-yl]-3-methyl-2-{N-methyl-1-[(3S)-1-(prop-2-enoyl)pyrrolidin-3-yl]formamido}butanamide
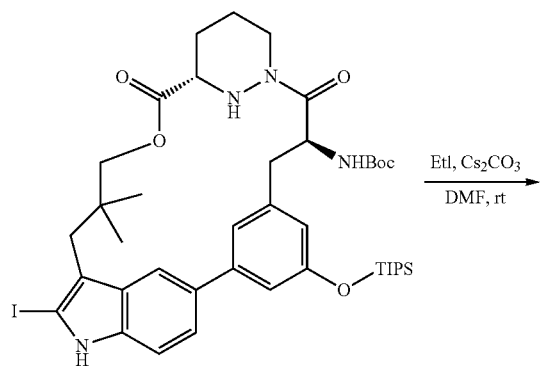
Intermediate 6
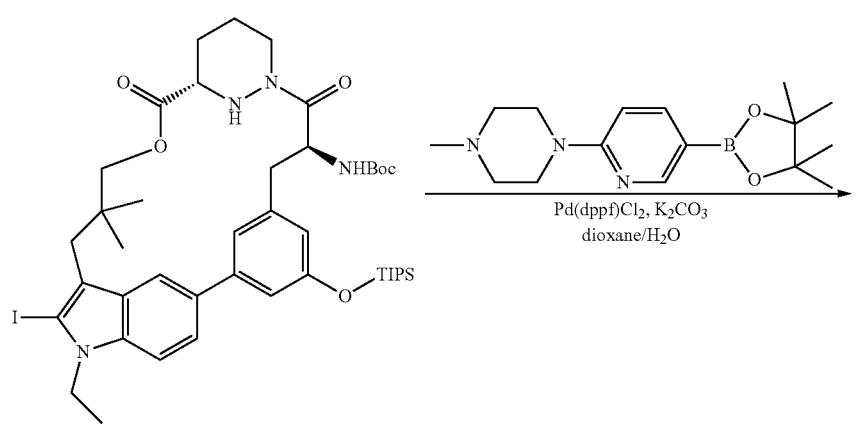
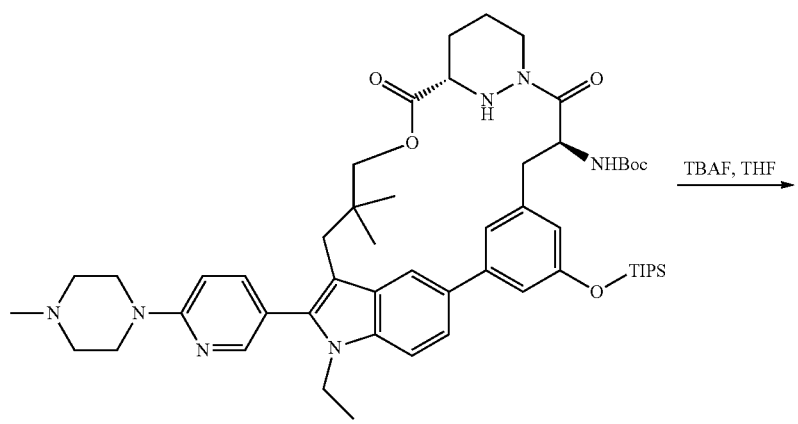

-continued

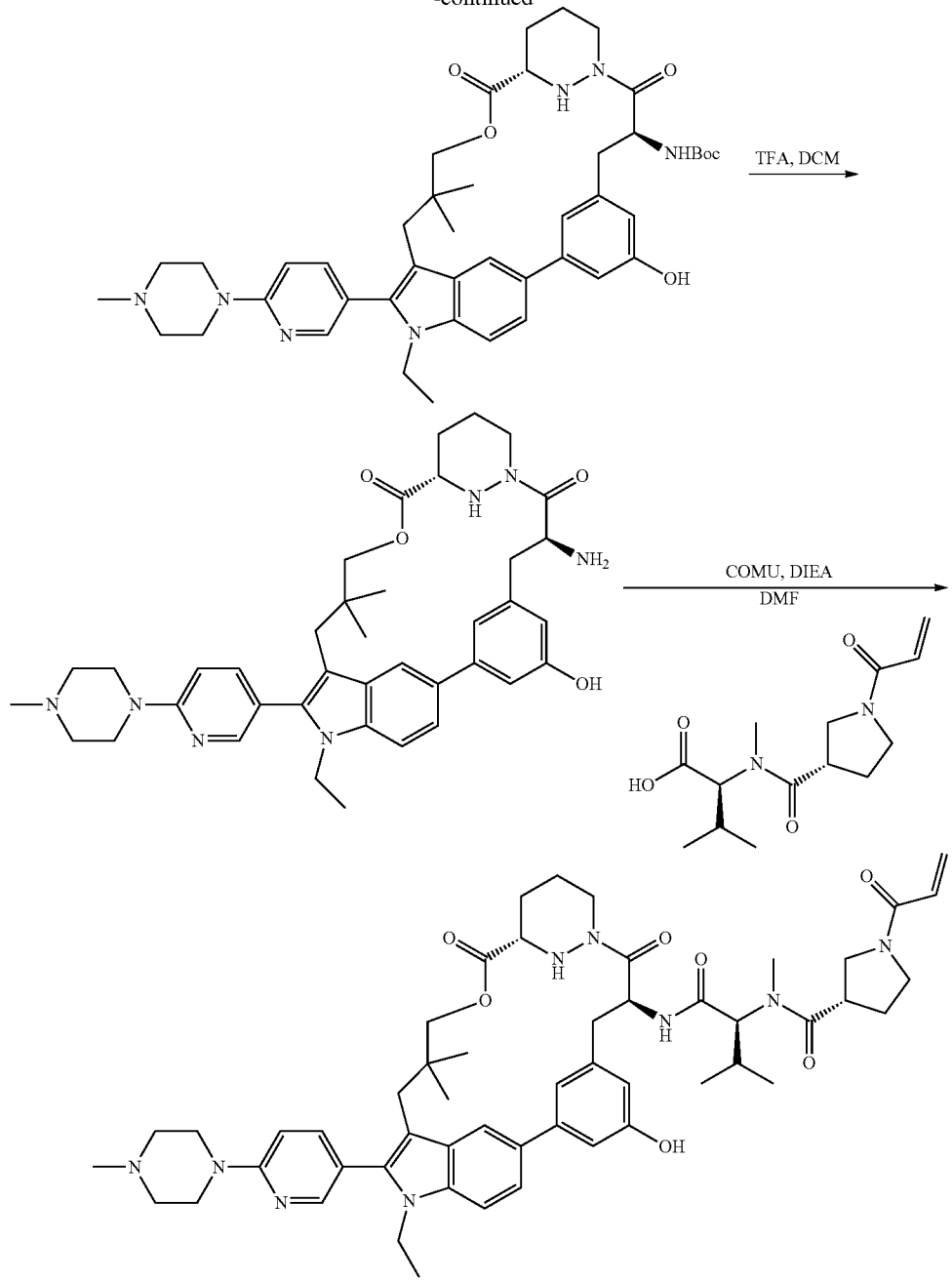

Step 1. To a mixture of tert-butyl ((6³S,4S)-1²-iodo-10,10-dimethyl-5,7-dioxo-25-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (240.00 mg, 0.279 mmol, 1.00 equiv) and Cs$_2$CO$_3$ (182 mg, 0.558 mmol, 2 equiv) in DMF (5.00 mL) was added ethyl iodide (113.45 mg, 0.727 mmol, 2.60 equiv) dropwise at 0° C. The reaction was stirred for 16 h at 25° C. The resulting mixture was diluted with water (10 mL) and extracted with EtOAc (3×10 mL). The combined organic layers were washed with brine (3×10 mL), and dried over anhydrous Na$_2$SO$_4$. The filtrate was concentrated under reduced pressure and the remaining residue was purified by silica gel column chromatography to afford tert-butyl ((6³S,4S)-1¹-ethyl-1²-iodo-10,10-dimethyl-5,7-dioxo-25-((triisopropylsilyl)oxy)-6¹, 6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (190 mg, 77% yield) as a yellow solid.

Step 2. A mixture of tert-butyl ((6³S,4S)-1¹-ethyl-1²-iodo-10,10-dimethyl-5,7-dioxo-25-((triisopropylsilyl)oxy)-6¹,6², 6³,6⁴,6⁵,6⁶-hexahydro-1¹H-8-oxa-1(5,3)-indola-6(1,3)-pyridazina-2(1,3)-benzenacycloundecaphane-4-yl) carbamate (500 mg, 0.54 mmol), 1-methyl-4-[5-(4,4,5,5-tetramethyl-1,3,2-dioxaborolan-2-yl)pyridin-2-yl]piperazine (257 mg, 0.8 mmol), Pd(dppf)Cl$_2$ (83 mg, 0.11 mmol) and K$_2$CO$_3$ (156 mg, 1.1 mmol) in 1,4-dioxane (25 mL) and H$_2$O (5 mL) under an atmosphere of Ar was stirred at 80° C. for 2 h. The mixture was concentrated under reduced pressure and the residue was purified by prep-TLC to afford tert-butyl ((6³S,4S)-1¹-ethyl-10,10-dimethyl-1²-(6-(4-methylpiperazin-1-yl)pyridin-3-yl)-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (400 mg, 76% yield) as a solid. LCMS (ESI): m/z [M+H] calc'd for $C_{53}H_{77}N_7O_6Si$ 935.6; found 936.6.

Step 3. A mixture of tert-butyl ((6³S,4S)-1¹-ethyl-10,10-dimethyl-1²-(6-(4-methylpiperazin-1-yl)pyridin-3-yl)-5,7-dioxo-2⁵-((triisopropylsilyl)oxy)-6¹,6²,6³,6⁴,6⁵,6⁶-hexahydro-11H-8-oxa-1(5,3)-indola-6(1,3)-pyridazina-2(1,3)-benzenacycloundecaphane-4-yl)carbamate (350 mg, 0.36 mmol) and 1M TBAF in THF (0.4 mL, 0.4 mmol) in THF (5 mL) was stirred at 0° C. for 1 h. The mixture was concentrated under reduced pressure and the residue was purified by silica gel column chromatography to give tert-butyl ((6³S,4S)-1¹-ethyl-2⁵-hydroxy-10,10-dimethyl-1²-(6-(4-methylpiperazin-1-yl)pyridin-3-yl)-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl) carbamate (290 mg, 100% yield) as a solid. LCMS (ESI): m/z [M+H] calc'd for $C_{44}H_{57}N_7O_6$ 779.4; found 780.4.

Step 4. A mixture of tert-butyl ((6³S,4S)-1¹-ethyl-2⁵-hydroxy-10,10-dimethyl-12-(6-(4-methylpiperazin-1-yl)pyridin-3-yl)-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (300 mg, 0.37 mmol) in TFA (5 mL) and DCM (5 mL) was stirred at rt for 1 h. The mixture was concentrated under reduced pressure to give (6³S,4S)-4-amino-1¹-ethyl-2⁵-hydroxy-10,10-dimethyl-1²-(6-(4-methylpiperazin-1-yl)pyridin-3-yl)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (300 mg, crude) as a solid. LCMS (ESI): m/z [M+H] calc'd for $C_{39}H_{49}N_7O_4$ 679.4; found 680.3.

Step 5. To a mixture of (6³S,4S)-4-amino-1¹-ethyl-2⁵-hydroxy-10,10-dimethyl-1²-(6-(4-methylpiperazin-1-yl)pyridin-3-yl)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (300 mg, 0.36 mmol) in DMF (3 mL) at 0° C. under an atmosphere of $N_2$ was added DIPEA (0.96 mL, 5.4 mmol) and (2S)-3-methyl-2-[N-methyl-1-[(3S)-1-(prop-2-enoyl)pyrrolidin-3-yl]formamido]butanoic acid (213 mg, 0.72 mmol), followed by dropwise addition of COMU (243 mg, 0.56 mmol). $H_2O$ was added at 0° C. and the mixture was extracted with EtOAc (3×10 mL). The combined organic layers were washed with brine (3×10 mL), dried over anhydrous $Na_2SO_4$, and filtered. The filtrate was concentrated under reduced pressure and the crude residue was purified by Prep-HPLC to give (2S)—N-[(8S,14S)-22-ethyl-4-hydroxy-18,18-dimethyl-21-[6-(4-methylpiperazin-1-yl)pyridin-3-yl]-9,15-dioxo-16-oxa-10,22,28-triazapentacyclo[18.5.2.1²,⁶0.1¹⁰,¹⁴0.0²³,²⁷]nonacosa-1(26),2,4,6(29),20,23(27),24-heptaen-8-yl]-3-methyl-2-{N-methyl-1-[(3S)-1-(prop-2-enoyl)pyrrolidin-3-yl]formamido}butanamide (45 mg, 13.2% yield) as a solid. LCMS (ESI): m/z [M+H] calc'd for $C_{53}H_{69}N_9O_7$ 943.5; found 944.8; ¹H NMR (400 MHz, DMSO-$d_6$) δ 9.39-9.23 (m, 1H), 8.64-8.60 (m, 1H), 8.19-8.16 (m, 1H), 8.15 (d, J=6.2 Hz, 1H), 7.86 (s, 1H), 7.66-7.62 (m, 1H), 7.56-7.54 (m, 1H), 7.50-7.43 (m, 1H), 7.13-7.11 (m, 1H), 7.03-6.95 (m, 1H), 6.70-6.47 (m, 2H), 6.17 (ddt, J=16.8, 6.4, 2.8 Hz, 1H), 5.76-5.63 (m, 1H), 5.45-5.33 (m, 1H), 5.11 (m, 1H), 4.75-4.72 (m, 1H), 4.28-4.24 (m, 1H), 4.11-3.98 (m, 4H), 3.91-3.76 (m, 1H), 3.73-3.71 (m, 1H), 3.59-3.56 (m, 7H), 3.51-3.40 (m, 2H), 3.08-2.94 (m, 1H), 2.94-2.92 (m, 2H), 2.92-2.87 (m, 2H), 2.86-2.83 (m, 2H), 2.80-2.65 (m, 2H), 2.83-2.82 (m, 3H), 2.28-2.25 (m, 3H), 2.08-2.05 (m, 2H), 2.02-1.96 (m, 1H), 1.87-1.78 (m, 1H), 1.74-1.66 (m, 1H), 1.56-1.48 (m, 1H), 1.11-1.08 (m, 4H), 0.99-0.92 (m, 2H), 0.89-0.87 (m, 5H), 0.82-0.73 (m, 2H).

Example A115. Synthesis of Two Atropisomers of (2S)—N-[(8S,14S,20P)-22-ethyl-21-{4-[(1S)-1-methoxyethyl]pyridin-3-yl}-18,18-dimethyl-9,15-dioxo-16-oxa-10,22,28-triazapentacyclo[18.5.2.1²,⁶0.1¹,¹⁴0.0²³,²⁷]nonacosa-1(26),2,4,6(29),20,23(27),24-heptaen-8-yl]-3-methyl-2-{N-methyl-1-[(3S)-1-(prop-2-enoyl)pyrrolidin-3-yl]formamido}butanamide

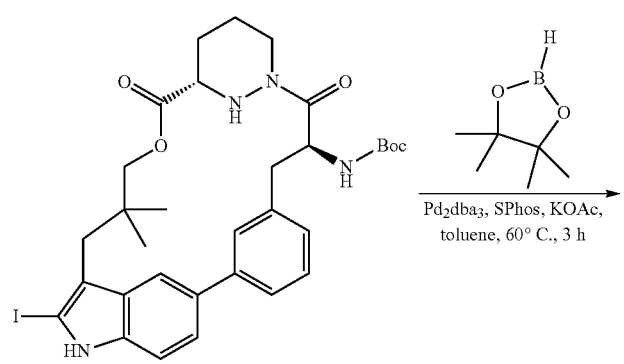

-continued
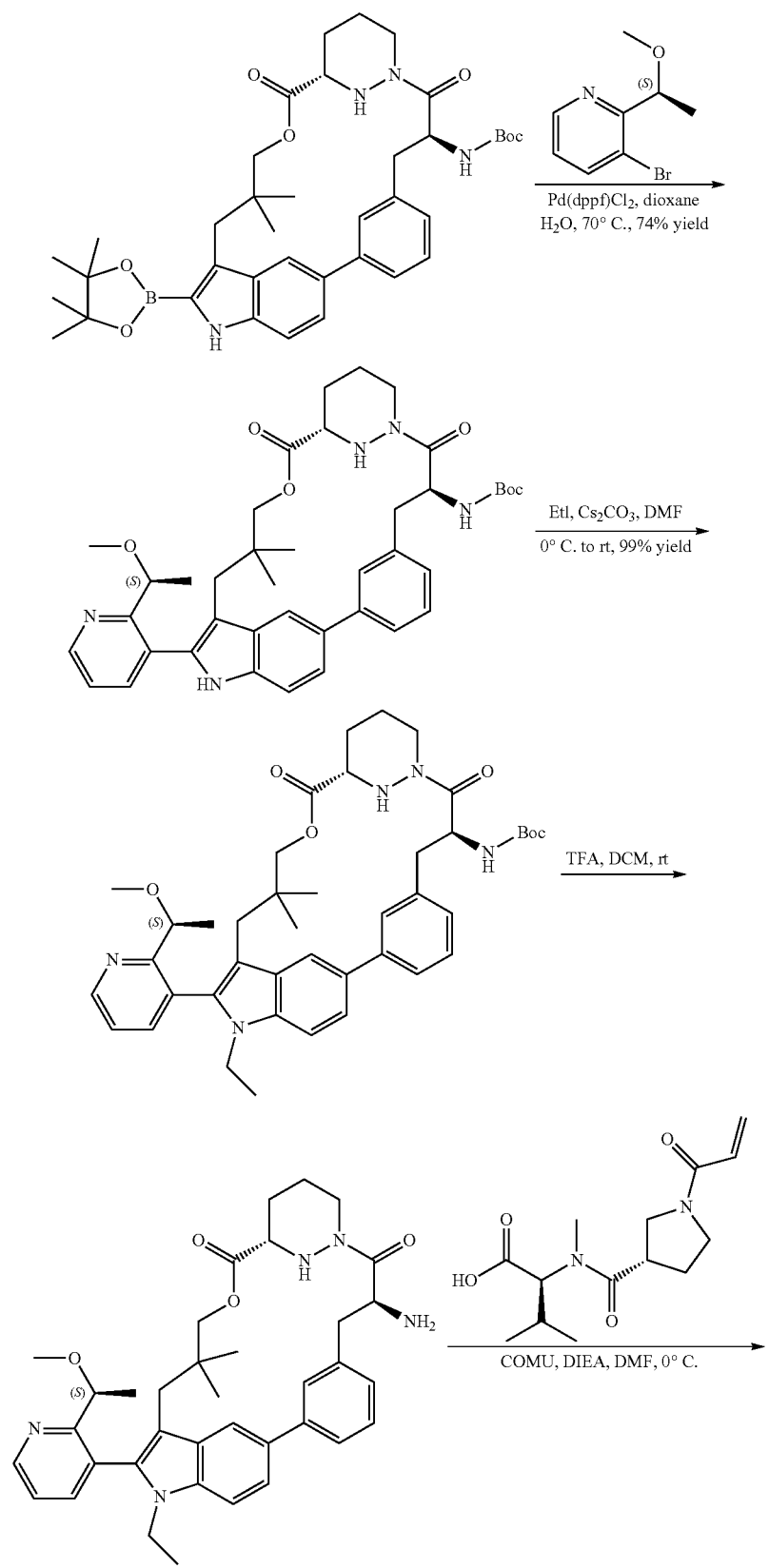

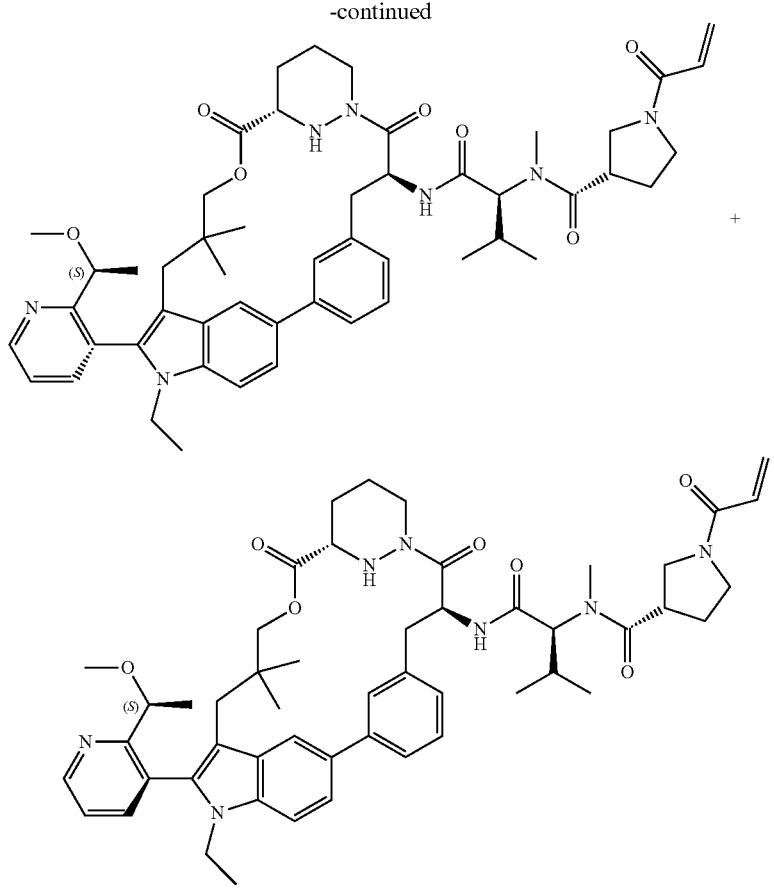

Step 1. A 1 L round-bottom flask was charged with tert-butyl (($6^3$S,4S)-$1^2$-iodo-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl) carbamate (22.00 g, 32.042 mmol, 1.00 equiv), toluene (300.00 mL), Pd$_2$(dba)$_3$ (3.52 g, 3.845 mmol, 0.12 equiv), S-Phos (3.95 g, 9.613 mmol, 0.30 equiv), and KOAc (9.43 g, 96.127 mmol, 3.00 equiv) at room temperature. To the mixture was added 4,4,5,5-tetramethyl-1,3,2-dioxaborolane (26.66 g, 208.275 mmol, 6.50 equiv) dropwise with stirring at room temperature. The resulting solution was stirred for 3 h at 60° C. The resulting mixture was filtered, and the filter cake was washed with EtOAc. The filtrate was concentrated under reduced pressure and the remaining residue was purified by silica gel column chromatography to afford tert-butyl (($6^3$S,4S)-10,10-dimethyl-5,7-dioxo-12-(4,4,5,5-tetramethyl-1,3,2-dioxaborolan-2-yl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (22 g, 90%) as a light yellow solid. ESI-MS m/z=687.3 [M+H]$^+$; Calculated MW: 686.4

Step 2. A mixture of tert-butyl (($6^3$S,4S)-10,10-dimethyl-5,7-dioxo-$1^2$-(4,4,5,5-tetramethyl-1,3,2-dioxaborolan-2-yl)-$6^1$,$6^2$,$6^3$,$6^4$,$6^5$,$6^6$-hexahydro-$1^1$H-8-oxa-1 (5,3)-indola-6(1,3)-pyridazina-2(1,3)-benzenacycloundecaphane-4-yl) carbamate (2.0 g, 2.8 mmol), 3-bromo-2-[(1S)-1-methoxyethyl]pyridine (0.60 g, 2.8 mmol), Pd(dppf)Cl$_2$ (0.39 g, 0.5 mmol), and K$_3$PO$_4$ (1.2 g, 6.0 mmol) in 1,4-dioxane (50 mL) and H$_2$O (10 mL) under an atmosphere of N$_2$ was heated to 70° C. and stirred for 2 h. The mixture was diluted with H$_2$O (50 mL) and extracted with EtOAc (3×50 mL). The combined organic layers were washed with brine (3×50 mL), dried over anhydrous Na$_2$SO$_4$, and filtered. The filtrate was concentrated under reduced pressure and the residue was purified by silica gel column chromatography to give tert-butyl (($6^3$S,4S)-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (1.5 g, 74% yield) as a solid. LCMS (ESI): m/z [M+H] calc'd for C$_{40}$H$_{49}$N$_5$O$_6$ 695.4; found 696.5.

Step 3. A mixture of tert-butyl (($6^3$S,4S)-$1^2$-(2-((S)-1-methoxyethyl)pyridin-3-yl)-10,10-dimethyl-5,7-dioxo-$6^1$, $6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl) carbamate (1.5 g, 2.1 mmol), Cs$_2$CO$_3$ (2.1 g, 6.3 mmol), and ethyl iodide (0.43 mL, 5.1 mmol) in DMF (50 mL) was stirred at 0° C. for 16 h. The mixture was quenched at 0° C. with H$_2$O and extracted with EtOAc (3×50 mL). The combined organic layers were washed with brine (3×50 mL), dried over anhydrous Na$_2$SO$_4$, and filtered. The filtrate was concentrated under reduced pressure and the residue was purified by silica gel column chromatography to give tert-butyl (($6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (1.5 g, 99% yield) as a solid. LCMS (ESI): m/z [M+H] calc'd for C$_{42}$H$_{53}$N$_5$O$_6$ 723.4; found 724.6.

Step 4. A mixture of tert-butyl (($6^3$S,4S)-$1^1$-ethyl-$1^2$-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1 (5,3)-indola-6(1,3)-pyridazina-2(1,3)-benzenacycloundecaphane-4-yl) carbamate (1.3 g, 1.7 mmol) in TFA (10 mL) and DCM (20 mL) was stirred at 0° C. for 2 h. The mixture was concentrated under reduced pressure to afford (6³S,4S)-4-amino-1¹-ethyl-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (1.30 g, crude) as a solid. LCMS (ESI): m/z [M+H] calc'd for $C_{37}H_{45}N_5O_4$ 623.3; found 624.4.

Step 5. Into a 40-mL vial purged and maintained with an inert atmosphere of Ar, was placed (6³S,4S)-4-amino-1¹-ethyl-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (250 mg, 0.4 mmol), (2S)-3-methyl-2-[N-methyl-1-[(3S)-1-(prop-2-enoyl)pyrrolidin-3-yl]formamido]butanoic acid (226 mg, 0.8 mmol), DIPEA (774 mg, 6.0 mmol), and DMF (3 mL). A solution of COMU (257 mg, 0.6 mmol) in DMF (2 mL) was added at 0° C. and the resulting mixture was stirred at 0° C. for 1 h. The mixture was filtered, the filtrate was concentrated under reduced pressure, and the residue was purified by prep-HPLC to give two atropisomers of (2S)—N-[(8S,14S,20P)-22-ethyl-21-{4-[(1 S)-1-methoxyethyl]pyridin-3-yl}-18,18-dimethyl-9,15-dioxo-16-oxa-10,22,28-triazapentacyclo[18.5.2.1²,⁶0.1¹⁰,¹⁴0.0²³,²⁷]nonacosa-1(26),2,4,6(29),20,23(27),24-heptaen-8-yl]-3-methyl-2-{N-methyl-1-[(3S)-1-(prop-2-enoyl)pyrrolidin-3-yl]formamido}butanamide (56 mg, 15% yield) and (46 mg, 13% yield) both as a solid. LCMS (ESI): m/z [M+H] calc'd for $C_{51}H_{65}N_7O_7$ 887.5; found 888.4; ¹H NMR (400 MHz, DMSO-$d_6$) δ 8.81 (s, 1H), 8.07 (s, 1H), 8.05-7.96 (m, 1H), 7.78-7.45 (m, 5H), 7.41-7.08 (m, 2H), 6.66-6.58 (m, 1H), 6.18 (d, J=17.0 Hz, 1H), 5.75-5.67 (m, 1H), 5.46-5.31 (m, 1H), 5.16-5.04 (m, 1H), 4.75 (dd, J=10.9, 4.5 Hz, 1H), 4.31-4.21 (m, 2H), 4.11-3.95 (m, 3H), 3.87-3.71 (m, 5H), 3.74-3.54 (m, 3H), 3.11 (s, 4H), 2.95 (d, J=9.7 Hz, 2H), 2.85-2.72 (m, 3H), 2.31-2.04 (m, 3H), 1.88-1.47 (m, 2H), 1.24-1.21 (m, 3H), 1.16-1.08 (m, 3H), 1.03-0.91 (m, 6H), 0.85-0.74 (m, 3H), 0.51-0.46 (m, 3H) and LCMS (ESI): m/z [M+H] calc'd for $C_{51}H_{65}N_7O_7$ 887.5; found 888.4; ¹H NMR (400 MHz, DMSO-$d_6$) δ 8.77 (s, 1H), 8.71-8.63 (m, 0.5H), 8.23-8.17 (m, 0.5H), 8.00 (s, 1H), 7.85 (t, J=9.9 Hz, 2H), 7.77-7.62 (m, 3H), 7.57-7.50 (m, 1H), 7.33-7.22 (m, 1H), 7.15-7.06 (m, 1H), 6.73-6.56 (m, 1H), 6.17 (ddd, J=16.7, 6.1, 2.7 Hz, 1H), 5.76-5.64 (m, 1H), 5.49-5.29 (m, 2H), 4.70 (dd, J=10.8, 3.5 Hz, 1H), 4.33-4.22 (m, 3H), 4.14-3.95 (m, 2H), 3.86-3.77 (m, 1H), 3.72-3.65 (m, 2H), 3.61 (t, J=10.6 Hz, 3H), 3.46-3.42 (m, 1H), 3.13 (d, J=4.8 Hz, 3H), 2.99 (d, J=14.4 Hz, 1H), 2.95-2.70 (m, 6H), 2.24-1.99 (m, 4H), 1.95-1.44 (m, 4H), 1.40 (d, J=6.1 Hz, 3H), 0.98-0.87 (m, 6H), 0.86-0.64 (m, 6H), 0.64-0.54 (m, 3H).

Example A2. Synthesis of (2S)—N-[(8S,14S)-4-amino-22-ethyl-21-[2-(2-methoxyethyl)phenyl]-18,18-dimethyl-9,15-dioxo-16-oxa-10,22,28-triazapentacyclo[18.5.2.1²,⁶0.1¹⁰,¹⁴0.0²³,²⁷]nonacosa-1(26),2,4,6(29),20,23(27),24-heptaen-8-yl]-3-methyl-2-{N-methyl-1-[(3S)-1-(prop-2-enoyl)pyrrolidin-3-yl]formamido}butanamide

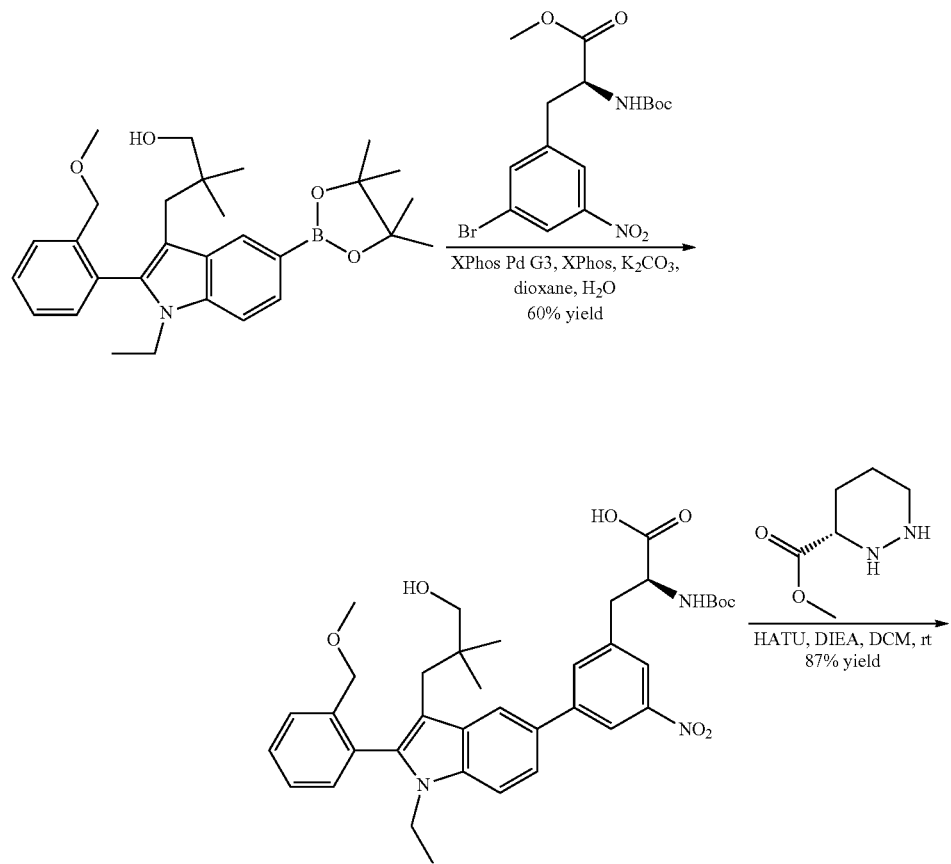

933 934
-continued
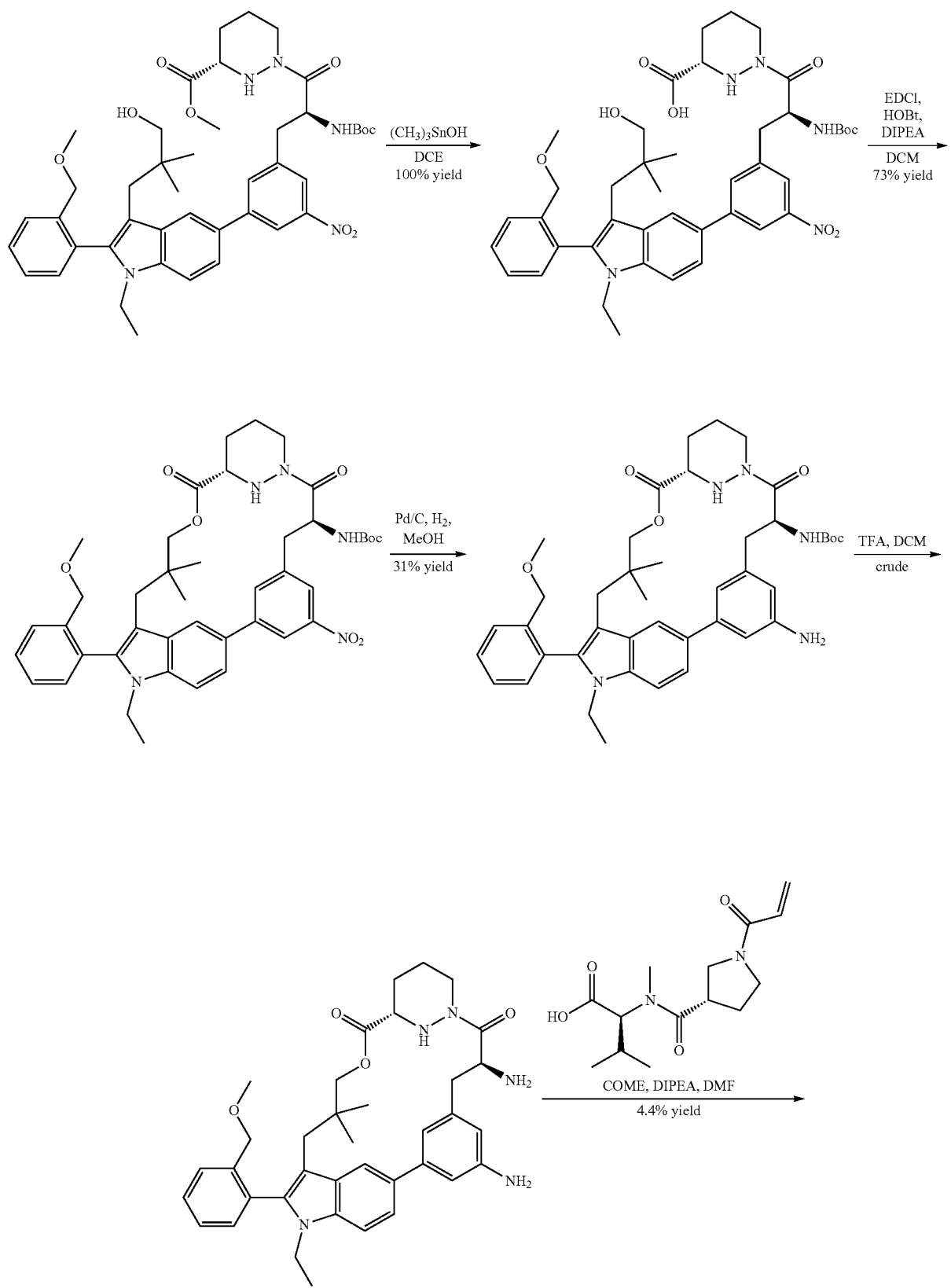

-continued

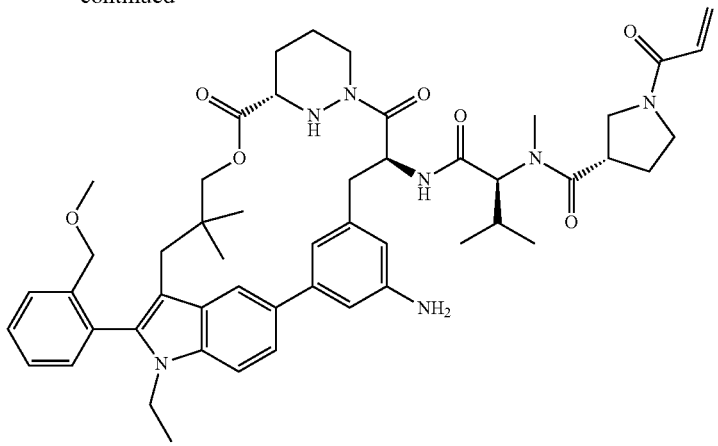

Step 1. Into a 25 mL sealed tube were added 3-[1-ethyl-2-[2-(methoxymethyl)phenyl]-5-(4,4,5,5-tetramethyl-1,3,2-dioxaborolan-2-yl)indol-3-yl]-2,2-dimethylpropan-1-ol (590 mg, 1.2 mmol), methyl (2S)-3-(3-bromo-5-nitrophenyl)-2-[(tert-butoxycarbonyl)amino]propanoate (747 mg, 1.9 mmol), XPhos Pd G3 (105 mg, 0.12 mmol), XPhos (71 mg, 0.15 mmol), $K_2CO_3$ (427 mg, 3.1 mmol), and 1,4-dioxane (2 mL) under an atmosphere of $N_2$ at rt. The mixture was heated to 60° C. and stirred overnight, then cooled and $H_2O$ added. The mixture was extracted with EtOAc (3×20 mL) and the combined organic layers were washed with brine (1×20 mL), dried over anhydrous $Na_2SO_4$, and filtered. The filtrate was concentrated under reduced pressure and the residue was purified by silica gel column chromatography to give (2S)-2-[(tert-butoxycarbonyl)amino]-3-[3-[1-ethyl-3-(3-hydroxy-2,2-dimethylpropyl)-2-[2-(methoxymethyl)phenyl]indol-5-yl]-5-nitrophenyl]propanoic acid (500 mg, 61% yield) as a solid. LCMS (ESI): m/z [M+H] calc'd for $C_{37}H_{45}N_3O_8$ 659.3; found 660.4.

Step 2. A mixture of (2S)-2-[(tert-butoxycarbonyl)amino]-3-[3-[1-ethyl-3-(3-hydroxy-2,2-dimethylpropyl)-2-[2-(methoxymethyl)phenyl]indol-5-yl]-5-nitrophenyl]propanoic acid (500 mg, 0.79 mmol), methyl (3S)-1,2-diazinane-3-carboxylate (164 mg, 1.1 mmol), DCM (6 mL), DIPEA (294 mg, 2.3 mmol) and HATU (432 mg, 1.1 mmol) was stirred at 0° C. for 1 h under an atmosphere of air. $H_2O$ was added and the mixture was extracted with DCM (3×20 mL), then the combined organic layers were dried over anhydrous $Na_2SO_4$, and filtered. The filtrate was concentrated under reduced pressure and the residue was purified by silica gel column chromatography to give methyl (3S)-1-[(2S)-2-[(tert-butoxycarbonyl)amino]-3-[3-[1-ethyl-3-(3-hydroxy-2,2-dimethylpropyl)-2-[2-(methoxymethyl)phenyl]indol-5-yl]-5-nitrophenyl]propanoyl]-1,2-diazinane-3-carboxylate (520 mg, 87% yield) as a solid. LCMS (ESI): m/z [M+H] calc'd for $C_{43}H_{55}N_5O_9$ 785.4; found 786.8.

Step 3. Into a 40 mL sealed tube were added methyl (3S)-1-[(2S)-2-[(tert-butoxycarbonyl)amino]-3-[3-[1-ethyl-3-(3-hydroxy-2,2-dimethylpropyl)-2-[2-(methoxymethyl)phenyl]indol-5-yl]-5-nitrophenyl]propanoyl]-1,2-diazinane-3-carboxylate (510 mg, 0.65 mmol), DCE (5 mL) and trimethyltin hydroxide (587 mg, 3.3 mmol) at rt under an atmosphere of air. The mixture was heated to 60° C. and stirred overnight, cooled, and diluted with DCM (20 mL). The mixture was washed with 0.1 N $KHSO_4$ (3×20 mL), dried over anhydrous $Na_2SO_4$, filtered, and the filtrate was concentrated under reduced pressure to give (3S)-1-[(2S)-2-[(tert-butoxycarbonyl)amino]-3-[3-[1-ethyl-3-(3-hydroxy-2,2-dimethylpropyl)-2-[2-(methoxymethyl)phenyl]indol-5-yl]-5-nitrophenyl]propanoyl]-1,2-diazinane-3-carboxylic acid (500 mg, 100%) as a solid. LCMS (ESI): m/z [M+H] calc'd for $C_{42}H_{53}N_5O_9$ 771.4; found 772.7.

Step 4. A mixture of (3S)-1-[(2S)-2-[(tert-butoxycarbonyl)amino]-3-[3-[1-ethyl-3-(3-hydroxy-2,2-dimethylpropyl)-2-[2-(methoxymethyl)phenyl]indol-5-yl]-5-nitrophenyl]propanoyl]-1,2-diazinane-3-carboxylic acid (490 mg, 0.64 mmol), DCM (100 mL), DIPEA (2.5 g, 19.0 mmol), HOBT (429 mg, 3.2 mmol), and EDCl (3.65 g, 19.0 mmol) at room temperature was stirred at rt overnight under an atmosphere of air. $H_2O$ was added and the mixture was extracted with DCM (3×60 mL), dried over anhydrous $Na_2SO_4$, and filtered. The filtrate was concentrated under reduced pressure and the residue was purified by silica gel column chromatography to give tert-butyl (($6^3$S,4S)-$1^1$-ethyl-$1^2$-(2-(methoxymethyl)phenyl)-10,10-dimethyl-$2^5$-nitro-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (350 mg, 73% yield) as a solid. LCMS (ESI): m/z [M+H] calc'd for $C_{42}H_{51}N_5O_8$ 753.4; found 754.2.

Step 5. A mixture of tert-butyl (($6^3$S,4S)-$1^1$-ethyl-$1^2$-(2-(methoxymethyl)phenyl)-10,10-dimethyl-$2^5$-nitro-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (200 mg, 0.27 mmol), MeOH (4 mL), and Pd on carbon (20 mg) was stirred at rt for 2 h under an atmosphere of $H_2$. The mixture was filtered, the filter cake was washed with MeOH (3×5 mL), and the filtrate was concentrated under reduced pressure to give tert-butyl (($6^3$S,4S)-$2^5$-amino-$1^1$-ethyl-$1^2$-(2-(methoxymethyl)phenyl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (60 mg, 31% yield) as a solid. LCMS (ESI): m/z [M+H] calc'd for $C_{42}H_{53}N_5O_6$ 723.4; found 724.4.

Step 6. Into an 8 mL vial were added tert-butyl (($6^3$S,4S)-$2^5$-amino-$1^1$-ethyl-$1^2$-(2-(methoxymethyl)phenyl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (50 mg, 0.07 mmol), DCM (1 mL), and TFA (158 mg, 1.4 mmol) at 0° C. under an atmosphere of air. The mixture was stirred for at 0° C. for 2 h then concentrated under reduced pressure to give ($6^3$S,4S)-$2^5$,4-diamino-11-ethyl-$1^2$-(2-(methoxymethyl)

phenyl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (45 mg) as a solid, which was used directly in the next step directly without further purification. LCMS (ESI): m/z [M+H] calc'd for $C_{37}H_{45}N_5O_4$ 623.3; found 624.4.

Step 7. Into an 8 mL vial were added (6³S,4S)-2⁵,4-diamino-1¹-ethyl-1²-(2-(methoxymethyl)phenyl)-10,10-dimethyl-6¹,6²,6³,6⁴,6⁵,6⁶-hexahydro-1¹H-8-oxa-1 (5,3)-indola-6(1,3)-pyridazina-2(1,3)-benzenacycloundecaphane-5,7-dione (40 mg, 0.06 mmol), DMF (1 mL), DIPEA (75 mg, 0.58 mmol), and COMU (41 mg, 0.1 mmol) at 0° C. under an atmosphere of air. The mixture was stirred at 0° C. for 1 h, then H₂O added. The mixture was extracted with EtOAc (3×30 mL), the combined organic layers were concentrated under reduced pressure, and purified by prep-HPLC to give (2S)—N-[(8S,14S)-4-amino-22-ethyl-21-[2-(2-methoxyethyl)phenyl]-18,18-dimethyl-9,15-dioxo-16-oxa-10,22,28-triazapentacyclo[18.5.2.1²,⁶0.1¹⁰,¹⁴0.0²³,²⁷]nonacosa-1(26),2,4,6(29),20,23(27),24-heptaen-8-yl]-3-methyl-2-{N-methyl-1-[(3S)-1-(prop-2-enoyl)pyrrolidin-3-yl]formamido}butanamide (2.5 mg, 4.4% yield) as a solid.

LCMS (ESI): m/z [M+H] calc'd for $C_{51}H_{65}N_7O_7$ 887.5; found 888.6; ¹H NMR (400 MHz, DMSO-d₆) δ 8.74-8.55 (m, 1H), 7.89 (d, J=9.6 Hz, 1H), 7.66-7.53 (m, 1H), 7.57-7.47 (m, 6H), 7.32 (t, J=6.4 Hz, 1H), 6.85 (d, J=8.4 Hz, 2H), 6.70-6.55 (m, 1H), 6.24-6.12 (m, 1H), 5.69 (ddd, J=14.8, 8.0, 3.9 Hz, 1H), 5.41 (s, 1H), 5.09-4.80 (m, 2H), 4.26 (d, J=10.1 Hz, 2H), 4.19 (s, 2H), 4.17-4.06 (m, 1H), 4.02 (dd, J=12.0, 3.9 Hz, 1H), 3.92 (d, J=8.0 Hz, 3H), 3.78 (d, J=8.7 Hz, 5H), 3.29 (s, 2H), 3.14 (d, J=1.9 Hz, 1H), 2.98-2.92 (m, 1H), 2.87-2.68 (m, 3H), 2.62 (d, J=12.5 Hz, 3H), 2.15-1.99 (m, 4H), 1.80 (s, 1H), 1.68-1.53 (m, 2H), 1.08 (t, J=7.1 Hz, 1H), 0.98-0.88 (m, 6H), 0.82 (dd, J=23.3, 16.4 Hz, 3H), 0.74 (t, J=7.2 Hz, 3H), 0.44 (s, 2H), 0.43 (s, 3H).

Example A118. Synthesis of (2S)—N-[(7S,13S)-21-ethyl-20-[2-(methoxymethyl)pyridin-3-yl]-17,17-dimethyl-8,14-dioxo-15-oxa-3-thia-9,21,27,28-tetraazapentacyclo[17.5.2.1²,⁵0.1⁹,¹³0.0²²,²⁶]octacosa-1(25),2(28),4,19,22(26),23-hexaen-7-yl]-3-methyl-2-{N-methyl-1-[(3S)-1-(prop-2-enoyl)pyrrolidin-3-yl]formamido}butanamide

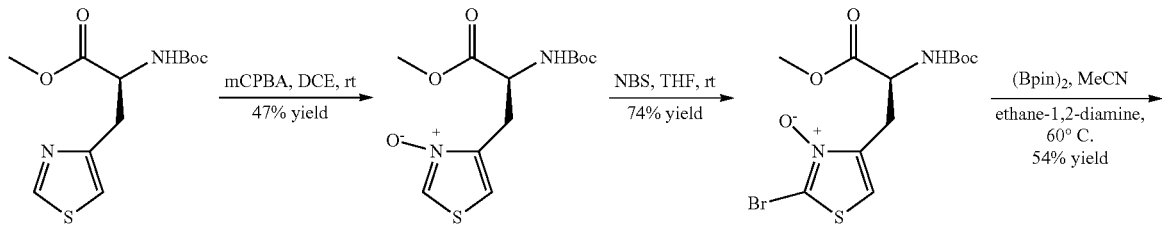

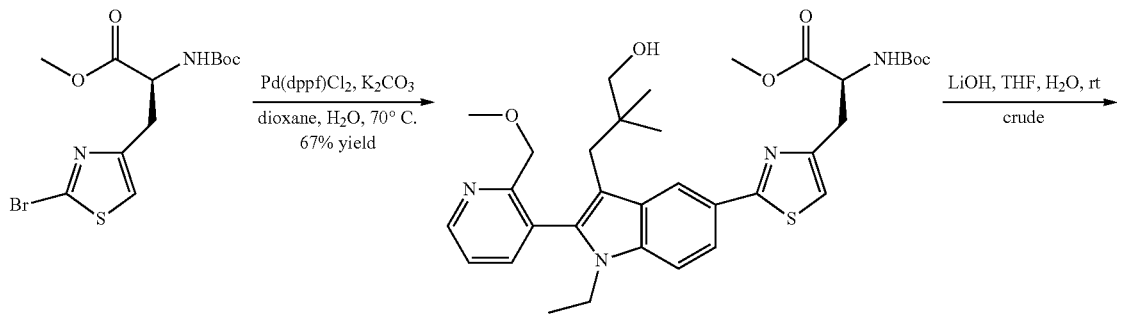

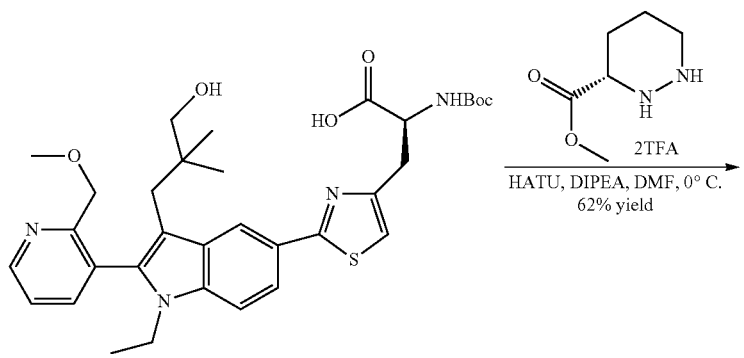

-continued
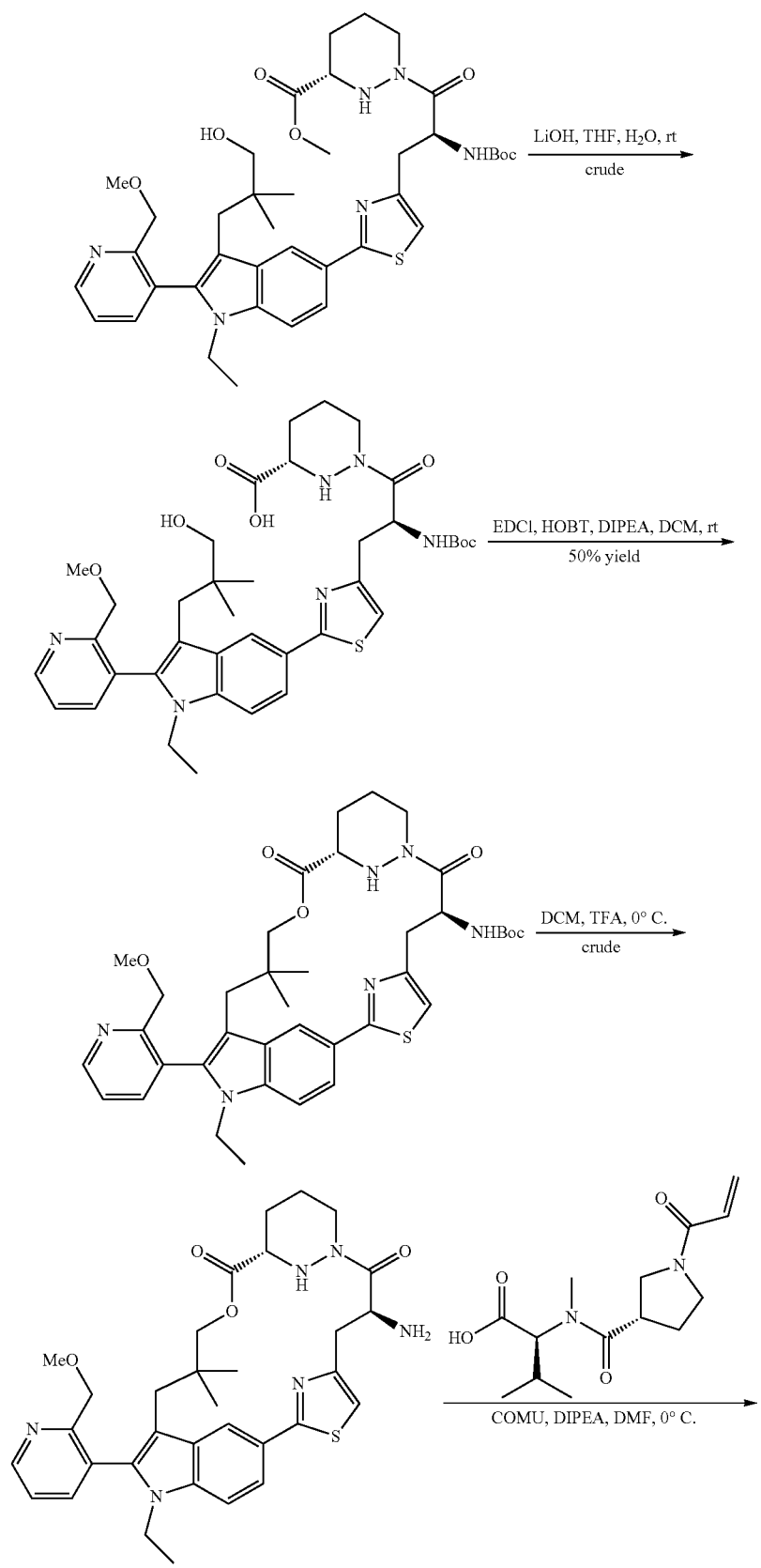

-continued

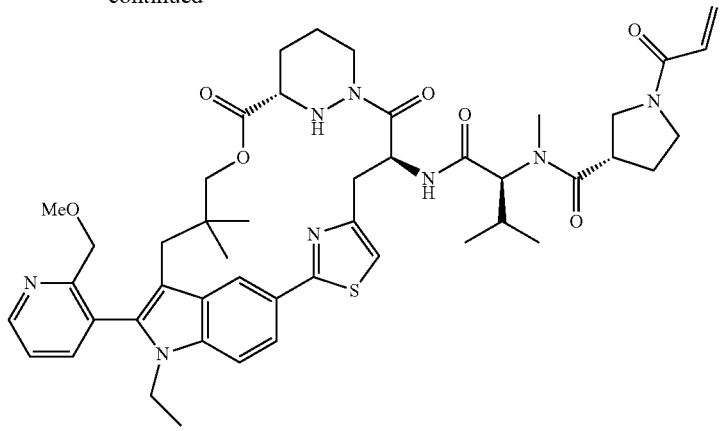

Step 1. A mixture of methyl (2S)-2-[(tert-butoxycarbonyl)amino]-3-(1,3-thiazol-4-yl)propanoate (2.08 g, 7.26 mmol) and mCPBA (1.88 g, 10.9 mmol) in DCE (15 mL) at 0° C. under an atmosphere of $N_2$ was diluted with DCM (100 mL). The mixture was allowed to warm to rt and stirred for 16 h, then diluted with DCM, washed with $H_2O$ (1×30 mL), dried over anhydrous $Na_2SO_4$, and filtered. The filtrate was concentrated under reduced pressure and the residue was purified by silica gel column chromatography to give 4-[(2S)-2-[(tert-butoxycarbonyl)amino]-3-methoxy-3-oxopropyl]-1,3-thiazol-3-ium-3-olate (1.15 g, 47% yield) as a solid. LCMS (ESI): m/z [M+H] calc'd for $C_{12}H_{18}N_2O_5S$ 302.1; found 303.2.

Step 2. To a mixture of 4-[(2S)-2-[(tert-butoxycarbonyl)amino]-3-methoxy-3-oxopropyl]-1,3-thiazol-3-ium-3-olate (1.15 g, 3.8 mmol) in THF at 0° C. under an atmosphere of $N_2$ was added NBS (0.74 g, 4.2 mmol) dropwise. The mixture was allowed to warm to rt and stirred for 2 h, then diluted with $H_2O$ (500 mL) and extracted with EtOAc (3×500 mL). The combined organic layers were washed with water (2×30 mL), dried over anhydrous $Na_2SO_4$, and filtered. The filtrate was concentrated under reduced pressure and the residue was purified by silica gel column chromatography to give 2-bromo-4-[(2S)-2-[(tert-butoxycarbonyl)amino]-3-methoxy-3-oxopropyl]-1,3-thiazol-3-ium-3-olate (1.2 g, 74% yield) as a solid. LCMS (ESI): m/z [M+H] calc'd for $C_{12}H_{17}BrN_2O_5S$ 380.0; found 381.0.

Step 3. To a stirred mixture of 2-bromo-4-[(2S)-2-[(tert-butoxycarbonyl)amino]-3-methoxy-3-oxopropyl]-1,3-thiazol-3-ium-3-olate (1.2 g, 3.2 mmol) and 4,4,5,5-tetramethyl-2-(tetramethyl-1,3,2-dioxaborolan-2-yl)-1,3,2-dioxaborolane (1.04 g, 4.1 mmol) in MeCN at 70° C. under an atmosphere of $N_2$ was added ethane-1,2-diamine (1.89 g, 31.5 mmol) in portions. The mixture was cooled to 60° C. and the mixture was stirred overnight, then diluted with water (500 mL) and extracted with EtOAc (3×400 mL). The combined organic layers were washed with brine (1×50 mL), dried over anhydrous $Na_2SO_4$, and filtered. The filtrate was concentrated under reduced pressure and the residue was purified by silica gel column chromatography to give methyl (2S)-3-(2-bromo-1,3-thiazol-4-yl)-2-[(tert-butoxycarbonyl)amino]propanoate (653 mg, 54% yield) as a solid.

Step 4. A 50 mL sealed tube was charged with 3-[1-ethyl-2-[2-(methoxymethyl)pyridin-3-yl]-5-(4,4,5,5-tetramethyl-1,3,2-dioxaborolan-2-yl)indol-3-yl]-2,2-dimethylpropan-1-ol (1.00 g, 2.1 mmol), $K_2CO_3$ (727 mg, 5.2 mmol), Pd(dppf)$Cl_2$ (153 mg, 0.21 mmol), and 2,4-dibromo-1,3-thiazole (1.0 g, 4.2 mmol) at rt under an atmosphere of $N_2$, then 1,4-dioxane (1.0 mL) and $H_2O$ (0.20 mL) were added. The mixture was heated to 70° C. and stirred for 4 h, then cooled, diluted with $H_2O$ (100 mL) and extracted with EtOAc (3×100 mL). The combined organic layers were washed with brine (3×100 mL), dried over anhydrous $Na_2SO_4$, and filtered. The filtrate was concentrated under reduced pressure and the residue was purified by silica gel column chromatography to give 3-[5-(4-bromo-1,3-thiazol-2-yl)-1-ethyl-2-[2-(methoxymethyl)pyridin-3-yl]indol-3-yl]-2,2-dimethylpropan-1-ol (727 mg, 67% yield) as a solid. LCMS (ESI): m/z [M+H] calc'd for $C_{34}H_{44}N_4O_6S$ 636.3; found 637.3.

Step 5. To a stirred mixture of methyl (2S)-2-[(tert-butoxycarbonyl)amino]-3-[2-[1-ethyl-3-(3-hydroxy-2,2-dimethylpropyl)-2-[2-(methoxymethyl)pyridin-3-yl]indol-5-yl]-1,3-thiazol-4-yl]propanoate (636 mg, 1.0 mmol) and LiOH·$H_2O$ (126 mg, 3.0 mmol) in THF at 0° C. under an atmosphere of $N_2$ was added $H_2O$ (1.24 mL) portionwise. The mixture was allowed to warm to rt and stirred for 1 h, then diluted with water (300 mL) and extracted with EtOAc (3×300 mL). The combined organic layers were washed with brine (1×100 mL), dried over anhydrous $Na_2SO_4$, filtered, and the filtrate concentrated under reduced pressure to give (2S)-2-[(tert-butoxycarbonyl)amino]-3-[2-[1-ethyl-3-(3-hydroxy-2,2-dimethylpropyl)-2-[2-(methoxymethyl)pyridin-3-yl]indol-5-yl]-1,3-thiazol-4-yl]propanoic acid (622 mg, crude), which was used in the next step directly without further purification. LCMS (ESI): m/z [M+H] calc'd for $C_{33}H_{42}N_4O_6S$ 622.3; found 623.2.

Step 6. To a stirred mixture of (2S)-2-[(tert-butoxycarbonyl)amino]-3-[2-[1-ethyl-3-(3-hydroxy-2,2-dimethylpropyl)-2-[2-(methoxymethyl)pyridin-3-yl]indol-5-yl]-1,3-thiazol-4-yl]propanoic acid (622 mg, 1.0 mmol) and methyl (3S)-1,2-diazinane-3-carboxylate (288 mg, 2.0 mmol) in DMF at 0° C. under an atmosphere of $N_2$ was added HATU (570 mg, 1.5 mmol). The mixture was stirred at 0° C. for 1 h, then diluted with EtOAc and washed with $H_2O$ (1×10 mL), dried over anhydrous $Na_2SO_4$, filtered, and the filtrate concentrated under reduced pressure to give methyl (3S)-1-[(2S)-2-[(tert-butoxycarbonyl)amino]-3-[2-[1-ethyl-3-(3-hydroxy-2,2-dimethylpropyl)-2-[2-(methoxymethyl)pyridin-3-yl]indol-5-yl]-1,3-thiazol-4-yl]propanoyl]-1,2-diazinane-3-carboxylate (550 mg, 62% yield) as a solid. LCMS (ESI): m/z [M+H] calc'd for $C_{39}H_{52}N_6O_7S$ 748.4; found 749.6.

Step 7. (3S)-1-[(2S)-2-[(tert-butoxycarbonyl)amino]-3-[2-[1-ethyl-3-(3-hydroxy-2,2-dimethylpropyl)-2-[2-(methoxymethyl)pyridin-3-yl]indol-5-yl]-1,3-thiazol-4-yl]propanoyl]-1,2-diazinane-3-carboxylic acid was synthesized in a manner similar to (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylic acid except methyl (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylate was substituted with methyl (3S)-1-[(2S)-2-[(tert-butoxycarbonyl)amino]-3-[2-[1-ethyl-3-(3-hydroxy-2,2-dimethylpropyl)-2-[2-(methoxymethyl)pyridin-3-yl]indol-5-yl]-1,3-thiazol-4-yl]propanoyl]-1,2-diazinane-3-carboxylate. LCMS (ESI): m/z [M+H] calc'd for $C_{38}H_{50}N_6O_7S$ 734.3; found 735.3.

Step 8. tert-butyl ((6³S,4S,2)-1¹-ethyl-1²-(2-(methoxymethyl)pyridin-3-yl)-10,10-dimethyl-5,7-dioxo-6¹,6²,6³,6⁴,6⁵,6⁶-hexahydro-1¹H-8-oxa-2(2,4)-thiazola-1(5,3)-indola-6(1,3)-pyridazinacycloundecaphane-4-yl)carbamate was synthesized in a manner similar to tert-butyl ((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate except (3S)-1-[(2S)-2-[(tert-butoxycarbonyl)amino]-3-[3-[1-ethyl-3-(3-hydroxy-2,2-dimethylpropyl)-2-[2-[(1 S)-1-methoxyethyl]pyridin-3-yl]indol-5-yl]-5-[(triisopropylsilyl)oxy]phenyl]propanoyl]-1,2-diazinane-3-carboxylic acid was substituted with (3S)-1-[(2S)-2-[(tert-butoxycarbonyl)amino]-3-[2-[1-ethyl-3-(3-hydroxy-2,2-dimethylpropyl)-2-[2-(methoxymethyl)pyridin-3-yl]indol-5-yl]-1,3-thiazol-4-yl]propanoyl]-1,2-diazinane-3-carboxylic acid. LCMS (ESI): m/z [M+H] calc'd for $C_{38}H_{48}N_6O_6S$ 716.3; found 717.4.

Step 9. To a stirred mixture of tert-butyl ((6³S,4S,Z)-1¹-ethyl-1²-(2-(methoxymethyl)pyridin-3-yl)-10,10-dimethyl-5,7-dioxo-6¹,6²,6³,6⁴,6⁵,6⁶-hexahydro-1¹H-8-oxa-2(2,4)-thiazola-1(5,3)-indola-6(1,3)- pyridazinacycloundecaphane-4-yl)carbamate (253 mg) in DCM at 0° C. under an atmosphere of N₂ was added TFA (1.0 mL) dropwise. The mixture was stirred at 0° C. for 1 h, then concentrated under reduced pressure and then repeated using toluene (20 mL×3) to give (6³S,4S,Z)-4-amino-1¹-ethyl-1²-(2-(methoxymethyl)pyridin-3-yl)-10,10-dimethyl-6¹,6²,6³,6⁴,6⁵,6⁶-hexahydro-1¹H-8-oxa-2(2,4)-thiazola-1(5,3)-indola-6(1,3)-pyridazinacycloundecaphane-5,7-dione (253 mg, crude) as a solid. LCMS (ESI): m/z [M+H] calc'd for $C_{33}H_{40}N_6O_4S$ 616.3; found 617.3.

Step 10. (2S)—N-[(7S,13S)-21-ethyl-20-[2-(methoxymethyl)pyridin-3-yl]-17,17-dimethyl-8,14-dioxo-15-oxa-3-thia-9,21,27,28-tetraazapentacyclo[17.5.2.1²,⁵0.1⁹,¹³0.0²²,²⁶]octacosa-1(25),2(28),4,19,22(26),23-hexaen-7-yl]-3-methyl-2-{N-methyl-1-[(3S)-1-(prop-2-enoyl)pyrrolidin-3-yl]formamido}butanamide was synthesized in a manner similar to (2S)—N-[(8S,14S)-4-amino-22-ethyl-21-[2-(2-methoxyethyl)phenyl]-18,18-dimethyl-9,15-dioxo-16-oxa-10,22,28-triazapentacyclo[18.5.2.1²,⁶0.1¹⁰,¹⁴0.0²³,²⁷]nonacosa-1(26),2,4,6(29),20,23(27),24-heptaen-8-yl]-3-methyl-2-{N-methyl-1-[(3S)-1-(prop-2-enoyl)pyrrolidin-3-yl]formamido}butanamide except (6³S,4S)-4-amino-1¹-ethyl-2⁵-hydroxy-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione was substituted with (6³S,4S,Z)-4-amino-1¹-ethyl-1²-(2-(methoxymethyl)pyridin-3-yl)-10,10-dimethyl-6¹,6²,6³,6⁴,6⁵,6⁶-hexahydro-1¹H-8-oxa-2(2,4)-thiazola-1(5,3)-indola-6(1,3)-pyridazinacycloundecaphane-5,7-dione. LCMS (ESI): m/z [M+H] calc'd for $C_{47}H_{60}N_8O_7S$ 880.4; found 881.6; ¹H NMR (400 MHz, DMSO-d₆) δ 8.75 (m, 1H), 8.55 (d, J=6.7 Hz, 1H), 8.32 (d, J=8.3 Hz, 1H), 7.99 (d, J=7.7 Hz, 1H), 7.65-7.51 (m, 3H), 7.11-6.92 (m, 1H), 6.72-6.56 (m, 1H), 6.18 (dd, J=16.8, 2.9 Hz, 1H), 5.82-5.65 (m, 1H), 5.61-5.46 (m, 1H), 5.02 (dd, J=24.2, 12.2 Hz, 1H), 4.69 (d, J=10.9 Hz, 1H), 4.37-4.11 (m, 5H), 4.05-3.79 (m, 4H), 3.76-3.50 (m, 6H), 3.47 (s, 2H), 3.08 (s, 3H), 3.04 (s, 1H), 2.98 (d, J=1.9 Hz, 1H), 2.95 (d, J=3.6 Hz, 2H), 2.83 (d, J=2.0 Hz, 2H), 2.24-2.03 (m, 4H), 1.81 (s, 2H), 1.56 (s, 1H), 1.11 (t, J=7.0 Hz, 2H), 1.02-0.87 (m, 8H), 0.80 (dd, J=24.6, 6.6 Hz, 3H), 0.41 (s, 2H), 0.31 (s, 1H).

Example A194. Synthesis of (2S)—N-[(7S,13S)-21-ethyl-20-[2-(methoxymethyl)pyridin-3-yl]-17,17-dimethyl-8,14-dioxo-15-oxa-4-thia-9,21,27,28-tetraazapentacyclo[17.5.2.1²,⁵0.1⁹,¹³0.0²²,²⁶]octacosa-1(25),2,5(28),19,22(26),23-hexaen-7-yl]-3-methyl-2-{N-methyl-1-[(3S)-1-(prop-2-enoyl)pyrrolidin-3-yl]formamido}butanamide

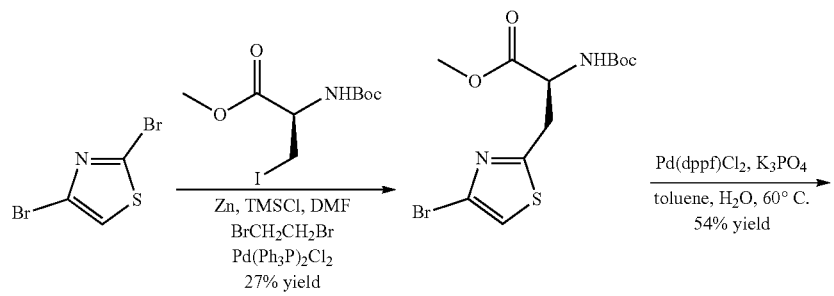

-continued
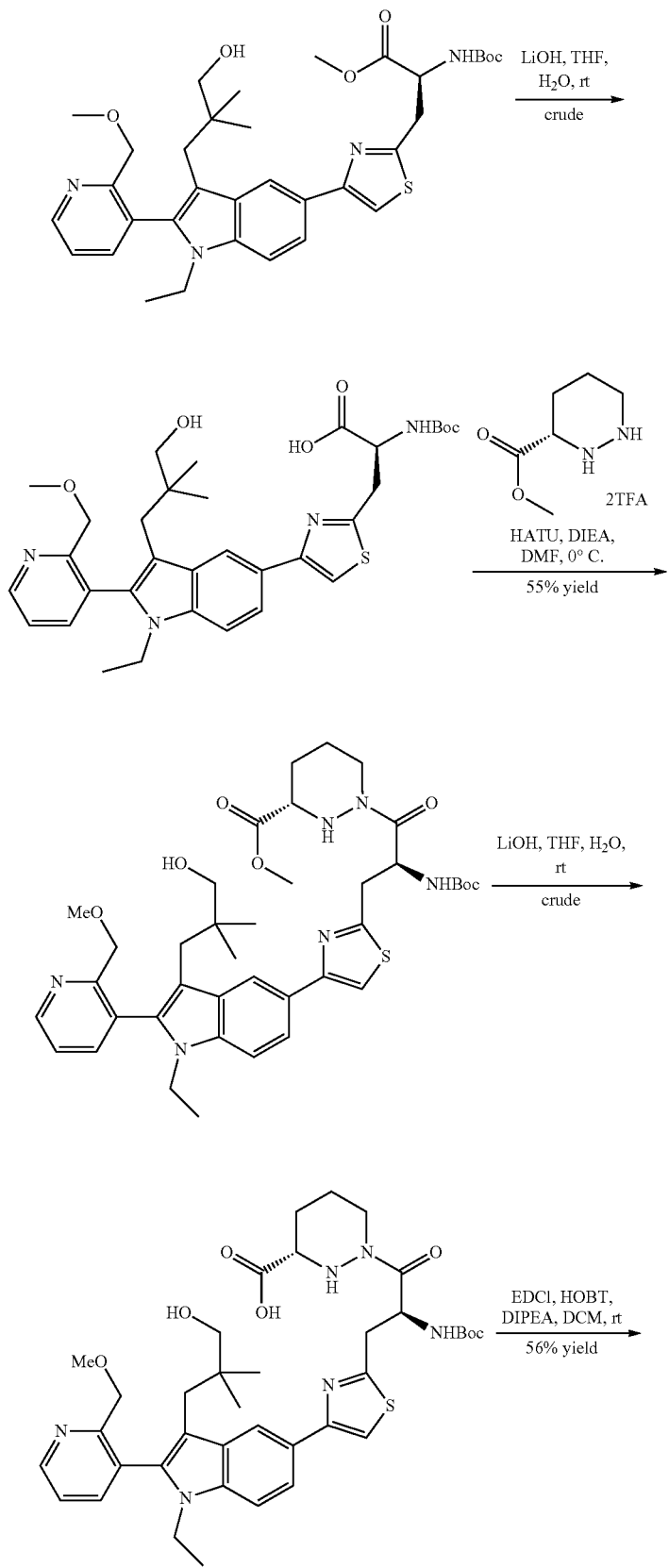

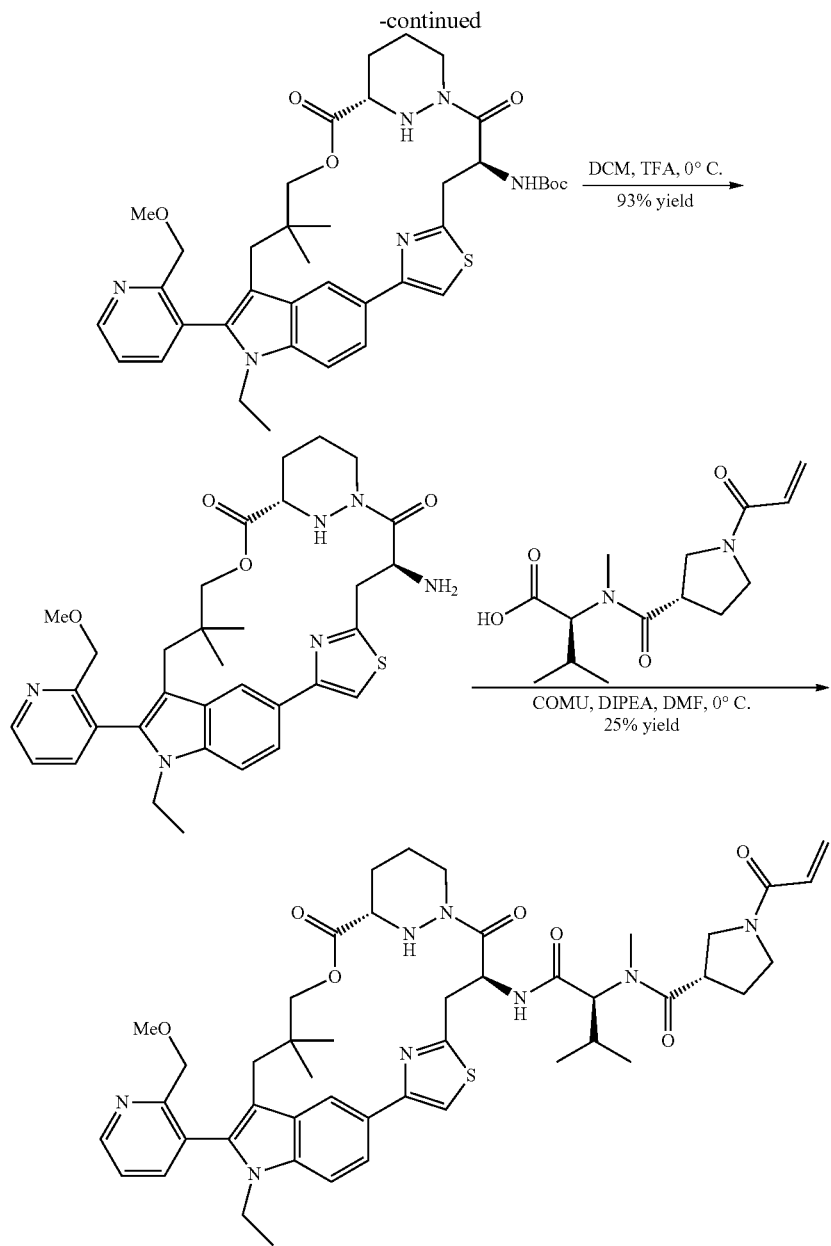

Step 1. A mixture of Zn (1.2 g, 182 mmol) and 1,2-dibromoethane (1.71 g, 9.1 mmol) and DMF (50 mL) was stirred for 30 min at 90° C. under an atmosphere of Ar. The mixture was allowed to rt, then TMSCl (198 mg, 1.8 mmol) was added dropwise over 30 min at rt. Methyl (2R)-2-[(tert-butoxycarbonyl) amino]-3-iodopropanoate (10.0 g, 30.4 mmol) in DMF (100 mL) was added dropwise over 10 min at rt. The mixture was heated to 35° C. and stirred for 2 h, then a mixture of 2,5-dibromo-1,3-thiazole (1.48 g, 60.8 mmol) and Pd(PPh$_3$)$_2$Cl$_2$ (2.1 g, 3.0 mmol) in DMF (100 mL) was added dropwise. The mixture was heated to 70° C. and stirred for 2 h, then filtered and the filtrate diluted with EtOAc (1 L) and washed with H$_2$O (3×1 L), dried with anhydrous Na$_2$SO$_4$, and filtered. The filtrate was concentrated under reduced pressure and the residue was purified by silica gel column chromatography to give methyl (2S)-3-(5-bromo-1,3-thiazol-2-yl)-2-[(tert-butoxycarbonyl) amino]propanoate (3 g, 27% yield) as a semi-solid. LCMS (ESI): m/z [M+H] calc'd for C$_{12}$H$_{17}$BrN$_2$O$_4$S 364.0; found 365.1.

Step 2. Into a 20 mL sealed tube were added 3-[1-ethyl-2-[2-(methoxymethyl)pyridin-3-yl]-5-(4,4,5,5-tetramethyl-1,3,2-dioxaborolan-2-yl)indol-3-yl]-2,2-dimethylpropan-1-ol (100 mg, 0.21 mmol), K$_3$PO$_4$ (111 mg, 0.52 mmol), Pd(dppf)Cl$_2$ (15 mg, 0.02 mmol), methyl (2S)-3-(4-bromo-1,3-thiazol-2-yl)-2-[(tert-butoxycarbonyl)amino]propanoate (153 mg, 0.42 mmol), toluene (1 mL), and H$_2$O (0.2 mL) at rt under an atmosphere of N$_2$. The mixture was heated to 60° C. and stirred for 3 h, cooled, diluted with H$_2$O (10 mL) and extracted with EtOAc (10 mL×3). The combined organic layers were washed with brine (3×10 mL), dried over anhydrous Na$_2$SO$_4$, and filtered. The filtrate was concentrated under reduced pressure and the residue was purified by silica gel column chromatography to give methyl (2S)-

2-[(tert-butoxycarbonyl)amino]-3-[4-[1-ethyl-3-(3-hydroxy-2,2-dimethylpropyl)-2-[2-(methoxymethyl)pyridin-3-yl]indol-5-yl]-1,3-thiazol-2-yl]propanoate (72 mg, 54% yield) as a solid. LCMS (ESI): m/z [M+H] calc'd for $C_{34}H_{44}N_4O_6S$ 636.3; found 637.2.

Step 3. A mixture of methyl (2S)-2-[(tert-butoxycarbonyl)amino]-3-[4-[1-ethyl-3-(3-hydroxy-2,2-dimethylpropyl)-2-[2-(methoxymethyl)pyridin-3-yl]indol-5-yl]-1,3-thiazol-2-yl]propanoate (40 mg, 0.06 mmol) and LiOH·H$_2$O (unspecified) in THF (1 mL) and H$_2$O (0.2 mL) was stirred at rt under an atmosphere of N$_2$ for 2 h. The mixture was acidified to pH 5 with aqueous NaHSO$_4$ and extracted with EtOAc (3×10 mL). The combined organic layers were washed with brine (3×10 mL), dried over anhydrous Na$_2$SO$_4$, filtered, and concentrated under reduced pressure to give (2S)-2-((tert-butoxycarbonyl)amino)-3-(4-(1-ethyl-3-(3-hydroxy-2,2-dimethylpropyl)-2-(2-(methoxymethyl)pyridin-3-yl)-1H-indol-5-yl)thiazol-2-yl)propanoic acid. The crude product was used in the next step directly without further purification. LCMS (ESI): m/z [M+H] calc'd for $C_{33}H_{42}N_4O_6S$ 622.3; found 623.3.

Step 4. Methyl (3S)-1-((2S)-2-((tert-butoxycarbonyl)amino)-3-(4-(1-ethyl-3-(3-hydroxy-2,2-dimethylpropyl)-2-(2-(methoxymethyl)pyridin-3-yl)-1H-indol-5-yl)thiazol-2-yl)propanoyl)hexahydropyridazine-3-carboxylate was synthesized in a manner similar to methyl (3S)-1-[(2S)-2-[(tert-butoxycarbonyl)amino]-3-[2-[1-ethyl-3-(3-hydroxy-2,2-dimethylpropyl)-2-[2-(methoxymethyl)pyridin-3-yl]indol-5-yl]-1,3-thiazol-4-yl]propanoyl]-1,2-diazinane-3-carboxylate except (2S)-2-[(tert-butoxycarbonyl)amino]-3-[2-[1-ethyl-3-(3-hydroxy-2,2-dimethylpropyl)-2-[2-(methoxymethyl)pyridin-3-yl]indol-5-yl]-1,3-thiazol-4-yl] propanoic acid was substituted with (2S)-2-((tert-butoxycarbonyl)amino)-3-(4-(1-ethyl-3-(3-hydroxy-2,2-dimethylpropyl)-2-(2-(methoxymethyl)pyridin-3-yl)-1H-indol-5-yl)thiazol-2-yl)propanoic acid. LCMS (ESI): m/z [M+H] calc'd for $C_{39}H_{52}N_6O_7S$ 748.4; found 749.4.

Step 5. (3S)-1-[(2S)-2-[(tert-butoxycarbonyl)amino]-3-[4-[1-ethyl-3-(3-hydroxy-2,2-dimethylpropyl)-2-[2-(methoxymethyl)pyridin-3-yl]indol-5-yl]-1,3-thiazol-2-yl]propanoyl]-1,2-diazinane-3-carboxylic acid was synthesized in a manner similar to (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylic acid except methyl (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylate was substituted with methyl (3S)-1-((2S)-2-((tert-butoxycarbonyl)amino)-3-(4-(1-ethyl-3-(3-hydroxy-2,2-dimethylpropyl)-2-(2-(methoxymethyl)pyridin-3-yl)-1H-indol-5-yl)thiazol-2-yl)propanoyl)hexahydropyridazine-3-carboxylate. LCMS (ESI): m/z [M+H] calc'd for $C_{38}H_{50}N_6O_7S$ 734.3; found 735.4.

Step 6. Tert-butyl ((6$^3$S,4S,Z)-1$^1$-ethyl-12-(2-(methoxymethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate was synthesized in a manner similar to tert-butyl ((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl) carbamate except (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-[(triisopropylsilyl)oxy]phenyl]propanoyl]-1,2-diazinane-3-carboxylic acid was substituted with (3S)-1-[(2S)-2-[(tert-butoxycarbonyl)amino]-3-[4-[1-ethyl-3-(3-hydroxy-2,2-dimethylpropyl)-2-[2-(methoxymethyl)pyridin-3-yl]indol-5-yl]-1,3-thiazol-2-yl]propanoyl]-1,2-diazinane-3-carboxylic acid. LCMS (ESI): m/z [M+H] calc'd for $C_{38}H_{48}N_6O_6S$ 716.3; found 717.3.

Step 7. (6$^3$S,4S,Z)-4-amino-1$^1$-ethyl-1$^2$-(2-(methoxymethyl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione was synthesized in a manner similar to (6$^3$S,4S)-4-amino-1$^1$-ethyl-1$^2$-(2-(methoxymethyl)pyridin-3-yl)-10,10-dimethyl-6$^1$,6$^2$,6$^3$,6$^4$,6$^5$,6$^6$-hexahydro-1$^1$H-8-oxa-2(2,4)-thiazola-1(5,3)-indola-6(1,3)-pyridazinacycloundecaphane-5,7-dione except tert-butyl ((6$^3$S,4S,Z)-1$^1$-ethyl-1$^2$-(2-(methoxymethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(2,4)-thiazola-1(5,3)-indola-6(1,3)-pyridazinacycloundecaphane-4-yl)carbamate was substituted with tert-butyl ((6$^3$S,4S,Z)-1$^1$-ethyl-12-(2-(methoxymethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl) carbamate. LCMS (ESI): m/z [M+Na] calc'd for $C_{33}H_{40}N_6O_4SNa$ 639.3; found 640.3.

Step 8. (2S)—N-[(7S,13S)-21-ethyl-20-[2-(methoxymethyl)pyridin-3-yl]-17,17-dimethyl-8,14-dioxo-15-oxa-4-thia-9,21,27,28-tetraazapentacyclo[17.5.2.1$^{2,5}$0.1$^{9,3}$0.0$^{22,26}$]octacosa-1(25),2,5(28),19,22(26),23-hexaen-7-yl]-3-methyl-2-{N-methyl-1-[(3S)-1-(prop-2-enoyl)pyrrolidin-3-yl]formamido}butanamide was synthesized in a manner similar to (2S)—N-[(7S,13S)-21-ethyl-20-[2-(methoxymethyl)pyridin-3-yl]-17,17-dimethyl-8,14-dioxo-15-oxa-3-thia-9,21,27,28-tetraazapentacyclo[17.5.2.1$^{2,5}$0.1$^{9,13}$0.0$^{22,26}$]octacosa-1(25),2(28),4,19,22(26),23-hexaen-7-yl]-3-methyl-2-{N-methyl-1-[(3S)-1-(prop-2-enoyl)pyrrolidin-3-yl]formamido}butanamide except (6$^3$S,4S)-4-amino-1$^1$-ethyl-2$^5$-hydroxy-1$^2$-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane- 5,7-dione was substituted with (6$^3$S,4S,Z)-4-amino-1$^1$-ethyl-1$^2$-(2-(methoxymethyl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione. LCMS (ESI): m/z [M+H] calc'd for $C_{47}H_{60}N_8O_7S$ 880.4; found 881.5; $^1$H NMR (400 MHz, DMSO-d$_6$) δ 8.70 (dt, J=16.2, 8.1 Hz, 1H), 8.54 (ddd, J=6.6, 4.7, 1.7 Hz, 1H), 8.50 (m, 1H), 7.96 (d, J=7.8 Hz, 1H), 7.88 (t, J=2.1 Hz, 2H), 6.70-6.57 (m, 2H), 6.24-6.13 (m, 2H), 5.75 (m, 1H), 5.55 (t, J=7.3 Hz, 1H), 5.46 (d, J=8.5 Hz, 1H), 5.14 (d, J=13.0 Hz, 1H), 4.84-4.75 (m, 1H), 4.35 (d, J=10.7 Hz, 1H), 4.28-4.19 (m, 4H), 3.91 (s, 3H), 3.87 (dd, J=10.4, 8.1 Hz, 1H), 3.78-3.70 (m, 2H), 3.63 (t, J=8.8 Hz, 2H), 3.61-3.49 (m, 2H), 2.87 (d, J=1.1 Hz, 2H), 2.79 (s, 1H), 2.38 (s, 1H), 2.18 (s, 1H), 2.13 (d, J=10.7 Hz, 4H), 1.96 (s, 2H), 1.81 (s, 1H), 1.53 (s, 2H), 1.11 (t, J=7.1 Hz, 2H), 0.99-0.89 (m, 7H), 0.93-0.81 (m, 2H), 0.78 (d, J=6.6 Hz, 2H), 0.28 (s, 3H).

Example A71. Synthesis of (2S)-2-(1-{1-[(2E)-4-(dimethylamino)but-2-enoyl]azetidin-3-yl}-N-methylformamido)-N-[(8S,14S)-22-ethyl-4-hydroxy-21-[2-(methoxymethyl)pyridin-3-yl]-18,18-dimethyl-9,15-dioxo-16-oxa-10,22,28-triazapentacyclo[18.5.2.1$^{2,6}$.0.1$^{10,14}$.0.0$^{23,27}$]nonacosa-1(26),2,4,6(29),20,23(27),24-heptaen-8-yl]-3-methylbutanamide

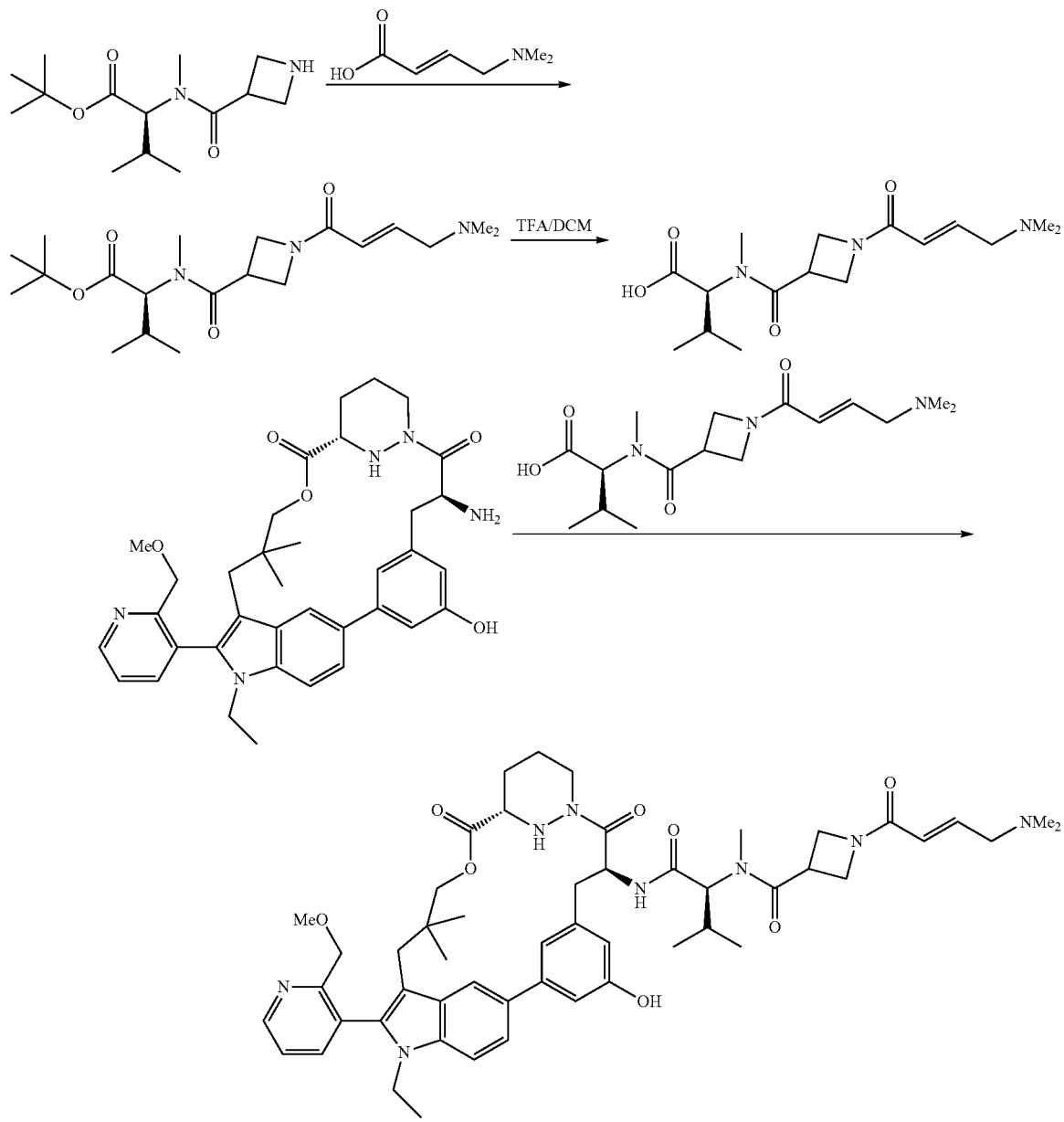

Step 1. To a mixture of tert-butyl N-(azetidine-3-carbonyl)-N-methyl-L-valinate (350 mg, 1.3 mmol) and (2E)-4-(dimethylamino)but-2-enoic acid (201 mg, 1.56 mmol) in DCM (8 mL) at 5° C. was added a solution of T3P, 50% in EtOAc (827 mg, 2.6 mmol) and DIPEA (1.7 g, 13 mmol) in DCM (2 mL). The mixture was stirred for 1 h, then diluted with EtOAc (20 mL) and H$_2$O (20 mL). The aqueous and organic layers were separated and the organic layer was washed with H$_2$O (3×10 mL), brine (10 mL), dried over anhydrous Na$_2$SO$_4$, and filtered. The filtrate was concentrated under reduced pressure and the residue was purified by prep-HPLC to give tert-butyl (E)-N-(1-(4-(dimethylamino)but-2-enoyl)azetidine-3-carbonyl)-N-methyl-L-valinate (200 mg, 39% yield) as a solid. LCMS (ESI): m/z [M+H] calc'd for C$_{20}$H$_{35}$N$_3$O$_4$ 381.3; found 382.3.

Step 2. To a mixture of tert-butyl (E)-N-(1-(4-(dimethylamino)but-2-enoyl)azetidine-3-carbonyl)-N-methyl-L-valinate (190 mg, 0.32 mmol) in DCM (3 mL) at rt was added TFA (1 mL). The mixture was stirred at rt for 1 h, then concentrated under reduced pressure to give (E)-N-(1-(4-(dimethylamino)but-2-enoyl)azetidine-3-carbonyl)-N-methyl-L-valine (190 mg, 90%) as a solid, which was used directly in the next step without further purification. LCMS (ESI): m/z [M+H] calc'd for $C_{16}H_{27}N_3O_4$ 325.2; found 326.2.

Step 3. To a mixture of $(6^3S,4S)$-4-amino-$1^1$-ethyl-$2^5$-hydroxy-$1^2$-(2-(methoxymethyl)pyridin-3-yl)-10,10-dimethyl-$6^1,6^2,6^3,6^4,6^5,6^6$-hexahydro-$1^1H$-8-oxa-1 (5,3)-indola-6(1,3)-pyridazina-2(1,3)-benzenacycloundecaphane-5,7-dione (172 mg, 0.27 mmol) and (E)-N-(1-(4-(dimethylamino)but-2-enoyl)azetidine-3-carbonyl)-N-methyl-L-valine (105 mg, 0.32 mmol) in DMF (2 mL) at 5° C. was added a mixture of HATU (133 mg, 0.297 mmol) and DIPEA (348 mg, 2.7 mmol) in DMF (1 mL). The mixture was stirred for 1 h, then diluted with EtOAc (20 mL) and $H_2O$ (20 mL). The aqueous and organic layers were separated, and the organic layer was washed with $H_2O$ (3×10 mL), brine (10 mL), dried over anhydrous $Na_2SO_4$, and filtered. The filtrate was concentrated under reduced pressure and the residue was purified by prep-TLC to give (2S)-2-(1-{1-[(2E)-4-(dimethylamino)but-2-enoyl]azetidin-3-yl}-N-methylformamido)-N-[(8S,14S)-22-ethyl-4-hydroxy-21-[2-(methoxymethyl)pyridin-3-yl]-18,18-dimethyl-9,15-dioxo-16-oxa-10,22,28-triazapentacyclo[$18.5.2.1^2,^60.1^{10,14}0.0^{23,27}$]nonacosa-1(26),2,4,6(29),20,23(27),24-heptaen-8-yl]-3-methylbutanamide (4.8 mg, 2% yield over 2 steps) as a solid. LCMS (ESI): m/z [M+H] calc'd for $C_{52}H_{68}N_8O_8$ 932.5; found 933.5; $^1$H NMR (400 MHz, $CD_3OD$) δ 8.71 (d, J=3.2 Hz, 1H), 8.50 (s, 1.5H), 8.08-7.85 (m, 2H), 7.65-7.44 (m, 3H), 7.32-7.14 (m, 1H), 7.07-6.95 (m, 1H), 6.80 (dt, J=22.1, 6.8 Hz, 1H), 6.55 (d, J=35.8 Hz, 1H), 6.30 (d, J=15.4 Hz, 1H), 5.56 (dd, J=13.8, 6.7 Hz, 1H), 4.76 (dd, J=19.8, 10.5 Hz, 1H), 4.54 (dd, J=15.9, 7.5 Hz, 2H), 4.48-4.38 (m, 2H), 4.36-4.23 (m, 3H), 4.22-4.14 (m, 1H), 3.96 (qd, J=15.6, 7.9 Hz, 3H), 3.77 (ddd, J=25.8, 23.4, 11.9 Hz, 2H), 3.58 (dd, J=17.2, 8.3 Hz, 2H), 3.38 (s, 2H), 3.25-3.11 (m, 3H), 3.05-2.94 (m, 1H), 2.94-2.81 (m, 4H), 2.73 (dd, J=20.9, 11.0 Hz, 1H), 2.45 (d, J=6.9 Hz, 5H), 2.32-2.07 (m, 3H), 1.92 (d, J=13.2 Hz, 1H), 1.72 (s, 1H), 1.64-1.51 (m, 1H), 1.18 (t, J=7.0 Hz, 2H), 1.00 (ddd, J=14.6, 11.8, 8.5 Hz, 6H), 0.92-0.81 (m, 4H), 0.55-0.41 (m, 3H).

Example A67. Synthesis of (2E)-4-(dimethylamino)-N-(6-{[(1S)-1-{[(8S,14S)-22-ethyl-4-hydroxy-21-[2-(methoxymethyl)pyridin-3-yl]-18,18-dimethyl-9,15-dioxo-16-oxa-10,22,28-triazapentacyclo[$18.5.2.1^2,^60.1^{10,14}0.0^{23,27}$]nonacosa-1(26),2,4,6(29),20,23(27),24-heptaen-8-yl]carbamoyl}-2-methylpropyl](methyl)carbamoyl}pyridin-3-yl)but-2-enamide

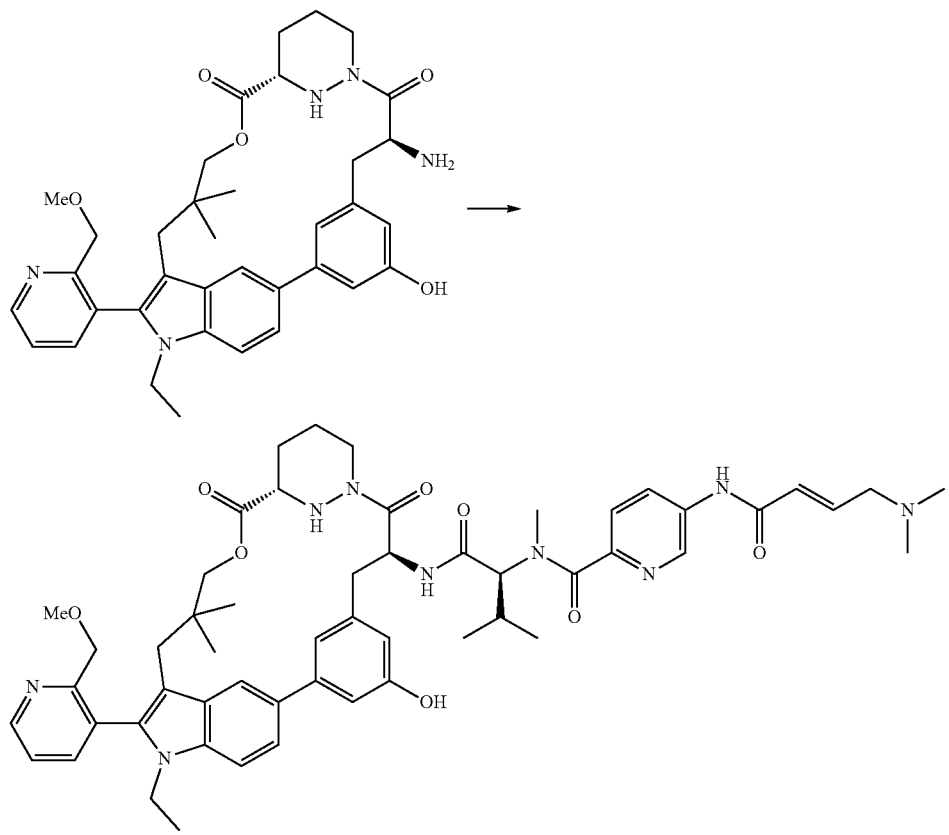

Step 1. To a mixture of $(6^3S,4S)$-4-amino-$1^1$-ethyl-$2^5$-hydroxy-$1^2$-(2-(methoxymethyl)pyridin-3-yl)-10,10-dimethyl-$6^1,6^2,6^3,6^4,6^5,6^6$-hexahydro-$1^1H$-8-oxa-1(5,3)-indola-6(1,3)-pyridazina-2(1,3)-benzenacycloundecaphane-5,7-dione TFA salt (225 mg, 0.28 mmol) and (E)-N-(5-(4-(dimethylamino)but-2-enamido)picolinoyl)-N-methyl-L-valine TFA salt (260 mg crude, 0.56 mmol) in DMF (5 mL)

at 0° C. were added DIPEA (0.46 mL, 2.8 mmol) followed by HATU (140 mg, 0.36 mmol). The mixture was stirred at 0-10° C. for 1 h, then concentrated under reduced pressure and the residue was purified by prep-HPLC to give (2E)-4-(dimethylamino)-N-(6-{[(1S)-1-{[(8S,14S)-22-ethyl-4-hydroxy-21-[2-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]carbamoyl}-2-methylpropyl](methyl)carbamoyl}pyridin-3-yl)but-2-enamide TFA salt (23.3 mg, 8% yield over 2 steps) as a solid. LCMS (ESI): m/z [M+Na] calc'd for $C_{54}H_{67}N_9O_8Na$ 992.5; found 992.4; $^1$H NMR (400 MHz, CD$_3$OD) δ 9.05 (d, J=2.5 Hz, 1H), 8.85-8.71 (m, 1H), 8.43 (ddd, J=33.3, 18.0, 2.6 Hz, 2H), 8.01-7.87 (m, 2H), 7.83-7.70 (m, 1H), 7.60-7.47 (m, 2H), 7.31-7.19 (m, 1H), 7.07-6.90 (m, 2H), 6.70-6.36 (m, 3H), 5.81-5.61 (m, 1H), 4.50-4.20 (m, 4H), 4.01-3.68 (m, 3H), 3.64-3.35 (m, 5H), 3.27-3.08 (m, 3H), 3.04-2.44 (m, 11H), 2.36-2.10 (m, 3H), 1.93 (d, J=13.0 Hz, 1H), 1.61 (dd, J=34.3, 21.6 Hz, 3H), 1.39-1.16 (m, 3H), 1.12-0.81 (m, 6H), 0.78-0.45 (m, 6H).

Example A54. Synthesis of (2S)-2-{1-[(3S)-1-[(2E)-4-(dimethylamino)but-2-enoyl]pyrrolidin-3-yl]-N-methylformamido}-N-[(8S,14S)-22-ethyl-4-hydroxy-21-[2-(methoxymethyl)pyridin-3-yl]-18,18-dimethyl-9,15-dioxo-16-oxa-10,22,28-triazapentacyclo[18.5.2.1$^{2,6}$0.1$^{10,14}$0.0$^{23,27}$]nonacosa-1(26),2,4,6(29),20,23(27),24-heptaen-8-yl]-3-methylbutanamide

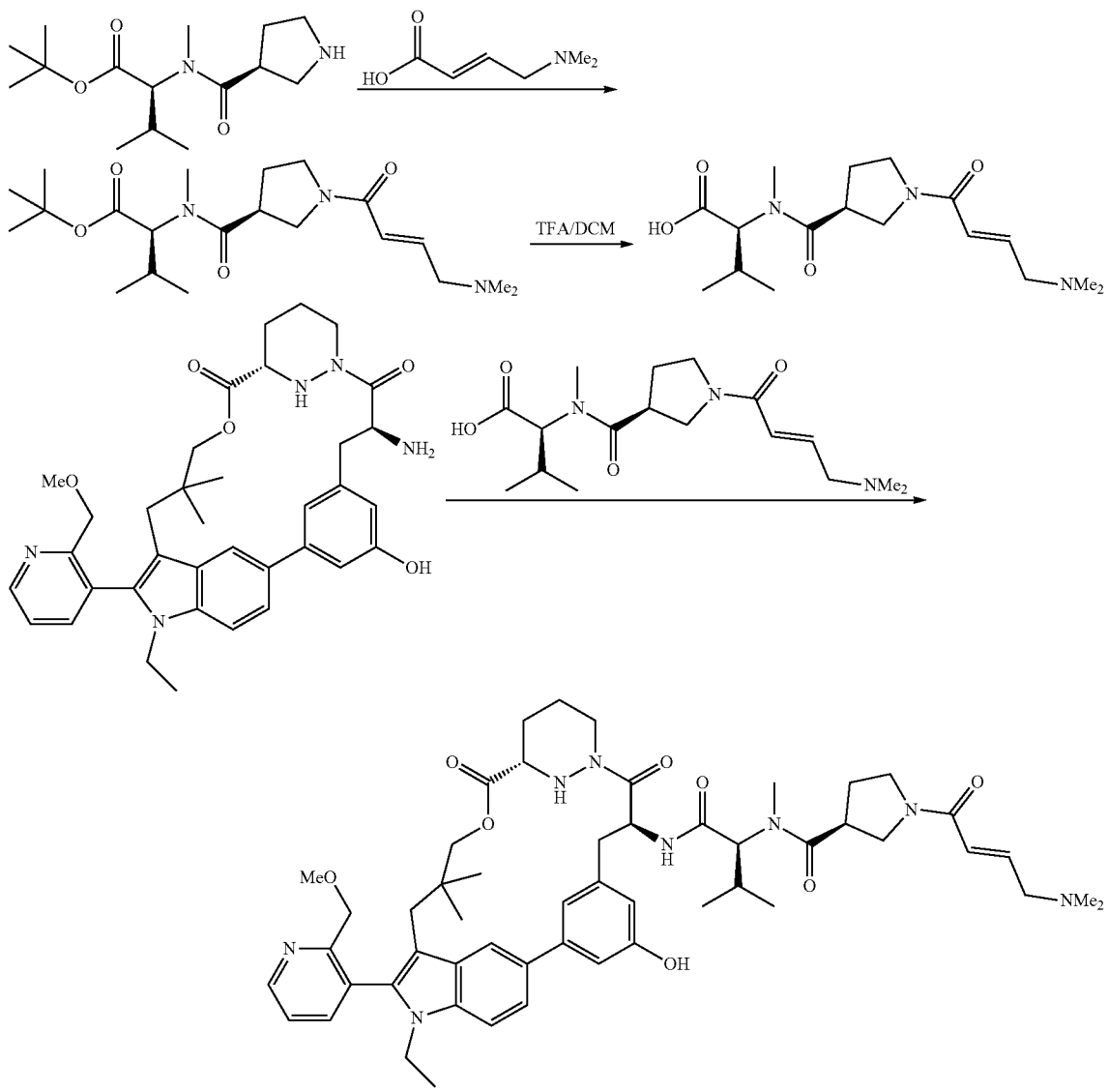

Step 1. To a mixture of tert-butyl N-methyl-N—((S)-pyrrolidine-3-carbonyl)-L-valinate (210 mg, 0.73 mmol) in DMF (4 mL) at rt were added 4-(dimethylamino)-4-methylpent-2-ynoic acid (450 mg, 2.9 mmol), DIPEA (1.2 mL, 7.3 mmol), and HATU (332 mg, 0.88 mmol). The mixture was stirred at rt for 1 h then diluted with EtOAc, and the mixture washed with H$_2$O, brine, dried over Na$_2$SO$_4$, and filtered. The filtrate was concentrated under reduced pressure and the residue was purified by silica gel column chromatography to give tert-butyl N—((S)-1-(4-(dimethylamino)-4-methylpent-2-ynoyl)pyrrolidine-3-carbonyl)-N- methyl-L-valinate (140 mg, 45% yield) as an oil. LCMS (ESI): m/z [M+H] calc'd for $C_{23}H_{39}N_3O_4$ 421.3; found 422.3.

Step 2. A mixture of tert-butyl N—((S)-1-(4-(dimethylamino)-4-methylpent-2-ynoyl)pyrrolidine-3-carbonyl)-N-methyl-L-valinate (130 mg, 0.31 mmol) in DCM (2 mL) and TFA (1 mL) was stirred at rt for 90 min. The mixture was concentrated under reduced pressure to give N—((S)-1-(4-(dimethylamino)-4-methylpent-2-ynoyl)pyrrolidine-3-carbonyl)-N-methyl-L-valine TFA salt (150 mg) as an oil, which was used directly in the next step without further purification. LCMS (ESI): m/z [M+H] calc'd for $C_{19}H_{31}N_3O_4$ 365.2; found 366.2.

Step 3. (3S)-1-(4-(dimethylamino)-4-methylpent-2-ynoyl)-N-((2S)-1-(((6³S,4S)-1¹-ethyl-2⁵-hydroxy-1²-(2-(methoxymethyl)pyridin-3-yl)-10,10-dimethyl-5,7-dioxo-6¹,6²,6³,6⁴,6⁵,6⁶-hexahydro-1¹H-8-oxa-1 (5,3)-indola-6(1,3)-pyridazina-2(1,3)-benzenacycloundecaphane-4-yl)amino)-3-methyl-1-oxobutan-2-yl)-N-methylpyrrolidine-3-carboxamide TFA salt was synthesized in a manner similar to 1-acryloyl-N-((2S)-1-(((6³S,4S)-1¹-ethyl-2⁵-hydroxy-1²-(2-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methylazetidine-3-carboxamide except (2S)-2-{1-[(3S)-1-[(2E)-4-(dimethylamino)but-2-enoyl]pyrrolidin-3-yl]-N-methylformamido}-N-[(8S,14S)-22-ethyl-4-hydroxy-21-[2-(methoxymethyl)pyridin-3-yl]-18,18-dimethyl-9,15-dioxo-16-oxa-10,22,28-triazapentacyclo[18.5.2.1²,⁶0.1¹⁰,¹⁴0.0²³,²⁷]nonacosa-1(26),2,4,6(29),20,23(27),24-heptaen-8-yl]-3-methylbutanamide TFA salt. (120 mg, 54% yield over 2 steps) as a solid. ¹H-NMR (400 MHz, CD₃OD) δ 8.76-8.68 (m, 1H), 8.44 (s, 1H), 8.02-7.94 (m, 1H), 7.94-7.84 (m, 1H), 7.65-7.43 (m, 3H), 7.27-7.14 (m, 1H), 7.06-6.96 (m, 1H), 6.65-6.48 (m, 1H), 5.62-5.46 (m, 1H), 4.81-4.57 (m, 1H), 4.46-4.22 (m, 3H), 4.10-3.35 (m, 11H), 3.26-2.93 (m, 6H), 2.91-2.51 (m, 4H), 2.42-2.09 (m, 9H), 1.95-1.87 (m, 1H), 1.85-1.40 (m, 6H), 1.38-1.10 (m, 6H), 1.07-0.81 (m, 9H), 0.56-0.38 (m, 3H). LCMS (ESI): m/z [M+H] $C_{52}H_{68}N_8O_8$ found 947.7.

Example A95. Synthesis of (2S)—N-[(8S,14S)-22-ethyl-4-hydroxy-21-[2-(methoxymethyl)pyridin-3-yl]-18,18-dimethyl-9,15-dioxo-16-oxa-10,22,28-triazapentacyclo[18.5.2.1²,⁶0.1¹,¹⁴0.0²³,²⁷]nonacosa-1(26),2,4,6(29),20,23(27),24-heptaen-8-yl]-3-methyl-2-{N-methyl-1-[(3S)-1-[4-(morpholin-4-yl)but-2-ynoyl]pyrrolidin-3-yl]formamido}butanamide

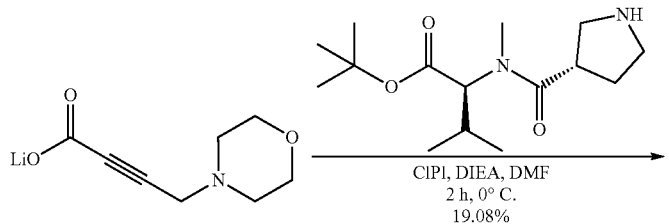

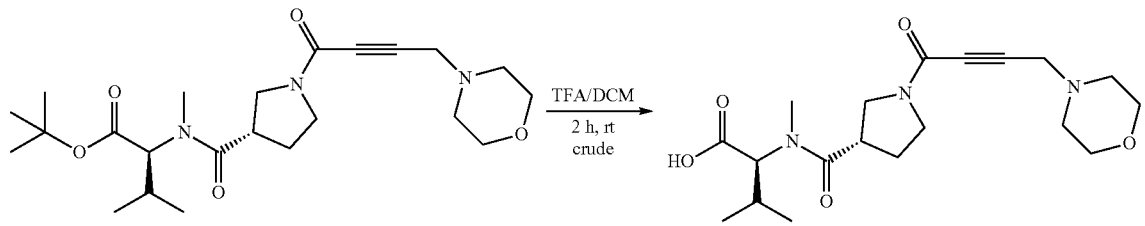

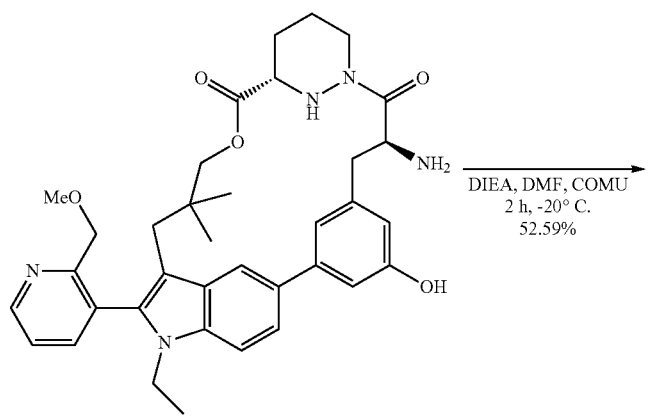

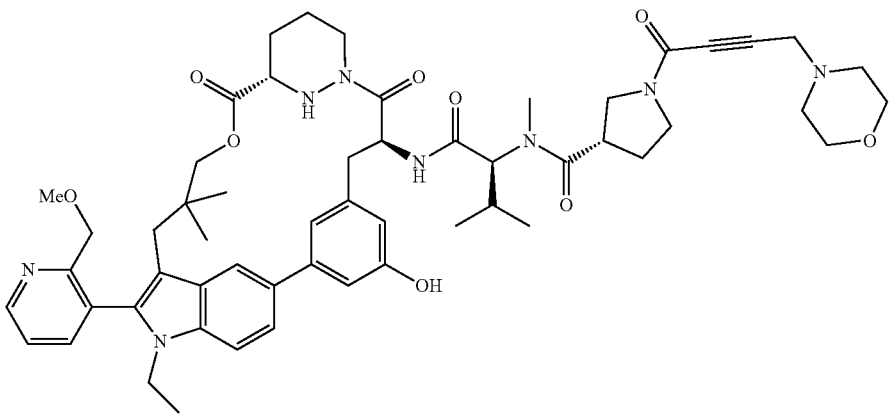

Step 1. A mixture of tert-butyl (2S)-3-methyl-2-[N-methyl-1-(3S)-pyrrolidin-3-ylformamido]butanoate (500 mg, 1.8 mmol), 4-(morpholin-4-yl)but-2-ynoic acid (1.49 g, 8.8 mmol), DIPEA (682 mg, 5.3 mmol) and CIP (635 mg, 2.3 mmol) in DMF (5 mL) was stirred at 0° C. for 2 h. The mixture was concentrated under reduced pressure and the residue was purified by silica gel column chromatography to give tert-butyl N-methyl-N—((S)-1-(4-morpholinobut-2-ynoyl)pyrrolidine-3-carbonyl)-L-valinate (150 mg, 19% yield) as an oil. LCMS (ESI): m/z [M+H] calc'd for $C_{23}H_{37}N_3O_5$ 435.3; found 436.5.

Step 2. A mixture of tert-butyl N-methyl-N—((S)-1-(4-morpholinobut-2-ynoyl)pyrrolidine-3-carbonyl)-L-valinate (250 mg, 0.57 mmol) in DCM (5 mL) and TFA (2.5 mL) was stirred at rt for 2 h. The mixture was concentrated under reduced pressure to give (2S)-3-methyl-2-[N-methyl-1-[(3S)-1-[4-(morpholin-4-yl)but-2-ynoyl]pyrrolidin-3-yl]formamido]butanoic acid (310 mg, crude) as an oil, which was used directly in the next step without further purification. LCMS (ESI): m/z [M+H] calc'd for $C_{19}H_{29}N_3O_5$ 379.2; found 380.2.

Step 3. A mixture of $(6^3S,4S)$-4-amino-$1^1$-ethyl-$2^5$-hydroxy-$1^2$-(2-(methoxymethyl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione (250 mg, 0.4 mmol), DIPEA (516 mg, 4.0 mmol), (2S)-3-methyl-2-[N-methyl-1-[(3S)-1-[4-(morpholin-4-yl)but-2-ynoyl]pyrrolidin-3-yl]formamido]butanoic acid (182 mg, 0.48 mmol), and COMU (205 mg, 0.48 mmol) in DMF (3 mL) was stirred at −20° C. for 2 h. The mixture was diluted with $H_2O$ (10 mL), then extracted with EtOAc (3×10 mL) and the combined organic layers were washed with brine (3×10 mL), dried over anhydrous $Na_2SO_4$, and filtered. The mixture was concentrated under reduced pressure and the residue was purified by reverse-phase silica gel column chromatography to give (2S)—N-[(8S,14S)-22-ethyl-4-hydroxy-21-[2-(methoxymethyl)pyridin-3-yl]-18,18-dimethyl-9,15-dioxo-16-oxa-10,22,28-triazapentacyclo[18.5.2.$1^2,^6$0.$1^{10,14}$0.$0^{23,27}$]nonacosa-1(26),2,4,6(29),20,23(27),24-heptaen-8-yl]-3-methyl-2-{N-methyl-1-[(3S)-1-[4-(morpholin-4-yl)but-2-ynoyl]pyrrolidin-3-yl]formamido}butanamide (207 mg, 53% yield) as a solid. LCMS (ESI): m/z [M+H] calc'd for $C_{55}H_{70}N_8O_9$ 986.5; found 987.8; $^1$H NMR (400 MHz, DMSO-$d_6$) δ 9.39-9.28 (m, 1H), 8.74 (t, J=4.8, 1H), 8.70-8.04 (m, 1H), 7.98-7.90 (m, 1.5H), 7.82 (d, J=7.7 Hz, 0.5H), 7.63-7.46 (m, 3H), 7.26-7.10 (m, 1H), 7.03 (s, 1H), 6.58-6.43 (m, 1H), 5.44-5.30 (m, 1H), 5.06 (q, 0.5H), 4.72 (t, J=11.0, 0.5H), 4.39-4.20 (m, 3H), 4.15 (d, J=11.1 Hz, 1H), 4.09-3.85 (m, 4H), 3.66 (s, 2H), 3.65-3.58 (m, 4H), 3.58-3.55 (m, 2H), 3.55-3.48 (m, 3H), 3.47-3.41 (m, 3H), 3.31 (s, 2H), 3.10 (s, 2H), 2.92 (s, 1H), 2.89-2.65 (m, 5H), 2.68 (s, 1H), 2.45-2.38 (m, 1H), 2.29-2.24 (m, 1H), 2.23-1.99 (m, 3H), 1.82 (d, J=12.1 Hz, 1H), 1.76-1.62 (m, 1H), 1.61-1.45 (m, 1H), 1.14-1.04 (m, 2H), 1.02-0.92 (m, 3H), 0.91-0.86 (m, 3H), 0.83-0.77 (m, 3H), 0.77-0.70 (m, 2H), 0.50-0.35 (m, 3H).

Example A145. Synthesis of two atropisomers of (2S)-2-{1-[(3S)-1-(but-2-ynoyl)pyrrolidin-3-yl]-N-methylformamido}-N-[(8S,14S,20M)-22-ethyl-4-hydroxy-21-{2-[(1S)-1-methoxyethyl]pyridin-3-yl}-18,18-dimethyl-9,15-dioxo-16-oxa-10,22,28-triazapentacyclo[18.5.2.$1^2,^6$0.$1^{10,14}$0.$0^{23,27}$]nonacosa-1(26),2,4,6(29),20,23(27),24-heptaen-8-yl]-3-methylbutanamide

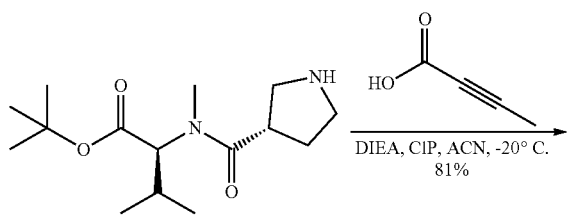

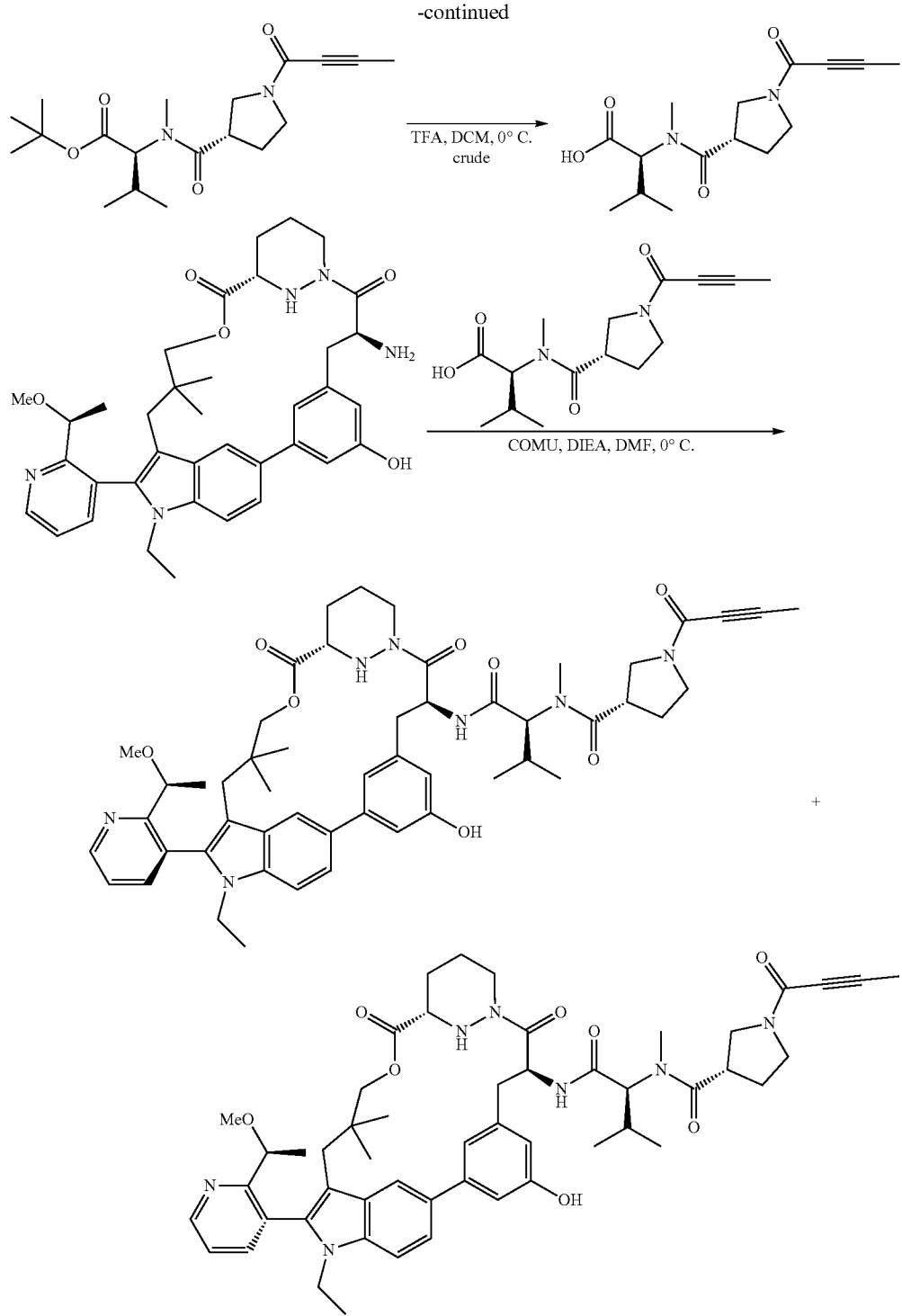

Step 1. To a mixture of but-2-ynoic acid (222 mg) and CIP (588 mg) in ACN (8 mL) at 0° C. under an atmosphere of Ar was added DIPEA (681 mg). The mixture was stirred at 0° C. then tert-butyl N-methyl-N—((S)-pyrrolidine-3-carbonyl)-L-valinate (500 mg) in ACN (3 mL) was added dropwise and the mixture stirred at 0° C. for 2 h. EtOAc was added and the mixture was washed with brine (3×20 mL), dried over anhydrous $Na_2SO_4$, and filtered. The filtrate was concentrated under reduced pressure and the residue was purified by silica gel column chromatography to give tert-butyl N—((S)-1-(but-2-ynoyl)pyrrolidine-3-carbonyl)-N-methyl-L-valinate as a solid. LCMS (ESI): m/z [M+H] calc'd for $C_{19}H_{30}N_2O_4$ 350.2; found 352.1.

Step 2. A mixture of tert-butyl N—((S)-1-(but-2-ynoyl) pyrrolidine-3-carbonyl)-N-methyl-L-valinate (200 mg) in DCM (4 mL) and TFA (2 mL) was stirred at 0° C. for 2 h. The mixture was concentrated under reduced pressure with azeotropic removal of $H_2O$ using toluene (4 mL×2) to give N—((S)-1-(but-2-ynoyl)pyrrolidine-3-carbonyl)-N-methyl-L-valinate as a solid. LCMS (ESI): m/z [M+H] calc'd for $C_{15}H_{22}N_2O_4$ 294.2; found 295.2.

Step 3. Two atropisomers of (2S)-2-{1-[(3S)-1-(but-2-ynoyl)pyrrolidin-3-yl]-N-methylformamido}-N-[(8S,14S,20M)-22-ethyl-4-hydroxy-21-{2-[(1 S)-1-methoxyethyl]pyridin-3-yl}-18,18-dimethyl-9,15-dioxo-16-oxa-10,22,28-triazapentacyclo[18.5.2.1$^{2,6}$.0.1$^{10,14}$.0.0$^{23,27}$]nonacosa-1(26),2,4,6(29),20,23(27),24-heptaen-8-yl]-3-methylbutanamide was synthesized in a manner similar to (2S)—N-[(8S,14S)-22-ethyl-4-hydroxy-21-[2-(methoxymethyl)pyridin-3-yl]-18,18-dimethyl-9,15-dioxo-16-oxa-10,22,28-triazapentacyclo[18.5.2.1$^{2,6}$.0.1$^{10,14}$.0.0$^{23,27}$]nonacosa-1(26),2,4,6(29),20,23(27),24-heptaen-8-yl]-3-methyl-2-{N-methyl-1-[(3S)-1-[4-(morpholin-4-yl)but-2-ynoyl]pyrrolidin-3-yl]formamido}butanamide except (2S)-3-methyl-2-[N-methyl-1-[(3S)-1-[4-(morpholin-4-yl)but-2-ynoyl]pyrrolidin-3-yl]formamido]butanoic acid was substituted with N—((S)-1-(but-2-ynoyl)pyrrolidine-3-carbonyl)-N-methyl-L-valinate. (43.3 mg, 12% yield) and (33 mg, 9% yield) both as solids. LCMS (ESI): m/z [M+H] calc'd for $C_{52}H_{65}N_7O_8$ 915.5; found 916.7; $^1$H NMR (400 MHz, DMSO-$d_6$) δ 9.34-9.27 (m, 1H), 8.78 (t, J=2.5 Hz, 1H), 8.68 (t, J=8.5 Hz, 0.5H), 8.20-8.11 (m, 0.6H), 7.95 (ddt, J=5.4, 3.5, 1.7 Hz, 2H), 7.63-7.60 (m, 1H), 7.61-7.49 (m, 2H), 7.13 (s, 1H), 7.03 (d, J=6.2 Hz, 1H), 6.60-6.49 (d, J=35.5 Hz, 1H), 5.43-5.39 (m, 1H), 5.12-5.00 (m, 0.7H), 4.74 (d, J=10.6 Hz, 0.4H), 4.32-4.25 (m, 1H), 4.18-3.85 (m, 5H), 3.81-3.45 (m, 8H), 3.18-3.02 (m, 5H), 2.93-2.80 (m, 4H), 2.80-2.70 (m, 2H), 2.42-2.36 (m, 1H), 2.31-2.20 (m, 1H), 2.18-1.96 (m, 6H), 1.85-1.74 (m, 1H), 1.74-1.63 (m, 1H), 1.62-1.42 (m, 1H), 1.32-1.16 (m, 4H), 1.15-1.05 (t, J=6.3 Hz, 4H), 1.04-0.95 (m, 2H), 0.95-0.85 (m, 5H), 0.68-0.52 (m, 4H), 0.52-0.37 (m, 4H), and LCMS (ESI): m/z [M+H] calc'd for $C_{52}H_{65}N_7O_8$ 915.5; found 916.7; $^1$H NMR (400 MHz, DMSO-$d_6$) δ 9.36-9.28 (m, 1H), 8.77 (dd, J=4.7, 1.8 Hz, 1H), 8.62-8.57 (m, 0.5H), 8.15-8.07 (m, 0.5H), 7.95 (s, 1H), 7.87-7.81 (m, 1H), 7.65-7.51 (m, 3H), 7.37-7.25 (m, 1H), 7.10-7.03 (m, 1H), 6.54 (d, J=35.5 Hz, 1H), 5.52-5.21 (m, 2H), 4.78-4.66 (m, 0.5H), 4.34-4.20 (m, 3H), 4.15-3.85 (m, 4H), 3.85-3.42 (m, 7H), 3.22-3.11 (m, 3H), 2.97-2.72 (m, 7H), 2.62-2.54 (m, 1H), 2.28-1.96 (m, 7H), 1.95-1.74 (m, 2H), 1.73-1.44 (m, 2H), 1.42-1.37 (m, 3H), 1.28-1.14 (m, 1H), 1.03-0.85 (m, 6H), 0.83-0.72 (m, 7H), 0.71-0.55 (m, 3H).

Example A28. Synthesis of (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1^[2,6]0.1^[10,14]0.0^[23,27]]nonacosa-1(26),2,4,6(29),20,23(27),24-heptaen-8-yl]-3-methyl-2-[N-methyl-1-[(3S)-1-(prop-2-enoyl)pyrrolidin-3-yl]formamido]butanamide

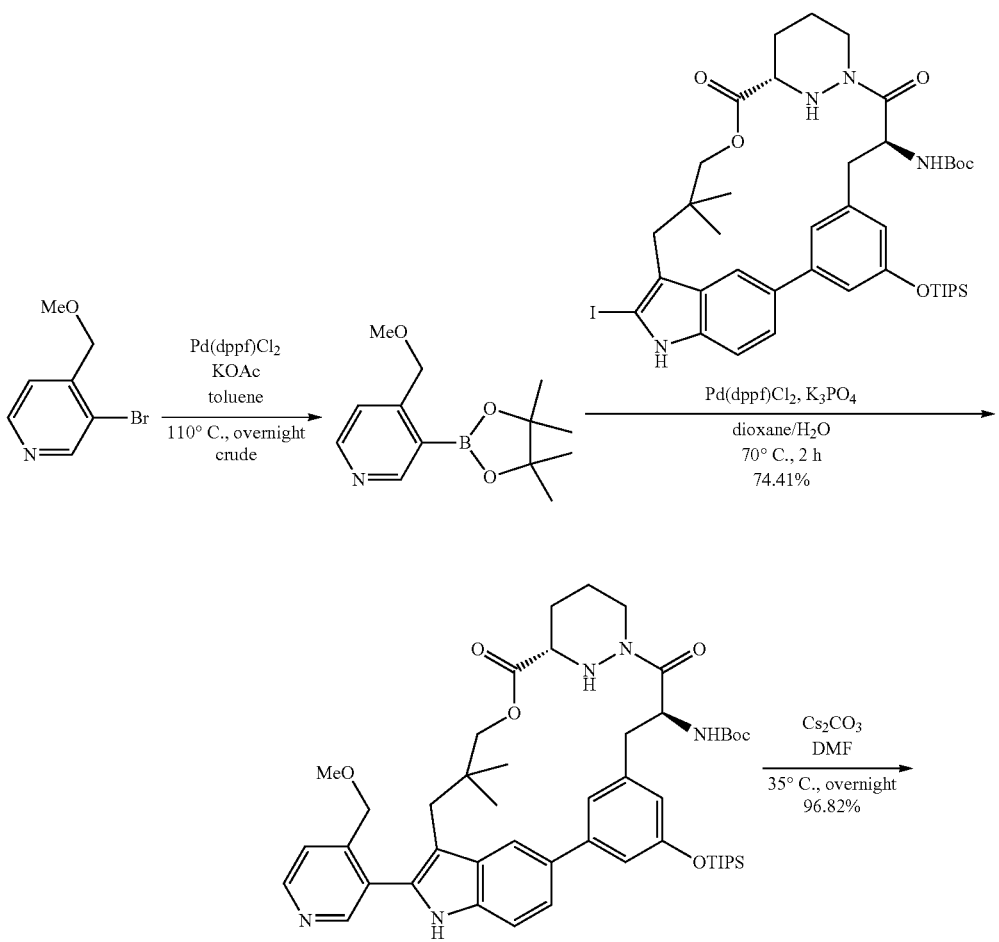

965 966

-continued

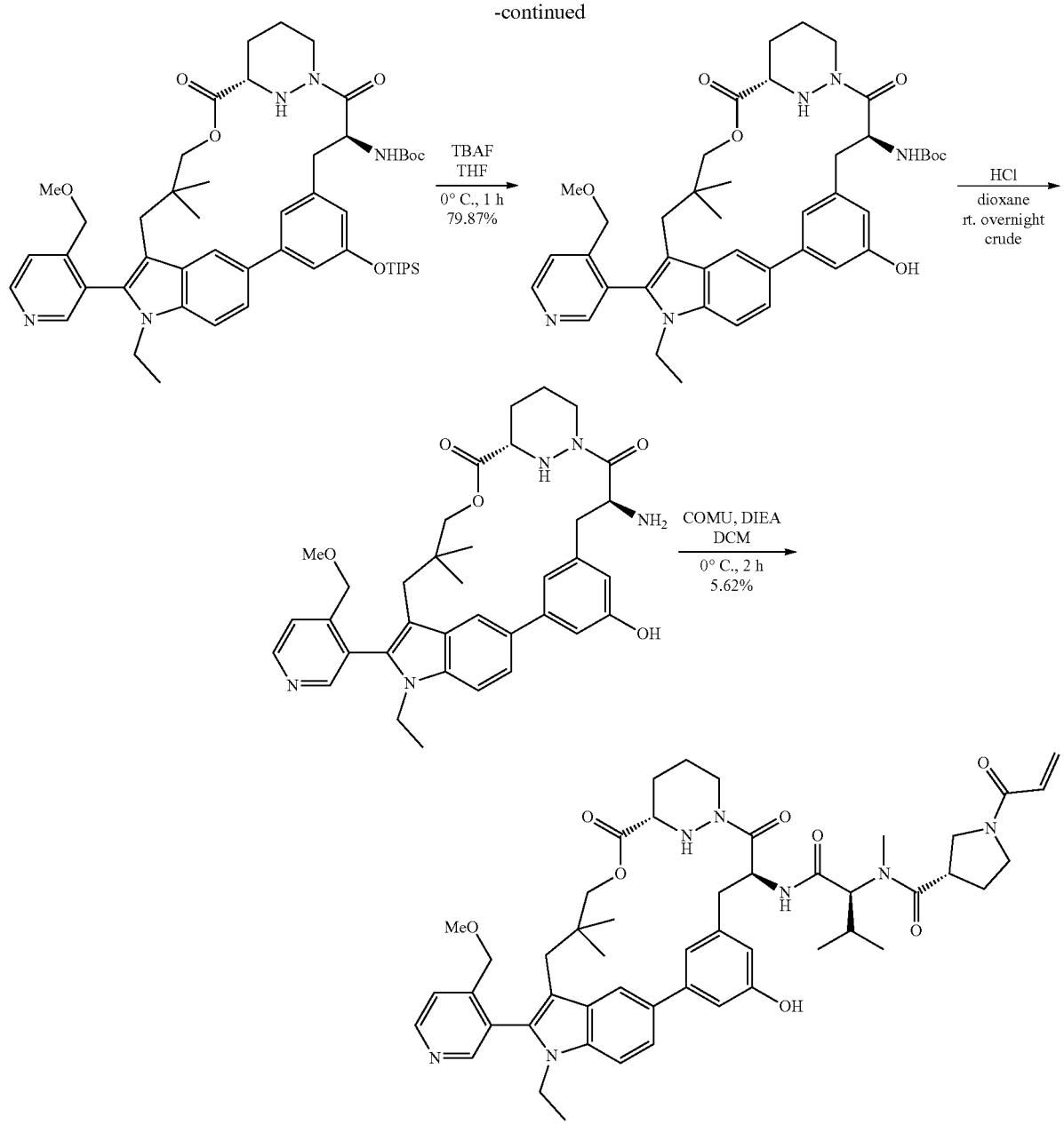

Step 1. To a mixture of 3-bromo-4-(methoxymethyl) pyridine (1.00 g, 5.0 mmol), 4,4,5,5-tetramethyl-2-(tetramethyl-1,3,2-dioxaborolan-2-yl)-1,3,2-dioxaborolane (1.51 g, 5.9 mmol) and KOAc (1.21 g, 12.3 mmol) in toluene (10 mL) at rt under an atmosphere of Ar was added Pd(dppf)Cl$_2$ (362 mg, 0.5 mmol). The mixture was heated to 110° C. and stirred overnight, then concentrated under reduced pressure to give 4-(methoxymethyl)-3-(4,4,5,5-tetramethyl-1,3,2-dioxaborolan-2-yl)pyridine, which was used directly in the next step directly without further purification. LCMS (ESI): m/z [M+H] calc'd for C$_{13}$H$_{20}$BNO$_3$ 249.2; found 250.3.

Step 2. To a mixture of 4-(methoxymethyl)-3-(4,4,5,5-tetramethyl-1,3,2-dioxaborolan-2-yl)pyridine (290 mg, 1.16 mmol), K$_3$PO$_4$ (371 mg, 1.75 mmol) and tert-butyl N-[(8S,14S)-21-iodo-18,18-dimethyl-9,15-dioxo-4-[(triisopropylsilyl)oxy]-16-oxa-10,22,28-triazapentacyclo[18.5.2.1ˆ[2,6]0.1ˆ[10,14]0.0ˆ[23,27]]nonacosa-1(26),2,4,6(29),20,23(27), 24-heptaen-8-yl]carbamate (500 mg, 0.58 mmol) in 1,4-dioxane (5 mL) and H$_2$O (1 mL) at rt under an atmosphere of Ar was added Pd(dppf)Cl$_2$ (43 mg, 0.06 mmol). The mixture was heated to 70° C. and stirred for 2 h, then H$_2$O added and the mixture extracted with EtOAc (2×10 mL). The combined organic layers were washed with brine (10 mL), dried over anhydrous Na$_2$SO$_4$, and filtered. The filtrate was concentrated under reduced pressure and the residue was purified by silica gel column chromatography to give tert-butyl N-[(8S,14S)-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaen-8-yl]carbamate (370 mg, 74% yield) as a foam. LCMS (ESI): m/z [M+H] calc'd for C$_{48}$H$_{67}$N$_5$O$_7$Si 853.6; found 854.6.

Step 3. A mixture of tert-butyl N-[(8S,14S)-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaen-8-yl]carbamate (350 mg, 0.41 mmol), Cs$_2$CO$_3$ (267 mg, 0.82 mmol) and EtI (128 mg, 0.82 mmol) in DMF (4 mL) was stirred at 35° C. overnight. H$_2$O was added and the mixture was extracted with EtOAc (2×15 mL). The combined organic layers were washed with brine (15 mL), dried over anhydrous Na$_2$SO$_4$, and filtered. The filtrate was concentrated under reduced pressure and the residue was purified by silica gel column chromatography to give tert-butyl N-[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaen-8-yl]carbamate (350 mg, 97% yield) as an oil. LCMS (ESI): m/z [M+H] calc'd for C$_{50}$H$_{71}$N$_5$O$_7$Si 881.5; found 882.6.

Step 4. A mixture of tert-butyl N-[(8S,14S)-22-ethyl-21-[4-(methoxymethyl)pyridin-3-yl]-18,18-dimethyl-9,15-dioxo-4-[(triisopropylsilyl)oxy]-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaen-8-yl]carbamate (350 mg, 0.4 mmol) and 1M TBAF in THF (0.48 mL, 0.480 mmol) in THF (3 mL) at 0° C. under an atmosphere of Ar was stirred for 1 h. The mixture was concentrated under reduced pressure and the residue was purified by silica gel column chromatography to give tert-butyl N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaen-8-yl]carbamate (230 mg, 80% yield) as an oil. LCMS (ESI): m/z [M+H] calc'd for C$_{41}$H$_{51}$N$_5$O$_7$ 725.4; found 726.6.

Step 5. To a mixture of tert-butyl N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaen-8-yl]carbamate (200 mg, 0.28 mmol) in 1,4-dioxane (2 mL) at 0° C. under an atmosphere of Ar was added 4M HCl in 1,4-dioxane (2 mL, 8 mmol). The mixture was allowed to warm to rt and was stirred overnight, then concentrated under reduced pressure to give (8S,14S)-8-amino-22-ethyl-4-hydroxy-21-[4-(methoxymethyl)pyridin-3-yl]-18,18-dimethyl-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaene-9,15-dione (200 mg). LCMS (ESI): m/z [M+H] calc'd for C$_{36}$H$_{43}$N$_5$O$_5$ 625.3; found 626.5.

Step 6. To a mixture of (2S)-3-methyl-2-[N-methyl-1-[(3S)-1-(prop-2-enoyl)pyrrolidin-3-yl]formamido]butanoic acid (108 mg, 0.38 mmol) and (8S,14S)-8-amino-22-ethyl-4-hydroxy-21-[4-(methoxymethyl)pyridin-3-yl]-18,18-dimethyl-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaene-9,15-dione (200 mg, 0.32 mmol) in DCM (3 mL) at 0° C. was added DIPEA (165 mg, 1.3 mmol) and COMU (274 mg, 0.64 mmol) in portions. The mixture was stirred at 0° C. for 2 h, H$_2$O added and extracted with EtOAc (2×10 mL). The combined organic layers were washed with brine (10 mL), dried over anhydrous Na$_2$SO$_4$, and filtered. The filtrate was concentrated under reduced pressure and the residue was purified by silica gel column chromatography then prep-HPLC to give (2S)—N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1ˆ[2,6]0.1ˆ[10,14]0.0ˆ[23,27]]nonacosa-1(26),2,4,6(29),20,23(27),24-heptaen-8-yl]-3-methyl-2-[N-methyl-1-[(3S)-1-(prop-2-enoyl)pyrrolidin-3-yl]formamido]butanamide (16 mg, 5.6% yield) as a solid. LCMS (ESI): m/z [M+H] calc'd for C$_{50}$H$_{63}$N$_7$O$_8$ 889.5; found 890.6; $^1$H NMR (400 MHz, DMSO-d$_6$) δ 9.33 (dd, J=9.1, 6.9 Hz, 1H), 8.79-8.46 (m, 2H), 7.93 (s, 1H), 7.68-7.58 (m, 2H), 7.53 (t, J=8.5 Hz, 1H), 7.26-6.98 (m, 2H), 6.71-6.47 (m, 2H), 6.24-6.07 (m, 1H), 5.80-5.60 (m, 1H), 5.49-5.18 (m, 1H), 4.45-4.07 (m, 4H), 4.08-3.87 (m, 3H), 3.87-3.64 (m, 4H), 3.64-3.40 (m, 5H), 3.34 (s, 2H), 3.30 (s, 2H), 3.23 (d, J=1.8 Hz, 1H), 2.94-2.74 (m, 6H), 2.16-2.01 (m, 3H), 1.82-1.47 (m, 3H), 1.08 (q, J=8.9, 8.0 Hz, 1H), 1.00-0.88 (m, 6H), 0.82 (d, J=10.8 Hz, 4H), 0.76-0.66 (m, 2H), 0.44 (d, J=14.2 Hz, 3H).

Example A316. Synthesis of (2R)-2-(((1-(4-(dimethylamino)-4-methylpent-2-ynoyl)azetidin-3-yl)oxy)methyl)-N-((6$^3$S,4S)-1$^1$-ethyl-1$^2$-(2-((S)—I-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-(5,3)-indola-6(1,3)-pyridazina-2(1,3)-benzenacycloundecaphane-4-yl)-3-methylbutanamide

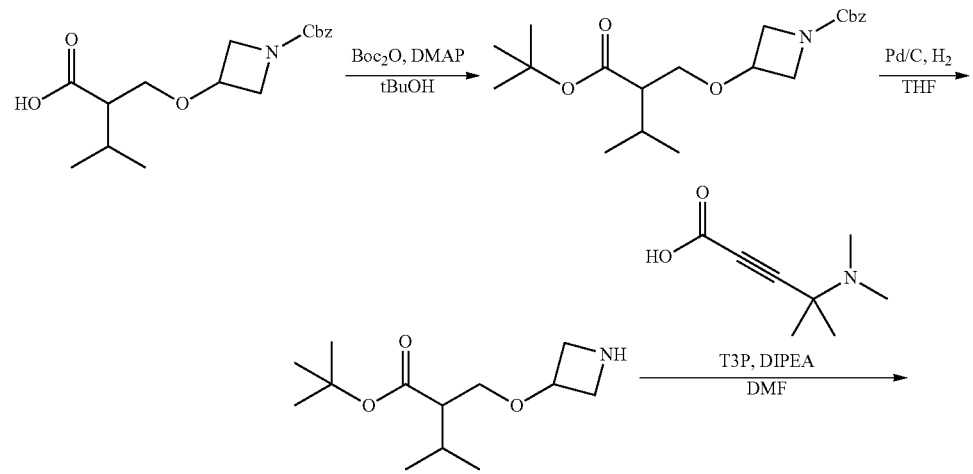

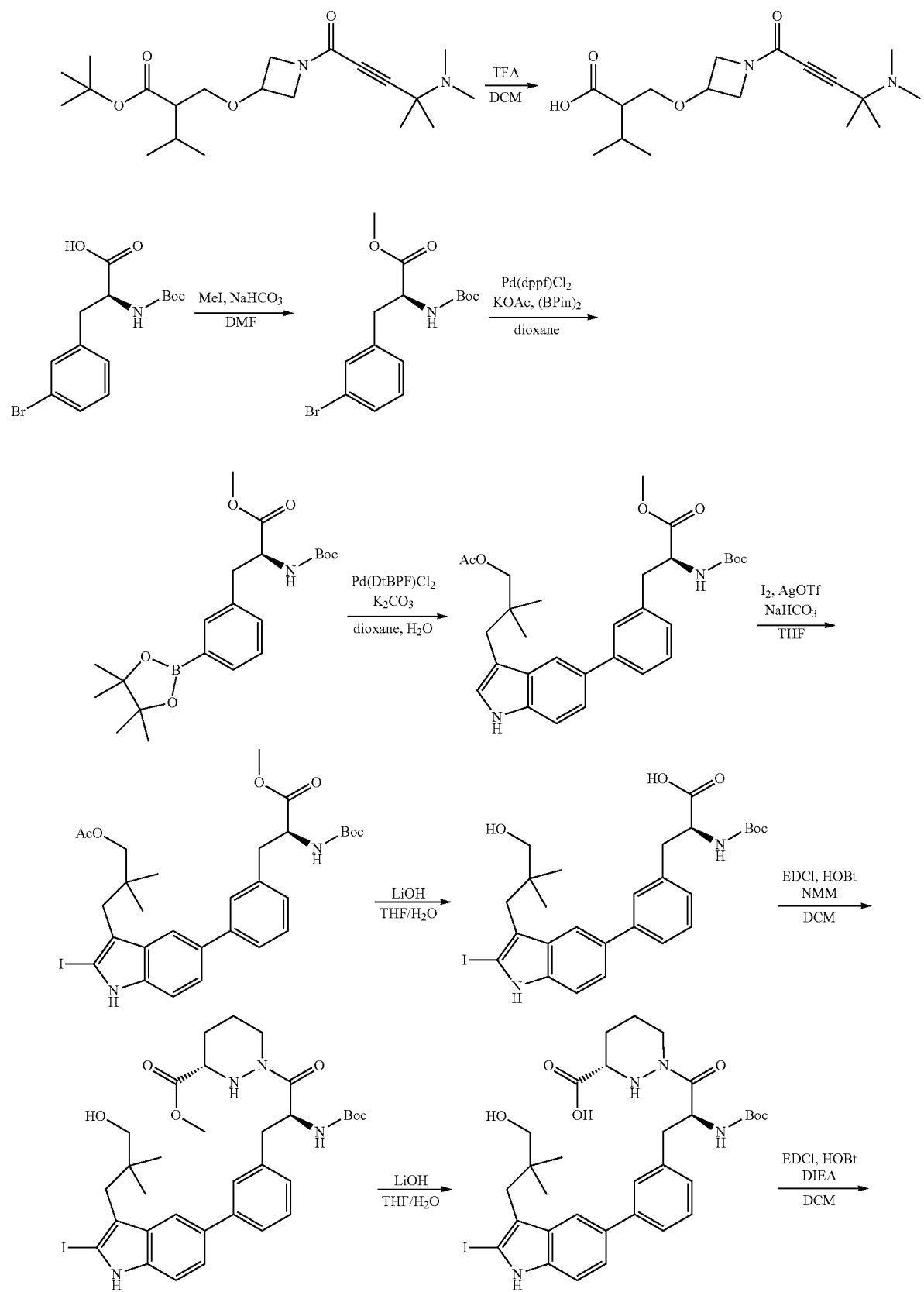

-continued
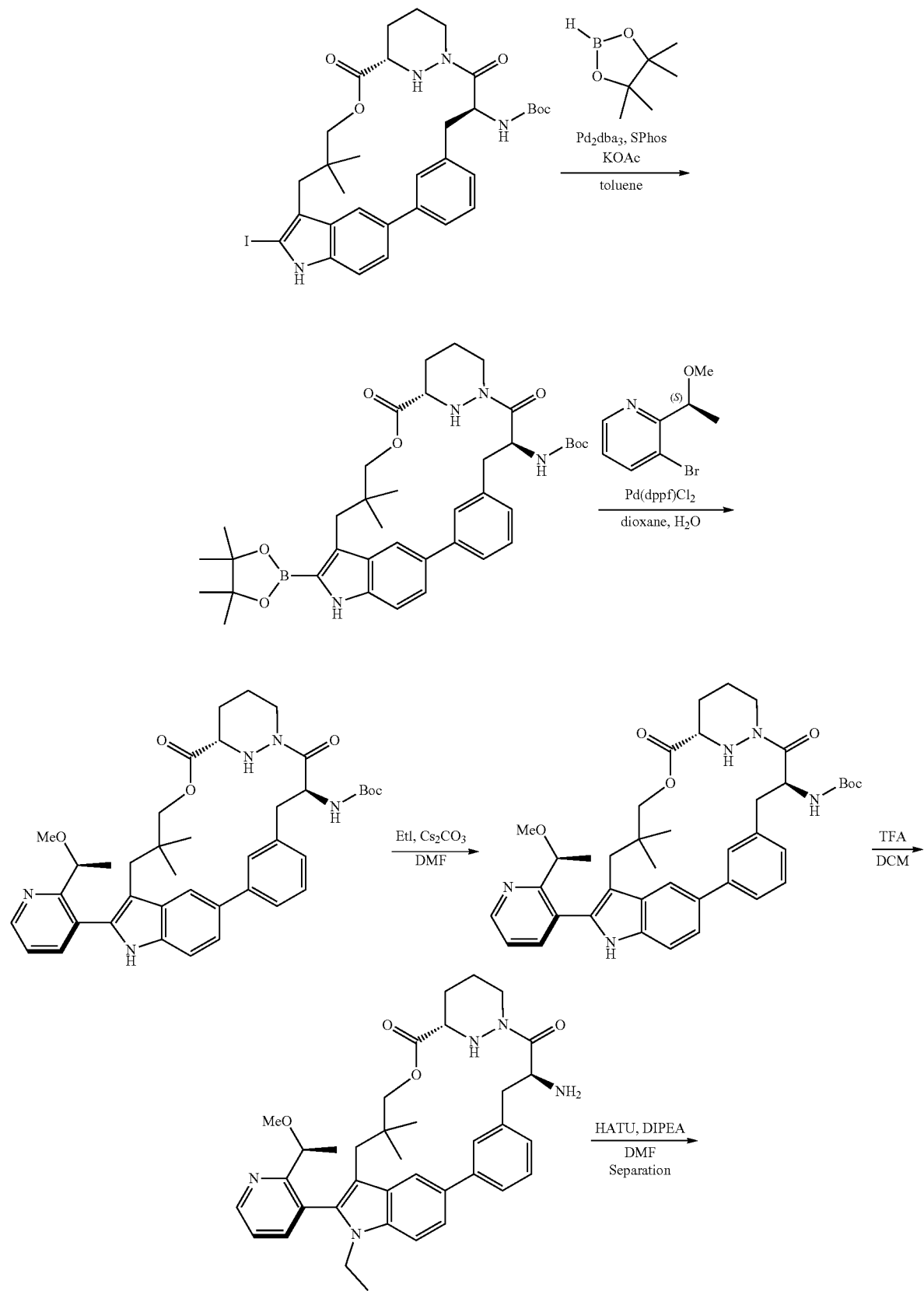

-continued

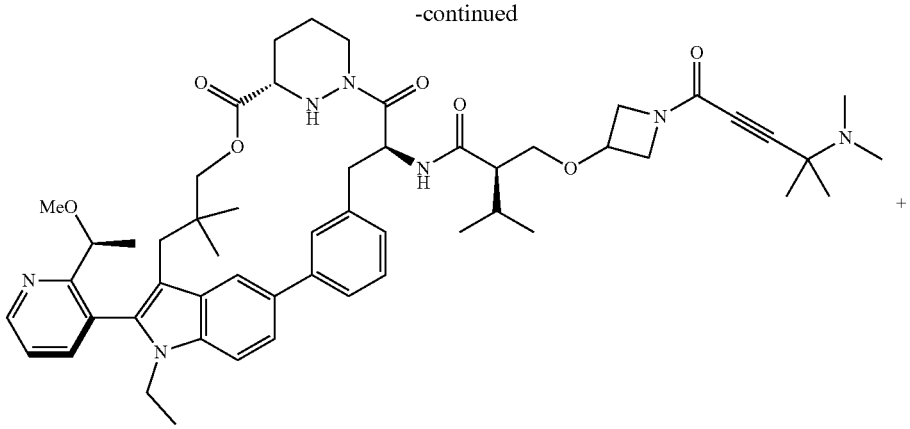

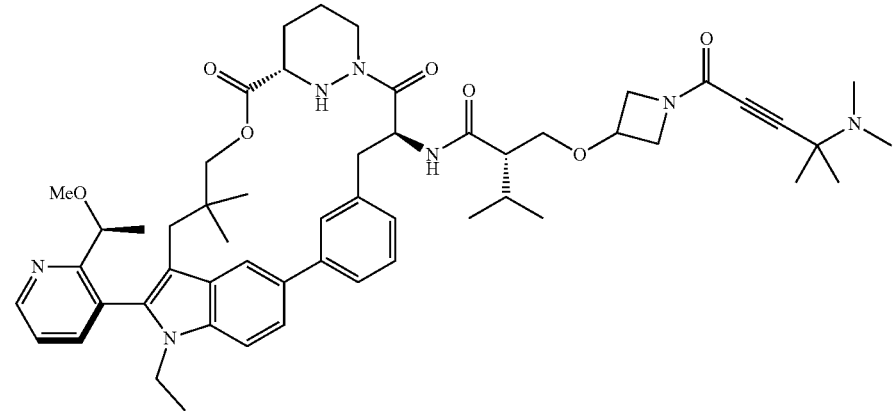

Step 1. To a mixture of 2-(((1-((benzyloxy)carbonyl)azetidin-3-yl)oxy)methyl)-3-methylbutanoic acid (650 mg, 2 mmol) and di-tert-butyl dicarbonate (883 mg, 4 mmol) in $^t$BuOH (10 mL) was added 4-dimethylaminopyridine (124 mg, 1 mmol). The mixture was heated to 30° C. and stirred for 1 h, then diluted with $H_2O$ (50 mL) and extracted with EtOAc (50 mL×3). The combined organic layers were concentrated under reduced pressure and the residue was purified by silica gel column chromatography to afford benzyl 3-(2-(tert-butoxycarbonyl)-3-methylbutoxy)azetidine-1-carboxylate (450 mg, 56% yield) as an oil. LCMS (ESI): m/z [M+Na] calc'd for $C_{21}H_{31}NO_5Na$ 400.2; found 400.2.

Step 2. A mixture of benzyl 3-(2-(tert-butoxycarbonyl)-3-methylbutoxy)azetidine-1-carboxylate (450 mg, 1.19 mmol) and Pd/C (50 mg) in THF (30 mL) was stirred for 2 h under an atmosphere of $H_2$ (15 psi). The mixture was filtered and the filtrate was concentrated under reduced pressure to give tert-butyl 2-((azetidin-3-yloxy)methyl)-3-methylbutanoate (300 mg, 100% yield) as an oil. LCMS (ESI): m/z [M+H] calc'd for $C_{13}H_{26}NO_3$ 243.2; found 244.2; $^1$H NMR (400 MHz, CDCl$_3$) δ 4.35-4.25 (m, 1H), 3.71-3.63 (m, 2H), 3.63-3.56 (m, 2H), 3.50 (t, J=8.0 Hz, 1H), 3.43 (dd, J=9.0, 4.0 Hz, 1H), 2.37-2.26 (m, 1H), 2.21 (br. s, 1H), 1.92-1.81 (m, 1H), 1.47 (s, 9H), 0.93 (d, J=6.8 Hz, 6H).

Step 3. To a mixture of tert-butyl 2-((azetidin-3-yloxy)methyl)-3-methylbutanoate (270 mg, 1.11 mmol), 4-(dimethylamino)-4-methylpent-2-ynoic acid (860 mg, 5.55 mmol) and DIPEA (1.56 g, 11.1 mmol) in DMF (20 mL) at 0° C. was added T$_3$P (2.12 g, 6.7 mmol). The mixture was stirred at 0° C. for 1 h, diluted with EtOAc (200 mL), then washed with $H_2O$ (30 mL×5), brine (30 mL), dried over anhydrous Na$_2$SO$_4$ and filtered. The filtrate was concentrated under reduced pressure and the residue was purified by silica gel column chromatography to give tert-butyl 2-(((1-(4-(dimethylamino)-4-methylpent-2-ynoyl)azetidin-3-yl)oxy)methyl)-3-methylbutanoate (200 mg, 47% yield) as an oil. LCMS (ESI): m/z [M+H] calc'd for $C_{21}H_{36}N_2O_4$ 380.3; found 381.3.

Step 4. To a mixture of tert-butyl 2-(((1-(4-(dimethylamino)-4-methylpent-2-ynoyl)azetidin-3-yl)oxy)methyl)-3-methylbutanoate (190 mg, 0.5 mmol) in DCM (4 mL) was added TFA (2 mL). The mixture was stirred for 1 h, then concentrated under reduced pressure to give 2-(((1-(4-(dimethylamino)-4-methylpent-2-ynoyl)azetidin-3-yl)oxy)methyl)-3-methylbutanoic acid (162 mg, 100% yield) as an oil, which was used directly in the next step without further purification. LCMS (ESI): m/z [M+H] calc'd for $C_{17}H_{28}N_2O_4$ 324.2; found 325.3.

Step 5. To a solution of (2S)-3-(3-bromophenyl)-2-[(tert-butoxycarbonyl)amino]propanoic acid (100 g, 290 mmol) in DMF (1 L) at room temperature was added NaHCO$_3$ (48.8 g, 581.1 mmol) and MeI (61.9 g, 435.8 mmol). The reaction mixture was stirred for 16 h and was then quenched with $H_2O$ (1 L) and extracted with EtOAc (3×1 L). The combined organic layers were washed with brine (3×500 mL), dried over Na$_2$SO$_4$, filtered, and concentrated under reduced pressure. The residue was purified by silica gel chromatography (13% EtOAc/pet. ether) to give methyl (S)-3-(3-bromophenyl)-2-((tert-butoxycarbonyl)amino)propanoate (109 g, crude). LCMS (ESI): m/z [M+Na] calc'd for $C_{15}H_{20}BrNO_4$ 380.05; found 380.0.

Step 6. To a stirred solution of methyl (2S)-3-(3-bromophenyl)-2-[(tert-butoxycarbonyl)amino]propanoate (108 g, 301.5 mmol) and bis(pinacolato)diboron (99.53 g, 391.93 mmol) in 1,4-dioxane (3.2 L) was added KOAc (73.97 g, 753.70 mmol) and Pd(dppf)Cl$_2$ (22.06 g, 30.15 mmol). The reaction mixture was heated to 90° C. for 3 h and was then cooled to room temperature and extracted with EtOAc (2×3 L). The combined organic layers were washed with brine (3×800 mL), dried over Na$_2$SO$_4$, filtered, and concentrated under reduced pressure. The residue was purified by silica gel chromatography (5% EtOAc/pet. ether) to give methyl (S)-2-((tert-butoxycarbonyl)amino)-3-(3-(4,4,5,5-tetramethyl-1,3,2-dioxaborolan-2-yl)phenyl)propanoate (96 g, 78.6% yield). LCMS (ESI): m/z [M+Na] calc'd for C$_{21}$H$_{32}$BNO$_6$ 428.22; found 428.1.

Step 7. To a mixture of methyl (2S)-2-[(tert-butoxycarbonyl)amino]-3-[3-(4,4,5,5-tetramethyl-1,3,2-dioxaborolan-2-yl)phenyl]propanoate (94 g, 231.9 mmol) and 3-(5-bromo-1H-indol-3-yl)-2,2-dimethylpropyl acetate (75.19 g, 231.93 mmol) in 1,4-dioxane (1.5 L) and H$_2$O (300 mL) was added K$_2$CO$_3$ (64.11 g, 463.85 mmol) and Pd(DtBPF)Cl$_2$ (15.12 g, 23.19 mmol). The reaction mixture was heated to 70° C. and stirred for 4 h. The reaction mixture was extracted with EtOAc (2×2 L) and the combined organic layers were washed with brine (3×600 mL), dried over Na$_2$SO$_4$, filtered, and concentrated under reduced pressure. The residue was purified by silica gel chromatography (20% EtOAc/pet. ether) to give methyl (S)-3-(3-(3-(3-acetoxy-2,2-dimethylpropyl)-1H-indol-5-yl)phenyl)-2-((tert-butoxycarbonyl)amino)propanoate (130 g, crude). LCMS (ESI): m/z [M+H] calc'd for C$_{30}$H$_{38}$N$_2$O$_6$ 523.28; found 523.1.

Step 8. To a solution of methyl (2S)-3-(3-[3-[3-(acetyloxy)-2,2-dimethylpropyl]-1H-indol-5-yl]phenyl)-2-[(tert-butoxycarbonyl)amino]propanoate (95.0 g, 181.8 mmol) and iodine (36.91 g, 145.41 mmol) in THF (1 L) at −10° C. was added AgOTf (70.0 g, 272.7 mmol) and NaHCO$_3$ (22.9 g, 272.65 mmol). The reaction mixture was stirred for 30 min and was then quenched by the addition of sat. Na$_2$S$_2$O$_3$ (100 mL) at 0° C. The resulting mixture was extracted with EtOAc (3×1 L) and the combined organic layers were washed with brine (3×500 mL), dried over Na$_2$SO$_4$, filtered, and concentrated under reduced pressure. The residue was purified by silica gel chromatography (50% EtOAc/pet. ether) to give methyl (S)-3-(3-(3-(3-acetoxy-2,2-dimethylpropyl)-2-iodo-1H-indol-5-yl)phenyl)-2-((tert-butoxycarbonyl)amino)propanoate (49.3 g, 41.8% yield). LCMS (ESI) m/z: [M+H] calcd for C$_{30}$H$_{37}$IN$_2$O$_6$: 649.18; found 649.1.

Step 9. To a solution of methyl (2S)-3-(3-[3-[3-(acetyloxy)-2,2-dimethylpropyl]-2-iodo-1H-indol-5-yl]phenyl)-2-[(tert-butoxycarbonyl)amino]propanoate (60 g, 92.5 mmol) in THF (600 mL) was added a solution of LiOH·H$_2$O (19.41 g, 462.5 mmol) in H$_2$O (460 mL). The resulting solution was stirred overnight and then the pH was adjusted to 6 with HCl (1M). The resulting solution was extracted with EtOAc (2×500 mL) and the combined organic layers was washed with sat. brine (2×500 mL), dried over Na$_2$SO$_4$, filtered, and concentrated under reduced pressure to give (S)-2-((tert-butoxycarbonyl)amino)-3-(3-(3-(3-hydroxy-2,2-dimethylpropyl)-2-iodo-1H-indol-5-yl)phenyl)propanoic acid (45 g, 82.1% yield). LCMS (ESI): m/z [M+Na] calc'd for C$_{27}$H$_{33}$IN$_2$O$_6$ 615.13; found 615.1.

Step 10. To a solution of (2S)-2-[(tert-butoxycarbonyl)amino]-3-[3-[3-(3-hydroxy-2,2-dimethylpropyl)-2-iodo-1H-indol-5-yl]phenyl]propanoic acid (30 g, 50.6 mmol) and methyl (3S)-1,2-diazinane-3-carboxylate (10.9 g, 75.9 mmol) in DCM (400 mL) was added NMM (40.97 g, 405.08 mmol), HOBT (2.05 g, 15.19 mmol), and EDCl (19.41 g, 101.27 mmol). The reaction mixture was stirred overnight and then the mixture was washed with sat. NH$_4$Cl (2×200 mL) and sat. brine (2×200 mL), and the mixture was dried over Na$_2$SO$_4$, filtered, and concentrated under reduced pressure to give methyl (S)-1-((S)-2-((tert-butoxycarbonyl)amino)-3-(3-(3-(3-hydroxy-2,2-dimethylpropyl)-2-iodo-1H-indol-5-yl)phenyl)propanoyl)hexahydropyridazine-3-carboxylate (14 g, 38.5% yield). LCMS (ESI): m/z [M+H] calc'd for C$_{33}$H$_{431}$N$_4$O$_6$ 718.23; found 719.4.

Step 11. To a solution of methyl (S)-1-((S)-2-((tert-butoxycarbonyl)amino)-3-(3-(3-(3-hydroxy-2,2-dimethylpropyl)-2-iodo-1H-indol-5-yl)phenyl)propanoyl)hexahydropyridazine-3-carboxylate (92 g, 128.0 mmol) in THF (920 mL) at 0° C. was added a solution of LiOH·H$_2$O (26.86 g, 640.10 mmol) in H$_2$O (640 mL). The reaction mixture was stirred for 2 h and was then concentrated under reduced pressure to give (S)-1-((S)-2-((tert-butoxycarbonyl)amino)-3-(3-(3-(3-hydroxy-2,2-dimethylpropyl)-2-iodo-1H-indol-5-yl)phenyl)propanoyl)hexahydropyridazine-3-carboxylic acid (90 g, crude). LCMS (ESI): m/z [M+H] calc'd for C$_{32}$H$_{411}$N$_4$O$_6$ 705.22; found 705.1.

Step 12. To a solution of (3S)-1-[(2S)-2-[(tert-butoxycarbonyl)amino]-3-[3-[3-(3-hydroxy-2,2-dimethylpropyl)-2-iodo-1H-indol-5-yl]phenyl]propanoyl]-1,2-diazinane-3-carboxylic acid (90 g, 127.73 mmol) in DCM (10 L) at 0° C. was added HOBt (34.52 g, 255.46 mmol), DIPEA (330.17 g, 2554.62 mmol) and EDCl (367.29 g, 1915.96 mmol). The reaction mixture was stirred for 16 h and was then concentrated under reduced pressure. The mixture was extracted with DCM (2×2 L) and the combined organic layers were washed with brine (3×1 L), dried over Na$_2$SO$_4$, filtered, and concentrated under reduced pressure. The residue was purified by silica gel chromatography (50% EtOAc/pet. ether) to give tert-butyl ((6$^3$S,4S)-1$^2$-iodo-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate (70 g, 79.8% yield). LCMS (ESI): m/z [M+H] calc'd for C$_{32}$H$_{39}$IN$_4$O$_5$ 687.21; found 687.1.

Step 13. A1 L round-bottom flask was charged with tert-butyl ((6$^3$S,4S)-1$^2$-iodo-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate (22.0 g, 32.042 mmol), toluene (300.0 mL), Pd$_2$(dba)$_3$ (3.52 g, 3.845 mmol), S-Phos (3.95 g, 9.613 mmol), and KOAc (9.43 g, 96.127 mmol) at room temperature. To the mixture was added 4,4,5,5-tetramethyl-1,3,2-dioxaborolane (26.66 g, 208.275 mmol) dropwise with stirring at room temperature. The resulting solution was stirred for 3 h at 60° C. The resulting mixture was filtered, and the filter cake was washed with EtOAc. The filtrate was concentrated under reduced pressure and the remaining residue was purified by silica gel column chromatography to afford tert-butyl ((6$^3$S,4S)-10,10-dimethyl-5,7-dioxo-12-(4,4,5,5-tetramethyl-1,3,2-dioxaborolan-2-yl)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate (22 g, 90% yield) as a solid. LCMS (ESI): m/z [M+H] calc'd for C$_{38}$H$_{51}$BN$_4$O$_7$ 687.3; found 687.4.

Step 14. A mixture of tert-butyl ((6$^3$S,4S)-10,10-dimethyl-5,7-dioxo-1$^2$-(4,4,5,5-tetramethyl-1,3,2-dioxaborolan- 2-yl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl) carbamate (2.0 g, 2.8 mmol), 3-bromo-2-[(1S)-1-methoxyethyl]pyridine (0.60 g, 2.8 mmol), Pd(dppf)Cl$_2$ (0.39 g, 0.5 mmol), and K$_3$PO$_4$ (1.2 g, 6.0 mmol) in 1,4-dioxane (50 mL) and H$_2$O (10 mL) under an atmosphere of N$_2$ was heated to 70° C. and stirred for 2 h. The mixture was diluted with H$_2$O (50 mL) and extracted with EtOAc (3×50 mL). The combined organic layers were washed with brine (3×50 mL), dried over anhydrous Na$_2$SO$_4$, and filtered. The filtrate was concentrated under reduced pressure and the residue was purified by silica gel column chromatography to give tert-butyl ((6³S,4S)-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (1.5 g, 74% yield) as a solid. LCMS (ESI): m/z [M+H] calc'd for C$_{40}$H$_{49}$N$_5$O$_6$ 695.4; found 696.5.

Step 15. To a solution of tert-butyl ((6³S,4S)-1²-(2-((S)-1-methoxyethyl) pyridin-3-yl)-10,10-dimethyl-5,7-dioxo-6¹,6²,6³,6⁴,6⁵,6⁶-hexahydro-1¹H-8-oxa-1(5,3)-indola-6(1, 3)-pyridazina-2(1,3)-benzenacycloundecaphane-4-yl) carbamate (20 g, 28.7 mmol) and Cs$_2$CO$_3$ (18.7 g, 57.5 mmol) in DMF (150 mL) at 0° C. was added a solution of ethyl iodide (13.45 g, 86.22 mmol) in DMF (50 mL). The resulting mixture was stirred overnight at 35° C. and was then diluted with H$_2$O (500 mL). The mixture was extracted with EtOAc (2×300 mL) and the combined organic layers were washed with brine (3×100 mL), dried over Na$_2$SO$_4$, filtered, and concentrated under reduced pressure. The residue was purified by silica gel chromatography to give tert-butyl ((6³S,4S)-1¹-ethyl-1²-(2-((S)-1-methoxyethyl) pyridin-3-yl)-10,10-dimethyl-5,7-dioxo-6¹,6²,6³,6⁴,6⁵,6⁶-hexahydro-1¹¹H-8-oxa-1(5,3)-indola-6(1,3)-pyridazina-2(1, 3)- benzenacycloundecaphane-4-yl)carbamate (4.23 g, 18.8% yield) and the atropisomer (5.78 g, 25.7% yield) as solids. LCMS (ESI): m/z [M+H] calc'd for C$_{42}$H$_{53}$N$_5$O$_6$ 724.4; found 724.6.

Step 16. A mixture of tert-butyl ((6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1 (5,3)-indola-6(1,3)-pyridazina-2(1,3)-benzenacycloundecaphane-4-yl) carbamate (1.3 g, 1.7 mmol) in TFA (10 mL) and DCM (20 mL) was stirred at 0° C. for 2 h. The mixture was concentrated under reduced pressure to afford (6³S,4S)-4-amino-1¹-ethyl-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (1.30 g, crude) as a solid. LCMS (ESI): m/z [M+H] calc'd for C$_{37}$H$_{45}$N$_5$O$_4$ 623.3; found 624.4.

Step 17. To a mixture of (6³S,4S)-4-amino-1¹-ethyl-1²-(2-((S)-1-methoxyethyl)pyridin-3-yl)-10,10-dimethyl-6¹,6², 6³,6⁴,6⁵,6⁶-hexahydro-1¹H-8-oxa-1(5,3)-indola-6(1,3)-pyridazina-2(1,3)-benzenacycloundecaphane-5,7-dione (258 mg, 0.41 mmol) and 2-(((1-(4-(dimethylamino)-4-methylpent-2-ynoyl)azetidin-3-yl)oxy)methyl)-3-methylbutanoic acid (162 mg, 0.5 mmol) in DMF (4 mL) at 0° C. was added a mixture of HATU (188 mg, 0.5 mmol) and DIPEA (534 mg, 4.14 mmol) in DMF (2 mL). The mixture was stirred at 0° C. for 1 h, then diluted with H$_2$O (30 mL) and extracted with EtOAc (30 mL×3). The combined organic layers were concentrated under reduced pressure and the residue was purified by silica gel column chromatography to give 2-(((1-(4-(dimethylamino)-4-methylpent-2-ynoyl)azetidin-3-yl)oxy)methyl)-N-((6³S,4S)-1¹-ethyl-1²-(2-((S)-1-methoxyethyl)pyridin-3-yl)-10,10-dimethyl-5,7-dioxo-6¹, 6²,6³,6⁴,6⁵,6⁶-hexahydro-1H-8-oxa-1(5,3)-indola-6(1,3)-pyridazina-2(1,3)-benzenacycloundecaphane-4-yl)-3-methylbutanamide (250 mg, 64% yield) as a solid. LCMS (ESI): m/z [M+H] calc'd for C$_{54}$H$_{71}$N$_7$O$_7$ 929.5; found 930.5; ¹H NMR (400 MHz, CD$_3$OD) δ 8.90-8.79 (m, 1H), 8.54-8.21 (m, 1H), 8.15-7.91 (m, 2H), 7.88-7.67 (m, 2H), 7.65-7.52 (m, 2H), 7.47-7.15 (m, 2H), 5.80-5.52 (m, 1H), 4.53-4.23 (m, 5H), 4.23-3.93 (m, 3H), 3.90-3.76 (m, 2H), 3.75-3.58 (m, 3H), 3.57-3.44 (m, 1H), 3.38 (s, 1H), 3.29-3.26 (m, 2H), 3.21-2.85 (m, 8H), 2.82-2.65 (m, 3H), 2.51-2.30 (m, 1H), 2.24-2.03 (m, 1H), 1.99-1.87 (m, 1H), 1.86-1.69 (m, 6H), 1.67-1.57 (m, 2H), 1.57-1.39 (m, 4H), 1.45-1.05 (m, 2H), 1.04-0.96 (m, 3H), 0.96-0.88 (m, 3H), 0.88-0.79 (m, 3H), 0.79-0.63 (m, 3H), 0.56 (s, 1H).

Step 18. 2-(((1-(4-(dimethylamino)-4-methylpent-2-ynoyl)azetidin-3-yl)oxy)methyl)-N-((6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1H-8-oxa-1(5,3)-indola-6(1,3)-pyridazina-2(1,3)-benzenacycloundecaphane-4-yl)-3-methylbutanamide (180 mg, 0.194 mmol) was purified by prep-HPLC to afford (2R)-2-(((1-(4-(dimethylamino)-4-methylpent-2-ynoyl)azetidin-3-yl)oxy)methyl)-N-((6³S, 4S)-1¹-ethyl-1²-(2-((S)-1-methoxyethyl)pyridin-3-yl)-10, 10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide (41.8 mg, 23.2% yield) as a solid. LCMS (ESI): m/z [M+H] calc'd for C$_{54}$H$_{71}$N$_7$O$_7$ 930.5; found 930.5; ¹H NMR (400 MHz, MeOD) δ 8.74 (d, J=4.0 Hz, 1H), 8.53-8.30 (m, 1H), 8.10-7.95 (m, 1H), 7.94-7.80 (m, 2H), 7.68 (t, J=8.0 Hz, 1H), 7.65-7.58 (m, 1H), 7.58-7.46 (m, 2H), 7.38-7.17 (m, 2H), 5.73-5.60 (m, 1H), 4.52-4.40 (m, 1H), 4.35-4.15 (m, 4H), 4.14-3.95 (m, 2H), 3.90-3.72 (m, 3H), 3.71-3.45 (m, 4H), 3.30-3.20 (m, 3H), 3.06-2.72 (m, 5H), 2.49-2.28 (m, 4H), 2.28-2.20 (m, 3H), 2.18-2.06 (m, 1H), 2.00-1.90 (m, 1H), 1.90-1.52 (m, 4H), 1.52-1.40 (m, 5H), 1.40-1.22 (m, 4H), 1.09-0.92 (m, 8H), 0.90-0.75 (m, 3H), 0.71-0.52 (m, 3H) and (2S)-2-(((1-(4-(dimethylamino)-4-methylpent-2-ynoyl)azetidin-3-yl)oxy)methyl)-N-((6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1 (5,3)-indola-6(1,3)-pyridazina-2(1,3)-benzenacycloundecaphane-4-yl)-3-methylbutanamide (51.2 mg, 28.4% yield) as a solid. LCMS (ESI): m/z [M+H] calc'd for C$_{54}$H$_{71}$N$_7$O$_7$ 930.5; found 930.3; ¹H NMR (400 MHz, MeOD) δ 8.74 (d, J=4.0 Hz, 1H), 8.28-8.20 (m, 0.6H), 8.11-7.98 (m, 1H), 7.97-7.80 (m, 2H), 7.73-7.48 (m, 4H), 7.46-7.36 (m, 0.4H), 7.33-7.26 (m, 1H), 7.25-7.13 (m, 1H), 5.79-5.66 (m, 1H), 4.54-4.43 (m, 1H), 4.42-4.01 (m, 7H), 3.90-3.75 (m, 2H), 3.73-3.48 (m, 4H), 3.27-3.12 (m, 3H), 3.08-2.99 (m, 1H), 2.96-2.85 (m, 2H), 2.84-2.69 (m, 2H), 2.69-2.49 (m, 6H), 2.41-2.29 (m, 1H), 2.15-2.05 (m, 1H), 1.95-1.85 (m, 1H), 1.84-1.71 (m, 1H), 1.71-1.38 (m, 11H), 1.14-1.00 (m, 3H), 1.00-0.71 (m, 9H), 0.70-0.56 (m, 3H).

Example A427. Synthesis of 3-((1-(4-(dimethyl-amino)-4-methylpent-2-ynoyl)azetidin-3-yl)oxy)-N-((6³S,4S,Z)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)propanamide

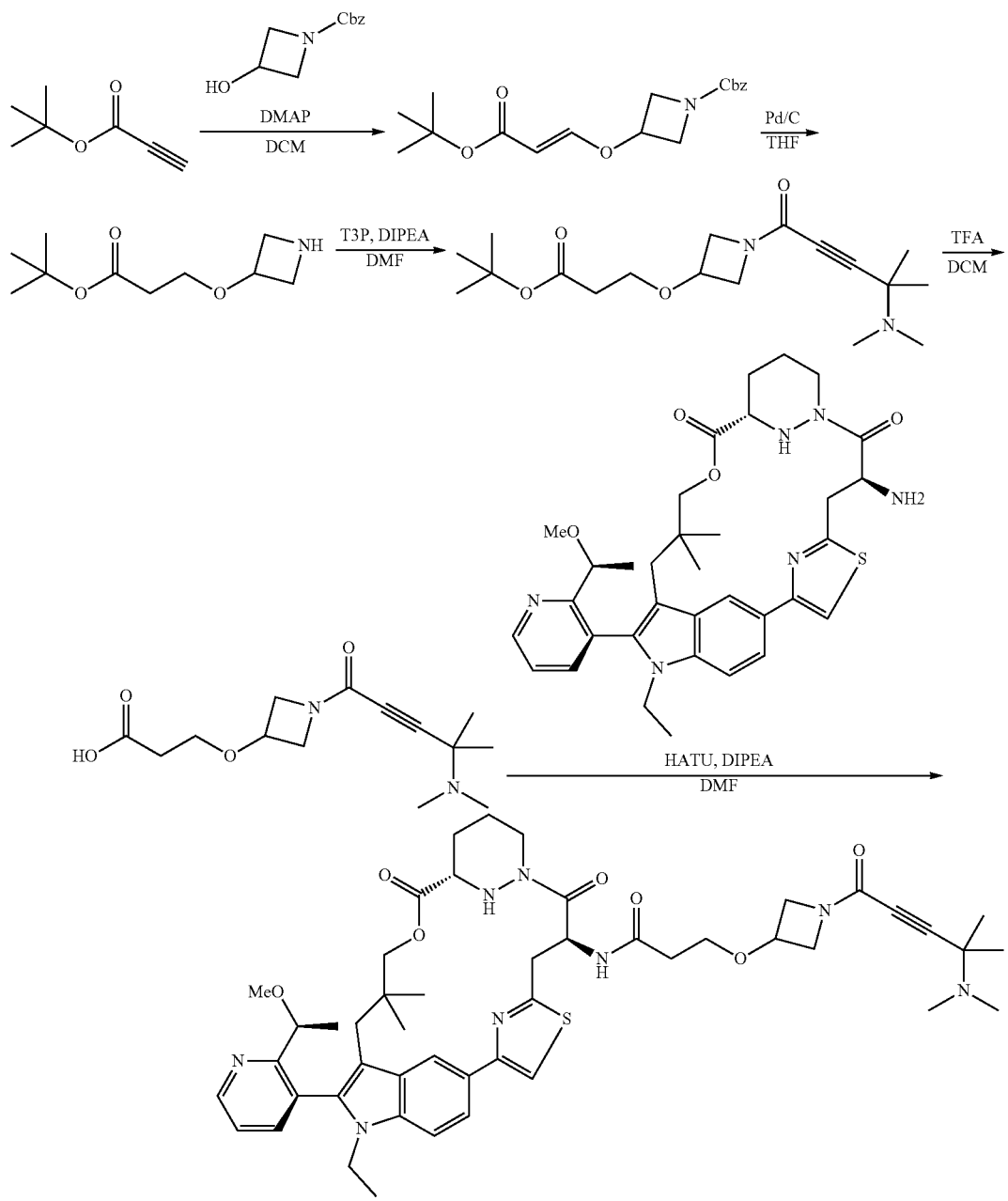

Step 1. To a mixture of tert-butyl prop-2-ynoate (5 g, 40 mmol) and [3-(3-hydroxyazetidin-1-yl)phenyl]methyl formate (4.1 g, 20 mmol) in DCM (150 mL) was added DMAP (9.8 g, 80 mmol). The mixture was stirred for 2 h, then diluted with H₂O and washed with H₂O (60 mL×3). The organic layer was dried over Na₂SO₄, filtered, the filtrate was concentrated under reduced pressure and the residue purified by silica gel column chromatography to give benzyl (E)-3-((3-(tert-butoxy)-3-oxoprop-1-en-1-yl)oxy)azetidine-1-carboxylate (6.6 g, 90% yield) as an oil. LCMS (ESI): m/z [M+Na] calc'd for C₁₈H₂₃NO₅Na 356.2; found 356.2.

Step 2. A mixture of benzyl (E)-3-((3-(tert-butoxy)-3-oxoprop-1-en-1-yl)oxy)azetidine-1-carboxylate (1.4 g, 4 mmol) and Pd/C (200 mg) in THF (10 mL) was stirred under an atmosphere of H₂ (1 atmosphere) for 16 h. The mixture was filtered and the filtrate and was concentrated under reduced pressure to give tert-butyl 3-(azetidin-3-yloxy)propanoate, which was used directly in the next step. LCMS (ESI): m/z [M+H] calc'd for $C_{10}H_{19}NO_3$ 201.1; found 202.2.

Step 3. To a mixture of tert-butyl 3-(azetidin-3-yloxy) propanoate (300 mg, 1.5 mmol) and 4-(dimethylamino)-4-methylpent-2-ynoic acid (2.3 g, 15 mmol) in DMF (15 mL) at 5° C. was added DIPEA (1.9 g, 15 mmol) and $T_3P$ (4.77 g, 7.5 mmol) dropwise. The mixture was stirred at 5° C. for 2 h, then $H_2O$ and EtOAc (80 mL) were added. The organic and aqueous layers were separated and the organic layer was washed with $H_2O$ (20 mL×3), brine (30 mL), dried over anhydrous $Na_2SO_4$ and filtered. The filtrate was concentrated under reduced pressure and the residue was purified by preparative-HPLC to afford tert-butyl 3-((1-(4-(dimethylamino)-4-methylpent-2-ynoyl)azetidin-3-yl)oxy)propanoate (60 mg, 12% yield) as an oil. LCMS (ESI): m/z [M+H] calc'd for $C_{18}H_{30}N_2O_4$ 338.2; found 339.2.

Step 4. A mixture tert-butyl 3-((1-(4-(dimethylamino)-4-methylpent-2-ynoyl)azetidin-3-yl)oxy)propanoate (70 mg, 0.21 mmol) in TFA/DCM (1:3, 2 mL) was stirred at 0-5° C. for 1 h, then concentrated under reduced pressure to give 3-({1-[4-(dimethylamino)-4-methylpent-2-ynoyl]azetidin-3-yl}oxy)propanoic acid (56 mg, 95% yield) as a solid. LCMS (ESI): m/z [M+H] calc'd for $C_{14}H_{22}N_2O_4$ 282.2; found 283.3.

Step 5. To a mixture of 3-((1-(4-(dimethylamino)-4-methylpent-2-ynoyl)azetidin-3-yl)oxy)propanoic acid (56 mg, 0.19 mmol), ($6^3$S,4S,Z)-4-amino-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane- 5,7-dione (90 mg, 0.14 mmol) and DIPEA (200 mg, 1.9 mmol) in DMF (1 mL) at 0° C. was added HATU (110 mg, 0.38 mmol) portion-wise. The mixture was stirred at 0° C. for 1 h, then $H_2O$ added and the mixture extracted with EtOAx (150 mL×2). The combined organic layers were washed with $H_2O$ (150 mL) and brine (150 mL), then dried over anhydrous $Na_2SO_4$ and filtered. The filtrate was concentrated under reduced pressure and the residue was purified by preparative-HPLC to give 3-((1-(4-(dimethylamino)-4-methylpent-2-ynoyl)azetidin-3-yl)oxy)-N-(($6^3$S,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl) propanamide (12.6 mg, 7.5% yield) as a solid. LCMS (ESI): m/z [M+H] calc'd for $C_{48}H_{62}N_8O_7S$ 894.5; found 895.3; $^1$H NMR (400 MHz, CD$_3$OD) δ 8.73 (dd, J=4.8, 1.6 Hz, 1H), 8.57 (s, 1H), 8.28 (s, 0.3H), 7.84 (m, 1H), 7.71 (m, 1H), 7.52 (m, 3H), 5.76 (dd, J=30.2, 7.8 Hz, 1H), 4.40 (m, 4H), 4.32-4.12 (m, 4H), 4.06 (dd, J=12.4, 6.0 Hz, 1H), 3.97-3.86 (m, 1H), 3.79-3.66 (m, 4H), 3.46 (dd, J=14.8, 4.8 Hz, 1H), 3.41-3.33 (m, 3H), 3.29-3.19 (m, 1H), 3.17-3.05 (m, 1H), 2.79 (m, 1H), 2.73-2.50 (m, 3H), 2.49-2.43 (m, 3H), 2.38 (s, 3H), 2.21 (dd, J=12.6, 9.6 Hz, 1H), 1.95 (d, J=12.8 Hz, 1H), 1.86-1.73 (m, 1H), 1.61 (dd, J=12.6, 3.6 Hz, 1H), 1.51 (s, 2H), 1.46-1.43 (m, 4H), 1.38-1.27 (m, 3H), 1.01-0.86 (m, 6H), 0.44 (d, J=11.6 Hz, 3H).

Example A716. Synthesis of (3S)-1-acryloyl-N-((2S)-1-((($6^3$S,4S)-1-ethyl-$1^2$-(2-((S)-1-methoxyethyl)pyridin-3-yl)-10,10-dimethyl-5,7-dioxo-$2^1$,$2^2$, $2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl)amino)-3-methyl-1-oxobutan-2-yl)-N-methylpyrrolidine-3-carboxamide

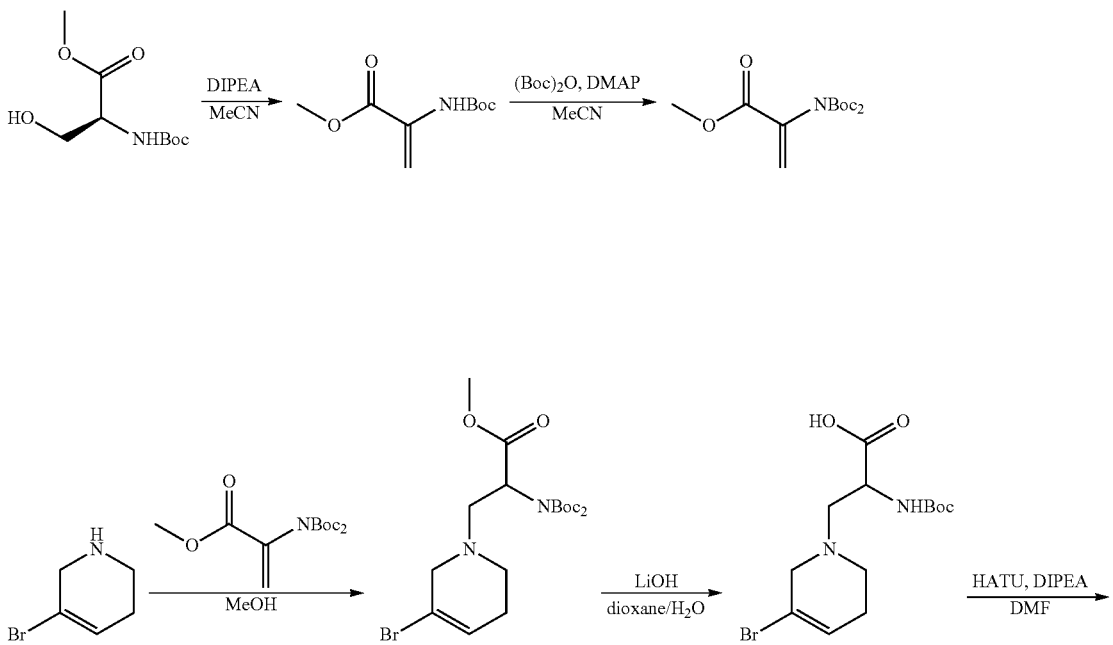

983
984
-continued
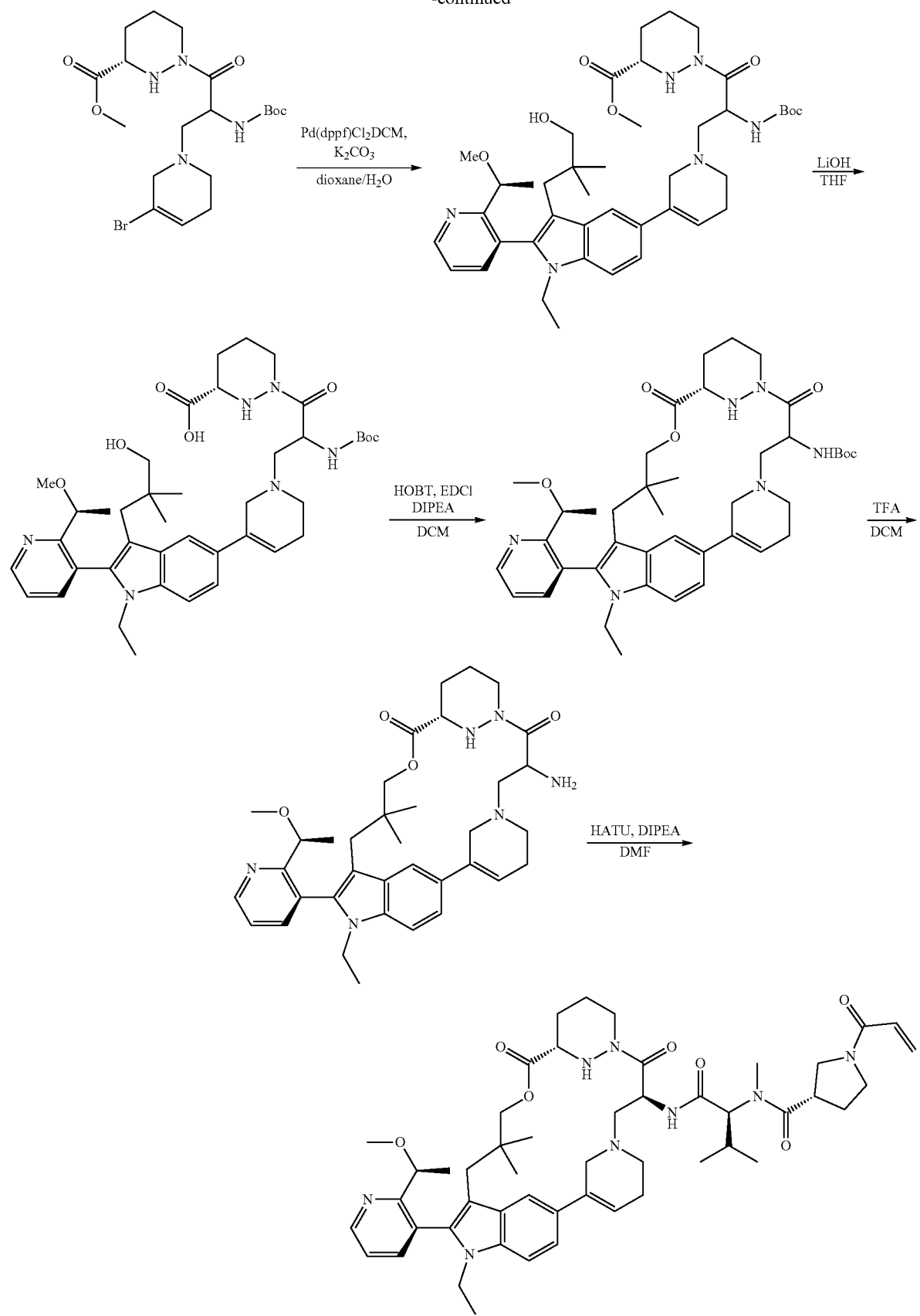

Step 1. To a solution of methyl (tert-butoxycarbonyl)-L-serinate (10 g, 45 mmol) in anhydrous MeCN (150 mL), was added DIPEA (17 g, 137 mmol). The reaction mixture was stirred at 45° C. for 2 h to give methyl 2-((tert-butoxycarbonyl)amino)acrylate in solution. LCMS (ESI): m/z [M+Na] calc'd for $C_9H_{15}NO_4$ 201.1; found 224.1.

Step 2. To a solution of methyl 2-((tert-butoxycarbonyl)amino)acrylate (12 g, 60 mmol) in anhydrous MeCN (150 mL) at 0° C., was added 4-DMAP (13 g, 90 mmol) and $(BoC)_2O$ (26 g, 120 mmol). The reaction was stirred for 6 h, then quenched with $H_2O$ (100 mL) and extracted with DCM (200 mL×3). The combined organic layers were washed with brine (150 mL), dried over anhydrous sodium sulfate, filtered and concentrated under reduced pressure. The residue was purified by silica gel column chromatography to give methyl 2-(bis(tert-butoxycarbonyl)amino)acrylate (12.5 g, 65% yield) as solid. LCMS (ESI): m/z [M+Na] calc'd for $C_{14}H_{23}NO_6$ 301.2; found 324.1.

Step 3. To a mixture of 5-bromo-1,2,3,6-tetrahydropyridine (8.0 g, 49 mmol) in MeOH (120 mL) under an atmosphere of Ar was added methyl 2-{bis[(tert-butoxy)carbonyl]amino}prop-2-enoate (22 g, 74 mmol). The mixture was stirred for 16 h, then concentrated under reduced pressure and the residue was purified by silica gel column chromatography to give methyl 2-(bis(tert-butoxycarbonyl)amino)-3-(5-bromo-3,6-dihydropyridin-1(2H)-yl)propanoate (12 g, 47% yield) as an oil. LCMS (ESI): m/z [M+H] calc'd for $C_{19}H_{31}BrN_2O_6$ 462.1; found 463.1.

Step 4. To a mixture of methyl 2-(bis(tert-butoxycarbonyl)amino)-3-(5-bromo-3,6-dihydropyridin-1(2H)-yl)propanoate (14 g, 30 mmol) in 1,4-dioxane (30 mL) and $H_2O$ (12 mL) was added LiOH (3.6 g, 151 mmol). The mixture was heated to 35° C. and stirred for 12 h, then 1M HCl was added and the pH adjusted to ~3-4. The mixture was extracted with DCM (300 mL×2) and the combined organic layers were dried over anhydrous $Na_2SO_4$ and filtered. The filtrate was concentrated under reduced pressure to give 3-(5-bromo-3,6-dihydropyridin-1(2H)-yl)-2-((tert-butoxycarbonyl)amino)propanoic acid (10 g, 85% yield) as a solid. LCMS (ESI): m/z [M+H] calc'd for $C_{13}H_{21}BrN_2O_4$ 348.1; found 349.0.

Step 5. To a mixture of 3-(5-bromo-3,6-dihydropyridin-1(2H)-yl)-2-((tert-butoxycarbonyl)amino)propanoic acid (10 g, 30 mmol), DIPEA (12 g, 93 mmol) and methyl (3S)-1,2-diazinane-3-carboxylate (5.4 g, 37 mmol) in DMF (100 mL) at 0° C. under an atmosphere of Ar was added HATU (13 g, 34 mmol). The mixture was stirred at 0° C. for 2 h, then $H_2O$ added and the mixture extracted with EtOAc (300 mL×2). The combined organic layers were dried over anhydrous $Na_2SO_4$, filtered, the filtrate was concentrated under reduced pressure and the residue was purified by preparative-HPLC to give methyl (3S)-1-(3-(5-bromo-3,6-dihydropyridin-1(2H)-yl)-2-((tert-butoxycarbonyl)amino)propanoyl)hexahydropyridazine-3-carboxylate (9.0 g, 55% yield) as a solid. LCMS (ESI): m/z [M+H] calc'd for $C_{19}H_{31}BrN_4O_5$ 474.1; found 475.1.

Step 6. A mixture of methyl (3S)-1-(3-(5-bromo-3,6-dihydropyridin-1(2H)-yl)-2-((tert-butoxycarbonyl)amino)propanoyl)hexahydropyridazine-3-carboxylate (9.0 g, 18 mmol), $K_2CO_3$ (4.5 g, 32 mmol), Pd(dppf)$Cl_2$·DCM (1.4 g, 2 mmol), 3-(1-ethyl-2-{2-[(1S)-1-methoxyethyl]pyridin-3-yl}-5-(4,4,5,5-tetramethyl-1,3,2-dioxaborolan-2-yl)indol-3-yl)-2,2-dimethylpropan-1-ol (9.8 g, 20 mmol) in 1,4-dioxane (90 mL) and $H_2O$ (10 mL) under an atmosphere of Ar was heated to 75° C. and stirred for 2 h. $H_2O$ was added and the mixture was extracted with EtOAc (200 mL×3). The combined organic layers were dried over $Na_2SO_4$, filtered, the filtrate was concentrated under reduced pressure and the residue was purified by silica gel column chromatography to give methyl (3S)-1-(2-((tert-butoxycarbonyl)amino)-3-(5-(1-ethyl-3-(3-hydroxy-2,2-dimethylpropyl)-2-(2-((S)-1-methoxyethyl)pyridin-3-yl)-1H-indol-5-yl)-3,6-dihydropyridin-1(2H)-yl)propanoyl)hexahydropyridazine-3-carboxylate (4.0 g, 25% yield) as a solid. LCMS (ESI): m/z [M+H] calc'd for $C_{42}H_{60}N_6O_7$ 760.5; found 761.4.

Step 7. To a mixture of methyl (3S)-1-(2-((tert-butoxycarbonyl)amino)-3-(5-(1-ethyl-3-(3-hydroxy-2,2-dimethylpropyl)-2-(2-((S)-1-methoxyethyl)pyridin-3-yl)-1H-indol-5-yl)-3,6-dihydropyridin-1(2H)-yl)propanoyl) hexahydropyridazine-3-carboxylate (4.1 g, 5.0 mmol) in THF (35 mL) at 0° C. was added LiOH (0.60 g, 27 mmol). The mixture was stirred at 0° C. for 1.5 h, then 1 M HCl added to adjust pH to ~6-7 and the mixture extracted with EtOAc (200 mL×3). The combined organic layers were dried over $Na_2SO_4$, filtered and the filtrate was concentrated under reduced pressure to give (3S)-1-(2-((tert-butoxycarbonyl)amino)-3-(5-(1-ethyl-3-(3-hydroxy-2,2-dimethylpropyl)-2-(2-((S)-1-methoxyethyl)pyridin-3-yl)-1H-indol-5-yl)-3,6-dihydropyridin-1 (2H)-yl)propanoyl) hexahydropyridazine-3-carboxylic acid (3.6 g, 80% yield) as a solid. LCMS (ESI): m/z [M+H] calc'd for $C_{41}H_{58}N_6O_7$ 746.4; found 747.4.

Step 8. To a mixture of (3S)-1-(2-((tert-butoxycarbonyl)amino)-3-(5-(1-ethyl-3-(3-hydroxy-2,2-dimethylpropyl)-2-(2-((S)-1-methoxyethyl)pyridin-3-yl)-1H-indol-5-yl)-3,6-dihydropyridin-1(2H)-yl)propanoyl)hexahydropyridazine-3-carboxylic acid (3.6 g, 5.0 mmol) and DIPEA (24 g, 190 mmol) in DCM (700 mL) under an atmosphere of Ar was added EDCl·HCl (28 g, 140 mmol) and HOBT (6.5 g, 50 mmol). The mixture was heated to 30° C. and stirred for 16 h at 30° C., then concentrated under reduced pressure. The residue was diluted with EtOAc (200 mL) and washed with $H_2O$ (200 mL×2), brine (200 mL), dried over $Na_2SO_4$ and filtered. The filtrate was concentrated under reduced pressure and the residue was purified by silica gel column chromatography to give tert-butyl ((6$^3$S)-1$^1$-ethyl-1$^2$-(2-((S)-1-methoxyethyl)pyridin-3-yl)-10,10-dimethyl-5,7-dioxo-2$^1$,2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-4-yl)carbamate (1.45 g, 40% yield) as a solid. LCMS (ESI): m/z [M+H] calc'd for $C_{41}H_{56}N_6O_6$ 728.4; found 729.4.

Step 9. To a mixture of tert-butyl ((6$^3$S)-1$^1$-ethyl-1$^2$-(2-((S)-1-methoxyethyl)pyridin-3-yl)-10,10-dimethyl-5,7-dioxo-2$^1$,2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-4-yl)carbamate (130 mg, 0.20 mmol) in DCM (1.0 mL) at 0° C. was added TFA (0.3 mL). The mixture was warmed to room temperature and stirred for 2 h, then concentrated under reduced pressure to give (6$^3$S)-4-amino-1$^1$-ethyl-1$^2$-(2-((S)-1-methoxyethyl)pyridin-3-yl)-10,10-dimethyl-2$^1$,2$^2$,2$^3$,2$^6$,6$^1$,6$^2$,6$^3$,6$^4$,6$^5$,6$^6$-decahydro-1¹H-8-oxa-1 (5,3)-indola-6(1,3)-pyridazina-2(5,1)-pyridinacycloundecaphane-5,7-dione, which was used directly in the next step directly without further purification. LCMS (ESI): m/z [M+H] calc'd for $C_{36}H_{48}N_6O_4$ 628.4; found 629.4.

Step 10. To a mixture of ((6³S)-4-amino-1¹-ethyl-1²-(2-((S)-1-methoxyethyl)pyridin-3-yl)-10,10-dimethyl-2¹,2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-5,7-dione (130 mg, 0.2 mmol), DIPEA (270 mg, 2.0 mmol) and (2S)-3-methyl-2-{N-methyl-1-[(3S)-1-(prop-2-enoyl)pyrrolidin-3-yl]formamido}butanoic acid (118 mg, 0.40 mmol) in DMF (3.0 mL) at 0° C. under an atmosphere of Ar was added HATU (87 mg, 0.30 mmol) in portions. The mixture was stirred at 0° C. for 1 h, then diluted with H₂O extracted with EtOAc (30 mL×2). The combined organic layers were dried over anhydrous Na₂SO₄, filtered, the filtrate was concentrated under reduced pressure and the residue was purified by preparative-HPLC to give (3S)-1-acryloyl-N-((2S)-1-(((6³S,4S)-1¹-ethyl-1²-(2-((S)-1-methoxyethyl)pyridin-3-yl)-10,10-dimethyl-5,7-dioxo-2¹,2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)amino)-3-methyl-1-oxobutan-2-yl)-N-methylpyrrolidine-3-carboxamide (17.2 mg, 10% yield) as a solid. LCMS (ESI): m/z [M+H] calc'd for $C_{50}H_{68}N_6O_4$ 892.5; found 893.5; ¹H NMR (400 MHz, CD₃OD) δ 8.74 (d, J=4.4 Hz, 1H), 7.93-7.90 (m, 1H), 7.56-7.51 (m, 3H), 7.43 (d, J=4.4 Hz, 1H), 6.63-6.53 (m, 2H), 6.33-6.23 (m, 2H), 5.83-5.70 (m, 1H), 4.73-4.70 (d, J=11.0 Hz, 1H), 4.48-4.45 (d, J=13.0 Hz, 1H), 4.12-4.10 (m, 3H), 3.86-3.81 (m, 4H), 3.79-3.75 (m, 1H), 3.72-3.69 (m, 3H), 3.57-3.47 (m, 2H), 3.21-3.09 (m, 1H), 3.07-3.04 (q, 4H), 3.02-2.95 (m, 3H), 2.86-2.82 (m, 3H), 2.66-2.48 (m, 2H), 2.29-2.17 (m, 4H), 2.11-1.98 (m, 2H), 1.95-1.91 (m, 1H), 1.45 (d, J=6.2 Hz, 3H), 1.23-1.16 (m, 2H), 1.09-1.04 (m, 1H), 0.97-0.93 (m, 3H), 0.92-0.81 (m, 5H), 0.67-0.63 (m, 3H).

Example A663. The synthesis of (2R)-2-(((1-(4-(dimethylamino)-4-methylpent-2-ynoyl)405yridine405-3-yl)oxy)methyl)-N-((6³S,4S)-1¹-ethyl-1²-(2-((S)-1-methoxyethyl)405yridine-3-yl)-10,10-dimethyl-5,7-dioxo-2¹,2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)-3-methylbutanamide

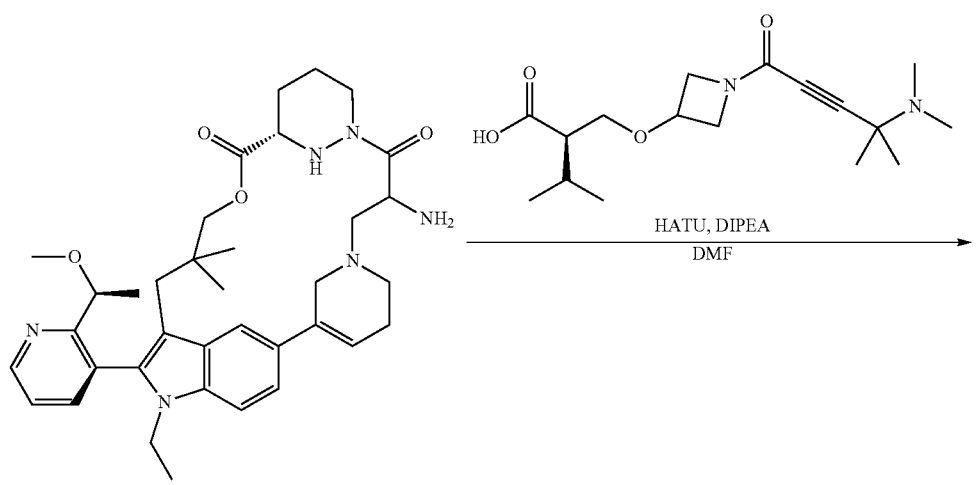

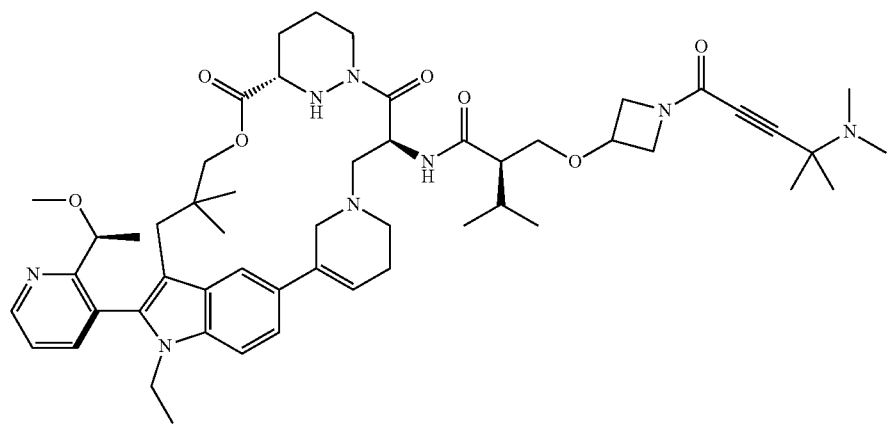

To a mixture of (6³S,4S)-4-amino-1-ethyl-1²-(2-((S)-1-methoxyethyl)405yridine-3-yl)-10,10-dimethyl-2¹,2²,2³,2⁶,6¹,6² 6³ 6⁴ 6⁵ 6⁶-decahydro-1¹H-8-oxa-1(5,3)-indola-6(1,3)-pyridazina-2(5,1)- pyridinacycloundecaphane-5,7-dione (100 mg, 0.16 mmol), 0-2-(((1-(4-(dimethylamino)-4-methylpent-2-ynoyl)405yridine405-3-yl)oxy)methyl)-3-methylbutanoic acid (80 mg, 0.24 mmol) and DIPEA (825 mg, 6.4 mmol) in DMF (2 mL) at 0° C., was added HATU (95 mg, 0.24 mmol). The reaction mixture was stirred at 0° C. for 1 h, then poured into H₂, (60 mL), extracted with EtOAc (80 mL×2). The combined organic layers were washed with H₂S (80 mL) and brine (80 mL, dried over anhydrous sodium sulfate, filtered and concentrated under reduced pressure. The residue was purified by silica gel chromatography to afford (2R)-2-(((1-(4-(dimethylamino)-4-methyl-pent-2-ynoyl)405yridine405-3-yl)oxy)methyl)-N-((6³S, 4S)-1¹-ethyl-1²-(2-((S)-1-methoxyethyl)405yridine-3-yl)-10,10-dimethyl-5,7-dioxo-2¹,2²,2³,2⁶,6¹,6²,6³,6⁴,6⁵,6⁶-decahydro-1¹H-8-oxa-1 (5,3)-indola-6(1,3)-pyridazina-2(5,1)-pyridinacycloundecaphane-4-yl)-3-methylbutanamide (55 mg, 36% yield) as solid. ¹H NMR (400 MHz, 00300) b 8.76-8.70 (m, 1H), 8.49 (dd, J=4.3, 1.4 Hz, 0.1H), 7.93-7.87 (m, 1H), 7.58-7.50 (m, 3H), 7.41 (dd, J=8.8, 3.2 Hz, 1H), 6.26 (d, J=16.8 Hz, 1H), 5.96 (t, J=9.6 Hz, 1H), 4.47 (d, J=12.8 Hz, 1H), 4.39-4.28 (m, 2H), 4.21-3.97 (m, 5H), 3.96-3.70 (m, 5H), 3.68-3.54 (m, 3H), 3.51-3.35 (m, 1H), 3.11 (d, J=22.7 Hz, 3H), 3.00-2.67 (m, 5H), 2.46-2.30 (m, 7H), 2.24 (s, 3H), 2.11 (d, J=12.4 Hz, 1H), 1.92 (d, J=13.2 Hz, 1H), 1.85-1.60 (m, 3H), 1.45 (d, J=7.8 Hz, 6H), 1.32 (d, J=16.0 Hz, 3H), 1.12 (dt, J=24.5, 6.8 Hz, 3H), 0.95 (m, 6H), 0.76 (in, 6H). LCMS (ESI): m/z [M+H] calc'd for C₅₃H₇₄N₈O₇ 934.6; found 935.5.

Example A646. The synthesis of (2R)-2-(((1-(4-(dimethylamino)-4-methylpent-2-ynoyl)azetidin-3-yl)oxy)methyl)-N-((6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(3,1)-piperidinacycloundecaphane-4-yl)-3-methylbutanamide

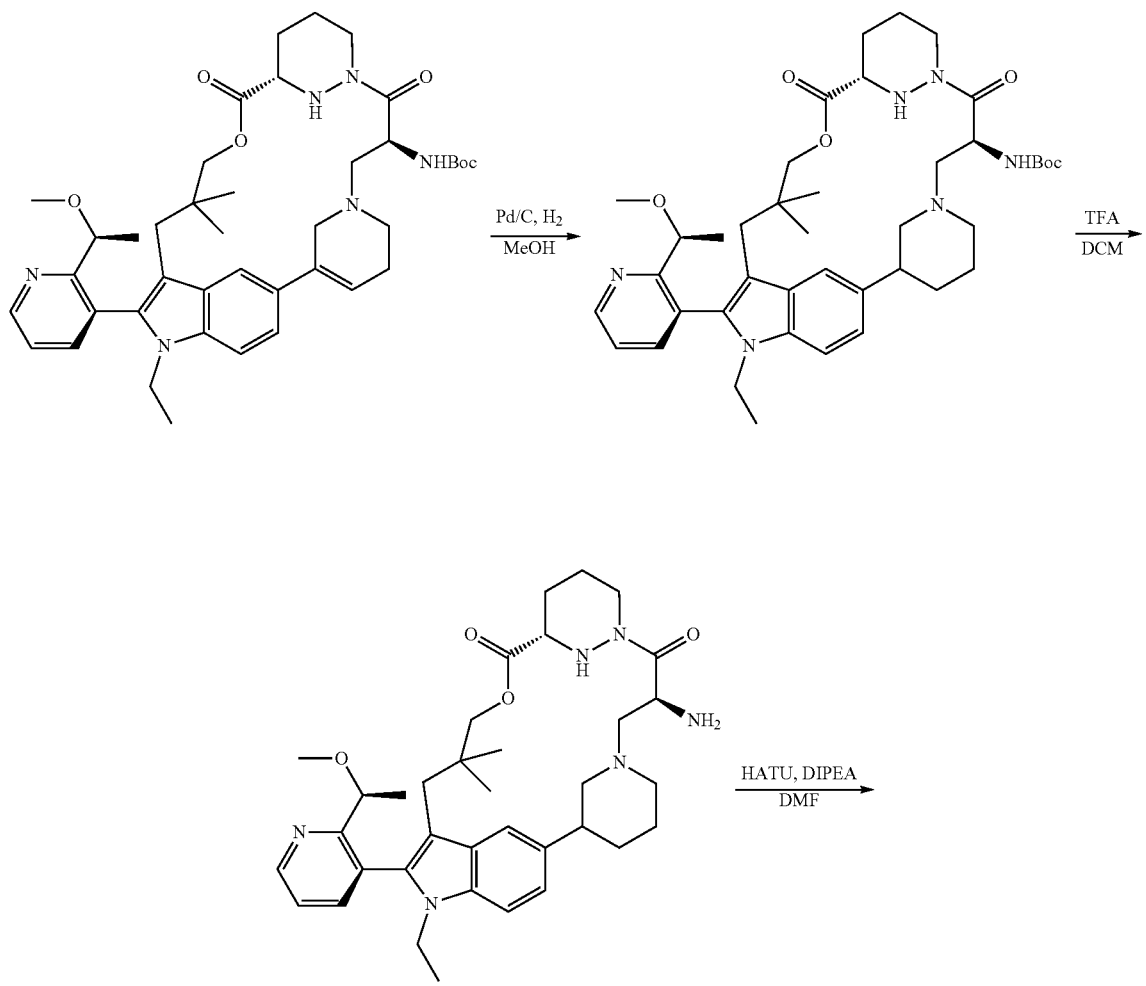

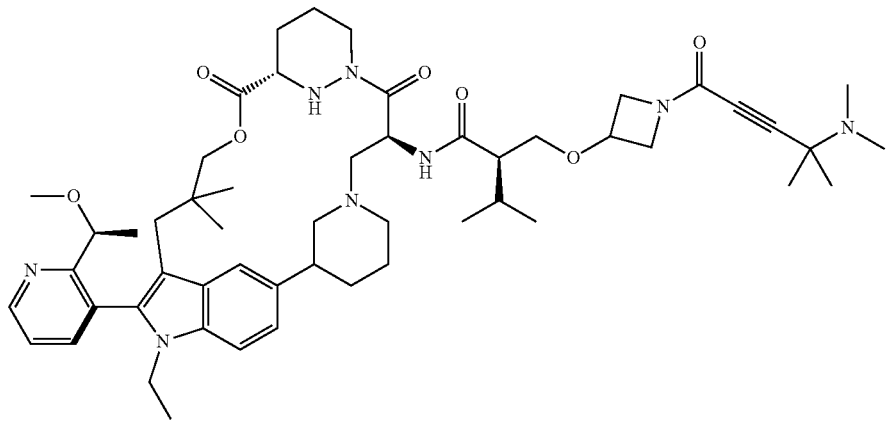

Step 1. A mixture of tert-butyl ((6³S)-1¹-ethyl-1²-(2-((S)-1-methoxyethyl)pyridin-3-yl)-10,10-dimethyl-5,7-dioxo-2¹,2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)carbamate (0.2 g, 0.28 mmol) and Pd/C (0.2 g, 2 mmol) in MeOH (10 mL) was stirred at 25° C. for 16 h under an H₂ atmosphere. The reaction mixture was filtered through Celite, concentrated under reduced pressure to afford tert-butyl ((6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(3,1)-piperidinacycloundecaphane-4-yl)carbamate as solid. LCMS (ESI): m/z [M+H] calc'd for C₄₁H₅₈N₆O₆ 730.4; found 731.4.

Step 2. To a solution of tert-butyl ((6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(3,1)-piperidinacycloundecaphane-4-yl)carbamate (150 mg, 0.2 mmol) in DCM (1.5 mL) at 0° C. was added TFA (0.5 mL). The reaction mixture was stirred at 20° C. for 1 h, then concentrated under reduced pressure to afford (6³S,4S)-4-amino-1¹-ethyl-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(3,1)-piperidinacycloundecaphane-5,7-dione as solid. LCMS (ESI): m/z [M+H] calc'd for C₃₆H₅₀N₆O₄ 630.4; found 631.4.

Step 3. To a mixture of (6³S,4S)-4-amino-1¹-ethyl-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(3,1)-piperidinacycloundecaphane-5,7-dione (240 mg, 0.4 mmol), DIPEA (982 mg, 2 mmol) and (R)-2-(((1-(4-(dimethylamino)-4-methylpent-2-ynoyl)azetidin-3-yl)oxy)methyl)-3-methylbutanoic acid (148 mg, 0.45 mmol) in DMF (4 mL) at 0° C. under argon atmosphere, was added HATU (173 mg, 0.46 mmol) in portions. The reaction mixture was stirred at 0° C. under an argon atmosphere for 1 h, then quenched with H₂O at 0° C. The resulting mixture was extracted with EtOAc (30 mL×2). The combined organic layers were dried over anhydrous sodium sulfate, filtered and concentrated under reduced pressure. The residue was purified by reverse phase chromatography to afford (2R)-2-(((1-(4-(dimethylamino)-4-methylpent-2-ynoyl)azetidin-3-yl)oxy)methyl)-N-((6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(3,1)-piperidinacycloundecaphane-4-yl)-3-methylbutanamide (150 mg, 38% yield) as solid. ¹H NMR (400 MHz, CD₃OD) δ 8.72 (d, J=4.8 Hz, 1H), 7.88 (d, J=8.0 Hz, 1H), 7.53-7.49 (m, 2H), 7.42 (d, J=8.4 Hz, 1H), 7.18 (d, J=8.4 Hz, 1H), 5.95-5.91 (m, 1H), 4.52-4.49 (m, 1H), 4.37-4.25 (m, 3H), 4.18-4.15 (m, 2H), 3.99-3.98 (m, 2H), 3.90-3.86 (m, 1H), 3.76-3.68 (m, 2H), 3.55-3.50 (m, 2H), 3.39-3.36 (m, 2H), 3.20 (s, 3H), 3.02 (s, 3H), 2.89-2.79 (m, 3H), 2.62-2.50 (m, 2H), 2.36 (s, 3H), 2.35-2.30 (m, 1H), 2.26 (s, 3H), 2.20-1.15 (m, 1H), 1.97-1.93 (m, 3H), 1.81-1.76 (m, 4H), 1.64-1.61 (m, 2H), 1.46-1.43 (m, 6H), 1.36 (d, J=14.8 Hz, 3H), 1.02 (s, 3H), 0.94 (m, 6H), 0.81 (s, 3H), 0.65 (s, 3H). LCMS (ESI): m/z [M+H] calc'd for C₅₃H₇₆N₈O₇ 936.6; found 937.5.

Example A740. Synthesis of (3S)-1-acryloyl-N-((2S)-1-(((2³S,6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(3,1)-piperidinacycloundecaphane-4-yl)amino)-3-methyl-1-oxobutan-2-yl)-N-methylpyrrolidine-3-carboxamide

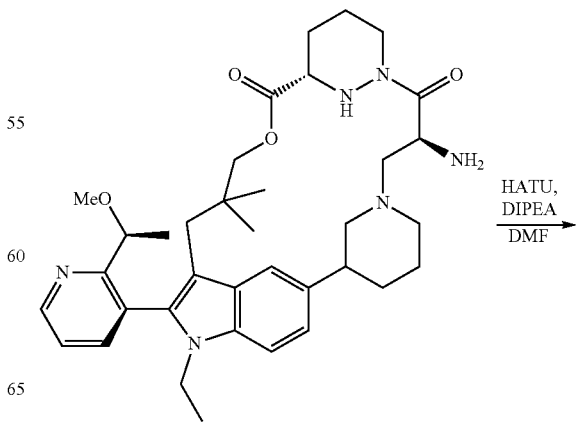

993

-continued

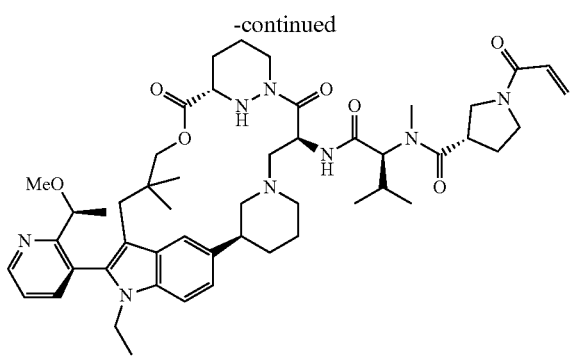

To a mixture of (6³S,4S)-4-amino-1¹-ethyl-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(3,1)-piperidinacycloundecaphane-5,7-dione (140 mg, 0.20 mmol), DIPEA (570 mg, 4.4 mmol) and (2S)-3-methyl-2-{N-methyl-1-[(3S)-1-(prop-2-enoyl)pyrrolidin-3-yl]formamido}butanoic acid (124 mg, 0.40 mmol) in DMF (3.0 mL) at 0° C. under an atmosphere of Ar was added HATU (100 mg, 0.30 mmol) in portions. The mixture was stirred at 0° C. for 1 h, then H₂O was added and the mixture extracted with EtOAc (2×30 mL). The combined organic layers were dried over anhydrous Na₂SO₄ and filtered. The filtrate was concentrated under reduced pressure and the residue was

994 purified by preparative-HPLC to give (3S)-1-acryloyl-N-((2S)-1-(((2³S,6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(3,1)-piperidinacycloundecaphane-4-yl)amino)-3-methyl-1-oxobutan-2-yl)-N-methylpyrrolidine-3-carboxamide (41 mg, 20% yield) as a solid. LCMS (ESI): m/z [M+H] calc'd for C₅₀H₇₀N₈O₇ 894.5; found 895.5; ¹H NMR (400 MHz, CD₃OD) δ 8.72 (d, J=4.8 Hz, 1H), 7.87 (d, J=7.6 Hz, 1H), 7.51-7.49 (m, 2H), 7.42-7.37 (m, 1H), 7.18-7.14 (m, 1H), 6.64-6.54 (m, 1H), 6.30-6.23 (m, 1H), 5.77-5.70 (m, 2H), 4.65-4.60 (m, 1H), 4.50-4.40 (m, 1H), 4.27-4.16 (m, 2H), 4.00-3.95 (m, 2H), 3.83-3.78 (m, 2H), 3.73-3.60 (m, 4H), 3.51-3.36 (m, 3H), 3.22-3.19 (m, 4H), 3.07 (d, J=6.8 Hz, 2H), 2.99 (d, J=12.0 Hz, 3H), 2.90-2.78 (m, 2H), 2.75-2.64 (m, 3H), 2.20-2.10 (m, 4H), 2.02-1.93 (m, 3H), 1.87-1.64 (m, 4H), 1.45 (d, J=4.8 Hz, 3H), 1.06-1.00 (m, 4H), 0.97-0.89 (m, 3H), 0.83-0.79 (m, 3H), 0.66 (s, 3H).

Example A534. (2S)-2-((S)-7-(4-(dimethylamino)-4-methylpent-2-ynoyl)-1-oxo-2,7-diazaspiro[4.4]nonan-2-yl)-N-((6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide

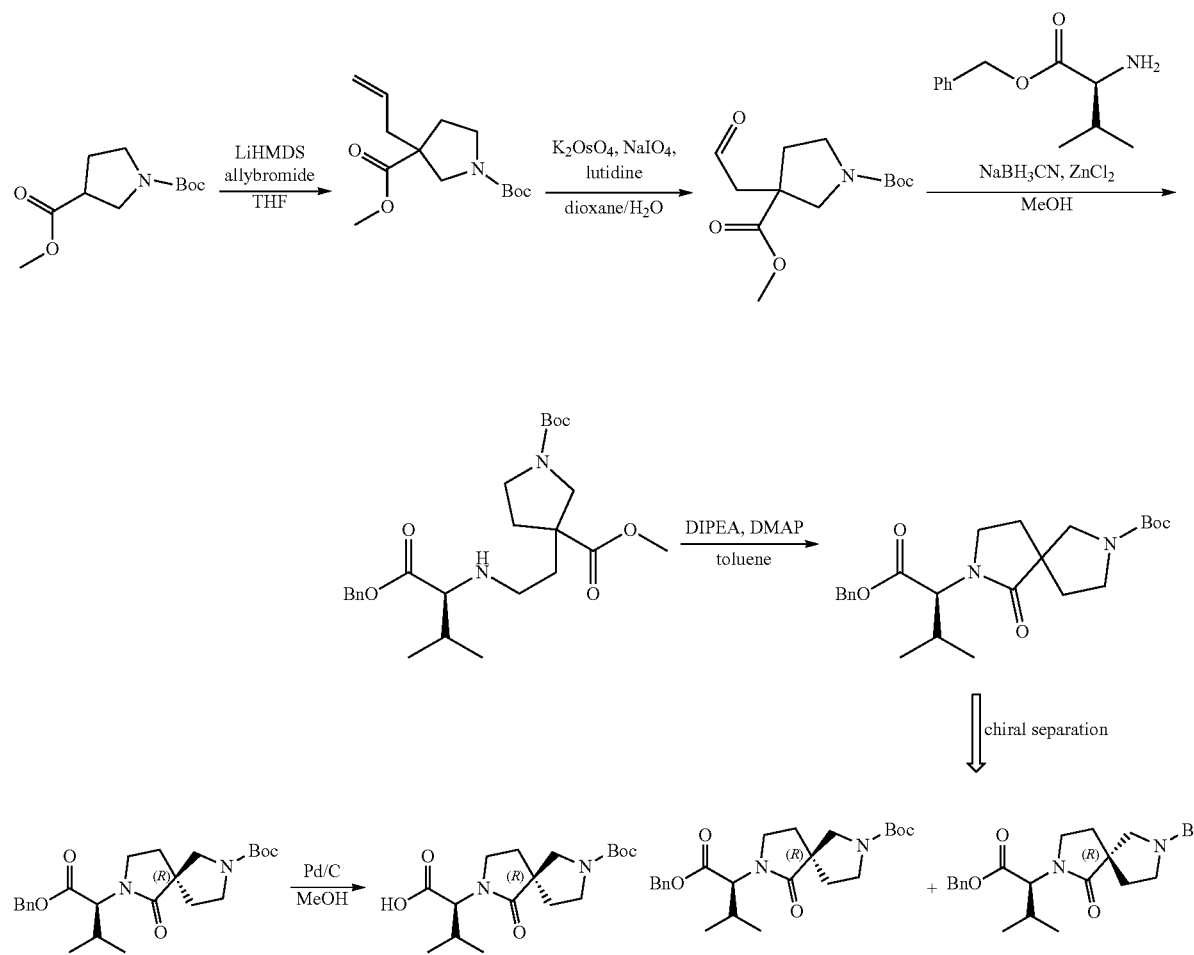

995
996
-continued
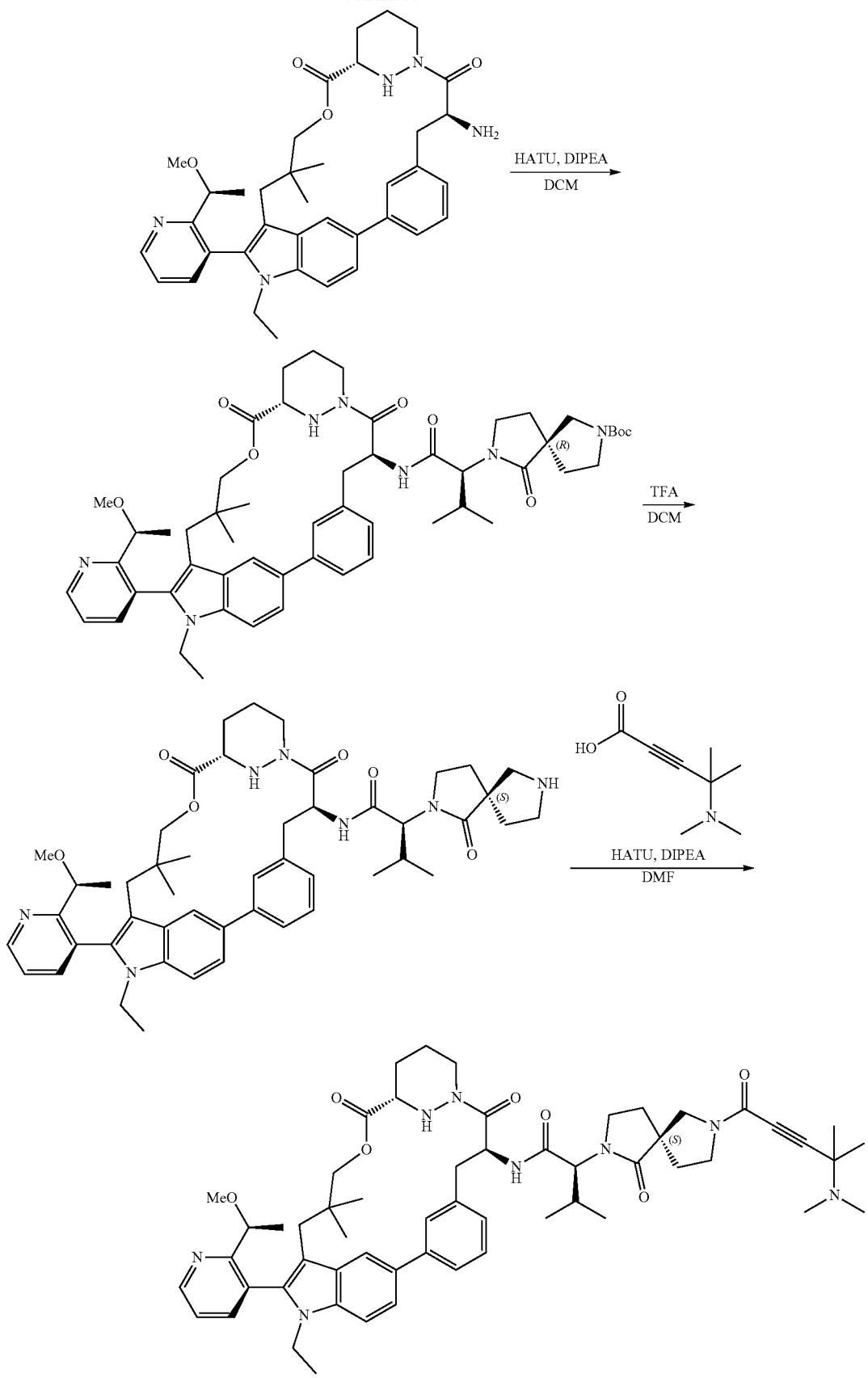

Step 1. To a mixture of 1-tert-butyl 3-methyl pyrrolidine-1,3-dicarboxylate (20.0 g, 87.2 mmol) in THF (150 mL) at −78° C. under an atmosphere of nitrogen was added 1M LiHMDS in THF (113.4 mL, 113.4 mmol). After stirring at −78° C. for 40 min, allyl bromide (13.72 g, 113.4 mmol) was added and the mixture was allowed to warm to room temperature and stirred for 4 h. The mixture was cooled to 0° C., saturated NaCl (30 mL) was added and the mixture extracted with EtOAc. The combined organic layers were dried over anhydrous $Na_2SO_4$ and filtered. The filtrate was concentrated under reduced pressure and the residue was purified by silica gel column chromatography to give 1-(tert-butyl) 3-methyl 3-allylpyrrolidine-1,3-dicarboxylate (17 g, 72% yield) as an oil. $^1$H NMR (300 MHz, $CDCl_3$) δ 5.80-5.60 (m, 1H), 5.16-5.02 (m, 2H), 3.71 (s, 4H), 3.42 (d, J=9.3 Hz, 2H), 3.27 (t, J=11.2 Hz, 1H), 2.42 (d, J=7.6 Hz, 2H), 2.38-2.24 (m, 1H), 2.05 (s, 1H), 1.85 (dt, J=14.3, 7.5 Hz, 1H), 1.46 (s, 10H), 1.27 (t, J=7.1 Hz, 1H).

Step 2. To a mixture of 1-(tert-butyl) 3-methyl 3-allylpyrrolidine-1,3-dicarboxylate (4.0 g, 14.9 mmol) and 2,6-dimethylpyridine (3.18 g, 29.7 mmol) in 1,4-dioxane (200 mL) and $H_2O$ (100 mL) at 0° C. was added $K_2OsO_4 \cdot 2H_2O$ (0.11 g, 0.3 mmol) in portions. The mixture was stirred for 15 min at 0° C., then $NaIO_4$ (6.35 g, 29.7 mmol) was added in portions. The mixture was stirred at room temperature for 3 h at room temperature, then cooled to 0° C. and saturated aqueous $Na_2S_2O_3$ (50 mL) added. The mixture was extracted with EtOAc (3×100 mL) and the combined organic layers were washed with 2 M HCl, then dried over anhydrous $Na_2SO_4$ and filtered. The filtrate was concentrated under reduced pressure to give 1-(tert-butyl) 3-methyl 3-(2-oxoethyl)pyrrolidine-1,3-dicarboxylate (4 g, 52% yield) as an oil. $^1$H NMR (300 MHz, $CDCl_3$) δ 5.80-5.60 (m, 1H), 5.16-5.04 (m, 2H), 3.72 (s, 3H), 3.41 (s, 3H), 3.28 (d, J=11.0 Hz, 1H), 2.44 (s, 2H), 2.31 (d, J=9.1 Hz, 1H), 1.85 (dt, J=12.7, 7.5 Hz, 1H), 1.69 (s, 1H), 1.47 (s, 10H).

Step 3. To a mixture of 1-(tert-butyl) 3-methyl 3-(2-oxoethyl)pyrrolidine-1,3-dicarboxylate (6.30 g, 23.2 mmol), in MeOH (70 mL) at 0° C. was added benzyl (2S)-2-amino-3-methylbutanoate (7.22 g, 34.8 mmol) and $ZnCl_2$ (4.75 g, 34.8 mmol). The mixture was warmed to room temperature and stirred for 30 min, then cooled to 0° C. and $NaCNBH_3$ (2.92 g, 46.4 mmol) was added in portions. The mixture was warmed to room temperature and stirred for 2 h, then cooled to 0° C. and saturated aqueous $NH_4Cl$ added. The mixture was extracted with EtOAc (3×200 mL) and the combined organic layers were washed with brine (150 mL), dried over anhydrous $Na_2SO_4$ and filtered. The filtrate was concentrated under reduced pressure and the residue was purified by silica gel column chromatography to give 1-(tert-butyl) 3-methyl 3-(2-(((S)-1-(benzyloxy)-3-methyl-1-oxobutan-2-yl)amino)ethyl)pyrrolidine-1,3-dicarboxylate (6.4 g, 54% yield) as an oil. LCMS (ESI): m/z [M+H] calc'd for $C_{25}H_{38}N_2O_6$ 462.3; found 463.4.

Step 4. To a mixture of 1-(tert-butyl) 3-methyl 3-(2-(((S)-1-(benzyloxy)-3-methyl-1-oxobutan-2-yl)amino)ethyl)pyrrolidine-1,3-dicarboxylate (4.50 g, 9.7 mmol) in toluene (50 mL) was added DIPEA (12.57 g, 97.3 mmol) and DMAP (1.19 g, 9.7 mmol). The resulting mixture was heated to 80° C. and stirred for 24 h, then concentrated under reduced pressure and the residue was purified by preparative-HPLC, then by chiral-HPLC to give tert-butyl (R)-7-((S)-1-(benzyloxy)-3-methyl-1-oxobutan-2-yl)-6-oxo-2,7-diazaspiro[4.4]nonane-2-carboxylate (1.0 g, 32% yield) and tert-butyl (S)-7-((S)-1-(benzyloxy)-3-methyl-1-oxobutan-2-yl)-6-oxo-2,7-diazaspiro[4.4]nonane-2-carboxylate (1.0 g, 32% yield) and as a an oil. LCMS (ESI): m/z [M+H] calc'd for $C_{24}H_{34}N_2O_5$ 430.5; found 431.2 and LCMS (ESI): m/z [M+H] calc'd for $C_{24}H_{34}N_2O_5$ 430.3; found 431.2.

Step 5. A mixture of tert-butyl (R)-7-((S)-1-(benzyloxy)-3-methyl-1-oxobutan-2-yl)-6-oxo-2,7-diazaspiro[4.4]nonane-2-carboxylate (4.0 g) and 10% Pd/C (1 g) in MeOH (40 mL) was stirred at room temperature under an atmosphere of $H_2$. The mixture was filtered through a pad of Celite pad and the filtrate was concentrated under reduced pressure to give (S)-2-((R)-7-(tert-butoxycarbonyl)-1-oxo-2,7-diazaspiro[4.4]nonan-2-yl)-3-methylbutanoic acid (4.9 g) as a solid. LCMS (ESI): m/z [M−H] calc'd for $C_{17}H_{28}N_2O_5$ 340.2; found 339.3.

Step 6. To a mixture of $(6^3S,4S)$-4-amino-$1^1$-ethyl-$1^2$-(2-((S)-1-methoxyethyl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione (500 mg, 0.8 mmol) in DCM at 0° C. were added DIPEA (829 mg, 6.4 mmol), ((S)-2-((R)-7-(tert-butoxycarbonyl)-1-oxo-2,7-diazaspiro[4.4]nonan-2-yl)-3-methylbutanoic acid (273 mg, 0.8 mmol) and HATU (396 mg, 1.0 mmol) in portions over 1 min. The mixture was allowed to warm to room temperature and stirred 2 h, then concentrated under reduced pressure and the residue was purified by preparative-TLC to give tert-butyl (5R)-7-((2S)-1-((($6^3$S,4S)-$1^1$-ethyl-$1^2$-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-6-oxo-2,7-diazaspiro[4.4]nonane-2-carboxylate (500 mg, 64% yield) as an oil. LCMS (ESI): m/z [M+H] calc'd for $C_{54}H_{71}N_7O_8$ 945.5; found 946.5.

Step 7. To a mixture of tert-butyl (5R)-7-((2S)-1-((($6^3$S,4S)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-6-oxo-2,7-diazaspiro[4.4]nonane-2-carboxylate (1.0 g, 1.06 mmol) in DCM (10 mL) at 0° C. was added TFA (3 mL) dropwise. The mixture was warmed to room temperature and stirred for 1 h, then concentrated under reduced pressure to give (2S)—N-(($6^3$S,4S)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)-3-methyl-2-((S)-1-oxo-2,7-diazaspiro[4.4]nonan-2-yl) butanamide (1.3 g). LCMS (ESI): m/z [M−H] calc'd for $C_{49}H_{63}N_7O_6$ 846.1; found 845.5.

Step 8. To a mixture of (2S)—N-(($6^3$S,4S)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)-3-methyl-2-((S)-1-oxo-2,7-diazaspiro[4.4]nonan-2-yl) butanamide (500 mg, 0.59 mmol) and DIPEA (764 mg, 5.9 mmol) in DMF (5 mL) at 0° C. were added 4-(dimethylamino)-4-methylpent-2-ynoic acid (110 mg, 0.71 mmol) and HATU (292 mg, 0.77 mmol) in portions. The mixture was warmed to room temperature and stirred for 1 h, then $H_2O$ (10 mL) was added and the mixture extracted with EtOAc (10 mL×3). The combined organic layers were washed with brine (10 mL), dried over anhydrous $Na_2SO_4$ and filtered. The filtrate was concentrated under reduced pressure and the residue was purified by preparative-HPLC to give (2S)-2-((S)-7-(4-(dimethylamino)-4-methylpent-2-ynoyl)-1-oxo-2,7-diazaspiro[4.4]nonan-2-yl)-N-(($6^3$S,4S)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1 (5,3)-indola-6(1,3)-pyridazina-2(1,3)-benzenacycloundecaphane- 4-yl)-3-methylbutanamide (177 mg, 28.94% yield) as a white solid. LCMS (ESI): m/z [M+H] calc'd for $C_{57}H_{74}N_8O_7$ 982.6; found 983.8; $^1$H NMR (400 MHz, DMSO-$d_6$) δ 8.76 (dd, J=4.7, 1.7 Hz, 1H), 8.52 (d, J=7.9 Hz, 1H), 7.99 (d, J=1.7 Hz, 1H), 7.83 (d, J=10.2 Hz, 2H), 7.74-7.58 (m, 3H), 7.53 (dd, J=7.7, 4.8 Hz, 1H), 7.24 (t, J=7.6 Hz, 1H), 7.12 (d, J=7.6 Hz, 1H), 5.32 (d, J=9.7 Hz, 2H), 4.33-4.20 (m, 4H), 4.03 (dd, J=15.0, 8.6 Hz, 2H), 3.88-3.82 (m, 1H), 3.63 (dq, J=20.5, 10.3 Hz, 4H), 3.42-3.34 (m, 2H), 3.21 (s, 1H), 3.13 (d, J=2.8 Hz, 3H), 2.87 (s, 2H), 2.83-2.72 (m, 2H), 2.69-2.62 (m, 1H), 2.21 (d, J=22.6 Hz, 6H), 2.12-1.76 (m, 7H), 1.75-1.47 (m, 2H), 1.46-1.28 (m, 9H), 0.99-0.89 (m, 6H), 0.79-0.71 (m, 6H), 0.52 (s, 3H).

Example A341. Synthesis of (3S)-1-acryloyl-N-((2S)-1-((((6$^3$S,4S)-2$^5$-(difluoromethyl)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide

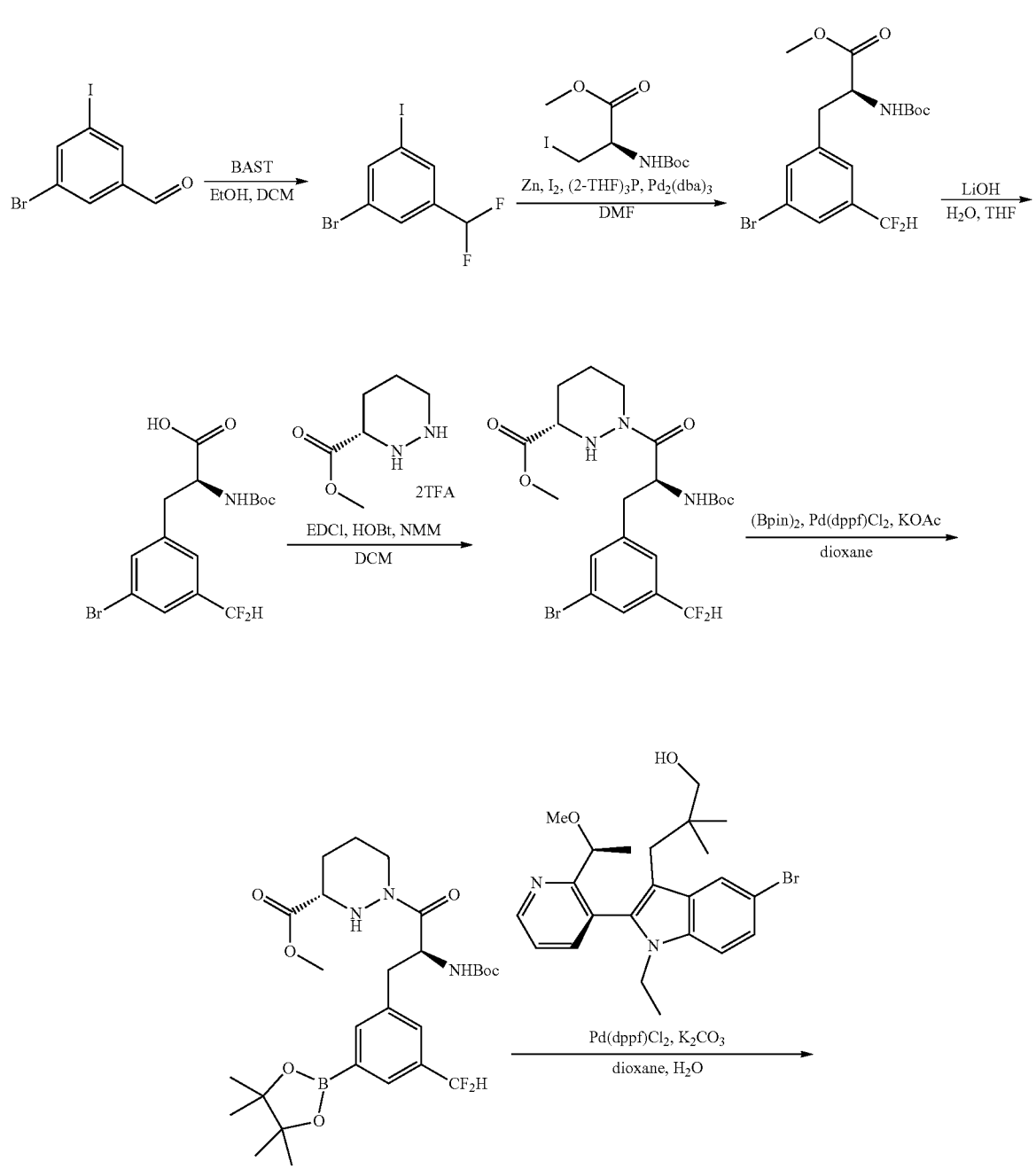

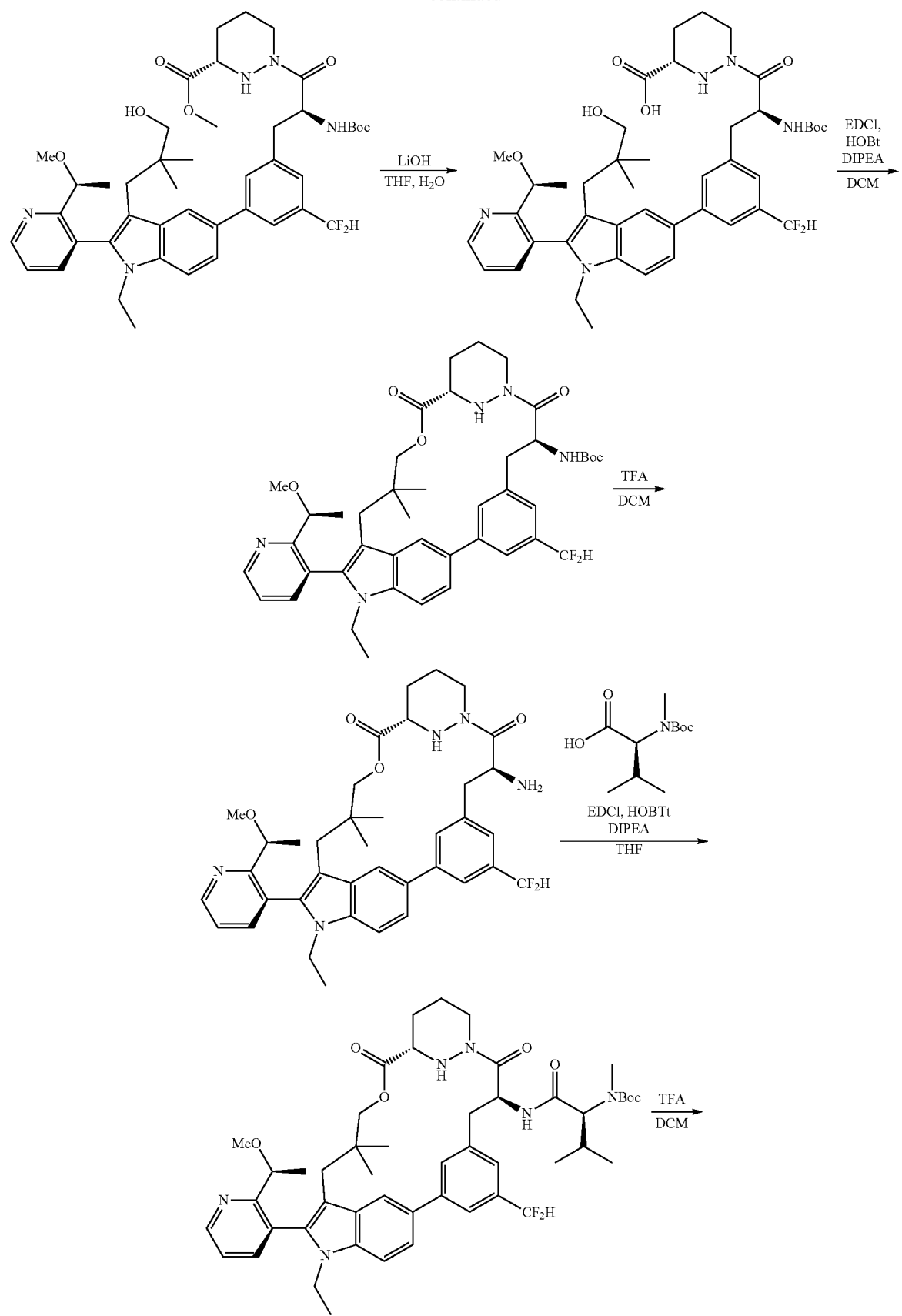

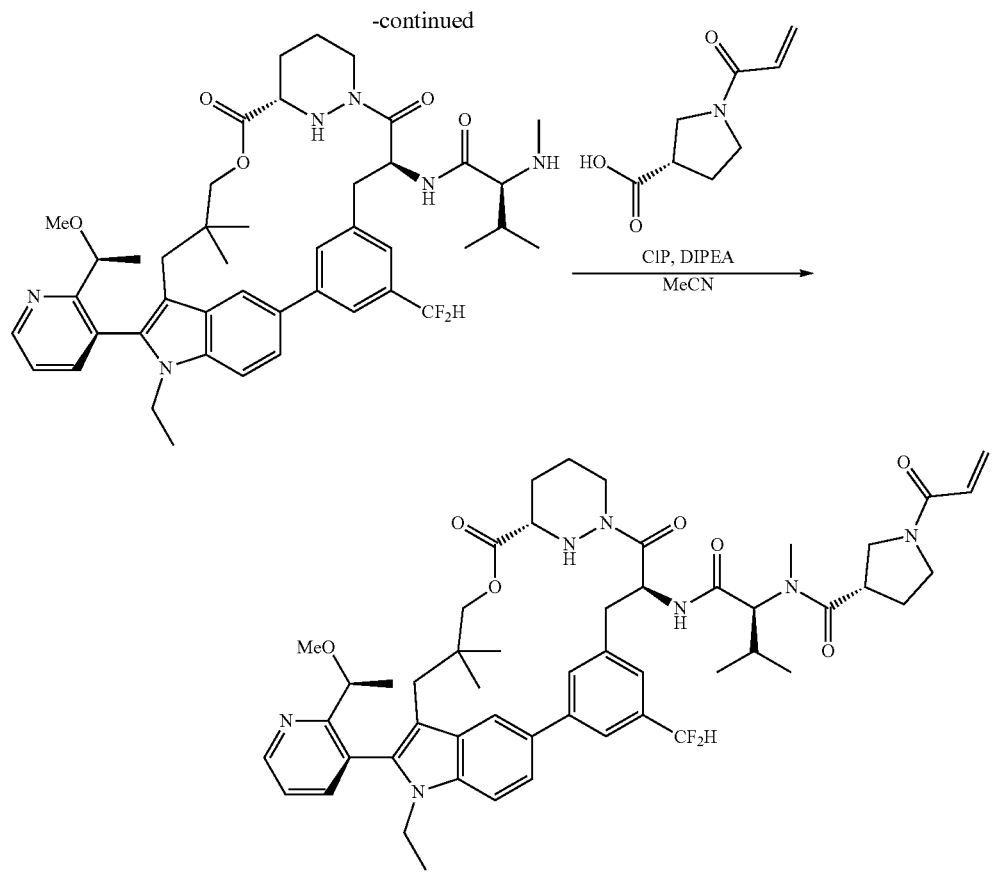

Step 1. To a mixture of 3-bromo-5-iodobenzaldehyde (4.34 g, 14.0 mmol) in DCM at 0° C. under an atmosphere of $N_2$ was added BAST (6.8 g, 30.7 mmol) and EtOH (129 mg, 2.8 mmol) dropwise. The mixture was heated with microwave heating at 27° C. for 14 h. $H_2O$ (500 mL) was added and the mixture was extracted with DCM (200 mL×3), the combined organic layers were concentrated under reduced pressure and the residue was purified by silica gel column chromatography to give 1-bromo-3-(difluoromethyl)-5-iodobenzene (3.2 g, 65% yield) as a solid. $^1$H NMR (300 MHz, DMSO-$d_6$) δ 8.16 (p, J=1.2 Hz, 1H), 7.94 (p, J=1.3 Hz, 1H), 7.81 (p, J=1.3 Hz, 1H), 7.00 (t, J=55.3 Hz, 1H).

Step 2. A mixture of Zn (2.28 g, 34.8 mmol) and 12 (442 mg, 1.74 mmol) in DMF (20 mL) under an atmosphere of Ar was stirred at 50° C. for 0.5 h. To this mixture was added a solution of methyl (methyl (R)-2-((tert-butoxycarbonyl) amino)-3-iodopropanoate (2.39 g, 7.25 mmol) in DMF (20 mL) and the mixture was stirred at 50° C. for 2 h. After cooling, the mixture was added to 1-bromo-3-(difluoromethyl)-5-iodobenzene (2.90 g, 8.7 mmol), $Pd_2(dba)_3$ (239 mg, 0.26 mmol) and tri-2-furylphosphine (162 mg, 0.7 mmol) in DMF (20 mL). The mixture was heated to 70° C. and stirred for 2 h, then $H_2O$ (200 mL) was added and the mixture extracted with EtOAc (200 mL×3). The combined organic layers were concentrated under reduced pressure and the residue was purified by silica gel column chromatography to give methyl (S)-3-(3-bromo-5-(difluoromethyl) phenyl)-2-((tert-butoxycarbonyl)amino)propanoate (560 mg, 19% yield) as a solid. $^1$H NMR (300 MHz, DMSO-$d_6$) δ 7.65 (d, J=10.0 Hz, 2H), 7.47 (s, 1H), 7.36 (d, J=8.4 Hz, 1H), 7.00 (t, J=55.6 Hz, 1H), 4.25 (td, J=9.6, 4.7 Hz, 1H), 3.64 (s, 3H), 3.11 (dd, J=13.6, 4.9 Hz, 1H), 3.00-2.80 (m, 1H), 1.32 (s, 9H).

Step 3. To a mixture of methyl (S)-3-(3-bromo-5-(difluoromethyl)phenyl)-2-((tert-butoxycarbonyl)amino)propanoate (650 mg, 1.6 mmol) in THF (1.5 mL) at 0° C. under an atmosphere of $N_2$ was added LiOH (114 mg, 4.8 mmol) in $H_2O$ (1.50 mL). The mixture was stirred at 0° C. for 1 h, then acidified to pH 5 with 1M HCl. The mixture was extracted with DCM/MeOH (10/1) (100 mL×3) and the combined organic layers were dried over anhydrous $Na_2SO_4$ and filtered. The filtrate was concentrated under reduced pressure to give (S)-3-(3-bromo-5-(difluoromethyl)phenyl)-2-((tert-butoxycarbonyl)amino)propanoic acid (500 mg), which was used directly in the next step without further purification. LCMS (ESI): m/z [M+H] calc'd for $C_{15}H_{18}BrF_2NO_4$ 393.0; found 392.1.

Step 4. To a mixture of methyl (3S)-1,2-diazinane-3-carboxylate (475 mg, 3.3 mmol) in DCM (10 mL) at 0° C. under an atmosphere of $N_2$ were added N-methylmorpholine (3.34 g, 33.0 mmol) and (S)-3-(3-bromo-5-(difluoromethyl) phenyl)-2-((tert-butoxycarbonyl)amino)propanoic acid (650 mg, 1.7 mmol) and HOBt (45 mg, 0.33 mmol) and EDCl (632 mg, 3.3 mmol). The mixture was warmed to room temperature and stirred for 16 h, then diluted with DCM (100 mL) and $H_2O$. The organic and aqueous layer was separated and the aqueous layer was extracted with DCM (100 mL×3). The combined organic layers were dried over anhydrous $Na_2SO_4$ and filtered. The filtrate was concentrated under reduced pressure and the residue was purified by silica gel column chromatography to give methyl (S)-1-

((S)-3-(3-bromo-5-(difluoromethyl)phenyl)-2-((tert-butoxycarbonyl)amino)propanoyl)hexahydropyridazine-3-carboxylate (510 mg, 56% yield) as a solid. LCMS (ESI): m/z [M+H] calc'd for $C_{21}H_{28}BrF_2N_3O_5$ 519.1; found 520.3.

Step 5. To a mixture of 4,4,5,5-tetramethyl-2-(tetramethyl-1,3,2-dioxaborolan-2-yl)-1,3,2-dioxaborolane (488 mg, 1.92 mmol) and methyl (S)-1-((S)-3-(3-bromo-5-(difluoromethyl)phenyl)-2-((tert-butoxycarbonyl)amino)propanoyl)hexahydropyridazine-3-carboxylate (500 mg, 0.96 mmol) in 1,4-dioxane (5 mL) was added Pd(dppf)Cl$_2$ (70 mg, 0.07 mmol) and KOAc (236 mg, 2.4 mmol) in portions. The mixture was heated to 90° C. and stirred for 4 h then diluted with H$_2$O (100 mL). The mixture was extracted with DCM (100 mL×3) and the combined organic layers were dried over anhydrous Na$_2$SO$_4$ and filtered. The filtrate was concentrated under reduced pressure and the residue was purified by silica gel column chromatography to give methyl (S)-1-((S)-2-((tert-butoxycarbonyl)amino)-3-(3-(difluoromethyl)-5-(4,4,5,5-tetramethyl-1,3,2-dioxaborolan-2-yl)phenyl)propanoyl)hexahydropyridazine-3-carboxylate (423 mg, 73% yield) as a solid. LCMS (ESI): m/z [M+H] calc'd for $C_{27}H_{40}BF_2N_3O_7$ 567.3; found 568.2.

Step 6. To a mixture of methyl (S)-1-((S)-2-((tert-butoxycarbonyl)amino)-3-(3-(difluoromethyl)-5-(4,4,5,5-tetramethyl-1,3,2-dioxaborolan-2-yl)phenyl)propanoyl)hexahydropyridazine-3-carboxylate (260 mg, 0.47 mmol), (S)-3-(5-bromo-1-ethyl-2-(2-(1-methoxyethyl)pyridin-3-yl)-1H-indol-3-yl)-2,2-dimethylpropan-1-ol and Pd(dppf)Cl$_2$ (34 mg, 0.05 mmol) in 1,4-dioxane (3 mL) and H$_2$O (0.6 mL) was added K$_2$CO$_3$ (163 mg, 1.12 mmol). The mixture was heated to 60° C. and stirred for 16 h, then diluted with H$_2$O (100 mL) and extracted with DCM (100 mL×3). The combined organic layers were dried over anhydrous Na$_2$SO$_4$ and filtered. The filtrate was concentrated under reduced pressure and the residue was purified by silica gel column chromatography to give methyl (S)-1-((S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoyl)hexahydropyridazine-3-carboxylate (350 mg, 78% yield) as a solid. LCMS (ESI): m/z [M+H] calc'd for $C_{44}H_{57}F_2N_5O_7$ 805.4; found 806.6.

Step 7. To a mixture of methyl (S)-1-((S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoyl)hexahydropyridazine-3-carboxylate (350 mg, 0.43 mmol) in THF (2.8 mL) at 0° C. was added LiOH H$_2$O (54 mg, 1.3 mmol) in H$_2$O (0.7 mL). The mixture was warmed to room temperature and stirred for 2 h, then acidified to pH 5 with 1M HCl and extracted with EtOAc (50 mL×3). The combined organic layers were dried over anhydrous Na$_2$SO$_4$, filtered and the filtrate was concentrated under reduced pressure to give (S)-1-((S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoyl)hexahydropyridazine-3-carboxylic acid (356 mg) was used directly in the next step without further purification. LCMS (ESI): m/z [M+H] calc'd for $C_{43}H_{55}F_2N_5O_7$ 791.4; found 792.6.

Step 8. To a mixture of S)-1-((S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoyl)hexahydropyridazine-3-carboxylic acid (356 mg, 0.45 mmol) and DIPEA (1.74 g, 13.5 mmol) in DCM were added EDCl (2.41 g, 12.6 mmol) and HOBt (304 mg, 2.3 mmol). The mixture was stirred for 16 h then H$_2$O was added and the mixture extracted with EtOAc (200 mL×3). The combined organic layers were washed with brine (50 mL×4), dried over anhydrous Na$_2$SO$_4$ and filtered. The filtrate was concentrated under reduced pressure and the residue was purified by silica gel column chromatography to give tert-butyl (($6^3$S,4S)-$2^5$-(difluoromethyl)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)carbamate (202 mg, 51% yield). LCMS (ESI): m/z [M+H] calc'd for $C_{43}H_{53}F_2N_5O_6$ 773.4; found 774.6.

Step 9. To a mixture of tert-butyl (($6^3$S,4S)-$2^5$-(difluoromethyl)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)carbamate (202 mg, 0.26 mmol) in DCM (2 mL) at 0° C. was added TFA (1.0 mL) dropwise. The mixture was stirred at 0° C. for 1.5 h, then concentrated under reduced pressure and dried azeotropically with toluene (3 mL×3) to give ($6^3$S,4S)-4-amino-$2^5$-(difluoromethyl)-$1^1$-ethyl-$1^2$-(2-((S)-1-methoxyethyl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione, which was used directly in the next without further purification. LCMS (ESI): m/z [M+H] calc'd for $C_{38}H_{45}F_2N_5O_4$ 673.3; found 674.5.

Step 10. To a mixture of ($6^3$S,4S)-4-amino-$2^5$-(difluoromethyl)-$1^1$-ethyl-$1^2$-(2-((S)-1-methoxyethyl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione (202 mg, 0.3 mmol) and (2S)-2-[(tert-butoxycarbonyl)(methyl)amino]-3-methylbutanoic acid (139 mg, 0.6 mmol) in THF under an atmosphere of Ar were added DIPEA (581 mg, 4.5 mmol), EDCl (86 mg, 0.45 mmol) and HOBt (61 mg, 0.45 mmol). The mixture was stirred for 16 h, then H$_2$O (100 mL) added and the mixture extracted with EtOAc (200 mL×3). The combined organic layers were washed with brine (50 mL×3), dried over anhydrous Na$_2$SO$_4$ and filtered. The filtrate was concentrated under reduced pressure and the residue was purified by silica gel column chromatography to give tert-butyl ((2S)-1-((($6^3$S,4S)-$2^5$-(difluoromethyl)-11-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)(methyl)carbamate (135 mg, 46% yield) as a solid. LCMS (ESI): m/z [M+H] calc'd for $C_{49}H_{64}F_2N_6O_7$ 886.5; found 887.6.

Step 11. To a mixture of tert-butyl ((2S)-1-((($6^3$S,4S)-$2^5$-(difluoromethyl)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)(methyl)carbamate (130 mg, 0.15 mmol) in DCM at 0° C. under an atmosphere of N$_2$ was added TFA (1.0 mL) dropwise. The mixture was stirred at 0° C. for 1.5 h, then concentrated under reduced pressure and dried azeotropically with toluene (3 mL×3) to give (2S)—N-(($6^3$S,4S)-$2^5$-(difluoromethyl)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)-3-methyl-2-(methylamino)butanamide (130 mg), which was used directly in the next step without further purification. LCMS (ESI): m/z [M+H] calc'd for $C_{44}H_{56}EF_2N_6O_5$ 786.4; found 787.6.

Step 12. To a mixture of (2S)—N-((6³S,4S)-2⁵-(difluoromethyl)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(methylamino)butanamide (130 mg, 0.17 mmol) and (3S)-1-(prop-2-enoyl)pyrrolidine-3-carboxylic acid (56 mg, 0.33 mmol) in MeCN (1.5 mL) at 0° C. under an atmosphere of $N_2$ were added DIPEA (427 mg, 3.3 mmol) and CIP (69 mg, 0.25 mmol). The mixture was stirred at 0° C. for 1 h, then $H_2O$ (100 mL) was added and the mixture extracted with EtOAc (200 mL×3). The combined organic layers were washed with brine (50 mL×3), dried over anhydrous $Na_2SO_4$ and filtered. The filtrate was concentrated under reduced pressure and the residue was purified by preparative-HPLC to give (3S)-1-acryloyl-N-((2S)-1-(((6³S,4S)-2⁵-(difluoromethyl)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide (58 mg, 36% yield) as a solid. LCMS (ESI): m/z [M+H] calc'd for $C_{52}H_{65}EF_2N_7O_7$ 937.4; found 938.1; ¹H NMR (400 MHz, DMSO-$d_6$) δ 8.78 (dd, J=4.8, 1.7 Hz, 1H), 8.43-8.21 (m, 1H), 8.02 (s, 2H), 7.93-7.81 (m, 2H), 7.76 (dd, J=9.3, 3.9 Hz, 1H), 7.66 (d, J=8.7 Hz, 1H), 7.56 (dd, J=7.7, 4.8 Hz, 1H), 7.34 (d, J=5.4 Hz, 1H), 7.20-6.86 (m, 1H), 6.80-6.40 (m, 1H), 6.15 (ddt, J=16.8, 4.9, 2.4 Hz, 1H), 5.90-5.60 (m, 1H), 5.59-5.19 (m, 2H), 4.71 (dd, J=10.7, 3.1 Hz, 1H), 4.40-4.17 (m, 3H), 4.12-3.90 (m, 3H), 3.85-3.71 (m, 1H), 3.61 (tdd, J=23.4, 9.9, 4.3 Hz, 6H), 3.40-3.30 (m, 2H), 3.11 (d, J=6.8 Hz, 3H), 3.08-2.90 (m, 2H), 2.87 (s, 2H), 2.84 (s, 3H), 2.69-2.30 (d, J=16.5 Hz, 1H), 2.30-1.79 (m, 5H), 1.75-1.45 (m, 2H), 1.40 (d, J=6.1 Hz, 3H), 1.05-0.85 (m, 6H), 0.85-0.66 (m, 6H), 0.57 (d, J=11.8 Hz, 3H).

Example A741. Synthesis of (3S)-1-acryloyl-N-((2S)-1-(((2³S,6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-piperidinacycloundecaphane-4-yl)amino)-3-methyl-1-oxobutan-2-yl)-N-methylpyrrolidine-3-carboxamide

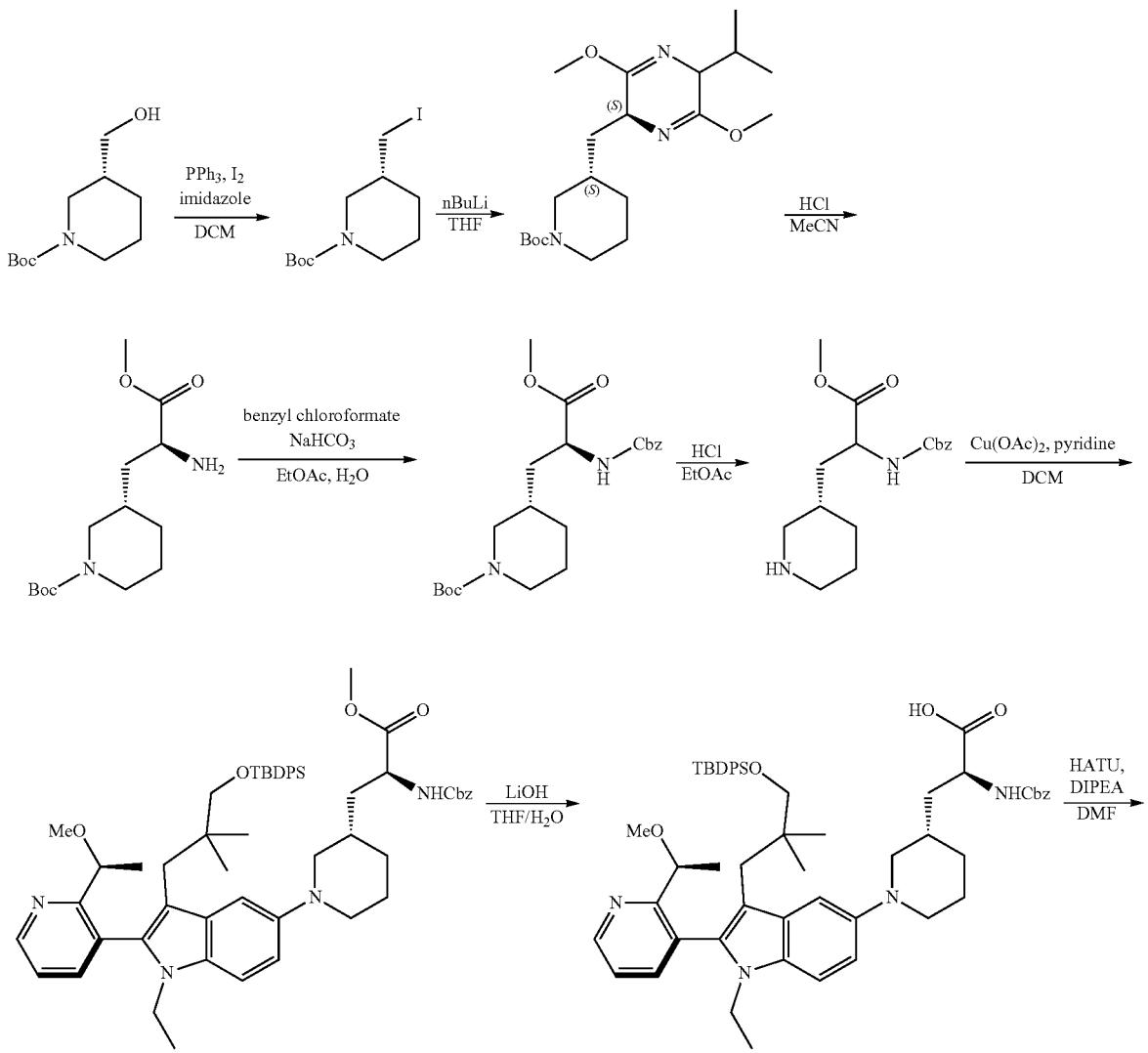

1009
1010
-continued
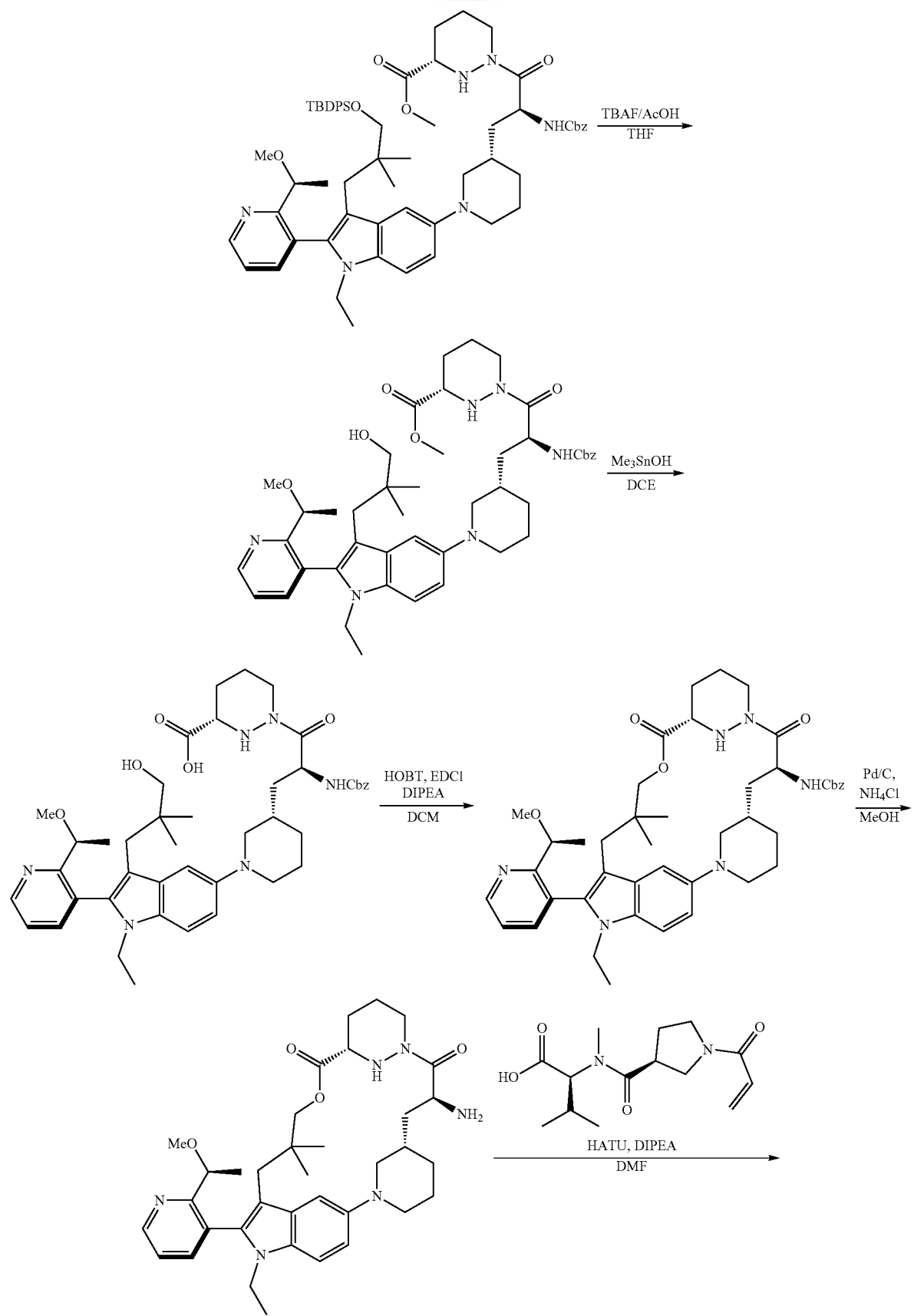

-continued

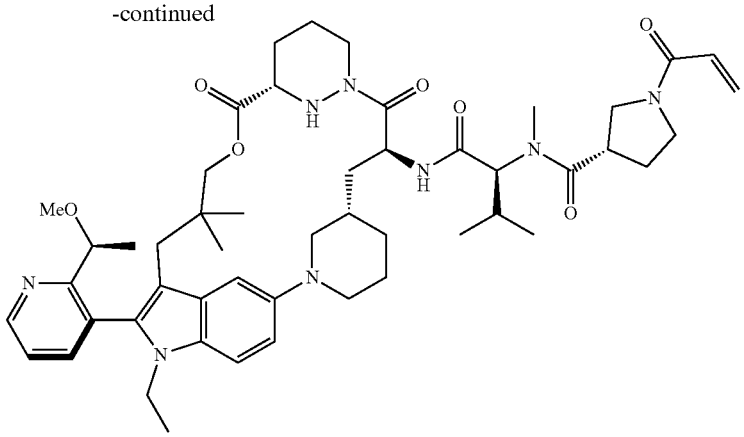

Step 1. A solution of tert-butyl (3R)-3-(hydroxymethyl) piperidine-1-carboxylate (10 g, 46.45 mmol) in DCM (200 mL) at 0° C., was added PPh₃ (15.8 g, 60.4 mmol), Imidazole (4.7 g, 69.7 mmol) and I₂ (14.1 g, 55.74 mmol). The reaction suspension was stirred at 20° C. for 17 h, then concentrated under reduced pressure. The residue was purified by silica gel column chromatography to afford tert-butyl (3R)-3-(iodomethyl) piperidine-1-carboxylate (10 g, 66% yield) as oil. LCMS (ESI): m/z [M+H] calc'd for C₁₁H₂₀INO₂ 325.1; found no mass.

Step 2. To a mixture of 3-isopropyl-2,5-dimethoxy-3,6-dihydropyrazine (10.8 g, 58.9 mmol) in THF (150 mL) at −60° C. under an atmosphere of N₂ was added n-BuLi (47 mL, 2.5 M in hexane, 117.7 mmol) dropwise. The mixture was warmed to 0° C. and was stirred for 2 h, then re-cooled to −60° C., and a solution of tert-butyl (3R)-3-(iodomethyl) piperidin-1-yl formate (9.60 g, 29.4 mmol) in THF (50 mL) was slowly added dropwise. The mixture was stirred at −60° C. for 2 h then warmed to room temperature and stirred for 2 h. Saturated NH₄Cl (150 mL) was slowly added and the mixture extracted with EtOAc (150 mL×2). The combined organic layers were washed with brine (200 mL), dried over anhydrous Na₂SO₄ and filtered. The filtrate was reduced under reduced pressure and the residue was purified by silica gel column chromatography to give tert-butyl (3S)-3-{[(2S)-5-isopropyl-3,6-dimethoxy-2,5-dihydropyrazin-2-yl]methyl}piperidin-1-yl formate (5.3 g, 46% yield) as a gum. LCMS (ESI): m/z [M+H] calc'd for C₂₀H₃₅N₃O₄ 381.5; found 382.3.

Step 3. A mixture of tert-butyl (3S)-3-{[(2S)-5-isopropyl-3,6-dimethoxy-2,5-dihydropyrazin-2-yl]methyl}piperidin-1-yl formate (5.30 g, 13.9 mol) in MeCN (4 mL) was added 1M HCl (27.7 mL, 27.7 mmol) dropwise. The mixture was stirred for 2 h, then saturated NaHCO₃ until ~pH 7-8, then extracted with DCM (30 mL×2). The combined organic layers was dried over anhydrous Na₂SO₄, filtered and concentrated under reduced pressure to give methyl (S)-tert-butyl 3-((S)-2-amino-3-methoxy-3-oxopropyl)piperidine-1-carboxylate (4.3 g, 95% yield) as an oil, which was used in next step without further purification. LCMS (ESI): m/z [M+H] calc'd for C₁₄H₂₆N₂O₄ 286.2; found 287.3.

Step 4. To a mixture of methyl (S)-tert-butyl 3-((S)-2-amino-3-methoxy-3-oxopropyl)piperidine-1-carboxylate (4.30 g, 15.0 mmol) in EtOAc (30 mL) and H₂O (20 mL) at −10° C. was added NaHCO₃(3.77 g, 44.88 mmol). The mixture was stirred at −10° C. for 10 min, then a solution of benzyl chloroformate (3.83 g, 22.44 mmol) was added dropwise. The mixture was warmed to 0° C. and stirred for 1 h, then H₂O (50 mL) was added and the mixture extracted with EtOAc (50 mL×2). The combined organic layers were dried over anhydrous Na₂SO₄, filtered, the filtrate was concentrated under reduced pressure to give tert-butyl (3S)-3-[(2S)-2-{[(benzyloxy)carbonyl] amino}-3-methoxy-3-oxopropyl]piperidine-1-carboxylate (4.0 g, 60% yield) as a gum. LCMS (ESI): m/z [M-Boc+H] calc'd for C₁₇H₂₄N₂O₄ 320.2; found 321.3.

Step 5. To a mixture of tert-butyl (3S)-3-[(2S)-2-{[(benzyloxy)carbonyl] amino}-3-methoxy-3-oxopropyl]piperidine-1-carboxylate (1.0 g, 2.38 mmol) in EtOAc (8 mL) was added 2M HCl in EtOAc (11.9 mL, 23.8 mmol). The mixture was stirred for 2 h, then saturated NaHCO₃ added until ~pH 8-9, and the mixture extracted with DCM (30 mL×3). The combined organic layer was dried over anhydrous Na₂SO₄, filtered and concentrated under reduced pressure to give (2S)-2-{[(benzyloxy)carbonyl]amino}-3-[(3S)-piperidin-3-yl]propanoate (740 mg, 91% yield) as a gum. LCMS (ESI): m/z [M+H] calc'd for C₁₇H₂₄N₂O₄ 320.2; found 321.2.

Step 6. To a mixture of (3-{3-[(tert-butyldiphenylsilyl)oxy]-2,2-dimethylpropyl}-1-ethyl-2-{2-[(1 S)-1-methoxyethyl]pyridin-3-yl}indol-5-yl)boranediol (5.47 g, 8.43 mmol) and methyl (2S)-2-{[(benzyloxy)carbonyl]amino}-3-[(3S)-piperidin-3-yl]propanoate (2.70 g, 8.43 mmol) in DCM (70 mL) was added Cu(OAc)₂ (6.06 g, 16.86 mmol) and pyridine (2.0 g, 25.3 mmol). The mixture was stirred under an atmosphere of O2 for 48 h, then diluted with DCM (200 mL) and washed with H₂O (150 mL×2). The organic layer was dried over anhydrous Na₂SO₄, filtered, concentrated under reduced pressure and the residue was purified by silica gel column chromatography to give methyl 2-{[(benzyloxy)carbonyl]amino}-3-[(3S)-1-(3-{3-[(tert-butyldiphenylsilyl)oxy]-2,2-dimethylpropyl}-1-ethyl-2-{2-[(1 S)-1-methoxyethyl]pyridin-3-yl}indol-5-yl)piperidin-3-yl]propanoate (3.6 g, 42% yield) as a solid. LCMS (ESI): m/z [M/2+H] calc'd for C₅₆H₇₀N₄O₆Si 462.3; found 462.3.

Step 7. To a mixture of methyl 2-{[(benzyloxy)carbonyl] amino}-3-[(3S)-1-(3-{3-[(tert-butyldiphenylsilyl)oxy]-2,2-dimethylpropyl}-1-ethyl-2-{2-[(1 S)-1-methoxyethyl]pyridin-3-yl}indol-5-yl)piperidin-3-yl]propanoate (3.60 g, 3.57 mmol) in THF (60 mL) and H₂O (30 mL) was added LiOH (342 mg, 14.28 mmol). The mixture was stirred for 2 h, then diluted with H₂O (150 mL), then 1M HCl was added slowly until ~pH 3-4 and the mixture extracted with EtOAc (200 mL×3). The combined organic layers were dried over anhydrous Na₂SO₄, filtered and the filtrate concentrated under reduced pressure to give 2-{[(benzyloxy)carbonyl]amino}-3-[(3S)-1-(3-{3-[(tert-butyldiphenylsilyl)oxy]-2,2-dimethylpropyl}-1-ethyl-2-{2-[(1 S)-1-methoxyethyl]pyridin-3-yl}indol-5-yl)piperidin-3-yl]propanoic acid (3.3 g, 85% yield) as a solid, which was used directly in the next step without further purification. LCMS (ESI): m/z [M/2+H] calc'd for $C_{55}H_{68}N_4O_6Si$ 455.3; found 455.3.

Step 8. To a mixture of methyl 2-{[(benzyloxy)carbonyl]amino}-3-[(3S)-1-(3-{3-[(tert-butyldiphenylsilyl)oxy]-2,2-dimethylpropyl}-1-ethyl-2-{2-[(1 S)-1-methoxyethyl]pyridin-3-yl}indol-5-yl)piperidin-3-yl]propanoate (3.30 g, 2.91 mmol) in DMF (40 mL) was added methyl (3S)-1,2-diazinane-3-carboxylate (0.42 g, 2.91 mmol), HATU (2.21 g, 5.82 mmol) and DIPEA (2.26 g, 17.46 mmol). The mixture was stirred for 3 h, then poured into ice-$H_2O$ and extracted with EtOAc (120 mL×2). The combined organic layers were washed with saturated $NaHCO_3$ (150 mL), brine (150 mL), dried over anhydrous $Na_2SO_4$ and filtered. The filtrate was concentrated under reduced pressure and the residue was purified by silica gel column chromatography to give methyl (3S)-1-[(2S)-2-{[(benzyloxy)carbonyl]amino}-3-[(3S)-1-(3-{3-[(tert-butyldiphenylsilyl)oxy]-2,2-dimethylpropyl}-1-ethyl-2-{2-[(1 S)-1-methoxyethyl]pyridin-3-yl}indol-5-yl)piperidin-3-yl]propanoyl]-1,2-diazinane-3-carboxylate (2.9 g, 95% yield) as a gum. LCMS (ESI): m/z [M/2+H] calc'd for $C_{61}H_{78}N_6O_7Si$ 518.3; found 518.3.

Step 9. To a mixture of methyl (3S)-1-[(2S)-2-{[(benzyloxy)carbonyl]amino}-3-[(3S)-1-(3-{3-[(tert-butyldiphenylsilyl)oxy]-2,2-dimethylpropyl}-1-ethyl-2-{2-[(1 S)-1-methoxyethyl]pyridin-3-yl}indol-5-yl)piperidin-3-yl]propanoyl]-1,2-diazinane-3-carboxylate (1.70 g, 1.64 mmol) was added a mixture of 1M TBAF in THF (19.68 mL, 19.68 mmol) and AcOH (1.18 g, 19.68 mmol). The reaction was heated to 60° C. and stirred for 22 h, then diluted with EtOAc (80 mL) and washed with saturated $NaHCO_3$ (80 mL), $H_2O$ (60 mL×2) and brine (60 mL). The organic layer was dried over anhydrous $Na_2SO_4$, filtered, the filtrate was concentrated under reduced pressure and the residue was purified by preparative-HPLC to give methyl (3S)-1-[(2S)-2-{[(benzyloxy)carbonyl]amino}-3-[(3S)-1-[1-ethyl-3-(3-hydroxy-2,2-dimethylpropyl)-2-{2-[(1 S)-1-methoxyethyl]pyridin-3-yl}indol-5-yl]piperidin-3-yl]propanoyl]-1,2-diazinane-3-carboxylate (1.0 g, 73% yield) as a solid. LCMS (ESI): m/z [M/2+H] calc'd for $C_{45}H_{60}N_6O_7$ 399.2; found 399.4.

Step 10. To a mixture m methyl (3S)-1-[(2S)-2-{[(benzyloxy)carbonyl]amino}-3-[(3S)-1-[1-ethyl-3-(3-hydroxy-2,2-dimethylpropyl)-2-{2-[(1 S)-1-methoxyethyl]pyridin-3-yl}indol-5-yl]piperidin-3-yl]propanoyl]-1,2-diazinane-3-carboxylate (1.0 g, 1.1 mmol) in 1,2-dichloroethane (10 mL) was added $Me_3SnOH$ (1.42 g 7.84 mmol). The mixture was heated to 65° C. and stirred for 10 h, then filtered and the filtrate was concentrated under reduced pressure to give (3S)-1-[(2S)-2-{[(benzyloxy)carbonyl]amino}-3-[(3S)-1-[1-ethyl-3-(3-hydroxy-2,2-dimethylpropyl)-2-{2-[(1 S)-1-methoxyethyl]pyridin-3-yl}indol-5-yl]piperidin-3-yl]propanoyl]-1,2-diazinane-3-carboxylic acid (1.0 g, 99% yield) as a gum. The product was used in the next step without further purification. LCMS (ESI): m/z [M/2+H] calc'd for $C_{44}H_{58}N_6O_7$ 392.2; found 392.3.

Step 11. To a mixture of (3S)-1-[(2S)-2-{[(benzyloxy)carbonyl]amino}-3-[(3S)-1-[1-ethyl-3-(3-hydroxy-2,2-dimethylpropyl)-2-{2-[(1 S)-1-methoxyethyl]pyridin-3-yl}indol-5-yl]piperidin-3-yl]propanoyl]-1,2-diazinane-3-carboxylic acid (1.0 g, 1.1 mmol) in DCM (30 mL) at 0° C. was added HOBT (1.51 g, 11.2 mmol), N-(3-dimethylaminopropyl)-N'-ethylcarbodiimide HCl (6.44 g, 33.6 mmol) and DIPEA (5.79 g, 44.8 mmol). The mixture was warmed to room temperature and stirred for 6 h, then diluted with $H_2O$ and extracted with EtOAc (100 mL×3). The combined organic layers were dried over anhydrous $Na_2SO_4$, filtered, the filtrate was concentrated under reduced pressure and the residue was purified by silica gel column chromatography to give benzyl N-[(6S,8S,14S)-22-ethyl-21-{2-[(1S)-1-methoxyethyl]pyridin-3-yl}-18,18-dimethyl-9,15-dioxo-16-oxa-2,10,22,28-tetraazapentacyclo [18.5.2.1^{2,6}0.1^{10,14}0.0^{23,27}]nonacosa-1(26),20,23(27),24-tetraen-8-yl]carbamate (340 mg, 36% yield) as a solid. LCMS (ESI): m/z [M+H] calc'd for $C_{44}H_{56}N_6O_6$ 383.2; found 383.3.

Step 12. A mixture of benzyl N-[(6S,8S,14S)-22-ethyl-21-{2-[(1 S)-1-methoxyethyl]pyridin-3-yl}-18,18-dimethyl-9,15-dioxo-16-oxa-2,10,22,28-tetraazapentacyclo [18.5.2.1^{2,6}0.1^{10,14}0.0^{23,27}]nonacosa-1(26),20,23(27),24-tetraen-8-yl]carbamate (250 mg, 0.33 mmol), Pd/C (100 mg) and $NH_4Cl$ (353 mg, 6.6 mmol) in MeOH (5 mL) was stirred under an atmosphere of $H_2$ for 4 h. The mixture was filtered through Celite and the filtrate was concentrated under reduced pressure. The residue was dissolved in DCM (30 mL) and washed with saturated $NaHCO_3$ (20 mL), $H_2O$ (20 mL) and brine (20 mL). The organic layer was dried over $Na_2SO_4$, filtered, and the filtrate concentrated under reduced pressure to give (6S,8S,14S)-8-amino-22-ethyl-21-{2-[(1 S)-1-methoxyethyl]pyridin-3-yl}-18,18-dimethyl-16-oxa-2,10,22,28-tetraazapentacyclo [18.5.2.1^{2,6}0.1^{10,14}0.0^{23,27}]nonacosa-1(26),20,23(27),24-tetraene-9,15-dione, which was used in next step without further purification. LCMS (ESI): m/z [M+H] calc'd for $C_{36}H_{50}N_6O_4$ 631.4; found 631.4.

Step 13. To a mixture of (6S,8S,14S)-8-amino-22-ethyl-21-{2-[(1S)-1-methoxyethyl]pyridin-3-yl}-18,18-dimethyl-16-oxa-2,10,22,28-tetraazapentacyclo[18.5.2.1^{2,6}0.1^{10,14}0.0^{23,27}]nonacosa-1(26),20,23(27),24-tetraene-9,15-dione (300 mg, 0.48 mmol), (2S)-3-methyl-2-{N-methyl-1-[(3S)-1-(prop-2-enoyl)pyrrolidin-3-yl]formamido}butanoic acid (136 mg, 0.48 mmol) and DIPEA (620 mg, 4.8 mmol) in DMF (5 mL) at 0° C. was added HATU (183 mg, 0.48 mmol). The mixture was stirred at 0-5° C. for 1 h, then diluted with EtOAc (50 mL), washed with $H_2O$ (50 mL×2), brine (50 mL), dried over $Na_2SO_4$ and filtered. The filtrate was concentrated under reduced pressure and the residue was purified by silica gel column chromatography to give (2S)—N-[(6S,8S,14S)-22-ethyl-21-{2-[(1 S)-1-methoxyethyl]pyridin-3-yl}-18,18-dimethyl-9,15-dioxo-16-oxa-2,10,22,28-tetraazapentacyclo [18.5.2.1^{2,6}0.1^{10,14}0.0^{23,27}]nonacosa-1(26),20,23(27),24-tetraen-8-yl]-3-methyl-2-{N-methyl-1-[(3S)-1-(prop-2-enoyl)pyrrolidin-3-yl]formamido}butanamide (90 mg, 20% yield) as a solid. LCMS (ESI): m/z [M+H] calc'd for $C_{50}H_{70}N_8O_7$ 895.5; found 895.4; $^1$H NMR (400 MHz, $CD_3OD$) δ 8.71 (dd, J=4.8, 1.5 Hz, 1H), 7.86 (dd, J=7.7, 1.5 Hz, 1H), 7.51 (dd, J=7.7, 4.8 Hz, 1H), 7.36 (dd, J=8.9, 1.9 Hz, 1H), 7.22 (d, J=12.1 Hz, 1H), 7.09 (dd, J=8.9, 1.9 Hz, 1H), 6.59 (dt, J=16.9, 9.9 Hz, 1H), 6.26 (ddd, J=16.8, 5.0, 1.9 Hz, 1H), 5.80-5.67 (m, 1H), 5.59-5.46 (m, 1H), 4.93 (d, J=12.4 Hz, 1H), 4.66 (dd, J=11.1, 6.4 Hz, 1H), 4.45 (d, J=12.6 Hz, 1H), 4.28-4.19 (m, 1H), 4.13 (dd, J=14.5, 7.2 Hz, 1H), 4.02-3.87 (m, 1H), 3.87-3.36 (m, 11H), 3.16 (s, 2H), 3.10 (d, J=3.4 Hz, 2H), 2.76 (dd, J=26.9, 13.5 Hz, 3H), 2.61 (s, 1H), 2.35-1.97 (m, 5H), 1.78 (dd, J=25.4, 22.1 Hz, 10H), 1.45 (d, J=6.2 Hz, 3H), 1.04 (d, J=6.2 Hz, 3H), 0.95 (dd, J=6.5, 1.8 Hz, 3H), 0.83 (d, J=6.6 Hz, 3H), 0.72 (d, J=31.8 Hz, 6H).

Example A715. Synthesis of benzyl ((2³S,6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-piperidinacycloundecaphane-4-yl)carbamate

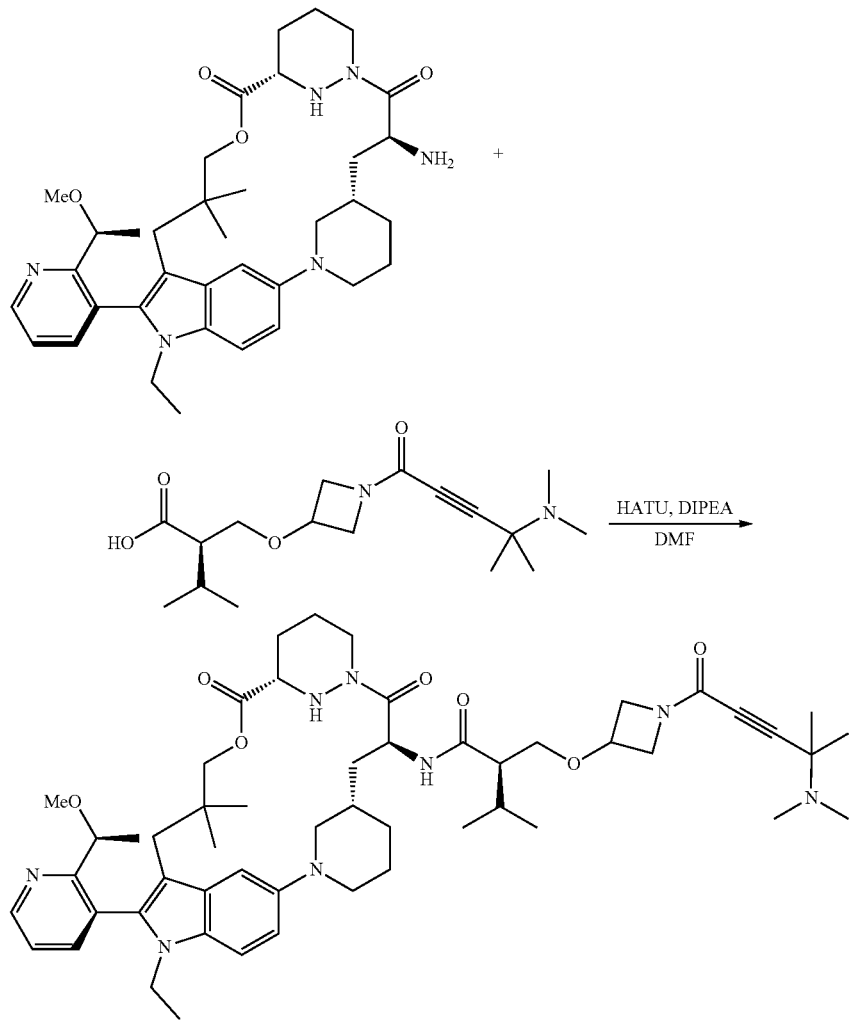

To a solution of ((2³S,6³S,4S)-4-amino-1¹-ethyl-1²-(2-((S)-1-methoxyethyl)pyridin-3-yl)-10,10-dimethyl-6¹,6²,6³, 6⁴,6⁵,6⁶-hexahydro-1¹H-8-oxa-1(5,3)-indola-6(1,3)-pyridazina-2(1,3)-piperidinacycloundecaphane-5,7-dione (50 mg, 0.08 mmol), (R)-2-(((1-(4-(dimethylamino)-4-methylpent-2-ynoyl)azetidin-3-yl)oxy)methyl)-3-methylbutanoic acid (26 mg, 0.08 mmol) and DIPEA (31 mg, 0.24 mmol) in DMF (1 mL) at 0° C., was added HATU (30 mg, 0.08 mmol). The reaction mixture was stirred at 0-5° C. for 1 h, then diluted with EtOAc (20 mL), washed with H₂O (20 mL×2) and brine (20 mL). The organic phase was separated and dried over anhydrous sodium sulfate, filtered and concentrated under reduced pressure. The residue was purified by silica gel column chromatography to give (2R)-2-(((1-(4-(dimethylamino)-4-methylpent-2-ynoyl)azetidin-3-yl)oxy)methyl)-N-((2³S,6³S,4S)-1¹-ethyl-1²-(2-((S)-1-methoxyethyl)pyridin-3-yl)-10,10-dimethyl-5,7-dioxo-6¹, 6²,6³,6⁴,6⁵,6⁶-hexahydro-1¹H-8-oxa-1(5,3)-indola-6(1,3)-pyridazina-2(1,3)-piperidinacycloundecaphane-4-yl)-3-methylbutanamide as solid. ¹H NMR (400 MHz, CD₃OD) δ 8.71 (d, J=4.7 Hz, 1H), 8.24 (s, 1H), 8.10 (dd, J=26.7, 7.8 Hz, 1H), 7.86 (d, J=7.7 Hz, 1H), 7.51 (dd, J=7.7, 4.8 Hz, 1H), 7.39 (dd, J=8.9, 3.1 Hz, 1H), 7.26 (d, J=16.6 Hz, 1H), 7.11 (d, J=8.8 Hz, 1H), 5.61 (s, 1H), 4.50-4.28 (m, 3H), 4.27-4.07 (m, 3H), 3.98 (ddd, J=25.6, 13.4, 5.1 Hz, 2H), 3.84-3.72 (m, 2H), 3.62 (dd, J=10.7, 4.8 Hz, 2H), 3.55 (d, J=7.1 Hz, 2H), 3.47 (d, J=6.5 Hz, 2H), 3.16 (s, 3H), 3.03-2.91 (m, 1H), 2.76 (dd, J=28.7, 15.2 Hz, 3H), 2.62 (s, 1H), 2.40 (t, J=7.0 Hz, 3H), 2.33 (dd, J=14.3, 5.0 Hz, 4H), 2.05 (d, J=11.6 Hz, 1H), 1.99-1.64 (m, 10H), 1.64-1.55 (m, 1H), 1.51-1.42 (m, 6H), 1.37 (d, J=12.3 Hz, 3H), 1.05 (s, 3H), 0.94 (ddd, J=9.3, 6.7, 2.0 Hz, 6H), 0.76 (d, J=3.8 Hz, 3H), 0.69 (s, 3H). LCMS (ESI): m/z [M+H] calc'd for C₅₃H₇₆N₈O₇ 936.6; found 937.4.

Example A347. Synthesis of (2S)—N-[(7S,13S)-21-ethyl-20-{2-[(1S)-1-methoxyethyl]pyridin-3-yl}-17,17-dimethyl-8,14-dioxo-15-oxa-4-thia-9,21,25,27,28-pentaazapentacyclo[17.5.2.1^{2,5}0.1 ^{9,13}0.0^{22,26}]octacosa-1(25),2,5(28),19,22(26),23-hexaen-7-yl]-3-methyl-2-{N-methyl-1-[(3S)-1-(prop-2-enoyl)pyrrolidin-3-yl]formamido}butanamide
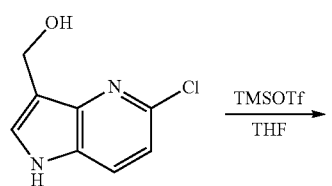
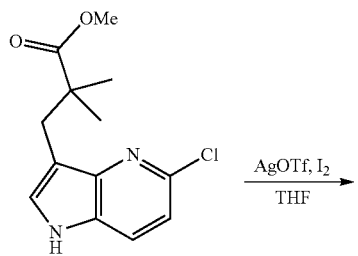
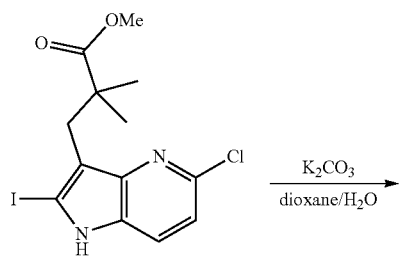
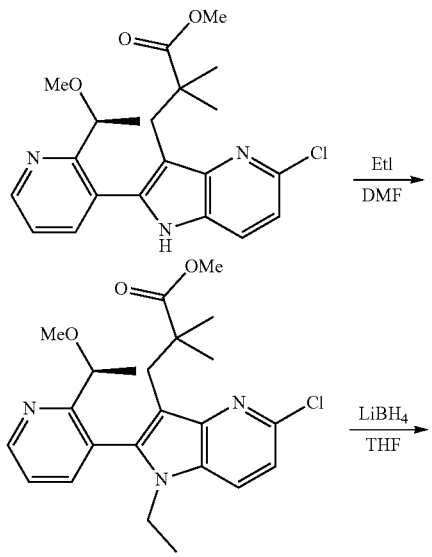
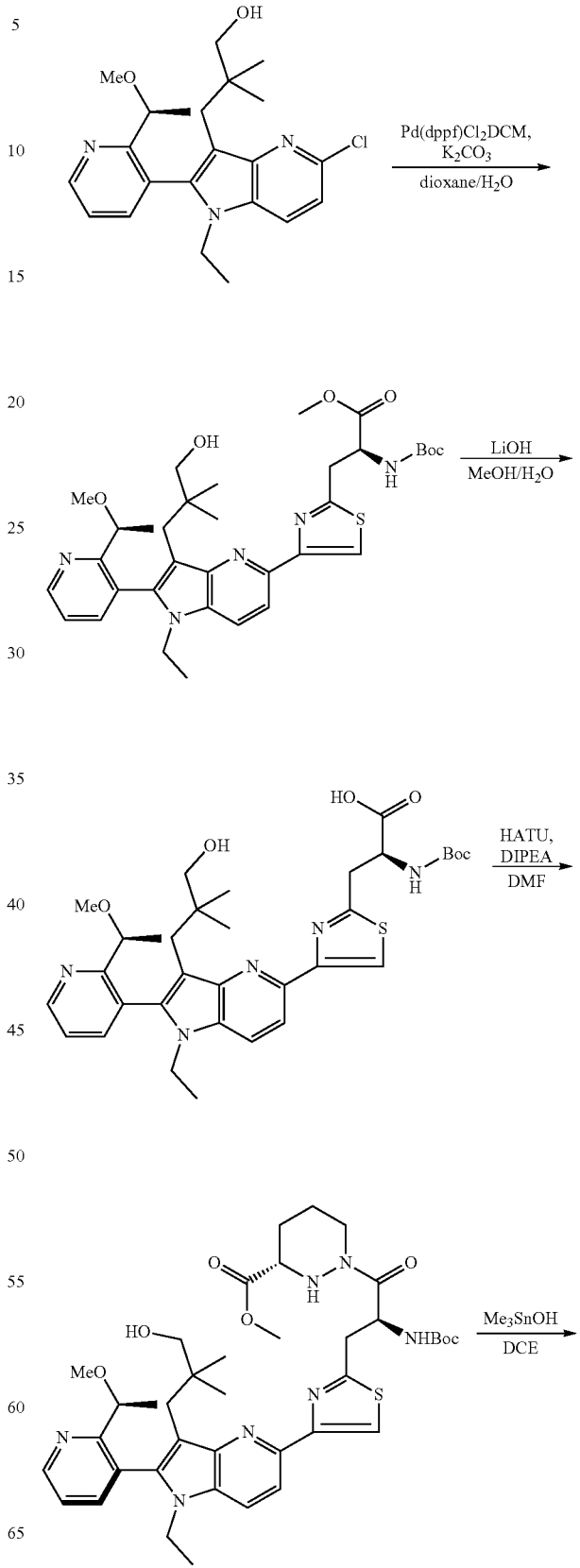

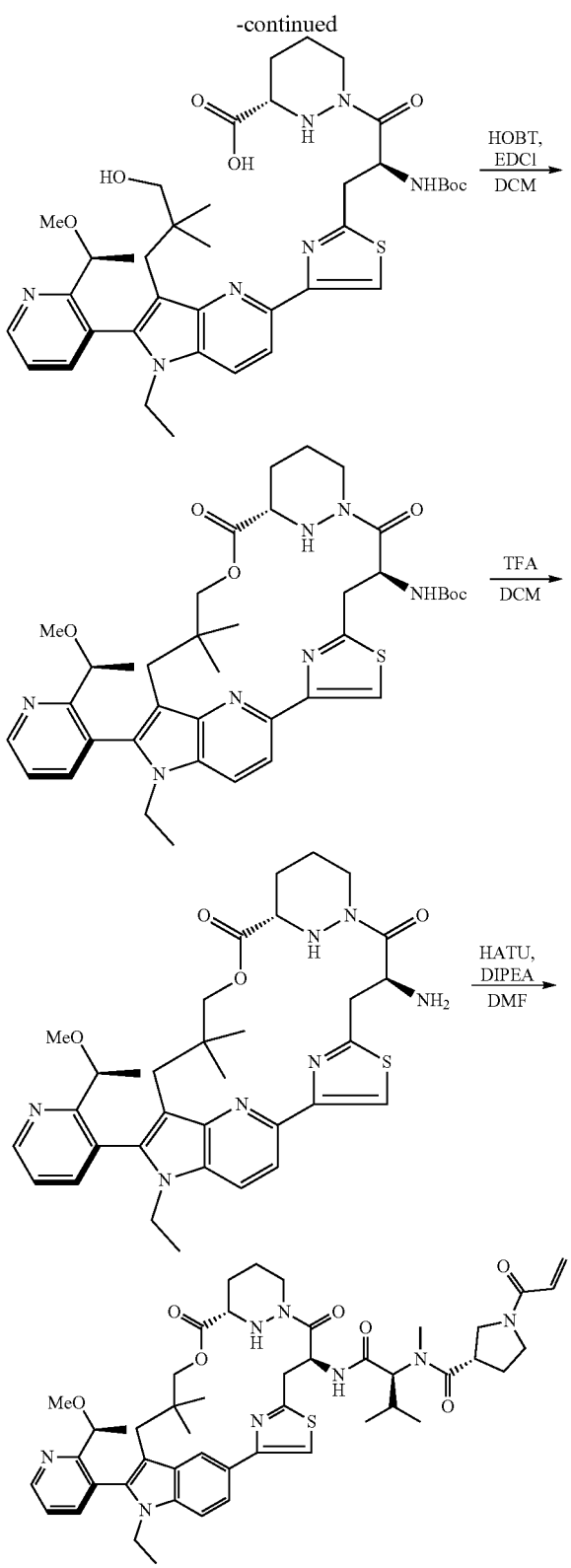

rated NaHCO$_3$(50 mL) and brine (50 mL×2). The organic layer was dried over Na$_2$SO$_4$, filtered and the filtrate was concentrated under reduced pressure. The residue was purified by silica gel column chromatography to give methyl 3-(5-chloro-1H-pyrrolo[3,2-b]pyridin-3-yl)-2,2-dimethylpropanoate (3.0 g, 59% yield) as a solid. LCMS (ESI): m/z [M+H] calc'd for C$_{13}$H$_{15}$ClN$_2$O$_2$ 266.1; found 267.1.

Step 2. To a mixture of methyl 3-(5-chloro-1H-pyrrolo[3,2-b]pyridin-3-yl)-2,2-dimethylpropanoate (3.0 g, 11 mmol) in anhydrous THF (50 mL) at 0° C. was added AgOTf (4.3 g, 17 mmol) and 12 (2.9 g, 11 mmol). The mixture was stirred at 0° C. for 2 h, then saturated Na$_2$SO$_3$ (20 mL) and EtOAc (50 mL) added. The mixture was filtered and the filtrate was washed with brine (50 mL), dried over Na$_2$SO$_4$ and filtered. The filtrate was concentrated under reduced pressure and the residue was purified by silica gel column chromatography to give methyl 3-(5-chloro-2-iodo-1H-pyrrolo[3,2-b]pyridin-3-yl)-2,2-dimethylpropanoate (2.3 g, 52% yield) as a solid. LCMS (ESI): m/z [M+H] calc'd for C$_{13}$H$_{15}$ClIN$_2$O$_2$ 392.0; found 393.0.

Step 3. To a mixture of methyl 3-(5-chloro-2-iodo-1H-pyrrolo[3,2-b]pyridin-3-yl)-2,2-dimethylpropanoate (2.3 g, 5.9 mmol) and 2-(2-(2-methoxyethyl)phenyl)-4,4,5,5-tetramethyl-1,3,2-dioxaborolane (1.6 g, 7.1 mmol) and K$_2$CO$_3$ (2.4 g, 18 mol) in 1,4-dioxane (25 mL) and H$_2$O (5 mL) under an atmosphere of N$_2$ was added Pd(dppf)Cl$_2$·DCM (480 mg, 0.59 mmol). The mixture was heated to 70° C. and for 4 h, then diluted with EtOAc (200 mL) and washed with brine (25 mL), dried over Na$_2$SO$_4$ and filtered. The filtrate was concentrated under reduced pressure and the residue was purified by silica gel column chromatography to give methyl (S)-3-(5-chloro-2-(2-(1-methoxyethyl)pyridin-3-yl)-1H-pyrrolo[3,2-b]pyridin-3-yl)-2,2-dimethylpropanoate (2.0 g, 84% yield) as a solid. LCMS (ESI): m/z [M+H] calc'd for C$_{21}$H$_{24}$ClN$_3$O$_3$ 401.2; found 402.2.

Step 4. A mixture of ethyl 3-(5-chloro-2-(2-((S)-1-methoxyethyl)pyridin-3-yl)-1H-pyrrolo[3,2-b]pyridin-3-yl)-2-methylpropanoate (2.0 g, 5.0 mmol), Cs$_2$CO$_3$ (3.3 g, 10 mmol) and EtI (1.6 g, 10 mmol) in DMF (30 mL) was stirred for 10 h. The mixture was diluted with EtOAc (100 mL) and washed with brine (20 mL×4), dried over Na$_2$SO$_4$ and filtered. The filtrate was concentrated under reduced pressure and the residue was purified by silica gel column chromatography to give two diastereomers of methyl (S)-3-(5-chloro-1-ethyl-2-(2-(1-methoxyethyl)pyridin-3-yl)-1H-pyrrolo[3,2-b]pyridin-3-yl)-2,2-dimethylpropanoate (0.7 g, 32% yield; 0.6 g, 28% yield) as a solid. LCMS (ESI): m/z [M+H] calc'd for C$_{23}$H$_{28}$ClN$_3$O$_3$ 429.2; found 430.2.

Step 5. To a mixture of methyl (S)-3-(5-chloro-1-ethyl-2-(2-(1-methoxyethyl)pyridin-3-yl)-1H-pyrrolo[3,2-b]pyridin-3-yl)-2,2-dimethylpropanoate (1.9 g, 4.4 mmol) in anhydrous THF (20 mL) at 0° C. was added LiBH$_4$ (200 mg, 8.8 mmol). The mixture was heated to 60° C. and stirred for 4 h, then saturated NH$_4$Cl (20 mL) and EtOAc (50 mL) added. The aqueous and organic layers were separated and the organic layer was washed with brine (30 mL), dried over Na$_2$SO$_4$ and filtered. The filtrate was concentrated under reduced pressure and the residue was purified by silica gel column chromatography to give (S)-3-(5-chloro-1-ethyl-2-(2-(1-methoxyethyl)pyridin-3-yl)-1H-pyrrolo[3,2-b]pyridin-3-yl)-2,2-dimethylpropan-1-ol (1.5 g, 85% yield) as a solid. LCMS (ESI): m/z [M+H] calc'd for C$_{22}$H$_{28}$ClN$_3$O$_2$ 401.2; found 402.2.

Step 6. To a mixture of (S)-3-(5-chloro-1-ethyl-2-(2-(1-methoxyethyl)pyridin-3-yl)-1H-pyrrolo[3,2-b]pyridin-3-yl)-2,2-dimethylpropan-1-ol (550 mg, 1.37 mmol), (S)-(2-(2-((tert-butoxycarbonyl)amino)-3-methoxy-3-oxopropyl)

Step 1. To a mixture of (5-chloro-1H-pyrrolo[3,2-b]pyridin-3-yl)methanol (3.5 g, 19 mmol), and ((1-methoxy-2-methylprop-1-en-1-yl)oxy)trimethylsilane (6.7 g, 38 mmol) in THF (50 ml) at 0° C. was added TMSOTf (3.8 g, 17 mmol) dropwise. The mixture was stirred at 0-5° C. for 2 h, then diluted with EtOAc (100 mL) and washed with satuthiazol-4-yl)boronic acid (907.4 mg, 2.74 mmol, 2 eq) and K$_2$CO$_3$ (568 mg, 4.11 mmol) in 1,4-dioxane (25 mL) and H$_2$O (5 mL) under an atmosphere of N$_2$ was added Pd(dppf)Cl$_2$·DCM (89 mg, 0.14 mmol). The mixture was heated to 70° C. and stirred for 4 h, then H$_2$O (50 mL) added and the mixture extracted with EtOAc (100 mL×3). The combined organic layers were washed with brine (50 mL), dried over Na$_2$SO$_4$ and filtered. The filtrate was concentrated under reduced pressure and the residue was purified by silica gel column chromatography to give methyl (S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoate (440 mg, 22% yield) as a solid, which was used directly in the next step. LCMS (ESI): m/z [M+H] calc'd for C$_{34}$H$_{45}$N$_5$O$_6$S 651.3; found 652.3.

Step 7. To a mixture of (2S)-methyl 2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoate (280 mg, 0.43 mmol) in MeOH (4 mL) was added a solution of LiOH (51 mg, 2.2 mmol) in H$_2$O (2 mL). The mixture was stirred for 5 h, then pH adjusted to ~3-4 by addition of 1M HCl. The mixture was diluted with H$_2$O (30 mL) and extracted with EtOAc (15 mL×3). The combined organic layers were washed with brine (10 mL), dried over anhydrous Na$_2$SO$_4$, filtered and the filtrate was concentrated under reduced pressure to give (2S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoic acid (280 mg) as solid, which was used directly in the next step without further purification. LCMS (ESI): m/z [M+H] calc'd for C$_{33}$H$_{43}$N$_5$O$_6$S 637.3; found 638.3.

Step 8. To a mixture of (2S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-pyrrolo[3,2-b]pyridin-5-yl)thiazol-2-yl)propanoic acid (274 mg, 0.43 mmol) and methyl (3S)-1,2-diazinane-3-carboxylate (280 mg, 0.64 mmol) in DMF (3 mL) at 0-5° C. was added a solution of HATU (245 mg, 0.64 mmol) and DIPEA (555 mg, 4.3 mmol) in DMF (2 mL). The mixture was stirred for 1 h, then diluted with EtOAc (20 mL) and H$_2$O (20 mL). The aqueous and organic layers were partitioned and the organic layer was washed with H$_2$O (20 mL×3), brine (20 mL), dried over anhydrous Na$_2$SO$_4$ and filtered. The filtrate was concentrated under reduced pressure and the residue was purified by silica gel column chromatography to give methyl (3S)-1-[(2S)-2-{[(tert-butoxy)carbonyl]amino}-3-{4-[1-ethyl-3-(3-hydroxy-2,2-dimethylpropyl)-2-{2-[(1 S)-1-methoxyethyl]pyridin-3-yl}pyrrolo[3,2-b]pyridin-5-yl]-1,3-thiazol-2-yl}propanoyl]-1,2-diazinane-3-carboxylate (230 mg, 70% yield) as a solid. LCMS (ESI): m/z [M+H] calc'd for C$_{39}$H$_{53}$N$_7$O$_7$S 763.4; found 764.3.

Step 9. To a mixture of methyl (3S)-1-[(2S)-2-{[(tert-butoxy)carbonyl]amino}-3-{4-[1-ethyl-3-(3-hydroxy-2,2-dimethylpropyl)-2-{2-[(1 S)-1-methoxyethyl]pyridin-3-yl}pyrrolo[3,2-b]pyridin-5-yl]-1,3-thiazol-2-yl}propanoyl]-1,2-diazinane-3-carboxylate (230 mg, 0.3 mmol) in DCE (3 mL) under an atmosphere of N$_2$ was added Me$_3$SnOH (300 mg). The mixture was heated to 65° C. and stirred for 16 h, then concentrated under reduced pressure. The residue was diluted with EtOAc (20 mL), washed with H$_2$O (20 mL) and brine (10 mL), dried over Na$_2$SO$_4$ and filtered. The filtrate was concentrated under reduced pressure to give (3S)-1-[(2S)-2-{[(tert-butoxy)carbonyl]amino}-3-{4-[1-ethyl-3-(3-hydroxy-2,2-dimethylpropyl)-2-{2-[(1 S)-1-methoxyethyl]pyridin-3-yl}pyrrolo[3,2-b]pyridin-5-yl]-1,3-thiazol-2-yl}propanoyl]-1,2-diazinane-3-carboxylic acid (200 mg) as a foam, which was used directly in the next step without further purification. LCMS (ESI): m/z [M+H] calc'd for C$_{38}$H$_{51}$N$_7$O$_7$S 749.4; found 750.3.

Step 10. To a mixture of (3S)-1-[(2S)-2-{[(tert-butoxy)carbonyl]amino}-3-{4-[1-ethyl-3-(3-hydroxy-2,2-dimethylpropyl)-2-{2-[(1 S)-1-methoxyethyl]pyridin-3-yl}pyrrolo[3,2-b]pyridin-5-yl]-1,3-thiazol-2-yl}propanoyl]-1,2-diazinane-3-carboxylic acid (245 mg, 0.32 mmol) in DCM (50 mL) at 0-5° C. were added HOBT (432 mg, 3.2 mmol), EDCl HCl (1.8 g, 9.6 mmol) and DIPEA (1.65 g, 12.8 mmol). The mixture was warmed to room temperature and stirred for 16 h, then concentrated under reduced pressure. The residue was diluted with EtOAc (20 mL) and H$_2$O (20 mL) and the aqueous and organic layers were partitioned. The organic layer was washed with H$_2$O (30 mL×3), brine (30 mL), dried over anhydrous Na$_2$SO$_4$ and filtered. The filtrate was concentrated under reduced pressure and the residue was purified by preparative-TLC to give tert-butyl ((6$^3$S,4S,2)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-pyrrolo[3,2-b]pyridina-6(1,3)-pyridazinacycloundecaphane-4-yl)carbamate (100 mg, 43% yield) as a solid. LCMS (ESI): m/z [M+H] calc'd for C$_{38}$H$_{49}$N$_7$O$_6$S 731.4; found 732.3.

Step 11. A mixture of tert-butyl ((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-pyrrolo[3,2-b]pyridina-6(1,3)-pyridazinacycloundecaphane-4-yl)carbamate (80 mg, 0.11 mmol) in DCM (0.6 mL) and TFA (0.2 mL) was stirred for 1 h. The mixture was concentrated under reduced pressure to give (6$^3$S,4S,Z)-4-amino-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-1$^{t1}$H-8-oxa-2(4,2)-thiazola-1(5,3)-pyrrolo[3,2-b]pyridina-6(1,3)-pyridazinacycloundecaphane-5,7-dione (72 mg, 95% yield) as a solid. LCMS (ESI): m/z [M+H] calc'd for C$_{33}$H$_{41}$N$_7$O$_4$S 631.3; found 632.3.

Step 12. To a mixture of (6$^3$S,4S,Z)-4-amino-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-pyrrolo[3,2-b]pyridina-6(1,3)-pyridazinacycloundecaphane-5,7-dione (120 mg, 0.39 mmol) and DIPEA (335 mg, 2.6 mmol) in DMF (1 mL) at 0° C. was added HATU (60 mg, 0.16 mmol). The mixture was stirred at 0° C. for 1 h, then diluted with H$_2$O (110 mL) and extracted with EtOAc (80 mL×2). The combined organic layers were washed with H$_2$O (100 mL), brine (100 mL), dried over anhydrous Na$_2$SO$_4$ and filtered. The filtrate was concentrated under reduced pressure and the residue was purified by preparative-TLC to give (3S)-1-acryloyl-N-((2S)-1-(((6$^3$S,4S,2)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-pyrrolo[3,2-b]pyridina-6(1,3)-pyridazinacycloundecaphane-4-yl)amino)-3-methyl-1-oxobutan-2-yl)-N-methylpyrrolidine-3-carboxamide (1.8 mg, 2% yield) as a solid. LCMS (ESI): m/z [M+H] calc'd for C$_{47}$H$_{61}$N$_9$O$_7$S 895.4; found 896.3; $^1$H NMR (400 MHz, CD$_3$OD) δ 8.72 (d, J=4.5 Hz, 1H), 7.98-7.77 (m, 3H), 7.72 (dd, J=12.0, 8.6 Hz, 1H), 7.54 (dd, J=7.6, 4.8 Hz, 1H), 6.67-6.54 (m, 1H), 6.26 (m, 1H), 5.79-5.58 (m, 2H), 4.83-4.75 (m, 1H), 4.39-4.16 (m, 4H), 4.02 (dd, J=28.0, 10.6 Hz, 2H), 3.89-3.65 (m, 6H), 3.50 (m, 4H), 3.34 (d, J=6.2 Hz, 3H), 3.12 (d, J=4.0 Hz, 2H), 3.00 (s, 1H), 2.73 (m, 1H), 2.48-2.37 (m, 1H), 2.31-2.07 (m, 4H), 1.88 (d, J=11.2 Hz, 1H), 1.71 (d, J=12.8 Hz, 1H), 1.44 (m, 7H), 0.97 (dd, J=6.2, 4.4 Hz, 3H), 0.92-0.84 (m, 8H), 0.41 (d, J=6.2 Hz, 3H).

Example 647. Synthesis of 1-(4-(dimethylamino)-4-methylpent-2-ynoyl)-N-((2S)-1-(((2²S,6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)amino)-3-methyl-1-oxobutan-2-yl)-4-fluoro-N-methylpiperidine-4-carboxamide
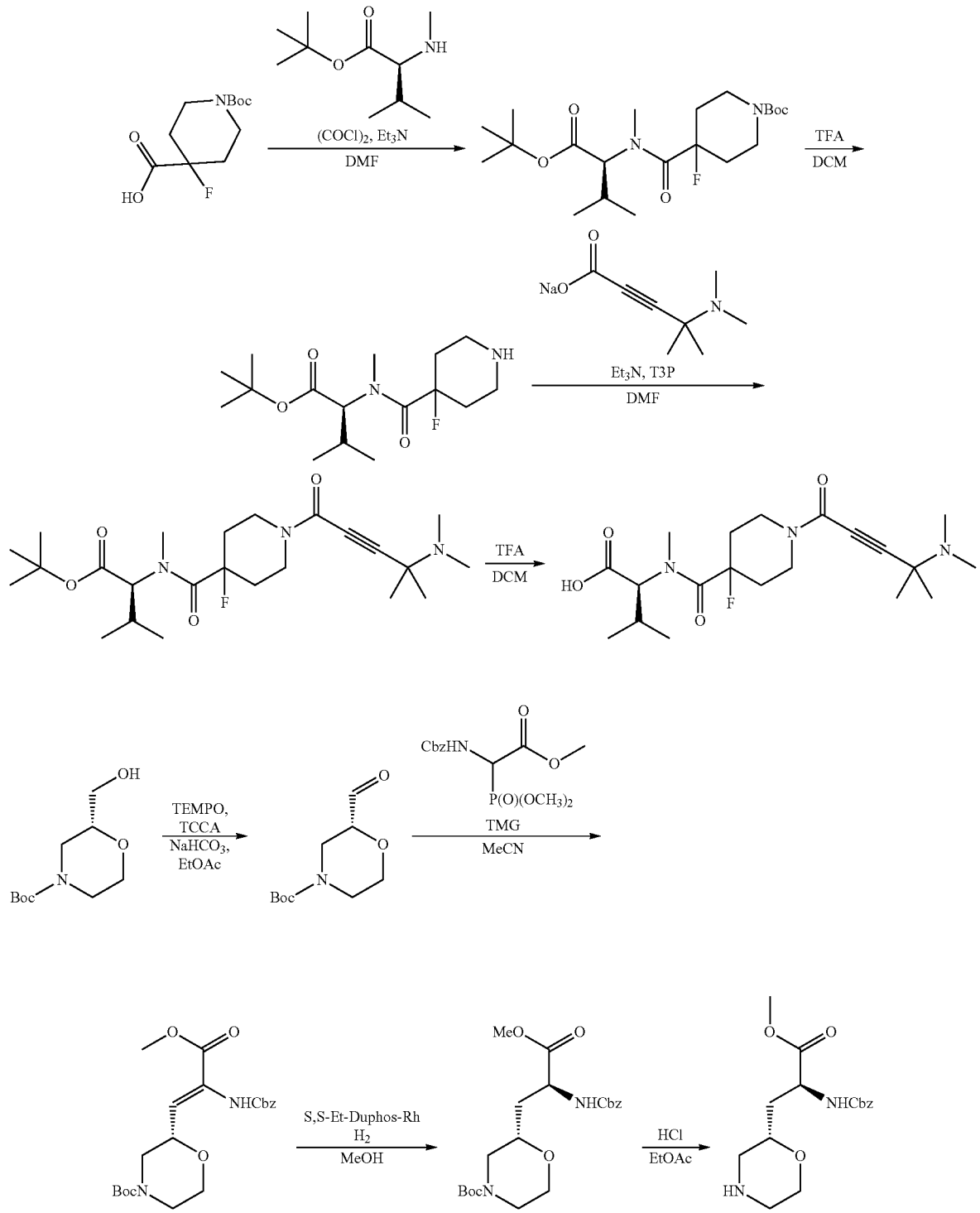

1025 1026
-continued
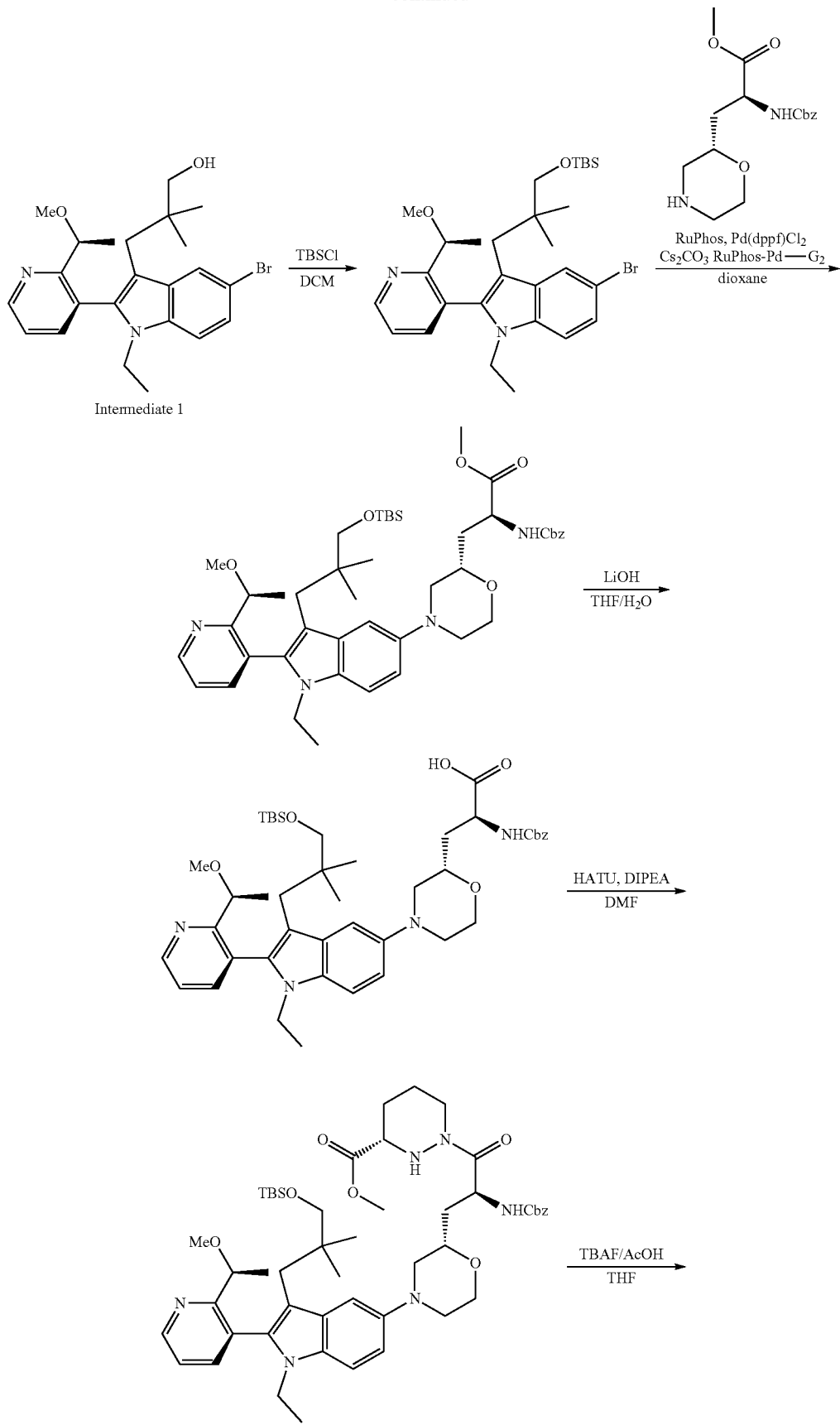

-continued
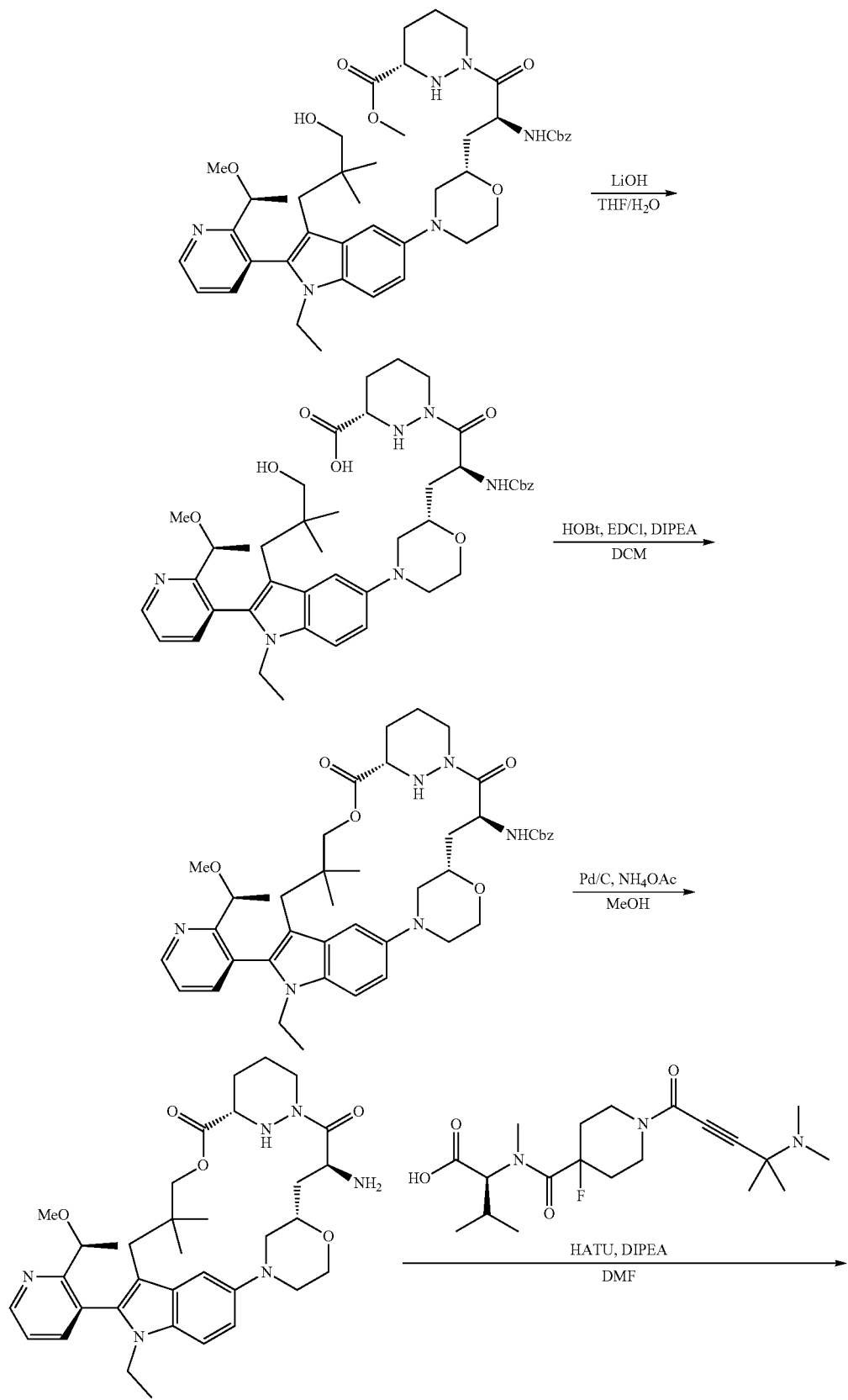

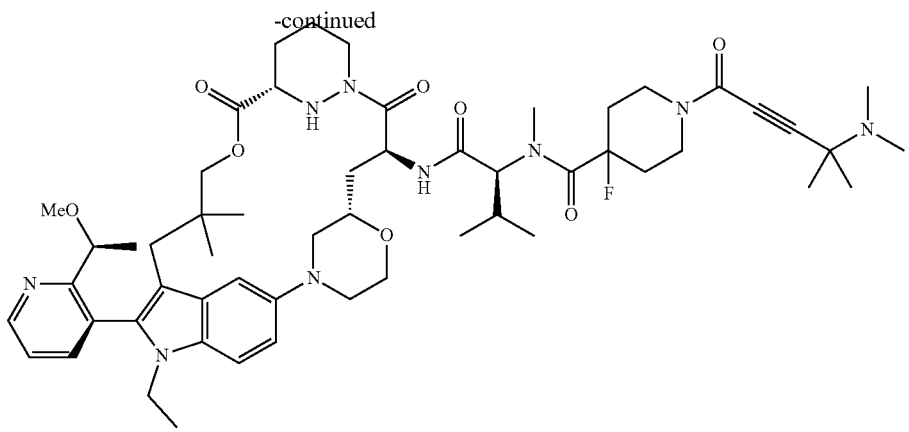

Step 1. A mixture of 1-[(tert-butoxy)carbonyl]-4-fluoropiperidine-4-carboxylic acid (2.0 g, 8.1 mmol) in DCM (20 mL) was added oxalic dichloride (1.34 g, 10.5 mmol) and DMF (30 mg, 0.4 mmol). The resulting solution was stirred at room temperature for 1 h. Et$_3$N (3.2 g, 3.2 mmol) and (2S)-3-methyl-2-(methylamino)butanoic acid (1.25 g, 9.5 mmol) were added and the mixture was stirred at room temperature for 1 h. H$_2$O (100 mL) was added and the mixture was extracted with EtOAc (50 mL×3). The combined organic layers were concentrated under reduced pressure and the residue was purified by silica gel column chromatography to give tert-butyl (S)-4-((1-(tert-butoxy)-3-methyl-1-oxobutan-2-yl)(methyl)carbamoyl)-4-fluoropiperidine-1-carboxylate (1.34 g, 45% yield) as a solid. LCMS (ESI): m/z [M+Na] calc'd for C$_{21}$H$_{37}$FN$_2$O$_5$Na 439.3; found 439.3.

Step 2. A mixture of tert-butyl (S)-4-((1-(tert-butoxy)-3-methyl-1-oxobutan-2-yl)(methyl)carbamoyl)-4-fluoropiperidine-1-carboxylate (290 mg, 0.70 mmol) in DCM (4 mL) and TFA (2 mL) was stirred at room temperature for 2 h, then concentrated under reduced pressure to give N-(4-fluoropiperidine-4-carbonyl)-N-methyl-L-valine, which was used directly in the next step without further purification. LCMS (ESI): m/z [M+H] calc'd for C$_{12}$H$_{21}$FN$_2$O$_3$ 260.2; found 261.2.

Step 3. To a solution of the tert-butyl N-(4-fluoropiperidine-4-carbonyl)-N-methyl-L-valinate (1.7 g, 5.3 mmol), sodium 4-(dimethylamino)-4-methylpent-2-ynoate (1.67 g, 9.4 mmol) and Et$_3$N (2.73 g, 36.9 mmol) in DMF (20 mL) stirred at 5° C. was added T$_3$P (4.11 g, 10.7 mmol, 50 wt % in EtOAc). The reaction mixture was stirred at 5° C. for 1 h. The resulting mixture was quenched with H$_2$O (100 mL) and extracted with EtOAc (50 mL×3). The combined organic layers were concentrated and purified by silica gel column chromatography to give tert-butyl N-(1-(4-(dimethylamino)-4-methylpent-2-ynoyl)-4-fluoropiperidine-4-carbonyl)-N-methyl-L-valinate (1.6 g, 74.0% yield) as a solid. LCMS (ESI): m/z [M+H] calc'd for C$_{24}$H$_{40}$FN$_3$O$_4$ 453.3; found 454.2.

Step 4. To a solution of tert-butyl N-(1-(4-(dimethylamino)-4-methylpent-2-ynoyl)-4-fluoropiperidine-4-carbonyl)-N-methyl-L-valinate (50 mg, 0.11 mmol) in DCM (2 mL) was added TFA (1 mL). The reaction mixture was stirred at 20° C. for 2 h, then concentrated under reduced pressure to afford crude N-(1-(4-(dimethylamino)-4-methylpent-2-ynoyl)-4-fluoropiperidine-4-carbonyl)-N-methyl-L-valine. It was used for the next step directly without further purification. LCMS (ESI): m/z [M+H] calc'd for C$_{20}$H$_{32}$FN$_3$O$_4$ 397.2; found 398.3.

Step 5. To a solution of tert-butyl (2R)-2-(hydroxymethyl)morpholin-4-yl formate (50 g, 230 mmol) in EtOAc (1 L) was added TEMPO (715 mg, 4.6 mmol) and NaHCO$_3$(58 g, 690 mmol) at 20° C. The mixture was cooled to −50° C., then TCCA (56 g, 241 mmol) in EtOAc (100 mL) was added dropwise over 30 min. The reaction mixture was warmed to 5° C. for 2 h, then quenched with 10% Na$_2$S$_2$O$_3$ (200 mL) and stirred for 20 min. The resulting mixture was filtered and the organic phase was separated from filtrate. The aqueous phase was extracted with EtOAc (100 mL×2). The combined organic layers were washed with H$_2$O (100 mL) and brine (100 mL), and dried over anhydrous Na$_2$SO$_4$. The organic layer was concentrated under reduced pressure to afford tert-butyl (2R)-2-formylmorpholin-4-yl formate (50 g, crude) as an oil.

Step 6. To a solution of tert-butyl (2R)-2-formylmorpholin-4-yl formate (49 g, 153 mmol) and methyl 2-{[(benzyloxy)carbonyl]amino}-2-(dimethoxyphosphoryl)acetate (60 g, 183 mmol) in CAN (300 mL) was added tetramethylguanidine (35 g, 306 mmol) at 0-10° C. The reaction mixture was stirred at 10° C. for 30 min then warmed to 20° C. for 2 h. The reaction mixture was diluted with DCM (200 mL) and washed with Citric acid (10%, 200 mL) and 10% NaHCO$_3$ aqueous solution (200 mL). The organic phase was concentrated under reduced pressure, and purified by silica gel column chromatography to afford tert-butyl (S,Z)-2-(2-(((benzyloxy)carbonyl)amino)-3-methoxy-3-oxoprop-1-en-1-yl)morpholine-4-carboxylate (36 g, 90% yield) as solid. LCMS (ESI): m/z [M+Na] calc'd for C$_{21}$H$_{28}$N$_2$O$_4$ 420.2; found: 443.1.

Step 7. To a solution of tert-butyl (S,Z)-2-(2-(((benzyloxy)carbonyl)amino)-3-methoxy-3-oxoprop-1-en-1-yl)morpholine-4-carboxylate (49 g, 0.12 mol) in MeOH (500 mL) was added (S,S)-Et-DUPHOS-Rh (500 mg, 0.7 mmol). The mixture was stirred at 25° C. under an H$_2$ (60 psi) atmosphere for 48 h. The reaction was concentrated and purified by chromatography to give tert-butyl (S)-2-((S)-2-(((benzyloxy)carbonyl)amino)-3-methoxy-3-oxopropyl)morpholine-4-carboxylate (44 g, 89.8% yield) as solid. LCMS (ESI): m/z [M+Na] calc'd for C$_{21}$H$_{30}$N$_2$O$_7$ 422.2; found: 445.2.

Step 8. To a stirred solution of tert-butyl (S)-2-((S)-2-(((benzyloxy)carbonyl)amino)-3-methoxy-3-oxopropyl)morpholine-4-carboxylate (2.2 g, 5.2 mmol) in EtOAc (2 mL) was added HCl/EtOAc (25 mL) at 15° C. The reaction was stirred at 15° C. for 2 h, then concentrated under reduced pressure to afford methyl (S)-2-(((benzyloxy)carbonyl)amino)-3-((S)-morpholin-2-yl)propanoate (1.51 g, 90.4% yield) as an oil. LCMS (ESI): m/z [M+H] calc'd for $C_{16}H_{22}N_2O_5$ 322.1; found 323.2.

Step 9. To a solution of 3-(5-bromo-1-ethyl-2-{2-[(1 S)-1-methoxyethyl]pyridin-3-yl}indol-3-yl)-2,2-dimethylpropan-1-ol (100 g, 0.22 mol) and 1H-imidazole (30.6 g, 0.45 mol) in DCM (800 mL) was added TBSCl (50.7 g, 0.34 mol) in DCM (200 mL) at 0° C. The reaction was stirred at 25° C. for 2 h. The resulting solution was washed with $H_2O$ (300 mL×3) and brine (200 mL×2), dried over anhydrous sodium sulfate, filtered and concentrated under reduced pressure. The residue was purified with silica gel column chromatography to give (S)-5-bromo-3-(3-((tert-butyldimethylsilyl)oxy)-2,2-dimethylpropyl)-1-ethyl-2-(2-(1-methoxyethyl)pyridin-3-yl)-1H-indole (138 g, 90% yield) as an solid. LCMS (ESI): m/z [M+H] calc'd for $C_{29}H_{43}BrN_2O_2Si$ 558.2; found 559.2.

Step 10. To a stirred solution of Intermediate 1 (50 g, 89.3 mmol) in dioxane (500 mL) was added methyl (2S)-2-{[(benzyloxy)carbonyl]amino}-3-[(2S)-morpholin-2-yl]propanoate from step 1 (31.7 g, 98.2 mmol), RuPhos (16.7 g, 35.7 mmol), Di-mu-chlorobis(2-amino-1,1-biphenyl-2-yl-C,N)dipalladium(II) (2.8 g, 4.4 mmol) and cesium carbonate (96 g, 295 mmol) followed by RuPhos-Pd-G2 (3.5 g, 4.4 mmol) at 105° C. under an $N_2$ atmosphere. The reaction mixture was stirred for 6 h at 105° C. under an $N_2$ atmosphere. The resulting mixture was filtered, and the filtrate was concentrated under reduced pressure. The residue was purified by prep-TLC chromatography to afford methyl (2S)-2-{[(benzyloxy)carbonyl]amino}-3-[(2S)-4-(3-{3-[(tert-butyldimethylsilyl)oxy]-2,2-dimethylpropyl}-1-ethyl-2-{2-[(1 S)-1-methoxyethyl]pyridin-3-yl}indol-5-yl)morpholin-2-yl]propanoate (55 g, 73% yield) as a solid. LCMS (ESI): m/z [M+H] calc'd for $C_{45}H_{64}N_4O_7Si$ 800.5; found 801.5.

Step 11. To a solution of methyl (2S)-2-{[(benzyloxy)carbonyl]amino}-3-[(2S)-4-(3-{3-[(tert-butyldimethylsilyl)oxy]-2,2-dimethylpropyl}-1-ethyl-2-{2-[(1 S)-1-methoxyethyl]pyridin-3-yl}indol-5-yl)morpholin-2-yl]propanoate (10 g, 12 mmol) in THF (270 mL) was added LiOH (1.3 g, 31 mmol) in $H_2O$ (45 mL) at 20° C. The reaction was stirred at 20° C. for 2 h, then treated with 1N HCl to adjust pH to 4-5 at 0-5° C. The resulting mixture was extracted with EtOAc (50 mL×2). The combined organic layers were washed with brine and dried over anhydrous $Na_2SO_4$. The organic phase was then concentrated under reduced pressure to afford (2S)-2-{[(benzyloxy)carbonyl]amino}-3-[(2S)-4-(3-{3-[(tert-butyldimethylsilyl)oxy]-2,2-dimethylpropyl}-1-ethyl-2-{2-[(1 S)-1-methoxyethyl]pyridin-3-yl}indol-5-yl)morpholin-2-yl]propanoic acid (9.5 g, 97% yield) as a solid. LCMS (ESI): m/z [M+H] calc'd for $C_{44}H_{62}N_4O_7Si$ 786.4; found 787.4.

Step 12. To a stirred solution of (2S)-2-{[(benzyloxy)carbonyl]amino}-3-[(2S)-4-(3-{3-[(tert-butyldimethylsilyl)oxy]-2,2-dimethylpropyl}-1-ethyl-2-{2-[(1 S)-1-methoxyethyl]pyridin-3-yl}indol-5-yl)morpholin-2-yl]propanoic acid (10 g, 12.7 mmol) in DMF (150 mL), was added methyl (S)-hexahydropyridazine-3-carboxylate (2 g, 14 mmol), then cooled to 0° C., DIPEA (32.8 g, 254 mmol) was added followed by HATU (9.7 g, 25.4 mmol) at 0-5° C. The reaction mixture was stirred at 0-5° C. for 1 h. The resulting mixture was diluted with EtOAc (500 mL) and $H_2O$ (200 mL). The organic layer was separated and washed with $H_2O$ (100 mL×2) and brine (100 mL), dried over anhydrous sodium sulfate. The solution was filtered and concentrated under reduced pressure, and the residue was purified by silica gel column chromatography to afford methyl (S)-1-((S)-2-(((benzyloxy)carbonyl)amino)-3-((S)-4-(3-(3-((tert-butyldimethylsilyl)oxy)-2,2-dimethylpropyl)-1-ethyl-2-(2-((S)-1-methoxyethyl)pyridin-3-yl)-1H-indol-5-yl)morpholin-2-yl)propanoyl)hexahydropyridazine-3-carboxylate (8 g, 70% yield) as a solid. LCMS (ESI): m/z [M+H] calc'd for $C_{50}H_{72}N_6O_8Si$ 912.5; found 913.4.

Step 13. A solution of methyl (S)-1-((S)-2-(((benzyloxy)carbonyl)amino)-3-((S)-4-(3-(3-((tert-butyldimethylsilyl)oxy)-2,2-dimethylpropyl)-1-ethyl-2-(2-((S)-1-methoxyethyl)pyridin-3-yl)-1H-indol-5-yl)morpholin-2-yl)propanoyl)hexahydropyridazine-3-carboxylate (8.5 g, 9 mmol) in THF (8 mL) was added a mixture of tetrabutylammonium fluoride (1M in THF, 180 mL, 180 mmol) and AcOH (11 g, 200 mmol) at 20° C. The reaction mixture was stirred at 75° C. for 3 h. The resulting mixture was diluted with EtOAc (150 mL) and washed with $H_2O$ (20 mL×6). The organic phase was concentrated under reduced pressure to give methyl (S)-1-((S)-2-(((benzyloxy)carbonyl)amino)-3-((S)-4-(1-ethyl-3-(3-hydroxy-2,2-dimethylpropyl)-2-(2-((S)-1-methoxyethyl)pyridin-3-yl)-1H-indol-5-yl)morpholin-2-yl)propanoyl)hexahydropyridazine-3-carboxylate (7.4 g, 100% yield) as solid. LCMS (ESI): m/z [M+H] calc'd for $C_{44}H_{58}N_6O_8$ 799.4; found 798.4.

Step 14. To a solution of methyl (S)-1-((S)-2-(((benzyloxy)carbonyl)amino)-3-((S)-4-(1-ethyl-3-(3-hydroxy-2,2-dimethylpropyl)-2-(2-((S)-1-methoxyethyl)pyridin-3-yl)-1H-indol-5-yl)morpholin-2-yl)propanoyl)hexahydropyridazine-3-carboxylate (8 g, 10 mmol) in THF (200 mL) was added lithium hydroxide (600 mg, 25 mmol) in $H_2O$ (30 mL). The reaction mixture was stirred at 20° C. for 1 h, then treated with 1 N HCl to adjust pH to 4-5 at 0-5° C., and extracted with EtOAc (500 mL×2). The organic phase was washed with brine, and concentrated under reduced pressure to afford (S)-1-((S)-2-(((benzyloxy)carbonyl)amino)-3-((S)-4-(1-ethyl-3-(3-hydroxy-2,2-dimethylpropyl)-2-(2-((S)-1-methoxyethyl)pyridin-3-yl)-1H-indol-5-yl)morpholin-2-yl)propanoyl)hexahydropyridazine-3-carboxylic acid (8 g, crude) as a solid. LCMS (ESI): m/z [M+H] calc'd for $C_{43}H_{56}N_6O_8$ 784.4; found 785.4.

Step 15. To a stirred solution of (S)-1-((S)-2-(((benzyloxy)carbonyl)amino)-3-((S)-4-(1-ethyl-3-(3-hydroxy-2,2-dimethylpropyl)-2-(2-((S)-1-methoxyethyl)pyridin-3-yl)-1H-indol-5-yl)morpholin-2-yl)propanoyl)hexahydropyridazine-3-carboxylic acid (8 g, 10.2 mmol) and DIPEA (59 g, 459 mmol) in DCM (800 mL) was added EDCI (88 g, 458 mmol) and HOBT (27.6 g, 204 mmol) at 25° C. under an argon atmosphere. The reaction mixture was stirred at 25° C. for 16 h. The resulting mixture was concentrated under reduced pressure, and the residue was purified by silica gel column chromatography to afford benzyl (($2^2$S,$6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-4-yl)carbamate (5 g, 66% yield) as a solid; LCMS (ESI): m/z [M+H] calc'd for $C_{43}H_{54}N_6O_7$ 766.4; found 767.4.

Step 16. To a solution of benzyl (($2^2$S,$6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^{i1}$H-8-oxa-2(4,2)-morpholina-1(5,3)-indola-6(1,3)-pyridazinacycloundecaphane-4-yl)carbamate (400 mg, 0.5 mmol) in MeOH (20 mL) was added Pd/C (200 mg) and ammonium acetate (834 mg, 16 mmol) at 20° C. under an $H_2$ atmosphere and the mixture was stirred for 2 h. Then resulting mixture was filtered and concentrated under reduced pressure. The residue was redissolved in DCM (20 mL) and washed with H$_2$O (5 mL×2), then concentrated under reduced pressure to afford (2$^2$S,6$^3$S,4S)-4-amino-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-5,7-dione (320 mg, 97% yield) as a solid. LCMS (ESI): m/z [M+H] calc'd for C$_{35}$H$_{48}$N$_6$O$_5$ 632.4; found 633.3.

Step 17. To a solution of the (2$^2$S,6$^3$S,4S)-4-amino-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-5,7-dione (50 mg, 0.079 mmol), N-(1-(4-(dimethylamino)-4-methylpent-2-ynoyl)-4-fluoropiperidine-4-carbonyl)-N-methyl-L-valine (47 mg, 0.12 mmol) in DMF (2 mL) stirred at 0° C. was added HATU (36 mg, 0.09 mmol) and DIPEA (153 mg, 1.2 mmol) dropwise. The reaction was stirred at 0° C. for 1 h. The resulting mixture was purified by reverse phase to afford 1-(4-(dimethylamino)-4-methylpent-2-ynoyl)-N-((2S)-1-(((2$^2$S,6$^3$S,4S)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphan-4-yl)amino)-3-methyl-1-oxobutan-2-yl)-4-fluoro-N-methylpiperidine-4-carboxamide (11.9 mg, 13.9% yield) as a solid. $^1$H NMR (400 MHz, CD$_3$OD) δ 8.71 (dd, J=4.8, 1.7 Hz, 1H), 7.86 (d, J=7.8 Hz, 1H), 7.51 (dd, J=7.8, 4.8 Hz, 1H), 7.39 (d, J=8.9 Hz, 1H), 7.15-7.04 (m, 2H), 5.67 (d, J=8.8 Hz, 1H), 4.62 (d, J=11.2 Hz, 1H), 4.46 (d, J=12.4 Hz, 1H), 4.39-4.27 (m, 2H), 4.23 (d, J=6.1 Hz, 1H), 4.17-4.08 (m, 1H), 3.93 (s, 2H), 3.86 (s, 1H), 3.84-3.76 (m, 2H), 3.74-3.65 (m, 2H), 3.63-3.51 (m, 2H), 3.27-3.23 (m, 1H), 3.22-3.11 (m, 6H), 3.0-2.89 (m, 2H), 2.85-2.75 (m, 2H), 2.74-2.55 (m, 2H), 2.36 (d, J=8.2 Hz, 6H), 2.32-2.21 (m, 2H), 2.20-2.02 (m, 5H), 1.92 (d, J=12.5 Hz, 2H), 1.69 (dd, J=43.8, 12.6 Hz, 2H), 1.46 (dt, J=8.0, 4.9 Hz, 9H), 1.03 (d, J=3.5 Hz, 3H), 0.90 (dd, J=48.3, 6.5 Hz, 6H), 0.77 (d, J=3.0 Hz, 3H), 0.69 (s, 3H). LCMS (ESI): m/z [M+H] calc'd for C$_{55}$H$_{78}$FN$_9$O$_8$ 1011.6; found 1012.5.

Example A375. Synthesis of (2R)-2-(((1-(4-(dimethylamino)-4-methylpent-2-ynoyl)azetidin-3-yl)oxy)methyl)-N-((2$^2$S,6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphan-4-yl)-3-methylbutanamide

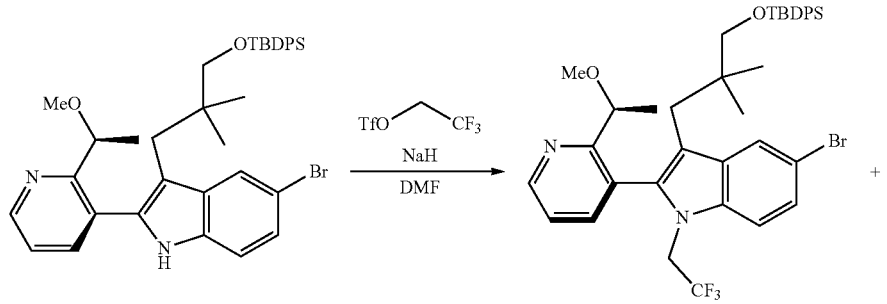

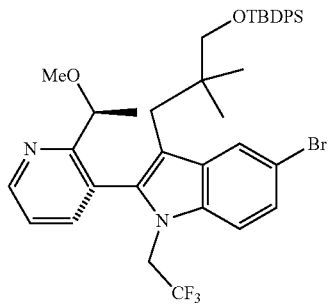

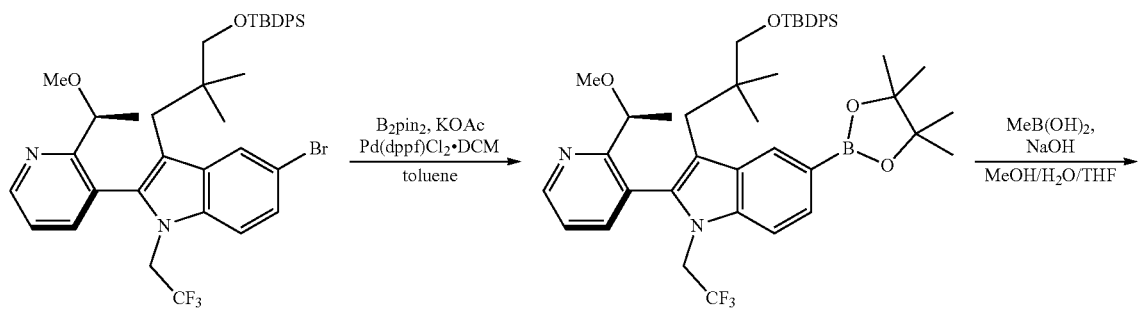

1035　　　　　　　　　　　　　　　1036
-continued
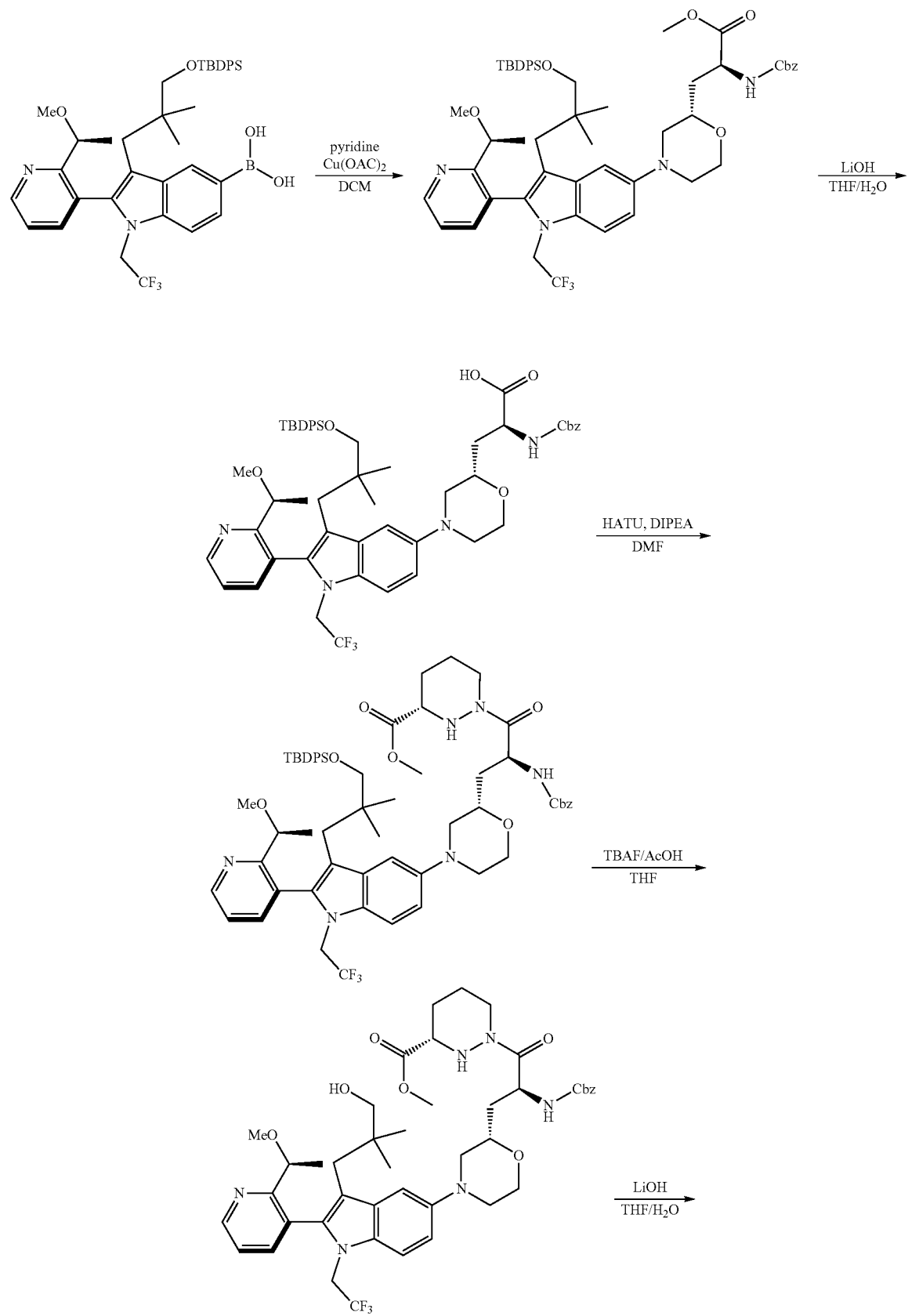

-continued
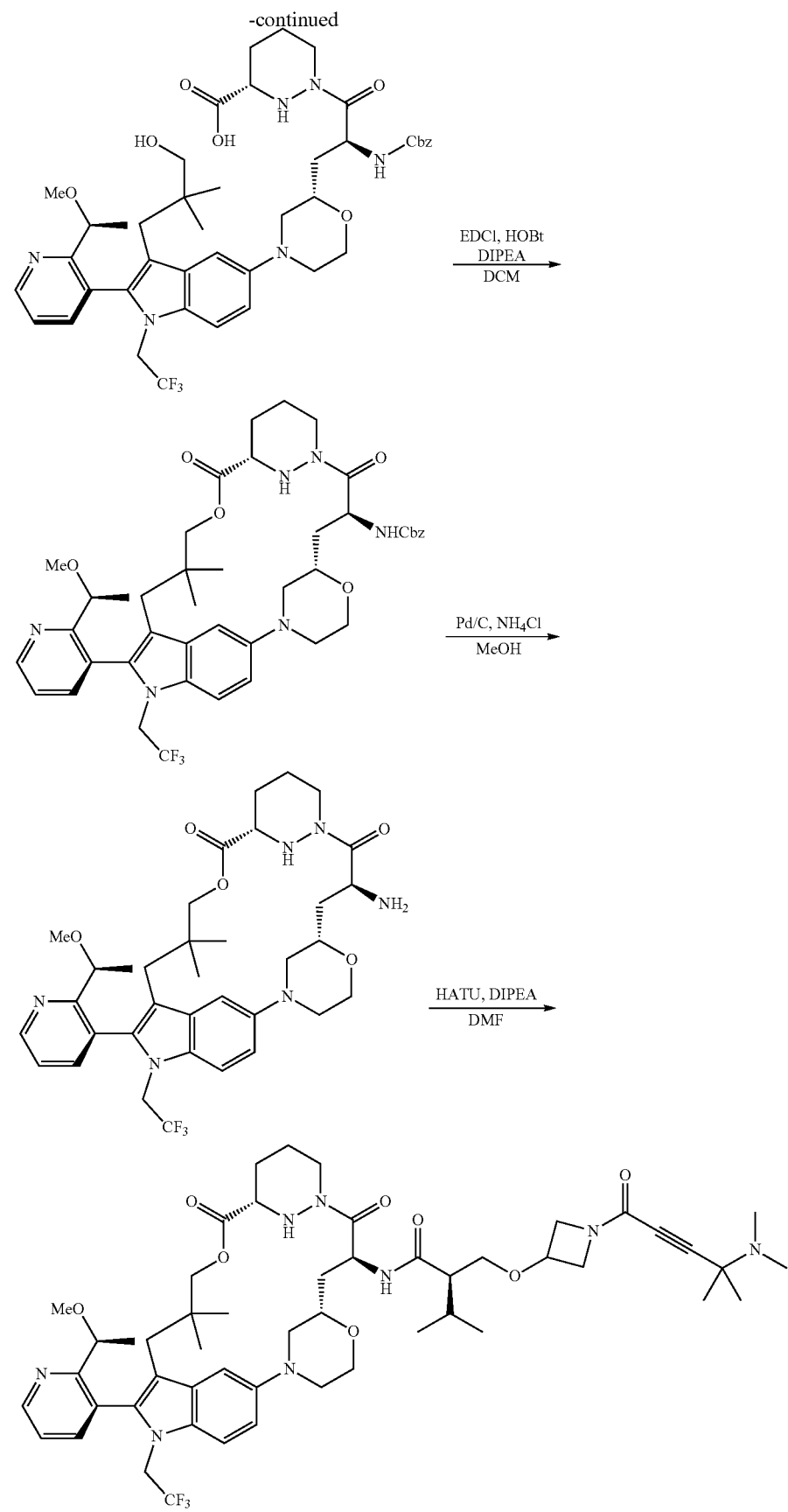

Step 1. To a mixture of 5-5-bromo-3-{3-[(tert-butyldiphenylsiyl)oxy]-2,2-dimethylpropyl}-2-{2-[(1 S)-1-methoxyethyl]pyridin-3-yl}-1H-indole (10.0 g, 15.2 mmol) in anhydrous DMF (120 mL) at 0° C. under an atmosphere of $N_4$ was added NaH, 60% dispersion in oil (1.2 g, 30.4 mmol) and 2,2,2-trifluoroethyl trifluoromethanesulfonate (35.4 g, 152 mmol). The mixture was stirred at 0° C. for 1 h, then saturated $NH_4Cl$ (30 mL) added and the mixture extracted with EtOAc (100 mL×3). The combined organic layers were washed with brine, dried over anhydrous $Na_2SO_4$ and filtered. The filtrate was concentrated under reduced pressure and the residue was purified by silica gel column chromatography to give (S)-5-bromo-3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indole (8 g) as an oil and the other atropisomer (6 g, 48% yield) as an oil. LCMS (ESI): m/z [M+H] calc'd for $C_{39}H_{44}BrF_3N_2O_2Si$ 736.2; found 737.1.

Step 2. To a mixture of (S)-5-bromo-3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indole (7.2 g, 9.7 mmol) in toulene (80 mL) under an atmosphere of $N_2$ was added 4,4,4',4',5,5,5',5'-octamethyl-2,2'-bi(1,3,2-dioxaborolane) (2.7 g, 10.6 mmol), KOAc (1.9 g, 19.4 mmol) and Pd(dppf)Cl$_2$ DCM (0.8 g, 0.1 mmol). The mixture was heated to 90° C. and stirred for 8 h, then saturated $NH_4Cl$ (30 mL) added and the mixture extracted with EtOAc (40 mL×3). The combined organic layers were dried over anhydrous $Na_2SO_4$ and filtered. The filtrate was concentrated under reduced pressure and the residue was purified by silica gel column chromatography to give (S)-3-(3-((tert-butyldiphenylsilyl)oxy)-2,2-dimethylpropyl)-2-(2-(1-methoxyethyl)pyridin-3-yl)-5-(4,4,5,5-tetramethyl-1,3,2-dioxaborolan-2-yl)-1-(2,2,2-trifluoroethyl)-1H-indole (6.1 g, 64% yield) as an oil. LCMS (ESI): m/z [M+H] calc'd for $C_{45}H_{56}BF_3N_2O_4Si$ 784.4; found 785.3.

Step 3. To a mixture of (S)-3-(3-((tert-butyldiphenylsilyl)oxy)-2,2-dimethylpropyl)-2-(2-(1-methoxyethyl)pyridin-3-yl)-5-(4,4,5,5-tetramethyl-1,3,2-dioxaborolan-2-yl)-1-(2,2,2-trifluoroethyl)-1H-indole (33 g, 42 mmol) in THF (120 mL) and MeOH (330 mL) at 0° C. under an atmosphere of $N_2$ was added MeB(OH)$_2$ (50.4 g, 841 mmol), then a mixture of NaOH (33.6 g, 841 mmol) in $H_2O$ (120 mL). The mixture was warmed to room temperature and stirred for 16 h, then concentrated under reduced pressure. $H_2O$ (500 mL) was added to the residue and the mixture extracted with EtOAc (300 mL×3). The combined organic layers were washed with brine (300 mL), $H_2O$ (300 mL), then concentrated under reduced pressure and the residue was purified by silica gel column chromatography to give (S)-(3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl) boronic acid (20 g, 68% yield) as a solid. LCMS (ESI): m/z [M+H] calc'd for $C_{39}H_{46}BF_3N_2O_4Si$ 702.3; found 703.3.

Step 4. Note: Three reactions were run in parallel—the yield reflects the sum of the products.

A mixture of (S)-(3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl)boronic acid (1.85 g, 5.6 mmol) and methyl (S)-2-(((benzyloxy)carbonyl)amino)-3-((S)-morpholin-2-yl)propanoate in DCM (150 mL) under air was added pyridine (1.35 g, 16.9 mmol) and Cu(OAc)$_2$ (2.0 g, 11.3 mmol). The mixture was stirred for 48 h, then concentrated under reduced pressure. $H_2O$ (300 mL) was added to the residue and the mixture was extracted with EtOAc (300 mL×2). The combined organic layers were washed with brine (100 mL), dried over anhydrous $Na_2SO_4$ and filtered. The filtrate was concentrated under reduced pressure and the residue was silica gel column chromatography to give methyl (S)-2-(((benzyloxy)carbonyl)amino)-3-((S)-4-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)morpholin-2-yl)propanoate (9.2 g, 55% yield) as a solid. LCMS (ESI): m/z [M/2+H] calc'd for $C_{55}H_{65}F_3N_4O_7Si$ 490.2; found 490.3.

Step 5. To a mixture of methyl (S)-2-(((benzyloxy)carbonyl)amino)-3-((S)-4-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)morpholin-2-yl) propanoate (10.8 g, 11.0 mmol) in THF (50 mL) was added LiOH (528 mg, 22 mmol) in $H_2O$ (10 mL). The mixture was stirred for 1 h, then cooled to 0-5° C. and acidified to pH-7 using 2N HCl (10 mL). The mixture was extracted with DCM (100 mL×2) and the combined organic layers were dried over $Na_2SO_4$ and filtered. The filtrate was concentrated under reduced pressure to give (S)-2-(((benzyloxy)carbonyl) amino)-3-((S)-4-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)morpholin-2-yl) propanoic acid (10.6 g, 100% yield) as a solid. LCMS (ESI): m/z [M/2+H] calc'd for $C_{54}H_{63}F_3N_4O_7Si$ 483.2; found 483.3.

Step 6. To a mixture of (S)-2-(((benzyloxy)carbonyl) amino)-3-((S)-4-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)morpholin-2-yl) propanoic acid (10.6 g, 11.0 mmol) and methyl (3S)-1,2-diazinane-3-carboxylate (15.8 g, 22.0 mmol) in DMF (150 mL) at 0° C. was added DIPEA (28.4 g, 220 mmol) and HATU (8.4 g, 22.0 mmol). The mixture was stirred at 0-5° C. for 1 h, then EtOAc (500 mL) was added and the mixture was washed with $H_2O$ (200 mL×2), brine (100 mL), dried over anhydrous $Na_2SO_4$ and filtered. The filtrate was concentrated under reduced pressure and the residue was purified by silica gel column chromatography to give methyl (S)-1-((S)-2-(((benzyloxy)carbonyl)amino)-3-((S)-4-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)morpholin-2-yl)propanoyl) hexahydropyridazine-3-carboxylate (11 g, 90% yield) as a solid. LCMS (ESI): m/z [M/2+H] calc'd for $C_{60}H_{73}F_3N_6O_8Si$ 546.3; found 546.3.

Step 7. To a mixture of methyl (S)-1-((S)-2-(((benzyloxy) carbonyl)amino)-3-((S)-4-(3-(3-((tert-butyldiphenylsilyl) oxy)-2,2-dimethylpropyl)-2-(2-((S)-1-methoxyethyl)pyridin-3-yl)-1-(2,2,2-trifluoroethyl)-1H-indol-5-yl)morpholin-2-yl)propanoyl)hexahydropyridazine-3-carboxylate (11.0 g, 10.1 mmol) in THF (10 mL) was added a mixture of AcOH (21.2 g, 353 mmol) and 1M TBAF in THF (300 mL, 300 mmol). The mixture was heated to 80° C. and stirred for 16 h, then concentrated under reduced pressure. EtOAc (800 mL) was added to the residue and the mixture was washed with $H_2O$ (80 mL×6), concentrated under reduced pressure and the residue was purified by preparative-HPLC to give methyl (S)-1-((S)-2-(((benzyloxy)carbonyl)amino)-3-((S)-4-(3-(3-hydroxy-2,2-dimethylpropyl)-2-(2-((S)-1-methoxyethyl)pyridin-3-yl)-1-(2,2,2-trifluoroethyl)-1H-indol-5-yl) morpholin-2-yl)propanoyl)hexahydropyridazine-3-carboxylate (7.9 g, 91% yield) as a solid. LCMS (ESI): m/z [M+H] calc'd for $C_{44}H_{55}F_3N_6O_8$ 852.4; found 853.3.

Step 8. To a mixture of methyl (S)-1-((S)-2-(((benzyloxy) carbonyl)amino)-3-((S)-4-(3-(3-hydroxy-2,2-dimethylpropyl)-2-(2-((S)-1-methoxyethyl)pyridin-3-yl)-1-(2,2,2-trifluoroethyl)-1H-indol-5-yl)morpholin-2-yl)propanoyl)

hexahydropyridazine-3-carboxylate (7.9 g, 9.3 mmol) in THF (50 mL) was added LiOH (443 mg, 18.5 mmol) in H$_2$O (10 mL). The mixture was stirred for 1 h, then cooled to 0-5° C. and acidified to ~pH 7 with 2N HCl (9 mL). The mixture was extracted with DCM (100 mL×2) and the combined organic layers were dried over Na$_2$SO$_4$ and filtered. The filtrate was concentrated under reduced pressure to give (S)-1-((S)-2-(((benzyloxy)carbonyl)amino)-3-((S)-4-(3-(3-hydroxy-2,2-dimethylpropyl)-2-(2-((S)-1-methoxyethyl)pyridin-3-yl)-1-(2,2,2-trifluoroethyl)-1H-indol-5-yl)morpholin-2-yl)propanoyl)hexahydropyridazine-3-carboxylic acid (7.6 g, 98% yield) as a solid. LCMS (ESI): m/z [M+H] calc'd for C$_{43}$H$_{53}$F$_3$N$_6$O$_8$ 838.4; found 839.3.

Step 9. To a mixture of (S)-1-((S)-2-(((benzyloxy)carbonyl)amino)-3-((S)-4-(3-(3-hydroxy-2,2-dimethylpropyl)-2-(2-((S)-1-methoxyethyl)pyridin-3-yl)-1-(2,2,2-trifluoroethyl)-1H-indol-5-yl)morpholin-2-yl)propanoyl)hexahydropyridazine-3-carboxylic acid (7.6 g, 9.0 mmol) and DIPEA (52.3 g, 405 mmol) in DCM (800 mL) under an atmosphere of Ar was added EDCI (77.6 g, 405 mmol) and HOBT (12 g, 90 mmol). The mixture was stirred for 16 h, then concentrated under reduced pressure. The residue was diluted with EtOAc (500 mL), washed with H$_2$O (100 mL×2) and filtered. The organic layer was concentrated under reduced pressure and the residue was purified by silica gel column chromatography to give benzyl ((2$^2$S,6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)carbamate (6.1 g, 74% yield) as a solid. LCMS (ESI): m/z [M+H] calc'd for C$_{43}$H$_{51}$F$_3$N$_6$O$_7$ 820.4; found 821.3.

Step 10. To a mixture of benzyl ((2$^2$S,6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)carbamate (700 mg, 0.85 mmol) in MeOH (30 mL) was added 10% Pd on C (317 mg) and NH$_4$Cl (909 mg). The mixture was stirred under an atmosphere of H$_2$ (1 atm) for 16 h, then filtered through Celite and the filter cake was washed with MeOH (150 mL). The filtrate was concentrated under reduced pressure, DCM (20 mL) was added to the residue and the mixture was washed with saturated NaHCO$_3$ (20 mL×3). The organic layer was concentrated under reduced pressure to give (2$^2$S,6$^3$S,4S)-4-amino-1$^2$-(2-((S)-1-methoxyethyl)pyridin-3-yl)-10,10-dimethyl-1$^1$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)- pyridazinacycloundecaphane-5,7-dione (660 mg, 95% yield) as a solid. LCMS (ESI): m/z [M+H] calc'd for C$_{35}$H$_{45}$F$_3$N$_6$O$_5$ 686.3; found 687.3; $^1$H NMR (400 MHz, CDCl$_3$) δ 8.80 (dd, J=4.7, 1.7 Hz, 1H), 7.66 (d, J=7.4 Hz, 1H), 7.43-7.30 (m, 2H), 7.12-7.01 (m, 2H), 4.90-4.83 (m, 1H), 4.68 (d, J=12.5 Hz, 1H), 4.57 (dd, J=16.2, 8.1 Hz, 1H), 4.24 (q, J=6.1 Hz, 1H), 4.08 (d, J=10.6 Hz, 1H), 3.97-3.82 (m, 4H), 3.80-3.68 (m, 2H), 3.55 (d, J=11.6 Hz, 1H), 3.21 (d, J=9.4 Hz, 1H), 2.93 (dd, J=19.9, 9.3 Hz, 3H), 2.66 (t, J=11.6 Hz, 1H), 2.47 (d, J=14.5 Hz, 1H), 2.19-2.04 (m, 4H), 1.96 (d, J=13.6 Hz, 2H), 1.80-1.71 (m, 2H), 1.66-1.59 (m, 1H), 1.47 (d, J=6.1 Hz, 3H), 0.88 (s, 3H), 0.42 (s, 3H).

Step 11. To a mixture of (2$^2$S,6$^3$S,4S)-4-amino-1$^2$-(2-((S)-1-methoxyethyl)pyridin-3-yl)-10,10-dimethyl-1$^1$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-5,7-dione (300 mg, 0.4 mmol), (2R)-2-[({1-[4-(dimethylamino)-4-methylpent-2-ynoyl]azetidin-3-yl}oxy)methyl]-3-methylbutanoic acid (157 mg, 0.48 mmol) and DIPEA (569.0 mg, 0.4 mmol) in DMF (5 mL) at 0° C. was added HATU (217 mg, 0.57 mmol). The mixture was stirred at 0° C. for 0.5 h, then diluted with H$_2$O and extracted with EtOAc (20 mL×3). The combined organic layers were washed with brine (20 mL×3), dried over Na$_2$SO$_4$ and filtered. The filtrate was concentrated under reduced pressure and the residue was purified by preparative-TLC to give (2R)-2-(((1-(4-(dimethylamino)-4-methylpent-2-ynoyl)azetidin-3-yl)oxy)methyl)-N-((2$^2$S,6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)-3-methylbutanamide (200 mg, 46% yield) as a solid. LCMS (ESI): m/z [M+H] calc'd for C$_{52}$H$_{71}$F$_3$N$_8$O$_8$ 992.5; found 993.4; $^1$H NMR (400 MHz, CD$_3$OD) δ 8.74 (m, 1H), 8.00 (m, 1H), 7.85 (d, J=7.7 Hz, 1H), 7.60-7.43 (m, 2H), 7.14 (t, J=9.5 Hz, 2H), 5.63 (s, 1H), 5.06 (m, 1H), 4.64 (s, 1H), 4.52-4.31 (m, 3H), 4.27-4.05 (m, 3H), 3.97 (m, 1H), 3.92-3.66 (m, 6H), 3.59 (m, 2H), 3.46 (m, 2H), 3.25 (d, J=5.3 Hz, 3H), 3.07-2.89 (m, 2H), 2.86-2.59 (m, 3H), 2.38-2.32 (m, 3H), 2.28 (s, 3H), 2.13 (m, 2H), 2.03-1.51 (m, 6H), 1.50-1.41 (m, 6H), 1.38 (d, J=7.5 Hz, 3H), 0.98 (t, J=8.7 Hz, 6H), 0.89 (t, J=6.4 Hz, 3H), 0.54 (d, J=8.4 Hz, 3H).

Example A722. Synthesis of 1-acryloyl-N-((2S)-1-(((6$^3$S,4S)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)amino)-3-methyl-1-oxobutan-2-yl)-4-fluoro-N-methylpiperidine-4-carboxamide

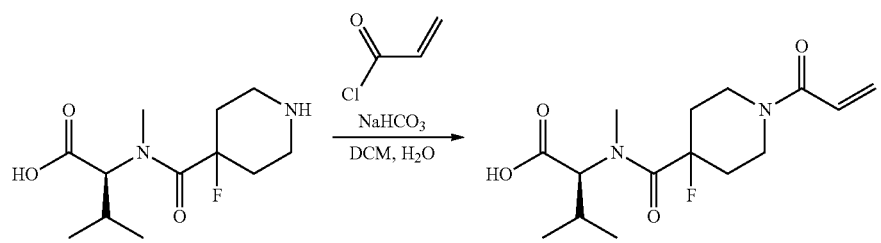

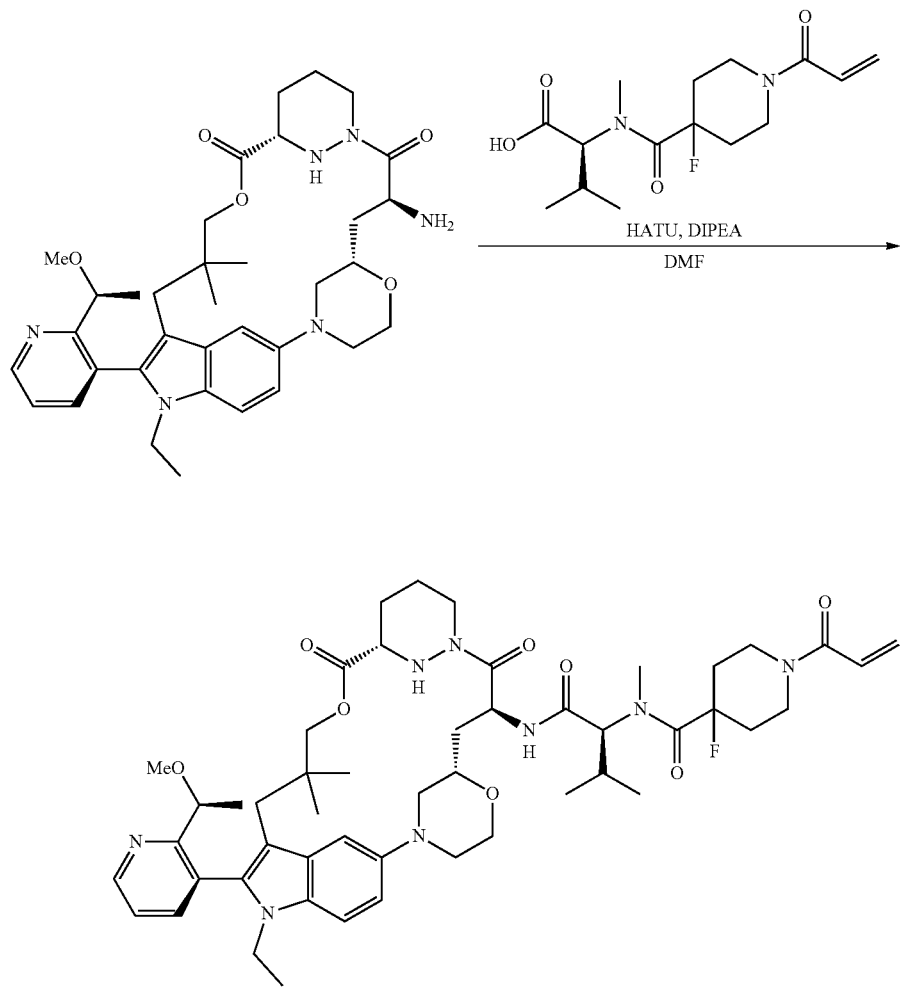

Step 1. To a mixture of N-(4-fluoropiperidine-4-carbonyl)-N-methyl-L-valine (190 mg, 0.73 mmol) and NaHCO$_3$ (306 mg, 3.6 mmol) in DCM (2 mL) and H$_2$O (1 mL) at −10° C. was added prop-2-enoyl chloride (132 mg, 1.45 mmol). The mixture was stirred at 0-5° C. for 1 h, then diluted with DCM (20 mL) and washed with H$_2$O (20 mL×2), brine (20 mL) and the organic layer dried over Na$_2$SO$_4$ and filtered. The filtrate was concentrated under reduced pressure and the residue was purified by silica gel column chromatography to give N-(1-acryloyl-4-fluoropiperidine-4-carbonyl)-N-methyl-L-valine (120 mg, 52% yield) as a solid. LCMS (ESI): m/z [M+H] calc'd for C$_{15}$H$_{23}$FN$_2$O$_4$ 314.2; found 315.2.

Step 2. To a mixture of (6$^3$S,4S)-4-amino-1$^1$-ethyl-12-(2-((S)-1-methoxyethyl)pyridin-3-yl)-10,10-dimethyl-6$^1$,6$^2$,6$^3$, 6$^4$,6$^5$,6$^6$-hexahydro-1$^1$H-8-oxa-2(4,2)-morpholina-1(5,3)-indola-6(1,3)-pyridazinacycloundecaphane-5,7-dione (153 mg, 0.24 mmol), N-(1-acryloyl-4-fluoropiperidine-4-carbonyl)-N-methyl-L-valine (106 mg, 0.34 mmol) in DMF (2 mL) at 5° C. was added HATU (110 mg, 0.29 mmol) and DIPEA (468 mg, 3.6 mmol) dropwise. The mixture was stirred at 5° C. for 1 h, then purified by preparative-HPLC to give 1-acryloyl-N-((2S)-1-(((6$^3$S,4S)-11-ethyl-12-(2-((S)-1-methoxyethyl)pyridin-3-yl)-10,10-dimethyl-5,7-dioxo-6$^1$, 6$^2$,6$^3$,6$^4$,6$^5$,6$^6$-hexahydro-1$^1$H-8-oxa-2(4,2)-morpholina-1(5,3)-indola-6(1,3)- pyridazinacycloundecaphane-4-yl)amino)-3-methyl-1-oxobutan-2-yl)-4-fluoro-N-methylpiperidine-4-carboxamide (69.5 mg, 29% yield) as a solid. LCMS (ESI): m/z [M+H] calc'd for C$_{50}$H$_{69}$FN$_8$O$_8$ 928.5; found 929.4; $^1$H NMR (400 MHz, CD$_3$OD) δ 8.71 (d, J=3.2 Hz, 1H), 7.86 (d, J=7.7 Hz, 1H), 7.51 (dd, J=7.7, 4.8 Hz, 1H), 7.39 (d, J=8.9 Hz, 1H), 7.18-7.02 (m, 2H), 6.80 (dd, J=16.8, 10.7 Hz, 1H), 6.23 (d, J=16.8 Hz, 1H), 5.77 (d, J=10.6 Hz, 1H), 5.67 (d, J=6.5 Hz, 1H), 4.61 (d, J=11.1 Hz, 1H), 4.44 (t, J=15.1 Hz, 2H), 4.23 (q, J=6.1 Hz, 1H), 4.18-4.10 (m, 1H), 4.09-4.01 (m, 1H), 3.99-3.83 (m, 3H), 3.83-3.65 (m, 4H), 3.58-3.46 (m, 2H), 3.27 (s, 1H), 3.21-3.11 (m, 6H), 3.00-2.91 (m, 2H), 2.85-2.75 (m, 2H), 2.73-2.64 (m, 1H), 2.62-2.54 (m, 1H), 2.36-2.21 (m, 2H), 2.19-2.01 (m, 5H), 1.92 (d, J=12.7 Hz, 2H), 1.79-1.57 (m, 2H), 1.44 (d, J=6.2 Hz, 3H), 1.04 (t, J=6.3 Hz, 3H), 0.98-0.81 (m, 6H), 0.76 (s, 3H), 0.68 (s, 3H).

Example A377. Synthesis of (2R)-2-(((1-(4-(dimethylamino)-4-methylpent-2-ynoyl)azetidin-3-yl)oxy)methyl)-N-(($2^2$S,$6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-4-yl)-3-methylbutanamide

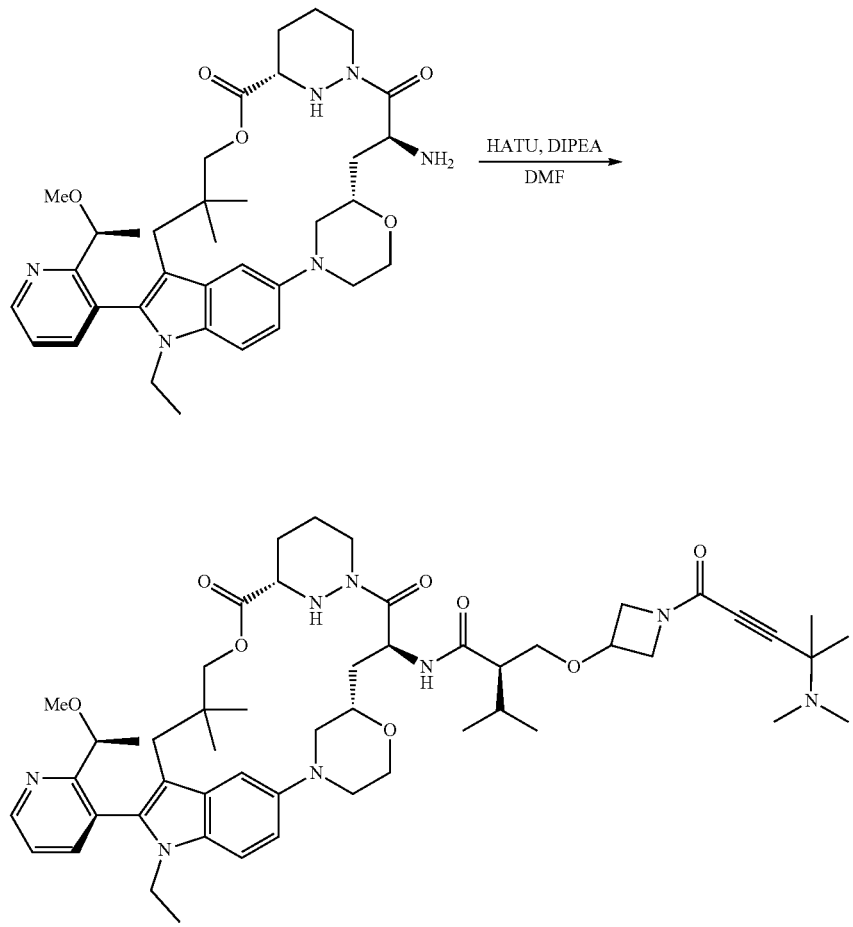

Step 1. (2R)-2-(((1-(4-(dimethylamino)-4-methylpent-2-ynoyl)azetidin-3-yl)oxy)methyl)-N-(($2^2$S,$6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-4-yl)-3-methylbutanamide was synthesized in a manner similar to (2R)-2-(((1-(4-(dimethylamino)-4-methylpent-2-ynoyl)azetidin-3-yl)oxy)methyl)-N-(($2^2$S,$6^3$S,4S)-12-(2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-4-yl)-3-methylbutanamide except ($2^2$S,$6^3$S,4S)-4-amino-$1^2$-(2-((S)-1-methoxyethyl)pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-5,7-dione was substituted with ($2^2$S,$6^3$S,4S)-4-amino-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-5,7-dione and 3-({1-[4-(dimethylamino)-4-methylpent-2-ynoyl]azetidin-3-yl}oxy)propanoic acid was substituted with (2R)-2-[({1-[4-(dimethylamino)-4-methylpent-2-ynoyl]azetidin-3-yl}oxy)methyl]-3-methylbutanoic acid to give the desired product (25.6 mg, 26% yield) as a solid. LCMS (ESI): m/z [M+H] calc'd for $C_{52}H_{74}N_8O_8$ 938.6; found 939.5; $^1$H NMR (400 MHz, $CD_3OD$) δ 8.72 (dd, J=4.8, 1.5 Hz, 1H), 7.97 (dd, J=20.0, 6.8 Hz, 1H), 7.87 (dd, J=5.8, 2.6 Hz, 1H), 7.54-7.51 (m, 1H), 7.41 (d, J=8.9 Hz, 1H), 7.14 (dd, J=36.0, 10.4 Hz, 2H), 5.65 (s, 1H), 4.49-4.33 (m, 3H), 4.27-4.08 (m, 4H), 3.96 (d, J=8.6 Hz, 2H), 3.87 (dd, J=10.8, 3.6 Hz, 2H), 3.79 (dd, J=10.8, 7.7 Hz, 3H), 3.69-3.58 (m, 3H), 3.43 (dd, J=23.9, 11.7 Hz, 2H), 3.17 (d, J=21.9 Hz, 3H), 3.00-2.95 (m, 1H), 2.70 (t, J=14.0 Hz, 8H), 2.34-2.24 (m, 1H), 2.05 (d, J=34.4 Hz, 3H), 1.92-1.82 (m, 2H), 1.69-1.62 (m, 5H), 1.57 (d, J=11.5 Hz, 3H), 1.45 (d, J=6.2 Hz, 3H), 1.33 (d, J=12.6 Hz, 1H), 1.05-0.93 (m, 10H), 0.80 (d, J=9.8 Hz, 3H), 0.64 (d, J=12.2 Hz, 2H).

Example A643. Synthesis of (2R)-2-(((1-(4-(dimethylamino)-4-methylpent-2-ynoyl)piperidin-4-yl)oxy)methyl)-N-((2²S,6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-3-methylbutanamide
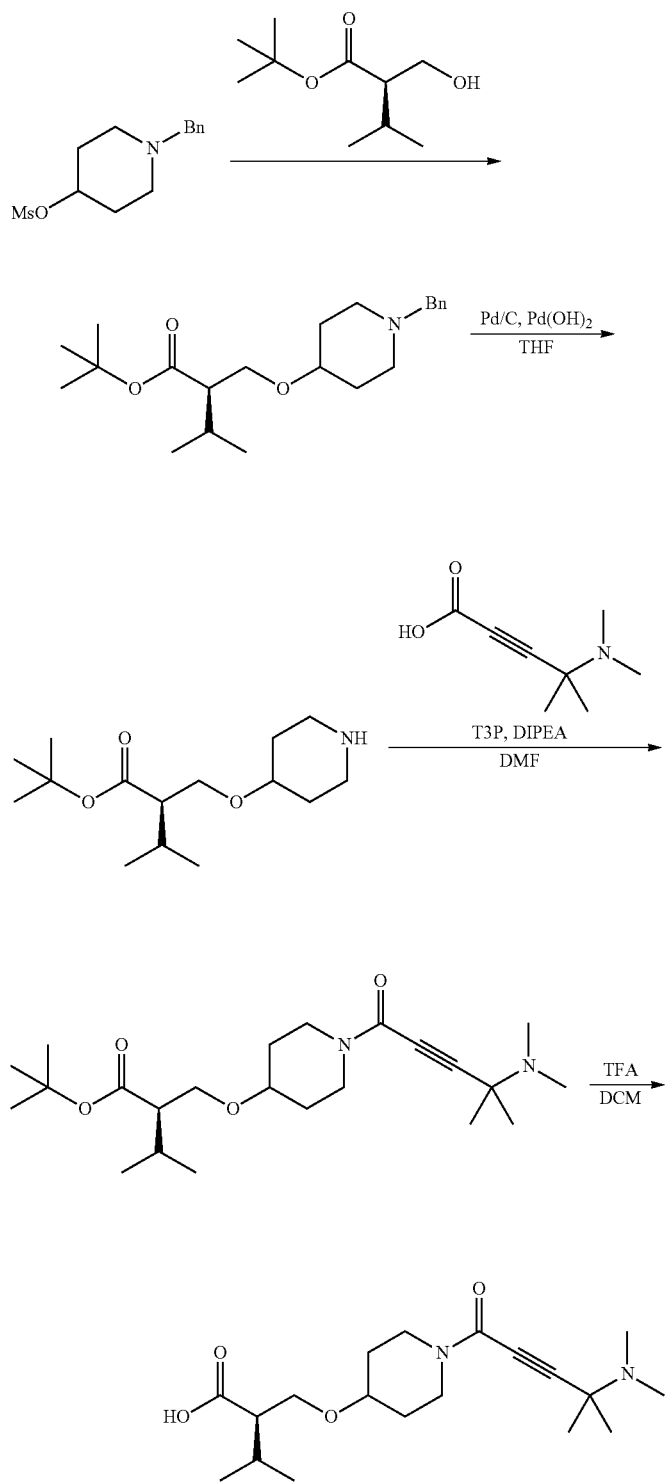

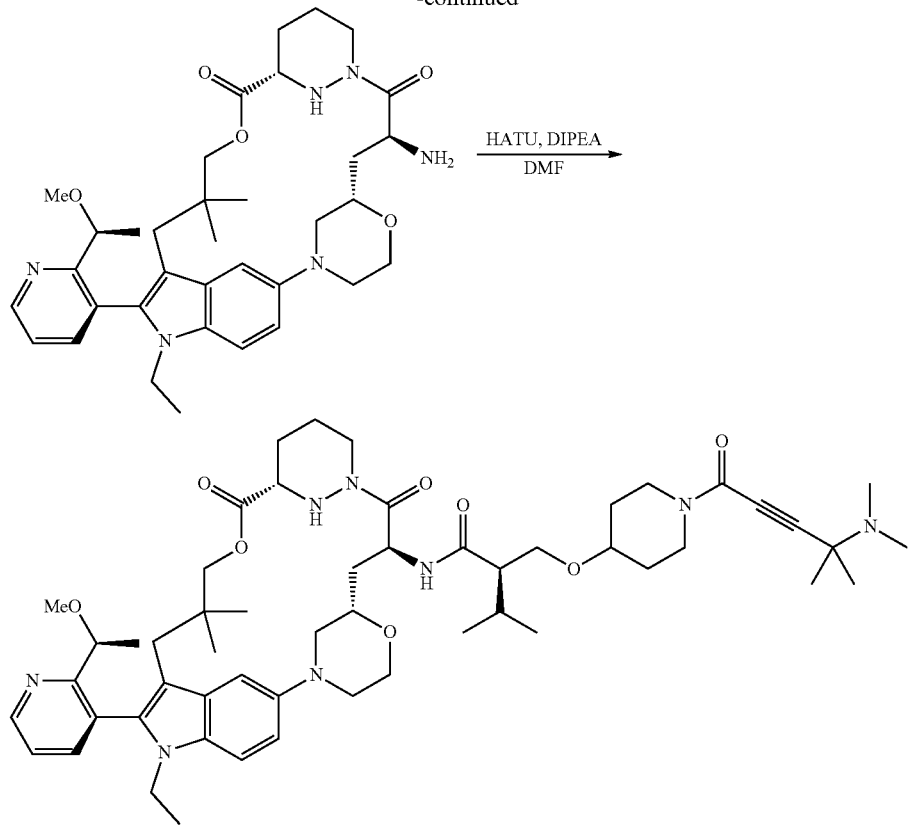

Step 1. A mixture of 1-(1-methylphenyl)piperidin-4-yl methanesulfonate (2 g, 7.4 mmol) and tert-butyl (2R)-2-(hydroxymethyl)-3-methylbutanoate (1.39 g, 7.4 mmol) was stirred at 120° C. for 1 h, then purified by silica gel column chromatography to give tert-butyl (R)-2-(((1-benzylpiperidin-4-yl)oxy)methyl)-3-methylbutanoate (800 mg, 28% yield) as an oil. LCMS (ESI): m/z [M+H] calc'd for $C_{22}H_{35}NO_3$ 361.3; found 362.3.

Step 2. A mixture of tert-butyl (R)-2-(((1-benzylpiperidin-4-yl)oxy)methyl)-3-methylbutanoate (700 mg, 1.9 mmol), 10% wet Pd/C (411 mg, 3.9 mmol) and 20% wet Pd(OH)$_2$/C (542 mg, 3.9 mmol) in THF (30 mL) was stirred under an atmosphere of H$_2$ (15 psi) for 16 h. The mixture was filtered and the filtrate was concentrated under reduced pressure to give tert-butyl (R)-3-methyl-2-((piperidin-4-yloxy)methyl) butanoate (440 mg, 80% yield) as a an oil. LCMS (ESI): m/z [M+H] calc'd for $C_{15}H_{29}NO_3$ 271.2; found 272.2.

Step 3. To a mixture of tert-butyl (R)-3-methyl-2-((piperidin-4-yloxy)methyl)butanoate (440 mg, 1.6 mmol) 4-(dimethylamino)-4-methylpent-2-ynoic acid (3.77 g, 24.3 mmol) and DIPEA (2.09 g, 16.2 mmol) in DMF (50 mL) at 0° C. was added T$_3$P (2.57 g, 8.1 mmol). The mixture was stirred at 0° C. for 1 h, then poured into H$_2$O (50 mL) and extracted with EtOAc (50 mL×3). The combined organic layers were washed with brine, concentrated under reduced pressure and the residue purified by silica gel column chromatography to give tert-butyl (R)-2-(((1-(4-(dimethylamino)-4-methylpent-2-ynoyl)piperidin-4-yl)oxy)methyl)-3-methylbutanoate (190 mg, 27% yield) as an oil. LCMS (ESI): m/z [M+H] calc'd for $C_{23}H_{40}N_2O_4$ 408.3; found 409.4.

Step 4. To a mixture of tert-butyl (R)-2-(((1-(4-(dimethylamino)-4-methylpent-2-ynoyl)piperidin-4-yl)oxy) methyl)-3-methylbutanoate (180 mg, 0.47 mmol) in DCM (2 mL) was added TFA (1 mL). The mixture was stirred at room temperature for 1 h, then concentrated under reduced pressure to give (R)-2-(((1-(4-(dimethylamino)-4-methylpent-2-ynoyl)piperidin-4-yl)oxy)methyl)-3-methylbutanoic acid (170 mg, 98% yield) as an oil. LCMS (ESI): m/z [M+H] calc'd for $C_{19}H_{32}N_2O_4$ 352.2; found 353.2.

Step 5. (2R)-2-(((1-(4-(dimethylamino)-4-methylpent-2-ynoyl)piperidin-4-yl)oxy)methyl)-N-(($2^2S,6^3S,4S$)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-2(4,2)-morpholina-1(5,3)-indola-6(1,3)-pyridazinacycloundecaphane-4-yl)-3-methylbutanamide was synthesized in a manner similar to (2R)-2-(((1-(4-(dimethylamino)-4-methylpent-2-ynoyl)azetidin-3-yl)oxy) methyl)-N-(($2^2S,6^3S,4S$)-12-(2-((S)-1-methoxyethyl)pyridin-3-yl)-10,10-dimethyl-5,7-dioxo-$1^1$-(2,2,2-trifluoroethyl)-$6^1,6^2,6^3,6^4,6^5,6^6$-hexahydro-$1^1$H-8-oxa-2(4,2)-morpholina-1(5,3)-indola-6(1,3)-pyridazinacycloundecaphane-4-yl)-3-methylbutanamide except ($2^2S,6^3S,4S$)-4-amino-$1^2$-(2-((S)-1-methoxyethyl) pyridin-3-yl)-10,10-dimethyl-$1^1$-(2,2,2-trifluoroethyl)-$6^1$, $6^2,6^3,6^4,6^5,6^6$-hexahydro-$1^1$H-8-oxa-2(4,2)-morpholina-1 (5,3)-indola-6(1,3)-pyridazinacycloundecaphane-5,7-dione was substituted with ($2^2S,6^3S,4S$)-4-amino-$1^1$-ethyl-$1^2$-(2-((S)-1-methoxyethyl)pyridin-3-yl)-10,10-dimethyl-$6^1,6^2,6^3$, $6^4,6^5,6^6$-hexahydro-$1^1$H-8-oxa-2(4,2)-morpholina-1(5,3)-indola-6(1,3)-pyridazinacycloundecaphane-5,7-dione and 3-({1-[4-(dimethylamino)-4-methylpent-2-ynoyl]azetidin-3-yl}oxy)propanoic acid was substituted with (2R)-2-[({1-

1051

[4-(dimethylamino)-4-methylpent-2-ynoyl]piperidin-4-yl}oxy)methyl]-3-methylbutanoic acid. (101 mg, 42% yield) as a solid. LCMS (ESI): m/z [M+H] calc'd for $C_{54}H_{78}N_8O_8$ 966.6; found 969.5; $^1$H NMR (400 MHz, CD$_3$OD) δ 8.70 (d, J=4.8 Hz, 1H), 7.81-7.76 (m, 1H), 7.56-7.46 (m, 1H), 7.43-7.34 (m, 1H), 7.24-7.01 (m, 2H), 5.66-5.54 (m, 1H), 4.50-4.40 (m, 1H), 4.31-4.22 (m, 1H), 4.19-4.08 (m, 1H), 4.02-3.82 (m, 4H), 3.80-3.53 (m, 10H), 3.47-3.34 (m, 2H), 3.26-3.15 (m, 3H), 2.98-2.57 (m, 5H), 2.37-2.30 (m, 3H), 2.27-2.18 (m, 4H), 2.15-2.02 (m, 2H), 2.00-1.80 (m, 4H), 1.78-1.71 (m, 2H), 1.68-1.55 (m, 3H),

1052

1.49-1.37 (m, 6H), 1.35-1.28 (m, 3H), 1.05-0.92 (m, 9H), 0.85-0.72 (m, 3H), 0.68-0.51 (m, 3H).

Example A328. Synthesis of two atropisomers of (3S)-1-acryloyl-N-((2S)-1-(((6$^3$S,4S)-1$^1$-ethyl-1$^2$-(2-((S)-1-methoxyethyl)-5-(4-methylpiperazin-1-yl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide

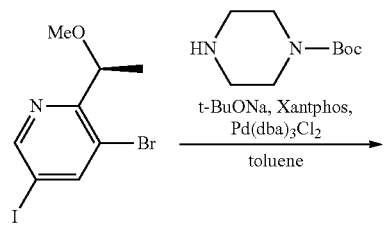

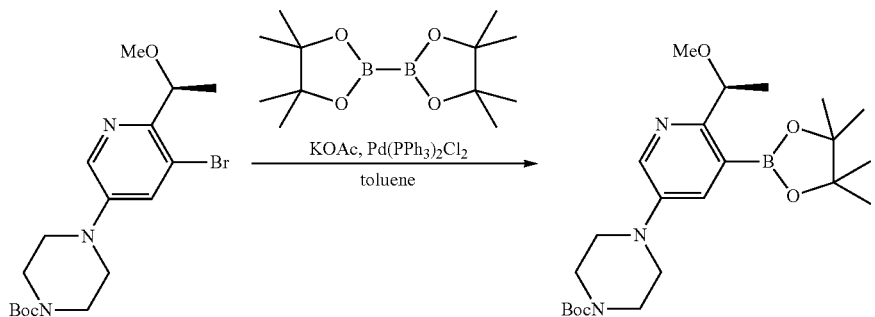

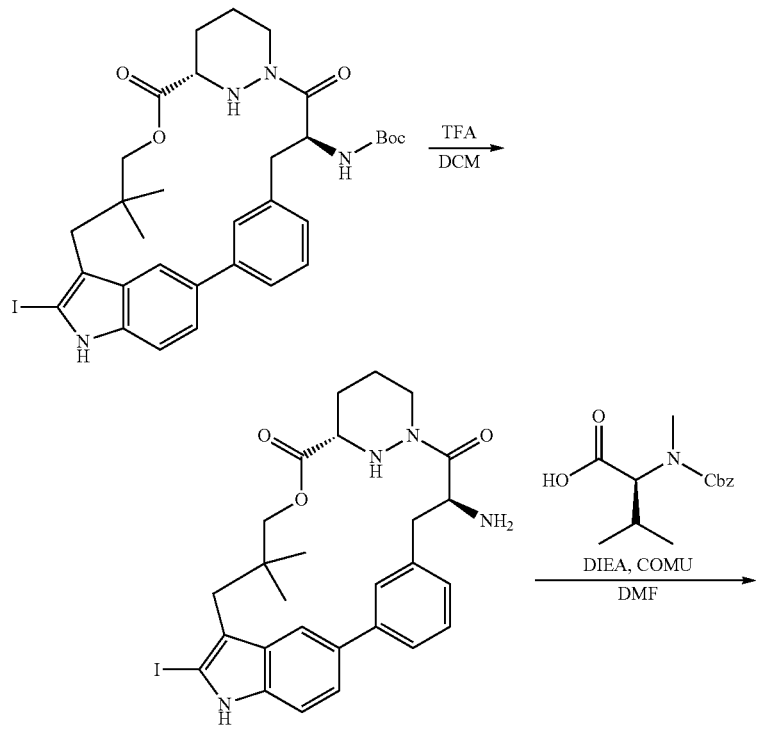

-continued
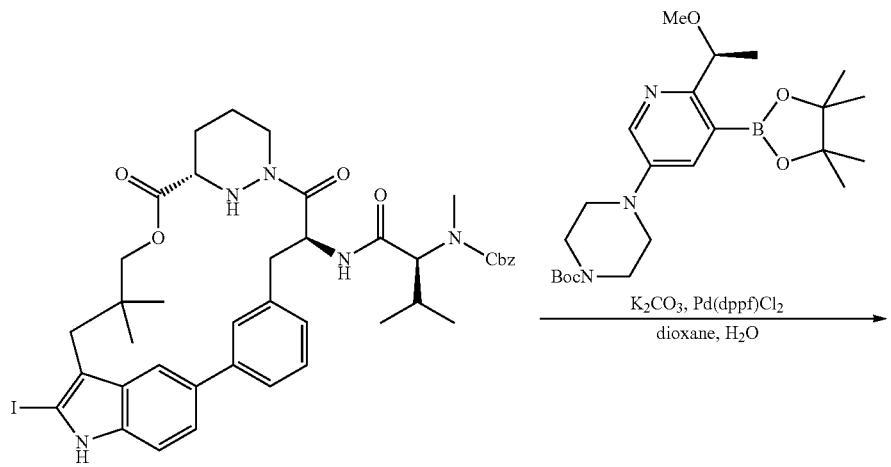
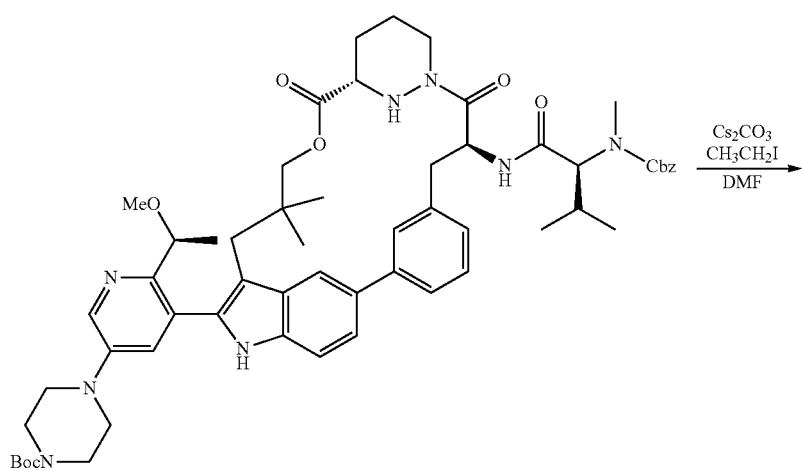
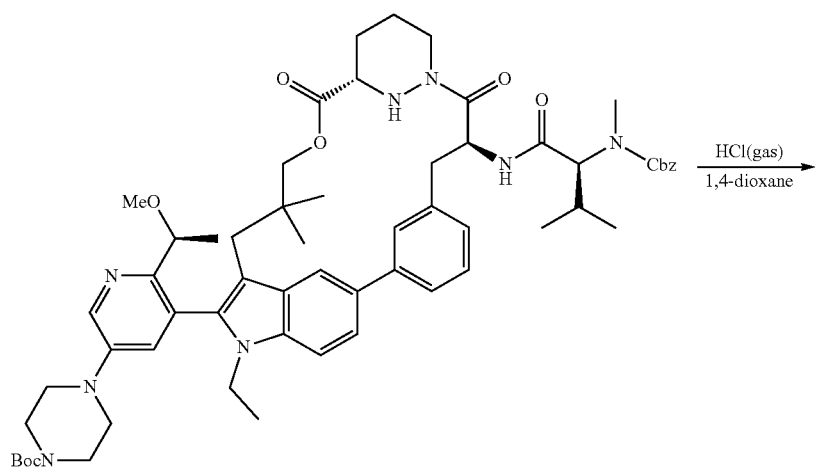

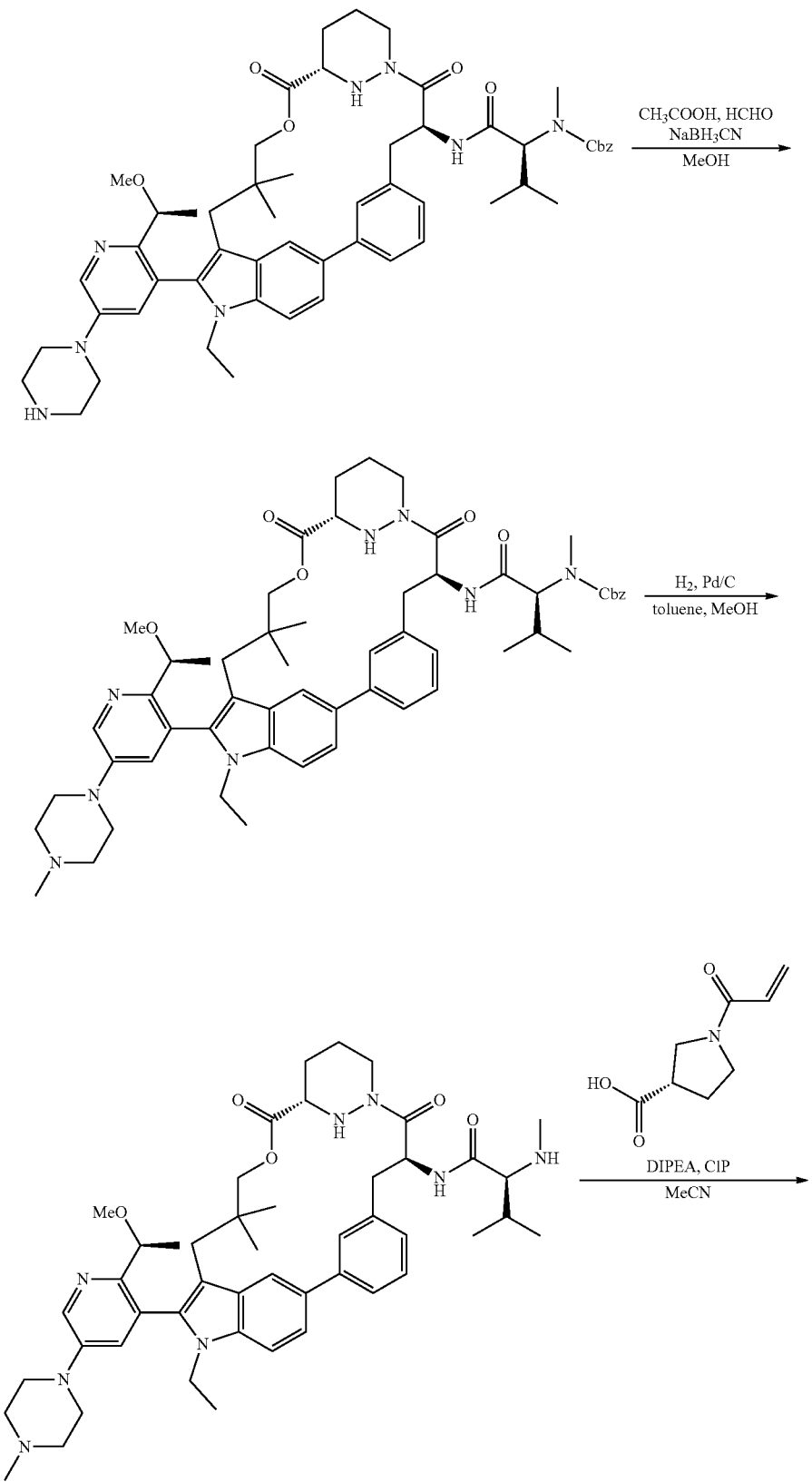

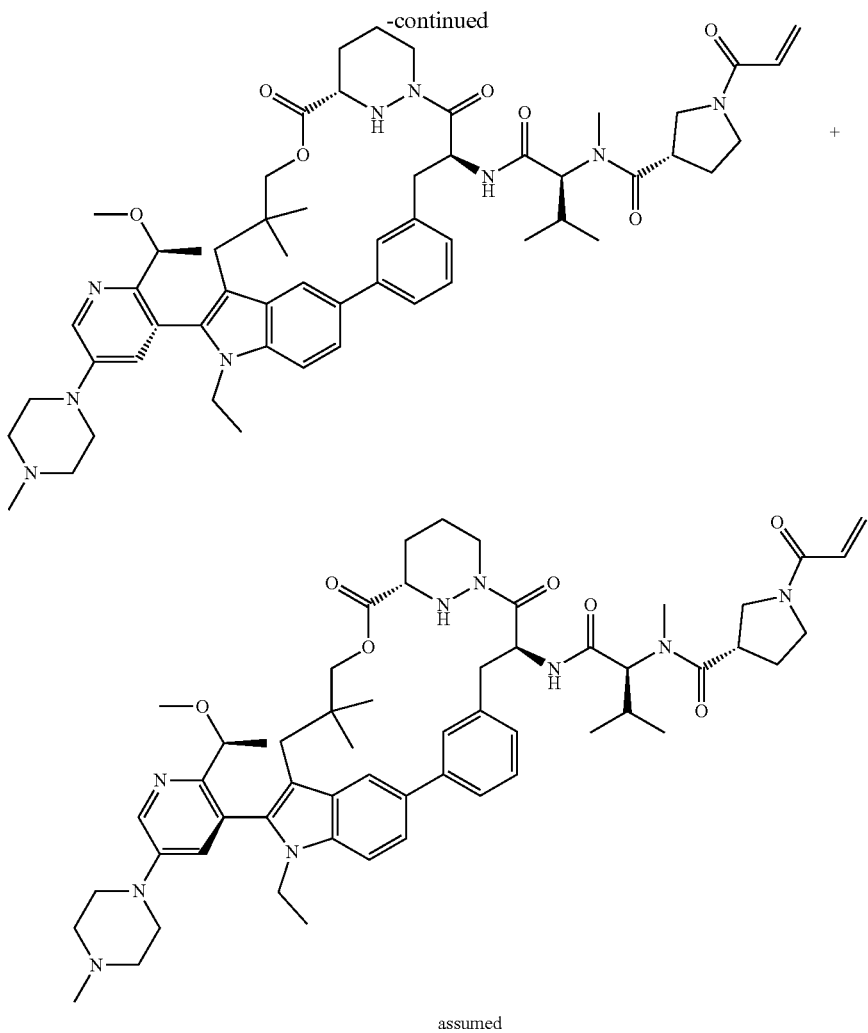

assumed

Step 1. To a mixture of 3-bromo-5-iodo-2-[(1S)-1-methoxyethyl]pyridine (2.20 g, 6.4 mmol) and tert-butyl piperazine-1-carboxylate (1.20 g, 6.4 mmol) in toluene (50 mL) under an atmosphere of Ar were added tBuONa (0.74 g, 7.7 mmol) and portion-wise addition of $Pd_2(dba)_3$ (0.59 g, 0.64 mmol), followed by portion-wise addition of Xantphos (0.74 g, 1.3 mmol). The mixture was heated to 100° C. and stirred for 16 h then $H_2O$ added and the mixture extracted with EtOAc (400 mL×3). The combined organic layers were washed with brine (150 mL×3), dried over anhydrous $Na_2SO_4$ and filtered. The filtrate was concentrated under reduced pressure and the residue was purified by preparative-HPLC to give tert-butyl 4-[5-bromo-6-[(1S)-1-methoxyethyl]pyridin-3-yl]piperazine-1-carboxylate (1.7 g, 61% yield) as a solid. LCMS (ESI): m/z [M+H] calc'd for $C_{17}H_{26}BrN_3O_3$ 399.1; found 400.1.

Step 2. A mixture of tert-butyl 4-[5-bromo-6-[(1 S)-1-methoxyethyl]pyridin-3-yl]piperazine-1-carboxylate (1.76 g, 4.4 mmol) and 4,4,4',4',5,5,5',5'-octamethyl-2,2'-bi(1,3,2-dioxaborolane) (1.67 g, 6.6 mmol) in toluene (18 mL) under an atmosphere of Ar were added KOAc (0.95 g, 9.7 mmol) and $Pd(PPh_3)_2Cl_2$ (0.31 g, 0.44 mmol) in portions. The mixture was heated to 80° C. and stirred for 16 h, then diluted with $H_2O$ and the mixture extracted with EtOAc (500 mL×3). The combined organic layers were washed with brine (100 mL×3), dried over anhydrous $Na_2SO_4$ and filtered. The filtrate was concentrated under reduced pressure and the residue was purified by silica gel column chromatography to give tert-butyl 4-[6-[(1 S)-1-methoxyethyl]-5-(4,4,5,5-tetramethyl-1,3,2-dioxaborolan-2-yl)pyridin-3-yl]piperazine-1-carboxylate (1.4 g, 68% yield) as a solid. LCMS (ESI): m/z [M+H] calc'd for $C_{23}H_{38}BN_3O_5$ 447.4; found 448.2.

Step 3. To a mixture of tert-butyl (($6^3$S,4S)-$1^2$-iodo-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (1.0 g, 1.5 mmol) in DCM (10 mL) at 0° C. under an atmosphere of $N_2$ was added TFA (5.0 mL, 67.3 mmol) in portions. The mixture was stirred at 0° C. for 1 h then concentrated under reduced pressure and dried azeotropically with toluene (3 mL×3) to give ($6^3$S, 4S)-4-amino-$1^2$-iodo-10,10-dimethyl-$6^1$,$6^2$,$6^3$,$6^4$,$6^5$,$6^6$-hexahydro-$1^1$H-8-oxa-1(5,3)-indola-6(1,3)-pyridazina-2(1, 3)-benzenacycloundecaphane-5,7-dione (1.0 g), which was used directly in the next step without further purification. LCMS (ESI): m/z [M+H] calc'd for $C_{27}H_{31}IN_4O_3$ 586.1; found 587.3.

Step 4. To a mixture of ($6^3$S,4S)-4-amino-$1^2$-iodo-10,10-dimethyl-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5, 7-dione (1.0 g, 1.7 mmol) in DMF (15 mL) at 0° C. under an atmosphere of $N_2$ were added DIPEA (2.20 g, 17.0 mmol) and (2S)-2-[[(benzyloxy)carbonyl](methyl)amino]-3-methylbutanoic acid (0.90 g, 3.4 mmol) in portions, followed by COMU (1.10 g, 2.6 mmol) in portions over 10 min. The mixture was stirred at 0° C. for 1.5 h, then diluted with $H_2O$ and the mixture was extracted with EtOAc (300 mL×3). The combined organic layers were washed with brine (100 mL×3), dried over anhydrous $Na_2SO_4$ and filtered. The filtrate was concentrated under reduced pressure and the residue was purified by preparative-HPLC to give benzyl ((2S)-1-(((6$^3$S,4S)-1$^2$-iodo-10,10-dimethyl-5,7-dioxo-6$^1$,6$^2$, 6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)(methyl)carbamate (790 mg, 53% yield) as a solid.

Step 5. To a mixture of benzyl ((2S)-1-(((6$^3$S,4S)-1$^2$-iodo-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)(methyl)carbamate (480 mg, 0.58 mmol) and tert-butyl 4-[6-[(1S)-1-methoxyethyl]-5-(4,4,5,5-tetramethyl-1,3,2-dioxaborolan-2-yl)pyridin-3-yl]piperazine-1-carboxylate (309 mg, 0.69 mmol) in 1,4-dioxane (8.0 mL) and $H_2O$ (1.6 mL) under an atmosphere of Ar were added $K_2CO_3$ (199 mg, 1.4 mmol) and Pd(dppf)$Cl_2$ (42 mg, 0.06 mmol) in portions. The mixture was heated to 70° C. and stirred for 16 h, then diluted with $H_2O$ and extracted with EtOAc (200 mL×3). The combined organic layers were washed with brine (150 mL×3), dried over anhydrous $Na_2SO_4$ and filtered. The filtrate was concentrated under reduced pressure and the residue was purified by silica gel column chromatography to give tert-butyl 4-(5-((6$^3$S,4S)-4-((S)-2-(((benzyloxy)carbonyl)(methyl)amino)-3-methylbutanamido)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-1$^2$-yl)-6-((S)-1-methoxyethyl)pyridin-3-yl)piperazine-1-carboxylate (335 mg, 51% yield) as a solid. LCMS (ESI): m/z [M+H] calc'd for $C_{58}H_{74}N_8O_9$ 1026.6; found 1027.4.

Step 6. To a mixture of tert-butyl 4-(5-((6$^3$S,4S)-4-((S)-2-(((benzyloxy)carbonyl)(methyl)amino)-3-methylbutanamido)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-1$^2$-yl)-6-((S)-1-methoxyethyl)pyridin-3-yl)piperazine-1-carboxylate (335 mg, 0.33 mmol) in DMF (5 mL) at 0° C. under an atmosphere of $N_2$ were added $Cs_2CO_3$ (234 mg, 0.72 mmol) and iodoethane (102 mg, 0.65 mmol) in portions. The mixture was warmed to room temperature and stirred for 16 h, then diluted with $H_2O$ and the mixture extracted with EtOAc (100 mL×3). The combined organic layers were washed with brine (50 mL×3), dried over anhydrous $Na_2SO_4$ and filtered. The filtrate was concentrated under reduced pressure and the residue was purified by preparative-TLC to give tert-butyl 4-(5-((6$^3$S,4S)-4-((S)-2-(((benzyloxy)carbonyl)(methyl) amino)-3-methylbutanamido)-1$^1$-ethyl-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-1$^2$-yl)-6-((S)-1-methoxyethyl)pyridin-3-yl)piperazine-1-carboxylate (320 mg, 84% yield) as a light yellow solid. LCMS (ESI): m/z [M+H] calc'd for $C_{60}H_{78}N_8O_9$ 1054.6; found 1055.8.

Step 7. A mixture of tert-butyl 4-(5-((6$^3$S,4S)-4-((S)-2-(((benzyloxy)carbonyl)(methyl)amino)-3-methylbutanamido)-1$^1$-ethyl-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1, 3)-benzenacycloundecaphane-1$^2$-yl)-6-((S)-1-methoxyethyl)pyridin-3-yl)piperazine-1-carboxylate (320 mg) in xx M HCl in 1,4-dioxane (3.0 mL) at 0° C. under an atmosphere of $N_2$ was stirred at room temperature for 2 h, then concentrated under reduced pressure to give benzyl ((2S)-1-(((6$^3$S,4S)-1$^1$-ethyl-1$^2$-(2-((S)-1-methoxyethyl)-5-(piperazin-1-yl)pyridin-3-yl)-10,10-dimethyl-5,7-dioxo-6$^1$, 6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)(methyl)carbamate, which was used directly in the next step further purification. LCMS (ESI): m/z [M+H] calc'd for $C_{55}H_{70}N_8O_7$ 954.5; found 955.3.

Step 8. To a mixture of benzyl ((2S)-1-(((6$^3$S,4S)-1$^1$-ethyl-1$^2$-(2-((S)-1-methoxyethyl)-5-(piperazin-1-yl)pyridin-3-yl)-10,10-dimethyl-5,7-dioxo-6$^1$,6$^2$,6$^3$,6$^4$,6$^5$,6$^6$-hexahydro-1$^{i1}$H-8-oxa-1(5,3)-indola-6(1,3)-pyridazina-2(1,3)-benzenacycloundecaphane-4-yl)amino)-3-methyl-1-oxobutan-2-yl)(methyl)carbamate (320 mg, 0.34 mmol) and HCHO (60 mg, 2.0 mmol) in MeOH (3.0 mL) at 0° C. under an atmosphere of $N_2$ were added $NaCNBH_3$ (42 mg, 0.67 mmol) and AcOH (60 mg, 1.0 mmol) in portions. The mixture was warmed to room temperature and stirred for 2 h, then diluted with $H_2O$ and the mixture extracted with DCM/MeOH (5:1) (200 mL×3). The combined organic layers were washed with brine (100 mL×3), dried over anhydrous $Na_2SO_4$ and filtered. The filtrate was concentrated under reduced pressure and the residue was purified by preparative-HPLC to give benzyl ((2S)-1-(((6$^3$S,4S)-1$^1$-ethyl-1$^2$-(2-((S)-1-methoxyethyl)-5-(4-methylpiperazin-1-yl)pyridin-3-yl)-10,10-dimethyl-5,7-dioxo-6$^1$,6$^2$,6$^3$,6$^4$,6$^5$, 6$^6$-hexahydro-1$^1$H-8-oxa-1(5,3)-indola-6(1,3)-pyridazina-2 (1,3)-benzenacycloundecaphane-4-yl)amino)-3-methyl-1-oxobutan-2-yl)(methyl)carbamate (160 mg, 59% yield) as a solid. LCMS (ESI): m/z [M+H] calc'd for $C_{56}H_{72}N_8O_7$ 968.6; found 969.6.

Step 9. To a mixture of benzyl ((2S)-1-(((6$^3$S,4S)-1$^1$-ethyl-1$^2$-(2-((S)-1-methoxyethyl)-5-(4-methylpiperazin-1-yl)pyridin-3-yl)-10,10-dimethyl-5,7-dioxo-6$^1$,6$^2$,6$^3$,6$^4$,6$^5$, 6$^6$-hexahydro-1$^1$H-8-oxa-1(5,3)-indola-6(1,3)-pyridazina-2 (1,3)-benzenacycloundecaphane-4-yl)amino)-3-methyl-1-oxobutan-2-yl)(methyl)carbamate (160 mg, 0.17 mmol) in toluene (10 mL) and MeOH (1.0 mL) was added Pd/C (130 mg, 1.2 mmol) in portions. The mixture was evacuated and re-filled with $H_2$ (×3), then stirred under an atmosphere of $H_2$ for 16 h. The mixture was filtered and the filtrate was concentrated under reduced pressure to give (2S)—N-((6$^3$S, 4S)-1$^1$-ethyl-1$^2$-(2-((S)-1-methoxyethyl)-5-(4-methylpiperazin-1-yl)pyridin-3-yl)-10,10-dimethyl-5,7-dioxo-6$^1$,6$^2$,6$^3$, 6$^4$,6$^5$,6$^6$-hexahydro-1$^1$H-8-oxa-1(5,3)-indola-6(1,3)-pyridazina-2(1,3)- benzenacycloundecaphane-4-yl)-3-methyl-2-(methylamino)butanamide (140 mg), which was used directly in the next step without further purification. LCMS (ESI): m/z [M+H] calc'd for $C_{48}H_{66}N_8O_5$ 834.5; found 835.5.

Step 10. To a mixture of (2S)—N-((6$^3$S,4S)-1$^1$-ethyl-1$^2$-(2-((S)-1-methoxyethyl)-5-(4-methylpiperazin-1-yl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)-3-methyl-2-(methylamino) butanamide (140 mg, 0.17 mmol) in ACN (2.0 mL) at 0° C. under an atmosphere of $N_2$ were added DIPEA (433 mg, 3.35 mmol), (3S)-1-(prop-2-enoyl)pyrrolidine-3-carboxylic acid (57 mg, 0.34 mmol) in portions and CIP (70 mg, 0.25 mmol) in portions over 10 min. The mixture was stirred at 0° C. for 1.5 h, then $H_2O$ added and the mixture extracted with EtOAc (150 mL×3). The combined organic layers were washed with brine (100 mL×3), dried over anhydrous Na$_2$SO$_4$ and filtered. The filtrate was concentrated under reduced pressure and the residue was purified by preparative-HPLC to give two atropisomers of (3S)-1-acryloyl-N-((2S)-1-(((6$^3$S,4S)-1$^1$-ethyl-1$^2$-(2-((S)-1-methoxyethyl)-5-(4-methylpiperazin-1-yl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide (40 mg, 24% yield) as a solid and (20 mg, 12% yield) as a solid. LCMS (ESI): m/z [M+H] calc'd for C$_{56}$H$_{75}$N$_9$O$_7$ 985.6; found 986.7; $^1$H NMR (400 MHz, DMSO-d$_6$) 8.47 (t, J=2.1 Hz, 1H), 8.00 (d, J=4.7 Hz, 1H), 7.78-7.59 (m, 3H), 7.58-7.48 (m, 1H), 7.42-7.30 (m, 1H), 7.23 (dq, J=8.0, 4.0, 3.5 Hz, 1H), 7.15-7.03 (m, 1H), 6.75-6.50 (m, 1H), 6.18 (dt, J=16.8, 2.7 Hz, 1H), 5.70 (tt, J=9.3, 2.7 Hz, 1H), 5.48-5.23 (m, 1H), 5.06 (dd, J=31.1, 12.3 Hz, 1H), 4.74 (dd, J=11.0, 4.3 Hz, 1H), 4.33-4.15 (m, 2H), 4.01 (ddd, J=36.1, 12.6, 7.6 Hz, 2H), 3.91-3.56 (m, 6H), 3.52-3.39 (m, 2H), 3.31-3.28 (m, 2H), 3.24 (d, J=5.7 Hz, 4H), 3.06 (s, 4H), 2.93 (d, J=9.8 Hz, 2H), 2.81 (d, J=5.4 Hz, 3H), 2.47-2.43 (m, 4H), 2.22 (s, 4H), 2.09 (tq, J=12.0, 7.4, 6.6 Hz, 3H), 1.81 (s, 1H), 1.74 (d, J=11.7 Hz, 1H), 1.56 (d, J=11.7 Hz, 1H), 1.20 (dd, J=6.3, 1.5 Hz, 3H), 1.10 (td, J=7.2, 2.4 Hz, 3H), 1.00-0.86 (m, 6H), 0.86-0.72 (m, 3H), 0.54 (d, J=3.5 Hz, 3H) and LCMS (ESI): m/z [M−H] calc'd for C$_{56}$H$_{75}$N$_9$O$_7$ 985.6; found 984.4; $^1$H NMR (400 MHz, DMSO-d$_6$) δ 8.46 (d, J=3.0 Hz, 2H), 7.98 (s, 1H), 7.89-7.83 (m, 1H), 7.76-7.57 (m, 3H), 7.24 (s, 2H), 7.07 (s, 1H), 6.70-6.58 (m, 1H), 6.17 (d, J=16.5 Hz, 1H), 5.73-5.67 (m, 1H), 5.36-5.30 (m, 1H), 4.31-3.97 (m, 6H), 3.83-3.77 (m, 2H), 3.74-3.49 (m, 6H), 3.48-3.41 (m, 1H), 3.40-3.37 (m, 2H) 3.28-3.24 (m, 4H), 3.07 (s, 3H), 2.88-2.82 (m, 1H), 2.80-2.64 (m, 7H), 2.49-2.44 (m, 4H), 2.22 (s, 3H), 2.04 (d, J=26.1 Hz, 3H), 1.85-1.79 (m, 1H), 1.67-1.55 (m, 2H), 1.35 (d, J=6.1 Hz, 3H), 1.27-1.22 (m, 1H), 1.05-0.93 (m, 4H), 0.89 (d, J=6.9 Hz, 2H), 0.79 (d, J=12.4 Hz, 5H), 0.73 (d, J=6.5 Hz, 1H), 0.56 (s, 3H).

Example A542. The synthesis of 1-(4-(dimethylamino)-4-methylpent-2-ynoyl)-4-fluoro-N-((2S)-1-(((6$^3$S,4S)-1$^2$-(2-((S)-1-methoxyethyl)-5-(4-methylpiperazin-1-yl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)-N-methylpiperidine-4-carboxamide

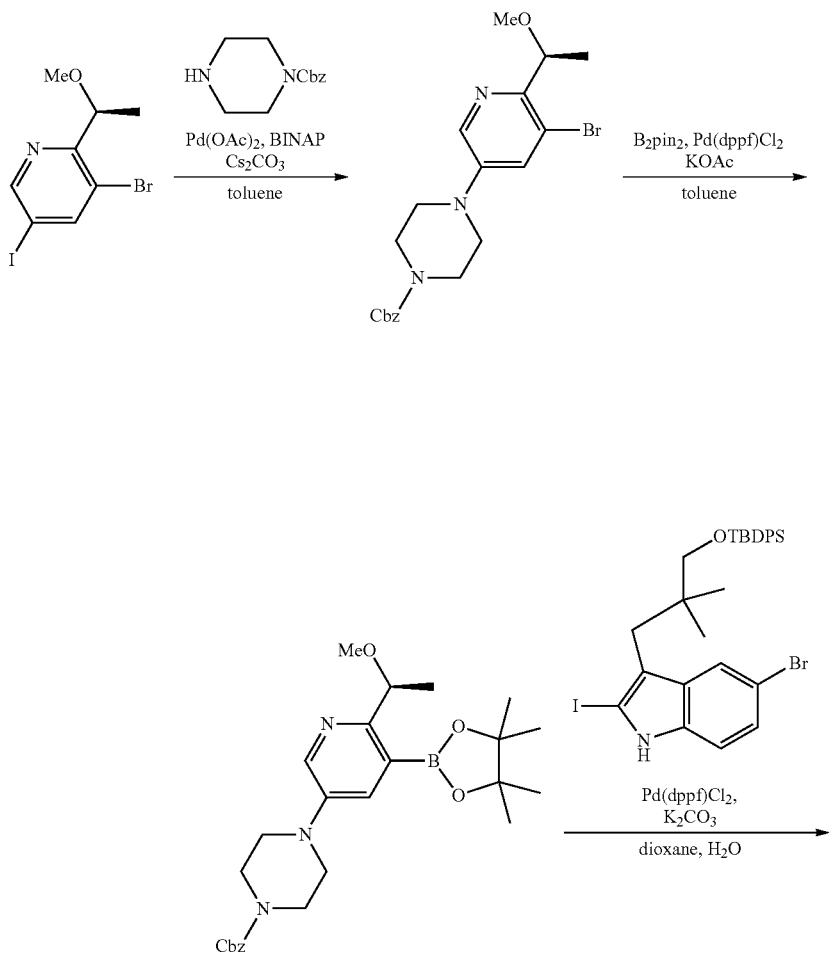

-continued
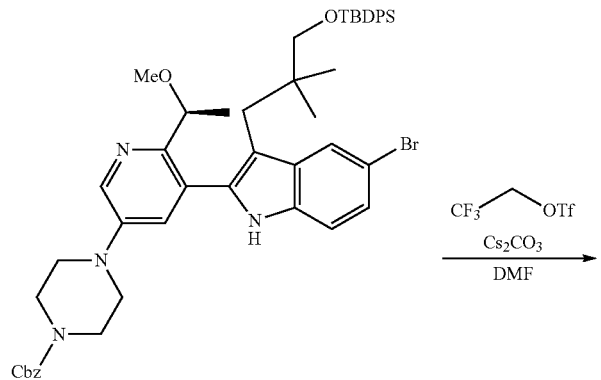
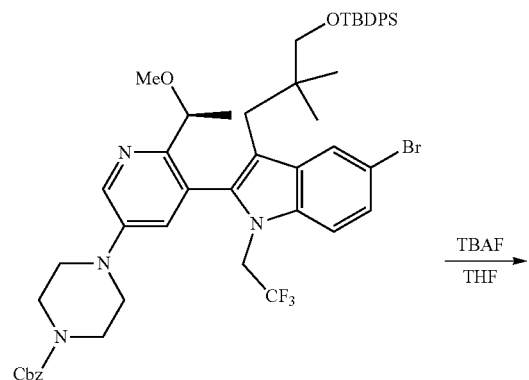
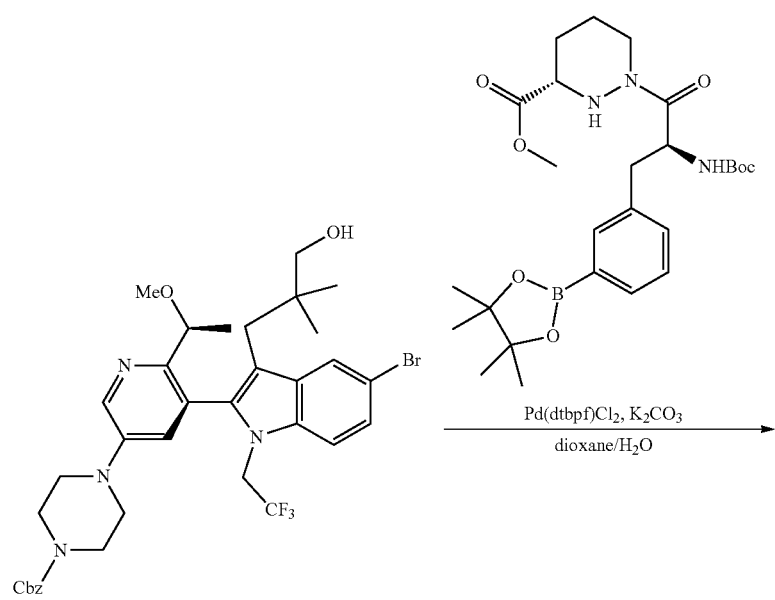

-continued
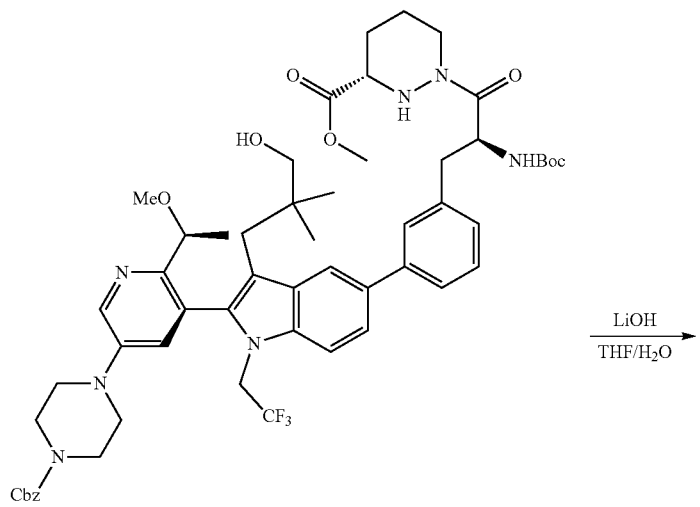
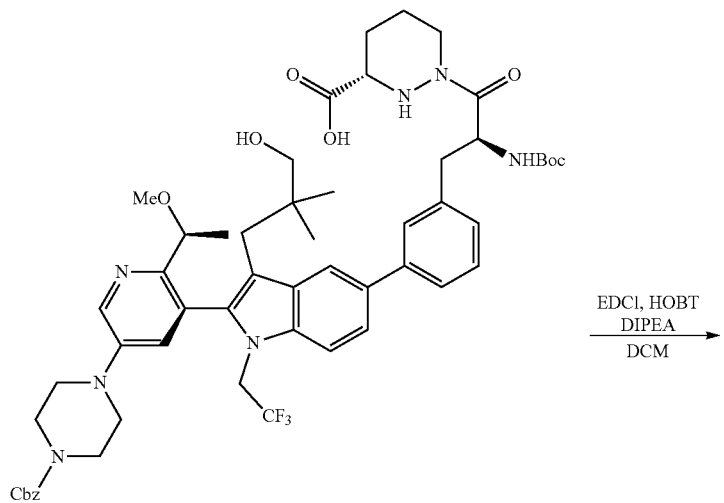
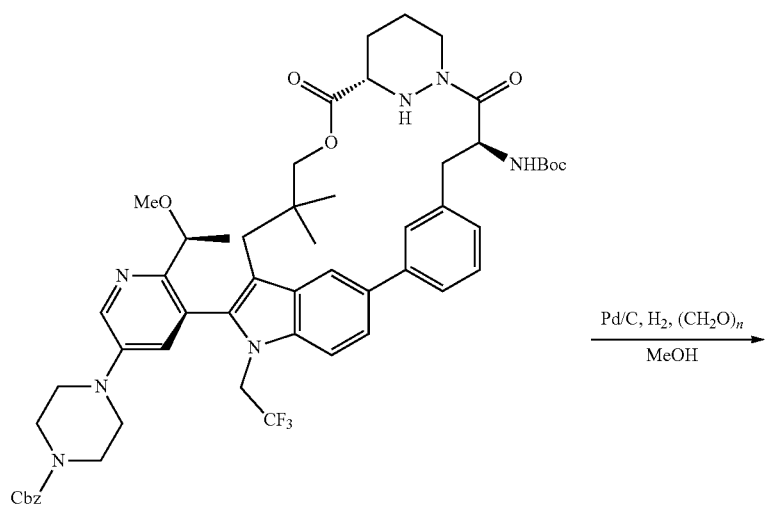

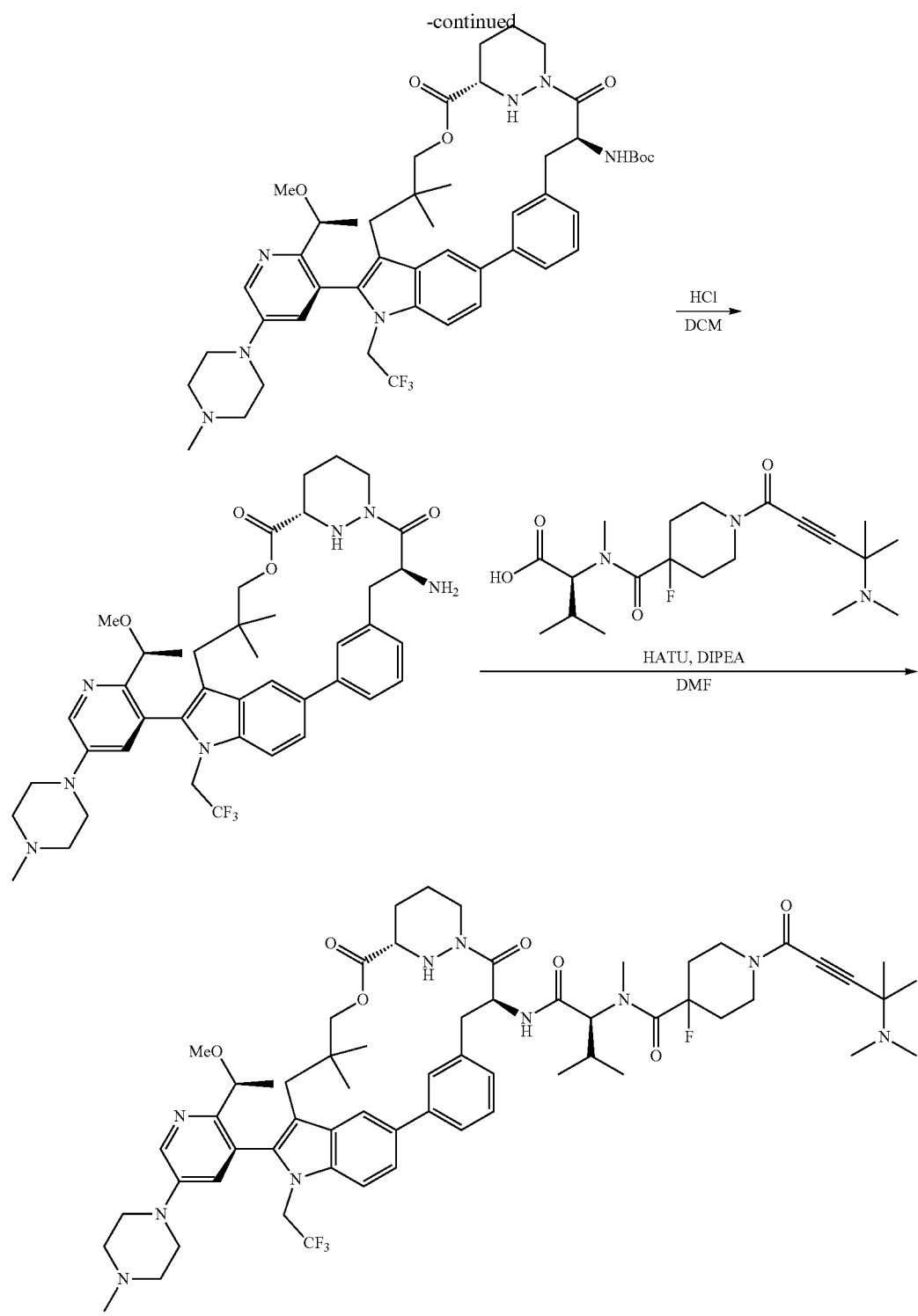

Step 1. To a solution of (S)-3-bromo-5-iodo-2-(1-methoxyethyl)pyridine (15 g, 43.86 mmol), and benzyl piperazine-1-carboxylate (8.7 g, 39.48 mmol) in toluene (150 mL) at 0° C., were added cesium carbonate (71.46 g, 219.32 mmol), BINAP (0.55 g, 0.88 mmol) and palladium acetate (0.49 g, 2.19 mmol) in portions. The reaction mixture was stirred at 90° C. for 12 h under an argon atmosphere. The resulting mixture was cooled down to room temperature, filtered and the filter cake was washed with EtOAc (150 mL×3). The filtrate was concentrated under reduced pressure. The residue was purified by silica gel column chromatography to afford benzyl (S)-4-(5-bromo-6-(1-methoxyethyl)pyridin-3-yl)piperazine-1-carboxylate (16 g, 84% yield) as solid. LCMS (ESI): m/z [M+H] calc'd for $C_{44}H_{58}N_6O_7$ 433.1; found 434.0.

Step 2. To a stirred solution of benzyl (S)-4-(5-bromo-6-(1-methoxyethyl)pyridin-3-yl)piperazine-1-carboxylate (22.7 g, 52.26 mmol), bis(pinacolato)diboron (19.91 g, 78.4 mmol) in toluene (230 mL) at 0° C., were added potassium acetate (12.82 g, 130.66 mmol) and Pd(dppf)Cl$_2$-DCM (4.26 g, 5.23 mmol) in portions. The reaction mixture was stirred at 90° C. for 6 h under an argon atmosphere. The resulting mixture was filtered and the filter cake was washed with EtOAc (200 mL×3). The filtrate was concentrated under reduced pressure. The residue was purified by silica gel column chromatography to afford benzyl (S)-4-(6-(1-methoxyethyl)-5-(4,4,5,5-tetramethyl-1,3,2-dioxaborolan-2-yl)pyridin-3-yl)piperazine-1-carboxylate (14.7 g, 58% yield) as solid. LCMS (ESI): m/z [M+H] calc'd for $C_{26}H_{36}BN_3O_5$ 481.3; found 482.3.

Step 3. To a stirred solution of 5-bromo-3-(3-((tert-butyldiphenylsilyl)oxy)-2,2-dimethylpropyl)-2-iodo-1H-indole (17.46 g, 27 mmol) in 1,4-dioxane (150 mL) and H$_2$O (30 mL) at 0° C., were added potassium carbonate (9.33 g, 67.51 mmol) and Pd(dppf)Cl$_2$ DCM (2.2 g, 2.7 mmol) in portions, followed by benzyl (S)-4-(6-(1-methoxyethyl)-5-(4,4,5,5-tetramethyl-1,3,2-dioxaborolan-2-yl) pyridin-3-yl) piperazine-1-carboxylate (13 g, 27 mmol). The reaction mixture was stirred at 70° C. for 12 h under an argon atmosphere. The resulting mixture was cooled to room temperature and quenched with H$_2$O, then extracted with EtOAc (200 mL×3). The organic phase was dried over anhydrous sodium sulfate and concentrated under reduced pressure. The residue was purified by silica gel column chromatography to afford benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate (20 g, 84.7% yield) as solid. LCMS (ESI): m/z [M+H] calc'd for $C_{49}H_{57}BN_4O_4Si$ 873.2; found 873.3.

Step 4. To a mixture of benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate (19 g, 21.74 mmol) and Cs$_2$CO$_3$ (49.58 g, 152.17 mmol) in DMF (190 mL) at 0° C. under argon atmosphere, was dropwise added 2,2,2-trifluoroethyl trifluoromethanesulfonate (50.46 g, 217.39 mmol). The reaction mixture was stirred at room temperature for 12 h under an argon atmosphere, then quenched with H$_2$O, extracted with EtOAc (200 mL×3). The combined organic layers were washed with brine (200 mL×3), dried over anhydrous sodium sulfate and concentrated under reduced pressure. The residue was purified by silica gel column chromatography to afford benzyl (S)-4-(5-(5-bromo-3-(3-((tert-butyldiphenylsilyl)oxy)-2,2-dimethylpropyl)-1-(2,2,2-trifluoroethyl)-1H-indol-2-yl)-6-(1-methoxyethyl)pyridin-3-yl)piperazine-1-carboxylate (17.6 g, 84.7% yield) as solid. LCMS (ESI): m/z [M+H] calc'd for $C_{51}H_{58}BF_3N_4O_4Si$ 954.2; found 955.3.

Step 5. To a solution of benzyl (S)-4-(5-(5-bromo-3-(3-((tert-butyldiphenylsilyl)oxy)-2,2-dimethylpropyl)-1-(2,2,2-trifluoroethyl)-1H-indol-2-yl)-6-(1-methoxyethyl)pyridin-3-yl)piperazine-1-carboxylate (18 g, 18.83 mmol), was added TBAF in THF (180.0 mL) at 0° C. The reaction mixture was stirred at 40° C. for 12 h under an argon atmosphere, then quenched with cold H$_2$O. The resulting mixture was extracted with EtOAc (200 mL×3). The combined organic layers were washed with brine (200 mL×3), dried over anhydrous sodium sulfate and concentrated under reduced pressure. The residue was purified by silica gel column chromatography to afford benzyl (S)-4-(5-(5-bromo-3-(3-hydroxy-2,2-dimethylpropyl)-1-(2,2,2-trifluoroethyl)-1H-indol-2-yl)-6-(1-methoxyethyl)pyridin-3-yl)piperazine-1-carboxylate (7.8 g, 57.7% yield) as solid. LCMS (ESI): m/z [M+H] calc'd for $C_{35}H_{40}BrF_3N_4O_4$ 716.2; found 717.1.

Step 6. A solution of benzyl (S)-4-(5-(5-bromo-3-(3-hydroxy-2,2-dimethylpropyl)-1-(2,2,2-trifluoroethyl)-1H-indol-2-yl)-6-(1-methoxyethyl)pyridin-3-yl)piperazine-1-carboxylate (1 g, 1.39 mmol) in 1,4-dioxane (10 mL) and H$_2$O (2 mL), was added methyl (S)-1-((S)-2-((tert-butoxycarbonyl)amino)-3-(3-(4,4,5,5-tetramethyl-1,3,2-dioxaborolan-2-yl)phenyl)propanoyl)hexahydropyridazine-3-carboxylate (1.08 g, 2.09 mmol), potassium carbonate (481.47 mg, 3.48 mmol) and Pd(dtbpf)Cl$_2$ (181.64 mg, 0.28 mmol) in portions at 0° C. The reaction mixture was stirred at 70° C. for 3 h under an argon atmosphere. The resulting mixture was cooled to room temperature, then quenched with H$_2$O and extracted with EtOAc (50 mL×3). The combined organic layers were washed with brine (20 mL×3), dried over anhydrous sodium sulfate and concentrated under reduced pressure. The residue was purified by silica gel chromatography to afford methyl (S)-1-((S)-3-(3-(2-(5-(4-((benzyloxy)carbonyl)piperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)phenyl)-2-((tert-butoxycarbonyl)amino)propanoyl)hexahydropyridazine-3-carboxylate (1.1 g, 77% yield) as solid. LCMS (ESI): m/z [M+H] calc'd for $C_{55}H_{68}F_3N_7O_9$ 1027.5; found 1028.3.

Step 7. To a solution of methyl (S)-1-((S)-3-(3-(2-(5-(4-((benzyloxy)carbonyl)piperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)phenyl)-2-((tert-butoxycarbonyl)amino)propanoyl)hexahydropyridazine-3-carboxylate (1.1 g, 1.07 mmol) in THF (8 mL) and H$_2$O (2 mL) at 0° C., was dropwise added LiOH (2.2 mL, 1M aqueous) under an argon atmosphere. The reaction mixture was stirred for 2 h then concentrated under reduced pressure. The residue was acidified to pH 5 with citric acid (1M) and extracted with EtOAc (20 mL×3). The combined organic layers were concentrated under reduced pressure. The residue was purified by reverse phase chromatography to afford (S)-1-((S)-3-(3-(2-(5-(4-((benzyloxy)carbonyl)piperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)phenyl)-2-((tert-butoxycarbonyl)amino)propanoyl) hexahydropyridazine-3-carboxylic acid (750 mg, 69% yield) as solid. LCMS (ESI): m/z [M+H] calc'd for $C_{54}H_{66}F_3N_7O_9$ 1013.5; found 1014.3.

Step 8. To a solution of (S)-1-((S)-3-(3-(2-(5-(4-((benzyloxy)carbonyl)piperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)phenyl)-2-((tert-butoxycarbonyl)amino)propanoyl)hexahydropyridazine-3-carboxylic acid (0.75 g, 0.74 mmol) in DCM (75 mL) at 0° C., were added in portions HOBT (0.5 g, 3.7 mmol), DIPEA (3.82 g, 29.58 mmol), and EDCl (4.25 g, 22.19 mmol) at 0° C. The reaction mixture was stirred at room temperature for 12 h under an argon atmosphere. The resulting mixture was concentrated under reduced pressure and extracted with EtOAc (100 mL×3). The combined organic layers were washed with brine (50 mL×3), dried over anhydrous sodium sulfate and concentrated under reduced pressure. The residue was purified by silica gel chromatography to afford benzyl 4-(5-((6$^3$S,4S)-4-((tert-butoxycarbonyl)amino)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-6(1,3)-pyridazina-2(1,3)-benzenacycloundecaphane-1$^2$-yl)-6-((S)-1-methoxyethyl)pyridin-3-yl)piperazine-1-carboxylate (0.5 g, 67.9% yield) as solid. LCMS (ESI): m/z [M+H] calc'd for $C_{54}H_{64}F_3N_7O_8$ 995.5; found 996.3.

Step 9. To a mixture of benzyl 4-(5-((($6^3$S,4S)-4-((tert-butoxycarbonyl)amino)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-$1^2$-yl)-6-((S)-1-methoxyethyl)pyridin-3-yl)piperazine-1-carboxylate (500 mg, 0.5 mmol) in MeOH (15 mL) at 0° C., was added paraformaldehyde (135.64 mg, 1.5 mmol), and Pd/C (750 mg) in portions. The reaction mixture was stirred at room temperature for 12 h under a hydrogen atmosphere. The resulting mixture was filtered and the filter cake was washed with EtOAc (50 mL×5). The filtrate was concentrated under reduced pressure. The residue was purified by silica gel chromatography to afford tert-butyl (($6^3$S,4S)-$1^2$-(2-((S)-1-methoxyethyl)-5-(4-methylpiperazin-1-yl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (350 mg, 79.6% yield) as an solid. LCMS (ESI): m/z [M+H] calc'd for $C_{47}H_{60}F_3N_7O_8$ 875.5; found 876.5.

Step 10. To a solution of tert-butyl (($6^3$S,4S)-$1^2$-(2-((S)-1-methoxyethyl)-5-(4-methylpiperazin-1-yl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (300 mg, 0.34 mmol) in DCM (2 mL) at 0° C., was dropwise added HCl in 1,4-dioxane (1 mL, 4M, 4 mmol). The reaction mixture was stirred at room temperature for 2 h, then concentrated under reduced pressure to give ($6^3$S,4S)-4-amino-$1^2$-(2-((S)-1-methoxyethyl)-5-(4-methylpiperazin-1-yl)pyridin-3-yl)-10,10-dimethyl-11-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5,7-dione hydrochloride (350 mg, crude) as solid. LCMS (ESI): m/z [M+H] calc'd for $C_{42}H_{52}F_3N_7O_4$ 775.4; found 766.4.

Step 11. To a solution of ($6^3$S,4S)-4-amino-$1^2$-(2-((S)-1-methoxyethyl)-5-(4-methylpiperazin-1-yl)pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5,7-dione hydrochloride (150 mg, 0.19 mmol) and N-(1-(4-(dimethylamino)-4-methylpent-2-ynoyl)-4-fluoropiperidine-4-carbonyl)-N-methyl-L-valine (154 mg, 0.39 mmol) in DMF (2 mL) at 0° C., was dropwise added a mixture of DIPEA (1 g, 7.72 mmol) and HATU (110 mg, 0.29 mmol) in DMF (0.2 mL). The reaction mixture was stirred at 0° C. for 2 h under an argon atmosphere, then quenched with $H_2O$. The resulting mixture was extracted with EtOAc (20 mL×3). The combined organic phase was washed with brine (10 mL×3), dried over anhydrous sodium sulfate and concentrated under reduced pressure. The residue was purified by reverse phase chromatography to afford 1-(4-(dimethylamino)-4-methylpent-2-ynoyl)-4-fluoro-N-((2S)-1-((($6^3$S,4S)-$1^2$-(2-((S)-1-methoxyethyl)-5-(4-methylpiperazin-1-yl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-N-methylpiperidine-4-carboxamide (39.5 mg, 17% yield) as solid. $^1$H NMR (400 MHz, DMSO-$d_6$) δ 8.48 (d, J=2.9 Hz, 1H), 8.32 (t, J=7.3 Hz, 1H), 7.97 (s, 1H), 7.82-7.69 (m, 3H), 7.66 (t, J=7.8 Hz, 1H), 7.33-7.07 (m, 3H), 5.50 (dd, J=16.7, 8.6 Hz, 1H), 5.33 (t, J=9.2 Hz, 1H), 5.16 (d, J=12.2 Hz, 1H), 4.94-4.80 (m, 1H), 4.64 (d, J=10.8 Hz, 1H), 4.33-4.16 (m, 3H), 4.12-4.02 (m, 2H), 3.71-3.50 (m, 3H), 3.25 (s, 3H), 3.21-3.16 (m, 3H), 3.14-3.05 (m, 1H), 2.96 (t, J=4.7 Hz, 4H), 2.84 (s, 1H), 2.82-2.72 (m, 2H), 2.59-2.53 (m, 1H), 2.47-2.40 (m, 4H), 2.22 (d, J=2.9 Hz, 9H), 2.18-2.12 (m, 2H), 2.11-1.99 (m, 3H), 1.87-1.78 (m, 1H), 1.74-1.62 (m, 1H), 1.59-1.48 (m, 1H), 1.40-1.32 (m, 9H), 1.01 (t, J=7.7 Hz, 1H), 0.89 (s, 5H), 0.83 (d, J=6.3 Hz, 1H), 0.77 (d, J=6.6 Hz, 2H), 0.38 (s, 3H).

LCMS (ESI): m/z [M+H] calc'd for $C_{44}H_{58}N_6O_7$ 1154.6; found 1155.7.

Example A735. Synthesis of 2-acryloyl-N-((2S)-1-((($6^3$S,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)amino)-3-methyl-1-oxobutan-2-yl)-N-methyl-5-oxa-2,9-diazaspiro[3.5]nonane-9-carboxamide

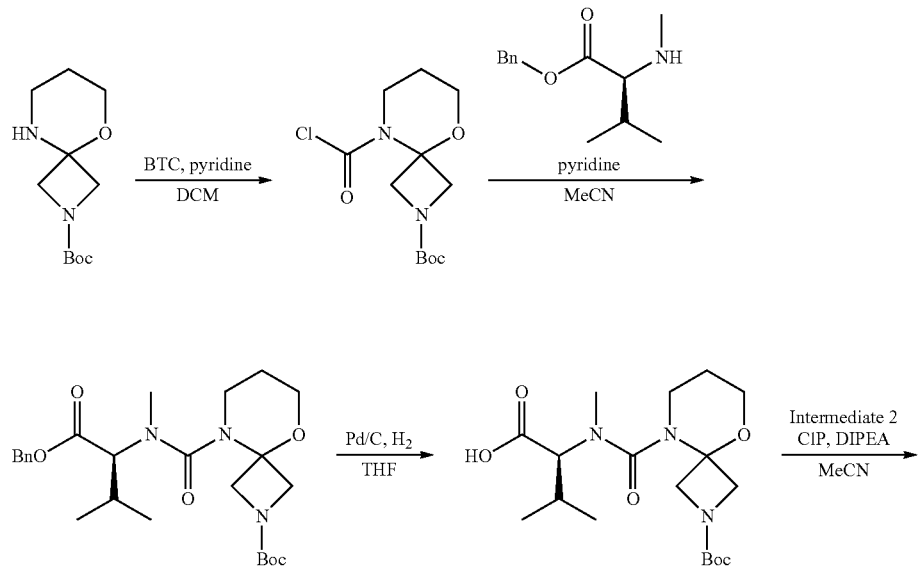

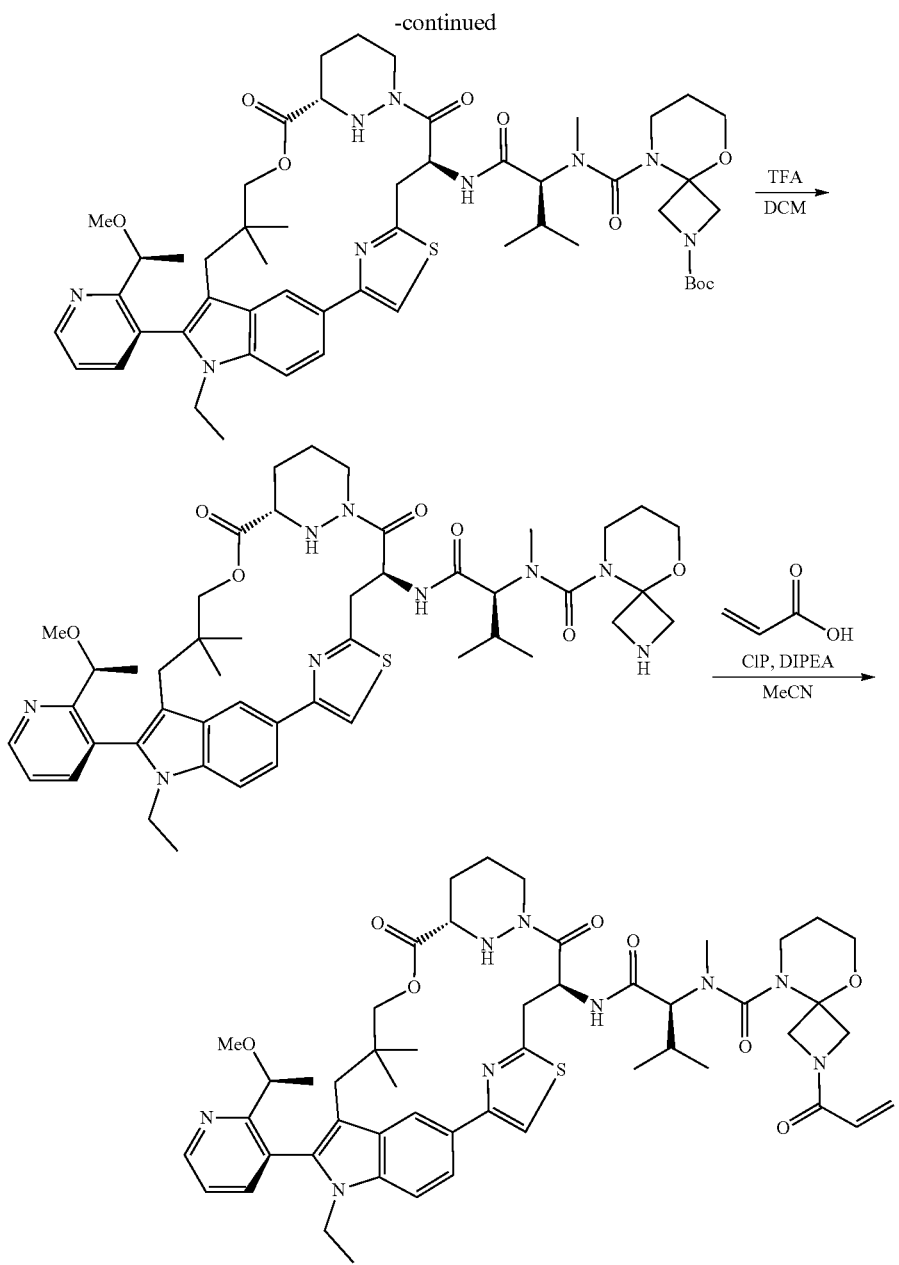

Step 1. To a stirred mixture of BTC (425.2 mg, 1.448 mmol) in DCM (10 mL) was added dropwise pyridine (1.04 g, 13.16 mmol) and tert-butyl 5-oxa-2,9-diazaspiro[3.5]nonane-2-carboxylate (1 g, 4.39 mmol), the reaction mixture was stirred at room temperature for 2 h. The resulting mixture was concentrated under reduced pressure to give crude tert-butyl 9-(chlorocarbonyl)-5-oxa-2,9-diazaspiro[3.5]nonane-2-carboxylate.

Step 2. To a stirred solution of tert-butyl 9-(chlorocarbonyl)-5-oxa-2,9-diazaspiro[3.5]nonane-2-carboxylate (2.5 g, crude) in MeCN (20 mL) were added dropwise pyridine (1.04 g, 13.16 mmol) and benzyl (2S)-3-methyl-2-(methylamino)butanoate (970.66 mg, 4.38 mmol) at room temperature. The reaction mixture was stirred at 80° C. for 12 h and concentrated under reduced pressure. The residue was purified by silica gel column chromatography to afford tert-butyl (S)-9-((1-(benzyloxy)-3-methyl-1-oxobutan-2-yl)(methyl) carbamoyl)-5-oxa-2,9-diazaspiro[3.5]nonane-2-carboxylate (783 mg, 37.6% yield, two steps) as an oil. LCMS (ESI): m/z [M+H] calc'd for $C_{25}H_{37}N_3O_6$ 475.3; found 476.3.

Step 3. A solution of tert-butyl (S)-9-((1-(benzyloxy)-3-methyl-1-oxobutan-2-yl)(methyl)carbamoyl)-5-oxa-2,9-diazaspiro[3.5]nonane-2-carboxylate (783 mg, 1.65 mmol) and 10 wt % palladium on carbon (226.29 mg) in THF (10 mL) was stirred for 2 h at 50° C. under a hydrogen atmosphere. The resulting mixture was cooled to room temperature, filtered and the filter cake was washed with MeCN (10 mL×3). The filtrate was concentrated under reduced pressure to give N-(2-(tert-butoxycarbonyl)-5-oxa-2,9-diazaspiro[3.5]nonane-9-carbonyl)-N-methyl-L-valine (591 mg, 98.8% yield) as solid. LCMS (ESI): m/z [M+H] calc'd for $C_{18}H_{31}N_3O_6$ 385.2; found 386.3.

Step 4. To a stirred solution of intermediate 2 (731 mg, 1.16 mmol) and DIPEA (2.25 g, 17.38 mmol) in MeCN (50 mL) was added CIP (644.31 mg, 2.32 mmol) and N-(2-(tert-butoxycarbonyl)-5-oxa-2,9-diazaspiro[3.5]nonane-9-carbonyl)-N-methyl-L-valine (446.68 mg, 1.16 mmol) at room temperature. The reaction mixture was stirred for 2 h then concentrated under reduced pressure. The residue was purified by silica gel column chromatography to afford tert-butyl 9-(((2S)-1-(((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)amino)-3-methyl-1-oxobutan-2-yl)(methyl)carbamoyl)-5-oxa-2,9-diazaspiro[3.5]nonane-2-carboxylate (752 mg, 65% yield) as solid. LCMS (ESI): m/z [M+H] calc'd for $C_{52}H_{71}N_9O_9S$ 997.5; found 996.6.

Step 5. To a stirred solution of tert-butyl 9-(((2S)-1-(((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)amino)-3-methyl-1-oxobutan-2-yl)(methyl)carbamoyl)-5-oxa-2,9-diazaspiro[3.5]nonane-2-carboxylate (752 mg, 0.75 mmol) in DCM (40 mL) was added TFA (10 mL) in portions at room temperature. The reaction mixture was stirred for 2 h, then concentrated under reduced pressure. To the residue was added saturated aqueous sodium bicarbonate (100 mL) and DCM (100 mL). The aqueous layer was separated and extracted with DCM (100 mL×2). The combined organic phase was dried over anhydrous sodium sulfate, filtrated and concentrated under reduced pressure to afford N-((2S)-1-(((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)amino)-3-methyl-1-oxobutan-2-yl)-N-methyl-5-oxa-2,9-diazaspiro[3.5]nonane-9-carboxamide (587 mg, 87% yield) as solid. LCMS (ESI): m/z [M+H] calc'd for $C_{47}H_{63}N_9O_7S$ 897.5; found 898.4.

Step 6. A stirred solution of N-((2S)-1-(((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)amino)-3-methyl-1-oxobutan-2-yl)-N-methyl-5-oxa-2,9-diazaspiro[3.5]nonane-9-carboxamide (586 mg, 0.65 mmol) in MeCN (10 mL) was added acrylic acid (47 mg, 0.65 mmol), DIPEA (421 mg, 3.26 mmol), CIP (362 mg, 1.3 mmol). The reaction mixture was stirred for 12 h and concentrated under reduced pressure. The residue was purified by reverse phase chromatography to afford 2-acryloyl-N-((2S)-1-(((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)amino)-3-methyl-1-oxobutan-2-yl)-N-methyl-5-oxa-2,9-diazaspiro[3.5]nonane-9-carboxamide (194 mg, 27% yield) as a solid. $^1$H NMR (400 MHz, DMSO-$d_6$) δ 8.78 (dd, J=4.8, 1.7 Hz, 1H), 8.48 (d, J=1.6 Hz, 2H), 7.85-7.65 (m, 3H), 7.65-7.42 (m, 2H), 6.30 (mm, 1H), 6.10 (m, J=17.0, 1H), 5.78-5.50 (m, J=10.3, 2H), 5.10 (dd, 1H), 4.40-3.80 (m, 14H), 3.60-3.10 (m, 10H), 2.94 (d, J=14.5 Hz, 1H), 2.85 (s, 4H), 2.42 (dd, 1H), 2.07 (dd, 2H), 1.80 (s, 2H), 1.55 (s, 3H), 1.32 (d, 3H), 0.95-0.75 (m, 12H), 0.33 (s, 3H). LCMS (ESI): m/z [M+H] calc'd for $C_{50}H_{65}N_9O_8S$ 951.5; found 952.6.

Example A720. Synthesis of (2R)-2-(((1-(4-(dimethylamino)-4-methylpent-2-ynoyl)azetidin-3-yl)oxy)methyl)-N-((6$^3$S,4S,Z)-1$^1$-ethyl-1$^2$-(2-((S)-1-methoxyethyl)pyridin-3-yl)-2$^1$,10,10-trimethyl-5,7-dioxo-6$^1$,6$^2$,6$^3$,6$^4$,6$^5$,6$^6$-hexahydro-1$^1$H,2$^1$H-8-oxa-1(5,3)-indola-6(1,3)-pyridazina-2(5,3)-triazolacycloundecaphane-4-yl)-3-methylbutanamide

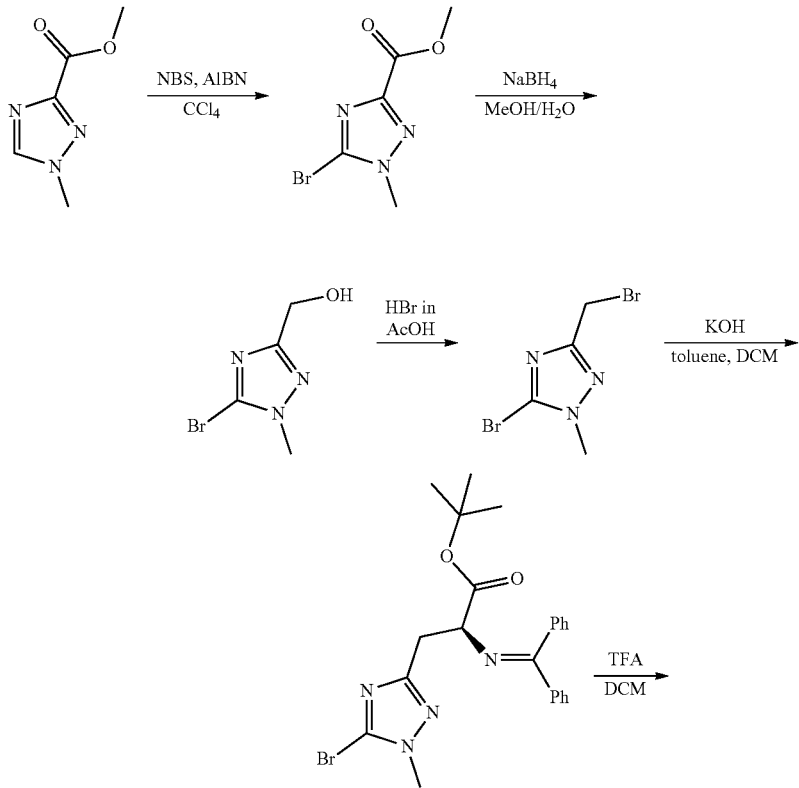

-continued
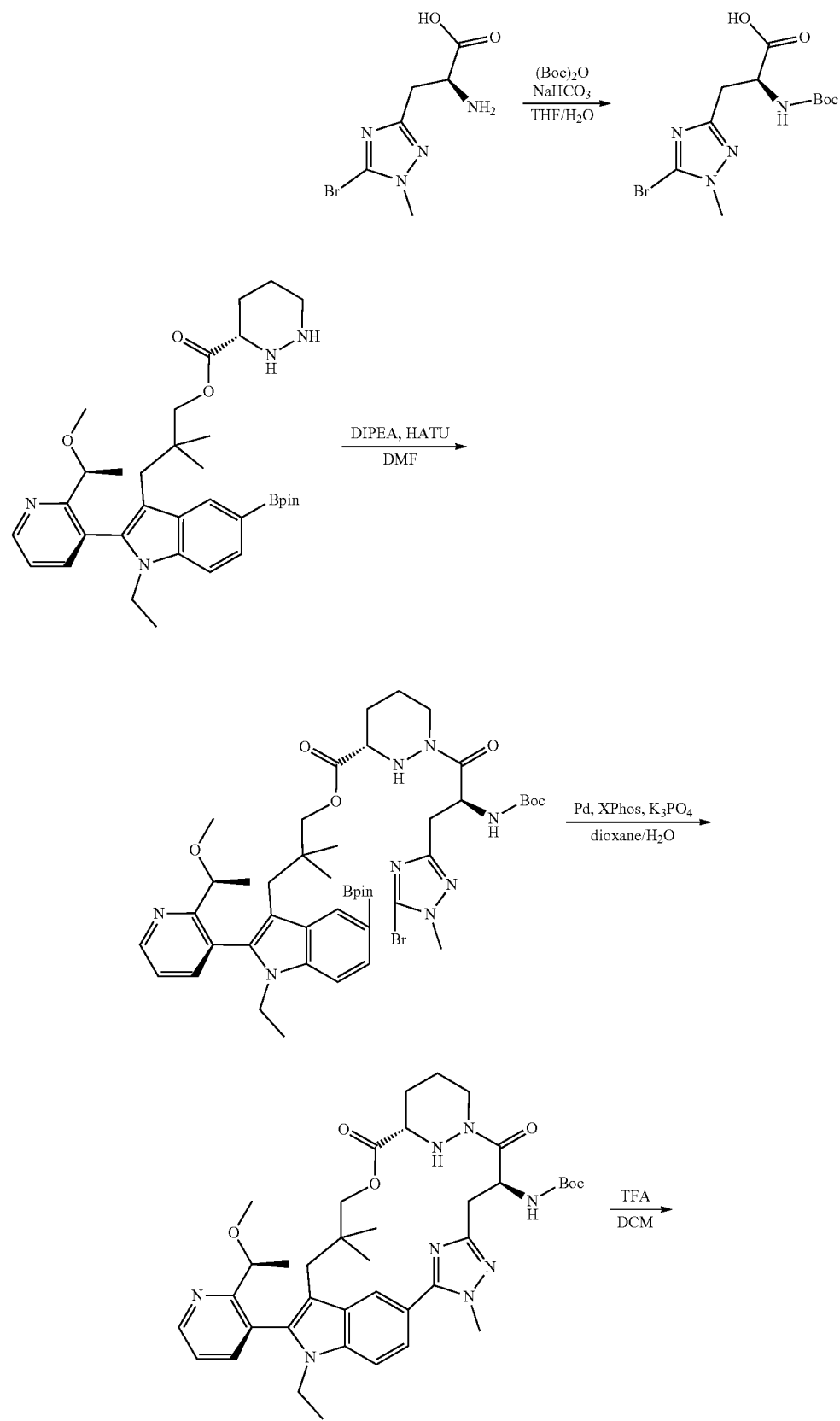

-continued
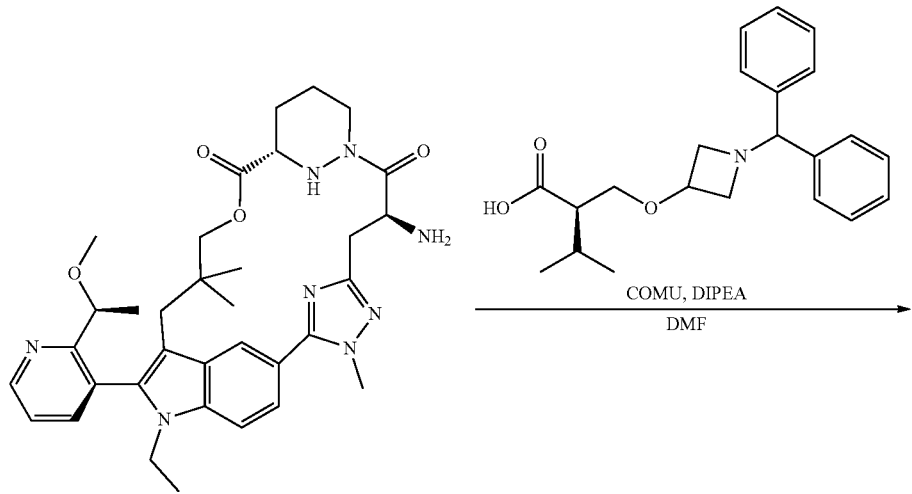
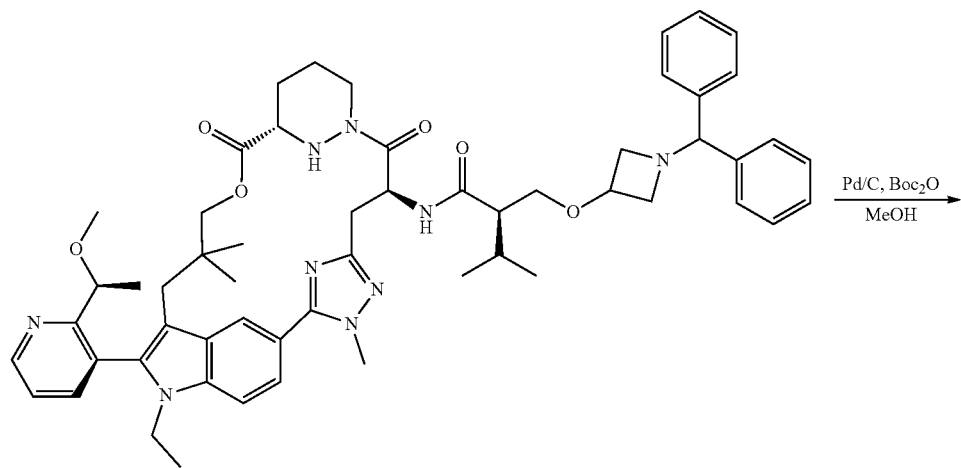
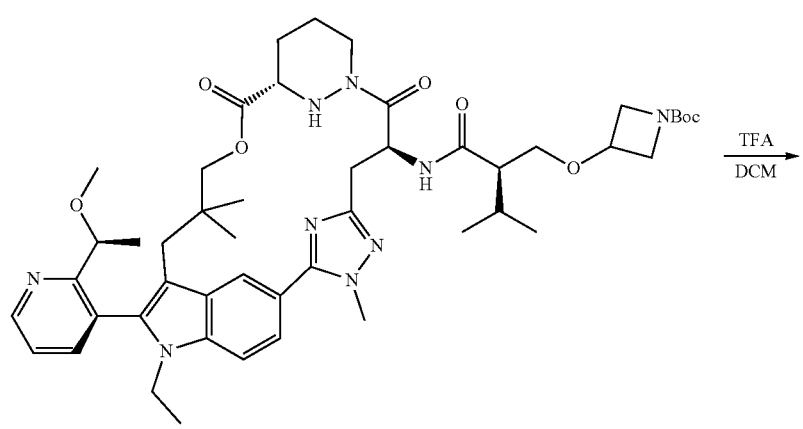

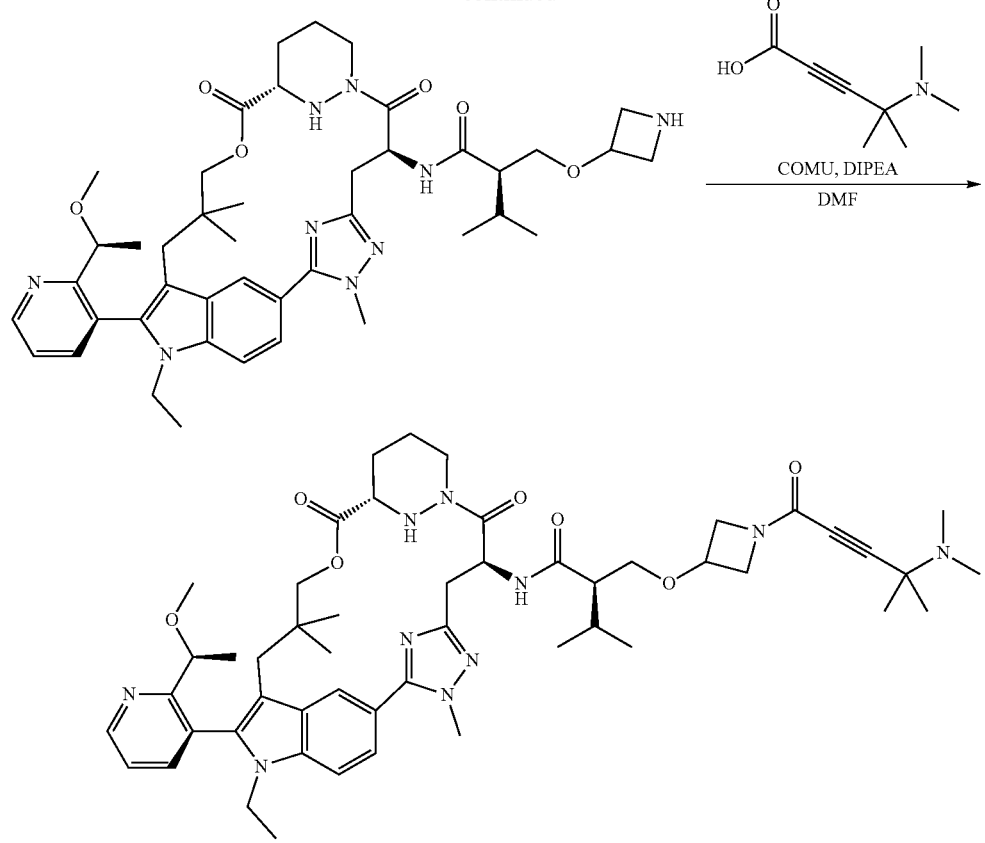

Step 1. To a stirred solution of methyl 1-methyl-1,2,4-triazole-3-carboxylate (7.0 g, 49.60 mmol) in CCl$_4$ (70. mL) was added NBS (13.24 g, 74.40 mmol) and AIBN (11.40 g, 69.44 mmol) in portions at 25° C. under an argon atmosphere. The resulting mixture was stirred for 24 h at 80° C. The resulting mixture was filtered, the filtrate was cooled to 20° C. and kept at 20° C. for 30 min. The resulting mixture was filtered. The filter cake was washed with H$_2$O (3×50 mL) and pet. ether (3×100 mL). The filter cake was dried under reduced pressure. This resulted in methyl 5-bromo-1-methyl-1,2,4-triazole-3-carboxylate (10 g, crude) as a light yellow solid. LCMS (ESI): m/z [M+H] calc'd for C$_5$H$_6$BrN$_3$O$_2$ 219.0; found 219.9.

Step 2. To a stirred solution of methyl 5-bromo-1-methyl-1,2,4-triazole-3-carboxylate (10.0 g, 45.50 mmol) in MeOH (150.0 mL) and H$_2$O (30.0 mL) was added NaBH$_4$ (6.88 g, 181.80 mmol) in portions at −5° C. under a nitrogen atmosphere. The resulting mixture was stirred for 2 h at 0-10° C. Desired product could be detected by LCMS. The reaction was quenched with brine (100 mL) at 0° C. The resulting mixture was extracted with pet. ether (100 mL). The aqueous layer was separated and filtered. The filter cake was washed with MeOH (2×50 mL). The filtrate was concentrated under reduced pressure to afford (5-bromo-1-methyl-1,2,4-triazol-3-yl)methanol (6 g, crude) as a light yellow solid. LCMS (ESI): m/z [M+H] calc'd for C$_4$H$_6$BrN$_3$O 191.98; found 192.0.

Step 3. A solution of (5-bromo-1-methyl-1,2,4-triazol-3-yl)methanol (6.0 g) and HBr in AcOH (144.0 mL) was stirred for overnight at 80° C. The mixture was neutralized to pH 9 with saturated NaHCO$_3$ (aq.). The resulting mixture was extracted with EtOAc (3×60 mL). The combined organic layers were washed with brine (3×100 mL), dried over anhydrous Na$_2$SO$_4$. After filtration, the filtrate was concentrated under reduced pressure. This resulted in 5-bromo-3-(bromomethyl)-1-methyl-1,2,4-triazole (6 g, crude) as a white solid. LCMS (ESI): m/z [M+H] calc'd for C$_4$H$_5$Br$_2$N$_3$ 253.89; found 253.8.

Step 4. To a stirred mixture of 5-bromo-3-(bromomethyl)-1-methyl-1,2,4-triazole (6.0 g, 23.54 mmol) and tert-butyl 2-[(diphenylmethylidene)amino]acetate (6.95 g, 23.54 mmol) in toluene (42 mL) and DCM (18.0 mL) was added (2R,4R,5S)-1-(anthracen-9-ylmethyl)-5-ethenyl-2-[(S)-(prop-2-en-1-yloxy)(quinolin-4-yl)methyl]-1-azabicyclo[2.2.2]octan-1-ium bromide (1.43 g, 2.35 mmol) in portions at 0° C. under argon atmosphere. The resulting mixture was stirred and KOH (60 mL) in H$_2$O was added. The resulting mixture was stirred for 24 h at −10° C. under an argon atmosphere. Desired product could be detected by LCMS. The reaction was quenched with sat. NH$_4$Cl (aq.) at 0° C. The resulting mixture was extracted with EtOAc (3×100 mL). The combined organic layers were washed with brine (1×200 mL), dried over anhydrous Na$_2$SO$_4$. After filtration, the filtrate was concentrated under reduced pressure. The residue was purified by Prep-TLC to afford tert-butyl (2S)-3-(5-bromo-1-methyl-1,2,4-triazol-3-yl)-2-[(diphenylmethylidene)amino]propanoate (5 g, 38.6% yield) as a yellow oil. LCMS (ESI): m/z [M+H] calc'd for C$_{21}$H$_{21}$BrN$_4$O$_2$ 469.12; found 469.1.

Step 5. To a stirred solution of tert-butyl (2S)-3-(5-bromo-1-methyl-1,2,4-triazol-3-yl)-2-[(diphenylmethylidene)amino]propanoate (5.0 g, 10.65 mmol) in DCM (50.0 mL)

was added TFA (25.0 mL) dropwise at 0° C. under argon atmosphere. The resulting mixture was stirred for 16 h at room temperature under an argon atmosphere. The resulting mixture was concentrated under reduced pressure to afford (2S)-2-amino-3-(5-bromo-1-methyl-1,2,4-triazol-3-yl)propanoic acid (6 g, crude) as a brown oil. LCMS (ESI): m/z [M+H] calc'd for $C_6H_9BrN_4O_2$ 249.00; found 249.0.

Step 6. To a stirred solution of (2S)-2-amino-3-(5-bromo-1-methyl-1,2,4-triazol-3-yl)propanoic acid (6.0 g, 24.09 mmol) in THF (36.0 mL) was added $NaHCO_3$ (10.14 g, 120.69 mmol), $Boc_2O$ (7.89 g, 36.14 mmol) in portions at 0° C. under an argon atmosphere. The resulting mixture was stirred for 16 h at room temperature. Desired product could be detected by LCMS. The resulting mixture was concentrated under reduced pressure. The mixture was purified by reverse phase chromatography to afford (2S)-3-(5-bromo-1-methyl-1,2,4-triazol-3-yl)-2-[(tert-butoxycarbonyl)amino]propanoic acid (3 g, 33.9% yield) as a white solid. LCMS (ESI): m/z [M+H] calc'd for $C_1H_{17}BrN_4O_4$ 349.05; found 349.0.

Step 7. To a stirred solution of 2-[[(2M)-1-ethyl-2-[2-[(1 S)-1-methoxyethyl]pyridin-3-yl]-5-(4,4,5,5-tetramethyl-1,3,2-dioxaborolan-2-yl)indol-3-yl]methyl]-2-methylpropyl (3S)-1,2-diazinane-3-carboxylate (1.0 g, 1.65 mmol) in DMF (10.0 mL) was added DIPEA (4.28 g, 33.08 mmol), (2S)-3-(5-bromo-1-methyl-1,2,4-triazol-3-yl)-2-[(tert-butoxycarbonyl)amino]propanoic acid (0.69 g, 1.98 mmol) and HATU (0.75 g, 1.99 mmol) in portions at 0° C. The resulting mixture was stirred for 2 h at 20° C. under an argon atmosphere. Desired product could be detected by LCMS. The resulting mixture was quenched with $H_2O$ (100 mL) and extracted with EtOAc (3×30 mL). The combined organic layers were washed with brine (3×100 mL), dried over anhydrous $Na_2SO_4$. After filtration, the filtrate was concentrated under reduced pressure. The residue was purified by reverse phase chromatography to afford 2-[[(2M)-1-ethyl-2-[2-[(1 S)-1-methoxyethyl]pyridin-3-yl]-5-(4,4,5,5-tetramethyl-1,3,2-dioxaborolan-2-yl)indol-3-yl]methyl]-2-methylpropyl (3S)-1-[(2S)-3-(5-bromo-1-methyl-1,2,4-triazol-3-yl)-2-[(tert-butoxycarbonyl)amino]propanoyl]-1,2-diazinane-3-carboxylate (800 mg, 46.5% yield) as a light yellow solid. LCMS (ESI): m/z [M+H] calc'd for $C_{45}H_{64}BBrN_8O_8$ 935.42; found 935.2.

Step 8. To a stirred solution of 2-[[(2M)-1-ethyl-2-[2-[(1 S)-1-methoxyethyl]pyridin-3-yl]-5-(4,4,5,5-tetramethyl-1,3,2-dioxaborolan-2-yl)indol-3-yl]methyl]-2-methylpropyl (3S)-1-[(2S)-3-(5-bromo-1-methyl-1,2,4-triazol-3-yl)-2-[(tert-butoxycarbonyl)amino]propanoyl]-1,2-diazinane-3-carboxylate (800.0 mg, 0.86 mmol) in dioxane (10.0 mL) were added $K_3PO_4$ (0.45 g, 2.12 mmol), XPhos (122.26 mg, 0.27 mmol), XPhos Pd G3 (0.22 g, 0.27 mmol) and $H_2O$ (2.0 mL) at room temperature. The resulting mixture was stirred for 3 h at 75° C. under an argon atmosphere. Desired product could be detected by LCMS. The resulting mixture was extracted with EtOAc (3×100 mL). The combined organic layers were washed with brine (3×60 mL), dried over anhydrous $Na_2SO_4$. After filtration, the filtrate was concentrated under reduced pressure. The residue was purified by reverse phase chromatography to afford tert-butyl ((6$^3$S,4S,Z)-1$^1$-ethyl-12-(2-((S)-1-methoxyethyl)pyridin-3-yl)-2$^1$,10,10-trimethyl-5,7-dioxo-6$^1$, 6$^2$,6$^3$,6$^4$,6$^5$,6$^6$-hexahydro-11H,2'H-8-oxa-1(5,3)-indola-6(1,3)-pyridazina-2(5,3)-triazolacycloundecaphane-4-yl)carbamate (400 mg, 56.8% yield) as a light yellow solid. LCMS (ESI): m/z [M+H] calc'd for $C_{39}H_{52}N_8O_6$ 729.41; found 729.3.

Step 9. To a solution of tert-butyl ((6$^3$S,4S,Z)-1$^1$-ethyl-1$^2$-(2-((S)-1-methoxyethyl)pyridin-3-yl)-2$^1$,10,10-trimethyl-5,7-dioxo-6$^1$,6$^2$,6$^3$,6$^4$,6$^5$,6$^6$-hexahydro-1$^1$H,2$^1$H-8-oxa-1(5,3)-indola-6(1,3)-pyridazina-2(5,3)-triazolacycloundecaphane-4-yl)carbamate (400.0 mg, 0.56 mmol) in DCM (1 mL) was added TFA (0.5 mL). The reaction was stirred for 1 h at room temperature under an argon atmosphere. After concentration, the mixture was neutralized to pH 8 with saturated $NaHCO_3$ (aq., 20 mL). The mixture was extracted with DCM (3×20 mL). The organic layers were dried over $Na_2SO_4$ and concentrated to afford (6$^3$S,4S,2)-4-amino-1$^1$-ethyl-1$^2$-(2-((S)-1-methoxyethyl)pyridin-3-yl)-2$^1$,10,10-trimethyl-6$^1$,6$^2$,6$^3$,6$^4$,6$^5$,6$^6$-hexahydro-1$^1$H,2$^1$H-8-oxa-1(5,3)-indola-6(1,3)-pyridazina-2(5,3)-triazolacycloundecaphane-5,7-dione (500 mg, crude) as a light yellow solid. ESI-MS m/z=629.3 [M+H]$^+$; Calculated MW:628.3. LCMS (ESI): m/z [M+H] calc'd for $C_{34}H_{44}N_8O_4$ 629.36; found 629.3.

Step 10. To a stirred solution of (6$^3$S,4S,2)-4-amino-1$^1$-ethyl-1$^2$-(2-((S)-1-methoxyethyl)pyridin-3-yl)-2$^1$,10,10-trimethyl-6$^1$,6$^2$,6$^3$,6$^4$,6$^5$,6$^6$-hexahydro-1$^1$H,2$^1$H-8-oxa-1(5,3)-indola-6(1,3)-pyridazina-2(5,3)-triazolacycloundecaphane-5,7-dione (170.0 mg, 0.27 mmol) and (R)-2-(((1-benzhydrylazetidin-3-yl)oxy)methyl)-3-methylbutanoic acid (114.68 mg, 0.32 mmol) in DMF (5 mL) were added DIPEA (698.86 mg, 5.41 mmol) and HATU (123.36 mg, 0.32 mmol) dropwise at 0° C. under an air atmosphere. The resulting mixture was stirred for 2 h at 0° C. The resulting mixture was diluted with 25 mL $H_2O$. The resulting mixture was extracted with EtOAc (3×25 mL). The combined organic layers were washed with brine (3×25 mL), dried over anhydrous $Na_2SO_4$. After filtration, the filtrate was concentrated under reduced pressure to afford (2R)-2-(((1-benzhydrylazetidin-3-yl)oxy)methyl)-N-((6$^3$S,4S,2)-1$^1$-ethyl-1$^2$-(2-((S)-1-methoxyethyl)pyridin-3-yl)-2$^1$,10,10-trimethyl-5,7-dioxo-6$^1$,6$^2$,6$^3$,6$^4$,6$^5$,6$^6$-hexahydro-1'H,2'H-8-oxa-1(5,3)-indola-6(1,3)-pyridazina-2(5,3)-triazolacycloundecaphane-4-yl)-3-methylbutanamide (180 mg, crude) as an off-white oil. LCMS (ESI): m/z [M+H] calc'd for $C_{56}H_{69}N_9O_6$ 964.54; found 964.4.

Step 11. To a stirred solution of (2R)-2-(((1-benzhydrylazetidin-3-yl)oxy)methyl)-N-((6$^3$S,4S,2)-1$^1$-ethyl-1$^2$-(2-((S)-1-methoxyethyl)pyridin-3-yl)-2$^1$,10,10-trimethyl-5,7-dioxo-6$^1$,6$^2$,6$^3$,6$^4$,6$^5$,6$^6$-hexahydro-1$^1$H,2'H-8-oxa-1(5,3)-indola-6(1,3)-pyridazina-2(5,3)-triazolacycloundecaphane-4-yl)-3-methylbutanamide (180.0 mg, 0.19 mmol) and Pd/C (90.0 mg, 0.85 mmol) in MeOH (10 mL) was added $Boc_2O$ (81.48 mg, 0.37 mmol) at room temperature under a hydrogen atmosphere. The resulting mixture was stirred overnight at room temperature. The resulting mixture was filtered, the filter cake was washed with MeOH (3×10 mL). The filtrate was concentrated under reduced pressure to afford tert-butyl 3-((2R)-2-(((6$^3$S,4S,2)-1$^1$-ethyl-1$^2$-(2-((S)-1-methoxyethyl)pyridin-3-yl)-2$^1$,10,10-trimethyl-5,7-dioxo-6$^1$,6$^2$,6$^3$,6$^4$,6$^5$, 6$^6$-hexahydro-1'H,2'H-8-oxa-1(5,3)-indola-6(1,3)-pyridazina-2(5,3)-triazolacycloundecaphane-4-yl)carbamoyl)-3-methylbutoxy)azetidine-1-carboxylate (80 mg, 47.7% yield) as an off-white solid. LCMS (ESI): m/z [M+H] calc'd for $C_{48}H_{67}N_9O_8$ 898.52; found 898.4.

Step 12. To a stirred solution of tert-butyl 3-((2R)-2-(((6$^3$S,4S,2)-1$^1$-ethyl-1$^2$-(2-((S)-1-methoxyethyl)pyridin-3-yl)-2$^1$,10,10-trimethyl-5,7-dioxo-6$^1$,6$^2$,6$^3$,6$^4$,6$^5$,6$^6$-hexahydro-1'H,2'H-8-oxa-1(5,3)-indola-6(1,3)-pyridazina-2(5,3)-triazolacycloundecaphane-4-yl)carbamoyl)-3-methylbutoxy)azetidine-1-carboxylate in DCM (2 mL) was added TFA (1.0 mL) dropwise at 0° C. under an air atmosphere. The resulting mixture was stirred for 1 h at 0° C. The resulting mixture was concentrated under reduced pressure to afford (2R)-2-((azetidin-3-yloxy)methyl)-N-((6$^3$S,4S,Z)-

1¹-ethyl-1²-(2-((S)-1-methoxyethyl)pyridin-3-yl)-2¹,10,10-trimethyl-5,7-dioxo-6¹,6²,6³,6⁴,6⁵,6⁶-hexahydro-1'H,2'H-8-oxa-1(5,3)-indola-6(1,3)-pyridazina-2(5,3)-triazolacycloundecaphane-4-yl)-3-methylbutanamide (85 mg, crude) as a yellow green oil.

Step 13. To a stirred solution of (2R)-2-((azetidin-3-yloxy)methyl)-N-((6³S,4S,2)-1¹-ethyl-1²-(2-((S)-1-methoxyethyl)pyridin-3-yl)-2¹,10,10-trimethyl-5,7-dioxo-6¹,6²,6³,6⁴,6⁵,6⁶-hexahydro-1'H,2'H-8-oxa-1(5,3)-indola-6(1,3)-pyridazina-2(5,3)-triazolacycloundecaphane-4-yl)-3-methylbutanamide (80.0 mg, 0.10 mmol) and 4-(dimethylamino)-4-methylpent-2-ynoic acid (38.90 mg, 0.25 mmol) in DMF (2 mL) were added DIPEA (518.27 mg, 4.01 mmol) and COMU (51.52 mg, 0.12 mmol) in portions at 0° C. The reaction mixture was stirred under an air atmosphere for 2 h. The crude product (150 mg) was purified by reverse phase chromatography to afford (2R)-2-(((1-(4-(dimethylamino)-4-methylpent-2-ynoyl)azetidin-3-yl)oxy)methyl)-N-((6³S,4S,Z)-1¹-ethyl-1²-(2-((S)-1-methoxyethyl)pyridin-3-yl)-2¹,10,10-trimethyl-5,7-dioxo-6¹,6²,6³,6⁴,6⁵,6⁶-hexahydro-1'H,2'H-8-oxa-1(5,3)-indola-6(1,3)-pyridazina-2(5,3)-triazolacycloundecaphane-4-yl)-3-methylbutanamide (15.3 mg, 16.3% yield) as an off-white solid. ¹H NMR (400 MHz, DMSO-d₆) δ 8.77 (dd, J=4.8, 1.7 Hz, 1H), 8.15 (d, J=1.7 Hz, 1H), 8.07 (d, J=8.1 Hz, 1H), 7.85-7.78 (m, 1H), 7.70 (d, J=8.6 Hz, 1H), 7.58-7.48 (m, 2H), 5.82 (s, 1H), 4.95 (d, J=11.7 Hz, 1H), 4.41-4.30 (m, 5H), 4.30 (d, J=8.2 Hz, 2H), 4.25 (d, J=5.6 Hz, 4H), 4.10 (td, J=17.1, 16.1, 9.1 Hz, 2H), 3.99-3.82 (m, 3H), 3.71-3.60 (m, 1H), 3.54-3.43 (m, 3H), 3.39 (s, 2H), 3.22 (d, J=1.6 Hz, 1H), 2.92 (d, J=13.6 Hz, 1H), 2.86-2.77 (m, 2H), 2.45 (s, 6H), 2.37 (q, J=7.7 Hz, 1H), 2.17 (d, J=6.6 Hz, 2H), 2.03 (d, J=10.2 Hz, 2H), 1.78-1.66 (m, 3H), 1.47 (t, J=10.9 Hz, 6H), 1.35-1.28 (m, 12H), 0.32 (s, 3H). LCMS (ESI): m/z [M+H] calc'd for $C_{51}H_{70}N_{10}O_7$ 935.55; found 935.3.

Example A692. Synthesis of (3S)-1-(4-(dimethylamino)-4-methylpent-2-ynoyl)-N-((2S)-1-(((6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(5,2)-oxazola-1(5,3)-indola-6(1,3)-pyridazinacycloundecaphane-4-yl)amino)-3-methyl-1-oxobutan-2-yl)-N-methylpyrrolidine-3-carboxamide

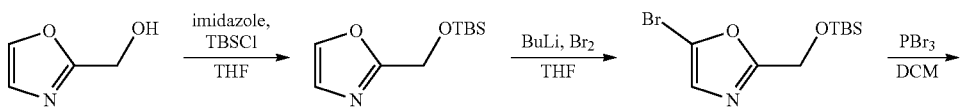

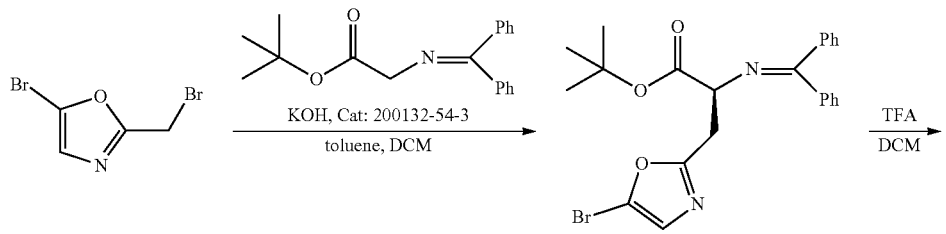

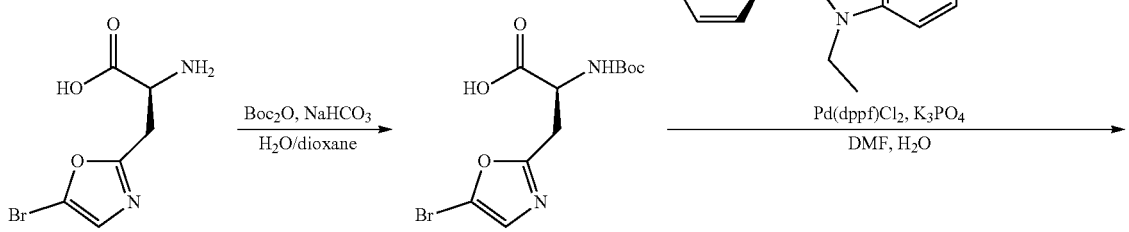

-continued
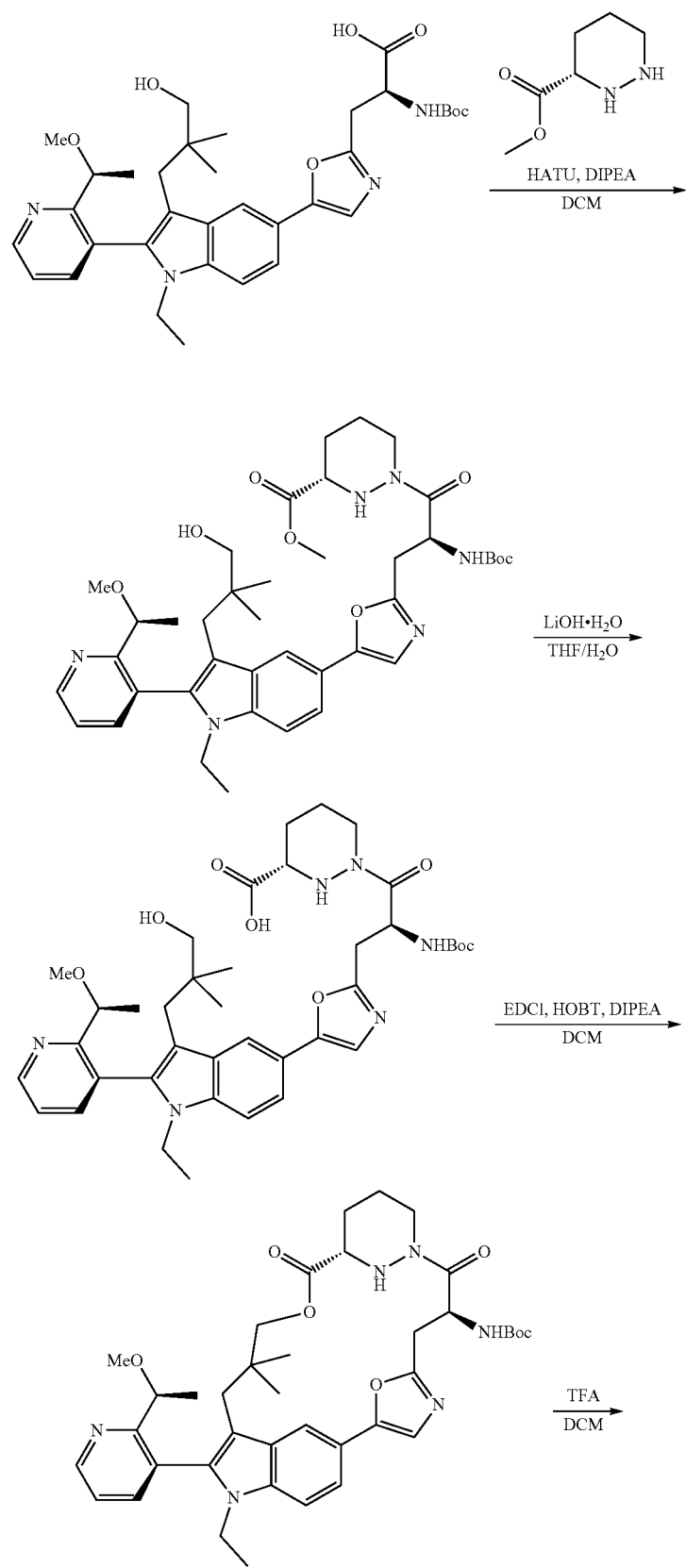

1089 1090
-continued
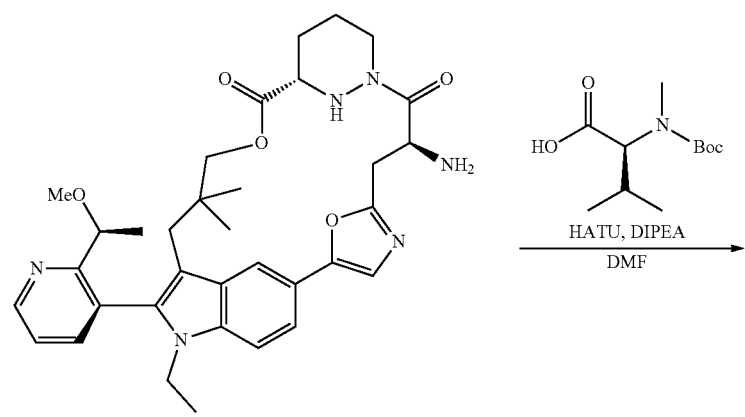
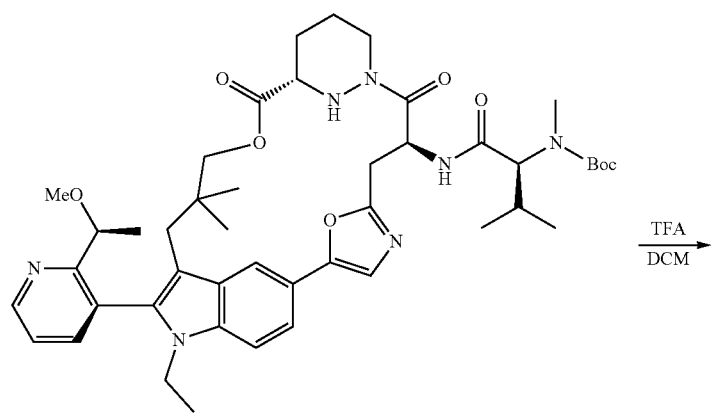
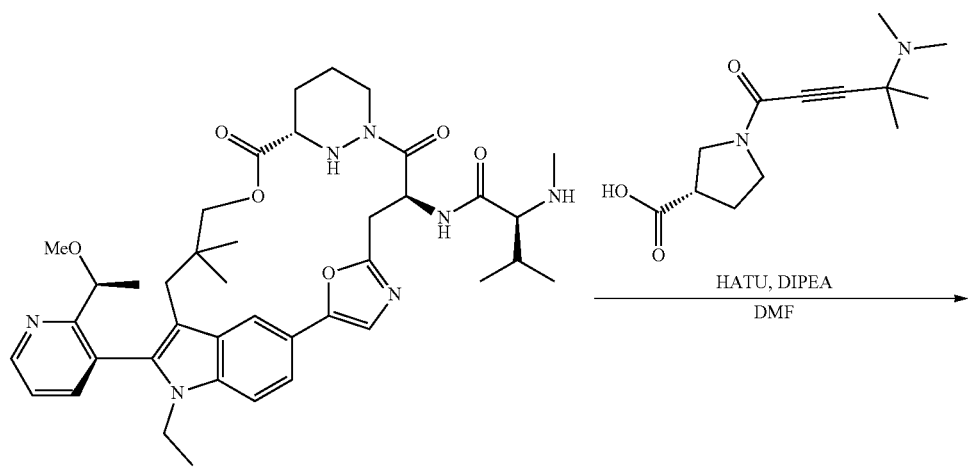

-continued

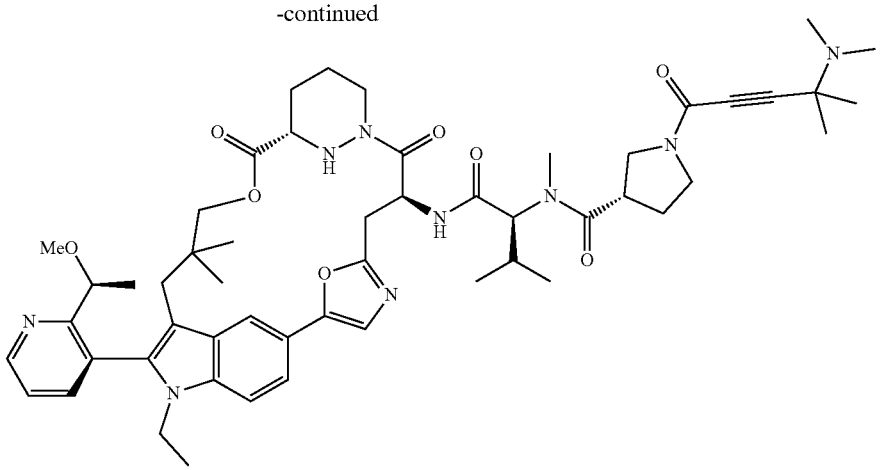

Step 1. To a solution of 1,3-oxazol-2-ylmethanol (5.0 g, 50.46 mmol) in THF (75 mL), were added imidazole (8.59 mg, 0.13 mmol), and TBSCl (11.41 mg, 0.08 mmol) at 0° C. The resulting solution was stirred for 5 h then concentrated under reduced pressure. The crude material was purified by silica gel column chromatography to afford 2-[[(tert-butyldimethylsilyl)oxy]methyl]-1,3-oxazole (10 g, 92.8% yield) as colorless oil. LCMS (ESI): m/z [M+H] calc'd for $C_{10}H_{19}NO_2Si$ 214.13; found 214.3.

Step 2. To a solution of 2-[[(tert-butyldimethylsilyl)oxy]methyl]-1,3-oxazole (10.0 g, 46.87 mmol) in THF (150.0 mL, 1851.45 mmol) at −78° C. was added n-BuLi (22.4 mL, 56.25 mmol) over 10 min and stirred for 30 min at −78° C. under an argon atmosphere. Then the solution of $Br_2$ (3.6 mL, 70.31 mmol) in THF (10 mL) was added over 10 min to the solution at −78° C. The resulting solution was slowly warmed to room temperature and stirred for 2 h. The resulting mixture was diluted with $NH_4Cl/H_2O$ (100 mL) and extracted with EtOAc (3×100 mL). The combined organic layers were dried over anhydrous $Na_2SO_4$. After filtration, the filtrate was concentrated under reduced pressure and purified by silica gel column chromatography to afford 5-bromo-2-[[(tert-butyldimethylsilyl)oxy]methyl]-1,3-oxazole (5.3 g, 38.6% yield) as yellow oil. LCMS (ESI): m/z [M+H] calc'd for $C_{10}H_{18}BrNO_2Si$ 292.04; found 292.0.

Step 3. To a solution of 5-bromo-2-[[(tert-butyldimethylsilyl)oxy]methyl]-1,3-oxazole (4.0 g, 13.69 mmol) in DCM (60.0 mL) was added $PBr_3$ (7.41 g, 27.37 mmol) at 0° C. under an argon atmosphere. The resulting solution was stirred for 4 h then diluted with $NaHCO_3/H_2O$ (30 mL). The mixture was extracted with EtOAc (3×40 mL). The organic layers were concentrated under reduced pressure and purified by silica gel column chromatography to afford 5-bromo-2-(bromomethyl)-1,3-oxazole (2.5 g, 75.7% yield) as yellow oil. LCMS (ESI): m/z [M+H] calc'd for $C_4H_3Br_2NO$ 239.87; found 241.9.

Step 4. A mixture of 5-bromo-2-(bromomethyl)-1,3-oxazole (9.0 g, 37.36 mmol), Cat:200132-54-3 (2.26 g, 3.74 mmol), DCM (45.0 mL), toluene (90.0 mL), KOH (20.96 g, 373.63 mmol), $H_2O$ (42 mL), and tert-butyl 2-[(diphenylmethylidene)amino]acetate (13.24 g, 44.82 mmol) at 0° C. was stirred for 4 h then diluted with $H_2O$ (30 mL). The mixture was extracted with DCM (3×40 mL). The organic layers were concentrated under reduced pressure and purified by reverse phase column chromatography to afford tert-butyl (2S)-3-(5-bromo-1,3-oxazol-2-yl)-2-[(diphenylmethylidene)amino]propanoate (4.8 g, 28.2% yield) as a yellow solid. LCMS (ESI): m/z [M+H] calc'd for $C_{23}H_{23}BrN_2O_3$ 455.10; found 457.1.

Step 5. A mixture of tert-butyl (2S)-3-(5-bromo-1,3-oxazol-2-yl)-2-[(diphenylmethylidene)amino]propanoate (1.20 g, 2.64 mmol), DCM (10.0 mL, 157.30 mmol), and TFA (5.0 mL, 67.32 mmol) at 0° C. was stirred for 2 h then concentrated under reduced pressure to afford (S)-3-(5-bromooxazol-2-yl)-2-((2,2,2-trifluoroacetyl)-14-azaneyl)propanoic acid (0.5 g, 81.3% yield) as a yellow solid. LCMS (ESI): m/z [M+H] calc'd for $C_6H_7BrN_2O_3$ 234.97; found 237.0.

Step 6. A mixture of (S)-3-(5-bromooxazol-2-yl)-2-((2,2,2-trifluoroacetyl)-14-azaneyl)propanoic acid (500.0 mg, 2.13 mmol), $Boc_2O$ (928.56 mg, 4.26 mmol), dioxane (2.50 mL), $H_2O$ (2.50 mL), and $NaHCO_3$ (714.84 mg, 8.51 mmol) at 0° C. was stirred for 3 h. The resulting solution was purified by reverse phase column chromatography to afford (2S)-3-(5-bromo-1,3-oxazol-2-yl)-2-[(tert-butoxycarbonyl)amino]propanoic acid (0.65 g, 91.1% yield) as a yellow solid. LCMS (ESI): m/z [M+H] calc'd for $C_{11}H_{15}BrN_2O_5$ 335.02; found 334.8.

Step 7. To a solution of (2S)-3-(5-bromo-1,3-oxazol-2-yl)-2-[(tert-butoxycarbonyl)amino]propanoic acid (500.0 mg, 1.49 mmol) and 3-[(2M)-1-ethyl-2-[2-[(1S)-1-methoxyethyl]pyridin-3-yl]-5-(4,4,5,5-tetramethyl-1,3,2-dioxaborolan-2-yl)indol-3-yl]-2,2-dimethylpropan-1-ol (808.16 mg, 1.64 mmol) in DMF (5.0 mL) and $H_2O$ (1.0 mL) were added $K_3PO_4$ (791.67 mg, 3.73 mmol) and Pd(dppf)$Cl_2$ (109.16 mg, 0.15 mmol). The resulting mixture was stirred for 2 h at 70° C. under an argon atmosphere. The mixture was purified by reverse phase column chromatography to afford (2S)-2-[(tert-butoxycarbonyl)amino]-3-[5-[(2M)-1-ethyl-3-(3-hydroxy-2,2-dimethylpropyl)-2-[2-[(1 S)-1-methoxyethyl]pyridin-3-yl]indol-5-yl]-1,3-oxazol-2-yl]propanoic acid (600 mg, 64.79% yield) as a light brown solid. LCMS (ESI): m/z [M+H] calc'd for $C_{34}H_{44}N_4O_7$ 621.33; found 621.3.

Step 8. To a stirred mixture of methyl (3S)-1,2-diazinane-3-carboxylate (627.10 mg, 4.350 mmol) and (2S)-2-[(tert-butoxycarbonyl)amino]-3-[5-[(2M)-1-ethyl-3-(3-hydroxy-2,2-dimethylpropyl)-2-[2-[(1S)-1-methoxyethyl]pyridin-3-yl]indol-5-yl]-1,3-oxazol-2-yl]propanoic acid (900.0 mg, 1.45 mmol) in DCM (10.0 mL) were added HATU (661.54 mg, 1.74 mmol) and DIPEA (3747.71 mg, 29.00 mmol) at 0° C. The resulting mixture was stirred for 2 h. Desired product could be detected by LCMS. The resulting mixture was concentrated under reduced pressure and the crude material was purified by silica gel column chromatography to afford methyl (3S)-1-[(2S)-2-[(tert-butoxycarbonyl)amino]-3-[5-[(2M)-1-ethyl-3-(3-hydroxy-2,2-dimethylpropyl)-2-[2-[(1 S)-1-methoxyethyl]pyridin-3-yl]indol-5-yl]-1,3-oxazol-2-yl]propanoyl]-1,2-diazinane-3-carboxylate (900 mg, 83.11%) as a brown yellow solid. LCMS (ESI): m/z [M+H] calc'd for $C_{40}H_{54}N_6O_8$ 747.41; found 747.2.

Step 9. To a stirred mixture of methyl (3S)-1-[(2S)-2-[(tert-butoxycarbonyl)amino]-3-[5-[(2M)-1-ethyl-3-(3-hydroxy-2,2-dimethylpropyl)-2-[2-[(1S)-1-methoxyethyl]pyridin-3-yl]indol-5-yl]-1,3-oxazol-2-yl]propanoyl]-1,2-diazinane-3-carboxylate (2000.0 mg, 2.68 mmol) in THF (18. mL) and $H_2O$ (6.0 mL) was added $LiOH \cdot H_2O$ (337.10 mg, 8.03 mmol) at 0° C. The resulting mixture was stirred for 2 h. Desired product could be detected by LCMS. The reaction was quenched with $H_2O$ at 0° C. and adjusted to pH 6 with 1 N HCl solution. The resulting mixture was extracted with EtOAc (3×50 mL). The combined organic layers were washed with brine (1×10 mL), dried over anhydrous $Na_2SO_4$. After filtration, the filtrate was concentrated under reduced pressure to afford (3S)-1-[(2S)-2-[(tert-butoxycarbonyl)amino]-3-[5-[(2M)-1-ethyl-3-(3-hydroxy-2,2-dimethylpropyl)-2-[2-[(1 S)-1-methoxyethyl]pyridin-3-yl]indol-5-yl]-1,3-oxazol-2-yl]propanoyl]-1,2-diazinane-3-carboxylic acid (1300 mg, 66.2% yield) as a yellow solid. LCMS (ESI): m/z [M+H] calc'd for $C_{39}H_{52}N_6O_8$ 733.39; found 733.3.

Step 10. To a stirred mixture of (3S)-1-[(2S)-2-[(tert-butoxycarbonyl)amino]-3-[5-[(2M)-1-ethyl-3-(3-hydroxy-2,2-dimethylpropyl)-2-[2-[(1 S)-1-methoxyethyl]pyridin-3-yl]indol-5-yl]-1,3-oxazol-2-yl]propanoyl]-1,2-diazinane-3-carboxylic acid (1.2 g, 1.64 mmol) and DIPEA (8.5 g, 65.50 mmol) in DCM (120.0 mL) were added HOBT (1.8 g, 13.10 mmol) and EDCl (7.8 g, 40.93 mmol) at 0° C. The resulting mixture was stirred for 2 h. Desired product could be detected by LCMS. The mixture was concentrated under reduced pressure and purified by silica gel column chromatography to afford tert-butyl (($6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(5,2)-oxazola-1(5,3)-indola-6(1,3)-pyridazinacycloundecaphane-4-yl)carbamate (660 mg, 56.4% yield) as a brown yellow solid. LCMS (ESI): m/z [M+H] calc'd for $C_{39}H_{50}N_6O_7$ 715.38; found 715.3.

Step 11. A mixture of tert-butyl (($6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(5,2)-oxazola-1(5,3)-indola-6(1,3)-pyridazinacycloundecaphane-4-yl)carbamate (20.0 mg, 0.028 mmol) and TFA (3.0 mL) in DCM (6.0 mL) at 0° C. was stirred for 2 h. Desired product could be detected by LCMS. The resulting mixture was concentrated under reduced pressure to afford ($6^3$S,4S)-4-amino-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(5,2)-oxazola-1(5,3)-indola-6(1,3)-pyridazinacycloundecaphane-5,7-dione (160 mg, crude) as a yellow green solid. LCMS (ESI): m/z [M+H] calc'd for $C_{34}H_{42}N_6O_5$ 615.33; found 615.2.

Step 12. To a stirred mixture of ($6^3$S,4S)-4-amino-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(5,2)-oxazola-1(5,3)-indola-6(1,3)-pyridazinacycloundecaphane-5,7-dione (180.0 mg, 0.293 mmol) and (2S)-2-[(tert-butoxycarbonyl)(methyl)amino]-3-methylbutanoic acid (135.45 mg, 0.59 mmol) in DMF (2.0 mL) were added HATU (133.60 mg, 0.35 mmol) and DIPEA (756.86 mg, 5.86 mmol) at 0° C. The resulting mixture was stirred for 2 h. Desired product could be detected by LCMS. The mixture was purified by reverse phase column chromatography to afford tert-butyl ((2S)-1-((($6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(5,2)-oxazola-1(5,3)-indola-6(1,3)-pyridazinacycloundecaphane-4-yl)amino)-3-methyl-1-oxobutan-2-yl)(methyl)carbamate (160 mg, 66% yield) as a brown yellow solid. LCMS (ESI): m/z [M+H] calc'd for $C_{45}H_{61}N_7O_8$ 828.47; found 828.4.

Step 13. To a stirred mixture of tert-butyl ((2S)-1-((($6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(5,2)-oxazola-1(5,3)-indola-6(1,3)-pyridazinacycloundecaphane-4-yl)amino)-3-methyl-1-oxobutan-2-yl)(methyl)carbamate (160.0 mg, 0.19 mmol) in DCM (2.0 mL) was added TFA (1.0 mL) at 0° C. The resulting mixture was stirred for 2 h. Desired product could be detected by LCMS. The resulting mixture was concentrated under reduced pressure to afford (2S)—N-(($6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(5,2)-oxazola-1(5,3)-indola-6(1,3)-pyridazinacycloundecaphane-4-yl)-3-methyl-2-(methylamino)butanamide (130 mg, crude) as a yellow solid. LCMS (ESI): m/z [M+H] calc'd for $C_{40}H_{53}N_7O_6$ 728.41; found 728.5.

Step 14. To a stirred mixture of ((2S)—N-(($6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(5,2)-oxazola-1(5,3)-indola-6(1,3)-pyridazinacycloundecaphane-4-yl)-3-methyl-2-(methylamino)butanamide (130.0 mg, 0.18 mmol) and (3S)-1-[4-(dimethylamino)-4-methylpent-2-ynoyl]pyrrolidine-3-carboxylic acid (180.25 mg, 0.72 mmol) in DMF (2.0 mL) were added DIPEA (461.64 mg, 3.57 mmol) and HATU (135.81 mg, 0.36 mmol) at 0° C. The resulting mixture was stirred for 2 h. Desired product could be detected by LCMS. The mixture was purified by reverse phase column chromatography to afford (3S)-1-(4-(dimethylamino)-4-methylpent-2-ynoyl)-N-((2S)-1-((($6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(5,2)-oxazola-1(5,3)-indola-6(1,3)-pyridazinacycloundecaphane-4-yl)amino)-3-methyl-1-oxobutan-2-yl)-N-methylpyrrolidine-3-carboxamide (55.3 mg, 31.3% yield) as a solid. $^1$H NMR (400 MHz, DMSO-$d_6$) δ 8.77 (dd, J=4.8, 1.7 Hz, 1H), 8.09-8.00 (m, 1H), 7.92 (s, 1H), 7.88-7.80 (m, 1H), 7.62 (d, J=8.7 Hz, 1H), 7.59-7.49 (m, 2H), 7.39-7.30 (m, 1H), 5.69 (p, J=8.8 Hz, 1H), 5.44 (d, J=12.1 Hz, 1H), 4.67 (d, J=10.7 Hz, 1H), 4.30-4.15 (m, 3H), 3.99 (dt, J=13.2, 6.4 Hz, 3H), 3.89-3.79 (m, 1H), 3.62 (ddd, J=30.5, 18.6, 11.4 Hz, 5H), 3.39 (dd, J=9.4, 3.8 Hz, 2H), 3.21-3.13 (m, 1H), 3.08 (d, J=15.0 Hz, 3H), 2.99-2.74 (m, 6H), 2.26-2.18 (m, 5H), 2.16 (s, 2H), 2.14-1.94 (m, 3H), 1.86-1.68 (m, 2H), 1.57 (q, J=9.2, 5.8 Hz, 1H), 1.44-1.27 (m, 9H), 0.94 (d, J=6.6 Hz, 4H), 0.89 (dd, J=6.5, 2.5 Hz, 2H), 0.80 (d, J=6.3 Hz, 2H), 0.77-0.69 (m, 4H), 0.58 (d, J=20.4 Hz, 3H). LCMS (ESI): m/z [M+H] calc'd for $C_{53}H_{71}N_9O_8$ 962.55; found 962.5.

Example A675. Synthesis of (2R)-2-(((1-(4-(dimethylamino)-4-methylpent-2-ynoyl)azetidin-3-yl)oxy)methyl)-N-((6³S,4S,Z)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(2,4)-oxazola-1(5,3)-indola-6(1,3)-pyridazinacycloundecaphane-4-yl)-3-methylbutanamide
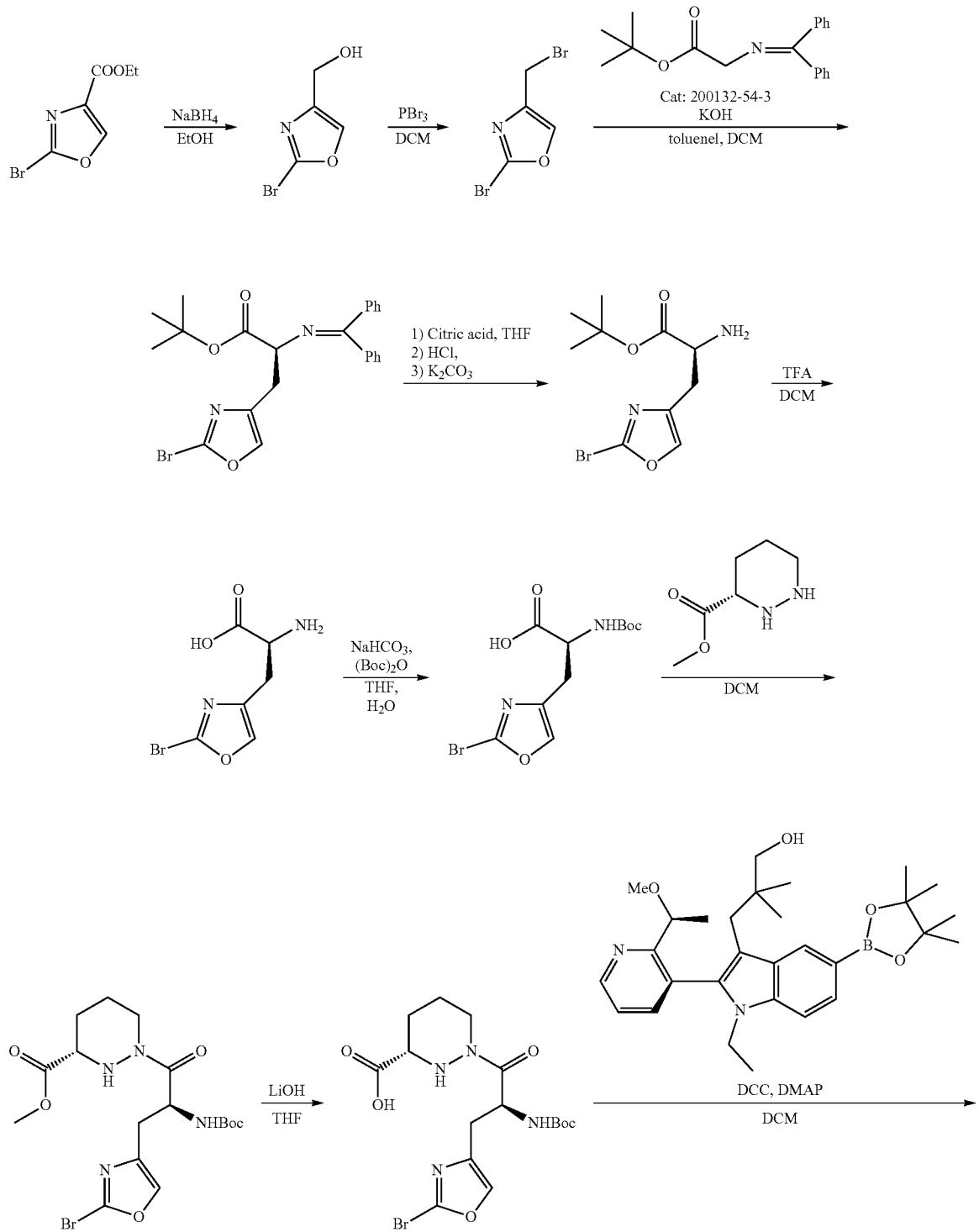

-continued
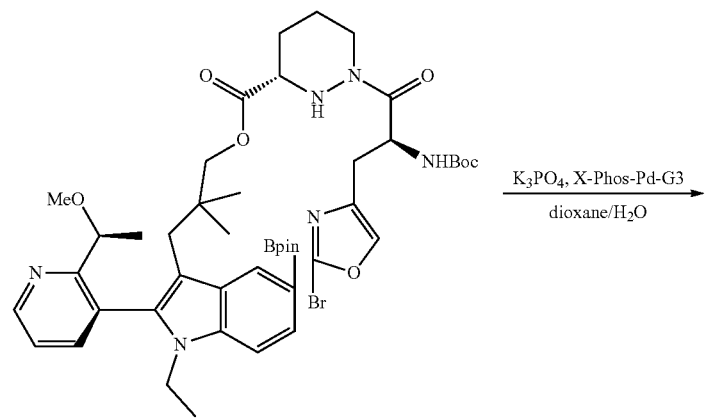
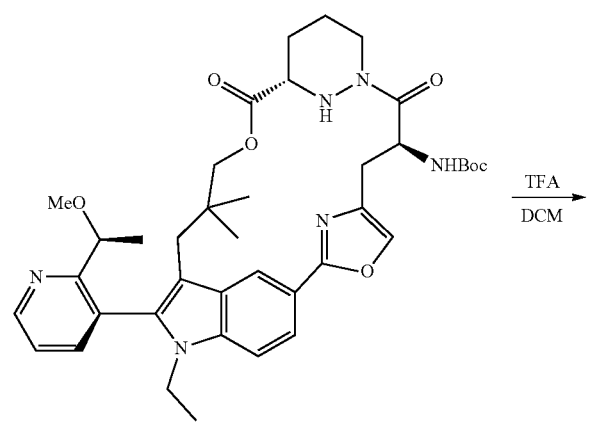
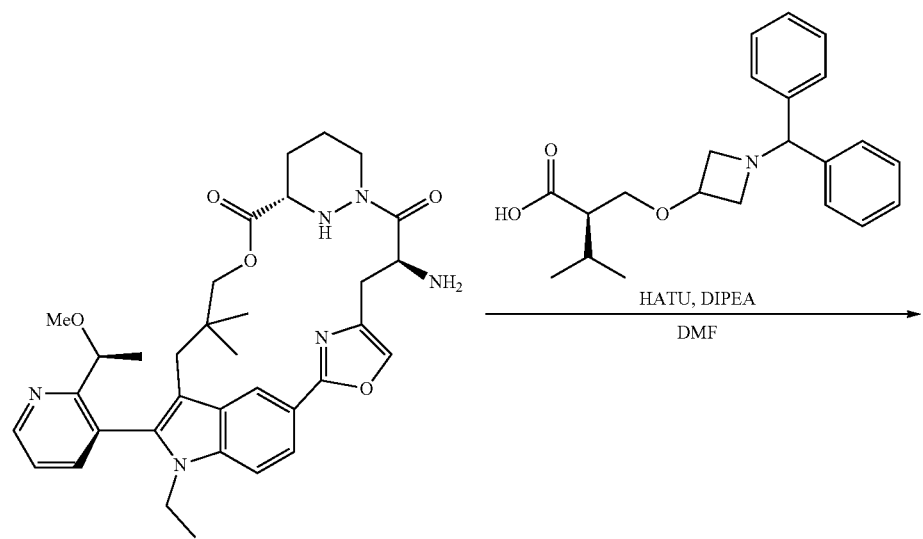

1099
-continued
1100
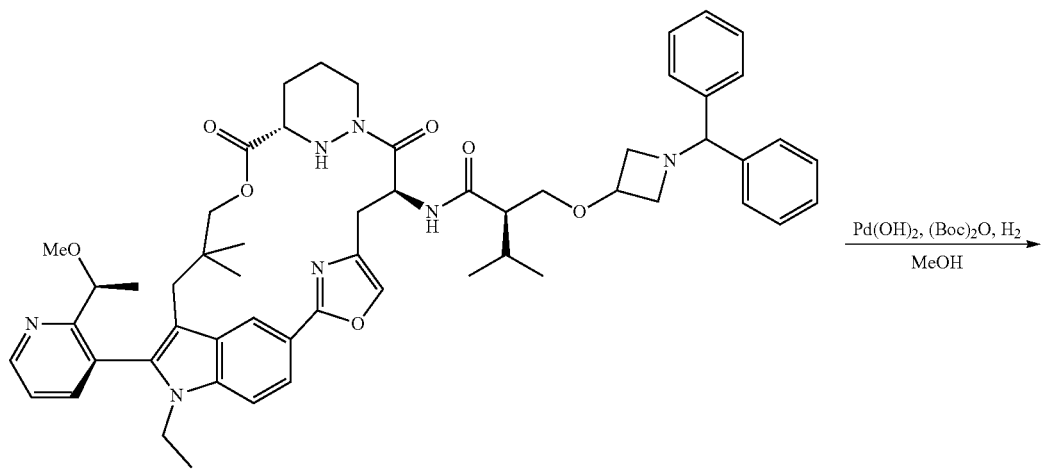
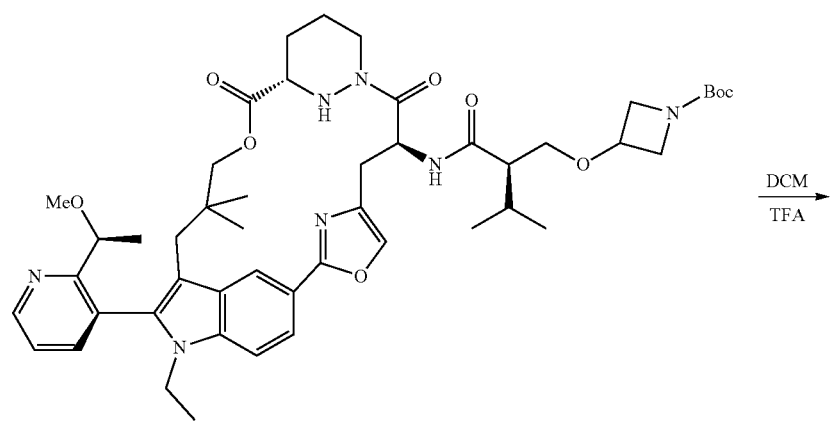
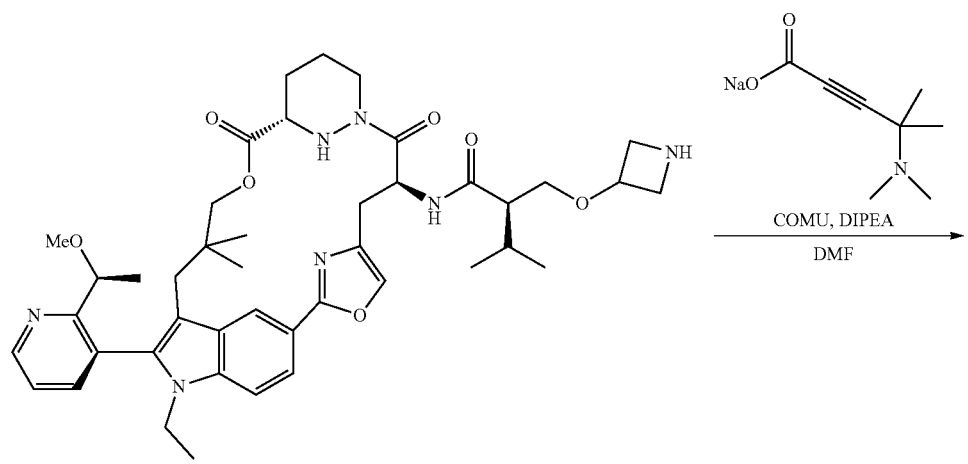

-continued

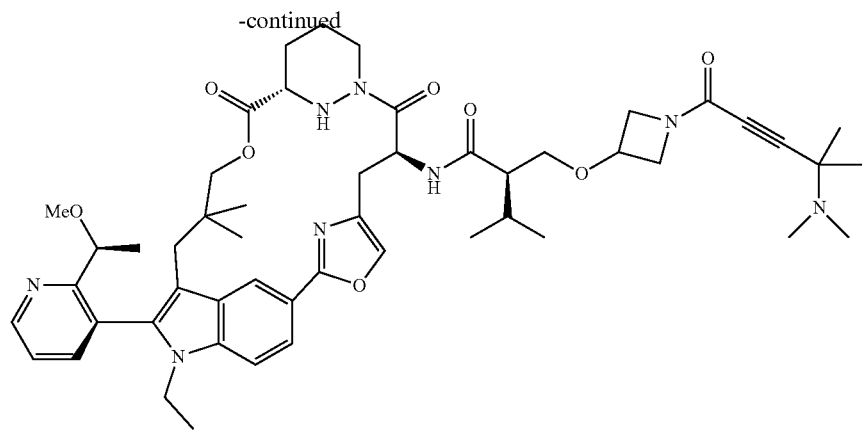

Step 1. A mixture of 2-bromo-4-(ethoxycarbonyl)-1,3-oxazol-5-ylium (6.83 g, −0.19 mmol), EtOH (100.0 mL) and NaBH$_4$ (4.72 g, 124.76 mmol) at 0° C. was stirred for 6 h at 0° C. under an air atmosphere. The reaction was quenched with H$_2$O at 0° C. The resulting mixture was extracted with EtOAc (3×100 mL). The combined organic layers were dried over anhydrous Na$_2$SO$_4$. After filtration, the filtrate was concentrated under reduced pressure to afford (2-bromo-1,3-oxazol-4-yl)methanol (4.122 g, 74.3% yield) as a solid. LCMS (ESI): m/z [M+H] calc'd for C$_4$H$_4$BrNO$_2$ 177.95; found 178.0.

Step 2. A mixture of (2-bromo-1,3-oxazol-4-yl)methanol (4.30 g, 24.16 mmol), DCM (50 mL) and phosphorus tribromide (9809.39 mg, 36.24 mmol) at 0° C. was stirred overnight at 0° C. under an air atmosphere. The reaction was quenched by the addition of NaHCO$_3$ (aq.) at 0° C. The resulting mixture was extracted with EtOAc (3×100 mL). The combined organic layers were dried over anhydrous Na$_2$SO$_4$. After filtration, the filtrate was concentrated under reduced pressure to afford 2-bromo-4-(bromomethyl)-1,3-oxazole (3.28 g, 56.4% yield) as a liquid. LCMS (ESI): m/z [M+H] calc'd for C$_4$H$_3$Br$_2$NO 239.87; found 239.9.

Step 3. A mixture of 2-bromo-4-(bromomethyl)-1,3-oxazole (3280.0 mg, 13.62 mmol), KOH (9M, 10 mL), 30 mL mixture of toluene/DCM (7/3) and tert-butyl 2-[(diphenylmethylidene)amino]acetate (5228.74 mg, 17.70 mmol) at −16° C. was stirred overnight under an air atmosphere. The resulting mixture was extracted with EtOAc (3×50 mL). The combined organic layers were dried over anhydrous Na$_2$SO$_4$. After filtration, the filtrate was concentrated under reduced pressure to afford tert-butyl (2S)-3-(2-bromo-1,3-oxazol-4-yl)-2-[(diphenylmethylidene)amino]propanoate (8.33 g, 80.6% yield) as a solid. LCMS (ESI): m/z [M+H] calc'd for C$_{23}$H$_{23}$BrN$_2$O$_3$ 455.10; found 455.1.

Step 4. A mixture of tert-butyl (2S)-3-(2-bromo-1,3-oxazol-4-yl)-2-[(diphenylmethylidene)amino]propanoate (4100.0 mg, 9.0 mmol) and citric acid (1 N) (40.0 mL, 0.21 mmol), in THF (40 mL) at room temperature was stirred overnight under an air atmosphere. The reaction was quenched by the addition of HCl (aq.) (100 mL) at 0° C. The aqueous layer was extracted with EtOAc (3×100 mL). K$_2$CO$_3$ (aq.) (200 mL) was added to the resulting mixture and extracted with EtOAc (3×100 mL). The organic layer was concentrated under reduced pressure to afford tert-butyl (2S)-2-amino-3-(2-bromo-1,3-oxazol-4-yl)propanoate (1730 mg, 66% yield) as a dark yellow solid. LCMS (ESI): m/z [M+H] calc'd for C$_{10}$H$_{15}$BrN$_2$O$_3$ 291.03; found 291.0.

Step 5. A mixture of tert-butyl (2S)-2-amino-3-(2-bromo-1,3-oxazol-4-yl)propanoate (1780.0 mg, 6.11 mmol), TFA (10.0 mL) and DCM (10.0 mL) at 0° C. was stirred overnight under an air atmosphere. The resulting mixture was concentrated under reduced pressure to afford (2S)-2-amino-3-(2-bromo-1,3-oxazol-4-yl)propanoic acid (1250 mg, 87% yield) as a dark yellow solid. LCMS (ESI): m/z [M+H] calc'd for C$_6$H$_7$BrN$_2$O$_3$ 234.97; found 234.9.

Step 6. A mixture of di-tert-butyl dicarbonate (4178.58 mg, 19.15 mmol), THF (10 mL), H$_2$O (10 mL), (2S)-2-amino-3-(2-bromo-1,3-oxazol-4-yl)propanoic acid (1500.0 mg, 6.38 mmol) and NaHCO$_3$ (3216.74 mg, 38.29 mmol) at room temperature was stirred overnight under an air atmosphere. The reaction was quenched with H$_2$O at room temperature. The resulting mixture was concentrated under reduced pressure. The resulting mixture was extracted with EtOAc (3×100 mL). The aqueous layer was acidified to pH 6 with 1M HCl (aq.). The resulting mixture was extracted with EtOAc (3×100 mL). The combined organic layers were dried over anhydrous Na$_2$SO$_4$. After filtration, the filtrate was concentrated under reduced pressure to afford (2S)-3-(2-bromo-1,3-oxazol-4-yl)-2-[(tert-butoxycarbonyl)amino]propanoic acid (920 mg, 43.0% yield) as an oil. LCMS (ESI): m/z [M+H] calc'd for C$_{11}$H$_{15}$BrN$_2$O$_5$ 335.02; found 335.0.

Step 7. A mixture of 3-(2-bromo-1,3-oxazol-4-yl)-2-[(tert-butoxycarbonyl)amino]propanoic acid (850.0 mg, 2.54 mmol), methyl 1,2-diazinane-3-carboxylate (1.88 g, 13.04 mmol), DIPEA (1966.68 mg, 15.22 mmol), DCM (30.0 mL) and HATU (1446.48 mg, 3.80 mmol) at 0° C. was stirred for 3 h under an air atmosphere. The resulting mixture was extracted with DCM (3×50 mL). The combined organic layers were dried over anhydrous Na$_2$SO$_4$. After filtration, the filtrate was concentrated under reduced pressure. The resulting mixture was purified by reverse flash chromatography to afford methyl 1-[3-(2-bromo-1,3-oxazol-4-yl)-2-[(tert-butoxycarbonyl)amino]propanoyl]-1,2-diazinane-3-carboxylate (610 mg, 52.1% yield) as a solid. LCMS (ESI): m/z [M+H] calc'd for C$_{17}$H$_{25}$BrN$_4$O 461.10; found 461.0.

Step 8. A mixture of methyl 1-[3-(2-bromo-1,3-oxazol-4-yl)-2-[(tert-butoxycarbonyl)amino]propanoyl]-1,2-diazinane-3-carboxylate (570.0 mg, 1.24 mmol), LiOH (2.0 mL, 1 M aq.) and THF (2.0 mL) at 0° C. was stirred for 3 h under an air atmosphere. The resulting mixture was concentrated under reduced pressure. The resulting mixture was extracted with EtOAc (3×50 mL). The combined aqueous layers were acidified to pH 5 with 1 N HCl (aq.). The aqueous phase was extracted with EtOAc (3×50 mL). The combined organic layers were dried over anhydrous $Na_2SO_4$. After filtration, the filtrate was concentrated under reduced pressure to afford 1-[3-(2-bromo-1,3-oxazol-4-yl)-2-[(tert-butoxycarbonyl)amino]propanoyl]-1,2-diazinane-3-carboxylic acid (500 mg, 90.5% yield) as a solid. LCMS (ESI): m/z [M+H] calc'd for $C_{16}H_{23}BrN_4O$ 447.09; found 446.8.

Step 9. A mixture of 1-[3-(2-bromo-1,3-oxazol-4-yl)-2-[(tert-butoxycarbonyl)amino]propanoyl]-1,2-diazinane-3-carboxylic acid (450.0 mg, 1.01 mmol), 3-[(2M)-1-ethyl-2-[2-[(1S)-1-methoxyethyl]pyridin-3-yl]-5-(4,4,5,5-tetramethyl-1,3,2-dioxaborolan-2-yl)indol-3-yl]-2,2-dimethylpropan-1-ol (743.19 mg, 1.51 mmol), DMAP (24.58 mg, 0.20 mmol), DCM (15.0 mL) and DCC (311.37 mg, 1.51 mmol) at 0° C. was stirred for 3 h under an air atmosphere. The resulting mixture was extracted with EtOAc (3×20 mL). The combined organic layers were dried over anhydrous $Na_2SO_4$. After filtration, the filtrate was concentrated under reduced pressure. The residue was purified by Prep-TLC to afford 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl(S)-1-((S)-3-(2-bromooxazol-4-yl)-2-((tert-butoxycarbonyl)amino)propanoyl)hexahydropyridazine-3-carboxylate (330 mg, 35.6% yield) as a white solid. LCMS (ESI): m/z [M+H] calc'd for $C_{45}H_{62}BBrN_6O_9$ 921.39; found 921.4.

Step 10. A mixture of 3-(1-ethyl-2-(2-((S)-1-methoxyethyl)pyridin-3-yl)-5-(4,4,5,5-tetramethyl-1,3,2-dioxaborolan-2-yl)-1H-indol-3-yl)-2,2-dimethylpropyl(S)-1-((S)-3-(2-bromooxazol-4-yl)-2-((tert-butoxycarbonyl)amino)propanoyl)hexahydropyridazine-3-carboxylate (290.0 mg, 0.33 mmol), $K_3PO_4$ (206.64 mg, 0.97 mmol), X-Phos (30.94 mg, 0.07 mmol), XPhos Pd G3 (54.93 mg, 0.07 mmol), dioxane (5. mL) and $H_2O$ (1.0 mL) at 70° C. was stirred for 4 h under an argon atmosphere. The resulting mixture was extracted with EtOAc (3×20 mL). The combined organic layers were dried over anhydrous $Na_2SO_4$. After filtration, the filtrate was concentrated under reduced pressure. The residue was purified by Prep-TLC to afford tert-butyl (($6^3S$,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-11H-8-oxa-2(2,4)-oxazola-1(5,3)-indola-6(1,3)-pyridazinacycloundecaphane-4-yl)carbamate (130 mg, 56.0% yield) as a solid. LCMS (ESI): m/z [M+H] calc'd for $C_{39}H_{50}N_6O_7$ 715.38; found 715.3.

Step 11. A mixture of tert-butyl (($6^3S$,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-11H-8-oxa-2(2,4)-oxazola-1(5,3)-indola-6(1,3)-pyridazinacycloundecaphane-4-yl)carbamate (120.0 mg), DCM (2.0 mL) and TFA (0.2 mL) at room temperature was stirred for 6 h under an air atmosphere. The resulting mixture was concentrated under reduced pressure. to afford ($6^3S$,4S,2)-4-amino-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-11H-8-oxa-2(2,4)-oxazola-1(5,3)-indola-6(1,3)-pyridazinacycloundecaphane-5,7-dione (90 mg, 87.2% yield) as a solid. LCMS (ESI): m/z [M+H] calc'd for $C_{34}H_{42}N_6O_5$ 615.33; found 615.3.

Step 12. A mixture of ($6^3S$,4S,2)-4-amino-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-5,7-dione (200.0 mg, 0.33 mmol), (2R)-2-(([1-(diphenylmethyl)azetidin-3-yl]oxy]methyl)-3-methylbutanoic acid (172.49 mg, 0.49 mmol), DIPEA (420.48 mg, 3.25 mmol), DMF (3.0 mL) and HATU (148.44 mg, 0.39 mmol) at 0° C. was stirred for 3 h under an air atmosphere. The resulting mixture was extracted with EtOAc (3×20 mL). The combined organic layers were dried over anhydrous $Na_2SO_4$. After filtration, the filtrate was concentrated under reduced pressure. The residue was purified by Prep-TLC to afford (2R)-2-(((1-benzhydrylazetidin-3-yl)oxy)methyl)-N-(($6^3S$,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-4-yl)-3-methylbutanamide (154 mg, 77.0% yield) as a solid. LCMS (ESI): m/z [M+H] calc'd for $C_{56}H_{67}N_7O_7$ 950.52; found 950.6.

Step 13. A mixture of (2R)-2-(((1-benzhydrylazetidin-3-yl)oxy)methyl)-N-(($6^3S$,4S,2)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-4-yl)-3-methylbutanamide (240.0 mg, 0.25 mmol), $(Boc)_2O$ (165.37 mg, 0.76 mmol), MeOH (5.0 mL) and $Pd(OH)_2$ (72.0 mg, 0.51 mmol) at room temperature was stirred overnight under an $H_2$ atmosphere. The resulting mixture was filtered, the filter cake was washed with MeOH (3×5 mL). The filtrate was concentrated under reduced pressure. The residue was purified by Prep-TLC to afford tert-butyl 3-((2R)-2-((($6^3S$,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-4-yl)carbamoyl)-3-methylbutoxy)azetidine-1-carboxylate (150 mg, 67.2% yield) as a solid. LCMS (ESI): m/z [M+H] calc'd for $C_{48}H_{65}N_7O_9$ 884.49; found 884.2.

Step 14. A mixture of tert-butyl 3-((2R)-2-((($6^3S$,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-11H-8-oxa-2(2,4)-oxazola-1(5,3)-indola-6(1,3)-pyridazinacycloundecaphane-4-yl)carbamoyl)-3-methylbutoxy)azetidine-1-carboxylate (150.0 mg), DCM (2.0 mL) and TFA (0.40 mL) at 0° C. was stirred for 3 h under an air atmosphere. The resulting mixture was concentrated under reduced pressure to afford (2R)-2-((azetidin-3-yloxy)methyl)-N-(($6^3S$,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-4-yl)-3-methylbutanamide (120 mg, 90.2% yield) as a solid. LCMS (ESI): m/z [M+H] calc'd for $C_{43}H_{57}N_7O_7$ 784.44; found 784.2.

Step 15. A mixture of (2R)-2-((azetidin-3-yloxy)methyl)-N-(($6^3S$,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-4-yl)-3-methylbutanamide (130.0 mg, 0.17 mmol), sodium 4-(dimethylamino)-4-methylpent-2-ynoate (44.07 mg, 0.25 mmol), DMF (3.0 mL), DIPEA (64.29 mg, 0.50 mmol) and COMU (106.46 mg, 0.25 mmol) at 0° C. was stirred for 3 h under an air atmosphere. The resulting mixture was extracted with EtOAc (3×20 mL). The combined organic layers were dried over anhydrous $Na_2SO_4$. After filtration, the filtrate was concentrated under reduced pressure. The crude product was purified by reverse phase chromatography to afford (2R)-2-(((1-(4-(dimethylamino)-4-methylpent-2-ynoyl)azetidin-3-yl)oxy)methyl)-N-(($6^3S$,4S,Z)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(2,4)-oxazola-1(5,3)-indola-6(1,3)-pyridazinacycloundecaphane-4-yl)-3-methylbutanamide (25 mg, 16.4% yield) as a solid. $^1$H NMR (400 MHz, DMSO-$d_6$) δ 8.77 (dd, J=4.8, 1.8 Hz, 1H), 8.55 (s, 1H), 8.14 (dd, J=8.3, 2.9 Hz, 1H), 7.82 (d, J=7.6 Hz, 1H), 7.76-7.65 (m, 3H), 7.54 (dd, J=7.7, 4.7 Hz, 1H), 7.54-7.02

(m, 1H), 5.72 (td, J=7.4, 3.4 Hz, 1H), 4.97 (d, J=11.9 Hz, 1H), 4.46-4.24 (m, 6H), 4.18-4.04 (m, 2H), 3.94 (dd, J=32.9, 7.8 Hz, 1H), 3.77-3.63 (m, 2H), 3.57 (s, 1H), 3.49 (s, 2H), 3.21 (s, 3H), 2.90 (d, J=14.6 Hz, 1H), 2.87-2.79 (m, 1H), 2.72 (td, J=15.5, 14.6, 3.1 Hz, 2H), 2.46 (s, 1H), 2.43-2.26 (m, 6H), 2.11-1.99 (m, 1H), 1.82-1.66 (m, 2H), 1.56-1.37 (m, 11H), 0.89 (dt, J=12.3, 7.7 Hz, 12H), 0.35 (s, 3H). LCMS (ESI): m/z [M+H] calc'd for $C_{51}H_{68}N_8O_8$ 921.52; found 921.5.

Example A607. The synthesis of (2R)-2-(((1-(4-(dimethylamino)-4-methylpent-2-ynoyl)azetidin-3-yl)oxy)methyl)-N-(($2^3$S,$6^3$S,4S)-$1^1$-ethyl-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-piperidinacycloundecaphane-4-yl)-3-methylbutanamide

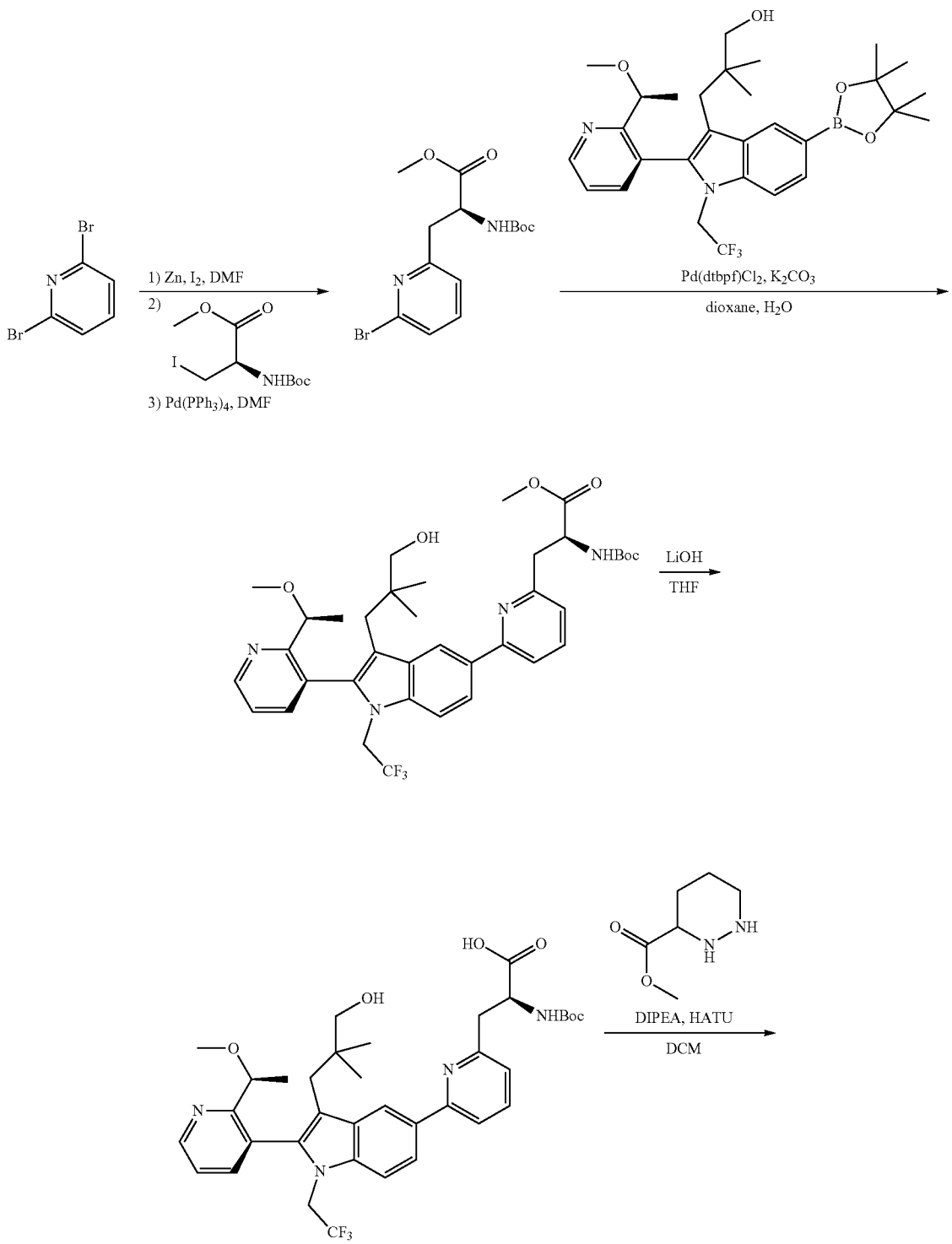

-continued
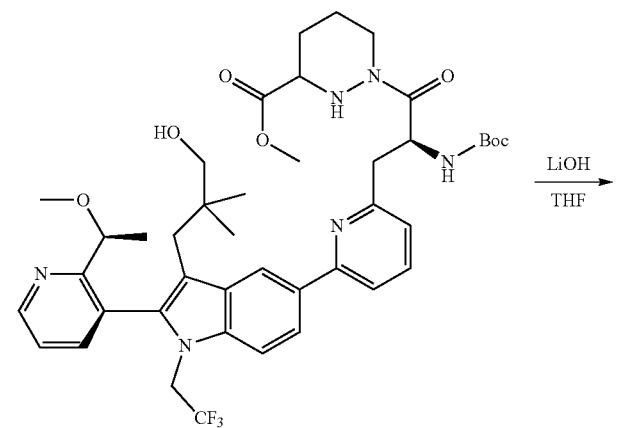
LiOH
THF
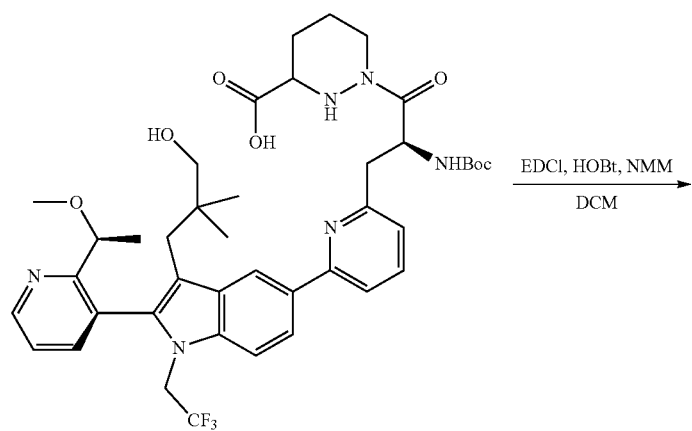
EDCl, HOBt, NMM
DCM
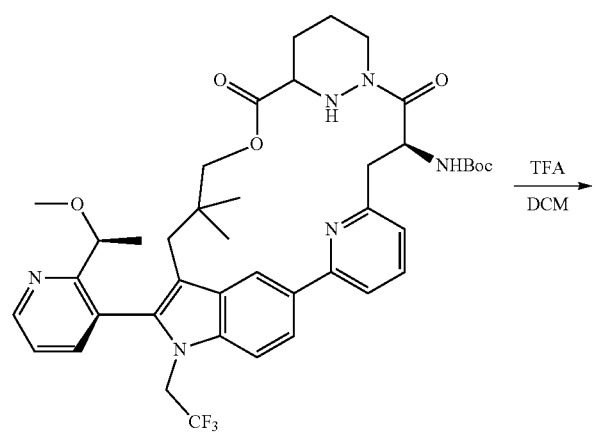
TFA
DCM

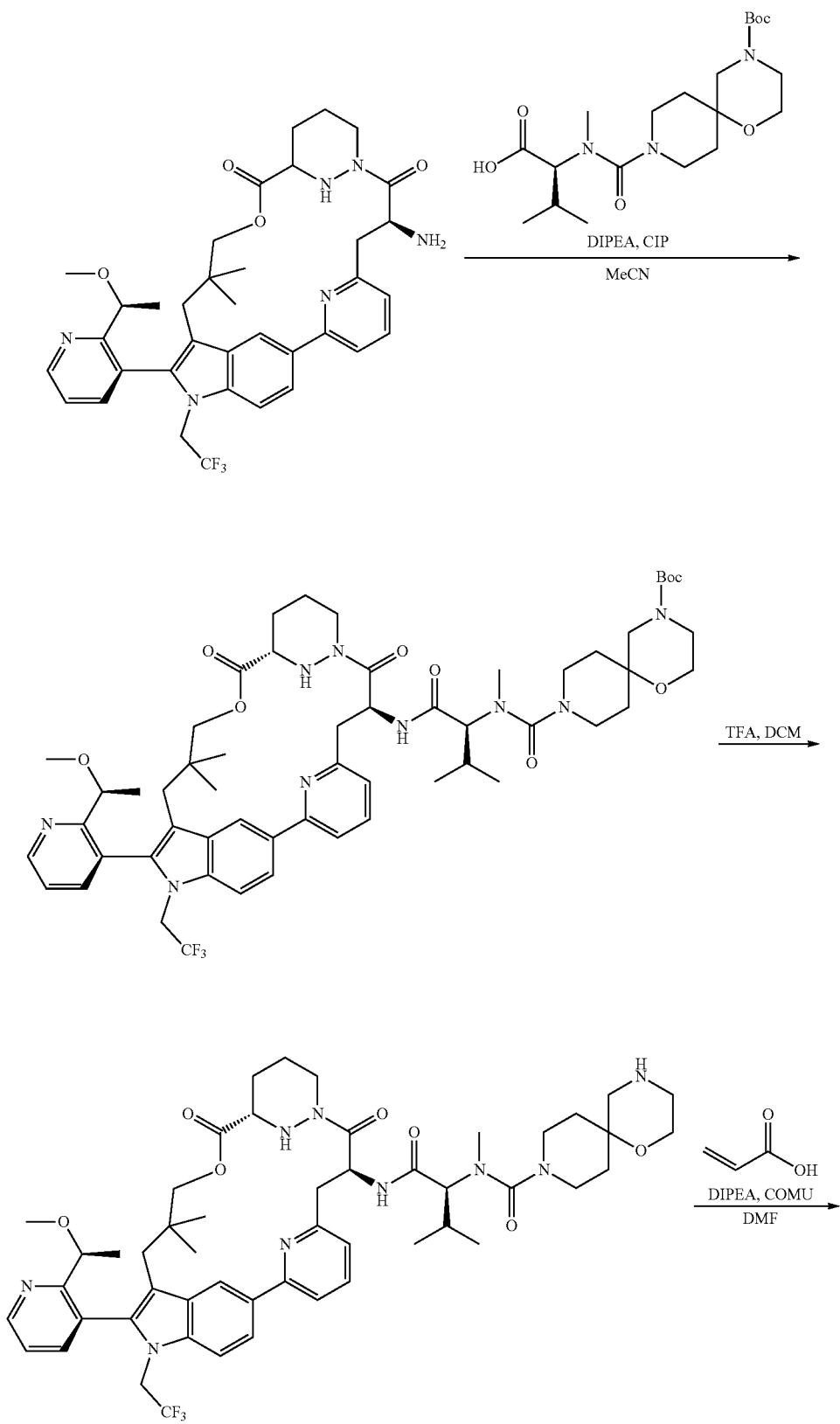

-continued

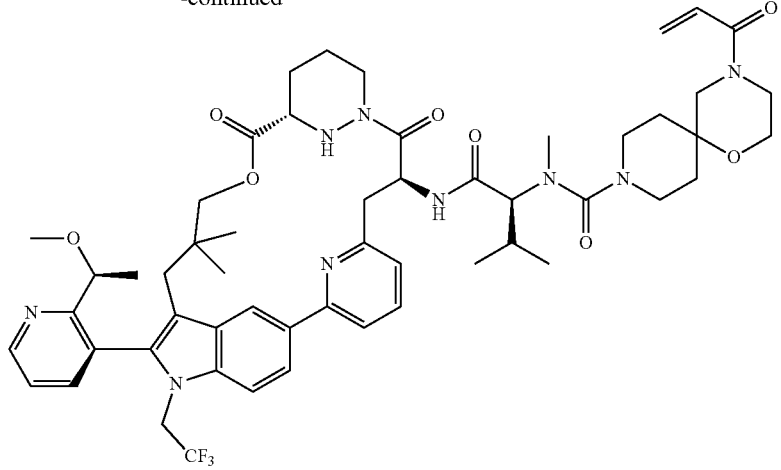

Step 1. A mixture of Zn (44.18 g, 675.41 mmol) and 12 (8.58 g, 33.77 mmol) in DMF (120 mL) was stirred for 30 min at 50° C. under an argon atmosphere, followed by the addition of methyl (2R)-2-[(tert-butoxycarbonyl) amino]-3-iodopropanoate (72.24 g, 219.51 mmol) in DMF (200 mL). The reaction mixture was stirred at 50° C. for 2 h under an argon atmosphere. Then a mixture of 2,6-dibromo-pyridine (40 g, 168.85 mmol) and Pd(PPh$_3$)$_4$ (39.02 g, 33.77 mmol) in DMF (200 mL) was added. The resulting mixture was stirred at 75° C. for 2 h, then cooled down to room temperature and extracted with EtOAc (1 L×3). The combined organic layers were washed with H$_2$O (1 L×3), dried over anhydrous sodium sulfate, filtered and concentrated under reduced pressure. The residue was purified by silica gel column chromatography to afford methyl (2S)-3-(6-bromopyridin-2-yl)-2-[(tert-butoxycarbonyl) amino] propanoate (41 g, 67% yield) as oil. LCMS (ESI): m/z [M+H] calc'd for C$_{14}$H$_{19}$BrN$_2$O$_4$ 358.1; found 359.1.

Step 2. To a solution of 3-[(2M)-2-[2-[(1 S)-1-methoxyethyl] pyridin-3-yl]-5-(4,4,5,5-tetramethyl-1,3,2-dioxaborolan-2-yl)-1-(2,2,2-trifluoroethyl) indol-3-yl]-2,2-dimethyl-propan-1-ol (45.0 g, 82.35 mmol) in dioxane (400 mL) and H$_2$O (80 mL), were added potassium carbonate (28.45 g, 205.88 mmol), methyl (2S)-3-(6-bromopyridin-2-yl)-2-[(tert-butoxycarbonyl) amino] propanoate (35.5 g, 98.8 mmol), Pd(dtbpf)Cl$_2$ (5.37 g, 8.24 mmol) at room temperature. The reaction mixture was stirred at 70° C. for 2 h under a nitrogen atmosphere. The resulting mixture was extracted with EtOAc (500 mL×3). The combined organic layers were washed with H$_2$O (300 mL×3), dried over anhydrous sodium sulfate, filtered and concentrated under reduced pressure. The residue was purified by silica gel chromatography to afford methyl (S)-2-((tert-butoxycarbonyl)amino)-3-(6-(3-(3-hydroxy-2,2-dimethylpropyl)-2-(2-((S)-1-methoxyethyl)pyridin-3-yl)-1-(2,2,2-trifluoroethyl)-1H-indol-5-yl)pyridin-2-yl)propanoate (48 g, 83% yield) as solid. LCMS (ESI): m/z [M+H] calc'd for C$_{37}$H$_{45}$F$_3$N$_4$O$_6$ 698.3; found 699.4.

Step 3. A solution of methyl (S)-2-((tert-butoxycarbonyl) amino)-3-(6-(3-(3-hydroxy-2,2-dimethylpropyl)-2-(2-((S)-1-methoxyethyl)pyridin-3-yl)-1-(2,2,2-trifluoroethyl)-1H-indol-5-yl)pyridin-2-yl)propanoate (52 g, 74.42 mmol) in THF (520 mL), was added LiOH (74.41 mL, 223.23 mmol) at 0° C. The reaction mixture was stirred at room temperature for 3 h. The resulting mixture was acidified to pH 5 with HCl (aq.) and extracted with EtOAc (1 L×3). The combined organic layers were washed with H$_2$O (1 L>3), dried over anhydrous sodium sulfate, filtered and concentrated under reduced pressure to afford (S)-2-((tert-butoxycarbonyl) amino)-3-(6-(3-(3-hydroxy-2,2-dimethylpropyl)-2-(2-((S)-1-methoxyethyl)pyridin-3-yl)-1-(2,2,2-trifluoroethyl)-1H-indol-5-yl)pyridin-2-yl)propanoic acid (50 g, 98% yield) as solid. LCMS (ESI): m/z [M+H] calc'd for C$_{36}$H$_{43}$F$_3$N$_4$O$_6$ 684.3; found 685.1.

Step 4. To a solution of (S)-2-((tert-butoxycarbonyl) amino)-3-(6-(3-(3-hydroxy-2,2-dimethylpropyl)-2-(2-((S)-1-methoxyethyl)pyridin-3-yl)-1-(2,2,2-trifluoroethyl)-1H-indol-5-yl)pyridin-2-yl)propanoic acid (55 g, 80.32 mmol) in DCM (600 mL), were added DIPEA (415.23 g, 3212.82 mmol), and HATU (45.81 g, 120.48 mmol) at 0° C. The reaction mixture was stirred at room temperature for 12 h and then quenched with H$_2$O. The resulting mixture was extracted with EtOAc (1 L×3). The combined organic layers were washed with H$_2$O (1 L), dried over anhydrous sodium sulfate, filtered and concentrated under reduced pressure. The residue was purified by silica gel column chromatography to afford methyl 1-((S)-2-((tert-butoxycarbonyl) amino)-3-(6-(3-(3-hydroxy-2,2-dimethylpropyl)-2-(2-((S)-1-methoxyethyl)pyridin-3-yl)-1-(2,2,2-trifluoroethyl)-1H-indol-5-yl)pyridin-2-yl)propanoyl)hexahydropyridazine-3-carboxylate (63 g, 96% yield) as solid. LCMS (ESI): m/z [M+H] calc'd for C$_{42}$H$_{53}$F$_3$N$_6$O$_7$ 810.4; found 811.3.

Step 5. A solution of methyl 1-((S)-2-((tert-butoxycarbonyl)amino)-3-(6-(3-(3-hydroxy-2,2-dimethylpropyl)-2-(2-((S)-1-methoxyethyl)pyridin-3-yl)-1-(2,2,2-trifluoroethyl)-1H-indol-5-yl)pyridin-2-yl)propanoyl) hexahydropyridazine-3-carboxylate (50 g, 61.66 mmol) in THF (500 mL) and 3M LiOH (61.66 mL, 184.980 mmol) at 0° C. was stirred at room temperature for 3 h, then acidified to pH 5 with HCl (aq.). The resulting mixture was extracted with EtOAc (800 mL×3). The combined organic layers were washed with H$_2$O (800 mL), dried over anhydrous sodium sulfate, filtered and concentrated under reduced pressure to afford 1-((S)-2-((tert-butoxycarbonyl)amino)-3-(6-(3-(3-hydroxy-2,2-dimethylpropyl)-2-(2-((S)-1-methoxyethyl)pyridin-3-yl)-1-(2,2,2-trifluoroethyl)-1H-indol-5-yl)pyridin-2-yl)propanoyl)hexahydropyridazine-3-carboxylic acid (48 g, 97% yield) as solid. LCMS (ESI): m/z [M+H] calc'd for C$_{41}$H$_{51}$F$_3$N$_6$O$_7$ 796.3; found 797.1.

Step 6. To a solution of 1-((S)-2-((tert-butoxycarbonyl) amino)-3-(6-(3-(3-hydroxy-2,2-dimethylpropyl)-2-(2-((S)-1-methoxyethyl)pyridin-3-yl)-1-(2,2,2-trifluoroethyl)-1H-indol-5-yl)pyridin-2-yl)propanoyl)hexahydropyridazine-3-carboxylic acid (50 g, 62.74 mmol) in DCM (10 L) at 0° C., were added DIPEA (243.28 g, 1882.32 mmol), EDCl (360.84 g, 1882.32 mmol) and HOBT (84.78 g, 627.44 mmol). The reaction mixture was stirred at room temperature for 3 h, quenched with H$_2$O and concentrated under reduced pressure. The residue was extracted with EtOAc (2 L×3). The combined organic layers were washed with H$_2$O (2 L×3), dried over anhydrous sodium sulfate, filtered and concentrated under reduced pressure. The residue was purified by silica gel column chromatography to afford tert-butyl ((4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(2,6)-pyridinacycloundecaphane-4-yl)carbamate (43.6 g, 89% yield) as solid. LCMS (ESI): m/z [M+H] calc'd for C$_{41}$H$_{49}$F$_3$N$_6$O$_6$ 778.3; found 779.3.

Step 7. To a solution of tert-butyl ((4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(2,6)-pyridinacycloundecaphane-4-yl)carbamate (300 mg) in DCM (10 mL), was added TFA (3 mL) at 0° C. The reaction mixture was stirred at room temperature for 1 h. The resulting mixture was diluted with toluene (10 mL) and concentrated under reduced pressure three times to afford (4S)-4-amino-1$^2$-(2-((S)-1-methoxyethyl)pyridin-3-yl)-10,10-dimethyl-1$^1$-(2,2,2-trifluoroethyl)-6$^1$,6$^2$,6$^3$,6$^4$,6$^5$,6$^6$-hexahydro-1$^{'1}$H-8-oxa-1(5,3)-indola-6(1,3)-pyridazina-2(2,6)-pyridinacycloundecaphane-5,7-dione (280 mg, crude) as oil. LCMS (ESI): m/z [M+H] calc'd for C$_{36}$H$_{41}$F$_3$N$_6$O$_4$ 679.2; found 678.3.

Step 8. To a solution of (4S)-4-amino-1$^2$-(2-((S)-1-methoxyethyl)pyridin-3-yl)-10,10-dimethyl-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(2,6)-pyridinacycloundecaphane-5,7-dione (140 mg, 0.21 mmol) in MeCN (2 mL), were added DIPEA (266.58 mg, 2.06 mmol), N-(4-(tert-butoxycarbonyl)-1-oxa-4,9-diazaspiro[5.5]undecane-9-carbonyl)-N-methyl-L-valine (127.94 mg, 0.31 mmol) and CIP (114.68 mg, 0.41 mmol) at 0° C. The reaction mixture was stirred at room temperature for 1 h. The resulting mixture was concentrated under reduced pressure. The residue was extracted with EtOAc (10 mL×3). The combined organic layers were washed with H$_2$O (10 mL×3), dried over anhydrous sodium sulfate, filtered and concentrated under reduced pressure. The residue was purified by silica gel chromatography to afford tert-butyl 9-(((2S)-1-(((6$^3$S,4S)-1$^2$-(2-((S)-1-methoxyethyl) pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(2,6)-pyridinacycloundecaphane-4-yl) amino)-3-methyl-1-oxobutan-2-yl) (methyl)carbamoyl)-1-oxa-4,9-diazaspiro [5.5] undecane-4-carboxylate (170 mg, 76% yield) as solid. LCMS (ESI): m/z [M+H] calc'd for C$_{56}$H$_{74}$F$_3$N$_9$O$_9$ 1073.5; found 1074.6.

Step 9. To a solution of tert-butyl 9-(((2S)-1-(((6$^3$S,4S)-1$^2$-(2-((S)-1-methoxyethyl) pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(2,6)-pyridinacycloundecaphane-4-yl) amino)-3-methyl-1-oxobutan-2-yl) (methyl)carbamoyl)-1-oxa-4,9-diazaspiro [5.5] undecane-4-carboxylate (160 mg, 0.15 mmol) in DCM (5 mL) at 0° C., was dropwise added TFA (1.5 mL). The reaction mixture was stirred at 0° C. for 1 h. The resulting mixture was diluted with toluene (10 mL) and concentrated under reduced pressure three times to afford N-((2S)-1-(((6$^3$S,4S)-1$^2$-(2-((S)-1-methoxyethyl) pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-11H-8-oxa-1(5,3)-indola-6(1,3)-pyridazina-2(2,6)-pyridinacycloundecaphane-4-yl) amino)-3-methyl-1-oxobutan-2-yl)-N-methyl-1-oxa-4,9-diazaspiro [5.5] undecane-9-carboxamide (150 mg, crude) as oil. LCMS (ESI): m/z [M+H] calc'd for C$_{51}$H$_{65}$F$_3$N$_9$O$_7$ 973.5; found 974.4.

Step 10. To a solution of N-((2S)-1-(((6$^3$S,4S)-1$^2$-(2-((S)-1-methoxyethyl) pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(2,6)-pyridinacycloundecaphane-4-yl) amino)-3-methyl-1-oxobutan-2-yl)-N-methyl-1-oxa-4,9-diazaspiro [5.5] undecane-9-carboxamide (150 mg, 0.15 mmol) in DMF (3 mL), were added DIPEA (199.01 mg, 1.54 mmol), acrylic acid (16.64 mg, 0.23 mmol) and COMU (98.39 mg, 0.23 mmol) at 0° C. The reaction mixture was stirred at room temperature for 1 h and concentrated under reduced pressure. The residue was extracted with EtOAc (10 mL×3). The combined organic layers were washed with H$_2$O (10 mL×3), dried over anhydrous sodium sulfate, filtered and concentrated under reduced pressure. The residue was purified by silica gel chromatography and reverse phase chromatography to afford 4-acryloyl-N-((2S)-1-(((6$^3$S,4S)-1$^2$-(2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-11H-8-oxa-1(5,3)-indola-6(1,3)-pyridazina-2(2,6)-pyridinacycloundecaphane-4-yl)amino)-3-methyl-1-oxobutan-2-yl)-N-methyl-1-oxa-4,9-diazaspiro[5.5] undecane-9-carboxamide (53 mg, 33% yield) as solid. $^1$H NMR (400 MHz, DMSO-d$_6$) δ 8.79 (dd, J=4.8, 1.9 Hz, 2H), 8.09 (d, J=31.4 Hz, 1H), 7.96 (d, J=8.9 Hz, 1H), 7.90-7.72 (m, 3H), 7.64 (t, J=7.8 Hz, 1H), 7.56 (dd, J=7.8, 4.7 Hz, 1H), 7.03 (s, 1H), 6.86 (dd, J=16.6, 10.4 Hz, 1H), 6.20 (d, J=14.0 Hz, 1H), 5.73 (d, J=12.2 Hz, 2H), 5.47 (s, 1H), 5.35 (d, J=11.8 Hz, 1H), 4.68 (s, 1H), 4.28 (d, J=12.5 Hz, 1H), 4.13 (d, J=6.4 Hz, 1H), 3.92 (s, 1H), 3.84-3.64 (m, 6H), 3.59 (d, J=14.0 Hz, 3H), 3.50 (s, 3H), 3.10 (s, 5H), 3.02 (d, J=13.3 Hz, 2H), 2.85 (d, J=12.1 Hz, 3H), 2.08-1.89 (m, 2H), 1.81 (s, 1H), 1.75-1.51 (m, 5H), 1.39 (d, J=6.1 Hz, 4H), 1.24 (s, OH), 0.91-0.66 (m, 10H), 0.53 (s, 3H). LCMS (ESI): m/z [M+H] calc'd for C$_{54}$H$_{68}$F$_3$N$_9$O$_8$ 1027.5; found 1028.1.

Example A590. The synthesis of (2R)-2-(((1-(4-(dimethylamino)-4-methylpent-2-ynoyl)azetidin-3-yl)oxy)methyl)-N-((6$^3$S,4S,Z)-1$^2$-(2-((S)-1-methoxyethyl)pyridin-3-yl)-10,10-dimethyl-5,7-dioxo-1$^1$-(2, 2,2-trifluoroethyl)-6',6$^2$,6$^3$,6$^4$,6$^5$,6$^6$-hexahydro-1$^1$H-8-oxa-2(5,3)-thiadiazola-1(5,3)-indola-6(1,3)-pyridazinacycloundecaphane-4-yl)-3-methylbutanamide

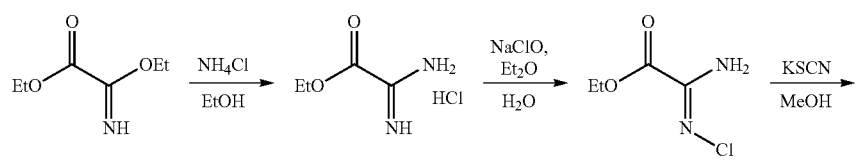

-continued
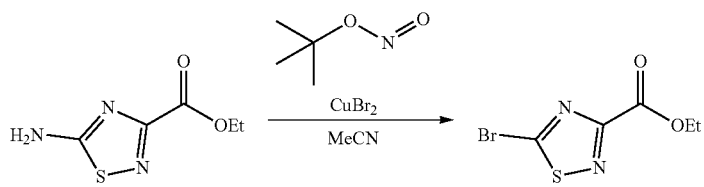
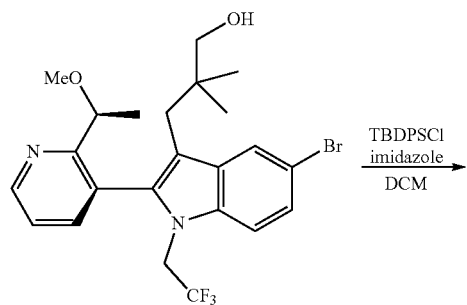
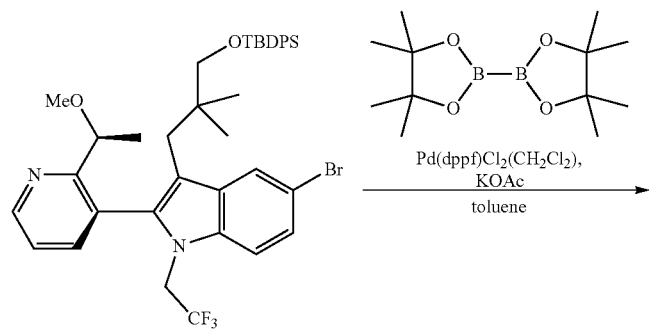
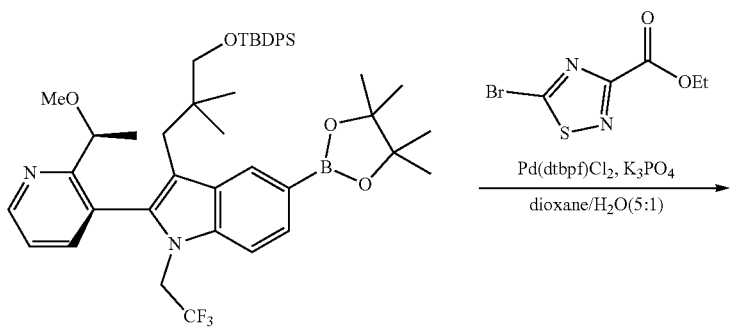
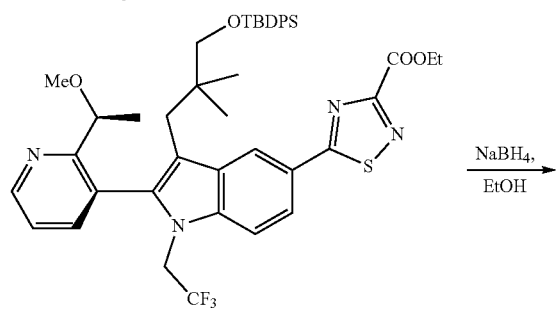

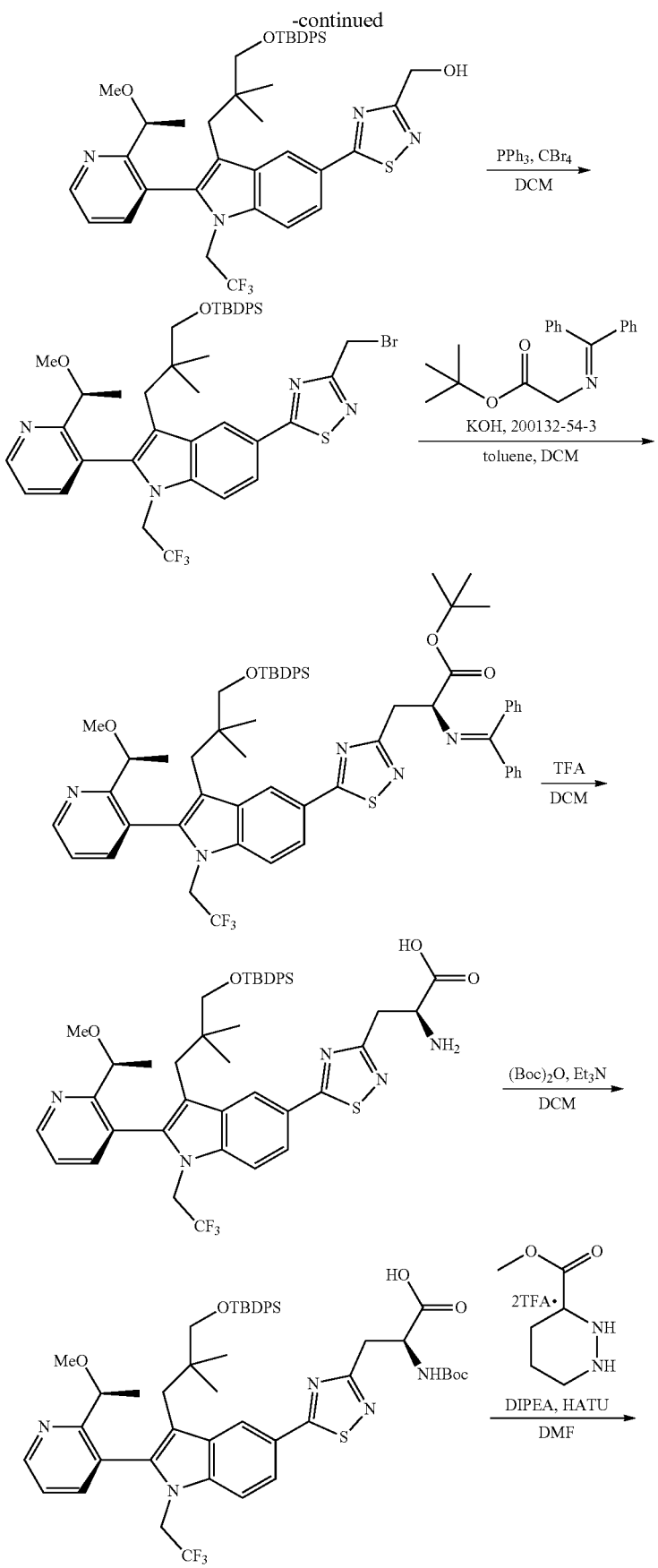

-continued
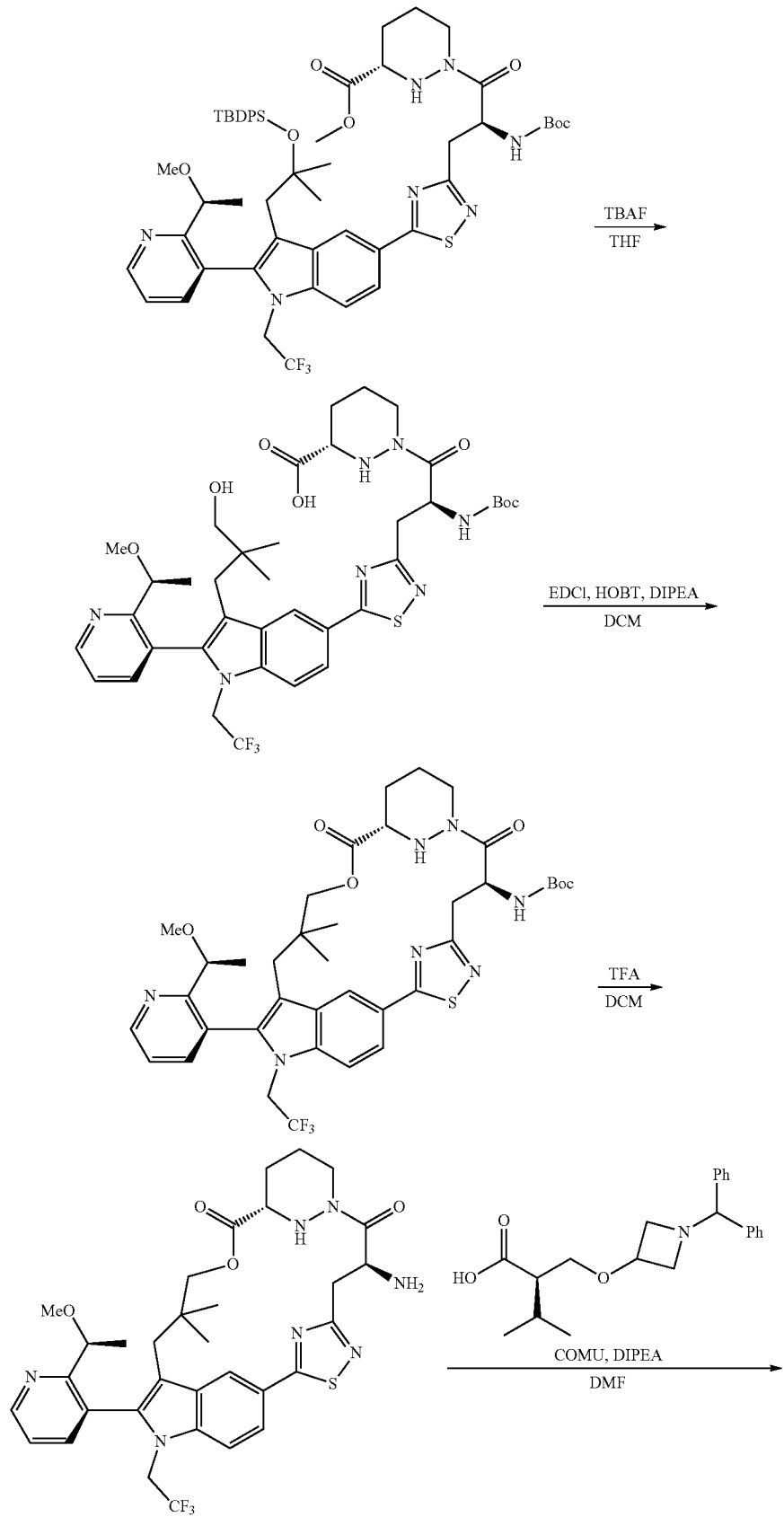

1121
-continued
1122
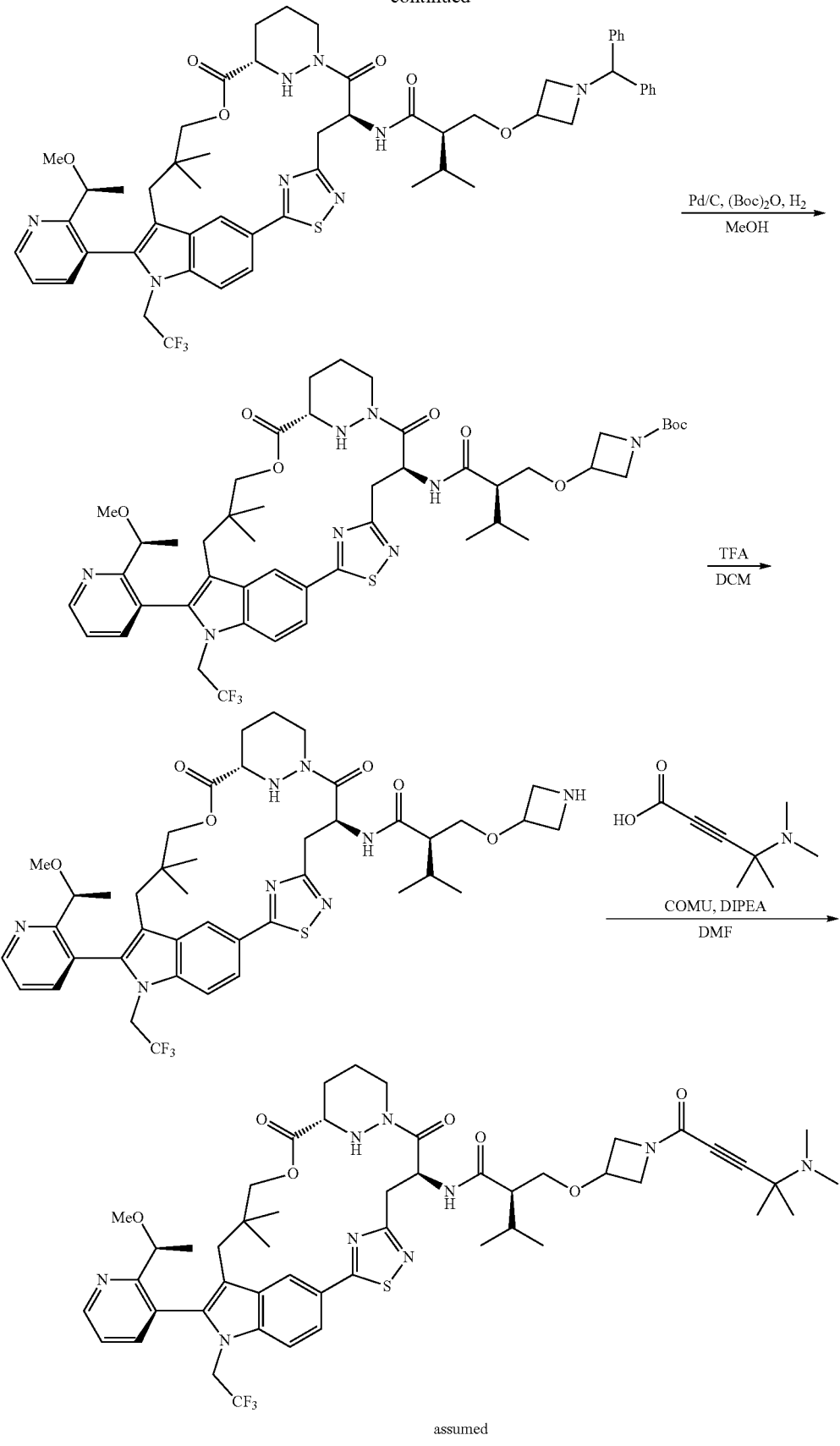
assumed

Step 1. To a mixture of ethyl 2-ethoxy-2-iminoacetate (25.0 g, 172.23 mmol) and EtOH (250.0 mL) at 0° C. was added ammonium chloride (9.21 g, 172.23 mmol) in portions then stirred for 4 h at room temperature under an argon atmosphere. The resulting mixture was concentrated under reduced pressure and washed with Et$_2$O (3×200 mL). The organic layers were combined and concentrated under reduced pressure. This resulted in ethyl 2-amino-2-iminoacetate hydrochloride (20 g, crude) as a light yellow solid. LCMS (ESI): m/z [M+H] calc'd for C$_4$H$_8$N$_2$O$_2$ 117.07; found 116.9.

Step 2. To a mixture of ethyl 2-amino-2-iminoacetate hydrochloride (13.30 g, 87.17 mmol), H$_2$O (50.0 mL) and Et$_2$O (100.0 mL) at 0° C. was added sodium hypochlorite pentahydrate (7.79 g, 104.60 mmol) dropwise. The resulting mixture was stirred for 3 h under an argon atmosphere. The mixture was extracted with Et$_2$O (3×200 mL). The resulting solution was washed with brine (3×100 mL). The organic phase was dried over anhydrous Na$_2$SO$_4$ and concentrated under reduced pressure to afford ethyl (2)-2-amino-2-(chloroimino) acetate (7 g, crude) as a light yellow solid. LCMS (ESI): m/z [M+H] calc'd for C$_4$H$_7$ClN$_2$O$_2$ 151.03; found 150.8.

Step 3. To a solution of ethyl (2)-2-amino-2-(chloroimino) acetate (8.40 g, 55.792 mmol) and MeOH (130.0 mL) at 0° C. was added potassium thiocyanate (5.42 g, 55.79 mmol) in portions. The resulting mixture was stirred for 4 h at room temperature under an argon atmosphere. The reaction was quenched with H$_2$O/Ice. The mixture was extracted with EtOAc (5×100 mL). The resulting organic phase was dried over anhydrous Na$_2$SO$_4$ and concentrated under reduced pressure. The residue was purified by silica gel column chromatography to afford ethyl 5-amino-1,2,4-thiadiazole-3-carboxylate (2.3 g, 23.8% yield) as a solid. LCMS (ESI): m/z [M+H] calc'd for C$_5$H$_7$N$_3$O$_2$S 174.03; found 173.8.

Step 4. To a solution of ethyl 5-amino-1,2,4-thiadiazole-3-carboxylate (5.80 g, 33.49 mmol), MeCN (90.0 mL) and CuBr$_2$ (11.22 g, 50.23 mmol) at 0° C. was added 2-methyl-2-propylnitrit (6.91 g, 66.98 mmol) dropwise under an argon atmosphere. The mixture was stirred for 30 min. The mixture was then stirred for 4 h at 50° C. The mixture was cooled to 0° C. and quenched with H$_2$O/Ice. The mixture was extracted with EtOAc (3×100 mL). The resulting organic phase was dried over anhydrous Na$_2$SO$_4$ and concentrated under reduced pressure. The residue was purified by silica gel chromatography to afford ethyl 5-bromo-1,2,4-thiadiazole-3-carboxylate (6.2 g, 78.1% yield) as a solid. LCMS (ESI): m/z [M+H] calc'd for C$_5$H$_5$BrN$_2$O$_2$S 236.93; found 237.1.

Step 5. To a solution of (S)-3-(5-bromo-2-(2-(1-methoxyethyl)pyridin-3-yl)-1-(2,2,2-trifluoroethyl)-1H-indol-3-yl)-2,2-dimethylpropan-1-ol (16.60 g, 33.24 mmol), DCM (170.0 mL) and imidazole (5.66 g, 83.10 mmol) at 0° C. was added tert-butyl-chlorodiphenylsilane (11.88 g, 43.21 mmol) dropwise. The resulting mixture was stirred for 3 h at room temperature under an argon atmosphere. The reaction was quenched with H$_2$O/Ice. The mixture was extracted with EtOAc (3×200 mL). The organic layer was washed with brine (3×100 mL), dried over anhydrous Na$_2$SO$_4$ and concentrated under reduced pressure. The residue was purified by silica gel column chromatography to afford (S)-5-bromo-3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indole (22 g, 89.7% yield) as a solid. LCMS (ESI): m/z [M+H] calc'd for C$_{39}$H$_{44}$BrF$_3$N$_2$O$_2$Si 737.24; found 737.0.

Step 6. To a solution of (S)-5-bromo-3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indole (28.0 g, 37.95 mmol), toluene (270.0 mL), KOAc (9.31 g, 94.88 mmol) and bis(pinacolato)diboron (19.27 g, 75.90 mmol) at 0° C. was added Pd(dppf)Cl$_2$·CH$_2$Cl$_2$ (6.18 g, 7.59 mmol) in portions. The resulting mixture was stirred for 3 h at 90° C. under an argon atmosphere. The mixture was cooled to room temperature and quenched with H$_2$O/Ice. The mixture was extracted with EtOAc (3×200 mL). The resulting organic phase was dried over anhydrous Na$_2$SO$_4$ and concentrated under reduced pressure. The residue was purified by silica gel column chromatography to afford (S)-3-(3-((tert-butyldiphenylsilyl)oxy)-2,2-dimethylpropyl)-2-(2-(1-methoxyethyl)pyridin-3-yl)-5-(4,4,5,5-tetramethyl-1,3,2-dioxaborolan-2-yl)-1-(2,2,2-trifluoroethyl)-1H-indole (28.2 g, 94.7% yield) as a solid. LCMS (ESI): m/z [M+H] calc'd for C$_{45}$H$_{56}$BF$_3$N$_2$O$_4$Si 785.41; found 785.4.

Step 7. To a solution of (S)-3-(3-((tert-butyldiphenylsilyl)oxy)-2,2-dimethylpropyl)-2-(2-(1-methoxyethyl)pyridin-3-yl)-5-(4,4,5,5-tetramethyl-1,3,2-dioxaborolan-2-yl)-1-(2,2,2-trifluoroethyl)-1H-indole (19.60 g, 24.97 mmol), 1,4-dioxane (200 mL), H$_2$O (40 mL), ethyl 5-bromo-1,2,4-thiadiazole-3-carboxylate (5.92 g, 24.97 mmol) and K$_3$PO$_4$ (13.25 g, 62.43 mmol) at 0° C. was added Pd(dtbpf)Cl$_2$ (1.63 g, 2.50 mmol) in portions. The resulting mixture was stirred for 1.5 h at 75° C. under an argon atmosphere. The mixture was cooled to 0° C. and quenched with H$_2$O/Ice and extracted with EtOAc (3×200 mL). The resulting organic phase was dried over anhydrous Na$_2$SO$_4$ and concentrated under reduced pressure. The residue was purified by silica gel column chromatography to afford ethyl (S)-5-(3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl)-1,2,4-thiadiazole-3-carboxylate (14 g, 68.8% yield) as a yellow solid. LCMS (ESI): m/z [M+H] calc'd for C$_{44}$H$_{49}$F$_3$N$_4$O$_4$SSi 815.33; found 815.2.

Step 8. To a solution of ethyl (S)-5-(3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl)-1,2,4-thiadiazole-3-carboxylate (13.60 g, 16.69 mmol) and EtOH (140.0 mL) at 0° C. was added NaBH$_4$ (3.16 g, 83.43 mmol) in portions. The resulting mixture was stirred for 3 h then quenched with H$_2$O/Ice. The resulting mixture was washed with brine (3×100 mL) and extracted with EtOAc (3×200 mL). The combined organic layers were dried over anhydrous Na$_2$SO$_4$ and concentrated under reduced pressure. The residue was purified by silica gel column chromatography to afford (S)-5-(3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl)-1,2,4-thiadiazol-3-ol (9.7 g, 75.2% yield) as a solid. LCMS (ESI): m/z [M+H] calc'd for C$_{42}$H$_{47}$F$_3$N$_4$O$_3$SSi 773.32; found 773.3.

Step 9. To a solution of (S)-5-(3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl)-1,2,4-thiadiazol-3-ol (9.70 g, 12.55 mmol), DCM (100.0 mL) and CBr$_4$ (8.32 g, 25.10 mmol) at 0° C. was added PPh$_3$ (6.58 g, 25.10 mmol) in DCM (20.0 mL) dropwise. The resulting mixture was stirred for 2 h under an argon atmosphere then quenched with H$_2$O/Ice. The mixture was extracted with DCM (3×200 mL). The resulting organic phase was dried over anhydrous Na$_2$SO$_4$ and concentrated under reduced pressure. The residue was purified by reverse flash chromatography to afford (S)-3-(bromomethyl)-5-(3-(3-((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl)-

1,2,4-thiadiazole (9.5 g, 90.6% yield) as a solid. LCMS (ESI): m/z [M+H] calc'd for $C_{42}H_{46}BrF_3N_4O_2SSi$ 835.23; found 834.9.

Step 10. To a stirred solution of (S)-3-(bromomethyl)-5-(3-(3-(((tert-butyldiphenylsilyl)oxy)-2,2-dimethylpropyl)-2-(2-(1-methoxyethyl)pyridin-3-yl)-1-(2,2,2-trifluoroethyl)-1H-indol-5-yl)-1,2,4-thiadiazole (9.40 g, 11.25 mmol), toluene (84.0 mL), DCM (36.0 mL), tert-butyl 2-[(diphenylmethylidene)amino]acetate (3.32 g, 11.25 mmol) and O-Allyl-N-(9-anthracenylmethyl)cinchonidinium bromide (0.68 g, 1.13 mmol) at 0° C. was added 9M KOH aqueous (94.0 mL) dropwise. The resulting mixture was stirred overnight under an argon atmosphere. The mixture was extracted with EtOAc (3×200 mL) and the organic phase was concentrated under reduced pressure. The residue was purified by silica gel column chromatography to afford tert-butyl (S)-3-(5-(3-(3-(((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)-1,2,4-thiadiazol-3-yl)-2-((diphenylmethylene)amino)propanoate (9 g, 76.2% yield) as a solid. LCMS (ESI): m/z [M+H] calc'd for $C_{61}H_{66}F_3N_5O_4SSi$ 1050.46; found 1050.8.

Step 11. To a solution of tert-butyl (S)-3-(5-(3-(3-(((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)-1,2,4-thiadiazol-3-yl)-2-((diphenylmethylene)amino)propanoate (8.0 g, 7.62 mmol) and DCM (40.0 mL) at 0° C. solution was added TFA (40.0 mL) dropwise. The resulting mixture was stirred overnight at room temperature then concentrated under reduced pressure. The residue was basified to pH 8 with NaHCO₃. The mixture was extracted with EtOAc (3×200 mL). The organic phase was concentrated under reduced pressure. The residue was purified by reverse flash chromatography to afford (S)-2-amino-3-(5-(3-(3-(((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)-1,2,4-thiadiazol-3-yl)propanoic acid (5 g, 79.1% yield) as a solid. LCMS (ESI): m/z [M+H] calc'd for $C_{44}H_{50}F_3N_5O_4SSi$ 830.34; found 830.2.

Step 12. To a solution of (S)-2-amino-3-(5-(3-(3-(((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)-1,2,4-thiadiazol-3-yl)propanoic acid (4.70 g, 5.66 mmol), DCM (50.0 mL) and Et₃N (2.86 g, 28.31 mmol) at 0° C. was added (Boc)₂O (1.36 g, 6.23 mmol) dropwise. The resulting mixture was stirred for 3 h at room temperature under an argon atmosphere then concentrated under reduced pressure and purified by reverse flash chromatography to afford (S)-2-((tert-butoxycarbonyl)amino)-3-(5-(3-(3-(((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)-1,2,4-thiadiazol-3-yl)propanoic acid (5 g, 94.9% yield) as a solid. LCMS (ESI): m/z [M+H] calc'd for $C_{49}H_{58}F_3N_5O_6SSi$ 930.39; found 930.3.

Step 13. To a mixture of (S)-2-((tert-butoxycarbonyl)amino)-3-(5-(3-(3-((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)-1,2,4-thiadiazol-3-yl)propanoic acid (5.30 g, 5.70 mmol), DMF (60.0 mL), methyl 1,2-diazinane-3-carboxylate (1.64 g, 11.40 mmol) and DIPEA (22.09 g, 170.94 mmol) at 0° C. was added HATU (2.82 g, 7.41 mmol) in DMF (5 mL) dropwise. The resulting mixture was stirred for 3 h at room temperature under an argon atmosphere. The reaction was then quenched with H₂O/Ice. The mixture was extracted with EtOAc (3×100 mL) and the organic phase was washed with brine (3×100 mL). The resulting mixture was dried over anhydrous Na₂SO₄ and concentrated under reduced pressure. The residue was purified by silica gel column chromatography to afford methyl (S)-1-((S)-2-((tert-butoxycarbonyl)amino)-3-(5-(3-(3-(((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)-1,2,4-thiadiazol-3-yl)propanoyl)hexahydropyridazine-3-carboxylate (5.6 g) as a solid. LCMS (ESI): m/z [M+H] calc'd for $C_{55}H_{68}F_3N_7O_7SSi$ 1056.47; found 1056.2.

Step 14. A mixture of methyl (S)-1-((S)-2-((tert-butoxycarbonyl)amino)-3-(5-(3-(3-(((tert-butyldiphenylsilyl)oxy)-2,2-dimethylpropyl)-2-(2-((S)-1-methoxyethyl)pyridin-3-yl)-1-(2,2,2-trifluoroethyl)-1H-indol-5-yl)-1,2,4-thiadiazol-3-yl)propanoyl)hexahydropyridazine-3-carboxylate (5.60 g, 5.30 mmol) and TBAF in THF (56.0 mL) was stirred overnight at 40° C. under an argon atmosphere. The reaction was quenched with sat. NH₄Cl (aq.). The mixture was extracted with EtOAc (3×100 mL) and the organic phase was concentrated under reduced pressure. The residue was purified by reverse flash chromatography to afford (S)-1-((S)-2-((tert-butoxycarbonyl)amino)-3-(5-(3-(3-hydroxy-2,2-dimethylpropyl)-2-(2-((S)-1-methoxyethyl)pyridin-3-yl)-1-(2,2,2-trifluoroethyl)-1H-indol-5-yl)-1,2,4-thiadiazol-3-yl)propanoyl)hexahydropyridazine-3-carboxylic acid (4.1 g, 96.2% yield) as a solid. LCMS (ESI): m/z [M+H] calc'd for $C_{38}H_{48}F_3N_7O_7S$ 804.34; found 804.3.

Step 15. To a solution of (S)-1-((S)-2-((tert-butoxycarbonyl)amino)-3-(5-(3-(3-hydroxy-2,2-dimethylpropyl)-2-(2-((S)-1-methoxyethyl)pyridin-3-yl)-1-(2,2,2-trifluoroethyl)-1H-indol-5-yl)-1,2,4-thiadiazol-3-yl)propanoyl)hexahydropyridazine-3-carboxylic acid (4.0 g, 5.0 mmol) and DCM (450.0 mL) at 0° C. were added DIPEA (51.45 g, 398.08 mmol), HOBt (6.72 g, 49.76 mmol) and EDCl (57.23 g, 298.55 mmol) in portions. The resulting mixture was stirred for 16 h at room temperature under an argon atmosphere. The reaction was quenched with H₂O/Ice and extracted with EtOAc (3×30 mL). The organic phase was concentrated under reduced pressure. The residue was purified by silica gel column chromatography to afford tert-butyl ((6³S,4S,Z)-1²-(2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(5,3)-thiadiazola-1(5,3)-indola-6(1,3)-pyridazinacycloundecaphane-4-yl)carbamate (1.7 g, 43.5% yield) as a solid. LCMS (ESI): m/z [M+H] calc'd for $C_{38}H_{46}F_3N_7O_6S$ 786.33; found 786.3.

Step 16. To a solution of ((6³S,4S,2)-1²-(2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(5,3)-thiadiazola-1(5,3)-indola-6(1,3)-pyridazinacycloundecaphane-4-yl)carbamate (300.0 mg, 0.38 mmol) and DCM (2.0 mL) at 0° C. was added TFA (1.0 mL) dropwise. The resulting mixture was stirred for 2 h at room temperature then concentrated under reduced pressure. The residue was basified to pH 8 with saturated NaHCO₃ (aq.). The mixture was extracted with EtOAc (3×20 mL). The organic phase was concentrated under reduced pressure to afford (6³S,4S,Z)-4-amino-1²-(2-((S)-1-methoxyethyl)pyridin-3-yl)-10,10-dimethyl-11-(2,2,2-trifluoroethyl)-6¹,6²,6³,6⁴,6⁵,6⁶-hexahydro-1¹H-8-oxa-2(5,3)-thiadiazola-1(5,3)-indola-6(1,3)-pyridazinacycloundecaphane-5,7-dione (270 mg, crude) as a solid. LCMS (ESI): m/z [M+H] calc'd for $C_{33}H_{38}F_3N_7O_4S$ 686.27; found 686.1.

Step 17. To a solution of (6³S,4S,Z)-4-amino-1²-(2-((S)-1-methoxyethyl)pyridin-3-yl)-10,10-dimethyl-1¹-(2,2,2-trifluoroethyl)-6¹,6²,6³,6⁴,6⁵,6⁶-hexahydro-1¹H-8-oxa-2(5,3)-thiadiazola-1(5,3)-indola-6(1,3)-pyridazinacycloundecaphane-5,7-dione (160.0 mg, 0.23 mmol), (R)-2-(((1-benzhydrylazetidin-3-yl)oxy)methyl)-3-methylbutanoic acid (123.70 mg, 0.35 mmol) and DMF (2.0 mL) at 0° C. were added DIPEA (603.09 mg, 4.660 mmol) and COMU (119.91 mg, 0.28 mmol) in DMF (0.5 mL). The resulting mixture was stirred for 2 h at room temperature under an argon atmosphere. The reaction was quenched with H₂O/Ice and extracted with EtOAc (3×20 mL). The organic phase was washed with brine (3×10 mL) and concentrated under reduced pressure. The residue was purified by Prep-TLC to afford (2R)-2-(((1-benzhydrylazetidin-3-yl)oxy)methyl)-N-(($6^3$S,4S,2)-1²-(2-((S)-1-methoxyethyl)pyridin-3-yl)-10,10-dimethyl-5,7-dioxo-1¹-(2,2,2-trifluoroethyl)-6¹,$6^2$,$6^3$,$6^4$,$6^5$,$6^6$-hexahydro-1¹¹H-8-oxa-2(5,3)-thiadiazola-1(5,3)-indola-6(1,3)-pyridazinacycloundecaphane-4-yl)-3-methylbutanamide (160 mg, 67.2% yield) as a solid. LCMS (ESI): m/z [M+H] calc'd for $C_{55}H_{63}F_3N_8O_6S$ 1021.46; found 1021.4.

Step 18. To a solution of (2R)-2-(((1-benzhydrylazetidin-3-yl)oxy)methyl)-N-(($6^3$S,4S,Z)-1²-(2-((S)-1-methoxyethyl)pyridin-3-yl)-10,10-dimethyl-5,7-dioxo-1¹-(2,2,2-trifluoroethyl)-6¹,$6^2$,$6^3$,$6^4$,$6^5$,$6^6$-hexahydro-1¹¹H-8-oxa-2(5,3)-thiadiazola-1(5,3)-indola-6(1,3)-pyridazinacycloundecaphane-4-yl)-3-methylbutanamide (160.0 mg, 0.16 mmol) and MeOH (5.0 mL) at 0° C. was added (Boc)₂O (85.49 mg, 0.39 mmol) dropwise followed by Pd/C (320.0 mg) in portions. The resulting mixture was stirred overnight at room temperature under a hydrogen atmosphere. The resulting mixture was filtered and the filter cake was washed with EtOAc (3×20 mL). The filtrate was concentrated under reduced pressure. The residue was purified by Prep-TLC to afford tert-butyl 3-((2R)-2-((($6^3$S,4S,2)-1²-(2-((S)-1-methoxyethyl)pyridin-3-yl)-10,10-dimethyl-5,7-dioxo-1¹-(2,2,2-trifluoroethyl)-6¹,$6^2$,$6^3$,$6^4$,$6^5$,$6^6$-hexahydro-1¹H-8-oxa-2(5,3)-thiadiazola-1(5,3)-indola-6(1,3)-pyridazinacycloundecaphane-4-yl)carbamoyl)-3-methylbutoxy)azetidine-1-carboxylate (80 mg, 53.5% yield) as a solid. LCMS (ESI): m/z [M+H] calc'd for $C_{47}H_{61}F_3NaOS$ 955.44; found 955.2.

Step 19. To a solution of tert-butyl 3-((2R)-2-((($6^3$S,4S,2)-1²-(2-((S)-1-methoxyethyl)pyridin-3-yl)-10,10-dimethyl-5,7-dioxo-1¹-(2,2,2-trifluoroethyl)-6¹,$6^2$,$6^3$,$6^4$,$6^5$,$6^6$-hexahydro-1¹H-8-oxa-2(5,3)-thiadiazola-1(5,3)-indola-6(1,3)-pyridazinacycloundecaphane-4-yl)carbamoyl)-3-methylbutoxy)azetidine-1-carboxylate (120.0 mg, 0.13 mmol) and DCM (0.80 mL) at 0° C. was added TFA (0.4 mL) dropwise and the resulting mixture was stirred for 2 h at room temperature. The mixture was basified to pH 8 with saturated NaHCO₃(aq.). The mixture was extracted with EtOAc (3×10 mL) and concentrated under reduced pressure. The residue was purified by reverse flash chromatography to afford (2R)-2-((azetidin-3-yloxy)methyl)-N-(($6^3$S,4S,2)-1²-(2-((S)-1-methoxyethyl)pyridin-3-yl)-10,10-dimethyl-5,7-dioxo-1¹-(2,2,2-trifluoroethyl)-6¹,$6^2$,$6^3$,$6^4$,$6^5$,$6^6$-hexahydro-1¹H-8-oxa-2(5,3)-thiadiazola-1(5,3)-indola-6(1,3)-pyridazinacycloundecaphane-4-yl)-3-methylbutanamide (40 mg, 37.2% yield) as a solid. LCMS (ESI): m/z [M+H] calc'd for $C_{42}H_{53}F_3N_8O_6S$ 855.38; found 855.3.

Step 20. To a solution of (2R)-2-((azetidin-3-yloxy)methyl)-N-(($6^3$S,4S,Z)-1²-(2-((S)-1-methoxyethyl)pyridin-3-yl)-10,10-dimethyl-5,7-dioxo-1¹-(2,2,2-trifluoroethyl)-6¹,$6^2$,$6^3$,$6^4$,$6^5$,$6^6$-hexahydro-1¹H-8-oxa-2(5,3)-thiadiazola-1(5,3)-indola-6(1,3)-pyridazinacycloundecaphane-4-yl)-3-methylbutanamide (32.0 mg, 0.037 mmol),4-(dimethylamino)-4-methylpent-2-ynoic acid (11.62 mg, 0.074 mmol) and DMF (0.50 mL) at 0° C. were added DIPEA (193.49 mg, 1.48 mmol) and COMU (19.23 mg, 0.044 mmol) in DMF (0.1 mL) dropwise. The resulting mixture was stirred for 2 h at room temperature under an argon atmosphere. The reaction was quenched with H₂O/Ice and extracted with EtOAc (3×20 mL). The organic phase was washed with brine (3×10 mL) and concentrated under reduced pressure. The crude product (60 mg) was purified by reverse phase chromatography to afford (2R)-2-(((1-(4-(dimethylamino)-4-methylpent-2-ynoyl)azetidin-3-yl)oxy)methyl)-N-(($6^3$S,4S,Z)-1²-(2-((S)-1-methoxyethyl)pyridin-3-yl)-10,10-dimethyl-5,7-dioxo-1¹-(2,2,2-trifluoroethyl)-6¹,$6^2$,$6^3$,$6^4$,$6^5$,$6^6$-hexahydro-1¹¹H-8-oxa-2(5,3)-thiadiazola-1(5,3)-indola-6(1,3)-pyridazinacycloundecaphane-4-yl)-3-methylbutanamide (11.7 mg, 30.9% yield) as a solid. ¹H NMR (400 MHz, DMSO-d₆) δ 8.80 (dd, J=4.7, 1.8 Hz, 1H), 8.58 (s, 1H), 8.30 (d, J=8.9 Hz, 1H), 7.92 (d, J=8.6 Hz, 1H), 7.84-7.69 (m, 2H), 7.56 (dd, J=7.8, 4.8 Hz, 1H), 5.78 (t, J=8.6 Hz, 2H), 5.10 (d, J=12.1 Hz, 1H), 4.91 (dd, J=16.9, 8.8 Hz, 1H), 4.31 (d, J=6.6 Hz, 6H), 4.05 (dd, J=16.3, 6.6 Hz, 2H), 3.87 (d, J=6.3 Hz, 1H), 3.75 (d, J=11.3 Hz, 1H), 3.61 (d, J=11.0 Hz, 1H), 3.53 (d, J=9.8 Hz, 1H), 3.45 (s, 3H), 3.25 (s, 1H), 3.09 (d, J=10.4 Hz, 1H), 3.01 (d, J=14.5 Hz, 1H), 2.79 (s, 1H), 2.45-2.35 (m, 2H), 2.20 (d, J=5.4 Hz, 6H), 2.15 (d, J=12.0 Hz, 1H), 1.81 (d, 2H), 1.74-1.65 (m, 1H), 1.54 (s, 1H), 1.41-1.30 (m, 9H), 1.24 (s, 1H), 0.94 (s, 3H), 0.90-0.81 (m, 5H), 0.29 (s, 3H). LCMS (ESI): m/z [M+H] calc'd for $C_{50}H_{64}F_3N_9O_7S$ 992.47; found 992.5.

The following table of compounds (Table 3) were prepared using the aforementioned methods or variations thereof, as is known to those of skill in the art.

TABLE 3

Exemplary Compounds Prepared by Methods of the Present Invention

| Ex# | LCMS (ESI): m/z [M + H] Found |
|---|---|
| A1 | 944.5 |
| A2 | 888.6 |
| A3 | 903.2 |
| A4 | 876.3 |
| A5 | 903.4 |
| A6 | 945.8 |
| A7 | 1058.1 |
| A8 | 960.8 |
| A9 | 921.7 |
| A10 | 928.8 |
| A11 | 936.4 |
| A12 | 942.5 |
| A13 | 932.5 |
| A14 | 917.5 |
| A15 | 961.5 |
| A16 | 890.6 |
| A17 | 875.4 |
| A18 | 918.5 |
| A19 | 975.6 |
| A20 | 934.5 |
| A21 | 903.3 |
| A22 | 903.6 |
| A23 | 844.6 |
| A24 | 887.6 |
| A25 | 921.4 |
| A26 | 930.4 |
| A27 | 915.6 |
| A28 | 890.6 |
| A29 | 903.5 |
| A30 | 902.7 |
| A31 | 901.4 |
| A32 | 1003.4 |
| A33 | 917.4 |
| A34 | 942.7 |
| A35 | 956.1 |
| A36 | 1005.5 |
| A37 | 917.5 |
| A38 | 959.5 |

TABLE 3-continued

Exemplary Compounds Prepared by
Methods of the Present Invention

| Ex# | LCMS (ESI): m/z [M + H] Found |
|---|---|
| A39 | 942.9 |
| A40 | 915.7 |
| A41 | 917.5 |
| A42 | 888.6 |
| A43 | 942.5 |
| A44 | 904.35 |
| A45 | 846.35 |
| A46 | 982.5 |
| A47 | 960.1 |
| A48 | 905.3 |
| A49 | 981.8 |
| A50 | 916.9 |
| A51 | 946.7 |
| A52 | 916.5 |
| A53 | 921.6 |
| A54 | 947.7 |
| A55 | 916.5 |
| A56 | 904.5 |
| A57 | 930.5 |
| A58 | 895.5 |
| A59 | 944.7 |
| A60 | 931.5 |
| A61 | 847.7 |
| A62 | 871.5 |
| A63 | 930.4 |
| A64 | 893.7 |
| A65 | 874.7 |
| A66 | 876.5 |
| A67 | 970.5 |
| A68 | 915.4 |
| A69 | 927.3 |
| A70 | 876.4 |
| A71 | 933.5 |
| A72 | 1003.5 |
| A73 | 903.6 |
| A74 | 885.5 |
| A75 | 904.7 |
| A76 | 904.5 |
| A77 | 860.6 |
| A78 | 1018.5 |
| A79 | 947.5 |
| A80 | 933.3 |
| A81 | 917.8 |
| A82 | 908.7 |
| A83 | 890.6 |
| A84 | 890.6 |
| A85 | 891.5 |
| A86 | 885.5 |
| A87 | 947.7 |
| A88 | 945.5 |
| A89 | 944.8 |
| A90 | 898 |
| A91 | 890.5 |
| A92 | 903.4 |
| A93 | 901.4 |
| A94 | 881.5 |
| A95 | 987.8 |
| A96 | 945.7 |
| A97 | 931.8 |
| A98 | 943.8 |
| A99 | 849.7 |
| A100 | 942.8 |
| A101 | 893.4 |
| A102 | 904.4 |
| A103 | 947.5 |
| A104 | 931.7 |
| A105 | 915.6 |
| A106 | 902.5 |
| A107 | 945.7 |
| A108 | 902.3 |
| A109 | 906.5 |
| A110 | 793.4 |
| A111 | 946.7 |
| A112 | 905.14 |
| A113 | 849.6 |
| A114 | 888.4 |
| A115 | 888.4 |
| A116 | 986.5 |
| A117 | 879.5 |
| A118 | 881.6 |
| A119 | 874.5 |
| A120 | 929.7 |
| A121 | 943.6 |
| A122 | 888.8 |
| A123 | 959.3 |
| A124 | 924.6 |
| A125 | 962.5 |
| A126 | 986.5 |
| A127 | 946.6 |
| A128 | 903.4 |
| A129 | 1001.2 |
| A130 | 930.5 |
| A131 | 959.5 |
| A132 | 940.5 |
| A133 | 969.7 |
| A134 | 990.5 |
| A135 | 933.5 |
| A136 | 875.4 |
| A137 | 889.5 |
| A138 | 929.4 |
| A139 | 930.4 |
| A140 | 943.7 |
| A141 | 943.8 |
| A142 | 901.7 |
| A143 | 852.3 |
| A144 | 886.7 |
| A145 | 916.7 |
| A146 | 963.4 |
| A147 | 864.4 |
| A148 | 885.5 |
| A149 | 947.5 |
| A150 | 902.7 |
| A151 | 904.5 |
| A152 | 885.5 |
| A153 | 949.6 |
| A154 | 907.5 |
| A155 | 944.5 |
| A156 | 943.7 |
| A157 | 943.5 |
| A158 | 904.5 |
| A159 | 904.5 |
| A160 | 858.5 |
| A161 | 947.4 |
| A162 | 973.5 |
| A163 | 989.4 |
| A164 | 947.5 |
| A165 | 960.3 |
| A166 | 907.7 |
| A167 | 918.5 |
| A168 | 907.4 |
| A169 | 859.4 |
| A170 | 874.3 |
| A171 | 867.5 |
| A172 | 883.6 |
| A173 | 900.5 |
| A174 | 848.4 |
| A175 | 959.5 |
| A176 | 944.5 |
| A177 | 935.4 |
| A178 | 930.4 |
| A179 | 849.5 |
| A180 | 849.5 |
| A181 | 918.8 |
| A182 | 1002.2 |
| A183 | 961.5 |
| A184 | 1003.5 |
| A185 | 928.5 |
| A186 | 992.5 |

TABLE 3-continued

Exemplary Compounds Prepared by Methods of the Present Invention

| Ex# | LCMS (ESI): m/z [M + H] Found |
|---|---|
| A187 | 945.5 |
| A188 | 960.4 |
| A189 | 1000.6 |
| A190 | 934.3 |
| A191 | 985.5 |
| A192 | 971.5 |
| A193 | 871.6 |
| A194 | 918.5 |
| A195 | 927.4 |
| A196 | 972.3 |
| A197 | 896.4 |
| A198 | 916.6 |
| A199 | 916.6 |
| A200 | 987.4 |
| A201 | 993.7 |
| A202 | 896.4 |
| A203 | 987.6 |
| A204 | 987.6 |
| A205 | 933.5 |
| A206 | 930.5 |
| A207 | 930.5 |
| A208 | 958.8 |
| A209 | 1015.7 |
| A210 | 906.5 |
| A211 | 905.5 |
| A212 | 901.3 |
| A213 | 969.5 |
| A214 | 933.6 |
| A215 | 890.3 |
| A216 | 916.4 |
| A217 | 930.5 |
| A218 | 983.5 |
| A219 | 917.4 |
| A220 | 996.5 |
| A221 | 915.4 |
| A222 | 930.05 |
| A223 | 920.01 |
| A224 | 983.5 |
| A225 | 982.7 |
| A226 | 873.7 |
| A227 | 887.7 |
| A228 | 911 |
| A229 | 896.7 |
| A230 | 905.5 |
| A231 | 912.4 |
| A232 | 849.4 |
| A233 | 905.4 |
| A234 | 1053.3 |
| A235 | 835.5 |
| A236 | 882.3 |
| A237 | 1015.4 |
| A238 | 971.5 |
| A239 | 869.4 |
| A240 | 884.4 |
| A241 | 987.4 |
| A242 | 877.4 |
| A243 | 863.5 |
| A244 | 1029.6 |
| A245 | 1029.5 |
| A246 | 501.4 |
| A247 | 985.5 |
| A248 | 896.4 |
| A249 | 984.5 |
| A250 | 927.4 |
| A251 | 985.5 |
| A252 | 927.3 |
| A253 | 990.4 |
| A254 | 933.3 |
| A255 | 930.7 |
| A256 | 890.4 |
| A257 | 947.4 |
| A258 | 990.3 |
| A259 | 933.3 |
| A260 | 918.4 |
| A261 | 975.5 |
| A262 | 919.4 |
| A263 | 976.5 |
| A264 | 990.5 |
| A265 | 933.5 |
| A266 | 945.5 |
| A267 | 987.5 |
| A268 | 973.5 |
| A269 | 487.3 |
| A270 | 959.4 |
| A271 | 861.3 |
| A272 | 847.6 |
| A273 | 861.6 |
| A274 | 930.5 |
| A275 | 916.3 |
| A276 | 892.8 |
| A277 | 895.7 |
| A278 | 879.5 |
| A279 | 895.4 |
| A280 | 954.6 |
| A281 | 916.6 |
| A282 | 952.5 |
| A283 | 931.4 |
| A284 | 889.5 |
| A285 | 839.4 |
| A286 | 877.4 |
| A287 | 894.7 |
| A288 | 879.3 |
| A289 | 908.7 |
| A290 | 971.6 |
| A291 | 978.5 |
| A292 | 987.5 |
| A293 | 921.4 |
| A294 | 902.8 |
| A295 | 916.4 |
| A296 | 930.8 |
| A297 | 938.4 |
| A298 | 952.6 |
| A299 | 966.7 |
| A300 | 919.6 |
| A301 | 907.7 |
| A302 | 895.8 |
| A303 | 895.4 |
| A304 | 897.5 |
| A305 | 968.6 |
| A306 | 968.7 |
| A307 | 952.6 |
| A308 | 952.7 |
| A309 | 933.6 |
| A310 | 926.8 |
| A311 | 944.7 |
| A312 | 897.5 |
| A313 | 976.5 |
| A314 | 893.3 |
| A316 | 930.5 |
| A317 | 982.6 |
| A318 | 883.5 |
| A319 | 916.5 |
| A320 | 886.6 |
| A321 | 900.6 |
| A322 | 1004.4 |
| A323 | 976.5 |
| A324 | 969.5 |
| A325 | 1033.7 |
| A326 | 997.5 |
| A327 | 906.6 |
| A328 | 986.7 |
| A329 | 890.5 |
| A330 | 895.6 |
| A331 | 879.5 |
| A332 | 942.5 |
| A333 | 919.6 |
| A334 | 930.7 |
| A335 | 924.5 |

TABLE 3-continued

Exemplary Compounds Prepared by
Methods of the Present Invention

| Ex# | LCMS (ESI): m/z [M + H] Found |
|---|---|
| A336 | 927.4 |
| A337 | 501.4 |
| A338 | 919.4 |
| A339 | 971.6 |
| A340 | 895.7 |
| A341 | 938.5 |
| A342 | 906.8 |
| A343 | 992.4 |
| A344 | 901.40 |
| A345 | 897.40 |
| A346 | 942.50 |
| A347 | 896.30 |
| A348 | 1,002.30 |
| A349 | 924.6 |
| A350 | 968.2 |
| A351 | 997.6 |
| A352 | 952.7 |
| A353 | 966.3 |
| A354 | 966.2 |
| A355 | 855.6 |
| A356 | 910.4 |
| A357 | 1091.0 |
| A358 | 902.5 |
| A359 | 904.7 |
| A360 | 924.5 |
| A361 | 967.5 |
| A362 | 936.6 |
| A363 | 961.4 |
| A364 | 946.5 |
| A365 | 995.6 |
| A366 | 921.5 |
| A367 | 950.6 |
| A368 | 924.5 |
| A369 | 924.5 |
| A370 | 1087.3 |
| A371 | 902.5 |
| A372 | 992.1 |
| A373 | 902.6 |
| A374 | 1,034.40 |
| A375 | 993.50 |
| A376 | 984.40 |
| A377 | 939.50 |
| A378 | 897.50 |
| A379 | 1005.6 |
| A380 | 949.4 |
| A381 | 921.5 |
| A382 | 938.5 |
| A383 | 938.5 |
| A384 | 924.5 |
| A385 | 938.3 |
| A386 | 938.4 |
| A387 | 938.5 |
| A388 | 938.5 |
| A389 | 936.5 |
| A390 | 924.5 |
| A391 | 1011.6 |
| A392 | 958.0 |
| A393 | 922.4 |
| A394 | 950.3 |
| A395 | 936.5 |
| A396 | 924.4 |
| A397 | 924.7 |
| A398 | 914.6 |
| A399 | 902.5 |
| A400 | 956.6 |
| A401 | 955.9 |
| A402 | 940.8 |
| A403 | 948.40 |
| A404 | 980.40 |
| A405 | 911.50 |
| A406 | 938.7 |
| A407 | 922.5 |
| A408 | 922.5 |
| A409 | 922.6 |
| A410 | 1046.9 |
| A411 | 990.7 |
| A412 | 912.7 |
| A413 | 914.7 |
| A414 | 983.5 |
| A415 | 950.5 |
| A416 | 924.6 |
| A417 | 936.7 |
| A418 | 938.5 |
| A419 | 922.3 |
| A420 | 936.7 |
| A421 | 924.5 |
| A422 | 910.5 |
| A423 | 1028.9 |
| A424 | 934.6 |
| A425 | 1012.5 |
| A426 | 912.5 |
| A427 | 895.30 |
| A428 | 951.30 |
| A429 | 911.50 |
| A430 | 938.5 |
| A431 | 952.3 |
| A432 | 924.2 |
| A433 | 924.2 |
| A434 | 924.7 |
| A435 | 910.5 |
| A436 | 924.6 |
| A437 | 912.5 |
| A438 | 898.5 |
| A439 | 1016.6 |
| A440 | 990.5 |
| A441 | 939.6 |
| A442 | 889.2 |
| A443 | 913.5 |
| A444 | 913.5 |
| A445 | 890.1 |
| A446 | 957.6 |
| A447 | 880.5 |
| A448 | 888.4 |
| A449 | 920.5 |
| A450 | 897.2 |
| A451 | 902.6 |
| A452 | 888.4 |
| A453 | 901.3 |
| A454 | 1044.6 |
| A455 | 949.2 |
| A456 | 1059.5 |
| A457 | 916.7 |
| A458 | 916.2 |
| A459 | 902.3 |
| A460 | 874.5 |
| A461 | 957.9 |
| A462 | 854.3 |
| A463 | 910.7 |
| A464 | 964.5 |
| A465 | 964.5 |
| A466 | 1033.7 |
| A467 | 874.5 |
| A468 | 879.6 |
| A469 | 902.6 |
| A470 | 900.6 |
| A471 | 900.6 |
| A472 | 964.6 |
| A473 | 854.3 |
| A474 | 914.4 |
| A475 | 914.40 |
| A476 | 983.6 |
| A477 | 907.5 |
| A478 | 900.5 |
| A479 | 993.6 |
| A480 | 902.2 |
| A481 | 930.6 |
| A482 | 974.6 |
| A483 | 847.5 |

TABLE 3-continued

Exemplary Compounds Prepared by Methods of the Present Invention

| Ex# | LCMS (ESI): m/z [M + H] Found |
|---|---|
| A484 | 847.4 |
| A485 | 938.4 |
| A486 | 893.5 |
| A487 | 900.6 |
| A488 | 888.5 |
| A489 | 962.6 |
| A490 | 896.5 |
| A491 | 910.2 |
| A492 | 910.5 |
| A493 | 910.5 |
| A494 | 886.3 |
| A495 | 907.5 |
| A496 | 900.4 |
| A497 | 902.7 |
| A498 | 902.6 |
| A499 | 998.7 |
| A500 | 897.5 |
| A501 | 906.3 |
| A502 | 949.2 |
| A503 | 920.6 |
| A504 | 920.8 |
| A505 | 920.0 |
| A506 | 879.3 |
| A507 | 897.4 |
| A508 | 942.4 |
| A509 | 942.4 |
| A510 | 899.3 |
| A511 | 919.5 |
| A512 | 900.5 |
| A513 | 983.7 |
| A514 | 983.7 |
| A515 | 985.7 |
| A516 | 985.7 |
| A517 | 892.6 |
| A518 | 920.6 |
| A519 | 920.4 |
| A520 | 990.6 |
| A521 | 990.6 |
| A522 | 945.3 |
| A523 | 945.4 |
| A524 | 914.5 |
| A525 | 914.4 |
| A526 | 1005.4 |
| A527 | 972.4 |
| A528 | 985.4 |
| A529 | 987.4 |
| A530 | 898.5 |
| A531 | 912.3 |
| A532 | 1013.6 |
| A533 | 999.3 |
| A534 | 983.4 |
| A535 | 919.5 |
| A536 | 961.7 |
| A537 | 961.6 |
| A538 | 999.7 |
| A539 | 960.4 |
| A540 | 1050.2 |
| A541 | 1078.7 |
| A542 | 1155.7 |
| A543 | 952.6 |
| A544 | 952.6 |
| A545 | 981.2 |
| A546 | 922.3 |
| A547 | 922.5 |
| A548 | 950.5 |
| A549 | 997.4 |
| A550 | 1025.6 |
| A551 | 997.5 |
| A552 | 950.4 |
| A553 | 974.6 |
| A554 | 957.5 |
| A555 | 1054.4 |
| A556 | 972.5 |
| A557 | 952.4 |
| A558 | 959.6 |
| A559 | 1011.7 |
| A560 | 1011.6 |
| A561 | 922.5 |
| A562 | 954.3 |
| A563 | 978.5 |
| A564 | 982.5 |
| A565 | 1039.3 |
| A566 | 1039.4 |
| A567 | 1039.4 |
| A568 | 1039.3 |
| A569 | 997.4 |
| A570 | 974.7 |
| A571 | 1038.5 |
| A572 | 1056.5 |
| A573 | 1063.5 |
| A574 | 990.6 |
| A575 | 1004.5 |
| A576 | 991.5 |
| A577 | 1062.3 |
| A578 | 1048.3 |
| A579 | 963.3 |
| A580 | 966.6 |
| A581 | 966.6 |
| A582 | 953.5 |
| A583 | 938.5 |
| A584 | 944.7 |
| A585 | 944.6 |
| A586 | 950.6 |
| A587 | 962.6 |
| A588 | 938.5 |
| A589 | 1016.6 |
| A590 | 992.5 |
| A591 | 1008.7 |
| A592 | 997.5 |
| A593 | 1020.5 |
| A594 | 1020.6 |
| A595 | 1000.6 |
| A596 | 966.7 |
| A597 | 946.6 |
| A598 | 979.6 |
| A599 | 958.7 |
| A600 | 887.4 |
| A601 | 985.5 |
| A602 | 1036.5 |
| A603 | 989.9 |
| A604 | 1006.1 |
| A605 | 1059.7 |
| A606 | 1032.6 |
| A607 | 1028.1 |
| A608 | 1027.1 |
| A609 | 966.6 |
| A610 | 945.6 |
| A611 | 1021.5 |
| A612 | 920.6 |
| A613 | 956.1 |
| A614 | 992.5 |
| A615 | 1010.5 |
| A616 | 1010.5 |
| A617 | 990.5 |
| A618 | 950.7 |
| A619 | 950.4 |
| A620 | 938.1 |
| A621 | 966.1 |
| A622 | 982.6 |
| A623 | 999.6 |
| A624 | 1019.5 |
| A625 | 1019.5 |
| A626 | 913.5 |
| A627 | 913.4 |
| A628 | 1046.5 |
| A629 | 952.2 |
| A630 | 967.6 |
| A631 | 942.5 |

TABLE 3-continued

Exemplary Compounds Prepared by
Methods of the Present Invention

| Ex# | LCMS (ESI): m/z [M + H] Found |
|---|---|
| A632 | 942.6 |
| A633 | 938.6 |
| A634 | 938.6 |
| A635 | 978.6 |
| A636 | 916.6 |
| A637 | 909.5 |
| A638 | 909.5 |
| A639 | 928.3 |
| A640 | 942.0 |
| A641 | 942.6 |
| A642 | 1047.5 |
| A643 | 966.6 |
| A644 | 944.4 |
| A645 | 986.5 |
| A646 | 937.5 |
| A647 | 1012.5 |
| A648 | 944.5 |
| A649 | 921.6 |
| A650 | 1007.6 |
| A651 | 964.2 |
| A652 | 1903.1 |
| A653 | 938.6 |
| A654 | 938.6 |
| A655 | 934.4 |
| A656 | 1005.5 |
| A657 | 960.7 |
| A658 | 1003.3 |
| A659 | 974.6 |
| A660 | 925.5 |
| A661 | 936.6 |
| A662 | 936.6 |
| A663 | 935.5 |
| A664 | 1047.5 |
| A665 | 1035.5 |
| A666 | 1035.2 |
| A667 | 936.3 |
| A668 | 965.6 |
| A669 | 1049.7 |
| A670 | 1047.7 |
| A671 | 964.6 |
| A672 | 997.9 |
| A673 | 1015.3 |
| A674 | 975.5 |
| A675 | 921.5 |
| A676 | 966.5 |
| A677 | 966.4 |
| A678 | 950.5 |
| A679 | 990.2 |
| A680 | 943.6 |
| A681 | 980.6 |
| A682 | 968.6 |
| A683 | 1000.6 |
| A684 | 915.0 |
| A685 | 977.6 |
| A686 | 922.5 |
| A687 | 936.4 |
| A688 | 936.5 |
| A689 | 1036.9 |
| A690 | 979.6 |
| A691 | 923.5 |
| A692 | 962.5 |
| A693 | 906.5 |
| A694 | 896.1 |
| A695 | 980.7 |
| A696 | 978.4 |
| A697 | 978.3 |
| A698 | 964.3 |
| A699 | 1003.3 |
| A700 | 927.2 |
| A701 | 993.7 |
| A702 | 950.6 |
| A703 | 985.5 |
| A704 | 938.6 |
| A705 | 925.5 |
| A706 | 952.5 |
| A707 | 1016.5 |
| A708 | 903.2 |
| A709 | 981.5 |
| A710 | 967.5 |
| A711 | 964.5 |
| A712 | 937.9 |
| A713 | 939.9 |
| A714 | 952.5 |
| A715 | 937.4 |
| A716 | 893.5 |
| A717 | 924.6 |
| A718 | 936.6 |
| A719 | 950.5 |
| A720 | 935.3 |
| A721 | 937.3 |
| A722 | 929.4 |
| A723 | 910.4 |
| A724 | 985.4 |
| A725 | 919.3 |
| A726 | 1010.4 |
| A727 | 1025.5 |
| A728 | 924.6 |
| A729 | 993.5 |
| A730 | 993.2 |
| A731 | 922.7 |
| A732 | 928.6 |
| A733 | 997.6 |
| A734 | 936.5 |
| A735 | 952.5 |
| A736 | 922.2 |
| A737 | 922.1 |
| A738 | 924.5 |
| A739 | 924.5 |
| A740 | 895.5 |
| A741 | 895.4 |

Blank = not determined

Matched Pair Analysis

Figure 1B:
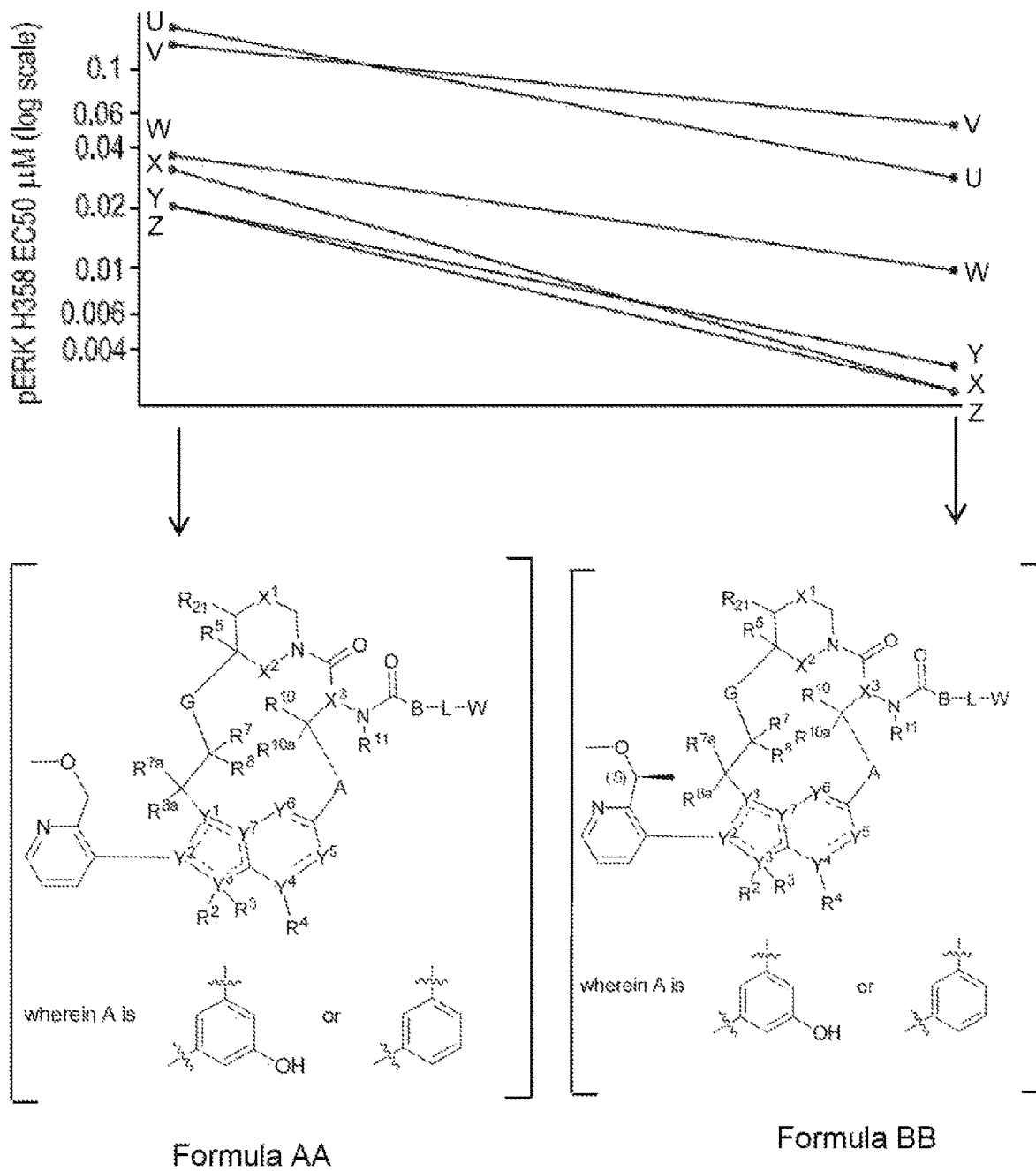

FIGS. 1A-1B compare the potency in two different cell-based assays of compounds of Formula BB of the present invention (points on the right) and corresponding compounds of Formula AA (points on the left) wherein a H is replaced with (S)Me. The y axes represent pERK EC50 (FIG. 1A) or CTG IC50 (FIG. 1B) as measured in an H358 cell line. Assay protocols are below. The linked points represent a matched pair that differs only between H and (S)Me substitution. Each compound of Formula BB demonstrated reduced potency in cell assays compared to the corresponding compound of Formula AA.

Biological Assays

Potency Assay: pERK

The purpose of this assay is to measure the ability of test compounds to inhibit K-Ras in cells. Activated K-Ras induces increased phosphorylation of ERK at Threonine 202 and Tyrosine 204 (pERK). This procedure measures a decrease in cellular pERK in response to test compounds. The procedure described below in NCI-H358 cells is applicable to K-Ras G12C.

Note: This protocol may be executed substituting other cell lines to characterize inhibitors of other RAS variants, including, for example, AsPC-1 (K-Ras G12D), Capan-1 (K-Ras G12V), or NCI-H1355 (K-Ras G13C).

NCI-H358 cells were grown and maintained using media and procedures recommended by the ATCC. On the day prior to compound addition, cells were plated in 384-well cell culture plates (40 µl/well) and grown overnight in a 37°

C., 5% $CO_2$ incubator. Test compounds were prepared in 10, 3-fold dilutions in DMSO, with a high concentration of 10 mM. On the day of assay, 40 nL of test compound was added to each well of cell culture plate using an Echo550 liquid handler (LabCyte®). Concentrations of test compound were tested in duplicate. After compound addition, cells were incubated 4 hours at 37° C., 5% $CO_2$. Following incubation, culture medium was removed and cells were washed once with phosphate buffered saline.

In some experiments, cellular pERK level was determined using the AlphaLISA SureFire Ultra p-ERK1/2 Assay Kit (PerkinElmer). Cells were lysed in 25 μL lysis buffer, with shaking at 600 RPM at room temperature. Lysate (10 μL) was transferred to a 384-well Opti-plate (PerkinElmer) and 5 μL acceptor mix was added. After a 2-hour incubation in the dark, 5 μL donor mix was added, plate was sealed, and incubated 2 hours at room temperature. Signal was read on an Envision plate reader (PerkinElmer) using standard AlphaLISA settings. Analysis of raw data was carried out in Excel (Microsoft) and Prism (GraphPad). Signal was plotted vs. the decadal logarithm of compound concentration, and $IC_{50}$ was determined by fitting a 4-parameter sigmoidal concentration response model.

In other experiments, cellular pERK was determined by In-Cell Western. Following compound treatment, cells were washed twice with 200 μL tris buffered saline (TBS) and fixed for 15 minutes with 150 μL 4% paraformaldehyde in TBS. Fixed cells were washed 4 times for 5 minutes with TBS containing 0.1% Triton X-100 (TBST) and then blocked with 100 μL Odyssey blocking buffer (LI-COR) for 60 minutes at room temperature. Primary antibody (pERK, CST-4370, Cell Signaling Technology) was diluted 1:200 in blocking buffer, and 50 μL was added to each well and incubated overnight at 4° C. Cells were washed 4 times for 5 minutes with TBST. Secondary antibody (IR-800CW rabbit, LI-COR, diluted 1:800) and DNA stain DRAQ5 (LI-COR, diluted 1:2000) were added and incubated 1-2 hours at room temperature. Cells were washed 4 times for 5 minutes with TBST. Plates were scanned on a Li—COR Odyssey CLx Imager. Analysis of raw data was carried out in Excel (Microsoft) and Prism (GraphPad). Signal was plotted vs. the decadal logarithm of compound concentration, and $IC_{50}$ was determined by fitting a 4-parameter sigmoidal concentration response model.

The following compounds exhibited a pERK EC50 of under 5 uM (H358 KRAS G12C): A48, A15, A272, A174, A163, A453, A447, A279, A240, A214, A225, A136, A226, A219, A228, A21, A12, A78, A424, A219, A378, A224, A4, A53, A187, A218, A213, A314, A220, A208, A24, A9, A126, A345, A46, A203, A210, A184, A469, A366, A113, A328, A693, A639, A364, A100, A249, A486, A307, A347, A33, A210, A192, A285, A468, A185, A612, A109, A284, A200, A2, A6, A606, A325, A139, A496, A393, A561, A125, A494, A547, A215, A258, A195, A259, A212, A637, A53, A63, A68, A178, A189, A205, A78, A254, A690, A563, A14, A19, A92, A576, A278, A331, A42, A67, A209, A350, A562, A652, A703, A623, A191, A241, A199, A193, A478, A251, A177, A222, A23, A59, A26, A211, A106, A279, A120, A7, A134, A521, A116, A467, A694, A729, A151, A110, A277, A340, A221, A723, A13, A442, A611, A50, A190, A553, A696, A211, A303, A613, A37, A146, A666, A688, A216, A390, A548, A238, A160, A183, A164, A451, A481, A524, A1, A186, A37, A635, A71, A269, A289, A489, A400, A731, A497, A568, A274, A253, A471, A720, A241, A179, A180, A426, A117, A363, A716, A423, A217, A708, A227, A3, A12, A8, A381, A84, A408, A85, A171, A263, A473, A258, A564, A118, A103, A565, A641, A655, A47, A11, A392, A169, A487, A640, A206, A449, A358, A192, A148, A4, A41, A5, A18, A301, A10, A65, A554, A159, A264, A99, A79, A142, A143, A25, A98, A80, A101, A730, A212, A359, A61, A441, A283, A413, A717, A145, A182, A62, A181, A233, A232, A634, A495, A34, A251, A539, A632, A54, A327, A37, A196, A607, A645, A35, A214, A225, A638, A40, A52, A268, A448, A575, A176, A593, A15, A17, A94, A170, A713, A93, A402, A64, A261, A399, A422, A214, A225, A625, A31, A119, A135, A281, A676, A709, A81, A32, A633, A39, A646, A662, A124, A732, A320, A81, A187, A354, A45, A570, A165, A66, A20, A455, A431, A270, A250, A457, A153, A404, A710, A541, A127, A373, A369, A557, A349, A598, A618, A60, A636, A499, A87, A156, A680, A477, A406, A330, A202, A535, A617, A737, A201, A302, A722, A209, A374, A631, A29, A555, A420, A380, A111, A306, A173, A628, A672, A51, A167, A588, A512, A194, A282, A412, A701, A583, A396, A678, A649, A27, A204, A626, A257, A614, A409, A172, A372, A353, A58, A728, A74, A619, A144, A183, A538, A445, A531, A360, A361, A459, A536, A344, A267, A574, A677, A530, A415, A30, A73, A152, A490, A702, A714, A483, A567, A43, A310, A319, A86, A321, A656, A739, A115, A130, A155, A608, A648, A168, A485, A738, A129, A650, A715, A488, A147, A121, A470, A115, A133, A510, A421, A309, A335, A387, A386, A734, A95, A430, A604, A458, A592, A384, A664, A197, A725, A89, A83, A586, A622, A305, A498, A668, A427, A630, A158, A644, A735, A70, A683, A352, A341, A719, A674, A70, A44, A501, A438, A698, A377, A417, A154, A433, A104, A184, A603, A280, A712, A237, A105, A394, A605, A517, A704, A566, A77, A356, A454, A600, A643, A112, A569, A529, A247, A463, A437, A718, A472, A461, A558, A48, A671, A395, A670, A681, A687, A382, A82, A686, A342, A436, A296, A16, A545, A533, A416, A149, A207, A371, A596, A675, A132, A419, A56, A579, A733, A573, A707, A597, A697, A75, A653, A362, A615, A332, A69, A162, A128, A432, A654, A22, A397, A526, A582, A418, A91, A260, A97, A191, A55, A581, A375, A522, A108, A367, A610, A552, A571, A57, A543, A661, A138, A196, A246, A337, A446, A265, A96, A509, A123, A627, A651, A682, A157, A572, A624, A691, A532, A462, A580, A695, A186, A316, A540, A590, A665, A244, A166, A587, A629, A595, A518, A519, A131, A502, A726, A452, A141, A181, A262, A338, A155, A389, A124, A275, A414, A546, A679, A425, A669, A28, A520, A88, A131, A589, A621, A182, A297, A594, A283, A194, A250, A336, A706, A252, A440, A107, A724, A525, A388, A175, A300, A333, A659, A346, A150, A476, A368, A528, A503, A504, A505, A684, A76, A736, A551, A383, A491, A492, A493, A410, A316, A295, A559, A511, A38, A140, A663, A334, A700, A692, A348, A584, A513, A657, A328, A515, A317, A135, A660, A351, A544, A281, A685, A602, A556, A385, A326, A464, A465, A403, A133, A299, A667, A255, A334, A256, A585, A642, A133, A443, A435, A560, A444, A439, A324, A120, A407, A527, A245, A370, A537, A247, A474, A475, A705, A323, A112, A298, A609, A673, A292, A599, A132, A145, A266, A601, A466, A549, A379, A727, A167, A711, A75, A76, A121, A357, A620, A316, A479, A290, A339, A322, A376, A456, A391, A291, A550, A343, A721, A689, A411, A578, A616, A534, A365, A658, A699, A577, A647, A591, A542, A279, A294.

Determination of Cell Viability in RAS Mutant Cancer Cell Lines
Protocol: CellTiter-Glo® Cell Viability Assay Note—The following protocol describes a procedure for monitoring cell viability of K-Ras mutant cancer cell lines in response to a compound of the invention. Other RAS isoforms may be employed, though the number of cells to be seeded will vary based on cell line used.

The purpose of this cellular assay was to determine the effects of test compounds on the proliferation of three human cancer cell lines (NCI-H358 (K-Ras G12C), AsPC-1 (K-Ras G12D), and Capan-1 (K-Ras G12V)) over a 5-day treatment period by quantifying the amount of ATP present at endpoint using the CellTiter-Glo® 2.0 Reagent (Promega).

Cells were seeded at 250 cells/well in 40 µL of growth medium in 384-well assay plates and incubated overnight in a humidified atmosphere of 5% $CO_2$ at 37° C. On the day of the assay, 10 mM stock solutions of test compounds were first diluted into 3 mM solutions with 100% DMSO. Well-mixed compound solutions (15 µL) were transferred to the next wells containing 30 µL of 100% DMSO, and repeated until a 9-concentration 3-fold serial dilution was made (starting assay concentration of 10 µM). Test compounds (132.5 nL) were directly dispensed into the assay plates containing cells. The plates were shaken for 15 seconds at 300 rpm, centrifuged, and incubated in a humidified atmosphere of 5% $CO_2$ at 37° C. for 5 days. On day 5, assay plates and their contents were equilibrated to room temperature for approximately 30 minutes. CellTiter-Glo® 2.0 Reagent (25 µL) was added, and plate contents were mixed for 2 minutes on an orbital shaker before incubation at room temperature for 10 minutes. Luminescence was measured using the PerkinElmer Enspire. Data were normalized by the following: (Sample signal/Avg. DMSO)*100. The data were fit using a four-parameter logistic fit.

Disruption of B-Raf Ras-Binding Domain ($BRAF^{RBD}$) Interaction with K-Ras by Compounds of the Invention (Also Called a FRET Assay or an MOA Assay)

Note—The following protocol describes a procedure for monitoring disruption of K-Ras G12C (GMP-PNP) binding to $BRAF^{RBD}$ by a compound of the invention. This protocol may also be executed substituting other Ras proteins or nucleotides.

The purpose of this biochemical assay was to measure the ability of test compounds to facilitate ternary complex formation between a nucleotide-loaded K-Ras isoform and Cyclophilin A; the resulting ternary complex disrupts binding to a $BRAF^{RBD}$ construct, inhibiting K-Ras signaling through a RAF effector. Data is reported as IC50 values.

In assay buffer containing 25 mM HEPES pH 7.3, 0.002% Tween20, 0.1% BSA, 100 mM NaCl and 5 mM $MgCl_2$, tagless Cyclophilin A, His6-K-Ras-GMPPNP, and GST-$BRAF^{RBD}$ were combined in a 384-well assay plate at final concentrations of 25 µM, 12.5 nM and 50 nM, respectively. Compound was present in plate wells as a 10-point 3-fold dilution series starting at a final concentration of 30 µM. After incubation at 25° C. for 3 hours, a mixture of Anti-His Eu-W1024 and anti-GST allophycocyanin was then added to assay sample wells at final concentrations of 10 nM and 50 nM, respectively, and the reaction incubated for an additional 1.5 hours. TR-FRET signal was read on a microplate reader (Ex 320 nm, Em 665/615 nm). Compounds that facilitate disruption of a K-Ras:RAF complex were identified as those eliciting a decrease in the TR-FRET ratio relative to DMSO control wells.

TABLE 4

Biological Assay Data for Representative Compounds of the Present Invention

| Ex# | H358 pERK (K-Ras G12C) EC50, uM | H358 Cell Viability (K-Ras G12C) IC50, uM | FRET (K-Ras G12C) IC50, uM | FRET (K-Ras G13C) IC50, uM |
|---|---|---|---|---|
| A208 | 0.013 | 0.004 | 0.023 | 7.48 |
| A193 | 0.067 | 0.054 | 0.295 | 10.2 |
| A186 | 0.013 | 0.005 | 0.038 | 0.94 |
| A89a | 0.003 | 0.0008 | 0.009 | 0.82 |
| A89b | 0.028 | 0.011 | 0.034 | 0.58 |

TABLE 5

Additional H358 Cell Viability assay data (K-Ras G12C, IC50, uM):

| IC50* | Examples |
|---|---|
| + | A104, A107, A108, A112, A120, A121, A123, A124, A128, A131, A131, A132, A133, A133, A135, A138, A140, A141, A145, A150, A155, A157, A162, A166, A167, A175, A181, A182, A183, A186, A191, A194, A196, A237, A244, A245, A246, A247, A250, A255, A256, A260, A266, A275, A28, A281, A283, A290, A291, A292, A295, A296, A298, A299, A300, A309, A316, A316, A316, A317, A322, A323, A324, A326, A328, A332, A333, A334, A334, A336, A337, A339, A343, A344, A346, A348, A351, A352, A356, A357, A365, A368, A370, A371, A375, A376, A377, A379, A38, A380, A382, A383, A384, A385, A388, A389, A391, A394, A395, A396, A397, A403, A407, A410, A411, A414, A416, A419, A425, A427, A435, A439, A440, A443, A444, A445, A446, A452, A454, A456, A461, A462, A463, A464, A465, A466, A472, A474, A475, A476, A479, A483, A485, A488, A491, A492, A493, A502, A503, A504, A505, A509, A511, A513, A515, A517, A518, A519, A520, A522, A525, A526, A527, A528, A532, A533, A534, A537, A540, A542, A543, A544, A546, A549, A55, A550, A551, A552, A556, A559, A56, A560, A566, A567, A57, A571, A572, A577, A578, A579, A581, A584, A585, A587, A589, A590, A591, A592, A594, A595, A596, A597, A599, A600, A601, A602, A604, A609, A610, A615, A616, A620, A621, A624, A627, A629, A631, A636, A642, A643, A644, A647, A657, A658, A659, A660, A661, A663, A665, A667, A673, A674, A675, A677, A684, A685, A686, A689, A691, A692, A699, A700, A704, A705, A706, A707, A711, A712, A714, A718, A721, A724, A726, A727, A733, A735, A736, A738, A75, A76, A76, A88, A91, A96 |
| ++ | A10, A105, A111, A112, A115, A115, A119, A12, A121, A124, A129, A130, A132, A133, A135, A143, A144, A145, A147, A149, A15, A152, A154, A155, A156, A158, A16, A165, A167, A168, A172, A173, A176, A181, A182, A184, A187, A194, A197, A20, A201, A202, A204, A207, A209, A212, A214, A214, A22, A225, A225, A232, A233, A238, A241, A247, A250, A251, A252, A257, A261, A262, A264, A265, A267, A268, A269, A27, A270, A280, A281, A282, A283, A297, A30, A302, A305, A306, A31, A310, A319, A320, A321, A327, A330, A335, A338, A34, A341, A342, A349, A35, A353, A354, A358, A359, A360, A361, A362, A363, A367, A369, A37, A372, A373, A374, A381, A386, A387, A39, A392, A393, A399, A40, A400, A402, A404, A406, A408, A409, A41, A412, A413, A415, A417, A418, A420, A421, A422, A423, A426, A43, A430, A431, A432, A433, A436, A437, A438, A44, A441, A442, A448, A449, A45, A451, A455, A457, A458, A459, A467, A468, A47, A470, A471, A473, A477, A478, A48, A481, A487, A489, A490, A495, A497, A498, A499, A5, A501, A51, A510, A512, A52, A524, A529, A530, A531, A535, A536, A538, A54, A541, A545, A555, A558, A564, A565, A568, A569, A573, A574, A575, |

TABLE 5-continued

Additional H358 Cell Viability assay data (K-Ras G12C, IC50, uM):

| IC50* | Examples |
|---|---|
|  | A58, A580, A582, A583, A586, A588, A598, A60, A603, A605, A607, A608, A61, A611, A613, A614, A617, A618, A619, A62, A622, A623, A625, A626, A628, A630, A633, A634, A637, A638, A64, A640, A641, A645, A646, A648, A649, A650, A651, A653, A654, A655, A656, A66, A662, A664, A666, A668, A669, A670, A671, A672, A676, A678, A679, A680, A681, A682, A683, A687, A69, A694, A695, A697, A698, A70, A70, A701, A702, A703, A708, A709, A710, A713, A715, A716, A717, A719, A720, A722, A723, A725, A728, A73, A730, A732, A734, A737, A739, A74, A75, A79, A81, A82, A83, A86, A87, A89, A93, A94, A95, A97, A98, A99 |
| +++ | A1, A100, A101, A103, A106, A109, A11, A110, A113, A114, A116, A117, A118, A120, A127, A13, A134, A139, A14, A142, A144, A146, A148, A151, A153, A159, A160, A164, A169, A17, A170, A171, A177, A18, A183, A185, A186, A19, A190, A191, A192, A192, A193, A195, A196, A199, A200, A205, A206, A209, A210, A211, A211, A212, A215, A216, A217, A219, A219, A221, A222, A226, A227, A23, A241, A249, A25, A251, A253, A254, A258, A258, A259, A26, A263, A274, A277, A278, A279, A284, A289, A29, A3, A301, A303, A304, A304, A304, A304, A308, A314, A32, A325, A328, A329, A33, A331, A340, A345, A347, A350, A355, A364, A366, A37, A37, A378, A390, A398, A4, A401, A42, A424, A447, A453, A469, A482, A484, A486, A494, A496, A50, A506, A507, A508, A514, A521, A523, A53, A53, A539, A547, A548, A553, A554, A557, A561, A562, A563, A570, A576, A59, A593, A6, A606, A612, A63, A632, A635, A639, A65, A652, A67, A68, A688, A690, A693, A696, A7, A71, A729, A731, A78, A8, A80, A81, A84, A85, A9, A92 |
| ++++ | A102, A12, A122, A125, A126, A136, A137, A148, A15, A161, A163, A174, A178, A179, A180, A184, A187, A188, A189, A198, A2, A203, A208, A21, A210, A210, A210, A211, A211, A213, A213, A214, A214, A215, A216, A217, A218, A220, A220, A221, A222, A223, A223, A224, A224, A225, A225, A228, A229, A230, A231, A231, A234, A235, A236, A239, A239, A24, A240, A242, A243, A248, A261, A271, A272, A273, A276, A279, A279, A283, A285, A286, A287, A288, A293, A307, A311, A312, A313, A318, A318, A32, A4, A405, A428, A429, A450, A46, A460, A48, A480, A49, A500, A516, A72, A78, A90 |

*Key:
++++: IC50 ≥ 1 uM
+++: 1 uM > IC50 ≥ 0.1 uM
++: 0.1 uM > IC50 ≥ 0.01 uM
+: IC50 < 0.01 uM

Additional Ras-Raf Disruption/FRET/MOA Assay Data (IC50, uM):

TABLE 6

| IC50* | Examples |
|---|---|
| + | none |
| ++ | A028, A075, A076, A076, A087, A112, A145, A155, A167, A181, A183, A184, A194, A233, A255, A256, A260, A262, A264, A265, A266, A268, A270, A275, A292, A294, A295, A298, A299, A300, A319, A333, A334, A334, A338, A367, A382, A383, A385, A388, A389, A418, A433, A464, A465, A479, A491, A492, A493, A527, A537, A542, A577, A596, A598, A602, A609, A621, A629, A664, A665, A679, A712, A734, A736 |

TABLE 6-continued

KRAS G12S FRET data

| IC50* | Examples |
|---|---|
| +++ | A004, A005, A012, A015, A016, A022, A027, A029, A032, A034, A037, A037, A041, A043, A044, A047, A048, A051, A052, A054, A055, A056, A057, A058, A064, A070, A070, A072, A074, A077, A079, A082, A083, A086, A088, A091, A093, A095, A096, A097, A101, A103, A105, A107, A123, A127, A128, A129, A131, A132, A135, A141, A147, A148, A149, A150, A153, A154, A158, A164, A166, A178, A182, A189, A193, A194, A196, A206, A207, A237, A241, A244, A245, A246, A247, A250, A251, A252, A257, A261, A261, A263, A267, A269, A280, A281, A281, A296, A297, A305, A306, A328, A336, A337, A349, A350, A351, A353, A354, A357, A360, A361, A368, A369, A379, A384, A386, A387, A393, A394, A395, A397, A406, A407, A408, A409, A410, A415, A416, A417, A419, A420, A421, A430, A431, A432, A435, A436, A437, A438, A443, A455, A463, A470, A490, A502, A515, A517, A518, A519, A529, A536, A538, A539, A541, A543, A544, A545, A548, A554, A555, A557, A558, A560, A564, A570, A571, A572, A573, A575, A578, A580, A581, A582, A583, A586, A591, A594, A603, A604, A605, A606, A608, A611, A612, A618, A620, A622, A624, A625, A630, A631, A632, A633, A634, A635, A636, A650, A651, A653, A654, A655, A656, A659, A661, A662, A667, A668, A669, A670, A671, A672, A677, A678, A680, A681, A682, A683, A684, A685, A686, A687, A689, A690, A695, A696, A697, A698, A699, A700, A701, A702, A704, A709, A710, A711, A713, A714, A717, A718, A719, A728, A729, A730, A731, A732, A737 |
| ++++ | A001, A003, A006, A007, A008, A010, A013, A014, A017, A018, A019, A020, A025, A030, A031, A033, A035, A036, A038, A039, A040, A045, A050, A053, A060, A061, A062, A063, A066, A067, A068, A069, A071, A073, A075, A081, A081, A089, A092, A098, A099, A104, A108, A109, A110, A111, A112, A113, A115, A115, A117, A119, A120, A121, A124, A125, A131, A132, A133, A133, A134, A135, A137, A140, A143, A145, A146, A151, A155, A159, A161, A162, A167, A168, A169, A172, A173, A175, A176, A179, A180, A181, A182, A183, A184, A186, A187, A197, A199, A202, A204, A209, A210, A211, A212, A213, A214, A214, A215, A216, A217, A221, A223, A225, A225, A226, A227, A238, A241, A247, A249, A250, A251, A253, A254, A258, A258, A259, A277, A278, A282, A283, A290, A291, A301, A302, A309, A310, A314, A317, A320, A321, A324, A325, A326, A327, A330, A331, A332, A335, A339, A340, A341, A342, A343, A344, A347, A348, A356, A358, A359, A363, A364, A365, A366, A370, A371, A372, A373, A376, A378, A380, A381, A390, A391, A392, A396, A399, A401, A402, A411, A412, A413, A414, A422, A423, A424, A425, A426, A427, A439, A440, A442, A444, A445, A446, A447, A449, A451, A452, A454, A456, A457, A458, A459, A461, A462, A466, A468, A469, A471, A472, A473, A474, A475, A476, A481, A485, A487, A488, A489, A495, A498, A499, A501, A503, A504, A505, A506, A507, A509, A510, A511, A512, A513, A520, A521, A522, A525, A526, A528, A530, A531, A532, A533, A534, A535, A540, A546, A547, A549, A550, A551, A552, A553, A559, A561, A562, A563, A565, A566, A567, A568, A569, A574, A579, A585, A588, A590, A592, A593, A595, A597, A600, A601, A607, A610, A616, A619, A623, A626, A628, A637, A638, A639, A640, A641, A642, A645, A647, A652, A658, A660, A673, A676, A688, A691, A692, A693, A694, A705, A706, A707, A716, A720, A722, A723, A725, A726, A727, A733, A738, A739 |
| +++++ | A002, A004, A009, A011, A012, A015, A021, A023, A024, A026, A032, A036, A037, A038, A042, A046, A048, A049, A053, A059, A065, A078, A078, A080, A084, A085, A090, A094, A100, A102, A106, A114, A116, A118, A120, A121, A122, A124, A126, A130, A133, A136, A138, A139, A142, A144, A144, A148, A152, A156, A157, A160, A163, A165, A170, A171, A174, A177, A185, A186, A187, A188, A190, A191, |

TABLE 6-continued

KRAS G12S FRET data

| IC50* | Examples |
|---|---|
|  | A191, A192, A192, A195, A196, A198, A200, A201, A203, A205, A208, A209, A210, A210, A210, A211, A211, A211, A212, A213, A214, A214, A215, A216, A217, A218, A218, A219, A219, A219, A219, A220, A220, A221, A222, A222, A223, A224, A224, A225, A225, A228, A229, A230, A231, A231, A231, A232, A234, A235, A236, A239, A239, A240, A242, A243, A248, A271, A272, A273, A274, A276, A279, A279, A279, A283, A283, A284, A285, A286, A287, A288, A289, A293, A303, A304, A304, A304, A307, A308, A311, A312, A313, A316, A316, A316, A318, A318, A322, A323, A328, A329, A345, A346, A352, A355, A362, A374, A375, A377, A398, A400, A403, A404, A405, A428, A429, A441, A448, A450, A453, A460, A467, A477, A478, A480, A482, A483, A484, A486, A494, A496, A497, A500, A508, A514, A516, A523, A524, A556, A576, A584, A587, A589, A599, A613, A614, A615, A617, A627, A643, A644, A646, A648, A649, A657, A663, A666, A674, A675, A703, A708, A715, A721, A724, A735 |

+++++: IC50 ≥ 10 uM
++++: 10 uM > IC50 ≥ 1 uM
+++: 1 uM > IC50 ≥ 0.1 uM
++: 0.1 uM > IC50 ≥ 0.01 uM
+: IC50 < 0.01 uM

TABLE 7

KRAS G12D FRET data

| IC50* | Examples |
|---|---|
| + | none |
| ++ | A183, A264, A265, A268, A319, A388, A464, A465, A664 |
| +++ | A028, A054, A075, A076, A076, A087, A107, A112, A123, A131, A145, A153, A155, A167, A184, A189, A194, A233, A247, A255, A256, A257, A260, A261, A262, A263, A266, A269, A270, A275, A292, A294, A295, A298, A300, A333, A334, A334, A338, A349, A353, A354, A367, A368, A382, A383, A384, A385, A386, A387, A389, A394, A407, A409, A417, A418, A432, A433, A436, A479, A491, A492, A493, A527, A529, A537, A542, A555, A577, A578, A594, A596, A598, A602, A603, A605, A608, A609, A612, A621, A622, A629, A633, A650, A651, A653, A654, A662, A665, A667, A669, A671, A678, A679, A681, A682, A683, A685, A696, A697, A698, A700, A701, A704, A709, A710, A711, A712, A719, A734, A736, A737 |
| ++++ | A005, A007, A012, A015, A016, A022, A029, A034, A037, A037, A038, A038, A039, A043, A044, A046, A047, A048, A051, A052, A055, A056, A057, A058, A067, A070, A070, A071, A072, A074, A077, A079, A082, A086, A088, A090, A091, A093, A096, A097, A101, A103, A105, A108, A110, A116, A120, A120, A121, A121, A127, A128, A129, A130, A131, A132, A133, A133, A133, A134, A135, A138, A139, A140, A141, A142, A144, A144, A147, A148, A149, A150, A152, A154, A155, A156, A157, A162, A163, A164, A166, A175, A178, A179, A180, A181, A182, A183, A194, A196, A207, A213, A218, A218, A220, A224, A224, A237, A241, A244, A245, A246, A247, A250, A251, A252, A253, A254, A258, A261, A267, A280, A281, A282, A296, A297, A299, A305, A306, A314, A326, A328, A330, A332, A336, A337, A341, A342, A350, A351, A356, A357, A358, A360, A361, A365, A366, A369, A370, A373, A379, A380, A381, A390, A393, A395, A396, A397, A406, A408, A410, A411, A412, A415, A416, A419, A420, A421, A422, A430, A431, A435, A437, A438, A440, A443, A444, A451, A454, A455, A456, A459, A463, A470, A476, A487, A488, A490, A499, A501, A502, A503, A504, A505, A510, A513, A515, A517, A518, A519, A520, A525, A534, A536, A538, A539, A541, A543, A544, A545, A546, A547, A548, A550, A551, A552, A553, A554, A557, A558, A559, A560, A561, A562, A564, A566, A567, A570, A571, A572, A573, A575, A580, A581, A582, A583, A586, A588, A591, A593, A595, A600, A604, A606, A607, A610, A611, A618, A619, A620, A623, A624, A625, A626, A630, A631, A632, A634, A635, A636, A640, A645, A647, A655, A656, A658, A659, A660, A661, A668, A670, A672, A673, A676, A677, A680, A684, A686, A687, A688, A689, A690, A691, A694, A695, A699, A702, A707, A713, A714, A717, A718, A722, A727, A728, A729, A730, A731, A732, A738, A739 |
| +++++ | A001, A002, A003, A004, A004, A006, A008, A009, A010, A011, A012, A013, A014, A015, A017, A018, A019, A020, A021, A023, A024, A025, A026, A027, A030, A031, A032, A032, A033, A035, A036, A036, A037, A040, A041, A042, A045, A048, A049, A050, A053, A053, A059, A060, A061, A062, A063, A064, A065, A066, A068, A069, A073, A075, A078, A078, A080, A081, A081, A083, A084, A085, A089, A092, A094, A095, A098, A099, A100, A102, A104, A106, A109, A111, A112, A113, A114, A115, A115, A117, A118, A119, A122, A124, A124, A125, A126, A132, A135, A136, A137, A143, A145, A146, A148, A151, A158, A159, A160, A161, A165, A167, A168, A169, A170, A171, A172, A173, A174, A176, A177, A181, A182, A184, A185, A186, A186, A187, A187, A188, A190, A191, A191, A192, A192, A193, A195, A196, A197, A198, A199, A200, A201, A202, A203, A204, A205, A206, A208, A209, A209, A210, A210, A210, A210, A211, A211, A211, A211, A212, A212, A213, A214, A214, A214, A214, A215, A215, A216, A216, A217, A217, A219, A219, A219, A219, A220, A221, A221, A222, A222, A223, A223, A225, A225, A225, A225, A226, A227, A228, A229, A230, A231, A231, A231, A232, A234, A235, A236, A238, A239, A239, A240, A241, A242, A243, A248, A249, A250, A251, A258, A259, A271, A272, A273, A274, A276, A277, A278, A279, A279, A279, A283, A283, A283, A284, A285, A286, A287, A288, A289, A290, A291, A293, A301, A302, A303, A304, A304, A304, A304, A307, A308, A309, A310, A311, A312, A313, A316, A316, A316, A317, A318, A318, A320, A321, A322, A323, A324, A325, A327, A328, A329, A331, A335, A339, A340, A343, A344, A345, A346, A347, A348, A352, A355, A359, A362, A363, A364, A371, A372, A374, A375, A376, A377, A378, A391, A392, A398, A399, A400, A401, A402, A403, A404, A405, A413, A414, A423, A424, A425, A426, A427, A428, A429, A439, A441, A442, A445, A446, A447, A448, A449, A450, A452, A453, A457, A458, A460, A461, A462, A466, A467, A468, A469, A471, A472, A473, A474, A475, A477, A478, A480, A481, A482, A483, A484, A485, A486, A489, A494, A495, A496, A497, A498, A500, A506, A507, A508, A509, A511, A512, A514, A516, A521, A522, A523, A524, A526, A528, A530, A531, A532, A533, A535, A540, A549, A556, A563, A565, A568, A569, A574, A576, A579, A584, A585, A587, A589, A590, A592, A597, A599, A601, A613, A614, A615, A616, A617, A627, A628, A637, A638, A639, A641, A642, A643, A644, A646, A648, A649, A652, A657, A663, A666, A674, A675, A692, A693, A703, A705, A706, A708, A715, A716, A720, A721, A723, A724, A725, A726, A733, A735 |

TABLE 8

KRAS G13C FRET data

| IC50* | Examples |
|---|---|
| + | A088, A096, A097, A107, A131, A132, A155, A175, A247, A250, A251, A252, A253, A255, A258, A262, A270, A292, A294, A297, A298, A299, A334, A336, A338, A474, A475, A529, A542, A683 |
| ++ | A031, A037, A038, A046, A067, A069, A071, A075, A076, A076, A090, A108, A112, A116, A121, A123, A124, A131, A132, A133, A133, A135, A140, A141, A145, A150, A155, A163, A167, A172, A178, A182, A183, A194, A196, A218, A224, A233, A244, A245, A246, A247, A249, A250, A251, A254, A256, A257, A258, A259, A260, A261, A263, A264, A265, A266, A267, A268, A275, A280, A281, A283, A295, A296, A300, A305, A306, A319, A333, A334, A337, A379, A383, A385, A388, A389, A394, A396, A397, A417, A418, A421, A432, A433, A438, A452, A464, A465, A479, A491, A492, A493, A517, A525, A527, A537, A538, A539, A540, A541, A545, A546, A552, A553, A554, A555, A564, A570, A571, A572, A573, A574, A575, A577, A578, A591, A594, A595, A597, A600, A602, A603, A604, A605, A606, A607, A608, A609, A610, A621, A622, A629, A630, A632, A650, A664, A668, A679, A680, A695, A698, A699, A706, A711, A714, A718, A719, A734, A736, A737 |
| +++ | A005, A012, A013, A016, A018, A022, A027, A028, A029, A033, A036, A037, A038, A043, A044, A047, A048, A049, A052, A054, A055, A056, A057, A070, A070, A072, A074, A077, A082, A086, A087, A091, A093, A095, A101, A105, A110, A117, A120, A125, A126, A127, A128, A129, A130, A135, A138, A142, A146, A147, A149, A153, A157, A158, A162, A164, A165, A166, A179, A180, A181, A184, A189, A196, A199, A207, A209, A213, A216, A218, A220, A220, A222, A224, A232, A237, A238, A241, A241, A261, A269, A277, A281, A302, A314, A322, A323, A324, A328, A332, A340, A341, A342, A344, A349, A350, A351, A353, A354, A356, A357, A358, A360, A361, A365, A366, A367, A368, A369, A370, A371, A372, A373, A380, A382, A384, A386, A387, A390, A393, A395, A401, A406, A407, A408, A409, A410, A411, A412, A415, A416, A419, A420, A422, A423, A425, A430, A431, A435, A436, A437, A439, A440, A443, A444, A445, A449, A451, A454, A455, A457, A458, A459, A463, A466, A470, A471, A476, A485, A487, A488, A490, A497, A501, A502, A503, A504, A505, A509, A510, A513, A515, A518, A519, A524, A534, A536, A543, A544, A547, A549, A550, A551, A557, A558, A559, A560, A561, A562, A563, A566, A567, A576, A580, A581, A582, A583, A586, A593, A596, A598, A601, A611, A612, A618, A619, A620, A624, A625, A631, A633, A634, A635, A636, A640, A642, A645, A647, A651, A652, A653, A654, A655, A658, A659, A660, A661, A662, A665, A667, A669, A670, A671, A672, A673, A678, A681, A682, A684, A685, A686, A687, A688, A689, A690, A692, A694, A696, A697, A700, A701, A702, A704, A707, A709, A710, A712, A717, A722, A725, A726, A727, A728, A729, A730, A731, A732, A733, A738, A739 |
| ++++ | A001, A003, A004, A006, A007, A008, A010, A014, A015, A017, A019, A020, A025, A030, A032, A034, A035, A039, A040, A041, A045, A051, A058, A060, A061, A063, A064, A068, A073, A075, A078, A078, A079, A081, A081, A083, A089, A092, A098, A099, A103, A104, A111, A112, A115, A115, A119, A120, A121, A124, A133, A134, A139, A144, A144, A145, A148, A152, A154, A156, A161, A167, A168, A169, A170, A171, A174, A176, A181, A182, A183, A186, A187, A191, A193, A194, A197, A200, A201, A204, A206, A212, A213, A214, A214, A217, A221, A225, A225, A225, A227, A235, A242, A278, A279, A282, A283, A283, A284, A289, A290, A291, A301, A307, A308, A309, A310, A316, A316, A317, A320, A321, A325, A326, A327, A330, A331, A335, A339, A343, A345, A346, A347, A348, A359, A362, A363, A364, A375, A376, A377, A378, A381, A391, A392, A398, A399, A400, A402, A403, A413, A414, A424, A426, A427, A441, A442, A446, A447, A456, A460, A461, A462, A467, A468, A469, A472, A473, A477, A480, A481, A483, A484, A486, A489, A494, A495, A496, A498, A499, A506, A507, A508, A511, A512, A514, A516, A520, A521, A522, A526, A528, A530, A531, A532, A533, A535, A548, A556, A565, A568, A569, A579, A584, A585, A588, A589, A590, A592, A599, A614, A616, A623, A626, A628, A637, A638, A639, A641, A643, A644, A648, A656, A657, A663, A674, A676, A677, A691, A693, A703, A705, A708, A713, A716, A720, A721, A723, A735 |
| +++++ | A210, A173, A109, A042, A062, A137, A303, A228, A666, A214, A225, A627, A675, A229, A015, A066, A184, A209, A328, A288, A011, A587, A448, A613, A617, A226, A240, A316, A113, A059, A002, A374, A223, A313, A190, A212, A219, A065, A032, A615, A143, A215, A080, A026, A050, A191, A219, A216, A217, A106, A649, A151, A053, A478, A222, A219, A037, A211, A404, A724, A085, A248, A202, A122, A159, A094, A004, A009, A012, A021, A023, A024, A036, A048, A053, A084, A100, A102, A114, A118, A136, A148, A160, A177, A185, A186, A187, A188, A192, A192, A195, A198, A203, A205, A208, A210, A210, A210, A211, A211, A211, A215, A219, A221, A223, A230, A231, A231, A231, A234, A236, A239, A239, A243, A271, A272, A273, A274, A276, A279, A279, A285, A286, A287, A293, A304, A304, A304, A304, A311, A312, A318, A318, A329, A352, A355, A405, A428, A429, A450, A453, A482, A500, A523, A646, A715 |

TABLE 9

KRAS G12V FRET data

| IC50* | Examples |
|---|---|
| + | None |
| ++ | A028, A075, A076, A076, A087, A112, A132, A145, A155, A167, A183, A184, A194, A233, A245, A262, A264, A265, A266, A268, A275, A292, A295, A298, A300, A305, A319, A333, A334, A338, A368, A383, A388, A389, A418, A464, A465, A479, A491, A492, A493, A527, A537, A542, A602, A609, A621, A629, A665, A679, A734 |
| +++ | A004, A005, A012, A015, A016, A022, A027, A029, A034, A037, A037, A041, A043, A044, A047, A048, A051, A052, A054, A055, A056, A057, A058, A069, A070, A072, A074, A077, A079, A082, A086, A088, A091, A093, A095, A096, A097, A101, A103, A105, A107, A123, A127, A128, A129, A131, A135, A141, A147, A148, A149, A150, A153, A154, A155, A162, A164, A166, A178, A180, A181, A182, A183, A189, A193, A194, A196, A206, A207, A209, A237, A238, A241, A244, A246, A247, A250, A251, A252, A253, A255, A256, A257, A258, A260, A261, A263, A267, A269, A270, A280, A281, A281, A294, A296, A297, A299, A306, A334, A336, A337, A349, A350, A353, A354, A357, A360, A361, A366, A367, A369, A373, A379, A380, A382, A384, A385, A386, A387, A394, A395, A397, A406, A407, A408, A409, A410, A415, A416, A417, A419, A420, A421, A431, A432, A433, A435, A436, A437, A438, A443, A444, A463, A490, A517, A518, A519, A529, A536, A538, A539, A543, A544, A545, A546, A548, A550, A554, A555, A564, A570, A571, A572, A577, A578, A580, A581, A582, A586, A591, A594, A596, A598, A603, A604, A605, A606, A608, A611, A612, A618, A620, A622, A624, A625, A630, A631, A632, A633, A634, A635, A650, A651, A653, A654, A655, A659, A660, A662, A664, A667, A668, A669, A670, A671, A672, A673, A678, A680, A681, A682, A683, A684, A685, A686, A687, A695, A696, A697, A698, A699, A700, A701, A702, A704, A709, A710, A711, A712, A714, A717, A718, A719, A728, A736, A737 |
| ++++ | A001, A003, A006, A007, A008, A010, A013, A017, A018, A025, A030, A031, A032, A035, A036, A038, A039, A040, A045, A046, A050, A060, A061, A062, A063, A064, A066, |

TABLE 9-continued

KRAS G12V FRET data

| IC50* | Examples |
|---|---|
|  | A067, A068, A070, A071, A073, A075, A080, A081, A081, A083, A089, A092, A098, A099, A104, A108, A109, A110, A111, A112, A113, A115, A115, A117, A120, A121, A124, A125, A131, A132, A133, A133, A134, A135, A137, A138, A140, A143, A145, A146, A151, A152, A158, A159, A161, A167, A168, A169, A172, A173, A175, A176, A179, A181, A182, A184, A186, A187, A191, A197, A199, A204, A210, A211, A212, A213, A215, A216, A217, A218, A221, A223, A224, A226, A227, A232, A241, A242, A247, A249, A251, A254, A258, A259, A261, A277, A278, A282, A283, A289, A290, A291, A301, A302, A307, A309, A310, A314, A316, A317, A320, A321, A324, A325, A326, A328, A330, A331, A332, A335, A339, A340, A341, A342, A343, A344, A346, A348, A351, A356, A358, A359, A362, A363, A364, A365, A370, A372, A375, A376, A378, A381, A390, A391, A392, A393, A396, A398, A399, A401, A402, A403, A411, A412, A413, A414, A422, A423, A424, A426, A427, A430, A439, A440, A445, A446, A447, A449, A451, A452, A454, A455, A456, A457, A458, A459, A461, A462, A466, A468, A469, A470, A472, A473, A474, A475, A476, A477, A481, A483, A485, A487, A488, A489, A495, A498, A499, A501, A502, A503, A504, A505, A506, A507, A509, A510, A511, A512, A513, A515, A520, A521, A522, A525, A526, A528, A530, A531, A532, A533, A534, A540, A541, A547, A549, A551, A552, A553, A556, A557, A558, A559, A560, A561, A562, A563, A565, A566, A567, A573, A574, A575, A579, A583, A584, A585, A588, A590, A592, A593, A595, A597, A599, A600, A601, A607, A610, A616, A619, A623, A626, A628, A636, A637, A638, A639, A640, A641, A642, A645, A647, A652, A656, A658, A661, A676, A677, A688, A689, A690, A691, A692, A693, A694, A703, A705, A706, A707, A708, A713, A716, A720, A721, A722, A723, A725, A726, A727, A729, A730, A731, A732, A733, A738, A739 |
| +++++ | A002, A004, A009, A011, A012, A014, A015, A019, A020, A021, A023, A024, A026, A032, A033, A036, A037, A038, A042, A048, A049, A053, A053, A059, A065, A078, A078, A084, A085, A090, A094, A100, A102, A106, A114, A116, A118, A119, A120, A121, A122, A124, A126, A130, A133, A136, A139, A142, A144, A144, A148, A156, A157, A160, A163, A165, A170, A171, A174, A177, A185, A186, A187, A188, A190, A191, A192, A192, A195, A196, A198, A200, A201, A202, A203, A205, A208, A209, A210, A210, A210, A211, A211, A211, A212, A213, A214, A214, A214, A214, A215, A216, A217, A218, A219, A219, A219, A219, A220, A220, A221, A222, A223, A224, A225, A225, A225, A225, A228, A229, A230, A231, A231, A231, A234, A235, A236, A239, A239, A240, A243, A248, A250, A271, A272, A273, A274, A276, A279, A279, A279, A283, A283, A284, A285, A286, A287, A288, A293, A303, A304, A304, A304, A304, A308, A311, A312, A313, A316, A316, A318, A322, A323, A327, A328, A329, A345, A347, A352, A355, A371, A374, A377, A400, A404, A405, A425, A428, A429, A441, A442, A448, A450, A453, A460, A467, A471, A478, A480, A482, A484, A486, A494, A496, A497, A500, A508, A514, A516, A523, A524, A535, A568, A569, A576, A587, A589, A613, A614, A615, A617, A627, A643, A644, A646, A648, A649, A657, A663, A666, A674, A675, A715, A724, A735 |

TABLE 10

KRAS WT FRET data

| IC50* | Examples |
|---|---|
| + | A388 |
| ++ | A075, A076, A076, A112, A132, A155, A167, A183, A194, A233, A256, A260, A261, A262, A263, A264, A265, A268, A270, A280, A294, A295, A296, A297, A298, A299, A300, A319, A333, A334, A338, A367, A382, A383, A385, A386, A387, A389, A418, A432, A433, A436, A464, A465, A479, A491, A492, A493, A527, A537, A542, A569, A594, A598, |

TABLE 10-continued

KRAS WT FRET data

| IC50* | Examples |
|---|---|
|  | A602, A603, A605, A609, A621, A629, A633, A664, A665, A667, A679, A704, A711, A712, A734, A736, A737 |
| +++ | A005, A012, A016, A022, A028, A029, A037, A037, A043, A052, A054, A056, A069, A070, A072, A074, A077, A082, A087, A088, A091, A093, A096, A097, A101, A105, A107, A110, A123, A128, A131, A141, A145, A147, A148, A149, A150, A153, A158, A164, A166, A180, A181, A182, A184, A189, A207, A244, A245, A246, A247, A250, A251, A252, A253, A254, A255, A257, A258, A259, A266, A267, A269, A275, A281, A281, A292, A305, A306, A334, A336, A337, A349, A350, A351, A353, A354, A356, A357, A358, A360, A361, A368, A369, A379, A384, A393, A394, A395, A397, A406, A407, A408, A409, A410, A415, A416, A417, A419, A420, A421, A430, A431, A435, A437, A438, A452, A454, A455, A457, A463, A490, A501, A517, A518, A519, A529, A536, A538, A539, A541, A543, A544, A545, A547, A548, A550, A552, A553, A554, A555, A557, A558, A564, A570, A571, A572, A573, A575, A577, A578, A580, A581, A582, A583, A586, A591, A595, A600, A604, A606, A607, A608, A610, A611, A612, A618, A620, A622, A624, A625, A630, A631, A632, A634, A635, A636, A647, A650, A651, A653, A654, A655, A656, A659, A660, A661, A662, A668, A669, A670, A671, A672, A676, A677, A678, A680, A681, A682, A683, A684, A685, A686, A687, A688, A690, A695, A696, A697, A698, A699, A700, A701, A702, A709, A710, A713, A714, A717, A718, A719, A722, A728, A729, A730, A731, A732, A738, A739 |
| ++++ | A004, A006, A007, A008, A010, A013, A014, A015, A017, A018, A019, A020, A025, A027, A030, A031, A032, A033, A034, A035, A036, A038, A039, A040, A041, A044, A045, A047, A048, A051, A055, A057, A058, A061, A063, A064, A067, A068, A071, A073, A075, A079, A081, A081, A083, A086, A089, A092, A095, A098, A103, A104, A108, A111, A112, A115, A115, A116, A117, A120, A121, A124, A125, A127, A129, A131, A132, A133, A133, A134, A135, A137, A138, A140, A145, A146, A152, A154, A155, A159, A161, A162, A163, A167, A168, A169, A172, A175, A178, A179, A181, A182, A183, A187, A193, A194, A196, A197, A199, A204, A206, A209, A212, A213, A214, A214, A214, A214, A216, A217, A222, A225, A225, A225, A225, A227, A232, A237, A238, A241, A241, A247, A249, A250, A251, A258, A261, A277, A278, A282, A283, A290, A291, A302, A309, A310, A314, A317, A320, A321, A324, A326, A328, A330, A331, A332, A335, A339, A340, A341, A342, A343, A344, A347, A348, A352, A359, A363, A364, A365, A366, A370, A371, A372, A373, A375, A376, A378, A380, A381, A390, A391, A392, A396, A398, A399, A401, A402, A411, A412, A413, A422, A423, A424, A426, A427, A439, A440, A443, A444, A445, A446, A447, A449, A451, A456, A458, A459, A461, A462, A466, A468, A469, A470, A471, A472, A473, A474, A475, A476, A477, A481, A483, A485, A487, A488, A489, A494, A495, A497, A498, A499, A502, A503, A504, A505, A506, A509, A510, A511, A512, A513, A515, A520, A521, A522, A525, A526, A528, A530, A531, A532, A533, A534, A540, A546, A549, A551, A556, A559, A560, A561, A562, A563, A566, A567, A574, A576, A579, A585, A588, A589, A590, A593, A597, A601, A616, A619, A623, A626, A637, A638, A639, A640, A641, A642, A645, A648, A652, A658, A673, A689, A691, A692, A693, A694, A703, A705, A706, A707, A708, A716, A720, A723, A725, A726, A727, A735 |
| +++++ | A001, A002, A003, A004, A009, A011, A012, A015, A021, A023, A024, A026, A032, A036, A037, A038, A042, A046, A048, A049, A050, A053, A053, A059, A060, A062, A065, A066, A078, A078, A080, A084, A085, A090, A094, A099, A100, A102, A106, A109, A113, A114, A118, A119, A120, A121, A122, A124, A126, A130, A133, A135, A136, A139, A142, A143, A144, A144, A148, A151, A156, A157, A160, A165, A170, A171, A173, A174, A176, A177, A184, A185, A186, A186, A187, A188, A190, A191, A191, A192, A192, A195, A196, A198, A200, A201, A202, A203, A205, A208, A209, A210, A210, A210, A210, A211, A211, A211, A211, A212, A213, A215, A215, A216, A217, A218, A218, A219, A219, A219, A219, A220, A220, A221, A221, A222, A223, A223, A224, A224, A226, A228, A229, A230, A231, A231, A231, A234, A235, A236, A239, A239, A240, A242, A243, |

TABLE 10-continued

KRAS WT FRET data

| IC50* | Examples |
|---|---|
| | A248, A271, A272, A273, A274, A276, A279, A279, A279, A283, A283, A284, A285, A286, A287, A288, A289, A293, A301, A303, A304, A304, A304, A304, A307, A308, A311, A312, A313, A316, A316, A316, A318, A318, A322, A323, A325, A327, A328, A329, A345, A346, A355, A362, A374, A377, A400, A403, A404, A405, A414, A425, A428, A429, A441, A442, A448, A450, A453, A460, A467, A478, A480, A482, A484, A486, A496, A500, A507, A508, A514, A516, A523, A524, A535, A565, A568, A584, A587, A592, A596, A599, A613, A614, A615, A617, A627, A628, A643, A644, A646, A649, A657, A663, A666, A674, A675, A715, A721, A724, A733 |

TABLE 11

KRAS G12C FRET data

| IC50* | Examples |
|---|---|
| + | A038, A075, A076, A088, A095, A096, A097, A107, A108, A112, A116, A120, A121, A129, A130, A131, A131, A132, A133, A133, A135, A140, A141, A145, A157, A162, A167, A175, A176, A182, A183, A184, A194, A196, A209, A244, A245, A246, A247, A247, A255, A256, A257, A266, A268, A270, A290, A291, A292, A294, A298, A299, A300, A316, A316, A316, A317, A322, A323, A324, A326, A333, A334, A337, A339, A343, A346, A348, A351, A365, A375, A376, A377, A379, A380, A381, A388, A391, A403, A407, A411, A414, A425, A427, A474, A475, A477, A479, A509, A527, A529, A534, A542, A543, A544, A549, A550, A551, A556, A577, A578, A579, A591, A599, A600, A601, A609, A620, A626, A627, A628, A638, A642, A647, A658, A660, A663, A667, A673, A684, A689, A691, A692, A699, A705, A707, A711, A721, A726, A727, A735 |
| ++ | A004, A005, A012, A015, A016, A020, A022, A027, A028, A029, A031, A032, A037, A037, A038, A043, A044, A047, A048, A051, A052, A054, A055, A056, A057, A058, A064, A067, A069, A070, A070, A071, A072, A074, A076, A077, A079, A082, A083, A086, A087, A091, A093, A103, A104, A105, A115, A121, A123, A124, A126, A127, A128, A132, A133, A134, A135, A138, A139, A142, A144, A148, A149, A150, A152, A153, A154, A155, A155, A156, A158, A164, A165, A166, A172, A178, A179, A181, A182, A183, A186, A187, A189, A191, A193, A196, A200, A201, A204, A207, A209, A214, A214, A225, A225, A233, A237, A238, A241, A241, A250, A250, A251, A251, A252, A253, A260, A261, A262, A263, A264, A265, A267, A269, A275, A280, A281, A283, A295, A296, A297, A305, A319, A328, A332, A334, A336, A338, A342, A344, A349, A350, A352, A353, A359, A361, A362, A363, A366, A367, A368, A370, A371, A382, A383, A384, A385, A386, A387, A389, A394, A396, A397, A400, A410, A416, A417, A418, A421, A423, A432, A433, A435, A436, A437, A438, A439, A440, A443, A444, A445, A448, A452, A454, A456, A458, A459, A463, A464, A465, A466, A476, A478, A485, A489, A490, A491, A492, A493, A499, A501, A503, A504, A505, A510, A513, A515, A517, A518, A519, A525, A526, A528, A532, A533, A536, A537, A538, A545, A552, A558, A559, A560, A566, A567, A568, A569, A572, A573, A575, A580, A581, A584, A585, A587, A589, A590, A592, A594, A595, A596, A597, A598, A602, A603, A610, A612, A614, A615, A616, A617, A621, A622, A624, A629, A632, A634, A636, A637, A643, A644, A645, A646, A649, A650, A651, A653, A657, A659, A661, A662, A664, A665, A668, A669, A671, A672, A674, A675, A678, A679, A681, A682, A683, A685, A686, A697, A698, A700, A701, A703, A704, A706, A709, A710, A712, A715, A719, A720, A722, A724, A730, A733, A734, A736, A737 |
| +++ | A001, A003, A006, A007, A008, A010, A011, A013, A014, A017, A018, A019, A023, A025, A026, A030, A033, A034, A035, A039, A040, A041, A042, A045, A046, A050, A053, A053, A060, A061, A062, A063, A065, A066, A068, A073, A075, A078, A078, A080, A081, A081, A089, A092, A094, A098, A099, A101, A109, A110, A111, A112, A113, A115, |

TABLE 11-continued

KRAS G12C FRET data

| IC50* | Examples |
|---|---|
| | A117, A118, A119, A120, A125, A137, A143, A144, A145, A146, A147, A151, A159, A160, A161, A167, A168, A169, A173, A174, A177, A180, A181, A184, A185, A188, A190, A191, A192, A194, A195, A197, A199, A205, A206, A208, A210, A211, A212, A213, A215, A216, A217, A218, A220, A221, A222, A223, A224, A226, A227, A229, A232, A249, A254, A258, A258, A259, A261, A277, A278, A281, A282, A284, A301, A302, A306, A310, A314, A320, A321, A327, A330, A331, A335, A340, A341, A347, A354, A356, A357, A358, A360, A364, A369, A372, A373, A374, A378, A390, A392, A393, A395, A399, A402, A404, A406, A408, A409, A412, A413, A415, A419, A420, A422, A424, A426, A430, A431, A442, A446, A447, A449, A451, A455, A457, A461, A462, A468, A469, A470, A471, A472, A473, A481, A483, A484, A486, A487, A488, A494, A495, A497, A498, A502, A506, A507, A508, A511, A512, A520, A522, A524, A530, A531, A539, A540, A541, A546, A547, A548, A553, A554, A555, A557, A561, A562, A563, A564, A565, A570, A571, A574, A576, A582, A583, A586, A588, A593, A604, A605, A606, A607, A608, A611, A613, A618, A619, A623, A625, A630, A631, A633, A635, A639, A640, A641, A648, A652, A654, A655, A656, A670, A676, A677, A680, A687, A688, A690, A693, A694, A695, A696, A702, A708, A713, A714, A716, A717, A718, A723, A725, A728, A729, A731, A732, A738, A739 |
| ++++ | A002, A004, A009, A012, A015, A021, A024, A032, A036, A037, A048, A049, A059, A084, A085, A090, A100, A102, A106, A124, A136, A148, A163, A170, A171, A186, A187, A192, A202, A203, A210, A211, A212, A214, A214, A216, A218, A219, A219, A220, A222, A224, A225, A225, A228, A235, A240, A242, A248, A272, A274, A276, A279, A283, A283, A289, A303, A307, A309, A313, A325, A328, A345, A398, A401, A405, A441, A453, A460, A467, A480, A496, A514, A516, A521, A523, A535, A666 |
| +++++ | A036, A114, A122, A198, A210, A210, A211, A211, A213, A215, A217, A219, A219, A221, A223, A230, A231, A231, A231, A234, A236, A239, A239, A243, A271, A273, A279, A279, A285, A286, A287, A288, A293, A304, A304, A304, A304, A308, A311, A312, A318, A318, A329, A355, A428, A429, A450, A482, A500 |

TABLE 12

KRAS G13D FRET data

| IC50* | Examples |
|---|---|
| + | None |
| ++ | A075, A076, A112, A155, A183, A260, A261, A262, A263, A264, A265, A267, A268, A270, A294, A296, A298, A300, A319, A333, A338, A388, A464, A465, A527, A537, A542, A664 |
| +++ | A028, A054, A096, A105, A107, A123, A128, A131, A132, A141, A145, A149, A150, A153, A158, A164, A167, A181, A182, A184, A189, A194, A196, A207, A233, A244, A245, A246, A247, A250, A251, A252, A253, A255, A256, A257, A258, A261, A266, A269, A275, A280, A281, A281, A292, A295, A297, A299, A305, A306, A334, A334, A336, A337, A349, A350, A353, A354, A357, A361, A367, A368, A379, A382, A383, A384, A385, A386, A387, A389, A394, A395, A397, A406, A407, A410, A415, A416, A417, A418, A421, A432, A433, A436, A438, A463, A479, A490, A491, A492, A493, A518, A519, A529, A536, A538, A543, A544, A545, A555, A558, A573, A577, A578, A580, A581, A582, A591, A594, A596, A598, A602, A603, A605, A606, A608, A609, A611, A612, A620, A621, A622, A624, A629, A631, A633, A650, A651, A653, A654, A655, A659, A661, A662, A665, A667, A669, A670, A671, A672, A678, A679, A681, A682, A683, A684, A685, A686, A687, A690, A695, A697, A698, A699, A700, A701, A704, A709, A710, A711, A712, A718, A719, A729, A730, A734, A736, A737 |
| ++++ | A016, A038, A069, A075, A088, A095, A103, A104, A108, A110, A111, A112, A116, A117, A120, A120, A121, A121, |

TABLE 12-continued

KRAS G13D FRET data

| IC50* | Examples |
|---|---|
| | A125, A127, A129, A130, A131, A132, A133, A133, A133, A134, A135, A138, A140, A142, A144, A144, A145, A146, A147, A148, A152, A154, A155, A156, A157, A159, A161, A162, A163, A166, A175, A178, A179, A180, A181, A182, A183, A187, A193, A194, A197, A206, A209, A212, A213, A232, A237, A238, A241, A241, A247, A249, A251, A254, A258, A259, A277, A278, A282, A290, A302, A314, A321, A326, A328, A330, A331, A332, A335, A339, A340, A341, A342, A344, A351, A356, A358, A359, A360, A363, A364, A365, A366, A369, A370, A372, A373, A380, A381, A390, A391, A393, A396, A399, A401, A408, A409, A411, A412, A413, A419, A420, A422, A424, A427, A430, A431, A435, A437, A439, A440, A443, A444, A445, A446, A449, A451, A452, A454, A455, A456, A457, A458, A459, A466, A468, A469, A470, A472, A473, A474, A475, A476, A485, A487, A488, A489, A499, A501, A502, A503, A504, A505, A509, A510, A511, A513, A515, A517, A520, A521, A522, A525, A534, A539, A540, A541, A546, A547, A548, A549, A550, A551, A552, A553, A554, A557, A559, A560, A561, A562, A563, A564, A566, A567, A570, A571, A572, A574, A575, A583, A586, A588, A593, A595, A597, A600, A601, A604, A607, A610, A616, A618, A619, A623, A625, A626, A630, A632, A634, A635, A636, A637, A638, A640, A641, A642, A645, A647, A652, A656, A658, A660, A668, A673, A676, A677, A680, A688, A689, A691, A693, A694, A696, A702, A706, A707, A713, A714, A717, A720, A722, A725, A726, A727, A728, A731, A732, A738, A739 |
| +++++ | A024, A065, A094, A102, A106, A109, A113, A114, A115, A115, A118, A119, A122, A124, A124, A126, A135, A136, A137, A139, A143, A148, A151, A160, A165, A167, A168, A169, A170, A171, A172, A173, A174, A176, A177, A184, A185, A186, A186, A187, A188, A190, A191, A191, A192, A192, A195, A196, A198, A199, A200, A201, A202, A203, A204, A205, A208, A209, A210, A210, A210, A211, A211, A211, A211, A212, A213, A214, A214, A214, A225, A225, A225, A226, A227, A228, A229, A230, A231, A231, A231, A234, A235, A236, A239, A239, A240, A242, A243, A248, A250, A271, A272, A273, A274, A276, A279, A279, A279, A283, A283, A283, A284, A285, A286, A287, A288, A289, A291, A293, A301, A303, A304, A304, A304, A307, A308, A309, A310, A311, A312, A313, A316, A316, A316, A317, A318, A320, A322, A323, A324, A325, A327, A328, A329, A343, A345, A346, A347, A348, A352, A355, A362, A371, A374, A375, A376, A377, A378, A392, A398, A400, A402, A403, A404, A405, A414, A423, A425, A426, A428, A429, A441, A442, A447, A448, A450, A453, A460, A461, A462, A467, A471, A477, A478, A480, A481, A482, A483, A484, A486, A494, A495, A496, A497, A498, A500, A506, A507, A508, A512, A514, A516, A523, A524, A526, A528, A530, A531, A532, A533, A535, A556, A565, A568, A569, A576, A579, A584, A585, A587, A589, A590, A592, A599, A613, A614, A615, A617, A627, A628, A639, A643, A644, A646, A648, A649, A657, A663, A666, A674, A675, A692, A703, A705, A708, A715, A716, A721, A723, A724, A733, A735 |

TABLE 13

KRAS Q61H FRET data

| IC50* | Examples |
|---|---|
| + | A297, A299, A388, A598, A621 |
| ++ | A012, A022, A075, A076, A077, A082, A087, A105, A148, A167, A181, A207, A262, A275, A281, A300, A333, A338, A349, A350, A353, A354, A367, A368, A379, A382, A383, A384, A385, A386, A387, A389, A394, A407, A416, A417, A463, A491, A492, A493, A537, A542, A543, A544, A545, A557, A577, A578, A580, A582, A586, A594, A596, A602, A603, A605, A606, A608, A609, A611, A612, A620, A622, A629, A631, A633, A650, A651, A653, A654, A655, A656, A661, A662, A664, A665, A667, A668, A669, A671, A672, A676, A678, A679, A681, A682, A683, A684, A686, A687, |

TABLE 13-continued

KRAS Q61H FRET data

| IC50* | Examples |
|---|---|
| | A696, A697, A698, A701, A702, A704, A709, A710, A711, A712, A718, A719, A734, A736, A737, A739 |
| +++ | A016, A045, A064, A074, A083, A086, A089, A104, A115, A166, A172, A193, A252, A277, A314, A328, A330, A332, A340, A341, A342, A344, A351, A356, A357, A358, A360, A361, A365, A366, A369, A372, A373, A390, A393, A468, A474, A475, A494, A502, A503, A504, A505, A522, A534, A538, A539, A540, A541, A546, A547, A548, A549, A551, A552, A553, A554, A555, A558, A559, A560, A561, A564, A566, A567, A570, A571, A572, A573, A574, A575, A581, A583, A588, A591, A593, A595, A597, A600, A604, A607, A610, A618, A619, A623, A624, A625, A626, A630, A632, A634, A635, A636, A640, A659, A660, A670, A673, A677, A680, A685, A688, A689, A690, A694, A695, A699, A700, A706, A713, A714, A717, A725, A728, A729, A730, A731, A732, A738 |
| ++++ | A023, A025, A026, A050, A053, A060, A061, A062, A080, A084, A085, A102, A113, A136, A143, A151, A160, A168, A202, A210, A211, A226, A227, A242, A278, A290, A301, A302, A303, A331, A335, A339, A343, A345, A346, A347, A348, A352, A359, A362, A363, A364, A370, A371, A376, A380, A381, A391, A392, A403, A427, A442, A447, A461, A472, A481, A495, A496, A498, A531, A550, A562, A563, A565, A568, A569, A576, A579, A584, A585, A589, A590, A592, A601, A616, A627, A637, A638, A639, A641, A642, A645, A647, A652, A658, A666, A674, A691, A692, A693, A703, A705, A707, A708, A716, A720, A721, A722, A723, A726, A727, A733, A735 |
| +++++ | A170, A171, A205, A240, A243, A248, A285, A304, A304, A313, A316, A329, A355, A374, A375, A377, A378, A482, A486, A507, A587, A599, A613, A614, A615, A617, A628, A643, A644, A646, A648, A649, A657, A663, A675, A715, A724 |

TABLE 14

NRAS G12C FRET data

| IC50* | Examples |
|---|---|
| + | A038, A075, A076, A088, A095, A096, A107, A108, A112, A116, A120, A121, A123, A129, A130, A131, A131, A132, A133, A133, A135, A140, A141, A145, A155, A157, A162, A167, A175, A176, A182, A183, A184, A194, A196, A209, A244, A245, A246, A247, A247, A250, A255, A257, A266, A268, A270, A290, A292, A294, A297, A298, A299, A300, A316, A316, A316, A323, A324, A326, A333, A334, A336, A337, A339, A343, A348, A351, A365, A375, A376, A377, A380, A388, A391, A407, A411, A414, A427, A435, A474, A475, A479, A509, A527, A529, A534, A537, A542, A543, A544, A550, A551, A556, A577, A578, A579, A591, A600, A601, A609, A612, A616, A620, A626, A627, A628, A638, A642, A647, A658, A660, A663, A667, A673, A684, A689, A691, A692, A699, A705, A707, A711, A721, A727, A735 |
| ++ | A016, A054, A069, A103, A104, A105, A115, A121, A124, A126, A127, A128, A132, A133, A134, A135, A138, A142, A144, A148, A149, A150, A152, A153, A154, A155, A158, A164, A165, A166, A172, A178, A179, A181, A182, A183, A186, A187, A189, A191, A196, A200, A204, A207, A233, A237, A241, A241, A250, A251, A252, A256, A260, A261, A262, A263, A264, A265, A267, A269, A275, A281, A291, A295, A296, A305, A317, A319, A322, A328, A332, A334, A338, A344, A346, A349, A350, A352, A353, A354, A361, A362, A363, A367, A368, A370, A371, A379, A381, A382, A383, A384, A385, A386, A387, A389, A394, A396, A397, A400, A403, A410, A417, A418, A419, A421, A423, A425, A432, A433, A436, A437, A438, A439, A440, A443, A444, A445, A448, A452, A454, A456, A458, A459, A463, A464, A465, A466, A476, A477, A478, A485, A489, A490, A491, A492, A493, A499, A501, A503, A504, A505, A510, A513, A515, A517, A518, A519, A525, A526, A528, A532, A533, A536, A538, A545, A549, A552, A558, A559, A560, A566, A567, A569, A572, A573, A574, A575, A580, A581, |

TABLE 14-continued

NRAS G12C FRET data

| IC50* | Examples |
|---|---|
| | A582, A584, A585, A587, A589, A590, A592, A594, A595, A596, A597, A598, A599, A602, A603, A610, A614, A615, A617, A621, A622, A624, A629, A631, A632, A633, A634, A636, A637, A643, A644, A645, A646, A649, A650, A651, A653, A654, A657, A659, A661, A662, A664, A665, A668, A669, A671, A672, A674, A675, A676, A678, A679, A681, A682, A683, A685, A686, A695, A697, A698, A700, A701, A703, A704, A706, A709, A710, A712, A715, A719, A720, A722, A724, A726, A730, A733, A734, A736, A737 |
| +++ | A065, A075, A094, A109, A111, A112, A113, A115, A117, A118, A119, A120, A137, A139, A143, A144, A145, A146, A147, A151, A156, A159, A161, A167, A169, A173, A177, A180, A181, A184, A185, A188, A190, A192, A193, A194, A195, A197, A199, A201, A206, A209, A210, A211, A212, A214, A225, A226, A227, A232, A238, A249, A253, A254, A258, A258, A259, A261, A277, A278, A280, A281, A282, A283, A301, A302, A306, A310, A314, A320, A321, A327, A330, A331, A335, A340, A341, A342, A347, A356, A357, A358, A359, A360, A364, A366, A369, A372, A373, A374, A378, A390, A392, A393, A395, A399, A402, A404, A406, A408, A409, A412, A413, A415, A416, A420, A422, A424, A430, A431, A442, A446, A447, A449, A451, A455, A457, A461, A462, A467, A468, A469, A470, A471, A472, A473, A481, A483, A486, A487, A488, A494, A495, A497, A498, A502, A506, A507, A508, A511, A512, A520, A522, A524, A530, A531, A539, A540, A541, A546, A547, A548, A553, A554, A555, A557, A561, A562, A563, A564, A565, A568, A570, A571, A576, A583, A586, A588, A593, A604, A605, A606, A607, A608, A611, A618, A619, A623, A625, A630, A635, A639, A640, A641, A648, A652, A655, A656, A670, A677, A680, A687, A688, A690, A693, A694, A696, A702, A708, A713, A714, A716, A717, A718, A723, A725, A728, A729, A731, A732, A738, A739 |
| ++++ | A024, A102, A106, A110, A124, A125, A136, A160, A163, A168, A170, A171, A174, A186, A187, A191, A192, A202, A203, A205, A208, A210, A211, A212, A213, A228, A229, A235, A240, A242, A248, A274, A276, A279, A283, A284, A289, A303, A307, A309, A313, A325, A328, A345, A398, A401, A426, A441, A453, A460, A480, A484, A496, A514, A516, A521, A523, A535, A613, A666 |
| +++++ | A114, A122, A148, A198, A210, A210, A211, A211, A213, A214, A214, A225, A225, A230, A231, A231, A231, A234, A236, A239, A239, A243, A271, A272, A273, A279, A279, A283, A285, A286, A287, A288, A293, A304, A304, A304, A304, A308, A311, A312, A318, A318, A329, A355, A405, A428, A429, A450, A482, A500 |

TABLE 15

NRAS Q61R FRET data

| IC50* | Examples |
|---|---|
| + | A388 |
| ++ | A367, A368, A382, A383, A385, A386, A387, A389, A407, A417, A491, A492, A493, A542, A577, A594, A596, A598, A602, A603, A609, A611, A612, A621, A629, A633, A655, A664, A665, A667, A669, A678, A679, A697, A704, A712, A719, A734, A736, A737 |
| +++ | A012, A022, A075, A076, A082, A087, A105, A148, A167, A181, A207, A262, A275, A281, A297, A299, A300, A314, A333, A338, A349, A350, A353, A354, A356, A357, A360, A361, A369, A379, A384, A393, A394, A416, A463, A502, A537, A538, A539, A541, A543, A544, A545, A546, A548, A554, A555, A570, A571, A572, A573, A575, A578, A580, A581, A582, A583, A586, A591, A593, A595, A597, A604, A605, A606, A607, A608, A610, A618, A619, A620, A622, A624, A625, A630, A631, A632, A634, A635, A636, A650, A651, A653, A654, A656, A659, A661, A662, A668, A670, A671, A672, A676, A677, A680, A681, A682, A683, A684, A685, A686, A687, A688, A690, A695, A696, A698, A699, A700, A701, A702, A706, A709, A710, A711, A713, A714, A717, A718, A728, A732, A738 |

TABLE 15-continued

NRAS Q61R FRET data

| IC50* | Examples |
|---|---|
| ++++ | A016, A064, A074, A077, A083, A086, A089, A104, A115, A166, A168, A193, A252, A277, A290, A328, A330, A332, A335, A339, A340, A341, A342, A343, A344, A347, A351, A352, A358, A359, A363, A364, A365, A366, A370, A372, A373, A380, A381, A390, A391, A392, A442, A461, A472, A474, A475, A481, A494, A495, A496, A498, A503, A504, A505, A522, A531, A534, A540, A547, A549, A550, A551, A552, A553, A557, A558, A559, A560, A561, A564, A566, A567, A574, A588, A600, A601, A623, A626, A638, A639, A640, A641, A647, A652, A658, A660, A673, A689, A691, A693, A694, A720, A722, A725, A727, A729, A730, A731, A739 |
| +++++ | A023, A025, A026, A045, A050, A053, A060, A061, A062, A080, A084, A085, A102, A113, A136, A143, A151, A160, A170, A171, A172, A202, A205, A210, A211, A226, A227, A240, A242, A243, A248, A278, A285, A301, A302, A303, A304, A304, A313, A316, A329, A331, A345, A346, A348, A355, A362, A371, A374, A375, A376, A377, A378, A403, A427, A447, A468, A482, A486, A507, A556, A562, A563, A565, A568, A569, A576, A579, A584, A585, A587, A589, A590, A592, A599, A613, A614, A615, A616, A617, A627, A628, A637, A642, A643, A644, A645, A646, A648, A649, A657, A663, A666, A674, A675, A692, A703, A705, A707, A708, A715, A716, A721, A723, A724, A726, A733, A735 |

TABLE 16

NRAS Q61K FRET data

| IC50* | Examples |
|---|---|
| + | A388 |
| ++ | A262, A297, A299, A338, A349, A350, A353, A354, A367, A368, A369, A382, A383, A384, A385, A386, A387, A389, A394, A407, A416, A417, A463, A491, A492, A493, A542, A543, A544, A545, A577, A580, A582, A594, A596, A598, A602, A603, A609, A611, A612, A620, A621, A622, A629, A631, A633, A650, A651, A653, A654, A655, A661, A662, A664, A665, A667, A668, A669, A671, A678, A679, A681, A682, A683, A686, A687, A696, A697, A698, A701, A702, A704, A709, A710, A711, A712, A718, A719, A734, A736, A737, A739 |
| +++ | A012, A022, A074, A075, A076, A077, A082, A086, A087, A105, A148, A167, A181, A207, A275, A277, A281, A300, A314, A330, A333, A340, A356, A360, A361, A379, A390, A393, A502, A537, A538, A539, A541, A546, A547, A548, A554, A555, A561, A570, A571, A572, A573, A574, A575, A578, A581, A583, A586, A588, A593, A595, A597, A604, A605, A606, A607, A608, A610, A618, A619, A623, A624, A625, A630, A632, A634, A635, A636, A656, A660, A670, A672, A676, A677, A680, A684, A685, A688, A690, A694, A695, A699, A700, A706, A713, A714, A717, A728, A729, A730, A731, A732, A738 |
| ++++ | A016, A025, A045, A050, A060, A061, A064, A080, A083, A089, A104, A115, A143, A151, A166, A168, A172, A193, A202, A210, A211, A227, A252, A278, A290, A328, A331, A332, A335, A339, A341, A342, A343, A344, A347, A351, A352, A357, A358, A359, A363, A364, A365, A366, A370, A372, A373, A380, A381, A391, A427, A442, A461, A468, A472, A474, A475, A481, A494, A495, A496, A498, A503, A504, A505, A522, A531, A534, A540, A549, A550, A551, A552, A553, A557, A558, A559, A560, A562, A563, A564, A566, A567, A576, A590, A591, A600, A601, A626, A637, A638, A639, A640, A641, A647, A652, A659, A673, A689, A691, A693, A705, A720, A722, A725, A727, A735 |
| +++++ | A023, A026, A053, A062, A084, A085, A102, A113, A136, A160, A170, A171, A205, A226, A240, A242, A243, A248, A285, A301, A302, A303, A304, A304, A313, A316, A329, A345, A346, A348, A355, A362, A371, A374, A375, A376, A377, A378, A392, A403, A447, A482, A486, A507, A556, A565, A568, A569, A579, A584, A585, A587, A589, A592, A599, A613, A614, A615, A616, A617, A627, A628, A642, A643, A644, A645, A646, A648, A649, A657, A658, A663, |

TABLE 16-continued

NRAS Q61K FRET data

| IC50* | Examples |
|---|---|
| | A666, A674, A675, A692, A703, A707, A708, A715, A716, A721, A723, A724, A726, A733 |

TABLE 17

NRAS WT FRET data

| IC50* | Examples |
|---|---|
| + | A388 |
| ++ | A075, A076, A087, A167, A262, A275, A297, A299, A300, A333, A338, A349, A367, A368, A382, A383, A385, A386, A387, A389, A407, A417, A491, A492, A493, A537, A542, A577, A594, A596, A598, A602, A603, A605, A609, A612, A621, A629, A633, A664, A665, A667, A669, A679, A697, A704, A709, A711, A712, A719, A734, A736, A737 |
| +++ | A012, A016, A022, A074, A077, A082, A086, A105, A148, A166, A181, A207, A252, A277, A281, A340, A350, A351, A353, A354, A356, A357, A358, A360, A361, A369, A379, A384, A393, A394, A416, A463, A502, A538, A539, A541, A543, A544, A545, A546, A547, A548, A550, A552, A554, A555, A557, A558, A564, A570, A571, A572, A573, A575, A578, A580, A581, A582, A583, A586, A591, A593, A595, A600, A604, A606, A607, A608, A610, A611, A618, A620, A622, A624, A625, A630, A631, A632, A634, A635, A636, A647, A650, A651, A653, A654, A655, A656, A659, A660, A661, A662, A668, A670, A671, A672, A676, A677, A678, A680, A681, A682, A683, A684, A685, A686, A687, A688, A690, A695, A696, A698, A699, A700, A701, A702, A710, A713, A714, A717, A718, A722, A728, A729, A730, A731, A732, A738, A739 |
| ++++ | A025, A045, A060, A061, A062, A064, A083, A089, A104, A115, A151, A168, A172, A193, A202, A210, A211, A227, A278, A290, A314, A328, A330, A331, A332, A335, A339, A341, A342, A343, A344, A347, A348, A352, A359, A362, A363, A364, A365, A366, A370, A371, A372, A373, A375, A376, A378, A380, A381, A390, A391, A392, A427, A447, A461, A468, A472, A474, A475, A481, A494, A495, A496, A498, A503, A504, A505, A507, A522, A531, A534, A540, A549, A551, A553, A556, A559, A560, A561, A562, A563, A566, A567, A574, A576, A579, A584, A585, A588, A589, A590, A597, A601, A616, A619, A623, A626, A637, A638, A639, A640, A641, A642, A645, A648, A652, A658, A673, A689, A691, A693, A694, A703, A705, A706, A707, A708, A716, A720, A721, A723, A725, A726, A727, A735 |
| +++++ | A023, A026, A050, A053, A080, A084, A085, A102, A113, A136, A143, A160, A170, A171, A205, A226, A240, A242, A243, A248, A285, A302, A303, A304, A304, A313, A316, A329, A345, A346, A355, A374, A377, A403, A442, A482, A486, A565, A568, A569, A587, A592, A599, A613, A614, A615, A617, A627, A628, A643, A644, A646, A649, A657, A663, A666, A674, A675, A692, A715, A724, A733 |

In Vitro Cell Proliferation Panels

Potency for inhibition of cell growth was assessed at CrownBio using standard methods. Briefly, cell lines were cultured in appropriate medium, and then plated in 3D methylcellulose. Inhibition of cell growth was determined by CellTiter-Glo® after 5 days of culture with increasing concentrations of compounds. Compound potency was reported as the 50% inhibition concentration (absolute IC50).

The assay took place over 7 days. On day 1, cells in 2D culture were harvested during logarithmic growth and suspended in culture medium at 1×105 cells/ml. Higher or lower cell densities were used for some cell lines based on prior optimization. 3.5 ml of cell suspension was mixed with 6.5% growth medium with 1% methylcellulose, resulting in a cell suspension in 0.65% methylcellulose. 90 µl of this suspension was distributed in the wells of 296-well plates. One plate was used for day 0 reading and 1 plate was used for the end-point experiment. Plates were incubated overnight at 37 C with 5% $CO_2$. On day 2, one plate (for t0 reading) was removed and 10 µl growth medium plus 100 µl CellTiter-Glo® Reagent was added to each well. After mixing and a 10 minute incubation, luminescence was recorded on an EnVision Multi-Label Reader (Perkin Elmer). Compounds in DMSO were diluted in growth medium such that the final, maximum concentration of compound was 10 µM, and serial 4-fold dilutions were performed to generate a 9-point concentration series. 10 µl of compound solution at 10 times final concentration was added to wells of the second plate. Plate was then incubated for 120 hours at 37 C and 5% $CO_2$. On day 7 the plates were removed, 100 µl CellTiter-Glo® Reagent was added to each well, and after mixing and a 10 minute incubation, luminescence was recorded on an EnVision Multi-Label Reader (Perkin Elmer). Data was exported to GeneData Screener and modeled with a sigmoidal concentration response model in order to determine the IC50 for compound response.

Not all cell lines with a given RAS mutation may be equally sensitive to a RAS inhibitor targeting that mutation, due to differential expression of efflux transporters, varying dependencies on RAS pathway activation for growth, or other reasons. This has been exemplified by the cell line KYSE-410 which, despite 8 having a KRAS G12C mutation, is insensitive to the KRAS G12C (OFF) inhibitor MRTX-849 (Hallin et al., Cancer Discovery 10:54-71 (2020)), and the cell line SW1573, which is insensitive to the KRAS G12C (OFF) inhibitor AMG510 (Canon et al., Nature 575:217-223 (2019)).

TABLE 18

IC50 values for various cancer cell lines with Compound B

| Cell Line | Histotype | Mutant | IC50* |
|---|---|---|---|
| NCI-H358 | Lung | KRAS G12C | very sensitive |
| MIA PaCa-2 | Pancreas | KRAS G12C | very sensitive |
| SW837 | Intestine/Large/Colorectum | KRAS G12C | very sensitive |
| KYSE-410 | HN/Esophagus | KRAS G12C | moderately sensitive |
| NCI-H727 | Lung | KRAS G12V | moderately sensitive |
| OVCAR-5 | Ovary | KRAS G12V | moderately sensitive |
| Capan-2 | Pancreas | KRAS G12V | moderately sensitive |
| NCI-H747 | Intestine/Large/Colorectum | other KRAS (G13D) | moderately sensitive |
| NCI-H441 | Lung | KRAS G12V | moderately sensitive |
| HEC-1-A | Uterus | KRAS G12D | moderately sensitive |
| NOZ | Liver/Bile duct | KRAS G12V | moderately sensitive |
| HCT116 | Intestine/Large/Colorectum | other KRAS (G13D) | moderately sensitive |
| Calu-6 | Lung | other KRAS (Q61K) | moderately sensitive |
| HuCCT1 | Liver/Bile duct | KRAS G12D | moderately sensitive |
| NCI-H2009 | Lung | other KRAS (G12A) | low sensitivity |
| NCI-H1975 | Lung | other MAPK (EGFR T790M, L858R) | low sensitivity |
| SW1573 | Lung | KRAS G12C | not sensitive |
| AGS | Stomach | KRAS G12D | low sensitivity |

TABLE 18-continued

IC50 values for various cancer cell lines with Compound B

| Cell Line | Histotype | Mutant | IC50* |
|---|---|---|---|
| AsPC-1 | Pancreas | KRAS G12D | low sensitivity |
| SNU-668 | Stomach | other KRAS (Q61K) | low sensitivity |
| HPAC | Pancreas | KRAS G12D | low sensitivity |
| NCI-H1838 | Lung | other MAPK (NF1 mut) | low sensitivity |
| NCI-H3122 | Lung | other MAPK (EML4-ALK(E13, A20)) | low sensitivity |
| NCI-H460 | Lung | other KRAS (Q61H) | low sensitivity |
| SW403 | Intestine/Large/Colorectum | KRAS G12V | low sensitivity |
| A549 | Lung | other KRAS (G12S) | low sensitivity |
| CAL-62 | HN/Thyroid | other KRAS (G12R) | low sensitivity |
| DV-90 | Lung | other KRAS (G13D) | low sensitivity |
| OZ | Liver/Bile duct | other KRAS (Q61L) | low sensitivity |
| A-375 | Skin | BRAF V600E | low sensitivity |
| BxPC-3 | Pancreas | other MAPK (BRAF V487_P492delinsA) | low sensitivity |
| SW48 | Intestine/Large/Colorectum | not MAPK (PIK3CA G914R, EGFR G719S) | low sensitivity |
| HCC1588 | Lung | KRAS G12D | low sensitivity |
| TOV-21G | Ovary | other KRAS (G13C) | low sensitivity |
| SW948 | Intestine/Large/Colorectum | other KRAS (Q61L) | low sensitivity |
| LS513 | Intestine/Large/Colorectum | KRAS G12D | low sensitivity |
| MeWo | Skin | other MAPK (NF1 mut) | low sensitivity |

*Key:
low sensitivity: IC50 ≥ 1 uM
moderately sensitive: 1 uM > IC50 ≥ 0.1 uM
very sensitive: IC50 < 0.1 uM

TABLE 19

Summary of IC50 results for various cancer cell lines with several compounds of the present invention (Compounds B and E-M)

| Cell Line | Histotype | Mutant | E | F | G | H | I | J | K | L | B | M |
|---|---|---|---|---|---|---|---|---|---|---|---|---|
| SW837 | Intestine/Large/Colorectum | KRAS G12C | V | V | V | V | V | V | V | V | V | V |
| MIA PaCa-2 | Pancreas | KRAS G12C | V | V | V | V | V | V | V | V | V | V |
| KYSE-410 | HN/Esophagus | KRAS G12C | L | L | L | L | L | L | L | L | L | L |
| H358 | Lung | KRAS G12C | V | V | V | V | V | V | V | V | V | V |
| H2122 | Lung | KRAS G12C | V | V | V | V | V | V | V | V | V | V |
| H1373 | Lung | KRAS G12C | V | V | V | V | V | V | V | V | V | V |
| H23 | Lung | KRAS G12C | V | V | V | V | V | V | V | V | V | V |
| H1792 | Lung | KRAS G12C | V | V | V | V | V | V | V | V | V | V |
| AsPC-1 | Pancreas | KRAS G12D | L | L | M | L | L | M | L | L | M | L |
| A375 | Skin | BRAF V600E | L | L | L | L | L | L | L | L | L | L |
| H1975 | Lung | other MAPK (EGFR T790M, L858R) | M | L | M | L | L | M | L | M | M | L |
| HCC1588 | Lung | KRAS G12D | L | L | L | L | L | L | L | L | L | L |
| H441 | Lung | KRAS G12V | M | M | M | L | M | V | L | M | V | L |

*Key:
(L) low sensitivity: IC50 ≥ 1 uM
(M) moderately sensitive: 1 uM > IC50 ≥ 0.1 uM
(V) very sensitive: IC50 < 0.1 uM In Vivo NSCLC K-Ras G12C Xenograft Models Compound A:

Methods:

The effects of a compound of the present invention, Compound A (H358 pERK K-Ras G12C EC50: 0.001 uM), on tumor cell growth in vivo were evaluated in the human non-small cell lung cancer NCI-H358 KRASG12C xenograft model using female BALB/c nude mice (6-8 weeks old). Mice were implanted with NCI-H358 tumor cells in 50% Matrigel (5×106 cells/mouse) subcutaneously in the flank. At the indicated tumor volume (dotted line, FIG. 2A), mice were randomized to treatment groups to start the administration of test articles or vehicle. Compound A was administered by oral gavage daily at the dose of 100 mg/kg. Body weight and tumor volume (using calipers) was measured twice weekly until study endpoints. Spaghetti plot (FIG. 2B) shows the tumor volume change in individual tumors during the course of treatment.

Figure 2A:
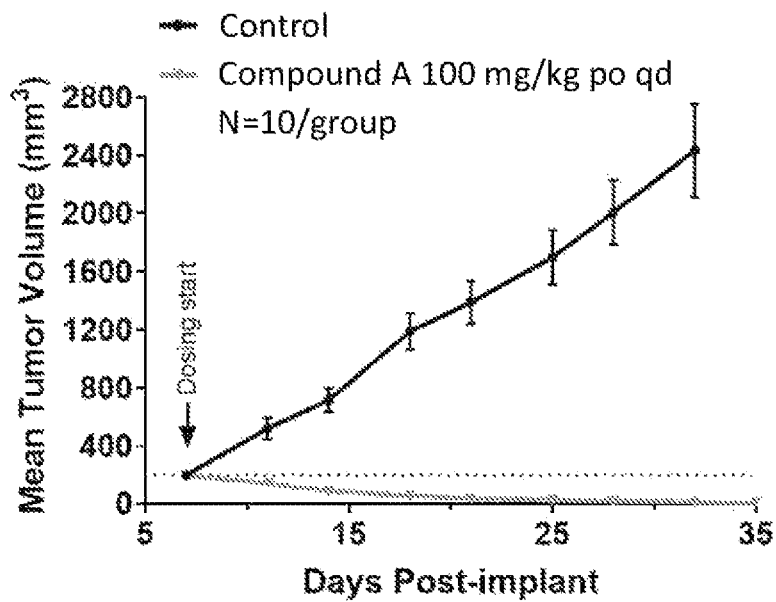
FIG. 2A and FIG. 2B: A compound of the present invention, Compound A, drove deep regressions in vivo in a NSCLC (KRAS G12C) xenograft model. Some animals exhibited complete responses (CR)=3 consecutive tumor measurements <30 mm3.
Figure 2B:
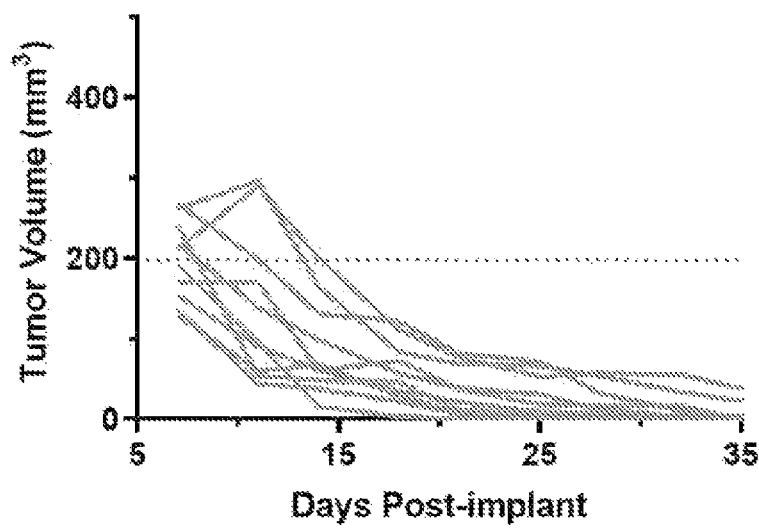

Results:

FIG. 2A shows Compound A dosed at 100 mg/kg by daily oral gavage led to tumor regression in NCI-H358 KRASG12C xenograft model, which is a sensitive model to KRASG12C inhibition alone. The spaghetti titer plot (FIG. 2B) displaying individual tumor growth is shown next to the tumor volume plot (FIG. 2A). Over the treatment course of 28 days, Compound A drove tumor regression in all 10 animals bearing NCI-H358 KRASG12C tumors.

Figure 3A:
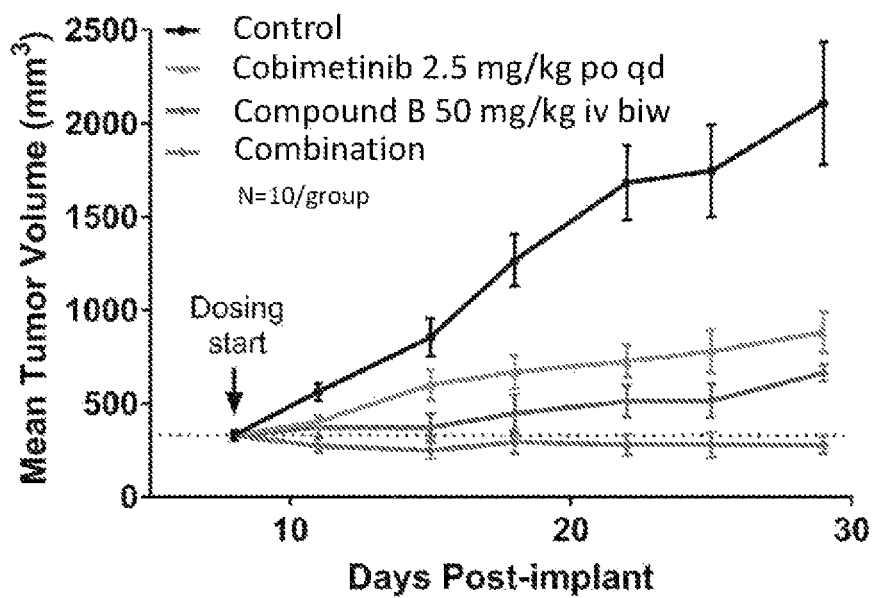
FIG. 3A and FIG. 3B: A compound of the present invention, Compound B, drove tumor xenograft regressions in combination with a MEK inhibitor, cobimetinib, in a NSCLC (KRAS G12C) model.
Figure 3B:
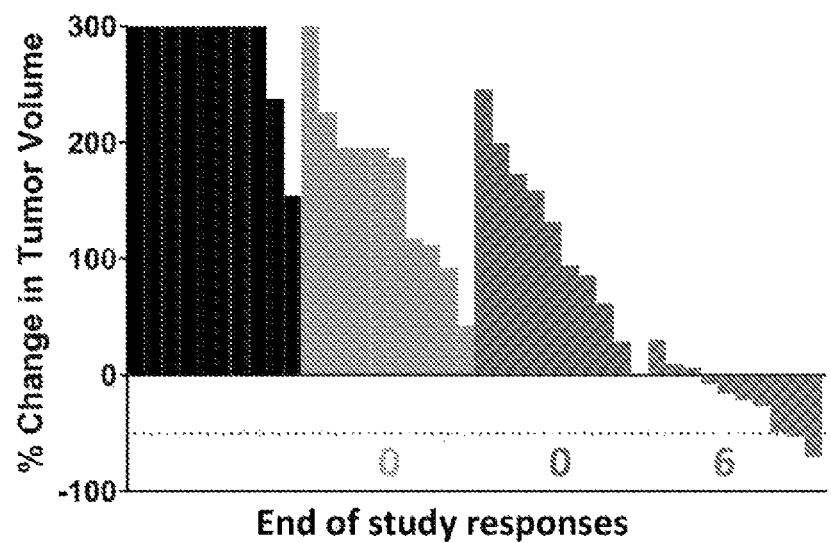
Figure 4A:
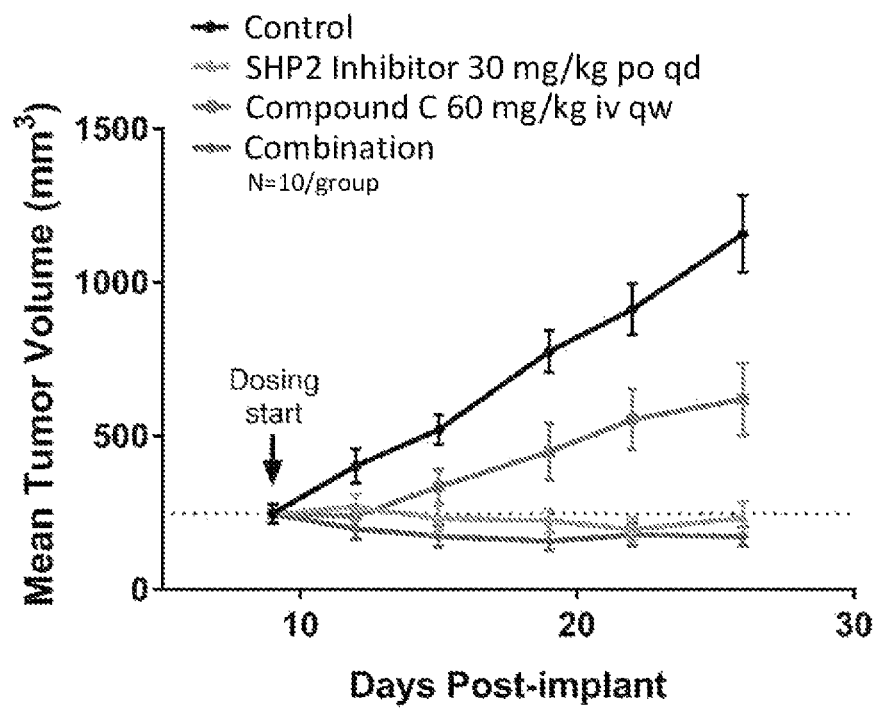
FIG. 4A and FIG. 4B: A compound of the present invention, Compound C, dosed weekly with daily SHP2 inhibitor, RMC-4550, drove xenograft regressions in a NSCLC (KRAS G12C) model.
Figure 4B:
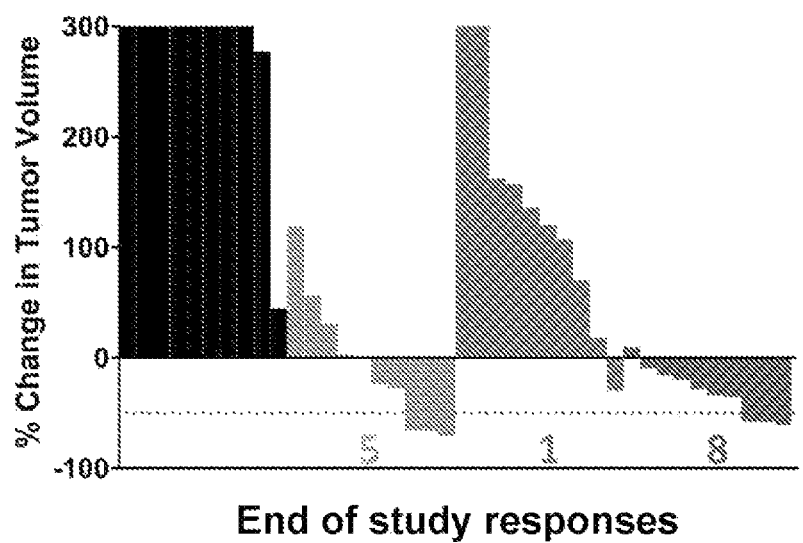
Figure 5:
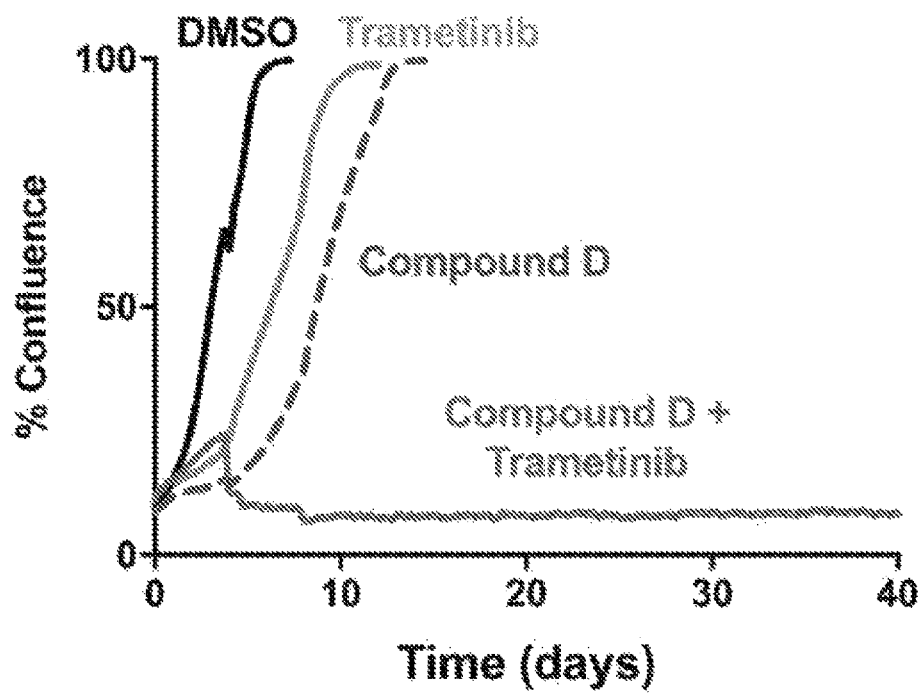
FIG. 5: A compound of the present invention, Compound D, combined with a MEK inhibitor, trametinib, suppressed in vitro growth durably in a long-term cell growth NSCLC (KRAS G12C) model.

Compound B:

Methods:

The combinatorial effect of a compound of the present invention, Compound B (H358 pERK K-Ras G12C EC50: 0.003 uM), with cobimetinib on tumor cell growth in vivo were evaluated in the human non-small cell lung cancer NCI-H358 KRASG12C xenograft model using female BALB/c nude mice (6-8 weeks old). Mice were implanted with NCI-H358 tumor cells in 50% Matrigel (5×106 cells/mouse) subcutaneously in the flank. At indicated tumor volume (dotted line, FIG. 3A), mice were randomized to treatment groups to start the administration of test articles or vehicle. Compound B was administered by intermittent (twice weekly) intravenous injection at the dose of 50 mg/kg. Cobimetinib was administered by daily oral gavage at 2.5 mg/kg. The combination of Compound B and cobimetinib at their respective single-agent dose and regimen was also tested. Body weight and tumor volume (using calipers) was measured twice weekly until study endpoints. End of study responses in individual tumors were plotted as a waterfall plot (FIG. 3B), and the numbers indicate number of tumor regression in each group. Tumor regression is defined as greater than 10% reduction of tumor volume at the end of study relative to initial volume.
Results:

FIG. 3A shows the combination of intermittent intravenous administration of Compound B at 50 mg/kg plus daily oral administration of cobimetinib at 2.5 mg/kg drove tumor regression, whereas each single agent led to tumor growth inhibition. End of study responses were shown as waterfall plots (FIG. 3B), which indicate 6 out 10 mice had tumor regression in the combination group, whereas no tumor regressions recorded in each single agent group.
Compound C:
Methods:

The combinatorial effect of a compound of the present invention, Compound C (H358 pERK K-Ras G12C EC50: 0.007 uM), with a SHP2 inhibitor, RMC-4550, on tumor cell growth in vivo were evaluated in the human non-small cell lung cancer NCI-H358 KRASG12C xenograft model using female BALB/c nude mice (6-8 weeks old). Mice were implanted with NCI-H358 tumor cells in 50% Matrigel (5×106 cells/mouse) subcutaneously in the flank. At indicated tumor volume (dotted line, FIG. 4A), mice were randomized to treatment groups to start the administration of test articles or vehicle. Compound C was administered by once weekly intravenous injection at the dose of 60 mg/kg. SHP2 inhibitor was administered by daily oral gavage at 30 mg/kg. The combination of Compound C and SHP2 inhibitor at their respective single-agent dose and regimen was also tested. Body weight and tumor volume (using calipers) was measured twice weekly until study endpoints. End of study responses in individual tumors were plotted as a waterfall plot (FIG. 4B), and the numbers indicate number of tumor regression in each group. Tumor regression is defined as greater than 10% reduction of tumor volume at the end of study relative to initial volume.
Results:

In FIG. 4A, the combinatorial activity of once weekly intravenous administration of Compound C at 60 mg/kg plus daily oral administration of SHP2 inhibitor at 30 mg/kg is shown. The combination treatment had similar anti-tumor activity as the single agent SHP2 inhibitor, but the combination treatment led to 8 out of 10 mice with tumor regression, whereas single agent SHP2 inhibitor led to 5 out of 10 mice with tumor regressions. Single agent Compound C administered once weekly via intravenous injection led to tumor growth inhibition with one tumor regression.
Cell Proliferation Assay
Methods:

NCI-H358 cells were plated in 12-well tissue culture plates at a density of 100,000 cells/well in RPMI 1640 (10% FBS, 1% PenStrep) and cultured overnight at 37° C., 5% $CO_2$. The following day, cells were treated with either trametinib (10 nM) or a compound of the present invention, Compound D (H358 pERK K-Ras G12C EC50: 0.024 uM), (17 nM). These concentrations represent the EC50 values from a 72-hour proliferation assay using the CellTiter-Glo® reagent (Promega). Additionally, cells were treated with the combination of trametinib and Compound D at the above indicated concentrations. The plate was placed in the Incucyte S3 live cell analysis system (37° C., 5% CO2) and confluence was measured by recording images at 6-hour intervals for a maximum of 40 days, or until wells reached maximal confluence. Media and drug were replaced at 3-4 day intervals. Data are plotted as % confluence over the time course of the experiment for each single agent and respective combination (FIG. 5).
Results:

As shown in FIG. 5, treatment of NCI-H358 cells with submaximal (EC50) concentrations of Compound D or MEK inhibitor results in a short period of growth inhibition, followed by proliferation. Cells reach maximal confluence in ~10 days after the addition of drug. The combination of the MEK inhibitor, trametinib, with Compound D resulted in complete and sustained inhibition of cell growth throughout the duration of the assay.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features set forth herein.

All publications, patents and patent applications are herein incorporated by reference in their entirety to the same extent as if each individual publication, patent or patent application was specifically and individually indicated to be incorporated by reference in its entirety.

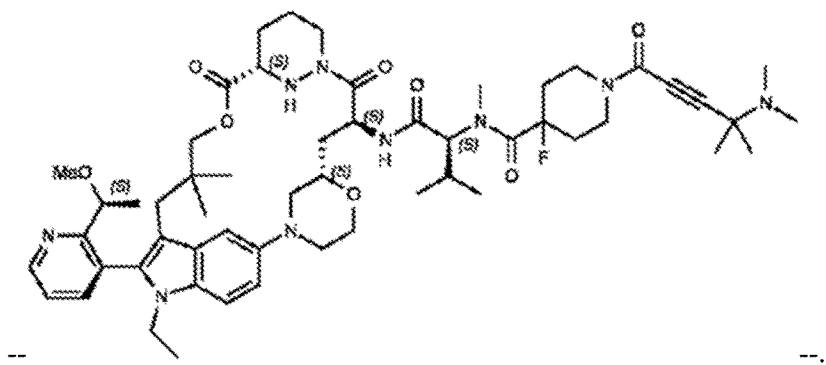

The invention claimed is:

1. A compound of the following structure:

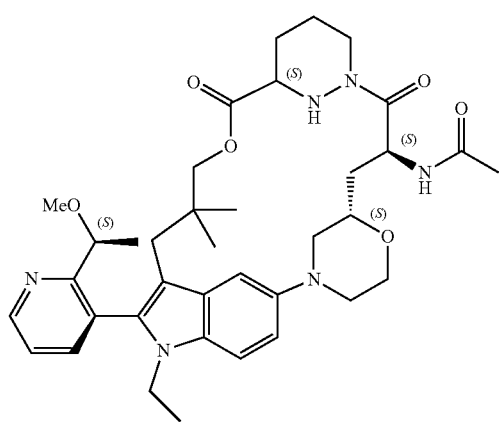

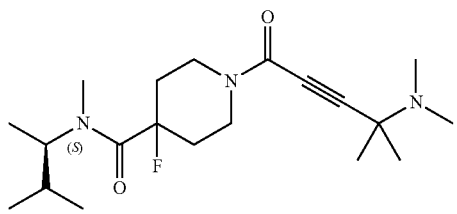

or a pharmaceutically acceptable salt thereof.

2. A compound of the following structure:
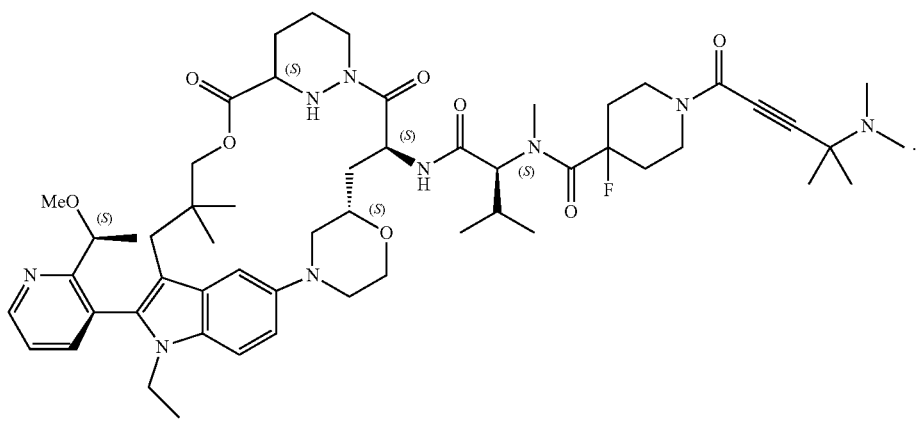
3. A pharmaceutical composition comprising a compound of the following structure:
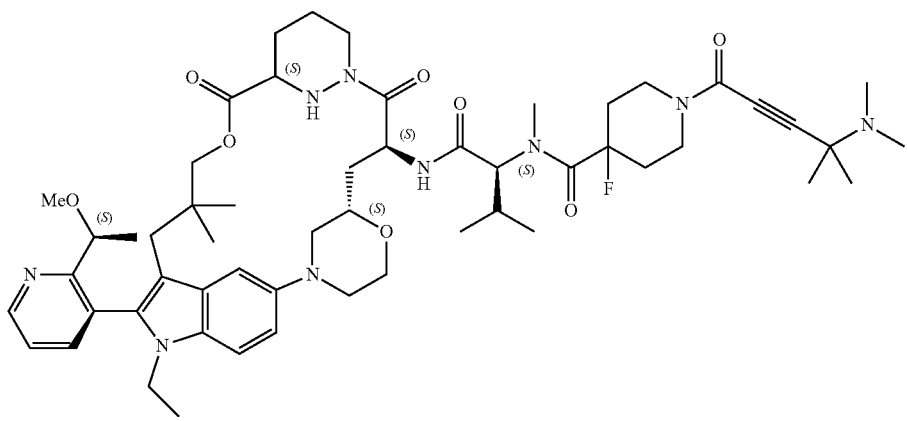
or a pharmaceutically acceptable salt thereof, and a pharmaceutically acceptable excipient.
4. A pharmaceutical composition comprising a compound of the following structure:
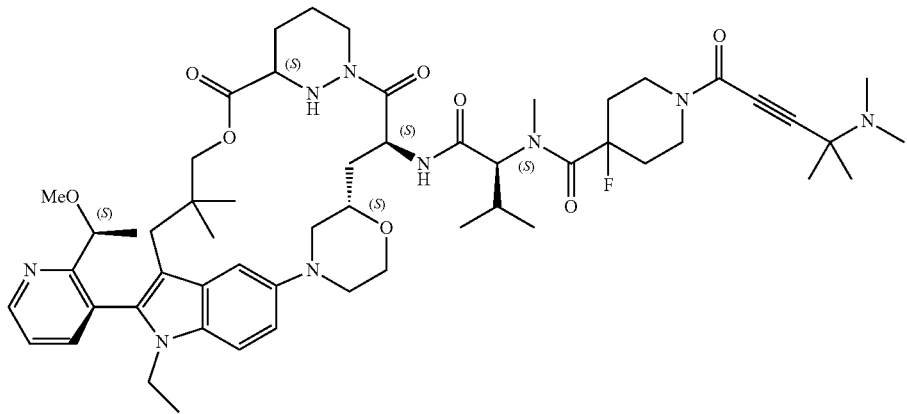
and a pharmaceutically acceptable excipient.
* * * * *

UNITED STATES PATENT AND TRADEMARK OFFICE
CERTIFICATE OF CORRECTION

PATENT NO. : 11,952,352 B2  
APPLICATION NO. : 18/161266  
DATED : April 9, 2024  
INVENTOR(S) : Adrian L. Gill et al.

Page 1 of 3

It is certified that error appears in the above-identified patent and that said Letters Patent is hereby corrected as shown below:

In the Claims

Column 1162, Compound of Claim 1, replace " 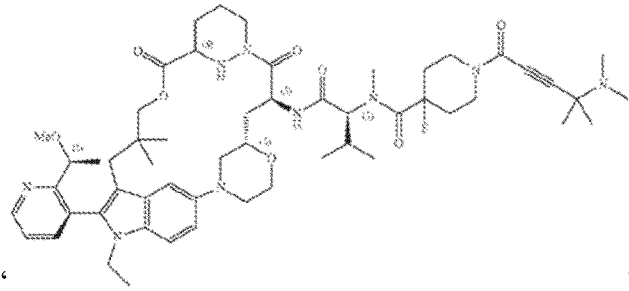 "

with -- 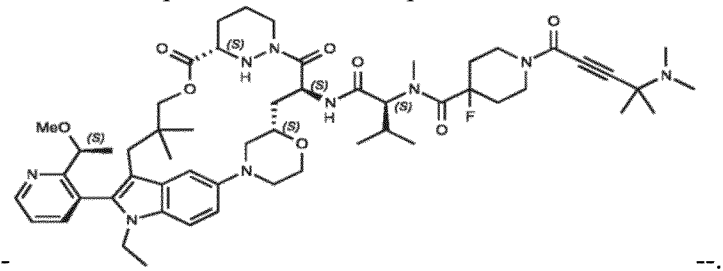 --.

Column 1163, Compound of Claim 2, replace " 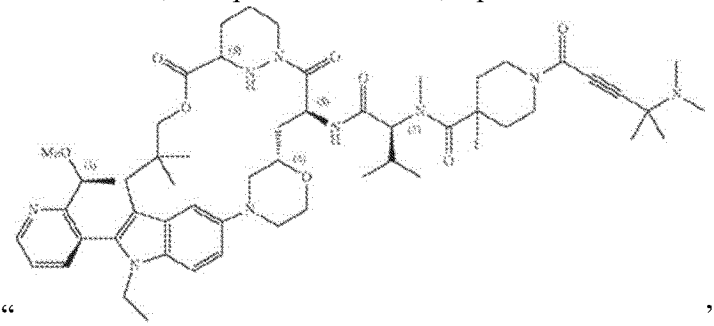 " with

Signed and Sealed this  
Twenty-fifth Day of February, 2025

Coke Morgan Stewart  
*Acting Director of the United States Patent and Trademark Office*

CERTIFICATE OF CORRECTION (continued)
U.S. Pat. No. 11,952,352 B2

Page 2 of 3

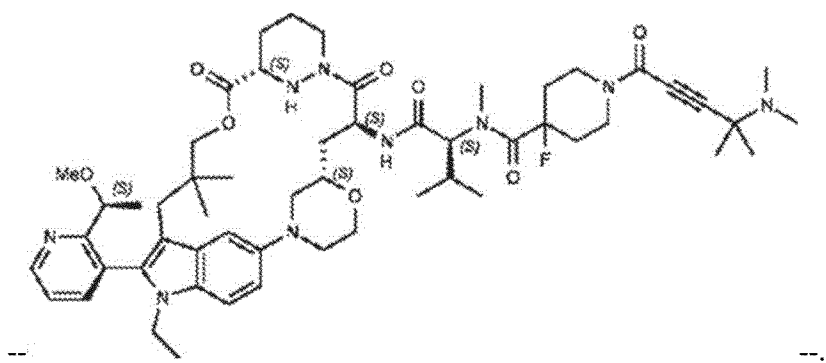

--.

Column 1163, Compound of Claim 3, replace

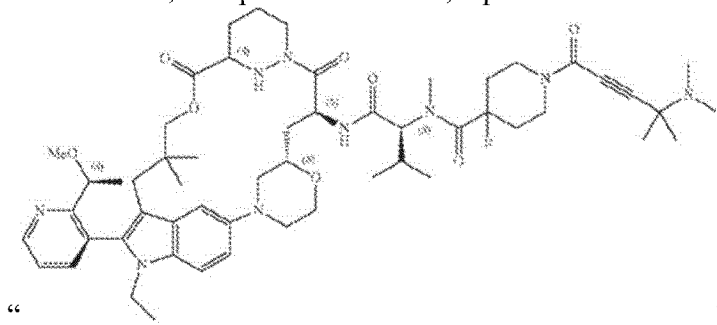

" " with

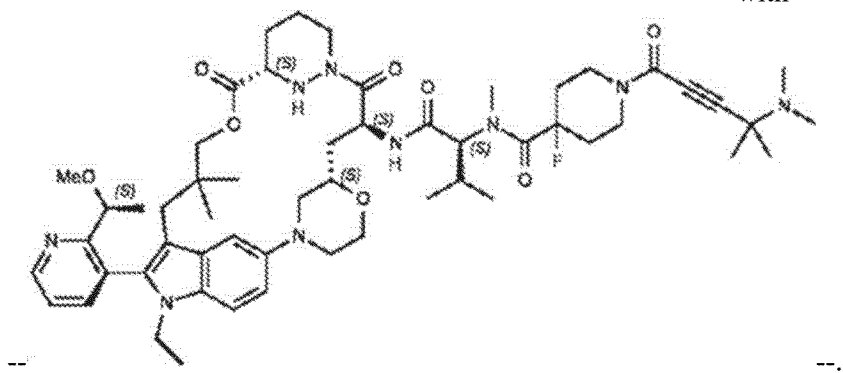

--.

Column 1163, Compound of Claim 4, replace

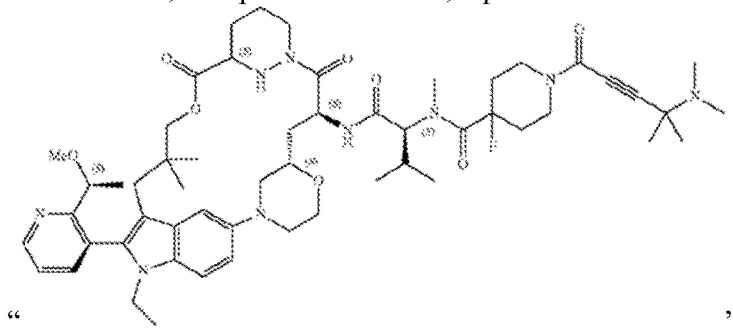

" " with

CERTIFICATE OF CORRECTION (continued)
U.S. Pat. No. 11,952,352 B2